(12) United States Patent
Baldwin et al.

(10) Patent No.: US 7,179,819 B2
(45) Date of Patent: Feb. 20, 2007

(54) VLA-4 INHIBITOR COMPOUNDS

(75) Inventors: John J. Baldwin, Gwynedd Valley, PA (US); Edward McDonald, Surrey (GB); Kevin Joseph Moriarty, Norristown, PA (US); Christopher Ronald Sarko, New Milford, CT (US); Nobuo Machinaga, Tokyo (JP); Atsushi Nakayama, Tokyo (JP); Jun Chiba, Tokyo (JP); Iimura Shin, Tokyo (JP); Yoshiyuki Yoneda, Tokyo (JP)

(73) Assignees: Daiichi Pharmaceutical Co., Ltd., Tokyo (JP); Pharmacopeia Drug Discovery, Inc., Cranbury, NJ (US)

( * ) Notice: Subject to any disclaimer, the term of this patent is extended or adjusted under 35 U.S.C. 154(b) by 81 days.

(21) Appl. No.: 10/787,905

(22) Filed: Feb. 26, 2004

(65) Prior Publication Data

US 2004/0229858 A1    Nov. 18, 2004

Related U.S. Application Data

(60) Division of application No. 10/034,585, filed on Dec. 28, 2001, now Pat. No. 6,756,378, which is a continuation of application No. PCT/US00/18079, filed on Jun. 30, 2000.

(60) Provisional application No. 60/141,601, filed on Jun. 30, 1999, provisional application No. 60/141,602, filed on Jun. 30, 1999, provisional application No. 60/141,692, filed on Jun. 30, 1999.

(51) Int. Cl.
*C07D 277/04*   (2006.01)
*A61K 31/425*   (2006.01)
*C07D 207/12*   (2006.01)

(52) U.S. Cl. ............... 514/326; 514/365; 546/209; 548/200

(58) Field of Classification Search ........... 548/200; 546/209; 514/326, 365
See application file for complete search history.

(56) References Cited

U.S. PATENT DOCUMENTS

| | | | |
|---|---|---|---|
| 5,795,876 A | 8/1998 | Wright et al. | 514/63 |
| 6,069,163 A | 5/2000 | Delaszlo | 514/403 |
| 6,306,887 B1 * | 10/2001 | Chupak et al. | 514/378 |
| 6,479,519 B1 | 11/2002 | Astles et al. | 514/332 |

FOREIGN PATENT DOCUMENTS

| | | |
|---|---|---|
| WO | WO 96/22966 | 8/1996 |
| WO | WO 97/03094 | 1/1997 |
| WO | WO 98/04913 | 2/1998 |
| WO | WO 98/53814 | 12/1998 |
| WO | WO 98/53817 | 12/1998 |
| WO | WO 98/53818 | 12/1998 |
| WO | WO 99/20272 | 4/1999 |
| WO | WO 99/23063 | 5/1999 |
| WO | WO 99/54321 | 10/1999 |

OTHER PUBLICATIONS

Singh et al., Immune therapy in inflammatory bowel disease and models of colitis, British Journal of Surgery, 88, pp. 1558-1569, 2001.*
Robinson, Medical Therapy of Inflammatory Bowel Disease for the 21st Century, Eur. J. Surg. Suppl 582, pp. 90-98, 1998.*
Agrez et al., The alphavbeta6 Integrin induces Gelatinase B Secretion in colon cancer cells, Int. J. Cancer, 81, pp. 90-97, 1999.*
Nip et al., The role of the integrin vitronectin receptor, alphavbeta3 in melanoma metastasis, Cancer and Metastasis Reviews, 14, pp. 241-252, 1995.*
Bremner et al., Therapy of Crohn's Disease in childhood, Expert Opin. Pharmacother. 3(7):809-825, 2002.*
Casanova et al., PubMed Abstract (Rev Neurol. 28(9):909-15), May 1999.*
Simone, Oncology: Introduction, Cecil Textbook of Medicine, 20th Edition, vol. 1, pp. 1004-1010, 1996.*
Tarkowski et al., PubMed Abstract (Int Arch Allergy Immunol. 121(1):25-33), Jan. 2000.*
Birner et al., Medline Abstract (European Journal of Immunology, vol. 29, Issue 4, pp. 1094-1100) Apr. 1999.*
Lobb et al., Medline Abstract (Expert Opinion on Investigational Drugs, vol. 8, Issue 7, pp. 935-945) Jul. 1999.*
Springer, Timothy A., "On a Roll with Cell Adhesion Molecules," *The Scientist*, pp. 10, 13 (Aug. 1998).
Springer, Timothy A., "Adhesion Receptors of the Immune System," *Nature*, 346:425-34 (Aug. 1990).

* cited by examiner

*Primary Examiner*—Deepak Rao
(74) *Attorney, Agent, or Firm*—Heslin Rothenberg Farley & Mesiti P.C.

(57) ABSTRACT

Compounds that selectively inhibit the binding of ligands to α4β1 integrin (VLA-4) and methods for their preparation are disclosed. In one embodiment, compounds of the invention are represented by Formula I:

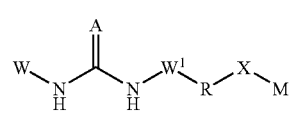

As selective inhibitors of VLA-4 mediated cell adhesion, compounds of the present invention are useful in the treatment of conditions associated with such adhesion, including, but not limited to, such conditions as inflammatory and autoimmune responses, diabetes, asthma, psoriasis, inflammatory bowel disease, transplantation rejection, and tumor metastasis. Also disclosed are methods of inhibiting VLA-4 mediated cell adhesion and methods of treating conditions associated with LA-4 mediated cell adhesion.

24 Claims, No Drawings

VLA-4 INHIBITOR COMPOUNDS

CROSS REFERENCE TO RELATED APPLICATIONS

This application is a divisional of U.S. application Ser. No. 10/034,585, filed Dec. 28, 2001 now U.S. Pat. No. 6,756,378. U.S. Ser. No. 10/034,585 is a continuation of PCT International Application PCT/US00/18079 filed Jun. 30, 2000, and published under PCT Article 21(2) in English as WO 01/00206 on Jan. 4, 2001. PCT/US00/18079 claimed benefit from U.S. Provisional Applications 60/141,601; 60/141,602 and 60/141,692, all filed Jun. 30, 1999. The entire contents of each of the prior applications are incorporated here by reference.

FIELD OF THE INVENTION

The present invention relates to compounds that selectively inhibit the binding of ligands to the adhesion receptor, $\alpha_4\beta_1$ integrin, also known as VLA-4. Compounds of the present invention are useful in the treatment and prevention of pathologies associated with VLA-4 mediated cell adhesion, such as inflammatory and autoimmune diseases, and tumor metastasis.

BACKGROUND OF THE INVENTION

A primary feature of such pathologies as inflammation and autoimmune diseases is the accumulation of activated leukocytes in affected tissues. The process by which leukocytes transmigrate from the circulation at a site of inflammation involves a cascade of interactions that can be divided into four major steps: tethering and rolling, activation, firm adhesion, and transmigration (Springer, T., *Ann. Rev. Physiol.*, 57:827 (1995)). Initially, leukocytes are lightly tethered to the endothelium and roll along its surface. This is followed by cell activation, mediated by soluble chemotactic stimuli, which initiates the development of a firmer bond between individual leukocytes and endothelial cells. The firm bond then results in the successful adhesion and transmigration of the leukocytes through endothelial cell junctions. The steps occur in series and each is essential for transmigration to occur. This also means that transmigration can be modulated at each step, thus providing a number of potential targets for pharmacological inhibition.

The receptors involved in leukocyte migration have, to a large extent, been characterized as belonging to particular cell adhesion molecule families (Carlos and Harlan, *Blood* 84:2068 (1994)). The initial attachment and rolling step is mediated by a family of adhesion receptors referred to as selecting. Firm adhesion is mediated by interaction of leukocyte surface integrins with molecules of the immunoglobulin superfamily expressed on the surface of the endothelium. Both integrins and the immunoglobulin-type adhesion molecules are also primarily involved in leukocyte transmigration. After transmigration, the leukocytes rely on integrins to traverse through the extracellular matrix and remain at the site of inflammation.

Integrins are a large family of heterodimeric glycoproteins composed of two noncovalently associated subunits, $\alpha$ and $\beta$ (Hynes, R, *Cell*, 69:11 (1992)). There are at least 16 different $\alpha$ subunits ($\alpha_1$–$\alpha_9\alpha_L$, $\alpha_M$, $\alpha_D$, $\alpha_X$, $\alpha_E$, $\alpha_{IIb}$, $\alpha_v$) and at least 9 different $\beta$ ($\beta_1$–$\beta_9$) subunits. Integrins are divided into sub-families, based upon the $\beta$ subunit. Leukocytes express a number of different integrins, including $\alpha_4\beta_1$, $\alpha_5\beta_1$, $\alpha_6\beta_1$, $\alpha_4\beta_7$, $\alpha_L\beta_2$, $\alpha_X\beta_2$, and $\alpha_v\beta_3$.

$\alpha_4\beta_1$ integrin, also known as very late antigen-4 (VLA-4) or CD49d/CD29, is expressed on monocytes, lymphocytes, eosinophils, and basophils, all of which are key effector cells in various inflammatory disorders (Helmer, M., *Ann. Rev. Immunol.*, 8:365 (1990)). $\alpha_4\beta_1$ integrin serves as a receptor for vascular cell adhesion molecule-1 (VCAM-1), as well as to the extracellular protein fibronectin (FN) (Elices et al., *Cell*, 60:577 (1990)). Anti-inflammatory effects and delayed disease progression have been demonstrated after in vivo monoclonal antibody blockade of the $\alpha_4\beta_1$/VCAM-1 pathway (Lobb et al., *J. Clin. Invest.*, 94:1722–28 (1994)). In a guinea pig model of pulmonary inflammation, anti-$\alpha_4$ inhibited both antigen-induced bronchial hyperreactivity and leukocyte recruitment in bronchoalveolar lavage fluid (Pretolani et al., *J. Exp. Med.* 180:795 (1994)). Antibodies to $\alpha_4$ or VCAM-1, prevented antigen-induced eosinophil infiltration of the mouse trachea (Nakajima et al., *J. Exp. Med.* 179:1145 (1994)). $\alpha_4$ or VCAM-1 monoclonal antibody treatment also delayed or prevented cutaneous delayed hypersensitivity response in mice and monkeys (Chisholm et al., *Eur. J. Immunol.* 23:682 (1993); Silber et al., *J. Clin. Invest.*, 93:1554 (1993); cardiac allograft rejection in mice, accompanied by specific immunosuppression (Isobe et al., *J. Immunol.*, 153:5810 (1994); graft-versus-host disease in mice after bone marrow transfer (Yang et al., *Proc. Natl. Acad. Sci. USA*, 90:10494, (1993); and experimental autoimmune encephalomyelitis in rats and mice (Yednock et al., *Nature*, 356:63 (1992);. Baron et al., *J. Exp. Med.* 177:57 (1993)).

Rational drug design studies have produced soluble VCAM-Ig fusion protein containing the two N-terminal domains of human VCAM-1 fused to a human IgG1 constant region. In vivo administration of the fusion protein significantly delays the onset of adoptively transferred autoimmune diabetes in nonobese diabetic mice (Jakubowski et al., *J. Immunol.*, 155:938 (1995)). Another approach has used three-dimensional crystallographic structures of VCAM-1 fragments to synthesize cyclic peptide antagonists that closely mimicked the $\alpha_4$ integrin binding loop in domain 1 of VCAM-1. Synthetic VCAM-1 peptide CQIDSPC, was able to inhibit the adhesion of VLA-4-expressing cells to purified VCAM-1 (Wang et al., *Proc. Natl. Acad. Sci. USA*. 92:5714 (1995)).

An additional strategy is to block the binding of $\alpha_4\beta_1$ to its other counter receptor, that is, an alternatively spliced region of fibronectin containing the connecting segment-1 (CS-1) motif (E. A. Wayner, *J. Cell. Biol.*, 116:489 (1992)). A synthetic CS-1 tetrapeptide (phenylacetic acid-Leu-Asp-Phe-d-Pro-amide) inhibited VLA-4-mediated lymphocyte adherence in vitro and reduced accelerated coronary arteriopathy in rabbit cardiac allografts (Molossi et al., *J. Clin. Invest.*, 95:2601 (1995)). Each of these studies provide evidence that selective inhibition of $\alpha_4\beta_1$/VCAM-1 mediated adhesion is a proven strategy in the treatment of autoimmune and allergic inflammatory diseases.

Moreover, while U.S. Pat. No. 5,821,231 and PCT Applications WO 96/22966, WO 97/03094, WO 98/04247 and WO 98/04913 describe compounds exhibiting VLA-4 inhibitory activity in in vitro binding assays, none of the described compounds have exhibited efficacy in oral administration.

Accordingly, despite these advances, there remains a need for small, non-peptidic, specific inhibitors of VLA-4 dependent cell adhesion that are orally bioavailable and that are suitable for the long-term treatment of chronic inflammatory diseases and other pathologies associated with leukocyte migration and adhesion.

SUMMARY OF THE INVENTION

The compounds of the present invention selectively inhibit the binding of ligands to $\alpha_4\beta_1$ and therefore, are useful for inhibition, prevention and suppression of VLA-4-mediated cell adhesion and the pathologies associated with that adhesion, such as, for example, inflammation, asthma, arthritis, diabetes, autoimmune responses, multiple sclerosis, psoriasis, transplantation rejection, and tumor metastasis.

In one embodiment, the present invention provides a compound represented by Formula I, or a salt thereof, $$W-\underset{H}{N}-\underset{H}{\overset{A}{C}}-\underset{H}{N}-W^1-R-X-M \quad \text{I}$$

wherein

W is chosen from aryl group, substituted aryl group, heteroaryl group and substituted heteroaryl group;

$W^1$ is chosen from arylene group, substituted arylene group, heteroarylene group and substituted heteroarylene group;

A is chosen from =O, =S and =NH;

R is chosen from a direct bond, alkyenylene group and —(CH$_2$)$_n$—, wherein n is chosen from 1 and 2;

X is chosen from —C(O)—, —CH$_2$— and S(O)$_2$;

M is chosen from

[structures]

is a divalent 4-, 5-, 6- or 7-membered heterocyclic moiety, wherein the nitrogen atom is the point of attachment to X;

$R^1$, $R^2$ and $R^3$ are independently chosen from —H, —OH, —NH$_2$, halogen atom, alkyl group, substituted alkyl group, aryl group, substituted aryl group, alkoxy group, substituted alkoxy group, monoalkylamino group, substituted monoalkylamino group, dialkylamino group, substituted dialkylamino group, cycloalkylamino group, substituted cycloalkylamino group, alkylsulfonylamino group, substituted alkylsulfonylamino group, arylsulfonylamino group, substituted arylsulfonylamino group, aryloxy group, substituted aryloxy group, heteroaryloxy group, substituted heteroaryloxy group, benzyloxy group and substituted benzyloxy group, or two of $R^1$, $R^2$ and $R^3$ taken together may form a 3-, 4-, 5-, 6-, or 7-membered carbocyclic or heterocyclic residues optionally substituted with from 1 to 3 substituents chosen independently from —OH, halogen atom, —NH$_2$, alkyl group, alkoxy group, aryl group, aryloxy group, alkylamino group, benzyloxy group and heteroaryl group;

$R^4$ is chosen from —H and lower alkyl group;

Y is a direct bond or a divalent radical chosen from —C(O)—, —C(O)NH—, alkenylene group, alkynylene group and —(CH$_2$)$_k$Y$^2$, wherein k is chosen from 1, 2 and 3; and $Y^2$ is a direct bond or a divalent radical chosen from —O—, —S—, —S(O), —S(O)$_2$— and —NY$^3$—, wherein $Y^3$ is chosen from —H and lower alkyl group;

Z is chosen from arylene group, substituted arylene group, heterocyclylene group, substituted heterocyclylene group, cycloalkylene group and substituted cycloalkylene group;

$A^1$ is a direct bond or a divalent radical chosen from alkenylene group, alkynylene group, —(CH$_2$)$_t$— and —O(CH$_2$)$_v$, wherein t is chosen from 1, 2 and 3; and v is chosen from 0, 1, 2, and 3; and $R^5$ is chosen from —OH, lower alkoxy group, —N(H)OH,

[structures]

is a divalent 4-, 5-, 6- or 7-membered heterocyclic moiety, wherein the nitrogen atom is the point of attachment to X;

$R^6$ and $R^7$ are independently chosen from —H, —OH, halogen atom, alkyl group and alkoxy group;

$Y^1$ is a divalent radical chosen from —O—, —S—, —S(O)—, —S(O)$_2$— and —NY$^4$—, wherein $Y^4$ is chosen from —H and lower alkyl group;

$Z^1$ is a divalent radical chosen from arylene group, substituted arylene group, heterocyclylene group, substituted heterocyclylene group, cycloalkylene group and substituted cycloalkylene group;

$A^2$ is a direct bond or a divalent radical chosen from alkenylene group, alkynylene group and —(CH$_2$)$_e$ wherein e is chosen from 1, 2 and 3; and $R^8$ is chosen from —OH, lower alkoxy group, —N(H)OH,

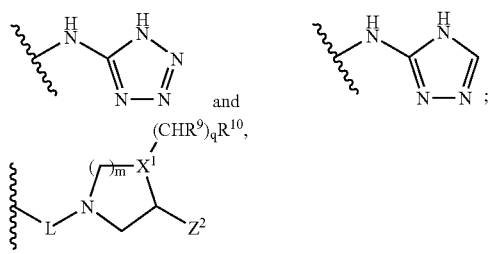

wherein
L is

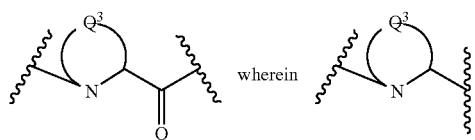 wherein

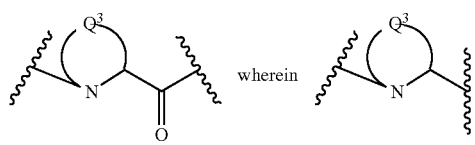 wherein is a divalent 4-, 5-, 6- or 7-membered heterocyclic moiety, optionally substituted with from 1 to 3 substitutents chosen independently from alkyl group, alkoxy group, hydroxyalkyl group, —OH, benzyloxy group, —NH$_2$, halogen atom, aryl group and heteroaryl group, said moiety may be fused to 1 or 2 additional carbocyclic or heterocyclic residues optionally substituted with from 1 to 3 substitutents chosen independently from alkyl group, aryloxy group, alkoxy group, hydroxyalkyl group, —OH, benzyloxy group, —NH$_2$, halogen atom, aryl group and heteroaryl group;

m and q are independently chosen from 0, 1, 2 and 3;
X$^1$ is chosen from —CH= and —N=;
R$^9$ is chosen from —H and lower alkyl group;
R$^{10}$ is chosen from —COOH, lower alkoxycarbonyl group,

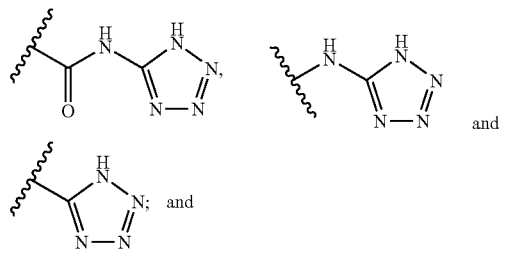

Z$^2$ is chosen from —H, COOH and lower alkoxycarbonyl group; and

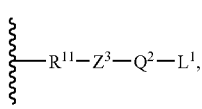

wherein
R$^{11}$ is chosen from —O—,

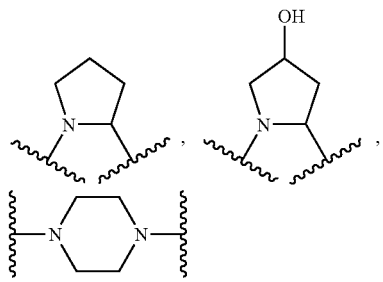

and —NR$^{12}$—
wherein
R$^{12}$ is chosen from —H, alkyl group, substituted alkyl group, cycloalkyl group, substituted cycloalkyl group, aryl group, substituted aryl group, benzyl group, substituted benzyl group, lower alkenyl group, substituted lower alkenyl group and lower alkynyl group
the left hand bond is the point of attachment to —X— and the right hand bond is the point of attachment to —Z$^3$;
Z$^3$ is chosen from a direct bond, a divalent aliphatic hydrocarbon moiety having 1 to 12 carbon atoms,
wherein
one or more carbon atoms may be replaced with —O— or —NR$^{13}$—
wherein
R$^{13}$ is chosen from —H and lower alkyl group, and
one or more hydrogen atoms attached to an aliphatic carbon atom may be replaced with lower alkyl group; and

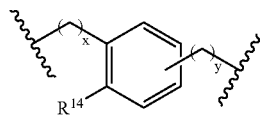

wherein
x is chosen from 0 and 1;
y is chosen from 1, 2, and 3; and
R$^{14}$ is chosen from —H, —OH and halogen atom,

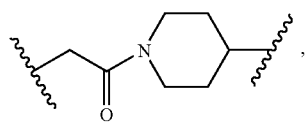

-continued

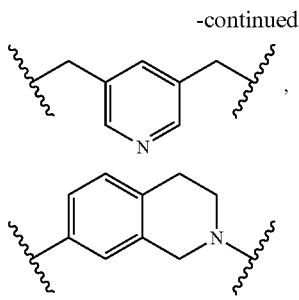

and, when $R^{11}$ is —$NR^{12}$,

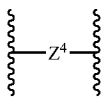

wherein

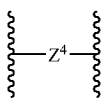

wherein
$Z^4$ is chosen from

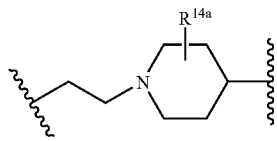

wherein
$R^{14a}$ is chosen from —H, —OH, lower alkyl group and halogen atom;

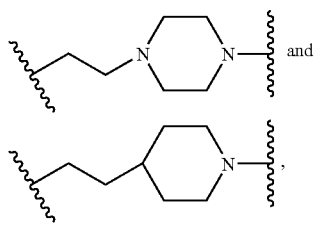

wherein the left hand bond is the point of attachment to $R^{11}$ and the right hand bond is the point of attachment to $Q^2$;
$Q^2$ is a divalent radical chosen from arylene group, substituted arylene group, heterocyclylene group, substituted heterocyclylene group, cycloalkylene group, substituted cycloalkylene group,

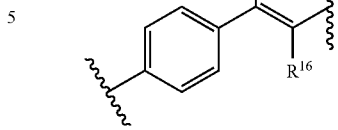

wherein $R^{15}$ and $R^{16}$ are independently chosen from —H, halogen atom and lower alkyl group; and

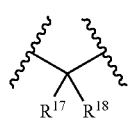

wherein $R^{17}$ and $R^{18}$ are independently chosen from —H, lower alkyl group, substituted lower alkyl group and lower alkenyl group; and
$L^1$ is chosen from —COOH and —COOR$^{19}$ wherein
$R^{19}$ is a lower alkyl group.

In a preferred embodiment of Formula I, M is

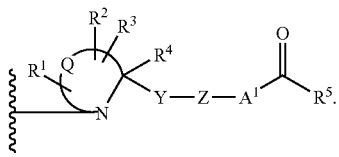

In this embodiment, more preferred compounds are those wherein A is =O, R is —(CH$_2$)$_n$— and X is —C(O)—. Y is preferably chosen from alkenylene group, alkynylene group, —(CH$_2$)$_k$Y$^2$, —CH$_2$S(O)— and —CH$_2$O—, and more preferably, Y is —CH$_2$O—.

Preferred compounds of this embodiment are those wherein W is unsubstituted phenyl group or phenyl group having one or two substituents chosen from lower alkyl group and halogen atom at the ortho positions thereof. $W^1$ is preferably unsubstituted phenylene group or phenylene group having a substituent chosen from methoxy group, lower alkyl group and halogen atom at the ortho position to —NH—.

In preferred compounds of this embodiment, A is preferably =O and $A^1$ is a direct bond or —(CH$_2$)$_r$—. More preferred compounds are those wherein $A^1$ is a direct bond and $R^5$ is —OH.

Preferred compounds of Formula I, wherein M is

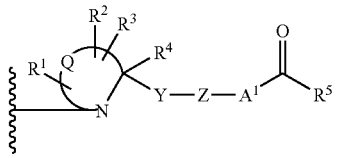

and A is =O are represented in Table 1. With respect to the representation of —W$^1$—, the lower bond is the point of attachment to —NH— and the upper bond is the point of attachment to —R—. The entry entitled ——R————R⁵ depicts that portion of the particular compound represented by

TABLE 1

| Mass Spectrum (M⁺ + 1) | W— | —W¹— | —R—R⁵ |
|---|---|---|---|
| 502.6 | 2-methylphenyl | 1,4-phenylene | 2-(3-(2-carboxyethoxy)phenyl)pyrrolidin-1-yl-propanoyl |
| 516.7 | 2-methylphenyl | 3-methoxy-1,4-phenylene | 2-(3-(2-carboxyethyl)phenyl)pyrrolidin-1-yl-propanoyl |
| 486.7 | 2-methylphenyl | 1,4-phenylene | 2-(3-(2-carboxyethyl)phenyl)pyrrolidin-1-yl-propanoyl |
| 508.7 | 2-methylphenyl | 1,4-phenylene | 2-(6-carboxynaphthalen-2-yl)pyrrolidin-1-yl-propanoyl |
| 507.0 | 2-chlorophenyl | 1,4-phenylene | 2-(4-(2-carboxyethyl)phenyl)pyrrolidin-1-yl-propanoyl |
| 501.6 | 2-methylphenyl | 1,4-phenylene | 2-(3-(2-(N-hydroxycarbamoyl)ethyl)phenyl)pyrrolidin-1-yl-propanoyl |

TABLE 1-continued

| Mass Spectrum (M⁺ + 1) | W— | —W¹— | —R—R⁵ |
|---|---|---|---|
| 486.6 | 2-methylphenyl | 1,4-phenylene | pyrrolidine-N-C(O)-CH₂- attached to 3-(CH₂CO₂H)phenyl |
| 553.6 | 2-methylphenyl | 1,4-phenylene | pyrrolidine-N-C(O)-CH₂- with 3-[CH₂CH₂C(O)NH-(1H-tetrazol-5-yl)]phenyl |
| 486.6 | 2-methylphenyl | 1,4-phenylene | pyrrolidine-N-C(O)-CH₂- with 4-(CH₂CH₂CO₂H)phenyl |
| 579.7 | 2-methylphenyl | 3-methoxy-1,4-phenylene | pyrrolidine-N-C(O)-CH₂- with 4-[C≡C-C₆H₄-C(O)NH-(1H-tetrazol-5-yl)] |
| 552.7 | 2-methylphenyl | 1,4-phenylene | pyrrolidine-N-C(O)-CH₂- with 3-[CH₂CH₂C(O)NH-(1H-1,2,4-triazol-3-yl)]phenyl |
| 496.6 | 2-methylphenyl | 1,4-phenylene | pyrrolidine-N-C(O)-CH₂- with 2-[(C≡C-CO₂H)]benzyl |

TABLE 1-continued
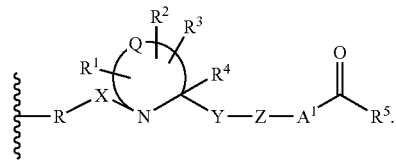
| Mass Spectrum (M⁺ + 1) | W— | —W¹— | —R—R⁵ |
|---|---|---|---|
| 500.6 | 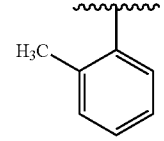 | 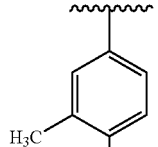 | 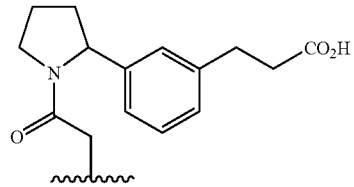 |
| 512.6 | 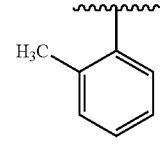 | 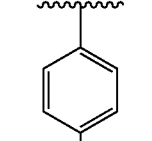 | 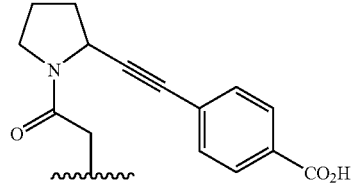 |
| 527.7 | 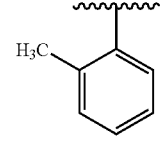 | 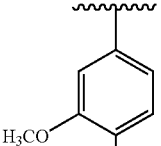 | 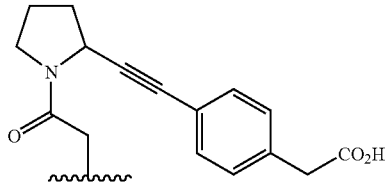 |
| 484 | 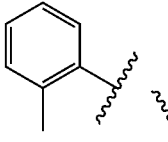 | 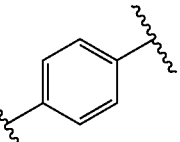 | 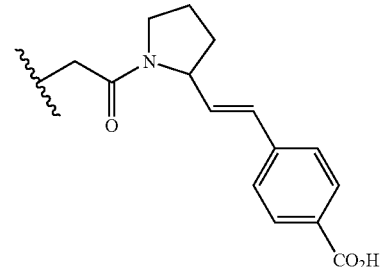 |
| 486 | 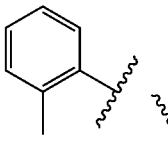 | 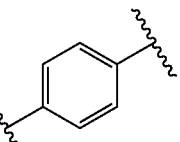 | 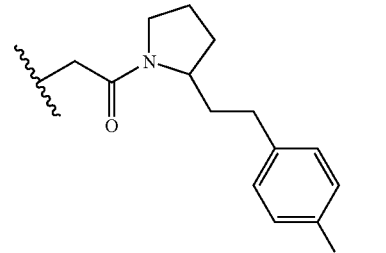 |
| 488 | 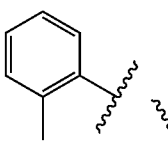 | 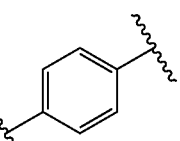 | 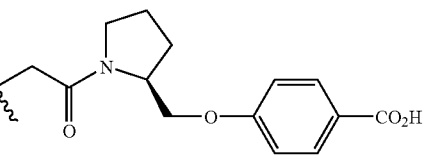 |

TABLE 1-continued
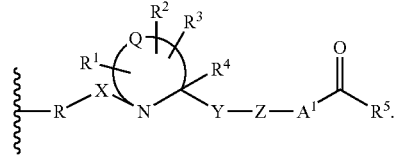
| Mass Spectrum (M⁺ + 1) | W— | —W¹— | —R—R⁵ |
|---|---|---|---|
| 504 | 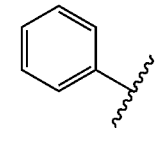 | 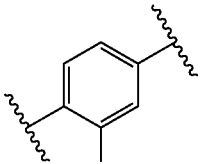 | 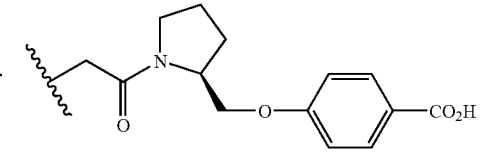 |
| 518 | 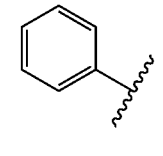 | 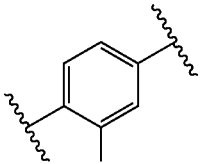 | 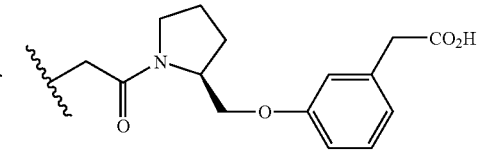 |
| 502 | 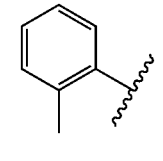 | 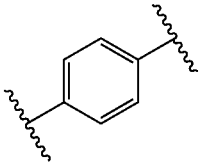 | 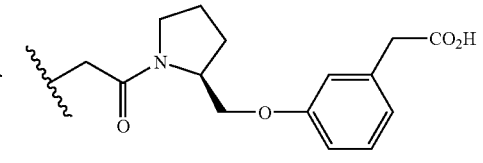 |
| 508 | 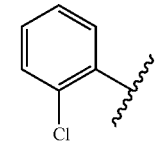 | 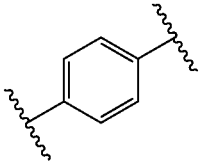 | 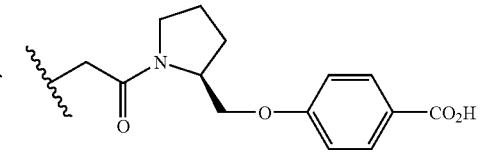 |
| 498 | 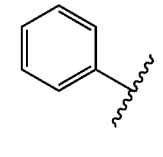 | 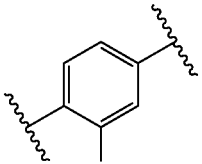 | 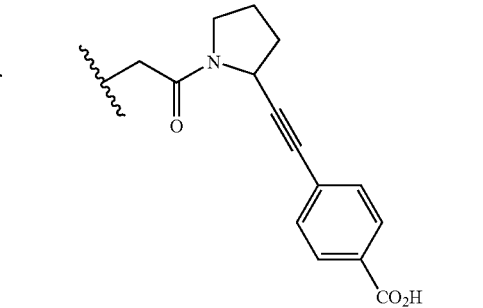 |

TABLE 1-continued
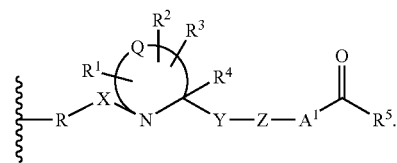
| Mass Spectrum (M⁺ + 1) | W— | —W¹— | —R—R⁵ |
|---|---|---|---|
| 512 | 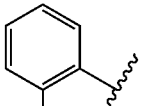 | 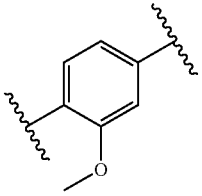 | 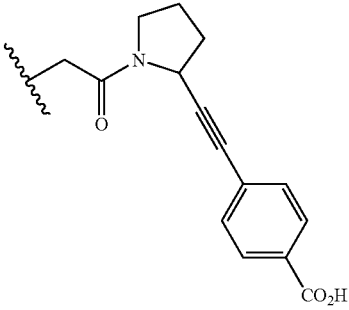 |
| 526 | 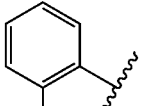 | 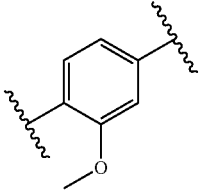 | 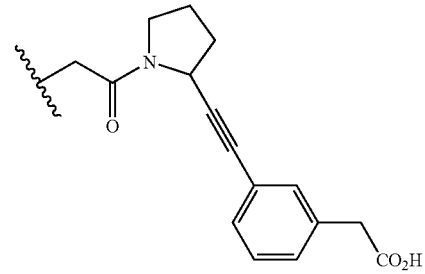 |
| 532 | 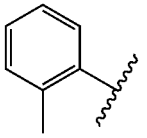 | 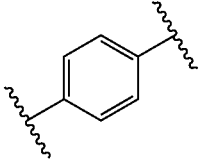 | 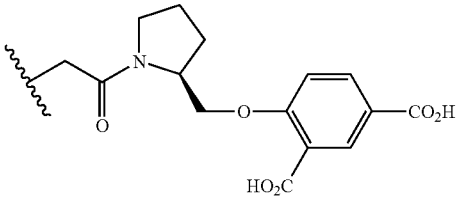 |
| 514 | 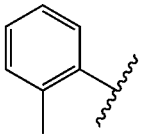 | 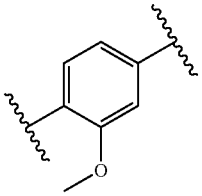 | 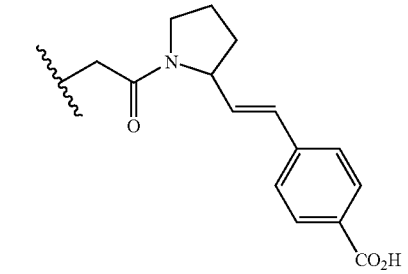 |
| 500 | 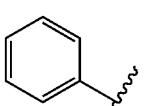 | 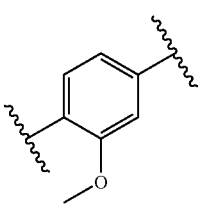 | 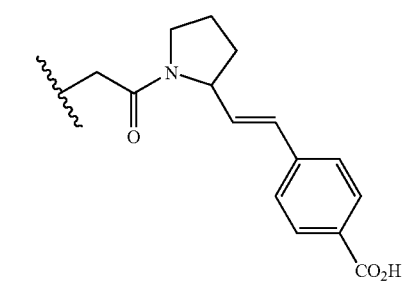 |

TABLE 1-continued
| Mass Spectrum (M⁺ + 1) | W— | —W¹— | —R—R⁵ |
|---|---|---|---|
| 516 | 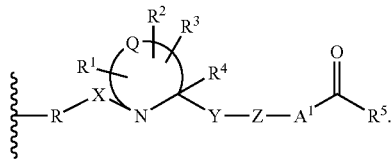 | 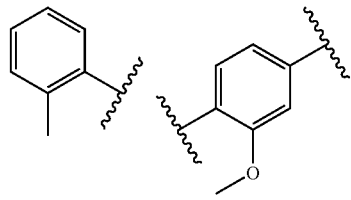 | 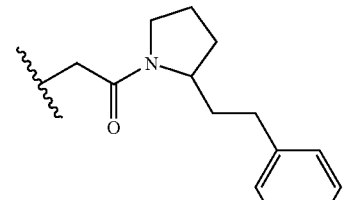 |
| 534 |  | 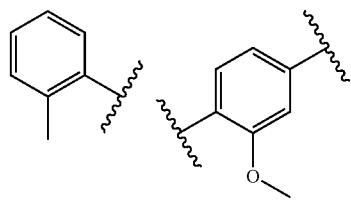 | 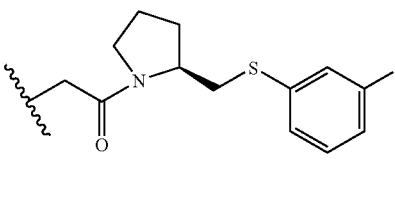 |
| 566 |  | 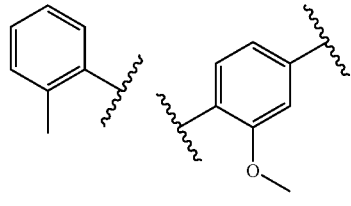 | 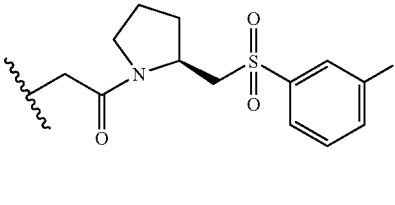 |
| 566 |  | 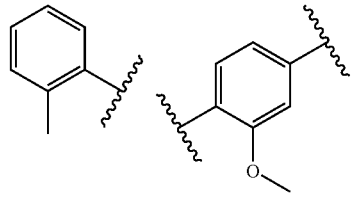 | 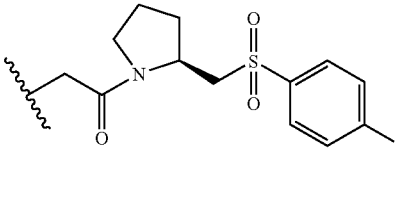 |
| 534 |  | 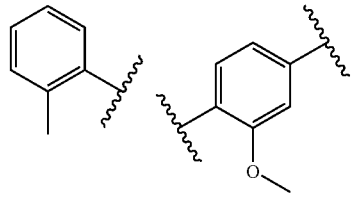 | 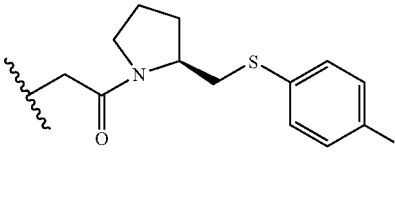 |
| 550 |  | 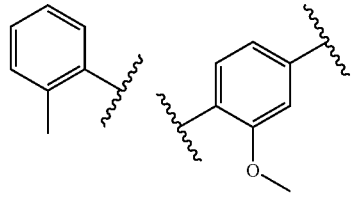 | 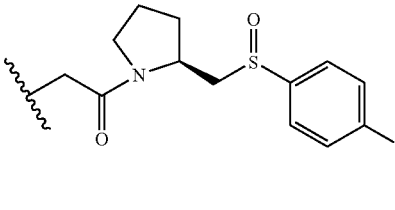 |

TABLE 1-continued
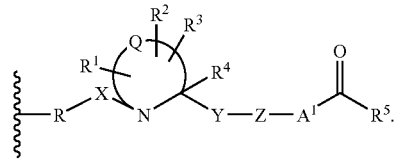

TABLE 1-continued
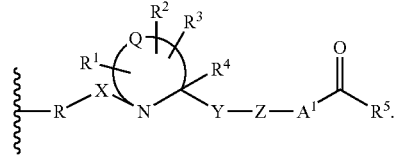
| Mass Spectrum (M+ + 1) | W— | —W¹— | —R—R⁵ |
|---|---|---|---|
| 563 | 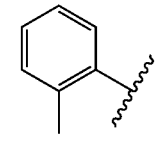 | 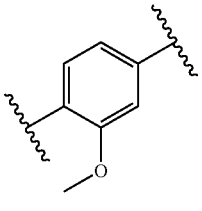 | 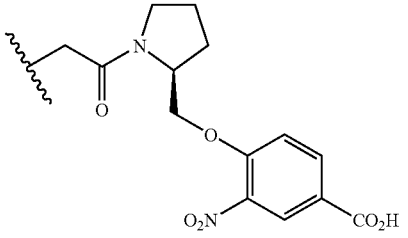 |
| 533 | 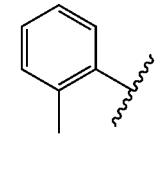 | 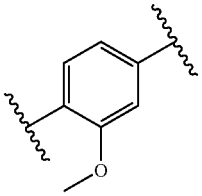 | 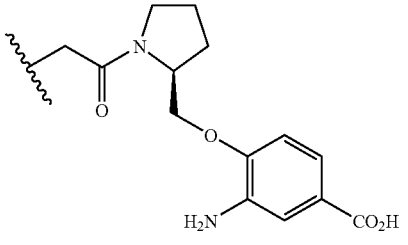 |
| 516 | 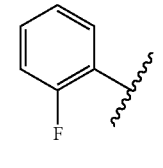 | 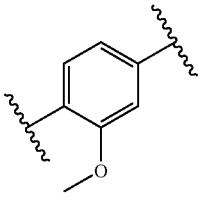 | 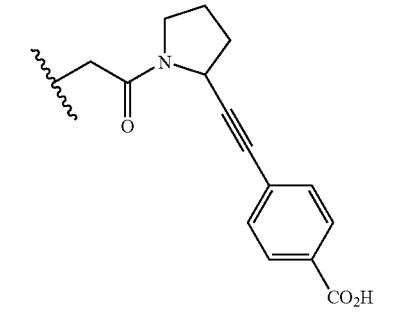 |
| 532 | 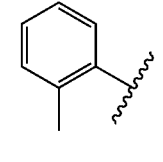 | 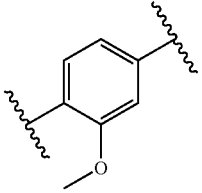 | 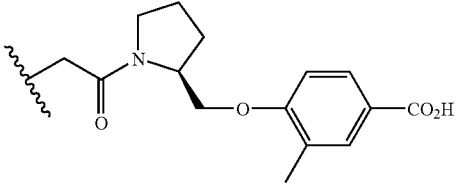 |
| 562 | 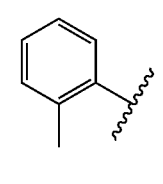 | 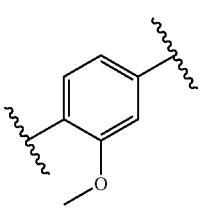 | 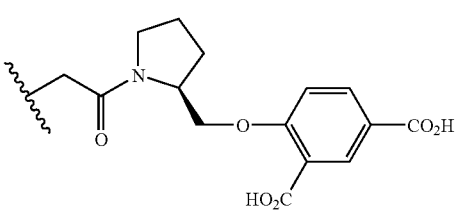 |

TABLE 1-continued
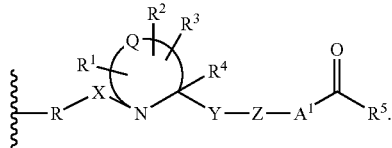
| Mass Spectrum (M+ + 1) | W— | —W¹— | —R—R⁵ |
|---|---|---|---|
| 542 | 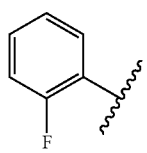 | 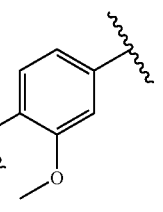 | 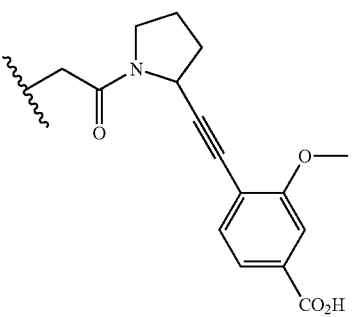 |
| 561 | 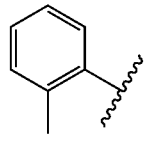 | 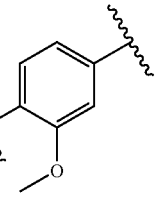 | 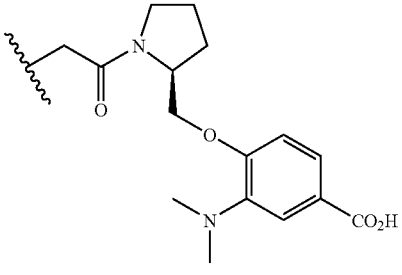 |
| 536 | 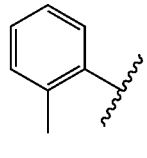 | 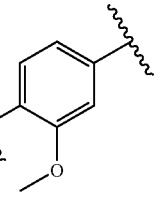 | 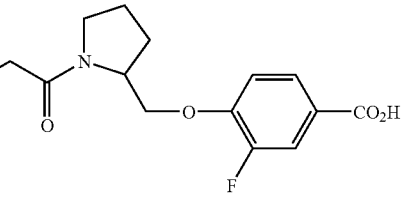 |
| 552 | 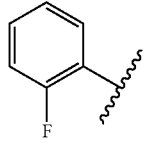 | 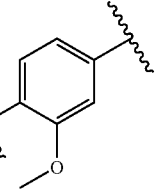 | 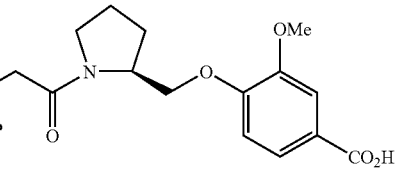 |
| 519 | 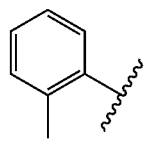 | 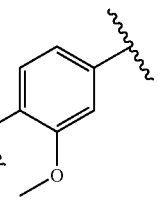 | 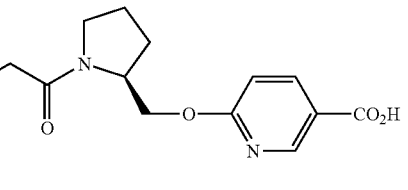 |

TABLE 1-continued
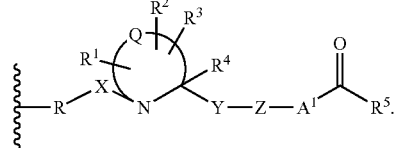

TABLE 1-continued

| Mass Spectrum (M+ + 1) | W— | —W¹— | —R—R⁵ |
|---|---|---|---|
| 575 | o-tolyl | 2-methoxyphenyl | pyrrolidine-acyl-CH₂-O-phenyl(NHAc)-CO₂H |
| 553 | o-tolyl | 2-methoxyphenyl | pyrrolidine-acyl-CH₂-O-(3-Cl-pyridyl)-CO₂H |
| 523 | 2-F-phenyl | 2-methoxyphenyl | pyrrolidine-acyl-CH₂-O-pyridyl-CO₂H |
| 524 | o-tolyl | 2-methoxyphenyl | pyrrolidine-acyl-CH₂-piperazine-CH₂-CO₂H |
| 517 | o-tolyl | 2-methoxyphenyl | pyrrolidine-acyl-CH₂-NH-phenyl-CO₂H |
| 535 | 2-F-phenyl | 2-methoxyphenyl | pyrrolidine-acyl-CH₂-N(Me)-phenyl-CO₂H |

TABLE 1-continued
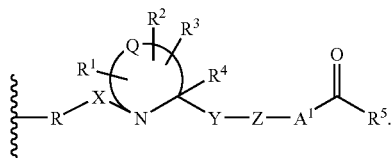
| Mass Spectrum (M⁺ + 1) | W— | —W¹— | —R—R⁵ |
|---|---|---|---|
| 521 | 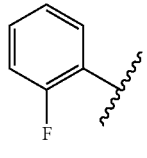 | 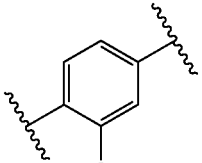 | 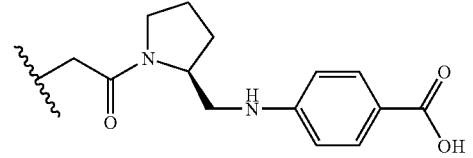 |
| 580 | 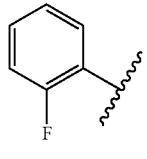 | 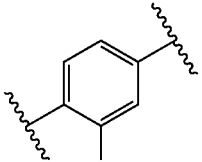 | 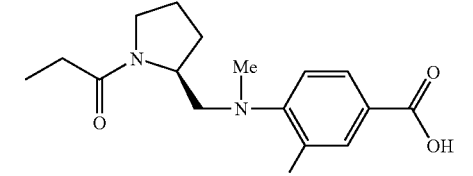 |
| 550 | 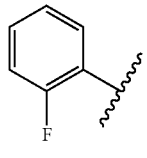 | 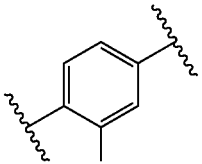 | 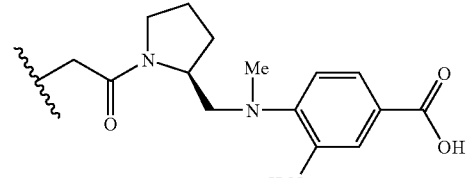 |
| 537 | 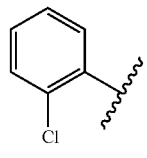 | 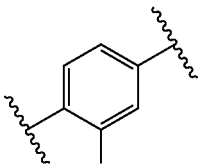 | 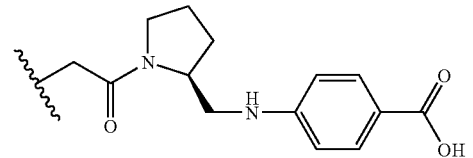 |
| 582 | 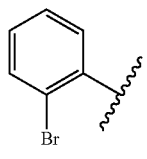 | 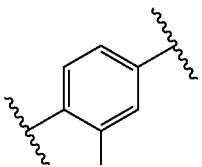 | 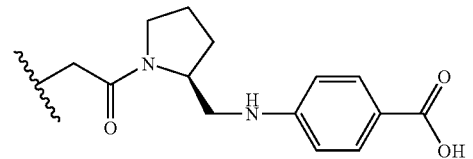 |
| 553 | 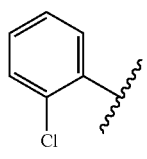 | 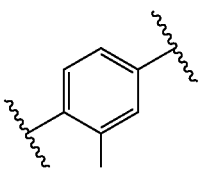 | 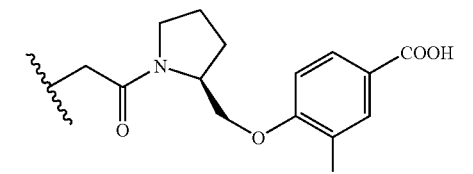 |

TABLE 1-continued
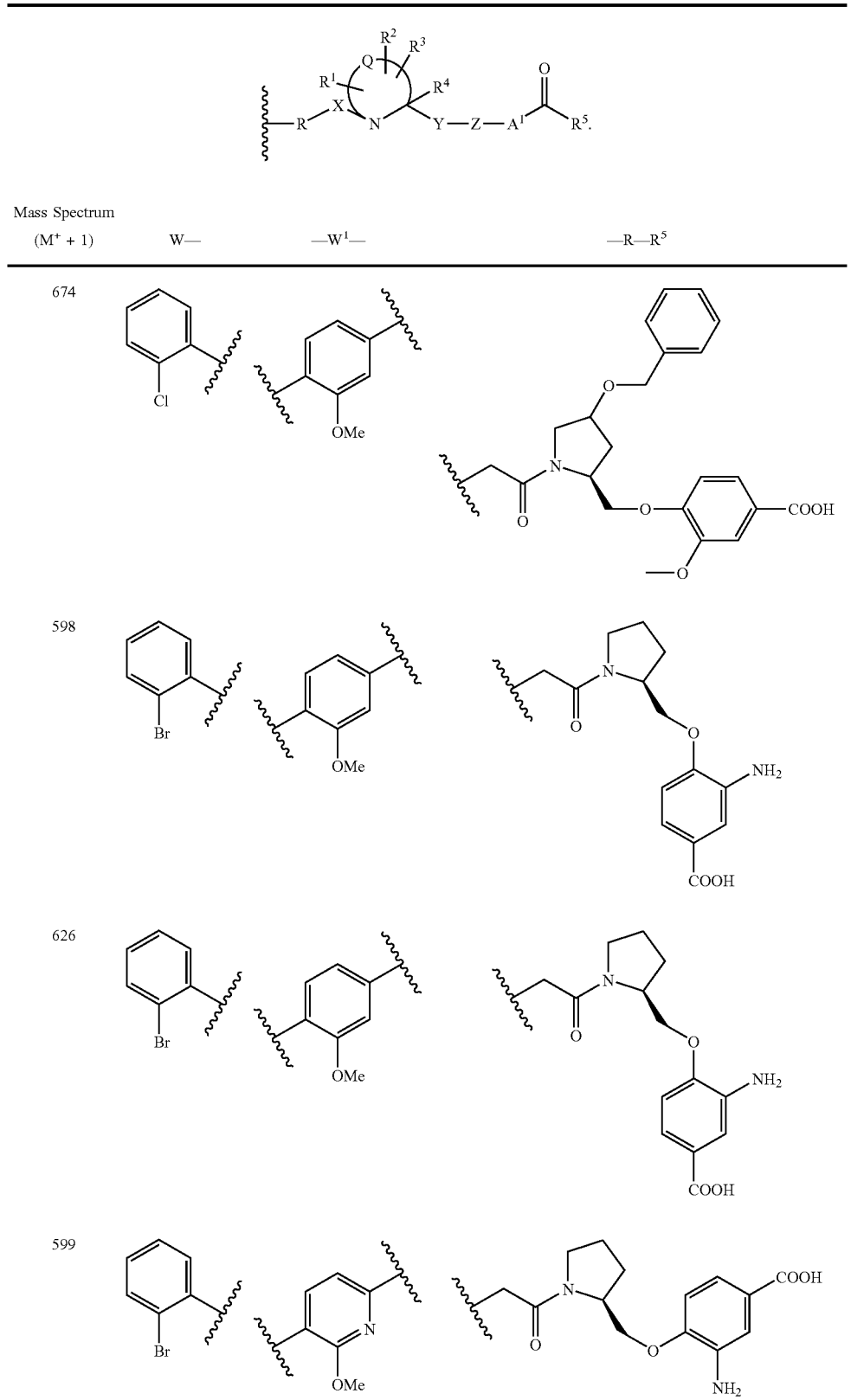

TABLE 1-continued

| Mass Spectrum (M⁺ + 1) | W— | —W¹— | —R—R⁵ |
|---|---|---|---|
| 554 | 2-Cl-phenyl | 3-methoxy-pyridin-2,6-diyl | pyrrolidine-N-C(O)-, 2-CH₂O-(3-NH₂-4-COOH-phenyl) |
| 537 | 2-Cl-phenyl | 2-OMe-phenyl-1,4-diyl | pyrrolidine-N-C(O)-, 2-CH₂NH-(4-COO-phenyl) |
| 582 | 2-Br-phenyl | 2-OMe-phenyl-1,4-diyl | pyrrolidine-N-C(O)-, 2-CH₂NH-(4-COO-phenyl) |
| 535 | 2-OH-phenyl | 2-OMe-phenyl-1,4-diyl | pyrrolidine-N-C(O)-, 2-CH₂O-(3-NH₂-4-COOH-phenyl) |
| 639 | 2-methyl-phenyl | 2-OMe-phenyl-1,4-diyl | 4-OBn-pyrrolidine-N-C(O)-, 2-CH₂O-(3-NH₂-4-COOH-phenyl) |
| 646 | 2-methyl-phenyl | 2-OMe-phenyl-1,4-diyl | 4-(2,4-diF-phenoxy)-pyrrolidine-N-C(O)-, 2-CH₂O-(4-COOH-phenyl) |

TABLE 1-continued
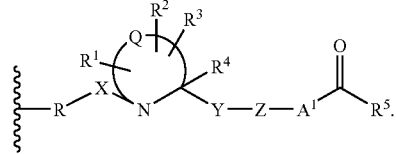
| Mass Spectrum (M⁺ + 1) | W— | —W¹— | —R—R⁵ |
|---|---|---|---|
| 629 | 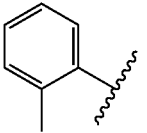 | 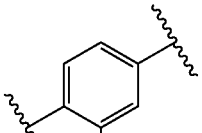 | 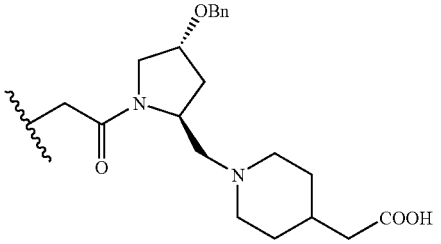 |
| 538 | 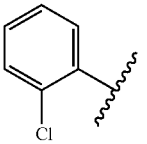 | 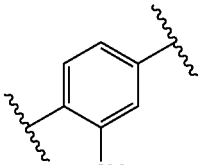 | 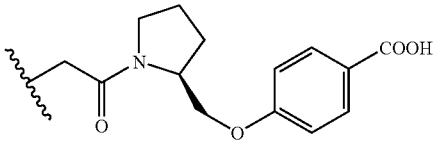 |
| 554 | 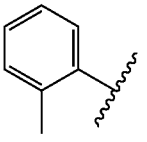 | 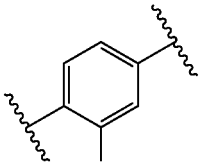 | 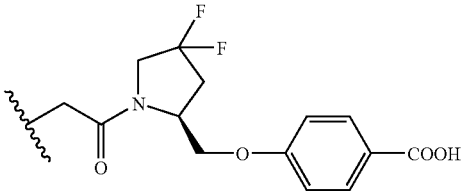 |
| 583 | 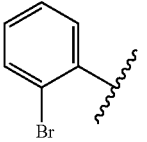 | 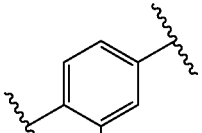 | 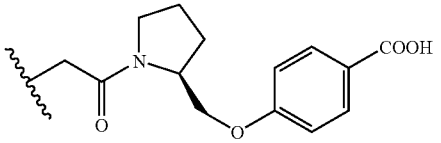 |
| 536 | 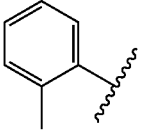 | 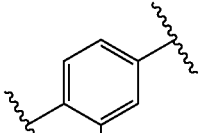 | 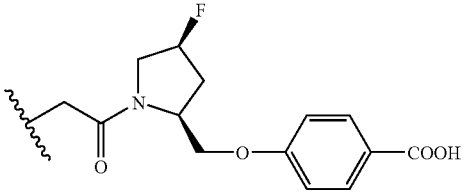 |
| 556 | 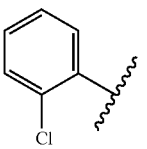 | 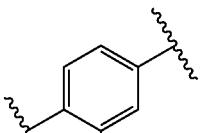 | 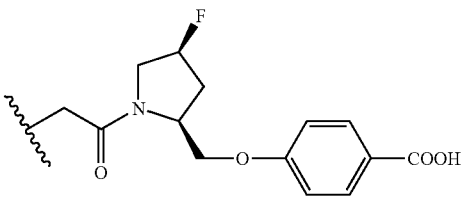 |

TABLE 1-continued

| Mass Spectrum (M⁺ + 1) | W— | —W¹— | —R—R⁵ |
|---|---|---|---|
| 538 | 2-chlorophenyl | 2-methoxy-1,4-phenylene | pyrrolidine-N-C(O)-CH₂- at 2-position, CH₂-NH-(5-pyridyl-2-COOH) |
| 518 | 2-methylphenyl | 2-methoxy-1,4-phenylene | pyrrolidine-N-C(O)-CH₂- at 2-position, CH₂-NH-(5-pyridyl-2-COOH) |
| 601 | 2-bromophenyl | 2-methoxy-1,4-phenylene | 4-fluoropyrrolidine-N-C(O)-CH₂- at 2-position, CH₂-O-(4-C₆H₄-COOH) |
| 516 | 2-methylphenyl | 2-methoxy-1,4-phenylene | pyrrolidine-N-C(O)-CH₂- at 2-position, CH₂-O-(4-C₆H₄-COOH) |
| 534 | 2-methylphenyl | 2-methoxy-1,4-phenylene | morpholine-N-C(O)-CH₂- at 3-position, CH₂-O-(4-C₆H₄-COOH) |
| 554 | 2-chlorophenyl | 2-methoxy-1,4-phenylene | morpholine-N-C(O)-CH₂- at 3-position, CH₂-O-(4-C₆H₄-COOH) |
| 542 | 2-methylphenyl | 2-methoxy-1,4-phenylene | 4-fluoropyrrolidine-N-C(O)-CH₂- at 2-position, CH₂-piperazine-CH₂-COOH |

TABLE 1-continued
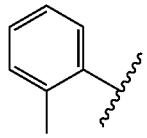
| Mass Spectrum (M+ + 1) | W— | —W¹— | —R—R⁵ |
|---|---|---|---|
| 561 | 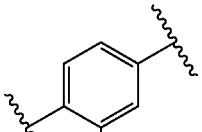 | 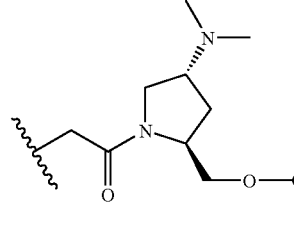 | 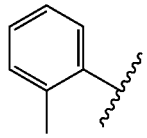 |
| 536 | 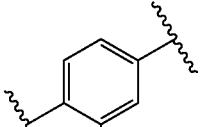 | 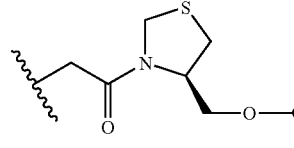 | 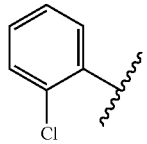 |
| 556 | 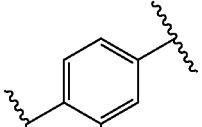 | 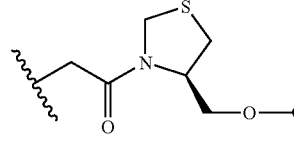 | 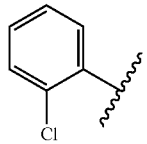 |
| 556 | 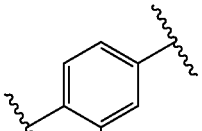 | 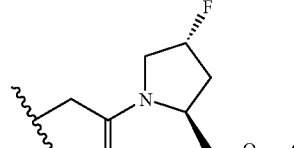 | 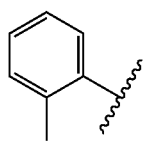 |
| 561 | 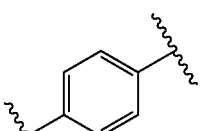 | 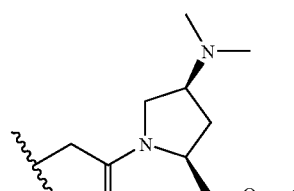 | 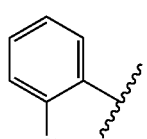 |
| 572 | 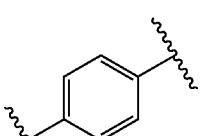 | 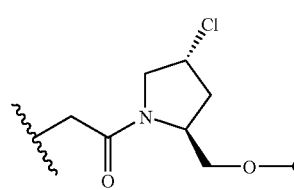 | |

TABLE 1-continued
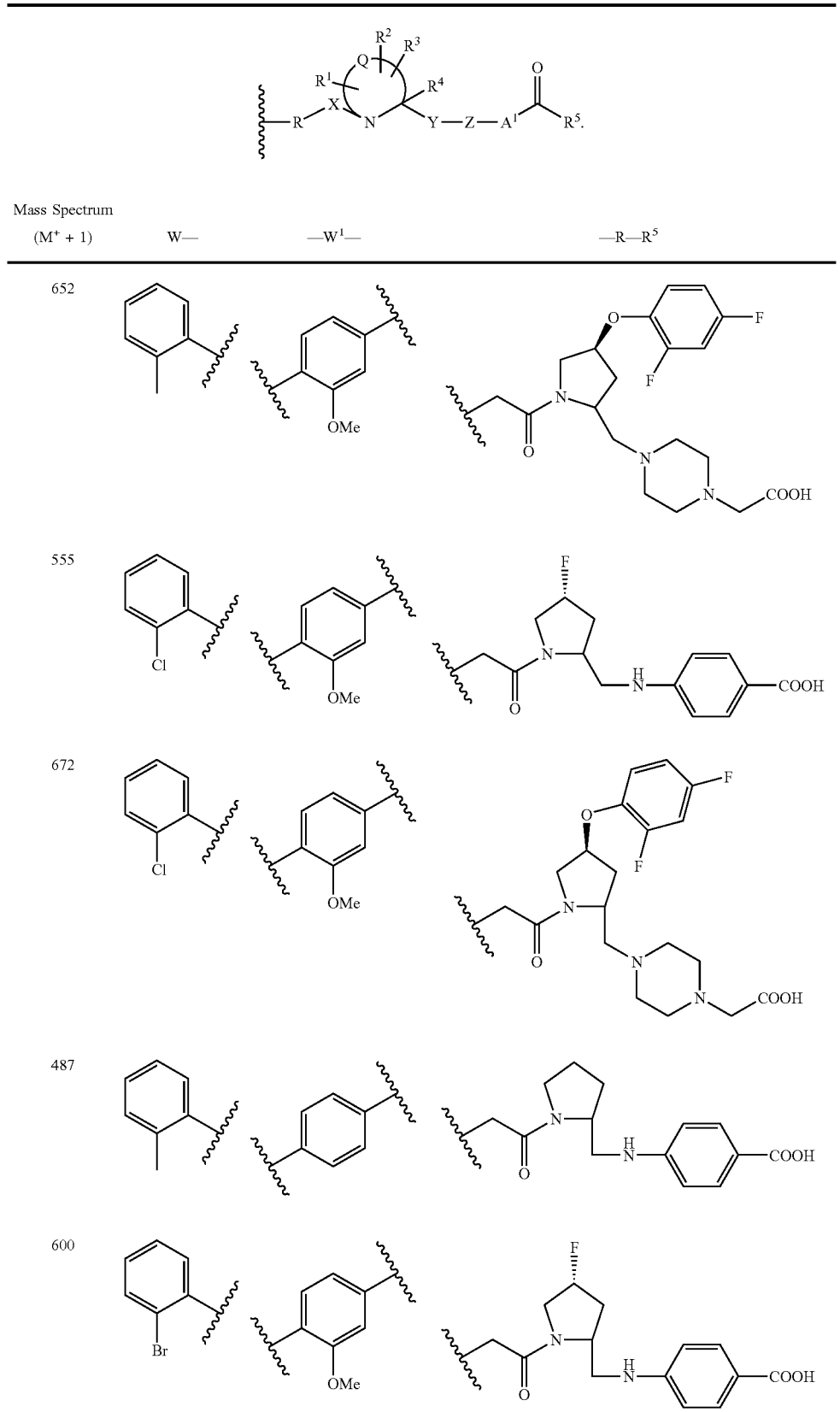

TABLE 1-continued
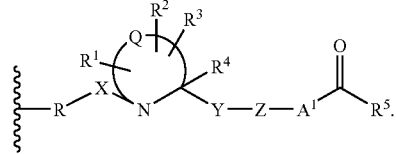

TABLE 1-continued
| Mass Spectrum (M⁺ + 1) | W— | —W¹— | —R—R⁵ |
|---|---|---|---|
| 581 | 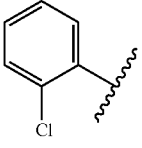 | 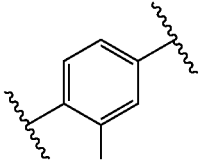 | 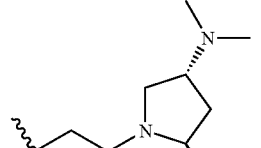 |
| 533 |  | 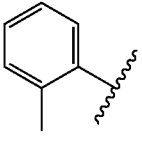 | 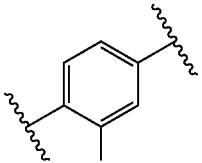 |
| 547 | 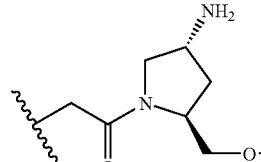 | 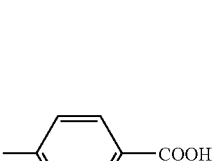 | 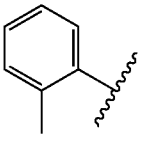 |
| 548 | 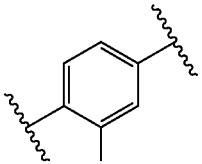 | 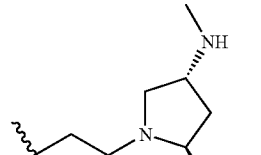 | 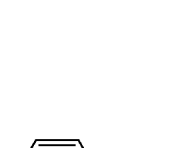 |
| 552 | 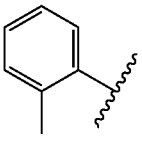 | 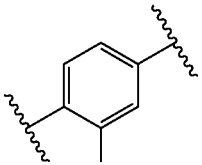 | 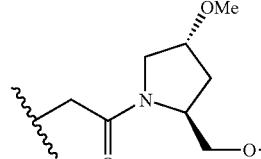 |
| 539 | 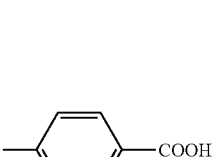 | 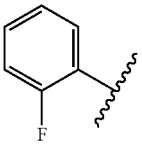 | 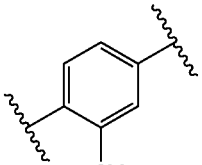 |

TABLE 1-continued
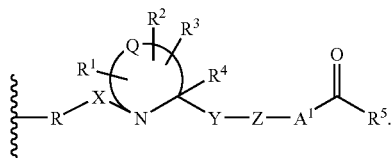
| Mass Spectrum (M+ + 1) | W— | —W¹— | —R—R⁵ |
|---|---|---|---|
| 584 | 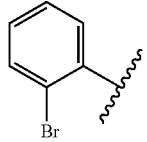 | 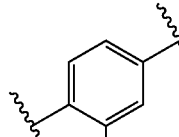 | 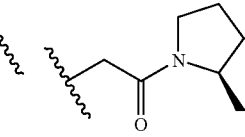 |
| 523 | 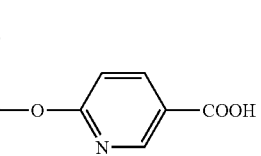 | 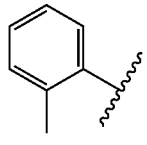 | 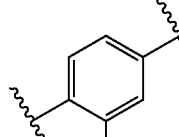 |
| 568 | 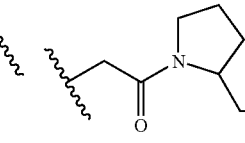 | 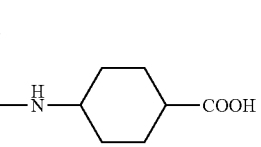 | 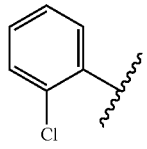 |
| 613 | 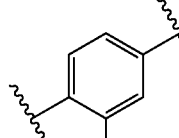 | 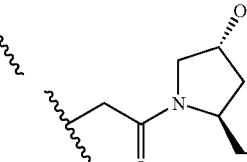 | 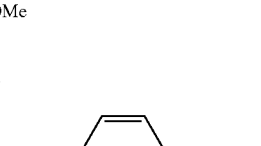 |
| 602 | 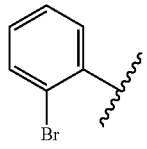 | 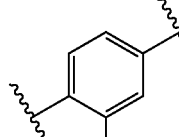 | 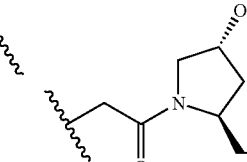 |
| 572 | 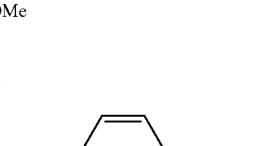 | 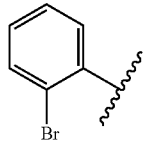 | 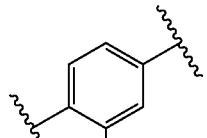 |

TABLE 1-continued
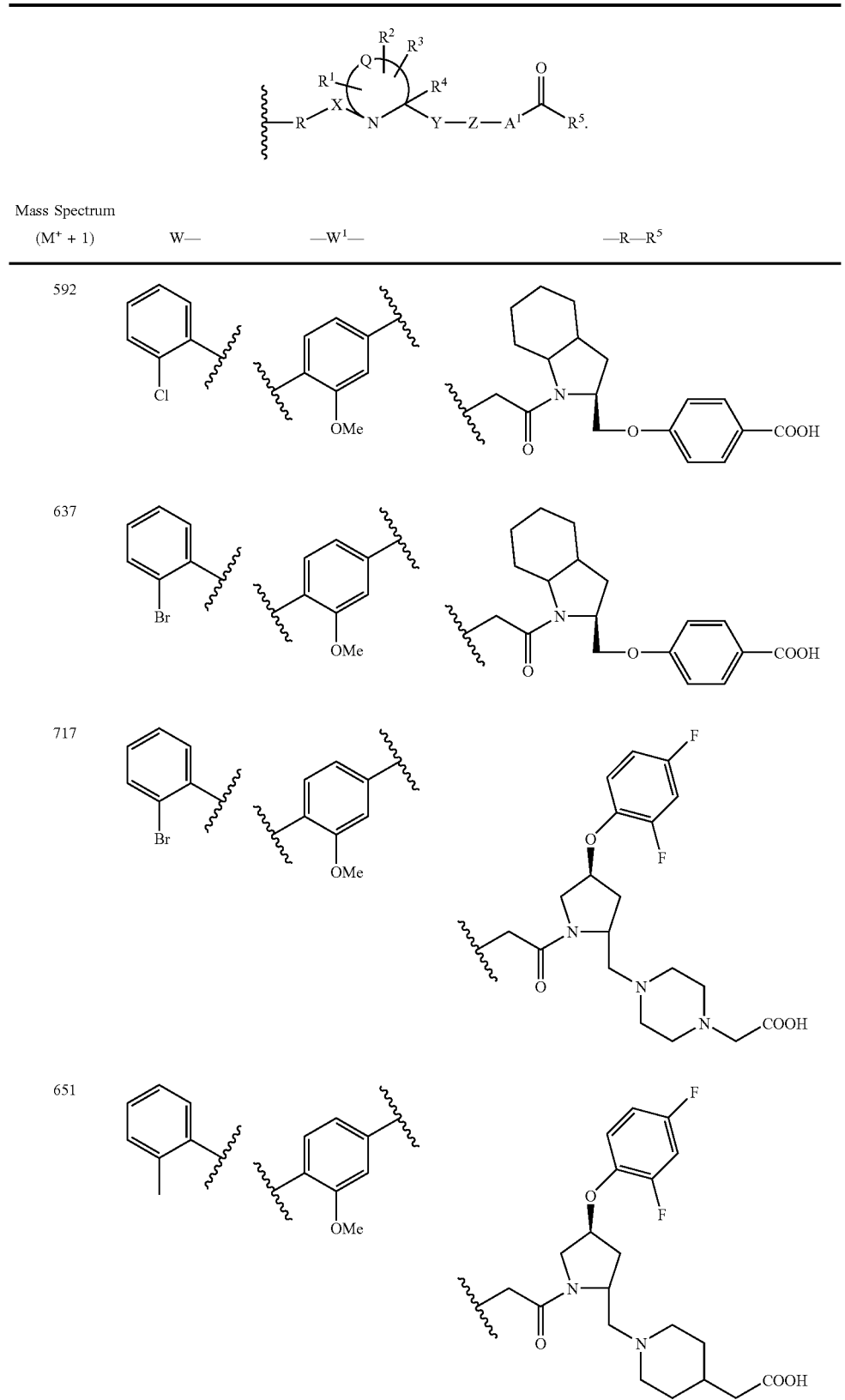

TABLE 1-continued
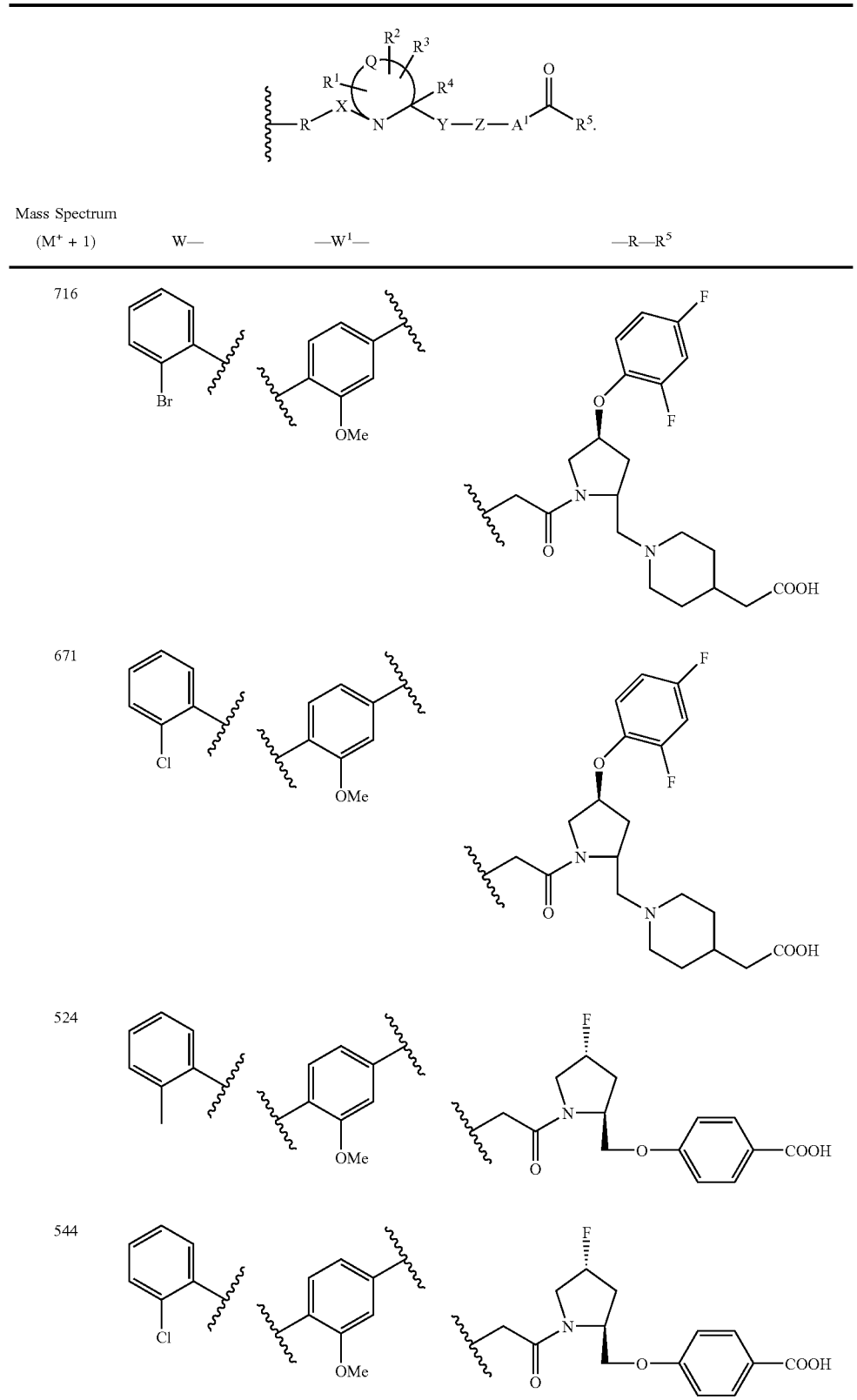
| Mass Spectrum (M+ + 1) | W— | —W¹— | —R—R⁵ |
|---|---|---|---|
| 716 | 2-Br-phenyl | 4-OMe-phenyl (2-OMe) | (2S,4R)-4-(2,4-difluorophenoxy)pyrrolidine-N-CH₂-(piperidine-4-CH₂COOH) |
| 671 | 2-Cl-phenyl | 4-OMe-phenyl (2-OMe) | (2S,4R)-4-(2,4-difluorophenoxy)pyrrolidine-N-CH₂-(piperidine-4-CH₂COOH) |
| 524 | 2-Me-phenyl | 4-OMe-phenyl (2-OMe) | (2S,4R)-4-F-pyrrolidine-2-CH₂O-(4-COOH-phenyl) |
| 544 | 2-Cl-phenyl | 4-OMe-phenyl (2-OMe) | (2S,4R)-4-F-pyrrolidine-2-CH₂O-(4-COOH-phenyl) |

TABLE 1-continued
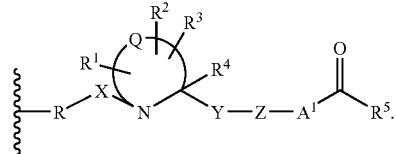
| Mass Spectrum (M+ + 1) | W— | —W¹— | —R—R⁵ |
|---|---|---|---|
| 506 | 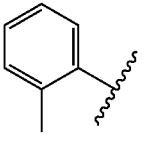 | 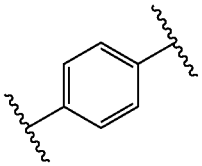 | 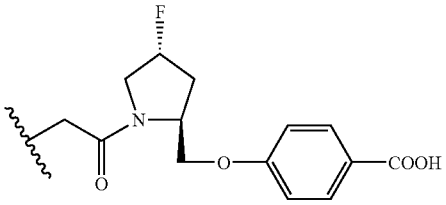 |
| 537 | 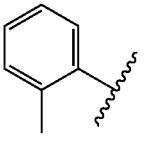 | 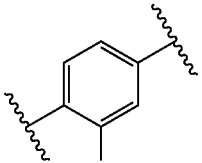 | 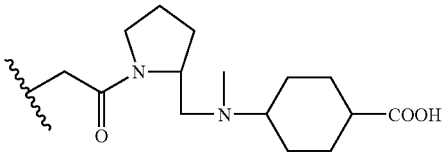 |
| 648 | 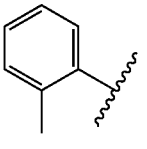 | 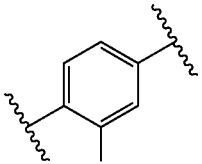 | 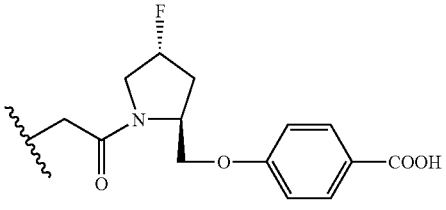 |
| 581 | 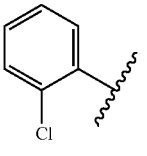 | 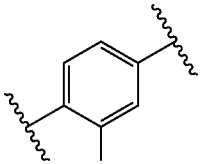 | 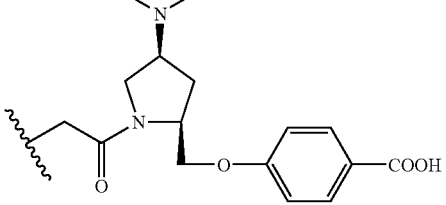 |
| 589 | 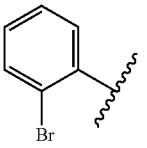 | 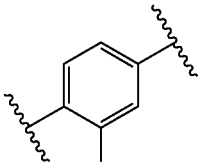 | 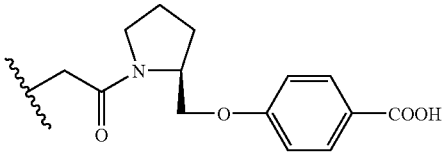 |
| 537 | 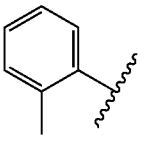 | 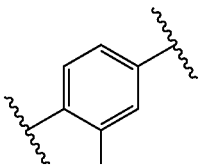 | 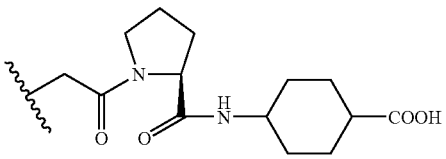 |

TABLE 1-continued
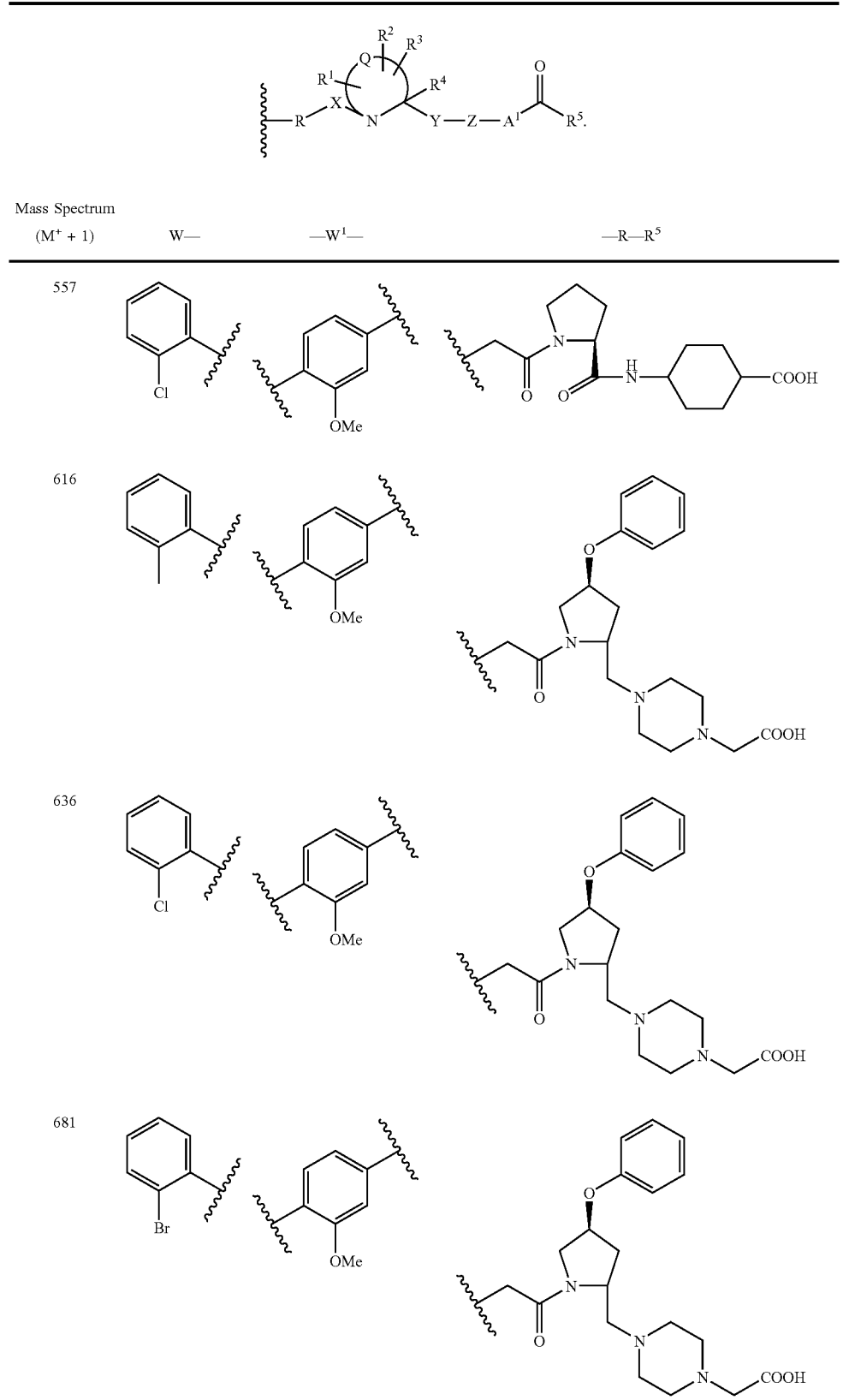

TABLE 1-continued
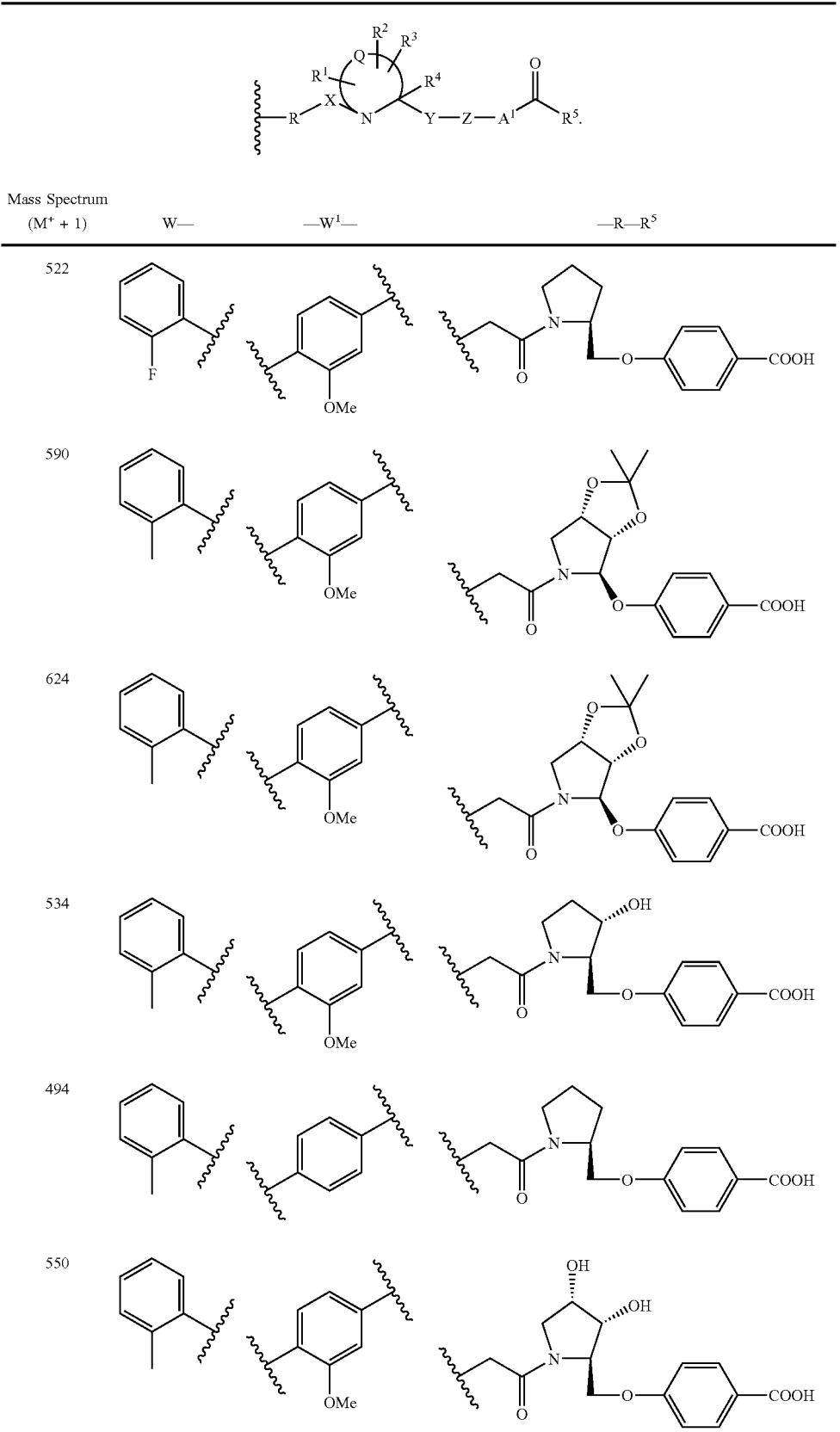

TABLE 1-continued

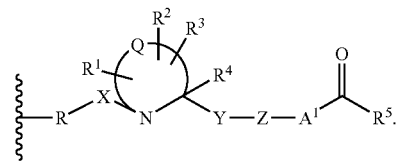

| Mass Spectrum (M+ + 1) | W— | —W¹— | —R—R⁵ |
|---|---|---|---|
| 570 | 2-Cl-phenyl | 4-OMe-phenyl | trans-3,4-dihydroxy-pyrrolidine with CH₂O-(4-COOH-phenyl) |
| 624 | 2-Me-phenyl | 4-phenyl | pyrrolidine with 3-O-(4-COOH-phenyl) and 2-CH₂O-(4-COOH-phenyl) |
| 674 | 2-Cl-phenyl | 4-OMe-phenyl | pyrrolidine with 3-O-(4-COOH-phenyl) and 2-CH₂O-(4-COOH-phenyl) |
| 661 | 2-Me-phenyl | 4-OMe-phenyl | pyrrolidine with 3-O-(2-naphthyl) and 2-CH₂O-(4-COOH-phenyl) |
| 654 | 2-Me-phenyl | 4-OMe-phenyl | pyrrolidine with 3-O-(4-COOH-phenyl) and 2-CH₂O-(4-COOH-phenyl) |
| 670 | 2-Me-phenyl | 4-OMe-phenyl | pyrrolidine with 3-O-(2-naphthyl) and 2-CH₂O-(4-COOH-phenyl) |

TABLE 1-continued

| Mass Spectrum (M⁺ + 1) | W— | —W¹— | —R—R⁵ |
|---|---|---|---|
| 680 | 2-chlorophenyl | 2-methoxy-1,4-phenylene | pyrrolidine with 2-naphthyloxy and CH₂O-C₆H₄-COOH |
| 636 | o-tolyl | 1,4-phenylene | pyrrolidine with (2-isopropyl-5-methylphenoxy) and CH₂O-C₆H₄-COOH |
| 666 | o-tolyl | 2-methoxy-1,4-phenylene | pyrrolidine with (2-isopropyl-5-methylphenoxy) and CH₂O-C₆H₄-COOH |
| 520 | o-tolyl | 2-methoxy-1,4-phenylene | 4-fluoropyrrolidine with CH₂O-C₆H₄-COOH |
| 540 | 2-chlorophenyl | 2-methyl-1,4-phenylene | 4-fluoropyrrolidine with CH₂O-C₆H₄-COOH |

TABLE 1-continued
| Mass Spectrum (M+ + 1) | W— | —W¹— | —R—R⁵ |
|---|---|---|---|
| 598 | 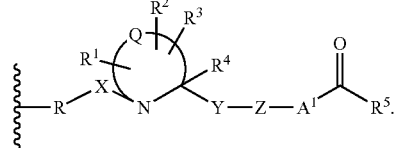 | 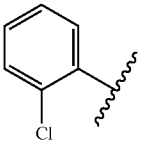 | 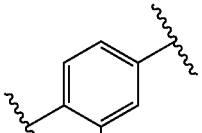 |
| 643 | 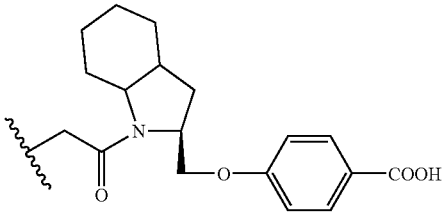 | 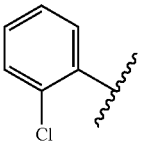 | 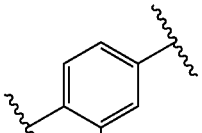 |
| 585 | 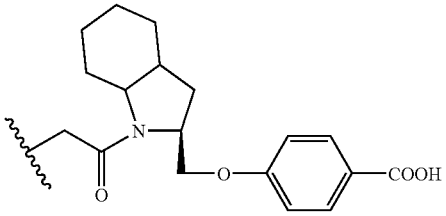 | 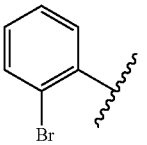 | 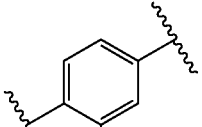 |
| 601 | 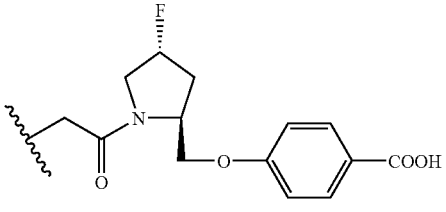 | 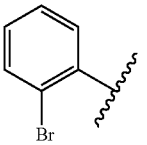 | 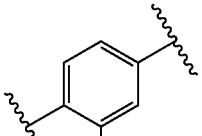 |
| 719 | 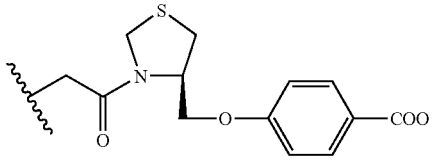 | 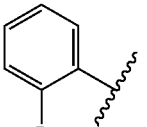 | 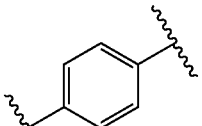 |
| 594 | 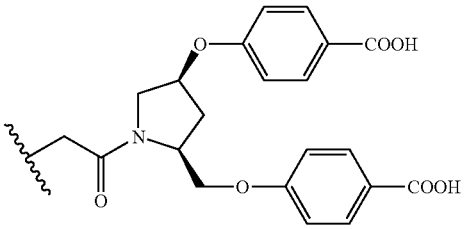 | 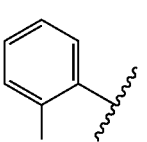 | 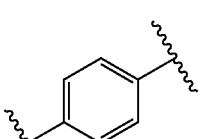 |

TABLE 1-continued
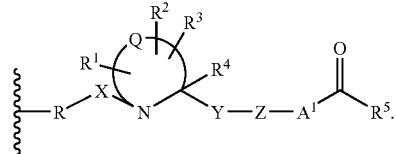
| Mass Spectrum (M⁺ + 1) | W— | —W¹— | —R—R⁵ |
|---|---|---|---|
| 686 | 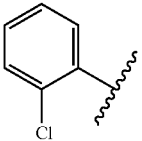 | 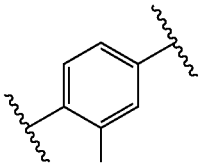 | 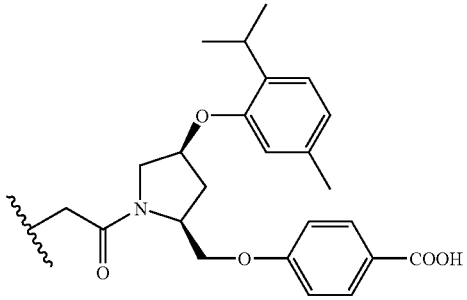 |
| 731 | 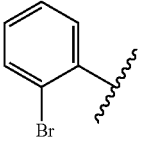 | 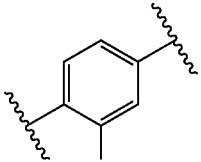 | 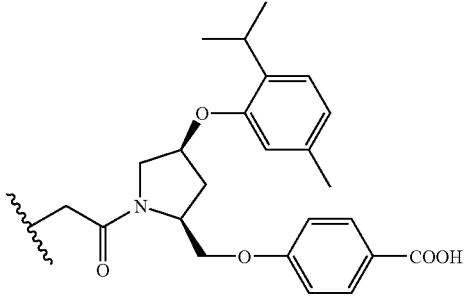 |
| 573 | 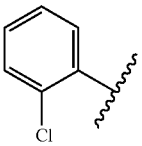 | 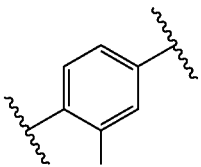 | 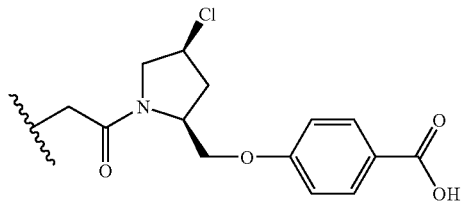 |
| 617 | 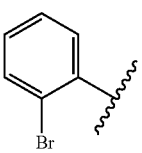 | 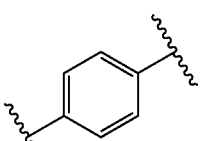 | 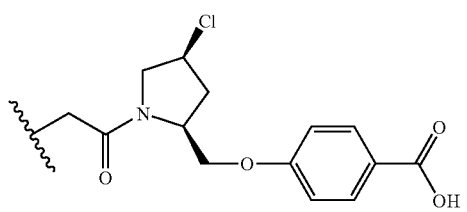 |
| 492 | 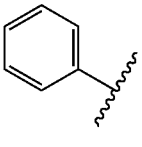 | 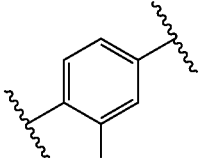 | 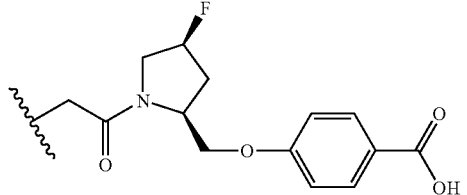 |

TABLE 1-continued
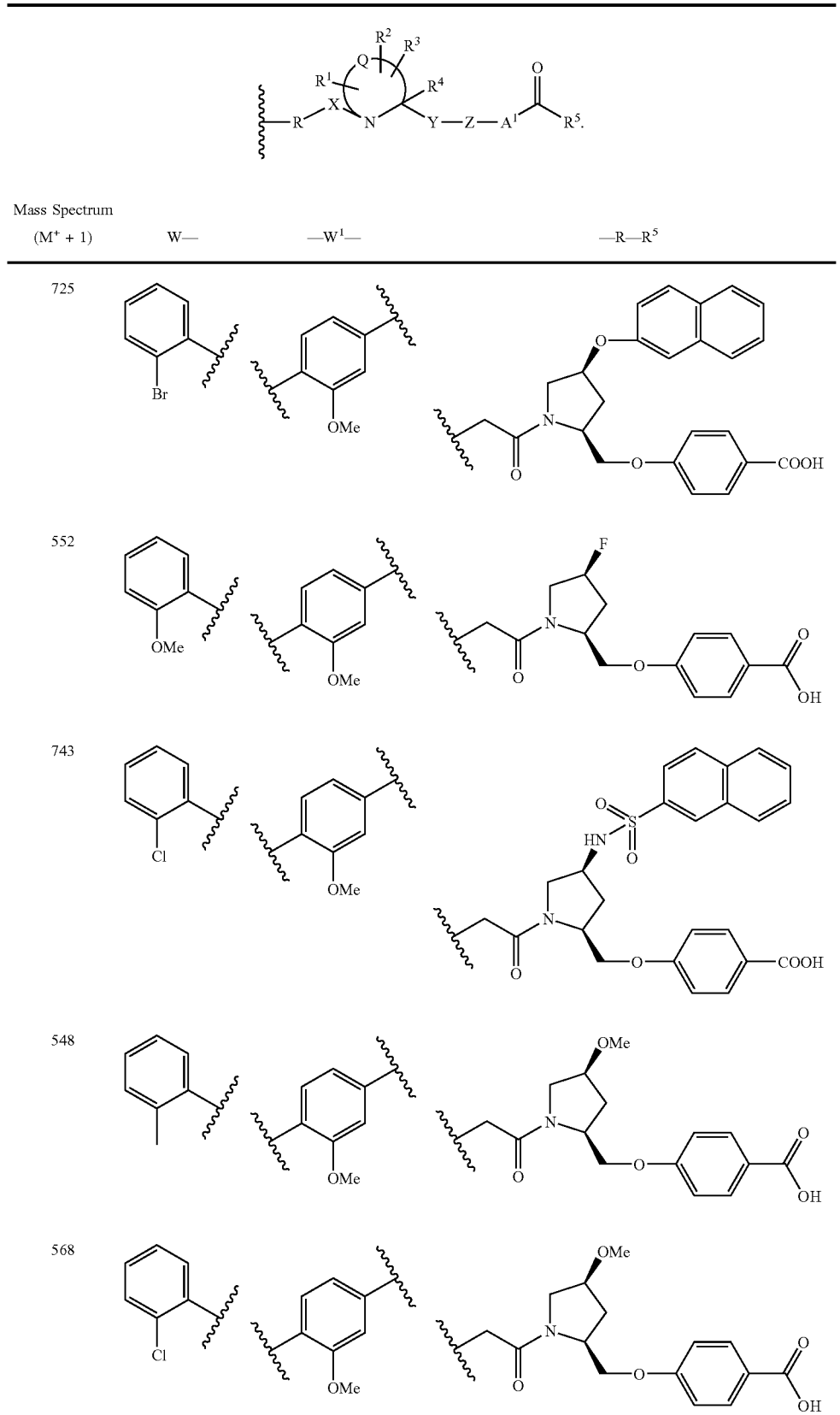

TABLE 1-continued
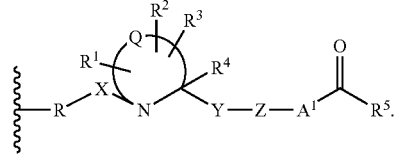
| Mass Spectrum (M⁺ + 1) | W— | —W¹— | —R—R⁵ |
|---|---|---|---|
| 613 | 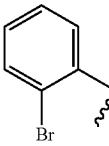 | 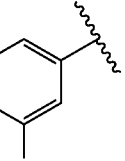 | 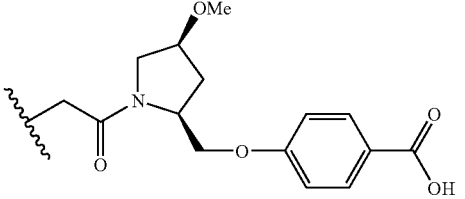 |
| 506 | 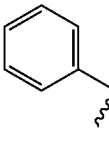 | 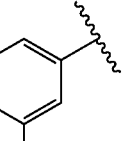 | 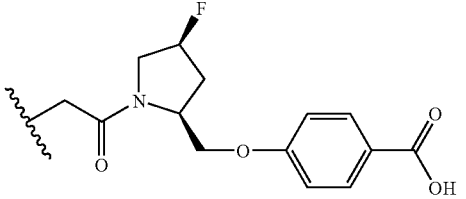 |
| 780 | 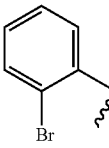 | 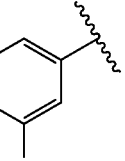 | 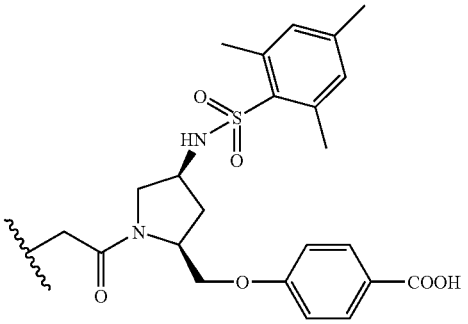 |
| 831 | 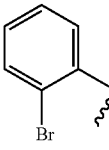 | 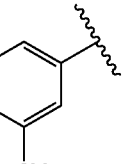 | 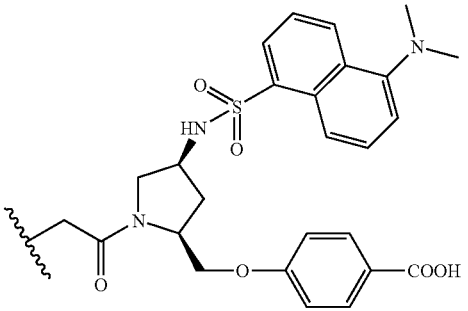 |
| 676 | 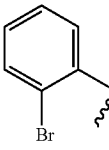 | 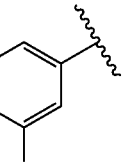 | 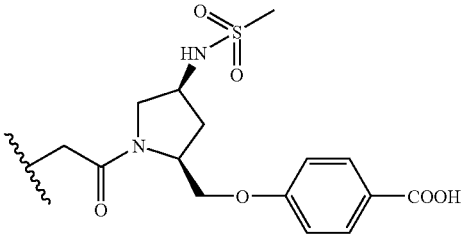 |

TABLE 1-continued

| Mass Spectrum (M⁺ + 1) | W— | —W¹— | —R—R⁵ |
|---|---|---|---|
| 524 | 2-F-phenyl | 4-Me-phenyl (1,4 with 3-Me) | pyrrolidine with 4-F, 2-CH₂O-(4-COOH-phenyl), N-acyl |
| 644 | 2-Cl-phenyl | 2-OMe-phenyl (1,4) | pyrrolidine with 3-OBn, 2-CH₂O-(4-COOH-phenyl), N-acyl |
| 689 | 2-Cl-phenyl | 2-OMe-phenyl (1,4) | pyrrolidine with 3-OBn, 2-CH₂O-(4-COOH-phenyl), N-acyl |
| 594 | 2-Me-phenyl | 1,4-phenyl | pyrrolidine with 3-OBn, 2-CH₂O-(4-COOH-phenyl), N-acyl |
| 681 | 2-Cl-phenyl | 2-OMe-phenyl (1,4) | pyrrolidine with 4-O-(quinolin-6-yl), 2-CH₂O-(4-COOH-phenyl), N-acyl |
| 726 | 2-Br-phenyl | 2-OMe-phenyl (1,4) | pyrrolidine with 4-O-(quinolin-6-yl), 2-CH₂O-(4-COOH-phenyl), N-acyl |

TABLE 1-continued
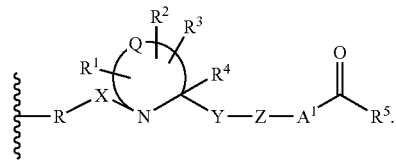
| Mass Spectrum (M⁺ + 1) | W— | —W¹— | —R—R⁵ |
|---|---|---|---|
| 590 | 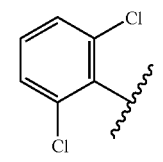 | 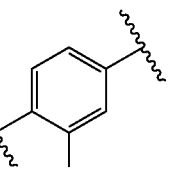 | 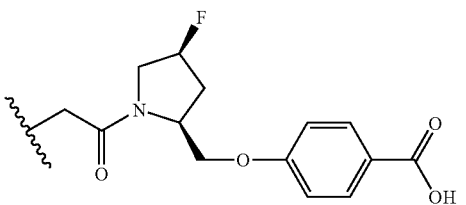 |
| 594 | 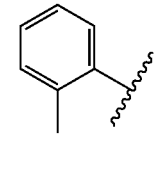 | 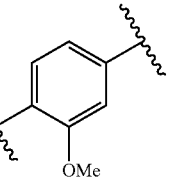 | 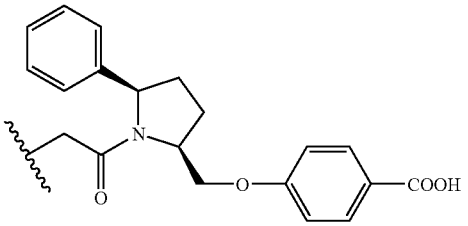 |
| 614 | 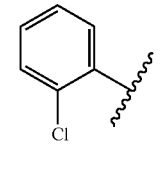 | 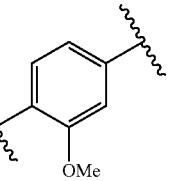 | 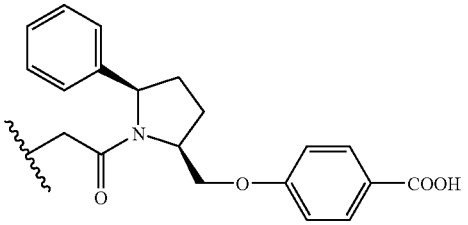 |
| 659 | 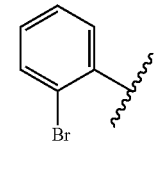 | 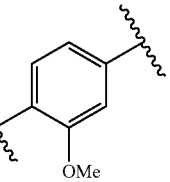 | 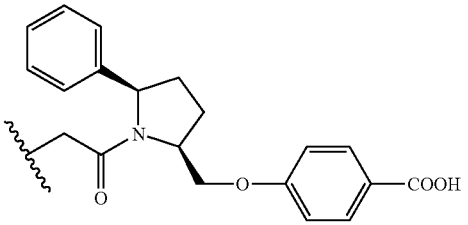 |
| 534 | 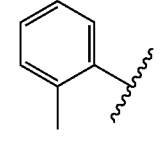 | 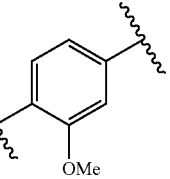 | 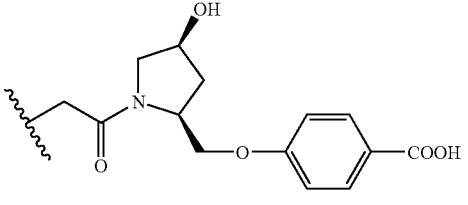 |
| 554 | 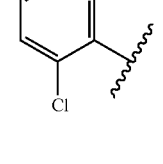 | 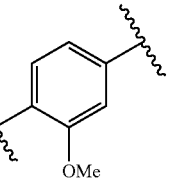 | 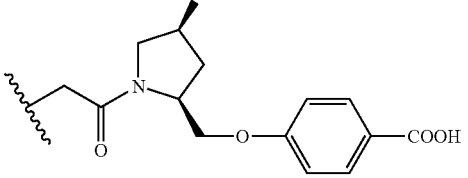 |

TABLE 1-continued

| Mass Spectrum (M+ + 1) | W— | —W¹— | —R—R⁵ |
|---|---|---|---|
| 599 | 2-Br-phenyl | 2-OMe-phenyl (1,4) | (4-OH)pyrrolidine-CH₂-O-C₆H₄-COOH |
| 571 | 2-Br-phenyl | phenyl (1,4) | (4-F)pyrrolidine-CH₂-O-C₆H₄-COOH |
| 648 | 2,6-diCl-phenyl | 2-OMe-phenyl (1,4) | (2-phenyl)pyrrolidine-CH₂-O-C₆H₄-COOH |
| 643 | 2-Br-phenyl | 2-OMe-phenyl (1,4) | (2-phenyl)pyrrolidine-CH₂-O-C₆H₄-COOH |
| 532 | 2-Me-phenyl | 2-Me-phenyl (1,4) | (4-OMe)pyrrolidine-CH₂-O-C₆H₄-COOH |
| 552 | 2-Cl-phenyl | 2-Me-phenyl (1,4) | (4-OMe)pyrrolidine-CH₂-O-C₆H₄-COOH |

TABLE 1-continued
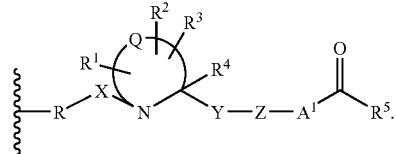
| Mass Spectrum (M⁺ + 1) | W— | —W¹— | —R—R⁵ |
|---|---|---|---|
| 597 | 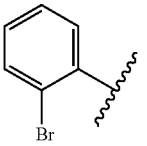 | 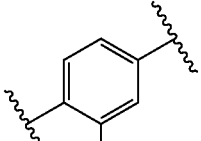 | 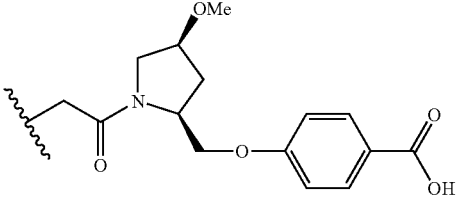 |
| 602 | 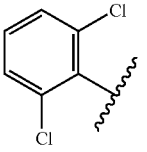 | 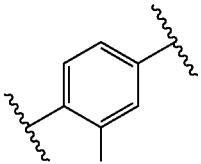 | 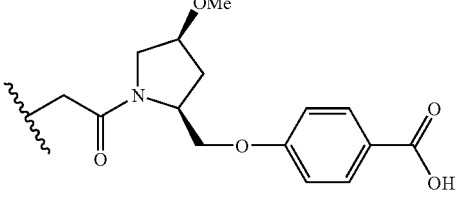 |
| 562 | 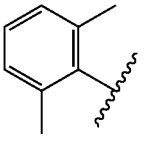 | 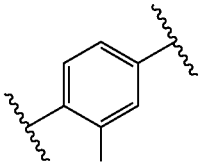 | 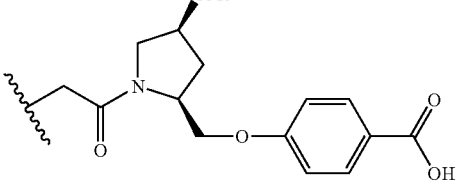 |
| 550 | 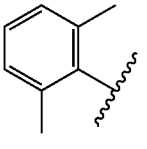 | 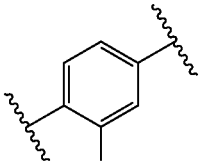 | 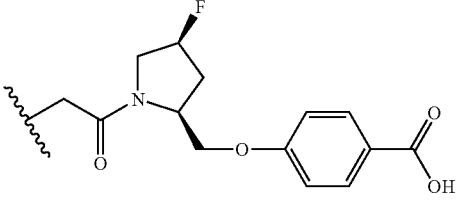 |
| 532 | 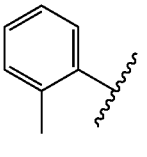 | 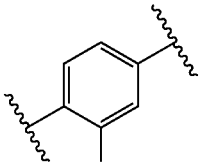 | 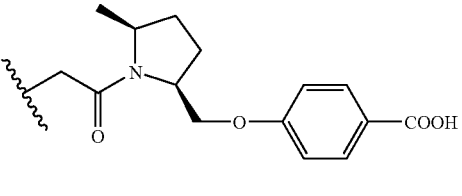 |
| 552 | 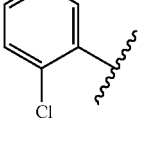 | 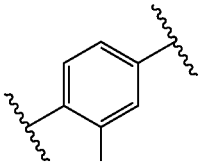 | 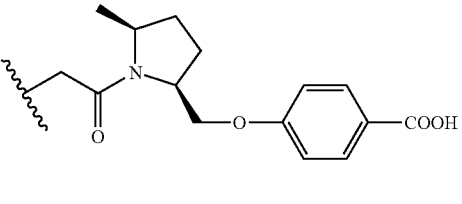 |

TABLE 1-continued
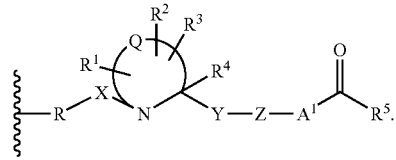
| Mass Spectrum (M⁺ + 1) | W— | —W¹— | —R—R⁵ |
|---|---|---|---|
| 528 | 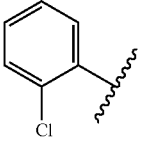 | 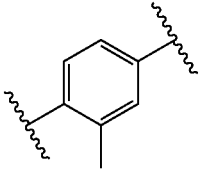 | 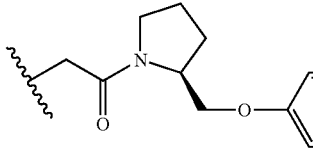 |
| 573 | 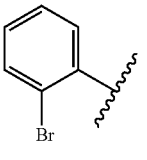 | 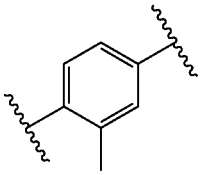 | 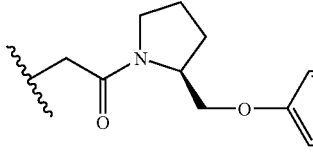 |
| 578 | 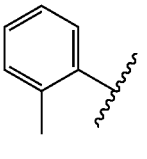 | 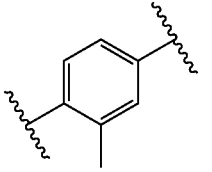 | 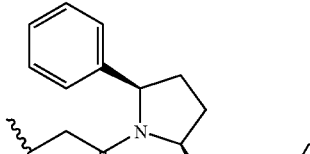 |
| 516 | 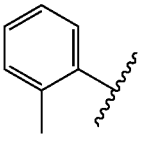 | 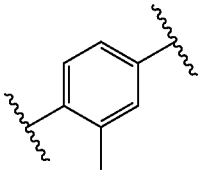 | 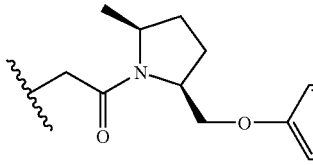 |
| 534 | 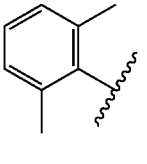 | 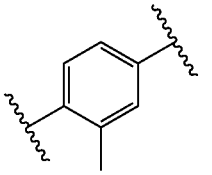 | 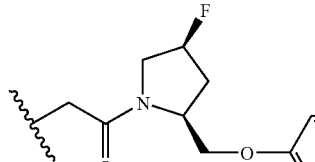 |
| 520 | 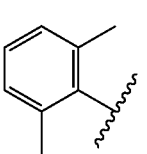 | | 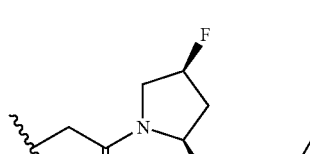 |

TABLE 1-continued
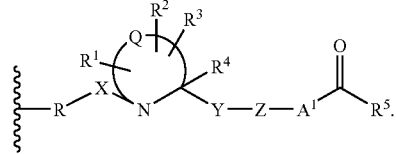
| Mass Spectrum (M⁺ + 1) | W— | —W¹— | —R—R⁵ |
|---|---|---|---|
| 536 | 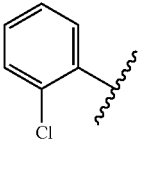 | 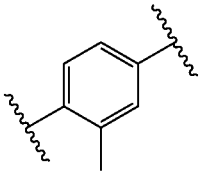 | 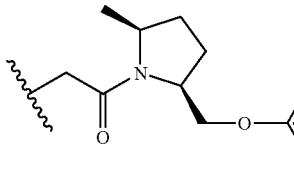 |
| 546 | 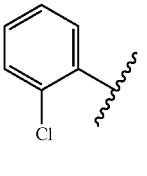 | 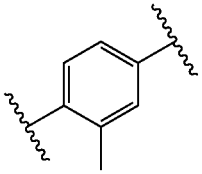 | 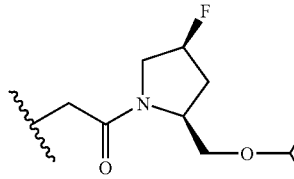 |
| 540 | 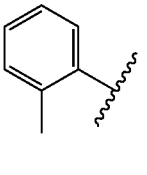 | 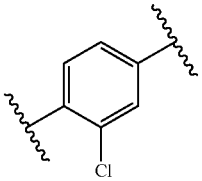 | 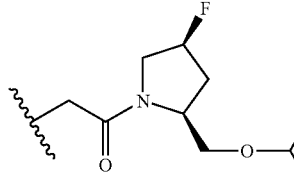 |
| 560 | 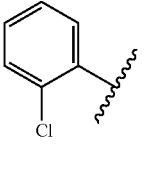 | 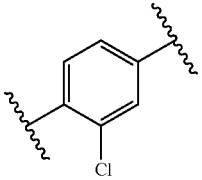 | 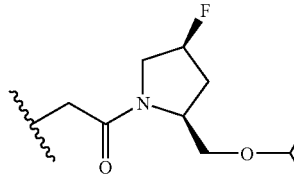 |
| 605 | 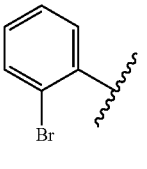 | 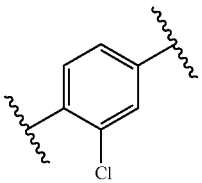 | 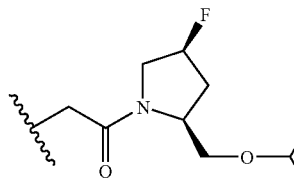 |
| 562 | 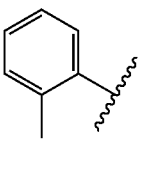 | 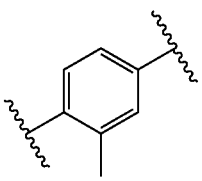 | 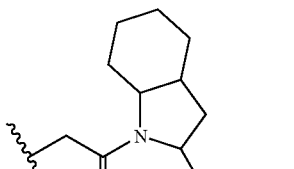 |

TABLE 1-continued
| Mass Spectrum (M⁺ + 1) | W— | —W¹— | —R—R⁵ |
|---|---|---|---|
| 582 | 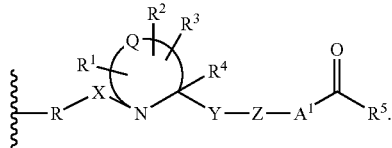 | 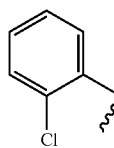 | 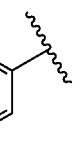 |
| 627 | 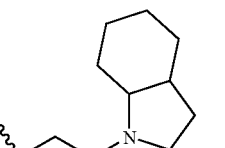 |  | 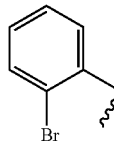 |
| 508 | 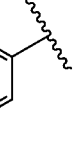 | 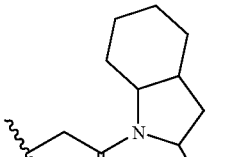 | 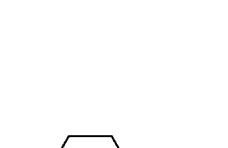 |
| 558 | 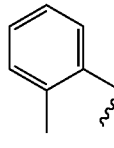 | 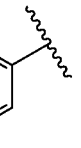 | 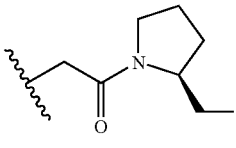 |
| 522 | 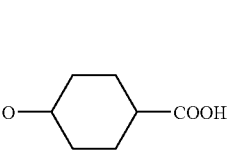 | 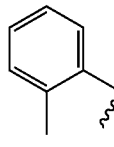 | 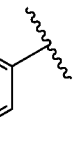 |
| 522 | 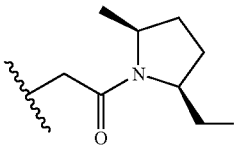 | 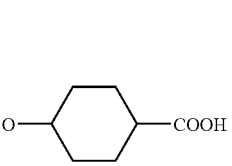 | 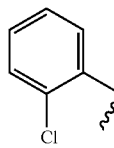 |

TABLE 1-continued
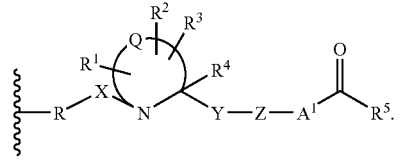
| Mass Spectrum (M+ + 1) | W— | —W1— | —R—R5 |
|---|---|---|---|
| 526 | 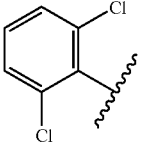 | 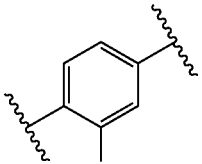 | 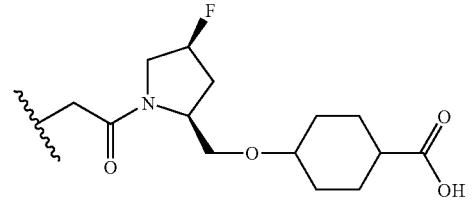 |
| 591 | 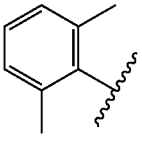 | 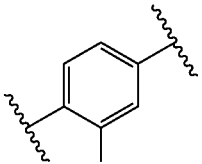 | 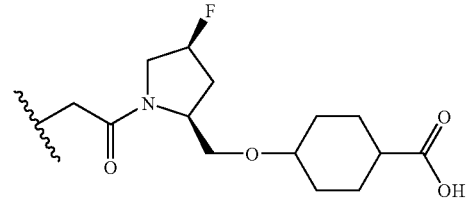 |
| 513 | 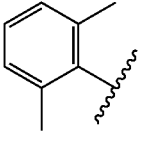 | 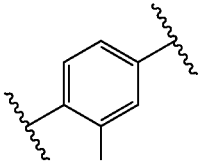 | 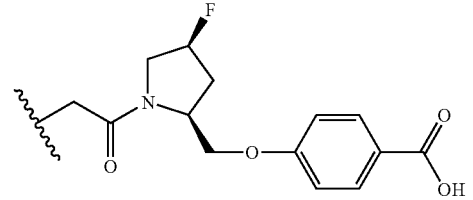 |
| 585 | 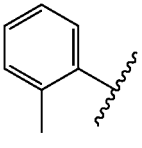 | 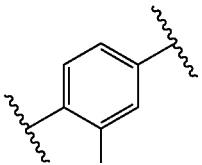 | 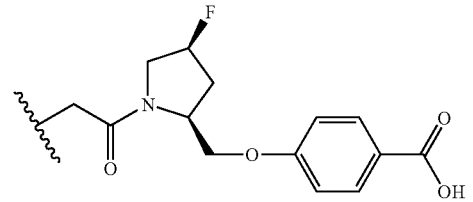 |
| 605 | 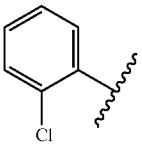 | 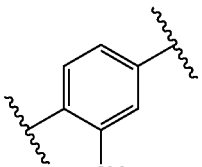 | 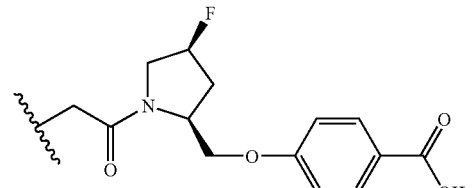 |
| 650 | 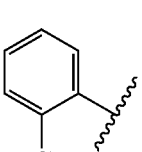 | 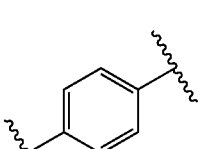 | 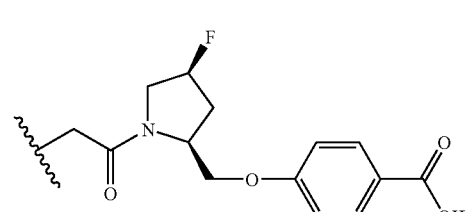 |

TABLE 1-continued
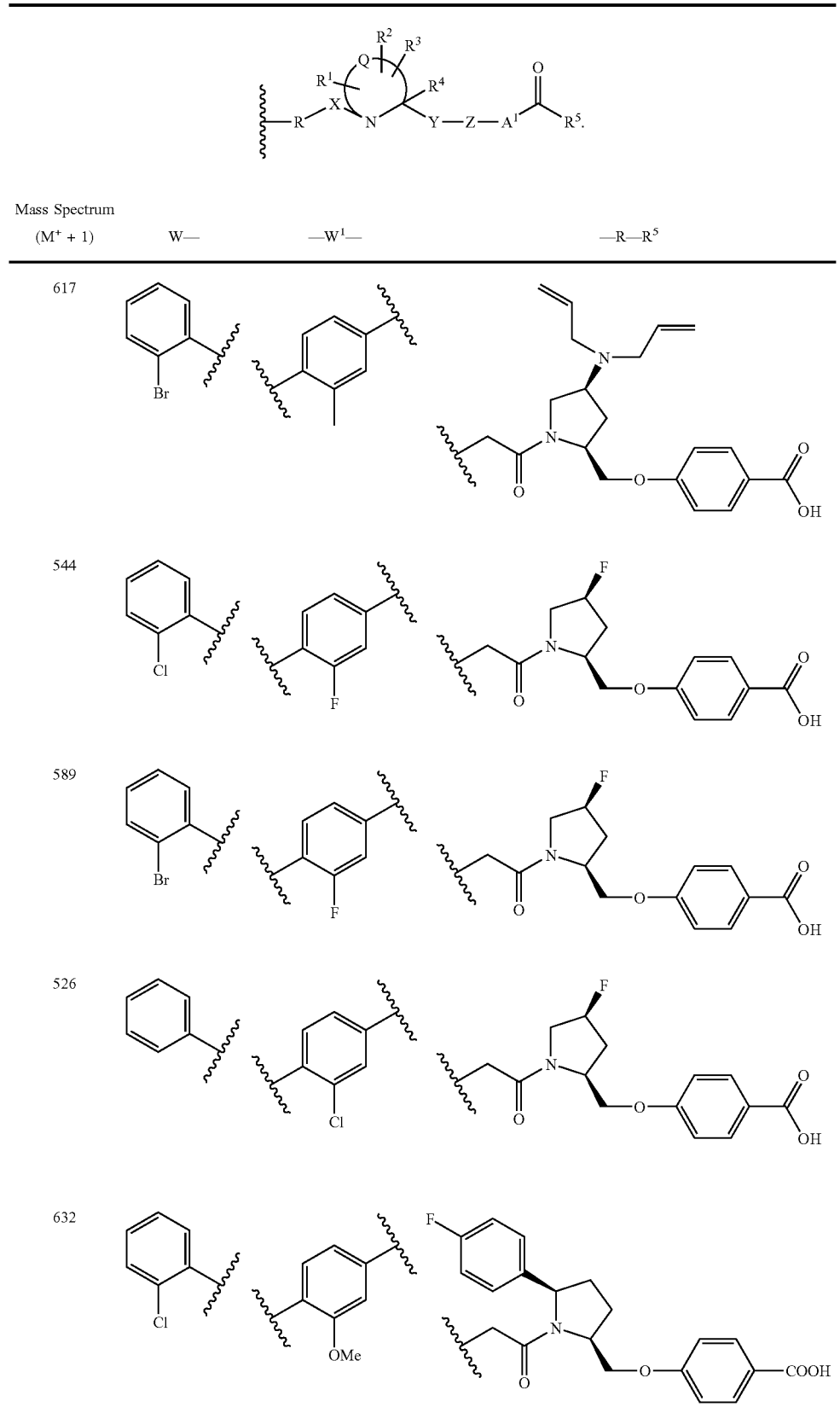

TABLE 1-continued
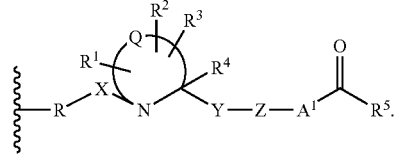
| Mass Spectrum (M⁺ + 1) | W— | —W¹— | —R—R⁵ |
|---|---|---|---|
| 616 | 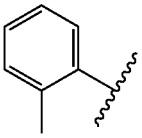 | 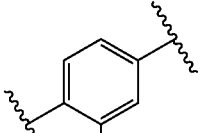 | 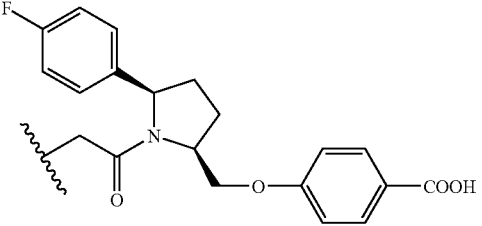 |
| 574 | 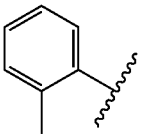 | 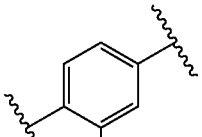 | 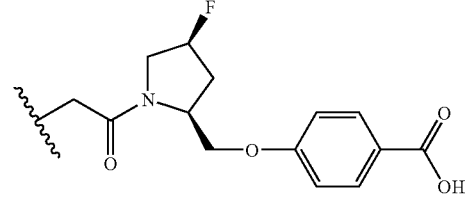 |
| 585 | 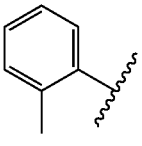 | 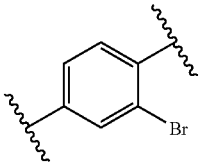 | 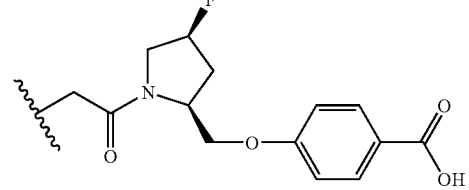 |
| 524 | 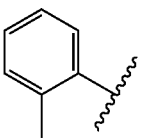 | 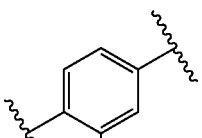 | 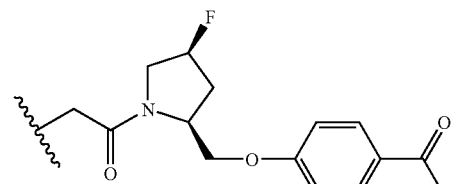 |
| 541 | 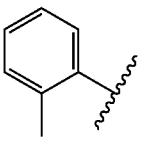 | 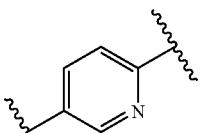 | 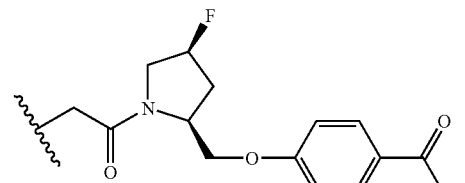 |
| 542 | 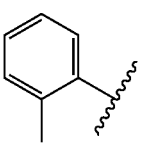 | 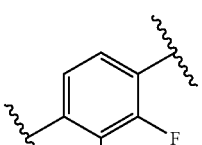 | 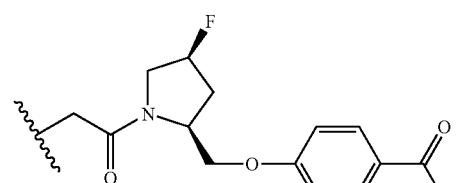 |

US 7,179,819 B2
TABLE 1-continued
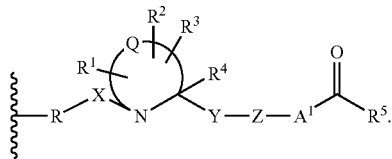
| Mass Spectrum (M⁺ + 1) | W— | —W¹— | —R—R⁵ |
|---|---|---|---|
| 542 | 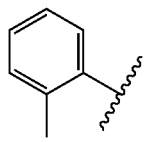 | 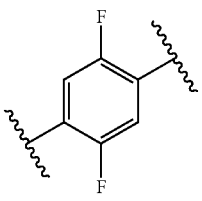 | 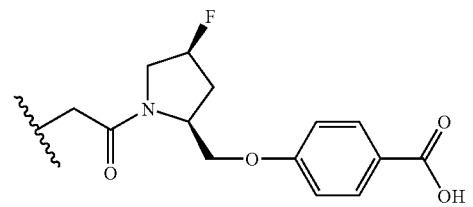 |
| 607 | 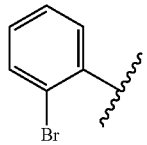 | 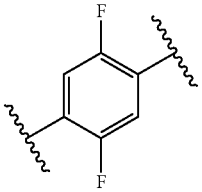 | 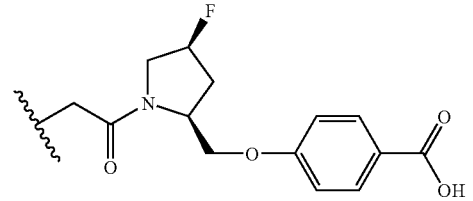 |
| 571 | 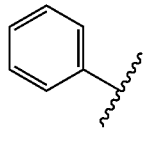 | 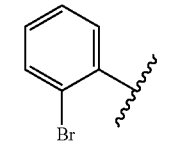 | 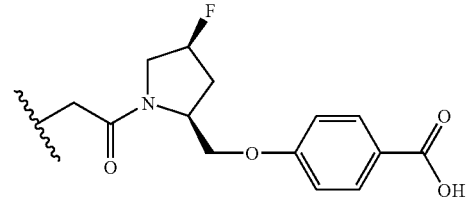 |
| 619 | 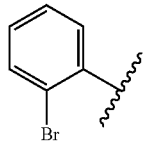 | 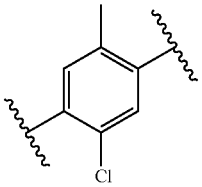 | 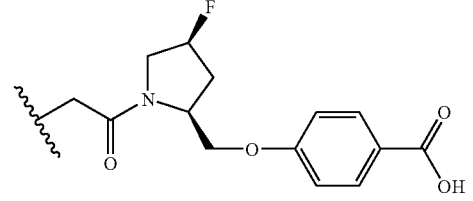 |
| 560 | 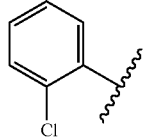 | 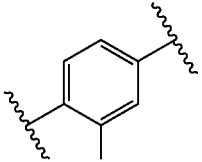 | 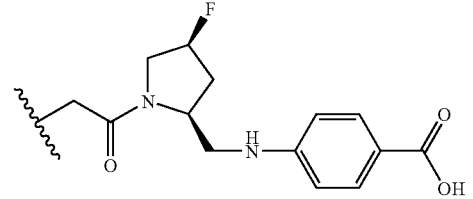 |

In another preferred embodiment of Formula I, M is

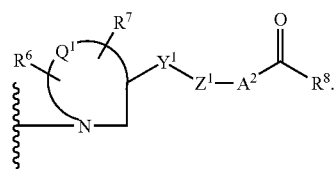

In this embodiment, more preferred compounds are those wherein A is =O, R is —(CH$_2$)$_n$— and X is —C(O)—. Y is preferably chosen from —O—, —S—, —S(O)—, —S(O)$_2$— and —NY$^4$, and more preferably, is —O—.

Preferred compounds of this embodiment are those wherein W is unsubstituted phenyl group or phenyl group having one or two substituents chosen from lower alkyl group and halogen atom at the ortho positions thereof. W$^1$ is preferably unsubstituted phenylene group or phenylene group having a substituent chosen from methoxy group, lower alkyl group and halogen atom at the ortho position to —NH—.

In this embodiment of Formula I, A is preferably =O and A$^2$ is a direct bond or —(CH2)$_e$—. More preferred compounds are those wherein A$^2$ is a direct bond and R$^8$ is —OH.

Preferred compounds of Formula I, wherein M is

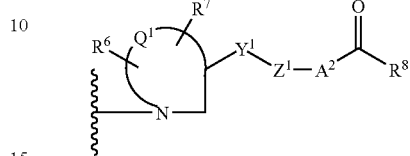

and A is =O, are represented in Table 2. With respect to the representation of —W$^1$, the lower bond is the point of attachment to —NH— and the upper bond is the point of attachment to —R—. The entry entitled —R———R$^8$ depicts that portion of the particular compound represented by

TABLE 2

TABLE 2-continued

| Mass Spec (M⁺ + 1) | W— | —W¹— | —R—R⁸ |
|---|---|---|---|
| 569 | 2-Br-phenyl | 2-OMe-phenyl (para linked) | pyrrolidine-N-C(O)-CH₂-, 3-O-(4-COOH-phenyl) |

In another preferred embodiment of Formula I, M is $$\text{-L-N}(\text{-}( \ )_m\text{-X}^1\text{-}(CHR^9)_q R^{10})\text{-CHZ}^2\text{-}$$

In this embodiment, preferred compounds are those wherein A is =O, R¹⁰ is —CO₂H and q is 0 or 1. More preferred are compounds wherein R¹⁰ is —CO₂H, q is 0 or 1, most preferably 0, and m is 2.

When A is =O, L is preferably chosen from

[structures: piperidine-2-carbonyl; 4-hydroxy-pyrrolidine-2-carbonyl; morpholine-3-carbonyl; pyrrolidine-2-carbonyl; piperazine-2-carbonyl; indoline-2-carbonyl]

-continued

[structures: 3,4-dihydroxy-pyrrolidine-2-carbonyl; 4-phenyl-pyrrolidine-2-carbonyl; 4-amino-pyrrolidine-2-carbonyl; 4-oxo-pyrrolidine-2-carbonyl; 4-(p-ClPh-O)-pyrrolidine-2-carbonyl; 4-PhO-pyrrolidine-2-carbonyl; 4-Ph-pyrrolidine-2-carbonyl; thiazolidine-4-carbonyl; octahydroindole-2-carbonyl; indoline-2-carbonyl; 4-(p-MeOPh-O)-pyrrolidine-2-carbonyl; 4-BnO-pyrrolidine-2-carbonyl]

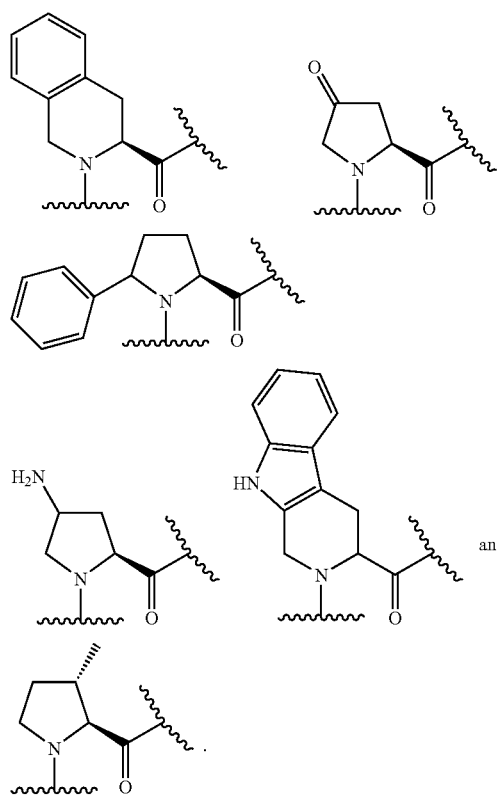
More preferably, L is chosen from
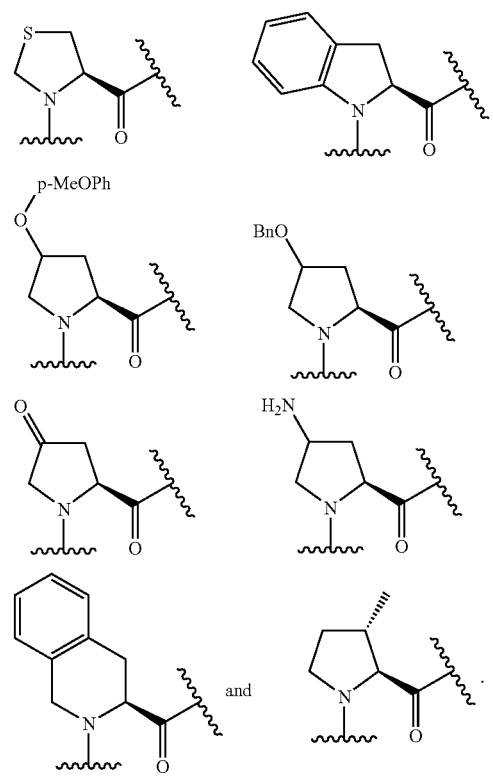
Most preferably, L is chosen from
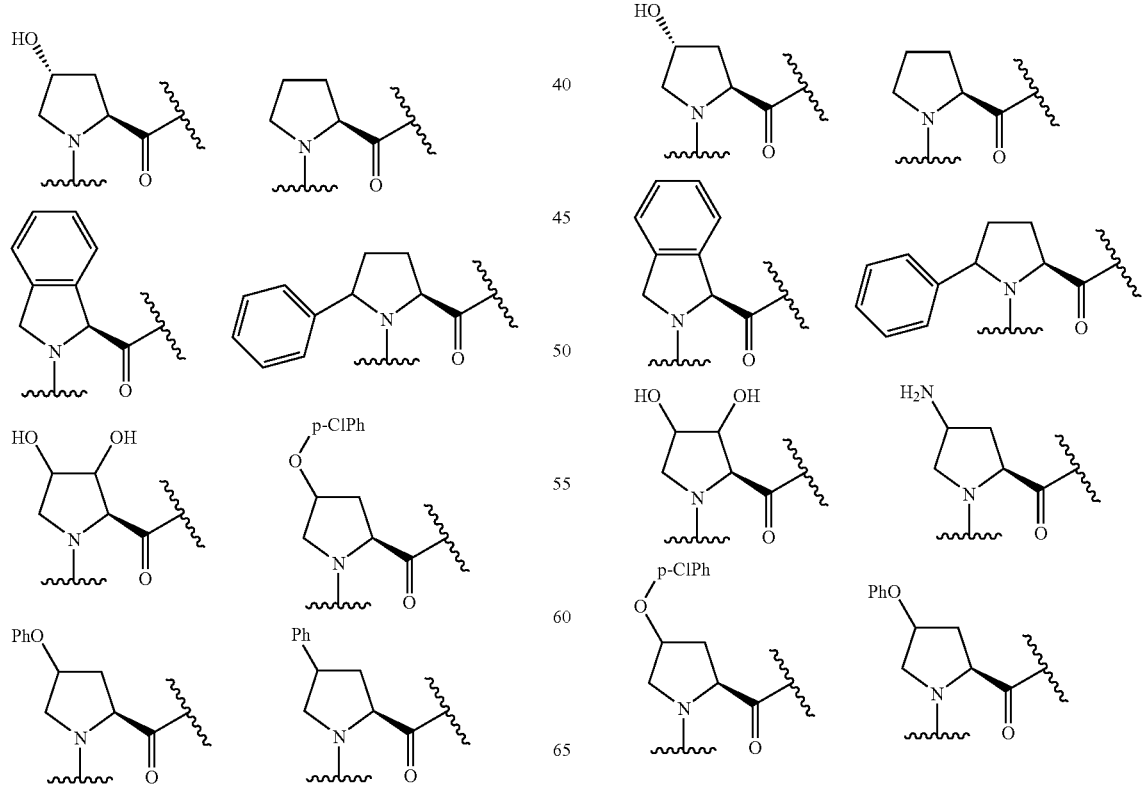

-continued

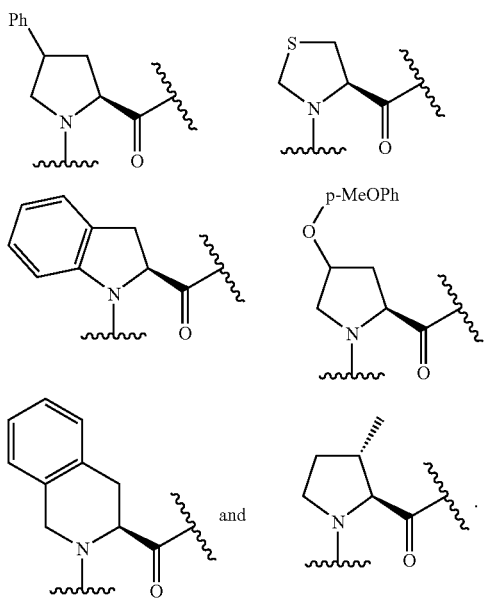

Preferred compounds of Formula I, wherein R is —CH$_2$— and X is =O, are those wherein W is unsubstituted phenyl group or phenyl group having one or two substituents chosen from lower alkyl group and halogen atom at the ortho positions thereof. W$^1$ is preferably unsubstituted phenylene group or phenylene group having a substituent chosen from methoxy group, lower alkyl group and halogen atom at the ortho position to —NH—.

Preferred compounds of Formula I, wherein M is

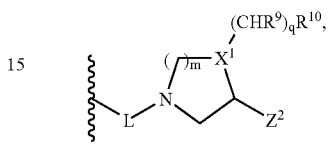

A is =O, R is —CH$_2$— and X is =O, are represented in Table 3. With respect to the representation of —W$^1$, the lower bond is the point of attachment to —NH— and the upper bond is the point of attachment to —R—. The entry entitled —N———Z$^2$ depicts that portion of the particular compound represented by

TABLE 3

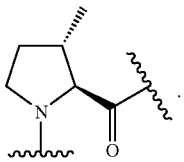

| Mass Spec (M$^+$ + 1) | W— | —W$^1$— | —L— | —N—Z$^2$ |
|---|---|---|---|---|
| 554.7 | o-H$_3$C-phenyl | 3-MeO, 4-substituted phenylene | 4-HO-pyrrolidine-2-carbonyl | piperazine-N-CH$_2$CO$_2$H |
| 493.6 | o-H$_3$C-phenyl | p-phenylene | azetidine-2-carbonyl | 4-(CH$_2$CO$_2$H)-piperidine |
| 540.6 | phenyl | 3-MeO, 4-substituted phenylene | 4-HO-pyrrolidine-2-carbonyl | piperazine-N-CH$_2$CO$_2$H |

TABLE 3-continued
| Mass Spec (M⁺ + 1) | W— | —W¹— | —L— | —N—Z² |
|---|---|---|---|---|
| 523.7 | 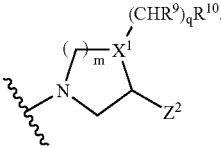 | 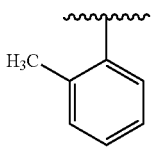 | 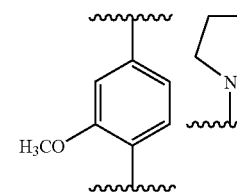 | 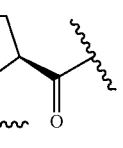 |
| 555.7 | 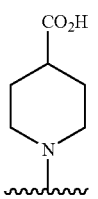 | 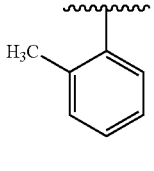 | 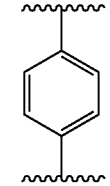 | 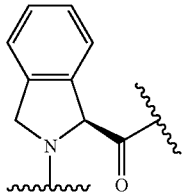 |
| 583.8 | 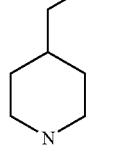 | 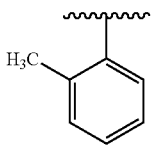 | 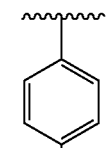 | 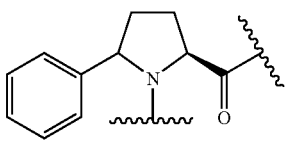 |
| 524.7 | 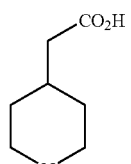 | 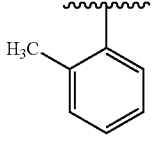 | 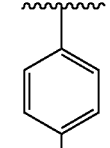 | 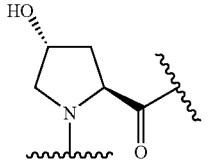 |
| 509.7 | 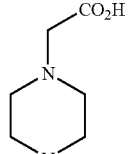 | 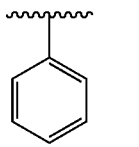 | 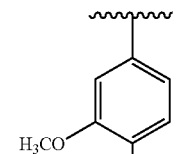 | 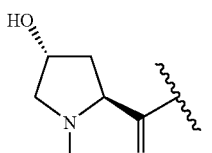 |
| 538.7 | 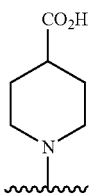 | 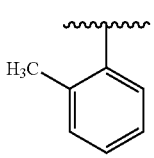 | 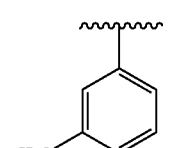 | 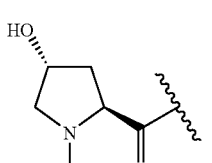 |

TABLE 3-continued
| Mass Spec (M⁺ + 1) | W— | —W¹— | —L— | —N—Z² |
|---|---|---|---|---|
| 554.7 | 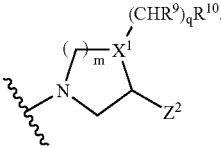 | 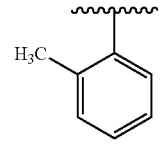 | 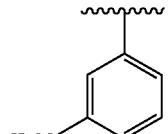 | 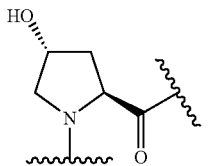 |
| 569.7 | 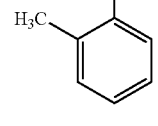 | 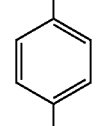 | 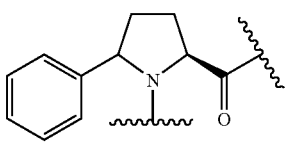 | 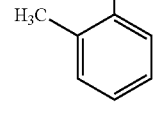 |
| 666.9 | 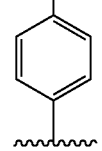 | 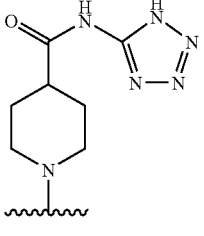 | 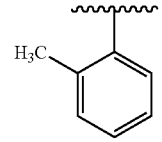 | 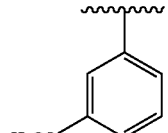 |
| 567.8 | 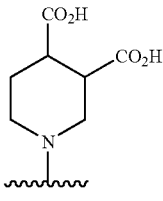 | 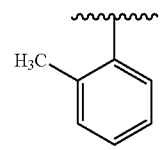 | 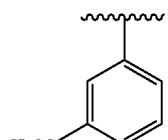 | 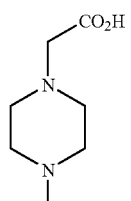 |
| 570.4 | 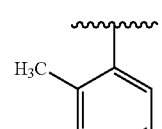 | 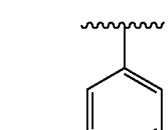 | | |
| 552.7 | | | | 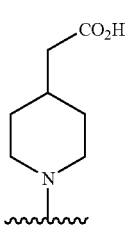 |

TABLE 3-continued

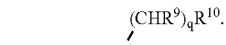

| Mass Spec (M+ + 1) | W— | —W¹— | —L— | —N—Z² |
|---|---|---|---|---|
| 619.5 | 2-Br-phenyl | 4-methoxyphenyl (3-OMe) | 4-hydroxy-pyrrolidine-2-carbonyl | 4-(carboxymethyl)piperazin-1-yl |
| 575.1 | 2-Cl-phenyl | 4-methoxyphenyl (3-OMe) | 4-hydroxy-pyrrolidine-2-carbonyl | 4-(carboxymethyl)piperazin-1-yl |
| 553.6 | 2-methylphenyl | 4-methoxyphenyl (3-OMe) | 4-oxo-pyrrolidine-2-carbonyl | 4-(carboxymethyl)piperazin-1-yl |
| 664.1 | 2-methylphenyl | 4-methoxyphenyl (3-OMe) | 4-(p-ClPh-O)-pyrrolidine-2-carbonyl | 4-(carboxymethyl)piperidin-1-yl |
| 629.7 | 2-methylphenyl | 4-methoxyphenyl (3-OMe) | 4-(PhO)-pyrrolidine-2-carbonyl | 4-(carboxymethyl)piperazin-1-yl |
| 555.6 | 2-methylphenyl | 4-phenyl | isoindoline-1-carbonyl | 4-(carboxymethyl)piperidin-1-yl |

TABLE 3-continued
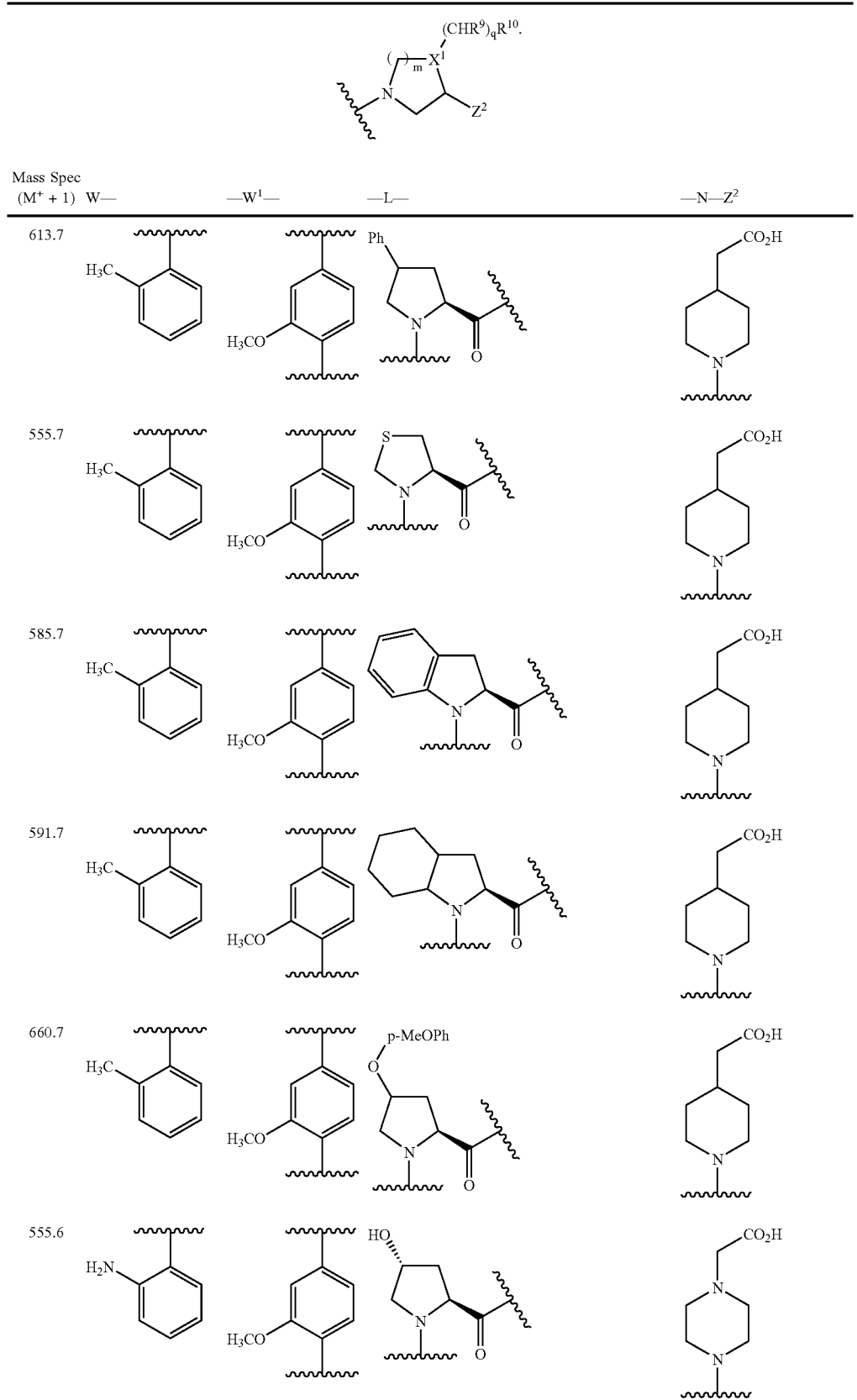

TABLE 3-continued

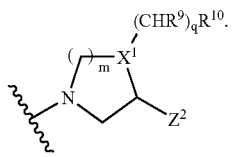

| Mass Spec (M+ + 1) | W— | —W¹— | —L— | —N—Z² |
|---|---|---|---|---|
| 556.6 | 2-hydroxyphenyl | 3-methoxy-1,4-phenylene | (4-hydroxy)prolyl carbonyl | 4-(carboxymethyl)piperazin-1-yl |
| 570.7 | 2-methoxyphenyl | 3-methoxy-1,4-phenylene | (4-hydroxy)prolyl carbonyl | 4-(carboxymethyl)piperazin-1-yl |
| 570.7 | 2-(hydroxymethyl)phenyl | 3-methoxy-1,4-phenylene | (4-hydroxy)prolyl carbonyl | 4-(carboxymethyl)piperazin-1-yl |
| 673.8 | 2-methylphenyl | 3-methoxy-1,4-phenylene | (4-benzyloxy)prolyl carbonyl | 3,4-dicarboxypiperidin-1-yl |
| 600.7 | 2-methylphenyl | 3-methoxy-1,4-phenylene | 1,2,3,4-tetrahydroisoquinolin-3-yl carbonyl | 4-(carboxymethyl)piperazin-1-yl |
| 552.7 | 2-methylphenyl | 3-methoxy-1,4-phenylene | (3-methyl)prolyl carbonyl | 4-(carboxymethyl)piperazin-1-yl |

TABLE 3-continued
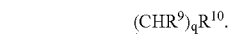
| Mass Spec (M⁺ + 1) | W— | —W¹— | —L— | —N—Z² |
|---|---|---|---|---|
| 668.8 | 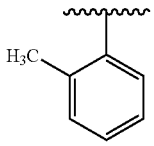 | 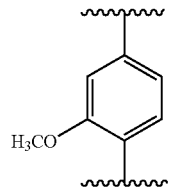 | 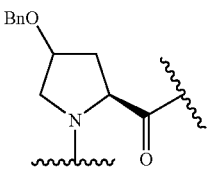 | 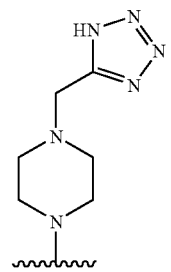 |
| 583.7 | 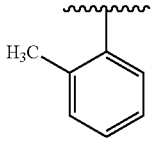 | 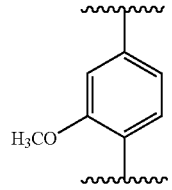 | 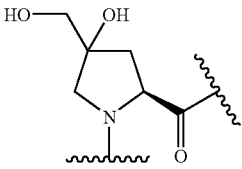 | 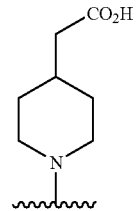 |
| 704.9 | 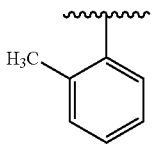 | 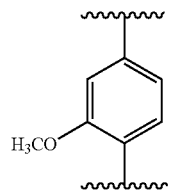 | 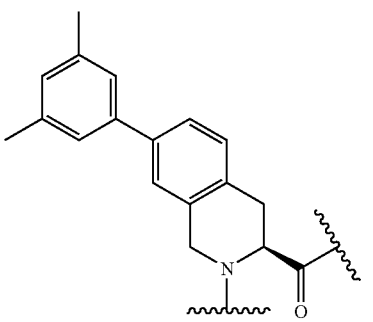 | 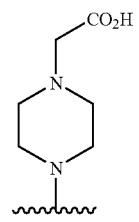 |
| 514.6 | 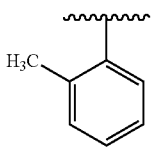 | 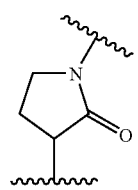 | 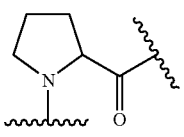 | 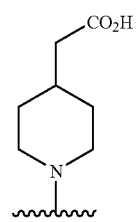 |
| 514.6 | 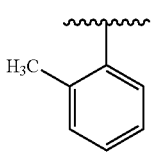 | 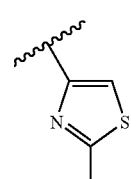 | 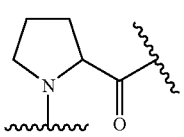 | 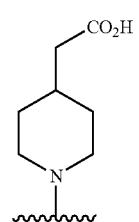 |

TABLE 3-continued

| Mass Spec (M+ + 1) | W— | —W¹— | —L— | —N—Z² |
|---|---|---|---|---|
| 562.6 | | | | |

Yet another preferred embodiment of Formula I includes compounds wherein M is

—R¹¹—Z³—Q²—L¹.

Preferably, A is =O, R is —CH$_2$— and X is =O. Preferably W is unsubstituted phenyl group or phenyl group having one or two substituents chosen from lower alkyl group and halogen atom at the ortho positions thereof. W¹ is preferably unsubstituted phenylene group or phenylene group having a substituent chosen from methoxy group, lower alkyl group and halogen atom at the ortho position to —NH—.

In compounds wherein Q² is

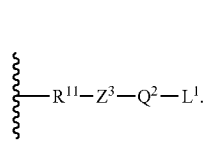

and Z³ is a divalent aliphatic hydrocarbon moiety, preferred compounds are those wherein R¹¹ is

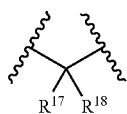

or —NR¹², more preferably NR¹², wherein R¹² is chosen from —H, lower allyl group and substituted lower alkyl group, most preferably dihydroxy lower alkyl group. Preferred choices for Z³ is a divalent aliphatic hydrocarbon moiety having 4, 5 or 6 carbon atoms. A preferred choice for W¹ is phenylene group having a substituent chosen from methoxy group, lower alkyl group and halogen atom at the ortho position to —NH—.

In compounds wherein Q² is

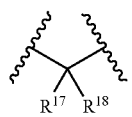

and Z³ is

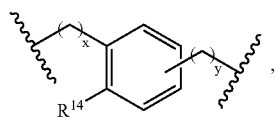

R¹¹ is preferably —NR¹²—. In these compounds, x and y are preferably 1. Preferred choices for R¹⁴ include —H. —OH and —F. A preferred choice for W¹ is phenylene group having a substituent chosen from methoxy group, lower alkyl group and halogen atom at the ortho position to —NH—.

In compounds wherein Q² is

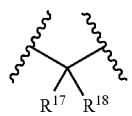

and Z³ is

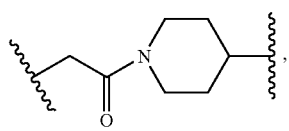

R¹¹ is preferably chosen from —O— and —NR¹²—, preferably wherein R¹² is chosen from —H and lower alkyl group. Preferably, $R^{17}$ and $R^{18}$ are each —H. A preferred choice for $W^1$ is phenylene group having a substituent chosen from methoxy group, lower alkyl group and halogen atom at the ortho position to —NH—.

In compounds wherein $Q^2$ is

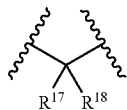

and $Z^3$ is

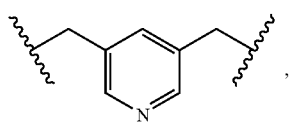

$R^{11}$ is preferably —$NR^{12}$—, wherein $R^{12}$ is preferably lower alkyl group. Preferred compounds of this embodiment also include those wherein at least one of $R^{17}$ and $R^{18}$ is lower alkyl group or substituted lower alkyl group.

In compounds wherein $Q^2$ is

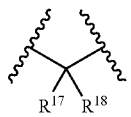

and $Z^3$ is

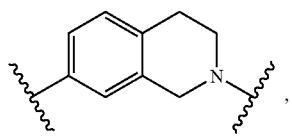

$R^{11}$ is preferably —NH— and $R^{17}$ and $R^{18}$ are each preferably —H. A preferred choice for $W^1$ is phenylene group having a substituent chosen from methoxy group, lower alkyl group and halogen atom at the ortho position to —NH—.

In compounds wherein $Q^2$ is chosen from aryl group, substituted aryl group and

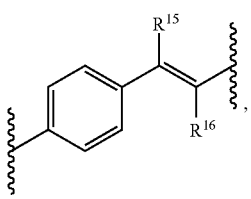

and more preferably from phenyl group and phenyl group substituted at the point of attachment to $Z^3$, $Z^3$ is preferably a divalent aliphatic hydrocarbon moiety.

Yet another embodiment of the invention is a compound represented by Formula II,

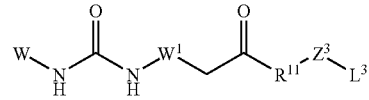

II wherein the substituents W, $W^1$, $R^{11}$ and $Z^3$ are defined as in Formula I, and $L^3$ is chosen from

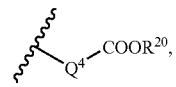

wherein $R^{20}$ is preferably chosen from —H and lower alkyl,

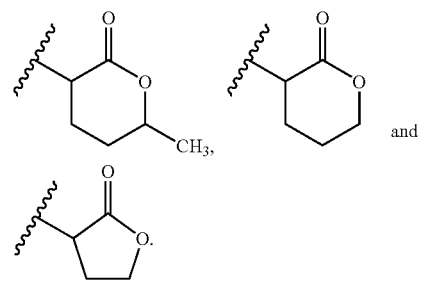

Still another embodiment of the invention is a compound represented by Formula III,

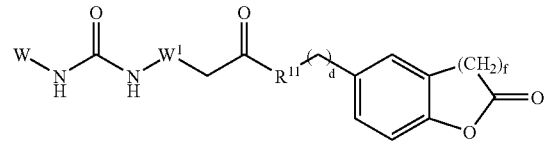

III wherein the substituents W, $W^1$, and $R^{11}$ are defined as in Formula I, and d is chosen from 0 and 1, and f is chosen from 1 and 2.

Preferred compounds of Formula I, wherein M is

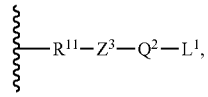

A is =O, R is —$CH_2$— and X is =O, are represented in Table 4. With respect to the representation of —$W^1$, the lower bond is the point of attachment to —NH— and the upper bond is the point of attachment to —R—. The entry entitled ——$R^{11}$——$L^1$ depicts that portion of the particular compound represented by TABLE 4
$$\text{—}R^{11}\text{—}Z^3\text{—}Q^2\text{—}L^1.$$
| Mass Spec (M⁺+ 1) | W— | —W¹— | —R¹¹—L¹ |
|---|---|---|---|
| 466.22 | 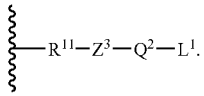 | 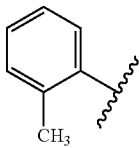 | 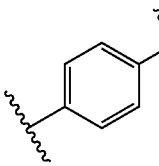 |
| 496.22 | 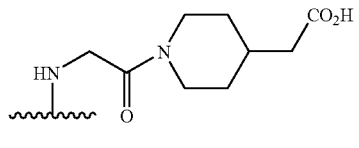 | 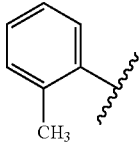 | 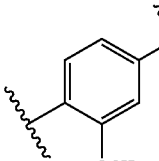 |
| 445.19 | 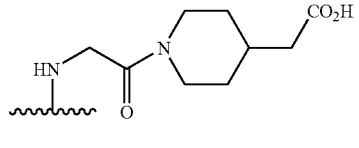 | 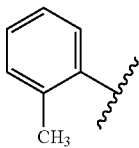 | 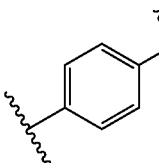 |
| 475.20 | 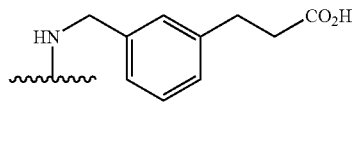 | 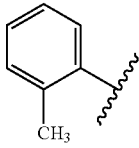 | 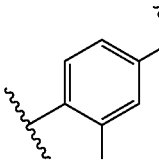 |
| 497.22 | 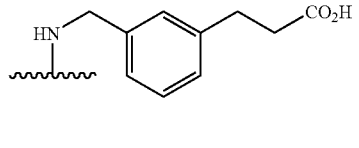 | 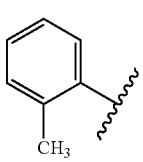 | 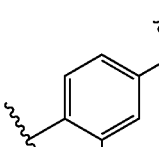 |
| 510.42 | 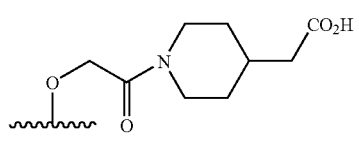 | 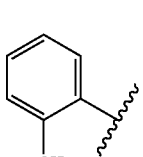 | 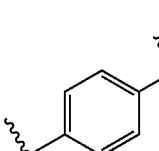 |
| 517.62 | 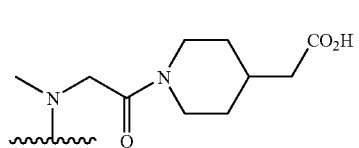 | 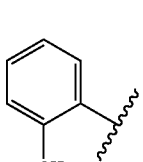 | 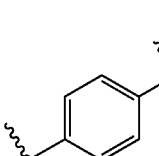 |

TABLE 4-continued
$$\text{―}R^{11}\text{―}Z^3\text{―}Q^2\text{―}L^1.$$
| Mass Spec (M⁺+ 1) | W— | —W¹— | —R¹¹—L¹ |
|---|---|---|---|
| 473.56 | 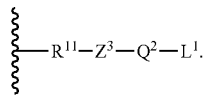 | 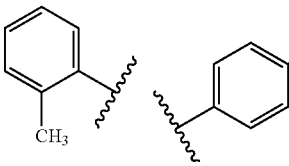 | 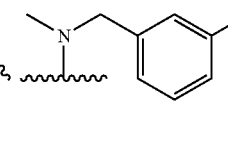 |
| 504.1 | 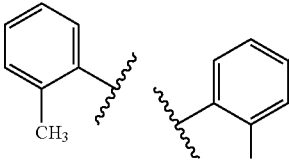 | 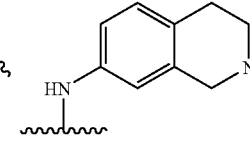 | 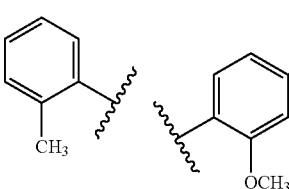 |
| 529.17 | 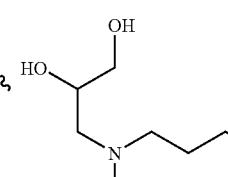 | 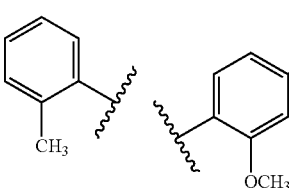 | 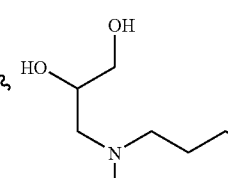 |
| 501.16 | 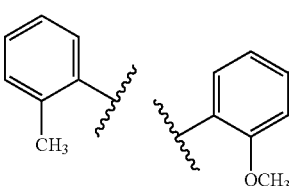 | 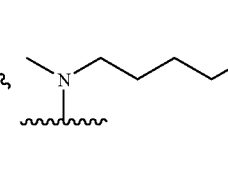 | 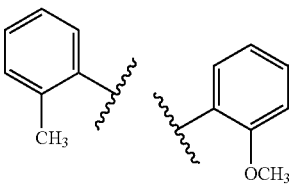 |
| 427.20 | | | 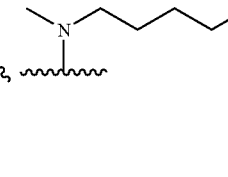 |
| 441.22 | | | 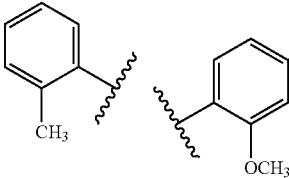 |
| 468.1 | | | 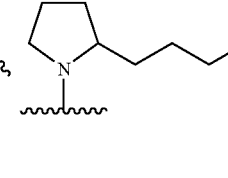 |

TABLE 4-continued
$$\text{—}R^{11}\text{—}Z^3\text{—}Q^2\text{—}L^1.$$
| Mass Spec (M⁺+ 1) | W— | —W¹— | —R¹¹—L¹ |
|---|---|---|---|
| 532.2 | 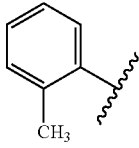 | 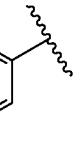 | 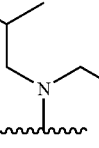 |
| 624.2 | 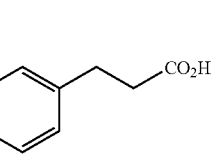 | 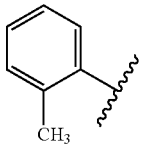 | 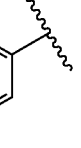 |
| 455.16 | 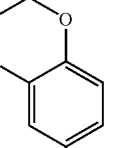 |  |  |
| 483.70 | 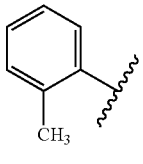 | 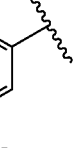 | 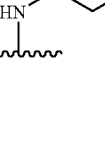 |
| 459.54 | 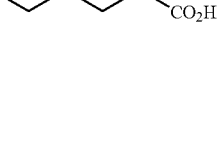 | 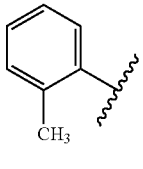 | 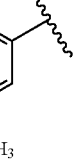 |
| 489.56 | 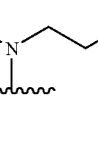 | 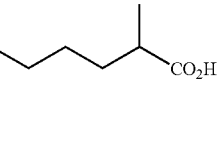 | 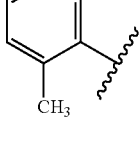 |
| 487.59 |  | 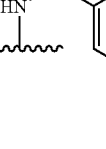 | 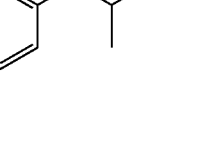 |

TABLE 4-continued
| Mass Spec (M⁺+ 1) | W— | —W¹— | —R¹¹—L¹ |
|---|---|---|---|
| 469.24 | 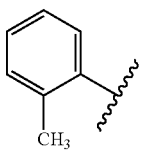 | 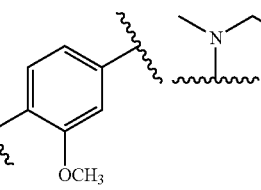 | 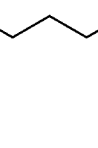 |
| 489.56 | 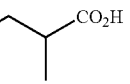 | 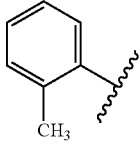 | 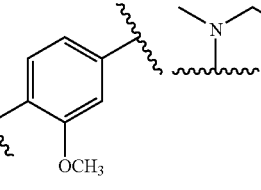 |
| 489.56 | 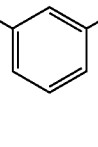 | 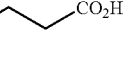 | 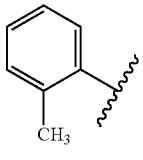 |
| 459.54 | 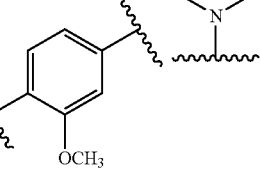 | 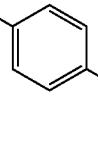 | 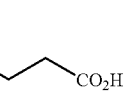 |
| 483.26 | 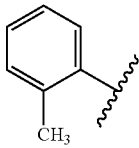 | 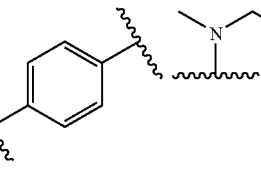 | 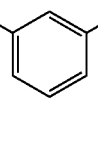 |
| 441.23 | 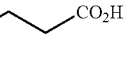 | 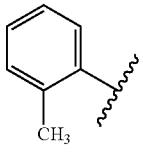 | 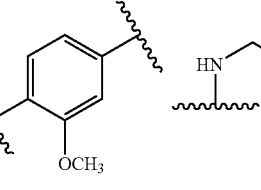 |
| 503.59 | 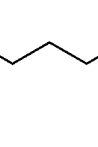 | 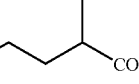 | 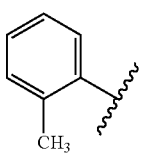 |

TABLE 4-continued
$$\{-R^{11}-Z^3-Q^2-L^1.$$
| Mass Spec (M⁺+ 1) | W— | —W¹— | —R¹¹—L¹ |
|---|---|---|---|
| 477.53 | 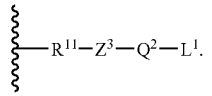 | 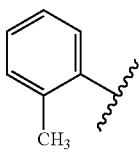 | 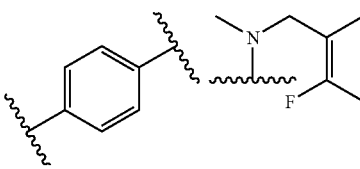 |
| 507.55 | 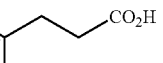 | 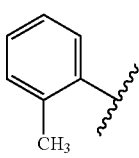 | 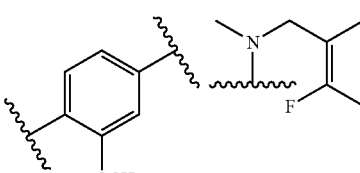 |
| 521.58 | 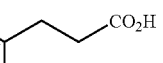 | 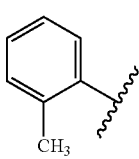 | 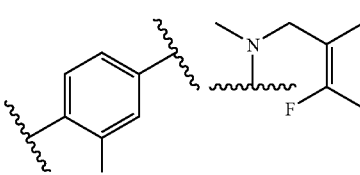 |
| | 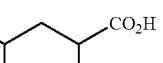 |  |  |
| |  | 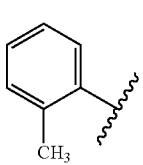 | 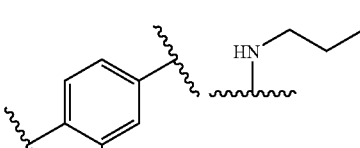 |
| 414.10 | 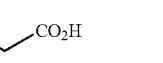 | 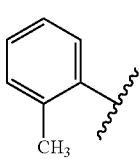 | 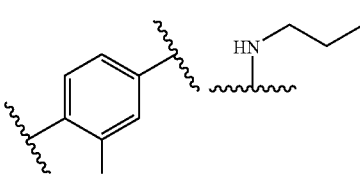 |
| 441.22 | 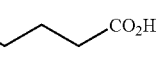 | | |

US 7,179,819 B2
TABLE 4-continued
| Mass Spec (M⁺+ 1) | W— | —W¹— | —R¹¹—L¹ |
|---|---|---|---|
| 511.47 | 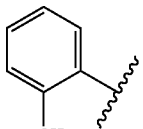 | 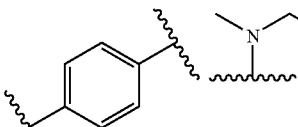 |  |
| 459.11 | 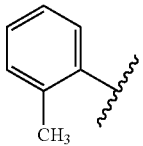 | 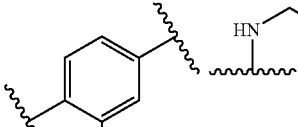 |  |
| 504.6 | 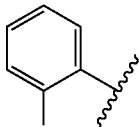 | 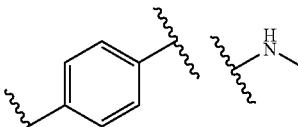 | 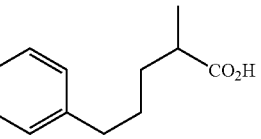 |
| 500.2 | 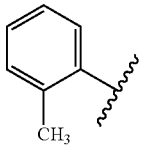 | 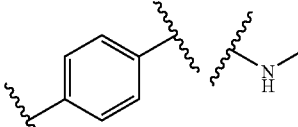 | 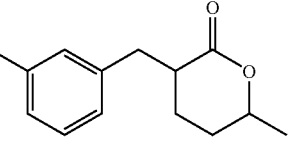 |
| 530.2 | 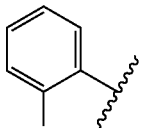 | 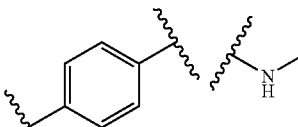 | 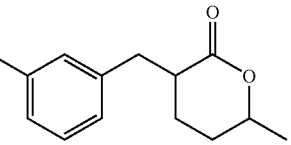 |
| 516.4 | 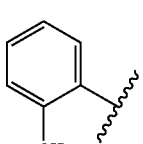 | 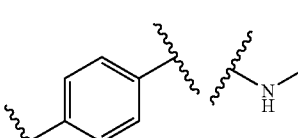 | 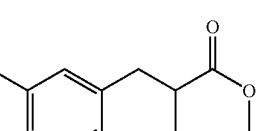 |
| 486.2 | 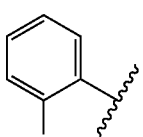 | 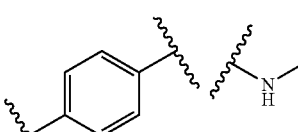 | 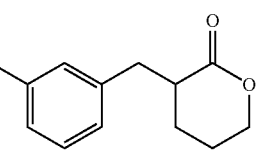 |

TABLE 4-continued
$$\text{−R}^{11}\text{−Z}^3\text{−Q}^2\text{−L}^1.$$
| Mass Spec (M⁺+ 1) | W— | —W¹— | —R¹¹—L¹ |
|---|---|---|---|
| 544.2 | 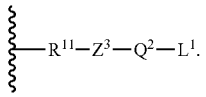 | | |
| 500.2 | 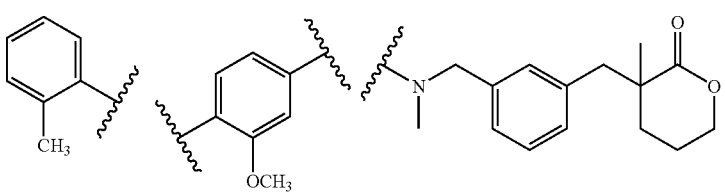 | | |
| 506.2 | 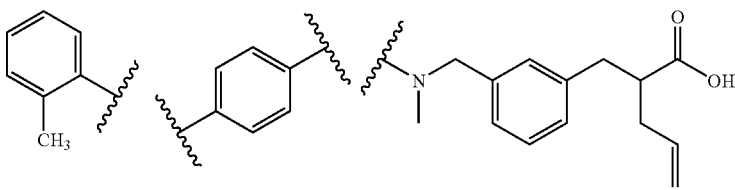 | | |
| 516.2 | 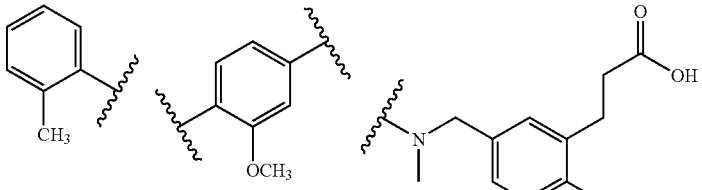 | | |
| 498.2 | 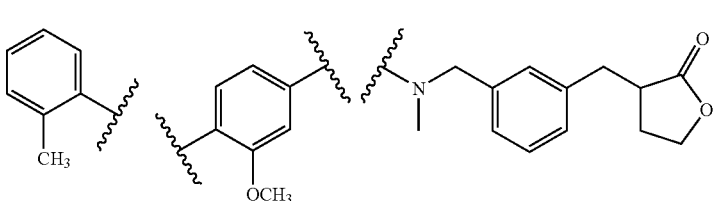 | | |
| 475.3 | 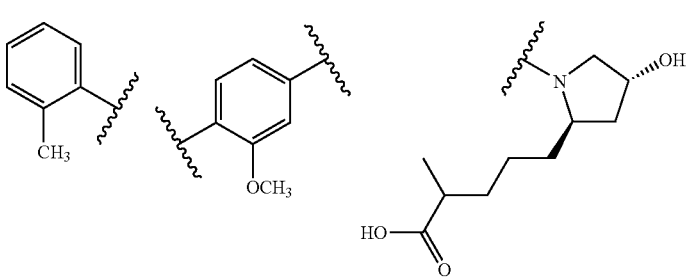 | | |

TABLE 4-continued
| Mass Spec (M⁺+ 1) | W— | —W¹— | —R¹¹—L¹ |
|---|---|---|---|
| 502.2 | 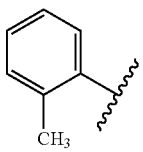 | 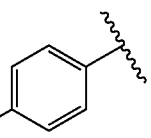 | 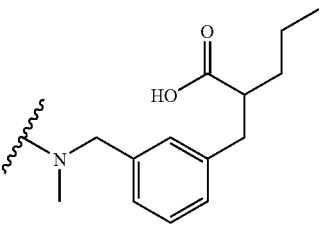 |
| 506.3 | 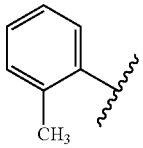 | 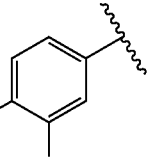 | 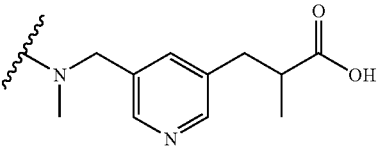 |
| 518.1 | 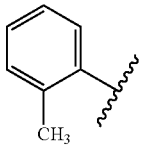 | 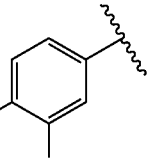 | 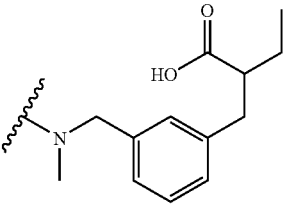 |
| 530.1 | 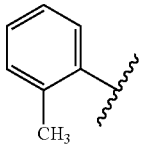 | 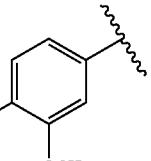 | 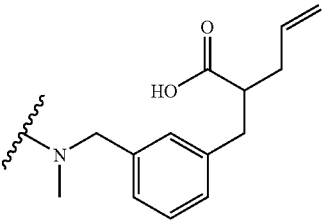 |
| 526 | 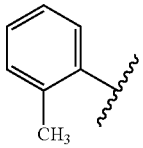 | 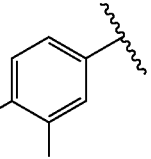 | 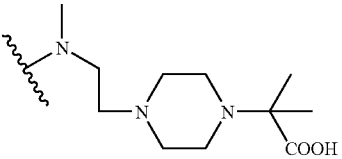 |
| 602 | 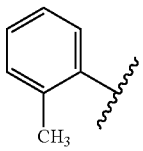 | 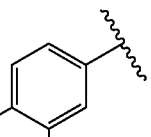 | 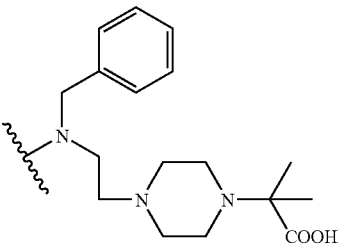 |

TABLE 4-continued
$\xi\text{—}R^{11}\text{—}Z^3\text{—}Q^2\text{—}L^1.$
Mass Spec
(M+ + 1)   W—   —W$^1$—   —R$^{11}$—L$^1$
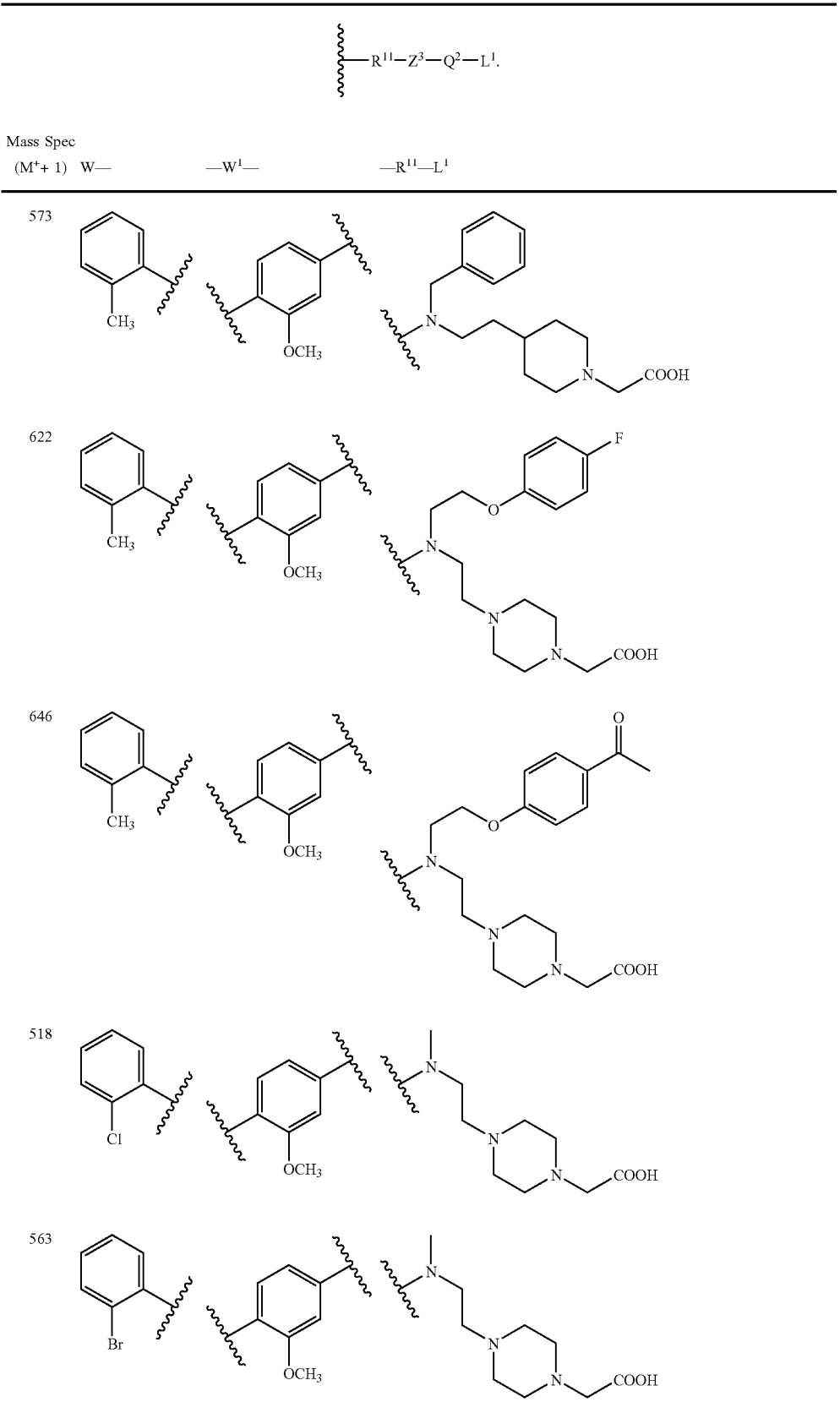

TABLE 4-continued
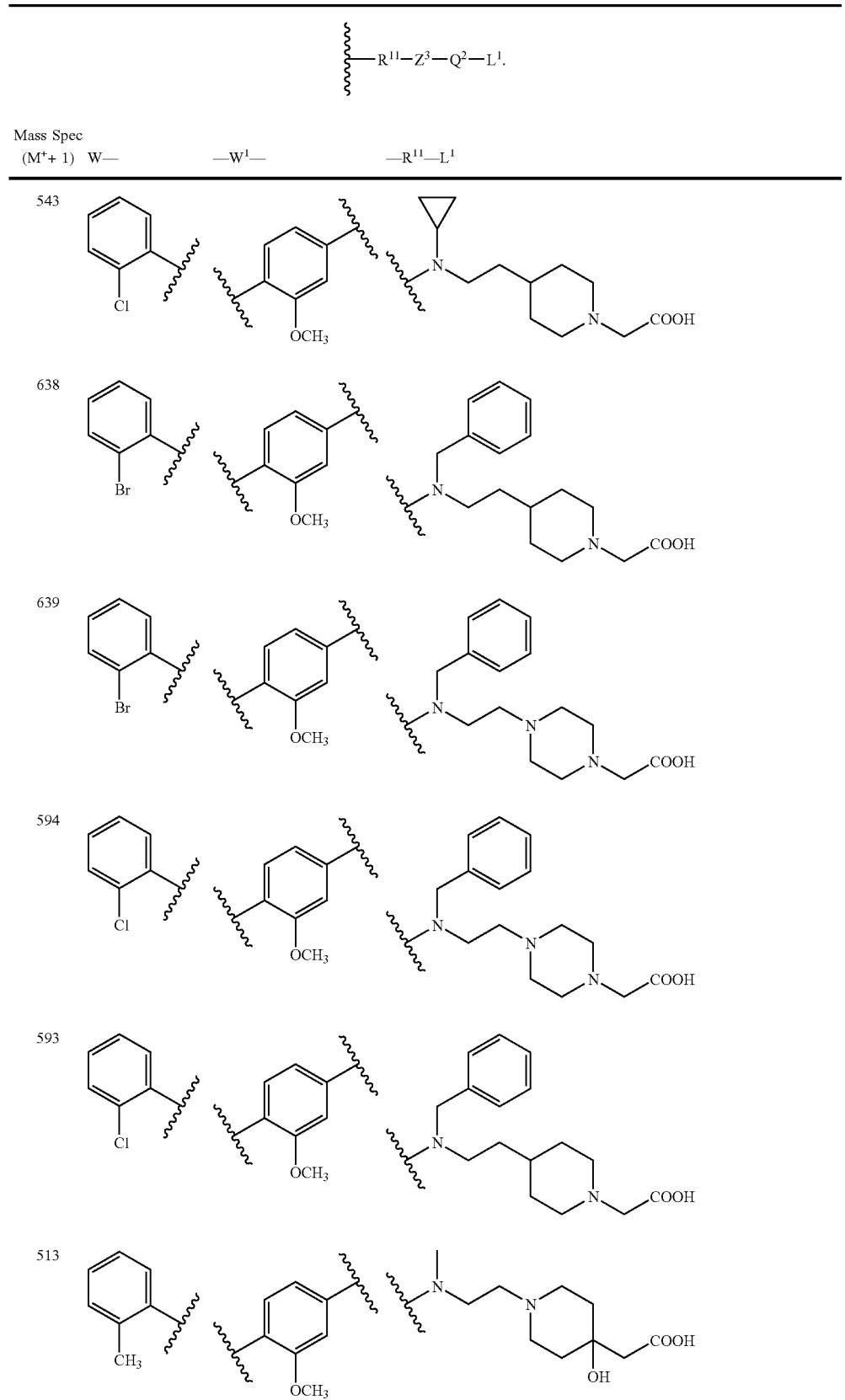

TABLE 4-continued
$$\substack{\xi\\\xi}-R^{11}-Z^3-Q^2-L^1.$$
| Mass Spec (M⁺+ 1) | W— | —W¹— | —R¹¹—L¹ |
|---|---|---|---|
| 638 | 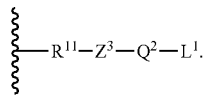 | 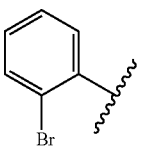 | 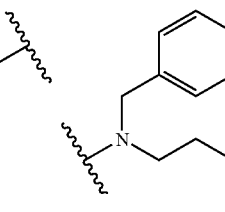 |
| 593 | 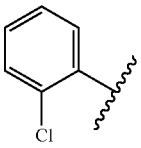 | 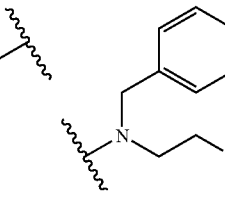 | 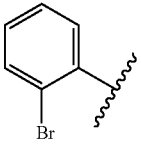 |
| 624 | 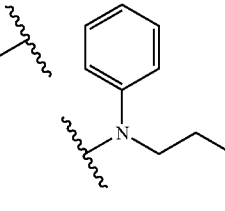 | 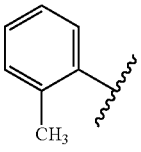 | 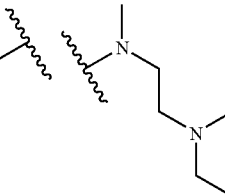 |
| 515 | 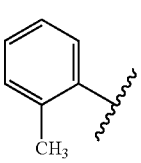 | 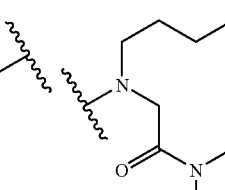 | 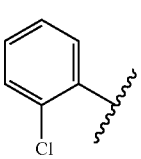 |
| 595 | 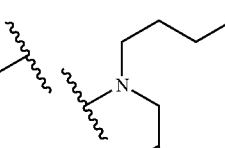 | | |
| 615 | | | |

TABLE 4-continued
$$-R^{11}-Z^3-Q^2-L^1.$$
| Mass Spec (M⁺+ 1) | W— | —W¹— | —R¹¹—L¹ |
|---|---|---|---|
| 514 | 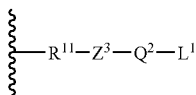 | 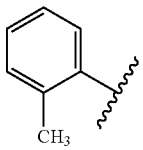 | 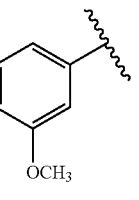 |
| 596 | 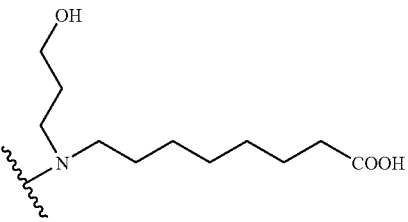 | 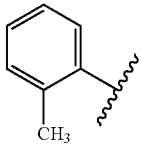 | 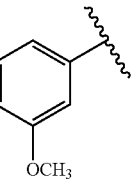 |
| 616 | 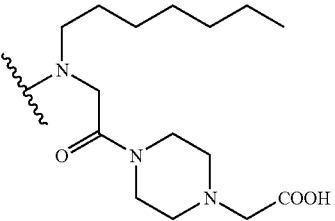 | 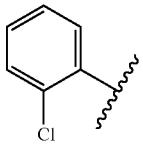 | 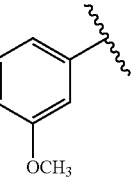 |
| 516 | 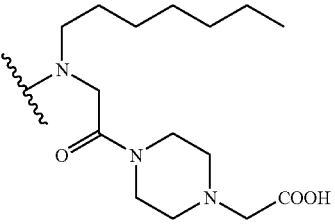 | 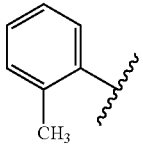 | 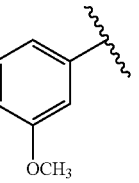 |
| 486 | 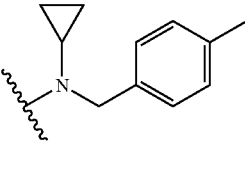 | 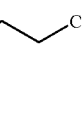 | 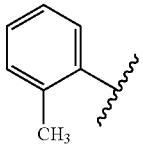 |
| 521.56 | 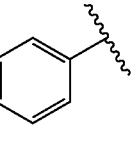 | 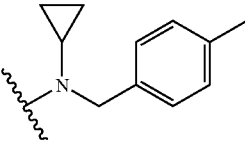 |  |

TABLE 4-continued
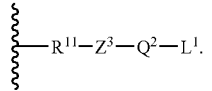
| Mass Spec (M⁺+ 1) | W— | —W¹— | —R¹¹—L¹ |
|---|---|---|---|
| 535.55 | 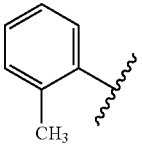 | 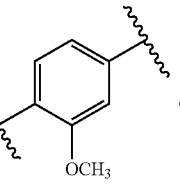 | 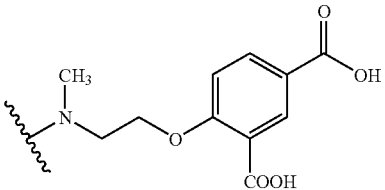 |
| 507.54 | 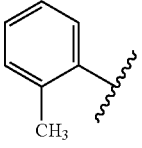 | 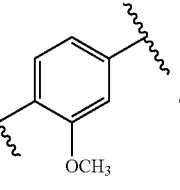 | 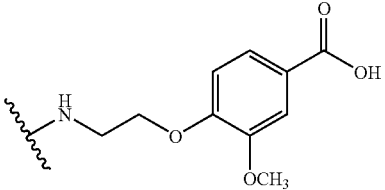 |
| 535.59 | 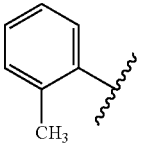 | 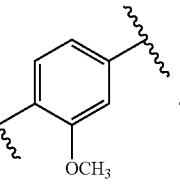 | 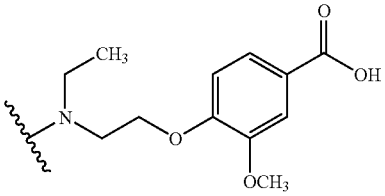 |
| 522.51 | 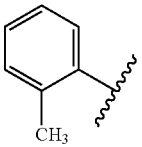 | 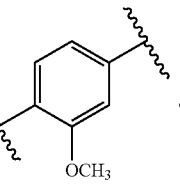 | 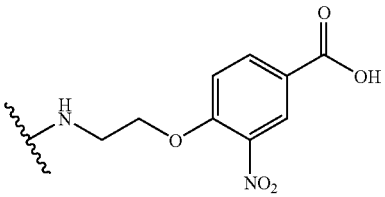 |
| 539.55 | 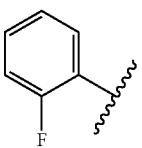 | 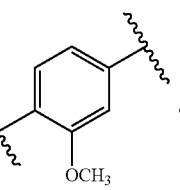 | 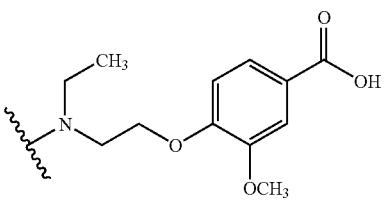 |
| 502.56 | 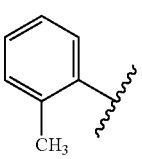 | 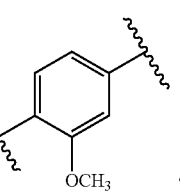 | 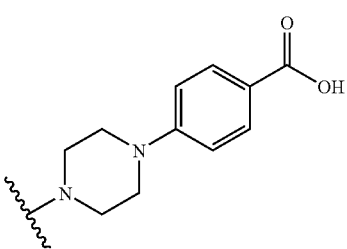 |

TABLE 4-continued
$$\begin{CD}\xi -R^{11}-Z^3-Q^2-L^1.\end{CD}$$
| Mass Spec (M⁺+ 1) | W— | —W¹— | —R¹¹—L¹ |
|---|---|---|---|
| 521.56 | 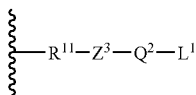 | 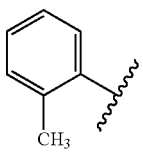 | 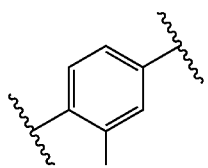 |
| 547.6 | 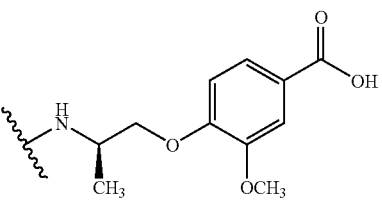 | 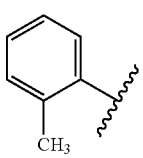 | 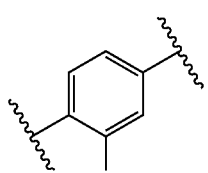 |
| 620.69 | 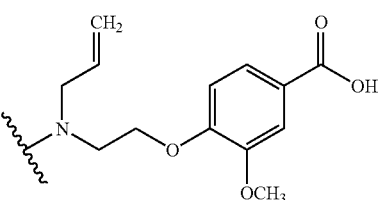 | 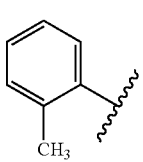 | 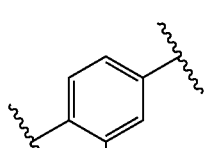 |
| 633.73 | 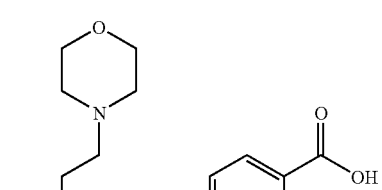 | 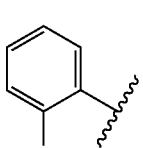 | 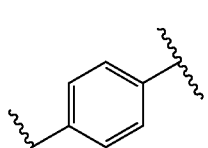 |
| 590.67 | 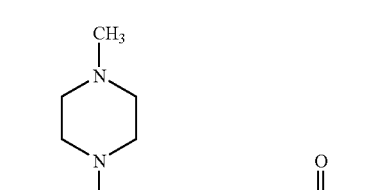 | 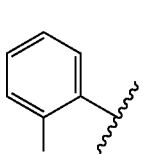 | 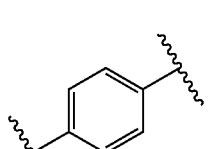 |

TABLE 4-continued

| Mass Spec (M⁺+ 1) | W— | —W¹— | —R¹¹—L¹ |
|---|---|---|---|
| 495.5 | 2-F-phenyl | 2-OCH₃-phenylene | N(CH₃)CH₂CH₂O-(4-carboxyphenyl) |
| 529.94 | 2-F-phenyl | 2-OCH₃-phenylene | N(CH₃)CH₂CH₂O-(3-Cl-4-carboxyphenyl) |
| 491.54 | 2-CH₃-phenyl | 2-OCH₃-phenylene | N(CH₃)CH₂CH₂O-(4-carboxyphenyl) |
| 525.98 | 2-CH₃-phenyl | 2-OCH₃-phenylene | N(CH₃)CH₂CH₂O-(3-Cl-4-carboxyphenyl) |
| 489.56 | 2-CH₃-phenyl | 2-OCH₃-phenylene | N(CH₃)CH₂CH₂CH₂-(4-carboxyphenyl) |
| 461.51 | 2-CH₃-phenyl | 1,4-phenylene | N(CH₃)CH₂CH₂O-(4-carboxyphenyl) |
| 495.95 | 2-CH₃-phenyl | 1,4-phenylene | N(CH₃)CH₂CH₂O-(3-Cl-4-carboxyphenyl) |

TABLE 4-continued
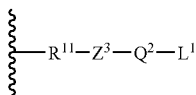
| Mass Spec (M⁺+ 1) | W— | —W¹— | —R¹¹—L¹ |
|---|---|---|---|
| 491.54 | 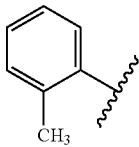 | 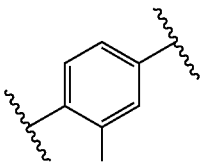 | 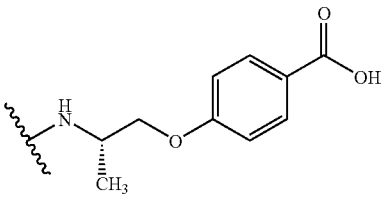 |
| 461.51 | 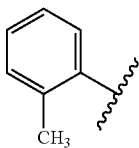 | 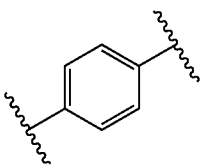 | 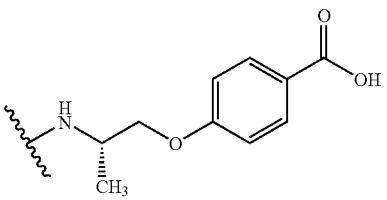 |
| 495.95 | 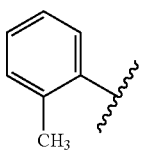 | 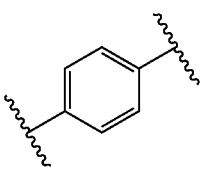 | 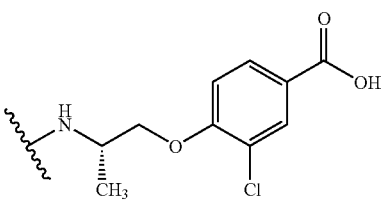 |
| 525.98 | 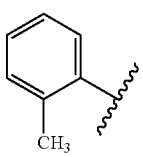 | 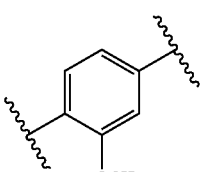 | 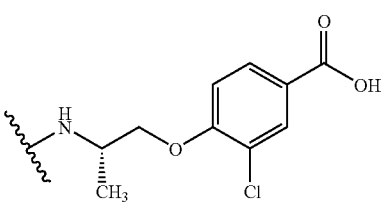 |
| 534.6 | 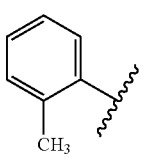 | 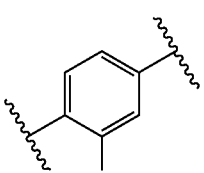 | 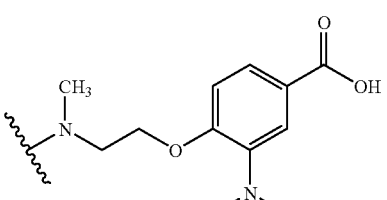 |
| 538.57 | 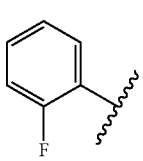 | 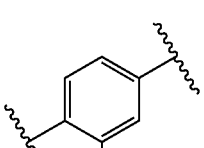 | 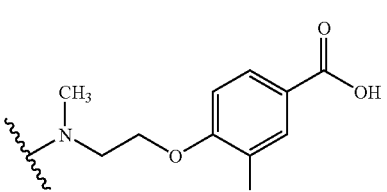 |

TABLE 4-continued
| Mass Spec (M⁺+ 1) | W— | —W¹— | —R¹¹—L¹ |
|---|---|---|---|
| 504.58 | 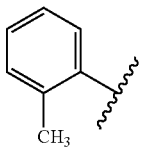 | 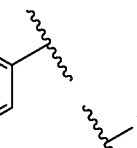 | 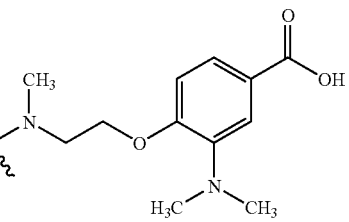 |
| 552.59 | 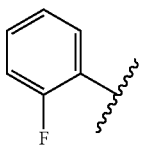 | 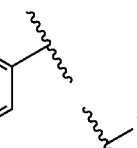 | 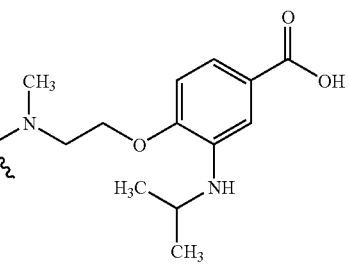 |
| 523.55 | 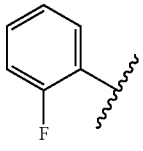 | 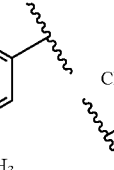 | 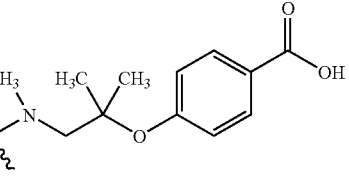 |
| 529.94 | 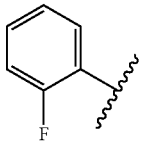 | 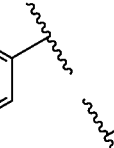 | 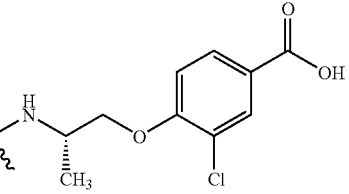 |
| 490.55 | 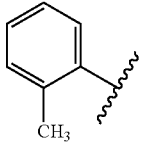 | 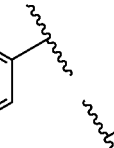 | 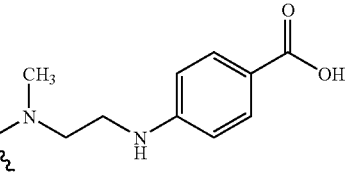 |
| 543.97 | 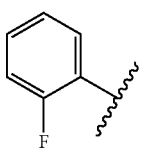 | 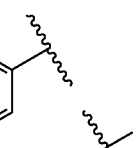 | 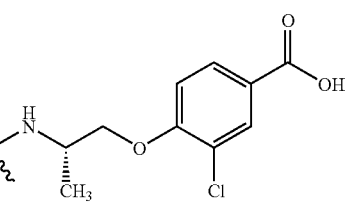 |

TABLE 4-continued
$$\text{—R}^{11}\text{—Z}^3\text{—Q}^2\text{—L}^1.$$
| Mass Spec (M$^+$+ 1) | W— | —W$^1$— | —R$^{11}$—L$^1$ |
|---|---|---|---|
| 540.01 | 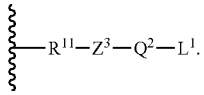 | 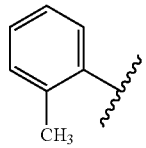 | 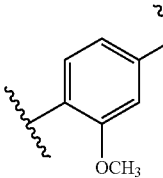 |
| 548.63 | 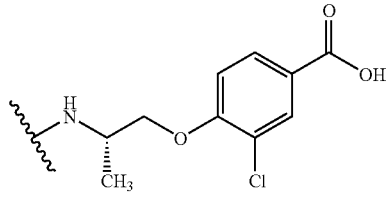 | 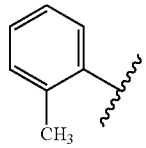 | 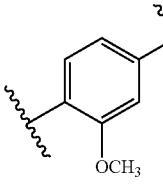 |
| 504.58 | 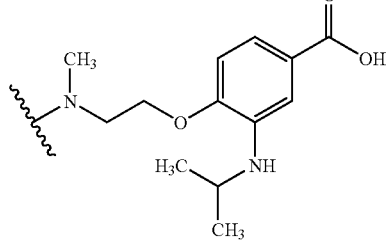 | 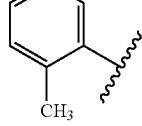 | 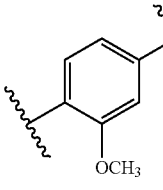 |
| 620.07 | 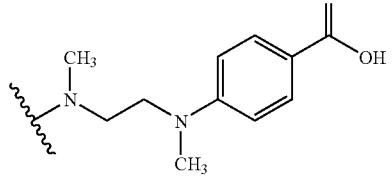 | 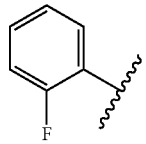 | 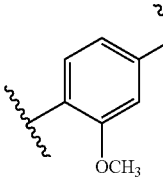 |
| 562.66 | 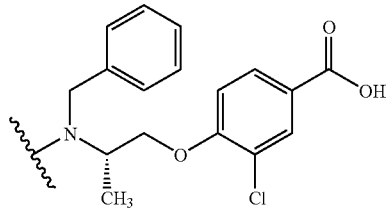 | 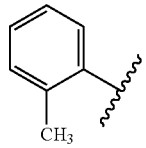 | 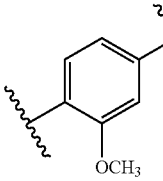 |

TABLE 4-continued
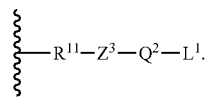

TABLE 4-continued
| Mass Spec (M⁺+ 1) | W— | —W¹— | —R¹¹—L¹ |
|---|---|---|---|
| 556.41 |  | 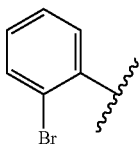 | 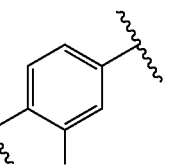 |
| 596.67 | 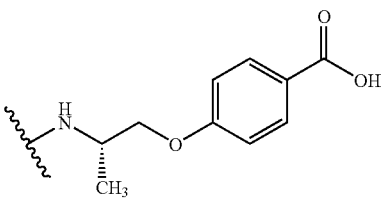 | 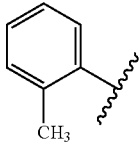 | 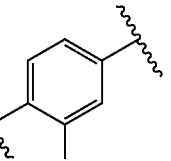 |
| 532.63 | 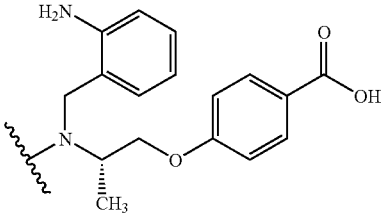 | 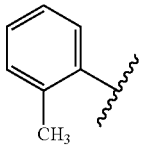 | 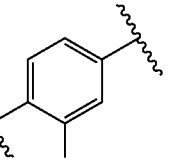 |
| 691.53 | 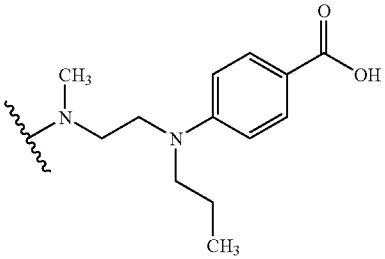 | 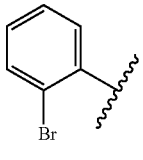 | 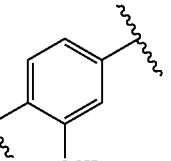 |
| 541.0 | 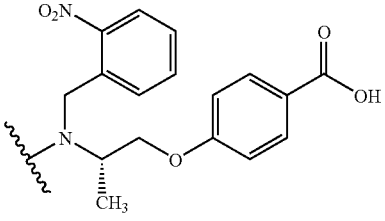 | 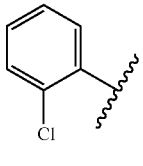 | 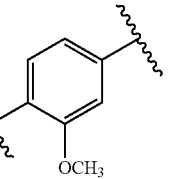 |
| 607 | 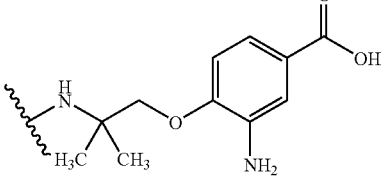 | 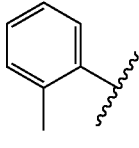 | 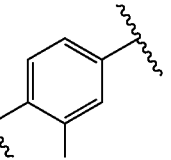 |

TABLE 4-continued

| Mass Spec (M⁺+ 1) | W— | —W¹— | —R¹¹—L¹ |
|---|---|---|---|
| 497 | 2-Cl-phenyl | 4-linked-2-OMe-phenyl | —NH-CH₂CH₂-NH-(4-COOH-phenyl) |
| 525 | 2-Cl-phenyl | 4-linked-2-OMe-phenyl | —N(Me)-CH₂CH₂-N(Me)-(4-COOH-phenyl) |
| 527 | 2-Cl-phenyl | 4-linked-2-OMe-phenyl | —N(Me)-CH₂CH₂-O-(3-NH₂-4-linked-COOH-phenyl) |
| 542 | 2-Cl-phenyl | 4-linked-2-OMe-phenyl | —N(CH₂CH₂OH)-CH₂CH₂-O-(4-COOH-phenyl) |
| 498 | 2-Cl-phenyl | 4-linked-2-OMe-phenyl | —NH-CH₂CH₂-O-(4-COOH-phenyl) |
| 543 | 2-Br-phenyl | 4-linked-2-OMe-phenyl | —NH-CH₂CH₂-O-(4-COOH-phenyl) |
| 611 | 2-Cl-phenyl | 4-linked-2-OMe-phenyl | —N(CH₂CH₂-morpholino)-CH₂CH₂-O-(4-COOH-phenyl) |

TABLE 4-continued $$\{-R^{11}-Z^3-Q^2-L^1.$$

| Mass Spec (M+ + 1) | W— | —W¹— | —R¹¹—L¹ |
|---|---|---|---|
| 477 | o-tolyl | 2-OMe-phenyl | —NH—CH₂CH₂—NH—C₆H₄—COOH |
| 512 | o-Cl-phenyl | 2-OMe-phenyl | —N(Me)—CH₂CH₂—O—C₆H₄—COOH |
| 518 | o-tolyl | 2-OMe-phenyl | —N(allyl)—CH₂CH₂—O—C₆H₄—COOH |
| 569 | o-tolyl | 2-OMe-phenyl | —N(CH₂-4-pyridyl)—CH₂CH₂—O—C₆H₄—COOH |
| 569 | o-tolyl | 2-OMe-phenyl | —N(CH₂-3-pyridyl)—CH₂CH₂—O—C₆H₄—COOH |
| 592 | o-tolyl | 2-OMe-phenyl | —N(CH₂-(2,2-dimethyl-1,3-dioxolan-4-yl))—CH₂CH₂—O—C₆H₄—COOH |
| 591 | o-tolyl | 2-OMe-phenyl | —N(CH₂CH₂-morpholino)—CH₂CH₂—O—C₆H₄—COOH |

TABLE 4-continued
$$\substack{\xi\\ \xi}-R^{11}-Z^3-Q^2-L^1.$$
| Mass Spec (M⁺+ 1) | W— | —W¹— | —R¹¹—L¹ |
|---|---|---|---|
| 569 | 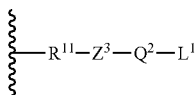 | 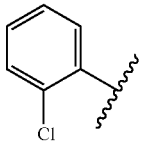 | 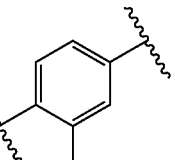 |
| 538 | 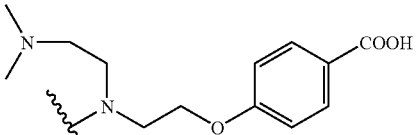 | 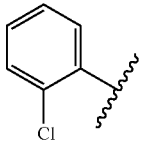 | 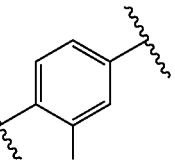 |
| 583 | 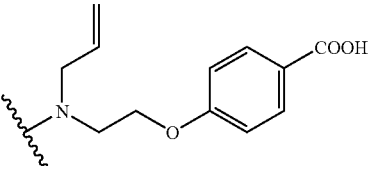 | 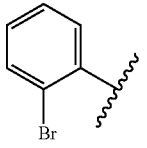 | 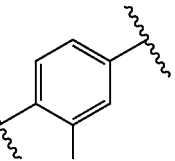 |
| 561 | 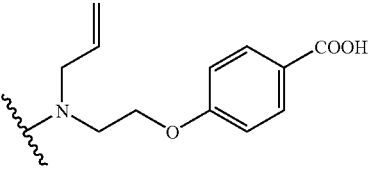 | 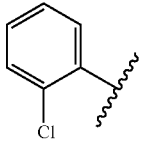 | 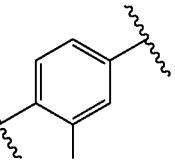 |
| 549 | 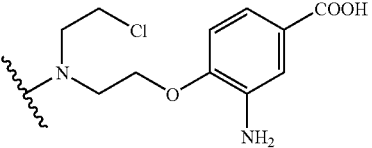 | 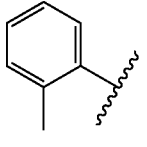 | 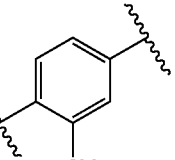 |
| 604 | 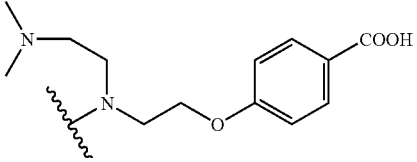 | 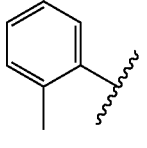 | 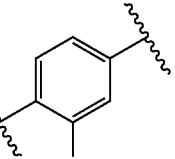 |
| 589 | 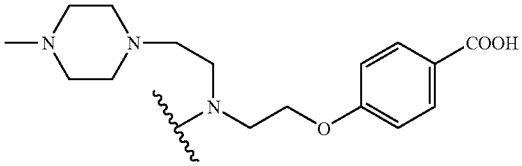 | 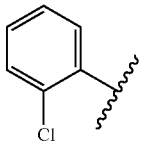 | 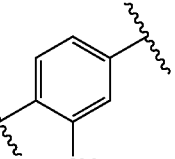 |

TABLE 4-continued
$$\{-R^{11}-Z^3-Q^2-L^1.$$
| Mass Spec (M⁺+ 1) | W— | —W¹— | —R¹¹—L¹ |
|---|---|---|---|
| 506 | 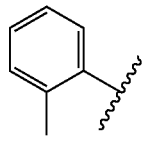 | 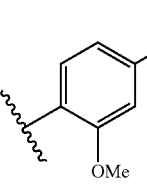 | 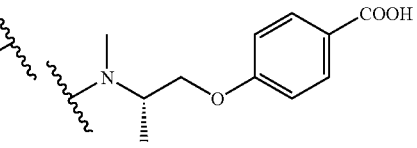 |
| 607 | 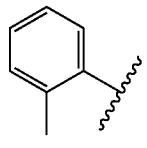 | 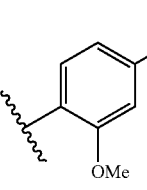 | 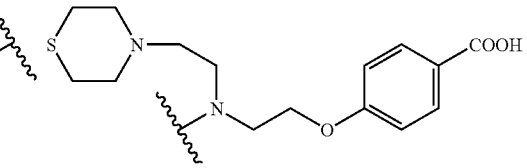 |
| 589 | 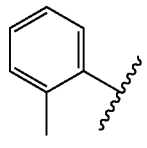 | 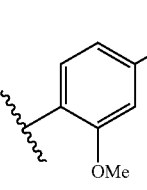 | 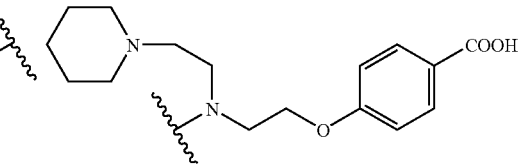 |
| 575 | 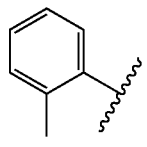 | 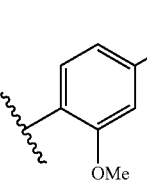 | 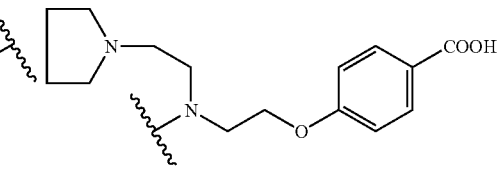 |
| 619 | 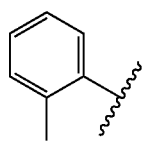 | 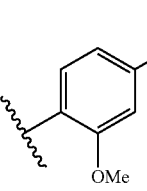 | 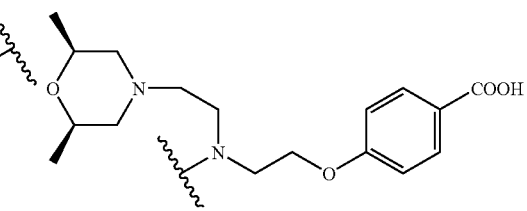 |
| 601 | 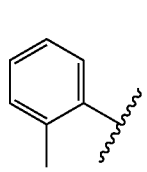 | 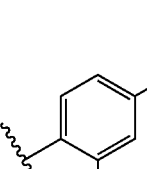 | 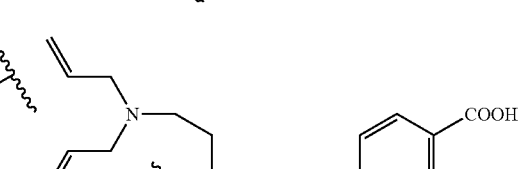 |
| 603 | 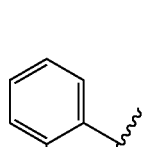 | 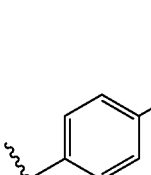 | 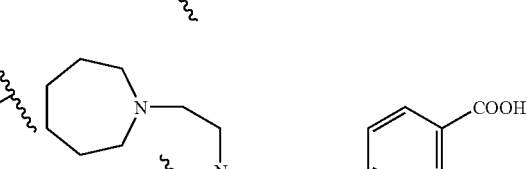 |

US 7,179,819 B2
167 168
TABLE 4-continued
$$\text{\}—R^{11}—Z^3—Q^2—L^1.}$$
| Mass Spec (M⁺+ 1) | W— | —W¹— | —R¹¹—L¹ |
|---|---|---|---|
| 617 | 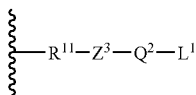 | 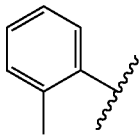 | 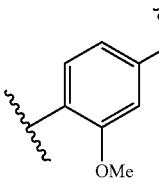 |
| 625 | 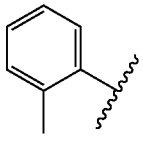 | 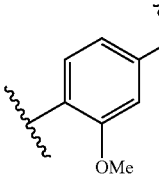 | 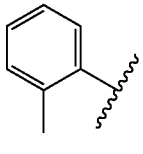 |
| 611 | 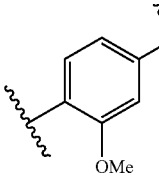 | 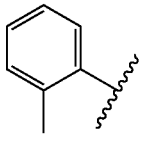 | 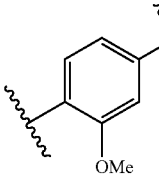 |
| 522 | 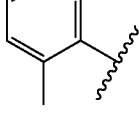 | 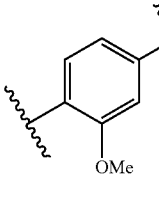 | 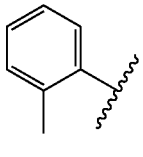 |
| 565 | 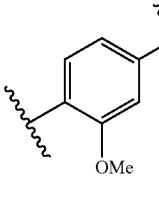 | | |
| 593 | | | |

TABLE 4-continued
$$\xi-R^{11}-Z^3-Q^2-L^1.$$
| Mass Spec (M⁺+ 1) | W— | —W¹— | —R¹¹—L¹ |
|---|---|---|---|
| 518 | 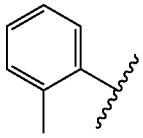 | 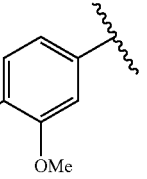 | 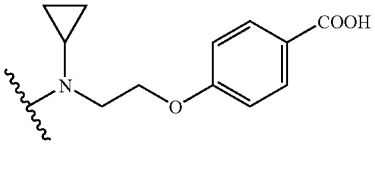 |
| 538 | 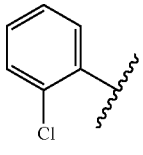 | 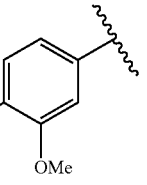 | 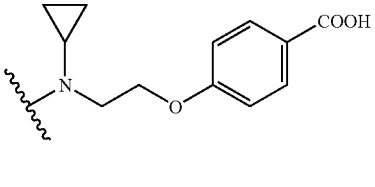 |
| 627 | 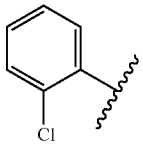 | 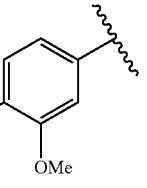 | 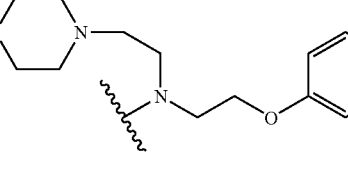 |
| 585 | 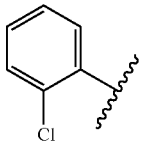 | 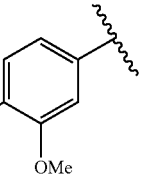 | 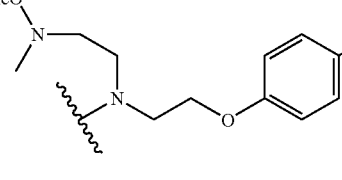 |
| 624 | 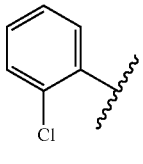 | 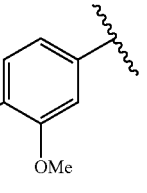 | 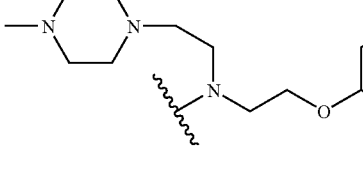 |
| 609 | 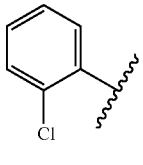 | 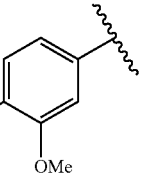 | 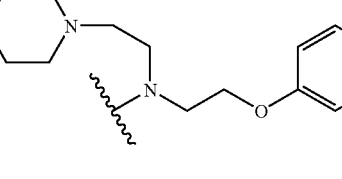 |
| 639 | 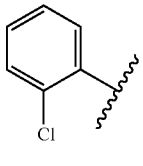 | 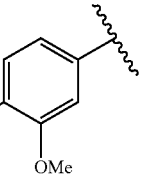 | 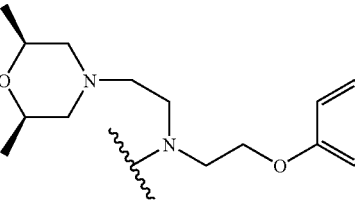 |

TABLE 4-continued $\{-R^{11}-Z^3-Q^2-L^1.$

| Mass Spec (M⁺+ 1) | W— | —W¹— | —R¹¹—L¹ |
|---|---|---|---|
| 623 | | | |
| 637 | | | |
| 595 | | | |
| 621 | | | |
| 645 | | | |
| 581 | | | |

TABLE 4-continued
$$\{-R^{11}-Z^3-Q^2-L^1.$$
| Mass Spec (M⁺+ 1) | W— | —W¹— | —R¹¹—L¹ |
|---|---|---|---|
| 637 | 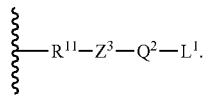 | 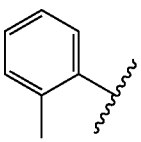 | 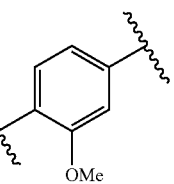 |
| 611 | 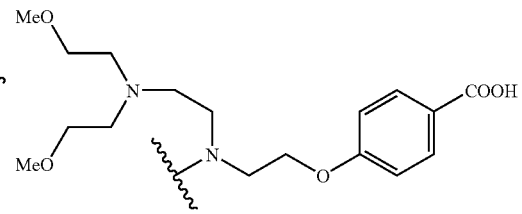 | 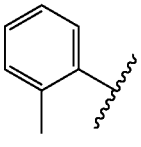 | 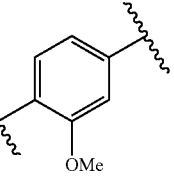 |
| 631 | 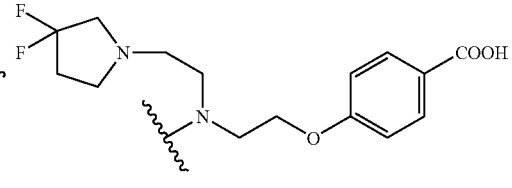 | 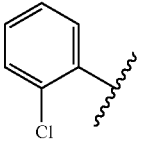 | 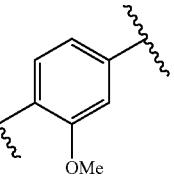 |
| 488 | 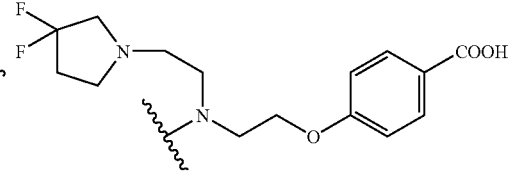 | 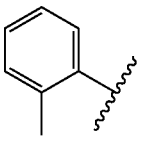 | 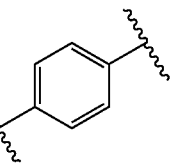 |
| 504 | 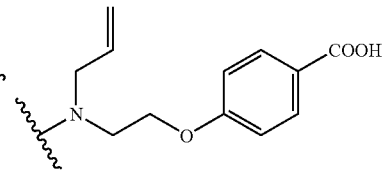 | 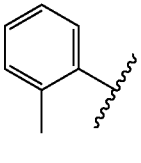 | 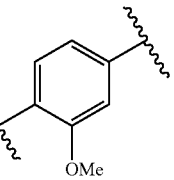 |
| 522 | 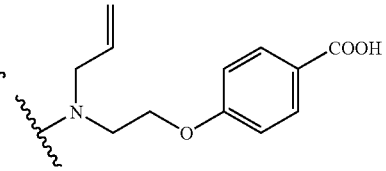 | 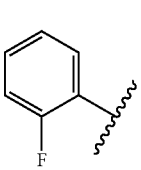 | 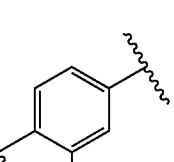 |
| 640 | 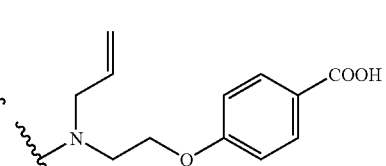 | 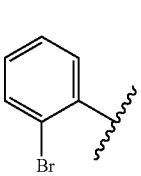 | 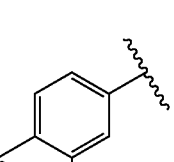 |

TABLE 4-continued $$-R^{11}-Z^3-Q^2-L^1.$$

| Mass Spec (M⁺+ 1) | W— | —W¹— | —R¹¹—L¹ |
|---|---|---|---|
| 676 | 2-Br-phenyl | 4-, 3-OMe-phenyl | 3,3-difluoropyrrolidinyl-N-CH₂CH₂-N(-)-CH₂CH₂-O-(4-COOH-phenyl) |
| 548 | 2-Me-phenyl | 4-, 3-OMe-phenyl | (CH₃)N(-)-CH₂CH₂-NH-(4-position of 2-NHAc, 1-COOH phenyl) |
| 613 | 2-Br-phenyl | 4-, 3-OMe-phenyl | (CH₃)N(-)-CH₂CH₂-NH-(4-position of 2-NHAc, 1-COOH phenyl) |
| 666 | 2-Br-phenyl | 4-, 3-OMe-phenyl | (allyl)₂N-CH₂CH₂-N(-)-CH₂CH₂-O-(4-COOH-phenyl) |
| 614 | 2-Br-phenyl | 4-, 3-OMe-phenyl | (CH₃)₂N-CH₂CH₂-N(-)-CH₂CH₂-O-(4-COOH-phenyl) |
| 626 | 2-Br-phenyl | 4-, 3-OMe-phenyl | cyclopropyl-NH-CH₂CH₂-N(-)-CH₂CH₂-O-(4-COOH-phenyl) |
| 630 | 2-Br-phenyl | 4-, 3-OMe-phenyl | (MeO)(Me)N-CH₂CH₂-N(-)-CH₂CH₂-O-(4-COOH-phenyl) |

TABLE 4-continued $$\{-R^{11}-Z^3-Q^2-L^1.$$

| Mass Spec (M⁺+ 1) | W— | —W¹— | —R¹¹—L¹ |
|---|---|---|---|
| 676 | 2-Br-phenyl | 2-OMe-phenyl (1,4) | N(Ph)CH₂CH₂N(Me)-, then N-CH₂CH₂-O-C₆H₄-COOH (para) |
| 506 | 2-Me-phenyl | 3-F-phenyl (1,4) | N(allyl)CH₂CH₂-O-C₆H₄-COOH |
| 526 | 2-Cl-phenyl | 3-F-phenyl (1,4) | N(allyl)CH₂CH₂-O-C₆H₄-COOH |
| 502 | 2-Me-phenyl | 3-Me-phenyl (1,4) | N(allyl)CH₂CH₂-O-C₆H₄-COOH |
| 514 | 2-Me-phenyl | 3-OMe-phenyl (1,4) | N(cyclopropyl)CH₂-C₆H₄-CH=CH-COOH |
| 484 | 2-Me-phenyl | phenyl (1,4) | N(cyclopropyl)CH₂-C₆H₄-CH=CH-COOH |
| 579 | 2-Br-phenyl | 3-OMe-phenyl (1,4) | N(cyclopropyl)CH₂-C₆H₄-CH=CH-COOH |

TABLE 4-continued
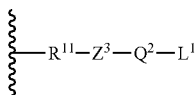
| Mass Spec (M⁺+ 1) | W— | —W¹— | —R¹¹—L¹ |
|---|---|---|---|
| 585 | 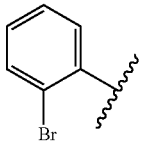 | 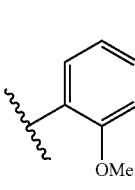 | 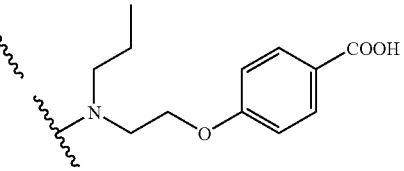 |
| 512 | 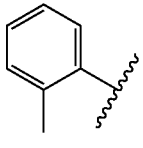 | 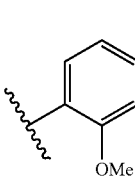 | 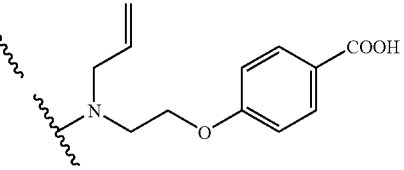 |
| 482 | 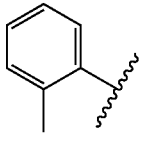 | 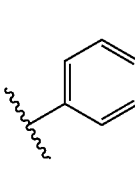 | 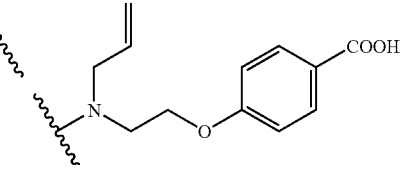 |
| 532 | 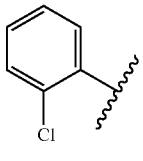 | 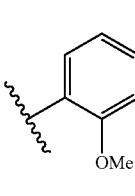 | 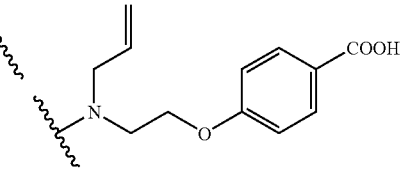 |
| 560 | 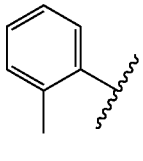 | 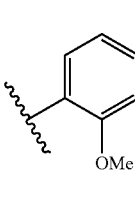 | 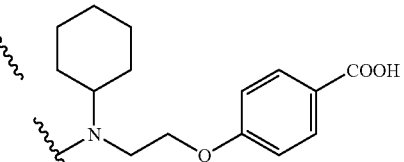 |
| 625 | 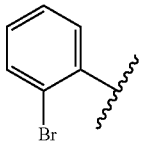 | 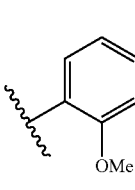 | 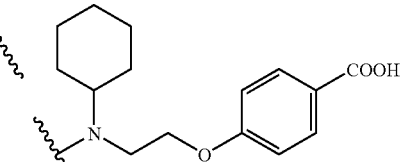 |
| 583 | 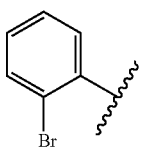 | 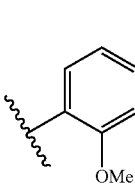 | 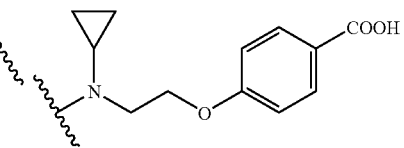 |

TABLE 4-continued
$$\{-R^{11}-Z^3-Q^2-L^1.$$
| Mass Spec (M⁺+ 1) | W— | —W¹— | —R¹¹—L¹ |
|---|---|---|---|
| 568 | 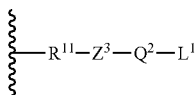 | 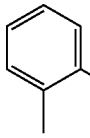 | 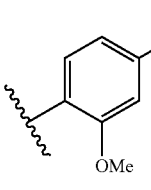 |
| 534 | 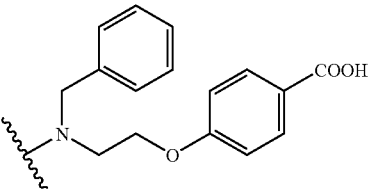 | 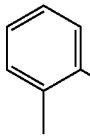 | 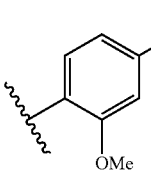 |
| 574 | 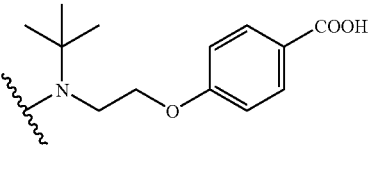 | 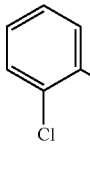 | 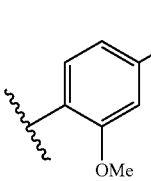 |
| 536 | 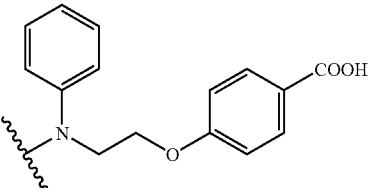 | 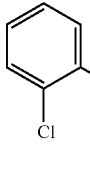 | 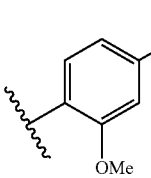 |
| 581 | 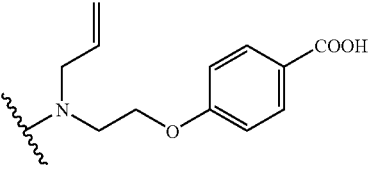 | 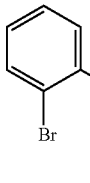 | 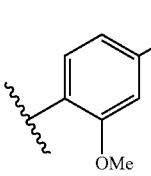 |
| 522 | 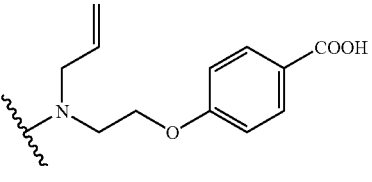 | 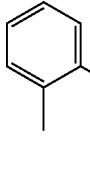 | 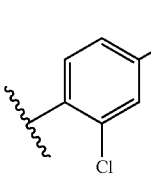 |
| 520 | 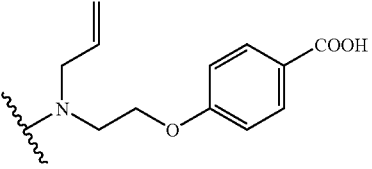 | 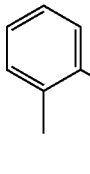 | 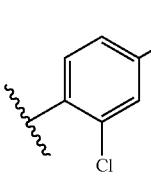 |

The principles of the present invention also encompass prodrugs in the scope of Formula I, and compounds representative thereof include those wherein $R^5$ or $R^8$ is a lower alkoxy group, and those wherein $R^{10}$ or $R^{19}$ is a lower alkoxycarbonyl group.

The principles of the present invention also provide a method for inhibiting cell adhesion, and in particular, VLA-4 mediated cell adhesion at $\alpha 4\beta 1$ receptor sites in a mammal, wherein the method comprises administering an effective amount of a compound represented by Formula I. As used herein, inhibiting cell adhesion is intended to include inhibiting, suppressing and preventing VLA-4 mediated cell adhesion-associated conditions, including but not limited to, inflammation and cell adhesion-associated immune or autoimmune responses.

The principles of the present invention therefore also provide a method of treating a condition associated with VLA-4 mediated cell adhesion, wherein the method comprises administering to a mammal in need of such treatment, an effective amount of a compound represented by Formula I. Such conditions include for example, but are not limited to, inflammatory and autoimmune responses, diabetes, asthma, arthritis, psoriasis, multiple sclerosis, inflammatory bowel disease, transplantation rejection, and tumor metastasis. As used herein, "treatment" of a mammal is intended to include prophylaxis as well.

The compounds of the present invention may be administered as a monotherapy, or in combination with antiinflammatory or immunosuppressive agents. Such combination therapies can involve the administration of the various pharmaceuticals as a single dosage form or as multiple dosage forms administered at the same time or at different times.

Any suitable route of administration may be employed for providing a patient with an effective amount of a compound of the present invention. Suitable routes of administration may include, for example, oral, rectal, nasal, buccal, parenteral (such as, intravenous, intrathecal, subcutaneous, intramuscular, intrasternal, intrahepatic, intralesional, intracranial, intra-articular, and intra-synovial), transdermal (such as, for example, patches), and the like. Due to their ease of administration, oral dosage forms, such as, for example, tablets, troches, dispersions, suspensions, solutions, capsules, soft gelatin capsules, and the like, may be preferred. Administration may also be by controlled or sustained release means and delivery devices. Methods for the preparation of such dosage forms are well known in the art.

Pharmaceutical compositions incorporating compounds of the present invention may include excipients, a pharmaceutically acceptable carrier, in addition to other therapeutic ingredients. Excipients such as starches, sugars, microcrystalline cellulose, diluents, lubricants, binders, coloring agents, flavoring agents, granulating agents, disintegrating agents, and the like may be appropriate depending upon the route of administration. Because of their ease of administration, tablets and capsules represent the most advantageous oral dosage unit forms. If desired, tablets may be coated by standard aqueous or nonaqueous techniques.

The compounds of the present invention may be used in the form of pharmaceutically acceptable salts derived from inorganic or organic bases. Suitable pharmaceutically acceptable base addition salts include, but are not limited to, ammonium salts, alkali metal salts, metallic salts made from aluminum, calcium, lithium, magnesium, potassium, sodium and zinc, organic salts made from chloroprocaine, choline, N,N'-dibenzylethylenediamine, dicyclohexylamine, diethanolamine, ethylenediamine, lysine, meglumine (N-methylglucamine) and procaine, as well as salts with amino acids, such as arginine, lysine, and so forth.

Where the compounds of the invention have a basic moiety, such as an amino group, the compounds may be used in the form of pharmaceutically acceptable non-toxic organic or inorganic acids. Such acids include acetic, benzenesulfonic, benzoic, camphorsulfonic, citric, ethanesulfonic, methanesulfonic, fumaric, gluconic, glutamic, hydrobromic, hydrochloric, lactic, maleic, malic, mandelic, nitric, pamoic, pantothenic, phosphoric, succinic, sulfuric, tartaric, p-toluenesulfonic acids, and the like. Particularly preferred are citric, hydrochloric, maleic, fumaric, phosphoric, sulfuric, tartaric and p-toluenesulfonic acids. Compounds of the invention may also be in the form of hydrates.

DETAILED DESCRIPTION OF THE INVENTION

Abbreviations & Definitions

The following terms and abbreviations have the indicated meaning throughout this disclosure.

| | |
|---|---|
| 293E HEK cells = | 293E human embryonic kidney cells |
| Ac = | acetyl |
| anti-α4-PE conjugated = | monoclonal antibody against integrin α4 subunit, phycoerythrin conjugated |
| anti-β1-FITC conjugated = | monoclonal antibody against integrin β1 subunit, fluorescein conjugated |
| α5β1 = | integrin α5β1, fibronectin receptor, VLA-5 |
| αvβ3 = | integrin αvβ3, vitronectin receptor |
| α4β7 = | integrin α4β7 |
| Bn = | benzyl |
| Boc = | t-butoxycarbonyl |
| BSA = | bovine serum albumin |
| c- = | cyclo- |
| cDNA = | complementary DNA |
| CHO cells = | Chinese Hamster Ovary cells |
| p-ClPh = | para-chlorophenyl |
| CMV promoter = | cytomegalovirus promoter |
| m-CPBA = | 3-chloroperoxybenzoic acid |
| DAST = | diethylaminosulfur trifluoride |
| DCM = | dichloromethane = methylene chloride = $CH_2Cl_2$ |
| DELFIA = | dissociation enhanced lanthanide fluor-immune assay |
| DIAD = | diisopropyl azodicarboxylate |

-continued

| | |
|---|---|
| DIC = | diisopropylcarbodiimide |
| DIEA = | N,N-diisopropylethylamine |
| DMAP = | 4-N,N-dimethylaminopyridine |
| DMEM = | Dulbecco's Modified Eagle's Medium |
| DMF = | N,N-dimethylformamide |
| DTPA = | Diethylenetriaminepentaacetic acid |
| EDC = | 1-ethyl-3-(3-dimethylaminopropyl)carbodiimide |
| Et$_2$O = | ethyl ether |
| FACS = | fluorescence cell sorting |
| Fmoc = | 9-fluorenylmethoxycarbonyl |
| GPIIb/IIIa = | integrin αIIbβ3, fibrinogen receptor |
| HEPES = | N-(2-hydroxyethyl)piperazine-N'-(2-ethanesulfonic acid) |
| HMDS = | 1,1,1,3,3,3-hexamethyldisilzane |
| HOAc = | acetic acid |
| HOBt = | 1-hydroxybenzotriazole |
| human IgG1 = | human immunoglobulin G1 |
| ICAM = | intracellular adhesion molecule |
| LDV = | Leu-Asp-Val |
| LFA-1 and Mac-1 = | Lymphocyte function-related antigen |
| LiHMDS = | lithium 1,1,1,3,3,3-hexamethyldisilazane |
| Me = | methyl |
| p-MeOPh = | para-methoxyphenyl |
| nM = | nanomolar |
| PBS = | phosphate buffered saline |
| PEG = | polyethylene glycol |
| Ph = | phenyl |
| PhOH = | phenol |
| PyBroP = | bromo-tris-pyrrolidinphosphonium hexafluorophosphate |
| RPMI medium = | Russell Park Memorial Institute medium |
| TFA = | trifluoroacetic acid |
| TFAA = | trifluoroacetic acid anhydride |
| THF = | tetrahydrofuran |
| TLC = | thin-layer chromatography |
| TMS = | trimethylsilyl |
| Ts = | toluenesulfonyl |
| VCAM-1 (D1D7) = | vascular cell adhesion molecule (containing one to seven immuloglobulin domains) |
| VCAM-IgG fusion protein = | a VCAM IgG fusion protein containing the one to seven immunoglobulin domains of human VCAM-1 (D1D7) attached above the hinge region of an IgG1 molecule |

"Alkyl group" is intended to include linear or branched hydrocarbon radicals and combinations thereof of 1 to 20 carbons. "Lower alkyl group" means alkyl groups of from 1 to about 10, preferably from 1 to about 8, and more preferably, from 1 to about 6 carbon atoms. Examples of such radicals include methyl, ethyl, n-propyl, isopropyl, n-butyl, isobutyl, sec-butyl, tert-butyl, pentyl, iso-amyl, hexyl, octyl groups and the like.

"Alkylene group" means a divalent radical formed by removing a hydrogen atom from an "alkyl group."

"Aryl group" means a radical formed from an aromatic hydrocarbon ring of 4 to about 16 carbon atoms, preferably of 6 to about 12 carbon atoms, and more preferably of 6 to about 10 carbon atoms. The rings may optionally be substituted with 1–3 substituents selected from alkyl, halogen, hydroxy, alkoxy, aryloxy, haloalkyl, phenyl and heteroaryl. Examples of aryl groups are phenyl, biphenyl, 3,4dichlorophenyl and naphthyl.

"Arylene group" means a divalent radical formed by removing a hydrogen atom from an "aryl group."

"Arylalkyl group" denotes a structure comprising an alkyl attached to an aryl ring. Examples include benzyl, phenethyl, 4-chlorobenzyl, and the like.

"Cycloalkyl group" refers to a saturated hydrocarbon ring radical of from 3 to 12 carbon atoms, and preferably from 3 to 8 carbon atoms. Examples include cyclopropyl, cyclobutyl, cyclopentyl, cyclohexyl, norbornyl, adamantyl, myrtanyl groups and the like. "Lower cycloalkyl group" refers to cycloalkyl of 3 to 6 carbons.

"Cycloalkylene group" means a divalent radical formed by removing a hydrogen atom from a "cycloalkyl group."

"Divalent $C_1$ to $C_{20}$ aliphatic hydrocarbon moiety" includes alkylene, cycloalkylene, alkenylene, alkynylene groups and combinations thereof. Examples include ethylene, propylene, propynylene, 2,4-heptadienylene groups and the like.

"Heterocyclyl group" refers to a cyclic radical having from 1 to 6 carbon atoms, preferably 3 to 6 carbon atoms, and from 1 to 4 heteroatoms chosen from O, N and S. Examples include: pyrrolyl, pyridinyl, pyrazolyl, triazolyl, pyrimidinyl, pyridazinyl, oxazolyl, thiazolyl, imidazolyl, indolyl, thienyl, furyl, azetidiyl, tetrazolyl, 2-pyrrolinyl, 3-pyrrolinyl, pyrrolindinyl, 1,3-dioxolanyl, imidazolinyl, imidazolidinyl, pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dithianyl, morpholinyl, thiomorpholinyl, pyrazinyl, piperazinyl, 1,3,5-triazinyl, 1,2,5-trithianyl, benzo(b)thiophenyl, benzimidazolyl, quinolinyl groups and the like.

"Heterocyclylene group" means a radical formed by removing a hydrogen atom from a "heterocyclyl group."

"Heteroaryl group" refers to an aromatic cyclic radical having from 1 to 12 carbon atoms, preferably 1 to 6 carbon atoms, and from 1 to 4 heteroatoms chosen from O, N and S; or a bicyclic 9- or 10-membered heteroaromatic ring system containing 1–4 heteroatoms selected from O, N and S. The methine H atoms of a heterocyclyl or heteroaryl structure may be optionally substituted with alkyl, alkoxy or halogen. Examples include: imidazolyl, pyridyl, indolyl, thienyl, benzopyranyl, thiazolyl, furyl, benzimidazolyl, quinolinyl, isoquinolinyl, quinoxalinyl, pyrimidinyl, pyrazinyl, tetrazolyl, pyrazolyl groups and the like.

"Heteroarylene group" means a divalent radical formed by removing a hydrogen atom from a "heteroaryl group."

"Alkoxy group" means a straight, branched or cyclic hydrocarbon configuration and combinations thereof, including from 1 to 20 carbon atoms, preferably from 1 to 8 carbon atoms, more preferably from 1 to 4 carbon atoms, and an oxygen atom at the point of attachment. Suitable alkoxy groups include methoxy, ethoxy, n-propoxy, isopropoxy, n-butoxy, iso-butoxy, sec-butoxy, tert-butoxy, cyclopropoxy, cyclohexyloxy groups and the like. "Lower alkoxy group" refers to alkoxy groups having from 1 to 4 carbon atoms.

"Alkenyl group" refers to an unsaturated acyclic hydrocarbon radical in so much as it contains at least one double bond. "Lower alkenyl group" refers to such radicals containing from 2 to 10 carbon atoms, preferably from 2 to 8 carbon atoms and more preferably from 2 to 6 carbon atoms. Examples of suitable alkenyl radicals include propenyl, buten-1-yl, isobutenyl, penten-1-yl, 2-methylbuten-1yl, 3-methylbuten-1-yl, hexen-1-yl, hepten-1-yl, and octen-1-yl groups and the like.

"Alkenylene group" means a divalent radical formed by removing a hydrogen atom from an "alkenyl group."

"Alkynyl group" refers to an unsaturated acyclic hydrocarbon radical containing at least one triple bond. Examples include ethynyl, propynyl groups, and the like.

"Alkynylene group" means a divalent radical formed by removing a hydrogen atom from an alkynyl group."

"Substituted alkyl group" means a linear or branched alkyl group wherein at least one hydrogen atom attached to an aliphatic carbon is replaced with a substituent such as alkyl, amino, alkoxy, hydroxy, aryl, cyano, carboxy, alkoxycarbonyl, monoalkylamino, alkyloxy, cyanoalkyl, cycloalkyl, alkylthio, alkylsulfinyl, alkylsulfonyl, arylthio, carboxyalkyl, alkoxycarbonylalkyl, haloalkyl, acylamino, dialkylamino, cyclicamino groups, halogen atom and nitro. Examples of such substituent groups include methyl, isopropyl, methoxy, ethoxy, propoxy, amino, methylamino, phenyl, naphthyl groups, chlorine, fluorine and the like.

"Substituted alkylene group" means a linear or branched alkylene group wherein at least one hydrogen atom attached to an aliphatic carbon is replaced with a substituent such as alkyl, amino, alkoxy, hydroxy, aryl, cyano, carboxy, alkoxycarbonyl, monoalkylamino, alkyloxy, cyanoalkyl, cycloalkyl, alkylthio, alkylsulfinyl, alkylsulfonyl, arylthio, carboxyalkyl, alkoxycarbonylalkyl, haloalkyl, acylamino, dialkylamino, cyclicamino groups, halogen atom and nitro.

"Substituted cycloalkyl group" means a cycloalkyl group wherein at least one hydrogen atom attached to a ring carbon atom is replaced with a substituent such as alkyl, amino, alkoxy, hydroxy, aryl, cyano, carboxy, alkoxycarbonyl, monoalkylamino, alkyloxy, cyanoalkyl, cycloalkyl, alkylthio, alkylsulfinyl, alkylsulfonyl, arylthio, carboxyalkyl, alkoxycarbonylalkyl, haloalkyl, acylamino, dialkylamino, cyclicamino groups, halogen atom and nitro.

"Substituted cycloalkyene group" means a cycloalkylene group wherein at least one hydrogen atom attached to a ring carbon is replaced with a substituent such as alkyl, amino, alkoxy, hydroxy, aryl, cyano, carboxy, alkoxycarbonyl, monoalkylamino, alkyloxy, cyanoalkyl, cycloalkyl, alkylthio, alkylsulfinyl, alkylsulfonyl, arylthio, carboxyalkyl, alkoxycarbonylalkyl, haloalkyl, acylamino, dialkylamino, cyclicamino groups, halogen atom and nitro.

"Substituted aryl group" means an aryl group wherein at least one methine hydrogen atom attached to an aromatic carbon is replaced with a substituent such as alkyl, amino, alkoxy, hydroxy, aryl, cyano, carboxy, alkoxycarbonyl, monoalkylamino, alkyloxy, cyanoalkyl, cycloalkyl, alkylthio, alkylsulfinyl, alkylsulfonyl, arylthio, carboxyalkyl, alkoxycarbonylalkyl, haloalkyl, acylamino, dialkylamino, cyclicamino groups, halogen atom and nitro.

"Substituted arylene group" means an arylene group wherein at least one hydrogen atom attached to an aromatic carbon is replaced with a substituent such as alkyl, amino, alkoxy, hydroxy, aryl, cyano, carboxy, alkoxycarbonyl, monoalkylamino, alkyloxy, cyanoalkyl, cycloalkyl, alkylthio, alkylsulfinyl, alkylsulfonyl, arylthio, carboxyalkyl, alkoxycarbonylalkyl, haloalkyl, acylamino, dialkylamino, cyclicamino groups, halogen atom and nitro.

"Substituted heteroaryl group" or "substituted heterocyclyl group" means a heteroaryl or heterocyclyl group wherein at least one hydrogen atom attached to a ring thereof is replaced with a substituent such as alkyl, amino, alkoxy, hydroxy, aryl, cyano, carboxy, alkoxycarbonyl, monoalkylamino, alkyloxy, cyanoalkyl, cycloalkyl, alkylthio, alkylsulfinyl, alkylsulfonyl, arylthio, carboxyalkyl, alkoxycarbonylalkyl, haloalkyl, acylamino, dialkylamino, cyclicamino groups, halogen atom and nitro.

"Substituted heteroarylene group" or "substituted heterocyclylene group" means a heteroarylene or heterocyclylene group wherein at least one hydrogen atom attached to a ring thereof is replaced with a substituent such as alkyl, amino, alkoxy, hydroxy, aryl, cyano, carboxy, alkoxycarbonyl, monoalkylamino, alkyloxy, cyanoalkyl, cycloalkyl, alkylthio, alkylsulfinyl, alkylsulfonyl, arylthio, carboxyalkyl, alkoxycarbonylalkyl, haloalkyl, acylamino, dialkylamino, cyclicamino groups, halogen atom and nitro.

"Substituted arylalkyl group" means an arylalkyl having one or more substituents such as alkyl, amino, alkoxy, hydroxy, aryl, cyano, carboxy, alkoxycarbonyl, monoalkylamino, alkyloxy, cyanoalkyl, cycloalkyl, alkylthio, alkylsulfinyl, alkylsulfonyl, arylthio, carboxyalkyl, haloalkyl, alkoxycarbonylalkyl, acylamino, dialkylamino, cyclicamino groups, halogen atom and nitro.

"Halogen" is intended to include for example, F, Cl, Br and I.

The term "prodrug" refers to a chemical compound that is converted to an active agent by metabolic processes in vivo. [See, e.g., N. Boder and J. J. Kaminski, *Ann. Rep. Med Chem.* 22:303 (1987) and H. Bundgarrd, *Adv. Drug Delivery Rev.*, 3:39(1989)]. The use of prodrug precursors of compounds of the present invention in any of the methods described herein is contemplated and is intended to be within the scope of the invention.

Terminology related to "protected," "protecting" and/or "deprotecting" functionalities is used throughout this application. Such terminology is well understood by persons of skill in the art and is used in the context of processes which involve sequential treatment with a series of reagents. In this context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups" for the functionalities involved.

In the case of the present invention, the functionalities that must be protected are amines. Suitable groups for that purpose are discussed in standard textbooks in the field of chemistry, such as *Protective Groups in Organic Synthesis* by T. W. Greene [John Wiley & Sons, New York, 1991], which is incorporated herein by reference. Particular attention is drawn to the chapter entitled "Protection for the Amino Group" (pages 309–405). Preferred protecting groups include BOC and Fmoc. Exemplary methods for protecting and deprotecting with these groups are found in Greene and Wuts on pages 318 and 327.

The materials upon which the syntheses described herein are performed are referred to as solid supports, beads, and resins. These terms are intended to include: (a) beads, pellets, disks, fibers, gels, or particles such as cellulose beads, pore-glass beads, silica gels, polystyrene beads optionally cross-linked with divinylbenzene and optionally grafted with polyethylene glycol, poly-acrylamide beads, latex beads, dimethylacrylamide beads optionally cross-linked with N,N'-bis-acryloyl ethylene diamine, glass particles coated with hydrophobic polymer, etc., i.e., material having a rigid or semi-rigid surface; and (b) soluble supports such as polyethylene glycol or low molecular weight, non-cross-linked polystyrene. The solid supports may, and usually do, have functional groups such as amino, hydroxy, carboxy, or halo groups; where amino groups are the most common.

Tentagel™ NH$_2$ (Rapp Polymere, Tubingen, Germany) is a preferred amine functionalized polyethylene glycol-grafted polystyrene resin. Tentagel™—S-PBB resin has a parahydroxy benzyl linker which can be cleaved by the use of 90% trifluoroacetic acid in dichloromethane. Techniques for functionalizing the surface of solid phases are well known in the art. Attachment of lysine to the amino groups on a bead (to increase the number of available sites) and subsequent attachment of linkers as well as further steps in a typical combinatorial synthesis are described, for example, in PCT application WO95/30642, the disclosure of which is incorporated herein by reference. In the synthesis described in WO95/30642, the linker is a photolytically cleavable linker, but the general principles of the use of a linker are well illustrated.

Optical Isomers—Diastereomers—Geometric Isomers

Some of the compounds described herein contain one or more asymmetric centers and may thus give rise to enantiomers, diastereomers, and other stereoisometric forms which may be defined in terms of absolute stereochemistry as (R)- or (S)-, or as (D)- or (L)- for amino acids. The present invention is meant to include all such possible diastereomers as well as their racemic and optically pure forms. Optically active (R)- and (S)-, or (D)- and (L)- isomers may be prepared using chiral synthons or chiral reagents, or resolved using conventional techniques. When the compounds described herein contain olefinic double bonds or other centers of geometric asymmetry, and unless specified otherwise, it is intended to include both (E)- and (Z)-geometric isomers. Likewise, all tautomeric forms are intended to be included. The configuration of any carbon-carbon double bond appearing herein is selected for convenience only and is not intended to designate a particular configuration; thus a carbon-carbon double bond depicted arbitrarily herein as trans may be cis, trans, or a mixture of the two in any proportion.

In view of the above definitions, other chemical terms used throughout this application can be easily understood by those of skill in the art. Terms may be used alone or in any combination thereof. The preferred and more preferred chain lengths of the radicals apply to all such combinations.

Utility

The compounds of the present invention have demonstrated utility as selective inhibitors at VLA-4 receptors. The inhibitory concentration (IC$_{50}$) and the VLA-4 selectivity of test compounds for an α4β1 receptor using in vitro assays are determined in direct binding assays and competitive assays with other integrin receptors such as β2 (LFA-1 and Mac-1), β3 (GPIIb/IIIa and αvβ3) and β1 ((α4β7). Compounds of the present invention have K$_i$ values <1 μM. Preferred compounds of the invention are those having K$_i$ values <300 nM, more preferably <100 nM, even more preferably <50 nM, and most preferably, <12 nM.

Examples of preferred compounds having a K$_i$ value <50 nM are shown below. These examples are provided by way of illustration only, and are not intended to limit the invention thereto.

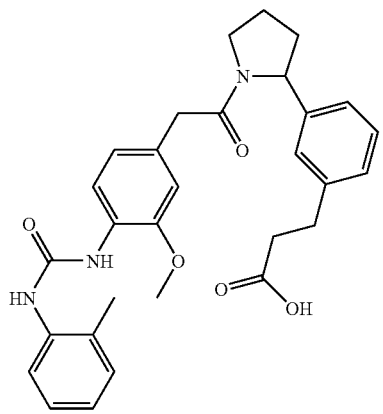

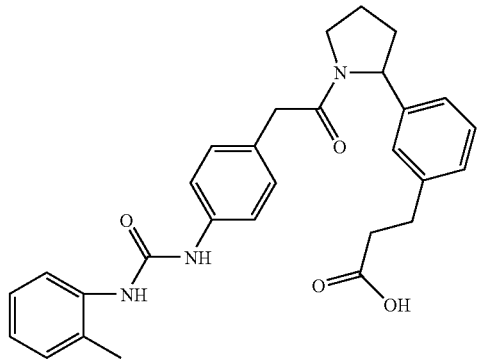

-continued
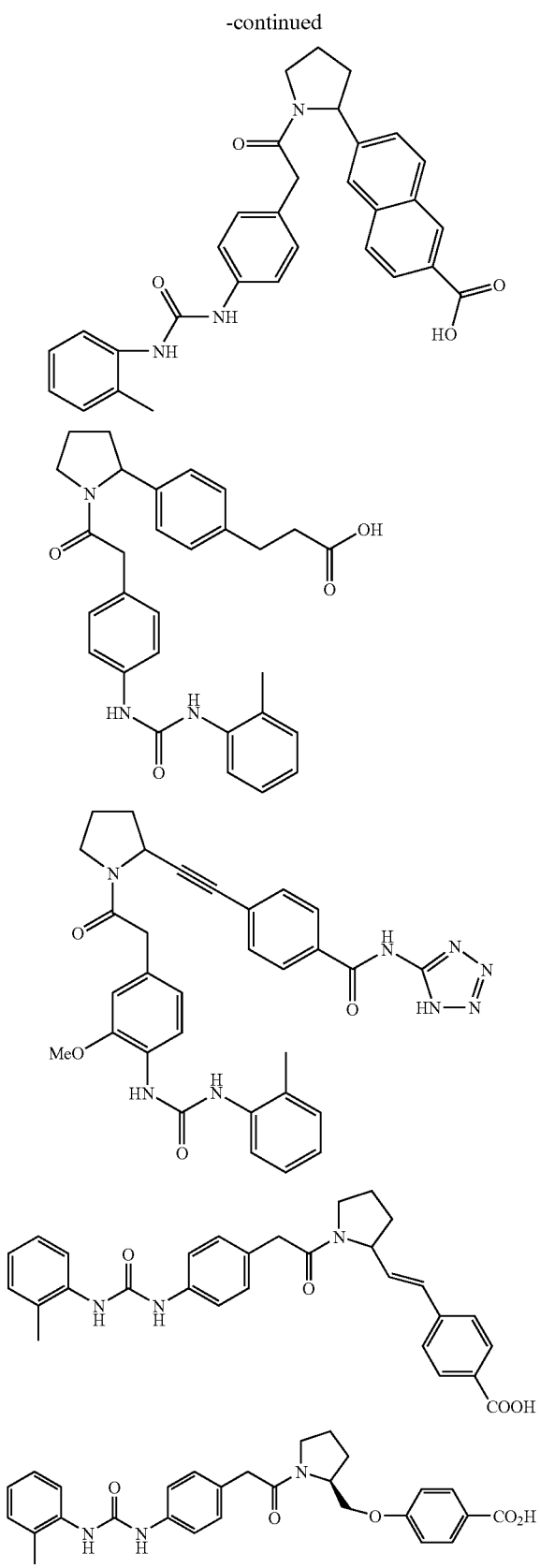
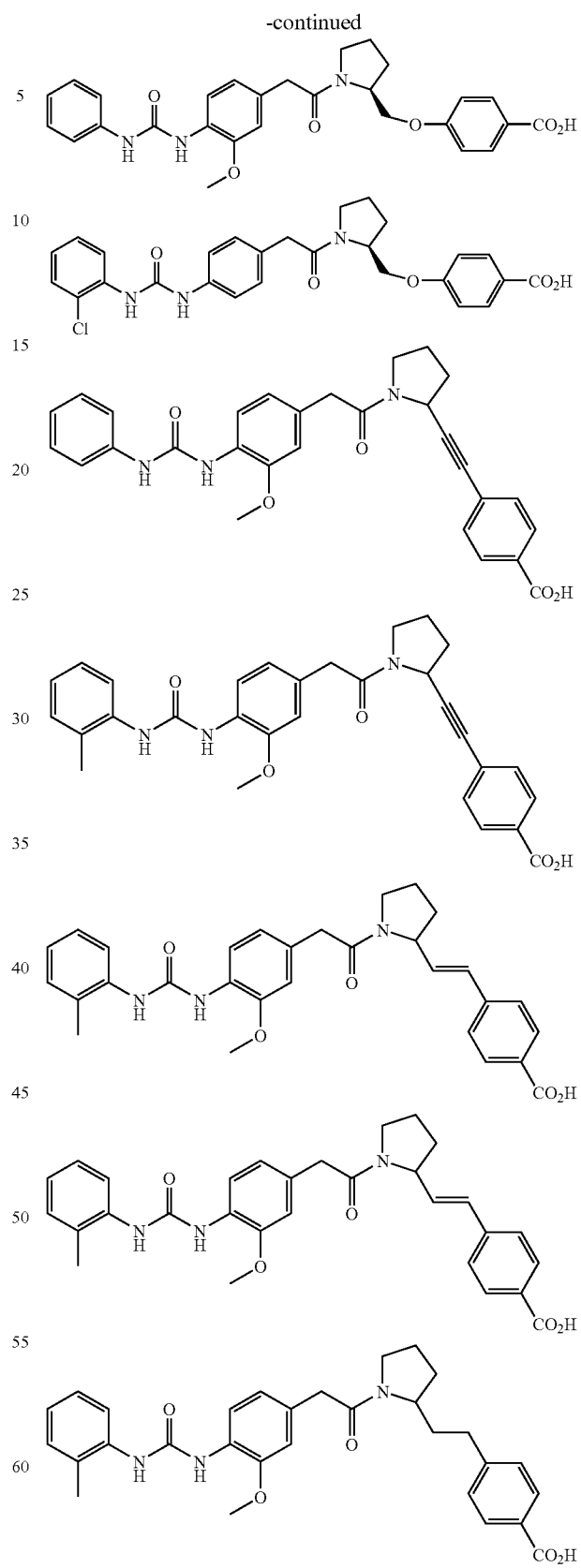

-continued
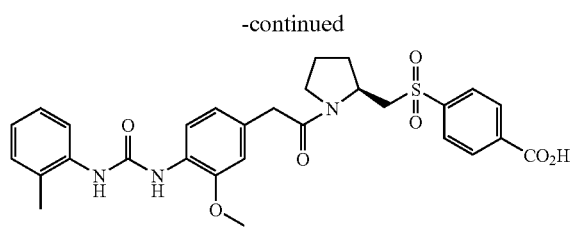
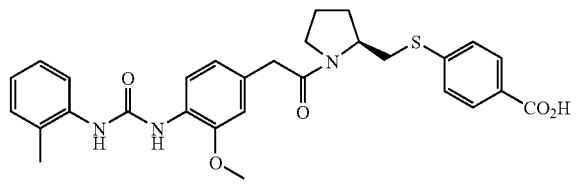
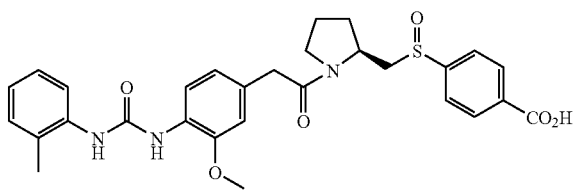
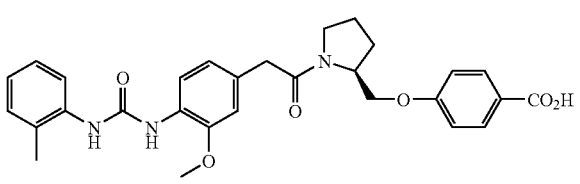
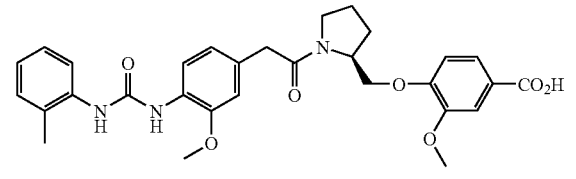
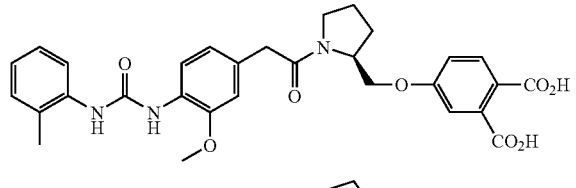

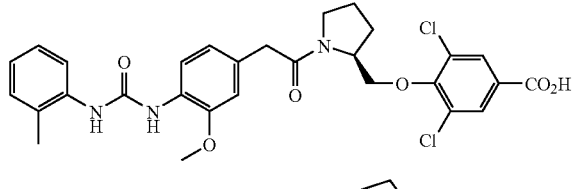
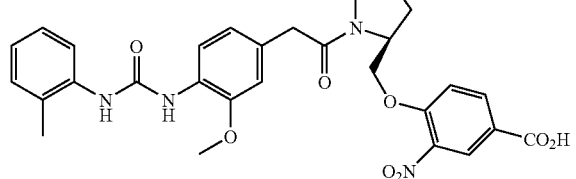
-continued
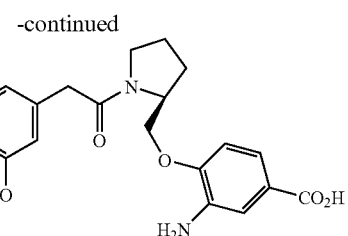
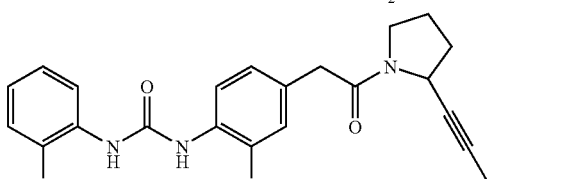
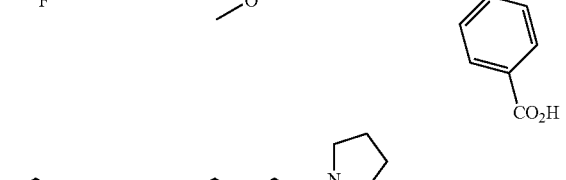
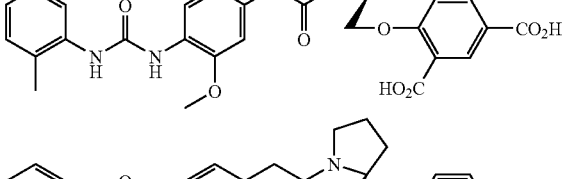
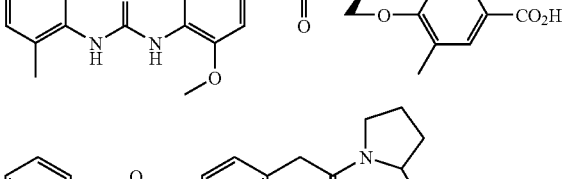
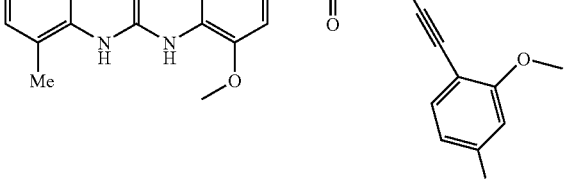
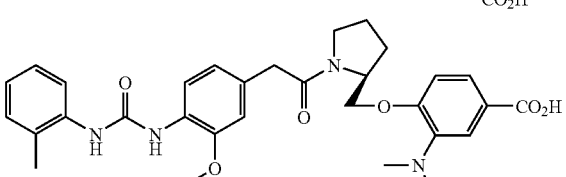
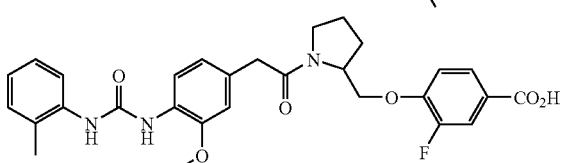
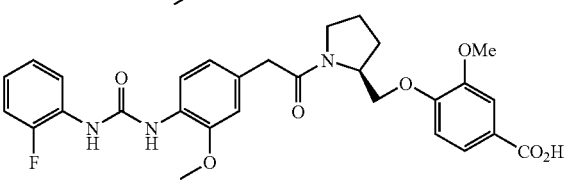

195
-continued
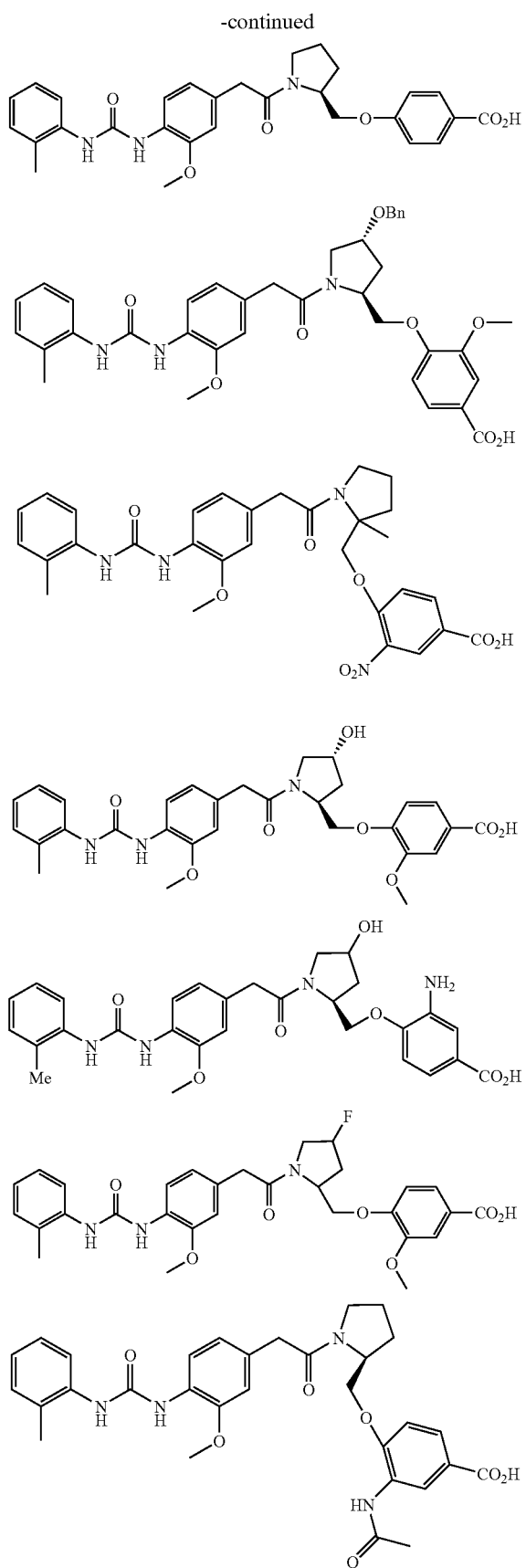
196
-continued
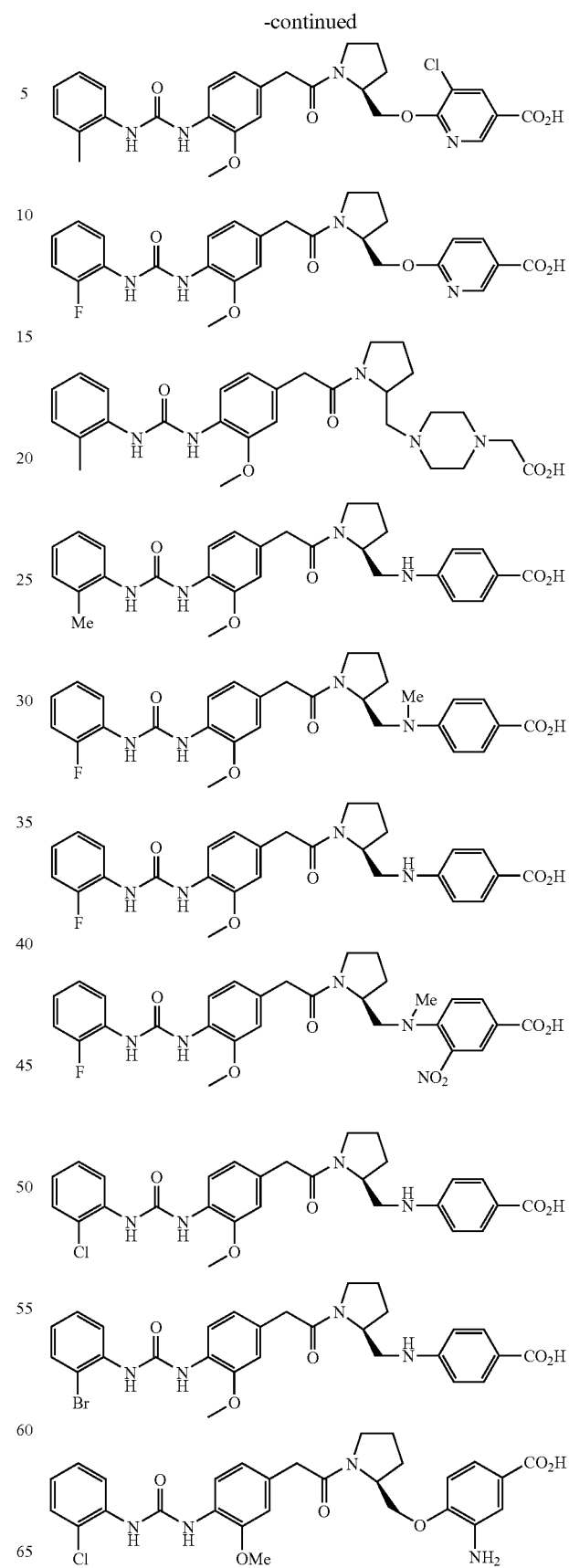

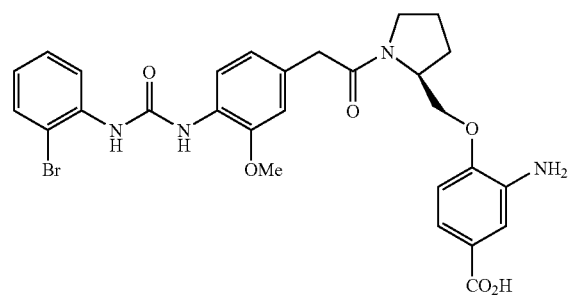
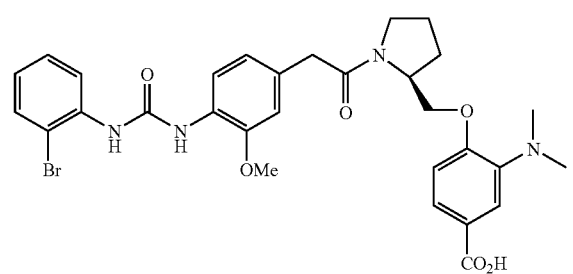
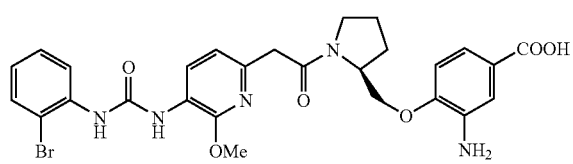
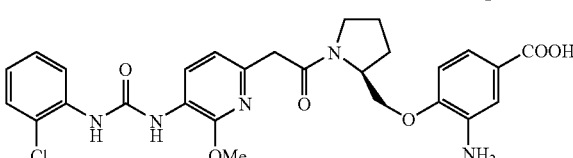
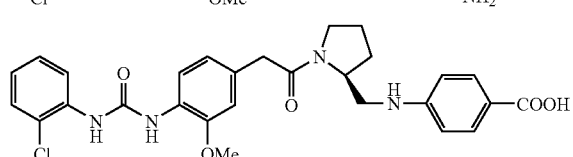
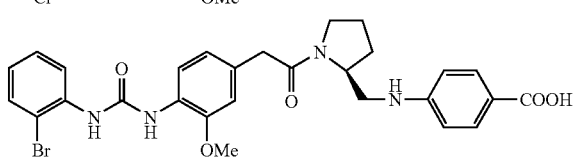
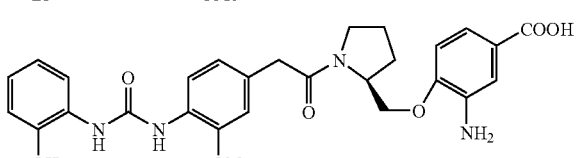
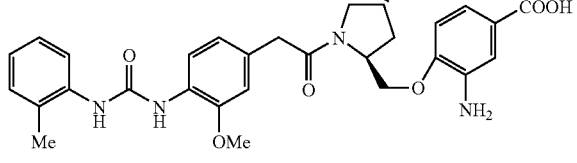
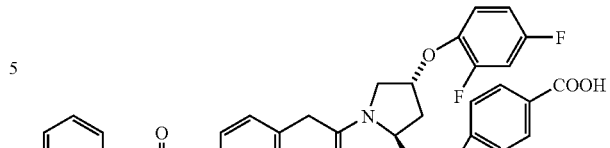
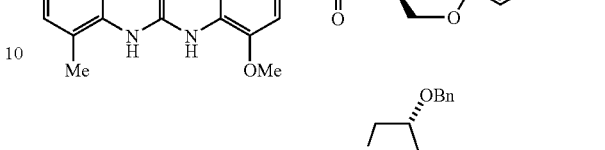
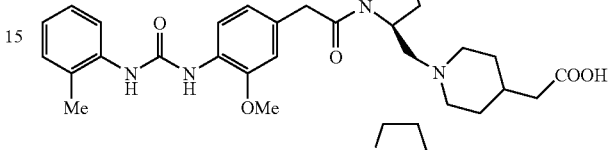
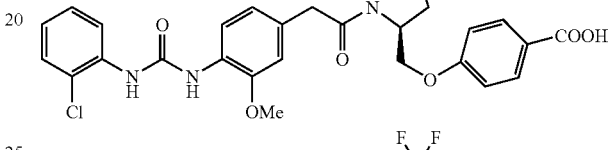
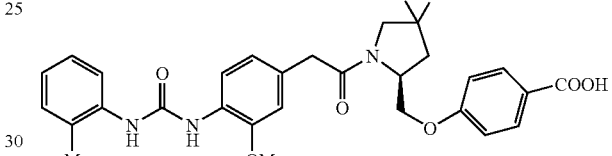
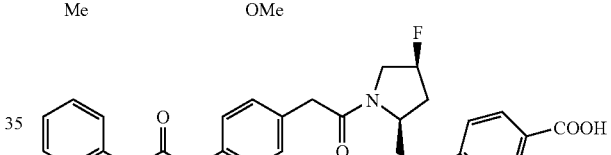
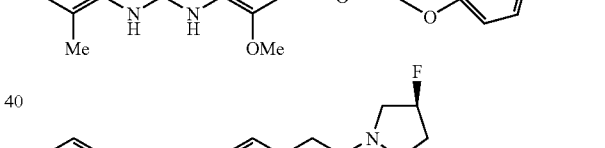
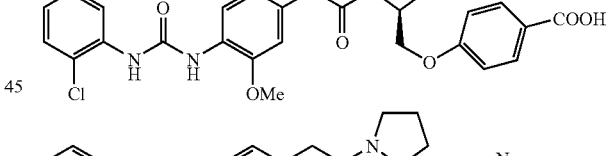
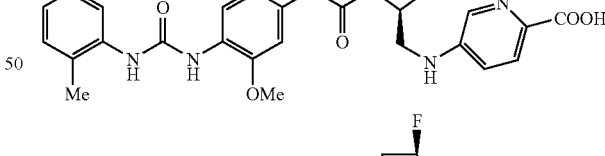
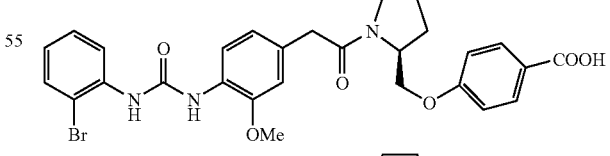
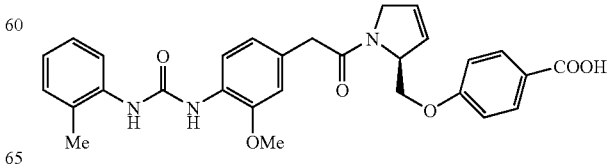

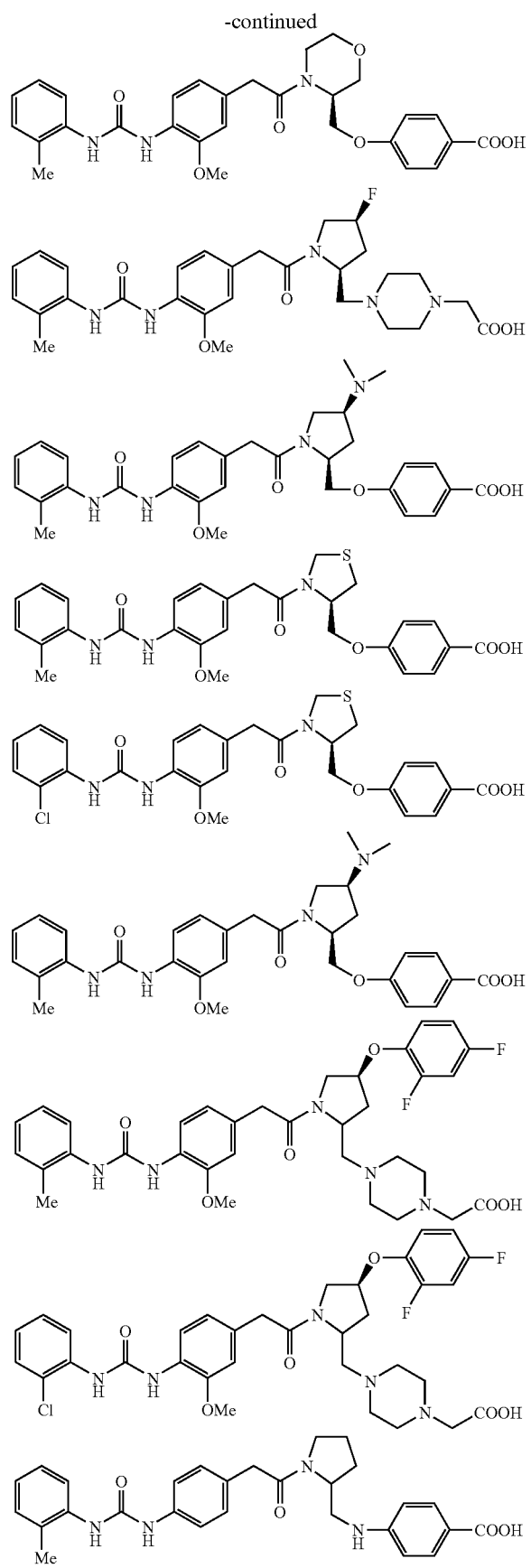

-continued
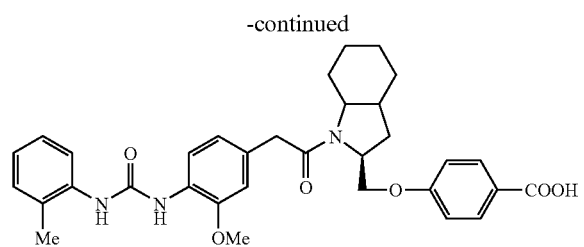
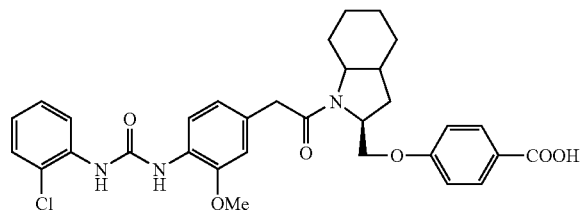
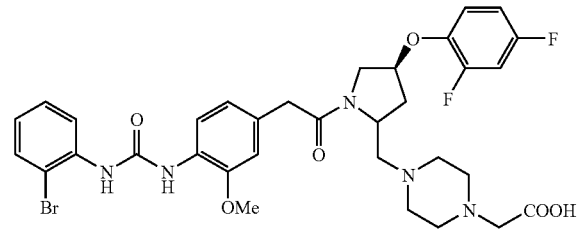
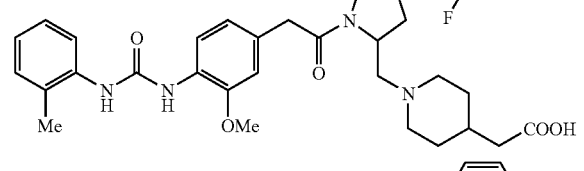
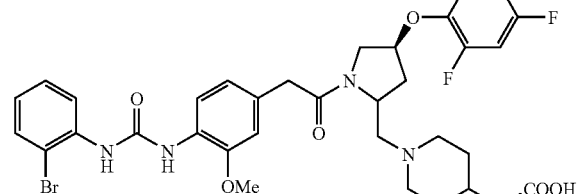
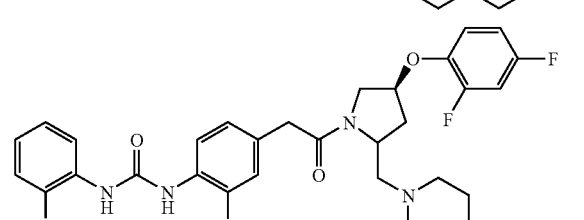
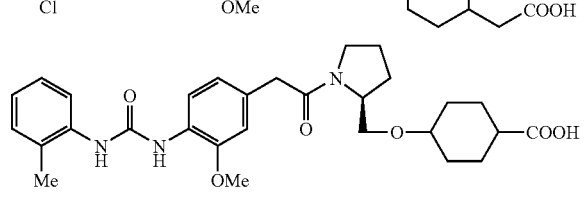
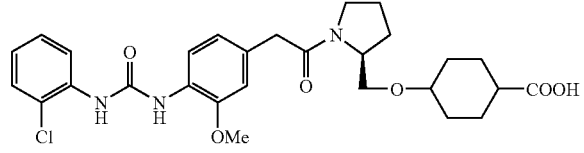
-continued
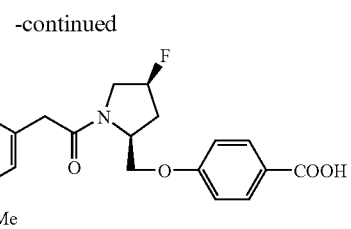
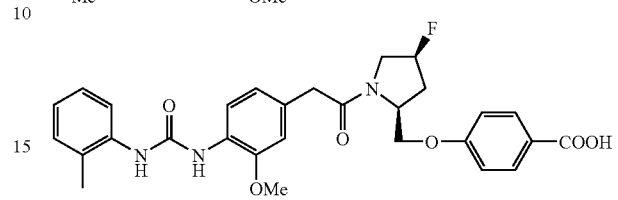
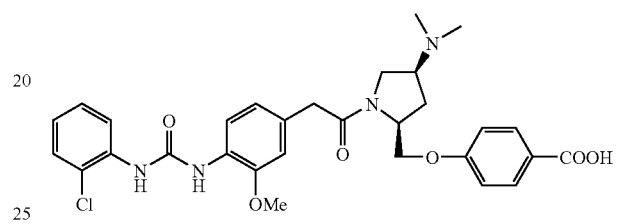
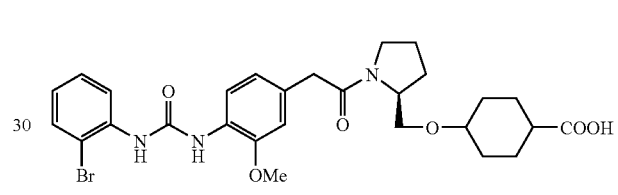
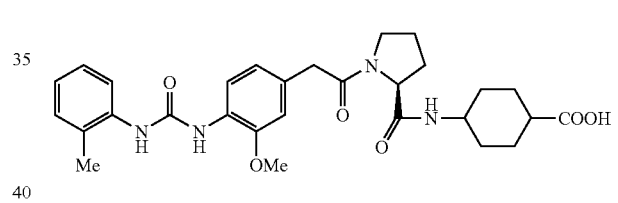
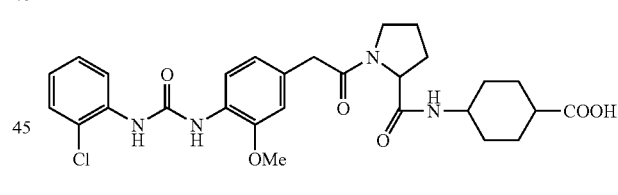
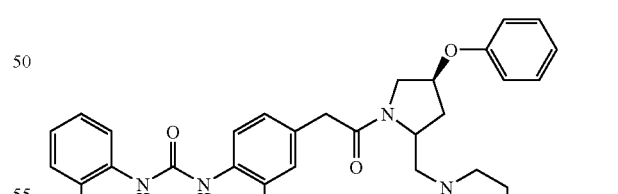
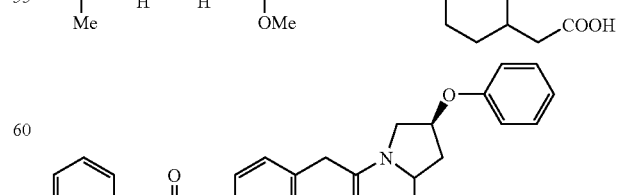
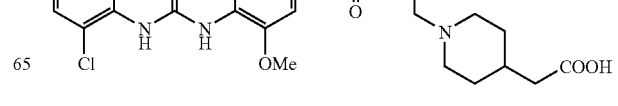

-continued
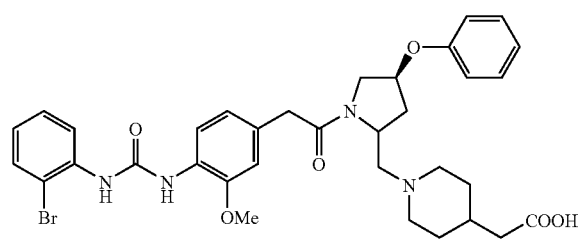
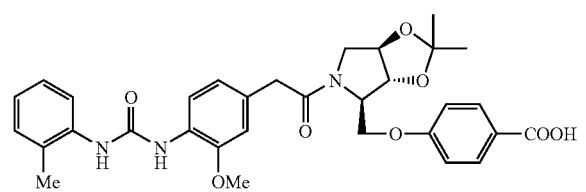
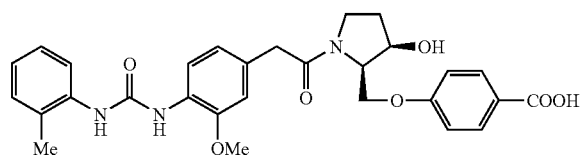
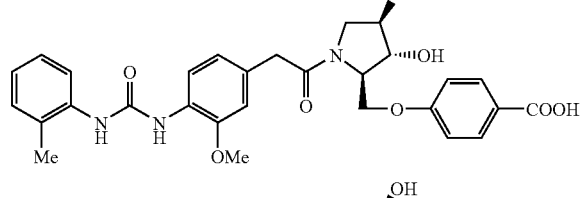
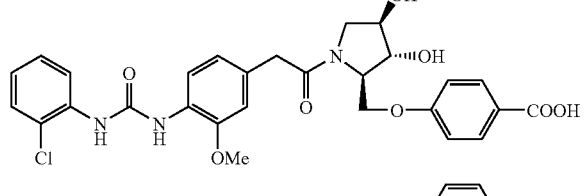
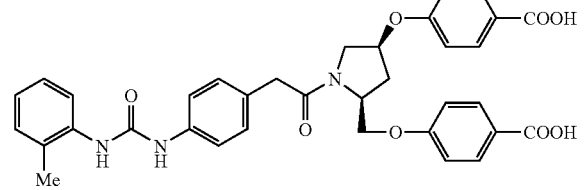
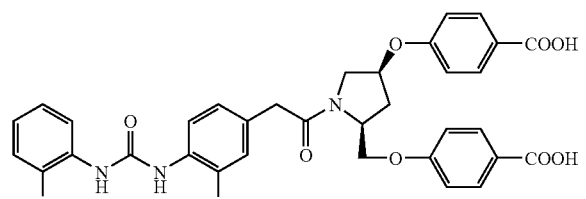
-continued
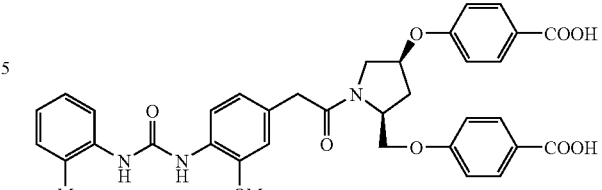
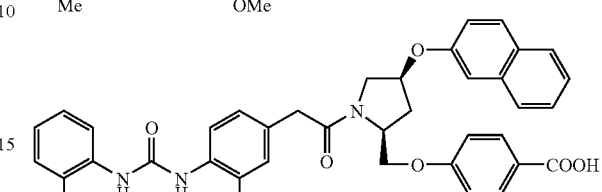
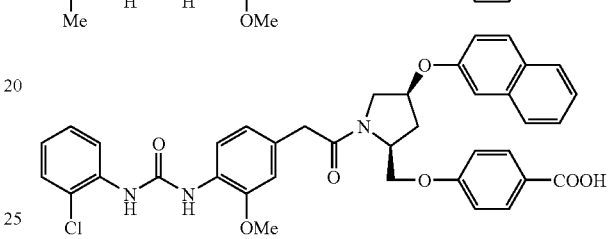
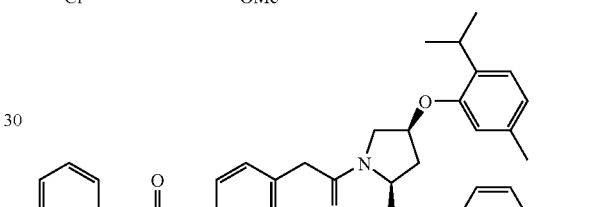
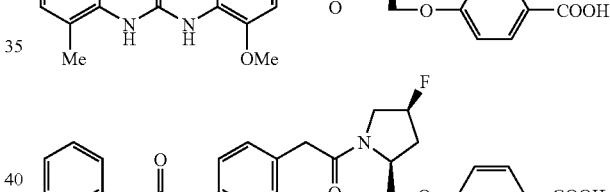
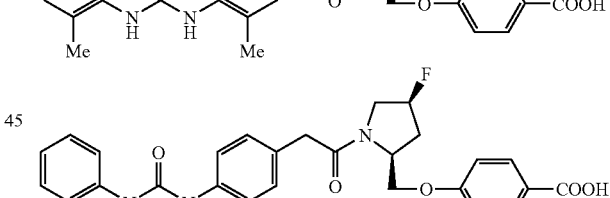
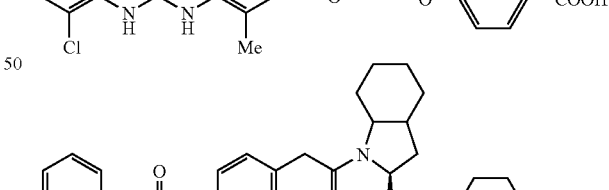

205
-continued
206
-continued
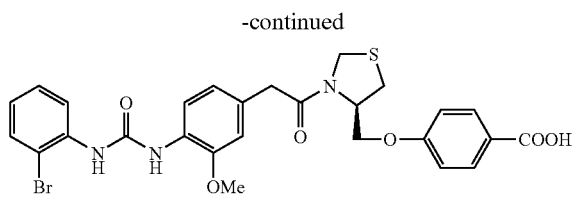
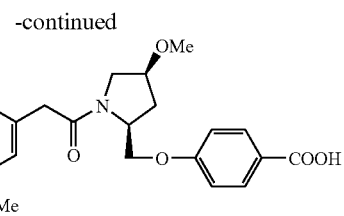

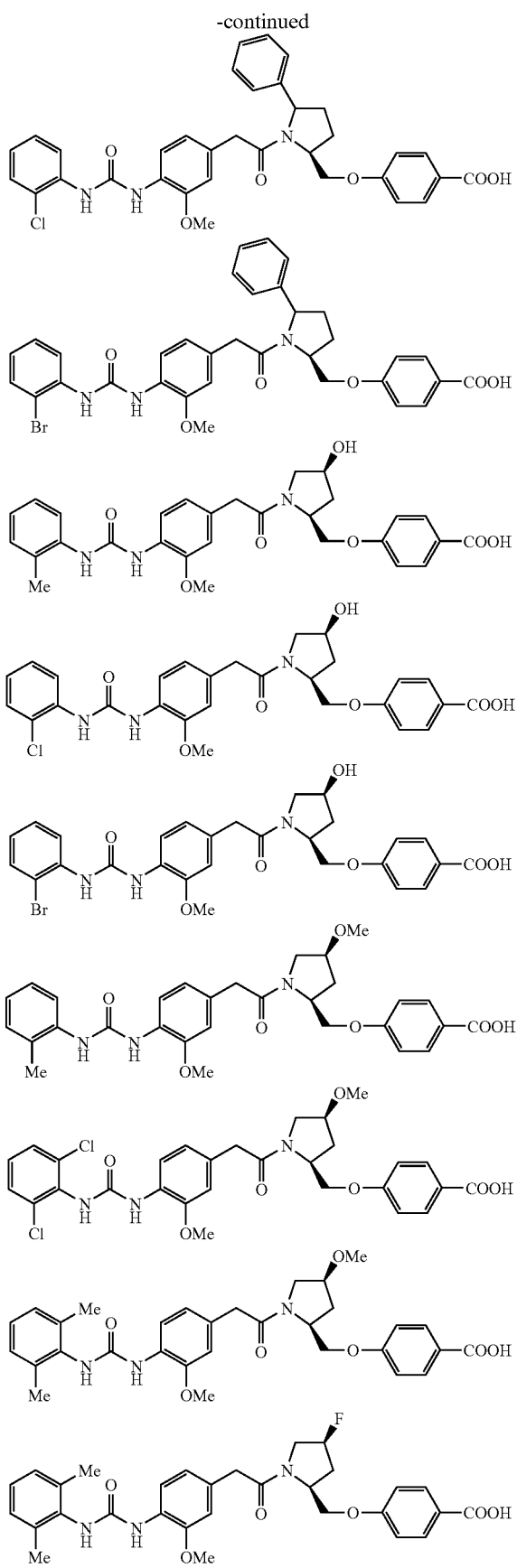
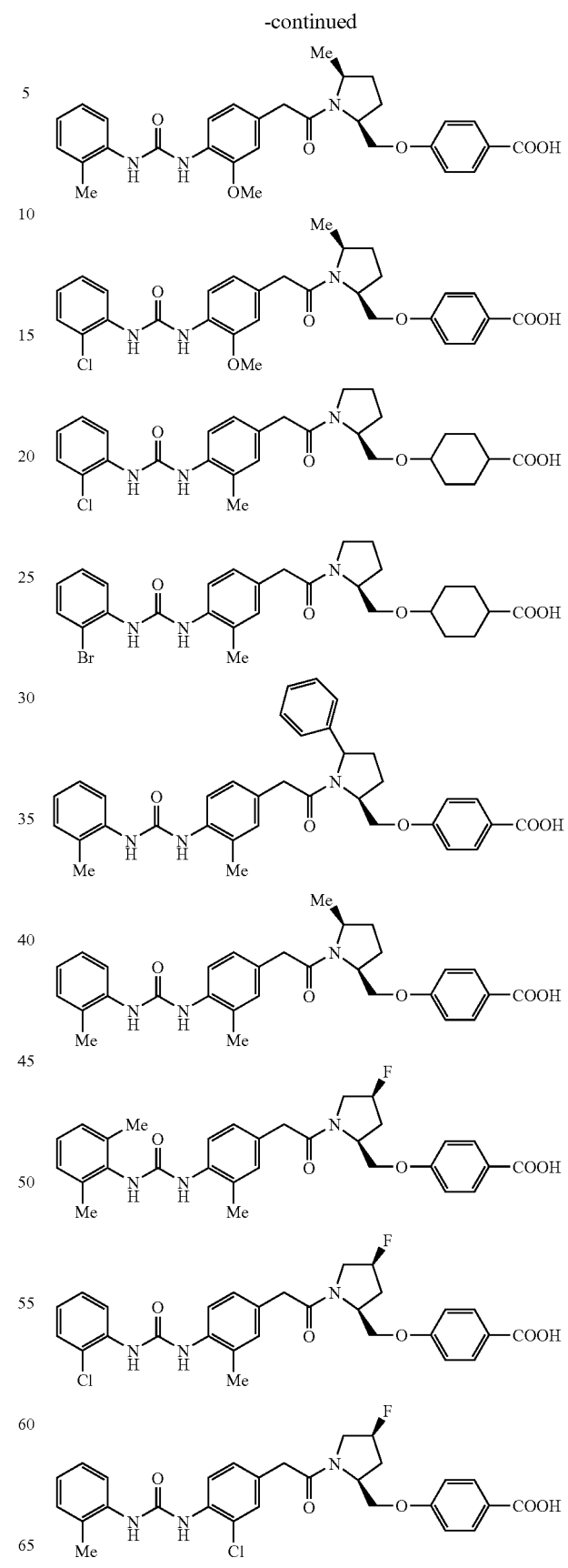

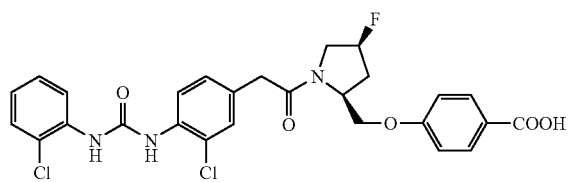
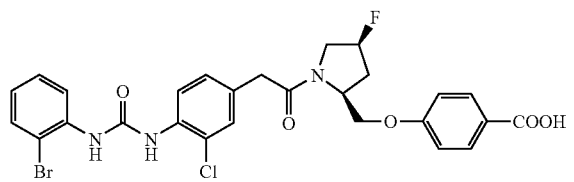
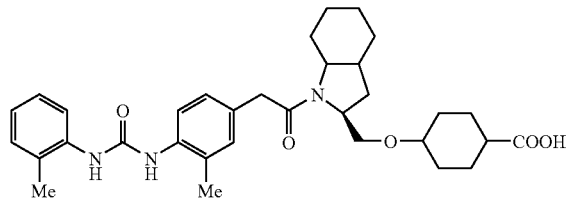
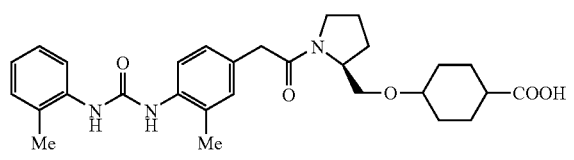
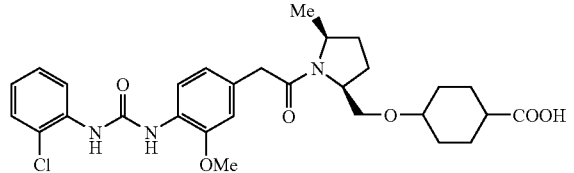
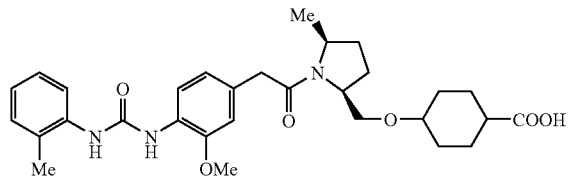
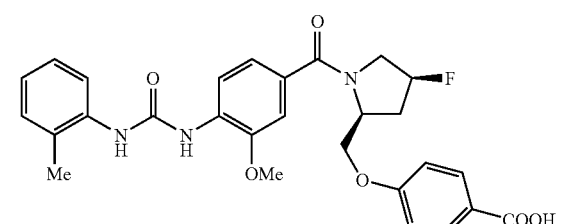
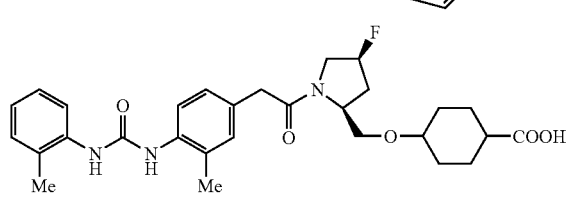
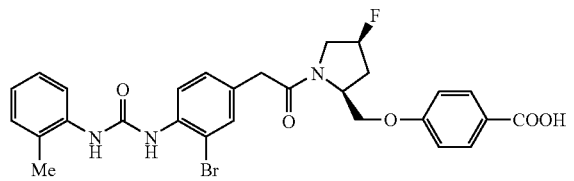
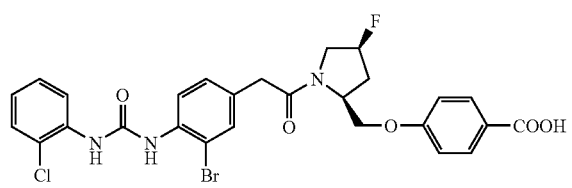
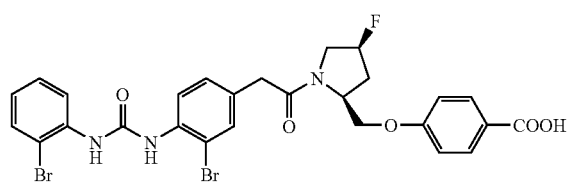
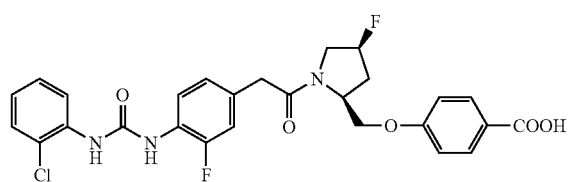
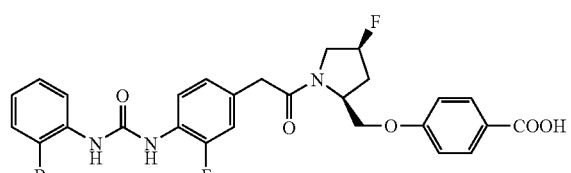
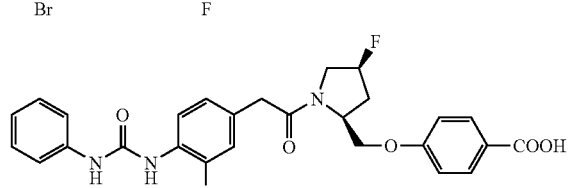
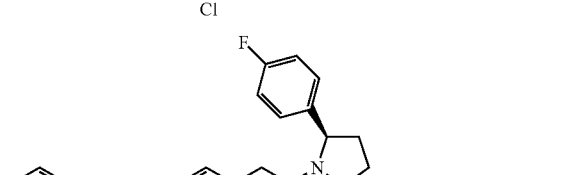
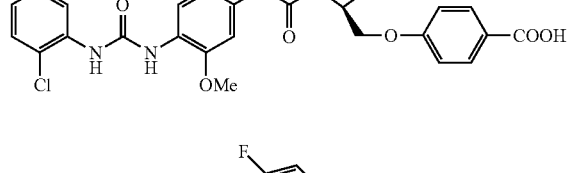
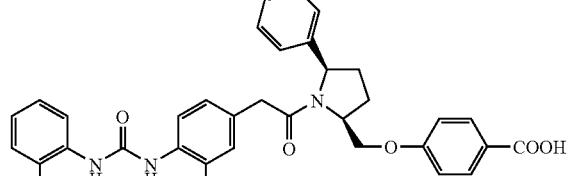
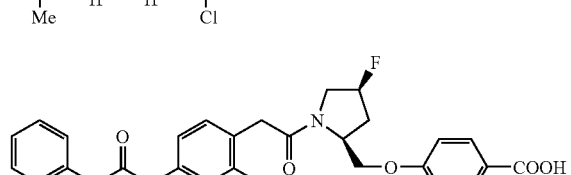
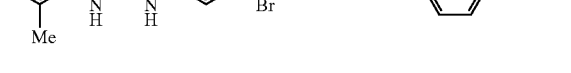

211
-continued
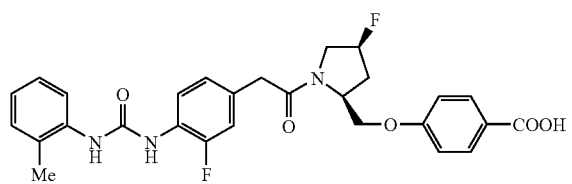
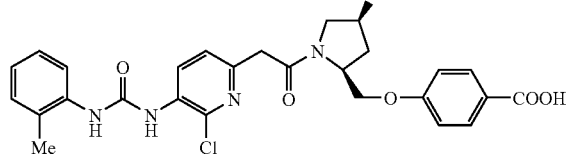
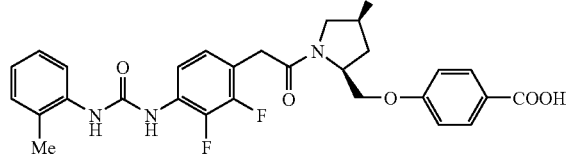
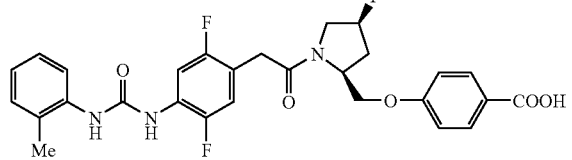
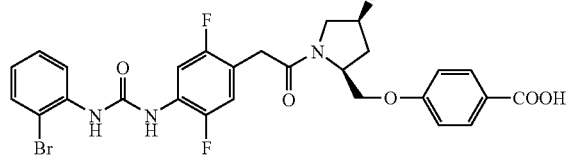
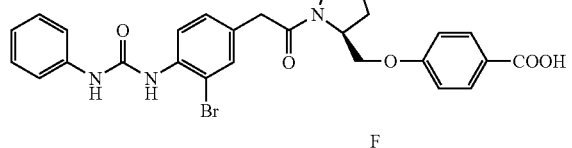
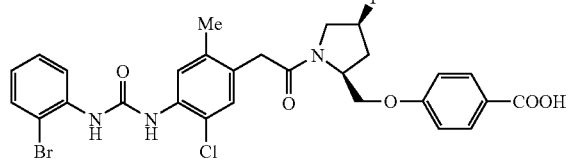
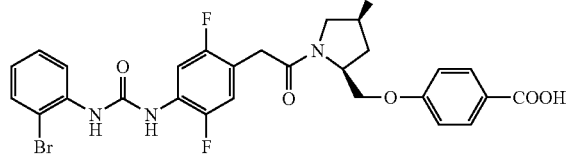
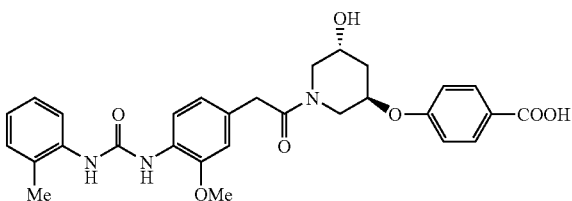
212
-continued
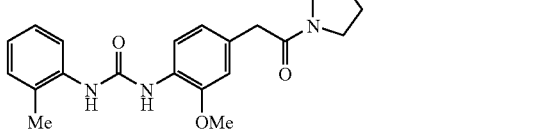
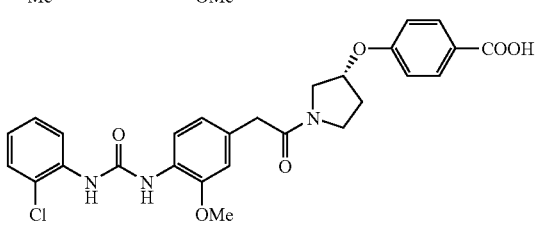
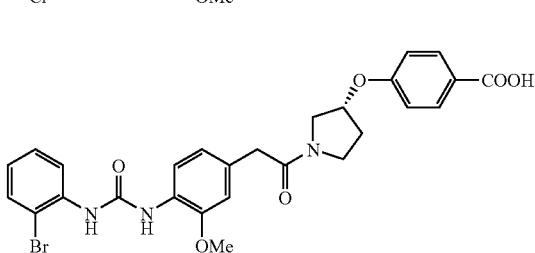
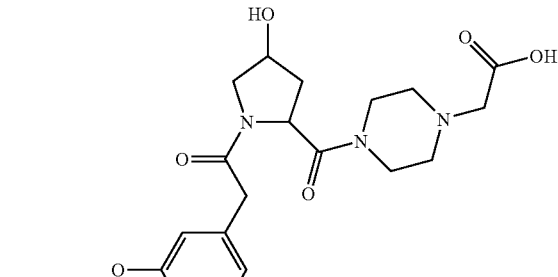
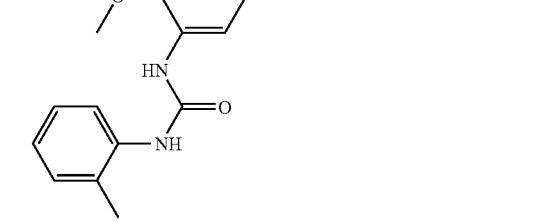
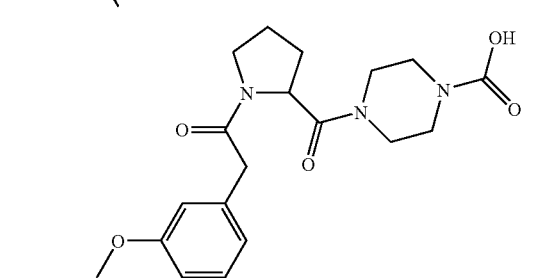
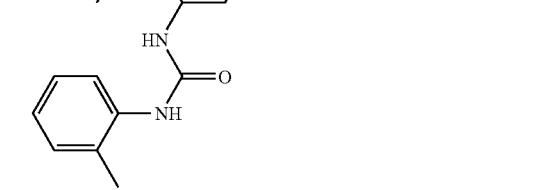

213
-continued
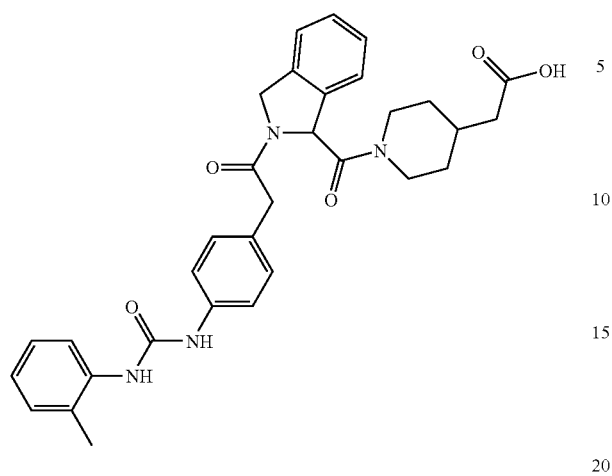
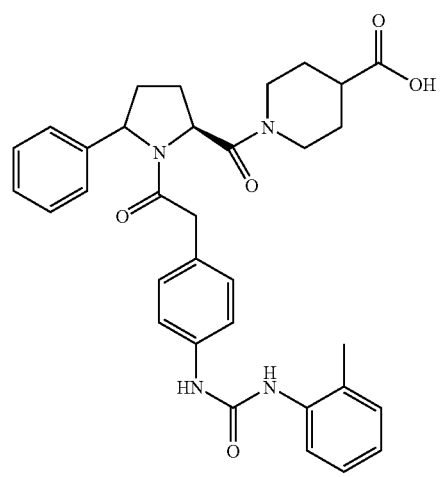
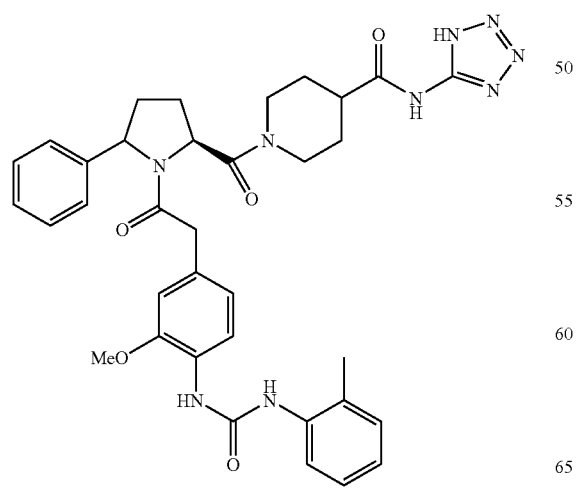
214
-continued
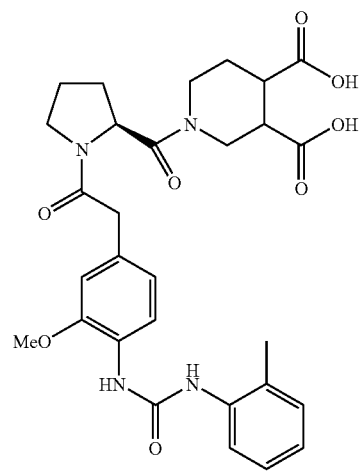
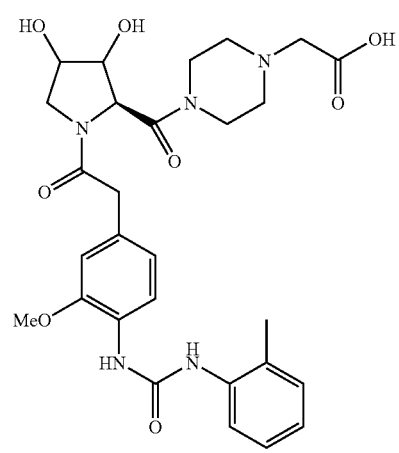
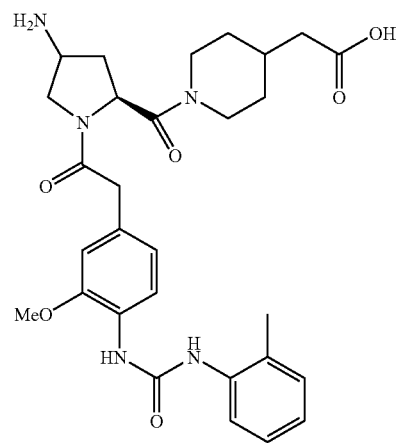

215
-continued
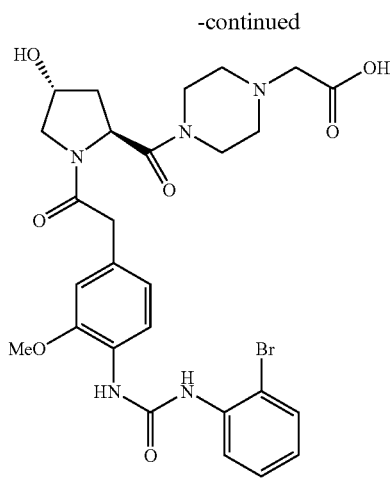
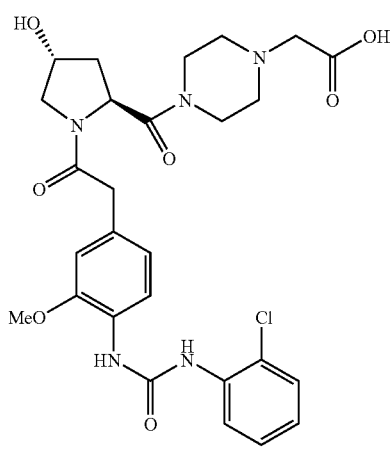
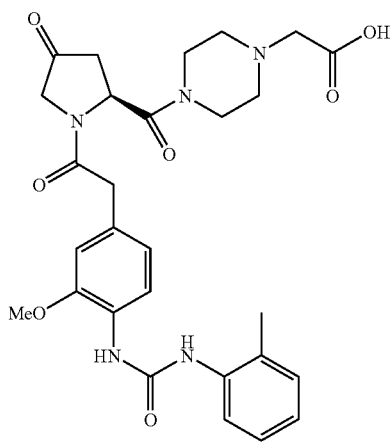
216
-continued
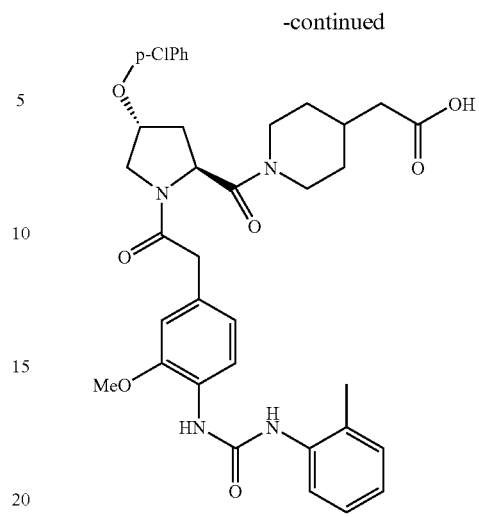
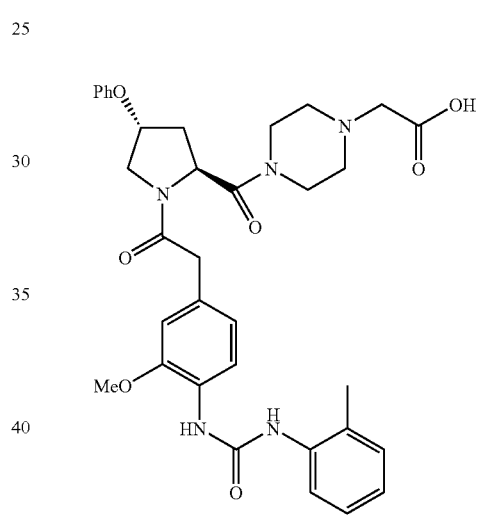
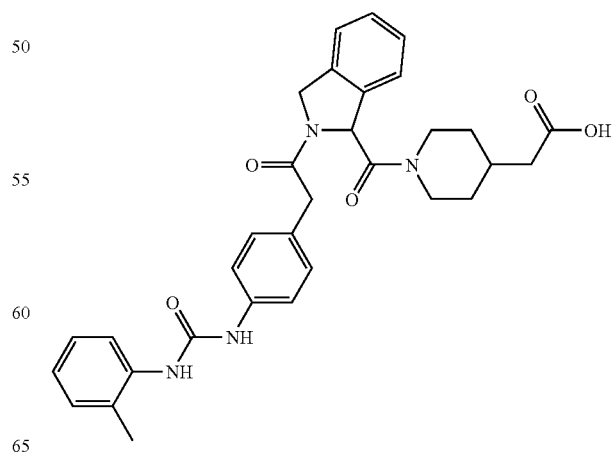

217
-continued
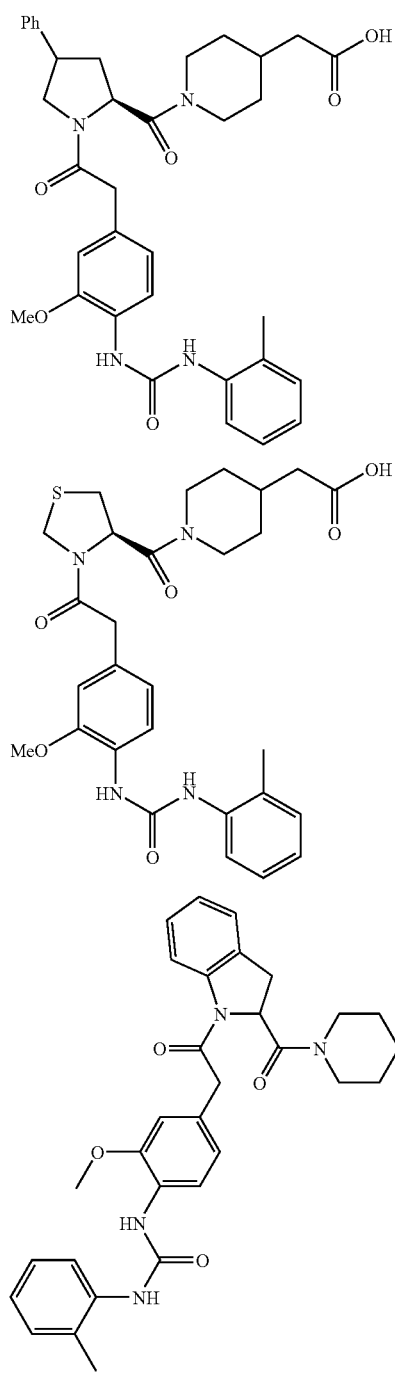
218
-continued
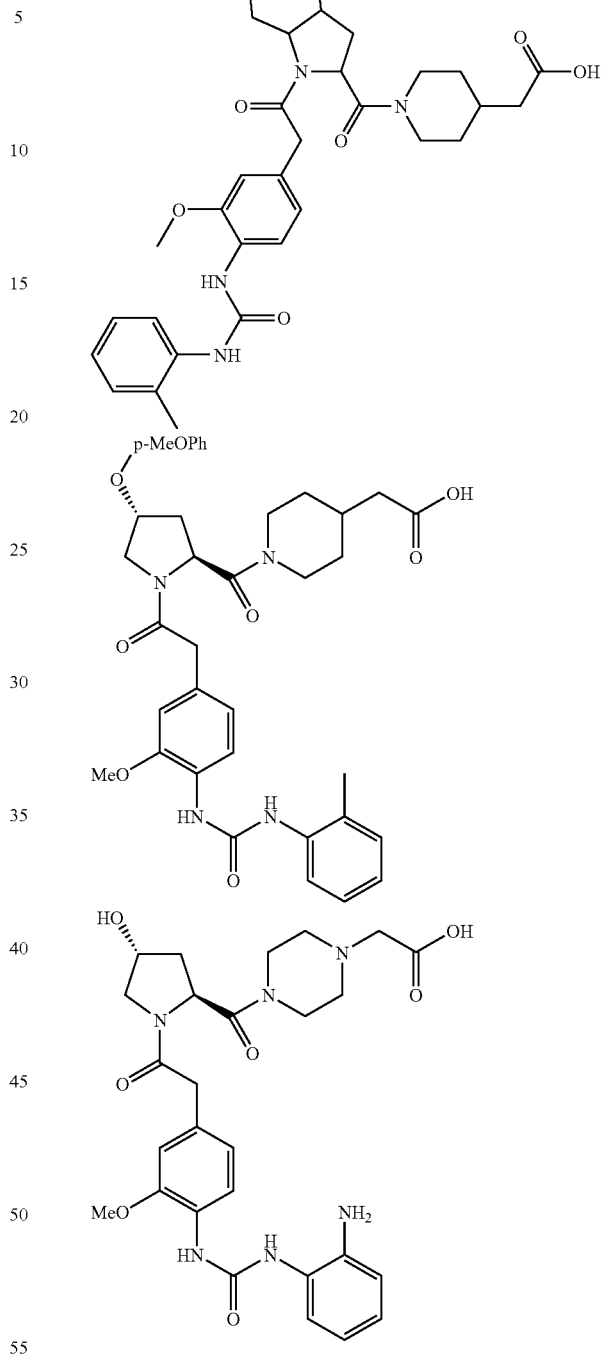

219
-continued
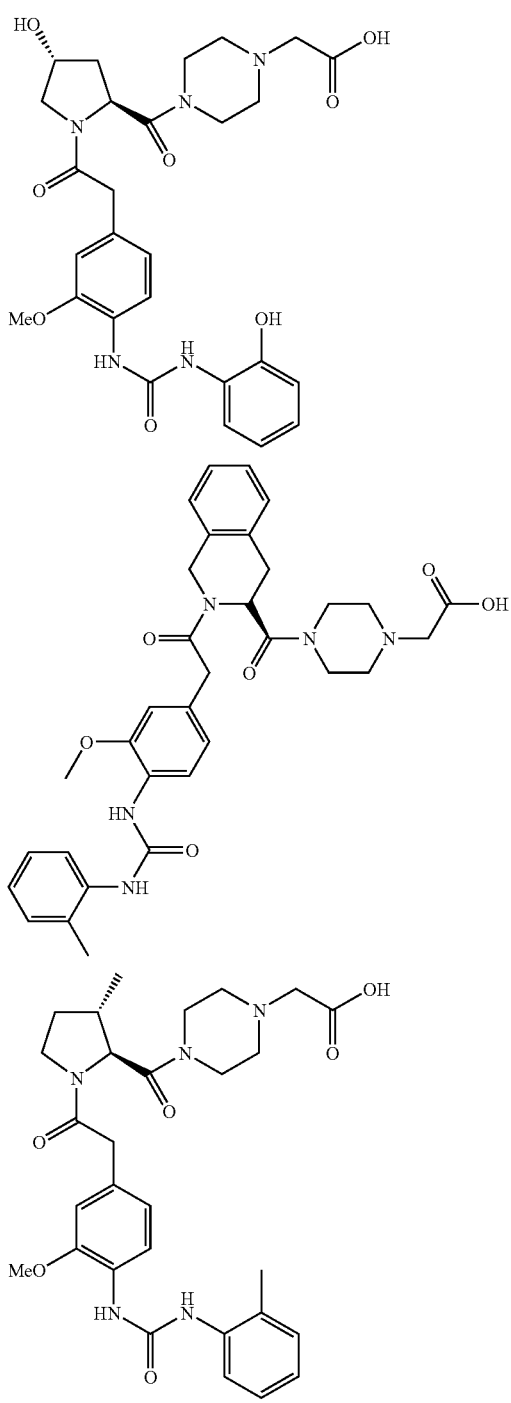
220
-continued
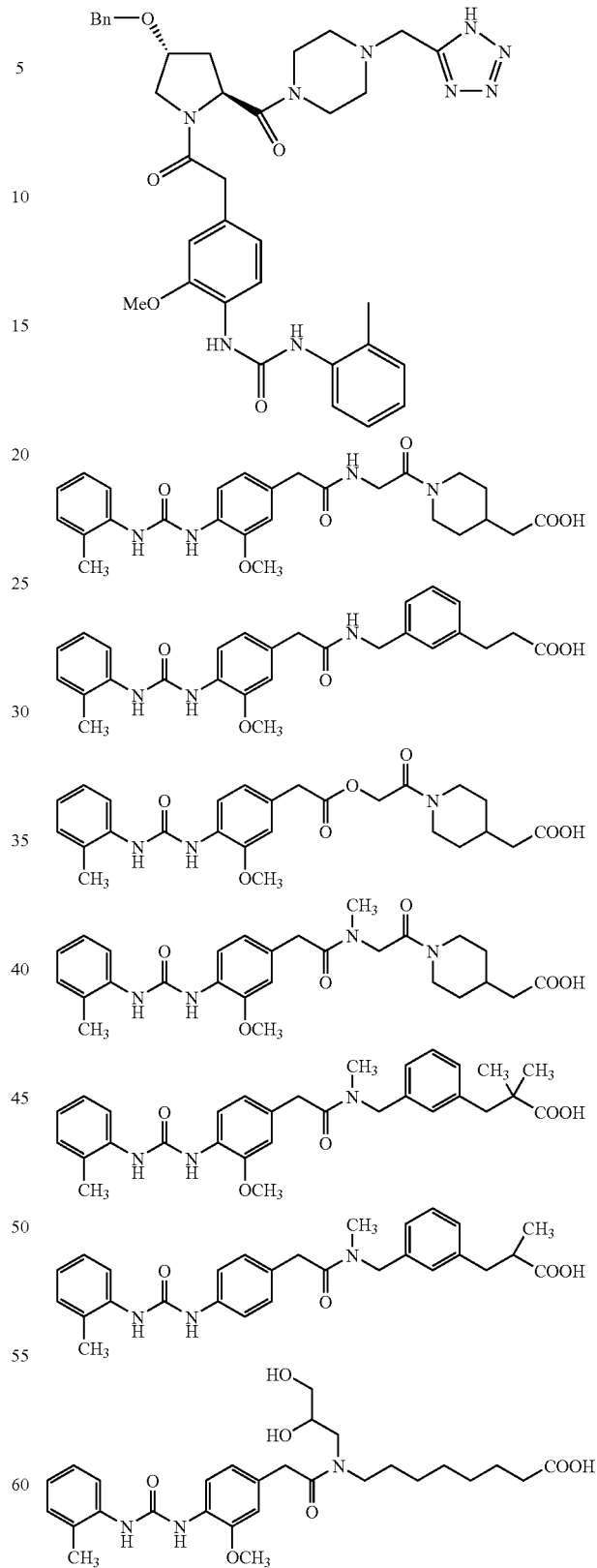

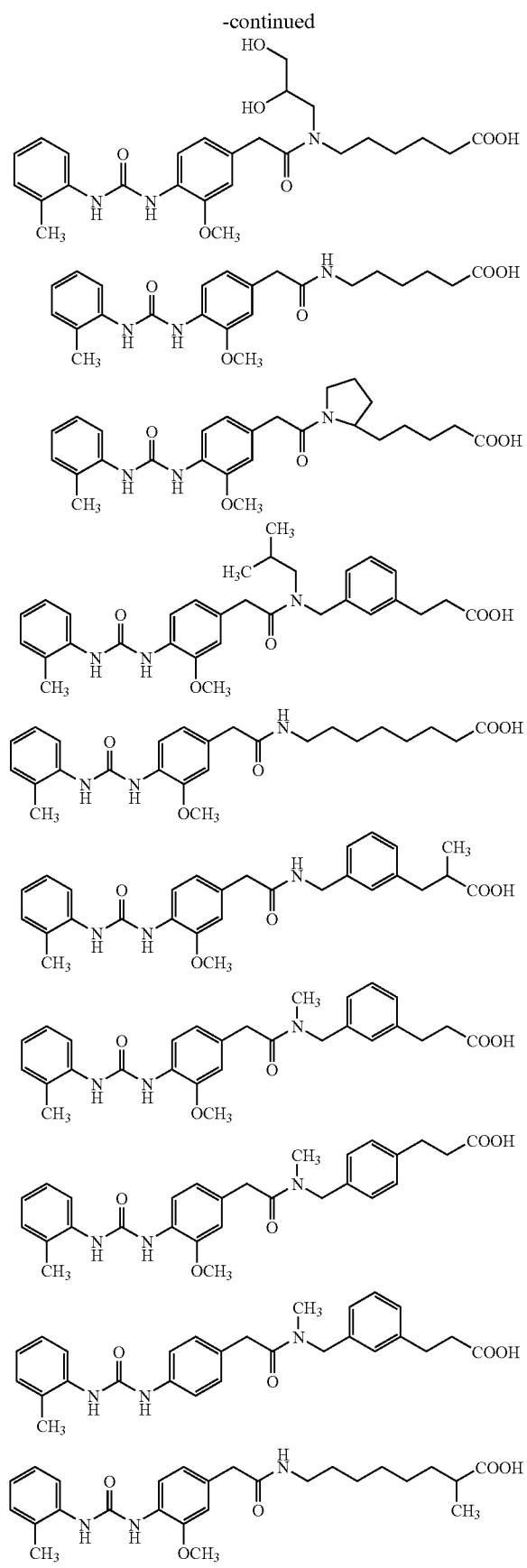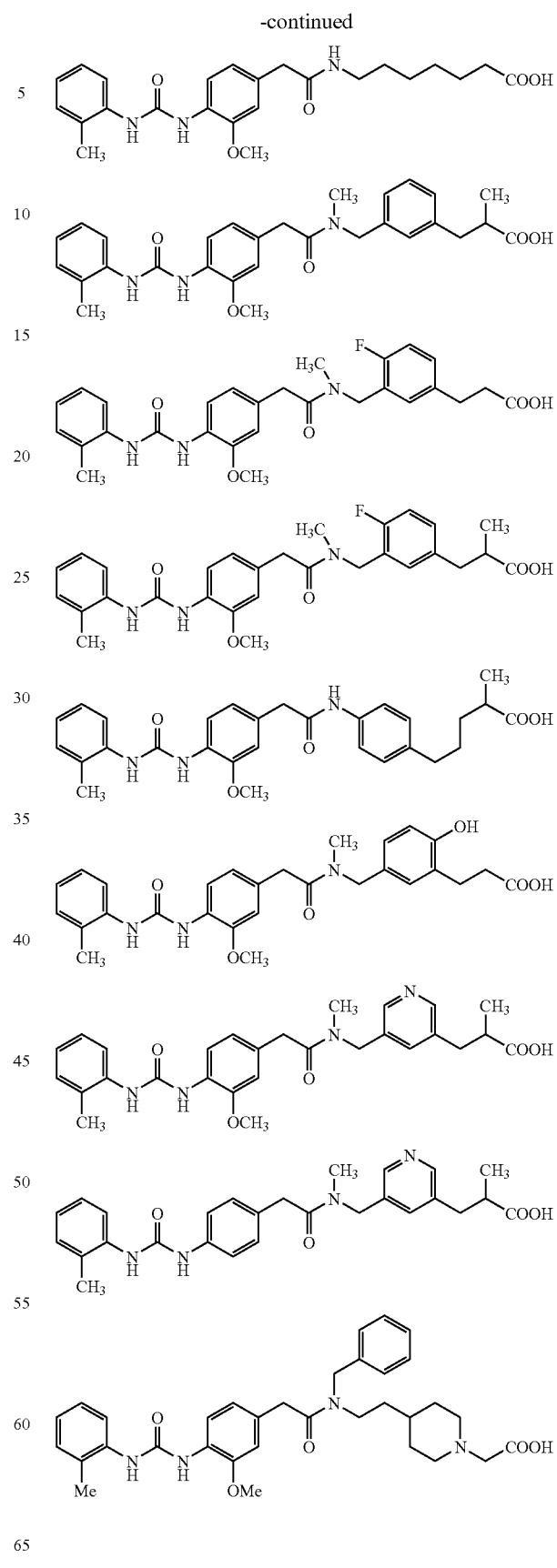

223
-continued
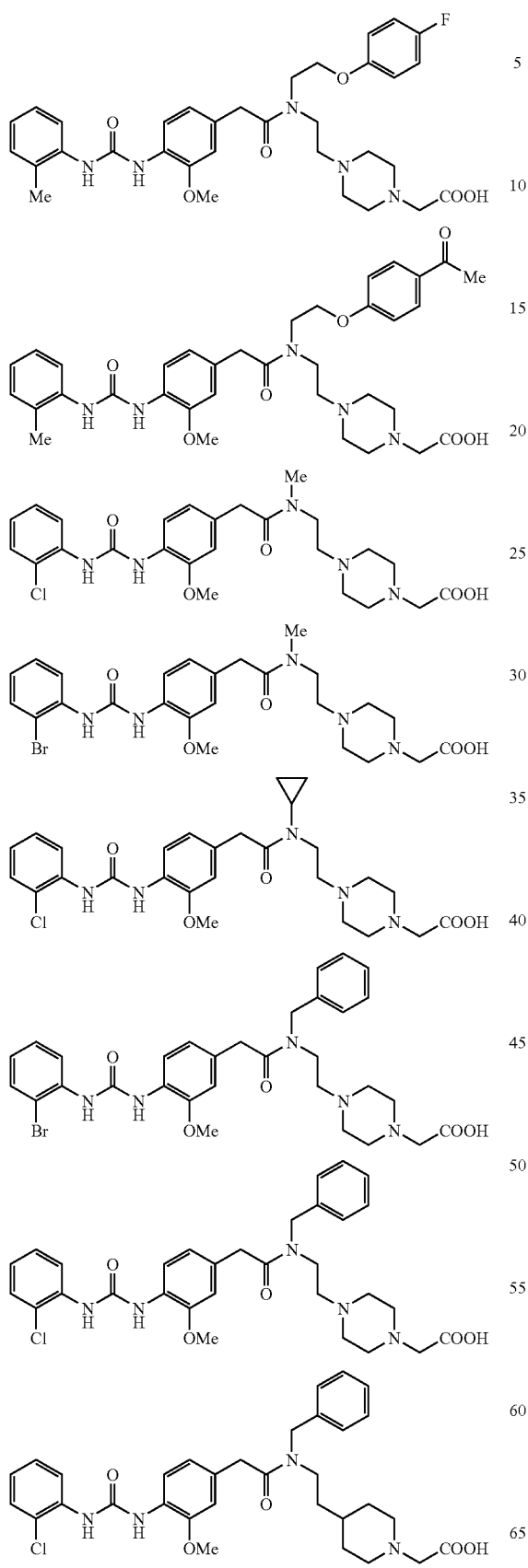
224
-continued
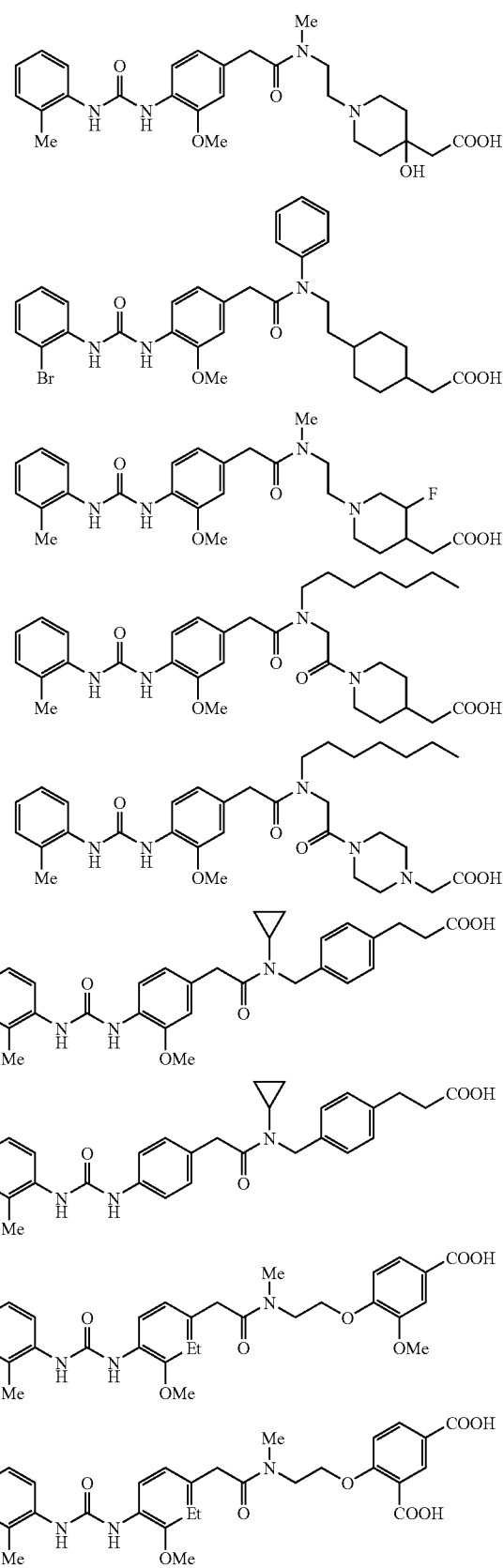

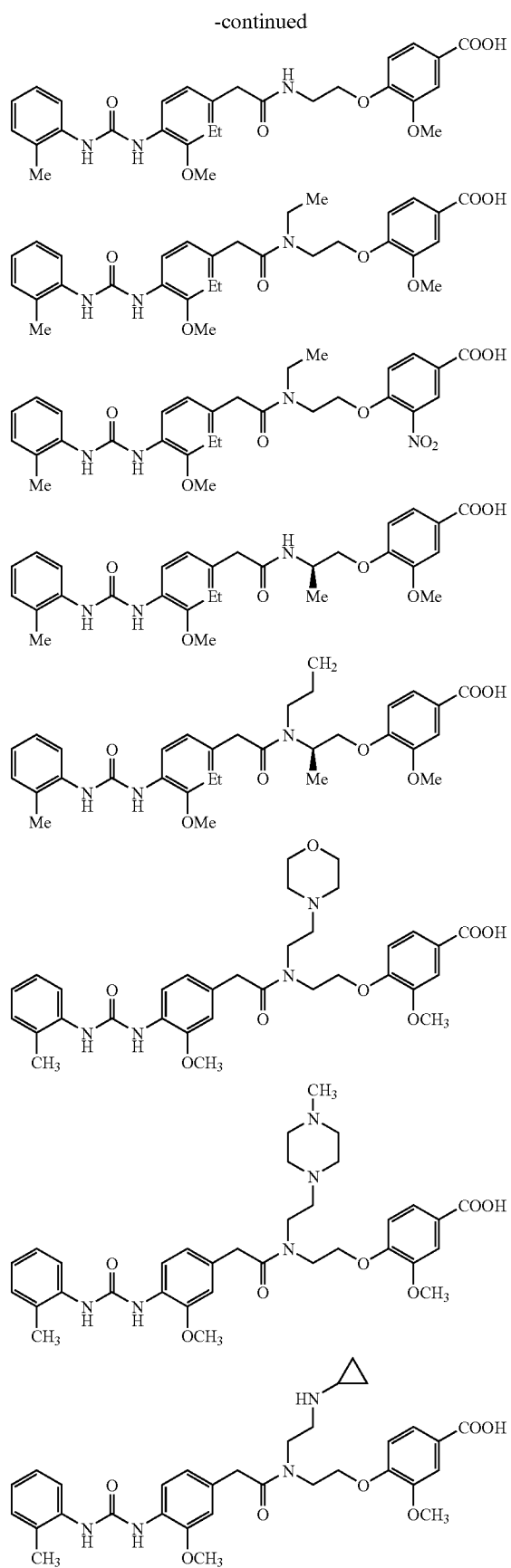
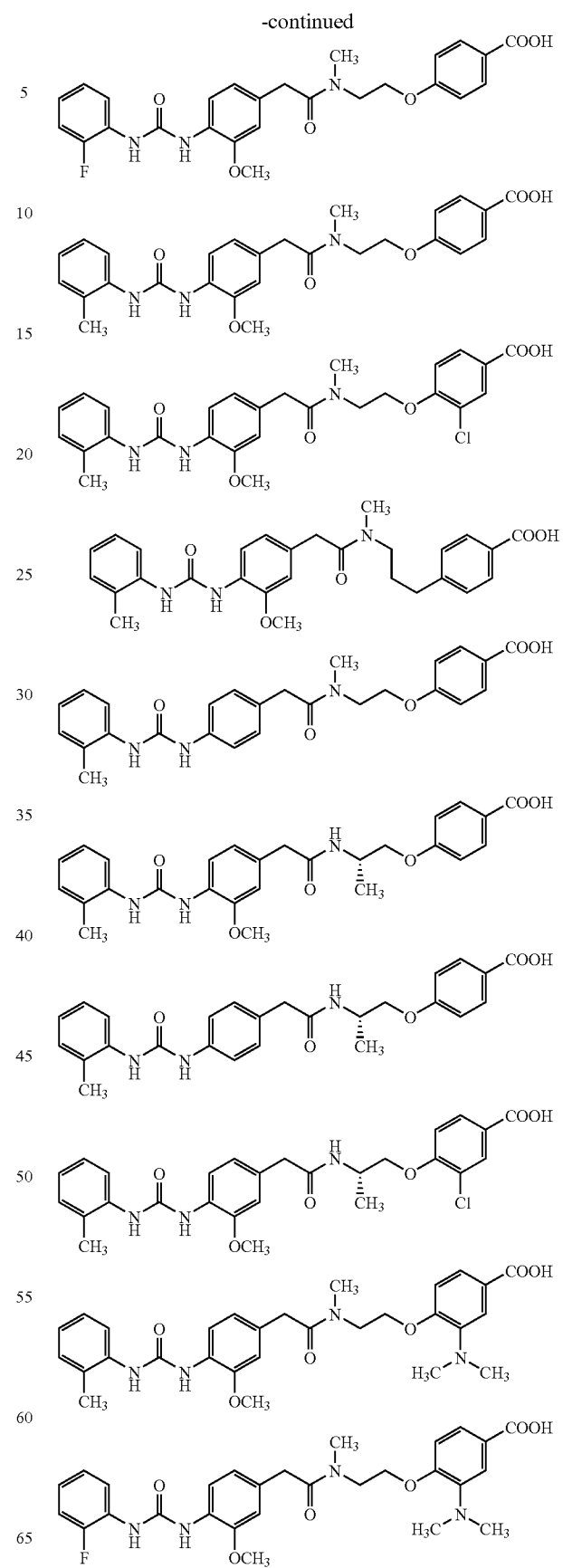

-continued
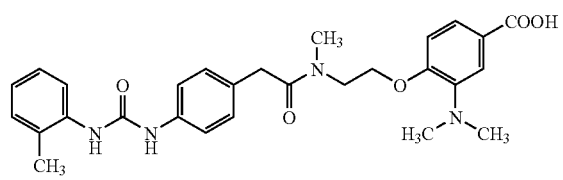
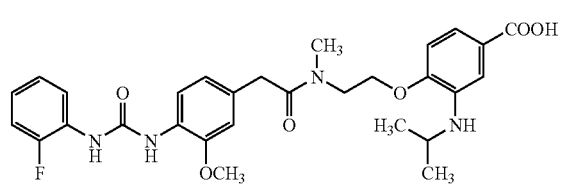
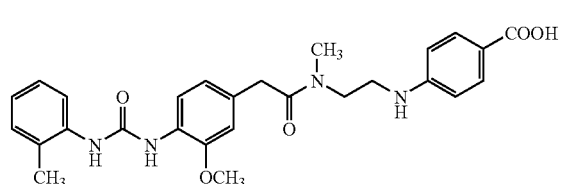
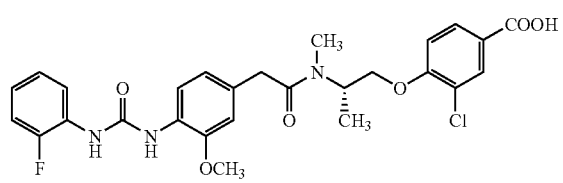
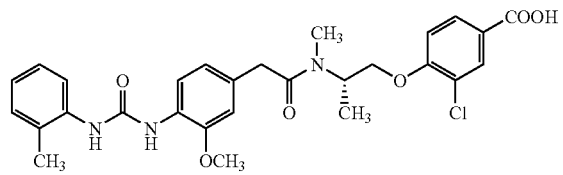
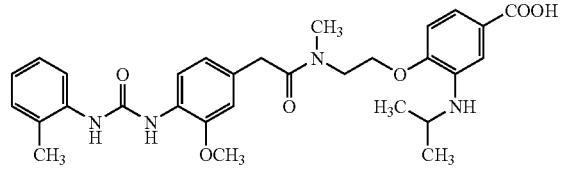
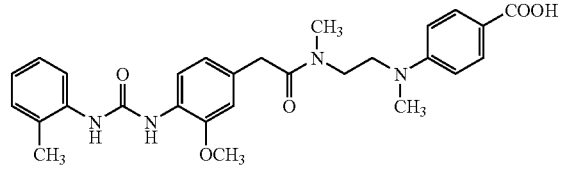
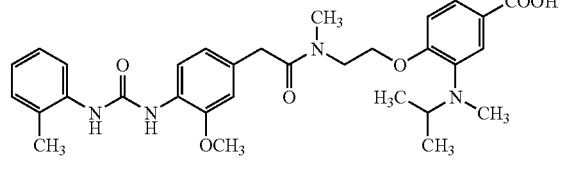
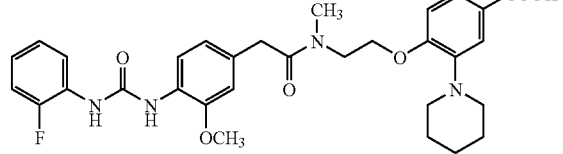
-continued
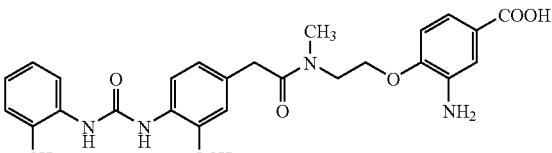
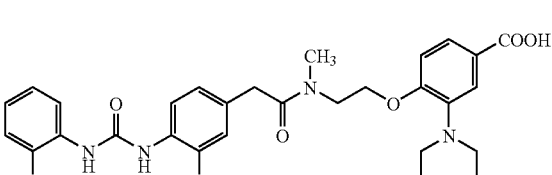
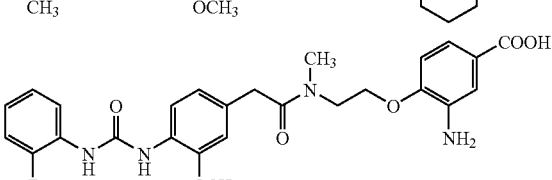
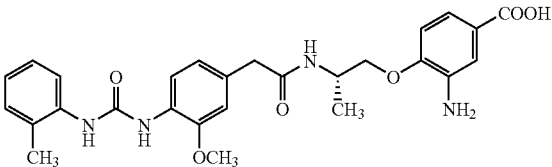
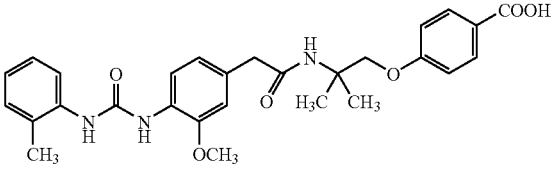
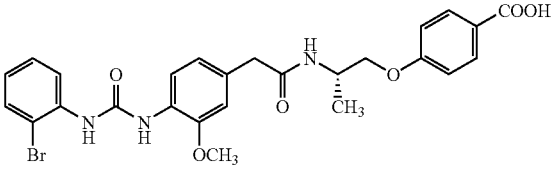
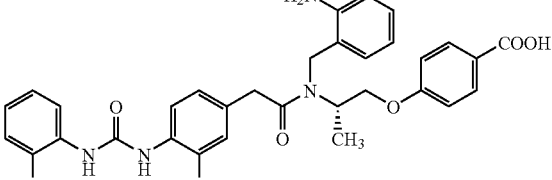
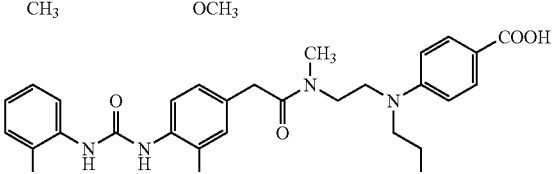
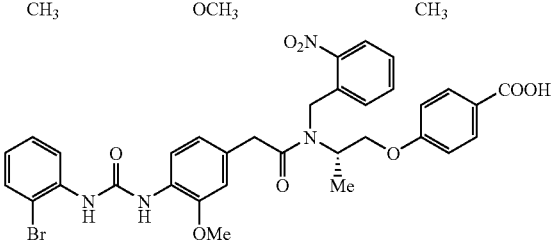

-continued
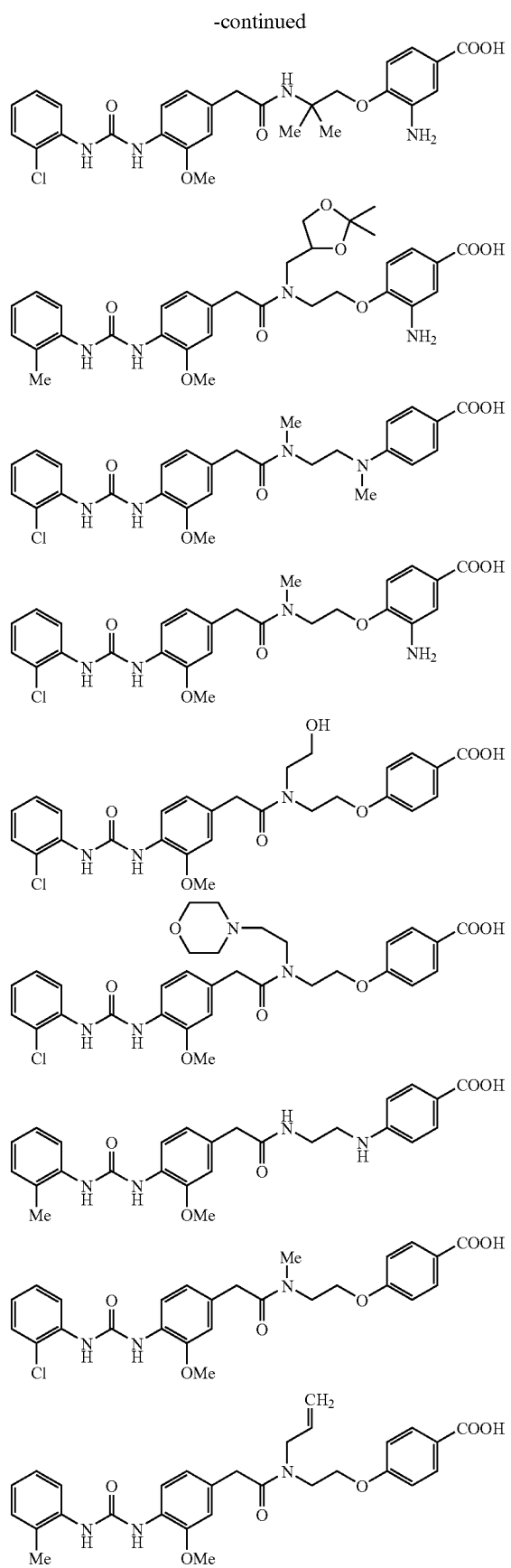
-continued
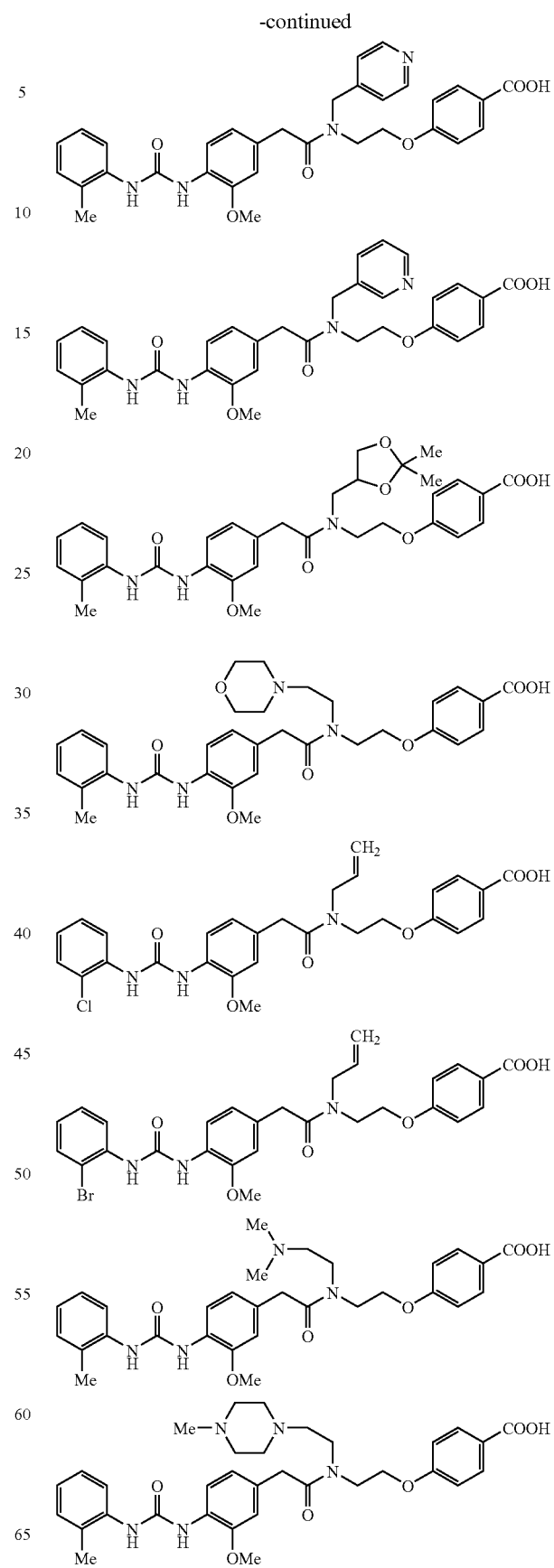

-continued
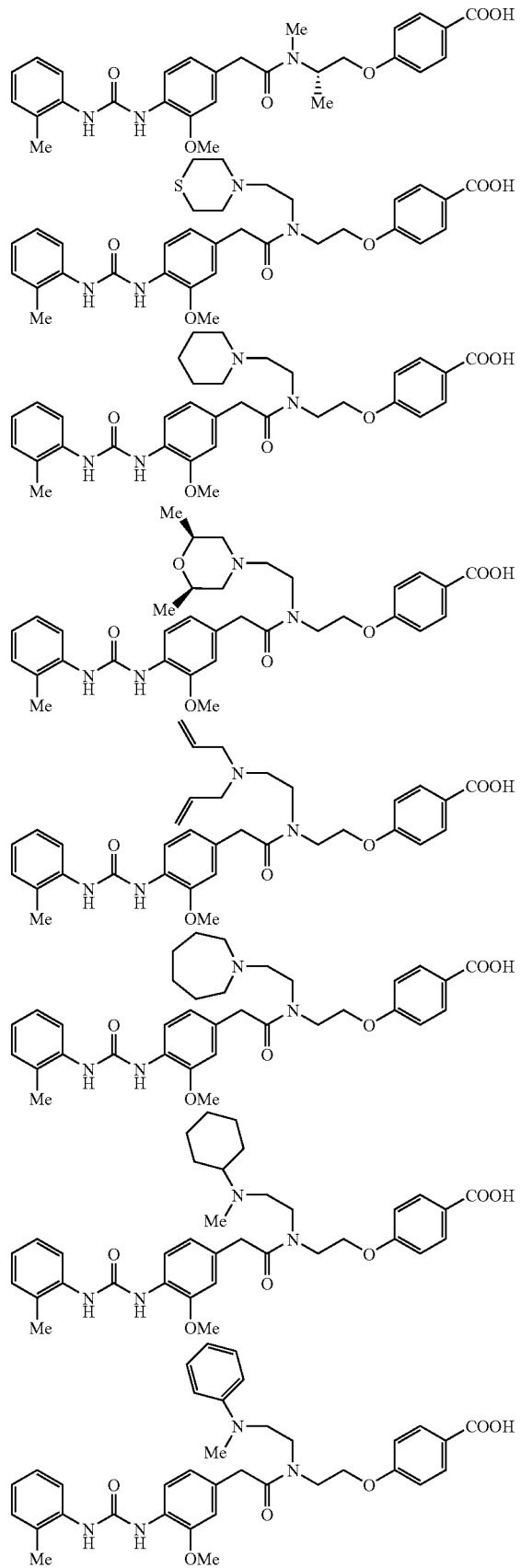
-continued
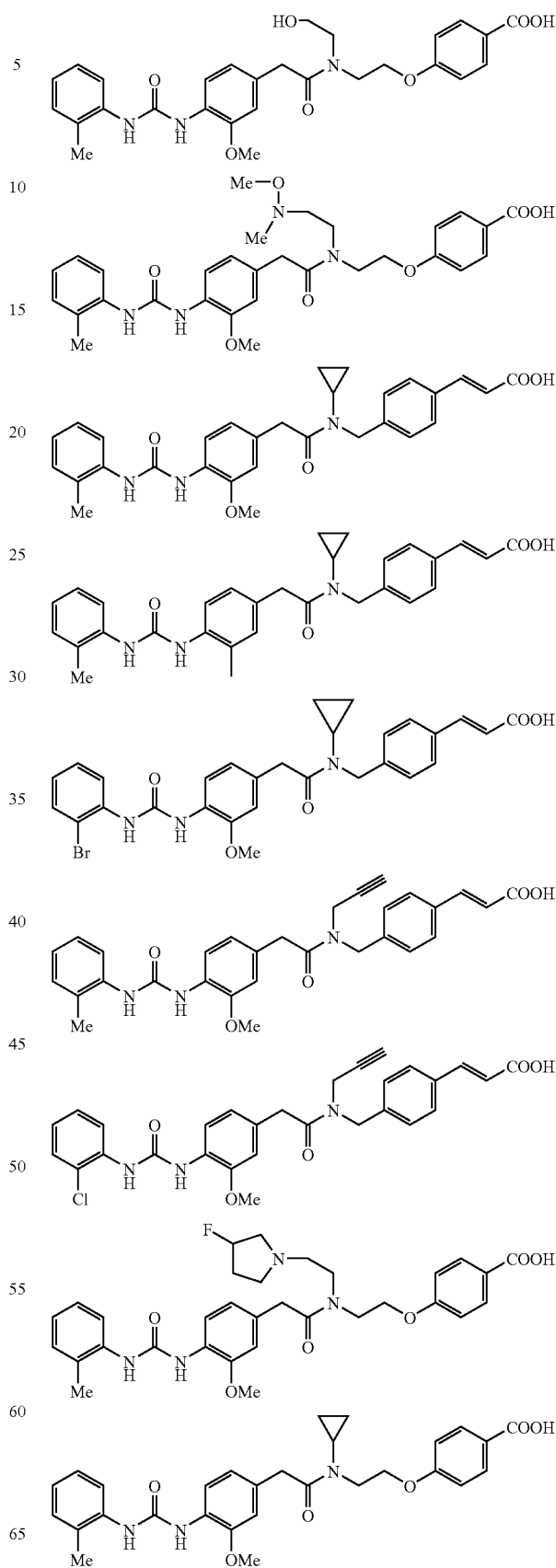

-continued
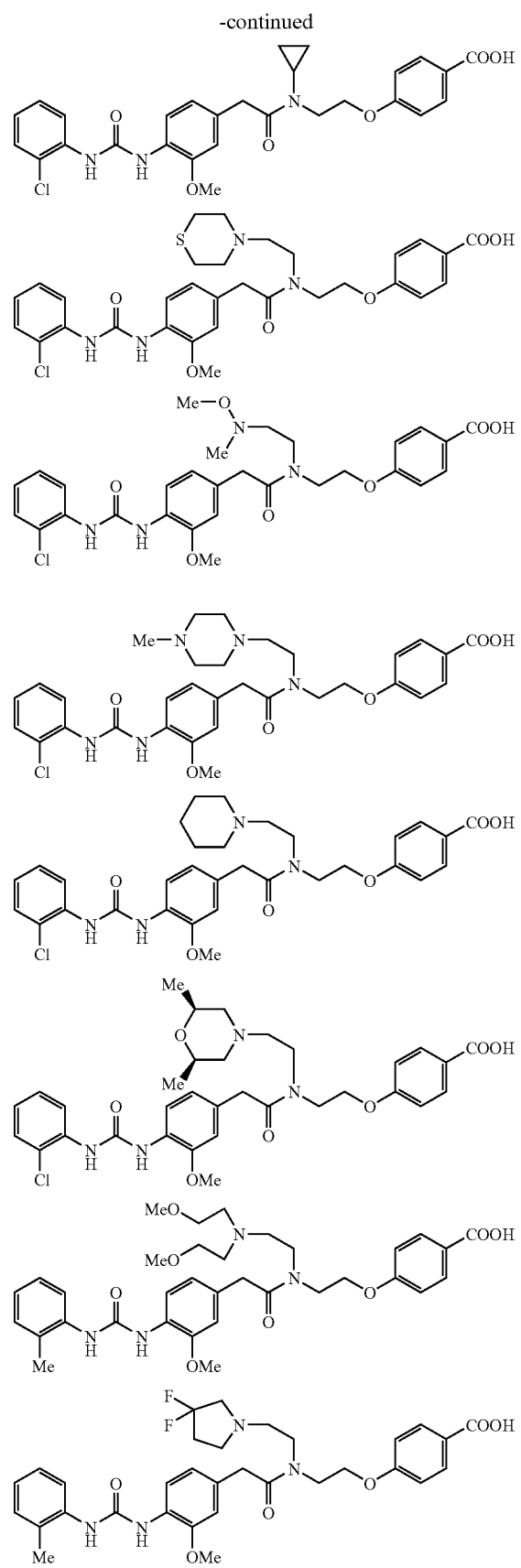
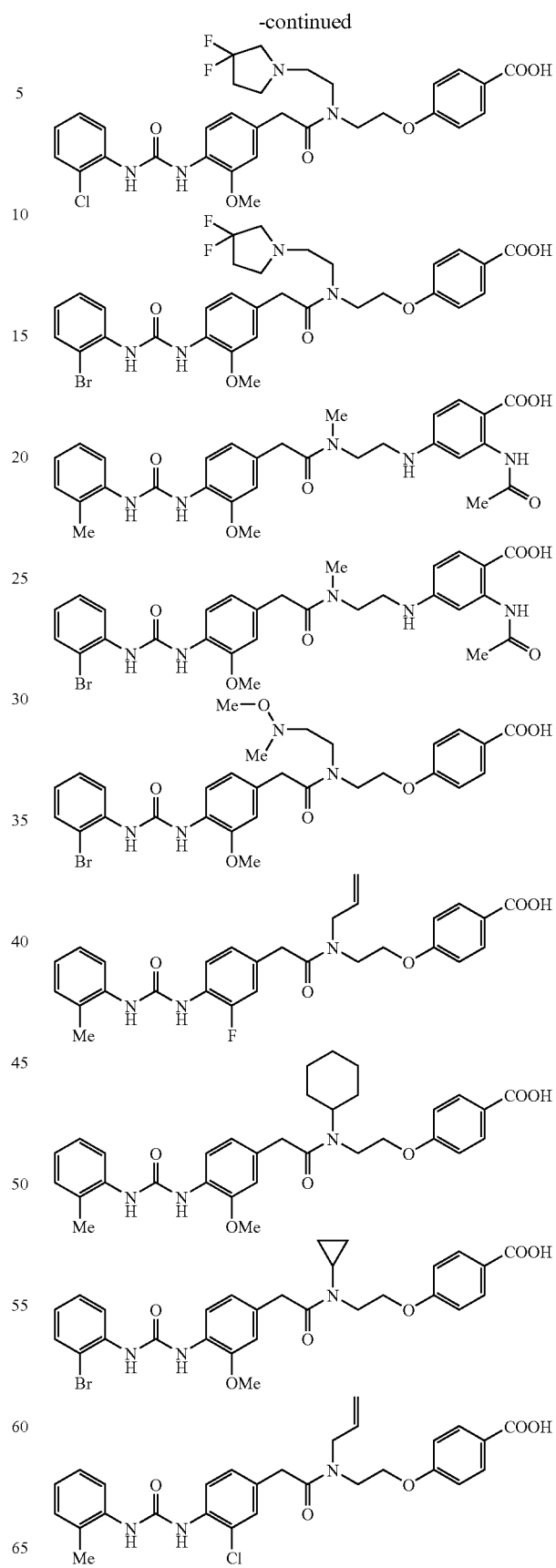

-continued

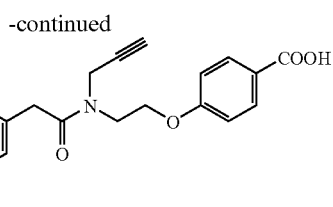

In vitro Assays

A direct binding assay was used to quantify the inhibitory activity of the compounds. In this assay, VLA-4-expressing cells were seeded in a 96-well microtiter plate. The cells were allowed to grow for 2 days until confluent. Various concentrations of the test compound were added together with 2 nM of the europium-labeled, VCAM-IgG fusion protein. The cells were allowed to incubate at room temperature in the microwells for at least 30 minutes. Following incubation, the microwells were emptied and washed. The amount of europium-labeled VCAM-IgG fusion protein bound was determined by time-resolved fluorescence measurement. Inhibition of binding was determined by quantifying the fluorescence bound to the plate for each of the various concentrations of test compound, as well as for controls containing no test compound.

The VLA4-expressing cells used in this assay was a CHO cell line stably transfected with the cDNA of the human $\alpha 4$ and $\beta 1$ subunits. Construction and maintenance of the cell line are described in the assay procedures. A VCAM IgG fusion protein containing the one to seven immunoglobulin domains of human VCAM-1 (D1D7) attached above the hinge region of an IgG1 molecule was labeled with europium chelates. The preparation and labeling of the fusion protein are described in the assay procedures.

The cell adhesion inhibitory activity of the test compound was determined by blocking the Jurkat cell attachment to the D1D7-VCAM IgG fusion protein. Jurkat cell is a human lymphocytic cell line expressing VLA-4 on cell surface. In this assay, each of the 96-well microtiter wells was coated with 75 ng of the VCAM IgG fusion protein. The wells were then blocked by the addition of 1% bovine serum albumin to remove nonspecific adhesive sites. Varying concentrations of the test compound were added together with the calcein-labeled Jurkat cells. The cells were allowed to adhere to the VCAM coated wells at room temperature for 1 hour in the dark. Following incubation, the plate was washed by immersing face down into a container filled with phosphate buffered saline. The wells were blotted dry on paper towel. Quantitation of the adhered cell was determined by fluorescence measurement. Decreased fluorescence indicated inhibition of cell adhesion by the test compound.

Specificity for $\alpha 4\beta 1$ of each test compound among other integrin receptors, namely, $\beta 2$ (LFA-1 and Mac-1), $\beta 3$ (GPIIb/IIIa and $\alpha v\beta 3$), $\beta 1$ ($\alpha 5\beta 1$) and $\beta 7$ ($\alpha 4\beta 7$) was examined. LFA-1 binds to ICAM-1 and mediates the emigration of leukocytes into inflammatory sites. Mac-1 binds to a number of ligands, including ICAM-1 and fibrinogen, and plays an important role in neutrophil phagocytosis and oxygen free radical generation. GPIIb/IIIa on platelet surface binds to fibrinogen in plasma and induces platelet aggregation. $\alpha v\beta 3$ binds to a number of extracellular matrix proteins, including vitronectin and mediates cell migration and prevents cell apoptosis. $\alpha 4\beta 7$ shares the same ligands as VLA-4 (VCAM-1, MAdCAM-1, and fibronectin), but with different preference. This receptor is expressed on lymphoid cells and is involved in lymphocyte migration to mucosal tissues.

Assays of LFA-1, Mac-1, GPIIb/IIIa and $\alpha v\beta 3$ involved coating the purified receptor on a 96-well microtiter plate. The specific ligands for these receptors were labeled with europium chelates. In the assays of LFA-1 and Mac-1, an ICAM-1 IgG fusion protein containing the one to five immunoglobulin domains of human ICAM-1 (D1D5) attached above the hinge region of an IgG1 molecule, was used. In the assays of GPIIb/IIIa and $\alpha v\beta 3$, europium-labeled fibrinogen and vitronectin, respectively, was used. The purified receptors were allowed to incubate in the wells with various concentrations of test compound, in the presence of europium-labeled ligands. Following incubation, the wells are emptied and washed. The amount of europium-labeled ligand bound was determined by time-resolved fluorescence measurement. Assay of $\alpha 4\beta 7$ is similar to the adhesion inhibition assay of VLA-4 described above, and uses the $\alpha 4\beta 7$-expressing cell, RPMI-8886. A MAdCAM-1 IgG fusion protein containing the one and two immunoglobulin domains of human MAdCAM-1 and mucin-like repeat domain, is used as the corresponding ligand for $\alpha 4\beta 7$.

$Eu^{3+}$-VCAM-1 IgG binding to CHO/VLA-4 cells may be determined as follows. 4B4 cells (CHO/VLA-4 cells) are distributed into each well of a 96-well microtiter plate at $3\times 10^4$/well. The plate is incubated at 37° C., 5% $CO_2$ for 48 hours and then washed twice with washing buffer, then blot dried. 50 µl of the inhibitor solution diluted with assay buffer (2% DMSO final) is added to each well, followed by 50 µl of $Eu^{3+}$-VCAM-1 IgG diluted with assay buffer at 2 nM. The plate is incubated at room temperature for at least 30 min. Each well is then washed four times with washing buffer and blot dried. 100 µl of DELFIA Enhancement solution is added to each well, followed by agitation of the plate at room temperature for 5 min. Fluorescence of each sample is then measured (e.g., DELFIA Fluorometer 1234, Wallace, Inc., USA). In this assay, the washing buffer comprises 25 mM-HEPES (pH 7.5), 150 mM NaCl, 1 mM $CaCl_2$, 1 mM $MgCl_2$, and 4 mM $MnCl_2$; the assay buffer comprises 25 mM HEPES (pH 7.5), 150 mM NaCl, 1 mM $CaCl_2$, 1 mM $MgCl_2$, 4 mM $MnCl_2$, 1% BSA, and 20 µM DTPA.

In Vivo Assays

The VLA-4 inhibitors may be further characterized in in vivo assays. One such assay examines the inhibition of eosinophil infiltration into the bronchoalveolar lavage fluid in the mouse (murine) model. In this assay, the animals are treated with cyclophosphamide on day 0. On days 2 and 14, the animals are immunized intraperitoneally with *Ascaris suum* extract. Seven days later, the animals are treated with various doses of the VLA-4 inhibitor. Shortly after drug administration, the animals are challenged with *Ascaris suum* extract by instillation into the trachea. Bronchoalveolar lavage of the animal is performed by instilling saline into the lung, 48 hours later. Total cell and eosinophil counts in the lavage are determined.

In the murine model of Ascaris-induced bronchial inflammation, one of the representative compounds (example number 32) inhibited eosinophil infiltration by 49% at an oral dosage of 30 mg/kg. By contrast, a representative prior art compound, 4-(N'-2-methylphenylurea)phenylacetyl-LDVP-OH, described in WO 97/03094, did not inhibit eosinophil infiltration (% inhibition=−2%) at an oral dosage of 50 mg/kg.

Other representative compounds were also tested in mice. The dosage, route of administration and inhibitory effect of representative compounds (hereinafter, all tested compounds are referenced by compound number provided in the Synthetic Examples) are shown in Table 5.

TABLE 5

|  | Dosage/Regimen | Route | % Inhibition of Eosinophil Infiltration |
|---|---|---|---|
| Compound 79 | 30 mg/kg b.i.d[1] × 2days | i.v. | 35.9 |
| Compound 90 | 10 mg/kg t.i.d[2] × 2 days | p.o. | 18.1 |
| Compound 90 | 30 mg/kg t.i.d. × 2 days | p.o. | 39.1 |
| Compound 90 | 50 mg/kg t.i.d. × 2 days | p.o. | 45.9 |
| Compound 90 | 30 mg/kg b.i.d. × 2 days | i.v | 47.3 |
| Compound 314 | 50 mg/kg t.i.d × 2days | p.o. | 18.9 |
| Compound 311 | 50 mg/kg t.i.d × 2 days | s.c. | 80.2 |
| Compound 311 | 50 mg/kg t.i.d × 2 days | p.o. | 42.5 |
| Compound 311 | 50 mg/kg t.i.d × 2 days | s.c. | 49.3 |

[1]two times a day (0 and 8 hrs)
[2]three times a day (0, 8 and 16 hrs)

The compounds of the present invention may also be further characterized in other in vivo assays, such as the eosioophil accumulation model tested in the rat. Fifty μg of Compound 48/80 was injected into the pleural cavities of male Sprague Dawley rats. After 24 hrs, each cavity was washed twice with Hank's Balanced Salt Solution containing 0.2% EDTA. Total cell and eosinophil counts were determined. Test compounds were given intraveneously, orally or subcutaneously, b.i.d. at 0 and 8 hours. The dosage, route of administration and inhibitory effect for the test compounds are shown in Table 6.

TABLE 6

|  | Dosage/Regimen | Route | % Inhibition of Eosinophil Infiltration |
|---|---|---|---|
| Compound 90 | 3 mg/kg 2 days | i.v. | 25.4 |
|  | 10 mg/kg 2 days | i.v. | 46.7 |
|  | 30 mg/kg 2 days | i.v. | 83.7 |
| Compound 90 | 50 mg/kg 2 days | p.o. | 50.5 |
| Compound 80 | 50 mg/kg 2 days | s.c. | 65.3 |
| Compound 92 | 50 mg/kg 2 days | s.c. | 43.1 |
| Compound 95 | 50 mg/kg 2 days | s.c. | 40.9 |

Mouse Bio-Assay Method

A compound was dissolved or suspended with an appropriate solvent at 1 mg/mL. Female Balb/c mice (7–9 weeks old) were given the compound orally. Blood samples were collected from the postcaval vein of the anesthetized mice after fifteen minutes. Serum was prepared and stored at −20° C. Serum concentration of the compound was determined from inhibitory activities of the diluted serum by a direct binding assay using VLA-4-expressing cells and VCAM-IgG fusion protein. Serum concentration determined by this method correlated well with the concentration determined by LC/MS/MS methodologies. The dosage, route of administration and resulting inhibitory effect for the test compounds are shown in Table 7.

TABLE 7

|  | Dosage | Minutes Post-Administration | Serum Concentration (ng/ml) |
|---|---|---|---|
| Compound 58 | 50 mg/kg | 30 | 3614 |
| Compound 68 | 10 mg/kg | 15 | 261 |
| Compound 78 | 10 mg/kg | 15 | 368 |
| Compound 79 | 10 mg/kg | 15 | 618 |
| Compound 80 | 10 mg/kg | 15 | 693 |
| Compound 90 | 10 mg/kg | 15 | 3659 |
| Compound 91 | 10 mg/kg | 15 | 2523 |
| Compound 92 | 10 mg/kg | 15 | 2162 |
| Compound 96 | 10 mg/kg | 15 | 3514 |
| Compound 97 | 10 mg/kg | 15 | 1733 |
| Compound 98 | 10 mg/kg | 15 | 2796 |
| Compound 102 | 10 mg/kg | 15 | 503 |
| Compound 124 | 10 mg/kg | 15 | 841 |
| Compound 134 | 10 mg/kg | 15 | 224 |
| Compound 146 | 10 mg/kg | 15 | 527 |
| Compound 156 | 10 mg/kg | 15 | 285 |
| Compound 158 | 10 mg/kg | 15 | 301 |
| Compound 166 | 10 mg/kg | 15 | 360 |
| Compound 179 | 10 mg/kg | 15 | 428 |
| Compound 309 | 10 mg/kg | 15 | 669 |
| Compound 311 | 10 mg/kg | 15 | 467 |
| Compound 314 | 50 mg/kg | 30 | 2309 |
| Compound 318 | 50 mg/kg | 30 | 2105 |
| Compound 319 | 50 mg/kg | 15 | 603 |
| Compound 323 | 50 mg/kg | 15 | 1423 |

Pharmakokinetic Evaluations

Pharmacokinetic parameters of exemplary compounds, in mouse, rat and monkey models, are shown in Tables 8, 9 and 10.

TABLE 8

| MOUSE | Dosage | AUC[1] (ng · h/mL) | MRT[2] (hr) | CL[3] (mL/min/kg) |
|---|---|---|---|---|
| Compound 68 | 10 mg/kg (i.v.) | 1595 (0–6 hr) | 0.2 | 104.5 |
|  |  | 1595 (0–∞) | 0.2 | 104.5 |
|  | 20 mg/kg (p.o.) | 1307 (0–6 hr) | 1.6 | 637.6 |
|  |  | 1751 (0–∞) | 4.1 | 476.0 |
| Compound 90 | 10 mg/kg (i.v.) | 8995 (0–6 hr) | 0.5 | 18.53 |
|  |  | 9219 (0–∞) | 0.7 | 18.08 |
|  | 10 mg/kg (p.o.) | 2540 (0–6 hr) | 1.2 | 65.62 |
|  |  | 2950 (0–∞) | 2.5 | 56.50 |
| Compound 80 | 10 mg/kg (i.v.) | 5259 (0–6 hr) | 0.4 | 31.69 |
|  |  | 5389 (0–∞) | 0.6 | 30.93 |
|  | 20 mg/kg (p.o.) | 2190 (0–6 hr) | 2.3 | 152.24 |
|  |  | 3615 (0–∞) | 6.5 | 92.21 |

[1]total area under the plasma concentration (measured by LC/MS/MS method) versus time curve
[2]mean residence time
[3]apparent plasma clearance

TABLE 9

| RAT | Dosage | AUC[1] (ng · h/mL) | MRT[2] (hr) | CL[3] (mL/min/kg) |
|---|---|---|---|---|
| Compound 90 | 10 mg/kg (i.v.) | 31915 (0–6 hr) | 0.8 | 5.23 |
|  |  | 33488 (0–∞) | 1.1 | 4.98 |
|  | 10 mg/kg (p.o.) | 11454 (0–6 hr) | 1.7 | 17.85 |
|  |  | 19968 (0–∞) | 8.8 | 9.99 |
| Compound 79 | 10 mg/kg (i.v.) | 5259 (0–6 hr) | 0.4 | 31.69 |
|  |  | 5389 (0–∞) | 0.6 | 30.93 |
|  | 10 mg/kg (p.o.) | 22119 (0–6 hr) | 0.5 | 8.5 |
|  |  | 24867 (0–∞) | 0.7 | 6.7 |
| Compound 68 | 10 mg/kg (i.v.) | 6345 (0–6 hr) | 0.63 | 26.45 |
|  |  | 6405 (0–∞) | 0.67 | 26.20 |

TABLE 9-continued

| RAT | Dosage | AUC[1] (ng · h/mL) | MRT[2] (hr) | CL[3] (mL/min/kg) |
|---|---|---|---|---|
| | 20 mg/kg (p.o.) | 1867 (0–6 hr) | 1.1 | 181.1 |
| | | 2086 (0–∞) | 2.0 | 162.7 |

[1]total area under the plasma concentration (measured by LC/MS/MS method) versus time curve
[2]mean residence time
[3]apparent plasma clearance Pharmacokinetic parameters and the time course of the serum concentration of a single intravenous dosage (2 mg/kg) of a representative compound and ATENOLOL {4-[2'-hydroxy-3'-isopropylamino) proppyxy]phenylacetamide; Sigma Chemical Co., code no. A-7655} are summarized in Tables 10 and 11 for the monkey model.

TABLE 10

| MONKEY | AUC[1] (ng · h/mL) | Cltot[2] (mL/min/kg) |
|---|---|---|
| Compound 195 | 8405 | 4.0 |
| ATENOLOL | 5021 | 6.7 |

[1]total area under the plasma concentration (measured by the LC/MS/MS method) versus time curve
[2]apparent plasma clearance

TABLE 11

| | TIME | | | | | |
|---|---|---|---|---|---|---|
| | 5 min | 30 min | 1 hr | 2 hr | 4 hr | 8 hr |
| Serum conc[1] (ng/ml) Compound 195 | 65447 | 3900 | 2225 | 772 | 194 | 28 |
| Serum conc[1] (ng/ml) ATENOLOL | 4057 | 1189 | 771 | 479 | 348 | 137 |

[1]measured by the LC/MS/MS method

Binding Assay of VCAM-1 to VLA-4 Expressing Cells

Preparation of VCAM IgG Fusion Protein

A VCAM IgG fusion protein containing the one to seven immunoglobulin domains of VCAM-1 (D1D7) ligated to the hinge (H), CH2 and CH3 regions of human IgG1 was used in the binding assay.

Construction of a Stable Cell Line Expressing D1D7-VCAM IgG Fusion Protein

An Epstein-Barr virus based, episomal plasmid containing a D1D7-VCAM IgG fusion gene under transcriptional control of the CMV promoter, was transfected into 293E human embryonic kidney cells. Stably transfected cells were selected using 250 µg/mL hygromycin in DMEM with 10% fetal calf serum. The cells secreted D1D7 VCAM IgG fusion protein into the medium cumulatively for up to 9 days.

Purification of D1D7 VCAM IgG Fusion Protein

The cells were cultured in DMEM with 10% fetal calf serum for 2 days, then changed to CCM5 medium and cultured for a further 10 days. The medium was centrifuged, filtered and then incubated overnight with Protein A Sepharose 4. The Protein A Sepharose was washed extensively and the D1D7 VCAM IgG fusion protein bound was eluted using 100 mM citric acid, pH 3.

Preparation of Europium Labeled-D1D7 VCAM IgG Fusion Protein

The D1D7-VCAM IgG fusion protein, at 1 mg/mL, was dialyzed against 50 mM NaHCO$_3$, 0.9% NaCl, pH 8.5. The fusion protein was added to one vial of europium-labeling reagent (DELFIA labeling kit from Wallac, Gaithersberg, Md.; catalog no. 1244-302) and incubated at room temperature in the dark overnight. The labeled protein was purified using a Sepharose G10 column and assayed for the europium content and protein concentration. The protein was stored at minus 80° C. until used.

Construction of Cell Line Expressing VLA-4 (CHO/VLA-4)

A CHO cell line stably transfected with the cDNA of α4 and β1 was used in the binding assay. The gene for human α4 was obtained from the American Type Culture Collection and recloned between the XhoI and Xba sites of the mammalian expression vector pCI-neo (Promega, Madison, Wis.). The β1 gene was amplified by PCR from human peripheral leukocyte cDNA and engineered such that the start codon was placed in the context of a consensus Kozak sequence. The gene was recloned into pCI-neo downstream of the CMV promoter and chimeric intron.

CHO-K1 cells were stably co-transfected with plasmids encoding the α4 and β1 genes, and single cells expressing high levels of VLA-4 were selected by fluorescence cell sorting (FACS). The antibodies used in FACS analysis were: anti-α4-PE conjugated (PharMingen, San Diego, Calif.) and anti-β1-FITC conjugated (Biosource, Camarillo, Calif.). A cell line 4B4, which expresses 400,000 and 300,000 sites/cell of the α4 and β1 subunit, respectively, was used in the binding assay. The subunit numbers were determined by FACS analysis, using Quantum Simply Cellular microbeads (Flow Cytometry Standards Corporation, Puerto Rico) as standards. The cells were maintained in F12 medium, containing 10% fetal bovine serum, 10 mM HEPES, pH 7.5, 0.5 mg/mL G418, using a 1:48 passage/week.

Binding Assay

CHO/VLA-4 cells were seeded in a 96-well microtiter plate at 30,000 cells/well and incubated at 37° C., 5% CO$_2$ for 48 hours until confluent. On the day of assay, the wells were emptied and washed twice with 350 µl of a washing buffer containing 25 mM HEPES, pH 7.5, 150 mM NaCl, 1 mM MgCl$_2$, 1 mM CaCl$_2$, 2 mM MnCl$_2$. The plate was then drained and blotted dry on paper towels to remove buffer.

The test compound was serially diluted in assay buffer (washing buffer together with 0.1% bovine serum albumin, 20 µM DTPA and 1% dimethysulfoxide), in the presence of 2 nM of europium-labeled D1D7-VCAM IgG fusion protein. Final concentrations used ranged from 0.1 nM-10 µM. 50 µl aliquot of the test compound mixture was added to duplicate wells in the plate. Control wells for total binding received no test compound. Non-specific binding wells contained an anti-α4 monoclonal antibody (L25.3, Becton Dickinson, Bedford, Mass.).

The cells were allowed to incubate with the test compound mixture, in the presence of europium-labeled D 1D7-VCAM IgG fusion protein at room temperature for at least 30 minutes. The cells were then washed three times with 350 µl of washing buffer, using a Skatron plate washer and blot dry. An 100 µl aliquot of DELFIA Enhancement solution was added to each well, followed by gentle agitation at room temperature for 10 minutes. The amount of europium-labeled VCAM-IgG fusion protein bound was determined by time-resolved fluorescence measurement (Model: Victor™, Wallac Inc., Gaithersberg, Md.).

Percent binding was calculated as: $[(F_T-F_{NS})-(F_I-F_{NS})]/(F_T-F_{NS})\times 100$ wherein $F_T$ and $F_{NS}$ is the fluorescence signal of the europium labeled D1D7-VCAM IgG fusion protein bound to cells, in the absence of test compound and containing an anti-α4 monoclonal antibody, respectively. $F_I$ is the fluorescence in wells containing a test compound. The $IC_{50}$ (concentration of the inhibitor to inhibit 50% binding of VACM to CHO/VLA-4 cell) was determined by a curve fitting routine, PRIZM (GraphPad Software, Inc., San Diego, Calif.).

Adhesion of VLA-4 Expressing Cell to VCAM-1

This secondary functional assay was used to determine the potency of a test compound in inhibiting VLA-4 mediated cell adhesion.

Preparation of VCAM Coated Plate

A 50 μl aliquot of the D1D7-VCAM IgG fusion protein (1.5 μg/mL in phosphate buffered saline, PBS) was added to each well of a 96-well Costar flat bottom plate (Costar, Franklin Lakes, N.J., catalog no. 2580). The plate was then incubated overnight at 4° C. On the day of assay, the wells were emptied and washed twice with 350 μl of PBS. The plate was then blocked with 100 μl of 1% bovine serum albumin (BSA, Sigma, cat# A9418) in PBS at room temperature for at least a hour.

Cell Preparation

Jurkat cell (clone E6-1) was obtained from American Type Cultured Collection and was maintained in RPMI medium, 10 mM HEPES, pH 7.5, 1 mM sodium pyruvate, 10% FCS, using a 1:64 passage/week. Just prior to running the assay, Jurkat cells were labeled with 5 μM of calcein-AM (Molecular Probe, Eugene, Oreg., catalog no. C1430) in RPMI medium, at room temperature for 30 min in the dark. Following labeling, cells were washed twice with RPMI medium and resupended at $1 \times 10^6$ cells/mL.

Cell Adhesion Assay

Immediately before the assay, the BSA solution was emptied from the VCAM-coated plate. The plate was then washed twice with RPMI medium. A 100 μl aliquot of the labeled Jurkat cells was added to each well, followed by the addition of 50 μl of the inhibitor solutions. Final inhibitor concentrations range from 1 nM to 10 μM and each concentration was tested in triplicates. The inhibitor and cells were allowed to incubate at room temp for 1 hr in the dark. Following the incubation, the plate was immersed gently into a container filled with PBS, then inverted face down under PBS. The wells were drained and blotted dry on a layer of paper towel. A 5 μl aliquot of 0.1% Triton X-100 was added to each well. The plate was incubated in the dark for 10 min. Adhesion of Jurkat cell was quantitated in a Millipore Cytofluor 2300 System plate reader set at 485 nM excitation and 530 nM emission. The $IC_{50}$ (concentration of the inhibitor to inhibit 50% Jurkat cell adhesion) was determined by a curve fitting routine, PRIZM (GraphPad Software, Inc., San Diego, Calif.).

Methods of Synthesis

Compounds of the present invention may be prepared by standard chemical synthesis methods, as well as by methods of combinatorial chemistry, such as that described in Published PCT application, WO 95/30642.

SYNTHETIC EXAMPLES

General methods of synthesis are illustrated by the following examples. The specific embodiments are presented by way of illustration only, and are not intended to limit the invention. Modifications and variations in any given material or process step will be readily apparent to one of skill in the art. Unless otherwise indicated, the solid-phase support used in certain examples is Tentagel™—S-PBB resin. This resin has a para-hydroxy benzyl linker which can be cleaved by the use of 90% trifluoroacetic acid in dichloromethane. The loading for this resin varies between 0.27 and 0.30 mmol/g and is not double loaded.

Example 1

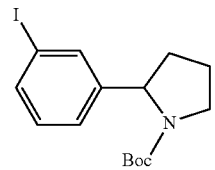

A

A three-necked 500 mL round-bottomed flask was charged with 200 mL of THF and NaH (1.5 g, 62.9 mmol). A solution of 1-vinyl-2-pyrrolidinone (6.9 g, 62.9 mmol) and methyl 3-iodobenzoate (15.0 g, 57.3 mmol) in THF (100 mL) was added dropwise to the flask over 15 min. After the addition was complete the reaction mixture was heated to reflux for 1 hr. The reaction vessel was allowed to cool to room temp and then 6 N HCl (100 mL) was carefully added. The reaction was concentrated in vacuo to remove the THF and then an additional aliquot of 6 N HCl (100 mL) was added and the reaction was refluxed for 14 hr. The reaction was quenched by the addition of $NaHCO_3$ until pH 9 and then the mixture was extracted 3× with EtOAc. The combined organics were dried over $MgSO_4$ and concentrated in vacuo to afford a yellow oil.

This oil was then placed in MeOH (100 mL) and cooled to minus 78° C. $NaBH_4$ (3.5 g, 96.5) was then added portionwise and the reaction was allowed to warm to room temp over 2 hr. The reaction was quenched by the addition of 6 N HCl until acidic and then made basic by the addition of 40% aqueous NaOH. The solution was extracted 3× with $CH_2Cl_2$, the combined organics were dried over $MgSO_4$, and then concentrated in vacuo to afford 11.4 g as a yellow oil.

The above amine was then Boc-protected by placing the amine in 50% dioxane:$H_2O$ (100 mL) and adding $K_2CO_3$ until basic. To this solution was added Boc-anhydride (9.1 g, 41 mmol) and then allowed to stir for 14 hr at room temp. The reaction was quenched by the addition of 1 N HCl until acidic. The solution was extracted 3× with EtOAc, dried over MgSO$_4$ and concentrated in vacuo to afford a yellow viscous oil. The oil was chromatographed (25% EtOAc:hexanes) to afford 7.0 g A.

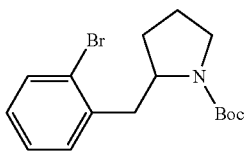

A'

Hydrochloric acid (gas) was bubbled through 15.8 g (73.5 mmol) 2-bromophenylacetic acid in 100 mL of methanol for 10 min. The resulting solution was partitioned between 100 mL water and 100 mL CH$_2$Cl. The organic layer was dried over MgSo$_4$ and the solvent was removed under reduced pressure to give 16.8 g (73.5 mmol) of methyl-2-brompophenylacetate which was combined with 9.0 g (80.8 mmol) of 1-vinyl-2-pyrrolidinone, and 100 mL of dry THF under argon in a 250 mL round-bottomed flask.

To this flask was added 3.5 g (147 mmol) sodium hydride (95%) and the solution was stirred for 10 min at room temp. A reflux condenser was added and the mixture was heated to reflux for 1 hr. The solution was cooled to room temp and the solvent was removed under reduced pressure. A solution of 30 mL aqueous hydrochloric acid and 50 mL water was added to the resultant mixture and was heated to reflux with no condenser until the solution temperature reached 96° C. at-which time a condenser was added and the solution was allowed to reflux for 16 hr. The solution was cooled to room temp, made basic with 150 mL of an aqueous solution of 40% sodium hydroxide, extracted with 3×125 mL CH$_2$Cl$_2$, and the combined organic layers were washed with a saturated aqueous solution of sodium chloride, dried over magnesium sulfate, and the solvent was removed under educed pressure to give 15.0 g (63.0 mmol, 86%) of 2-(2-bromobenzyl)-1-pyrolline.

To a solution of 15 g (63 mmol) of 2-(2-bromobenzyl)-1pyrroline in a solution of 80:20 methanol:aqueous acetic acid cooled to minus 78° C. was added, in portions over a 15 min period, 5.3 g (140.0 mmol) sodium borohydride. The mixture was allowed to stir for 1 hr warming to room temp at which time the solvent was removed under reduced pressure, 150 mL of water was added and the solution was made basic with an aqueous solution of sodium hydroxide which was extracted 10×100 mL CH$_2$Cl$_2$ which resulted in emulsions. The combined organic layers were washed with a saturated aqueous solution of sodium bicarbonate, dried over magnesium sulfate and the solvent was removed in vacuo to give 14.6 g (60.8 mmol, 97%) of the benzyl proline.

To a solution of 14.6 g(60.8 mmol) of the benzyl proline in a solution of 70 mL of saturated aqueous sodium bicarbonate and 70 mL dioxane was added 15.1 g (67.0 mmol) of di-t-butyl-dicarbonate and the mixture was stirred for 16 hr at room temp. The solution was partitioned between a 200 mL aqueous solution of hydrochloric acid and 200 mL ethyl acetate. The ethyl acetate layer was washed with 200 mL of a saturated aqueous solution of sodium chloride, dried over MgSO$_4$ and the solvent was removed under reduced pressure to give a residue which was purified by flash column chromatography (20%–100% ethyl acetate/hexane) to give 11.5 g (33.8 mol, 56%) pure A'.

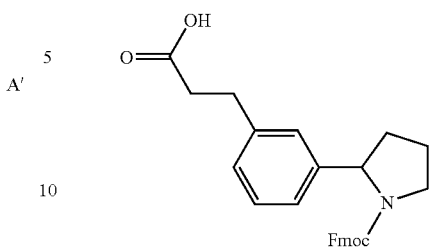

1

A (1.88 g, 5.0 mmol) was placed in a 100 mL round-bottomed flask and dissolved in DMF (50 mL). To this solution was added Pd(OAc)$_2$ (23 mg, 0.3 mmol), P(o-Tol)$_3$ (12 mg, 0.3 mmol), methyl acrylate (0.47 g, 5.5 mmol), and NaOAc (0.5 g, 5.5 mmol). This mixture was then heated to 80° C. for 14 hr. The reaction mixture was then cooled to room temp and 1 N HCl (100 mL) was added. The solution was then extracted 3× with EtOAc, dried over MgSO$_4$, and then concentrated in vacuo to afford a brown oil. This oil was chromatographed with 25% EtOAc:hexanes to afford 1.32 g of the alkene ester as a colorless viscous oil.

The alkene ester (1.32 g, 4.1 mmol) was then subjected to hydrogenation. The alkene was placed in a Parr hydrogenation bottle, EtOAc (10 mL) and 10% Pd/C (100 mg) was added under inert atmosphere. The bottle was then pressurized with hydrogen at 45 psi and shaken for 4 hr at room temp. The solution was then filtered through celite and concentrated in vacuo to afford 1.29 g of the alkane ester.

The alkane ester (1.29 g, 4.0 mmol) was dissolved in THF (30 mL), MeOH (20 mL), and water (10 mL) and saponified with LiOH (200 mg, 8.0 mmol). The reaction was stirred at room temp for 3 hr and then poured into 1 N HCl (50 mL). This solution was then extracted 3× with EtOAc, dried over MgSO$_4$, and then concentrated in vacuo to afford 1.02 g of the alkane acid as a yellow solid.

The alkane acid (1.02 g, 3.3 mmol) was then deprotected by the addition of a 25% TFA/CH$_2$Cl$_2$ solution and stirred for 2 hr at room temp. The resulting mixture was then concentrated in vacuo and immediately protected by dissolving the deprotected acid in 50% dioxane/water, adding K$_2$CO$_3$ (1.2 g), and Fmoc-Cl (1.08 g, 4.0 mmol). This mixture was stirred at room temp for 14 hr and then poured in 1 N HCl (100 mL). The solution was then extracted 3× with EtOAc, dried over MgSO$_4$, and then concentrated in vacuo to afford 495 mg 1 as a white crystalline solid.

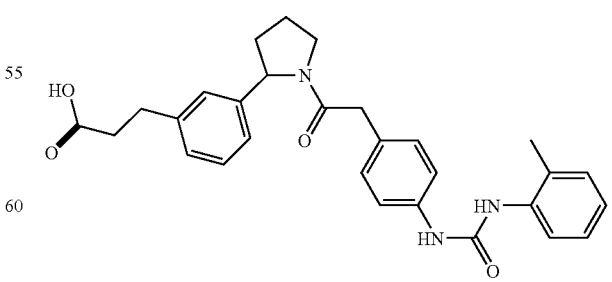

1'

The dried resin (500 mg, 0.14 mmol) was placed into a small shaker vessel. The vessel was then charged with 9 mL of DMF (2 mg, 0.42 mmol), DIC (102 mg, 0.84 mmol), and DMAP (17 mg, 0.14 mmol). The vessel was subsequently shaken for 16 hr at room temp. The contents were drained and the resin was washed 3× with DMF, MeOH, and CH₂Cl₂. The Fmoc group was then removed by the addition of 10 mL of 50% piperidine/DMF to the shaker vessel and shaking for 2 hr at room temp. The resulting amine resin was washed 3× with DMF, MeOH, and CH₂Cl₂.

To the above resin was added 9 mL of DMF, 4-[N'-(o-Tolylurea)]-phenylacetic acid (132 mg, 0.42 mmol), PyBroP (196 mg, 0.42 mmol), and DIEA (107 mg, 0.84 mmol). The contents were shaken for 14 hr at room temp and then drained and washed 3× with DMF, MeOH, and CH₂Cl₂. The compound was then cleaved from the resin and the filtrate was collected and then concentrated in vacuo. The resulting oil was triturated by taking up the oil in MeOH and slowly adding in Et₂O until a precipitate formed. This precipitate was collected and dried in vacuo to afford 67 mg 1' as a white crystalline solid.

Example 2

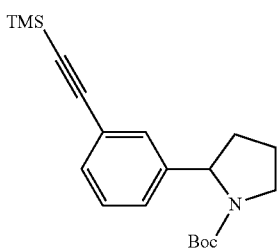

2

A (4.2 g, 11.3 mmol) was placed in a 100 mL round-bottomed flask and dissolved in NEt₃ (50 mL). To this solution was added Pd(PPh₃)₂Cl₂ (0.16 g, 0.23 mmol), CuI (21 mg, 0.12 mmol), and trimethylsilylacetylene (1.38 g, 13.5 mmol). This mixture was stirred at room temp for 14 hr. The reaction mixture was quenched by the addition of 1 N HCl (100 mL). The solution was then extracted 3× with EtOAc, dried over MgSO₄, and then concentrated in vacuo to afford a yellow oil. This oil was chromatographed with 15% EtOAc:hexanes to afford 3.8 g 2 as a colorless viscous oil.

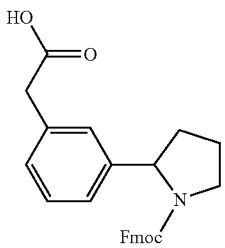

3

A solution of dicyclohexylborane was generated by the addition of borane-THF (12.0 mL, 12 mmol), at 0° C. to a solution of cyclohexene (2.3 mL) in 6 mL of anhydrous THF. This solution was stirred for an additional 1 hr at 0° C. The acetylene (2) (2.0 g, 5.84 mmol) was then added dropwise over 15 min at 0° C. and then allowed to warm to room temp over 1 hr. The reaction mixture was then diluted with MeOH (20 mL) and then recooled to 0° C. A solution of 2 N NaOH (6 mL) and 30% H₂O₂ (3.5 mL) was then added dropwise. The reaction mixture was then stirred at 0° C. for 1 hr and then warmed to 40° C. for 2.5 hr. The mixture was then cooled to room temp and an additional 6 mL of 2 N NaOH was added. The organics were removed in vacuo and the remaining aqueous solution was extracted 3× Et₂O and the organics were discarded. The aqueous extracts were then acidified with 1 N HCl and extracted with EtOAc dried over MgSO₄, and then concentrated in vacuo to afford 1.7 g of the phenylacetic acid as a tan crystalline solid.

The acid (1.7 g, 5.6 mmol) was then deprotected by the addition of a 25% TFA/CH₂Cl₂ solution and stirred for 2 hr at room temp. The resulting mixture was then concentrated in vacuo and immediately protected by dissolving the deprotected acid in 50% dioxane/water, adding K₂CO₃ (15 g), and Fmoc-Cl (1.4 g, 5.5 mmol). This mixture was stirred at room temp for 14 hr and then poured in 1 N HCl (100 mL). The solution was then extracted 3× with EtOAc, dried over MgSO₄, and then concentrated in vacuo to afford 1.7 g 3 as a white crystalline solid.

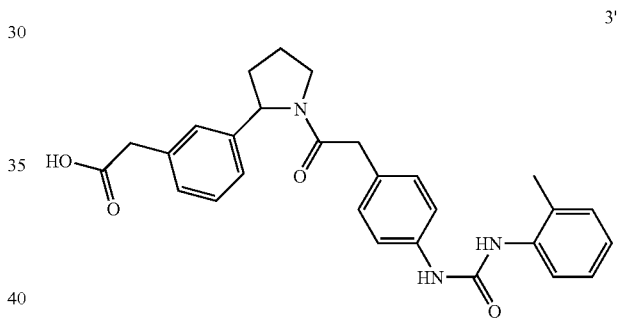

3'

The dried resin (500 mg, 0.14 mmol) was placed into a small shaker vessel. The vessel was then charged with 9 mL of DMF, 3 (180 mg, 0.42 mmol), DIC (102 mg, 0.84 mmol), and DMAP (17 mg, 0.14 mmol). The vessel was subsequently shaken for 16 hr at room temp. The contents were drained and the resin was washed 3× with DMF, MeOH, and CH₂Cl₂. The Fmoc group was then removed by the addition of 10 mL of 50% piperidine/DMF to the shaker vessel and shaking for 2 hr at room temp. The resulting amine resin was washed 3× with DMF, MeOH, and CH₂Cl₂.

To the above resin was added 9 mL of DMF, 4-[N'-(o-Tolylurea)]-phenylacetic acid (132 mg, 0.42 mmol), PyBroP (196 mg, 0.42 mmol), and DIEA (107 mg, 0.84mmol). The contents were shaken for 14 hr at room temp and then drained and washed 3× with DMF, MeOH, and CH₂Cl₂. The compound was then cleaved from the resin and the filtrate was collected and then concentrated in vacuo. The resulting oil was triturated by taking up the oil in MeOH and slowly adding in Et₂O until a precipitate formed. This precipitate was collected and dried in vacuo to afford 52 mg 3' as a white crystalline material.

Example 3

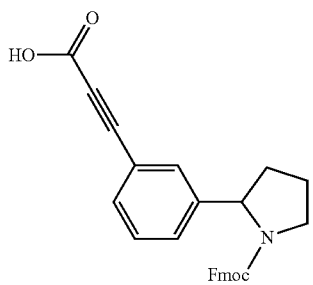

The acetylene (2) was deprotected by placing 2 (0.75 g, 2.1 mmol) in MeOH (25 mL) and adding to this solution KOH (1.4 g). The resulting solution was stirred at room temp for 1 hr. The reaction mixture was then concentrated in vacuo and acidified with 1 N HCl. The resulting aqueous solution was extracted 3×EtOAc, the combined organics were dried over $MgSO_4$, and then concentrated in vacuo to afford 0.56 g of the deprotected acetylene as a brown oil.

The deprotected acetylene (0.56 g, 2.0 mmol) was then placed into THF (50 mL) and cooled to −78° C. LiHMDS (1 M soln, 4.7 mL) was then added dropwise and the reaction was stirred for 30 min. $CO_2$ gas was then bubbled through the reaction mixture for 15 min and the reaction was then poured onto $CO_2$ solid. The reaction was quenched by the addition of 1 N HCl (100 mL) and the aqueous solution was extracted 3×EtOAc, the combined organics were dried over $MgSO_4$, and then concentrated in vacuo to afford the propionic acid (0.71 g) as a white solid.

The alkane acid (0.71 g) was then deprotected by the addition of a 25% $TFA/CH_2Cl_2$ solution and stirred for 2 hr at room temp. The resulting mixture was then concentrated in vacuo and immediately protected by dissolving the deprotected acid in 50% dioxane/water, adding $K_2CO_3$ (15 g), and Fmoc-Cl (1.29 g, 4.9 mmol). This mixture was stirred at room temp for 14 hr and then poured in 1 N HCl (100 mL). The solution was then extracted 3× with EtOAc, dried over $MgSO_4$, and then concentrated in vacuo to afford 4 as a brown oil. The oil was then chromatographed with 5% MeOH/dichloromethane to afford 110 mg of the desired compound.

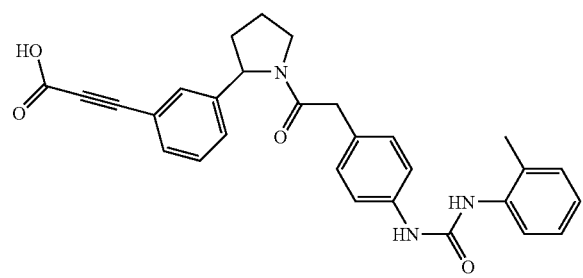

4'

The dried resin (500 mg, 0.14 mmol) was placed into a small shaker vessel. The vessel was then charged with 9 mL of DMF, 4 (184 mg, 0.42 mmol), DIC (102 mg, 0.84 mmol), and DMAP (17 mg, 0.14 mmol). The vessel was subsequently shaken for 16 hr at room temp. The contents were drained and the resin was washed 3× with DMF, MeOH, and $CH_2Cl_2$. The Fmoc group was then removed by the addition of 10 mL of 50% piperidine/DMF to the shaker vessel and shaking for 2 hr at room temp. The resulting amine resin was washed 3× with DMF, MeOH, and $CH_2Cl_2$.

To the above resin was added 9 mL of DMF, 4-[N'-(o-Tolylurea)]-phenylacetic acid (132 mg, 0.42 mmol), PyBroP (196 mg, 0.42 mmol), and DIEA (107 mg, 0.82 mmol). The contents were shaken for 14 hr at room temp and then drained and washed 3× with DMF, MEOH, and $CH_2Cl_2$. The compound was then cleaved from the resin and the filtrate was collected and then concentrated in vacuo. The resulting oil was triturated by taking up the oil in MeOH and slowly adding in $Et_2O$ until a precipitate formed. This precipitate was collected and dried in vacuo to afford 27 mg 4' as a white crystalline material.

Example 4

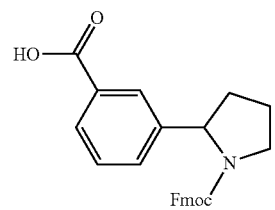

5

The iodide (A) (0.5 g, 1.3 mmol) was placed into THF (20 mL) and cooled to minus 78° C. Butyllithium (2.21 mL, 1.6M soln) was added dropwise and then the cooling bath was removed and gaseous $CO_2$ was bubbled through for 10 min. The reaction mixture was poured onto dry ice and then 1 M HCl (100 mL) was added. The mixture was extracted 3×EtOAc, the combined organics were dried over $MgSO_4$, and then concentrated in vacuo to afford 0.32 g of the benzoic acid as a white crystalline solid.

The benzoic acid (0.32 g, 1.68 mmol) was then deprotected by the addition of a 25% $TFA/CH_2Cl_2$ solution and stirred for 2 hr at room temp. The resulting mixture was then concentrated in vacuo and immediately protected by dissolving the deprotected acid in 50% dioxane/water, adding $K_2CO_3$ (15 g), and Fmoc-Cl (0.44 g, 1.67 mmol). This mixture was stirred at room temp for 14 hr and then poured in 1 N HCl (100 mL). The solution was then extracted 3× with EtOAc, dried over $MgSO_4$, and then concentrated in vacuo to afford 0.38 g 5 as a white crystalline solid.

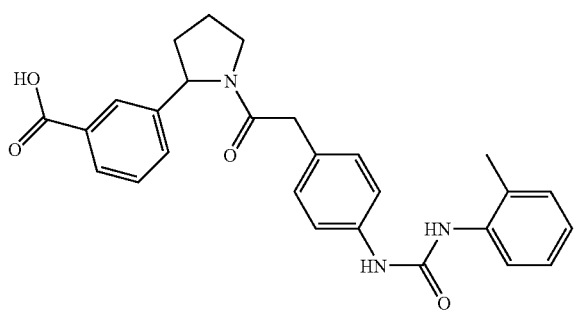

5'

The dried resin (500 mg, 0.14 mmol) was placed into a small shaker vessel. The vessel was then charged with 9 mL of DMF, 5 (173 mg, 0.42 mmol), DIC (102 mg, 0.84 mmol), and DMAP (17 mg, 0.14 mmol). The vessel was subsequently shaken for 16 hr at room temp. The contents were drained and the resin was washed 3× with DMF, MeOH, and $CH_2Cl_2$. The Fmoc group was then removed by the addition of 10 mL of 50% piperidine/DMF to the shaker vessel and shaking for 2 hr at room temp. The resulting amine resin was washed 3× with DMF, MeOH, and $CH_2Cl_2$.

To the above resin was added 9 mL of DMF, 4-[N'-(o-Tolylurea)]-phenylacetic acid (132 mg, 0.42 mmol), PyBroP (196 mg, 0.42 mmol), and DIEA (107 mg, 0.84 mmol). The contents were shaken for 14 hr at room temp and then drained and washed 3× with DMF, MeOH, and $CH_2Cl_2$ The compound was then cleaved from the resin and the filtrate was collected and then concentrated in vacuo. The resulting oil was triturated by taking up the oil in MeOH and slowly adding in $Et_2O$ until a precipitate formed. This precipitate was collected and dried in vacuo to afford 51 mg 5' as a white crystalline material.

Example 5

(E)-4-[2-[1-[4-[N'-(2-methylphenyl)ureido]phenylacetyl]-2-pyrrolidinyl]ethenyl]benzoic acid

6

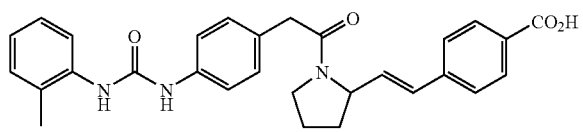

To a cold (minus 78° C.), stirred solution of triethyl 4-phosphonomethylbenzoate (904 mg, 3.01 mmol) in THF (20 mL) was added LiHMDS (1.0 M in THF, 3 mL, 3.00 mmol) and the stirring was continued for 1 hr at the same temp. N-Boc prolinal (500 mg, 2.51 mmol) in THF (10 mL) was added to this mixture and the mixture was allowed to warm to room temp for over 1 hr. After being stirred for 2 hr, the mixture was quenched by water and extracted with EtOAc. The extract was washed with brine (200 mL), dried over $MgSO_4$, and evaporated. The residue was chromatographed on silica-gel with n-hexane-EtOAc (8:1, v/v) as eluent to give 713 mg (82%) ethyl (E)-4-[2-[1-(tert-butoxycarbonyl)-2-pyrrolidinyl]ethenyl]benzoate as a colorless crystalline solid. mp 68–70° C.; IR (KBr) 1710, 1697, 1681 cm$^{-1}$; $^1$H-NMR (CDCl$_3$) δ1.39 (12 H, series of m), 1.77–1.93 (3 H, m), 2.11 (1 H, m), 3.47 (2 H, m), 4.34–454 (total 3 H, m), 6.22 (1 H, m), 6.43 (1 H, d, J=14.2 Hz), 7.39 (2 H, J=8.3 Hz), 7.97 (2 H, d, J=8.3 Hz); MS (FAB) m/z 346 (M$^+$+1); Anal. Calcd for $C_{20}H_{27}NO_4$: C, 69.54; H, 7.88; N, 4.05. Found: C, 69.52; H, 8.08; N, 4.07.

To a stirred solution of ethyl (E)-4-[2-[1-(tert-butoxycarbonyl)-2-pyrrolidinyl]ethenyl]benzoate (700 mg, 2.03 mmol) in $CH_2Cl_2$ (3 mL) was added TFA (3 mL) and the resulting mixture was stirred for 3 hr. The mixture was concentrated and the residue was made basic by the addition of sat. $NaHCO_3$. The mixture was extracted with $CHCl_3$ (2×100 mL). The combined extracts were dried over $Na_2CO_3$ and concentrated in vacuo to give 434 mg (87%) ethyl (E)-4-[2-(2-pyrrolidinyl) ethenyl]benzoate as a brown oil. $^1$H-NMR (CDCl$_3$) δ 1.39 (3 H, t, J=7.3 Hz), 1.52–2.06 (4 H, series of m), 2.93–2.99 (1 H, m), 3.07–3.13 (1 H, m), 3.74 (1 H, q, J=7.3 Hz), 4.37 (2 H, q, J=7.3 Hz), 6.34 (1 H, dd, J=15.6, 7.3 Hz), 6.54 (1 H, d, J=15.6 Hz), 7.41 (2 H, d, J=8.3 Hz), 7.97 (2 H, d, J=8.3 Hz).

A mixture of ethyl (E)-4-[2-(2-pyrrolidinyl)ethenyl]benzoate (434 mg, 1.77 mmol), pentafluorophenyl 4-[N'-(2-methylphenyl)ureido]phenylacetate (797 mg, 1.77 mmol), $Et_3N$ (0.37 mL, 2.66 mmol) in DMF (15 mL) was stirred for 15 hr. The mixture was diluted with EtOAc (300 mL). The solution was washed with brine (2×200 mL), dried over $MgSO_4$, and evaporated off in vacuo. The residue was chromatographed on silica-gel with $CHCl_3$-EtOAc (4:1) as eluent to give 906 mg (q.y.) ethyl (E)-4-[2-[1-[4-[N'-(2-methylphenyl)ureido]phenylacetyl]-2-pyrrolidinyl]ethenyl] benzoate as a brown oil. $^1$H-NMR (CDCl$_3$) δ 1.39 (3 H, t, J=7.3 Hz), 1.83–2.20 (4 H, series of m), 2.24 (3 H, d, J=4.9 Hz), 3.63 (4 H, m), 4.36 (2 H, q, J=7.3 Hz), 4.62 and 4.84 (total 1 H, m), 6.18–6.47 (2 H, m), 7.03–8.02 (14 H, series of m).

A stirred mixture of ethyl (E)-4-[2-[1-[4-[N'-(2-methylphenyl)ureido]phenylacetyl]-2-pyrrolidinyl]ethenyl]benzoate (906 mg, 1.77 mmol) in 0.25 N NaOH (14 mL) and THF (14 mL) was heated under reflux for 3 days. The mixture was poured into ice-1 N HCl (200 mL) and the precipitate was collected with suction. The solid was recrystallized from $CHCl_3$-MeOH-n-hexane to give 453 mg (53%) 6 as a light yellow crystalline powder. mp 165–168° C.; IR (KBr) 3282, 2974, 2663, 2537, 1700, 1685 cm$^{-1}$; $^1$H-NMR (DMSO-d$_6$) δ 1.74–2.12 (4 H, m), 2.24 (3 H, d, J=4.9 Hz), 3.35–3.66 (4 H, m), 4.67–4.74 (1 H, m), 6.25–6.41 (1 H, m), 6.53 (1 H, s), 6.93 (1 H, t, J=7.3 Hz), 7.08–7.92 (12 H, series of m), 9.00 (1 H, m), 12.87 (1 H, br s); MS (FAB) m/z 484 (M$^+$+1); Anal. Calcd for $C_{29}H_{29}N_3O_4 \cdot 0.5H_2O$: C, 70.71; H, 6.14; N, 8.39. Found: C, 70.46; H, 6.07; N, 8.39.

Example 6

4-[2-[1-[4-[N'-(2-methylphenyl)ureido]pheny-lacetyl]-2-pyrrolindinyl]ethyl]benzoic acid

7

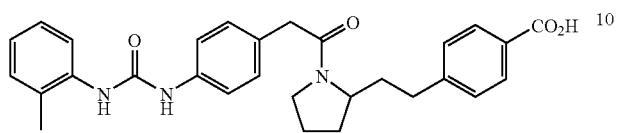

A mixture of (E)-4-[2-[1-[4-[N'-(2-methylphenyl)ureido]phenylacetyl]-2-pyrrolidinyl]ethenyl]benzoate (200 mg, 0.414 mmol) and 5% Pd/C (200 mg) in MeOH (20 mL) was hydrogenated at 1 atm for 1 hr with vigorously stirring. The mixture was filtered and the filtrate was concentrated. The residue was chromatographed on silica-gel with $CHCl_3$-MeOH (4:1) as eluent to give 201 mg (q.y.) 7 as a colorless crystalline powder. mp 180–190° C.; IR (KBr) 3345, 3124, 3060, 3027, 2960, 2927, 2875, 1706, 1672 $cm^{-1}$; $^1$H-NMR (DMSO-$d_6$) δ 1.04–3.96 (total 16 H, series of m), 6.91–7.41 (9 H, m), 7.79–7.90 (3 H, m), 8.23 (1 H, br s), 9.31 (1 H, br s); MS (FAB) m/z 486 ($M^+$+1); Anal. Calcd for $C_{29}H_{31}N_3O_4 \cdot 2.25H_2O$: C, 66.21; H, 6.80; N, 7.99. Found: C, 65.97; H, 6.20; N, 7.72.

Example 7

(S)-4-[2-[1-[4-[N'-(2-methylphenyl)ureido]pheny-lacetyl]pyrrolidinyl]methoxy]benzoic acid

8

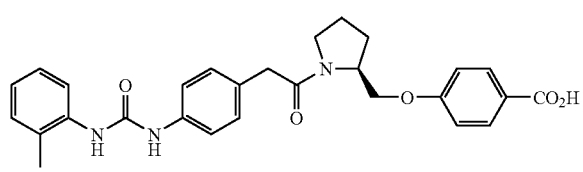

(S)-4-[2-[1-[3-methoxy-4-(N'-phenylureido)pheny-lacetyl]pyrrolidinyl]methoxy]benzoic acid

9

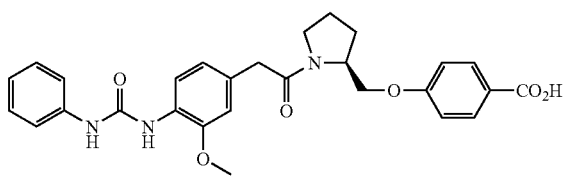

(S)-4-[2-[1-[4-[N'-(2-chlorophenyl)ureido]pheny-lacetyl]pyrrolidinyl]methoxy]benzoic acid

10

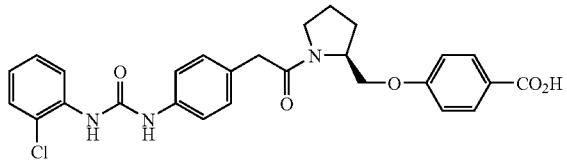

8,9 and 10 To a stirred mixture of Boc-prolinol (3.00 g, 14.9 mmol), ethyl p-hydroxybenzoate (2.40 g, 14.5 mmol), and triphenylphosphine (3.91 g, 14.9 mol) in THF (80 mL) was added dropwise diethyl azodicarboxylate (2.86 g, 16.4 mmol) at room temp. After the addition was completed, the resulting mixture was heated under reflux for 2 hr. After cooling, the mixture was concentrated in vacuo. The residue was dissolved in EtOAc and washed successively with 1 N NaOH, water, brine. The EtOAc layer was dried over $MgSO_4$ and evaporated in vacuo. The residue was purified by column chromatography on silica gel with EtOAc-n-hexane (1:4, v/v) as eluent to give 4.88 g (93%) ethyl (S)-4-(1-tert-butoxycarbonyl-2-pyrrolidinyl)methoxybenzoate as an oil.

To the above ethyl (S)-4-(1-tert-butoxycarbonyl-2-pyrrolidinyl)methoxybenzoate was added MeOH (100 mL) and 1 N NaOH (50 mL). The mixture was stirred for 15 hr at room temp. After removal of MeOH under a reduced pressure, water (50 mL) was added to the residual solution. The aqueous solution was washed with $Et_2O$ (×2) and then acidified by the addition of 1 N HCl. The mixture was extracted with EtOAc., washed with water, brine, dried over $MgSO_4$ and evaporated in vacuo to afford 4.26 g (95%) (S)-4-(1-tert-butoxycarbonyl-2-pyrrolidinyl) methoxybenzoic acid as a crystalline solid.

To the above (S)-4-(1-tert-butoxycarbonyl-2-pyrrolidinyl)methoxybenzoic acid was added $CH_2Cl_2$ (10 ml) and TFA (10 mL). The mixture was stirred at room temp for 1 hr $Et_2O$ was added to the mixture and resulting solid was collected. The solid was dissolved in water (100 mL), dioxane (50 mL) and $NaHCO_3$ (4.4 g). Fmoc-Cl (3.34 g, 12.9 mmol) was added to the solution, and the resulting mixture was stirred for 20 hr at room temp. The mixture was washed with $Et_2O$ (×2) and aqueous layer was separated. The layer was acidified by the addition of 1 N HCl. The mixture was extracted with EtOAc. The extract was washed with water, brine, dried over $MgSO_4$ and evaporated in vacuo to afford 5.36 g (91%) (S)-4-(1-Fmoc-2-pyrrolidinyl) methoxybenzoic acid as a viscous oil, which was crystallized on standing.

Wang resin (0.71 mmol/g, 400 mg) was suspended in a solution of (S)-4-(1-Fmoc-2-pyrrolidinyl) methoxybenzoic acid (500 mg, 1.13 mol), DMAP (35 mg, 0.29 mmol), HOBt (40 mg, 0.30 mmol) and DIC (0.45 mL, 2.9 mmol) in a mixture of DMF (3 mL) and $CH_2Cl_2$ (7 mL). The mixture was shaken for 20 hr and drained. The resin was washed with DMF (×3), MeOH (×3), $CH_2Cl_2$ (×3) and dried under a reduced pressure to give 522 mg of resin, which was used to prepare 8, 9 and 10.

8 To the above resin (115 mg) was added a solution of piperidine-DMF (50% v/v, 4 mL) and the mixture was shaken for 1 hr. The resin was washed with DMF (×3), MeOH (×3), CH$_2$Cl$_2$ (×3). To the resin was added DMF (4 mL), CH$_2$Cl$_2$ (2 mL), 4-[N'-(2-methylphenyl)ureido]phenylacetic acid (70 mg, 0.25 mmol), PyBrop (115 mg, 0.25 mmol) and DIEA (0.13 mL, 0.75 mmol). The mixture was shaken for 21 hr and drained. The resin was washed with DMF (×3), MeOH (×3), CH$_2$Cl$_2$ (×3). To the resin was added a solution of TFA in CH$_2$Cl$_2$ (50% v/v, 4 mL) and the mixture was shaken for 2 hr. The mixture was filtered and the filtrate was concentrated in vacuo. The residue was purified by Sep-Pak column. After removal of the solvent, Et$_2$O was added to the residue and resulting solid was collected to afford 25 mg 8 as a pale yellow crystalline material. MS (FAB) m/z 488 (M$^+$+1)

9 To the above resin (60 mg) was added a solution of piperidine in DMF (50% v/v, 3 mL) and the mixture was shaken for 2 hr. The resin was washed with DMF (×3), MeOH (×3), CH$_2$Cl$_2$ (×3). To the resin was added DMF (2 mL), CH$_2$Cl$_2$ (1 mL) 3-methoxy-4-(N'-phenylureido) phenylacetic acid (40 mg, 0.13 mmol), PyBrop (60 mg, 0.13 mmol) and DIEA (0.060 mL, 0.34 mmol). The mixture was shaken for 40 hr and drained. The resin was washed with DMF (×3), MeOH (×3), CH$_2$Cl$_2$ (×3). To the resin was added a solution of TFA in CH$_2$Cl$_2$ (30% v/v, 3 mL) and the mixture was shaken for 5 hr. The mixture was filtered and the filtrate was concentrated in vacuo. The residue was purified by Sep-Pak column. After removal of the solvent, Et$_2$O was added to the residue and the solid was collected to afford 8 mg 9 as a crystalline solid. MS (FAB) m/z 504 (M$^+$+1)

10 To the above resin (637 mg) was added a solution of piperidine in DMF (50% v/v, 20 mL) and the mixture was shaken for 4 hr. The resin was washed with DMF (×3), MeOH (×3), CH$_2$Cl$_2$ (×3). To the resin was added DMF (12 mL), CH$_2$Cl$_2$ (8 mL), 4-(Fmoc-amino)phenylacetic acid (530 mg, 1.42 mmol), PyBrop (660 mg, 1.43 mmol) and DIEA (0.62 mL, 3.56 mmol). The mixture was shaken for 60 hr and drained. The resin was washed with DMF (×3), MeOH (×3), CH$_2$Cl$_2$ (×3) and dried under a reduced pressure to afford 617 mg of the resin. 57 mg of this resin was added Piperidine in DMF (40% v/v, 2 mL). The mixture was shaken for 1 hr. The resin was washed with DMF (×3), MeOH (×3), CH$_2$Cl$_2$ (×3). 2-chlorophenyl isocyanate (0.050 mL, 0.41 mmol) was added to a suspension of resin in THF (1 mL) and CH$_2$Cl$_2$ (1 mL). The mixture was shaken for 20 hr and drained. The resin was washed with DMF (×3), MeOH (×3), CH$_2$Cl$_2$ (×3). To the resin was added a solution of TFA in CH$_2$Cl$_2$ (25% v/v, 2 mL) and the mixture was shaken for 1.5 hr. The mixture was filtered and the filtrate was concentrated in vacuo. The residue was purified by Sep-Pak column. After removal of the solvent, Et$_2$O was added to the residue and the solid was collected to afford 2 mg 10 as a crystalline solid. MS (FAB) m/z 508

Example 8

(S)-3-[2-[1-[3-methoxy-4-(N'-phenylureido)phenylacetyl]pyrrolidinyl]methoxy]phenylacetic acid

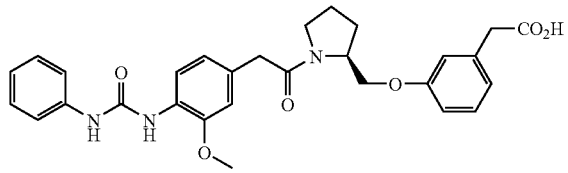

11

(S)-3-[2-[1-[4-[N'-(2-methylphenyl)ureido]phenylacetyl]pyrrolidinyl]methoxy]phenylacetic acid

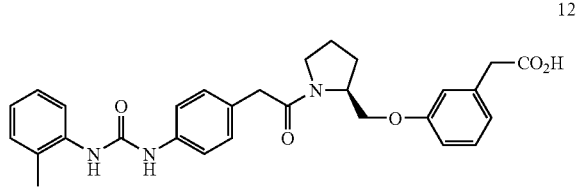

12

11 and 12 To a stirred mixture of Boc-prolinol (3.51 g, 17.5 mmol), methyl m-hydroxyphenylacetate (2.90 g, 17.5 mmol), triphenylphosphine (4.60 g, 17.6 mol) in THF (50 mL) was added dropwise diethyl azodicarboxylate (3.05 g, 17.5 mmol) at room temp. After the addition was completed, the mixture was heated under reflux for 3 hr. After cooling, the mixture was concentrated in vacuo. The residue was dissolved in EtOAc, washed successively with 1 N NaOH, water, brine and dried over MgSO$_4$. After removal of the solvent, the residue was purified by column chromatography on silica-gel with EtOAc-hexane (1:4, v/v) as eluent to give 5.49 g (90%) methyl (S)-3-(1-tert-butoxycarbonyl-2-pyrrolidinyl) methoxyphenylacetate as an oil.

A mixture of the above methyl (S)-3-(1-tert-butoxycarbonyl-2-pyrrolidinyl) methoxy phenylacetate in MeOH (60 mL) and 1 N NaOH (20 mL) was stirred for 8 hr at room temp. After removal of the solvent under a reduced pressure, water (50 mL) was added to the residue. The mixture was extracted with Et$_2$O (×2), and the aqueous layer was acidified by the addition of 1 N HCl. The mixture was extracted with EtOAc. The extract was washed with water, brine, dried over MgSO$_4$ and then concentrated in vacuo to afford 4.43 g (88%) (S)-3-(1-tert-butoxycarbonyl-2-pyrrolidinyl)methoxy phenylacetic acid as a viscous oil.

A mixture of the above (S)-3-(1-tert-butoxycarbonyl-2-pyrrolidinyl) methoxyphenyl acetic acid in CH$_2$Cl$_2$ (10 mL) and TFA (10 mL) was stirred for 1 hr at room temp. Et$_2$O was added to the mixture and allowed to stand. Upper layer was removed by decantation to give an oil. A mixture of this oil in water (100 mL), dioxane (30 mL) and NaHCO$_3$ (6.0 g) was added Fmoc-Cl (2.86 g, 11.1 mmol) and the mixture was stirred for 20 hr at room temp. The mixture was extracted with Et$_2$O (×2), and the aqueous layer was acidified by the addition of 1 N HCl. The mixture was extracted with EtOAc. The extract was washed with water, brine, dried over MgSO₄ and concentrated in vacuo to afford 5.08 g (81%) (S)-3-(1-Fmoc-2-pyrrolidinyl)methoxyphenylacetic acid as a viscous oil.

Wang resin (0.71 mmol/g, 400 mg) was suspended in a solution of (S)-3-(1-Fmoc-2-pyrrolidinyl) methoxyphenylacetic acid (520 mg, 1.14 mol), DMAP (35 mg, 0.29 mmol), HOBt (40 mg, 0.30 mmol) and DIC (0.45 mL, 2.9 mmol) in a mixture of DMF (3 mL) and CH₂Cl₂ (7 mL). The mixture was shaken for 20 hr and drained. The resin was washed with DMF (×3), MeOH (×3), CH₂Cl₂ (×3) and dried under a reduced pressure to give 593 mg of resin, which was used for the preparation of 11 and 12.

11 A mixture of the above resin (70 mg) in piperidine-DMF (40% v/v, 3 mL) was shaken for 1 hr. The resin was washed with DMF (×3), MeOH (×3), CH₂Cl₂ (×3). To the resin was added DMF (1.5 mL), CH₂Cl₂ (1.5 mL) 3-methoxy-4-(N'-phenylureido) phenylacetic acid (42 mg, 0.14 mmol), PyBrop (70 mg, 0.15 mmol) and DEA (0.065 mL, 0.37 mmol). The mixture was shaken for 15 hr and drained. The resin was washed with DMF (×3), MeOH (×3), CH₂Cl₂ (×3). To the resin was added a solution of TFA in CH₂Cl₂ (25% v/v, 2 mL) and the mixture was shaken for 3 hr. The mixture was filtered and the filtrate was concentrated in vacuo. The residue was purified by Sep-Pak column. After removal of the solvent, Et₂O was added to the residue and the solid was collected to afford 8 mg 11 as a crystalline solid. MS (FAB) m/z 518 (M⁺+1)

12 A mixture of the above resin (70 mg) in piperidine—DMF (40% v/v, 3 mL) was shaken for 1 hr. The resin was washed with DMF (×3), MeOH (×3), CH₂Cl₂ (×3). To the resin was added DMF (1.5 mL), CH₂Cl₂ (1.5 mL), 4-[N'-(2-methylphenyl)ureido]phenylacetic acid (40 mg, 0.14 mmol), PyBrop (70 mg, 0.15 mmol) and DIEA (0.065 mL, 0.37 mmol). The mixture was shaken for 15 hr and drained. The resin was washed with DMF (×3), MeOH (×3), CH₂Cl₂ (×3). A mixture of the resin in TFA-CH₂Cl₂ (25% v/v, 2 mL) was shaken for 3 hr. The mixture was filtered and the filtrate was concentrated in vacuo. The residue was purified by Sep-Pak column.

After removal of the solvent, Et₂O was added to the residue and the solid was collected to afford 11 mg 12 as a crystalline solid. MS (FAB) m/z 502 (M⁺+1)

Example 9

4-[2-[1-[3-methoxy4-(N'-phenylureido)phenylacetyl]-2-pyrrolidinyl]ethynyl]benzoic acid

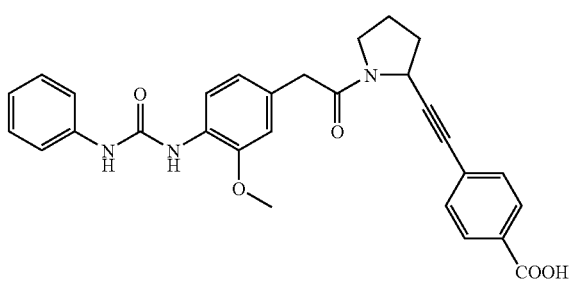

13

To a stirred cold (minus 50°) solution of N-boc-prolinal (5.98 g, 30 mmol) and PPh₃ (62.95 g, 240 mmol) in CH₂Cl₂ (200 mL) was slowly added a solution of CBr₄ (39.80 g, 120 mmol) in CH₂Cl₂ (50 mL), and the stirring was continued for 1 hr at 0° C. To this mixture was added sat. NaHCO₃ and the mixture was extracted with CHCl₃. The extract was washed with H₂O, dried over MgSO₄, and evaporated. The residue was chromatographed on silica-gel with CHCl₃ and n-hexane-AcOEt (4:1, v/v) as eluent to give 7.84 g (74%) 1-(tert-butoxycarbonyl)-2-(2,2-dibromoethenyl) pyrrolidine as colorless plates. mp 61–63; IR (KBr) 1693 cm⁻¹; ¹H-NMR (CDCl₃) δ 1.46 (9 H, s), 1.72–2.19 (4H, m), 3.35–3.45 (2H, m), 4.35 (1H, br s), 6.36 (1H, br s); MS (FAB) m/z 352, 354, 356, 358; Anal. Calcd for C₁₁H₁₇NO₂Br₂: C, 37.21; H, 4.83; N, 3.94. Found: C, 37.14; H, 4.83; N, 4.00.

To a stirred cold (minus 78° C.) solution of 1-(tert-butoxycarbonyl)-2-(2,2-dibromoethenyl) pyrrolidine (7.81 g, 22 mmol) in THF (200 mL) was added n-BuLi (1.59 M in hexane, 28 mL, 44 mmol) over 10 min, and the stirring was continued for 2 hr at the same temp. The reaction was quenched by the addition of sat. NH₄Cl and extracted with EtOAc. The extract was washed with brine, dried over MgSO₄, and evaporated. The residue was chromatographed on silica-gel with n-hexane-AcOEt (10:1, v/v) as eluent to give 4.15 g (97%) 1-(tert-butoxycarbonyl)-2-ethynyl pyrrolidine as a light yellow oil. ¹H-NMR (CDCl₃) δ 1.48 (9 H, s), 1.82–2.21 (4 H, m), 3.30–3.45 (2 H, m), 4.41–4.52 (1 H, m).

A suspension of ethyl 4-iodobenzoate (1.7 mL, 10 mmol), Pd(PPh₃)₄ (578 mg, 0.5 mmol), and CuI (190 mmol, 1 mmol) in i-Pr₂NH (20 mL) was stirred for 0.5 hr under N₂. To this mixture was added a solution of 1-(tert-butoxycarbonyl)-2-ethynylpyrrolidine (1.95 g, 10 mmol) in i-Pr₂NH (20 mL) for over 10 min. After stirring for 3 hr at room temp, the mixture was poured into H₂O and extracted with EtOAc. The extract was washed with brine, dried over MgSO₄, and evaporated. The residue was chromatographed on silica-gel with n-hexane-AcOEt (10:1, v/v) as eluent to give 2.77 g (81%) 1-(tert-butyloxycarbonyl)-2-(2-(4-ethoxycarbonylphenyl)ethynyl) pyrrolidine as a colorless oil. ¹H-NMR (CDCl₃) δ 1.37 (3 H, t, J=6.8 Hz), 1.49 (9 H, s), 1.85–2.12 (4 H, m), 3.37–3.51 (2 H, m), 4.37 (2 H, q, J=6.8 Hz), 4.54–4.77 (1 H, m), 7.44 (2 H, d, J=7.8 Hz), 7.96 (2 H, d, J=7.8 Hz)

To a stirred solution of 1-(tert-butoxycarbonyl)-2-[2-(4-ethoxycarbonylphenyl) ethynyl]pyrrolidine (2.75 g, 8 mmol) in CH₂Cl₂ (5 mL) was added TFA (5 mL), and the resulting mixture was stirred overnight. The mixture was concentrated in vacuo and made basic with sat. NaHCO₃ and extracted with CHCl₃. The extract was washed with brine, dried over MgSO₄, evaporated to give 1.95 g (q.y.) 2-[2-(4-ethoxycarbonylphenyl) ethynyl]pyrrolidine as a light yellow oil. ¹H-NMR (CDCl₃) δ 1.38 (3 H, t, J=6.8 Hz), 1.82–2.16 (4 H, m), 3.01–3.48 (2 H, m), 4.00–4.11 (1 H, m), 4.37 (2H, q, J=6.8 Hz), 4.54–4.77 (1 H, m), 7.44–7.46 (2 H, m), 7.95–7.97 (2 H, m).

A mixture of 3-methoxy-4-(N'-phenylureido)phenylacetic acid (180 mg, 0.6 mmol), 2-(2-(4-ethoxycarbonylphenyl) ethynyl)pyrrolidine (146 mg, 0.6 mmol), EDC (173 mg, 0.9 mmol), DMAP (73 mg, 0.6 mmol), and cat. HOBt in DMF (10 mL) was stirred overnight. The mixture was poured into 1 N HCl and the solid was collected with suction. The residue was dissolved in CHCl₃ and dried over MgSO₄. After removal of the solvent, the residue was chromatographed on silica-gel with CHCl₃-MeOH (10:1, v/v) as eluent to give 192 mg (61%) ethyl 4-[2-[1-[3-methoxy-4-(N'-phenylureido)phenylacetyl]-2-pyrrolidinyl]ethynyl] benzoate as a light yellow amorphous solid. ¹H-NMR (CDCl₃) δ 1.38 (3 H, t, J=6.8 Hz), 1.98–2.24 (4 H, m), 3.48–3.89 (2 H, m), 3.53 (2 H, s), 3.62 (3 H, s), 4.33–4.40 (2 H, m), 4.78–5.04 (1 H, m), 6.77–8.00 (14 H, m).

To a stirred solution of ethyl 4-[2-[1-[3-methoxy-4-(N'-phenylureido) phenylacetyl]-2-pyrrolidinyl]ethynyl]benzoate (184 mg, 0.35 mmol) in THF (5 mL) was added 0.25 N NaOH (4 mL). The resulting mixture was stirred overnight. The mixture was poured into H$_2$O and made acidic by the addition of 1 N HCl (1 mL). The solid was collected with suction and dissolved in CHCl$_3$. The solution was dried over MgSO$_4$ and evaporated. The residue was recrystallized from CHCl$_3$-n-hexane to give 65 mg (37%) 13 as a white crystalline powder. mp 154–157; IR (KBr) 3346, 2952, 2615, 1712, 1693 cm$^{-1}$; $^1$H-NMR (CDCl$_3$) δ 1.92–2.29 (4 H, m), 3.32–3.82 (2 H, m), 3.78 (2 H, s), 3.80 (3 H, s), 4.87–5.11 (1 H, m), 6.77–9.26 (14 H, m), 13.10 (1 H, br s); MS (FAB) m/z 498 (M$^+$+1).

Example 10

4-[2-[1-[3-methoxy-4-[N'-(2-methylphenyl)ureido] phenylacetyl]-2-pyrrolidinyl]ethynyl]benzoic acid

14

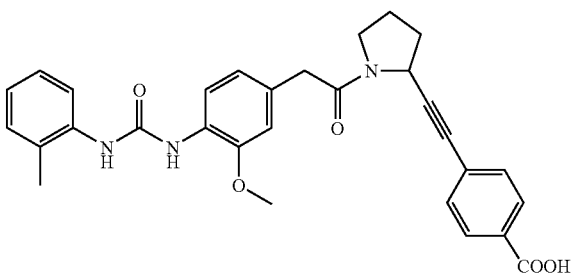

A mixture of 3-methoxy-4-[N'-(2-methylphenyl)ureido] phenylacetic acid (1.45 g, 4.6 mmol), 2-(2-(4-ethoxycarbonylphenyl)ethynyl)pyrrolidine (1.12 g, 4.6 mmol), EDC 1.32 g (6.9 mmol), DMAP (562 mg, 4.6 mmol) in DMF (20 ml-) was stirred overnight. The mixture was poured into 1 N HCl and the solid was collected with suction. The solid was dissolved in CHCl$_3$ and dried over MgSO$_4$. After removal of the solvent, the residue was chromatographed on silica-gel with CHCl$_3$-MeOH (100:1, v/v) as eluent to give 2.20 g (89%) ethyl 4-[2-[1-[3-methoxy-4-(N'-(2-methylphenyl) ureido]phenylacetyl]-2-pyrrolidinyl]ethynyl]benzoate as a white amorphous solid.

$^1$H-NMR (CDCl$_3$) δ 1.37–1.41 (3 H, m), 1.94–2.22 (4 H, m), 2.29 (3 H, s), 3.41–3.89 (2 H, m), 3.62 (3 H, s), 3.69 (2 H, s), 4.34–4.40 (2 H, m), 4.72–5.01 (1 H, m), 6.33 (1 H, br s), 6.80–8.06 (12 H, m).

To a stirred solution of ethyl 4-[2-[1-[3-methoxy4-(N'-(2-methylphenyl)ureido]phenyl acetyl]-2-pyrrolidinyl]ethynyl] benzoate (2.16 g, 4 mmol) in THF (30 mL) was added 0.25 N NaOH (32 mL) and the stirring was continued overnight. The mixture was poured into H$_2$O and acidified by the addition of 1 N HCl (8 mL). The resulting precipitate was collected with suction and dissolved in CHCl$_3$. The solution was dried over MgSO$_4$ and evaporated. The residue was recrystallized from CHCl$_3$-n-hexane to give 555 mg (27%) 14 as a white crystalline powder. mp 161–164; IR (KBr) 3338, 2954, 2875, 1707, 1691 cm$^{-1}$; $^1$H-NMR (CDCl$_3$) δ 1.96–2.10 (4 H, m), 2.24 (3 H, s), 3.32–3.81 (2 H, m), 3.62 (2 HI s), 3.81 (3 H, s), 4.87–5.10 (1 H, m), 6.76–8.58 (13 H, m); MS (FAB) m/z 512 (M$^+$+1)

Example 11

4-[2-[1-[3-methoxy-4-[N'-(2-methylphenyl)ureido] phenylacetyl]-2-pyrrolidinyl]ethynyl]phenylacetic acid

15

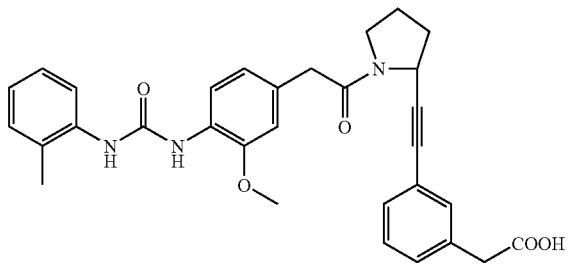

A mixture of 3-methoxy4-[N'-(2-methylphenyl)ureido] phenylacetic acid (141 mg, 0.45 mmol), 2-[2-(3-ethoxycarbonylmethylphenyl)ethynyl]pyrrolidine (116 mg, 0.45 mmol), EDC (130 mg, 0.68 mmol), DMAP (55 mg, 0.45 mmol), cat. HOBt in DMF (10 mL) was stirred overnight. The mixture was poured into 1 N HCl and the solid was collected by filtration. The solid was dissolved in CHCl$_3$, dried over MgSO$_4$, and evaporated. The residue was chromatographed on silica -gel with CHCl$_3$-MeOH (100:1 v/v) as eluent to give an oil, which was dissolved in THF (5 mL). 0.25 N NaOH (4 mL) was added to this solution with stirring. After stirring overnight, the mixture was poured into 1 N HCl (20 mL). The resulting precipitate was collected with suction and dissolved in CHCl$_3$ The solution was dried over MgSO$_4$ and evaporated. The residue was chromatographed on silica-gel with CHCl$_3$-MeOH (5:1, v/v) as eluent to give 92 mg (39%) 15 as a white amorphous solid. $^1$H-NMR (CDCl$_3$) δ 1.96–2.18 (7 H, m), 3.50–3.88 (9 H, m), 4.78–4.98 (2 H, m), 6.72–7.99 (14 H, m); MS (FAB) m/z 526. (M$^+$+1).

Example 12

4-[1-[4-[N'-(2-methylphenyl)ureido]phenylacetyl]-2-pyrrolidinylmethoxy]isophthalic acid

16

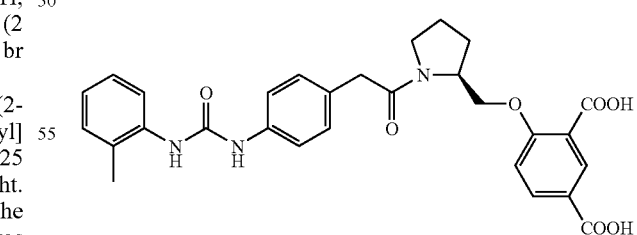

To a stirred solution of pentafluorophenyl ester of 4-[N'-(2-methylphenyl)ureido]phenylacetic acid (2.32 g, 5.15 mmol), dimethyl (S)-4-(2-pyrrolidinylmethoxy)isophthalate (1.51 g, 5.15 mmol) in DMF (20 mL) was added Et$_3$ N (1.0 mL, 6.65 mmol), and the mixture was stirred overnight. The resulting mixture was diluted with EtOAc. The solution was washed with brine, dried over MgSO$_4$, and evaporated off in vacuo. The residue was purified by column chromatography on silica-gel with CHCl$_3$-MeOH (10:1, v/v) as eluent to give 1.58 g (55%) dimethyl 4-[1-[4-[N'-(2-methylphenyl)ureido] phenylacetyl]-2-pyrrolidinylmethoxy]isophthalate as a yellow crystalline solid. $^1$H-NMR (CDCl$_3$) δ 1.87–2.25 (m, total 7 H), 3.50–3.65 (m, 4 H), 3.85 (s, 3 H), 3.89 (s, 3 H), 4.18–4.31 (m, 2 H), 4.44 (m, 1 H), 6.95–8.45 (m, total 13 H).

To a stirred solution of dimethyl 4-[1-[4-[N'-(2-methylphenyl)ureido]phenylacetyl]-2-pyrrolidinylmethoxy] isophthalate (1.56 g, 2.79 mmol) in THF (30 mL) was added 0.25 N NaOH (20 mL), and the reaction mixture was heated under reflux overnight. The resulting mixture was poured into 1 N HCl, and solid was collected. The crude solid was washed with Et$_2$O to give 574 mg (39%) 16 as a yellow amorphous solid. IR (KBr) 1710 cm$^-$; $^1$H-NMR (DMSO-d$_6$) δ 1.83–2.18 (m, 4 H), 2.24 (s, 3 H), 3.36–4.28 (m, 8 H) 6.91–9.02 (series of m, total 13 H), 12.89 (br s, 1 H); MS (FAB) m/z 532 (M$^+$+1).

Example 13

4-[2-[1-[3-methoxy-4-[N'-(2-methylphenyl)ureido] phenylacetyl]-2-pyrrolidinyl]ethenyl]benzoic acid

17

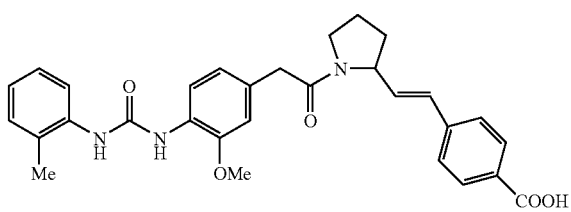

To a stirred solution of the 4-[2-[2-(N-tert-butoxycarbonyl)pyrrolydinylethenyl]benzonitrile (2.26 g, 7.57 mmol) in CH$_2$Cl$_2$ (23 mL) was added dropwise a 1.5M solution of diisopropylaluminum hydride (toluene solution) (6.06 mL, 9.09 mmol) at 0° C. for over 15 min.

The resulting solution was stirred for 3 hr at 0° C. The solution was quenched by the addition of sat.NH$_4$Cl. The resulting mixture was filtered through Celite, and the filtrate was extracted with EtOAc. The filtrate was washed with brine, dried over Na$_2$SO$_4$ and evaporated in vacuo to afford 1.89 g (83%) 4-[2-[2-(N-tert-butoxy carbonyl)pyrrolidinyl] ethenyl]benzaldehyde as a yellow syrup.

To a stirred solution of NaOH (1.00 g, 25.1 mmol) in water(10 mL) was added a solution of AgNO$_3$ (2.13 g, 12.5 mmol) in CH$_3$CN (10 mL) at 0° C. for over 0.5 hr. To the stirred above mixture was added dropwise a solution of 4-[2-[2-(N-tert-butoxycarbonyl) pyrrolydinyl]ethenyl]benzaldehyde (1.89 g, 6.27 mmol) in CH$_3$CN (10 mL) at 0° C. for over 20 min. After the resulting mixture was stirred for a further 3 hr at room temp. The mixture was filtered with suction, and then washed with hot water. After the filtrate was washed with EtOAc, the aqueous layer was acidified by carefully adding 1 N HCl, and then extracted with CHCl$_3$. The extract was dried over Na$_2$SO$_4$ and evaporated in vacuo to afford 0.700 g (35% for 2 steps) 4-[2-[2-(N-tert-butoxycarbonyl) pyrrolidinyl]ethenyl]benzoic acid as a pale yellow crystalline material.

To a stirred solution of 4-[2-(2-(N-tert-butoxycarbonyl) pyrrolidinyl) ethenyl]benzoic acid (0.700 g, 2.21 mmol) in MeOH-benzene(1:4, v/v, 30 mL) was added dropwise a 2 M-n-hexane solution of TMSCHN$_2$ (1.32 mL, 2.65 mmol) at room temp. After the solution was stirred for 0.5 hr at room temp, the solution was evaporated in vacuo. The resulting oily residue was chromatographed on silica-gel with EtOAc-n-hexane(1:6, v/v) as eluent to afford 0.64 g (88%) methyl 4-12-[2-(N-tert-butoxycarbonyl) pyrrolidinyl]ethenyl]benzoic as a pale yellow crystalline material.

To a stirred solution of methyl 4-[2-[2-(N-tert-butoxycarbonyl)pyrrolidinyl]ethenyl]benzoate (0.64 g, 1.93 mmol) in CH$_2$Cl$_2$ (5 mL) was added TFA (5 mL) at room temp. After the mixture was stirred for 1 hr at room temp, the mixture was evaporated in vacuo, The residue was treated with sat. NaHCO$_3$ and extracted with CHCl$_3$. The extract was dried over Na$_2$SO$_4$ and evaporated in vacuo to afford 0.45 g (100%) methyl 4-[2-(2-pyrrolidinyl)ethenyl]benzoate as a yellow crystalline material.

To a stirred mixture of 3-methoxy-4-[N'-(2-methylphenyl)ureido]phenylacetic acid (285 mg, 0.906 mmol), methyl 4-[2-(2-pyrrolydinyl)ethenyl]benzoate (210 mg, 0.906 mmol) in DMF (4 mL) was added 1-ethyl-3-(3dimethylaminopropyl)carbodiimide (EDC) (209 mg, 1.09 mmol), 1-hydroxybenzotriazole (HOBt) (147 mg, 1.09 mmol) and 4-dimethylaminopyridine (DMAP) (11 mg, 0.0906 mmol) at room temp. After the resulting mixture was stirred for 48 hr at room temp, the mixture was poured into ice-1 N HCl and extracted with EtOAc. The extract was dried over Na$_2$SO$_4$ and evaporated in vacuo. The residue was chromatographed on silica-gel with acetone-toluene (1:4 to 1:1, v/v) as eluent to afford 0.47 g (98%) methyl 4-[2-[1-[3-methoxy-4-[N'-(2-methylphenyl)ureido]phenylacetyl]-2-pyrrolidinyl]ethenyl] benzoate as a white crystalline material.

To a stirred solution of methyl 4-[2-[1-[3-methoxy-4-[N'-(2-methylphenyl) ureido]phenyl acetyl]-2-pyrrolidinyl]ethenyl]benzoate (0.47 g, 0.891 mmol) in THF (5 mL) was added 0.25 N NaOH (5.36 mL). The resulting mixture was stirred at room temp for 20 hr. The mixture was acidified with 1 N HCl. The mixture was extracted with EtOAc. The extract was washed with brine, dried over Na$_2$SO$_4$ and evaporated in vacuo to afford 430 mg (94%) 17 as a white crystalline material. $^1$H-NMR (400 MHz, DMSO-d$_6$) δ 1.78–2.13 (4H, m), 2.50 (3H, s), 3.44–3.68 (4H, m), 3.75 and 3.82 (3H, s), 4.71 (1H, m), 6.26–8.59 (15H, m).

Example 14

4-[2-[1-[3-methoxy-4-(N'-phenylureido)phenylacetyl]-2-pyrrolidinyl]ethenyl]benzoic acid

18

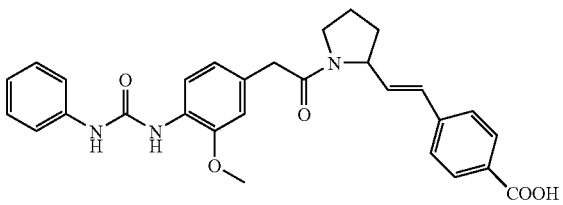

To a stirred solution of 3-methoxy-4-(N'-phenylureido) phenylacetic acid (305 mg, 1.01 mmol), methyl 4-[2-(2-pyrrolydinyl)ethenyl]benzoate (235 mg, 1.01 mmol) in DMF (4 mL) was added 1-ethyl-3-(3-dimethylaminopropyl)carbodiimide (232 mg, 1.21 mmol), 1-hydroxybenzotriazole (HOBt) (164 mg, 1.21 mmol), and 4-dimethylaminopyridine (DMAP) (12 mg, 0.101 mmol) at room temp. After the mixture was stirred for 48 hr, the mixture was acidified by the addition of 1 N HCl. The mixture was extracted with EtOAc. The extract was washed with brine, dried over Na₂SO₄ and evaporated in vacuo to give an oily residue. The residue was chromatographed on silica-gel with acetone:toluene (1:4 to 1:1, v/v) as eluent to afford 0.43 g (83%) methyl 4-[2-[1-[3-methoxy4-(N'-phenylureido) phenylacetyl]-2-pyrrolidinyl]ethenyl]benzoate acid as a white crystalline material.

To a stirred solution of methyl 4-[2-[1-[3-methoxy-4-(N'-phenylureido) phenylacetyl]-2-pyrrolidinyl]ethenyl]benzoate (0.43 g, 0.837 mmol) in THF (5 mL) was added a solution of 0.25 N NaOH (5.04 mL) at room temp. After the resulting mixture was stirred for 20 hr, the mixture was acidified by the carefully addition of 1 N HCl. The mixture was extracted with EtOAc. The extract was washed with brine, dried over Na₂SO₄ and evaporated in vacuo to afford 397 mg (95%) 18 as a white crystalline material. $^1$H-NMR (400 MHz, DMSO-d₆) δ 1.78–2.13 (4H, m), 3.17–3.68 (4H, m), 3.74, 3.82 (3H, s), 4.71 (1H, m), 6.27–9.28 (16H, m).

Example 15

4-[2-[1-[3-methoxy-4-[N'-(2-methylphenyl)ureido]phenylacetyl]-2-pyrrolidinyl]ethyl]benzoic acid

19

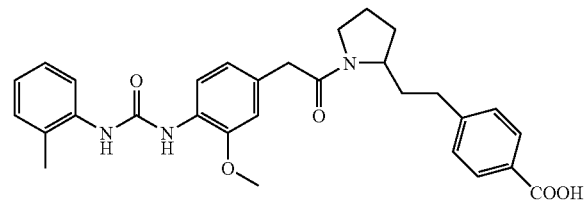

A mixture of 4-[2-[1-[3-methoxy-4-[N'(2-methylphenyl)ureido]phenylacetyl]-2-pyrrolidinyl]ethenyl]benzoic acid (184 mg, 0.358 mmol) and 5% Pd—C(368 mg) in MeOH was hydrogenated in an atmospheric pressure at room temp. After the mixture was stirred for 21 hr at room temp, insoluble catalyst was filtered off and the filtrate was evaporated in vacuo. The residue was chromatographed on silica-gel with MeOH—CHCl₃ (1:4 to 1:3, v/v) as eluent to afford 123 mg (66%) 19 as a white crystalline material. $^1$H-NMR (DMSO-d₆) δ 1.55–2.03 (m, 6H), 2.24 (s, 3H), 2.60 (m, 2H), 3.17–3.59 (m, 4H), 3.83 (s, 3H), 3.97 (m, 1H), 6.61–8.57 (m, 13H); MS (FAB) m/z 516 (M⁺+1).

Example 16

3-[1-[3-methoxy-4-[N'-(2-methylphenyl)ureido]phenylacetyl]-2-pyrrolidinyl]methylthiobenzoic acid

20

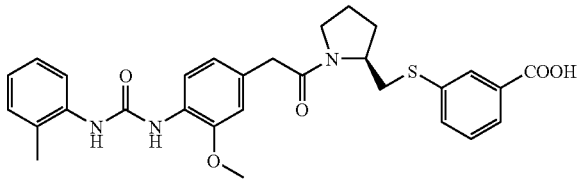

To a solution of m-iodophenol (20.0 g, 90.9 mmol) in DMF (200 mL) was added 1,4-diazabicyclo[2,2,2]octane (20.4 g, 181.8 mmol) and dimethylthiocarbamoyl chloride (16.9 g, 136.4 mmol). The resulting cloudy solution was stirred for 0.5 hr at 35° C. and then heated at 75° C. for 0.5 hr. After cooling, 300 mL of water was added to the mixture. The solid was collected, washed with water and dried under a reduced pressure to give 27.63 g (99%) O-m-iodophenyl dimethylthio carbamate as a pale yellow crystalline powder. IR(KBr) 1540, 1463, 1278, 1193, 1166, 1124 cm⁻¹; $^1$H-NMR (400 MHz, CDCl₃) δ 3.33 (s, 3H), 3.45 (s, 3H), 7.05–7.14 (m, 2H), 7.43 (d, J=1.9 Hz, 1H), 7.58 (dd, J=1.0, 7.8 Hz, 1H); MS (FAB) m/z 307 (M⁺+1); Anal. Calcd for C₉H₁₀INOS: C, 35.19; H, 3.28; N, 4.56. Found: C, 35.23; H, 3.40; N, 4.41.

A solution of O-m-iodophenyl dimethylthiocarbamate (10.0 g, 32.6 mmol) in Ph₂O (25 mL) was heated at 230° C. for 10 hr. After cooling, the reaction mixture was chromatographed on silica-gel with n-hexane-EtOAc (5:1, v/v)as eluent to give 9.31 g (93%) S-m-iodophenyl dimethylthio carbamate as a pale yellow oil. $^1$H-NMR (400 MHz, CDCl₃) δ 3.08 (br s, 6H), 7.11 (t, J=7.8 Hz, 1H), 7.46 (d, J=7.3 Hz, 1H), 7.71 (d, J=7.3 Hz, 1H), 7.85 (s, 1); MS (FAB) m/z 307 (M⁺+1).

To a solution of S-m-iodophenyl dimethylthiocarbamate (5.01 g, 16.31 mmol) in MeOH (20 mL) was added 28%-MeONa in MeOH (3.46 mL, 17.94 mmol). The resulting mixture was stirred at room temp for 3.5 hr and then heated at 70° C. overnight. After cooling, 1 N HCl was added. The solvent was removed under a reduced pressure and the residue was diluted with EtOAc. The solution was washed with H₂O, brine, and dried over Na₂SO₄. The organic layer was concentrated under a reduced pressure. The residue was chromatographed on silica-gel with n-hexane-AcOEt (10:1, v/v) as eluent to afford 3.42 g (89%) m-iodothiophenol as an oil. $^1$H-NMR (400 MHz, CDCl₃) δ 3.45 (s, 1H), 6.95 (t, J=7.8 Hz, H), 7.23 (d, J=7.8 Hz 1H), 7.48 (d, J=7.3 Hz, 1H), 7.64 (t, J=1.5 Hz, 1H); MS(EI) m/z 236(M⁺).

To a stirred solution of N-(tert-butoxycarbonyl)-2-pyrrolidinylmethanol (4.30 g, 20.0 mmol) in pyridine (40 mL) was added p-TsCl (5.72 g, 30.0 mmol). The resulting mixture was stirred at room temp for 3 hr. The reaction mixture was quenched. with H₂O, and evaporated off. The residue was diluted with EtOAc and washed with 1 N HCl, brine, and dried over Na₂SO₄. The solvent was removed under a reduced pressure and the residue was chromatographed on silica-gel with n-hexane-EtOAc (2:1, v/v) as eluent to afford 5.76 g (81%) N-(tert-butoxycarbonyl)-2-pyrrolidinylmethyl p-toluenesulfonate as a colorless oil. $^1$H-NMR (400 MHz, CDCl₃) δ 1.36 and 1.41 (s each, total 9H), 1.82 (br m, 2H), 1.96 (br m, 2H), 2.44 (s, 3H), 3.30 (br m, 2H), 3.89 (br s, 1H), 3.96 (br s, 1H), 4.09 (br m, 1H), 7.34 (br s, 2H), 7.77 (d, J=8.3 Hz, 2H); MS (FAB) m/z 356 (M⁺+1).

To a stirred mixture of m-iodothiophenol (2.67 g, 11.31 mmol) and N-(tert-butoxy carbonyl)-2-pyrrolidinylmethyl p-toluenesulfonate (3.34 g, 9.43 mmol) in pyridine (9.4 mL) was added 8 N KOH (1.77 mL). The resulting mixture was stirred at room temp overnight. The reaction mixture was diluted with EtOAc. The solution was washed with H₂O, sat. NH₄Cl solution, brine, and dried over Na₂SO₄. The organic layer was concentrated under a reduced pressure and the residue was chromatographed on silica-gel with n-hexane-EtOAc (5:1, v/v) as eluent to afford 1.79 g (45%) [N-(tert-butoxycarbonyl)-2-pyrrolidinyl]methyl 3-iodophenyl sulfide as an oil. ¹H-NMR (400 MHz, CDCl₃) δ 1.45 (s, 9H), 1.78–2.01 (br m, 4H), 2.71 (dt, 1H), 3.32–3.49 (br m, 3H), 3.90–4.02 (br m, 1H), 7.12 (d, J=7.8 Hz, 1H), 7.18 (d, J=7.8 Hz, 1H), 7.57 (dd, J=2.0, 8.3 Hz, 2H); MS (FAB) m/z 420 (M⁺+1).

To a stirred solution of [1-(tert-butoxycarbonyl)-2-pyrrolidinyl]methyl 3-iodophenyl sulfide (1.76 g, 4.20 mmol) in DMSO (20 mL) and MeOH (16 mL) was added Et₃N (1.28 mL, 9.24 mmol), Pd(OAc)₂ (47.1 mg, 0.21 mmol), and 1,3-bis(diphenylphosphino)propane (86.6 mg, 0.21 mmol), then CO gas was bubbled for 5 min. The resulting mixture was stirred at 70° C. overnight. After cooling, the mixture was concentrated. The residue was diluted with EtOAc and washed with brine, and dried over Na₂SO₄. The solvent was removed under a reduced pressure and the residue was chromatographed on silica-gel with n-hexane-EtOAc (5:1, v/v) as eluent to afford 1.28 g (87%) methyl 3-[1-(tert-butoxycarbonyl)-2-pyrrolidinyl]methylthiobenzoate as an oil. ¹H-NMR (400 MHz, CDCl₃) δ 1.42 and 1.45 (each s, 9H), 1.79–2.05 (br m, 4H) 2.83 (dt, J=10.8, 30.3 Hz, 1H), 3.34–3.54 (br m, 3H), 3.92 (s, 3H), 3.92 and 4.05 (d, J=7.8 Hz, 1H), 7.36 (t, J=7.8 Hz, 1H), 7.63 (br d, J=14.7 Hz, 1H), 7.83 (br d, J=12.7 Hz, 1H), 8.04 (s, 1H); MS (FAB) m/z 352 (M⁺+1).

To a stirred solution of methyl 3-[1-(tert-butoxycarbonyl)-2-pyrrolidinyl]methylthio benzoate (1.46 g, 4.16 mmol) in CH₂Cl₂ (30 mL) was added TFA (15 mL) at 0° C. The resulting mixture was stirred at room temp for 1 hr. The solvent was removed under a reduced pressure and the residue was treated with 1 N NaOH and extracted with CHCl₃. The extract was washed with brine, dried over Na₂SO₄, and concentrated under a reduced pressure to afford 947 mg (91%) methyl 3-(2-pyrrolidinyl) methylthio benzoate as a brown oil. ¹H-NMR (400 MHz, CDCl₃) δ 1.45–1.54 (m, 1H), 1.72–2.00 (m, 4H) 2.88–3.10 (m, 4H), 3.30 (m, 1H), 3.92 (s, 3H), 7.34 (t, J=7.8 Hz, 1H), 7.52 (m, 1H), 7.84 (m, 1H), 8.01 (t, J=2.0 Hz, 1H); MS (FAB) m/z 252 (M⁺+1).

The mixture of 3-methoxy-4-[N'-(2-methylphenyl)ureido]phenylacetic acid (1.18 g, 3.77 mmol), EDC (1.08 g, 5.65 mmol), DMAP (23 mg, 0.19 mmol) and HOBt (25 mg, 0.19 mmol) in DMF (5 mL) was stirred at room temp for 1 hr methyl 3-(2-pyrrolidinyl)methylthio benzoate (947 mg, 3.77 mmol) was added to the mixture and the resulting mixture was stirred overnight. After DMAP (460 mg, 3.77 mmol) and HOBt (835 mg, 6.18 mmol) was added and stirred for a further 5 hr. The reaction mixture was diluted with EtOAc. The solution was washed with brine and dried over Na₂SO₄. The solvent was removed under a reduced pressure. The residue was chromatographed on silica-gel with n-hexane-EtOAc (2:3, v/v) a eluent to afford 294.3 mg (14%) methyl 3-[1-[3-methoxy-4-[N'-(2-methylphenyl)ureido ]phenylacetyl]-2-pyrrolidinyl]methylthio benzoate as a pale yellowish amorphous. IR (KBr) 2875, 1724, 1620, 1284, 1182 cm⁻¹; ¹H-NMR (400 MHz, CDCl₃) δ 1.86–2.05 (m, 4H), 2.3 1 (s, 3H), 2.84 (dd, J=9.3, 13.7 Hz, 1H), 3.43–3.59 (m, 5H), 3.73 (s, 3H), 3.92 (s, 3H), 4.33 (m, 1H), 6.16 (s, 1H), 6.77–6.80 m, 2H), 7.04 (s, 1H), 7.16 (t, J=8.3 Hz, 1H), 7.38 (t, J=7.8 Hz, 1H), 7.49 (t, J=7.8 Hz, 1H), 7.73 (dt, J=1.0, 7.8 Hz, 1H), 7.79 (dd, J=2.0, 6.8 Hz, 1H), 8.01 (d, J=2.0 Hz, 1H), 8.05 (dd, J=2.4, 7.8 Hz, 1H); MS (FAB) m/z 548 (M⁺+1).

To a stirred solution of methyl 3-[1-[3-methoxy-4-[N'-(2-methylphenyl)ureido]phenylacetyl]-2-pyrrolidinyl]methylthiobenzoate (148.2 mg, 0.271 mmol) in THF (7.4 mL) and H₂O (1.8 mL) was added LiOH (19.4 mg, 0.812 mmol), and the resulting mixture was stirred for 9 hr at room temp. The mixture was treated with 1 N HCl and extracted with CHCl₃. The extract was washed with brine and dried over Na₂SO₄. The solvent was removed under a reduced pressure and the residue was purified by preparative TLC eluting with CHCl₃-MeOH (10:1, v/v), and crystallized from n-hexane-EtOAc to afford 89.7 mg (62%) 20 as a white powder. IR (KBr) 2960, 1708 cm⁻; ¹H-NMR (400 MHz, DMSO-d₆) δ 1.82–2.01 (m, 4H), 2.24 (s, 3H), 2.93 (dd, J=9.3, 12.7 Hz, 1H), 3.40–3.54 (m, 5H), 3.86 (s, 3H), 4.13 (br m, 1H), 6.74 (d, J=8.3 Hz, 1H), 6.87 (d, J=1.5 Hz, 1), 6.94 (t, J=7.8 Hz, 1H), 7.10–7.17 (m, 2H), 7.42 (t, J=7.8Hz, 1H), 7.70 (d, J=7.8 Hz, 1H), 7.74 (d, J=8.3 Hz, 1H), 7.79 (d, J=7.8 Hz, 1H), 7.84 (s, 1H), 8.00 (d, J=8.3 Hz, 1H), 8.48 (s, 1H), 8.57 (s, 1H); MS (FAB) m/z 534 (M⁺+1).

Example 17

3-[[1-[3-methoxy-4-[N'-(2-methylphenyl)ureido] phenylacetyl]-2-pyrrolidinyl]methylsulfonyl]benzoic acid

21

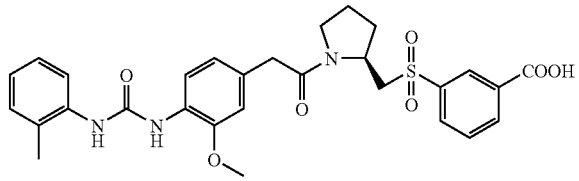

To a stirred solution of methyl 3-[1-[3-methoxy-4-[N'-(2-methyl phenyl)ureido]phenylacetyl]-2-pyrrolidinyl]methylthiobenzoate (131.8 mg, 0.241 mmol) in CH₂Cl₂ (3 mL) was added m-CPBA (130.5 mg, 0.529 mmol) at 0° C. The reaction mixture was stirred at room temp for 0.5 hr. The mixture was diluted with CHCl₃, and quenched with sat. Na₂S₂O₃ solution The organic layer was separated, washed with sat. NaHCO₃ solution, brine, and dried over Na₂SO₄. The solvent was removed under a reduced pressure to afford methyl 3-[[1-[3-methoxy-4-[N'-(2-methylphenyl) ureido] phenyl acetyl]-2-pyrrolidinyl]-methylsulfonyl]benzoate as an amorphous solid. To a stirred solution of this crude compound in THF (7.4 mL) and H₂O (1.8 mL) was added LiOH (17.3 mg, 0.723 mmol), and the stirring was continued overnight at room temp. The reaction mixture was diluted with CHCl₃ and washed with 1 N HCl, then brine, and dried over Na₂SO₄. The solvent was removed under a reduced pressure and the residue was purified by preparative TLC with CHCl₃-MeOH (10:1, v/v) as eluent, and the crude solid was recrystallized from n-hexane-EtOAc to afford 69.9 mg (51%) 21 as a white crystalline powder. mp 243–245; IR (KBr) 3354, 2974, 1533 cm$^{-1}$; $^1$H-NMR (400 MHz, DMSO-d$_6$) δ 1.80–2.00 (m, 4H), 2.24 (s, 3H), 3.19–3.62 (m, 6H), 3.82 (s, 3H), 4.18 (m, 1H); 6.67 (d, J=8.8 Hz, 1H), 6.80 (d, J=1.0 Hz, 1H), 6.93 (t, J=7.3 Hz, 1H), 7.10–7.17 (m, 2H), 7.66 (t, J=7.8 Hz, 1H), 7.78 (d, J=8.3 Hz, 1H), 7.91–7.99 (m, 2H), 8.20 (d, J=7.3 Hz, 1H), 8.34 (s, 1H), 8.48 (s, 1H), 8.56 (s, 1H); MS (FAB) m/z 566 (M$^+$+1); Anal. Calcd for C$_{29}$H$_{31}$N$_3$O$_7$S.1HCl.1H$_2$O: C, 56.17; H, 5.53; N, 6.78. Found: C, 55.92; H, 5.58; N, 6.71.

Example 18

4-[[1-[3-methoxy-4-[N'-(2-methylphenyl)ureido]phenylacetyl]-2-pyrrolidinyl]methylsulfonyl]benzoic acid

22

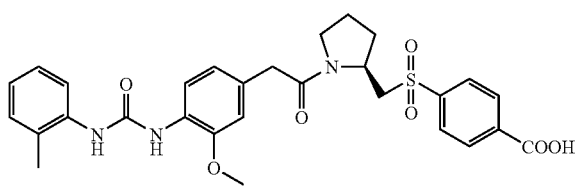

To a stirred solution of methyl 4-[[1-[3-methoxy4-[N'-(2-methyl phenyl)ureido]phenylacetyl]-2-pyrrolidinyl]methylthio]benzoate (300 mg, 0.548 mmol) in CH$_2$Cl$_2$ (6 mL) was added m-CPBA (297 mg, 1.206 mmol) at 0° C., and the reaction mixture was stirred at room temp for 1 hr. The mixture was diluted with CHCl$_3$, and quenched with sat. Na$_2$S$_2$O$_3$ solution. The separated organic layer was washed with sat. NaHCO$_3$ solution, brine, and dried over Na$_2$SO$_4$. The solvent was removed under a reduced pressure to afford methyl 4-[[1-[3-methoxy-4-[N'-(2-methylphenyl)ureido]phenylacetyl]-2-pyrrolidinyl]-methylsulfonyl]benzoate as a crude yellow oil. To a stirred solution of this crude compound in THF (4.4 mL) and H$_2$O (11.1 mL) was added LiOH (39.4 mg, 1.643 mmol), and the stirring was continued overnight at room temp. The reaction mixture was diluted with CHCl$_3$ and washed with 1 N HCl, brine, and dried over Na$_2$SO$_4$. The solvent was removed under a reduced pressure and the residue was purified by preparative TLC eluting with CHCl$_3$-MeOH (10:1, v/v), and crystallized from n-hexane-EtOAc to afford 128.0 mg (41%) 22 as a white powder. IR (KBr) 3388, 2974, 1537, 1298, 1155 cm$^{-1}$; $^1$H-NMR (400 MHz, DMSO-d$_6$) δ 1.80–1.98 (m, 4H), 2.24 (s, 3H), 2.54 (s, 1H), 3.20–3.70 (m, 5H), 3.82 (s, 3H), 4.16 (br m, 1H), 6.67 (dd, J=1.5, 8.3 Hz, 1H), 6.80 (d, J=1.5 Hz, 1H), 6.93 (d, J=7.3 Hz, 1H), 7.10–7.16 (m, 2H), 7.78 (d, J=7.3 Hz, 1H), 7.95 (d, J=8.3 Hz, 2H), 7.98 (d, J=8.3 Hz, 1H), 8.14 (d, J=8.3 Hz, 2H), 8.49 (s, 1H), 8.57 (s, 1H); MS (FAB) m/z 566 (M$^+$+1); Anal. Calcd for C$_{29}$H$_{31}$N$_3$O$_7$S.3H$_2$O: C, 56.21; H, 6.02; N, 6.78. Found: C, 56.76; H, 5.37; N, 6.70.

Example 19

4-[[1-[3-methoxy-4-[N'-(2-methylphenyl)ureido]phenylacetyl]-2-pyrrolidinyl]methylthio]benzoic acid

23

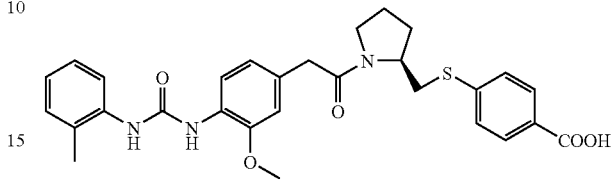

To a stirred solution of p-iodophenol (20.0 g, 90.9 mmol) in DMF (200 mL) was added 1,4-diazabicyclo[2,2,2]octane (20.4 g, 181.8 mmol) and dimethylthiocarbamoyl chloride (16.9 g, 136.4 mmol). The resulting solution was stirred for 3.5 hr at 75° C. After cooling, 300 mL of water was added. The solid was collected with suction and was dissolved in EtOAc. The EtOAc layer was washed with water, dried over Na$_2$SO$_4$, and evaporated under a reduced pressure. The crude solid was recrystallized from H$_2$O to give the 26.75 g (96%) O-p-iodophenyl dimethylthiocarbamate as a pale a yellow crystalline powder. IR (KBr) 1479, 1207, 827 cm$^{-1}$; $^1$H-NMR (400 MHz, CDCl$_3$) δ 3.37 (s, 3H), 3.45 (s, 3H), 6.83 (d, J=8.8 Hz, 2H), 7.69 (d, J=8.3 Hz, 2H); MS (FAB) m/z 307 (M$^+$+1); Anal. Calcd for C$_9$H$_{10}$INOS: C, 35.19; H, 3.28; N, 4.56. Found: C, 35.17; H, 3.35; N, 4.44.

A stirred solution of O-p-iodophenyl dimethylthiocarbamate (10.0 g, 32.6 mmol) in Ph$_2$O (25 mL) was heated at 230° C. for 5.5 hr. After cooling, the reaction mixture was chromatographed on silica-gel with n-hexane-EtOAc (3:1, v/v) as eluent to give 2.55 g (26%) S-p-iodophenyl dimethylthio carbamate as a white crystalline powder. IR (KBr) 3299, 1651, 1469, 1371 cm$^{-1}$; $^1$H-NMR (400 MHz, CDCl$_3$) δ 3.03 (br s, 3H), 3.08 (br s, 3H), 7.21 (d, J=8.3 Hz, 2H), 7.70 (d, J=8.3 Hz, 2H); MS (FAB) m/z 308 (M$^+$+1); Anal. Calcd for C$_9$H$_{10}$INOS: C, 35.19; H, 3.28; N, 4.56. Found: C, 35.49; H, 3.28; N, 4.43.

To a solution of S-p-iodophenyl dimethylthiocarbamate (2.55 g, 8.31 mmol) in MeOH (10 mL) was added MeONa (495 mg, 9.14 mmol), and the resulting mixture was stirred at 70° C. overnight. After cooling, 1 N HCl was added and the mixture was concentrated under a reduced pressure. The residue was diluted with EtOAc and washed with H$_2$O, brine, and dried over Na$_2$SO$_4$. The organic layer was concentrated under a reduced pressure and the residue was chromatographed on silica-gel with n-hexane EtOAc (5:1, v/v) as eluent to afford 1.75 g (89%) p-iodothiophenol as a pale yellow crystalline solid. IR (KBr) 2559, 1097, 1002, 806 cm$^{-1}$; $^1$H-NMR (400 MHz, CDCl$_3$) δ 3.43 (s, 1H), 7.10 (d, J=8.3 Hz, 2H), 7.53 (d, J=8.3 Hz, 2H); MS (FAB) m/z 236 (M$^+$+1); Anal. Calcd for C$_6$H$_5$IS: C, 30.53; H, 2.13. Found: C, 30.57; H, 2.15.

To a stirred mixture of p-iodothiophenol (1.75 g, 7.43 mmol) and N-(tert-butoxycarbonyl)-2-pyrrolidinylmethyl p-toluenesulfonate (2.39 g, 6.75 mmol) in pyridine (12.7 mL) was added 8 N KOH (1.27 mL) at room temp, and the resulting mixture was stirred for 4 hr at the same temp. The reaction mixture was diluted with EtOAc. The solution was washed with H$_2$O, sat. NH$_4$Cl, brine, and dried over Na$_2$SO$_4$. The organic layer was concentrated under a reduced pressure. The residue was chromatographed on silica-gel with n-hexane-EtOAc (5:1, v/v) as eluent to afford 1.49 g (530%) [N-(tert-butoxycarbonyl)-2-pyrrolidinyl]methyl 4-iodophenyl sulfide as a pale yellowish oil. $^1$H-NMR (400 MHz, CDCl$_3$) δ (s, 9H), 1.78–2.01 (br m, 4H), 2.71 (dt, 1H), 3.32–3.49 (br m, 3H), 3.90–4.02 (br m, 1H), 7.12 (d, J=7.8 Hz, 1H), 7.18 (d, J=7.8 Hz, 1), 7.57 (dd, J=2.0,8.3 Hz, 2H);MS(FAB)m/z 420(M$^+$+1).

To a stirred solution of [1-(tert-butoxycarbonyl)-2-pyrrolidinyl]methyl 4-iodophenyl sulfide (1.49 g, 3.56 mmol) in DMSO (16 mL) and MeOH (13 mL) was added Et$_3$N (1.09 mL, 7.84 mmol), Pd(OAc)$_2$ (40 mg, 0.178 mmol), and 1,3-bis(diphenylphosphino)propane (73.4 mg, 0.178 mmol). To the stirred resulting mixture was induced CO gas for 5 min, and the mixture was stirred at 70° C. overnight. After cooling, the mixture was concentrated to a small volume. The residue was diluted with EtOAc, washed with brine, and dried over Na$_2$SO$_4$. The solvent was removed under a reduced pressure and the residue was chromatographed on silica-gel with n-hexane-EtOAc (5:1, v/v) as eluent to afford 1.16 g (93%) methyl 4-[1-(tert-butoxycarbonyl)-2-pyrrolidinyl]methylthiobenzoate as an oil. $^1$H-NMR (400 MHz, CDCl$_3$) δ 1.51 and 1.47 (each s, 9H), 1.78–2.05 (br m, 4H) 2.77 (dt, J=10.8, 37.1 Hz, 1H), 3.34–3.58 (m, 3H), 3.89 (s, 3H), 4.03 (br d, J=27.3 Hz, 1H), 7.38 (d, J=7.3 Hz, 1H), 7.47 (d, J=7.3 Hz, 1H), 7.92 (br s, 2H); MS (FAB) m/z 352 (M$^+$+1).

To a stirred solution of methyl 4-[1-(tert-butoxycarbonyl)-2-pyrrolidinyl]methylthio benzoate (1.16 g, 3.32 mmol) in CH$_2$Cl$_2$ (20 mL) was added TFA (4 mL), and the mixture was stirred at room temp for 1.5 hr. The solvent was removed under a reduced pressure and the residue was treated with 1 N NaOH. The mixture was extracted with CHCl$_3$. The extract was washed with brine, dried over KOH, and concentrated under a reduced pressure to afford 767 mg (92%) methyl 4-(2-pyrrolidinyl) methylthio benzoate as a yellow oil. $^1$H-NMR (400 MHz, CDCl$_3$) δ (dt, J=3.9, 12.7 Hz, 1H), 1.85–2.09 (m, 2H) 2.13 (m, 1H), 3.11–3.27 (m, 3H), 3.40 (dd, J=6.8, 13.2 Hz, 1H), 3.54 (dd, J=7.3, 15.1 Hz, H), 3.89 (s, 3H), 5.07 (br, 1H), 7.38 (d, J=8.3 Hz, 2H), 7.91 (d, J=8.3 Hz, 2H); MS (FAB) m/z 252 (M$^+$+1).

To a stirred mixture of 3-methoxy-4-[N'-(2-methylphenyl)ureido]phenylacetic acid (1.30 g, 4.136 mmol), Et$_3$N (0.63 mL, 4.549 mmol) in DMF (20 mL) was added pentafluorophenyl trifluoroacetate at 0° C. The resulting mixture was stirred at room temp for 1 hr. The mixture was poured into water (60 mL) and precipitate was collected with suction. The crude solid was washed with 0.1 N HCl, H$_2$O, n-hexane, and dried at 40° C. to afford 1.91 g (96%) pentafluorophenyl 3-methoxy-4-[N'-(2-methylphenyl) ureido]phenylacetate as a pale brownish crystalline powder. IR (KBr) 1785, 1224, 1216 cm$^{-1}$; $^1$H-NMR (400 MHz, CDCl$_3$) δ 2.29 (s, 3H), 3.76 (s, 3H), 3.90 (s, 2H), 6.49 (s, 1H), 6.81 (d, J=1.5 Hz, 1H), 6.91 (dd, J=1.5, 8.3 Hz, 1H), 7.15 (t, J=7.3 Hz, 3H), 7.24 (m, 1H), 7.50 (d, J=7.8 Hz, 1H), 8.17 (d, J=7.8 Hz, 1H); MS (FAB) m/z 481 (M$^+$+1); Anal. Calcd for C$_{30}$H$_{33}$N$_3$O$_5$S.1/4H$_2$O: C, 57.51; H, 3.57; N, 5.83. Found: C, 57.40; H, 3.75; N, 5:68.

A mixture of pentafluorophenyl 3-methoxy-4-[N'-(2-methylphenyl)ureido]phenylacetate (1.47 g, 3.05 mmol), methyl 4-(2-pyrrolidinyl)methylthiobenzoate (767 mg, 3.05 mmol), Et$_3$N (0.51 mL, 3.66 mmol) in DMF (15 mL) was stirred overnight at room temp. The reaction mixture was diluted with EtOAc, washed with brine, and dried over Na$_2$SO$_4$. The solvent was removed under a reduced pressure and the residue was chromatographed on silica-gel with n-hexane-EtOAc (1:2, v/v) as eluent to afford 1.366 g (82%) methyl 4-[[1-[3-methoxy-4-[N'-(2-methylphenyl)ureido] phenylacetyl]-2-pyrrolidinyl]methylthio]benzoate as a white crystalline powder. IR (KBr) 1785, 1224, 1216 cm$^{-1}$; $^1$H-NMR (400 MHz, CDCl$_3$) δ 1.88–1.99 (m, 4H), 2.30 (s, 3H), 2.75 (dd, J=9.8, 13.2 Hz, 1H), 3.43–3.55 (m, 3H), 3.56 (s, 2H), 3.64 (dd, J=1.1, 14.2 Hz, 1H), 3.73 (s, 3H), 3.88 (s, 3H), 4.33 (m, 1H), 6.29 (s, 1H), 6.78–6.81 (m, 2H), 7.11–7.26 (m, 5H), 7.50 (d, J=8.3 Hz, 3H), 7.93 (d, J=8.8 Hz, 2H), 8.07 (d, J=7.8 Hz, 1H); MS (FAB) m/z 548 (M$^+$+1); Anal. Calcd for C$_{30}$H$_{33}$N$_3$O$_5$S.1/4H$_2$O: C, 65.26; H, 6.12; N, 7.61. Found: C, 65.48; H, 6.20; N, 7.47.

To a stirred solution of methyl 4-[[1-[3-methoxy-4-[N'-(2-methylphenyl)ureido]phenylacetyl]-2-pyrrolidinyl]methylthio]benzoate (300 mg, 0.548 mmol) in THF (5.5 mL) and H$_2$O (1.1 mL) was added LiOH (39.4 mg, 1.643 mmol), and the reaction mixture was stirred at room temp overnight and at 50° C. for 9 hr. The mixture was diluted with CHCl$_3$. The solution was washed with 1 N HCl, brine, and dried over Na$_2$SO$_4$. The solvent was removed under a reduced pressure, and the obtained crude solid was recrystallized from n-hexane-EtOAc-MeOH to afford 218.6 mg (75%) 23 as a white crystalline powder. IR (KBr) 3318, 2952, 1596, 1536, 1299, 1155 cm$^{-1}$; $^1$H-NMR (400 MHz, DMSO-d$_6$) δ 1.82–2.05 (m, 4H), 2.25 (s, 3H), 2.91 (dd, J=9.8, 13.2 Hz, 1H), 3.47–3.52 (m, 3H), 3.57 (s, 2H), 3.87 (s, 3H), 4.14 (br m, 1H), 6.76 (d, J=1.5, 8.3 Hz, 1H), 6.89 (d, J=1.5 Hz, 1H), 6.94 (t, J=7.3 Hz, 1H), 7.11–7.19 (m, 2H), 7.57 (d, J=8.3 Hz, 2H), 7.80 (d, J=8.3 Hz, 1H), 7.83 (d, J=8.3 Hz, 2H), 8.02 (d, J=8.3 Hz, 1H), 8.49 (s, 1H), 8.58 (s, 1H); MS (FAB) m/z 534 (M$^+$+1); Anal. Calcd for C$_{29}$H$_{31}$N$_3$O$_5$S.5/4H$_2$O: C, 62.63; H, 6.07; N, 7.36; S, 5.77. Found: C, 62.62; H, 5.74; N, 7.36; S, 5.67.

Example 20

4-[[1-[3-methoxy-4-[N'-(2-methylphenyl)ureido] phenylacetyl]-2-pyrrolidinyl]methylsulfinyl]benzoic acid

24

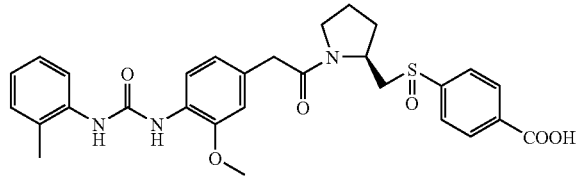

To a stirred solution of methyl 4-[[1-[3-methoxy4-[N'-(2-methyl phenyl)ureido]phenylacetyl]-2-pyrrolidinyl]methylthio]benzoate (264 mg, 0.482 mmol) in CH$_2$Cl$_2$ (5.2 mL) was added m-CPBA (118.8 mg, 0.482 mmol) at 0° C., and the mixture was stirred at room temp for 1 hr. The mixture was diluted with CHCl$_3$, and quenched with sat. Na$_2$S$_2$O$_3$. The separated organic layer was washed with sat. NaHCO$_3$, brine, and dried over Na$_2$SO$_4$. The solvent was removed under a reduced pressure to afford methyl 4-[[1-[3-methoxy-4-[N'-(2-methylphenyl)ureido]phenylacetyl]-2 pyrrolidinyl] methylsulfinyl]benzoate as a crude amorphous solid. To a stirred solution of this crude compound in THF (4 mL) and H$_2$O (1mL) was added LiOH (34.6 mg, 1.45 mmol), and the stirring was continued overnight at room temp. The mixture was diluted with CHCl$_3$, washed with 1 N HCl, brine, and dried over Na$_2$SO$_4$. The solvent was removed under a reduced pressure, and the obtained crude solid was recrystallized from n-hexane-CHCl₃-MeOH to afford 193.2 mg (73%) 24 as a white crystalline powder. IR (KBr) 3338, 2956, 1708, 1529, 1299, 1207, 1155 cm$^{-1}$; $^1$H-NMR (400 MHz, DMSO-d$_6$) δ 1.70–2.06 (m, 4H), 2.24 (s, 3H), 2.90 (dd, J=8.3, 13.2 Hz, 1H), 3.02–3.08 (m, 1H), 3.16–3.25 (m, 1H), 3.41–3.60 (m, 3H), 3.84 (s, 3H), 4.40 (br s, 1H), 6.74 (d, J=7.8 Hz, 1H), 6.87 (s, 1H), 6.94 (d, J=7.3 Hz, 1H), 7.11–7.17 (m, 2H), 7.75–7.81 (m, 3H), 7.98–8.05 (m, 1H), 8.10 (d, J=8.3 Hz, 2H), 8.46 (s, 1H), 8.56 (s, 1H); MS (FAB) m/z 550 (M$^+$+1), 572 (M$^+$+Na); Anal. Calcd for $C_{29}H_{31}N_3O_6S \cdot 3/2H_2O$: C, 60.40; H, 5.94; N, 7.29. Found: C, 60.15; H, 5.82; N, 6.90.

Example 21

(S)-4-[1-[3-methoxy-4-[N'-(2-methylphenyl)ureido]phenylacethyl]-2-pyrrolidinylmethoxy]benzoic acid.

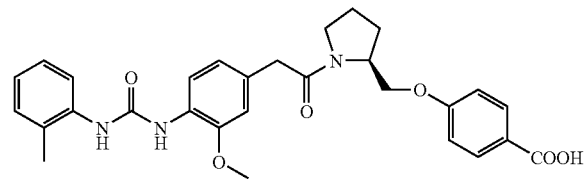

25

To a stirred solution of methyl 4-hydroxybenzoate (1.96 g, 12.88 mmol), N-Boc-prolinol (2.59 g, 12.87 mmol) and PPh$_3$ (4.06 g, 15.48 mmol) in THF (40 mL) was added DIAD (3.10 mL, 15.74 mmol). The resulting mixture was heated under reflux for 14 hr. The mixture was evaporated off in vacuo and the residue was purified by column chromatography on silica-gel with n-hexane-EtOAc (6:1, v/v) as eluent to give 3.34 g (77%) methyl (S)-4-[1-(tert-butoxycarbonyl)-2-pyrrolidinylmethoxy]benzoate as an oil. $^1$H-NMR (CDCl$_3$) δ 1.48 (s, 9 H), 1.67 (d, J=9.3 Hz, 1 H), 1.87–2.03 (m, 3 H), 3.36–3.43 (m, 2H), 3.87 4.09 (m,11H), 4.13–4.20 (m, 2 H, 6.94 (d, J=8.3 Hz, 2H), 7.98 (d, J=8.3 Hz, 2H).

A mixture of methyl (S)-4-[1-(tert-butoxycarbonyl)-2-pyrrolidinylmethoxy]benzoate (3.34 g, 9.96 mmol) in TFA (20 mL) and CH$_2$Cl$_2$ (35 mL) was stirred at room temp for 15 hr. The mixture was concentrated in vacuo and made basic with sat. NaHCO$_3$. The mixture was extracted with CHCl$_3$, washed with brine, and dried over Na$_2$CO$_3$. The organic layer was evaporated to give 1.70 g (73%) methyl (S)-4-(2-pyrrolidinylmethoxy)benzoate as a yellow oil. $^1$H-NMR (CDCl$_3$) δ 1.54–1.61 (m, 1 H), 1.77–1.86 (m, 2 H), 1.87–1.97 (m, 1 H), 2.00 (bs, 1 H), 2.93–3.06 (m, 2 H), 3.52–3.57 (m, 1 H), 3.88 (s, 3 H), 3.90–3.99 (m, 2 H), 6.92 (d, J=9.0 Hz, 2 H), 7.98 (d, J=9.0 Hz, 2 H)

A mixture of 3-methoxy4-[N'-(2-methylphenyl)ureido]phenylacetic acid (428 mg, 1.36 mmol), methyl (S)-4-(2-pyrrolidinylmethoxy)benzoate (330 mg, 1.40 mmol), EDC (312 mg, 1.63 mg), HOBt (220 mg, 1.63 mmol), and a catalytic amount of DMAP in DMF (15 mL) was stirred for 6 hr. The resulting mixture was diluted with EtOAc, washed with 0.5 N HCl, sat. NaHCO$_3$, brine, and dried over MgSO$_4$. The solvent was evaporated off in vacuo to give an oily residue, which was purified by column chromatography on silica-gel with CHCl$_3$-MeOH (50:1, v/v) as eluent to give 540 mg (75%) methyl (S)-4-[1-[3-methoxy-4-[N'-(2-methylphenyl)ureido]phenylacetyl]-2-pyrrolidinylmethoxy]benzoate as an oil. $^1$H-NMR (CDCl$_3$) δ 1.81–2.12 (m, 4 H) 2.88 (bs, 3 H), 3.48–3.61 (m, total 7 H), 3.88 (s, 3 H), 4.10–4.21 (m, 2 H), 4.42–4.46 (m, 1 H), 6.75–8.08 (series of m, total 13 H).

To a stirred solution of methyl (S)-4-[1-[3-methoxy-4-[N'-(2-methylphenyl) ureido]phenylacetyl]-2-pyrrolidinylmethoxy]benzoate (540 mg, 1.02 mmol) in THF (10 mL) was added 0.25 N NaOH (10 mL). The resulting mixture was heated under reflux for 16 hr. The mixture was poured into 1 N HCl and the solid was collected. The crude solid was washed with Et$_2$O to give 278 mg (53%) 25 as a white amorphous solid. IR (KBr) 1708 cm$^{-1}$; $^1$H-NMR (DMSO-d$_6$) δ 1.83–2.14 (m, 4 H), 2.21 (s, 3 H), 2.46 (s, 2 H), 3.78 (s, 3 H), 3.95–4.02 (m, 1 H), 4.13–4.16 (m, 1 H), 4.24 (bs, 1 H), 6.51–7.98 (series of m, 12 H), 8.43 (s, 1 H), 8.53 (s, 1 H), 12.57 (bs, 1 H); MS (FAB) m/z 517 (M$^+$).

Example 22

1-[1-[3-methoxy-4-[N'-(2-methylphenyl)ureido]benzoyl]-L-prolyl]-4-piperidinylacetic acid

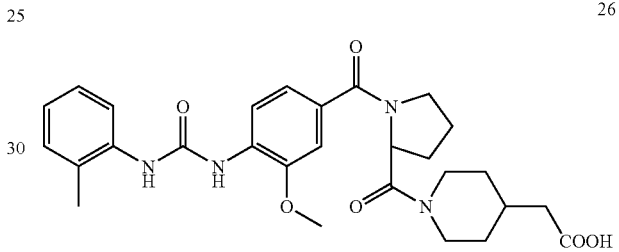

26

A mixture of 3-methoxy-4-nitrobenzoic acid (229 mg, 1.16 mmol), tert-butyl 4-(1-prolylpiperidinyl)acetate (344 mg, 1.16 mmol), HOBt (188 mg, 1.39 mmol), DMAP (14.2 mg, 0.116 mmol), and EDC (267 mg, 1.39 mmol) in DMF (7 mL) was stirred for 22 hr at room temp. The mixture was diluted with EtOAc (50 mL) and washed successively with 1 N HCl, sat. NaHCO$_3$, and H$_2$O. The organic layer was dried over Na$_2$SO$_4$ and evaporated in vacuo. The residue was chromatographed on silica-gel with MeOH:CHCl$_3$ (1:30, v/v) as eluent to afford 520 mg (94%) tert-buty 1-(3-methoxy-4-nitrobenzoyl)prolyl-4-(1-piperidinyl)acetate as a white crystalline material. $^1$H-NMR (CDCl$_3$) δ 1.12–1.33 and 1.62–2.23 (each m, 9H), 1.44 (s, 9H), 2.65, 3.13,3.47, 3.67, 4.44, and 4.61 (each m, 8H), 3.99 (s, 3H), 5.05 (m, 1H), 7.21 (d, J=8.3 Hz, 1H), 7.31 (s, 1H), 7.86 (d, J=8.3 Hz, 1H).

A stirred mixture of tert-buty 1-(3-methoxy-4-nitrobenzoyl)prolyl-4-(1-piperidinyl) acetate (0.52 g, 1.09 mmol) and 5% Pd—C (2.08 g) in MeOH (10 mL) was hydrogenated under an atmospheric pressure for 94 hr at room temp. Insoluble catalyst was removed, and the filtrate was evaporated in vacuo. The residue was chromatographed on silica-gel with MeOH:CHCl$_3$ (1:40 to 1:6, v/v) as eluent to afford 279 mg (57%) tert-buty 1-(4-amino-3-methoxybenzoyl)prolyl-4-(1-piperidinyl)acetate as a white crystalline material. $^1$H-NMR (CDCl$_3$) δ 1.16–2.17, 2.69, 3.06, 3.67, 4.12, and 4.59 (each m, 17H), 3.86 (s, 3H), 5.10 (m, 1H), 6.64 (m, 1H), 7.12 (each m, 2H).

To a stirred solution of tert-buty 1-(4-amino-3-methoxybenzoyl)-L-prolyl-4-(1-piperidinyl) acetate (279 mg, 0.627 mmol) and Et$_3$N (0.0876 mL, 0.627 mmol) in THF (4 mL) was added dropwise o-tolyl isocyanate (0.0777 mL, 0.627 mmol) at room temp, and the resulting mixture was stirred for a further 21 hr at room temp. Ice water was added to the mixture and the precipitate was collected with suction. The crude solid was purified by silica-gel column chromatography with MeOH:CHCl$_3$ (1:40, v/v) as eluent to afford 254 mg (70%) tert-butyl 1-[1-[3-methoxy-4-[N'-(2-methylphenyl)ureido]benzoyl]-L-prolyl]-4-(1-piperidinyl)acetate as a crystalline solid. $^1$H-NMR (CDCl$_3$) δ 1.43 (s, 9H), 1.13–1.25 and 1.76–2.14 (each m, 9H), 2.60, 3.18, 3.71, 4.06, and 4.57 (each m, 8H), 3.67 (s, 3H), 5.06 (m, 1H), 6.63, and 6.90 (s, 2H), 6.98–7.23, and 7.64 (each m, 5H), 7.56 (d, J=7.8 Hz, 1H), 8.21 (d, J=8.8 Hz, 1H).

A solution of tert-butyl 1-[1-[3-methoxy-4-[N'-(2-methylphenyl)ureido]benzoyl]prolyl]-4-(1-piperidinyl)acetate (254 mg, 0.440 mmol) in CH$_2$Cl$_2$ (6 mL) and TFA (6 mL) was stirred for 5 hr at room temp. The mixture was poured into ice water. The solid was collected with suction, washed with water and air-dried to afford 179 mg (78%) 26 as a white crystalline solid. $^1$H-NMR (DMSO-d$_6$) δ 0.47, 1.05, 1.44, and 1.62–1.99 (each m, 9H), 2.49 (s, 3H), 2.15–2.30, 2.35, 2.56, 2.78, 3.09, 3.04–3.80, 4.05, 4.15, and 4.32 (each m, 8H), 3.92 (s, 3H), 4.92 (m, 1H), 6.82, 6.95, 7.11, 7.77, 8.20, 8.57, and 8.75 (m, 9H); MS (FAB) m/z 523 (M$^+$+1); Anal. Calcd for C$_{28}$H$_{34}$N$_4$O$_6$: C, 64.35; H, 6.56; N, 10.72. Found: C, 55.58; H, 5.89; N, 8.75.

Example 23

(S)-3-methoxy-4-[1-[3-methoxy-4-[N'-(2-methylphenyl)ureido]phenylacetyl]-2-pyrrolidinyl methoxylbenzoic acid

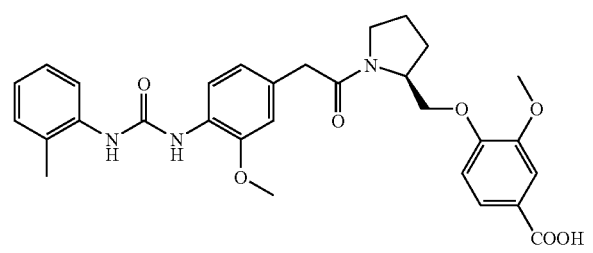

27

To a stirred solution of ethyl 4-hydroxy-3-methoxybenzoate (3.00 g, 15.29 mmol), (S)-N-Boc-prolinol (3.08 g, 15.30 mmol), Ph$_3$P (4.81 g, 18.34 mmol) in THF (50 mL) was added DIAD (3.61 mL, 18.33 mmol) at 0° C. The resulting mixture was heated under reflux 6.5 hr. After cooling to room temp, the mixture was evaporated and purified by column chromatography on silica-gel with CHCl$_3$-MeOH (50:1, v/v) as eluent to give ethyl (S)-3-methoxy-4-[1-(tert-butoxycarbonyl)-2-pyrrolidinyl methoxy]benzoate as a gum. The above ethyl (S)-3-methoxy-4-[1-(tert-butoxycarbonyl)-2-pyrrolidinylmethoxy]benzoate was dissolved in CH$_2$Cl$_2$ (50 mL) and TFA (45 mL). The mixture was stirred for 2 days at room temp. The resulting mixture was concentrated in vacuo and made basic with sat. NaHCO$_3$. The mixture was extracted with CH$_2$Cl$_2$, washed with brine, and dried over MgSO$_4$. The solvent was evaporated and the residue was purified by column chromatography on silica-gel with CHCl$_3$-MeOH (20:1, v/v) as eluent to give 3.27 g (77% for 2 steps) ethyl (S)-3-methoxy-4-(2-pyrrolidinylmethoxy) benzoate as a yellow oil. $^1$H-NMR (CDCl$_3$) δ 1.39 (t, 3 H, J=7.1 Hz), 1.52–1.59 (m, 1 H), 1.76–1.88 (m, 2 H), 1.92–2.01 (m, 1H), 2.92–3.06 (m, 2 H), 3.56–3.63 (m, 1 H), 3.90 (s, 3 H), 3.91–4.02 (m, 2 H), 4.35 (q, 2 H, J=7.1 Hz), 6.89 (d, 1 H, J=8.3 Hz), 7.54 (d, 1 H, J=2.0 Hz), 7.65 (dd, 1 H, J=2.0, 8.3 Hz).

To a stirred solution of ethyl (S)-3-methoxy-4-(2-pyrrolidinylmethoxy)benzoate (424 mg, 1.52 mmol) in DMF (8 mL) was added pentafluorphenyl ester of 3-methoxy-4-[N'-(2-methylphenyl) ureido]phenylacetic acid (728 mg, 1.52 mmol) and Et$_3$N (0.26 mL, 1.87 mmol). And the resulting mixture was stirred at room temp overnight. The mixture was diluted with EtOAc, washed with 1 N HCl, sat. NaHCO$_3$, brine, and dried over MgSO$_4$. The solvent was evaporated off in vacuo and the residue was purified by column chromatography on silica-gel with CHCl$_3$-MeOH (50:1, v/v) as eluent to give 830 mg (95%) ethyl (S)-3-methoxy-4-[1-[3-methoxy-4-[N'-(2-methylphenyl)ureido] phenyl acetyl]-2-pyrrolidinyl methoxy]benzoate as an amorphous solid. $^1$H-NMR (CDCl$_3$) δ 1.38 (t, 3 H, J=7.3 Hz), 1.88–2.20 (m, 4 H, m), 2.24 (m, 3 H), 3.44–3.50 (m, 1 H), 3.53–3.58 (m, 7 H), 3.82 (s, 3 H), 4.09–4.17 (m, 1 H), 4.22–4.25 (m, 1 H), 4.35 (q, 2 H, J=7.3 Hz), 4.38–4.49 (m, 1 H), 6.71–6.78 (m, 1 H), 6.99 (d, 1 H, J=8.3 Hz), 7.04–7.07 (m, 1H), 7.16–7.19 (m, 2 H), 7.49–7.66 (m, 3 H), 8.06 (d, 1 H, J=8.3 Hz).

To a stirred solution of ethyl (S)-3-methoxy-4-[[1-[3-methoxy-4-[N'-2-methylphenyl) ureido]phenylacetyl]-2-pyrrolidinyl]methoxy]benzoate (760 mg, 1.32 mmol) in THF (10 mL) was added 0.25 N NaOH (10 mL), and the resulting mixture was heated under reflux overnight. After cooling to room temp, the mixture was poured into 1 N HCl (100 mL) and the solid was collected. The crude solid was washed with Et$_2$O to give 429 mg (59%) 27 as a yellow amorphous solid. mp 132–135; IR (KBr) 1707 cm$^-$; $^1$H-NMR (DMSO-d$_6$) δ 1.84–2.18 (m, 4 H), 2.25 (s, 3 H), 2.49–2.51 (m, 2 H), 3.29–3.59 (m, 4 H), 3.80 (s, 3 H), 3.82 (s, 3 H), 4.00–4.05 (m, 1 H), 6.53–8.01 (m, 10 H), 8.45 (s, 1 H), 8.54 (s, 1 H), 12.63 (bs, 1 H); MS (FAB) m/z 548 (M$^+$+1).

Example 24

(S)-4-[1-[3-methoxy-4-[N'-(2-methylphenyl)ureido] phenylacetyl]-2-pyrrolidinylmethoxy]phthalic acid

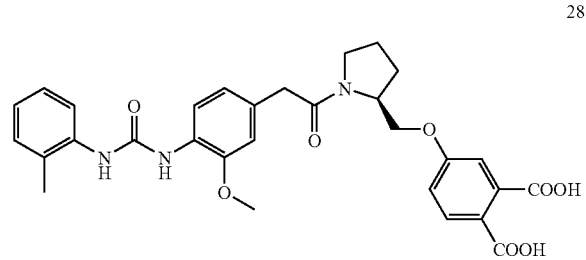

28

To a stirred solution of dimethyl 4-hydroxyphthalate (3.00 g, 14.27 mmol), N-Boc-prolinol (2.87 g, 14.26 mmol), Ph$_3$P (4.49 g, 17.12 mmol) in THF (50 mL) was added DIAD (3.40 mL, 17.27 mmol) at 0° C. Then the resulting mixture was heated under reflux overnight. The resulting mixture was evaporated and the residue was purified by column chromatography on silica-gel with n-hexane-EtOAc (3:1, v/v) as eluent to give 5.75 g (q.y.) dimethyl (S)-4-[1-(tert-butoxycarbonyl)-2-pyrrolidinyl methoxy]phthalate as an oil. $^1$H-NMR (CDCl$_3$) δ 1.47 (s, 9 H), 1.86–2.05 (m, 4 H), 3.36–3.40 (m, 2 H), 3.87 (m, 3 H), 3.91 (s, 3 H), 3.96–4.19 (m, 3 H), 7.03–7.24 (m, 2 H), 7.80 (m, 1H).

To a solution of dimethyl (S)-4-[1-(tert-butoxycarbonyl)-2-pyrrolidinylmethoxy]phthalate (5.75 g, 14.62 mmol) in CH$_2$Cl$_2$ (25 mL) was added TFA (20 mL), and the resulting mixture was stirred for 50 min at room temp. The resulting mixture was concentrated in vacuo and made basic with sat. NaHCO$_3$. The mixture was extracted with CH$_2$Cl$_2$, washed with brine, dried over MgSO$_4$, and evaporated off in vacuo. The residue was purified by column chromatography on silica-gel with CHCl$_3$-MeOH (50:1, v/v) as eluent to give 790 mg (18%) dimethyl (S)-4-(2pyrrolidinylmethoxy) phthalate as a brown oil. $^1$H-NMR (CDCl$_3$) δ 1.48–1.57 (m, 1 H), 1.72–1.84 (m, 2 H), 1.89–1.98 (m, 2 H), 2.91–3.03 (m, 2 H), 3.48–3.54 (m, 1 H), 3.82–3.97 (m, total 8 H), 6.98 (dd, 1 H, J=2.4, 8.8 Hz), 7.06 (d, 1 H, J=2.4 Hz), 7.78 (d, 1 H, J=8.8 Hz).

To a stirred solution of dimethyl (S)-4-(2-pyrrolidinylmethoxy)phthalate (212 mg, 0.72 mmol) in DMF (8 mL) was added pentafluorophenyl ester of the 3-methoxy-4-[N'-(2-methylphenyl)ureido]phenylacetic acid (346 mg, 0.72 mmol) and Et$_3$N (120 ml, 0.86 mmol), and the mixture was stirred overnight. The resulting mixture was diluted with EtOAc, washed with 1 N HCl, sat. NaHCO$_3$, brine, and dried over MgSO$_4$. The solvent was evaporated off in vacuo to give 413 mg (97%) dimethyl (S)-4-[1-[3-methoxy-4-[N'-(2-methylphenyl)ureido]phenylacetyl]-2-pyrrolidinylmethoxy]phthalate as an oil. $^1$H-NMR (CDCl$_3$) δ 1.92–2.12 (m, 4 H), 2.29 (br s, 3 H), 3.51–3.64 (m, 7 H), 3.87 (s, 3 H), 3.89 (s, 3 H), 4.10–4.19 (m, 2 H), 4.44 (m, 1 H), 6.73–8.02 (series of m, total 12 H).

To a stirred solution of dimethyl (S)-4-[1-[3-methoxy-4-[N'-(2-methylphenyl)ureido]phenylacetyl]-2-pyrrolidinylmethoxy]phthalate (413 mg, 0.70 mmol) in THF (10 mL) was added 0.25 N NaOH (10 mL) at room temp, and then the resulting mixture was heated under reflux overnight. After cooling to room temp, the reaction mixture was poured into 1 N HCl (100 mL). The solid was collected, washed with water and air-dried. The crude solid was washed with Et$_2$O to give 310 mg (79%) 28 as a yellow amorphous solid. IR (KBr) 1701 cm$^{-1}$; $^1$H-NMR (DMSO-d$_6$) δ 1.87–2.18 (m, 4 H), 2.25 (s, 3 H), 2.50 (s, 2 H), 3.38–3.60 (m, 4 H), 3.83 (s, 3 H), 400–4.14 (m, 1 H), 6.74–8.02 (series of m, 10 H), 8.46 (s, 1 H), 8.54 (s, 1 H); MS (FAB) m/z 562 (M$^+$+1).

Example 25

3-chloro-4-[[1-[3-methoxy-4-[N'-(2-methylphenyl) ureido]phenylacetyl]-2-pyrrolidinyl]methoxy]benzoic acid

29

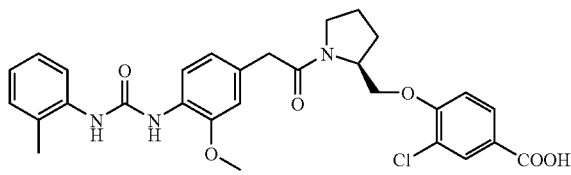

To a stirred solution of methyl 3-chloro-4-hydroxybenzoate (600 mg, 3,215 mmol), N-tert-butoxycalbonylprolinol (647,1 mg, 3,215 mmol), and Ph$_3$P (1.01 g, 3.858 mmol) in THF (10 mL) was added dropwise diisopropyl azodicarboxylate (DIAD) (0.8 mL, 3.890 mmol) at room temp and the mixture was stirred for 3 days at room temp, and for 18 hr at 70° C. The reaction mixture was evaporated off in vacuo, and the residue was chromatographed on silica-gel with n-hexane:EtOAc (5:1, v/v) as eluent to give 1.147 g (97%) methyl 3-chloro-[1-(tert-butoxycarbonyl)-2-pyrrolidinyl]methoxy benzoate as an oil. $^1$H-NMR (400 MHz, CDCl$_3$) δ 1.46, 1.48 (s each, 9H), 1.59–1.63 (br, 1H), 1.88 (br s, 1H), 2.05 (s, 1H), 2.05–2.21 (m, 2H), 3.34–3.45 (br m, 1.5H), 3.89 (s, 3H), 3.97 (br m, 0.5H), 4.21 (br s, 2H, 7.05 (d, J=8.8 Hz, 1H), 7.90 (dd, J=2.0, 8.8 Hz, 1H), 8.04 (d, J=2.0 Hz, 1H); MS (FAB) m/z 370 (M$^+$+1).

To a stirred solution of methyl 3-chloro-[1-(tert-butoxycarbonyl)-2-pyrrolidinyl]methoxy benzoate (1.14 g, 3.10 mmol) in CH$_2$Cl$_2$ (20 mL) was added TFA (5 mL) at 0° C., and the reaction mixture was stirred at room temp for 2 hr. The solvent was removed under a reduced pressure and the residue was treated with 1 N NaOH. The mixture was extracted with CHCl$_3$. The extract was washed with brine, dried over KOH, and concentrated under a reduced pressure to afford 741 mg (89%) methyl 3-chloro-4-(2-pyrrolidinyl) methoxybenzoate as a yellow oil. $^1$H-NMR (400 MHz, CDCl$_3$) δ 1.60–1.67 (m, 1H), 1.78–2.02 (m, 3H), 2.93–2.98 (m, 1H), 3.03–3.09 (m, 1H), 3.59 (dt, J=2.0, 9.3 Hz, 1H), 3.89 (s, 3H), 3.98 (dd, J=6.3, 8.8 Hz, 1H), 4.05 (dd, J=4.9, 9.3 Hz, 1H), 6.93 (d, J=8.8 Hz, 1H), 7.90 (dd, J=2.0, 8.8 Hz, 1H), 8.04 (d, J=2.0 Hz, 1H); MS (FAB) m/z 270 (M$^+$+1).

The mixture of pentafluorophenyl 3-methoxy-4-[N'-(2-methylphenyl)ureido] phenylacetate (500 mg, 1.04 mmol), methyl 3-chloro-4-(2-pyrrolidinyl)methoxybenzoate (281 mg, 1.04 mmol), Et$_3$N (0.17 mL, 1.25 mmol) in DMF (5 mL) was stirred for 1 hr at room temp. The mixture was diluted with EtOAc, washed with brine, and dried over Na$_2$SO$_4$. The solvent was removed under a reduced pressure, and the residue was chromatographed on silica-gel with n-hexane-EtOAc (1:3, v/v) as eluent to afford methyl 3-chloro-4-[[1-[3-methoxy-4-[N'-(2-methylphenyl)ureido] phenylacetyl]-2-pyrrolidinyl]methoxy]benzoate (620 mg, 1.04 mmol) as a white crystalline solid. To a stirred solution of this compound in THF (8 mL) and H$_2$O (2 mL) was added LiOH (74.9 mg, 3.126 mmol), and the mixture was stirred at room temp for 2 days. The mixture was diluted with CHCl$_3$, and treated with 1 N HCl. The solution was washed with brine, dried over Na$_2$SO$_4$, and evaporated in vacuo. The crude solid was recrystallized from n-hexane-EtOAc-CHCl$_3$ to afford 561.2 mg (98%) 29 as a white crystalline material. IR (KBr) 1676, 1599, 1487, 1267, 758, 754 cm$^1$; $^1$H-NMR (400 MHz, DMSO-d$_6$) δ 1.82–2.24 (m, 4H), 2.25 (s, 3H), 3.48–3.60 (m, 4H), 3.78 (s, 3H), 4.18 (m, 2H), 4.31 (m, 1H), 6.74 (dd, J=1.5, 8.3 Hz, 1H), 6.84 (d, J=2.0 Hz, 1H), 6.91–6.95 (m, 1H), 7.11–7.17 (m, 3H), 7.79 (dd, J=2.0, 8.3 Hz, 2H), 7.85 (d, J=2.0 Hz, 1H), 7.98 (d, J=8.3 Hz, 1H), 8.53 (s, 1H), 8.58 (s, 1H); MS (FAB) m/z 552 (M$^+$+1).

Example 26

3,5-dichloro-4-[[1-[3-methoxy-4-[N'-(2-methylphenyl)ureido]phenylacetyl]-2-pyrrolidinyl]methoxy]benzoic acid

30

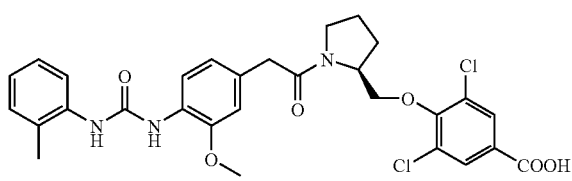

To a stirred solution of methyl 3,5-dichloro-4-hydroxybenzoate (600 mg, 2.714 mmol), N-tert-butoxycarbonylprolinol (546 mg, 2.714 mmol), and Ph$_3$P (854 mg, 3.257 mmol) in THF (10 mL) was added dropwise DIAD (0.68 mL, 3.283 mmol) at room temp and the mixture was stirred for 3 days at room temp, and for 18 hr at 70° C. The reaction mixture was concentrated and the residue was chromatographed on silica-gel with n-hexane-EtOAc (6:1, v/v) as eluent to give 988.8 mg (90%) methyl 4-[1-(tert-butoxycarbonyl)-2-pyrrolidinyl]methoxy-3,5-dichlorobenzoate a pale yellowish oil. $^1$H-NMR (400 MHz, CDCl$_3$) δ 1.44 (s, 9H), 1.88–2.15 (br m, 3H), 2.34 (br s, 1H), 3.40–3.44 (m, 2H), 3.92 (s, 3H), 3.92, 4.14 (m, 1H), 4.18 (br s, 2H), 7.98 (s, 2H); MS (FAB) m/z 404 (M$^+$+1).

To a stirred solution of methyl 4-[1-(tert-butoxycarbonyl)-2-pyrrolidinyl]methoxy-3,5-dichlorobenzoate (988 mg, 3.248 mmol) in CH$_2$Cl$_2$ (20 mL) was added TFA (5 mL) at 0° C., and the reaction mixture was stirred at room temp for 2 hr. The solvent was removed under a reduced pressure and the residue was treated with 1 N NaOH. The solution was extracted with CHCl$_3$. The extract was washed with brine, dried over Na$_2$SO$_4$, and concentrated under a reduced pressure to afford 672 mg (68%) methyl 3,5-dichloro-4-(2-pyrrolidinyl)methoxybenzoate as a pale yellowish oil. $^1$H-NMR (400 MHz, CDCl$_3$) δ 1.62–1.69 (m, 1H), 1.78–1.86 (m, 2H), 1.89–1.99 (m, 1H), 2.92–2.98 (m, 1H), 3.04–3.09 (m, 1H), 3.55–3.60 (m, 1H), 3.91 (s, 3H), 4.01 (dd, J=6.8, 8.8 Hz, 1H), 4.08 (dd, J=4.9, 8.8 Hz, 1H), 7.97 (s, 2H); MS (FAB) m/z 304 (M$^+$+1).

A mixture of pentafluorophenyl 3-methoxy-4-[N'-(2-methylphenyl)ureido]phenylacetate (385.8 mg, 0.803 mmol), methyl 3,5dichloro-4-(2-pyrrolidinyl)methoxybenzoate (244.3 mg, 0.803 mmol), Et$_3$N (0.13 mL, 0.964 mmol) in DMF (4 mL) was stirred for 1 hr at room temp. The mixture was diluted with EtOAc, washed with brine, and dried over Na$_2$SO$_4$. The solvent was removed under a reduced pressure, and the residue was chromatographed on silica-gel with n-hexane:EtOAc (1:2, v/v) as eluent to afford methyl 3,5-dichloro-4-[1-[3-methoxy4-[N'-(2-methylphenyl)ureido]phenylacetyl]-2-pyrrolidinyl]methoxy]benzoate as an oil. To a stirred solution of this compound in THF (8 mL) and H$_2$O (2 mL) was added LiOH (57.7 mg, 2.409 mmol), and the mixture was stirred at room temp overnight. The mixture was concentrated in vacuo, and the residue was diluted with CHCl$_3$. The solution was washed with 1 N HCl, brine, and dried over Na$_2$SO$_4$. The solvent was removed under a reduced pressure, and the obtained crude solid was recrystallized from n-hexane-MeOH—CHCl$_3$ to afford 428.2 mg (91%) 30 as a white crystalline powder. IR (KBr) 1618, 1535, 1454, 1257, 754 cm$^{-1}$; $^1$H-NMR (400 MHz, DMSO-d$_6$) δ 1.83–2.24 (m, 4H), 2.24 (s, 3H), 3.50–3.58 (m, 4H), 3.84 (s, 3H), 3.98–4.05 (m, 1H), 4.15 (dd, J=2.9, 8.7 Hz, 1H), 4.29 (br m, 1H), 6.74 (d, J=8.3 Hz, 1H), 6.87 (s, 1H), 6.93 (t, J=7.3 Hz, 1H), 7.11 (d, J=7.8 Hz, 1H), 7.16 (d, J=8.3 Hz, 1H), 7.79 (d, J=8.3 Hz, 1H), 7.86 (s, 1H), 7.87 (d, J=9.8 Hz, 1H), 7.99 (d, J=8.3 Hz, 1H), 8.49 (s, 1H), 8.58 (s, 1H); MS (FAB) m/z 586 (M$^+$+1)

Example 27

4-[1-[3-methoxy-4-[N'-(2-methylphenyl)ureido]phenylacetyl]-2-pyrrolidinylmethoxy]-3-nitrobenzoic acid

31

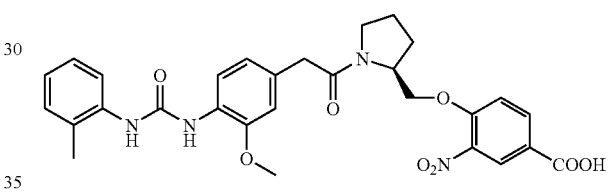

To a stirred solution of 4-hydroxy-3-nitrobenzoic acid (3.00 g, 0.0164mol) in MeOH-benzene (1:4, v/v) was added dropwise 2.0 M-n-hexane solution of TMSCHN$_2$ (8.2 mL, 0.0164mol) at room temp. After the resulting solution was stirred for 4 hr at room temp, the mixture was evaporated off in vacuo. The oily residue was chromatographed on silica-gel with CHCl$_3$ as eluent to afford 4.23 g (79%) methyl 4-hydoroxy-3-nitrobenzoate as a pale yellow crystalline material.

To a stirred mixture of N-tert-butoxycarbonylprolinol (1.02 g, 5.07 mmol), methyl 4-hydroxy-3-nitrobenzoate (1.00 g, 5.07 mmol), and Ph$_3$P (1.46 g, 5.58 mmol) in THF (10 mL) was added dropwise diisopropyl azodicarboxylate (DIAD) (95%) (1.16 mL, 5.58 mmol) at 0° C. The resulting mixture was heated under reflux for 46 hr. After cooling, the mixture was evaporated off in vacuo. The residue was dissolved in CH$_2$Cl$_2$ (10 mL) and added TFA (10 mL). After the solution was stirred for 0.5 hr at room temp, the solution was evaporated in vacuo. Water was added to the residue and washed with EtOAc. The aqueous layer was neutralized by the addition of sat. NaHCO$_3$ and extracted with EtOAc. The extract was dried over Na$_2$SO$_4$ and evaporated in vacuo to afford 0.698 g (49%) methyl 3-nitro-4-(2-pyrrolidinylmethoxy) benzoate as a gum.

A mixture of methyl 3-nitro-4-(2-pyrrolidinylmethoxy) benzoate (0.668 g, 2.38 mmol), 3-methoxy-4-[N'-(2-methylphenyl)ureido]phenylacetic acid (1.12 g, 3.57 mmol), 1-hydroxybenzo triazole (HOBt) (0.482 g, 3.57 mmol), 4-dimethylaminopyridine(DMAP) (43.6 mg, 0.357 mmol), and 1-ethyl-3-(3-dimethylaminopropyl)carbodiimide (EDC) (0.684 g, 3.57 mmol) in DMF (10 mL) was stirred for 15 hr at room temp. EtOAc was added to the mixture and washed successively with 1 N HCl, sat. NaHCO₃, and brine. The organic layer was dried over Na₂SO₄ and evaporated in vacuo. The residue was chromatographed on silica-gel with EtOH—CHCl₃ (1:20, v/v) as eluent to afford 0.927 g (68%) methyl 4-[1-[3-methoxy-4-[N'-(2-methylphenyl)ureido]phenylacethyl]-2-pyrrolidinylmethoxy]-3-nitrobenzoate as a yellow crystalline material.

A mixture of methyl 4-[1-[3-methoxy-4-[N'-(2-methylphenyl)ureido]phenylacethyl]-2-pyrrolidinylmethoxy]-3-nitrobenzoate (0.917 g, 1.59 mmol) in THF (10 mL) and 1 N NaOH (2.38 mL, 2.38 mmol) was heated under reflux for 2 hr. After cooling, the mixture was poured into ice water and extracted with EtOAc. The extract was washed with brine, dried over Na₂SO₄ and evaporated in vacuo to afford 0.826 g (92%) 31 as a yellow crystalline solid. $^1$H-NMR (400 MHz, CDCl₃) δ 1.91, 2.09 (1H, 3H, each m), 2.28 (3H, s), 3.54–3.62 (4H, m), 3.64 (3H, s), 4.15, 4.59 (each 1H, each d, J=7.8 Hz), 4.46 (1H, m), 6.66, 7.22 (each 1H, each s), 6.72 (1H, d, J=8.3 Hz), 7.11–7.28 (4H, m), 7.46 (1H, d, J=7.8 Hz), 7.74 (1H, d, J=7.8 Hz), 7.85 (1H, s), 8.17 (1H, dd, J=2.0, 8.8 Hz), 8.48 (1H, d, J=2.4 Hz); MS (FAB) m/z 563 (M⁺+1).

Example 28

3-amino-4-[1-[3-methoxy-4-[N'-(2-methylphenyl)ureido]phenylacetyl]-2-pyrrolidinylmethoxy]benzoic acid

32

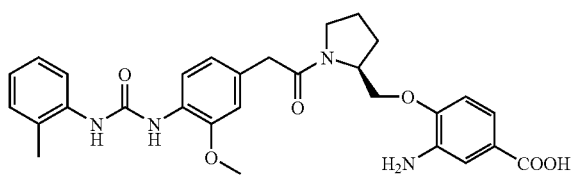

A stirred mixture of 4-[1-[3-methoxy-4-[N'-(2-methylphenyl)ureido]phenylacethyl]-2-pyrrolidinylmethoxy]-3-nitrobenzoic acid (101 mg, 0.190 mmol) and 5% Pd—C (0.247 g) in methanol was hydrogenated at 1 atm for 48 hr. Insoluble catalyst was removed, and the filtrate was evaporated in vacuo. The residue was chromatographed on silica-gel with EtOH—CHCl₃ (1:1, v/v) as eluent to afford 61.0 mg (60%) 32 as a crystalline. material. $^1$H-NMR (400 MHz, DMSO-d₆) δ 1.95 (4H, m), 2.23 (3H, s), 3.60, 3.91, 4.10, 4.34 (5H, each m), 3.81 (3H, s), 4.88 (2H, m); 6.74 (1H, d, J=8.3 Hz), 6.86–7.28 (5H, m), 7.78 (1H, d, J=7.8 Hz), 7.99 (1H, d, J=8.3 Hz), 8.01 (1H, s), 8.45, 8.55 (each 1H, each s); MS (FAB) m/z 533 (M⁺+1).

Example 29

4-[2-[1-[4-[N'-(2-fluorophenyl)ureido)-3-methoxyphenylacetyl]-2-pyrrolidinyl]ethynyl]benzoic acid

33

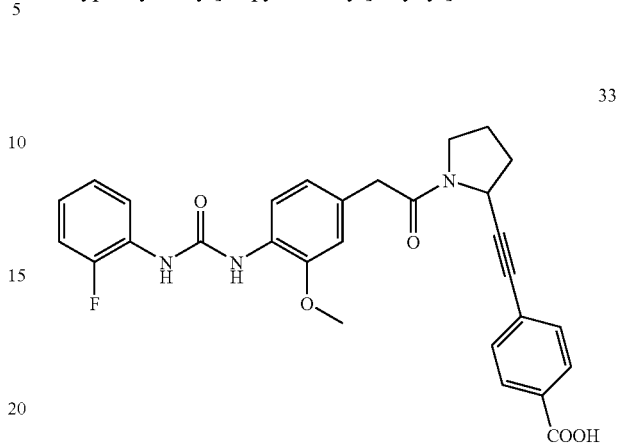

To a stirred solution of benzyl 4-amino-3-methoxyphenylacetate (1.36 g, 5 mmol) in THF (20 mL) was added 2-fluorophenyl isocyanate (561 ul, 5 mmol) and a catalytic amount of Et₃N. The resulting mixture was stirred for 3 hr. The mixture was quenched by the addition of H₂O (10 mL) and extracted with EtOAc. The extract was washed with brine, dried over MgSO₄, and evaporated. The residue was chromatographed on silica-gel with CHCl₃ as eluent to give 2.06 g (q.y.) benzyl 4-[N'-(2-fluorophenyl)ureido]-3-methoxyphenylacetate as a green oil. $^1$H-NMR (CDCl)₃ δ 3.63 (2H, s), 3.82 (3H, s), 5.14 (2H, s), 6.79–7.37 (12H, m), 8.01 (1H, d, J=7.8 Hz), 8.09–8.14 (1H, m).

To a stirred solution of benzyl 4-[N'-(2-fluorophenyl)ureido]-3-methoxyphenylacetate (2.04 g, 5 mmol) in THF (40 mL) was added 0.25 N NaOH (40 mL). The resulting mixture was stirred overnight. The mixture was poured into 1 N HCl (10 mL), and the resulting precipitate was collected with suction. The residue was recrystallized from CHCl₃-EtOH to give 1.04 g (66%) 4-[N'-(2-fluorophenyl)ureido]-3-methoxyphenylacetic acid as a white crystalline powder. mp 185 –188 (d); $^1$H-NMR (DMSO-d₆) δ 3.50 (2H, s), 3.82 (3H, s), 6.78 (1H, dd, J=1.4 and 8.3 Hz), 6.92 (1H, d, J=1.4 Hz), 6.95–7.01 (1H, m), 7.10–7.14 (1H, m), 7.19–7.24 (1H, m), 8.01 (1H, d, J=8.3 Hz), 8.14–8.18 (1H, m), 8.72 (1H, s), 9.17 (1H, s); MS (FAB) m/z 319 (M⁺+1); Anal. Calcd for C₁₆H₁₅N₂O₄F: C, 60.37; H, 4.75; N, 8.80. Found: C, 60.20; H, 4.82; N, 8.67.

A mixture of 4-[N'-(2-fluorophenyl)ureido]-3-methoxyphenylacetic acid (255 mg, 0.8 mmol), 2-[2-(4-ethoxycarbonylphenyl)ethynyl]pyrrolidine (195 mg, 0.8 mmol), EDC (230 mg, 1.2 mmol), DMAP (98 mg, 0.8 mmol) in DMF (20 mL) was stirred overnight. The reaction mixture was poured into 1 N HCl and the resulting precipitate was collected with suction and dissolve in CHCl₃. The solution was dried over MgSO₄ and evaporated. The residue was chromatographed on silica gel with CHCl₃-MeOH (100:1, v/v) as eluent to give the desired compound, which was dissolved in THF (8 mL). 0.25 N NaOH (8 mL) was added to this solution and the resulting mixture was stirred overnight. The mixture was poured into 1 N HCl and extracted with CHCl$_3$. The extract was washed with brine, dried over MgSO$_4$, and evaporated. The residue was recrystallized from CHCl$_3$-n-hexane to give 144 mg (37%) 33 as a pale yellow crystalline powder. mp 152–155 (d); $^1$H-NMR (DMSO-d$_6$) δ 1.92–2.27 (4 H, m), 2.50 (2 H, s), 3.33–3.78 (2 H, m), 3.80 and 3.82 (total 3 H, s, each), 4.88–5.12 (1 H, m), 6.77–7.24 and 7.99–8.20 (total 7 H, m), 7.48 and 7.52 (2 H, d, J=8.3 Hz, each), 7.91 (2H, d, J=8.3 Hz), 8.72 (1H, s), 9.18 (1H, s), 13.11 (1H, br-s); MS (FAB) m/z 516 (M$^+$+1); Anal. Calcd for C$_{29}$H$_{26}$N$_3$O$_5$F.2H$_2$O: C, 63.15; H, 5.48; N, 7.62. Found: C, 63.58; H, 5.15; N, 7.22.

Example 30

4-[[1-[3-methoxy-4-[N'-(2-methylphenyl)ureido]phenylacetyl]-2-pyrrolidinyl]methoxy]-3-methylbenzoic acid

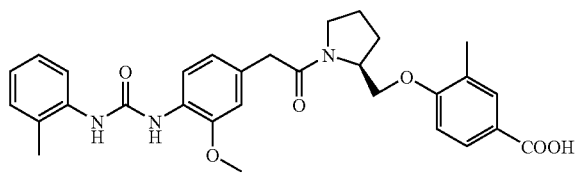

34

To a stirred solution of 4-iodo-2-methylphenol (465 mg, 1.987 mmol), N-tert-butoxycarbonylprolinol (400 mg, 1.987 mmol), and Ph$_3$P (625 mg, 2.384 mmol) in THF (7 mL) was added dropwise DIAD (0.5 mL, 2.404 mmol) at room temp, and the mixture was stirred for 13 hr at 70° C. The reaction mixture was concentrated in vacuo and the residue was chromatographed on silica-gel with n-hexane-EtOAc (9:1, v/v) as eluent to give 645.3 mg (78%) 4-[1-(tert-butoxycarbonyl)-2-pyrrolidinyl]methoxy-1-iodo-3-methylbenzene as a pale yellow oil. $^1$H-NMR (400 MHz, CDCl$_3$) δ 1.47 (s, 9H), 1.83–1.89 (m, 1H), 1.96–2.04 (m, 3H), 2.16 (s, 3H), 3.37–3.43 (br m, 2H), 3.81, 3.94 (br m each, 1H), 4.08–4.18 (m, 2H), 6.62 (br s, 1H), 7.42 (s, 2H); MS (FAB) m/z 418 (M$^+$+1).

To a stirred solution of 4-[1-(tert-butoxycarbonyl)-2-pyrrolidinyl]methoxy-1iodo-3-methylbenzene (645.3 mg, 1.546 mmol) in DMSO (7 mL) and MEOH (6 mL) was added Et$_3$N (0.47 mL, 3.401 mmol), Pd(OAc)$_2$ (17.4 mg, 0.077 mmol) and 1,3-bis(diphenylphosphino) propane (31.46 mg, 0.077 mmol). To the stirred mixture was induced CO gas for 10 min. The mixture was stirred at 70° C. for 2 days and concentrated. The residue was diluted with EtOAc, washed with brine, and dried over Na$_2$SO$_4$. The solvent was removed under a reduced pressure, and the residue was chromatographed on silica-gel with n-hexane-EtOAc (5:1, v/v) as eluent to afford 301.6 mg (56%) methyl4-[1-(tert-butoxycarbonyl)-2-pyrrolidinyl]methoxy-3-methylbenzoate as an oil. $^1$H-NMR (400 MHz, CDCl$_3$) δ 1.47 (s, 9H), 1.86–2.10 (br m, 4H), 2.33 (s, 3H), 3.32–3.50 (br m, 2H), 3.88 (s, 3H), 3.88, 4.04 (br m each, 1H), 4.13–4.20 (m, 2H), 6.89 (br m, 1H), 7.82 (s, 1H), 7.85 (dd, J=2.0, 8.8 Hz, 1H); MS (FAB) m/z 350 (M$^+$+1).

To a stirred solution of methyl 4-[1-(tert-butoxycarbonyl)-2-pyrrolidinyl]methyloxy-3-methylbenzoate (301.6 mg, 0.863 mmol) in CH$_2$Cl$_2$ (6 mL) was added TFA (1.2 mL) at 0° C., and the mixture was stirred at room temp for 1 hr. The solvent was removed under a reduced pressure, and the residue was made basic by the addition of 1 N NaOH. The mixture was extracted with CHCl$_3$. The extract was washed with brine, dried over Na$_2$SO$_4$, and concentrated under a reduced pressure to afford 192.5 mg (90%) methyl 3-methyl-4-(2-pyrrolidinyl)methoxybenzoate as an oil. $^1$H-NMR (400 MHz, CDCl$_3$) δ 1.58–1.65 (m, 1H), 1.78–2.00 (m, 3H), 2.24 (s, 3H), 2.97 (dt, J=6.8, 10.2 Hz, 1H), 3.05 (dt, J=5.9, 6.8 Hz, H), 3.54–3.58 (m, 1H), 3.87 (s, 3H), 3.92 (dd, J=6.3, 9.3 Hz, 1H), 3.99 (dd, J=4.9, 9.3 Hz, 1H), 6.81 (d, J=8.3 Hz, 1H), 7.83 (s, 1H), 7.85 (dd, J=2.0, 8.3 Hz, 1H); MS (FAB) m/z 250 (M$^+$+1).

A mixture of pentafluorophenyl 3-methoxy4-[N'-(2-methylphenyl)ureido]phenylacetate (211.3 mg, 0.44 mmol), methyl 3-methyl-4-(2-pyrrolidinyl)methoxybenzoate (109.7 mg, 0.44 mmol), Et$_3$N (73.6 ul, 0.528 mmol) in DMF (2 mL) was stirred for 1.5 hr at room temp. The reaction mixture was diluted with EtOAc. The solution was washed with brine and dried over Na$_2$SO$_4$. The solvent was removed under a reduced pressure, and the residue was chromatographed on silica-gel with n-hexane-EtOAc (1:3, v/v) as eluent to afford methyl 4-[[1-[3-methoxy-4-[N'-(2-methylphenyl)ureido]phenylacetyl]-2-pyrrolidinyl]methoxy]-3-methyl benzoate (241.6 mg, q.y.) as an oil. To a stirred solution of this compound in THF (4.4 mL) and H$_2$O (1.1 mL) was added LiOH (32 mg, 1.32 mmol), and the reaction mixture was stirred at room temp overnight. The mixture was diluted with CHCl$_3$, and acidified by the addition of 1 N HCl. The solution was washed with brine and dried over Na$_2$SO$_4$. The solvent was removed under a reduced pressure, and the obtained crude solid was recrystallized from n-hexane-EtOAc-CHCl$_3$-MeOH to afford 126.3 mg (54%) 34 as a white crystalline powder. IR (KBr) 1685, 1606, 1454, 1257, 752 cm$^{-1}$; $^1$H-NMR (400 MHz, DMSO-d$_6$) δ 1.87–2.10 (m, 4H), 2.12 (s, 3H), 2.25 (s, 3H), 3.51–3.71 (m, 4H), 3.76 (s, 3H), 4.08–4.18 (m, 2H), 4.34 (m, 1H), 6.74 (dd, J=1.5, 9.8 Hz, 1H), 6.84 (d, J=1.5 Hz, 1H), 6.94 (t, J=6.8 Hz, 1H), 7.06 (d, J=8.8 Hz, 1H), 7.12 (d, J=7.8 Hz, 1H), 7.16 (d, J=7.8 Hz, 1H), 7.72 (s, 1H), 7.76 (dd, J=2.0, 8.3 Hz, 1H), 7.79 (d, J=7.8 Hz, 1H), 7.99 (d, J=8.3 Hz, 1H), 8.46 (s, 1H), 8.54 (s, 1H); MS (FAB) m/z 532 (M$^+$+1); Anal. Calcd for C$_{30}$H$_{33}$N$_3$O$_6$.1/2H$_2$O: C, 66.65; H, 6.34; N, 7.77. Found: C, 66.16; H. 6.37; N, 7.50.

Example 31

(S)-4-[1-[3-methoxy-4-[N'-(2-methylphenyl)ureido]phenylacetyl]-2-pyrrolidinylmethoxy]isophthalic acid

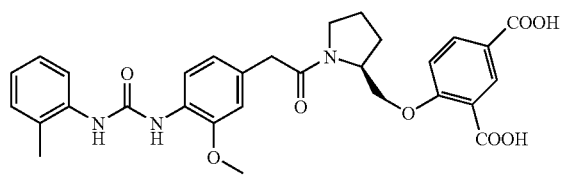

35

To a solution of dimethyl 4-acetoxyisophthalate (1.52 g, 6.03 mmol) in MeOH (70 mL) was added sat. NaHCO$_3$, and the resulting mixture was stirred for 3 hr at room temp. The resulting mixture was poured into 1 N HCl and extracted with EtOAc. The extract was washed with sat. NaHCO$_3$, brine, and dried over MgSO₄. The solvent was evaporated to give 1.27 g (q.y.) dimethyl 4-hydroxy isophthalate as a white crystalline powder. ¹H-NMR (CDCl₃) δ 3.91 (s, 3 H), 3.99 (s, 3 H), 7.01 (d, 1 H, J=8.8 Hz), 8.11 (dd, 1 H, J=2.4, 8.8 Hz), 8.55 (d, 1 H, J=2.4 Hz)

To a stirred solution of dimethyl 4-hydroxyisophthalate (1.27 g, 6.04 mmol), (S)-N-Boc-Prolinol (1.22 g, 6.06 mmol), PPh₃ (1.90 g, 7.24 mmol) in THF (30 mL) was added DIAD (1.43 mL, 7.26 mmol) at room temp. The resulting stirred mixture was then heated under reflux for 15 hr. After cooling to room temp, the resulting mixture was evaporated and the residue was purified by column chromatography on silica-gel with n-hexane-EtOAc (3:1, v/v) as eluent to give 2.10 g (88%) dimethyl (S)-4-[1-(tert-butoxycarbonyl)-2-pyrrolidinylmethoxy]isophthalate as a yellow oil. ¹H-NMR (CDCl₃) δ 1.26 (s, 9 H), 1.85–2.16 (m, 3 H), 3.36–3.46 (m, 2 H), 3.90 (s, 6 H), 4.11–4.31 (m, 2 H), 4.95–5.02 (m, 2 H), 7.09 (dd, H, J=9.3, 24.9 Hz), 8.11–8.14 (m, 1 H), 8.46 (d, 1 H, J=9.3 Hz)

A mixture of dimethyl (S)-4-[1-(tert-butoxycarbonyl)-2-pyrrolidinylmethoxy]isophthalate (2.01 g, 5.11 mmol), TFA (20 mL), and CH₂Cl₂ (25 mL) was stirred for 1.5 hr at room temp. The resulting mixture was concentrated in vacuo and made basic with sat. NaHCO₃. The mixture was extracted with CH₂Cl₂, washed with brine, dried over Na2CO₃, and evaporated. The residue was purified by column chromatography on silica-gel with CHCl₃-MeOH (9:1, v/v) as eluent to give 0.80 g (53%) dimethyl (S)-4-(2-pyrrolidinylmethoxy)isophthalate as a yellow oil. ¹H-NMR (CDCl₃) δ 1.71 (m, 1 H), 1.89 (m, 2 H), 2.00 (m, 1 H), 3.05–3.13 (m, 2 H), 3.67 (m, 1 H), 3.90 (s, 3 H), 3.91 (s, 3 H), 4.05–4.18 (m, 2 H), 7.00 (d, 1 H, J=8.8 Hz), 8.14 (dd, 1 H, J=2.4, 8.8 Hz), 8.50 (d, 1 H, J=2.4 Hz).

To a stirred solution of dimethyl (S)-4-(2-pyrrolidinylmethoxy)isophthalate (616 mg, 2.10 mmol) in DMF (13 mL) was added pentafluoro ester of 3-methoxy4-[N'-(2-methylphenyl)ureido]phenylacetic acid (1.00 g, 2.08 mmol) and Et₃N (425 μl, 3.12 mmol), and the resulting mixture was stirred for 3.5 hr at room temp. The resulting mixture was diluted with EtOAc, washed with 1 N HCl, sat. NaHCO₃, brine, and dried over Na₂SO₄. After removal of the solvent, the residue was purified by column chromatography on silica-gel with CHCl₃-MeOH (50:1, v/v) as eluent to give 1.41 g(q.y.) dimethyl (S)-4-[1-[3-methoxy-4-[N'-(2-methylphenyl)ureido]phenylacetyl]-2-pyrrolidinylmethoxy] isophthalate as a yellow oil. ¹H-NMR (CDCl₃) δ 1.86–2.29 (m, 4 H), 2.30 (s, 3 H), 3.47–3.57 (m, 2 H), 3.58 (s, 3 H), 3.59 (s, 2 H), 3.83 (s, 3 H), 3.91 (s, 3 H), 4.22–4.37 (m, 2 H), 4.42–4.47 (m, 1 H), 6.44–8.46 (series of m, 12 H).

To a stirred solution of dimethyl (S)-4-[1-[3-methoxy-4-[N'-(2-methylphenyl)ureido]phenyl acetyl]-2-pyrrolidinylmethoxy]isophthalate (1.41 g, 2.39 mmol) in THF (20 mL) was added 0.25 N NaOH (20 mL), and the resulting mixture was then heated under reflux overnight. After cooling to room temp, the mixture was poured into 1 N HCl (150 mL) and the solid was collected. The crude solid was recrystallized from CHCl₃-MeOH to give 140 mg (10%) 35 as a white crystalline powder. ¹H-NMR (CDCl₃) δ 1.83–2.18 (m, 4 H), 2.24 (s, 3H), 3.44–3.55 (m, 4H), 3.59 (s, 2 H), 3.80 (s, 3 H), 4.05–4.24 (m, 2 H), 4.28–4.32 (m, 1 H), 6.73–8.55 (series of m, total 12 H); MS (FAB) m/z 562 (M⁺+1); Anal. Calcd. for C₃₀H₃₁N₃O₈.4H₂O: C, 56.87; H, 6.20; N, 6.63. Found: C, 56.73; H, 5.56: N, 6.52.

Example 32

3-methoxy4-[2-[1-[3-methoxy4-[N'-(2-methylphenyl)ureido]phenylacetyl]-2-pyrrolidinyl]ethynyl] benzoic acid

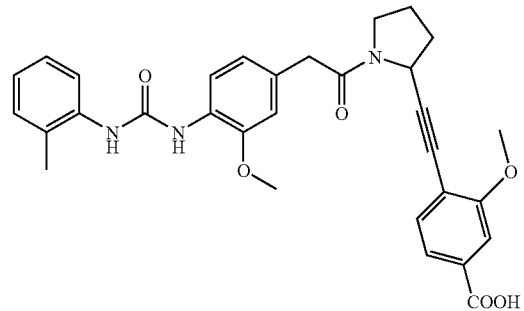

36

A stirred mixture of methyl 3-methoxy-4-nitrobenzoate (1.20 g, 5.7 mmol) and 5% Pd—C (1.0 g) in EtOH (30 mL) and THF (20 mL) was hydrogenated overnight at 1 atm. The mixture was filtered and the filtrate was evaporated. The residue was chromatographed on silica-gel with CHCl₃ as eluent, and the solid obtained was further purified by recrystallization from CHCl₃-n-hexane to give 805 mg (78%) methyl 4-amino-3-methoxybenzoate as white plates. mp 126–128; IR (KBr) 3475, 1700 cm⁻¹; ¹H-NMR (CDCl₃) δ 3.86 (3H, s), 3.89 (3H, s), 4.21 (2H, br s), 6.66 (1H, d, J=8.3 Hz), 7.45 (1H, d, J=1.9 Hz), 7.54 (1H, dd, J=1.9 and 8.3 Hz); MS (FAB) m/z 182 (M⁺+1); Anal. Calcd for C₉H₁₁NO₃: C, 59.66; H, 6.12; N, 7.73. Found: C, 59.65; H. 6.15; N, 7.65.

A stirred solution of methyl 4-amino-3-methoxybenzoate (725 mg, 4 mmol) in EtOH (10 mL) was added to dil.H₂SO₄ (prepared from H₂SO₄ 0.5 mL and H₂O 10 mL) at 0° C. A solution of NaNO₂ (331 mg, 4.8 mmol) in H₂O (10 mL) was added to the mixture. After stirring for 0.5 hr at the same temp, the mixture was poured into a cooled (0° C.), stirred suspended solution of KI (1.83 g, 11 mmol) and cat. Cu in H₂O (100 mL). The mixture was vigorously stirred for 1 hr at room temp and extracted with CHCl₃. The extract was washed with brine, dried over MgSO₄, and evaporated. The residue was chromatographed on silica-gel with n-hexane-EtOAc (10:1, v/v) as eluent to give a mixture of methyl 4-iodo-3-methoxybenzoate and methyl 3-methoxybenzoate (748 mg) as a colorless oil.

To this oil was added Pd(PPh₃)₄ (150 mg, 0.13 mmol), CuI (57 mg, 0.3 mmol) and i-Pr₂NH (10 mL). The mixture was stirred for 1 hr under N₂ and a solution of 1-(tert-butoxycarbonyl)-2-ethynylpyrrolidine (488 mg, 2.5 mmol) in i-Pr₂NH (10 mL) was added to the mixture. After stirring for 2 hr, the mixture was poured into H₂O and extracted with EtOAc. The extract was washed with brine, dried over MgSO₄, and evaporated. The residue was chromatographed on silica-gel with n-hexane-EtOAc (5:1, v/v) as eluent to give 431 mg (48%) 1-(tert-butoxycarbonyl)-2-[2-(2-methoxy-4-methoxycarbonylphenyl) ethynyl]pyrrolidine as a yellow oil. ¹H-NMR (CDCl₃) δ 1.49 (9 H, s), 1.77–2.14 (4 H, m), 3.36–3.51 (2 H. m), 3.90 (3 H, s), 3.91 (3 H, s), 4.60–4.81 (1 H, m), 7.36–7.39 (1 H, s), 7.51 (1 H, s), 7.55–7.57 (1 H, m).

To a stirred solution of 1-(tert-butoxycarbonyl)-2-[2-(2-methoxy-4-methoxycarbonyl phenyl)ethynyl]pyrrolidine (395 mg, 1.1 mmol) in CH$_2$Cl$_2$ (3 mL) was added TFA (3 mL). The resulting mixture was stirred for 1 hr. The mixture was concentrated in vacuo and made basic by the addition of sat. NaHCO$_3$, and extracted with CHCl$_3$. The extract was washed with H$_2$O, dried over MgSO$_4$, and evaporated to give 238 mg (84%) 2-[2-(2-methoxy4-methoxycarbonylphenyl) ethynyl]pyrrolidine as a yellow oil. $^1$H-NMR (CDCl$_3$) δ 1.81–2.16 (4 H, m), 2.97–3.17 (2 H, m), 3.91 (6 H, s), 4.13–4.15 (1 H, m), 7.41 (1 H, d, J=8.3 Hz), 7.51 (1 H, s), 7.56 (1 H, d, J=8.3 Hz).

A mixture of 2-[2-(2-methoxy-4-methoxycarbonylphenyl)ethynyl]pyrrolidine (233 mg, 0.9 mmol), 3-methoxy-4-[N'-(2-methylphenyl)ureido]phenylacetic acid (314 mg, 1 mmol), EDC (268 mg, 1.4 mmol), DMAP (110 mg, 0.9 mmol) in DMF (10 mL) was stirred overnight. The mixture was poured into 1 N HCl and the resulting solid was collected with suction. The solid obtained was dissolved in CHCl$_3$, and the solution was dried over MgSO$_4$ and evaporated. The residue was subjected to short column chromatography on silica-gel with EtOAc as eluent to give an oil. The oil was dissolved in THF (5 mL) and 0.25 N NaOH was added to this solution with stirring. The solution was poured into ice-1 N HCl to give a solid. The solid was collected, washed with water, and air-dried. The crude solid was recrystallized from CHCl$_3$-n-hexane to give 215 mg (44%) 36 as a white crystalline powder. mp 141–145; IR (KBr) 3338, 2956, 2935, 2875, 2593, 1711 cm$^{-1}$; $^1$H-NMR (DMSO-d$_6$) δ 1.91–2.14 (4 H, m), 2.24 (3 H, s), 3.38–3.68 (4 H, m), 4.88–5.08 (1 H, m), 6.76–8.56 (12 H, m); MS (FAB) m/z 542 (M$^+$+1).

Example 33

3-N,N-dimethylamino-4-[1-[3-methoxy-4-[N'-(2-methylphenyl)ureido]phenylacetyl]-2-pyrrolidinylmethoxy]benzoic acid

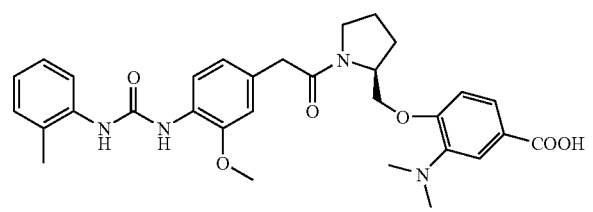

37

A stirred mixture of methyl 4-hydroxy-3-nitrobenzoate (3.22 g, 0.0163 mol) and 5% Pd—C (12.9 g) in MeOH (30mL) was hydrogenated under an atmospheric pressure for 70 hr at room temp. Insoluble catalyst was removed, and the filtrate was evaporated in vacuo. The residue was chromatographed on silica-gel with EtOH—CHCl$_3$ (1:20, v/v) as eluent to afford 1.89 g (69%) methyl 3-amino-4-hydroxybenzoate as a pale brown syrup.

A stirred mixture of methyl 3-amino-4-hydroxybenzoate (1.07 g, 6.40 mmol) and 5% Pd—C (2.14 g) in MeOH (20 mL) and 37% aq. formaldehyde (1.08 mL, 0.0122mol) and 1 N HCl (6.1 mL) was hydrogenated under an atmospheric pressure for 26 hr at room temp. Insoluble catalyst was removed, and the filtrate was evaporated in vacuo. The residue was chromatographed on silica-gel with EtOAc-n-hexane (1:10, v/v) as eluent to afford 0.817 g (70%) methyl 3-(N,N-dimethylamino)-4-hydroxybenzoate as a syrup.

To a stirred mixture of methyl 3-(N, N-methylamino)-4-hydroxybenzoate (0.817 g, 4.18 mmol), N-tert-butoxycarbonylprolinol (0.926 g, 4.60 mmol), Ph$_3$P (1.21 g, 4.60 mmol) in THF (20 mL) was added dropwise DIAD (95%) (0.953 mL, 4.60 mmol) at 0° C. The resulting mixture was heated under reflux for 41 hr. After cooling, the mixture was evaporated off in vacuo. The residue was chromatographed on silica-gel with EtOAc-n-hexane (1:10 to 1:6, v/v) as eluent to give a syrup which was used for the subsequent reaction without further purification. This syrup was dissolved in CH$_2$Cl$_2$ (10 mL) and added TFA (10 mL). After the solution was stirred for 5 hr at room temp, the solution was evaporated in vacuo. Water was to the residue and washed with CHCl$_3$. The aqueous layer was neutralized by the addition of sat. NaHCO$_3$ and extracted with CHCl$_3$. The extract was dried over Na$_2$SO$_4$ and evaporated in vacuo to afford 1.03 g (89%) methyl 3-(N, N-dimethylamino)-4-(2-pyrrolidinylmethoxy)benzoate as a gum.

A mixture of methyl 3-(N, N-dimethylamino)-4-(2-pyrrolidinylmethoxy)benzoate (0.529 g, 1.90 mmol), 3-methoxy-4-[N'-(2-methylphenyl)ureido]phenylacetic acid (0.597 g, 1.90 mmol), HOBt (0.308 g, 2.28 mmol), 4-dimethylaminopyridine(DMAP) (23.2 mg, 0.190 mmol), and 1-ethyl-3-(3-dimethylaminopropyl)carbodiimide (EDC) (0.437 g, 2.28 mmol) in DMF (10 mL) was stirred for 15 hr at room temp. The mixture was neutralized by the carefully addition of 1 N HCl and extracted with EtOAc. The extract was dried over Na$_2$SO$_4$ and evaporated in vacuo to afford 0.607 g (56%) methyl 3-N,N-dimethylamino-4-[1-[3-methoxy-4-[N'-(2-methylphenyl)ureido]-phenylacetyl]-2-pyrrolidinyl methoxy]benzoate as a white crystalline material.

A mixture of methyl 3-N,N-dimethylamino-4-[1-[3-methoxy-4-[N'-(2-methylphenyl) ureido]-phenylacetyl]-2-pyrrolidinylmethoxy]benzoate (0.600 g, 1.04 mmol) in THF (10 mL) and 0.25 N NaOH (5 mL, 1.25 mmol) was stirred for 21 hr at room temp. CHCl$_3$ was added to the mixture and extracted with a mixture of water(100 mL)-1 N NaOH (4 mL). The extract was neutralized with sat. NH$_4$Cl and extracted with CHCl$_3$. The extract was dried over Na$_2$SO$_4$ and evaporated in vacuo to afford 428 mg (70%) 37 as a white crystalline solid. $^1$H-NMR (400 MHz, DMSO-d$_6$) δ 1.88, 1.99 and 2.11 (4H, each m), 2.24 (3H, s), 2.67 (6H, s), 3.33 (2H, m), 3.58 (2H, m), 4.05–4.32 (3H, m), 6.75 (1H, d, J=7.3 Hz), 6.92–6.95 (1H, m), 7.05 (1H, d, J=8.3 Hz), 7.11–7.17 (2H, m), 7.42 (1H, s), 7.52 (1H, d, J=7.8 Hz), 7.79 (1H, d, J=7.8 Hz), 8.00 (1H, d, J=7.8 Hz), 8.31 (1H, s), 8.46, 8.55 (each 1H, each s); MS (FAB) m/z 533 (M$^+$+).

Example 34

3-fluoro-4-[[1-[3-methoxy-4-[N'-(2-methylphenyl) ureido]phenylacetyl]-2-pyrrolidinyl]methoxy]benzoic acid

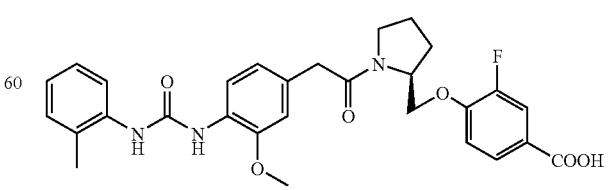

38

To a stirred solution of 4-bromo-2-fluorophenol (217 ul, 2.002 mmol), N-tert-butoxycarbonyl prolinol (403 mg, 2.002 mmol), and Ph$_3$P (630 mg, 2.403 mmol) in THF (7 mL) was added DIAD (477 ul, 2.423 mmol) at room temp. The resulting mixture was stirred for 6 hr at room temp and then overnight at 70° C. The mixture was concentrated in vacuo and the residue was chromatographed on silica-gel with n-hexane-EtOAc (5:1, v/v) as eluent to give 549.4 mg (73%) 1-bromo-4-[1-(tert-butoxycarbonyl)-2-pyrrolidinyl]methoxy-3-fluorobenzene as an oil. $^1$H-NMR (400 MHz, CDCl$_3$) δ 1.46 (s, 9H), 1.85 (br m, 1H), 1.90–2.10 (br s, 3H), 3.30–3.47 (m, 2H), 3.85, 4.04 (br s each, 1H), 4.11–4.20 (m, 2H), 6.82–6.98 (m, 1H), 7.13–7.26 (m, 2H); MS (FAB) m/z 374 (M$^+$+1).

To a stirred solution of 1-bromo4-[1-(tert-butoxycarbonyl)-2-pyrrolidinyl]methoxy-3-fluorobenzene (549.4 mg, 1.468 mmol) in DMSO (6 mL) and MeOH (5 mL) was added Et$_3$N (448 ul, 3.229 mmol), Pd(OAc)$_2$ (36.2 mg, 0.161 mmol), and 1,3-bis(diphenylphosphino)propane (66.4 mg, 0.161 mmol). To the mixture was induced CO gas for 10 min. The resulting mixture was stirred at 70° C. for 2 days under a current of CO. After the mixture was concentrated, the residue was diluted with EtOAc. The solution was washed with brine and dried over Na$_2$SO$_4$. The solvent was removed under a reduced pressure and the residue was chromatographed on silica-gel eluting with n-hexane:EtOAc (5:1, v/v) as eluent to afford 323.0 mg (62%) methyl 4-[1-(tert-butoxycarbonyl)-2-pyrrolidinyl]methoxy-3-fluorobenzoate as a pale yellow oil. $^1$H-NMR (400 MHz, CDCl$_3$) δ 1.47 (s, 9H), 1.87 (br s, 1H), 1.95–2.10 (m, 3H), 3.34–3.44 (br m, 2H), 3.89 (s, 3H), 3.94 and 4.11–4.26 (br m each, 3H), 7.03–7.11 (m, 1H), 7.75–7.80 (m, 2H); MS (FAB) m/z 354 M$^+$+1).

To a stirred solution of methyl 4-[1-(tert-butoxycarbonyl)-2-pyrrolidinyl]methoxy-3-fluorobenzoate (323.0 mg, 0.914 mmol) in CH$_2$Cl$_2$ (6.5 mL) was added TFA (1.3 mL) at 0° C., and the mixture was stirred 1.5 hr at room temp. The solvent was removed under a reduced pressure and the residue was made basic by the addition of 1 N NaOH. The mixture was extracted with CHCl$_3$. The extract was washed with brine, dried over Na$_2$SO$_4$, and concentrated under a reduced pressure to afford 174.8 mg (76%) methyl 3-fluoro4-(2-pyrrolidinyl)methoxybenzoate as a brownish oil. $^1$H-NMR (400 MHz, CDCl$_3$) δ 1.54–1.63 (m, 1H), 1.76–2.02 (m, 3H), 2.93–3.07 (m, 2H), 3.57 (ddd, J=4.9, 6.9, 14.3 Hz, 1H), 3.89 (s, 3H), 3.97 (dd, J=6.8, 9.3 Hz, 1H), 4.04 (dd, J=5.0, 8.8 Hz, 1H), 6.98 (t, J=17.6 Hz, 1H), 7.73 (dd, J=2.0, 11.7 Hz, 1H), 7.78 (dt, J=2.0, 8.8 Hz, 1H); MS (FAB) m/z 253 (M$^+$+1).

A mixture of pentafluorophenyl 3-methoxy-4-[N'-(2-methylphenyl)ureido]phenylacetate (324.5 mg, 0.676 mmol), methyl 3-fluoro4-(2-pyrrolidinyl)methoxybenzoate (171.1 mg, 0.676 mmol), Et$_3$N (113 ul, 0.811 mmol) in DMF (5 mL) was stirred for 2 hr at room temp. The mixture was diluted with EtOAc, washed with brine, and dried over Na$_2$SO$_4$. The solvent was removed under a reduced pressure and the residue was chromatographed on silica-gel with n-hexane:EtOAc (1:2, v/v) as eluent to afford methyl 3-fluoro-4-[[1-[3-methoxy-4-[N'-(2-methylphenyl)ureido]phenylacetyl]-2-pyrrolidinyl]methoxy]benzoate (365.1 mg, 0.664 mmol) as an oil. To a stirred solution of this compound in THF (4.4 mL) and H$_2$O (1.1 mL) was added LiOH (46.3 mg, 1.932 mmol), and the reaction mixture was stirred at room temp overnight. The mixture was diluted with CHCl$_3$ and acidified by the addition of 1 N HCl. The separated organic layer was washed with brine and dried over Na$_2$SO$_4$. The solvent was removed under a reduced pressure, and the obtained crude solid was recrystallized from n-hexane-EtOAc—CHCl$_3$ to afford 102 mg (30%) 38 as a white crystalline powder. mp 123–126; IR (KBr) 1616, 1537, 1282, 756 cm$^{-1}$; $^1$H-NMR (400 MHz, DMSO-d$_6$) δ 1.87–2.09 (m, 4H), 2.25 (s, 3H), 3.48–3.57 (m, 2H), 3.60 (s, 2H), 3.83 (s, 3H), 4.11–4.16 (m, 1H), 4.24 (dd, J=2.9, 9.8 Hz, 1H), 4.28–4.34 (br s, 1H), 6.74 (dd, J=1.5, 8.3 Hz, 1H), 6.87 (s, 1H), 6.94 (t, J=7.3 Hz, 1), 7.12 (d, J=7.8 Hz, 1H), 7.15 (t, J=8.3 Hz, 1H), 7.34 (t, J=8.8 Hz, 1H), 7.66 (dd, J=2.0, 12.2 Hz, 1H), 7.73 (d, J=9.3 Hz, 1H), 7.79 (d, J=8.3 Hz, 1H), 7.99 (d, J=7.8 Hz, 1H), 8.46 (s, 1H), 8.55 (s, 1H); MS (FAB) m/z 536 (M$^+$+1); Anal. Calcd for C$_{29}$H$_{30}$N$_3$O$_6$.0.5H$_2$O: C, 63.96; H. 5.74; N, 7.72; F; 3.49. Found: C, 64.11; H, 5.80; N, 7.39; F, 3.54.

Example 35

4-[1-[4-[N'-(2-fluorophenyl)ureido]-3-methoxyphenylacetyl]-2-pyrrolidinyl]methoxy-3-methoxy benzoic acid

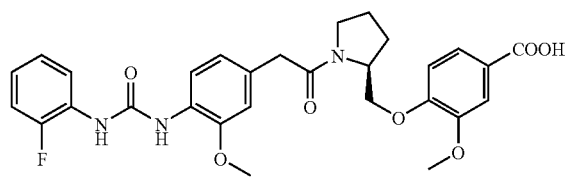

39

A mixture of 4-[N'-(2-fluorophenyl)ureido]-3-methoxyphenylacetic acid (318 mg, 1 mmol), 2-(2-methoxy-4-ethoxycarbonyl)phenoxymethylpyrrolidine (279 mg, 1 mmol), EDC (288 mg, 1.5 mmol), and DMAP (122 mg, 1 mmol) in DMF (20 mL) was stirred overnight. The mixture was poured into 1 N HCl and the resulting solid was collected with suction. The solid was dissolved in CHCl$_3$ and dried over MgSO$_4$. After removal of the solvent, the residue was chromatographed on silica-gel with CHCl$_3$:MeOH (100:1, v/v) as eluent to give an oil, which was dissolved in THF:MeOH (4:1, v/v, 10 mL). 0.25 N NaOH (8 mL) was added to the solution and the resulting stirred -mixture was heated under reflux for 3 hr. The mixture was poured into 1 N HCl. The resulting solid was collected with suction, dissolved in CHCl$_3$, dried over MgSO$_4$, and evaporated. The residue was recrystallized from CHCl$_3$-n-hexane-ether to give 329 mg (60%) 39 as a white crystalline powder. mp 140–144; IR (KBr) 3338, 2956, 2875, 2607, 1709 cm$^{-1}$; $^1$H-NMR (CDCl$_3$) δ 1.95–2.25 (4 H, m), 3.45–4.50 (12 H, m), 6.66–8.15 (12 H, m); MS (FAB) m/z 552 (M$^+$+1).

Example 36

2-[[1-[3-methoxy-4-[N'-(2-methylphenyl)ureido]phenylacetyl]-2-pyrrolidinyl]methoxy]pyridine-5-carboxylic acid

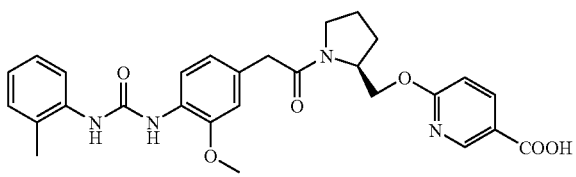

To a stirred solution of 6-hydroxynicotinic acid (500 mg, 3.594 mmol) in benzene (8 mL) and MeOH (2 mL) was added dropwise TMSCHN$_2$ (1.97 mL, 3.953 mmol) at 0° C., and the mixture was stirred overnight at room temp. The reaction mixture was quenched by the addition of AcOH, and the resulting mixture was concentrated in vacuo. The residue was chromatographed on silica-gel with n-hexane-EtOAc (1:3, v/v) as eluent to give 269.8 mg (49%) methyl 2-hydroxypyridine-5-carboxylate as a white crystalline powder. IR (KBr) 3062, 1657, 1654, 1612, 1435, 1300, 1113,775, 642 cm$^{-1}$; $^1$H-NMR (400 MHz, CDCl$_3$) δ 3.87 (s, 3H), 6.58 (d, J=9.8 Hz, 1H), 7.99 (dd, J=2.4, 9.8 Hz, 1H), 8.19 (d, J=2.4 Hz, 1H); MS (FAB) m/z 154 (M$^+$+1); Anal. Calcd for C$_7$H$_7$NO$_3$.1/4H$_2$O: C, 53.33; H, 4.80; N, 8.89. Found: C, 53.58; H, 4.65; N, 8.87.

To a stirred solution of methyl 2-hydroxypyridine-5-carboxylate (269.8 mg, 1.762 mmol), N-tert-butoxycarbonylprolinol (354.6 mg, 1.762 mmol), and Ph$_3$P (554.6 mg, 2.114 mmol) in THF (10 mL) was slowly added DIAD (0.42 mL, 2.114 mmol) at room temp, and the resulting mixture was stirred for 6 hr at 70° C. The reaction mixture was concentrated and the residue was chromatographed on silica-gel with n-hexane:EtOAc (5:1, v/v) as eluent to give 262.5 mg (44%) methyl 2-[[1-(tert-butoxycarbonyl)-2-pyrrolidinyl]methoxy]pyridine-5-carboxylate as an oil. $^1$H-NMR (400 MHz, CDCl$_3$) δ 1.47 (s, 9H), 1.85–1.98 (m, 4H), 3.37 (br s, 2H), 3.92 (s, 3H), 4.12–4.33 (br m, 2H),4.4 (br s, 1H),6.75(m, 1H),8.15 (m, 1H), 8.79 (m, 1H); MS (FAB) m/z 337 (M$^+$+1).

To a stirred solution of methyl 2-[[1-(tert-butoxycarbonyl)-2-pyrrolidinyl]methoxy]pyridine-5-carboxylate (262.5 mg, 0.870 mmol) in CH$_2$Cl$_2$ (5.3 mL) was added TFA (1.1 mL) at 0° C., and the resulting mixture was stirred at room temp for 1 hr. The solvent was removed under a reduced pressure and the residue was made basic by the addition of the 1 N NaOH, and extracted with CHCl$_3$. The extract was washed with brine, dried over Na$_2$SO$_4$, and concentrated under a reduced pressure to afford 173.1 mg (94%) methyl 2-[(2-pyrrolidinyl)methoxy]pyridine-5-carboxylate as a pale yellowish oil. $^1$H-NMR (400 MHz, CDCl$_3$) δ 1.49–1.58 (ddt, J=6.8, 8.8 Hz, 1H), 1.72–1.87 (m, 2H), 1.90–1.99 (m, 1H), 2.92–3.05 (m, 2H), 3.50–3.57 (ddd, J=4.4,7.3, 15.1 Hz, 1H), 3.91 (s, 3H), 4.23 (dd, J=7.8, 10.7 Hz, 1H), 4.38 (dd, J=4.4, 10.7 Hz, 1H), 6.78 (d, J=8.8 Hz, 1H), 8.15 (dd, J=2.4, 8.8 Hz, 1H), 8.80 (d, J=2.4 Hz, 1H); MS (FAB) m/z 237 (M$^+$+1).

A mixture of pentafluorophenyl 3-methoxy4-[N'-(2-methylphenyl)ureido]phenylacetate (351.7 mg, 0.732 mmol), methyl 2-[(2-pyrrolidinyl)methoxy]pyridine-5-carboxylate (173.0 mg, 0.732 mmol), Et$_3$N (122.4 μl, 0.878 mmol) in DMF (5.2 mL) was stirred for 1 hr at room temp. The mixture was diluted with EtOAc, washed with brine, and dried over Na$_2$SO$_4$. The solvent was removed under a reduced pressure and the residue was chromatographed on silica-gel with n-hexane:EtOAc (1:5, v/v) as eluent to afford methyl 2-[[1-[3-methoxy-4-[N'-(2-methylphenyl) ureido] phenylacetyl]-2-pyrrolidinyl]methoxy]pyridine-5-carboxylate (338.4 mg, 87%) as an oil. To a stirred solution of this compound in THF (5.6 mL) and H$_2$O (1.4 mL) was added LiOH (45.7 mg, 1.91 mmol), and the reaction mixture was stirred at room temp overnight. The mixture was diluted with CHCl$_3$, and treated with sat. NH$_4$Cl, washed with brine, dried over Na$_2$SO$_4$. The solvent was removed under a reduced pressure, and the obtained crude solid was recrystallized from n-hexane-Et$_2$O—CHCl$_3$-MeOH to afford 193.8 mg (59%) 40 as a white crystalline powder. mp 125–128; IR (KBr) 1716, 1600, 1533, 1255 cm$^{-1}$; $^1$H-NMR (400 MHz, DMSO-d$_6$) δ 1.67–2.03 (m, 4H), 2.50 (s, 3H), 3.33–3.42 (m, 1H), 3.52 (m, 2H), 3.58 (d, J=4.4 Hz, 1H), 3.83 (s, 3H), 4.27–4.31 (m, 2H), 4.42–4.47 (m, 1H), 6.73 (d, J=7.8 Hz, 1H), 6.87–6.95 (m, 3H), 7.11–7.17 (m, 2H), 7.79 (d, J=8.3 Hz, 1H), 7.99 (d, J=8.3 Hz, 1H), 8.14 (dd, J=2.0, 8.8 Hz, 1H), 8.46 (s, 1H), 8.56 (s, 1H), 8.69 (d, J=2.0 Hz, 1H), 13.06 (br s, 1H); MS (FAB) m/z 519 (M$^+$+1); Anal. Calcd for C$_{28}$H$_{30}$N$_4$O$_6$.1/2H$_2$O: C, 63.75; H, 5.92; N, 10.62. Found: C, 63.61; H, 5.94; N, 10.27.

Example 37

3-methoxy-4-[2-[4-[N'-(2-methylphenyl)ureido]benzyl]4-thiazolyl]methoxybenzoic acid

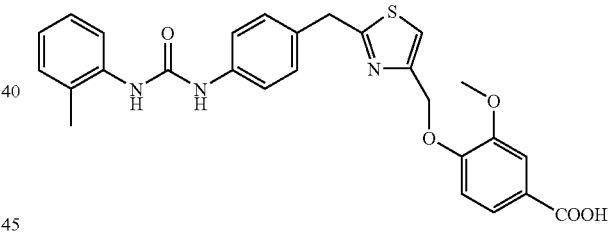

To a stirred solution of phosphorous pentasulfide (27.4 g, 123.34 mmol) and freshly prepared anhydrous Na$_2$S (4.8 g, 61.67 mmol) in THF (200 mL) was added p-nitrobenzyl cyanide (2.0 g, 12.33 mmol) at room temp. The resulting mixture was stirred for 17 hr at room temp. The mixture was diluted with EtOAc and washed with 10% K$_3$PO$_4$. The aqueous layer was extracted with CH$_2$Cl$_2$. The extract was dried over Na$_2$SO$_4$ and concentrated in vacuo. The residue was chromatographed on silica-gel with n-hexane:EtOAc (5:1 to 2:1, v/v) as eluent to give 1.53 g (64%) 4-nitrobenzyl carbothioamide as a pale yellow crystalline material. IR (KBr) 1529, 1446, 1326, 1315, 858 cm$^{-1}$; $^1$H-NMR(400 MHz, CDCl$_3$) δ 4.15 (s, 2H), 7.51 (d, J=8.3 Hz, 2H), 8.24 (d, J=8.8 Hz, 2H); MS (FAB) m/z 197 M$^+$+1); Anal. Calcd for C$_{88}$N$_2$O$_2$S: C, 48.97; H, 4.11; N, 14.28; S; 16.34. Found: C, 48.69; H, 4.06; N, 14.07; S; 16.10.

To a stirred solution of 4-nitrobenzylcarbothioamide (502.0 mg, 2.558 mmol) in EtOH (5 mL) was added 1,3-dichloro-2-propanone (649.6 mg, 5.16 mmol) and the mixture was heated under reflux for 1 hr. The mixture was concentrated and the residue was diluted with CHCl$_3$. The solution was washed with 1 N NaOH, brine, and dried over Na$_2$SO$_4$. The solvent was removed under a reduced pressure and the residue was chromatographed on silica-gel with n-hexane:EtOAc (4:1, v/v) as eluent to afford 495.2 mg (72%) 4-[2-(4-nitrobenzyl)thiazolyl]methyl chloride as a pale yellow oil. $^1$H-NMR (400 MHz, CDCl$_3$) δ 4.43 (s, 2H), 4.68 (s, 2H), 7.23 (s, 1H), 7.49 (d, J=8.8 Hz, 2H), 8.20 (d, J=8.8 Hz, 2H); MS (FAB) m/z 269 (M$^+$+1).

To a stirred solution of vanillic acid ethyl ester (308.0 mg, 1.570 mmol) and MeONa (89 mg, 1.570 mmol) in MeOH (6.5 mL) was added a solution of 4-[2-(4-nitrobenzyl)thiazolyl]methyl chloride (211.0 mg, 0.785 mmol) in MeOH (1.4 mL) at 0° C. The resulting mixture was stirred at room temp for 16 hr, and heated under reflux for 1 day. The solvent was removed under a reduced pressure and the residue was extracted with CHCl$_3$. The extract was washed with H$_2$O, brine, and dried over Na$_2$SO$_4$. The solvent was removed under a reduced pressure and the residue was chromatographed on silica-gel with n-hexane:EtOAc (2:1, v/v) as eluent to afford 201.7 mg (60%) ethyl 3-methoxy-4-[2-(4-nitrobenzyl)-4-thiazolyl]methoxybenzoate as a pale yellow oil. $^1$H-NMR (400 MHz, CDCl$_3$) δ 1.39 (t, J=7.3 Hz, 3H), 3.93 (s, 3H), 4.36 (q, J=7.3 Hz, 2H), 4.44 (s, 2H), 5.31 (s, 2H), 6.97 (d, J=8.3 Hz, 1H), 7.28 (s, 1H), 7.48 (d, J=8.8 Hz, 2H), 7.57 (d, J=2.0 Hz, 1H), 7.64 (dd, J=2.0, 8.3 Hz, 1H), 8.20 (d, J=8.8 Hz, 2H); MS (FAB) m/z 429 (M$^+$+1).

A stirred solution of ethyl 3-methoxy-4-[2-(4-aminobenzyl)-4-thiazolyl methoxybenzoate (201.7 mg, 0.471 mmol) and 5% Pd/C (40 mg) in EtOH (8 mL) was hydrogenated at 1 atm for 24 hr. The mixture was filtered and the filtrate was concentrated. The residue was chromatographed on silica-gel with n-hexane:EtOAc (1:1, v/v) as eluent to afford 87.8 mg (47%) ethyl 3-methoxy-4-[2-(4-aminobenzyl)-4-thiazolyl]methoxybenzoate as a yellowish crystalline powder. $^1$H-NMR (400 MHz, CDCl$_3$) δ 1.38 (t, J=7.3 Hz, 3H), 3.93 (s, 3H), 4.21 (s, 2H), 4.35 (q, J=7.3 Hz, 2H), 5.30 (s, 2H), 6.66 (dd, J=2.0, 6.4 Hz, 2H), 6.97 (d, J=8.3 Hz, 1H), 7.09 (d, J=8.3 Hz, 2H), 7.18 (s, 1H), 7.56 (d, J=2.0 Hz, 1H), 7.64 (dd, J=2.0, 8.3 Hz, 1H); MS (FAB) m/z 399 (M$^+$+1).

To a solution of ethyl 3-methoxy-4-[2-(4-aminobenzyl)-4-thiazolyl]methoxybenzoate (87.8 mg, 0.220 mmol) in THF (2.0 mL) was added triethylamine (30.5 ul, 0.220 mmol) and o-tolyl isocyanate (30 μl), and the reaction mixture was stirred at room temp for 21 hr. The reaction mixture was poured into ice-water and the resulting precipitates filtered off. The filtrate was extracted with CHCl$_3$, washed with H$_2$O, and brine. The extract was dried over Na$_2$SO$_4$. The solvent was removed under a reduced pressure to afford 110.4 mg (94%) ethyl 3-methoxy4-[2-[4-[N'-(2-methylphenyl) ureido]benzyl]-4-thiazolyl]methoxybenzoate as a pale yellow crystalline powder. 1H-NMR (400 MHz, CDCl$_3$) δ 1.38 (t, J=7.3 Hz, 3H), 2.28 (s, 3H), 3.92 (s, 3H), 4.28 (s, 2H), 4.35 (q, J=7.3 Hz, 2H), 5.29 (s, 2H), 6.20 (s, 1H), 6.47 (s, 1H), 6.97 (d, J=8.8 Hz, 1H), 7.20 (s, 1H), 7.24 (s, 2H), 7.27 (s, 2H), 7.33 (d, J=8.3 Hz, 2H), 7.49 (d, J=7.3 Hz, 1H), 7.56 (d, J=2.0 Hz, 1H), 7.63 (dd, J=2.0, 8.3 Hz, 1H); MS (FAB) m/z 532 (M$^+$+1).

To a stirred solution of ethyl 3-methoxy-4-[2-[4-[N'(2-methylphenyl)ureido]benzyl]-4-thiazolyl]methoxybenzoate in THF (1.6 mL) and H$_2$O (0.4 mL) was added LiOH (6.0 mg, 0.249 mmol), and the mixture was stirred at room temp for 1 hr, and heated under reflux for 8 hr. The mixture was concentrated and diluted with CHCl$_3$. The solution was made basic by the addition of 1 N NaOH. The aqueous extract was acidified by the addition of 1 N HCl and extracted with CHCl$_3$. The extract was washed with brine and dried over Na$_2$SO$_4$. The solvent was removed under a reduced pressure and the obtained crude solid was recrystallized from n-hexane-EtOAc-EtOH to afford 59.6 mg (57%) 41 as a white crystalline powder. mp 243–245; IR (KBr) 3282, 1685, 1637, 1600, 1554, 1516, 1278, 1234, 763, 748 cm$^{-1}$; $^1$H-NMR (400 MHz, DMSO-d$_6$) δ 2.27 (s, 3H), 3.83 (s, 3H), 4.30 (s, 2H), 5.21 (s, 2H), 6.97 (t, J=7.3 Hz, 1H), 7.15–7.24 (m, 3H), 7.29 (d, J=8.8 Hz, 2H), 7.47 (d, J=8.3 Hz, 2H), 7.50 (s, 1H), 7.58 (d, J=8.3 Hz, 1H), 7.62 (s, 1H), 7.86 (d, J=7.8 Hz, 1H), 7.97 (s, 1H), 9.09 (s, 1H), 12.70 (br s, 1H); MS (FAB) m/z 504 (M$^+$+1); Anal. Calcd for C$_{27}$H$_{25}$N3O$_5$S.1/4H$_2$O: C, 63.83; H, 5.06; N, 8.27. Found: C, 63.74; H, 4.99; N, 8.10.

Example 38

4-[[1-[3-methoxy-4-[N'-(2-methylphenyl)ureido]phenylacetyl]-2-methyl-2-pyrrolidinyl]methoxy]-3-nitrobenzoic acid

42

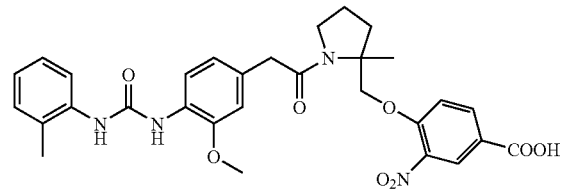

To a stirred solution of the N-tert-butoxycarbonylproline (6.00 g, 0.0279mol) in MeOH:benzene (1:4, v/v) was added dropwise 2.0 M-n-hexane solution of TMSCHN$_2$ (16.7 mL, 0.0334mol) at room temp. After the resulting solution was stirred for 1 hr at room temp, the mixture was evaporated off in vacuo to afford 6.39 g (100%) N-tert-butoxycarbonylproline methyl ester as a yellow syrup. $^1$H-NMR (CDCl$_3$) δ 1.41 (s, 9H), 1.85–1.98 (m, 4H), 2.21–2.28 (m, 2H), 3.72 (s, 3H), 4.29 (m, 1H).

To a stirred solution of diisopropylamine (2.02 mL, 0.0144mol) in THF (30 mL) was added dropwise 1.59 M n-hexane solution of n-BuLi (9.06 mL, 0.0144mol) at minus 78° C. for over 5 min. The resulting solution was stirred for 20 min at minus 78° C. To the solution was added dropwise N-tert-butoxycarbonylproline methyl ester (3.00 g, 0.0131 mmol) in THF (30 mL) at minus 78° C. for over 5 min. The resulting solution was stirred for 10 min at minus 78° C. To the solution was added dropwise MeI (0.900 mL, 0.0144 mol) at minus 78° C. The resulting solution was stirred for 30 min at minus 78° C. The solution was quenched by the addition of sat. NH$_4$Cl. The resulting mixture was extracted with CHCl$_3$. The extract was washed with water, dried over Na$_2$SO$_4$, and evaporated in vacuo to afford 3.20 g (q.y.) N-tert-butoxycarbonyl-2-methylproline methyl ester as a yellow syrup. $^1$H-NMR (CDCl$_3$) δ 1.33 (s, 9H), 1.38 (s, 3H), 1.72–2.20 (m, 4H) 3.27–3.59 (m, 2H) 3.63 (d, J=6.3 Hz, 3H).

To a stirred solution of N-tert-butoxycarbonyl-2-methyl-proline methyl ester (3.20 g, 0.0131 mol) in THF (20 mL) was added 1 N NaOH (15.7 mL) at room temp. After the resulting mixture was stirred for 24 hr, the mixture was diluted with water and washed with EtOAc. The separated aqueous layer was acidified by the addition of 1 N HCl, and extracted with EtOAc. The extract was dried over Na$_2$SO$_4$ and evaporated in vacuo to afford 1.71 g(57%) N-tert-butoxycarbonyl-2-methylproline as a yellow syrup. $^1$H-NMR (CDCl$_3$) δ 1.42 (s, 9H), 1.48 (s, 3H), 1.88–2.31 (m, 4H), 3.34–3.57 (m, 2H), 9.35 (br s, 1H)

To a stirred solution of N-tert-butoxycarbonyl-2-methyl-proline (1.10 g, 4.80 mmol) in THF (20 mL) was added dropwise BH$_3$-SMe$_2$ (0.546 mL, 5.76 mmol) at room temp. After the resulting mixture was stirred for 6 hr at 80° C., the mixture was evaporated in vacuo. The residue was diluted with MeOH, washed with n-hexane (3×), and evaporated in vacuo to afford 0.648 g (60%) N-tert-butoxycarbonyl-2-hydroxymethyl-2-methylpyrrolidine as a yellow syrup. $^1$H-NMR (CDCl$_3$) δ 1.47 (s, 9H), 1.76–2.05 (m, 4H), 3.28–3.48 (m, 2H), 3.66 (m, 2H, d).

To a stirred solution of N-tert-butoxycarbonyl-2-hydroxymethyl-2-methylpyrrolidine (0.648 g, 3.01 mmol), methyl 4-hydroxy-3-nitrobenzoate (0.593 g, 3.01 mmol), and Ph$_3$P (0.868 g, 3.31 mmol) in THF (10 mL) was added dropwise DIAD (95%) (0.686 mL, 3.31 mmol) at 0° C. After the resulting mixture was stirred for 24 hr at 80° C., the mixture was evaporated in vacuo. The residue was diluted with CH$_2$Cl$_2$ (5 mL) and added TFA (5 mL). After the resulting mixture was stirred for 2 hr at room temp, the mixture was evaporated in vacuo. The residue was diluted with 0.5 N HCl and extracted with CHCl$_3$. The aqueous layer was neutralized with sat. NaHCO$_3$, and extracted with CHCl$_3$. The extract was dried over Na$_2$SO$_4$ and evaporated in vacuo to afford 0.188 g (21%) methyl 3-nitro4-(2-methyl-2-pyrrolidinylmethoxy) benzoate as a yellow syrup.

A mixture of methyl 3-nitro4-(2-methyl-2-pyrrolidinyl-methoxy)benzoate (0.188 g, 0.920 mmol), 3-methoxy-4-[N'-(2-methylphenyl)ureido]phenylacetic acid (0.289 g, 0.920 mmol), HOBt (0.149 g, 1.10 mmol), DMAP. (11.2 mg, 0.0920 mmol) and EDC (0.211 g, 1.10 mmol) in DMF (5 mL) was stirred for 14 hr at room temp. EtOAC was added to the mixture and the solution was washed successively with 0.5 N HCl, sat. NaHCO$_3$, and brine. The organic layer was dried over Na$_2$SO$_4$ and evaporated in vacuo to afford 0.489 g (q.y.) methyl 4-[[1-[3-methoxy4-[N'-(2-methylphenyl)ureido]phenylacetyl]-2-methyl-2-pyrrolidinyl]methoxy]-3-nitrobenzoate as a yellow crystalline material. $^1$H-NMR (CDCl$_3$) δ 1.26 (d, J=5.9 Hz), 1.85–4.50 (m, 10H), 2.30 (s, 3H), 3.67 (s, 2H), 3.92 (s, 3H), 6.36 (s, 2H), 6.75–7.52 (m, 7H), 8.02 (d, J=7.8 Hz, 1H), 8.15 (d, J=8.8 Hz, 1H), 8.47 (s, 1H).

A stirred mixture of 4-[1-[3-methoxy-4-[N'-(2-methylphenyl)ureido]phenylacetyl]-2-methyl-2-pyrrolidinyl] methoxy]-3-nitrobenzoate (0.489 g, 0.828 mmol) in MEOH (5 mL) and 1N NaOH (1.24 mL) was heated under reflux for 2 hr After cooling, the mixture was diluted with water and extracted with CHCl$_3$. The aqueous layer was acidified with 1 N HCl, and extracted with CHCl$_3$. The extract was dried over Na$_2$SO$_4$ and evaporated in vacuo to afford 0.366 g (99%) 42 as a yellow crystalline material.

Example 39

4-[4-hydroxy-1-[3-methoxy-4-[N'-(2-methylphenyl) ureido]phenylacetyl]-2-pyrrolidinylmethoxy]-3-methoxybenzoic acid

43

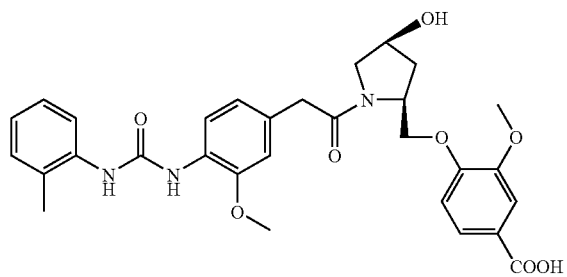

A stirred mixture of 4-[4-benzyloxy-1-[3-methoxy-4-[N'-(2-methylphenyl)ureido]phenylacetyl]-2-pyrrolidinyl-methoxy]-3-methoxybenzoate (440 mg, 0.645 mmol) and 5% Pd/C (400 mg) in AcOH:EtOH (1:1, v/v, 100 mL) was hydrogenated at 1 atm for 5 hr. The mixture was filtered to remove the catalyst and the filtrate was concentrated in vacuo. The residue was chromatographed on silica-gel with CHCl$_3$:EtOH (10:1, v/v) as eluent to give 90 mg (24%) ethyl 4-[4-hydroxy-1-[3-methoxy-4-[N'-(2-methylphenyl)ureido] phenylacetyl]-2-pyrrolidinylmethoxy]-3-methoxybenzoate as a pale yellow oil. $^1$H-NMR (CDCl$_3$) δ 1.39 (3 H, t, J=7.3 Hz), 2.04–2.37 (total 5 H, m), 3.44–4.70 (16 H, series of m), 6.63 (1 H, s), 6.70–6.80 (2 H, m), 6.84 (1 H, d, J=8.3 Hz), 7.11 (1H, t, J=7.8 Hz), 7.20–7.24 (3 H, m), 7.45 (1 H, d, J=2.0 Hz), 7.59 (2 H,dd, J=8.3, 2.0 Hz), 8.01 (1 H, d, J=7.8 Hz).

A stirred mixture of ethyl 4-[4-hydroxy-1-[3-methoxy-4-[N'-(2-methylphenyl)ureido]phenylacetyl]-2-pyrrolidinyl-methoxy]-3-methoxybenzoate (90 mg, 0.152 mmol) in 0.25 N NaOH (5 mL, 1.25 mmol) and THF (5 mL) was heated under reflux overnight. The mixture was poured into ice-1 N HCl (200 mL). The precipitate was collected with suction and recrystallized from CHCl$_3$-MeOH-n-hexane to give 40 mg (47%) 43 as a colorless amorphous solid. $^1$H-NMR (DMSO-d$_6$) δ 1.92–2.11 (2 H, m), 2.24 (3 H, s), 3.31–5.07 (14 H, series of m), 6.73 (1 H, d, J=8.3 Hz), 6.84 (1 H, s), 6.93 (1 H, t, J=7.8 Hz), 7.01–7.17 (3 H, m), 7.44 (1 H, s), 7.52 (1 H, d, J=8.8 Hz), 7.79 (1 H, d, J=8.3 Hz), 7.99 (1 H, d, J=7.8 Hz), 8.46 (1 H, s), 8.55 (1 H, s), 12.67 (1 H, br s); MS (FAB) m/z 564 (M$^+$+1).

Example 40

(2S,4R)-3-amino4-[4-hydroxy-1-[3-methoxy4-[N'-(2-methylphenyl)ureido]phenylacetyl]-2-pyrrolidi-nyl]methoxybenzoic acid

44

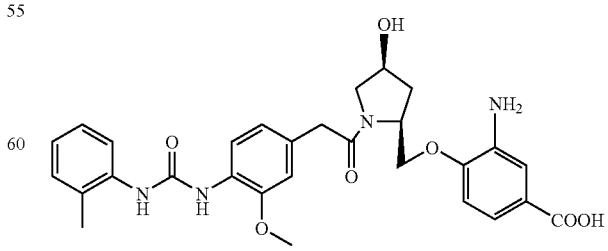

To a stirred solution of (2S,4R)4-benzyloxy-1-(tert-butoxycarbonyl)-2-prolinol (891 mg, 2.9 mmol), methyl 4-hydroxy-3-nitrobenzoate (572 mg, 2.9 mmol),and PPh₃ (839 mg, 3.2 mmol) in THF (6 mL) was added DIAD (630 mL, 3.2 mmol) and the mixture was heated under reflux overnight. After removal of the solvent, the residue was chromatographed on silica-gel with n-hexane:EtOAc (1:1) and toluene:EtOAc (10:1, v/v) as eluent to give 700 mg (50%) methyl (2S,4R)-4-[4-benzyloxy-1-(tert-butoxycarbonyl)-2-pyrrolidinyl]methoxy-3-nitrobenzoate as a pale yellow oil.

To a stirred solution of methyl (2S, 4R)4-[4-benzyloxy-1-(tert-butoxycarbonyl)-2-pyrrolidinyl]methoxy-3-nitrobenzoate (681 mg, 1.4 mmol) in CH₂Cl₂ (2 mL) was added TFA (2 mL), and the resulting mixture was stirred for 2 hr. After the reaction mixture was concentrated, the residue was made basic by the addition of sat. NaHCO₃ and extracted with CHCl₃. The extract was washed with H₂O, dried over MgSO₄, and evaporated to give 511 mg (95%) methyl (2S,4R)-4-[4-benzyloxy-2-pyrrolidinyl]methoxy-3-nitrobenzoate as a yellow oil.

A mixture of 3-methoxy-4-[N'-(2-methylphenyl)ureido] phenylacetic acid (409 mg, 1.3 mmol), methyl (2S,4R)4-(benzyloxy-2-pyrrolidinyl)methoxy-3-nitrobenzoate (502 mg, 1.3 mmol), EDC (383 mg, 2 mmol), and DMAP (159 mg, 1.3 mmol) in DMF (20 mL) was stirred for 3 days. The mixture was poured into 1 N HCl and the resulting precipitate was collected with suction. The residue was dissolved in CHCl₃ and dried over MgSO₄. After removal of solvent, the residue was chromatographed on silica-gel with CHCl₃: MeOH (200: 1, v/v) as eluent to give 680 mg (91%) methyl (2S,4R)4-[4-benzyloxy-1-[3-methoxy-4-[N'-(2-methylphenyl)ureido]phenylacetyl]-2-pyrrolidinyl]methoxy-3-nitrobenzoate as a white amorphous solid.

A solution of methyl (2S,4R)4-[4-benzyloxy-1-[3-methoxy-4-[N'-(2-methylphenyl) ureido]phenylacetyl]-2-pyrrolidinyl]methoxy-3-nitrobenzoate (676 mg, 0.99 mmol) and 5% Pd—C (1 g) in EtOH:AcOH (1:1, v/v, 30 mL) was hydrogenated at 1 atm for 6 hr. The mixture was filtered and the filtrate was evaporated to give an oil, which was made basic by the addition of sat. NaHCO₃. The mixture was extracted with EtOAc. The extract was washed with brine, dried over MgSO₄, and evaporated. The residue was recrystallized from CHCl₃-EtOH-n-hexane as eluent to give 120 mg (22%) 44 as a pale yellow crystalline powder. MS (FAB) m/z 549 (M⁺+1)

Example 41

4-[[4-fluoro-1-[3-methoxy-4-[N'-(2-methylphenyl) ureido]phenylacetyl]-2-pyrrolidinyl]methoxy]-3-methoxybenzoic acid

45

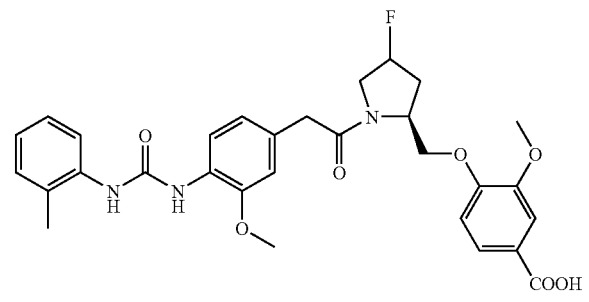

A stirred mixture of ethyl 4-[4-benzyloxy-1-(tert-butoxycarbonyl)-2-pyrrolidinyl]methoxy-3-methoxybenzoate (1.189 g, 2.449 mmol) and 5% Pd—C (240 mg) in EtOH (10 mL) was hydrogenated overnight at room temp. The mixture was filtered to remove the catalyst and the filtrate was concentrated in vacuo to give ethyl 4-[1-(tert-butoxycarbonyl)-4-hydroxy-2-pyrrolidinyl]methoxy-3-methoxybenzoate (735.3 mg, 76%) as a pale yellow oil. To a stirred cold (minus 78° C.) solution of DAST (0.491 mL, 3.718 mmol) in CH₂Cl₂ (7.4 mL) was added dropwise a solution of this compound in CH₂Cl₂ (2 mL), and the resulting mixture was stirred overnight. The mixture was quenched with water and extracted with CHCl₃. The extract was washed with brine and dried over Na₂SO₄. The solvent was removed under a reduced pressure and the residue was chromatographed on silica-gel with n-hexane:EtOAc (3:1, v/v) as eluent to afford 418.7 mg (57%) ethyl 4-[1-(tert-butoxycarbonyl)-4-fluoro-2-pyrrolidinyl]methoxy-3-methoxybenzoate as an oil. ¹H-NMR (400 MHz, CDCl₃) δ 1.39 (t, J=7.3 Hz, 3H), 1.49 (s, 9H), 2.16 (br m, 1H), 2.58 (dd, J=15.6, 19.0 Hz, 1H), 3.60–3.75 (m, 2H), 3.91 (s, 3H), 3.97 (t, J=9.3 Hz, 1), 4.35 (q, J=7.3 Hz, 2H), 4.33–4.53 (m, 2H), 5.25 (d, J=52.7 Hz, 1H), 7.04 (dd, J=7.8, 56.2 Hz, 1H), 7.55 (s, 1H), 7.65 (br s, 1H); MS (FAB) m/z 398 (M⁺+1).

To a stirred solution of ethyl 4-[1-(tert-butoxycarbonyl) 4-fluoro-2-pyrrolidinyl]methoxy-3-methoxybenzoate (482.2 mg, 1.213 mmol) in CH₂Cl₂ (10.0 mL) was added TFA (1.9 mL) at 0° C., and the mixture was stirred at room temp for 2 hr. The solvent was removed under a reduced pressure and the residue was made basic by the addition of 1 N NaOH and extracted with CHCl₃. The extract was washed with brine, dried over Na₂SO₄, and concentrated under a reduced pressure to afford 348.7 mg (97%) ethyl 4-(4-fluoro-2-pyrrolidinyl)methoxy-3-methoxybenzoate as a brownish oil. ¹H-NMR (400 MHz, CDCl₃) δ 1.39 (t, J=6.8 Hz, 3H), 1.97 (ddt, J=1.5, 5.4, 14.7 Hz, 1H), 2.27 (dddd, J=5.9, 8.8, 14.7, 32.7 Hz, 1H), 3.02 (ddd, J=3.9, 13.1, 35.2 Hz, 1H), 3.36 (dd, J=12.7, 21.5 Hz, 1H), 3.65 (m, 1H), 3.90 (s, 3H), 4.09 (m, 1H), 4.35 (q, J=6.8 Hz, 2H), 5.17, 5.31 (br m each, 1H), 6.90 (d, J=8.3 Hz, 1H), 7.75 (d, J=2.0 Hz, 1H), 7.65 (dd, J=2.0, 8.3 Hz, 1H); MS (FAB) m/z 298 (M⁺+1).

A mixture of pentafluorophenyl 3-methoxy-4-[N'-(2-methylphenyl)ureido]phenylacetate (404.0 mg, 0.840 mmol), ethyl 4-(4-fluoro-2-pyrrolidinyl)methoxy-3-methoxybenzoate (250.0 mg, 0.840 mmol), Et₃N (141 µl, 1.009 mmol) in DMF (4.0 mL) was stirred for 1 hr at room temp. The mixture was diluted with EtOAc, washed with water, brine, and dried over Na₂SO₄. The solvent was removed under a reduced pressure and the residue was chromatographed on silica-gel with n-hexane:EtOAc (1:3, v/v) to afford 502 mg (q.y.) of ethyl 4-[[4-fluoro-1-[3-methoxy-4-[N'-(2-methylphenyl)ureido]phenylacetyl]-2-pyrrolidinyl]methoxy]-3-methoxybenzoate as a yellow oil. To a stirred solution of this compound in THF (8.0 mL) and H₂O (2.0 mL) was added LiOH (60.4 mg, 2.520 mmol), and the mixture was stirred at room temp. overnight, and 50° C. for 1 day. The mixture was diluted with CHCl₃, and extracted with 1 N NaOH. The aqueous layer was acidified by the addition of 1 N HCl and extracted with CHCl₃. The extract was washed with brine and dried over Na₂SO₄. The solvent was removed under a reduced pressure and the obtained crude solid was recrystallized from EtOAc—CHCl₃-EtOH-n-hexane to afford 294.8 mg (62%) 45 as a white crystalline powder. IR (KBr) 2958, 2937, 1687, 1601, 1531, 1454, 1419, 1267, 1214, 1029 cm⁻¹; ¹H-NMR (400 MHz, DMSO-d₆) δ 1.86–2.09 (m, 5H), 2.06 (s, 3H), 2.25 (s, 3H), 3.47–3.67 (m, 6H), 3.76 (s, 3H), 4.05–4.12 (m, 2H), 4.30–4.31 (m, 1H), 6.51 (s, 1H), 6.55 (s, 1H), 6.73–6.95 (m, 2H), 7.11–7.17 (m, 2H), 7.64 (s, 1H), 7.79 (d, J=7.8 Hz, 1H), 7.99 (d, J=7.8 Hz, 1H), 8.47 (s, 1H), 8.55 (s, 1H); MS (FAB) m/z 566 (M$^+$+1); Anal. Calcd for $C_{30}H_{32}FN_3O_7 \cdot 1/2H_2O$: C, 62.71; H, 5.79; F, 3.31; N, 7.31. Found: C, 63.13; H. 6.17; F, 3.12; N, 7.04.

Example 42

3-acetylamino-4-[1-[3-methoxy-4-[N'-(2-methylphenyl)ureido]phenylacetyl]-2-pyrrolidinyl methoxy] benzoic acid

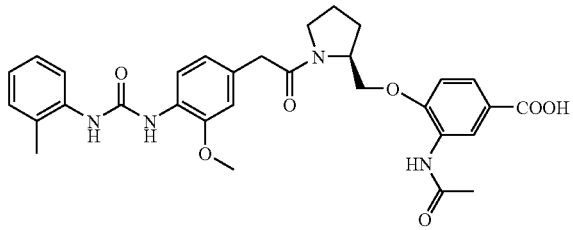

46

A solution of 3-amino-4-[1-[3-methoxy-4-[N'-(2-methylphenyl)ureido]phenylacetyl]-2-pyrrolidinylmethoxy]benzoic acid (130 mg, 0.244 mmol) and DMAP (2.9 mg, 0.0244 mmol) in pyridine (5 mL) and acetic anhydride (5 mL) was stirred for 2 hr at room temp. The mixture was evaporated off in vacuo (exess acetic anhydride was azeotropically removed with toluene). Water was added to the residue, and extracted with CHCl$_3$. The extract was dried over Na$_2$SO$_4$ and evaporated in vacuo. The residue was chromatographed on silica-gel with MeOH:CHCl$_3$ (1:15 to 1:1, v/v) as eluent to afford 29 mg (21%) 46 as a white crystalline material. $^1$H-NMR (DMSO-d$_6$) δ 1.80–2.30 (m, 4H), 2.04 (s, 3H), 2.26 (s, 3H), 3.33 (s, 3H), 3.40–4.80 (m, 7H), 6.59 (s, 1H), 6.74 (d, J=8.3 Hz, 1H), 6.79 (d, J=8.8 Hz, 1H), 7.07–7.57 (m, 6H), 7.75 (d, J=8.8 Hz, 1H), 8.07 (d, J=8.3 Hz, 1H), 8.41 and 8.96 (each s, each 1H); MS (FAB) m/z 575 (M$^+$+1).

Example 43

3-chloro-2-[[1-[3-methoxy-4-[N'-(2-methylphenyl) ureido]phenylacetyl]-2-pyrrolidinyl]methoxy]pyridine-5-carboxylic acid

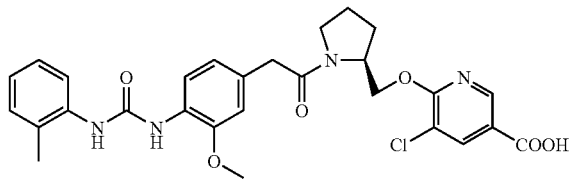

47

To a stirred solution of 3-chloro-2-hydroxypyridine-5-carboxylic acid (1 g, 5.762 mmol) in benzene (16 mL) and MeOH (4 mL) was added dropwise TMSCHN$_2$ (3.17 mL, 6.338 mmol) at 0° C., and the resulting mixture was stirred overnight at room temp. The reaction mixture was quenched by the addition of AcOH and the mixture was evaporated off. The residue was suspended in water and precipitate was collected. The crude solid was washed with Et$_2$O, and dried under a reduced pressure to give 728.1 mg (67%) methyl 3-chloro-2-hydroxypyridine-5-carboxylate as a white crystalline powder. IR (KBr) 1655, 1282, 1245, 769 cm$^{-1}$; $^1$H-NMR (400 MHz, DMSO-d$_6$) δ 3.79 (s, 3H), 8.01 (s, 1H), 8.06 (s, 1H); MS (FAB) m/z 188 (M$^+$+1); Anal. Calcd for $C_7H_6ClNO_3$: C, 44.82; H, 3.22; Cl, 18.90; N, 7.47. Found: C, 44.74; H, 3.22; Cl, 19.00; N, 7.34.

To a stirred solution of methyl 3-chloro-2-hydroxypyridine-5-carboxylate (300 mg, 1.599 mmol), N-tert-butoxycalbonylprolinol (321.9 mg, 1.599 mmol), and Ph$_3$P (503 mg, 1.919 mmol) in THF (3 mL) was slowly added DIAD (378 μl, 1.919 mmol) at room temp, and the mixture was stirred for 13 hr at 70° C. The mixture was concentrated and the residue was chromatographed on silica-gel with n-hexane-EtOAc (3:1, v/v) as eluent to give 235.6 mg (40%) methyl 3-chloro-2-[[1-(tert-butoxycarbonyl)-2-pyrrolidinyl] methoxy]pyridine-5-carboxylate as a pale yellowish oil. $^1$H-NMR (400 MHz, CDCl$_3$) δ 1.46 (s, 9H), 1.87 (m, 1H), 2.05 (br s, 3H), 3.43 (br s, 2H), 3.92 (s, 3H), 4.17, 4.26 (br s each, 1H), 4.45–4.51 (m, 1H), 4.50 (s, 1H), 8.21 (s, 1H), 8.67 (d, J=2.0 Hz, 1H); MS (FAB) m/z 371 (M$^+$+1).

To a stirred solution of methyl 3-chloro-2-[[1-(tert-butoxycarbonyl)-2-pyrrolidinyl]methoxy]pyridine-5-carboxylate (235.6 mg, 0.635 mmol) in CH$_2$Cl$_2$ (5.0 mL) was added TFA (1.0 mL) at 0° C., and the reaction mixture was stirred at room temp for 2 hr. The solvent was removed under a reduced pressure. The residue was made basic by the addition of 1N NaOH and extracted with CHCl$_3$. The extract was dried over Na$_2$SO$_4$, concentrated under a reduced pressure to afford 172.3 mg (q.y.) methyl 3-chloro-2-[(2-pyrrolidinyl) methoxy]pyridine-5-carboxylate as a pale yellowish oil. $^1$H-NMR (400 MHz, CDCl$_3$) δ 1.55–1.63 (m, 1H), 1.76–1.99 (m, 3H), 2.93–2.99 (m, 1H), 3.02–3.08 (m, 1H), 3.57–3.62 (m, 1H), 3.92 (s, 3H), 4.33 (dd, J=7.3, 10.7 Hz, 1H), 4.44 (dd, J=4.4, 10.7 Hz, 1H), 8.21 (d, J=2.0 Hz, 1H), 8.67 (d, J=2.0 Hz, 1H); MS (FAB) m/z 271 (M$^+$+1).

The mixture of pentafluorophenyl 3-methoxy-4-[N'-(2-methylphenyl)ureido]phenylacetate (317.0 mg, 0.660 mmol), methyl 3chloro-2-[(2-pyrrolidinyl)methoxy]pyridine-5-carboxylate (172.0 mg, 0.635 mmol), Et$_3$N (105 ul, 0.756 mmol) in DMF (2.0 mL) was stirred for 1 hr at room temp. The mixture was diluted with EtOAc, washed with brine, and dried over Na$_2$SO$_4$. The solvent was removed under a reduced pressure to afford methyl 3chloro-2-[[1-[3-methoxy-4-[N'-(2-methylphenyl)ureido]phenylacetyl]-2-pyrrolidinyl]methoxy]pyridine-5-carboxylate as a brownish oil. To a stirred solution of this compound in THF (6.0 mL) and H$_2$O (2.0. mL) was added LiOH (45.3 mg, 1.89 mmol), and the reaction mixture was stirred for 5 hr at room temp. The mixture was diluted with n-hexane and extracted with 1N-NaOH. The aqueous layer was acidified by the addition of 1 N HCl and extracted with CHCl$_3$. The extract was washed with brine, dried over Na$_2$SO$_4$. The solvent was removed under a reduced pressure and the obtained crude solid was recrystallized from n-hexane-EtOAc-EtOH to afford 242.2 mg (70%/0) 47 as an orange crystalline powder. mp 122–125; IR (KBr) 3354, 1709, 1593, 1535, 1454, 1257 cm$^{-1}$; $^1$H-NMR (400 MHz, DMSO-d$_6$) δ 1.67–2.03 (m, 4H), 2.50 (s, 3H), 3.33–3.42 (m, 1H), 3.52 (m, 2H), 3.58 (d, J=4.4 Hz, 1H), 3.83 (s, 3H), 4.27–4.31 (m, 2H), 4.42–4.47 (m, 1H), 6.73 (d, J=7.8 Hz, 1H), 6.87–6.95 (m, 3H), 7.11–7.17 (m, 2H), 7.79 (d, J=8.3 Hz, 1H), 7.99 (d, J=8.3 Hz, 1H), 8.14 (dd, J=2.0, 8.8 Hz, 1H), 8.46 (s, 1H), 8.56 (s, 1H), 8.69 (d, J=2.0 Hz, 1H), 13.06 (br s, 1H); MS (FAB) m/z 553 (M$^+$+1); Anal. Calcd for $C_{28}H_{29}ClN_4O_6$: C, 60.81; H, 5.29; N, 10.31. Found: C, 60.98; H, 5.50; N, 9.46.

Example 44

2-[[1-[4-[N'-(2-fluorophenyl)ureido]-3-methoxyphenylacetyl]-2-pyrrolidinyl]methoxy]pyridine-5-carboxylic acid

48

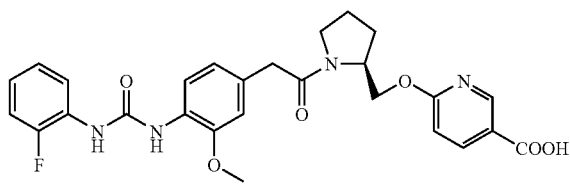

To a stirred solution of 6-hydroxynicotinic acid (2 g, 14.38 mmol) in benzene (32 mL) and MEOH (8 mL) was added dropwise TMSCHN$_2$ (1.97 mL, 3.953 mmol) at 0° C., and the resulting mixture was stirred for 2 hr at room temp. The mixture was quenched by the addition of AcOH and concentrated in vacuo. The residue was suspended in water and the solid was collected. The crude solid was washed with Et$_2$O, and dried in vacuo to give 1.566 g (71%) methyl 2-hydroxypyridine-5-carboxylate as a pale brown crystalline powder. IR (KBr) 1655, 1645, 1610, 1433, 1300, 1113, 777, 642 cm$^{-1}$; $^1$H-NMR (400 MHz, DMSO-d$_6$) δ 3.77 (s, 3H), 6.37 (d, J=9.8 Hz, 1H), 7.99 (dd, J=2.4, 9.8 Hz, 1H), 8.03 (d, J=2.4 Hz, 1H); MS (FAB) m/z 154 (M$^+$+1); Anal. Calcd for C$_7$H$_7$NO$_3$: C, 54.90; H, 4.61; N, 9.15. Found: C, 54.89; H, 4.60; N, 9.13.

To a stirred solution of methyl 2-hydroxypyridine-5-carboxylate (1.00 g, 6.529 mmol), N-tert-butoxycarbonyl-prolinol (1.31 g, 6.529 mmol), and Ph$_3$P (2.06 g, 7.836 mmol) in THF (10 mL) was added DIAD (1.54 mL, 7.836 mmol) at room temp, and the resulting mixture was stirred for 13 hr at 70° C. The mixture was concentrated and the residue was chromatographed on silica-gel with n-hexane:EtOAc (3:1, v/v) as eluent to give 712.3 mg (32%) methyl 2-[[1-(tert-butoxycarbonyl)-2-pyrrolidinyl]methoxy]pyridine-5-carboxylate as a pale yellow oil. $^1$H-NMR (400 MHz, CDCl$_3$) δ 1.47 (s, 9H), 1.85–1.98 (m, 4H), 3.37 (br s, 2H), 3.92 (s, 3H), 4.12–4.33 (br m, 2H), 4.48 (br s, 1H), 6.75 (m, 1H), 8.15 (m, 1H), 8.79 (m, 1H); MS (FAB) m/z 337 (M$^+$+1).

To a stirred solution of methyl 2-[[1-(tert-butoxycarbonyl)-2-pyrrolidinyl]methyloxy]pyridine-5-carboxylate (232.3 mg, 0.691 mmol) in CH$_2$Cl$_2$ (4.6 mL) was added TFA (0.9 mL) at 0° C., and the reaction mixture was stirred at room temp for 2 hr. The solvent was removed under a reduced pressure and the residue was made basic by the addition of 1 N NaOH. The aqueous solution was extracted with CHCl$_3$, washed with brine, and the dried over Na$_2$SO$_4$. The solvent was evaporated under a reduced pressure to afford 146.2 mg (90%) methyl 2-(2-pyrrolidinyl)methoxypyridine-5-carboxylate as an oil. $^1$H-NMR (400 MHz, CDCl$_3$) δ 1.49–1.58 (m, 1H), 1.72–2.18 (m, 3H), 2.92–3.05 (m, 2H), 3.50–3.57 (m, 1H), 3.91 (s, 3H), 4.23 (dd, J=8.0, 10.7 Hz, 1H), 4.38 (dd, J=4.4, 10.3 Hz, 1H), 6.78 (d, J=8.8 Hz, 1H), 8.15 (dd, J=2.4, 8.8 Hz, 1H), 8.80 (d, J=2.4 Hz, 1H); MS (FAB) m/z 237 (M$^+$+1).

The mixture of pentafluorophenyl 4-[N'-(2-fluorophenyl)ureido]-3-methoxy-phenylacetate (314.8 mg, 0.650 mmol), methyl 2-[(2-pyrrolidinyl)methoxy]pyridine-5-carboxylate (146.2 mg, 0.619 mmol), Et$_3$N (103 ul, 0.743 mmol) in DMF (1.5 mL) was stirred for 1 hr at room temp. The mixture was diluted with Et$_2$O, washed with brine, and dried over Na$_2$SO$_4$. The solvent was removed under a reduced pressure to afford methyl 2-[[1-[4-[N'-(2-fluorophenyl)ureido]-3-methoxyphenylacetyl]-2-pyrrolidinyl]methoxy]pyridine-5-carboxylate as a crude pale yellow oil.

To a stirred solution of this compound in THF (6.0 mL) and H$_2$O (2.0 mL) was added LiOH (44.5 mg, 1.857 mmol), and the reaction mixture was stirred for 17 hr at room temp. The mixture was diluted with n-hexane and made basic by the addition of 1 N NaOH. The aqueous layer was acidified by 1 N HCl and extracted with CHCl$_3$. The extract was washed with brine, and dried over Na$_2$SO$_4$. The solvent was removed under a reduced pressure and the obtained crude solid was recrystallized from n-hexane-EtOAc-EtOH to afford 202.5 mg (63%) 48 as a white crystalline powder. IR (KBr) 1602, 1537, 1456, 1265, 752 cm$^{-1}$; H-NMR (400 MHz, DMSO-d$_6$) δ 1.67–2.03 (m, 4H), 2.50 (s, 3H), 3.33–3.42 (m, 1H), 3.52 (m, 2H), 3.58 (d, J=4.4 Hz, 1H), 3.83 (s, 3H), 4.27–4.31 (m, 2H), 4.42–4.47 (m, 1H), 6.73 (d, J=7.8 Hz, 1H), 6.87–6.95 (m, 3H), 7.11–7.17 (m, 2H), 7.79 (d, J=8.3 Hz, 1H), 7.99 (d, J=8.3 Hz, 1H), 8.14 (dd, J=2.0, 8.8 Hz, 1H), 8.46 (s, 1H), 8.56 (s, 1H), 8.69 (d, J=2.0 Hz, 1H), 13.06 (br s, 1H); MS (FAB) m/z 523 (M$^+$+1); Anal. Calcd for C$_{27}$H$_{27}$FN$_4$O$_6$·1/2H$_2$O: C, 61.01; H, 5.31; N, 10.54. Found: C, 61.52; H, 5.39; N, 10.01.

Example 45

4-[1-[3-methoxy-4-[N'-(2-methylphenyl)ureido]phenylacetyl]-2-pyrrolidinylmethyl]-1-piperazinyl acetic acid

49

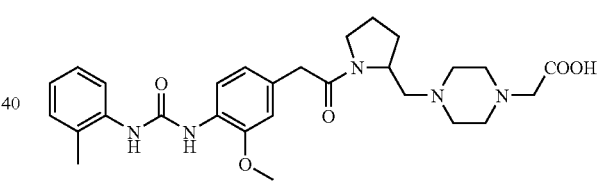

To a stirred suspension of 1-benzylpiperazine (5 g, 28.4 mmol) and K$_2$CO$_3$ (5.89 g, 42.6 mmol) in DMF (30 mL) was added ethyl bromoacetate (4.74 g, 28.4 mmol) at room temp. The resulting mixture was stirred for a further 3 hr. The mixture was diluted with EtOAc (300 mL), washed with brine (2×100 mL), dried over MgSO$_4$ and evaporated. The residue was chromatographed on silica-gel with CHCl$_3$:EtOH (10:1, v/v) as eluent to give 7.45 g (q.y.) ethyl 4-benzyl-1piperazinylacetate as a yellow oil. $^1$H-NMR (CDCl$_3$) δ 1.27 (3 H, t, J=7.3 Hz), 2.88–2.96 (8 H, m), 3.20 (2 H, s), 3.52 (2 H, s), 4.18 (2 H, q, J=7.3 Hz), 7.22–7.32 (5 H, m).

A stirred solution of ethyl 4-benzyl-1-piperazinylacetate (2.00 g, 7.62 mmol) and 5% Pd/C (2 g) in AcOH:EtOH (1:1, 40 mL) was hydrogenated at 1 atm for 8 hr. The mixture was filtered and the filtrate was concentrated in vacuo. The residue was made basic by the addition of saturated NaHCO$_3$ and extracted with CHCl$_3$ (2×200 mL). The combined extracts were dried over K$_2$CO$_3$ and evaporated to give 1.16 g (88%) ethyl 1-piperazinylacetate as a yellow oil. $^1$H-NMR (CDCl$_3$) δ 1.26–1.30 (3 H, m), 1.67 (1 H, br s), 2.55 (4 H, m), 2.92–2.96(4 H, m), 3.19–3.20 (2 H, m), 4.16–4.22 (2 H, m).

To a stirred solution of N-Boc-L-prolinol (1.00 g, 5.02 mmol) and ethyl 1-piperazinyl acetate (864 mg, 5.02 mmol) in MeOH:AcOH (10:1, v/v, 11 mL) was added NaBH$_3$CN (664 mg, 10.0 mmol) at room temp. After being stirred overnight, the mixture was poured into ice water (100 mL) and made basic by the addition of NaHCO$_3$. The mixture was extracted with CHCl$_3$ (2×200 mL). The combined extracts were dried over Na$_2$CO$_3$ and evaporated. The residue was chromatographed on silica-gel with CHCl$_3$:EtOH (10:1, v/v) as eluent to give 1.20 g (67%) ethyl 4-[1-(tert-butoxy carbonyl)-2-pyrrolidinylmethyl]-1-piperazinylacetate as a colorless oil. $^1$H-NMR (CDCl$_3$) δ 1.27 (3 H, t, J=7.3 Hz), 1.46–1.47 (9 H, m), 1.79–3.96 (total 19 H, series of m), 4.19 (2 H, q, J=7.3 Hz).

A mixture of ethyl 4-[1-(tert-butoxycarbonyl)-2-pyrrolidinylmethyl]-1-piperazinylacetate (1.20 g, 3.38 mmol) in TFA (5 mL) and CH$_2$Cl$_2$ (5 mL) was stirred overnight. After removal of the solvent, the residue was made basic by the addition of sat. NaHCO$_3$. The mixture was extracted with CHCl$_3$ (2×200 mL). The combined extracts were dried over Na$_2$CO$_3$ and evaporated to give 386 mg (45%) ethyl 4-(2-pyrrolidinylmethyl)-1-piperazinylacetate as a yellow oil. MS (FAB) 256 (M$^+$+1).

To a stirred solution of ethyl 4-(2-pyrrolidinylmethyl)-1-piperazinylacetate (380 mg, 1.49 mmol) and 3-methoxy-4-[N'-(2-methylphenyl)ureido]phenylacetic acid (468 mg, 1.49 mmol) in DMF (10 mL) was added EDC.HCl (428 mg, 2.24 mmol), HOBt, and DMAP (cat.). After being stirred overnight, the mixture was diluted with EtOAc (300 mL), washed with brine (2×200 mL), and dried over MgSO$_4$. After removal of the solvent, the residue was chromatographed on silica-gel with CHCl$_3$:EtOH (9:1, v/v) as eluent to give 257 mg (31%) ethyl 4-[1-[3-methoxy-4-[N'-(2-methylphenyl) ureido]phenylacetyl]-2-pyrrolidinylmethyl]-1-piperazinylacetate as a yellow foam. $^1$H-NMR (CDCl$_3$) δ 1.24–1.29 (3 H, m), 1.69–4.24 (total 29 H, series of m), 6.41 (1 H, m), 6.81 (2 H, m), 7.13–7.26 (4 H, m), 7.52 (1 H, d, J=7.3 Hz), 8.04 (1 H, d, J=8.3 Hz).

To a stirred solution of ethyl 4-[1-[3-methoxy-4-[N'-(2-methylphenyl)ureido]phenylacetyl]-2-pyrrolidinylmethyl]-1-piperazinylacetate (250 mg, 0.453 mmol) in THF (4 mL) was added 0.25 N NaOH (3.6 mL). The resulting mixture was stirred overnight. The mixture was adjusted to pH 7.5 by the addition of 1 N HCl and extracted with CHCl$_3$:MEOH (4:1, 3×100 mL). The combined extracts were dried over MgSO$_4$ and evaporated. The crude solid was recrystallized from CHCl$_3$-MeOH-n-hexane to give 40 mg (17%) 49 as a colorless crystalline powder. mp 160–170° C.; $^1$H-NMR (DMSO-d$_6$) δ 1.74–4.08 (total 27 H, series of m), 6.73 (1 H, d, J=7.8 Hz), 6.87 (1 H, s), 6.93 (H, t, J=7.8 Hz), 7.11–7.17 (2 H, m), 7.79 (1H, d, J=7.8 Hz), 8.00 (1 H, dd, J=7.8, 2.4 Hz), 8.47 (1 H, s), 8.56 (1 H, s); MS (FAB) 524 (M$^{30}$1); Anal. Calcd for C$_{28}$H$_{37}$N$_5$O$_5$.HCl.H$_2$O: C, 58.17; H, 6.97; N, 12.11. Found: C, 58.26; H, 7.26; N, 11.53.

Example 46

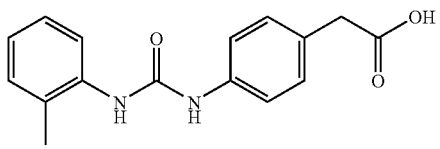

50

To a suspension of 4-aminophenylacetic acid (10 g, 66 mmol) in 1:1 CH$_2$Cl$_2$:acetone (100 mL) was added o-tolyisocyanate (8.8 g, 66 mmol). The mixture was heated to reflux for 4 hr at which time a white precipitate had formed. The precipitate was filtered and the solid washed generously with 1:1 CH$_2$Cl$_2$:acetone. The solid was recrystallized with hot methanol and dried under vacuum to yield 14.1 g (75% yield) of the desired 4-(o-tolylureido)phenylacetic acid 50.

Example 47

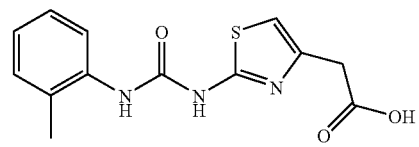

51

To a suspension of 2-amino-4-thiazoleacetic acid (4 g, 25 mmol) in 1:1 CH$_2$Cl:acetone (100 mL) was added o-tolyisocyanate (3.5 g, 26 mmol). The mixture was heated to reflux for 8 hr at which time a yellow precipitate had formed. the precipitate was filtered and the solid washed generously with 1:1 CH$_2$Cl$_2$:acetone. The solid was recrystallized with hot methanol and dried under vaccum to yield 4.8 g (66% yield) of the desired 2-(o-tolylureido)-4-thiazoleacetic acid 51.

Example 48

4-[[1-[3-methoxy-4-[N'-(2-methylphenyl)ureido] phenylacetyl]-2-pyrrolidinylmethylamino]benzoic acid

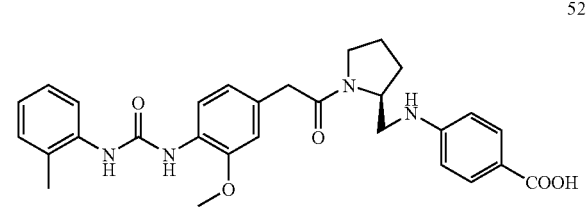

52

A stirred mixture of methyl 4-aminobenzoate (1.52 g, 10.04 mmol) and 1-tert-butoxy carbonyl prolinal (3.00 g, 15.06 mmol) in toluene (30 mL) was heated under reflux for 3 hr. After cooling to room temp, the solvent was evaporated in vacuo. The solid was dissolved in MeOH (27 mL) and AcOH (3 mL), then NaBH$_3$CN (1.33 g, 20.08 mmol) was added to the mixture, and the resulting mixture was stirred overnight at room temp. The reaction mixture was quenched with water, and the solvent was removed under a reduced pressure. Water was added to the residue, and extracted with EtOAc. The extract was washed with H$_2$O, brine, and dried over Na$_2$SO$_4$. The solvent was removed under a reduced pressure, and the residue was chromatographed on silica-gel with n-hexane-EtOAc (3:1, v/v) as eluent to afford 2.17 g (65%) 4-[1-(tert-butoxycarbonyl)-2-pyrrolidinylmethylamino]benzoate as a pale yellow oil. $^1$H-NMR (400 MHz, CDCl$_3$) δ 1.48 (s, 9H), 1.51–2.09 (m, 4H), 3.05–3.07 and 3.43–3.48 (br m, 1H), 3.18 (br s, 1H), 3.36 (br s, 2H), 3.84 (s, 1H), 4.06–4.08, 4.20–4.24 (br m each, 1H), 6.49–6.65 (m, 2H), 7.84 (d, J=8.3 Hz, 2H); MS (FAB) m/z 335 (M$^+$+1).

To a stirred solution of methyl 4-[1-(tert-butoxycarbonyl)-2-pyrrolidinylmethylamino]benzoate (2.17 g, 6.490 mmol) in CH$_2$Cl$_2$ (44 mL) was added TFA (8.7 mL) at 0° C., and the resulting mixture was stirred overnight at room temp. The solvent was removed under a reduced pressure and the residue was treated with 1 N NaOH. The mixture was extracted with CH$_2$Cl$_2$. The extract was washed with brine, dried over Na$_2$SO$_4$, and the solvent was concentrated under a reduced pressure to afford 1.34 g (88%) methyl 4-(2-pyrrolidinylmethylamino)benzoate as a brown oil, which is used to the subsequent reaction without further purification.

The mixture of the above methyl 4-(2-pyrrolidinylmethylamino)benzoate (397.8 mg, 1.69 mmol), 3-methoxy-4-[N'-(2-methylphenyl)ureido]phenylacetic acid (587.1 mg, 1.87 mmol), EDC (HCl) (486 mg, 2.54 mmol), HOBt (23 mg, 0.17 mmol), and DMAP (21 mg, 0.17 mmol) in DMF (4 mL) was stirred overnight at room temp. The mixture was diluted with EtOAc, washed with brine, and dried over Na$_2$SO$_4$. The solvent was removed under a reduced pressure. The residue was chromatographed on-silica-gel with CHCl$_3$-MeOH (50:1, v/v) as eluent to afford 882 mg (98%) methyl 4-[1-[3-methoxy-4-[N'-(2-methylphenyl)ureido]phenylacetyl]-2-pyrrolidinyl methylamino]benzoate as a brown amorphous solid, which is used to the subsequent reaction without further purification.

To a stirred solution of the above methyl 4-[1-[3-methoxy-4-[N'-(2-methylphenyl)ureido]phenylacetyl]-2-pyrrolidinylmethylamino]benzoate (882 mg, 1.662 mmol) in THF (18 mL) and MeOH (5.0 mL) was added 1 N NaOH (5.0 mL, 5.000 mmol), and the mixture was heated under reflux for 3 days. The mixture was concentrated. The residue was treated with 1 N HCl and extracted with CH$_2$Cl$_2$. The extract was washed with brine, dried over Na$_2$SO$_4$, and evaporated in vacuo. The solid was recrystallized from n-hexane-diisopropyl ether-CHCl$_3$-MeOH to afford 180.5 mg (21%) 52 as a pale yellow amorphous solid. IR(KBr) 1604, 1535, 1511, 1454, 1255, 1224, 1174 cm$^{-1}$; $^1$H-NMR (400 MHz, DMSO-d$_6$) δ 1.79–1.99 (br m, 4H), 2.25 (s, 3H), 2.90–2.94 (m, 1H), 3.35–3.62 (m, 6H), 3.87 (s, 3H), 4.12–4.15 (br s, 1H), 6.63–6.78 (m, 4H), 6.89–6.95 and 7.11–7.17 (m each, 3H), 7.65 (d, J=8.3 Hz, 2H), 7.80 (d, J=8.3 Hz, 1H), 8.02 (d, J=8.3 Hz, 1H), 8.47 (s, 1H), 8.57 (s, 1H), 12.0 (br s, 1H); MS (FAB) m/z 517 (M$^+$+1); Anal Calcd for C$_{29}$H$_4$N$_{32}$O$_5$.1H$_2$O: C, 65.15; H, 6.41; N, 10.48. Found: C, 65.45; H, 6.33; N, 10.02.

Example 49

4-[N-[1-[3-methoxy-4-[N'-(2-methylphenyl)ureido]phenylacetyl]-2-pyrrolidinylmethyl]-N-methylamino]benzoic acid

53

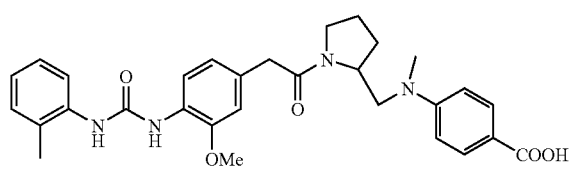

To a mixture of methyl 4-[N-(2-pyrrolidinyl)methylamino]benzoate (600 mg, 1.794 mmol), 37%-formaldehyde (1.79 mL, 23.32 mmol), and NaBH$_3$CN (368 mg, 5.561 mmol) in CH$_3$CN (6.0 mL) was added dropwise AcOH (0.205 mL, 3.588 mmol), and the resulting mixture was stirred for 2 hr at room temp. The reaction mixture was quenched by the addition of sat. NaHCO$_3$, and extracted with EtOAc. The extract was washed with brine and dried over Na$_2$SO$_4$. The solvent was removed under a reduced pressure, and the residue was chromatographed on silica-gel with n-hexane-EtOAc (3:1, v/v) as eluent to afford 645 mg (100%) methyl 4-[N-[1-(tert-butoxycarbonyl)-2-pyrrolidinylmethyl]-N-methylamino]benzoate as a colorless oil. $^1$H-NMR (400 MHz, CDCl$_3$) δ 1.50 (s, 9H), 1.76–1.91 (m, 4H), 3.07 (s, 3H), 3.15–3.43 (m, 3H), 3.67–3.71 (m, 1H), 3.85 (s, 3H), 4.11–4.17 (m, 1H), 4.37 (s, 1H), 6.75 (d, J=8.3 Hz, 2H), 7.89 (d, J=8.8 Hz, 2H); MS (FAB) m/z 349 (M$^+$+1).

To a stirred solution of methyl 4-[N-[1-(tert-butoxycarbonyl)-2-pyrrolidinylmethyl]-N-methylamino]benzoate (645 mg, 1.794 mmol) in CH$_2$Cl$_2$ (6.5 mL) was added TFA (1.3 mL) at 0° C., and the mixture was stirred overnight at room temp. The solvent was removed under a reduced pressure and the residue was treated with 1 N NaOH solution. The mixture was extracted with CH$_2$Cl$_2$. The extract was washed with brine, dried over Na$_2$SO$_4$, and the solvent was concentrated under a reduced pressure to afford 363.2 mg (82%) of methyl 4-[N-(2-pyrrolidinyl)methyl-N-methyl]aminobenzoate as a yellowish oil, which is used to the subsequent reaction without further purification.

The mixture of methyl 4-[N-(2-pyrrolidinyl)methyl-V-methyl]aminobenzoate (191.8 mg, 0.772 mmol), 3-methoxy-4-(N'-2-methylphenylureido)phenylacetic acid (258.1 mg, 0.811 mmol), EDC (hydrochloride) (221.9 mg, 1.158 mmol), HOBt (10.0 mg, 0.077 mmol), and DMAP (9.4 mg, 0.077 mmol) in DMF (2.0 mL) was stirred for 3 hr at room temp. The reaction mixture was diluted with Et$_2$O, washed with brine, and dried over Na$_2$SO$_4$. The solvent was removed under a reduced pressure to afford 482.5 mg methyl 4-[N-[1-[3-methoxy-4-[N'-(2-methylphenyl)ureido]phenylacetyl]-2-pyrrolidinylmethyl]-N-methylamino]benzoate as a white amorphous powder, which is used to the subsequent reaction without further purification.

To a stirred solution of methyl 4-[N-[1-[3-methoxy-4-[N'-(2-methylphenyl)ureido]phenyl acetyl]-2-pyrrolidinylmethyl]-N-methylamino]benzoate in THF (5.0 mL) was added 1 N NaOH (6.2 mL, 6.2 mmol), and the mixture was heated under reflux for 3 days. The reaction mixture was concentrated in vacuo. The residue was neutralized with 1 N HCl, and extracted with CH$_2$Cl$_2$. The extract was washed with sat. NH$_4$Cl, brine, dried over Na$_2$SO$_4$, and evaporated in vacuo. The crude solid was recrystallized from n-hexane-CHCl$_3$-MeOH-isopropylether to afford 102.8 mg (25%, 2steps) 53 as a pale yellow amorphous solid. mp 144–146; IR (KBr) 3325, 1600, 1529, 1454, 1284, 1257, 1184 cm$^{-1}$; $^1$H-NMR (400 M , DMSO-d$_6$) δ 1.73–1.91 (m, 3H), 2.03–2.11 (m, 1H), 3.03 (s, 3H), 3.16 (dd, J=9.3, 14.2 Hz, 1H), 3.37–3.60 (m, 4H), 3.76–3.80 (m, 1H), 3.86 (s, 3H), 4.25 (br s, 1H), 6.75 (dd, J=1.5, 8.3 Hz, 1H), 6.86 (d, J=1.5 Hz, 1H), 6.90 (d, J=8.8 Hz, 2H), 6.95–7.01 (m, 1H), 7.12 (t, J=7.8 Hz, 1H), 7.20–7.25 (m, 1H), 7.73 (d, J=8.8 Hz, 2H), 8.01 (d, J 7.8 Hz, 1H), 8.16–8.20 (m, 1H), 8.73 (s, 1H), 9.19 (d, J=2.0 Hz, 1H), 12.0 (br s, 1H); MS (FAB) m/z 535 (M$^+$+1); Anal. Calcd for C$_{29}$H$_{31}$,FN$_4$O$_5$.1/2H$_2$O: C, 64.08; H, 5.93; N, 10.31; F, 3.49. Found: C, 64.17; H, 5.84; N, 10.06; F, 3.26.

Example 50

4-[N'-[1-[-4-[N'-(2-fluorophenyl)ureido]-3-methoxyphenylacetyl]-2-pyrrolidinylmethyl]-N-methylamino]-3-nitrobenzoic acid

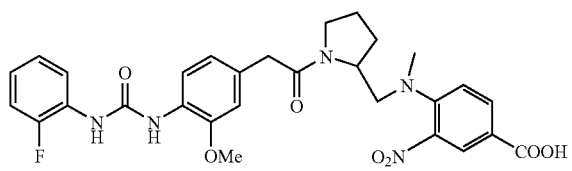

54

To a mixture of methyl 4-fluoro-3-nitrobenzoate (1.58 g, 4.666 mmol) and [1-(tert-butoxycarbonyl)-2-pyrrolidinyl]methylamine (500 mg, 2.333 mmol) in DMF (8.0 mL) was added $K_2CO_3$ (967 mg, 6.999 mmol), the resulting mixture was stirred for 3 hr at room temp. The reaction mixture was diluted with EtOAc, washed with water, and dried over $Na_2SO_4$. The solvent was removed under a reduced pressure, and the residue was chromatographed on silica-gel with n-hexane-EtOAc (3:1, v/v) as eluent to afford 834.9 mg (91%) of methyl 4-[N-[1-(tert-butoxycarbonyl)-2-pyrrolidinylmethyl]-N-methyl]amino-3-nitrobenzoate as a pale yellow oil, which is used to the subsequent reaction without further purification.

To a ice-cooling solution of the above oil in $CH_2Cl_2$ (8.3 mL) was added TFA (1.7 mL), and the reaction mixture was stirred overnight at room temp. The solvent was removed under a reduced pressure. The residue was treated with IN-NaOH and extracted with $CHCl_3$. The extract was washed with brine, dried over $Na_2SO_4$, and evaporated under a reduced pressure to afford 553.6 mg (90%) methyl 4-[N-(2-pyrrolidinylmethyl)-N-methyl]amino-3-nitrobenzoate as a pale yellow oil. $^1$H-NMR (400 MHz, $CDCl_3$) δ 1.31–1.40 (m, 1H), 1.74–2.05 (m, 4H), 2.73–2.79 (m, 1H), 2.81–2.99 (m, 1H), 2.94 (s, 3H), 3.29–3.55 (m, 2H), 3.89 (s, 3H), 7.14 (d, J=9.3 Hz, 1H), 7.98 (dd, J=2.0, 8.8 Hz, 1H), 8.42 (d, J=2.0 Hz, M1); MS (FAB) m/z 294 ($M^+$+1).

A mixture of 3-methoxy-4-[N'-(2-fluorophenyl)ureido]phenylacetic acid (630.0 mg, 1.979 mmol), methyl 3-nitro-4-[N-(2-pyrrolidinyl)methyl-N-methylamino]benzoate (553.0 mg, 1.885 mmol), EDC(Hydrochloride) (542.0 mg, 2.827 mmol), HOBt (25.5 mg, 0.189 mmol), and DMAP (23.1 mg, 0.189 mmol) in DMF (5.0 mL) was stirred at room temp. for 2 hr. The mixture was diluted with $Et_2O$, washed with brine, and dried over $Na_2SO_4$. The solvent was removed under a reduced pressure, and the residue was chromatographed on silica-gel with $CHCl_3$-MeOH (30:1, v/v) as eluent to afford 1.18 g (100%) methyl 4-[N-[1-[3-methoxy4-[N'-(2-fluorophenyl)ureido]phenylacetyl]-2-pyrrolidinyl methyl]-N-methylamino]-3-nitrobenzoate as a yellow foam, which is used to the subsequent reaction without further purification.

To a stirred solution of the above methyl 4-[N-[1-[3-methoxy-4-[N'-(2-fluorophenyl) ureido]phenylacetyl]-2-pyrrolidinylmethyl]-N-methylamino]-3-nitrobenzoate (2.50 mg, 0.421 mmol) in THF (3.0 mL) was added 1 N NaOH (1.5 mL, 1.500 mmol), and the mixture was heated under reflux overnight. After cooling, the mixture was concentrated to a small volume. The residue was treated with 1 N HCl, and extracted with $CHCl_3$. The extract was washed with brine, dried over $Na_2SO_4$, and evaporated in vacuo. The crude solid was recrystallized from n-hexane-diethyl ether-$CHCl_3$-MeOH to afford 194.9 mg (80%) of 54 as a yellow amorphous solid. IR (KBr) 1685, 1610, 1529, 1454, 1284, 1259, 1228 $cm^{-1}$; $^1$H-NMR (400 MHz, DMSO-$d_6$) δ 1.63–1.91 (m, 3H), 2.04–2.07 (br s, 1H), 2.60 (br s, 1H), 2.80 (s, 1H), 2.99 (s, 2H), 3.05–3.10 (m, 1H), 3.32–3.58 (m, 3H), 3.76–3.81 (m, 1H), 3.81 (s, 3H), 4.25 (br s, 1H), 6.68 (t, J=3.9 Hz, 1H), 6.71 (d, J=8.8 Hz, 1H), 6.81–6.96 (m, 1H), 7.07 (t, J=7.3 Hz, 1H), 7.17 (dd, J=7.8, 9.8 Hz, 1H), 7.48 (t, J=7.8 Hz, 1H), 7.85 (d, J=8.8 Hz, 1H), 7.97 (t, J=8.8 Hz, 1H), 8.11–8.20 (m, 2H), 8.68 (s, 1H), 9.14 (s, 1H), 12.8 (br s, 1H); MS (FAB) m/z 580 ($M^+$+1); Anal. Calcd for $C_{29}H_{30}FN_5O_7 \cdot 1/4H_2O$: C, 59.63; H, 5.26; N, 11.99; F, 3.25.Found: C, 59.68;H, 5.34;N, 11.80; F, 3.21.

Example 51

3-amino-4-[N-methyl-[1-[4-[N'-(2-fluorophenyl)ureido]-3-methoxy-phenylacetyl]-2-pyrrolidinyl methyl]-N-methylamino]benzoic acid

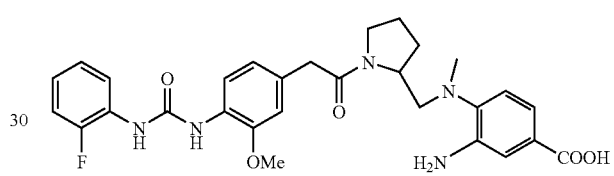

55

A stirred solution of methyl 4-[N-[1-[4-[N'-(2-fluorophenyl)ureido]-3-methoxy-phenylacetyl]-2-pyrrolidinylmethyl]-N-methylamino]-3-nitrobenzoate (901.0 mg, 1.518 mmol) in MeOH (18.0 mL) was hydrogenated over 5% Pd—C (1.35 g) at 45 psi overnight. The mixture was filtered and the filtrate was concentrated in vacuo. The residue was made basic with 1 N NaOH solution and extracted with $CHCl_3$. The extract was washed with brine, dried over $Na_2SO_4$, and the solvent was removed under a reduced pressure. The residue was chromatographed on silica-gel with $CHCl_3$-MeOH (24:1, v/v) as eluent to afford 283.7 mg (48%) methyl 3-amino-4-[N-[1-[4[-N'-(2-fluorophenyl)ureido]-3-methoxy-phenylacetyl]-2-pyrrolidinylmethyl]-N-methylamino]benzoate as a brownish amorphous solid, which was used to the subsequent reaction without further purification.

To a stirred solution of the above compound in THF (3.0 mL) was added 1 N NaOH solution (1.5 mL, 1.500 mmol), and the mixture was refluxed overnight. The mixture was concentrated, treated with 1 N HCl, and extracted with $CHCl_3$. The extract was washed with brine, dried over $Na_2SO_4$, and evaporated in vacuo. The solid was recrystallized from n-hexane-diethyl ether-$CHCl_3$-MeOH to afford 179.8 mg (65%) 55 as a white amorphous solid. IR (KBr) 1614, 1601, 1537, 1454, 1228, 1219, 1184 $cm^{-1}$; $^1$H-NMR (400 MHz, DMSO-$d_6$) δ 1.60–2.20 (m, 4H), 2.61–2.68 (m, 1H), 2.89 (s, 3H), 3.13–3.18 (m, 1H), 3.40–3.61 (m, 4H), 3.85 (s, 3H), 4.01 (br m, 1H), 4.93 (br s, 2H), 6.50–7.31 (m, 8H), 8.01 (dd, J=2.9, 8.3 Hz, 1H), 8.18 (t, J=8.3 Hz, 1H), 8.71 (s, 1H), 9.17(d, J=1.5 Hz, 1H), 12.3 (br s, 1H); MS (FAB) m/z 550 ($M^+$+1); Anal. Calcd for $C_{29}H_{32}FN_5O_5 \cdot 1/4H_2O$: C, 62.86; H, 5.91; N, 12.64; F, 3.43. Found: C, 62.71; H, 6.00; N, 12.39; F, 3.16.

Example 52

4-[1-[4-[N'-(2-methylphenyl)ureido]phenylacetyl]-2-pyrrolidinyl]methylamino]benzoic acid

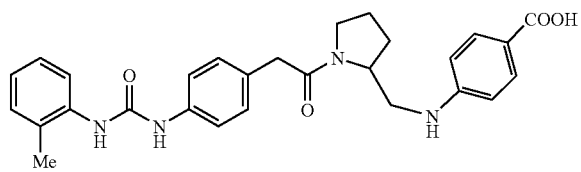

56

To a stirred mixture of methyl 4-[(2-pyrrolidinyl)methylamino]benzoate (220 mg, 0.94 mmol), 4-[N'-(2-methylphenyl)ureido]phenylacetic acid (285 mg, 0.94 mmol), 4-DMAP (140 mg, 1.13 mmol) and catalytic amount of HOBT in DMF (7 ml) was added EDC.HCl (220 mg, 1.13 mmol) at room temperature. The resulting mixture was stirred at room temperature for 20 hr. The mixture was pored into ice-water. The solid was collected, washed with water and air-dried. The crude solid was purified by silica-gel (20 ml) column chromatography with CHCl$_3$-EtOAc (3:1, v/v) to CHCl$_3$-EtOH (9:1, v/v) as eluent to give methyl 4-[1-[4-[N'-(2-methylphenyl)ureido]phenyl acetyl]-2-pyrrolidinyl]methylamino]benzoate (400 mg, 85%) as a gum. $^1$H-NMR (CDCl$_3$) δ 1.75–2.05 (series of m, 4 H), 2.24 (s, 3 H), 3.18 and 3.27 (each m, each 1 H), 3.51 (m, 2 H), 3.60 (s, 2 H), 3.83 (s, 3 H), 4.52 (m, 1 H), 6.52 (m, 3 H), 6.81 (s, 1 H), 7.11–7.25 (series of m, 7 H), 7.53 (m, 1 H), 7.81 (d, J=8.8 Hz, 2H).

A mixture of methyl 4-[1-[4-[N'-(2-methylphenyl)ureido]phenylacetyl]-2-pyrrolidinyl]methylamino]benzoate (280 mg, 0.56 mmol) in THF (3 ml) and 0.25 N NaOH (6.8 ml, 1.75 mmol) was stirred for 3 hr at 60–70° C. After cooling, the mixture was poured into ice-1 N HCl (3 ml). The solid was collected, washed with water and air-dried. The crude crystalline material was recrystallized from CHCl$_3$-EtOH-IPE to give 56 (180 mg, 66%) as fine needles. MW 486.56 IR (KBr) n 3367, 3294, 1712, 1606, 1539 cm$^{-1}$; $^1$H-NMR (CDCl$_3$-DMSO-d$_6$) δ 1.80–2.05 (series of m, 4 H), 2.26 (s, 3 H), 2.94 (m, 1), 3.38 and 3.56 (series of m, 3 H), 3.57 (s, 2H), 4.23 (m, 2 H), 6.48 (br s, 1 H), 6.69 (d, J=8.8 Hz, 2H), 6.91 (t, J=7 Hz, 1 H), 6.91 (m, 4H 7.39 (d, J=8.3 Hz, 2H), 7.66 (d, J=8.8 Hz, 2H), 7.80 (m, 2 H), 8.88 (s, 1 H), 11.76 (s, 1 H); MS(FAB) m/z 487 (M$^+$+1); Anal. Calcd for C$_{28}$H$_{30}$N$_4$O$_4$.0.75×H$_2$O: C, 67.24; H, 6.45; N, 11.20. Found: C, 67.13; H, 6.32; N, 11.01.

Example 53 methyl 4-[1-[4-[N'-(2-chlorophenyl)ureido]-3-methoxylphenylacetyl]-(2S)-pyrrolidinyl]methoxybenzoate

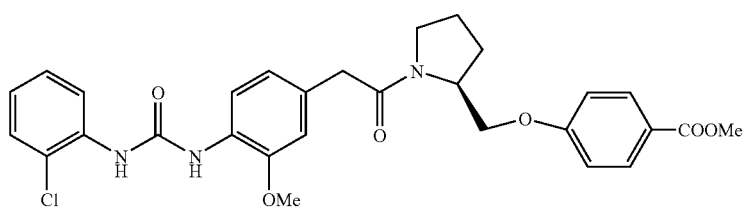

57

4-[1-[4-[N'-(2-chlorophenyl)ureido]-3-methoxylphenylacetyl]-(2S)-pyrrolindinyl]methoxybenzoic acid

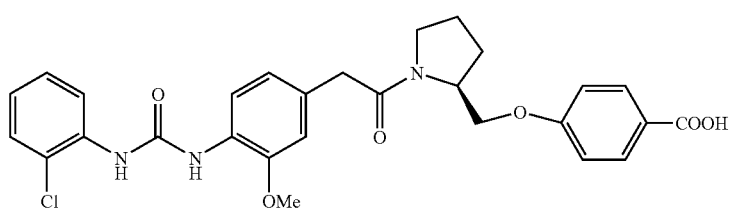

58

To a stirred solution of 2S-pyrrolidinemethanol (15.1 g, 149.5 mmol) in dioxane (100 ml) was added a solution of (Boc)$_2$O (32.6 g, 164.4 mmol) in dioxane (100 ml). The reaction mixture was stirred at room temperature for 18 hr, and concentrated in vacuo. The residue was purified by column chromatography on silica gel with EtOAc-hexane (1:5 v/v) as eluent to give (1-tert-butoxycarbonyl-(2S)-pyrrolidinyl)methanol (31.6 g, quant.) as a colorless oil. $^1$H-NMR (CDCl$_3$) δ 1.47 (s, 9H), 1.60–2.00 (m, 3H), 3.25–3.70 (4H, m), 3.92–4.00 (m, 1H).

To a stirred solution of (1-tert-butoxycarbonyl-(2S)-pyrrolidinyl)methanol (4.02 g, 20.0 mmol), methyl 4-hydroxybenzoate (3.04 g, 20.0 mmol) and Ph$_3$P (6.28 g, 24.0 mmol) in THF (50 ml) was added DIAD (4.85 g, 24.0 mmol) at 0° C. The reaction mixture was stirred at room temperature for 18 hr. The mixture was concentrated in vacuo. The residue was purified by column chromatography on silica gel with n-hexane-EtOAc (5:1, v/v) as eluent to give methyl 4-(1-tert-butoxycarbonyl-(2S)-pyrrolidinyl)methoxybenzoate (5.4 g, 81%) as a pale yellow oil. $^1$H-NMR (CDCl$_3$) δ 1.47 (s, 9H), 1.88–2.04 (m, 4H), 3.41 (m, 2H), 3.91 (s, 3H), 3.90–3.92 (m, 1H), 4.11–4.16 (m, 2H), 6.94 (d, J=8.6 Hz, 2H), 7.94 (d, J=8.3 Hz, 2H).

To a stirred solution of methyl 4-(1-tert-butoxycarbonyl-2S-pyrrolidinyl)methoxybenzoate (2.1 g, 6.27 mmol) in CH$_2$Cl$_2$ (9.0 ml) was added TFA (6.0 ml) at 0° C. The reaction mixture was stirred at room temperature for 0.5 hr. The mixture was concentrated in vacuo. Sat. NaHCO$_3$ was added to the residue, and extracted with CH$_2$Cl$_2$. The extract was washed with brine, dried over Na$_2$SO$_4$, and concentrated in vacuo. The crude product was used to the subsequent reaction without further purification. To a stirred solution of the crude product (470 mg, 2.0 mmol), 4-[N'-(2-chlorophenyl) uredio]-3-methoxyphenylacetic acid (669 mg, 2.0 mmol), HOBt (405 mg, 3.0 mmol), and triethylamine (554 ml, 4.0 mmol) in THF (10.0 ml) and MeCN (10.0 ml) was added EDC.HCl (576 mg, 3.0 mmol) at 0° C. The reaction mixture was stirred at room temperature for 16 hr, and concentrated in vacuo. Water was added to the residue, and extracted with EtOAc. The extract was washed with sat. NaHCO$_3$, then dried over Na$_2$SO$_4$, and concentrated in vacuo. The residue was purified by column chromatography on silica gel with n-hexane-EtOAc (1:4, v/v) as eluent to give 57 (900 mg, 82%) as a colorless oil. MW 552.02 $^1$H-NMR (CDCl$_3$) δ 2.04–2.10 (m, 4H), 3.51–3.70 (m, 6H), 3.87 (s, 3H), 4.11–4.18 (m, 2H), 6.77–6.88 (m, 4H), 7.23–7.34 (m, 4H), 7.91–7.96 (m, 2H), 8.17–8.19 (m, 1H).

The mixture was stirred at 70° C. for 24 hr. The mixture was concentrated in vacuo, water was added thereto, and neutralized with 1 N HCl. The resulting solid was collected, washed with water, and dried in vacuo to 58 (640 mg, 94%) as a white crystalline solid. MW 537.99 mp 126–130° C.; IR (KBr) 3324, 2938, 2877, 1604, 1533, 1249, 1166, 750 cm$^{-}$; $^1$H-NMR (DMSO-d$_6$) δ 1.93–2.05 (m, 4H), 3.52–3.61 (m, 5H), 3.82 (s, 3H), 3.99–4.01 (m, 2H), 4.18–4.20 (m, 1H), 4.29 (m, 1H), 6.74–6.76 (d, 1H, J=8.3 Hz), 6.87 (s, 1H), 6.99–7.04 (m, 3H), 7.25–7.29 (m, 1H), 7.41–7.43 (d, 1H, J=8.1 Hz), 7.86–7.91 (m, 2H), 7.95–7.97 (m, 1H), 8.09–8.11 (d, 1H, J=8.3 Hz), 8.87–8.92 (m, 1H); MS (FAB) m/z 538 (M$^+$+1); Anal. calcd for C$_{28}$H$_{28}$N$_3$O$_6$·0.5H$_2$O: C, 61.48; H, 5.34; N, 7.68; Cl, 6.48. Found: C, 61.46; H, 5.36; N, 7.62; Cl, 6.50. For Na salt of 58: Anal. Calcd for C$_{28}$H$_{27}$N$_3$O$_6$·Na·1.5H$_2$O: C, 57.29; H, 5.15; N, 7.16. Found: C, 57.48; H, 5.04; N, 6.99.

Example 54

4-[1-[4-[N'-(2-bromophenyl)ureido]-3-methoxylphenylacetyl]-(2S)-pyrrolidinyl]methoxybenzoic acid To a stirred solution of methyl 4-(2S-pyrrolidinyl)methoxybenzoate (470 mg, 2.0 mmol), 4-[N'-(2-bromophenyl) uredio]-3-methoxyphenylacetic acid (758 mg, 2.0 mmol), HOBt (405 mg, 3.0 mmol), and triethylamine (554 ml, 3.0 mmol) in THF (10.0 ml) and MeCN (10.0 ml) was added EDC.HCl (576 mg, 3.0 mmol) at 0° C. The reaction mixture was stirred at room temperature for 16 hr, and concentrated in vacuo. Water was added to the residue, and extracted with EtOAc. The extract was washed with sat. NaHCO$_3$, then dried over Na$_2$SO$_4$, and concentrated in vacuo. The residue was purified by column chromatography on silica gel with n-hexane-EtOAc (1:4, v/v) as eluent to give methyl 4-[1-[4-[N'-(2-bromophenyl)ureido]-3-methoxylphenylacetyl]-(2S)-pyrrolidinyl]methoxybenzoate (1.0 g, 84%) as a colorless oil. $^1$H-NMR (CDCl$_3$) δ 2.04–2.10 (m, 4H), 3.52–3.54 (m, 1H), 3.62 (s, 2H), 3.70 (s, 3H), 3.88 (s, 3H), 4.13–4.19 (m, 2H), 6.79–6.94 (m, 4H), 7.20–7.31 (m, 1H), 7.91–8.12 (m, 2H), 8.13–8.15 (m, 1H).

To a stirred solution of methyl 4-[1-[4-[N'-(2-bromophenyl)ureido]-3-methoxylphenylacetyl]-(2S)-pyrrolidinyl]methoxybenzoate (780 mg, 1.31 mmol) in THF (10.0 ml) and MeOH (5.0 ml) was added 1 N NaOH (2.0 ml, 2.0 mmol). The mixture was stirred at 70° C. for 24 hr. The mixture was concentrated in vacuo, water was added thereto, and neutralized with 1 N HCl. The resulting solid was collected, washed with water, and dried in vacuo to give 59 (730 mg, 96%) as a white crystalline solid. MW 582.44 mp 120–125° C.; IR (KBr) 3318, 2938, 1604, 1529, 1166, 1025 cm$^{-1}$; $^1$H-NMR (DMSO-d$_6$) δ 1.92–1.96 (m, 4H), 3.52–3.60 (m, 5H), 3.82 (s, 3H), 3.98–4.02 (m, 1H), 4.16–4.19 (m, 1H), 4.29 (m, 1H), 6.75 (d, J=8.3 Hz, 1H), 6.87 (m, 1H), 6.94–7.04 (m, 3H), 7.29–7.33 (m, 1H), 7.57–7.59 (m, 1H), 7.85–7.96 (m, 4H), 8.72 (s, 1H), 8.91 (s, 1H); MS (FAB) m/z 582 (M$^+$+1); Anal. calcd for C$_{28}$H$_{28}$N$_3$O$_6$Br·1.0H$_2$O: C, 56.01; H, 5.04; N, 7.00; Br, 13.31. Found: C, 56.12; H, 4.98; N, 6.96; Br, 13.57.

Example 55

3-amino-4-[1-[4-[N'-(2-hydroxyphenyl)ureido]-3-methoxyphenylacetamido]-2-pyrrolidinyl methoxy]benzoic acid

60

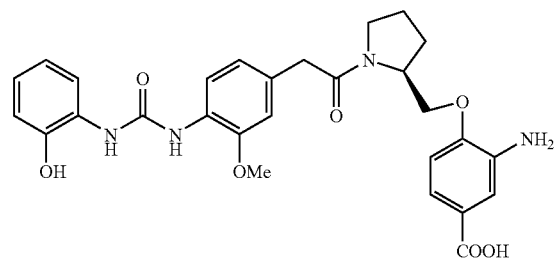

To a stirred solution of 2-nitrophenol (10.0 g, 72.0 mmol) and K$_2$CO$_3$ (9.96 g, 72.0 mmol) in DMF (150 mL) was

59

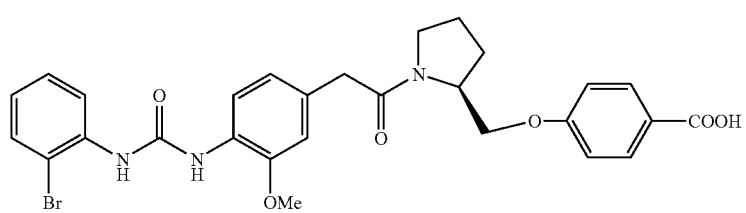

added dropwise benzyl bromide (9.40 mL, 79.2 mmol) at 0° C. After being stirred at room temperature for 3 hr, the reaction mixture was diluted with water, which was extracted with Et₂O. The extracts were washed with brine, dried over Na₂SO₄, and concentrated to dryness. Chromatography of the residue with hexane-EtOAc (2:1, v/v) as eluent gave 2-benzyloxy nitrobenzene (14.7 g, 89%) as a yellow oil. ¹H-NMR (CDCl₃) δ 5.24 (s, 2H), 7.04 (t, J=7.8 Hz, 1H), 7.12 (d, J=7.8 Hz, 1H), 7.31–7.50 (m, 5H), 7.51 (d, J=1.5 Hz, 1H), 7.86 (dd, J=7.8, 1.5 Hz, 1H).

To a stirred solution of 2-benzyloxynitrobenzene (9.92 g, 43.3 mmol) and NiCl₂ (20.3 g, 157 mmol) in MeOH (350 mL) was added portionwise NaBH₄ (8.09 g, 214 mmol) at 0° C. After disappearing of the starting material (monitored by TLC), the mixture was evaporated off. The black precipitate was dissolved in 1 N HCl, then acidic solution was alkalified by the addition of 1 N NaOH and extracted with EtOAc. The extracts were washed brine, dried over Na₂SO₄, and concentrated to dryness. Chromatography of the residue with CHCl₃ as eluent gave 2-benzyloxy aniline (8.60 g, 100%) as a reddish oil. ¹H-NMR (CDCl₃) δ 3.71 (broad s , 2H), 5.06 (s, 2H), 6.68–6.86 (m, 4H), 7.32–7.44 (m, 51); FAB-MS m/z 200 (M⁺+1).

To a solution of 2-benzyloxyaniline (1.15 g, 5.77 mmol) in benzene (60 mL) was added triphosgene (1.27 g, 6.35 mmol) and Et₃N (2.60 mL, 17.3 mmol) at 0° C. The reaction mixture was heated under reflux for 20 hr. The resulting mixture was filtrated and washed with hexane, and the filtrate was concentrated to leave a residual oil, which was chromatographed with hexane-EtOAc (4:1, v/v) as eluent to afford tert-butyl 4-[N'-(2-benzyloxyphenyl)ureido]-3-methoxy phenylacetate (2.38 g, 89%) as a yellow oil. ¹H-NMR (CDCl₃) δ 1.44 (s, 9H), 3.44 (s, 2H), 3.78 (s, 3H), 5.07 (s, 2H), 6.73 (dd, J=8.0, 1.7 Hz, 1H), 6.78 (d, J=1.7 Hz, 1H), 6.90–6.98 (m, 3H), 7.07 (s, 1H), 7.29 (s, 1H), 7.33–7.38 (m, 5H), 7.91 (d, J=8.0 Hz, 1H), 8.14 (m, 1H).

To a solution of tert-butyl 4-[N'-(2-benzyloxyphenyl)ureido]-3-methoxyphenylacetate (2.35 g, 5.08 mmol) in CH₂Cl₂ (25 mL) was added TFA (25 mL) at 0° C. After being stirred at room temperature for 3 hr, the mixture was concentrated. The residue was dissolved in 1 N NaOH and washed with Et₂O. The basic water layer was poured into ice-1 N HCl and the resulting mixture was extracted with CHCl₃-MeOH (4:1, v/v). The extracts were washed with brine, dried over Na₂SO₄, and concentrated to dryness. The residue was dissolved in isopropyl ether and hexane was added to this solution until the crystallization was completed. The solid was collected to give 4-[N'-(2-benzyloxyphenyl)ureido]-3-methoxyphenylacetic acid (1.59 g, 77%) as a brownish solid. ¹H-NMR (DMSO-d₆) δ 3.50 (s, 2H), 3.85 (s, 3H), 5.26 (s, 2H), 6.76 (d, J=8.3 Hz, 1H), 6.83–6.89 (m, 2H), 6.91 (s, 1H), 7.01 (dd, J=8.3, 2.3 Hz, 1H), 7.31 (t, J=7.3 Hz, 1H), 7.39 (t, J=7.3 Hz, 2H), 7.49 (d, J=7.3 Hz, 2H), 7.97 (d, J=8.3 Hz, 1H), 8.04 (d, J=8.3 Hz, 1H), 8.80 (s, 1H), 8.86 (s, 1H), 12.24 (broad s, 1H); FAB-MS m/z 407 (M⁺+1).

To a solution of 4-[N'-(2-benzyloxyphenyl)ureido]-3-methoxyphenylacetic acid (1.12 g, 2.76 mmol), methyl 4-(2-pyrrolidinylmethoxy)-3-nitrobenzoate (890 mg, 2.76 mmol), HOBt (74.0 mg, 0.55 mmol), DMAP (67.0 mg, 0.55 mmol), and Et₃N (0.58 mL, 4.13 mmol) in THF (15 mL) was added EDC.HCl (792 mg, 4.13 mmol). After being stirred at room temperature for 12 hr, the reaction mixture was diluted with water and extracted with EtOAc. The extracts were washed with brine, dried over Na₂SO₄, and concentrated to dryness. Chromatography of the residue with EtOAc as eluent gave methyl 4-[1-[4-[N'-(2-benzyloxyphenyl)ureido]-3-methoxyphenylacetamido ]-2-pyrrolidinylmethoxy]-3-nitrobenzoate (1.52 g, 82%) as a yellow amorphous solid. ¹H-NMR (CDCl₃) δ 1.91 (m, 1H), 1.95–2.17 (m, 3H), 3.47–3.53 (m, 2H), 3.56 (s, 2H), 3.60 (m, 1H), 3.68 (s, 3H), 3.90 (s, 3H), 4.11 (d, J=7.3 Hz, 1 H), 4.45 (m, 1H), 5.08 (s, 2H), 6.70 (dd, J=8.3, 1.9 Hz, 1H), 6.75 (d, J=1.9 Hz, 1H), 6.91–6.99 (m, 31H), 7.16 (s, 1H), 7.18 (d, J=8.3 Hz, 1H), 7.33–7.40 (m, 6H), 7.91 (d, J=8.3 Hz, 1H), 8.11–8.16 (m, 2H), 8.46 (s, 1H).

A solution of methyl 4-[1-[4-[N'-(2-benzyloxyphenyl)ureido]-3-methoxyphenylacetamido]-2-pyrrolidinylmethoxy]-3-nitrobenzoate (1.52 g, 2.27 mmol) in MeOH (20 mL) and THF (5 mL) was hydrogenated over 5% Pd—C (wet, 52.2%; 1.21 g) under hydrogen atmosphere (4 kg/cm²) at room temperature After being stirred for 17 hr, the catalyst was filtered off and the filtrate was concentrated to dryness. Chromatography of the residue with EtOAc as eluent gave methyl 3-amino-4-[1-[4-[N'-(2-hydroxyphenyl)ureido]-3-methoxyphenylacetamido]-2-pyrrolidinylmethoxy]benzoate (1.12 g, 90%) as a brownish amorphous solid. ¹H-NMR (CDCl₃) δ 1.97–2.10 (m, 4H), 3.44 (s, 3H), 3.52–3.63 (m, 2H), 3.85 (s, 3H), 4.10–4.18 (m, 2H), 4.53 (m, 1H), 6.65–6.67 (m, 4H), 6.93–7.02 (m, 3H), 7.33 (d, J=2.2 Hz, 1H), 7.36 (dd, J=8.3, 2.2 Hz, 1H), 7.60 (s, 1H), 7.69 (d, J=8.3 Hz, 1H), 8.08 (s, 1H), 9.47 (broad s, 1H); FAB-MS m/z 549 (M⁺+1).

To a solution of methyl 3-amino-4-[1-[4-[N'-(2-hydroxyphenyl)ureido]-3-methoxyphenyl acetamido]-2-pyrrolidinylmethoxy]benzoate (1.12 g, 2.04 mmol) in THF -MeOH (4:1, v/v; 20 mL) was added 1 N NaOH (4.20 mL, 4.20 mmol). After being stirred at room temperature for 24 hr, the reaction mixture was concentrated. The residue was diluted with water and neutralized with 1 N HCl at 0° C. The mixture was extracted with CHCl₃-MeOH (4:1, v/v), which was washed with brine, dried over Na₂SO₄, and concentrated to dryness. Chromatography of the residue with CHCl₃:MeOH (5:1, v/v) as eluent gave 60 (352 mg, 32%) as a pale yellow amorphous solid. MW 534.56 IR (KBr) 3282, 3062, 3025, 2952, 2865, 1629, 1546, 1509, 1454, 1419 cm⁻¹; ¹H-NMR (DMSO-d₆) δ 1.87–2.04 (m, 4H), 3.48–3.57 (m, 2H), 3.60 (s, 2H), 3.79 (s, 3H), 3.94 (dd, J=9.5, 7.6 Hz, 1H), 4.12 (dd, J=9.5, 3.9 Hz), 4.35 (m, 1H), 4.87 (broad s, 1H), 6.70–6.91 (m, 6H), 7.16 (dd, 1H, J=8.3, 2.0 Hz, 1H), 7.26 (d, J=2.0 Hz, 1H), 7.96 (d, J=8.3 Hz, 1H), 7.97 (d, J=8.3 Hz, 1H), 8.80 (s, 1H), 8.82 (s, 1H); FAB-MS m/z 535 (M⁺+1); Anal. Calcd for C₂₈H₃₀N₄O₇.4.5H₂O: C, 55.63; H, 6.39; N, 9.10. Found: C, 55.08; H. 5.06; N, 8.69.

Example 56

5-[[1-[4-[N'-(2-chlorophenyl)ureido]-3-methoxyphenylacetyl]-2-pyrrolidinyl]methylamino]pyridine-2-carboxylic acid

61

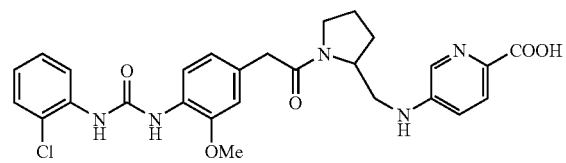

5-[[1-[3-methoxy-4-[N'-(2-methylphenyl)ureido]phenylacetyl]-2-pyrrolidinyl]methylamino]pyridine-2-carboxylic acid

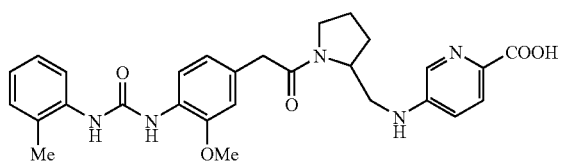

To a stirred solution of 5-(methoxycarbonyl)pyridine-2-carboxylic acid (2.5 g, 13.8 mmol) and 4-DMAP (340 mg, 2.8 mmol) in tert-BuOH (15 ml) was added Boc$_2$O (6 g, 27.6 mmol) at room temperature. After stirring for 2 hr at room temperature, ice and 0.2 N HCl (20 ml) was added to the mixture and extracted with CH$_2$Cl$_2$. The extracts were washed with sat. NaHCO$_3$, dried over Na$_2$SO$_4$, and evaporated. The residue was chromatographed on silica gel (50 ml) with CH$_2$Cl$_2$ as eluent to give methyl 6-tert-butoxycarbonylnicotinate (2.92 g, 89%) as needles. IR (KBr) 2729, 1736, 1720, 1590, 1570 cm$^{-1}$; MS (FAB) m/z 238 (M$^+$+1); Anal. Calcd for C$_{12}$H$_{15}$NO$_4$: C, 60.75; H, 6.37; N, 5.90. Found: C, 60.72; H, 6.46; N, 5.78.

A mixture of methyl 6-tert-butoxycarbonylnicotinate (1.2 g, 5.06 mmol) in THF (15 ml) and 0.25 N NaOH (40 ml, 10 mol) at an ambient temperature for 0.5 hr. The mixture was poured into ice-1 N HCl (10 ml). The solid was collected, washed with water and air-dried. The crude solid was recrystallized from CHCl$_3$-EtOH-IPE to afford 6-tert-butoxycarbonylnicotinic acid (850 mg, 76%) as needles. IR (KBr) n3095, 1728, 1705 cm$^{-1}$; $^1$H-NMR (DMAO-d$_6$) δ 1.63 (s, 9 H), 8.09 (m, 1 H), 8.17 (m, 1 H), 8.42 (dt, J=2.4 and 8.3 Hz, 1 H), 9.21 (t, J=2.4 and 8.8 Hz, 1 H); MS (FAB) m/z 224 (M$^+$+1); Anal. Calcd for C$_{29}$H$_{33}$N$_3$O$_6$: C, 36.18; H, 3.18; N, 3.84. Found: C, 36.85; H, 3.35; N, 3.79.

To a stirred mixture of 6-tert-butoxycarbonylnicotinic acid (1.9 g, 8.51 mmol) and triethylamine (1.17 g, 11.49 mmol) in tert-BuOH (30 ml) and toluene (30 ml) was added a solution of diphenyl phosphoryl azide (2.93 g, 10.64 mmol) in toluene (3 ml) at room temperature. The resulting mixture was then heated at reflux for 5 hr. After cooling, ice and 1 N HCl (5 ml) was added to the mixture and extracted with toluene. The extracts were washed with brine, dried over Na$_2$SO$_4$, and evaporated. The residue was chromatographed on silica gel (50 ml) with toluene-EtOAc (5:1, v/v) as eluent to give tert-butyl 5-tert-butoxycarbonyamino-2-pyridinecarboxylate (1.9 g, 76%) as a gum. $^1$H-NMR (CDCl$_3$) δ 1.53 (s, 9 H), 1.63 (s, 9 H), 6.82 (br s, 1 H), 8.01 (d, J=8.8 Hz, 1H), 8.17 (m, 1H), 8.46 (d, J=2.4 Hz, 1H).

To a stirred mixture of tert-butyl 5-tert-butoxycarbonyamino-2-pyridinecarboxylate (1.9 g, 6.45 mmol) in CH$_2$Cl$_2$ (20 ml) was added TFA (5 ml). The mixture was evaporated off, and the residue was dissolved in EtOH (30 ml). HCl-gas was induced to the solution with stirring at 0–10° C. for 10 min. The resulting stirred mixture was then heated at reflux for 10 hr. After cooling, N$_2$-gas was induced to remove of large excess of HCl-gas for 15 min. the mixture was evaporated off. The residue was alkalized by the addition of sat. NaHCO$_3$, and extracted with CH$_2$Cl$_2$. The extracts were washed with brine, dried over Na$_2$SO$_4$, and evaporated. The residue was chromatographed on silica gel (30 ml) with CHCl$_3$-EtOH (98:2, v/v) as eluent to give ethyl 5-amino-2-pyridine carboxylate (700 mg, 65%) as a crystalline material. IR (KBr) n 3423, 3190, 1708, 1657, 15873338, 3296, 1691, 1641 cm$^{-1}$; $^1$H-NMR (CDCl$_3$)δ 1.42 (t, J=7.0 Hz, 3 H), 4.11 (br s, 1 H), 4.43 (q, J=7.0 Hz, 2 H), 6.99 (dd, J=2.7 and 8.5 Hz, 1 H), 7.95 (d, J=8.5 Hz, 1H), 8.16 (d, J=2.7 Hz, 1 H); MS (FAB) m/z 167 (M$^+$); Anal. Calcd for C$_{27}$H$_{29}$ClN$_4$O$_6$: C, 57.47; H, 6.63; N, 16.76. Found: C, 57.27; H, 5.99; N, 16.72.

A stirred mixture of ethyl 5-amino-2-pyridinecarboxylate (660 mg, 3.95 mmol) and 1-tert-butoxycarbonyprolinal (1.1 g, 5.33 mmol) in toluene (10 ml) was heated at reflux for 1 hr, during which time water was azeotropically removed with Dean-Stark water-trap. After cooling, the mixture was evaporated in vacuo. The residue was dissolved in MeOH—AcOH (9:1, v/v, 30 ml). To the stirred solution was added NaBH$_3$CN (500 mg, 7.90 mmol) at 0–5° C. The resulting mixture was stirred for a further 12 hr at room temperature. The mixture was poured into ice-sat NaHCO$_3$ (50 ml), and extracted with CH$_2$Cl$_2$. The extracts were washed with brine, dried over Na$_2$SO$_4$, and evaporated. The residue was chromatographed on silica gel (50 ml) with CHCl$_3$-EtOAc (98:2, v/v) as eluent to give ethyl 5-[N-[2-(1-tert-butoxycarbony)pyrrolidinyl]methylamino]pyridine-2-carboxylate (1.1 g, 70%) as a gum. $^1$H-NMR (CDCl$_3$) δ 1.38 (s, 9 H), 1.42 (s, 6 H), 3.93 (s, 3 H), 4.29 (s, 2 H), 4.67 (br s, 1 H), 7.15 (d, J=8.8 Hz, 1 H), 8.18 (dd, J=1.7 and 8.8 Hz, 1 H), 8.52 (d, J=1.7 Hz, 1H).

A mixture of ethyl 5-[[2-(1-tert-butoxycarbony)pyrrolidinyl]methylamino]pyridine-2-carboxylate (800 mg, 2.29 mmol) in CH$_2$Cl$_2$ (17 ml) and TFA (3 ml) was stirred at room temperature for 3 hr. The mixture was evaporated, and the residue was made basic with sat. NaHCO$_3$. The mixture was extracted with CH$_2$Cl$_2$. The extracts were washed with brine, dried over Na$_2$SO$_4$-Na$_2$CO$_3$, and evaporated to give ethyl 5-[(2-pyrrolidinyl)methylamino]pyridine-2-carboxylate (460 mg, 81%) as a gum. $^1$H-NMR (CDCl$_3$) δ 1.32 (t, J=7 Hz, 3 H), 1.58–2.10 (series of m, 4 H), 3.12–3.28 (series of m, 3 H), 3.65 (m, 1 H), 4.30 (be q, J=7 Hz, 2 H), 6.27 (br, 1 H), 6.59 (dd, J=2.4 and 8.5 Hz, 1 H), 7.65 (d, J=8.5 Hz, 1 H), 7.94 (d, J=2.4 Hz, 1H).

To a stirred mixture of ethyl 5-[(2-pyrrolidinyl)methylamino]pyridine-2-carboxylate (220 mg, 0.88 mmol), 4-[N'-(2-chlorophenyl)ureido]-3-methoxyphenylacetic acid (300 mg, 0.88 mmol), 4-DMAP (135 mg, 1.10 mmol) in DMF (7 ml) was added EDC.HCl (215 mg, 1.10 mmol) at room temperature. The resulting mixture was stirred at room temperature for 20 hr. The mixture was pored into ice-water. The solid was collected, washed with water and air-dried. The crude solid was purified by silica gel (30 ml) column chromatography with CHCl$_3$-EtOH (98:2, v/v) as eluent and crystallized with Et$_2$O to give 5-[1-[4-[N'-(2-chlorophenyl)ureido]-3-methoxyphenylacetyl]-2-pyrrolidinyl]methylamino]pyridine-2-carboxylate (420 mg, 84%) as fine needles. IR (KBr) 3319, 1703, 1628, 1585, 1529 cm$^{-1}$; $^1$H-NMR (CDCl$_3$)δ 1.38 (t, J=7 Hz, 3 H), 1.73–2.17 (series of m, 4 H), 3.19 and 3.54 (each m, each 1 H), 3.63 (s, 2 H), 3.70 (s, 3 H), 4.39 (be q, J=7 Hz, 2 H), 4.55 (m, 1 H), 6.02 (br s, 1 H), 6.78–6.84 (series of s and m, 3 H), 6.98 (dt, J=2.4 and 8.0 Hz, 1 H), 7.16 (s, 1 H), 7.21–7.26 (series of m, 3 H), 7.34 (dd, J=2.4 and 8.0 Hz, 1 H), 7.90 (d, J=8.3 Hz, 1H), 7.98 (m, 2H), 8.16 (dd, J=1.2 and 8.8 Hz, 1H); MS (FAB) m/z 566 (M$^+$+1); Anal. Calcd for $C_{29}H_{32}ClN_5O_5 \cdot H_2O$: C, 59.63; H, 5.87; N, 12.37. Found: C, 60.06; H, 5.76; N, 11.95.

A mixture of ethyl 5-[[1-[4-[N'-(2-chlorophenyl)ureido]-3-methoxyphenylacetyl]-2-pyrrolidinyl]methylamino]pyridine-2-carboxylate (300 mg, 0.53 mmol) in THF:MeOH (1:1, v/v, 16 ml) and 0.25 N NaOH (11 ml, 2.75 mmol) was stirred for 3 hr at room temperature. The mixture was poured into ice-1 N HCl (3 ml). The solid was collected, washed with water and air-dried. The crude crystalline material was collected with $CH_2Cl_2-Et_2O$ to give 61 (180 mg, 63%) as an amorphous solid. MW 537.99 IR (KBr) 3319, 1701, 1620, 1585, 1533 cm$^{-1}$; $^1$H-NMR (CDCl$_3$) δ $^1$H-NMR (DMSO-d$_6$) δ 1.80–2.05 (series of m, 4 H), 2.99 (m, 1 H), 3.50–3.59 (series of m, 3 H), 3.60 (s, 2 H), 3.86 (s, 3 H), 4.11 (m, 1 H), 6.78 (d, J=8.5 Hz, 1 H), 6.91 (s, 1 H), 6.94 (m, 1 H), 7.02 (m, 1 H), 7.14 (dd, J=2.5 and 8.5 Hz, 1H), 7.28 (t, J=7.0 Hz, 1H), 7.45 (d, 8.0 Hz, 1 H), 7.78 (d, J=8.8 Hz, 1 H), 7.97 (d, J=8.3 Hz, 1H), 8.08 (br s, 1H), 8.11 (m, 1 H), 8.89 (s, 1 H), 8.94 (s, 1 H); MS (FAB) m/z 538 (M$^+$+1); Anal. Calcd for $C_{27}H_{28}ClN_5O_5 \cdot 1.5 \times H_2O$: C, 57.39; H, 5.53; N, 12.39. Found: C, 57.37; H, 5.54; N, 11.74.

To a stirred mixture of ethyl 5-[(2-pyrrolidinyl)methylamino]pyridine-2 carboxylate (230 mg, 0.923 mmol), 3-methoxy-4-[N'-(2-methylphenyl)ureido]phenylacetic acid (290 mg, 0.923 mmol), 4-DMAP (145 mg, 1.15 mmol) in DMF (7 ml) was added EDC.HCl (225 mg, 1.15 mmol) at room temperature. The resulting mixture was stirred at room temperature for 20 hr. The mixture was pored into ice-water. The solid was collected, washed with water and air-dried. The crude solid was purified by silica gel (30 ml) column chromatography with CHCl$_3$-EtOH (98:2, v/v) as eluent to give ethyl 5-[[1-[3-methoxy4-[N'-(2-methylphenyl)ureido]phenylacetyl]-2-pyrrolidinyl]methylamino]pyridine-2-carboxylate (400 mg, 80%) as fine needles. IR (KBr) n 3325, 1709, 1618, 1585, 1531 cm$^-$; $^1$H-NMR (CDCl$_3$) δ 1.39 (t, J=7 Hz, 3 H), 1.73–2.07 (series of m, 4 H), 2.28 (s, 3 H), 3.12 and 3.49 (each m, each 1 H), 3.60 (s, 2 H), 4.39 (br q, J=7 Hz, 2 H), 4.53 (m, 1 H), 6.07 (br s, 1 H), 6.23 (br s, 1 H), 6.75–6.77 (series of s and m, 2 H), 6.82 (dd, J=3.0 and 8.5 Hz, 1 H), 7.09–7.22 (series of m, 3 H), 7.49 (d, J=8.0 Hz, 1 H), 7.90 (d, J=8.5 Hz, 1H), 7.98 (d, J=2.6 Hz, 1H), 8.06 (d, J=8.8 Hz, 1H); MS (FAB) m/z 546 (M$^+$+1); Anal. Calcd for $C_{30}H_{35}N_5O_5 \cdot 1.5 \times H_2O$: C, 52.92; H, 6.69; N, 12.23. Found: C, 63.11; H, 6.48; N, 11.96.

A mixture of ethyl 5-[[1-[3-methoxy-4-[N'-(2-methylphenyl)ureido]phenylacetyl]-2-pyrrolidinyl]methylamino]pyridine-2-carboxylate (D914-596) (290 mg, 0.53 mmol) in THF:MeOH (1:1, v/v, 16 ml) and 0.25 N NaOH (11 ml, 2.75 mmol) was stirred for 3 hr at room temperature. The mixture was poured into ice-1 N HCl (3 ml). The solid was collected, washed with water and air dried. The crude crystalline material was collected with $CH_2Cl_2-Et_2O$ to give 62 (170 mg, 62%) as an amorphous solid. MW 517.58 IR (KBr) 3283, 1701, 1618, 1529 cm$^-$; $^1$H-NMR (CDCl$_3$) δ $^1$H-NM (DMSO-d$_6$) δ 1.78–2.04 (series of m, 4 H), 2.25 (s, 3 H), 2.95–3.55 (series of m, 4 H), 3.59 (s, 2 H), 3.87 (s, 3 H), 4.11 (m, 1 H), 6.75–7.24 (series of m, 7 H), 7.83–7.97 (series of m, 3H), 8.01 (d, J=8.3 Hz, 1 H), 8.13 (d, J=2.6 Hz, 1H), 8.47(s, 1 H), 8.57 (s, 1 H); MS (FAB) m/z 518 (M$^+$+1); Anal. Calcd for $C_{28}H_{31}N_5O_5 \cdot 2.5 \times H_2O$: C, 60.50; H, 6.39; N, 12.60. Found: C, 60.31; H, 6.28; N, 12.10.

Example 57

2-[1-[[4-[N'-(2-chlorophenyl)ureido]-3-methoxyphenylacetyl]-2-pyrrolidinyl]methoxy]pyridine-5-carboxylic acid

63

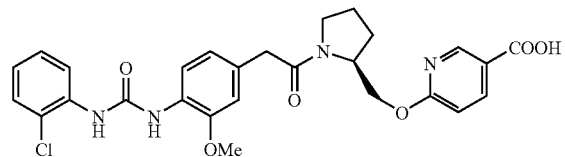

To a stirred solution of methyl 2-hydroxy-5-pyridinecarboxylate (2.0 g, 13.06 mmol), PPh$_3$ (4.2 g, 15.93 mmol) and 1-tert-butoxycarbony-(L)-prolinol (2.63 g, 13.06 mmol) in THF (25 ml) was added a solution of DIAD (3.3 g, 15.67 mmol) in THF (5 ml) at 0–10° C. The resulting stirred mixture was then heated at reflux for 3 hr. After cooling, the mixture was evaporated in vacuo. The residue was chromatographed on silica-gel (120 ml) with n-hexane-EtOAc (4:1, v/v) as eluent to give methyl 2-[2-(1-tert-butoxycarbony)pyrrolidinyl]methoxypyridine-5-carboxylate (3.0 g, 68%) as a gum. $^1$H-NMR (CDCl$_3$) δ 1.46 (s, 9 H), 1.82–2.04 (series of m, 4 H), 3.45 (m, 2 H), 3.91 (s, 3 H), 4.10–4.32 (series of m, 2 H), 4.48 (m, 1 H), 6.32 (br, 1 H), 6.75 (d, J=8.8 Hz, 1 H), 8.15 (dd, J=2 and 8.8 Hz, 1 H), 8.79 (d, J=2 Hz, 1H).

A mixture of methyl 2-[2-(1-tert-butoxycarbony)pyrrolidinyl]methoxypyridine-5-carboxylate (2.9 g, 8.62 mmol) in $CH_2Cl_2$ (80 ml) and TFA (20 ml) was stirred at room temperature for 3 hr. The mixture was evaporated, and the residue was alkalized with sat. NaHCO$_3$. The mixture was extracted with $CH_2Cl_2$. The extracts were washed with brine, dried over $Na_2SO_4-Na_2CO_3$, and evaporated to give methyl 2-(2-pyrrolidinyl)methoxypyridine-5-carboxylate (1.2 g, 59%) as a gum. $^1$H-NMR (CDCl$_3$)δ 1.58–2.050 (series of m, 4 H), 2.90–3.02 (series of m, 2 H), 3.87 and 3.90 (each s, 3 H), 4.23 (m, 1 H), 4.37 (m, 1 H), 6.33 (br, 1 H), 6.78 (d, J=8.5 Hz, 1 H), 8.15 (dd, J=2.2 and 8.8 Hz, 1 H), 8.79 (d, J=2.2 Hz, 1H).

To a stirred mixture of methyl 2-(2-pyrrolidinyl)methoxypyridine-5-carboxylate (370 mg, 1.57 mmol), 4-[N'-(2-chlorophenyl)ureido]-3-methoxyphenylacetic acid (525 mg, 1.57 mmol), 4-DMAP (230 mg, 1.88 mmol) in DMF (10 ml) was added EDC.HCl (360 mg, 1.88 mmol) at room temperature. The resulting mixture was stirred at room temperature for 20 hr. The mixture was pored into ice-water. The solid was collected, washed with water and air-dried. The crude solid was purified by silica-gel (30 ml) column chromatography with CHCl$_3$-EtOH (98:2, v/v) as eluent and crystallized with Et$_2$O to give methyl 2-[1-[4-[N'-(2-chlorophenyl)ureido]-3-methoxyphenyl acetyl]-2-pyrrolidinylmethoxy]pyridine-5-carboxylate (600 mg, 69%) as an amorphous solid. $^1$H-NMR (CDCl$_3$) δ 0.21 and 2.01 (each m, 4 H), 3.45–4.50 (series of s and m, 13 H which contains amide-isomers), 6.58–8.83 (series of s and m, 12 H which contains amide-isomers)

A mixture of methyl 2-[1-[4-[N'-(2-chlorophenyl)ureido]-3-methoxyphenylacetyl]-2-pyrrolidinylmethoxy]pyridine-5-carboxylate (230 mg, 0.415 mmol) in THF (1 ml) and 0.25N NaOH (4 ml, 1 mmol) was stirred for 14 hr at room temperature and for 3 hr at 60° C. After cooling, the mixture was poured into ice-1 N HCl (2 ml). The solid was collected, washed with water and air-dried. The crude crystalline material was purified by preparative TLC plate with CHCl$_3$-EtOH (9:1, v/v) as eluent and crystallized with Et$_2$O to give 63 (150 mg, 67%) as an amorphous solid. MW 538.98 IR (KBr) 3329, 1709, 1601, 1533 cm$^{-1}$; $^1$H-NMR (CDCl$_3$) δ 1.85–2.05 (series of m, 4 H), 3.50–3.60 (series of m, 2 H), 3.82 (s, 3 H), 3.86 (s, 2 H), 4.29 (m, 1 H), 4.42 (m, 1 H), 6.72–7.05 (series of m, 4 H), 7.28 (m, 1 H), 7.43 (d, J=8 Hz, 2 H), 7.95 (d, J=8.3 Hz, 1 H), 8.09 (d, J=8.3 Hz, 2 H), 8.64 (m, 1 H), 8.89 (s, 1 H), 8.93 (s, 1 H); MS (FAB) m/z 539 (M$^+$+1); Anal. Calcd for C$_{27}$H$_{28}$ClN$_4$O$_6$·1.3×H$_2$O: C, 57.55; H, 5.47; N, 9.94. Found: C, 57.94; H, 5.00; N, 9.45.

Example 58

5-[1-[4-[N'-(2-bromophenyl)ureido]-3-methoxyphenylacetyl]-2-pyrrolidinylmethoxy]pyridine-2-carboxylic acid

64

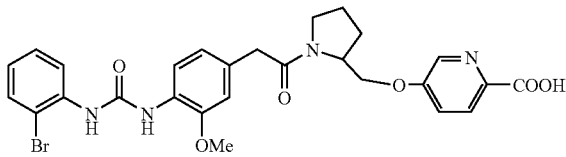

To a stirred mixture of methyl 5-(2-pyrrolidinyl)methoxypyridine-2-carboxylate (370 mg, 1.57 mmol), 4-[N'-(2-bromophenyl)ureido]-3-methoxyphenylacetic acid (595 mg, 1.57 mmol), 4-DMAP (230 mg, 1.88 mmol) in DMF (10 ml) was added EDC.HCl (360 mg, 1.88 mmol) at room temperature. The resulting mixture was stirred at room temperature for 20 hr. The mixture was pored into ice-water. The solid was collected, washed with water and air-dried. The crude solid was purified by silica-gel (30 ml) column chromatography with CHCl$_3$-EtOH (98:2, v/v) as eluent and crystallized with Et$_2$O to give methyl 5-[1-[4-[N'-(2-bromophenyl)ureido]-3-methoxyphenyl acetyl]-2-pyrrolidinylmethoxy]pyridine-2-carboxylate (650 mg, 69%) as an amorphous solid. IR (KBr) n 3323, 1720, 1624, 1601, 1527 cm$^{-1}$; $^1$H-NMR (CDCl$_3$) δ 1.22 and 2.00 (each m, 4 H), 3.48–4.55 (series of s and m, 13 H which contains amide-isomers), 6.93–8.82 (series of s and m, 12 H which contains amide-isomers); MS (FAB) m/z 597 (M$^{30}$ −1) and 599 (M$^+$+1); Anal. Calcd for C$_{28}$H$_{30}$BrN$_4$O$_6$·1.0×H$_2$O: C, 54.55; H, 5.23; N, 9.09. Found: C, 54.13; H, 5.03; N, 9.33.

A mixture of methyl 5-[1-[4-[N'-(2-bromophenyl)ureido]-3-methoxyphenylacetyl]-2-pyrrolidinylmethoxy]pyridine-2-carboxylate (300 mg, 0.5 mmol) in THF:MeOH (1:1, v/v, 2 ml) and 0.25 N NaOH (4 ml, 1 mmol) was stirred for 3 hr at room temperature and for 5 hr at 60° C. After cooling, the mixture was poured into ice-1 N HCl (2 ml). The solid was collected, washed with water and air-dried. The crude crystalline material was purified by preparative TLC plate with CHCl$_3$-EtOH (9:1, v/v) as eluent and crystallized with Et$_2$O to give 64 (180 mg, 62%) as an amorphous solid. MW 583.43 IR (KBr) n 3319, 1705, 1685, 1601, 1529 cm$^{-1}$; $^1$H-NMR (DMSO-d$_6$) δ 1.82–2.05 (series of m, 4 H), 3.48–3.58 (series of m, 2 H), 3.82 (s, 3 H), 3.86 (s, 2 H), 4.42–4.55 (series of m, 3 H), 6.72–6.98 (series of m, 4 H), 7.32 (t, J=8 Hz, 1 H), 7.60 (d, J=8 Hz, 1 H), 7.95 (m, 2 H), 8.08 (m, 1 H), 8.63 (m, 1 H), 8.64 (m, 1 H), 8.89 (s, 1 H), 8.93 (s, 1 H); MS (FAB) m/z 583 (M$^+$); Anal. Calcd for C$_{27}$H$_{28}$BrN$_4$O$_6$·2.0×H$_2$O: C, 52.26; H, 5.20; N, 9.03. Found: C, 52.72; H, 4.63; N, 8.50.

Example 59

4-[1-[3-[N'-(2-bromophenyl)ureido]-2-methoxy-6-pyridylacetyl]-(4S)-fluoro-(2S)-pyrrolidinyl methoxy]benzoic acid

65

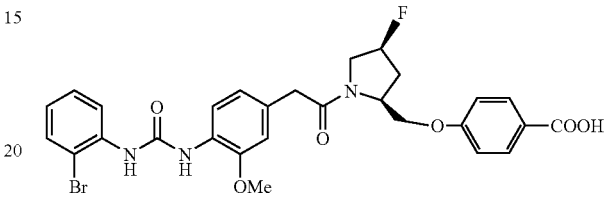

To a stirred solution of ethyl 3-amino-2-methoxy-6-pyridylacetate (1.61 g, 7.66 mmol) in THF (10 ml) were added 2-bromophenylisocyanate (948 ml, 7.66 mmol) and Et$_3$ N (107 ml, 0.776 mmol). After stirring overnight, the mixture was poured into H$_2$O (100 ml) and extracted with CHCl$_3$-MeOH (4:1, 2×200 ml). The combined extracts were dried over MgSO$_4$ and evaporated. The residue was recrystallized from CHCl$_3$-MeOH-hexane to give ethyl 3-[N'-(2-bromophenyl)ureido]-2-methoxy-6-pyridylacetate (2.91 g, 93%) as a colorless crystalline powder. mp 160–163° C.; $^1$H-NMR (DMSO-d$_6$) δ 1.19 (dt, J=7.1, 0.7 Hz, 3 H), 3.69 (s, 2 H), 3.95 (s, 3 H), 4.07–4.13 (m, 2 H), 6.90 (d, J=7.8 Hz, 1 H), 6.99 (t, J=7.8 Hz, 1 H), 7.33 (t, J=7.8 Hz, 1 H), 7.61 (d, J=7.8 Hz, 1 H), 7.96 (dd, J=7.8, 1.5 Hz, 1 H), 8.31 (d, J=7.8 Hz, 1 H), 8.82 (s, 1 H), 9.12 (s, 1 H); MS (FAB) m/z 408 (M$^+$), 410 (M$^+$+2); Anal. Calcd for C$_{17}$H$_{18}$BrN$_3$O$_4$·0.25 H$_2$O: C, 49.47; H, 4.52; 9.96. Found: C, 49.34; H, 4.48; N, 9.96.

A mixture of ethyl 3-[N'-(2-bromophenyl)ureido]-2-methoxy-6-pyridylacetate (2.90 g, 7.10 mmol), 0.25 N NaOH (56.8 ml, 14.2 mmol), and THF (50 ml) was stirred for 5 h. The mixture was neutralized with 1 N HCl and the resulting precipitate was collected by filtration. The residue was recrystallized from CHCl$_3$-MeOH-hexane to give 3-[N'-(2-bromophenyl)ureido]-2-methoxy-6-pyridylacetic acid (2.40 g, 89%) as a colorless crystalline powder. mp 195–197° C.; $^1$H-NMR (DMSO-d$_6$) δ 3.59 (s, 2 H), 3.95 (s, 3 H), 6.88 (d, J=8.1 Hz, 1 H), 6.97–7.01 (m, 1 H), 7.33 (t, J=7.3 Hz, 1H), 7.61 (d, J=8.1 Hz, 1 H), 7.95–7.97 (m, 1 H), 8.29 (d, J=8.1 Hz, 1H), 8.81 (s, 1 H), 9.10 (s, 1 H), 12.35 (br s, 1 H); Anal. Calcd for C$_{15}$H$_{14}$BrN$_3$O$_4$: C, 47.39; H, 3.71; N, 11.05. Found: C, 47.27; H, 3.59; N, 10.86.

To a stirred solution of 3-[N'-(2bromophenyl)ureido]-2-methoxy-6-pyridylacetic acid (751 mg, 1.97 mmol) and methyl (4S)-fluoro-(2S)-pyrrolidinylmethoxybenzoate (500 mg, 1.97 mmol) in DMF (10 ml) were added EDC.HCl (566 mg, 2.96 mmol), DMAP (cat.), and HOBt (cat.). After stirring overnight, the mixture was partitioned between EtOAc (200 ml) and brine (200 ml). The phases were separated. The organic phase was washed with brine (100 ml), dried over MgSO$_4$, and evaporated. The resulting residue was chromatographed on silica gel with CHCl$_3$-MeOH (20:1) as eluent to give methyl 4-[1-[3-[N'-(2-bromophenyl)ureido]-2-methoxy-6-pyridylacetyl]-(4S)-fluoro-(2S)-pyrrolidinylmethoxy]benzoate (1.16 g, 96%) as a yellow viscous solid.

A mixture of methyl 4-[1-[3-[N'-(2-bromophenyl)ureido]-2-methoxy-6-pyridylacetyl]-(4S)-fluoro-(2S)-pyrrolidinyl-methoxy]benzoate (1.16 g, 1.88 mmol), 0.25 N NaOH (15 ml, 3.75 mmol), and THF (15 ml) was stirred overnight. The mixture was neutralized with 1 N HCl and extracted with CHCl$_3$-MeOH (4:1, 2×200 ml). The combined extracts were dried over MgSO$_4$ and evaporated. The resulting residue was chromatographed on silica gel with CHCl$_3$-MeOH (40:1 to 10:1) as eluent to give 65 as a pale yellow amorphous solid. MW 601.42 $^1$H-NMR (DMSO-d$_6$) δ 2.27–2.39 (m, 2 H), 3.33–4.84 (series of m, 10 H), 5.33–5.53 (m, 1 H), 6.87–6.90 (m, 1 H), 6.99 (t, 1 H, J=7.6 Hz), 7.08 (d, 2 H, J=9.0 Hz), 7.34 (t, 1 H, J=7.6 Hz), 7.61 (d, 1 H, J=7.8 Hz), 7.88 (d, 2 H, J=9.0 Hz), 7.97 (d, 1 H, J=8.3 Hz), 8.28–8.32 (m, 1 H), 8.81–8.82 (m, 1 H), 9.10–9.12 (m, 1 H), 12.66 (br s, 1 H); MS (FAB) m/z 601 (M$^+$), 603 (M$^+$+2); Anal. Calcd for C$_{27}$H$_{26}$BrFN$_4$O$_6$: C, 53.92; H, 4.36; N, 9.32. Found: C, 52.37; H, 4.62; N, 8.38.

Example 60

4-[(4S)-fluoro-1[4-[N'-(2-methylphenyl)ureido]phenylacetyl]-(2S)-pyrrolidinylmethoxy]benzoic acid

66

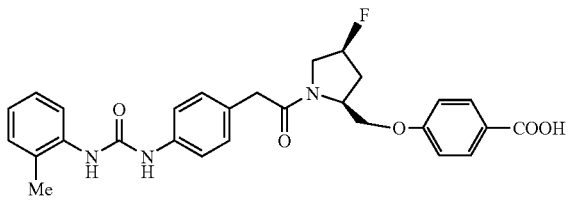

To a stirred solution of 4-[N'-(2-methylphenyl)ureido] phenylacetic acid (337 mg, 1.18 mmol) and methyl 4-[(4S)-fluoro-(2S)-pyrrolidinylmethoxy]benzoate (300 mg, 1.18 mmol) in DMF (10 ml) were added EDC.HCl (339 mg, 1.77 mmol), HOBt (cat.) and DMAP (cat.). The reaction mixture was stirred overnight. The mixture was partitioned between EtOAc (200) and H$_2$O (200 ml) and the organic phase was separated. The organic phase was washed with brine (200 ml), dried over MgSO$_4$, and evaporated. The residue was chromatographed on silica gel with CHCl$_3$-MeOH (50:1) to give methyl 4-[(4S)-fluoro-1[4-[N'-(2-methylphenyl)ureido]phenylacetyl]-(2S)-pyrrolidinyl methoxy]benzoate (613 mg, quant) as a yellow viscous oil. $^1$H-NMR (CDCl$_3$)δ 2.03–2.55 (series of m, total 5 H), 3.47–4.21 (series of m, total 7 H), 4.44–4.60 (m, 3 H), 5.21 and 5.34 (m, each, total 1 H), 6.87–7.16 (m, 8 H), 7.52–7.55 (m, 3 H), 7.93 (d, J=8.8 Hz, 2 H), 7.99 (d, J=8.8 Hz, 1 H).

To a stirred solution of methyl 4-[(4S)-fluoro-1-[4-[N'-(2-methylphenyl)ureido]phenylacetyl]-(2S)-pyrrolidinyl-methoxy]benzoate (613 mg, 1.18 mmol) in THF (10 ml) was added 0.25 N NaOH (9.4 ml, 2.36 mmol). The mixture was refluxed for 1 day. After cooling to rt, the mixture was poured into 1 N HCl (50 ml) and extracted with CHCl$_3$-MeOH (5:1, 2×200 ml). The combined extracts were dried over MgSO$_4$ and evaporated. The residue was chromatographed on silica gel with CHCl$_3$-MeOH (10:1) to give 66 (378 mg, 63%) as a colorless amorphous solid. MW 505.54

$^1$H-NMR (DMSO-d$_6$)δ 0.08–2.30 (m, total 5 H), 3.47–4.63 (series of m, 7 H), 5.30–5.50 (m, 1 H), 6.94 (t, J=7.3 Hz, 1 H), 7.02–7.17 (m, 6 H), 7.37–7.41 (m, 2 H), 7.82–7.96 (m, 4 H), 9.05 (s, 1 H); MS (FAB) m/z 506 (M$^+$+1); Anal. Calcd for C$_{28}$H$_{28}$FN3O$_5$.1.75 H$_2$O: C, 62.62; H, 5.91; N, 7.82. Found: C, 62.23; H, 5.63; N, 7.18.

Example 61

4-[(4S)-fluoro-1[3-methoxy-4-[N'-(2-methylphenyl) ureido]phenylacetyl]-(2S)-pyrrolidinyl methoxy] benzoic acid

67

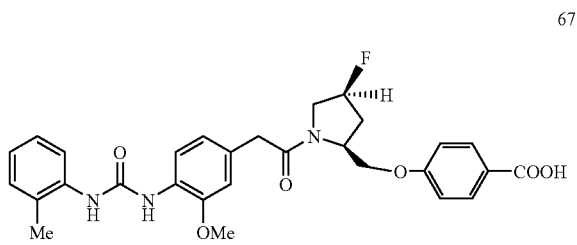

To a stirred solution of 1-(tert-butoxycarbonyl)-(4S)-fluoro-(2S)-proline (1.85 g, 7.93 mmol) in THF (15 ml) was added BH$_3$.DMS (0.75 ml, 7.93 mmol) at room temperature. After being heated at reflux for 5 h with stirring, the mixture was cooled to room temperature and concentrated in vacuo. The resulting residue was quenched by the addition of H$_2$O (100 ml) and extracted with CHCl$_3$ (2×200 ml). The combined extracts were washed with brine (100 ml), dried over MgSO$_4$, and evaporated. The residue was chromatographed on silica gel with CHCl$_3$-EtOAc (4:1) as eluent to give 1-(tert-butoxycarbonyl)-(4S)-fluoro-(2S)-pyrrolidinyl-methanol (1.76 g, quant) as a colorless oil. $^1$H-NMR (CDCl$_3$) δ 1.48 (s, 9 H), 1.64 (m, 1 H), 1.97–2.28 (m, 2 H), 3.53–3.87 (series of m, 4 H), 4.09–4.25 (m, 1 H), 5.09 and 5.22 (m, each, total 1 H).

To a stirred mixture of 1-(tert-butoxycarbonyl)-(4S)-fluoro-(2S)-pyrrolidinylmethanol (500 mg, 2.28 mmol), methyl 4-hydroxybenzoate (416 mg, 2.74 mmol), Ph$_3$P (719 mg, 2.74 mmol) in THF (10 ml) was added DIAD (0.54 ml, 2.74 mmol) at room temperature. The mixture was heated to reflux for 5 h with stirring. After cooling to room temperature, the mixture was concentrated in vacuo. The residue was chromatographed on silica gel with CHCl$_3$-EtOAc as eluent (10:1 to 4:1) to give methyl 4-[1-(tert-butoxycarbonyl)-(4S)-fluoro-(2S)-pyrrolidinyl methoxy]benzoate (597 mg, 74%) as a colorless oil. $^1$H-NMR (CDCl$_3$) δ 1.49–1.59 (m, 9 H), 2.05–2.21 (m, 1 H), 3.56–4.43 (series of m, 8 H), 5.19 and 5.32 (m, each, total 1 H), 6.97 (m, 2 H), 7.98 (d, J=8.5 Hz, 2 H).

A mixture of methyl 4-[1-(tert-butoxycarbonyl)-(4S)-fluoro-(2S)-pyrrolidinylmethoxy]benzoate (590 mg, 1.67 mmol) and TFA (5 ml) in CH$_2$Cl$_2$ (5 ml) was stirred for 3 h. After the mixture was concentrated in vacuo, the residue was made basic with sat. NaHCO$_3$ and extracted with CHCl$_3$ (2×200 ml). The combined extracts were dried over K$_2$CO$_3$ and evaporated to give methyl 4-[(4S)-fluoro-(2S)-pyrrolidinylmethoxy]benzoate (414 mg, 98%) as a yellow solid. $^1$H-NMR (CDCl$_3$) δ 1.89–2.02 (m, 1 H), 2.16–2.31 (m, 1 H), 2.98 (m, 1 H), 3.35 (m, 1 H), 3.46–3.68 (m, 1 H), 3.86 (s, 3 H), 4.00–4.08 (m, 2 H), 5.16 and 5.29 (t, each, J=4.7 Hz, total 1 H), 6.91 (d, J=8.8 Hz, 2 H), 7.96 (d, J=8.8 Hz, 2 H).

A mixture of methyl 4-[(4S)-fluoro-(2S)-pyrrolidinyl-methoxy]benzoate (205 mg, 0.810 mmol), 3-methoxy-4-[N'-(2-methylphenyl)ureido]phenylacetic acid (254 mg, 0.810 mmol), EDC.HCl (233 mg, 1.22 mmol), HOBt (cat.), and DMAP (cat.) in DMF (10 ml) was stirred overnight. The mixture was diluted with EtOAc (200 ml), washed with brine (2×100 ml), dried over MgSO$_4$, and evaporated. The residue was chromatographed on silica gel with CHCl$_3$-MeOH (20:1) as eluent to give methyl 4-[(4S)-fluoro-1-[3-methoxy-4-[N-'(2-methylphenyl)ureido]phenylacetyl]-(2S)-pyrrolidinylmethoxy]benzoate (445 mg, quant) as a light brown viscous. $^1$H-NMR (CDCl$_3$)δ 2.05–2.55 (m, total 6 H), 3.55–4.13 (m, 11 H), 4.48–4.60 (m, 2 H), 5.20 and 5.33 (each m, total 1 H), 6.29 (s, 1 H), 6.79 (m, 2 H), 6.96 (d, J=8.8 Hz, 2 H), 7.11–7.25 (m, 3 H), 7.48 (d, J=7.6 Hz, 1 H), 7.93–8.09 (m, 4 H).

A mixture of methyl 4-[(4S)-fluoro-1-[3-methoxy-4-[N'-(2-methylphenyl)ureido]phenylacetyl]-(2S)-pyrrolidinyl-methoxy]benzoate (445 mg, 1.62 mmol) and 0.25 N NaOH (15 ml, 3.75 mmol) in THF (15 ml) was stirred overnight at room temperature then for 2 h at reflux. The mixture was acidified with 1 N HCl and extracted with CHCl$_3$-MeOH (4:1, 2×200 ml). The combined extracts were dried over MgSO$_4$ and evaporated. The residue was chromtographed on silica gel with CHCl$_3$-MeOH (10:1) as eluent to give 67 (260 mg, 30%) as a pale yellow amorphous solid. MW 535.56 $^1$H-NMR (DMSO-d$_6$) δ 2.25–2.51 (m, 5 H), 3.33–4.41 (series of m, 10 H), 5.30–5.50 (m, 1 H), 6.75–7.17 (m, 7 H), 7.79 (d, J=8.1 Hz, 1 H), 7.87–8.04 (m, 3 H), 8.48 (m, 1 H), 8.58 (m, 1 H); MS (FAB) m/z 536 M$^+$+1); Anal.Calcd for C$_{29}$H$_{30}$FN$_3$O$_6$.H$_2$O: C, 62.92; H, 5.83; N, 7.59. Found: C, 62.40; H, 5.82; N, 6.93.

Example 62

4-[1-[4-[N'-(2-Bromophenyl)ureido]-3-methoxyphe-nylacetyl]-(4S)-fluoro-(2S)-pyrrolidinyl methoxy] benzoic acid

68

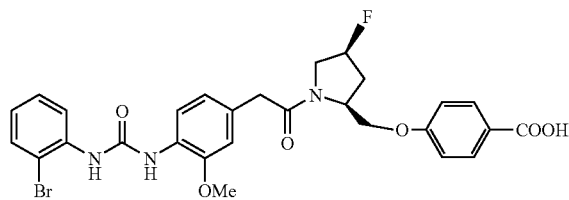

A mixture of methyl 4-[(4S)-fluoro-(2S)-pyrrolidinyl-methoxy]benzoate (501 mg, 1.98 mmol), 4-[N'-(2-bromophenyl)ureido]-3-methoxyphenylacetic acid (750 mg, 1.98 mmol), EDC.HCl (569 mg, 2.97 mmol), HOBt (cat.) and DMAP (cat.) in DMF (10 ml) was stirred overnight. The mixture was diluted with EtOAc (300 ml), washed with brine (100 ml), dried over MgSO$_4$ and evaporated. The residue was chromatographed on silica gel with CHCl$_3$-EtOAc (4:1) to CHCl$_3$-MeOH (10:1) as eluent to give methyl 4-[1-[4-[N'-(2-bromophenyl)ureido]-3-methoxyphenyl acetyl]-(4S)-fluoro-(2S)-pyrrolidinylmethoxy]benzoate (1.29 g,quant) as a brown viscous oil. $^1$H-NMR (CDCl$_3$) δ 2.05–2.58 (m, 2 H), 3.49–4.17 (series of m, 12 H), 4.52–4.65 (m, 2 H), 6.82–7.33 (series of m, 8), 7.53 (dd, J=8.1, 1.5 Hz, 1H), 7.95–8.02 (m, 4H), 8.14 (dd, J=8.3, 1.7 Hz, 1H).

A mixture of methyl 4-[f-[4-[N'-(2-bromophenyl)ureido]-3-methoxyphenylacetyl]-(4S)-fluoro-(2S)-pyrrolidinyl-methoxy]benzoate (1.29 g, 2.10 mmol) and 0.25 N NaOH (17 ml, 4.20 mmol) in THF (20 ml) was refluxed for 5 h with stirring. The mixture was poured into ice-cooled 1 N HCl (100 ml) and extracted with CHCl$_3$-MeOH (4:1, 2×200 ml). The combined extracts were dried over MgSO$_4$ and evaporated. The residue was chromatographed on silica gel with CHCl$_3$-MeOH (10:1) as eluent to give 68 (860 mg, 68%) as a colorless amorphous solid. MW 600.43 $^1$H-NMR (DMSO-d$_6$) δ 2.24–2.31 (m, 2 H), 3.21–4.63 (series of m, 10 H), 5.31–5.51 (m, 1 H), 6.74–7.10 (m, 5 H), 7.32 (t, J=7.8 Hz, 1 H), 7.60 (d, J=7.8 Hz, 2 H), 7.87–7.99 (m, 4 H), 8.74–8.75 (m, 1 H), 8.92–8.94 (m, 1 H); MS (FAB) m/z 601 (M$^+$+1); Anal. Calcd for C$_{28}$H$_{27}$BrFN$_3$O$_6$.2 H$_2$O: C, 52.84; H, 4.91; N, 6.60. Found: C, 52.38; H, 4.62; N, 5.99. For Na salt of 68: mp 180–182° C.; Anal. Calcd for C$_{28}$H$_{27}$BrFN$_3$NaO$_6$.0.75 H$_2$O: C, 52.88; H, 4.36; N, 6.61. Found: C, 52.97; H, 4.36; N, 6.61.

Example 63

4-[1-[4-[N'-(2-chlorophenyl)ureido]-3-methoxyphe-nylacetyl]-(4S)-fluoro-(2S)-pyrrolidinyl methoxy] benzoic acid

69

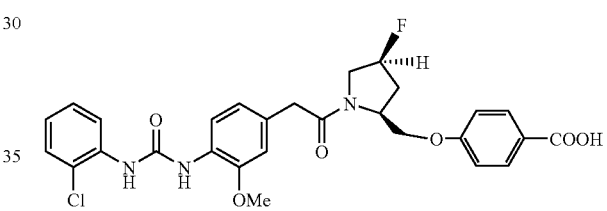

A mixture of methyl 4-[(4S)-fluoro-(2S)-pyrrolidinyl-methoxy]benzoate (205 mg, 0.810 mmol), 3-methoxy-4-[N'-(2-methylphenyl)ureido]phenylacetic acid (254 mg, 0.810 mmol), EDC.HCl (233 mg, 1.22 mmol), HOBt (cat.) and DMAP (cat.) in DMF (10 ml) was stirred overnight. The mixture was diluted with EtOAc (200 ml), washed with brine (2×100 ml), dried over MgSO$_4$, and evaporated. The residue was chromatographed on silica gel with CHCl$_3$-MeOH (20:1) as eluent to give methyl 4-[1-[4-[N'-(2-chlorophenyl)ureido]-3-methoxyphenylacetyl]-(4S)-fluoro-(2S)-pyrrolidinylmethoxy]benzoate (376 mg, 81%) as a yellow foam. $^1$H-NMR (CDCl$_3$) δ 2.07–2.56 (m, 2 H), 3.57–4.14 (series of m, 11 H), 4.50–4.61 (m, 2 H), 5.22 and 5.35 (series of m, total 1 H), 6.80–7.33 (series of m, 9 H), 7.93–8.00 (m, 3 H), 8.16 (d, J=8.1 Hz, 1 H).

A mixture of methyl methyl 4-[1-[4-[N'-(2-chlorophenyl) ureido]-3-methoxyphenylacetyl]-(4S)-fluoro-(2S)-pyrrolidinylmethoxy]benzoate (376 mg, 0.660 mmol) and 0.25 N NaOH (15 ml, 3.75 mmol) in THF (15 ml) was stirred overnight at room temperature then for 2 h at reflux. The mixture was acidified with 1 N HCl and extracted with CHCl$_3$-MeOH (4:1, 2×200 ml). The combined extracts were dried over MgSO$_4$ and evaporated. The residue was chromtographed on silica gel with CHCl$_3$-MeOH (20:1). as eluent to give 69 (260 mg, 30%) as a pale yellow amorphous solid. MW 555.98 $^1$H-NMR (DMSO-d$_6$)δ 2.24–2.501 (m, 2 H), 3.48–4.65 (series of m, 10 H), 5.30–5.50 (m, 1 H), 6.75–7.08 (m, 5 H), 7.29 (t, J=7.3 Hz, 1 H), 7.43–7.45 (m, 1H), 7.89–7.98 (m, 2 H), 7.99 (d, J=8.3 Hz, 1 H), 8.09 (d, J=7.1 Hz, 1H), 8.90–8.96 (m, 21H); MS (FAB) m/z 556 (M⁺+1); Anal. Calcd for $C_{28}H_{27}ClFN_3O_6 \cdot 1/4H_2O$: C, 60.00; H, 4.95; N, 7.50. Found: C, 59.67; H, 5.08; N, 7.10.

Example 64

4-[1-[4-[N'-(2-bromophenyl)ureido]phenylacetyl]-(4S)-fluoro-(2S)-pyrrolidinylmethoxy]benzoic acid

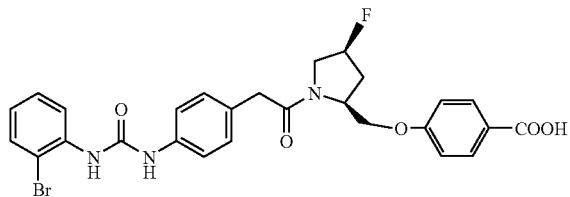

Methyl 4-[1-(4-benzyloxycarbonylaminophenylacetyl)-(4S)-fluoro-(2S)-pyrrolidinylmethoxy]benzoate (300 mg, 0.576 mmol) was tsdded EtOH-THF (5:1, 30 ml) and the solution was hydrogenated over 5% Pd/C (300 ml) for 12 h while stirring. The mixture was filtered to remove the catalyst. The filtrate was concentrated under a reduced pressure. The residue was chromatographed on silica gel with $CHCl_3$-MeOH (20:1) as eluent to give methyl 4-[1-(4aminophenylacetyl)-(4S)-fluoro-(2S)-pyrrolidinylmethoxy]benzoate (200 mg, 90%) as a yellow oil. $^1$H-NMR ($CDCl_3$) δ 2.01–2.56 (series of m, 2 H), 3.50–4.14 (series of m, 5 H), 4.45–4.62 (m, 2 H), 5.21 and 5.34 (each m, total 1 H), 6.60–6.65 (m, 2 H), 6.88 (d, J=8.8 Hz, 0.5 H), 6.99–7.05 (m, 3.5 H), 7.95–8.00 (m, 2 H). methyl 4-[1-(4-aminophenylacetyl)-(4S)-fluoro-(2S)-pyrrolidinylmethoxy]benzoate (200 mg, 0.518 mmol) was dissolved THF (10 ml). $Et_3$ N (108 ul, 0.776 mmol) and 2-bromophenylisocyanate (96 ul, 0.776 mmol) were added to the solution. The mixture was stirred overnight and diluted with EtOAc (200 ml). The solution was washed with brine (100 ml), dried over $MgSO_4$, and the solvent was removed under a reduced pressure. The residue was chromatographed on silica gel with $CHCl_3$-EtOAc (4:1) to $CHCl_3$-MeOH (10:1) as eluent to give methyl 4-[1-[4-[N'-(2-bromophenyl) ureido]phenylacetyl]-(4S)-fluoro-(2S)-pyrrolidinylmethoxy]benzoate (303 mg, quant) as a yellow oil. $^1$H-NMR ($CDCl_3$) δ 2.08–2.60 (series of m, 2 H), 3.56–4.69 (series of m, 10 H), 5.28 and 5.40 (m, each, total 1), 6.84–6.92 (m, 3 H), 7.03–7.10 (m, 3 H), 7.14 (d, J=8.1 Hz, 1 H), 7.23 (t, J=8.1 Hz, 1 H), 7.39–7.44 (m, 2 H), 7.89 (d, J=8.1 Hz, 1 H), 7.98–8.03 (m, 2H), 8.09 (d, J=8.1 Hz, 1H).

Methyl 4-[1-[4-[N'-(2-bromophenyl)ureido]phenylacetyl]-(4S)-fluoro-(2S)-pyrrolidinyl-methoxy]benzoate (300 mg, 0.513 mmol) was dissolved THF (5 ml), and 0.25 N NaOH (4.0 ml, 1.00 mmol) was added to this solution. After being stirred for 3 days, the mixture was poured into 1 N HCl (100 ml), and extracted with $CHCl_3$-MeOH (5:1, 2×200 ml). The combined extracts were dried over $MgSO_4$ and the solvent was removed under a reduced pressure. The residue was chromatographed on silica gel with $CHCl_3$-MeOH (10:1) to give 70 (209 mg, 71%) as a colorless amorphous solid. MW 570.41 $^1$H-NMR (DMSO-$d_6$)δ 2.24–2.51 (m, 2 H), 3.36–4.64 (series of m, 7 H), 5.31–5.50 (m, 1 H), 6.97 (t, J=7.8 Hz, 1 H), 7.04 (d, J=8.5 Hz, 1 H), 7.09 (d, J=8.8 Hz, 1 H), 7.14–7.20 (m, 2 H), 7.34 (t, J=7.8 Hz, 1 H), 7.38–7.43 (m, 2 H), 7.61 (d, J=8.1 Hz, 1 H), 7.87–7.92 (m, 2 H), 8.08 (d, J=8.1 Hz, 1 H), 8.15 (s, 1 H), 9.45–9.47 (m, 1 H), 12.66 (br s, 1 H); MS (FAB) m/z 572 (M⁺+2), 570 (M⁺); Anal. Calcd for $C_{27}H_{25}BrFN_3O_5 \cdot 1.5 H_2O$: C, 54.28; H, 4.72; N, 7.03. Found: C, 54.67; H, 4.51; N, 6.61.

Example 65

4-[1-[4-[N'-(2-iodophenyl)ureido]-3-methoxyphenylacetyl]-(4S)-fluoro-(2S)-pyrrolidinylmethoxy]benzoic acid

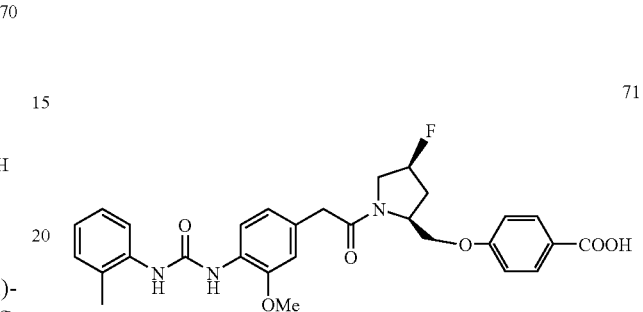

To a stirred solution of tert-butyl 4-amino-3-methoxyphenylacetate (1.94 g, 8.16 mmol) in THF (20 ml) was added 2-iodophenylisocyanate (2.0 g, 8.16 mmol) and $Et_3$ N (114 μl, 0.816 mmol). After stirring overnight, the mixture was poured into 1 N HCl (200 ml). The resulting precipitate was collected by filtration and dissolved in $CHCl_3$ (200 ml). The solution was dried over $MgSO_4$ and evaporated to give tert-butyl 4-[N'-(2-iodophenyl)ureido]-3-methoxyphenylacetate (3.93 g, quant) as a pale yellow amorphous solid. $^1$H-NMR ($CDCl_3$)δ 1.44 (s, 9 H), 3.49 (s, 2 H), 3.85 (s, 3 H), 6.78–6.88 (m, 4 H), 7.07 (s, 1 H), 7.31–7.35 (m, 1 H), 7.76 (dd, J=7.8, 1.5 Hz, 1 H), 7.95 (d, J=8.3 Hz, 1 H), 7.99 (dd, J=8.3, 1.5 Hz, 1 H). MS (ESI), m/z 483 (M⁺+1).

A stirred mixture of tert-butyl 4-[N'-(2-iodophenyl)ureido]-3-methoxyphenylacetate (3.93 g, 8.16 mmol) and TFA (5 ml) in $CH_2Cl_2$ (5 ml) was refluxed for 3 h. After cooling to rt, the mixture was concentrated in vacuo and $H_2O$ (50 ml) was added to this residue. The resulting precipitate was collected by filtration and purified by column chromatography on silica gel with $CHCl_3$-MeOH (9:1) as eluent to give 4-[N-(2-iodophenyl)ureido]-3-methoxyphenylacetic acid (2.89 g, 83%) as a pale yellow crystalline powder. $^1$H-NMR (DMSO-$d_6$)δ 3.62 (s, 2 H), 3.88 (s, 3), H), 6.78 (d, J=8.3 Hz, 1 H), 6.83–6.87 (m, 1 H), 6.94 (s, 1 H), 7.32–7.36 (m, 1 H), 7.69 (dd, J=8.3, 1.5 Hz, 1 H), 7.84 (dd, J=8.3, 1.5 Hz, 1 H), 7.97–8.00 (m, 1 H), 8.55 (m, 1 H), 8.82 (m, 1 H), 12.26 (br s, 1 H).

A mixture of 4-[N'-(2-iodophenyl)ureido]-3-methoxyphenylacetic acid (505 mg, 1.18 mmol), methyl 4-[(4S)-fluoro-(2S)-pyrrolidinylmethoxy]benzoate (300 mg, 1.18 mmol), EDC.HCl (339 mg, 1.77 mmol), DMAP (catatlytic amount) and HOBt (catalytic amount) in DMF (10 ml) was stirred overnight. The mixture was diluted with EtOAc (300 ml) and washed with brine (2×200 ml). The solution was dried over $MgSO_4$ and evaporated. The resulting residue was chromatographed on silica gel with $CHCl_3$-EtOAc (4:1) as eluent to give methyl 4-[1-[4-[N'-(2-iodophenyl)ureido]-3-methoxyphenylacetyl]-(4S)-fluoro-(2S)-pyrrolidinylmethoxy]benzoate (500 mg, 64%) as a colorless viscous oil. $^1$H-NMR ($CDCl_3$) δ 07–2.58 (m, 2 H), 3.59–4.20 (m, 11 H), 4.51–4.64 (m, 1 H), 5.24 and 5.37 (m, each, total 1 H), 6.80–6.91 (m, 5 H), 6.98 (d, J=8.8 Hz, 2 H), 7.34 (t, J=7.8 Hz, 1 H), 7.78 (dd, J=7.8, 1.2 Hz, 1 H), 7.95–8.02 (m, 4 H).

To a stirred solution of methyl 4-[1-[4-[N'-(2-iodophenyl)ureido]-3-methoxyphenyl acetyl]-(4S)-fluoro-(2S)-pyrrolidinylmethoxy]benzoate (500 mg, 0.756 mmol) in THF (6 ml) was added 0.25 N NaOH (6 ml). The stirring was continued overnight at room temperature then 5 h at reflux. After cooling to rt, the solution was poured into 1 N HCl (100 ml) and extracted with CHCl$_3$-MeOH (4:1, 2×200 ml). The combined extracts were dried over MgSO$_4$ and evaporated. The residue was chromatographed on silica gel with CHCl$_3$-MeOH (10:1) as eluent to give 71 (295 mg, 60%) as a colorless amorphous solid. MW 647.43 $^1$H-NMR (DMSO-d$_6$)δ 2. 2.09–2.31 (m, 2 H), 3.33–4.41 (series of m, 10 H), 5.30–5.50 (m, 1 H), 6.77–6.92 (m, 3 H), 7.03–7.09 (m, 2 H), 7.34 (t, J=8.1 Hz, 1 H), 7.69 (dd, J=8.3, 1.5 Hz, 1 H), 7.83–7.99 (m, 4 H), 8.54 (m, 1 H), 8.82 (m, 1 H); MS (FAB) m/z 648 (M$^+$+1); Anal. Calcd for C$_{28}$H$_{27}$FIN$_3$O$_4$: C, 51.94; H, 4.20; N, 6.49. Found: C, 51.17; H, 4.53; N, 5.76.

Example 66

4-[(4S)-fluoro-1-[4-(N'-phenylureido)phenylacetyl]-(2S)-pyrrolidinylmethoxy]benzoic acid

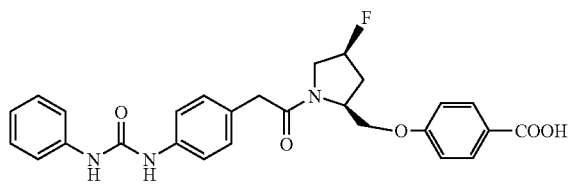

72

To a stirred solution of ethyl 4-aminophenylacetate (6.43 g, 35.9 mmol) and Et$_3$ N (5.50 ml, 39.5 mmol) in THF (70 ml) was added phenyl isocyanate (3.90 ml, 35.9 mmol), and the reaction mixture was stirred at room temperature for 4 days. Resulting precipitate was collected under a reduced pressure and the filtrate was washed with n-hexane to give ethyl 4-(N'-phenylureido) phenylacetate (9.64 g, 90%) as a white crystalline powder. mp 153–155° C.; $^1$H-NMR (CDCl$_3$)δ 1.26 (t, J=7.1 Hz, 3 H), 3.52 (s, 2 H), 4.15 (q, J=7.1 Hz, 2 H), 6.98–7.04 (m, 1 H), 7.07–7.11 (m, 4 H), 7.18–7.25 (m, 5 H), 7.42 (s, 1 H); MS (FAB) m/z 299 (M$^+$+1); Anal. Calcd for C$_{17}$H$_{18}$N$_2$O$_3$: C, 68.44; H, 6.08; N, 9.39. Found: C, 68.22; H, 6.10; N, 9.36.

To a stirred solution of ethyl 4-(N'-phenylureido)phenylacetate (9.64 g, 32.3 mmol) in THF (80 ml) was added 0.5 N NaOH (80 ml) and the reaction mixture was heated under reflux for 5 hr. After cooled to room temperature, the mixture was poured into ice-1 N HCl. The resulting precipitate was collected under a reduced pressure and the crude solid was recrystallized from MEOH—CHCl$_3$ to give 4-(N'-phenylureido)phenylacetic acid (8.14 g, 93%) as a white crystalline powder. MS (FAB) m/z 271 (M$^+$+1); Anal. Calcd for C$_{15}$H$_{14}$N$_2$O$_3$: C, 66.66; H, 5.22; N, 10.36. Found: C, 66.45; H, 5.22; N, 10.30.

A mixture of 4-(N'-phenylureido)phenylacetic acid (310 mg, 1.15 mmol), methyl 4-[(4S)-fluoro-(2S)-pyrrolidinylmethoxy]benzoate (287 mg, 1.13 mmol), EDC.HCl (260 mg, 1.36 mmol), HOBt (185 mg, 1.37 mmol), and Et$_3$ N (190 ml, 1.36 mmol) in DMF (5 ml) was stirred at room temperature overnight. The mixture was diluted with H$_2$O, and extracted with EtOAc. The extract was washed with brine, dried over Na$_2$SO$_4$, and evaporated. The residue was purified by column chromatography on silica-gel with CHCl$_3$-MeOH (100:1 to 50:1, v/v) as eluent to give methyl 4-[(4S)-fluoro-1[4-(N'-phenylureido)phenylacetyl]-(2S)-pyrrolidinylmethoxy]benzoate (570 mg, 99%) as a pale yellow foam. $^1$H-NMR (CDCl$_3$) δ 2.07–2.58 (m, 2 H), 3.55–3.56 (m, 1 H), 3.69–3.98 (series of s and m, total 6 H), 4.01–4.08 and 4.21–4.25 (each m, 1 H), 4.46–4.65 (m, 2 H), 5.23–5.25 and 5.38 (each m, 1 H), 6.88–7.07 (m, 7 H), 7.15–7.20 (m, 2 H), 7.28–7.30 (m, 2 H), 7.34 and 7.46 (each s, 1 H), 7.71 and 7.81 (each s, 1 H), 7.91–7.95 and 7.99–8.01 (each m, 2 H); MS (ESI) m/z 506 (M$^+$+1).

To a stirred solution of methyl 4-[(4S)-fluoro-1-[4-(N'-phenylureido)phenylacetyl]-(2S)-pyrrolidinylmethoxy]benzoate (570 mg, 1.13 mmol) in THF (5 ml) was added 0.5 N NaOH (5 ml), and the reaction mixture was heated under reflux for 5 hr. After cooled to room temperature, the mixture was poured into ice-1 N HCl, and the resulting precipitate was collected under a reduced pressure. The crude solid was recrystallized from MeOH—CHCl$_3$-IPE to give 72 (348 mg, 63%) as a white crystalline powder. MW 491.51 mp 169–171° C.; $^1$H-NMR (DMSO-d$_6$) δ 2.24–2.36 (m, 2 H), 3.47–4.08 (m, 5 H), 4.20–4.64 (m, 2 H), 5.31–5.50 (m, 1 H), 6.94–7.46 (series of m, total 11 H), 7.87–7.92 (m, 2 H), 8.64–8.67 (m, 2 H), 12.63 (br s, 1 H); MS (FAB) m/z 492 (M$^+$+1); Anal. Calcd for C$_{27}$H$_{26}$FN$_3$O$_6$.1/4H$_2$O: C, 65.38; H, 5.38; N, 8.47; F, 3.83. Found: C, 65.13; H, 5.38; N, 8.25; F, 3.78

Example 67

4-[(4S)-fluoro-1-[3-methyl-4-(N'-phenylureido)phenylacetyl]-(2S)-pyrrolidinylmethoxy]benzoic acid

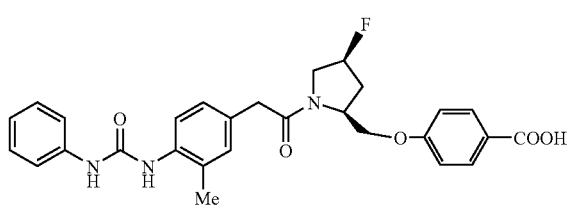

73

To a stirred solution of tert-butyl 4-amino-3-methylphenylacetate (1.20 g, 5.42 mmol) and Et$_3$N (830 ml, 5.95 mmol) in THF (10 ml) was added phenyl isocyanate (650 ml, 5.98 mmol) and the reaction mixture was stirred at room temperature overnight. The reaction mixture was concentrated to a small volume and diluted with n-hexane. Resulting precipitate was collected under a reduced pressure and the filtrate was washed with n-hexane to give tert-butyl 3-methyl4-(N'-phenylureido)phenylacetate (1.12 g, 61%) as a white crystalline powder. mp 143–145° C.; $^1$H-NMR (CDCl$_3$) δ 1.47 (s, 9 H), 2.09 (s, 3 H), 3.47 (s, 2 H), 6.44 (s, 1 H), 7.01–7.07 (m, 4 H), 7.16–7.27 (m, 2 H), 7.30–7.33 (m, 2 H), 7.45–7.47 (m, 1 H).

To a stirred solution of tert-butyl 3-methyl4-(N'-phenylureido)phenylacetate (1.12 g, 3.29 mmol) in CH$_2$Cl$_2$ (10 ml) was added TFA (10 ml) and the reaction mixture was stirred at room temperature for 4 hr. The reaction mixture was concentrated to a small volume and poured into ice-H$_2$O. The resulting precipitate was collected under a reduced pressure and the crude solid was recrystallized from MeOH—CHCl$_3$ to give 3-methyl4-(N'-phenylureido)phenylacetic acid (680 mg, 73%) as white needles. $^1$H-NMR (DMSO-d$_6$) δ 2.22 (s, 3 H), 3.46 (s, 2 H), 6.93–7.05 (m, 3 H), 7.25–7.29 (m, 2 H), 7.43–7.46 (m, 2 H), 7.72–7.74 (m, 1 H), 7.90 (s, 1 H), 8.98 (s, 1 H), 12.26 (br s, 1 H); Anal. Calcd for $C_{16}H_{16}N_2O_3$: C, 67.59; H, 5.67; N, 9.85. Found: C, 67.47; H, 5.68; N, 9.73.

A mixture of 3-methyl-4-(N'-phenylureido)phenylacetic acid (301 mg, 1.06 mmol), methyl 4-[(4S)-fluoro-(2S)-pyrrolidinylmethoxy]benzoate (268 mg, 1.06 mmol), EDC.HCl (243 mg, 1.27 mmol), HOBt (172 mg, 1.27 mmol), and Et$_3$N (180 ml, 1.29 mmol) in DMF (5 ml) was stirred at room temperature overnight. The mixture was diluted with H$_2$O, and extracted with EtOAc. The extract was washed with brine, dried over Na$_2$SO$_4$, and evaporated. The residue was purified by column chromatography on silica-gel with CHCl$_3$-MeOH (100:1 to 60:1, v/v) as eluent to give methyl 4-[(4S)-fluoro-1-[3-methyl-4-(N'-phenylureido)phenylacetyl]-(2S)-pyrrolidinylmethoxy]benzoate (550 mg, q.y.) as a white foam. $^1$H-NMR (CDCl$_3$) δ 1.79 and 1.87 (each s, 3 H), 2.04–2.61 (m, 2 H), 3.52–3.54 (m, 1 H), 3.73–4.27 (series of s and m, total 7 H), 4.47–4.67 (m, 2 H), 5.26–5.27 and 5.40 (each m, 1 H), 6.79–6.99 (m, 6 H), 7.14–7.18 (m, 2 H), 7.27–7.31 (m, 2 H), 7.40–7.44 (m, 1 H), 7.89–8.01 (m, 3 H); MS (ESI) m/z 520 (M$^+$+1).

To a stirred solution of methyl 4-[(4S)-fluoro-1-[3-methyl-4-(N'-phenylureido) phenylacetyl]-(2S)-pyrrolidinylmethoxy]benzoate (550 mg, 1.06 mmol) in THF (5 ml) was added 0.5 N NaOH (5 ml), and the reaction mixture was heated under reflux for 2 hr. After cooled to room temperature, the mixture was poured into ice-1 N HCl, and the resulting precipitate was collected under a reduced pressure. The crude solid was recrystallized from MeOH—CHCl$_3$-IPE to give 73 (226 mg, 42%) as a white crystalline powder. MW 505.54 mp 130–135° C.; $^1$H-NMR (DMSO-d$_6$) δ 2.18–2.30 (series of s and m, total 5 H), 3.47–3.92 (series of m, total 5 H), 4.03–4.63 (m, 2 H), 5.31–5.50 (m, 1 H), 6.94–7.10 (m, 5 H), 7.26–7.30 (m, 2 H), 7.45–7.47 (m, 2 H), 7.70–7.75 (m, 1 H), 7.87–7.92 (m, 3 H), 8.96–8.98 (m, 1 H), 12.63 (br s, 1 H); MS (ESI) m/z 506 (M$^+$+1); Anal. Calcd for $C_{28}H_{28}FN_3O_5 \cdot 1/2H_2O$: C, 65.36; H, 5.68; N, 8.17; F, 3.69. Found: C, 65.61; H, 5.71; N, 7.84; F, 3.60.

Example 68

4-[(4S)-fluoro-1-[4-[N'-(2-fluorophenyl)ureido]-3-methylphenylacetyl]-(2S)-pyrrolidinylmethoxy]benzoic acid

74

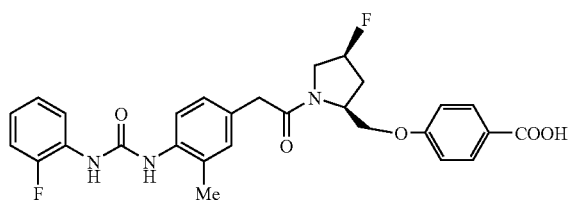

To a stirred solution of tert-butyl 4-amino-3-methylphenylacetate (1.09 g, 4.93 mmol) and Et$_3$N (755 ml, 5.42 mmol) in THF (10 ml) was added 2-fluorophenyl isocyanate (610 μl, 5.44 mmol) and the reaction mixture was stirred at room temperature overnight. The reaction mixture was concentrated to a small volume and diluted with n-hexane. Resulting precipitate was collected under a reduced pressure and the filtrate was washed with n-hexane to give tert-butyl 4-[N'-(2-fluorophenyl)ureido]-3-methylphenylacetate (1.31 g, 74%) as a white crystalline powder. mp 89–91° C.; $^1$H-NMR (CDCl$_3$) δ 1.47 (s, 9 H), 2.06 (s, 3 H), 3.49 (s, 2 H), 6.62 (s, 1 H), 6.92–7.09 (m, 5 H), 7.21 (br s, 1 H), 7.49–7.51 (m, 1 H), 8.10–8.15 (m, 1 H); Anal. Calcd for $C_{20}H_{23}FN_2O_3$: C, 67.02; H, 6.47; N, 7.82; F, 5.30. Found: C, 66.74; H, 6.35; N, 7.85; F, 5.69.

To a stirred solution of tert-butyl 4-[N'-(2-fluorophenyl)ureido]-3-methylphenylacetate (1.25 g, 3.49 mmol) in CH$_2$Cl$_2$ (10 ml) was added TFA (10 ml) and the reaction mixture was stirred at room temperature overnight. The reaction mixture was concentrated to a small volume and poured into ice-H$_2$O. The resulting precipitate was collected under a reduced pressure and the crude solid was recrystallized from MeOH—CHCl$_3$-IPE to give 4-[N'-(2-fluorophenyl)ureido]-3-methylphenylacetic acid (830 mg, 79%) as white needles. $^1$H-NMR (DMSO-d$_6$) δ 2.23 (s, 3 H), 3.47 (s, 2 H), 6.96–7.30 (m, 5 H), 7.74–7.76 (m, 1 H), 8.17–8.20 (m, 1 H), 8.33 (s, 1 H), 8.94 (s, 1 H), 12.27 (br s, 1 H); Anal. Calcd for $C_{16}H_{15}FN_2O_3$: C, 63.57; H, 5.00; N, 9.27; F, 6.28. Found: C, 63.28; H, 5.00; N, 9.14; F, 6.43.

A mixture of 4-[N'-(2-fluorophenyl)ureido]-3-methylphenylacetic acid (321 mg, 1.06 mmol), methyl 4-[(4S)-fluoro-(2S)-pyrrolidinylmethoxy]benzoate (269 mg, 1.06 mmol), EDC.HCl (244 mg, 1.27 mmol), HOBt (172 mg, 1.27 mmol), and Et$_3$N (177 ml, 1.27 mmol) in DMF (5 ml) was stirred at room temperature overnight. The mixture was diluted with H$_2$O, and extracted with EtOAc. The extract was washed with brine, dried over Na$_2$SO$_4$, and evaporated. The residue was purified by column chromatography on silica-gel with CHCl$_3$-MeOH (100:1, v/v) as eluent to give methyl 4-[(4S)-fluoro-1-[4-[N'-(2-fluorophenyl)ureido]-3-methylphenylacetyl]-(2S)-pyrrolidinyl methoxy]benzoate (560 mg, 98%) as a white foam. $^1$H-NMR (CDCl$_3$)δ 1.78 and 1.86 (each s, 3 H), 2.16–2.65 (m, 2 H), 3.58–3.61 (m, 1 H), 3.74–4.15 (series of s and m, total 7 H), 4.29–4.34 and 4.46–4.49 (each m, 1 H), 4.64–4.73 (m, 1 H), 5.29–5.34 and 5.43–5.47 (each m, 1 H), 6.84–6.97 (m, 6 H), 7.04–7.07 (m, 1 H), 7.21 (br s, 1 H), 7.55–7.59 (m, 1 H), 7.85–8.02 (m, 3 H), 8.18–8.22 (m, 1 H); MS (ESI) m/z 538 (M$^+$+1).

To a stirred solution of methyl 4-[(4S)-fluoro-1-[4-[N'-(2-fluorophenyl)ureido]-3-methylphenylacetyl]-(2S)-pyrrolidinylmethoxy]benzoate (560 mg, 1.04 mmol) in THF (5 ml) was added 0.5 N NaOH (5 ml), and the reaction mixture was heated under reflux for 5 hr. After cooled to room temperature, the mixture was poured into ice-1 N HCl, and the resulting precipitate was collected under a reduced pressure. The crude solid was recrystallized from MeOH—CHCl$_3$-IPE to give 74 (297 mg, 42%) as a white crystalline powder. MW 523.53 mp 137–143° C.; $^1$H-NMR (DMSO-d$_6$)δ 2.20–2.31 (series of s and m, total 5 H), 3.56–3.92 (series of m, total 5 H), 4.03–4.63 (m, 2 H), 5.31–5.50 (m, 1 H), 6.96–7.26 (series of m, total 7 H), 7.72–7.77 (m, 1 H), 7.87–7.92 (m, 2 H), 8.17–8.22 (m, 1 H), 8.32–8.36 (m, 1 H), 8.94–8.95 (m, 1 H), 12.66 (br s, 1 H); MS (ESI) m/z 524 (M$^+$+1); Anal. Calcd for $C_{28}H_{27}F_2N_3O_5$: C, 64.24; H, 5.20; N, 8.03; F, 7.26. Found: C, 64.44; H, 5.75; N, 7.40; F, 6.73.

Example 69

4-[(4S)-fluoro-1-[4-[N'-(2-trifluoromethylphenyl)ureido]phenylacetyl]-(2S)-pyrrolidinylmethoxy]benzoic acid

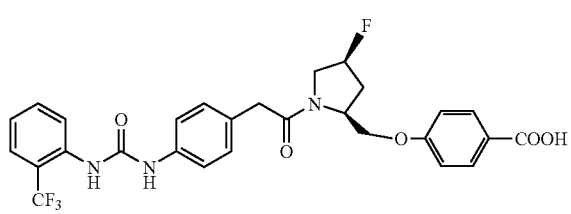

75

To a stirred solution of ethyl 4-aminophenylacetate (1.13 g, 6.31 mmol) and Et₃N (965 ml, 6.92 mmol) in THF (10 ml) was added 2-trifluoromethylphenyl isocyanate (953 ml, 6.31 mmol) and the reaction mixture was stirred at room temperature for 2 days. Resulting precipitate was collected under a reduced pressure and the filtrate was washed with n-hexane to give ethyl 4-[N'-(2-trifluoromethylphenyl)ureido]phenylacetate (1.93 g, 84%) as white needles. mp 137–139° C.; $^1$H-NMR (CDCl₃) δ 1.25–1.29 (m, 3 H), 3.59 (s, 2 H), 4.15–4.20 (m, 2 H), 7.05 (br s, 1 H), 7.13–7.23 (m, 6 H), 7.47–7.51 (m, 1 H), 7.54–7.56 (m, 1 H), 8.01–8.03 (m, 1 H).

To a stirred solution of ethyl 4-[N'-(2-trifluoromethylphenyl)ureido]phenylacetate (1.93 g, 5.27 mmol) in THF (10 ml) was added 1 N NaOH (10 ml) and the reaction mixture was heated under reflux for 5 hr. After cooled to room temperature, the mixture was poured into ice-1 N HCl. The resulting precipitate was collected under a reduced pressure and the crude solid was recrystallized from MeOH—CHCl₃-IPE to give 4-[N'-(2-trifluoromethylphenyl)ureido]phenylacetic acid (910 mg, 51%) as a white crystalline powder. mp 224–225° C.; $^1$H-NMR (DMSO-d₆) δ 3.50 (s, 2 H), 7.18 (d, J=8.3 Hz, 2 H), 7.25–7.29 (m, 1 H), 7.40 (d, J=8.3 Hz, 2 H), 7.62–7.69 (m, 2 H), 7.95–7.97 (m, 1 H), 8.06 (s, 1 H), 9.37 (s, 1 H), 12.27 (br s, 1 H); Anal. Calcd for C₁₆H₁₃F₃N₂O₃: C, 56.81; H, 3.87; N, 8.28; F, 16.85. Found: C, 56.68; H, 3.87; N, 8.16; F, 16.89.

A mixture of 4-[N'-(2-trifluoromethylphenyl)ureido]phenylacetic acid (302 mg, 0.89 mmol), methyl 4-[(4S)-fluoro-(2S)-pyrrolidinylmethoxy]benzoate (226 mg, 0.89 mmol), EDCHCl (205 mg, 1.07 mmol), HOBt (145 mg, 1.07 mmol), and Et₃N (150 ml, 1.08 mmol) in DMF (5 ml) was stirred at room temperature for 3 days. The mixture was diluted with H₂O, and extracted with EtOAc. The extract was washed with brine, dried over Na₂SO₄, and evaporated. The residue was purified by column chromatography on silica-gel with CHCl₃-MeOH (100:1 to 60:1, v/v) as eluent to give methyl 4-[(4S)-fluoro-1-[4-[N'-(2-trifluoromethylphenyl)ureido]phenylacetyl]-(2S)-pyrrolidinylmethoxy]benzoate (463 mg, 90%) as a pale yellow foam. $^1$H-NMR (CDCl₃) δ 2.09–2.60 (m, 2 H), 3.56–4.12 (series of s and m, total 8 H), 4.26–4.65 (m, 2 H), 5.26–5.29 and 5.39–5.42 (each m, total 1 H), 6.87–6.93 (m, 2 H), 6.99–7.13 (m, 5 H), 7.30–7.33 (m, 1 H), 7.44–7.53 (m, 2 H), 7.88–7.92 (m, 1 H), 7.99–8.04 (m, 2 H), 8.09–8.15 (m, 1 H); MS (ESI) m/z 574 (M⁺+1).

To a stirred solution of methyl 4-[(4S)-fluoro-1-[4-[N'-(2-trifluoromethylphenyl)ureido]phenylacetyl]-2S)-pyrrolidinylmethoxy]benzoate (460 mg, 0.80 mmol) in THF (5 ml) was added 0.5 N NaOH (5 ml), and the reaction mixture was heated under reflux for 5 hr. After cooled to room temperature, the mixture was poured into ice-1 N HCl, and the resulting precipitate was collected under a reduced pressure. The crude solid was recrystallized from MeOH—CHCl₃-IPE to give 75 (169 mg, 38%) as a white crystalline powder. MW 559.51 mp 130–135° C.; $^1$H-NMR (DMSO-d₆) δ 2.24–2.30 (m, 2 H), 3.51–4.24 (series of m, total 5 H), 4.38–4.40 and 4.61 (each m, total 2 H), 5.31–5.50 (m, 1 H), 7.03–7.42 (series of m, total 7 H), 7.62–7.69 (m, 2 H), 7.87–8.07 (m, 4 H), 9.36–9.37 (m, 1 H), 12.64 (br s, 1 H); MS (ESI) m/z 560 (M⁺+1); Anal. Calcd for C₂₈H₂₅F₄N₃O₅: C, 60.11; H, 4.50; N, 7.51; F, 13.58. Found: C, 60.10; H, 4.85; N, 7.01; F, 12.90.

Example 70

4-[(4S)-fluoro-1-[3-methoxy-4-[N'-(2-trifluoromethylphenyl)ureido]phenylacetyl]-(2S)-pyrrolidinyl methoxy]benzoic acid

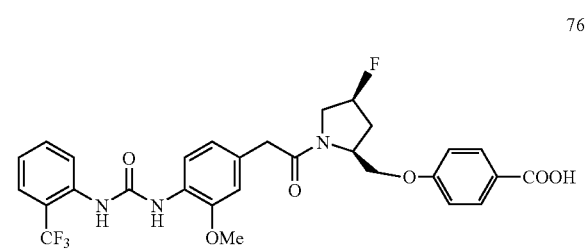

76

To a stirred solution of tert-butyl 4-amino-3-methoxyphenylacetate (1.11 g, 4.68 mmol) and Et₃N (720 ml, 5.17 mmol) in THF (10 ml) was added 2-trifluoromethylphenyl isocyanate (707 ml, 4.68 mmol) and the reaction mixture was stirred at room temperature for 2 days. The reaction mixture was concentrated to a small volume and diluted with n-hexane. Resulting precipitate was collected under a reduced pressure and washed with n-hexane to give tert-butyl 3-methoxy-4-[N'-(2-trifluoromethylphenyl)ureido] phenylacetate (1.11 g, 56%) as a white crystalline powder. mp 131–133° C.; $^1$H-NMR (CDCl₃) δ 1.44 (s, 9 H), 3.49 (s, 2 H), 3.85 (s, 3 H), 6.83–6.88 (m, 3 H), 6.98 (br s, 1 H), 7.17–7.21 (m, 1 H), 7.52–7.59 (m, 2 H), 7.89–7.91 (m, 1 H), 8.04–8.06 (m, 1 H).

To a stirred solution of tert-butyl 3-methoxy-4-[N'-(2-trifluoromethylphenyl)ureido] phenylacetate (1.11 g, 2.62 mmol) in CH₂Cl₂ (10 ml) was added TFA (10 ml), and the reaction mixture was stirred at room temperature for 4 hr. The reaction mixture was concentrated to a small volume and poured into ice-H₂O. The resulting precipitate was collected under a reduced pressure and the crude solid was recrystallized from MeOH—CHCl₃-IPE to give 3-methoxy-4-[N'-(2-trifluoromethylphenyl)ureido]phenylacetic acid (839 mg, 87%) as a white crystalline powder. mp 218–220°

C.; ¹H-NMR (DMSO-d₆) δ 3.51 (s, 2 H), 3.87 (s, 3 H), 6.76–6.79 (m, 1 H), 6.93–6.94 (m, 1 H), 7.27–7.30 (m, 1 H), 7.61–7.69 (m, 2 H), 7.82–7.84 (m, 1 H), 7.97–7.99 (m, 1 H), 8.71 (s, 1 H), 8.89 (s, 1 H), 12.30 (br s, 1 H); Anal. Calcd for $C_{17}H_{15}F_3N_2O_4$: C, 55.44; H, 4.11; N, 7.61; F, 15.47. Found: C, 55.30; H, 4.08; N, 7.63; F, 15.13.

A mixture of 3-methoxyl4-[N'-(2-trifluoromethylphenyl)ureido]phenylacetic acid (353 mg, 0.96 mmol), methyl 4-[(4S)-fluoro-(²S)-pyrrolidinylmethoxy]benzoate (243 mg, 0.96 mmol), EDC.HCl (221 mg, 1.15 mmol), HOBt (156 mg, 1.15 mmol), and Et₃ N (160 ml, 1.15 mmol) in DMF (5 ml) was stirred at room temperature overnight. The mixture was diluted with H₂O, and extracted with EtOAc. The extract was washed with brine, dried over Na₂SO₄, and evaporated. The residue was purified by column chromatography on silica-gel with CHCl₃-MeOH (100:1 to 60:1, v/v) as eluent to give methyl 4-[(4S)-fluoro-1-[3-methoxy-4-[N'-(2-trifluoromethylphenyl)ureido]phenylacetyl]-(2S)-pyrrolidinylmethoxy]benzoate (570 mg, 98%) as a white foam. ¹H-NMR (CDCl₃) δ 2.05–2.58 (m, 2 H), 3.56–4.21 (series of m, total 11 H), 4.05–4.64 (m, 2 H), 5.23–5.25 and 5.36–5.37 (each m, total 1 H), 6.79–6.82 (m, 2 H), 6.89–7.00 (m, 2 H), 7.16–7.20 (m, 2 H), 7.39–7.43 (m, 1 H), 7.51–7.59 (m, 2 H), 7.93–8.02 (m, 4 H); MS (ESI) m/z 604 (M⁺+1).

To a stirred solution of methyl 4-[(4S)-fluoro-1-[3-methoxy-4-[N'-(2-trifluoromethylphenyl)ureido] phenylacetyl]-(2S)-pyrrolidinylmethoxy]benzoate (570 mg, 0.94 mmol) in THF (5 ml) was added 0.5 N NaOH (5 ml), and the reaction mixture was heated under reflux for 2 hr. After cooled to room temperature, the mixture was poured into ice-1 N HCl, and the resulting precipitate was collected under a reduced pressure. The crude solid was recrystallized from MeOH—CHCl₃-IPE to give 76 (234 mg, 42%) as a white crystalline powder. MW 589.54 mp 129–132° C.; ¹H-NMR (DMSO-d₆)δ 2.23–2.29 (m, 2 H), 3.544.38 (series of s and m, total 8 H), 4.40–4.61 (m, 2 H), 5.30–5.36 and 5.43–5.49 (each m, total 1 H), 6.72–6.91 (m, 2 H), 7.02–7.08 (m, 2 H), 7.25–7.29 (m, 1 H), 7.59–7.67 (m, 2 H), 7.81–7.99 (m, 4 H), 8.69–8.70 (m, 1 H), 8.87–8.90 (m, 1 H), 12.67 (br s, 1 H); MS (ESI) m/z 589 (M⁺+1); Anal. Calcd for $CH_{27}F_4N_3O_6$: C, 59.08; H, 4.62; N, 7.13. Found: C, 59.22; H, 5.10; N, 6.58.

Example 71

4-[(4S)-fluoro-1-[3-methyl-4-[N'-(2-trifluoromethylphenyl)ureido]phenylacetyl]-(2S)-pyrrolidinylmethoxy]benzoic acid

77

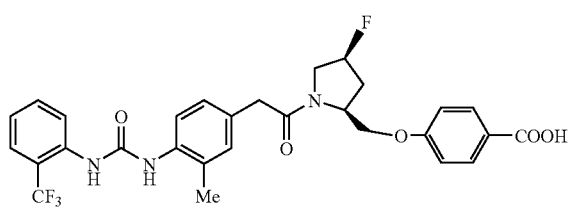

To a stirred solution of tert-butyl 4-amino-3-methylphenylacetate (927 mg, 4.19 mmol) and Et₃ N (645 μl, 4.63 mmol) in THF (10 ml) was added 2-trifluoromethylphenyl isocyanate (633 μl, 4.19 mmol) and the reaction mixture was stirred at room temperature for 2 days. The reaction mixture was concentrated to a small volume and diluted with n-hexane. Resulting precipitate was collected under a reduced pressure and the filtrate was washed with n-hexane to give tert-butyl 3-methyl-4-[N'-(2-trifluoromethylphenyl)ureido]phenylacetate (1.06 g, 62%) as a white crystalline powder. mp 178–180° C.; ¹H-NMR (CDCl₃) δ 1.44 (s, 9 H), 2.25 (s, 3 H), 3.51 (s, 2 H), 6.38 (br s, 1 H), 7.12–7.18 (m, 3 H), 7.36–7.37 (m, 1 H), 7.49–7.53 (m, 2 H), 8.13–8.16 (m, 1 H).

To a stirred solution of tert-butyl 3-methyl-4-[N'-(2-trifluoromethylphenyl)ureido]phenylacetate (1.06 g, 2.60 mmol) in CH₂Cl₂ (10 ml) was added TFA (10 ml) and the reaction mixture was stirred at room temperature for 4 hr. The reaction mixture was concentrated to a small volume and poured into ice-H₂O. The resulting precipitate was collected under a reduced pressure and the crude solid was recrystallized from MeOH—CHCl₃-IPE to give 3-methyl-4-[N'-(2-trifluoromethylphenyl)ureido]phenylacetic acid (702 mg, 77%) as a white crystalline powder. mp 262–263° C.; ¹H-NMR (DMSO-d₆) δ 2.24 (s, 3 H), 3.48 (s, 2 H), 7.03 (d, J=8.3 Hz, 1 H), 7.08 (s, 1 H), 7.26–7.30 (m, 1 H), 7.61–7.69 (m, 3 H), 7.88 (d, J=8.3 Hz, 1 H), 8.39 (s, 1 H), 8.55(s, 1 H), 12.28 (br s, 1 H); Anal. Calcd for $C_{17}H_{15}F_3N_2O_3$: C, 57.96; H, 4.29; N, 7.95; F, 16.18. Found: C, 57.73; H, 4.23; N, 7.92; F, 16.05.

A mixture of 3-methyl-4-[N'-(2-trifluoromethylphenyl)ureido]phenylacetic acid (359 mg, 1.02 mmol), methyl 4-[(4S)-fluoro-(2S)-pyrrolidinylmethoxy]benzoate (258 mg, 1.02 mmol), EDC.HCl (234 mg, 1.22 mmol), HOBt (165 mg, 1.22 mmol), and Et₃ N (170 μl, 1.22 mmol) in DMF (5 ml) was stirred at room temperature overnight. The mixture was diluted with H₂O, and extracted with EtOAc. The extract was washed with brine, dried over Na₂SO₄, and evaporated. The residue was purified by column chromatography on silica-gel with CHCl₃-MeOH (100:1 to 60:1, v/v) as eluent to give methyl 4-[(4S)-fluoro-1-[3-methyl-4-[N'-(2-trifluoromethylphenyl)ureido]phenylacetyl]-(2S)-pyrrolidinylmethoxy]benzoate (612 mg, q.y.) as a white foam. ¹H-NMR (CDCl₃) δ 1.92 and 2.00 (each s, total 3 H), 2.09–2.61 (m, 2 H), 3.56–4.29 (series of m, total 8 H), 4.45–4.48 and 4.59–4.64 (each m, total 2 H), 5.24–5.30 and 5.38–5.44 (each m, total 1 H), 6.90–7.14 (m, 5 H), 7.22–7.53 (m, 5 H), 7.90–7.92 (m, 1 H), 8.00–8.06 (m, 2 H); MS (ESI) m/z 588 (M⁺+1).

To a stirred solution of methyl 4-[(4S)-fluoro-1-[3-methyl-4-[N'-(2-trifluoromethylphenyl) ureido]phenylacetyl]-(2S)-pyrrolidinylmethoxy]benzoate (610 mg, 1.04 mmol) in THF (5 ml) was added 0.5 N NaOH (5 ml), and the reaction mixture was heated under reflux for 2 hr. After cooled to room temperature, the mixture was poured into ice-1 N HCl, and the resulting precipitate was collected under a reduced pressure. The crude solid was recrystallized from MeOH—CHCl₃-IPE to give 77 (186 mg, 31%) as a white crystalline powder. MW 573.54 mp 123–126° C.; ¹H-NMR (DMSO d₆) δ 2.19–2.29 (series of s and m, total 5 H), 3.64–4.21 (series of m, total 5 H), 4.36–4.60 (m, 2 H), 5.30–5.36 and 5.43–5.49 (each m, total 1 H), 6.97–7.08 (m, 4 H), 7.24–7.28

(m, 1 H), 7.59–7.68 (m, 3 H), 7.85–7.90 (m, 3 H), 8.37–8.39 (m, 1 H), 8.54–8.55 (m, 1 H), 12.67 (br s, 1 H); MS (ESI) m/z 573 ($M^+$).

Example 72

4-[(4S)-fluoro-1-[3-methyl-4-[N'-(2-methylphenyl)ureido]phenylacetyl]-(2S)-pyrrolidinyl]methoxybenzoic acid

78

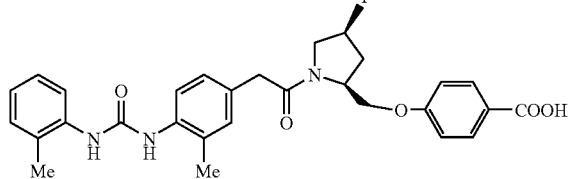

A mixture of 3-methyl-4-[N'-(2-methylphenyl)ureido]phenylacetic acid (250 mg, 0.84 mmol), methyl 4-[(4S)-fluoro-(2S)-pyrrolidinyl]methoxybenzoate (400 mg, 1.06 mmol), EDC.HCl (242 mg, 1.26 mmol) and DMAP (154 mg, 1.26 mmol) in DMF (5 ml) was stirred at room temperature for 21 h. The mixture was poured into ice water and extracted with EtOAc. The combined extracts were washed with ice water and brine. After dried over $Na_2SO_4$, the extracts were concentrated in vacuo. The residue was chromatographed on silica gel [50 g, $CHCl_3$/MeOH (50/1)], and then was purified on TLC [$CHCl_3$/acetone (10/1)] to give methyl 4-[(4S)-fluoro-1-[3-methyl-4-[N'-(2-methylphenyl)ureido]phenylacetyl]-(2S)-pyrrolidinyl]methoxybenzoate (342 mg, 76%) as a colorless amorphous solid. IR (KBr) 3356, 2951, 1716, 1651, 1604, 1537, 1252 $cm^{-1}$; $^1$H-NMR ($CDCl_3$) δ 2.07 (d, J=6.6 Hz, 2H), 2.12 (s, 3H), 2.27 (m, 1H), 2.24 (s, 3H), 2.30–2.59 (m, 1H), 3.60 (d, J=5.3 Hz, 1H), 3.65–4.23 (m, 3H), 3.87 (s, 3H), 4.50–4.62 (m, 1H), 5.31 (d, J=52.4 Hz, 1H), 6.23 (d, J=11.2 Hz, 1H), 6.26 (d, J=11.9 Hz, 1H), 6.87–7.27 (m, 8H), 7.54–7.65 (m, 3H), 7.94–8.01 (m, 2H); MS (FAB) m/z 534 ($M^++1$); Anal. Calcd for $C_{30}H_{32}FN_3O_5 \cdot 0.7H_2O$: C, 65.97; H, 6.16; F, 3.48; N, 7.69. Found: C, 66.04; H, 6.07; F, 3.55; N, 7.64.

To a stirred solution of methyl 4-[(4S)-fluoro-1-[3-methyl-4-[N'-(2-methylphenyl)ureido]phenylacetyl]-(2S)-pyrrolidinyl]methoxybenzoate (227 mg, 0.425 mmol) in THF (3.4 ml) was added 0.25 N NaOH (3.4 ml). After stirring at room temperature for 4 days, the mixture was acidified with 1 N HCl and extracted with $CHCl_3$-MeOH (10/1). The combined extracts were dried over $Na_2SO_4$ and concentrated in vacuo. The residue was purified on preparative-TLC [$CHCl_3$/MeOH (10/1)] to give 78 (190 mg, 86%) as a colorless amorphous solid. MW 519.56 IR (KBr) 3356, 2974, 1604, 1537, 1454, 1252 $cm^{-1}$; $^1$H-NMR (DMSO-$d_6$) δ 2.24 (s, 3H), 2.26 (s, 3H), 3.60 (d, J=3.7 Hz, 2H), 3.65–4.65 (m, 8H), 5.31–5.50 (m, 1H), 6.92–7.18 (m, 7H), 7.67–7.92 (m, 4H), 8.22–8.32 (m, 2H); MS (FAB) m/z 520 ($M^++1$); Anal. Calcd for $C_{29}H_{30}FN_3O_7 \cdot 1.1H_2O$: C, 64.58; H 6.02; F, 3.52; N, 7.79. Found: C, 64.71; H, 5.90; F, 3.24; N, 7.51.

Example 73

4-[1-[4-[N'-(2-chlorophenyl)ureido]-3-methylphenylacetyl]-(4S)-fluoro-(2S)-pyrrolidinyl]methoxybenzoic acid

79

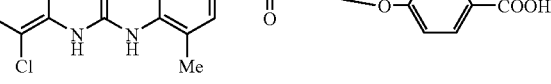

To a stirred mixture of tert-butyl 4-amino-3-methylphenylacetate (1.00 g, 4.52 mmol), 2-chlorophenyl isocyanate (0.55 ml, 4.52 mmol) in THF (10 ml) was added $Et_3N$ (0.13 ml, 0.90 mmol) at room temperature. After 6 h stirring, the reaction mixture was concentrated in vacuo. The residue was triturated by the addition of n-hexane, to give tert-butyl 4-[N'-(2-chlorophenyl) ureido]-3-methylphenylacetate (1.57 g, 93%) as a pale yellow powder. mp 104–106° C. (dec.); $^1$H-NMR ($CDCl_3$) δ 1.45 (s, 9H), 2.28 (s, 3H), 3.51 (s, 2H), 6.33 (br, 1H), 6.96 (t, J=7.6 Hz, 1H), 7.08 (br, 1H), 7.16–7.30 (m, 4H), 7.42 (m, 1H), 8.2 (d, J=8.1 Hz, 1H).

To a stirred solution of tert-butyl 4-[N'-(2-chlorophenyl)ureido]-3-methylphenylacetate (1.57 g, 4.19 mmol) in $CH_2Cl_2$ (10 ml) was added TFA (6 ml) at room temperature. After 4 h stirring, the mixture was concentrated in vacuo. The residue was triturated by the addition of water to give 4-[N'-(2-chlorophenyl)ureido]-3-methylphenylacetic acid (1.33 g, 100%) as a yellow powder. mp 243–245° C. (dec.); $^1$H-NMR ($CDCl_3$) δ 2.24 (s, 3H), 3.47 (s, 2H), 6.99–7.08 (m, 3H), 7.28 (t, J=7.6 Hz, 1H), 7.44 (dt, J=8.0, 2.4 Hz, 1H), 7.66 (dd, J=8.3, 1.9 Hz, 1H), 8.13 (dd, J=6.1, 1.7 Hz, 1H), 8.61 (d, J=6.3 Hz, 2H); MS (ESI), m/z 319 ($M^++1$), 321 ($M^++3$); Anal. Calcd for $C_{16}H_{15}ClN_2O_3 \cdot 0.7TFA$: C, 59.33; H, 4.65; Cl, 10.85; N, 8.57. Found: C, 59.23; H, 4.64; Cl, 10.90; N, 8.40.

A mixture of $^4$-[N'-($^2$-chlorophenyl)ureido]-3-methylphenylacetic acid (252 mg, 0.79 mmol), methyl $^4$-[(4S)-fluoro-(2S)-pyrrolidinyl]methoxybenzoate (200 mg, 0.79 mmol), EDC.HCl (227 mg, 1.20 mmol) and DMAP (147 mg, 1.20 mmol) in DMF (5 ml) was stirred at room temperature for 17 h. The mixture was poured into ice water and extracted with EtOAc. The combined extracts were washed with ice water and brine. After dried over $Na_2SO_4$, the extracts were concentrated in vacuo. The residue was purified on TLC [$CHCl_3$/acetone (10/1)], to give methyl 4-[1-[4-[N'-(2-chlorophenyl)ureido]-3-methylphenylacetyl]-(4S)-fluoro-(2S)-pyrrolidinyl]methoxybenzoate (390 mg, 89%) as a colorless amorphous solid. IR (KBr) 3340, 2951, 1712, 1624, 1604, 1533, 1438 $cm^{-1}$; $^1$H-NMR ($CDCl_3$) δ 1.92–2.05 (m, 3H), 2.07–2.63 (m, 2H), 3.61 (d, J=8.8 Hz), 3.70–4.15 (m, 5H), 4.25–4.67 (m, 2H), 5.26–5.44 (m, 1H), 6.84–8.19 (m, 13H); MS (FAB) m/z 554 ($M^++1$), 556 ($M^++3$).

To a stirred solution of methyl 4-[1-[4-[N'-(2-chlorophenyl)ureido]-3-methylphenyl acetyl]-(4S)-fluoro-(2S)-pyrrolidinyl]methoxybenzoate (268 mg, 0.484 mmol) in THF (3.8 ml) was added 0.25 N NaOH (3.8 ml). After stirring at room temperature for 1 days, the mixture was acidified with 1 N HCl and extracted with $CHCl_3$-MeOH (10/1). The combined extracts were dried over $Na_2SO_4$ and concentrated in vacuo. The residue was purified on TLC [$CHCl_3$/MeOH (10/1)] to give 79 (124 mg, 47%) as a colorless amorphous solid. MW 539.98 IR (KBr) 3346, 2976, 1709, 1685, 1604, 1533, 1439 cm$^{-1}$; $^1$H-NMR (DMSO-$d_6$) δ 2.20 (s, 3H, one of isomers), 2.24 (s, 3H, one of isomers), 2.30 (m, 1H), 3.60 (s, 2H), 3.71–4.62 (m, 6H), 5.30–5.50 (m, 1H), 7.01–7.09 (m, 5H), 7.28 (t, J=7.8 Hz, 1H), 7.44 (d, J=8.1 Hz, 1H), 7.66 (t, J=8.1 Hz, 1H), 7.87 (d, J=7.1 Hz, 2H), 8.13 (d, J=7.9 Hz, 1H), 8.62 (d, J=6.1 Hz, 2H); MS (FAB) m/z 540 (M$^+$+1), 542 (M$^+$+3). For Na salt: Anal. Calcd for $C_{28}H_{27}ClFN_3$.$Na.0.5EtOH.1.5H_2O$: C, 56.91; H, 5.27; Cl, 5.79; F, 3.10; N, 6.87. Found: C, 56.60; H, 4.98; Cl, 5.88; F, 3.08; N, 6.52.

Example 74

4-[1-[4-[N'-(2-bromophenyl)ureido]-3-methylphenylacetyl]-(4S)-fluoro-(2S)-pyrrolidinyl]methoxybenzoic acid

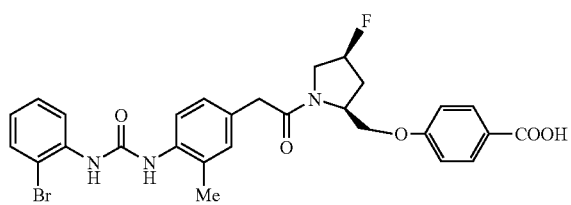

80

To a stirred mixture of tert-butyl 4-amino-3-methylphenylacetate (780 mg, 3.30 mmol), 2-bromo phenyl isocyanate (0.41 ml, 3.30 mmol) in THF (7 ml) was added $Et_3$ N (0.092 ml, 0.66 mmol) at room temperature. After 3 h stirring, the reaction mixture was concentrated in vacuo. The residue was triturated by the addition of n-hexane, to give tert-butyl 4-[N'-(2-bromophenyl) ureido]-3-methylphenylacetate (1.57 g, 93%) as a pale yellow powder. mp 138–145° C. (dec.); $^1$H-NMR (CDCl$_3$) δ 1.44 (s, 9H), 2.33 (s, 3H), 3.51 (s, 2H), 6.90 (dt, J=9.0, 1.4 Hz, 1H), 6.98 (br, 1H), 7.18–7.31 (m, 4H), 7.39 (dd, J=8.1, 2.9 Hz, 1H), 7.44 (d, J=8.0 Hz, 1H), 8.22 (d, J=8.3 Hz, 2H); Anal. Calcd for $C_{20}H_{22}BrN_2O_3.0.2H_2O$: C, 56.80; H, 5.58; N, 6.62. Found: C, 56.85; H, 5.42; N, 6.62.

To a stirred solution of tert-butyl 4-[N'-(2-bromophenyl) ureido]-3-methylphenylacetate (1.27 g, 3.03 mmol) in $CH_2Cl_2$ (10 ml) was added TFA (5 ml) at room temperature. After 1 h stirring, the mixture was concentrated in vacuo. The residue was triturated by the addition of water, to give 4-[N'-(2-bromophenyl)ureido]-3-methylphenylacetic acid (1.05 g, 95%) as a pale yellow powder. mp 245–248° C. (dec.); $^1$H-NMR (CDCl$_3$) δ 2.24 (s, 3H), 3.48 (s, 2H), 6.96 (dt, J=7.3, 1.5 Hz, 1H), 7.02 (d, J=8.3 Hz, 1H), 7.07 (s, 1H), 7.32 (t, J=8.1 Hz, 1H), 7.59–7.66 (m, 2H), 8.44 (s, 1H), 8.62 (s, 1H); MS (ESI), m/z 363 (M$^+$+1), 365 (M$^+$+3); Anal. Calcd for $C_{16}H_{15}BrN_2O_3.0.7H_2O$: C, 51.13; H, 4.40; Br, 21.26; N, 7.45. Found: C, 50.84; H, 4.62; Br, 21.72; N, 7.18.

A mixture of 4-[N'-(2-bromophenyl)ureido]-3-methylphenylacetic acid (287 mg, 0.79 mmol), methyl 4-[(4S)-fluoro-(2S)-pyrrolidinyl]methoxybenzoate (200 mg, 0.79 mmol), EDC.HCl (228 mg, 1.20 mmol), HOBT (160 mg, 1.19 mmol) and $Et_3$ N (0.55 ml, 3.95 mmol) in DMF (5 ml) was stirred at room temperature for 4 days. The mixture was poured into ice water and extracted with EtOAc. The combined extracts were washed with ice water and brine. After dried over $Na_2SO_4$, the extracts were concentrated in vacuo. The residue was purified on TLC [CHCl/acetone (10/1)], to give methyl 4-[(2S,4S)-1-[4-[N'-(2-chlorophenyl)ureido]-3-methylphenylacetyl]-4-fluoro-2-pyrrolidinyl]methoxybenzoate (440 mg, 93%) as a colorless amorphous solid. $^1$H-NMR (CDCl$_3$) δ 1.90 and 1.97 (eachs, 3H, amide isomers), 2.05–2.62 (m, 2H), 3.58 (d, J=8.1 Hz, 1H), 3.77 (m, 1H), 3.86 and 3.89 (eachs, 3H, amide isomers), 3.92–4.64 (m, 5H), 5.24–5.42 (m, 1H), 6.83–7.23 (m, 6H), 7.41–7.62 (m, 4H), 7.86–8.09 (m, 3H); MS (ESI), m/z 598 (M$^+$+1), 600 (M$^+$+3).

To a stirred solution of methyl 4-[1-[4-[N'-(2-bromophenyl)ureido]-3-methylphenyl acetyl]-(4S)-fluoro-(2S)-pyrrolidinyl]methoxybenzoate (440 mg, 0.74 mmol) in THF (6.0 ml), 0.25 N NaOH (6.0 ml) was added. After stirring at room temperature for 1 days, the mixture was acidified with 1 N HCl and extracted with $CHCl_3$-MeOH (10/1). The combined extracts were dried over $Na_2SO_4$ and concentrated in vacuo. The residue was purified on TLC [$CHCl_3$/MeOH (10/1)] to give 80 (229 mg, 53%) as a colorless amorphous solid. MW 584.44 IR (KBr) 3325, 2972, 1709, 1604, 1529, 1252 cm$^{-1}$; $^1$H-NMR (DMSO-$d_6$) δ 2.25 (s, 3H), 2.31 (m, 1H), 3.17 (s, 1H), 3.60 (d, J=4.7 Hz, 2H), 3.83 4.67 (m, 5H), 5.31–5.51 (m, 1H), 6.97 (t, J=7.3 Hz, 1H), 7.02–7.09 (m, 5H), 7.33 (t, J=8.0 Hz, 1H), 7.61 (d, J=7.8 Hz, 1H), 7.64 (d, J=8.3 Hz, 1H), 7.87 (d, J=8.3 Hz, 2H), 7.90 (d, J=8.8 Hz, 1H), 8.44–8.65 (m, 2H); MS (ESI), m/z 584 (M$^+$+1), 586 (M$^+$+3); Anal. Calcd for $C_{28}H_{27}BrFN_3O_7.0.4H_2O$: C, 56.84; H, 4.74; Br, 13.51; F, 3.21; N, 7.10. Found: C, 56.91; H, 4.93; Br, 13.23; F, 3.15; N, 6.88. For Na salt of 80: Anal. Calcd for $C_{28}H_{27}BrFN_3O_7.Na.1.8H_2O$: C, 52.64; H, 4.67; Br, 12.51; F, 2.97; N, 6.58. Found: C, 53.04; H, 4.67; Br, 12.95; F, 3.28; N, 6.11.

Example 75

4-[1-[4-[N'-(2-chlorophenyl)ureido]-3-methylphenylacetyl]-(2S)-pyrrolidinyl]methoxybenzoic acid

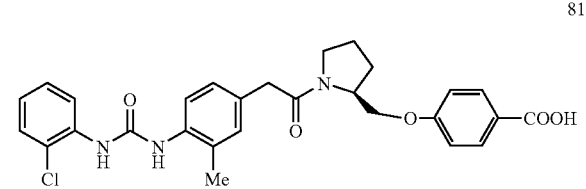

81

To a stirred solution of methyl 4-(1-tert-butoxycarbonyl-(2S)-pyrrolidinyl)methoxybenzoate (2.0 g, 5.9 mmol) in EtOH (10.0 ml) was added concd HCl (3.0 ml) at 0° C. The reaction mixture was stirred at room temperature for 4.0 hr. The mixture was concentrated in vacuo. The resulting solid was collected and washed with EtOH-$Et_2O$ to give methyl 4-(2S-pyrrolidinyl)methoxybenzoate HCl salt (1.4 g, 87%) as a white crystalline solid. $^1$H-NMR (CDCl$_3$) δ 1.90–2.25 (m, 4H), 3.25–3.45 (m, 2H), 3.88 (s, 3H), 3.90–4.00 (m, 1H), 4.25–4.45 (m, 2H), 6.96 (d, J=8.5 Hz, 2H), 7.95 (d, J=8.5 Hz, 2H).

To a stirred solution of methyl 4-[(2S)-pyrrolidinyl]methoxybenzoate HCl salt (135 mg, 0.5 mmol), 4-[N'-(2-chlorophenyl)uredio]-3-methylphenylacetic acid (159 mg, 0.5 mmol), HOBt (68 mg, 0.5 mmol), and triethylamine (278 ml, 2.0 mmol) in THF (5.0 ml) and MeCN (5.0 ml) was added EDC.HCl (144 mg, 0.75 mmol) at 0° C. The reaction mixture was stirred at room temperature for 16 hr, and concentrated in vacuo. Water was added to the residue, and extracted with EtOAc. The extract was washed with sat. NaHCO$_3$, then dried over Na$_2$SO$_4$, and concentrated in vacuo. The residue was purified by column chromatography on silica gel with n-hexane-EtOAc(1:2 ,v/v) as eluent to give methyl 4-[1-[4-[N'-(2-chlorophenyl)ureido]-3-methylphenylacetyl]-2-pyrrolidinyl]methoxybenzoate (220 mg, 82%) as a colorless oil. $^1$H-NMR (CDCl$_3$) δ 1.91 and 1.97 (each s, total 3H), 2.00–2.20 (m, 4H), 3.55–3.65 (m, 4H), 3.87 and 3.89(each s, total 3H), 4.10–4.20 (m, 2H), 4.51 (m, 1H); 6.86–7.04 (m, 6H), 7.20–7.53 (m, 4H), 7.89–8.01 (m, 2H), 8.22 (d, J=8.3 Hz, 1H).

To a stirred solution of methyl 4-[1-[4-[N'-(2-chlorophenyl)ureido]-3-methylphenylacetyl]-2S-pyrrolidinyl]methoxybenzoate (220 mg, 0.41 mmol) in THF (8.0 ml) and MeOH (4.0 ml) was added 1 N NaOH (0.8 ml, 0.8 mmol). The mixture was stirred at 70° C. for 24 hr. The mixture was concentrated in vacuo, water was added thereto, and neutralized with 1 N HCl. The resulting solid was collected, washed with water, and dried in vacuo to give 81 (220 mg, quant) as a white crystalline solid. MW 521.99 mp 122–124° C.; IR (KBr) 3340, 1710, 1685, 1604, 1533, 1511, 1438 cm$^{-1}$; $^1$H-NMR (DMSO-d$_6$) δ 1.81–2.11 (m, 4H), 2.18 and 2.20 (each s, total 3H), 3.45–3.80 (m, 4H), 3.95–4.05 (m, 1H), 4.12–4.20 (m, 1H), 4.21–4.31 (m, 1H), 6.99–7.06 (m, 5H), 7.26–7.30 (m, 1H), 7.44 (d, J=7.8 Hz, 1H), 7.62–7.64 (m, 1H), 7.85–7.90 (m, 2H), 8.13 (d, J=6.8 Hz, 1H), 8.60–8.62 (m, 2H); MS (FAB) m/z 522 (M$^+$+1); Anal. calcd for C$_{28}$H$_{28}$N$_3$O$_5$Cl.0.2H$_2$O: C, 63.99; H, 5.45; N, 7.99. Found: C, 63.90; H, 5.40; N, 7.72.

Example 76

4-[1-[4-[N'-(2-bromophenyl)ureido]-3-methylphenylacetyl]-(2S)-pyrrolidinyl]methoxybenzoic acid

82

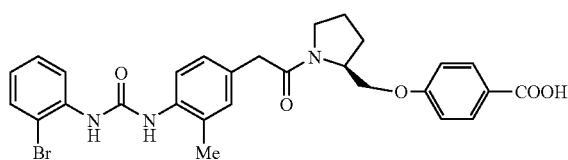

To a stirred solution of methyl [(2S)-pyrrolidinyl]methoxybenzoate HCl salt (135 mg, 0.5 mmol), 4-[N'-(2-bromophenyl)uredio]-3-methylphenylacetic acid (181 mg, 0.5 mmol), HOBt (68 mg, 0.5 mmol), and triethylamine (278 ml, 2.0 mmol) in THF (5.0 ml) and MeCN (5.0 ml) was added EDC.HCl (144 mg, 0.75 mmol) at 0° C. The reaction mixture was stirred at room temperature for 16 hr, and concentrated in vacuo. Water was added to the residue, and extracted with EtOAc. The extract was washed with sat. NaHCO$_3$, then dried over Na$_2$SO$_4$, and concentrated in vacuo. The residue was purified by column chromatography on silica gel with n-hexane-EtOAc (1/2, v/v) as eluent to give methyl 4-[1-[4-[N-(2-bromophenyl)ureido]-3-methylphenylacetyl]-(2S)-pyrrolidinyl]methoxybenzoate (290 mg, quant) as a colorless oil. $^1$H-NM (CDCl$_3$) δ 1.95 and 2.01 (each s, total 3H), 2.00–2.20 (m, 4H), 3.50–3.65 (m, 4H), 3.87 and 3.89 (each s, total 3H), 4.10–4.20 (m, 2H), 4.50 (m, 1H), 6.85–7.06 (m, 6H), 7.24–7.28 (m, 1H), 7.40–7.44 (m, 3H), 7.89–8.16 (m, 2H), 8.17–8.18 (m, 1H).

To a stirred solution of methyl 4-[1-[4-[N'-(2-bromophenyl)ureido]-3-methylphenylacetyl]-2S-pyrrolidinyl]methoxybenzoate (290 mg, 0.5 mmol) in THF (8.0 ml) and MeOH (4.0 ml) was added 1 N NaOH (1.0 ml, 1.0 mmol). The mixture was stirred at 70° C. for 24 hr. The mixture was concentrated in vacuo, water was added thereto, and neutralized with 1 N HCl. The resulting solid was collected, washed with water, and dried in vacuo to give 82 (240 mg, 85%) as a white crystalline solid. MW 566.44 mp 125–130° C.; IR (KBr) 3340, 1604, 1529, 1434 cm$^{-1}$; $^1$H-NMR (DMSO-d$_6$) δ 1.80–2.10 (m, 4H), 2.18 and 2.20 (each s, total 3H), 3.45–3.80 (m, 4H), 3.95–4.05 (m, 1H), 4.15–4.20 (m, 1H), 4.25–4.30 (m, 1H), 6.94–7.06 (m, 5H), 7.30–7.34 (m, 1H), 7.59–7.62 (m, 2H), 7.85–7.90 (m, 2H), 8.01 (d, J=8.1 Hz, 1H), 8.44 (s, 1H), 8.62 (s, 1H); MS (FAB) m/z 566 (M$^+$); Anal. calcd for C$_{28}$H$_{28}$N$_3$O$_5$Br.0.5H$_2$O: C, 58.44; H, 5.08; N, 7.30. Found: C, 58.57; H. 4.99; N, 7.18.

Example 77

4-[1-[3-methyl-4-[N'-(2-methylphenyl)ureido]phenylacetyl]-(2S)-pyrrolidinylmethoxy]benzoic acid

83

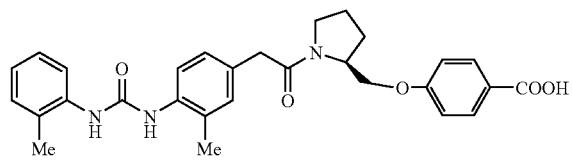

A mixture of 3-methyl-4-[N'-(2-methylphenyl)ureido]phenylacetic acid (438 mg, 1.47 mmol), methyl 4-[(2S)-pyrrolidinylmethoxy]benzoate (420 mg, 1.79 mmol), EDC.HCl (410 mg, 2.14 mmol), HOBt (228 mg, 1.69 mmol) and Et$_3$ N (240 ml, 1.72 mmol) in DMF (5 ml) was stirred at room temperature overnight. The mixture was diluted with H$_2$O and extracted with EtOAc. The extract was washed with brine, dried over Na$_2$SO$_4$, and evaporated. The residue was purified by column chromatography on silicagel with CHCl$_3$-MeOH (50:1 to 25:1, v/v) as eluent to give methyl 4-[1-[3-methyl4-[N'-(2-methylphenyl)ureido]phenylacetyl]-(2S)-pyrrolidinylmethoxy]benzoate (760 mg, quant.) as a white foam. $^1$H-NMR (CDCl$_3$) δ 1.89 (s, 3 H), 1:94–2.14 (m, 4 H), 2.16 (s, 3 H), 3.50–3.69 (m, 4 H), 3.87 (s, 3 H), 4.09–4.17 (m, 2 H), 4.42–4.45 (m, 1 H), 6.85–7.02 (m, 6 H), 7.10–7.16 (m, 3 H), 7.51–7.53 (m, 1 H), 7.62–7.64 (m, 1 H), 7.91–7.94 (m, 2 H); MS (FAB) m/z 516 (M$^+$+1).

To a stirred solution of methyl 4-[1-[3-methyl4-[N'-(2-methylphenyl)ureido]phenylacetyl]-(2S)-pyrrolidinylmethoxy]benzoate (420 mg, 0.71 mmol) in THF (7 ml) was added 0.5 N NaOH (7 ml) and the reaction mixture was heated under reflux for 2 hr. After cooled to room temperature, the mixture was poured into ice-1 N HCl and the resulting precipitate was collected under a reduced pressure. The crude solid was purified by recrystallization from CHCl$_3$-IPE to give 83 (526 mg, 69%) as a white crystalline powder. MW 501.57 mp 191–193° C.; $^1$H-NMR (DMSO-d$_6$) δ 1.87–2.10 (m, 4 H), 2.20 (s, 3 H), 2.26 (s, 3 H), 3.44–3.79 (series of m, total 4 H), 3.99–4.45 (series of m, total 3 H), 6.91–7.17 (series of m, total 7 H), 7.66–7.68 (m, 1 H), 7.80–7.90 (m, 3 H), 8.19–8.21 (m, 2 H), 12.62 (br s, 1 H); MS (FAB) m/z 502 (M⁺+1); Anal. Calcd for $C_{29}H_{31}N_3O_5 \cdot 1/4H_2O$: C, 68.83; H, 6.27; N, 8.30. Found: C, 68.81; H, 6.17; N, 8.23.

Example 78

4-[(4S)-fluoro-1-[4-[N'-(2-methoxyphenyl)ureido]-3-methylphenylacetyl]-(2S)-pyrrolidinyl methoxy]benzoic acid

84

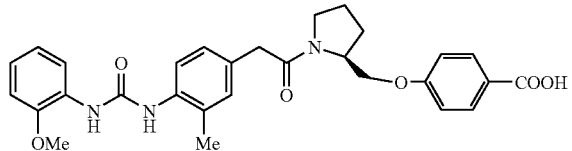

To a stirred solution of tert-butyl 4-amino-3-methylphenylacetate (1.36 g, 6.15 mmol) and triethylamine (170 ml, 1.23 mmol) in THF (30 ml) was added 2-methoxyphenyl isocyanate (820 ml, 6.15 mmol), and the resulting mixture was stirred for 27 h. The mixture was concentrated to a small volume in vacuo, and hexane was added to the residue to give precipitate, which was collected by filtration to give tert-butyl 4-[N'-(2-methoxyphenyl)ureido]-3-methylphenylacetate (1.74 g, 76%) as a white crystalline material. mp 157–158° C.; ¹H-NMR (CDCl₃) δ 1.46 (s, 9 H), 2.30 (s, 3 H), 3.50 (s, 2 H), 3.76 (s, 3 H), 6.43 (s, 1 H), 6.83 (br d, J=8.4 Hz, 1 H), 6.95 (br d, J=8.0 Hz, 1 H), 6.98–6.99 (m, 2 H), 7.13 (br s, 1 H), 7.23 (br s, 1 H), 7.48 (d, J=8.8 Hz, 1 H), 8.14 (d, J=8.4 Hz, 1 H); MS (ESI) m/z 371 (M⁺+H).

To a stirred solution of tert-butyl 4-[N'-(2-methoxyphenyl)ureido]-3-methylphenylacetate (1.32 g, 3.56 mmol) in CH₂Cl₂ (15 ml) was added trifluoroacetic acid (10 ml), and the resulting mixture was heated under reflux for 30 min. The mixture was concentrated in vacuo and added water to give precipitate which was collected by filtration. The crude solid was recrystallized from EtOH/hexane to give 4-[N'-(2-methoxyphenyl)ureido]-3-methylphenylacetic acid (932 mg, 83%) as a white powder. mp 260–264° C.; ¹H-NMR (CD₃OD) δ 2.30 (s, 3 H), 3.55 (s, 2 H), 4.87 (s, 3 H), 6.87–6.92 (m, 2 H), 6.97–6.99 (m, 2 H), 7.10–7.24 (m, 2 H), 7.53–7.58 (m, 1 H), 8.04 (d, J=7.2 Hz, 1 H); MS (ESI) m/z 314 (M⁺).

To a stirred solution of 4-[N'-(2-methoxyphenyl)ureido]-3-methylphenylacetic acid (336 mg, 1.07 mmol), methyl 4-[(4S)-fluoro-(2S)-pyrrolidinylmethoxy]benzoate (271 mg, 1.07 mmol) and N,N-dimethylaminopyridine (130 mg, 1.07 mmol) in DMF (10 ml) was added EDC.HCl (226 mg, 1.18 mmol) at rt, and the resulting mixture was stirred for 20 h. The mixture was poured into 1N-HCl aq. and extracted with EtOAc. The organic layer was washed with brine, drying over anhydrous Na₂SO₄, then concentrated in vacuo. The residue was chromatographed on silica gel with CHCl₃-MeOH (10:1) as eluent to give methyl 4-[(4S)-fluoro-1-[4-[N'-(2-methoxyphenyl)ureido]-3-methylphenylacetyl]-(2S)-pyrrolidinylmethoxy]benzoate (583 mg, 99%) as a colorless amorphous solid. ¹H-NMR (CDCl₃) mixture of rotamars, δ 2.05 and 2.12 (s, total 3 H), 2.05–2.61 (m, 2 H), 3.55–4.73 (series of m, 13 H), 4.51–4.66 (m, 2 H), 5.26–5.40 (m, 1 H), 6.72–7.01 (series of m, 8 H), 7.38–8.13 (series of m, 3 H); MS (ESI) m/z 550 (M⁺+H).

To a stirred solution of methyl 4-[(4S)-fluoro-1-[4-[N'-(2-methoxyphenyl)ureido]-3-methylphenylacetyl]-(2S)-pyrrolidinylmethoxy]benzoate (557 mg, 1.01 mmol) in MeOH-THF (1:1, 10 ml) was added 1.0N-NaOH aq. (4.05 ml, 4.05 mmol) at rt, and the resulting mixture was heated at 60° C. for 2 h. The mixture was poured into 1N-HCl aq. and extracted with EtOAc. The organic layer was washed with brine, drying over anhydrous Na₂SO₄, then concentrated in vacuo. The residue was chromatographed on silica gel with CHCl₃-MeOH (10:1) as eluent to give 84 (492 mg, 91%) as a colorless amorphous solid. MW 535.56 ¹H-NMR (CD₃OD), mixture of rotamars, δ 2.96 (s, 3 H), 2.11–2.45 (m, 2 H), 3.64–4.15 (series of m, 5 H), 3.91 (s, 3 H), 4.41–4.45 (m, 1 H), 4.52–4.61 (m, 1 H), 5.25–5.38 (m, 1 H), 6.84–7.10 (series of m, 7 H), 7.54–7.58 (m, 1 H), 7.93 (d, J=8.8 Hz, 2 H), 8.02 (d, J=8.8 Hz, 2 H); MS (ESI) m/z 536 (M⁺+H), 538 (M⁺+Na⁺).

Example 79

4-[(4S)-fluoro-1-[4-[N'-(2-methoxyphenyl)ureido]phenylacetyl]-(2S)-pyrro-lidinylmethoxy]benzoic acid

85

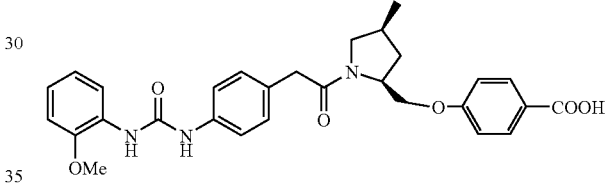

To a stirred solution of ethyl 4-amino-3-methylphenylacetate (1.32 g, 7.37 mmol) and triethylamine (205 ml, 1.47 mmol) in THF (20 ml) was added 2-methoxyphenyl isocyanate (980 ml, 7.37 mmol), and the resulting mixture was stirred for 23 h. The mixture was concentrated to a small volume in vacuo and hexane was added to the residue to give precipitate, which was collected to give ethyl 4-[N'-(2-methoxyphenyl)ureido]phenylacetate (2.44 g, quant.) as a white crystalline material. mp 107–109° C.; ¹H-NMR (CDCl₃) δ 1.26 (t, J=7.1 Hz, 3 H), 3.56 (s, 3 H), 3.79 (s, 3 H), 4.15 (q, J=7.1 Hz, 2 H), 6.82–6.85 (m, 1 H), 6.91–7.00 (m, 2 H), 7.08 (s, 1 H), 7.17 (d, J=8.5 Hz, 2 H), 7.27 (d, J=8.6 Hz, 2 H), 7.33 (s, 1 H), 8.07–8.10 (m, 1 H); MS (ESI) m/z 329 (M⁺+H).

To a stirred solution of ethyl 4-[N'-2-methoxyphenyl)ureido]phenylacetate (2.22 g, 6.78 mmol) in MeOH (30 ml) was added 1.0 M-NaOH aq. (10.2 ml, 10.2 mmol), and the resulting mixture was stirred overnight. 1N-HCl (aq.) was added and the mixture was concentrated in vacuo. Water was added to the residue to give precipitate, which was collected by filtration. The crude solid was recrystallized from EtOH/hexane to give 4-[N'-(2-methoxyphenyl)ureido]phenylacetic acid as a white powder (1.87 g, 92%). mp 165–168° C.; ¹H-NMR (CD₃OD) δ 2.30 (s, 3 H), 3.55 (s, 2 H), 4.87 (s, 3 H), 6.87–6.92 (m, 2 H), 6.97–6.99 (m, 2 H), 7.10–7.24 (m, 2 H), 7.53–7.58 (m, 1 H), 8.04 (d, J=7.2 Hz, 1 H); MS (ESI) m/z 300 (M⁺).

To a stirred solution of 4-[N'-(2-methoxyphenyl)ureido]phenylacetic acid (353 mg, 1.18 mmol), methyl 4-[(4S)-fluoro-(2S)-pyrrolidinylmethoxy]benzoate (298 mg, 1.18 mmol) and N,N-dimethylaminopyridine (144 mg, 1.18 mmol) in DMF (10 ml) was added EDC.HCl (226 mg, 1.18 mmol) at rt, and the resulting mixture was stirred for 22 h. The mixture was poured into 1N-HCl aq. and extracted with EtOAc. The organic layer was washed with brine, drying over anhydrous $Na_2SO_4$, then concentrated in vacuo. The residue was chromatographed on silica gel with $CHCl_3$-MeOH (10:1) to give methyl 4-[(4S)-fluoro1-[4-[N'-(2-methoxyphenyl)ureido]phenylacetyl]-(2S)-pyrrolidinyl-methoxy]benzoate (594 mg, 94%) as a colorless amorphous solid. $^1$H-NMR ($CDCl_3$) mixture of rotamers, δ 2.05–2.58 (series of m, 2 H), 3.55–4.25 (series of m, 5 H), 3.77 (s, 3 H), 3.87–3.90 (m, 3 H), 4.50–4.63 (m, 2 H), 5.23–5.37 (m, 1 H), 6.81–6.84 (m, 1 H), 6.91–6.99 (m, 4 H), 7.09–7.12 (m, 2 H), 7.18–7.26 (m, 2 H), 7.45–7.53 (m, 2 H), 7.91–8.03 (m, 2 H), 8.10–8.12 (m, 1 H); MS (ESI) m/z 536 ($M^+$+H).

To a stirred solution of methyl 4-[(4S)-fluoro-1-[4-[N'-(2-methoxyphenyl)ureido]phenylacetyl]-(2S)-pyrrolidinyl-methoxy]benzoate (568 mg, 1.06 mmol) in MeOH-THF (1:1, 10 ml) was added 1.0N-NaOH aq. (4.24 ml, 4.24 mmol) at rt, and the resulting mixture was heated at 60° C. for 1 h. The mixture was poured into 1N-HCl aq. and extracted with EtOAc. The organic layer was washed with brine, drying over anhydrous $Na_2SO_4$, then concentrated in vacuo. The residue was chromatographed on silica gel with $CHCl_3$-MeOH (10:1) as eluent to give 85 (516 mg, 93%) as a colorless amorphous solid. MW 521.54 $^1$H-NMR ($CD_3OD$), mixture of rotamers, δ 2.12–2.46 (m, 2 H), 3.65–4.19 (series of m, 5 H), 3.88 (s, 3 H), 4.42–4.45 (m, 1 H), 4.52–4.62 (m, 1 H), 5.24–5.39 (m, 1 H), 6.85–6.91 (m, 1 H), 6.94–7.03 (series of m, 4 H), 7.14–7.19 (m, 2 H), 7.35–7.40 (m, 2 H), 7.92–7.96 (m, 2 H), 8.02–8.04 (m, 1 H); MS (ESI) m/z 521 ($M^+$+H), 544 ($M^+$+$Na^+$).

Example 80

4-[(4S)-fluoro-1-[4-[N'-(2-methoxyphenyl)ureido]-3-methoxyphenylacetyl]-(2S)-pyrrolidinyl methoxy] benzoic acid

86

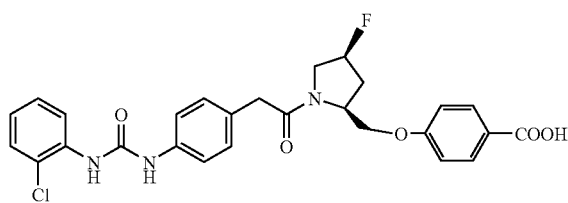

To a stirred solution of tert-butyl 4-amino-3-methoxy-lphenylacetate (1.41 g, 5.94 mmol) and triethylamine (165 ml, 1.19 mmol) in THF (20 ml) was added 2-methoxyphenyl isocyanate (790 ml, 5.94 mmol), and the resulting mixture was stirred for 4 days. The mixture was concentrated to a small volume in vacuo, and hexane was added to the residue to give precipitate, which was collected to give tert-butyl 4-[N'-(2-methoxyphenyl)ureido]-3-methoxylphenylacetate (2.06 g, 90%) as a white crystalline material. mp 132–134° C.; $^1$H-NMR ($CDCl_3$) δ 1.46 (s, 9 H), 3.50 (s, 2 H), 3.87 (s, 3 H), 3.88 (s, 3 H), 6.84 (s, 1 H), 6.87–6.90 (m, 2 H), 6.98–7.03 (m, 2 H), 7.12 (s, 1 H), 7.16 (s, 1 H), 8.06 (d, J=8.4 Hz, 1 H), 8.13 (dd, J=7.2, 2.0 Hz, 1 H); MS (ESI) m/z 387 ($N^+$+H).

To a stirred solution of tert-butyl 4-[N'-(2-methoxyphenyl)ureido]-3-methoxylphenyl-acetate (2.01 g, 5.20 mmol) in $CH_2Cl_2$ (15 ml) was added trifluoroacetic acid (10 ml), and the resulting mixture was heated under reflux for 30 min. The mixture was concentrated in vacuo. Water was added to the residue to give precipitate, which was collected by filtration. The crude solid was recrystallized from EtOH/hexane to give 4-[N'-(2-methoxyphenyl)ureido]-3-methoxy phenylacetic acid as white powder (1.40 g, 82%). mp 182–185° C.; $^1$H-NMR ($CD_3OD$) δ 3.55 (s, 2 H), 3.88 (s, 3 H), 3.89 (s, 3 H), 6.80–6.99 (m, 5 H), 7.94 (d, J=8.4 Hz, 1 H), 8.00 (d, J=7.2 Hz, 1 H); MS (ESI) m/z 330 ($M^+$).

To a stirred solution of 4-[N'-(2-methoxyphenyl)ureido]-3-methoxyphenylacetic acid (353 mg, 1.07 mmol), methyl 4-[(4S)-fluoro-(2S)-pyrrolidinylmethoxy]benzoate (271 mg, 1.07 mmol) and N,N-dimethylaminopyridine (131 mg, 1.07 mmol) in DMF (10 ml) was added EDC.HCl (224 mg, 1.18 mmol) at rt, and the resulting mixture was stirred for 14 h. The mixture was poured into 1N-HCl aq. and extracted with EtOAc. The organic layer was washed with brine, drying over anhydrous $Na_2SO_4$, then concentrated in vacuo. The residue was chromatographed on silica gel with $CHCl_3$-MeOH (10:1) as eluent to give methyl 4-[(4S)-fluoro-1-[4-[N'-(2-methoxyphenyl) ureido]-3-methoxyphenylacetyl]-(2S)-pyrrolidinylmethoxy]benzoate (372 mg, 61%) as a colorless amorphous solid. $^1$H-NMR ($CDCl_3$), mixture of rotamers, δ 2.04–2.57 (series of m, 2 H), 3.58–4.18 (series of m, 5 H), 3.79 and 3.83 (s, total 3 H), 3.86 (s, 3 H), 3.87 (s, 3 H), 4.51–4.63 (m, 2 H), 5.22–5.36 (m, 1 H), 6.80–6.89 (m, 3 H), 6.94–7.03 (m, 4 H), 7.15–7.25 (m, 2 H), 7.94–8.01 (m, 2 H), 8.04–8.11 (m, 2 H); MS (ESI) m/z 566 ($M^+$+H).

To a stirred solution of methyl 4-[(4S)-fluoro-1-[4-[N'-(2-methoxyphenyl)ureido]-3-methoxy phenyl-acetyl]-(2S)-pyrrolidinylmethoxy]benzoate (356 mg, 0.63 mmol) in MeOH-THF (1:1, 10 ml) was added 1.0N-NaOH aq. (1.88 ml, 1.88 mmol) at rt, and the resulting mixture was heated at 60° C. for 2 h. The mixture was poured into 1N-HCl aq. and extracted with EtOAc. The organic layer was washed with brine, drying over anhydrous $Na_2SO_4$, then concentrated in vacuo. The residue was chromatographed on silica gel with $CHCl_3$-MeOH (10:1) as eluent to give 86 (335 mg, 97%) as a colorless amorphous solid. MW 551.56 $^1$H-NMR ($CD_3OD$), mixture of rotamers, δ 2.14–2.48 (m, 2 H), 3.69–4.20 (series of m, 5 H), 3.88 (s, 3 H), 3.89 (s, 3 H), 4.46–4.57 (m, 2 H), 5.27–5.41 (m, 1 H), 6.79–7.04 (m, 7 H), 7.90–8.02 (m, 4 H); MS (ESI) m/z 552 ($M^+$+H).

Example 81

4-[1-[4-[N'-(2,6-dichlorophenyl)ureido]phenylacetyl]-(4S)-fluoro-(2S)-pyrrolidinyl]methoxy benzoic acid

87

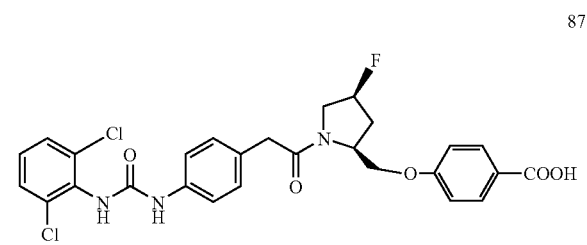

To a mixture of ethyl 4-aminophenylacetate (1.62 g, 9.04 mmol) and 2,6-dichlorophenyl isocyanate (1.70 g, 9.04 mmol) in THF (40 ml) was added Et₃N (0.25 ml, 1.81 mmol) at room temperature. After 2 h stirring, the reaction mixture was concentrated in vacuo. The residue was triturated by the addition of n-hexane, to give ethyl 4-[N'-(2,6-dichlorophenyl)ureido]phenyl acetate (3.19 g, 96%) as a colorless powder. mp 168–170° C. (dec.); ¹H-NMR (CDCl₃) δ 1.25 (t, J=7.1 Hz, 3H), 3.56 (s, 2H), 4.14 (q, J=7.1 Hz, 2H), 6.50 br, 1H), 6.67 (br, 1H), 7.12–7.52 (m, 7H).

To a stirred solution of ethyl 4-[N'-(2,6-dichlorophenyl)ureido]phenylacetate (3.19 g, 8.69 mmol) in THF (70 ml), 0.25 N NaOH (70 ml) was added. After stirring at room temperature for 17 h, the solvent was concentrated in vacuo. The residue was triturated by the addition of water, to give 4-[N'-(2,6-dichlorophenyl)ureido]phenylacetic acid (2.44 g, 82%) as colorless powder. mp 262–263° C. (dec.); ¹H-NMR (DMSO-d₆) δ 3.48 (s, 2H), 7.14 (d, J=8.3 Hz, 2H), 7.31 (t, J=8.3 Hz, 1H), 7.37 (d, J=8.3 Hz, 2H), 7.52 (d, J=8.0 Hz, 2H), 8.18 (s, 1H), 8.90 (s, 1H), 12.22 (br, 1H); MS (ESI) m/z 339 (M⁺+1), 341 (M⁺+3), 343 (M⁺+5).

A mixture of 4-[N'-(2,6dichlorophenyl)ureido]phenylacetic acid (268 mg, 0.79 mmol), methyl 4-[(2S, 4S)-4-fluoro-2-pyrrolidinyl]methoxybenzoate (200 mg, 0.79 mmol), EDC.HCl (227 mg, 1.19 mmol), HOBT (161 mg, 1.19 mmol) and Et₃N (0.55 ml, 3.95 mmol) in DMF (4 ml) was stirred at room temperature for 18 h. The mixture was poured into ice water and extracted with EtOAc. The combined extracts were washed with ice water and brine. After dried over Na₂SO₄, the extracts were concentrated in vacuo. The residue was purified on TLC [CHCl₃/MeOH (10/1)], to give tmethyl 4-[1-[4-[N'-(2,6-dichlorophenyl)ureido]phenylacetyl]-(4S)-fluoro-(2S)-pyrrolidinyl]methoxybenzoate (465 mg, 100%) as a colorless amorphous solid. ¹H-NMR (CDCl₃) δ 2.05–2.57 (m, 2H), 3.60 (d, 2H, J=3.4 Hz), 3.64–3.84 (m, 2H), 3.88 and 3.89 (each s, 3H, amide isomers), 3.92–4.63 (m, 3H), 5.22–5.38 (m, 1H), 6.87 and 6.89 (each d, each J=7.9 Hz, 2H, amide isomers), 7.01–7.17 (m, 6H), 7.28 (m, 2H), 7.36 (br, 1H), 7.92 (d, J=8.8 Hz, 1H), 7.79 (d, J=8.8 Hz, 1H); MS (ESI) m/z 574 (M⁺+1), 576 (M⁺+3), 578 (M⁺+5).

To a solution of methyl 4-[(2S, 4S)-1-[4-[N'-(2,6-dichlorophenyl)ureido]phenylacetyl]-4-fluoro-2-pyrrolidinyl]methoxybenzoate (465 mg, 0.809 mmol) in THF (40 ml), 0.25 N NaOH (40 ml) was added. After stirring at room temperature for 11 h, the mixture was acidified with 1 N HCl and extracted with CHCl₃-MeOH (10/1). The combined extracts were dried over Na₂SO₄ and concentrated in vacuo. The residue was purified on TLC [CHCl₃MeOH (10/1)], to give 87 (340 mg, 75%) as a colorless powder. MW 560.40 mp 168–172° C. (dec.); IR (KBr) 3340, 1711, 1685, 1604, 1240, 773 cm⁻¹; ¹H-NMR (DMSO-d₆) δ 2.22–2.30 (m, 2H), 3.61 (d, J=7.4 Hz, 2H), 3.70–4.75 (m, 6H), 5.30–5.49 (m, 1H), 7.02–7.18 (m, 5H), 7.28–7.41 (m, 4H), 7.52 (dd, J=8.0, 2.9 Hz, 2H), 7.86 (m, 2H), 8.29 (br, 1H), 9.01 (br, 1H), 12.66 (br, 1H); MS (ESI) m/z 560 (M⁺+1), 562 (M⁺+3), 564 (M⁺+5); Anal. Calcd for C₂₇H₂₄Cl₂FN₃O₅.0.5H₂O: C, 56.95; H, 4.43; Cl, 12.45; F, 3.34; N, 7.38. Found: C, 57.04; H, 4.34; Cl, 12.98; F, 3.27; N, 7.21.

Example 82

4-[1-[4-[N'-(2,6-dichlorophenyl)ureido]-3-methoxyphenylacetyl]-(4S)-fluoro-(2S)-pyrrolindinyl]methoxybenzoic acid

88

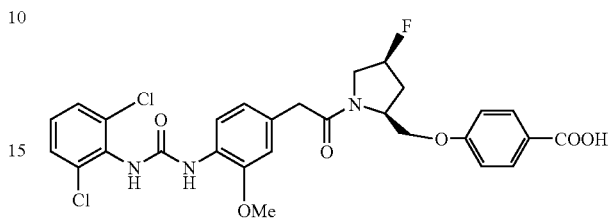

To a mixture of tert-butyl 4-amino-3-methoxyphenylacetate (2.15 g, 9.04 mmol), 2,6-dichlorophenyl isocyanate (1.70 g, 9.04 mmol) in THF (40 ml) was added Et₃N (0.25 ml, 9.04 mmol) at room temperature. After 18 h stirring, the reaction mixture was concentrated in vacuo. The residue was triturated by the addition of n-hexane, to give tert-butyl 4-[N'-(2,6-dichlorophenyl)ureido]-3-methoxyphenylacetate (2.27 g, 59%) as a colorless powder. mp 177–181° C. (dec.); ¹H-NMR (CDCl₃) δ 1.43 (s, 9H), 3.74 (s, 2H), 3.83 (s, 3H), 6.34 (s, 1H), 6.81 (s, 1H), 6.84 (d, J=8.3 Hz, 1H), 7.06 (br, 1H), 7.27 (t, J=8.1 Hz, 1H), 7.39 (d, J=8.1 Hz, 2H), 8.04 (d, J=8.3 Hz, 1H).

To a stirred solution of tert-butyl 4-[N'-(2,6-dichlorophenyl)ureido]-3-methoxyphenylacetate (2.27 g, 5.34 mmol) in CH₂Cl₂ (50 ml) was added TFA (20 ml) at room temperature. After 2 h stirring, the mixture was concentrated in vacuo. The residue was triturated by the addition of water, to give 4-[N'-(2,6-dichlorophenyl)ureido]-3-methoxyphenylacetic acid (1.50 g, 76%) as a colorless powder. mp 246–249° C. (dec.); ¹H-NMR (DMSO-d₆) δ 3.49 (s, 2H), 3.88 (s, 3H), 6.75 (d, J=8.3 Hz, 1H), 6.93 (s, 1H), 7.30 (t, J=7.8 Hz, 1H), 7.52 (d, J=8.0 Hz, 2H), 7.97 (d, J=8.0 Hz, 1H), 8.40 (s, 1H), 8.86 (s, 1H), 12.23 (br, 1H); MS (ESI) m/z 369 (M⁺+1), 371 (M⁺+3), 373 (M⁺+5).

A mixture of 4-[N'-(2,6-dichlorophenyl)ureido]-3-methoxyphenylacetic acid (288 mg, 0.78 mmol), methyl 4-[(2S, 4S)-4-fluoro-2-pyrrolidinyl]methoxybenzoate (200 mg, 0.79 mmol), EDC.HCl (227 mg, 1.19 mmol), HOBT (161 mg, 1.19 mmol) and Et₃N (0.55 ml, 3.95 mmol) in DMF (4 ml) was stirred at room temperature for 18 h. The mixture was poured into ice water and extracted with EtOAc. The combined extracts were washed with ice water and brine. After dried over Na₂SO₄, the extracts were concentrated in vacuo. The residue was chromatographed on silica gel [50 g, CHCl₃/MeOH(40/1)] to give methyl 4-[1-[4-[N'-(2,6-dichlorophenyl)ureido]-3-methoxyphenyl acetyl]-(4S)-fluoro-(2S)-pyrrolidinyl]methoxybenzoate (530 mg, 100%) as a colorless amorphous solid. ¹H-NMR (CDCl₃) δ 2.03–2.62 (m, 2H), 3.61 (d, 2H, J=4.7 Hz), 3.62–3.66 (m, 2H), 3.73 and 3.77 (each s, 3H, amide isomers), 3.78–3.85 (m, 1H), 3.87 and 3.88 (each s, 3H, amide isomers), 3.95–4.63 (m, 4H), 5.22–5.36 (m, 1H), 6.82 (s, 1H), 6.88 (d, J=8.8 Hz, 1H), 6.95 (d, J=8.8 Hz, 2H), 7.14–7.25 (m, 1H), 7.38 (d, J=8.1 Hz, 2H), 7.94–8.10 (m, 3H); MS (ESI) m/z 604 (M⁺+1), 606 (M⁺+3), 608 (M⁺+5).

To a solution of methyl 4-[1-[4-[N'-(2,6-dichlorophenyl)ureido]-3-methoxyphenylacetyl]-(4S)-fluoro-(2S)-pyrrolidinyl]methoxybenzoate (530 mg, 0.78 mmol) in THF (40 ml), 0.25 N NaOH (40 ml) was added. After stirring at room temperature for 11 h, the mixture was acidified with 1 N HCl and extracted with CHCl$_3$-MeOH (10/1). The combined extracts were dried over Na$_2$SO$_4$ and concentrated in vacuo. The residue was purified on TLC [CHCl$_3$/MeOH (10/1)]to give 88 (420 mg, 75%) as a colorless amorphous solid. MW 590.43 mp 162–168° C. (dec.); IR (KBr) 3346, 2974, 1709, 1604, 1533, 1254 cm$^{-1}$; $^1$H-NMR (DMSO-d$_6$) δ 1.98–2.36 (m, 2H), 3.58 (s, 2H), 3.78–3.95 (m, 6H), 4.02–4.68 (m, 2H), 5.31–5.50 (m, 1H), 6.71–7.09 (m, 4H1), 7.31 (t, J=7.8 Hz, 1H), 7.53 (d, J=8.1 Hz, 2H), 7.87 (d, J=8.1 Hz, 2H), 7.88–8.00 (m, 1H), 8.30–8.40 (m, 1H), 8.89 (s, 1H); MS (ESI) m/z 590 (M$^+$+1), 592 (M$^+$+3), 594 (M$^+$+5); Anal. Calcd for C$_{28}$H$_{26}$Cl$_2$FN$_3$O$_6$·1.5H$_2$O: C, 54.47; H, 4.73; F, 3.08; N, 6.81. Found: C, 54.53; H, 4.49; F, 2.93; N, 6.65.

Example 83

4-[(2S, 4S)-1-[4-[N'-(2,6-Dichlorophenyl)ureido]-3-methylphenylacetyl]4-fluoro-2-pyrrolidinyl]methoxybenzoic acid

89

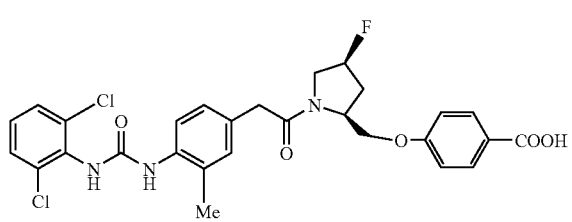

To a mixture of tert-butyl 4-amino-3-methylphenylacetate (1.88 g, 8.51 mmol), 2,6-dichlorophenyl isocyanate (1.60 g, 8.51 mmol) in THF (40 ml) was added Et$_3$N (0.24 ml, 1.70 mmol) at room temperature. After 3 h stirring, the reaction mixture was concentrated in vacuo. The residue was triturated by the addition of n-hexane, to give tert-butyl 4-[N'-(2,6-dichlorophenyl)ureido]-3-methylphenylacetate (2.58 g, 74%) as a colorless powder. mp 243–244° C. (dec.); $^1$H-NMR (CDCl$_3$) δ 1.45 (s, 9H), 2.30 (s, 3H), 3.49 (s, 2H), 6.24 (s, 2H), 7.12–7.16 (m, 3H), 7.35 (d, J=8.3 Hz, 2H), 7.51 (d, J=7.8 Hz, 1H).

To a stirred solution of tert-butyl 4-[N'-(2,6-dichlorophenyl)ureido]-3-methylphenylacetate (2.58 g, 6.30 mmol) in CH$_2$Cl$_2$ (50 ml) was added TFA (20 ml) at room temperature. After 2 h stirring, the mixture was concentrated in vacuo. The residue was triturated by the addition of water, to give 4-[N'-(2,6-dichlorophenyl)ureido]-3-methylphenylacetic acid (2.12 g, 95%) as a colorless powder. mp 274–283° C. (dec.); $^1$H-NMR (DMSO-d$_6$) δ 2.24 (s, 3H), 3.46 (s, 2H), 7.00 (d, J=8.6 Hz, 1H), 7.06 (s, 1H), 7.30 (t, J=7.8 Hz, 1H), 7.52 (d, J=8.3 Hz, 2H1), 7.65 (d, J=8.2 Hz, 1H), 8.12 (s, 1H), 8.50 (s, 1H), 12.22 (br, 1H); MS (ESI) m/z 353 (M$^+$+1), 355 (M$^+$+3), 357 (M$^+$+5).

A mixture of 4-[N'-(2,6-dichlorophenyl)ureido]-3-methylphenylacetic acid (181 mg, 0.51 mmol), methyl 4-[(2S, 4S)4-fluoro-2-pyrrolidinyl]methoxybenzoate (130 mg, 0.51 mmol), EDC·HCl (147 mg, 0.77 mmol), HOBT (104 mg, 0.77 mmol) and Et$_3$N (0.35 ml, 2.55 mmol) in DMF (4 ml) was stirred at room temperature for 18 h. The mixture was poured into ice water and extracted with EtOAc. The combined extracts were washed with ice water and brine. After dried over Na$_2$SO$_4$, the extracts were concentrated in vacuo.

The residue was purified on TLC [CHCl$_3$/MeOH (20/1)], to give methyl 4-[1-[4-[N'-(2,6dichlorophenyl)ureido]-3-methylphenylacetyl]-(4S)-fluoro-(2S)-pyrrolidinyl]methoxybenzoate (283 mg, 94%) as a colorless amorphous solid. $^1$H-NMR (CDCl$_3$) δ 1.95–2.61 (m, 3H), 3.55 (br, 2H), 3.67–3.81 (m, 2H), 3.87 (s, 6H), 3.89–4.68 (m, 2H), 5.23–5.43 (m, 1H), 6.81–7.10 (m, 6H), 7.13–7.43 (m, 3H), 7.56 (br, 1H, one of isomers), 7.73 (br, 1H, one of isomers), 7.89–8.00 (m, 2H); MS (ESI) m/z 588 (M$^+$+1), 590 (M$^+$+3), 592 (M$^+$+5).

To a solution of methyl 4-[1-[4-[N'-(2,6-dichlorophenyl)ureido]-3-methylphenylacetyl]-(4S)-fluoro-(2S)-pyrrolidinyl]methoxybenzoate (283 mg, 0.48 mmol) in THF (20 ml), 0.25 N NaOH (20 ml) was added. After stirring at room temperature for 11 h, the mixture was extracted with EtOAc. The remaining aqueous layer was acidified with 1 N HCl and extracted with EtOAc. The combined extracts were dried over Na$_2$SO$_4$ and concentrated in vacuo. The residue was on TLC [CHCl$_3$/MeOH (20/1)] to give 89 (450 mg, 67%) as a pale brown amorphous solid. MW 574.43 mp 174–180° C. (dec.); IR (KBr) 3330, 3288, 1711, 1685, 1604, 1512, 1242 cm$^{-1}$; $^1$H-NMR (DMSO-d$_6$) δ 2.24 (m, 3H), 3.61 (d, 2H, J=6.1 Hz), 3.72–4.68 (m, 7H), 5.30–5.50 (m, 1H), 6.97–7.20 (m, 4H), 7.29–7.68 (m, 5H), 7.87 (m, 2H), 8.10–8.95 (m, 1H), 12.65 (br, 1H); MS (ESI) m/z 574 (M$^+$+1), 576 (M$^+$+3), 578 (M$^+$+5); Anal. Calcd for C$_{28}$H$_{26}$Cl$_2$FN$_3$O$_5$·0.5H$_2$O:C, 57.64; H, 4.66; Cl, 12.15, F, 3.26; N, 7.20. Found: C, 57.37; H, 4.44; Cl, 12.64; F, 3.23; N, 7.25.

Example 84

4-[1-[3-chloro-4-[N'-(2-methylphenyl)ureido]phenylacetyl]-(4S)-fluoro-(2S)-pyrrolidinyl]methoxybenzoic acid

90

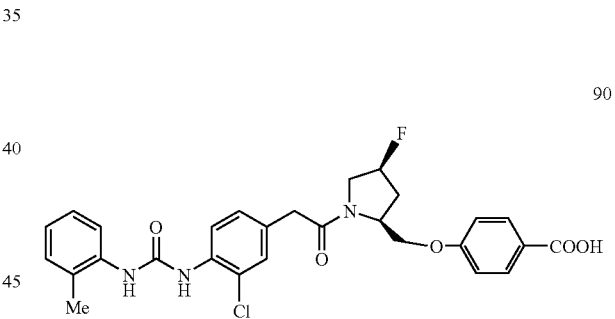

To a stirred solution of 3-chlorophenylacetic acid (21.76 g, 127.6 mmol) in dichloroethane (100 ml) was added MeOH (15:6 ml, 383 mmol) and H$_2$SO$_4$ (1 ml) at room temperature. After 20 minutes stirring, the mixture was heated at 80° C. for 2 h. The reaction mixture was poured into ice water and extracted with CHCl$_3$. The combined extracts were washed with aq. NaHCO$_3$ and brine. After dried over Na$_2$SO$_4$, the extract was concentrated in vacuo to give methyl 3-chlorophenylacetate (25.4 g, 100%) as a colorless oil. $^1$H-NMR (CDCl$_3$) δ 3.60 (s, 2H), 3.70 (s, 3H), 7.15–7.26 (m, 4H).

To a stirred mixture of methyl 3-chlorophenylacetate (25.4 g, 128 mmol) in H$_2$SO$_4$ (44 ml) was added HNO$_3$ (5.5 ml, 138 mmol) at 0° C. The reaction mixture was gradually raised to room temperature for 4 h. The reaction mixture was poured into ice water and extracted with EtOAc.

The combined extracts were washed with aq. NaHCO$_3$ and brine. After dried over Na$_2$SO$_4$, the extracts were concentrated in vacuo. The residue was chromatographed on silica gel [1 kg, n-hexane/EtOAc (40/1)] to give methyl 3-chloro-4-nitrophenylacetate (11.4 g, 36%) as a yellow oil. $^1$H-NMR (CDCl$_3$) δ 3.69 (s, 2H), 3.74 (s, 3H), 7.33 (dd, J=8.3, 1.5 Hz, 1H), 7.49 (d, J=1.5 Hz, 1H), 7.87 (d, J=8.3 Hz, 1H).

A mixture of methyl 3-chloro-4-nitrophenylacetate (10.9 g, 47.5 mmol), reduced iron powder (8.58 g, 153.6 mmol), AcONa.3H$_2$O (6.05 g, 44.5 mmol) and AcOH (17.6 ml) in MeOH/H$_2$O (100/400 ml) was heated at 110° C. for 1 h. After cooled to room temperature, the reaction mixture was filtered through Celite and the filtered cake was washed with MeOH. The combined filtrate were evaporated and extracted with EtOAc. The combined extracts were washed with brine, dried over Na$_2$SO$_4$ and concentrated in vacuo. The residue was chromatographed on silica gel [150 g, CHCl$_3$/EtOAc (10/1)] to give methyl 4-amino-3-chlorophenylacetate (4.58 g, 48%) as a red oil. $^1$H-NMR (CDCl$_3$) δ 3.49 (s, 2H), 3.68 (s, 3H), 4.01 (br, 2H), 6.70 (d, J=7.4 Hz, 1H), 6.96 (dd, J=8.1, 2.0 Hz, 1H), 7.17 (d, J=2.0 Hz, 1H).

To a mixture of methyl 4-amino-3-chlorophenylacetate (1.00 g, 5.01 mmol) and 2-methylphenyl isocyanate (0.60 ml, 5.01 mmol) in THF (20 ml) was added Et$_3$N (0.14 ml, 1.00 mmol) at room temperature. After 1 day stirring, 2-methylphenyl isocyanate (0.60 ml, 5.01 mmol) was added to the reaction mixture and stirred 17 h. The reaction mixture was concentrated in vacuo. The residue was triturated by the addition of n-hexane to give methyl 3-chloro-4-[N'-(2-methylphenyl) ureido]phenylacetate (1.23 g, 74%) as a colorless powder. $^1$H-NMR (CDCl$_3$) δ 2.34 (s, 3H), 3.54 (s, 2H), 3.68 (s, 3H), 6.24 (br, 1H1), 6.99 (br, 1H), 7.15 (dd, J=8.3, 2.0 Hz, 1H), 7.21–7.31 (m, 5H), 7.44 (d, J=7.6 Hz, 1H), 8.20 (d, J=8.5 Hz, 1H); MS (ESI) m/z 333 (M$^+$+1), 335 (M$^+$+3).

To a stirred solution of methyl 3-chloro-4-[N'-(2-methylphenyl)ureido]phenylacetate (1.23 g, 3.70 mmol) in THF (30 ml) was added 0.25 N NaOH (30 ml). After stirring at room temperature for 14 h, the solvent was concentrated in vacuo. The residue was triturated by the addition of 1 N HCl and dried over 60° C. for 2 days under a reduced pressure to give 3-chloro-4-[N'-(2-methylphenyl) ureido]phenylacetic acid (1.22 g, 100%) as colorless powder. $^1$H-NMR (DMSO-d$_6$) δ .26 (s, 3H), 3.40 (s, 2H), 6.95 (t, J=7.3 Hz, 1H), 7.11 (d, J=7.6 Hz, 2H), 7.16 (d, J=7.3 Hz, 1H), 7.32 (s, 1H), 7.76 (d, J=8.0 Hz, 1H), 7.94 (dd, J=9.3, 1.0 Hz, 1H), 8.72 (s, 2H); MS (ESI) m/z 319 (M$^+$+1), 321 (M$^+$+3), 341 (M$^+$+Na).

A mixture of 3-chloro-4-[N'-(2-methylphenyl)ureido]phenylacetic acid (319 mg, 1.00 mmol), methyl 4-[(4S)-fluoro-(2S)-pyrrolidinyl]methoxybenzoate (253 mg, 1.00 mmol), EDC.HCl (288 mg, 1.50 mmol), HOBT (203 mg, 1.50 mmol) and Et$_3$N (0.70 ml, 5.00 mmol) in DMF (4 ml) was stirred at room temperature for 15 h. The mixture was poured into ice water and extracted with EtOAc. The combined extracts were washed with ice water and brine. After dried over Na$_2$SO$_4$, the extracts were concentrated in vacuo. The residue was purified on TLC [CHCl$_3$/acetone (5/1)] to give methyl 4-[1-[3-chloro-4-[N'-(2-methylphenyl)ureido]phenylacetyl]-(4S)-fluoro-(2S)-pyrrolidinyl]methoxybenzoate (480 mg, 87%) as a colorless amorphous solid. $^1$H-NMR (CDCl$_3$) δ 2.10–2.60 (m, 2H), 2.29 (s, 3H), 3.56 (d, J=6.8 Hz, 1H), 3.71–3.84 (m, 1H), 3.87 and 3.89 (each s, 3H, amide isomers), 3.91–4.20 (m, 3H), 4.49–4.60 (m, 2H), 5.32 (dt, J=53.0, 4.2 Hz, 1H), 6:80 (br, 1H), 6.89 and 6.95 (each d, J=8.8 Hz, 2H, amide isomers), 7.09–7.26 (m, 6H), 7.50 (d, J=7.3 Hz, 1H), 7.94 and 8.00 (each d, J=8.8 Hz, 2H, amide isomers), 8.10 and 8.15 (each d, J=8.3 Hz, 1H, amide isomers); MS (FAB) m/z 554 (M$^+$+1), 556 (M$^+$+3).

To a solution of methyl 4-[1-[3-chloro-4-[N'-(2-methylphenyl)ureido]phenylacetyl]-(4S)-fluoro-(2S)-pyrrolidinyl]methoxybenzoate (480 mg, 0.866 mmol) in THF (30 ml) was added 0.25 N NaOH (30 ml). After stirring at room temperature for 2 days, the mixture was concentrated under a reduced pressure and acidified with 1 N HCl. The precipitates were collected, washed with water and dried under a reduced pressure to give 90 (374 mg, 80%) as a colorless powder. MW 539.98 IR (KBr) 3354, 3060, 2976, 1709, 1604, 1244 cm$^-$; $^1$H-NMR (DMSO-d$_6$) δ 2.27 (s, 3H), 2.31 (s, 2H), 3.66 (d, J=7.2 Hz, 2H), 3.71–4.67 (m, 5H), 5.32–5.53 (m, 1H), 6.97 (t, J=7.3 Hz, 1H), 7.04–7.22 (m, 5H), 7.32 and 7.35 (each d, J=1.7 Hz, 1H, amide isomers), 7.77 (d, J=7.6 Hz, 1H), 7.87 and 7.90 (each d, J=9.0 Hz, 2H, amide isomers), 8.01 and 8.03 (each d, J=8.5 Hz, 1H, amide isomers), 8.57 and 8.59 (each s, 1H, amide isomers), 8.63 and 8.65 (each s, 1H, amide isomers), 12.63 (s, 1H); MS (ESI) m/z 540 (M$^+$+1), 542 (M$^+$+3).

Example 85

4-[1-[3-chloro-4-[N'-(2-chlorophenyl)ureido]phenylacetyl]-(4S)-fluoro-(2S)-pyrrolidinyl]methoxy benzoic acid

91

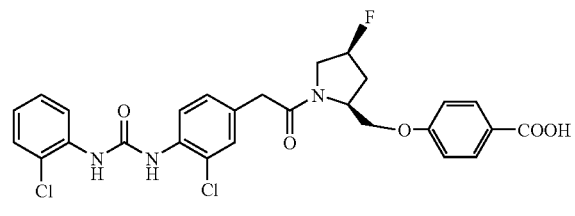

To a mixture of methyl 4-amino-3-chlorophenylacetate (1.00 g, 5.01 mmol) and 2-chlorophenyl isocyanate (0.60 ml, 5.01 mmol) in THF (20 ml) was added Et$_3$N (0.14 ml, 1.00 mmol) at room temperature. After 1 day stirring, 2-chlorophenyl isocyanate (0.60 ml, 5.01 mmol) was added to the reaction mixture and stirred 17 h. The reaction mixture was concentrated in vacuo. The residue was triturated by the addition of n-hexane to give methyl 3-chloro-4-[N'-(2-chlorophenyl) ureido]phenylacetate (1.35 g, 76%) as a colorless powder. $^1$H-NMR (CDCl$_3$) δ 3.58 (s, 3H), 3.71 (s, 2H), 7.04 (m, 3M), 7.18 (dd, J=8.5, 2.0 Hz, 1H), 7.27–7.39 (m, 3H), 8.07 (m, 2M); MS (ESI) m/z 353 (M$^+$+1), 355 (M$^+$+3), 357 (M$^+$+5).

To a stirred solution of methyl 3-chloro-4-[N'-(2-chlorophenyl)ureido]phenylacetate (1.35 g, 3.82 mmol) in THF (30 ml) was added 0.25 N NaOH (30 ml). After stirring at room temperature for 14 h, the solvent was concentrated in vacuo. The residue was triturated by the addition of 1 N HCl and dried at 60° C. for 2 days under a reduced pressure to give 3-chloro-4-[N'-(2-chlorophenyl) ureido]phenylacetic acid (1.12 g, 86%) as colorless powder. $^1$H-NMR (DMSO-d$_6$) δ 3.52 (s, 2H), 7.05 (m, 1H), 7.17 (d, J=8.5 Hz, 1H), 7.30 (d, J=7.6 Hz, 1H), 7.37 (s, 1H), 7.46 (dd, J=8.0, 1.5 Hz, 1H), 7.95 (dd, J=8.3, 1.2 Hz, 1H), 8.07 (d, J=8.3 Hz, 1H), 9.00 (d, J=8.0 Hz, 2H); MS (FAB) m/z 339 (M$^+$+1), 341 (M$^+$+3), 343 (M$^+$+5).

A mixture of 3-chloro-4-[N'-(2-chlorophenyl)ureido]phenylacetic acid (339 mg, 1.00 mmol), methyl 4-[(2S, 4S)-4-fluoro-2-pyrrolidinyl]methoxybenzoate (253 mg, 1.00 mmol), EDC.HCl (288 mg, 1.50 mmol), HOBT (203 mg, 1.50 mmol) and Et$_3$N (0.70 ml, 5.00 mmol) in DMF (4 ml)

was stirred at room temperature for 15 h. The mixture was poured into ice water and extracted with EtOAc. The combined extracts were washed with ice water and brine. After dried over Na$_2$SO$_4$, the extracts were concentrated in vacuo. The residue was chromatographed on silica gel [50 g, CHCl$_3$/acetone(10/1)] to give methyl 4-[1-[3-chloro-4-[N'-(2-chlorophenyl)ureido]phenylacetyl]-(4S)-fluoro-(2S)-pyrrolidinyl]methoxybenzoate (550 mg, 96%) as a colorless amorphous solid. $^1$H-NMR (CDCl$_3$) δ 2.14–2.64 (m, 2H), 3.59 (d, J=11.2 Hz, 2H), 3.78–3.82 (m, 1H), 3.86 and 3.89 (each s, 3H, amide isomers), 3.91–4.28 (m, 2H), 4.50–4.79 (m, 2H), 5.34 and 5.39 (each dt, J=52.5, 4.4 Hz, 1H, amide isomers), 6.89–6.98 (m, 3H), 7.09–7.13 (m, 2H), 7.22 (dt J=7.3, 2.2 Hz, 1H), 7.29 (dd, J=8.1, 2.0 Hz, 1H), 7.79 and 7.86 (each s, 1H, amide isomers), 7.86–8.03 (m, 4H), 8.11 (dd, J=8.3, 1.0 Hz, 1H); MS (FAB) m/z 574 (M$^+$+1), 576 (M$^+$+3), 578 (M$^+$+5).

To a solution of methyl 4-[1-[3-chloro-4-[N'-(2-chlorophenyl)ureido]phenylacetyl]-(4S)-fluoro-(2S)-pyrrolidinyl]methoxybenzoate (550 mg, 0.957 mmol) in THF (30 ml) was added 0.25 N NaOH (30 ml). After stirring at room temperature for 2 days, the mixture was concentrated under a reduced pressure and acidified with 1 N HCl. The precipitates were collected, washed with water and dried under a reduced pressure to give 91 (437 mg, 82%) as a colorless powder. MW 560.40 IR (KBr) 3348, 3072, 2954, 1703, 1604,1529, 1439 cm$^{-1}$; $^1$H-NMR (DMSO-d$_6$) δ 2.25–2.42 (m, 2H), 3.67 (d, J=8.3 Hz, 2H), 3.81–4.68 (m, 5H), 5.39 and 5.46 (each d, J=54.4 Hz, 1H, amide isomers), 7.04–7.10 (m, 3H), 7.18 (d, J=8.3 Hz, 1H), 7.31 (t, J=8.3 Hz, 1H), 7.33 and 7.37 (each s, 1H, amide isomers), 7.47 (d, J=8.1 Hz, 1H), 7.88 (dd, J=9.0, 3.2 Hz, 2H), 7.98 (dd, J=8.5, 3.0 Hz, 1H) m, 1H), 8.09 (d, J=8.3 Hz, 1H), 8.99 (d, J=2.9 Hz, 1H), 9.02 (s, 1H), 12.64 (s, 1H); MS (ESI) m/z 560 (M$^+$+1), 562 (M$^+$+3), 564 (M$^+$+5); Anal. Calcd for C$_{27}$H$_{24}$Cl$_2$FN$_3$O$_5$.0.2H$_2$O: C, 57.50; H, 4.36; N, 7.45; Cl, 12.57; F, 3.37. Found: C, 57.72; H, 4.47; N, 7.14; Cl, 12.44; F, 3.44.

Example 86

4-[1-[4-[N'-(2-bromophenyl)ureido]-3-chlorophenylacetyl]-(4S)-fluoro-(2S)-pyrrolidinyl]methoxybenzoic acid

92

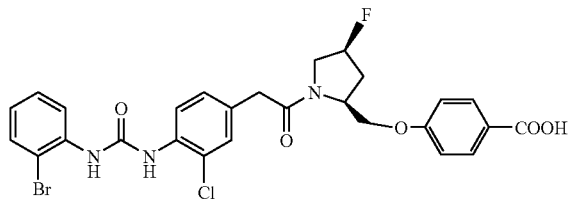

To a mixture of methyl 4-amino-3-chlorophenylacetate (1.00 g, 5.01 mmol) and 2-bromophenyl isocyanate (0.62 ml, 5.01 mmol) in THF (20 ml) was added Et$_3$ N (0.14 ml, 1.00 mmol) at room temperature. After 1 day stirring, 2-bromophenyl isocyanate (0.60 ml, 5.01 mmol) was added to the reaction mixture and stirred 24 h. The reaction mixture was concentrated in vacuo. The residue was triturated by the addition of n-hexane to give methyl 4-[N'-(2-bromophenyl) ureido]-3-chlorophenylacetate (1.34 g, 67%) as a colorless powder. $^1$H-NMR (CDCl$_3$) δ 3.58 (s, 3H), 3.70 (s, 2H), 6.98 (m, 3H), 7.19 (dd, J=8.3, 1.9 Hz, 1H), 7.32 (m, 1H), 7.51 (m, 2H), 8.05 (m, 1H); MS (ESI) m/z 398 (M$^+$+1), 400 (M$^+$+3), 402 (M$^+$+5).

To a stirred solution of methyl 4-[N'-(2-bromophenyl) ureido]-3-chlorophenylacetate (1.34 g, 3.37 mmol) in THF (30 ml) was added 0.25 N NaOH (30 ml). After stirring at room temperature for 14 h, the solvent was concentrated in vacuo. The residue was triturated by the addition of 1 N HCl and dried at 60° C. for 2 days under a reduced pressure to give 4-[N'-(2-bromophenyl)ureido]-3-chlorophenylacetic acid (1.03 g, 80%) as colorless powder. $^1$H-NMR (DMSO-d$_6$) δ 3.56 (s, 2H), 7.00 (m, 1H), 7.17 (dd, J=9.0, 1.7 Hz, 1H), 7.32–7.40 (m, 2H), 7.62 (dd, J=8.0, 1.2 Hz, 1H), 7.95 (m, 2H), 8.83 (s, 1), 9.01 (s, H), 12.41 (br, 1H); MS(FAB) m/z 385 (M$^+$+2), 386(M$^+$+4), 388 (M$^+$+6).

A mixture of 4-[N'-(2-bromophenyl)ureido]-3-chlorophenylacetic acid (384 mg, 1.00 mmol), methyl 4-[(4S)-fluoro-(2S)-pyrrolidinyl]methoxybenzoate (253 mg, 1.00 mmol), EDC.HCl (288 mg, 1.50 mmol), HOBT (203 mg, 1.50 mmol) and Et$_3$ N (0.70 ml, 5.00 mmol) in DMF (4 ml) was stirred at room temperature for 15 h. The mixture was poured into ice water and extracted with EtOAc. The combined extracts were washed with ice water and brine. After dried over Na$_2$SO$_4$, the extracts were concentrated in vacuo. The residue was chromatographed on silica gel [50 g, CHCl$_3$/acetone(10/1)] to give methyl 4-[1-[4-[N'-(2-bromophenyl)ureido]-3-chlorophenylacetyl]-(4S)-fluoro-(2S)-pyrrolidinyl]methoxybenzoate (530 mg, 86%) as a colorless amorphous solid. $^1$H-NMR (CDCl$_3$) δ 2.14–2.63 (m, 2H), 3.58 (d, J=10.0 Hz, 1H), 3.73–3.83 (m, 1H), 3.86 and 3.89 (each s, 3H, amide isomers), 3.90–4.29 (m, 3H), 4.50–4.69 (m, 2H), 5.33 and 5.37 (each m, 1H, amide isomers), 6.88–6.93 (m, 3H), 7.11–7.14 (m 2H), 7.26 (m, 1H), 7.46 (d, J=8.1 Hz, 1H), 7.62–7.78 (m, 2H), 7.89 and 7.93 (each m, 2H, amide isomers), 8.01 (dd, J=8.8, 1.7 Hz, 2H); MS (FAB) m/z 618 (M$^+$), 620 (M$^+$+2), 622 (M$^+$+4).

To a solution of methyl 4-[1-[4-[N'-(2-bromophenyl)ureido]-3-chlorophenylacetyl]-(4S)-fluoro-(2S)-pyrrolidinyl] methoxybenzoate (530 mg, 0.856 mmol) in THF (30 ml) was added 0.25 N NaOH (30 ml). After stirring at room temperature for 2 days, the mixture was concentrated under a reduced pressure and acidified with 1 N HCl. The mixture was extracted with CHCl$_3$/MeOH (10/1). The combined extracts were washed with ice water and brine. After dried over Na$_2$SO$_4$, the extracts were concentrated in vacuo. The residue was chromatographed on silica gel [20 g, CHCl$_3$/acetone(10/1)-CHCl$_3$/MeOH(10/1)] to give 92 (59 mg, 11%) as a colorless amorphous solid. MW 604.85 IR (KBr) 3329, 3060, 2976, 1712, 1526, 1435 cm$^{-1}$; $^1$H-NMR (DMSO-d$_6$) δ 2.31 (m, H), 3.48–4.68 (m, 7H), 5.32–5.53 (m, 1H), 6.99–7.19 (m, 4H), 7.36 (s, 1H), 7.63 (dd, J=6.7, 1.2 Hz, 1H), 7.86–8.18 (m, 4H), 8.83 (s, 1H), 9.02 (s, 1H), 12.67 (br, 1H); MS (ESI) m/z 604 (M$^+$+1), 606 (M$^+$+3), 608 (M$^+$+5); Anal. Calcd for C$_{27}$H$_{24}$BrClFN$_3$O$_5$.0.5H$_2$O: C, 52.83; H, 4.10; N, 6.85; Cl, 5.78; F, 3.09. Found: C, 53.24; H, 4.32; N, 6.43; Cl, 6.01; F, 3.07.

Example 87

4-[1-[3-chloro-4-(N'-phenylureido)phenylacetyl]-(4S)-fluoro-(2S)-pyrrolidinyl]methoxybenzoic acid

93

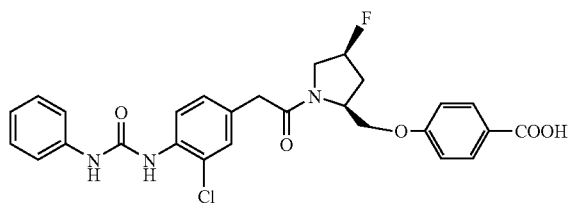

To a mixture of methyl 4-amino-3-chlorophenylacetate (1.31 g, 6.56 mmol) and phenyl isocyanate (0.71 ml, 6.56 mmol) in THF (20 ml) was added $Et_3N$ (0.19 ml, 1.33 mmol) at room temperature. After 15 h stirring, the reaction mixture was concentrated in vacuo. The residue was triturated by the addition of n-hexane to give methyl 3-chloro-4-(N'-phenylureido)phenylacetate (1.79 g, 86%) as a pale brown solid. $^1$H-NMR (CDCl$_3$) δ 3.56 (s, 2H), 3.70 (s, 3H), 6.70 (m, 1H), 7.06 (s, 1H), 7.14–7.18 (m, 2H), 7.26 (dd, J=7.8, 1.9 Hz, 1H), 7.33–7.38 (m, 4H), 8.14 (dd, J=8.3, 3.0 Hz, 1H); MS (ESI) m/z 319 (M$^+$+1), 321 (M$^+$+3).

To a stirred solution of methyl 3-chloro-4-(N'-phenylureido)phenylacetate (1.79 g, 5.62 mmol) in THF (30 ml) was added 0.25 N NaOH (30 ml). After stirring at room temperature for 20 h, the solvent was concentrated in vacuo. The residue was triturated by the addition of 1 N HCl and dried at 60° C. for 2 days under a reduced pressure to give 3-chloro-4-(N'-phenylureido) phenylacetic acid (1.58 g, 92%) as pale brown solid. $^1$H-NMR (DMSO-d$_6$) δ 3.55 (s, 2H), 6.99 (t, J=7.3 Hz, 1H), 7.17 (d, J=8.3 Hz, 1H1), 7.29 (t, J=7.6 Hz, 2H), 7.36 (s, 1H), 7.46 (d, J=8:0 Hz, 2H), 8.07 (d, J=8.3 Hz, 1H), 8.28 (s, 1H), 9.37 (s, 1H), 12.37 (br, 1H).

A mixture of 3-chloro-4-(N'-phenylureido)phenylacetic acid (305 mg, 1.00 mmol), methyl 4-[(2S, 4S)4-fluoro-2-pyrrolidinyl]methoxybenzoate (253 mg, 1.00 mmol), EDC.HCl (288 mg, 1.50 mmol), HOBT (203 mg, 1.50 mmol) and Et$_3$ N (0.70 ml, 5.00 mmol) in DMF (4 ml) was stirred at room temperature for 17 h. The mixture was poured into ice water and extracted with EtOAc. The combined extracts were washed with ice water and brine. After dried over Na$_2$SO$_4$, the extracts were concentrated in vacuo. The residue was chromatographed on silica gel [30 g, CHCl$_3$/acetone(20/1)] to give methyl 4-[1-[3-chloro-4-(N'phenylureido)phenylacetyl]-(4s)-fluoro-(2S)-pyrrolidinyl]methoxybenzoate (720 mg, 100%) as a colorless amorphous solid. MS (FAB) m/z 540 (M$^+$+1), 542 (M$^+$+3).

To a solution of methyl 4-[1-[3-chloro-4-(N'-phenylureido)phenylacetyl]-(4S)-fluoro-(2S)-pyrrolidinyl]methoxybenzoate (720 mg, 1.00 mmol) in THF/MeOH (30/30 ml) was added 0.25 N NaOH (30 ml). After stirring at room temperature for 2 h, the reaction mixture was heated at 50° C. for 22 h. After removed the solvent, the resulting residue was acidified with 1 N HCl. The precipitates were collected, washed with water and dried under a reduced pressure to give 93 [412 mg, 78% (2 Steps)] as a colorless powder. MW 525.96 IR (KBr) 3346, 3302, 2976, 1712, 1604, 1240 cm$^{-1}$; $^1$H-NMR (DMSO-d$_6$) δ 2.25–2.31 (m, 2H), 3.66 (d, J=7.8 Hz, 2H), 3.71–4.67 (m, 5H), 5.31–5.52 (m, 1H), 6.99 (t, J=7.3 Hz, 1H), 7.04 and 7.07 (each d, J=8.7 Hz, 2H, amide isomers), 7.14–7.18 (m, 1H), 7.29 (t, J=7.3 Hz, 2H), 7.35 (d, J=1.7 Hz, 1H), 7.46 (d, J=7.8 Hz, 2H), 7.87 and 7.90 (each d, J=9.0 Hz, 2H, amide isomers), 8.04 and 8.06 (each d, J=8.5 Hz, 1H, amide isomers), 8.26 and 8.28 (each s, 1H, amide isomers), 9.36 (s, 1H), 12.63 (s, 1H); MS (ESI) m/z 526 (M$^+$+1), 528 (M$^+$+3); Anal. Calcd for $C_{27}H_{25}ClFN_3O_5.0.5H_2O$: C, 60.62; H, 4.90; N, 7.85; Cl, 6.63; F, 3.55. Found: C, 61.00; H, 5.19; N, 7.40; Cl, 6.66; F, 3.39.

Example 88

4-[1-[3-bromo-4-[N'-(2-methylphenyl)ureido]phenylacetyl]-(4S)-fluoro-(2S)-pyrrolidinyl]methoxybenzoic acid

94

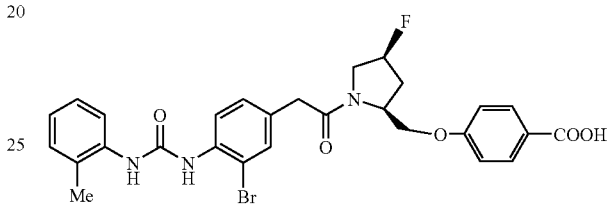

To a stirred solution of 3-bromophenylacetic acid (10.2 g, 47.4 mmol) in dichloroethane (50 ml) was added MEOH (5.8 ml, 142 mmol) and H$_2$SO$_4$ (0.5 ml) at room temperature. After 20 minutes stirring, the mixture was heated at 80° C. for 7 h. The reaction mixture was poured into ice water and extracted with CHCl$_3$. The combined extracts were washed with aq. NaHCO$_3$ and brine. After dried over Na$_2$SO$_4$, the extracts were concentrated in vacuo to give methyl 3-bromophenyl acetate (10.8 g, 99%) as a colorless oil. $^1$H-NMR (CDCl$_3$) δ 3.60 (s, 2H), 3.71 (d, J=1.0 Hz, 3H), 7.18–7.44 (m, 4H).

To a stirred mixture of methyl 3-chlorophenylacetate (10.8 g, 47.1 mmol) in H$_2$SO$_4$ (15.1 ml) was added HNO$_3$ (2.8 ml, 70.7 mmol) at 0° C. The reaction mixture was gradually raised to room temperature for 5.5 h. The reaction mixture was poured into ice water and extracted with CHCl$_3$. The combined extracts were washed with aq. NaHCO$_3$ and brine. After dried over Na$_2$SO$_4$, the extracts were concentrated in vacuo. The residue was chromatographed on silica gel [500 g, n-hexane/EtOAc (10/1)] to give methyl 3-bromo-4-nitrophenylacetate (3.69 g, 29%) as a yellow oil. $^1$H-NMR (CDCl$_3$) δ 3.68 (s, 2H), 3.73 (s, 3H), 7.38 (dd, J=8.3, 1.2 Hz, 1H), 7.67 (d, J=1.3 Hz, 1H), 7.83 (d, J=8.3 Hz, 1H).

A mixture of methyl 3-bromo-4-nitrophenylacetate (14.8 g, 53.8 mmol), reduced iron powder (9.62 g, 172 mmol), AcONa.3H$_2$O (7.32 g, 53.8 mmol) and AcOH (20.0 ml) in MeOH/H$_2$O (150/600 ml) was heated at 90° C. for 1 h. After cooled to room temperature, the reaction mixture was filtered through Celite and the filtered cake was washed with MeOH. The combined filtrate were evaporated and extracted with EtOAc. The extracts were washed with brine, dried over Na$_2$SO$_4$ and concentrated in vacuo. The residue was chromatographed on silica gel [400 g, CHCl$_3$/EtOAc (20/1)] to give methyl 4-amino-3-bromophenylacetate (9.01 g, 69%) as a brown oil. $^1$H-NMR (CDCl$_3$) δ 3.48 (s, 2H), 3.68 (s, 3H), 4.05 (br, 2H), 6.69 (d, J=8.3 Hz, 1H), 7.00 (dd, J=8.1, 2.0 Hz, 1H), 7.32 (d, J=2.0 Hz, 1H).

To a mixture of methyl 4-amino-3-bromophenylacetate (587 mg, 2.40 mmol) and 2-methylphenyl isocyanate (0.287 ml, 2.40 mmol) in THF (2 ml) was added Et₃N (33 ml, 0.24 mmol) at room temperature. After 21 h stirring, the reaction mixture was concentrated in vacuo. The residue was triturated by the addition of n-hexane to give methyl 3-bromo-4-[N'-(2-methylphenyl)ureido]phenylacetate (650 mg, 72%) as a pale brown powder. $^1$H-NMR (CDCl₃) δ2.34 (s, 3H), 3.53 (s, 2H), 3.68 (s, 3H), 6.18 (br, 1H), 6.96 (br, 1H), 7.18–7.33 (m, 4H), 7.29 (d, J=4.4 Hz, 1H), 7.30 (d, J=7.3 Hz, 1H), 8.19 (d, J=8.3 Hz, 1H); MS (ESI) m/z 377 (M$^+$), 379 (M$^+$+2).

To a stirred solution of methyl 3-bromo-4-[N'-(2-methylphenyl)ureido]phenylacetate (650 mg, 1.72 mmol) in THF (10 ml) was added 0.25 N NaOH (10 ml). After stirring at room temperature for 14 h, the solvent was concentrated in vacuo. The residue was triturated by the addition of 1 N HCl and dried at 60° C. for 2 days under a reduced pressure to give 3-bromo-4-[N'-(2-methylphenyl)ureido]phenylacetic acid (1.22 g, 100%) as colorless powder. $^1$H-NMR (DMSO-d₆) δ 2.26 (s, 3H), 3.32 (s, 2H), 6.93 (m, 2H), 7.10–7.17 (m, 4H), 7.76 (d, J=8.1 Hz, 2H), 8.52 (s, 1H); MS (ESI) m/z 385 (M$^+$+Na), 387 (M$^+$+2+Na).

A mixture of 3-bromo-4-[N'-(2-methylphenyl)ureido]phenylacetic acid (80 mg, 0.22 mmol), methyl 4-[(4S)-fluoro-(2S)-pyrrolidinyl]methoxybenzoate (56 mg, 0.22 mmol), EDC.HCl (63 mg, 0.33 mmol), HOBT (45 mg, 0.33 mmol) and Et₃N (0.15 ml, 1.10 mmol) in DMF (1 ml) was stirred at room temperature for 18 h. The mixture was poured into ice water and extracted with EtOAc. The combined extracts were washed with ice water and brine. After dried over Na₂SO₄, the extracts were concentrated in vacuo. The residue was purified on TLC [CHCl₃/acetone (5/1)] to give methyl 4-[1-[3-bromo-4-[N'-(2-methylphenyl)ureido]phenylacetyl]-(4S)-fluoro-(2S)-pyrrolidinyl]methoxybenzoate (140 mg, 100%) as a yellow oil. $^1$H-NMR (CDCl₃) δ 2.30 (s, 3H), 2.55 (m, 1H), 3.56 (d, J=6.4 Hz, 2H), 3.70–3.84 (m, 3H), 3.87 (s, 3H), 3.99–4.59 (m, 3H), 5.23–5.38 (m, 1H), 6.83–6.94 (m, 2H), 6.95 (d, J=8.8 Hz, 1H), 7.07–7.26 (m, 5H), 7.36–7.63 (m, 2H), 7.94–8.15 (m, 3H); MS (ESI) m/z 598 (M$^+$+1), 600 (M$^+$+3).

To a solution of methyl 4-[1-[3-bromo-4-[N'-(2-methylphenyl)ureido]phenylacetyl]-(4S)-fluoro-(2S)-pyrrolidinyl]methoxybenzoate (140 mg, 0.22 mmol) in THF (10 ml) was added 0.25 N NaOH (10 ml). After stirring at room temperature for 14 h, the mixture was concentrated under a reduced pressure and acidified with 1 N HCl. The precipitates were collected, washed with water and dried under a reduced pressure to give 94 (109 mg, 85%) as a colorless powder. MW 584.43 IR (KBr) 3313, 3060, 2976, 1687, 1604, 1525, 1244 cm$^{-1}$; $^1$H-NMR (DMSO-d₆) δ 2.27 (s, 3H), 2.29 (m, 2H), 3.66 (d, J=8.1 Hz, 2H), 3.72–4.68 (m, 5H), 5.31–5.53 (m, 1H), 6.92–6.99 (m, 1H), 7.04 and 7.07 (each d, J=8.3 Hz, 2H, amide isomers), 7.11–7.21 (m, 3H), 7.48 and 7.51 (s, 1H, amide isomers), 7.75 and 7.79 (each d, J=8.1 Hz, 1H, amide isomers), 7.86–7.92 (m, 3H), 8.45 and 8.47 (each s, 1H, amide isomers), 8.59 (s, 1H), 12.64 (s, 1H); MS (FAB) m/z 584 (M$^+$+1), 586 (M$^+$+3); Anal. Calcd for C₂₈H₂₇BrFN₃O₅: C, 57.54; H, 4.66; N, 7.19; Br, 13.67; F, 3.25. Found: C, 57.93; H, 4.97; N, 7.04; Br, 13.35; F, 2.89.

Example 89

4-[1-[3-bromo-4-[N'-(2-chlorophenyl)ureido]phenylacetyl]-(4S)-fluoro-(2S)-pyrrolindinyl]methoxybenzoic acid

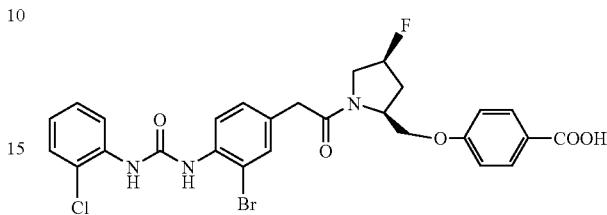

95

To a mixture of methyl 4-amino-3-bromophenylacetate (587 mg, 2.40 mmol) and 2-chlorophenyl isocyanate (0.29 ml, 2.40 mmol) in THF (2 ml) was added Et₃N (33 ml, 0.24 mmol) at room temperature. After 21 h stirring, the reaction mixture was concentrated in vacuo. The residue was triturated by the addition of n-hexane to give methyl 3-bromo-4-[N'-(2-chlorophenyl)ureido]phenylacetate (710 mg, 74%) as a pale brown powder. $^1$H-NMR (CDCl₃) δ 3.57 (s, 2H), 3.70 (s, 3H), 7.02–7.28 (m, 2H), 7.36 (d, J=6.8 Hz, 1H), 7.48 (s, 1H), 8.00–8.11 (m, 2H); MS (ESI) m/z 397 (M$^+$), 399 (M$^+$+2), 401 (M$^+$+4).

To a stirred solution of methyl 3-bromo-4-[N'-(2-chlorophenyl)ureido]phenylacetate (710 mg, 1.79 mmol) in THF (10 ml) was added 0.25 N NaOH (10 ml). After stirring at room temperature for 14 h, the solvent was concentrated in vacuo. The residue was triturated by the addition of 1 N HCl and dried at 60° C. for 2 days under a reduced pressure to give 3-bromo-4-[N'-(2-chlorophenyl) ureido]phenylacetic acid (643 mg, 94%) as colorless powder. $^1$H-NMR (DMSO-d₆) δ 3.56 (s, 2H), 7.05 (m, 1H), 7.21 (dd, J=8.6, 1.7 Hz, 1H), 7.29 (t, J=7.8 Hz, 1H), 7.46 (d, J=8.1 Hz, 1H), 7.46 (d, J=8.1 Hz, 1H), 7.53 (d, J=1.7 Hz, 1H), 7.83 (d, J=8.3 Hz, 1H), 8.06 (d, J=7.6 Hz, 1H), 8.86 (s, 1H), 8.89 (s, 1H), 12.40 (s, 1H); MS (ESI) m/z 382 (M$^+$+1), 384(M$^+$+3).

A mixture of 3-bromo-4-[N'-(2-chlorophenyl)ureido]phenylacetic acid (384 mg, 1.00 mmol), methyl 4-[(4S)-fluoro-(2S)-pyrrolidinyl]methoxybenzoate (253 mg, 1.00 mmol), EDC.HCl (288 mg, 1.50 mmol), HOBT (203 mg, 1.50 mmol) and Et₃N (0.70 ml, 5.00 mmol) in DMF (4 ml) was stirred at room temperature for 18 h. The mixture was poured into ice water and extracted with EtOAc. The combined extracts were washed with ice water and brine. After dried over Na₂SO₄, the extracts were concentrated in vacuo. The residue was chromatographed on silica gel [30 g, CHCl₃/acetone(10/1)]to give methyl 4-[1-[3-bromo-4-[N'-(2-chlorophenyl)ureido]phenylacetyl]-(4S)-fluoro-(2S)-pyrrolidinyl]methoxybenzoate (640 mg, 100%) as a colorless amorphous solid. $^1$H-NMR (CDCl₃) δ 2.07–2.46 (m, 2H), 2.59 (t, J=18.4 Hz, 1H), 3.57 (d, J=10.5 Hz, 2H), 3.63–4.67 (m, 7H), 5.26–5.44 (m, 1H), 6.89–6.96 (m, 3H), 7.13 (d, J=7.6 Hz, 1H), 7.1 (t, J=7.3 Hz, 1H), 7.26–7.29 (m, 2H), 7.52–7.94 (m, 4H), 8.01(d, J=8.5 Hz, 1H), 8.09 (d, J=8.5 Hz, 1H); MS (FAB) m/z 618 (M$^+$), 620 (M$^+$+3), 622 (M$^+$+5).

To a solution of methyl 4-[1-[3-bromo-4-[N'-(2-chlorophenyl)ureido]phenylacetyl]-(4S)-fluoro-(2S)-pyrrolidinyl]methoxybenzoate (640 mg, 1.00 mmol) in THF (40 ml) was added 0.25 N NaOH (40 ml). After stirring at room temperature for 14 h, the mixture was concentrated under a reduced pressure and acidified with 1 N HCl. The precipitates were collected, washed with water and dried under a reduced pressure to give 95 (522 mg, 86%) as a pale yellow powder. MW 604.85 IR (KBr) 3317, 3072, 1709, 1685, 1604, 1529, 1290 cm$^{-1}$; $^1$H-NMR (DMSO-d$_6$) δ 2.24–2.50 (m, 2H), 3.67 (d, J=8.3 Hz, 2H), 3.73–4.68 (m, 5H), 5.31–5.52 (m, 1H), 7.03–7.09 (m, 3H), 7.22 (dt, J=8.3, 1.7 Hz, 1H), 7.30 (d, J=7.3 Hz, 1H), 7.46 (dd, J=8.0, 1.4 Hz, 1H), 7.49 and 7.52 (each d, J=2.0 Hz, 1H, amide isomers), 7.80–7.91 (m, 3H), 8.07 (dd, J=8.3, 1.2 Hz, 1H), 8.85 and 8.86 (each s, 1H, amide isomers), 8.96 and 8.97 (each s, 1H, amide isomers), 12.62 (s, 1H); MS (FAB) m/z 605 (M$^+$+1), 607 (M$^+$+3), 609 (M$^+$+3), 626 (M$^+$+1+Na); Anal. Calcd for C$_{27}$H$_{24}$BrClFN$_3$O$_5$.0.8H$_2$O: C, 52.37; H, 4.17; N, 6.79; F, 3.07. Found: C, 52.63; H, 4.12; N, 6.62; F, 2.97.

Example 90

4-[1-[3-bromo4-[N':(2-bromophenyl)ureido]phenylacetyl]-(4S)-fluoro-(2S)-pyrrolidinyl]methoxybenzoic acid

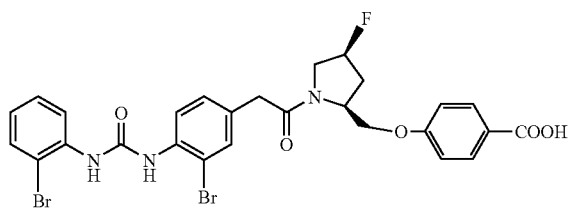

96

To a mixture of methyl 4-amino-3-bromophenylacetate (587 mg, 2.40 mmol) and 2-bromophenyl isocyanate (0.30 ml, 2.40 mmol) in THF (2 ml) was added Et$_3$N (33 ml, 0.24 mmol) at room temperature. After 4 h stirring, the reaction mixture was concentrated in vacuo. The residue was triturated by the addition of n-hexane to give methyl 3-bromo-4-[N'-(2-bromophenyl)ureido]phenylacetate (770 mg, 73%) as a pale brown powder. $^1$H-NMR (CDCl$_3$) δ 3.55 (s, 2H), 3.70 (s, 3H), 6.97 (dd, J=7.3, 1.5 Hz, 1H), 7.22 (dd, J=8.5, 2.2 Hz, 1H), 7.29–7.33 (m, 2H), 7.48 (d, J=1.0, 2.2 Hz, 1H), 7.54 (dd, J=8.0, 1.2 Hz, 1H), 8.01 (m, 2H); MS (ESI) m/z 443 (M$^+$+1), 445 (M$^+$+3), 447 (M$^+$+5).

To a stirred solution of methyl 3-bromo-4-[N'-(2-bromophenyl)ureido]phenylacetate (770 mg, 1.74 mmol) in THF (10 ml) was added 0.25 N NaOH (10 ml). After stirring at room temperature for 14 h, the solvent was concentrated in vacuo. The residue was triturated by the addition of 1 N HCl and dried at 60° C. for 2 days under a reduced pressure to give 3-bromo-4-[N'-(2-bromophenyl) ureido]phenylacetic acid (702 mg, 94%) as colorless powder. $^1$H-NMR (DMSO-d$_6$) δ 3.56 (s, 2H), 6.99 (dt, J=7.8, 1.5 Hz, 1H), 7.21 (dd, J=8.3, 1.7 Hz, 1H), 7.33 (dt, J=7.1, 1.5 Hz, 1H), 7.53 (d, J=1.7 Hz, 1H), 7.62 (dd, J=8.1, 1.5 Hz, 1H), 7.82 (d, J=8.3 Hz, 1H), 7.93 (dd, J=8.1, 1.5 Hz, 1H), 8.82 (s, 1H), 8.86 (s, 1H), 12.39 (s, 1H); MS (ESI) m/z 428 (M$^+$+1), 430(M$^+$+3).

A mixture of 3-bromo-4-[N'-(2-chlorophenyl)ureido]phenylacetic acid (428 mg, 1.00 mmol), methyl 4-[(2S, 4S)-4-fluoro-2-pyrrolidinyl]methoxybenzoate (253 mg, 1.00 mmol), EDC.HCl (288 mg, 1.50 mmol), HOBT (203 mg, 1.50 mmol) and Et$_3$N (0.70 ml, 5.00 mmol) in DMF (4 ml) was stirred at room temperature for 18 h. The mixture was poured into ice water and extracted with EtOAc. The combined extracts were washed with ice water and brine. After dried over Na$_2$SO$_4$, the extracts were concentrated in vacuo. The residue was chromatographed on silica gel [30 g, CHCl$_3$/acetone(10/1)]to give methyl 4-[1-[3-bromo-4-[N'-(2-bromophenyl)ureido]phenylacetyl]-(4S)-fluoro-(2S)-pyrrolidinyl]methoxybenzoate (720 mg, 100%) as a colorless amorphous solid. $^1$H-NMR (CDCl$_3$) δ 2.07–2.45 (m, 2H), 2.58 (m, 1H), 3.58 (d, J=9.0 Hz, 2H), 3.63–4.69 (m, 9H), 5.26–5.43 (m, 1H), 6.88–6.99 (m, 3H), 7.16 (d, J=8.3 Hz, 1H), 7.23–7.32 (m, 2H), 7.46 (dd, J=8.1, 1.5 Hz, 1H), 7.51–8.20 (m, 5H); MS (FAB) m/z 664 (M$^+$), 666 (M$^+$+3), 668 (M$^+$+5).

To a solution of methyl 4-[1-[3-bromo-4-[N'-(2-bromophenyl)ureido]phenylacetyl]-(4S)-fluoro-(2S)-pyrrolidinyl]methoxybenzoate (720 mg, 1.00 mmol) in THF (40 ml) was added 0.25 N NaOH (40 ml). After stirring at room temperature for 14 h, the mixture was concentrated in vacuo and acidified with 1 N HCl. The mixture was extracted with CHCl$_3$/MeOH (10/1). The combined extracts were washed with ice water and brine. After dried over Na$_2$SO$_4$, the extracts were concentrated in vacuo. The residue was chromatographed on silica gel [20 g, CHCl$_3$/acetone (10/1)-CHCl$_3$/MeOH(20/1)] and triturated by the addition of ether to give 96 (489 mg, 75%) as a colorless amorphous solid. MW 649.30 IR (KBr) 3450, 3313, 3070, 1709, 1684, 1525, 1435 cm$^{-1}$; $^1$H-NMR (DMSO$_{d6}$) δ 2.25–2.50 (m, 2H), 3.67 (d, J=8.3 Hz, 2H), 3.73–4.68 (m, 5H), 5.31–5.53 (m, 1H), 6.98–7.08 (m, 3H), 7.21 (d, J=8.2 Hz, 1H), 7.34 (t, J=8.8 Hz, 1H), 7.50 and 7.53 (each s, 1H, amide isomers), 7.62 (d, J=8.0 Hz, 1H), 7.80–7.96 (m, 4H), 8.82 (s, 1H), 8.85 and 8.86 (each s, 1H, amide isomers), 12.63 (br, 1H); MS (FAB) m/z 650 (M$^+$+1), 652 (M$^+$+3), 654 (M$^+$+3), 672 (M$^+$+Na); Anal. Calcd for C$_{27}$H$_{24}$Br$_2$FN$_3$O$_5$.0.9H$_2$O: C, 48.73; H, 3.91; N, 6.31; F, 2.85. Found: C, 48.96; H, 3.98; N, 5.92; F, 2.77.

Example 91

4-[1-[4-[N'-(2-methylphenyl)ureido]-2,3 difluorophenylacetyl]-(4S)-fluoro-(2S)-pyrrolidinyl methoxy]benzoic acid.

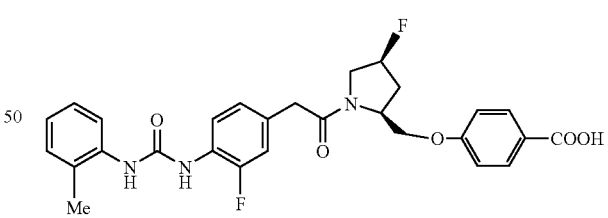

97

To a stirred solution of tert-butyl ethyl malonate (5.35 ml, 28.2 mmol) in DMF (150 ml) was added NaH (60% in oil, 3.38 g, 84.7 mmol) at rt. After 20 min, 2,3-difluoronitrobenzene (5 g, 28.2 mmol) in DMF (50 mL) was added dropwise via dropping funnel. Following the addition, the mixture was stirred for 3 hours at rt. The mixture was poured into ice-water and sat. NH$_4$Cl (100 mL). The mixture was extracted with EtOAc and the combined organic layer was washed with 1M HCl and brine, dried over MgSO$_4$, filtered and concentrated. The residue was dissolved to dichloromethane (20 mL), and added TFA (20 mL) at rt. The mixture was refluxed for 18 h. The mixture was evaporated in vacuo, coevaporated with toluene (20 mL×2). The residue was chromatographed on silica gel (middle pressure chromatography system:YAMAZEN YFLC-5404-FC, linear gradient hexane-EtOAc 10:0 to 1:1, φ50 mg×300 mg, 15 mL/min) to give ethyl 2,3-difluoro-4-nitrophenylacetic acid (5.85 g, 85%) as a yellow oil. $^1$H-NMR (CDCl$_3$) δ 1.30 (m, 3 H), 3.78 (s, 2 H), 4.22 (m, 2 H), 7.22 (m, 1 H), 7.84 (m, 1 H); MS (FAB) m/z 246 (M$^+$+1).

To a stirred solution of ethyl 2,3-difluoro-4-nitrophenylacetate (5.85 g, 23.9 mol) in EtOH (100 mL), was added SnCl$_2$ (16.1 g, 71.6 mmol) at rt. The stirring was continued for 18 hours at reflux. After removal of the solvent, the residue was dissolved in CHCl$_3$ (100 mL) and poured into ice water-4M NaOH (40 mL of 4M NaOH in 300 mL of ice-water), extracted with CHCl$_3$ (100 mL×2), dried over anhydrous MgSO$_4$, and concentrated under a reduced pressure. The residue was chromatographed on silica gel (middle pressure chromatography system YAMAZEN YFLC-5404, linear gradient of hexane-EtOAc from 9:1 to 7:3, φ50 mg×500 mg, 15 ml/min) to give ethyl 4-amino-2,3-difluorophenylacetic acid (1.94 g, 38%) as a colorless oil. $^1$H-NMR (CDCl$_3$) δ 1.25 (t, J=7.3 Hz, 3 H), 3.55 (d, J=1.0 Hz, 2 H), 3.78 (br s, 2 H), 4.15 (dd, J=7.2 Hz, 14.2 Hz, 2 H), 6.49 (dt, J=1.8, 8.2 Hz, 1 H), 6.78 (m, 1 H); MS (FAB) m/z 216 (M$^+$+1).

To a stirred solution of ethyl 4-amino-2,3-difluorophenylacetate (323 mg, 1.5 mmol) in DMF (8 mL), were added triethylamine (0.209 ml, 1.5 mmol) and 2-methylphenyl isocyanate (0.372 ml, 3.0 mmol) at rt. The stirring was continued for 48 hour at 80° C. The reaction mixture was evaporated in vacuo, and the solid was suspended to n-hexane. The solid was collected through filtration. The solid was dissolved in THF-MeOH (1:1, v/v, 20 mL), and was added 4M NaOH (10 mL) at rt. The stirring was continued for 18 hours at rt. The reaction was poured into 1M HCl, and the resulting precipitate was collected through filtration. The solid was recrystallized with CHCl$_3$-n-hexane to give 4-[(2-methylphenyl)ureido]-2,3-difluorophenylacetic acid (200 mg, 42%) as a white solid. $^1$H-NMR (CDCl$_3$) δ 2.30 (s, 3 H), 3.35 (s, 2 H), 6.98 (m, 1 H), 7.04 (m, 1 H), 7.18 (d, J=7.3 Hz, 2 H), 7.69 (d, J=8.1 Hz, 1 H), 7.90 (m, 1 H); MS (FAB) m/z 321 (M$^+$+1).

To a stirred solution of methyl 4-(4-S-4-fluoro-2-pyrrolidinyl)methoxy benzoate (63 mg, 0.25 mmol) and 4-[N'-(2-methylphenyl)ureido]-2,3 difluorophenylacetic acid (82 mg, 0.25 mmol) in DMF (5 mL), were added EDC.HCl (72 mg, 0.38 mmol), HOBt (69 mg, 0.48 mmol), and DMAP (cat.), and the stirring was continued overnight at rt. The mixture was diluted with EtOAc (50 mL), washed with 1M NaOH, 1M HCl, and brine, dried over anhydrous MgSO4, and concentrated under a reduced pressure. The residue was dissolved in THF-MeOH-H$_2$O (21 mL, 1:1:1, v/v/v) and the stirring was continued for 6 h at rt. The mixture was poured into 1M HCl and extracted with CHCl$_3$-MeOH (9:1, v/v). The combined organic phase was dried over anhydrous MgSO4, and concentrated under a reduced pressure. The residue was purified with TLC (Whatman, PLK-5F, CHCl$_3$/MeOH, 20:1, v/v) to give 97 (69 mg, 51%) as a white powder. MW 541.52 IR (KBr) 3340, 1604, 1540, 1251, 1168, 754 cm$^{-1}$; $^1$H-NMR (DMSO-d$_6$) δ 2.25 (s, 3 H), 2.32 (m, 2 H), 3.68–4.40 (m, 7 H), 5.32–5.55 (m, 1 H), 6.98 (m, 2 H), 7.05 (d, J=8.8 Hz, 2 H), 7.83 (d,.J=8.8 Hz, 2 H), 7.82–7.92 (m, 2 H), 8.40 (s, 1 H), 9.14 (s, 1 H); MS (ESI) m/z 564 (M$^+$+Na); Anal. Calcd for C$_{28}$H$_{26}$F$_3$N$_3$O$_5$.2.0H$_2$O: C, 58.23; H, 5.24; N, 7.28. Found: C, 58.07, H, 4.84; N, 7.03.

Example 92

4-[1-[4-[N'-(2-methylphenyl)ureido]-2,5-difluorophenylacetyl]-(4S)-fluoro-(2S)-pyrrolidinyl methoxy]benzoic acid

98

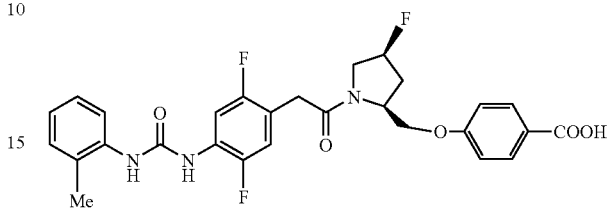

To a stirred solution of di-tert-butyl ethyl malonate (6.32 ml, 28.2 mmol) in DMF (150 ml), was added NaH (60% in oil, 3.38 g, 84.7 mmol) at rt. After 20 min, 2,5-difluoronitrobenzene (5 g, 28.2 mmol) in DMF (50 mL) was added dropwise via dropping funnel. Following the addition, the mixture was stirred for 3 hours at rt. The mixture was poured into ice-water and sat. NH$_4$Cl (100 mL). The mixture was extracted with EtOAc and the combined organic layer was washed with 1M HCl and brine, dried over MgSO$_4$, filtered and concentrated. The residue was dissolved to dichloromethane (20 mL), and added TFA (20 mL) at rt. The mixture was refluxed for 18 h. The mixture was evaporated in vacuo, coevaporated with toluene (20 mL×2). The residue was dissolved in MeOH (150 mL), and added conc. H$_2$SO$_4$ (5 mL). The mixture was refluxed for 18 h. The mixture was diluted with EtOAc (300 mL), washed with water, 1M HCl, and brine, dried over anhydrous MgSO$_4$, and concentrated under a reduced pressure. The residue was chromatographed on silica gel (middle pressure chromatography system: YAMAZEN YFLC-5404-FC, linear gradient hexane-EtOAc 10:0 to 1:1, φ50 mg×300 mg, 15 mL/min) to give ethyl 2,5-difluoro-4-nitrophenylacetic acid (6.53 g, 90%) as a yellow oil. $^1$H-NMR (CDCl$_3$) δ 3.75 (s, 2 H), 3.76 (s, 3 H), 7.29 (dd, J=5.8 Hz, 10.5 Hz, 1 H), 7.81 (dd, J=6.0 Hz, 8.4 Hz, 1 H); MS (ESI) m/z 232 (M$^+$+1).

To a stirred solution of ethyl 2,5-difluoro-4-nitrophenylacetate (5.88 g, 25.4 mol) in EtOH (100 mL), was added SnCl$_2$ (17.2 g, 76.3 mmol) at rt. The stirring was continued for 18 hours at reflux. After removal of the solvent, the residue was dissolved in CHCl$_3$ (100 mL) and poured into ice water-4M NaOH (40 mL of 4M NaOH in 300 mL of ice-water), extracted with CHCl$_3$ (100 mL×2), dried over anhydrous MgSO$_4$, and concentrated under a reduced pressure. The residue was chromatographed on silica gel (middle pressure chromatography system YAMAZEN YFLC-5404, linear gradient of hexane-EtOAc from 9:1 to 7:3, φ50 mg×500 mg, 15 ml/min) to give ethyl 4-amino-2,5-difluorophenylacetic acid (2.85 g, 52%) as a colorless oil. $^1$H-NMR (CDCl$_3$) δ 1.28 (t, J=7.3 Hz, 3 H), 3.51 (s, 2 H), 3.78 (br s, 2 H), 4.15 (dd, J=7.2 Hz, 14.2 Hz, 2 H), 6.47 (dd, J=7.5, 10.4 Hz, 1 H), 6.88 (dd, J=6.7, 11.0 Hz, 1 H); MS (FAB) m/z 216 (M$^+$+1).

To a stirred solution of ethyl 4-amino-2,5-difluorophenylacetate (323 mg, 1.5 mmol) in DMF (8 mL), were added triethylamine (0.209 ml, 1.5 mmol) and 2-methylphenyl isocyanate (0.372 ml, 3.0 mmol) at rt. The stirring was continued for 48 hour at 80° C. The reaction mixture was evaporated in vacuo, and the solid was suspended to n-hexane. The solid was collected through filtration. The solid was dissolved in THF-MeOH (1:1, v/v, 20 mL), and was added 4M NaOH (10 mL) at rt. The stirring was continued for 18 hours at rt. The reaction was poured into 1M HCl, and the resulting precipitate was collected through filtration. The solid was recrystallized with CHCl₃-n-hexane to give 4-[(2-methylphenyl)ureido]-2,5-difluorophenylacetic acid (214 mg, 46%) as a white solid. ¹H-NMR (CDCl₃) δ 2.30 (s, 3 H), 3.35 (m, 2 H), 7.02 (m, 2 H), 7.18 (d, J=7.3 Hz, 2 H), 7.69 (d, J=7.8 Hz, 1 H), 8.03 (m, 1 H); MS (FAB) m/z 321 (M⁺+1).

To a stirred solution of methyl 4-[(4S)-fluoro-(2S)-pyrrolidinyl]methoxybenzoate (63 mg, 0.25 mmol) and 2,5-difluoro-4-[N'-(2-methylphenyl)ureido]phenylacetic acid (82 mg, 0.25 mmol) in DMF (5 mL) was added EDC.HCl (72 mg, 0.38 mmol), HOBt (69 mg, 0.48 mmol), and DMAP (cat.), and the stirring was continued overnight at rt. The mixture was diluted with EtOAc (50 mL), washed with 1M NaOH, 1M HCl, and brine, dried over anhydrous MgSO4, and concentrated under a reduced pressure. The residue was dissolved in THF-MeOH-H₂O (21 mL, 1:1:1, v/v/v) and the stirring was continued for 6 h at rt. The mixture was poured into 1M HCl and extracted with CHCl₃-MeOH (9:1, v/v). The combined organic phase was dried over anhydrous MgSO4, and concentrated under a reduced pressure. The residue was purified with TLC (Whatman, PLK-5F, CHCl₃/MeOH, 20:1, v/v) to give 98 (69 mg, 51%) as a white powder. MW 541.52 IR-ATR: 3351, 1604, 1537, 1167, 754 (cm⁻¹); ¹H-NMR (DMSO) δ 2.25 (s, 3 H), 2.32 (m, 2 H), 3.68–4.70 (m, 7 H), 5.32–5.55 (m, 1 H), 6.97 (t, J=7.6 Hz, 1 H), 7.06 (d, J=8.5 Hz, 2 H), 7.20 (m, 3 H), 7.87 (d, J=8.8 Hz, 2 H), 7.83–8.04 (m, 2 H), 8.45 (s, 1 H), 9.18 (s, 1 H); MS (ESI) m/z 564 (M⁺+Na); Anal. Calcd for C₂₈H₂₆F₃N₃O₅.1.75 H₂O: C, 58.69; H, 5.19; N, 7.33. Found: C, 58.54, H, 4.85; N, 6.98.

Example 93

4-[1-[4-[N'-(2-chlorophenyl)ureido]-3-methoxyphenylacetyl]-4-fluoro-2-pyrrolidinyl]methylamino benzoic acid

99

4-[1-[4-[N'-(2-bromophenyl)ureido]-3-methoxyphenylacetyl]-4-fluoro-2-pyrrolidinyl]methylamino benzoic acid

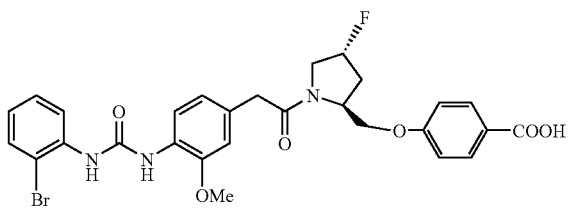

100

To a stirred solution of methyl1-tert-butoxycarbonyl-4-fluoropyrrolidine-2-carboxylate(1.2 g, 4.85 mmol) in MeOH (5 ml) was added 1 N NaOH (5 ml) and the mixture was stirred at room temperature for 1 hr. The mixture was concentrated in vacuo, water was added thereto, and neutralized with 1 N HCl. The mixture was extracted with EtOAc. The extract was washed with water, then dried over Na₂SO₄, and concentrated in vacuo to give 1-tert-butoxycarbonyl-4-fluoropyrrolidine-2-carboxylic acid (1.1 g, quant) as a colorless oil. ¹H-NMR (CDCl₃) δ 1.47 (br s, 9H), 2.78–2.83 (br s, 3H), 4.37 (s, 2H), 6.73–6.76 (m, 3H), 7.17 (m, 1H).

To a stirred solution of 1-tert-butoxycarbonyl-4-fluoropyrrolidine-2-carboxylic acid (1.1 g, 4.7 mmol) in THF (10.0 ml) was added BH₃.THF(1.0 M solution in THF, 10.0 ml, 10.0 mmol) at 0° C. After stirred at room temperature for 1.0 h. After cooled, the mixture was concentrated in vacuo. Water was added thereto at 0° C., and extracted with EtOAc. The extract was washed with water, then dried over Na₂SO₄, and concentrated in vacuo to give 1-tert-butoxycarbonyl-4-fluoro-2-pyrrolidinylmethanol (1.0 g, quant) as a a colorless oil. ¹H-NMR (CDCl₃) δ 1.48 (s, 9H), 2.29–2.39 (m, 1H), 3.38–3.59 (m, 2H), 3.74–3.88 (m, 2H), 4.09–4.14 (m, 2H), 4.85 (m, 1H), 5.03 (br s, 1H), 5.16 (br s, 1H).

To a stirred solution of oxalyl chloride (0.28 ml, 2.3 mmol) in CH₂Cl₂ (20.0 ml) was added DMSO (0.39 ml) at −78° C. After 5 minutes, to the mixture was added 1-tert-butoxycarbonyl-4-fluoro-2-pyrrolidinylmethanol (500 mg, 2.28 mmol) in CH₂Cl₂ (5.0 ml). The mixture was stirred for 30 minutes at −78° C., and triethylamine (1.6 ml) was added. The mixture was stirred for 30 minutes at −78° C., and stirred for 30 minutes at room temperature. Water was added to the mixture, and extracted with CH₂Cl₂. The organic layer was dried over Na₂SO₄, and concentrated in vacuo. The crude product was used to the subsequent reaction without further purification. To a stirred solution of the crude product, methyl 4-aminobenzoate(302 mg, 2.0 mmol), and AcOH (0.13 ml) in DCE (10 ml) was added NaBH(OAc)₃ (656 mg, 3.09 mmol) at 0° C. The reaction mixture was stirred at room temperature for 18 hr. The mixture was concentrated in vacuo. Sat. NaHCO₃ was added to the residue, and extracted with CH₂Cl₂. The extract was washed with brine, dried over Na₂SO₄, and concentrated in vacuo. The residue was purified by column chromatography on silica gel with EtOAc-n-hexane (1:3, v/v) as eluent to give methyl 4-(1-tert-butoxycarbonyl-4-fluoro-2-pyrrolidinyl) methylaminobenzoate (541 mg, 77%) as a pale yellow oil. ¹H-NMR (CDCl₃) δ 1.55–1.59 (m, 1H), 2.16–2.27 (m, 1H), 2.89–3.03 (m, 2H), 3.19–3.28 (m, 2H), 3.69–3.73 (m, 1H), 3.84 (s, 3H), 5.15 and 5.29 (each s, total 1H), 6.55–6.58 (m, 2H), 7.84–7.86 (m, 2H).

To a stirred solution of methyl 4-(1-tert-butoxycarbonyl-4-fluoro-2-pyrrolidinyl)methylamino benzoate (541 mg, 1.53 mmol) in CH₂Cl₂ (8.0 ml) was added TFA (4.0 ml) at 0° C. The reaction mixture was stirred at room temperature for 0.5 hr. The mixture was concentrated in vacuo. Sat. NaHCO₃ was added to the residue, and extracted with CH₂Cl₂. The extract was washed with brine, dried over Na₂SO₄, and concentrated in vacuo. The crude product was used to the subsequent reaction without further purification. To a stirred solution of the crude product(151 mg, 0.6 mmol), 4-[N'-(2-chlorophenyl)uredio]-3-methoxyphenylacetic acid (201 mg, 0.6 mmol), HOBt (94 mg, 0.7 mmol), and triethylamine (167 μl, 1, 1.2 mmol) in THF (10.0 ml) and MeCN (10.0 ml) was added EDC.HCl (173 mg, 0.9 mmol) at 0° C. The reaction mixture was stirred at room temperature for 16 hr, and concentrated in vacuo. Water was added to the residue, and extracted with EtOAc. The extract was washed with sat. NaHCO₃, 2-M citric acid, and sat. NaHCO₃, then dried over Na₂SO₄, and concentrated in vacuo. The residue was purified by column chromatography on silica gel with n-hexane-EtOAc(1:2, v/v) as eluent to give methyl 4-[1-[4-[N'-(2-chlorophenyl)ureido]-3-methoxyphenylacetyl]-4-fluoro-2-pyrrolidinyl]methylaminobenzoate (320 mg, 94%) as an amorphous solid. ¹H-NMR (CDCl₃) δ 1.80–1.95 (m, 1H), 2.42–2.58 (m, 1H), 3.20–3.51 (m, 3H), 3.51–3.76 (m, 5H), 3.84 (s, 3H), 3.85–3.98 (m, 1H), 4.67–4.70 (m, 1H), 5.10 and 5.23 (s, each, total 1H), 5.50 (br s, 1H), 6.49–6.52 (m, 2H), 6.78–6.81 (m, 2H), 6.97–7.01 (m, 1H), 7.14–7.18 (m, 2H), 7.24–7.36 (m, 2H), 7.80–7.82 (m, 2H), 7.99–8.01 (m, 1H), 8.15–8.18 (m, 1H).

To a stirred solution of methyl 4-[1-[4-[N'-(2-chlorophenyl)ureido]-3-methoxyphenyl acetyl]-4-fluoro-2-pyrrolidinyl]methylaminobenzoate (320 mg, 0.56 mmol) in THF (5.0 ml) and MeOH (3.0 ml) was added 1 N NaOH (0.8 ml, 0.8 mmol). The mixture was stirred at 70° C. for 24 hr. The mixture was concentrated in vacuo, water was added thereto, and neutralized with 1N HCl. The resulting solid was collected, washed with water, and dried in vacuo to give 99 (280 mg, 90%) as a white crystalline solid. MW 555.00 mp 132–136° C.; IR (KBr) 3332, 2937, 1602, 1531, 1174, 752 cm⁻¹; ¹H-NMR (DMSO-d₆) δ 2.00–2.40 (m, 2H), 3.50–3.90 (m, 4H), 3.75–3.85 (m, 5H), 4.27 (m, 1H), 5.23 and 5.37 (each s, total 1H), 6.51–7.03 (m, 5H), 7.25–7.29 (m, 1H), 7.41–7.44 (m, 1H), 7.64–7.68 (m, 2H), 7.92–8.10 (m, 2H), 8.87–8.94 (m, 2H); Anal. calcd for C₂₈H₂₈N₄O₅FCl.0.6H₂O: C, 59.44; H, 5.20; N, 9.90. Found: C, 59.41; H, 5.19; N, 9.72.

To a stirred solution of methyl 4-(1-tert-butoxycarbonyl-4-fluoro-2-pyrrolidinyl)methylamino benzoate (541 mg, 1.53 mmol) in CH₂Cl₂ (8.0 ml) was added TFA (4.0 ml) at 0° C. The reaction mixture was stirred at room temperature for 0.5 hr. The mixture was concentrated in vacuo. Sat. NaHCO₃ was added to the residue, and extracted with CH₂Cl₂. The extract was washed with brine, dried over Na₂SO₄, and concentrated in vacuo. The crude product was used to the subsequent reaction without further purification. To a stirred solution of the crude product (151 mg, 0.6 mmol), 4-[N'-(2-bromophenyl)uredio]-3-methoxyphenylacetic acid (227 mg, 0.6 mmol), HOBt (94 mg, 0.7 mmol), and triethylamine (167 μl, 1.2 mmol) in THF (10.0 ml) and MeCN (10.0 ml) was added EDC.HCl (173 mg, 0.9 mmol) at 0° C. The reaction mixture was stirred at room temperature for 16 hr, and concentrated in vacuo. Water was added to the residue, and extracted with EtOAc. The extract was washed with sat. NaHCO₃, 2-M citric acid, and sat. NaHCO₃, then dried over Na₂SO₄, and concentrated in vacuo. The residue was purified by column chromatography on silica gel with n-hexane-EtOAc (2:3, v/v) as eluent to give methyl 4-[1-[4-[N'-(2-bromophenyl)ureido]-3-methoxyphenylacetyl]-4-fluoro-2-pyrrolidinyl]methylamino benzoate (280 mg, 76%) as a colorless oil. ¹H-NMR (CDCl₃) δ 1.80–1.98 (m, 1H), 1.42–1.58 (m, 1H), 3.20–3.52 (m, 3H), 3.67–3.79 (m, 5H), 3.84 (s, 3H), 3.94–3.97 (m, 1H), 4.68–4.71 (m, 1H), 5.10 and 5.23 (each s, total 1H), 5.51 (br s, 1H), 6.50–6.52 (m, 2H), 6.79–7.07 (m, 5H), 7.25–7.33 (m, 1H), 7.51–7.53 (m, 1H), 7.80–7.83 (m, 2H), 7.98–8.00 (m, 1H), 8.11–8.14 (m, 1H).

To a stirred solution of methyl 4-[1-[4-[N'-(2-bromophenyl)ureido]-3-methoxyphenyl acetyl]-4-fluoro-2-pyrrolidinyl]methylaminobenzoate (280 mg, 0.46 mmol) in THF (8.0 ml) and MeOH (8.0 ml) was added 1 N NaOH (2.8 ml, 2.8 mmol). The mixture was stirred at 70° C. for 18 hr. The mixture was concentrated in vacuo, water was added thereto, and neutralized with 1N HCl. The resulting solid was collected, washed with water, and dried in vacuo to give 100 (260 mg, 95%) as a white crystalline solid. MW 599.45 mp 131–135° C.; IR (KBr) 3332, 2935, 1602, 1529, 1174 cm⁻¹; ¹H-NMR (DMSO-d₆) δ 1.95–2.01 (m, 1H), 2.20–2.35 (m, 1H), 3.10–3.20 (m, 1H), 3.50–3.70 (m, 3H), 3.80–3.85 (m, 5H), 4.27 (m, 1H), 5.24 and 5.37 (each s, total 1H), 6.54–6.99 (m, 5H), 7.30–7.33 (m, 1H), 7.58–7.94 (m, 3H), 7.94–7.98 (m, 2H), 8.73 (m, 1H), 8.93 (m, 1H); Anal. calcd for C₂₈H₂₈N₄O₅BrF.0.7H₂O: C, 54.95; H, 4.84; N, 9.15. Found: C, 54.98; H, 4.81; N, 8.93.

Example 94

4-[1-[3-methoxy-4-[N'-(2-methylphenyl)ureido]phenylacetyl]-(4R)-fluoro-(2S)-pyrrolidinyl methoxy] benzoic acid

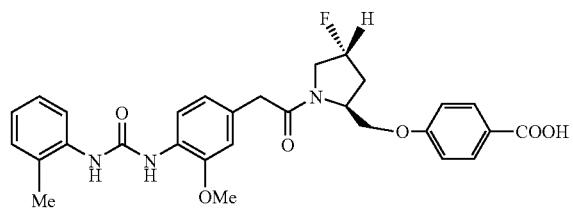

101

A mixture of methyl 4-[(4R)-fluoro-(2S)-pyrrolidinylmethoxy]benzoate (634 mg, 2.50 mmol), 3-methoxy-4-[N'-(2-methylphenyl)ureido]phenylacetic acid (787 mg, 2.50 mmol), EDC.HCl (718 mg, 3.75 mmol), HOBt (cat.), DMAP (cat.) and DMF (10 ml) was stirred overnight. The mixture was diluted with EtOAc (300 ml). The solution was washed with brine (2×100 ml), dried over MgSO₄, and concentrated in vacuo. The residue was chromatographed on silica gel with CHCl₃-EtOAc (4:1) as eluent to give methyl 4-[1-[3-methoxy-4-[N'-(2-methylphenyl)ureido]phenylacetyl]-(4R)-fluoro-(2S)-pyrrolidinylmethoxy]benzoate (1.37 g, quant) as a pale yellow viscous solid. ¹H-NMR (CDCl₃) δ 2.24 (s, 3 H), 2.26–2.47 (m, 2 H), 3.46 (s, 3 H), 3.49–3.64 (m, 4 H), 3.87 (s, 3 H), 4.06 (dd, J=9.5, 2.0 Hz, 1 H), 4.51–4.62 (m, 2 H), 5.20 and 5.33 (br s, each, total 1H), 6.63 (s, 1 H), 6.72 (d, J=8.3 Hz, 1 H), 6.77 (d, J=9.0 Hz, 2 H), 7.05 (t, J=7.6 Hz, 1 H), 7.16–7.20 (m, 3 H), 7.53 (s, 1 H), 7.63 (d, J=7.8 Hz, 1 H), 7.91 (d, J=9.0 Hz, 2 H), 8.07 (d, J=8.1 Hz, 1 H).

A mixture of methyl 4-[1-[3-methoxy-4-[N'-(2-methylphenyl)ureido]phenylacetyl]-(4R)-fluoro-(2S)-pyrrolidinylmethoxy]benzoate (1.37 g, 2.49 mmol), 0.25 N NaOH (20 ml, 5.00 mmol), and THF (20 ml) was stirred for 3 days. The mixture was poured into 1 N HCl (100 ml) and extracted with CHCl$_3$-MeOH (5:1, 2×200 ml). The combined extracts were dried over MgSO$_4$ and concentrated in vacuo. The residue was chromatographed on silica gel with CHCl$_3$-MeOH (20:1 to 4:1) to give 101 (930 mg, 70%) as a pale yellow amorphous solid. MW 535.56 $^1$H-NMR (DMSO-d$_6$) δ 2.24–2.41 (m, total 5 H), 3.42–4.66 (series of m, 10 H), 5.31 and 5.44 (br s, each, total 1 H), 6.71–7.16 (series of m, 7 H), 7.79 (d, J=8.1 Hz, 1 H), 7.85–7.89 (m, 2 H), 7.98–8.00 (m, 1 H), 8.47 (s, 1 H), 8.55 (s, 1 H); MS(FAB) m/z 536 (M$^+$+1).

Example 95

4-[(4S)-chloro-1-[3-methoxy-4-[N'-(2-chlorophenyl)ureido]phenylacetyl]-(2S)-pyrrolidinyl]methoxybenzoic acid

102

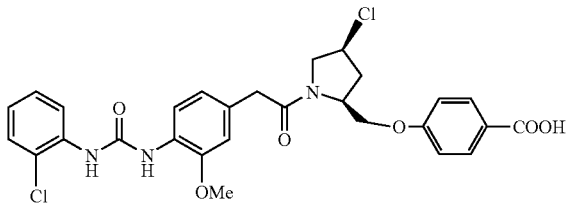

To a stirred solution of methyl 4-(trans-1-tert-butoxycarbonyl-4-hydroxy-(2S)-pyrrolidinyl) methoxybenzoate (351 mg, 1.0 mmol) and Ph$_3$P (393 mg, 1.5 mmol) in CHCl$_3$ (5.0 ml) was added CCl$_4$ (5.0 ml) at room temperature. The reaction mixture was stirred at 50° C. for 24 hr. The reaction mixture was concentrated in vacuo. The residue was purified by column chromatography on silica gel with n-hexane to n-hexane-EtOAc(4:1, v/v) as eluent to give methyl 4-(cis-1tert-butoxycarbonyl-4-chloro-(2S)-pyrrolidinyl)methoxybenzoate (340 mg, 92%) as a pale yellow oil. $^1$H-NMR (CDCl$_3$) δ 1.48 (s, 9H), 2.38–2.65 (m, 2H), 3.50–3.60 (m, 1H), 3.88 (s, 3H), 3.89–4.05 (m, 1H), 4.26–4.41 (m, 4H), 6.95–6.97 (m, 2H), 7.98 (d, J=8.5 Hz, 2H).

To a stirred solution of methyl 4-(1-tert-butoxycarbonyl-(4S)-chloro-(2S)-pyrrolidinyl) methoxybenzoate (369 mg, 1.0 mmol) in CH$_2$Cl$_2$ (3.0 ml) was added TFA (3.0 ml) at 0° C. The reaction mixture was stirred at room temperature for 0.5 hr. The mixture was concentrated in vacuo. Sat. NaHCO$_3$ was added to the residue, and extracted with CH$_2$Cl$_2$. The extract was washed with brine, dried over Na$_2$SO$_4$, and concentrated in vacuo. The crude product was used to the subsequent reaction without further purification. To a stirred solution of the crude product (185 mg, 0.5 mmol), 4-[N'-(2-chlorophenyl)uredio]-3-methoxyphenylacetic acid (167 mg, 0.5 mmol), HOBt (68 mg, 0.5 mmol), and triethylamine (208 ml, 1.5 mmol) in THF (8.0 ml) and MeCN (8.0 ml) was added EDC.HCl (144 mg, 0.75 mmol) at 0° C. The reaction mixture was stirred at room temperature for 16 hr, and concentrated in vacuo. Water was added to the residue, and extracted with EtOAc. The extract was washed with sat. NaHCO$_3$, 2-M citric acid, and sat. NaHCO$_3$, then dried over Na$_2$SO$_4$, and concentrated in vacuo. The residue was purified by column chromatography on silica gel with n-hexane-EtOAc (1:2, v/v) as eluent to give methyl 4-[(4S)-chloro-1-[3-methoxy-4-[N'-(2-chlorophenyl)ureido]phenylacetyl]-(2S)-pyrrolidinyl]methoxy benzoate (210 mg, 72%) as a colorless oil. $^1$H-NMR (CDCl$_3$) δ 3.35–3.50 (m, 1H), 3.55–3.65 (m, 1H), 3.61–3.66 (m, 3H), 3.75 (s, 3H), 3.88 (s, 3H), 3.994.04 (m, 1H), 4.35–4.40 (m, 3H), 4.48–4.53 (m, 1H), 6.77–7.10 (m, 7H), 7.25–7.36 (m, 2H), 7.93–8.00 (m, 2H), 8.18 (d, J=8.0 Hz, 1H).

To a stirred solution of methyl 4-[(4S)-chloro-1-[3-methoxy-4-[N'-(2-chlorophenyl) ureido]phenylacetyl]-(2S)-pyrrolidinyl]methoxybenzoate(210 mg, 0.35 mmol) in THF (6.0 ml) and MeOH (3.0 ml) was added 1 N NaOH (0.7 ml, 0.7 mmol). The mixture was stirred at 70° C. for 18 hr. The mixture was concentrate in vacuo, water was added thereto, and neutralized with 1 N HCl. The resulting solid was collected, washed with water, and dried in vacuo to give 102 (200 mg, 98%) as a white crystalline solid. MW 572.44 mp 126–131° C.; IR (KBr) 3330, 1685, 1604, 1533, 1438 cm$^{-1}$; $^1$H-NMR (DMSO-d$_6$) δ 2.15–2.25 (m, 1H), 2.58–2.63 (m, 1H), 3.58–3.78 (m, 3H), 3.83 (s, 3H), 4.13–4.42 (m, 4H), 4.73 (m, 1H), 6.75–7.45 (m, 7H), 7.86–8.10 (m, 4H), 8.90 (s, 1H), 8.95 (s, 1H); MS (FAB) m/z 572 (M$^+$+1); Anal. calcd for C$_{28}$H$_{27}$N$_3$O$_6$Cl: C, 58.75; H, 4.75; N, 7.34. Found: C, 58.93; H, 4.85; N, 7.15.

Example 96

4-[1-[4-[N'-(2-bromophenyl)ureido]-3-methoxyphenylacetyl]-(4S)-chloro-(2S)-pyrrolidinyl]methoxybenzoic acid

103

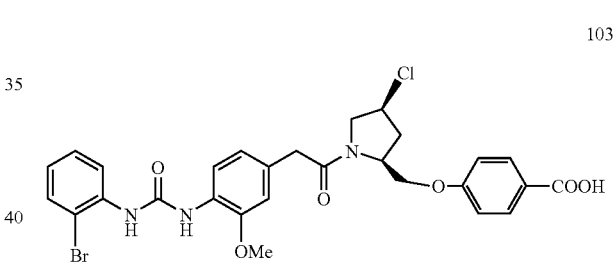

To a stirred solution of methyl 4-[1-tert-butoxycarbonyl-(4S)-chloro-(2S)-pyrrolidinyl]methoxybenzoate (369 mg, 1.0 mmol) in CH$_2$Cl$_2$ (3.0 ml) was added TFA (3.0 ml) at 0° C. The reaction mixture was stirred at room temperature for 0.5 hr. The mixture was concentrated in vacuo. Sat. NaHCO$_3$ was added to the residue, and extracted with CH$_2$Cl$_2$. The extract was washed with brine, dried over Na$_2$SO$_4$, and concentrated in vacuo. The crude product was used to the subsequent reaction without further purification. To a stirred solution of the crude product (185 mg, 0.5 mmol), 4-[N'-(2-bromophenyl)uredio]-3-methoxyphenylacetic acid (190 mg, 0.5 mmol), HOBt (68 mg, 0.5 mmol), and triethylamine (208 ml, 1.5 mmol) in THF (8.0 ml) and MeCN (8.0 ml) was added EDC.HCl (144 mg, 0.75 mmol) at 0° C. The reaction mixture was stirred at room temperature for 16 hr, and concentrated in vacuo. Water was added to the residue, and extracted with EtOAc. The extract was washed with sat. NaHCO$_3$, 2-M citric acid, and sat. NaHCO$_3$, then dried over Na$_2$SO$_4$, and concentrated in vacuo. The residue was purified by column chromatography on silica gel with n-hexane-EtOAc (1:2, v/v) as eluent to give methyl 4-[1-[4-[N'-(2-bromophenyl)ureido]-3-methoxyphenylacetyl]-(4S)-chloro-(2S)-pyrrolidinyl]methoxybenzoate (260 mg, 83%) as a colorless oil. $^1$H-NMR (CDCl$_3$) δ 2.32–2.50 (m, 1H), 2.53–2.65 (m, 1H), 3.61–3.67 (m, 3H), 3.75 (s, 3H), 3.88 (s, 3H), 3.99–4.03 (m, 1H), 4.35–4.40 (m, 3H), 4.45–4.55 (m, 1H), 6.78–7.10 (m, 7H), 7.28–7.33 (m, 1H), 7.52 (d, J=8.0 Hz, 1H), 7.94–7.99 (m, 3H), 8.14 (d, J=8.3 Hz, 1H).

To a stirred solution of methyl 4-[1-[4-[N'-(2-bromophenyl)ureido]-3-methoxyphenyl acetyl]-(4S)-chloro-(2S)-pyrrolidinyl]methoxybenzoate (260 mg, 0.4 mmol) in THF (6.0 ml) and MeOH (3.0 ml) was added 1 N NaOH (0.8 ml, 0.8 mmol). The mixture was stirred at 70° C. for 24 hr. The mixture was concentrate in vacuo, water was added thereto, and neutralized with 1 N HCl. The resulting solid was collected, washed with water, and dried in vacuo to give 103 (210 mg, 83%) as a white crystalline solid. MW 616.89 mp 127–132° C.; IR (KBr) 3330, 1685, 1604, 1529, 1434 cm$^{-1}$; $^1$H-NMR (DMSO-d$_6$) δ 2.18–2.28 (m, 1H), 2.60–2.70 (m, 1H), 3.55–3.75 (m, 3H), 3.83 (s, 3H), 4.12–4.42 (m, 4H), 4.60–4.75 (m, 1H), 6.75–7.06 (m, 5H), 7.30–7.34 (m, 1H), 7.60 (d, J=7.3 Hz, 1H), 7.86–7.94 (m, 5H), 8.75 (s, 1H), 8.94 (s, 1H); MS (FAB) m/z 616 (M$^+$), 618 (M$^+$+2); Anal. calcd for $C_{28}H_{27}N_3O_6ClBr$: C, 54.52; H, 4.41; N, 6.81. Found: C, 54.98; H, 4.54; N, 6.66.

Example 97

4-[(4R)-chloro-1-[3-methoxy-4-[N'-(2-methylphenyl)ureido]phenylacetyl]-(2S)-pyrrolidinyl methoxy]benzoic acid

104

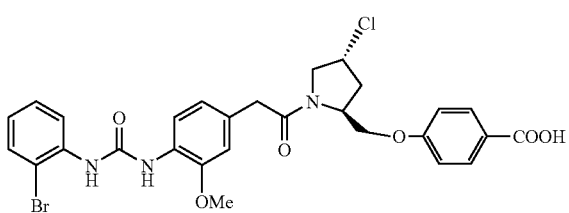

4-[(4R)-chloro-1-[4-[N'-(2-chlorophenyl)ureido]-3-methoxyphenylacetyl]-(2S)-pyrrolidinyl methoxy]benzoic acid

105

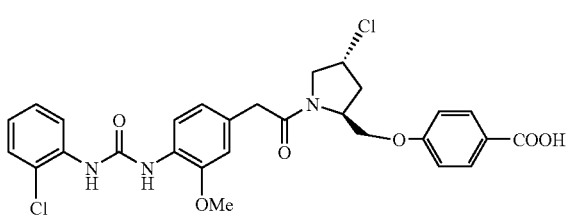

To a stirred solution of methyl 1-(tert-butoxycarbonyl)-(4S)-hydroxy-(2S)-pyrrolidinylcarboxylate (1.81 g, 7.34 mmol) in CCl$_4$—CH$_2$Cl$_2$ (20 ml, 1:1, v/v) was added Ph$_3$P (3.87 mmol, 14.75 mmol) and the reaction mixture was stirred at room temperature for 2 hr. To the mixture was added EtOH (5 ml) and the reaction mixture was stirred at room temperature overnight. After removal of the solvent, the residue was purified by column chromatography on silica-gel with n-hexane-EtOAc (3:1, v/v) as eluent to give Synthesis of methyl 1-(tert-butoxycarbonyl)-(4R)-chloro-(2S)-pyrrolidinylcarboxylate (1.36 g, 70%) as a colorless oil. $^1$H-NMR (CDCl$_3$) δ 1.42 (s, 9 H), 2.32–2.39 (m, 1 H), 2.49–2.54 (m, 1 H), 3.66–3.92 (series of s and m, total 5 H), 4.44–4.55 (m, 2 H); MS(FAB) m/z 264 (M$^+$+1).

To a stirred solution of methyl 1-(tert-butoxycarbonyl)-(4R)-chloro-(2S)-pyrrolidinyl carboxylate (1.35 g, 5.12 mmol) in THF. (10 ml) was added 0.5 N NaOH (10 ml) and the reaction mixture was heated under reflux for 1.5 hr. After cooled to room temperature, the mixture was poured into ice-1 N HCl and the mixture was extracted with CHCl$_3$-MeOH (9:1, v/v). The extract was washed with brine, dried over Na$_2$SO$_4$ and evaporated to give 1-(tert-butoxycarbonyl)-(4R)-chloro-(2S)-pyrrolidinylcarboxylic acid (1.28 g, quant.) as a colorless oil. $^1$H-NMR (CDCl$_3$) δ 1.44 (s, 9 H), 2.37–2.54 (m, 2 H), 3.68–3.88 (m, 2 H), 4.42–4.45 (m, 2 H).

To a stirred solution of I-(tert-butoxycarbonyl)-(4R)-chloro-(2S)-pyrrolidinylcarboxylic acid (1.28 g, 5.13 mmol) in THF (20 ml) was added dropwise BH$_3$.DMS (0.60 ml, 6.33 mmol) via a syringe and the reaction mixture was stirred at room temperature for 1 hr. After removal of the solvent, the residue was dissolved in CH$_2$Cl$_2$. The solution was washed with H$_2$O, brine, dried over Na$_2$SO$_4$, and evaporated. The residue was purified by column chromatography on silica-gel with CHCl$_3$-MeOH (50:1, v/v) as eluent to give 1-(tert-butoxycarbonyl)-(4R)-chloroprolinol (0.88 g, 730%) as a colorless oil. $^1$H-NMR (CDCl$_3$) δ 1.48 (s, 9 H), 1.98 (m, 1 H), 2.26–2.32 (m, 1 H), 3.56–3.65 (m, 2 H), 3.77 (m, 2 H), 4.24 (m, 1 H), 4.41–4.46 (m, 2 H); MS(FAB) m/z 236 (M$^+$+1).

To a cooled (0° C.), stirred solution of methyl 4-hydroxybenzoate (560 mg, 3.68 mmol), 1-(tert-butoxycarbonyl)-(4R)-chloroprolinol (870 mg, 3.69 mmol), Ph$_3$P (1.16 g, 4.42 mmol) in THF (15 ml) was added DIAD (870 ml, 4.42 mmol) and the reaction mixture was heated under reflux for 10 hr. After cooled to room temperature, the mixture was evaporated. The residue was purified by column chromatography on silica-gel with n-hexane-EtOAc (5:1, v/v) as eluent to give methyl 4-[1-(tert-butoxycarbonyl)-(4R)-chloro-(2S)-pyrrolidinylmethoxy]benzoate (890 mg, 65%) as a white solid. mp 116–120° C.; $^1$H-NMR (CDCl$_3$) δ 1.47 (s, 9 H), 2.39–2.53 (m, 2 H), 3.69–3.70 and 4.13–4.17 (m, total 3 H), 3.88 (s, 3 H), 4.30–4.41 (m, 2 H), 4.50–4.55 (m, 1 H), 6.90–6.92 (m, 2 H), 7.96–7.98 (m, 2 H); MS(FAB) m/z 370 (M$^+$+1); Anal. Calcd for $C_{18}H_{24}ClNO_5$: C, 58.46; H, 6.54; Cl; 9.59; N, 3.79. Found: C, 58.35; H, 6.56; Cl, 9.75; N, 3.77.

To a stirred solution of methyl 4-[1-(tert-butoxycarbonyl)-(4R)-chloro-(2S)-pyrrolidinylmethoxy]benzoate (840 mg, 2.27 mmol) in CH$_2$Cl$_2$ (10 ml) was added TFA (10 ml) and the reaction mixture was stirred at room temperature overnight. The mixture was concentrated in vacuo and made basic by sat. NaHCO$_3$. The mixture was extracted with CHCl$_3$, washed with brine, dried over Na$_2$SO$_4$, and evaporated to give methyl 4-[(4R)-chloro-(2S)-pyrrolidinylmethoxy]benzoate (580 mg, 95%) as a white solid. mp 61–64° C.; $^1$H-NMR (CDCl$_3$) δ 1.85 (br s, 1 H), 2.03–2.10 (m, 1 H), 2.29–2.35 (m, 1 H), 3.19–3.31 (m, 2 H), 3.88 (s, 3 H), 3.92–4.06 (m, 3 H), 4.53–4.56 (m, 1 H), 6.91 (d, J=8.8 Hz, 2 H), 7.98 (d, J=8.8 Hz, 2 H); MS (FAB) m/z 270 (M$^+$+1).

A mixture of 3-methoxy-4-[N'-(2-methylphenyl)ureido] phenylacetic acid (385 mg, 1.22 mmol), methyl 4-[(4R)-chloro-(2S)-pyrrolidinylmethoxy]benzoate (330 mg, 1.22 mmol), EDC.HCl (281 mg, 1.47 mmol), HOBt (200 mg, 1.48 mmol) and Et$_3$N (205 ml, 1.47 mmol) in THF (10 ml) was stirred at room temperature overnight. The mixture was diluted with H₂O and extracted with EtOAc. The extract was washed with brine, dried over Na₂SO₄ and evaporated. The residue was purified by column chromatography on silica-gel with CHCl₃-MeOH (100:1 to 50:1, v/v) as eluent to give methyl 4-[(4R)-chloro-1-[3-methoxy-4-[N'-(2-methylphenyl)ureido]phenylacetyl]-(2S)-pyrrolidinylmethoxy]benzoate (670 mg, 97%) as a white foam. $^1$H-NMR (CDCl₃) δ 2.28 (s, 3 H), 2.33–2.57 (m, 2 H), 3.50 (s, 3 H), 3.59–3.60 (m, 2 H), 3.75–3.82 (m, 2 H), 3.88 (s, 3 H), 4.06–4.09 (m, 1 H), 4.51–4.63 (m, 3 H), 6.65–6.80 (m, 5 H), 7.09–7.13 (m, 1 H), 7.20–7.27 (m, 3 H), 7.56–7.58 (m, 1 H), 7.91–7.93 (m, 2 H), 8.05–8.07 (m, 1 H); MS(FAB) m/z 566 (M⁺+1).

To a stirred solution of methyl 4-[(4R)-chloro-1-[3-methoxy-4-[N'-(2-methylphenyl) ureido]phenylacetyl]-(2S)-pyrrolidinylmethoxy]benzoate (480 mg, 0.85 mmol) in THF (5 ml) was added 0.5 N NaOH (5 ml) and the reaction mixture was heated under reflux for 2 hr. After cooled to room temperature, the mixture was poured into ice-1 N HCl and the resulting precipitate was collected under a reduced pressure. The crude solid was dissolved in CHCl₃-MeOH and evaporated. The residue was washed with Et₂O to give 104 (355 mg, 76%) as a white amorphous solid. MW 552.02 mp 128–132° C.; $^1$H-NMR (DMSO-d₆) δ 2.25 (s, 3 H), 2.29–2.46 (m, 2 H), 3.57–3.73 (m, 2 H), 3.78 (s, 3 H), 3.81–3.99 (m, 2 H), 4.11–4.31 (m, 2 H), 4.43–4.45 and 4.64–4.67 (each m, total 1 H), 4.83–4.85 (m, 1 H), 6.71–7.17 (m, 7 H), 7.78–7.80 (m, 1 H), 7.87–7.91 (m, 2 H), 7.99–8.01 (m, 1 H), 8.47 (s, 1 H), 8.56 (s, 1 H), 12.66 (br s, 1 H); MS(FAB) m/z 552 (M⁺+1); Anal. Calcd for C₂₉H₃₀ClN₃O₆·3/4H₂O: C, 61.59; H, 5.61; Cl, 6.27; N, 7.43. Found: C, 61.56; H, 5.51; Cl, 6.68; N, 7.26.

A mixture of 4-[N'-(2-chlorophenyl)ureido]-3-methoxyphenylacetic acid (400 mg, 1.19 mmol), methyl 4-[(4R)-chloro-(2S)-pyrrolidinylmethoxy]benzoate (320 mg, 1.19 mmol), EDC.HCl (275 mg, 1.43 mmol), HOBt (195 mg, 1.44 mmol) and Et₃N (200 ml, 1.43 mmol) in THF (10 ml) was stirred at room temperature overnight. The mixture was diluted with H₂O and extracted with EtOAc. The extract was washed with brine, dried over Na₂SO₄, and evaporated. The residue was purified by column chromatography on silica-gel with CHCl₃-MeOH (100:1, v/v) as eluent to give methyl 4-[(4R)-chloro-1-[4-[N'-(2-chlorophenyl)ureido]-3-methoxyphenylacetyl]-,(2S)-pyrrolidinylmethoxy]benzoate (690 mg, 98%) as a pale yellow foam. $^1$H-NMR (CDCl₃) δ 2.35–2.41 (m, 1 H), 2.49–2.59 (m, 1 H), 3.55 (s, 3 H), 3.57–3.70 (m, 2 H), 3.73–3.86 (m, 2 H), 3.88 (s, 3 H), 4.06–4.09 (m, 1 H), 4.54–4.66 (m, 3 H), 6.67–6.81 (m, 4 H), 6.95–6.99 (m, 1 H), 7.23–7.25 (m, 1 H), 7.29–7.33 (m, 1 H), 7.47–7.49 (m, 2 H), 7.90–7.99 (m, 3 H), 8.18–8.21 (m, 1 H); MS(FAB) m/z 586 (M⁺+1).

To a stirred solution of methyl 4-[(4R)-chloro-1-[4-[N'-(2-chlorophenyl)ureido]-3-methoxyphenylacetyl]-(2S)-pyrrolidinylmethoxy]benzoate (410 mg, 0.70 mmol) in THF (5 ml) was added 0.5 N NaOH (5 ml) and the reaction mixture was heated under reflux for 5 hr. After cooled to room temperature, the mixture was poured into ice-1 N HCl and the resulting precipitate was collected under a reduced pressure. The crude solid was dissolved in CHCl₃-MeOH and evaporated. The residue was washed with Et₂O to give 105 (282 mg, 70%) as an amorphous solid. MW 572.44 mp 131–136° C.; $^1$H-NMR (DMSO-d₆) δ 2.29–2.35 (m, 1 H), 2.44–2.47 (m, 1 H), 3.58–3.74 (m, 2 H), 3.78 (s, 3 H), 3.81–3.99 (m, 2 H), 4.10–4.32 (m, 2 H), 4.44–4.46 and 4.66 (each m, total 1 H), 4.84 (m, 1 H), 6.74–7.04 (m, 5 H), 7.26–7.30 (m, 1 H), 7.43–7.45 (m, 1 H), 7.87–7.91 (m, 2 H), 7.96 (d, J=8.3 Hz, 1 H), 8.09 (d, J=8.3 Hz, H), 8.90 (s, 1 H), 8.94 (s, 1 H); Anal. Calcd for C₂₈H₂₇Cl₂N₃O₆·3/4H₂O: C, 57.39; H, 4.90; Cl, 11.66; N, 7.17. Found: C, 57.57; H, 4.94; Cl, 11.66; N, 6.89.

Example 98

4-[(4S)-hydroxy-1-[4-[N'-(2-methylphenyl)ureido]phenylacetyl]-(2S)-pyrrolidinyl]methoxybenzoic acid

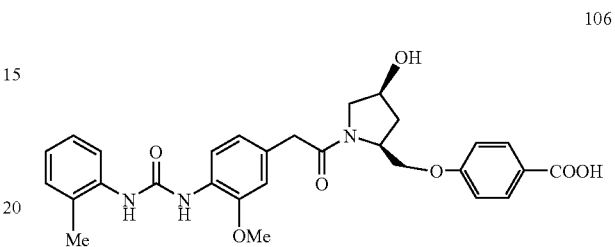

106

To a stirred solution of methyl 4-[(4S)-acetoxy-1-tert-butoxycarbonyl-(2S)-pyrrolidinyl]methoxy benzoate (2.31 g, 5.87 mmol) in CH₂Cl₂ (46 ml) was added TFA (10 ml) at room temperature. After 3.5 h stirring, the mixture was concentrated in vacuo. The residue was diluted by the addition of CH₂Cl₂ and 1 N NaOH, which were extracted with CH₂Cl₂ The combined extracts were washed with brine, dried over Na₂SO₄, which was concentrated in vacuo. The residue was chromatographed on silica gel [100 g, CHCl₃/MeOH(20/1)] to give tmethyl 4-[(4S)-acetoxy-(2S)-pyrrolidinyl]methoxybenzoate (1.89 mg, 100%) as a pale purple solid. $^1$H-NMR (CDCl₃) δ 2.10 (s, 3H), 2.14 (m, 1H), 2.65 (m, 1H), 3.52–3.63 (m, H), 3.89 (s, 3H), 4.18 (m, 1H), 4.28 (d, J=5.9 Hz, 2H), 5.38 (m, 1H), 6.93 (d, J=8.8 Hz, 2H), 7.99 (d, J=8.8 Hz, 2H).

A mixture of 3-methoxy-4-[N'-(2-methylphenyl)ureido] phenylacetic acid (343 mg, 1.09 mmol), methyl 4-[(4S)-acetoxy-(2S)-pyrrolidinyl]methoxybenzoate (320 mg, 1.09 mmol), EDC.HCl (313 mg, 1.64 mmol), HOBT (222 mg, 1.64 mmol) and Et₃N (0.76 ml, 5.45 mmol) in DMF (7 ml) was stirred at room temperature for 16 h. The mixture was poured into ice water and extracted with EtOAc. The combined extracts were washed with ice water and brine. After dried over Na₂SO₄, the extracts were concentrated in vacuo. The residue was chromatographed on silica gel [50 g, CHCl₃/Aectone (5/1)], to give methyl 4-[(4S)-acetoxy-1-[3-methoxy-4-[N'-(2-methylphenyl) ureido]phenylacetyl]-(2S)-pyrrolidinyl]methoxybenzoate (520 mg, 81%) as a brown amorphous solid. $^1$H-NMR (CDCl₃) δ 2.00 (s, 3H, one of isomers), 2.03 (s, 3H, one of isomers), 2.28 (m, 5H), 3.54 (s, 1H), 3.58 (s, 2H), 3.64 (s, 1H), 3.67 and 3.69 (each s, 3H, amide isomers), 3.85 (d, J=5.4 Hz, 1H), 3.88 (s, 3H), 4.04 (t, J=9.3 Hz, 1H), 5.27–5.34 (m, 1H), 6.51 (m, 1H), 6.76–6.89 (m, 2H), 6.94 (d, J=8.1 Hz, 1H), 7.14 (m, 1H), 7.25 (m, 4H), 7.53 (d, J=8.3 Hz, 1H), 7.96 (d, J=8.0 Hz, 1H), 8.00–8.10 (m, 2H); MS (ESI) m/z 590 (M⁺+1).

To a solution of methyl 4-[(4S)-acetoxy-1-[4-[N'-(2-methylphenyl)ureido]phenylacetyl]-(2S)-pyrrolidinyl]methoxybenzoate (520 mg, 0.882 mmol) in THF (30 ml), 0.25 N NaOH (30 ml) was added. After stirring at room temperature for 2 days, the mixture was extracted with EtOAc. The aqueous layer was acidified with 1 N HCl and extracted with CHCl₃-MeOH (10/1). The combined extracts were washed with brine. After dried over Na₂SO₄, the extracts were concentrated in vacuo. The residue was crystallized by the addition of CHCl$_3$, EtOH and ether to give 106 (68 mg, 14%) as a colorless powder. MW 533.57 mp 148–152° C. (dec.); IR (KBr) 3356, 2939, 1687, 1604, 1533, 1454, 1255 cm$^{-1}$; $^1$H-NMR (DMSO-d$_6$) δ 1.95–2.09 (m, 2H), 2.25 (s, 3H), 3.59 (d, J=5.9 Hz, 2H), 3.71 (m, 1H), 3.81 and 3.85 (each s, 3H, amide isomers), 4.13–4.47 (m, 4H), 5.19 (br, 1H), 6.70–7.21 (m, 7H), 7.79 (d, J=7.9 Hz, 1H), 7.86 (d, J=8.8 Hz, 21), 8.01 (d, J=8.3 Hz, 1H), 8.47 (s, 1H), 8.57 (s, 1H); MS (ESI) m/z 533 (M$^+$+1); Anal. Calcd for C$_{29}$H$_{31}$N$_3$O$_7$.1H$_2$O: C, 63.15; H, 6.03; N, 7.62. Found: C, 63.29; H, 5.76; N, 7.46.

Example 99

4-[1-[4-[N'-(2-chlorophenyl)ureido]-3-methoxyphenylacetyl]-(4S)-hydroxy-(2S)-pyrrolidinyl]methoxybenzoic acid

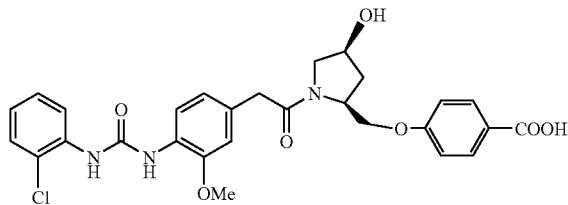

107

A mixture of 4-[N'-(2chlorophenyl)ureido]-3-methoxyphenylacetic acid (342 mg, 1.02 mmol), methyl 4-[(2S, 4S)-4-acetoxy-2-pyrrolidinyl]methoxybenzoate (300 mg, 1.02 mmol), EDC.HCl (293 mg, 1.53 mmol), HOBT (207 mg, 1.53 mmol) and Et$_3$ N (0.71 ml, 5.10 mmol) in DMF (6 ml) was stirred at room temperature for 15 h. The mixture was poured into ice water and extracted with EtOAc. The combined extracts were washed with ice water and brine. After dried over Na$_2$SO$_4$, the extracts were concentrated in vacuo. The residue was chromatographed on silica gel [50 g, CHCl$_3$/Aectone (5/1)], to give methyl 4-[(4S)-acetoxy-1-[4-[N'-(2-chlorophenyl)ureido]-3-methoxyphenylacetyl]-(2S)-pyrrolidinyl]methoxybenzoate (510 mg, 82%) as a pale brown amorphous solid. $^1$H-NMR (CDCl$_3$) δ 2.01 and 2.04 (each s, 3H, amide isomers), 2.17 (m, 2H), 3.56–3.66(m, 3H), 3.61 (s, 3H), 3.88 (s, 3H), 3.89(m, 1H), 4.07 (t, J=9.6 Hz, 1H), 4.45 (dd, J=9.2, 3.4 Hz, 1H), 4.56 (m, 1H), 5.31–5.39 (m, 1H), 6.80–7.01 (m, 4H), 7.23 (d, J=8.1 Hz, 4H), 7.34 (d, J=8.1 Hz, 1 H), 7.95 (d, J=8.5 Hz, 1H), 8.00 (m, 1H), 8.18 (d, J=8.3 Hz, 1H); MS (ESI) m/z 610 (M$^+$+1), 612 (M$^+$+3).

To a solution of methyl 4-[(4S)-acetoxy-1-[4-[N'-(2-chlorophenyl)ureido]-3-methoxyphenylacetyl]-(2S)-pyrrolidinyl]methoxybenzoate (510 mg, 0.836 mmol) in THF (30 ml), 0.25 N NaOH (30 ml) was added. After stirring at room temperature for 2 days, the mixture was extracted with EtOAc. The aqueous layer was acidified with 1 N HCl and extracted with CHCl$_3$-MeOH (10/1). The combined extracts were washed with brine. After dried over Na$_2$SO$_4$, the extracts were concentrated in vacuo. The residue was crystalized by the addition of EtOH and ether to give 107 (22 mg, 5%) as a colorless powder. MW 553.99 mp 138–142° C. (dec.); IR (KBr) 3334, 2939, 1685, 1604, 1533, 1439, 1248 cm$^{-1}$; $^1$H-NMR (DMSO-d$_6$) δ 1.93–2.14 (m, 2H), 3.60 (d, J=5.7 Hz, 2H), 3.71 (m, 1H), 3.81 and 3.85 (each s, 3H, amide isomers), 4.14–4.50 (m, 4H), 5.19 (br, 1H), 6.72 and 6.76 (each m, 1H, amideisomers), 6.85 and 6.90 (each s, 1H, amide isomers), 7.00–7.08 (m, 3H), 7.28 (t, J=7.3 Hz, 1H), 7.43 (dd, J=8.1, 1.2 Hz, 1H), 7.86–7.95 (m, 2H), 7.97 (d, J=8.1 Hz, 1H), 8.10 (dd, J=8.3, 1.5 Hz, 1H), 8.90 (s, 1H), 8.94 (s, 1H), 12.64 (br, 1H); MS (ESI) m/z 554 (M$^+$+1), 556 (M$^+$+3); Anal. Calcd for C$_{28}$H$_{28}$ClN$_3$O$_7$: C, 60.71; H, 5.05; Cl, 6.40; N, 7.58. Found: C, 60.47; H, 5.37; Cl, 6.31; N, 7.19.

Example 100

4-[(4S)-acetoxy-1-[4-[N'-(2-bromophenyl)ureido]phenylacetyl]-(2S)-pyrrolidinyl]methoxybenzoic acid

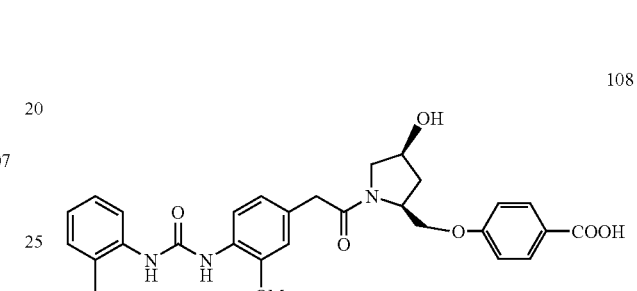

108

A mixture of 4-[N'-(2-bormophenyl)ureido]-3-methoxyphenylacetic acid (387 mg, 1.02 mmol), methyl 4-[(4S)-acetoxy-(2S)-pyrrolidinyl]methoxybenzoate (300 mg, 1.02 mmol), EDC.HCl (293 mg, 1.53 mmol), HOBT (207 mg, 1.53 mmol) and Et$_3$ N (0.71 ml, 5.10 mmol) in DMF (6 ml) was stirred at room temperature for 15 h. The mixture was poured into ice water and extracted with EtOAc. The combined extracts were washed with ice water and brine. After dried over Na$_2$SO$_4$, the extracts were concentrated in vacuo. The residue was chromatographed on silica gel [50 g, CHCl$_3$/Aectone (5/1)], to give methyl 4-[(4S)-acetoxy-1-[4-[N'-(2-bromophenyl)ureido]phenylacetyl]-2S)-pyrrolidinyl]methoxybenzoate (510 mg, 76%) as a yellow oil. $^1$H-NMR (CDCl$_3$) δ 2.01 and 2.04 (each s, 31, amide isomers), 2.31 (m, 2H), 3.54–3.68 (m, 3H), 3.76 (s, 2H), 3.88 (s, 3H), 3.89–4.58 (m, 4H), 5.31–5.36 (m, 1H), 6.81–6.96 (m, 51), 7.19–7.32 (m, 31), 7.51 (d, J=8.0 Hz, 1H), 7.93–8.00 (m, 311), 8.13 (d, J=8.3 Hz, 1H); MS (ESI) m/z 654 (M$^+$+1), 656 (M$^+$+3).

To a solution of methyl 4-[(4S)-acetoxy-1-[4-[N'-(2-bromophenyl)ureido]phenylacetyl]-(2S)-pyrrolidinyl]methoxybenzoate (510 mg, 0.779 mmol) in THF (30 ml), 0.25 N NaOH (30 ml) was added. After stirring at room temperature for 2 days, the mixture was extracted with EtOAc. The remaining aqueous layer was acidified with 1 N HCl and extracted with CHCl$_3$-MeOH (10/1). The combined extracts were washed with brine. After dried over Na$_2$SO$_4$, the extracts were concentrated in vacuo. The residue was crystalized by the addition of EtOH and ether, to give 108 (87 mg, 19%) as a pale brown powder. MW 598.44 mp 143–151° C. (dec.); IR (KBr) 3332, 2937, 1685, 1604, 1529, 1529, 1435 cm$^-$; $^1$H-NMR (DMSO-d$_6$) δ 1.92–2.14 (m, 2H), 3.60 (d, J=5.9 Hz, 2H), 3.72 (m, 1H), 3.81 and 3.85 (each s, 3H, amide isomers), 4.14–4.49 (m, 4H), 5.19 (br, 1H), 6.72 and 6.75 (each m, 1H, amide isomers), 6.85 and 6.90 (each m, 1H, amide isomers), 6.97 (t, J=6.1 Hz, 1H), 7.06 (d, J=8.8 Hz, 2H), 7.32 (t, J=7.1 Hz, 1H), 7.60 (dd, J=7.8, 1.2 Hz, 1H), 7.86 (d, J=8.8 Hz, 2H), 7.87–7.97 (m, 3l1), 8.74 (s, 1H), 8.93 (s, 1H), 12.60 (br, 1H); MS (ESI) m/z 559 (M$^+$+1), 561 (M$^+$+3); Anal. Calcd for $C_{28}H_{28}BrN_3O_7 \cdot 0.1 H_2O$: C, 56.03; H, 4.74; Br, 13.31; N, 7.06. Found: C, 55.80; H, 4.84; Br, 13.64; N, 6.66.

Example 101

4-[1-[4-[N'-(2-chlorophenyl)ureido-3-methoxyphenylacetyl]-(4R)-hydroxy-(2S)-pyrrolidinyl methoxy]benzoic acid

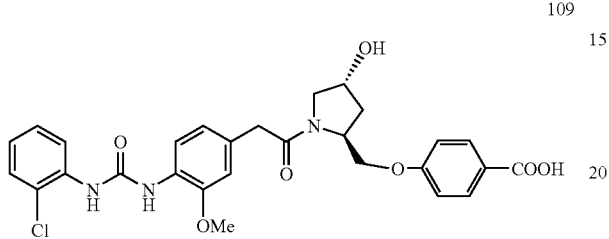

109

To a stirred solution of methyl 4-[(4R)-acetoxy-1(tert-butoxycarbonyl)-($^2$S)-pyrrolidinylmethoxy]benzoate (835 mg, 2.12 mmol) in $CH_2Cl_2$ (5 ml) was added TFA (5 ml) and the reaction mixture was stirred at room temperature for 1 hr. The mixture was concentrated in vacuo and made basic by sat. $NaHCO_3$. The mixture was extracted with $CHCl_3$, washed with brine, dried over $K_2CO_3$ and evaporated-to give methyl 4-[(4R)-acetoxy-(2S)-pyrrolidinylmethoxy]benzoate (580 mg, 95%) as a brown oil. $^1$H-NMR ($CDCl_3$) δ 1.86–1.93 (m, 1 H), 2.00–2.12 (series of s and m, total 5 H), 3.03–3.29 (m, 1 H), 3.73–3.80 (m, 1 H), 3.88 (s, 3 H), 3.93–4.01 (m, 2 H), 5.27–5.30 (m, 1 H), 6.91 (d, J=9.0 Hz, 2 H), 7.98 (d, J=9.0 Hz, 2 H); MS (FAB) m/z 294 (M$^+$+1).

A mixture of 4-[N'-(2-chlorophenyl)ureido]-3-methoxyphenylacetic acid (365 mg, 1.09 mmol), methyl 4-[(4R)-acetoxy-(2S)-pyrrolidinylmethoxy]benzoate (320 mg, 1.09 mmol), EDC.HCl (250 mg, 1.30 mmol), HOBt (180 mg, 1.33 mmol) and $Et_3$ N (182 ml, 1.31 mmol) in THF (5 ml) was stirred at room temperature for 2 days. The mixture was diluted with $H_2O$ and extracted with EtOAc. The extract was washed with brine, dried over $Na_2SO_4$ and evaporated. The residue was purified by column chromatography on silica-gel with $CHCl_3$-MeOH (50:1, v/v) as eluent to give methyl 4-[(4R)-acetoxy-1-[4-[N-(2-chlorophenyl)ureido]-3-methoxyphenyl acetyl]-(2S)-pyrrolidinylmethoxy]benzoate (500 mg, 75%) as a white foam. $^1$H-NMR ($CDCl_3$) δ 2.01 (s, 3 H), 2.03–2.05 (m, 1 H), 2.20–2.26 (m, 1 H), 2.37–2.43 (m, 1 H), 3.59 (s, 2 H), 3.62 (s, 3 H), 3.66–3.87 (m, 2 H), 3.89 (s, 3 H), 4.07–4.09 (m, 1 H), 4.48–4.51 (m, 1 H), 4.59 (m, 1 H), 6.70–6.82 (m, 4 H), 6.97–7.01 (m, 1 H), 7.24–7.35 (m, 4 H), 7.92–7.98 (m, 3 H), 8.12–8.21 (m, 1 H); MS (FAB) m/z 610 (M$^+$+1).

To a stirred solution of methyl 4-[(4R)-acetoxy-1-[4-[N'-(2-chlorophenyl)ureido]-3-methoxyphenylacetyl]-(2S)-pyrrolidinylmethoxy]benzoate (500 mg, 0.82 mmol) in THF (5 ml) was added 0.5 N NaOH (5 ml) and the reaction mixture was heated under reflux overnight. After cooled to room temperature, the mixture was poured into ice-1 N HCl and the resulting precipitate was collected under a reduced pressure. The crude solid was purified by recrystallization from $CHCl_3$-IPE to give 109 (223 mg, 49%) as a white crystalline powder. MW 553.99 mp 137–142° C.; $^1$H-NMR (DMSO-$d_6$) δ 1.95–2.09 (m, 2 H), 3.41–3.43 (m, 1 H), 3.57 (m, 3 H), 3.78 (s, 3 H), 4.07–4.40 (series of m, total 4 H), 5.07 (m, 1 H), 6.72–6.74 (m, 1 H), 6.85 (m, 1 H), 6.99–7.03 (m, 3 H), 7.25–7.29 (m, 1 H), 7.42–7.43 (m, 1 H), 7.85–7.87 (m, 2 H), 7.93–7.95 (m, 1 H), 8.07–8.09 (m, 1 H), 8.88 (s, 1 H), 8.92 (s, 1 H), 12.65 (br s, 1 H); MS (FAB) m/z 554 (M$^+$+1); Anal. Calcd for $C_{28}H_{28}ClN_3O_7 \cdot 1/2H_2O$: C, 59.73; H, 5.19; Cl, 6.30; N, 7.46. Found: C, 59.58; H, 5.32; Cl, 6.99; N, 7.21.

Example 102

4-[(4R)-hydroxy-1-[3-methoxy-4-[N'-(2-methylphenyl)ureido]phenylacetyl]-(2S)-pyrrolidinyl methoxy]benzoic acid

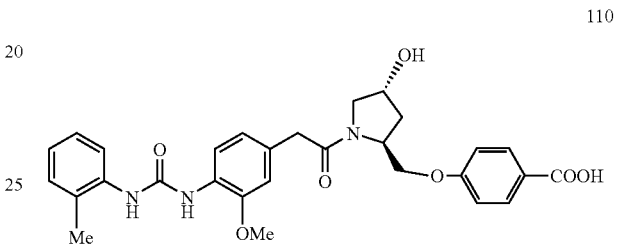

110

A mixture of 3-methoxy-4-[N'-(2-methylphenyl)ureido]phenylacetic acid (320 mg, 1.02 mmol), methyl 4-[(4R)-acetoxy-(2S)-pyrrolidinylmethoxy]benzoate (300 mg, 1.02 mmol), EDC.HCl (235 mg, 1.23 mmol), HOBt (166 mg, 1.23 mmol) and $Et_3$ N (171 ml, 1.23 mmol) in THF (5 ml) was stirred at room temperature for 2 days. The mixture was diluted with $H_2O$ and extracted with EtOAc. The extract was washed with brine, dried over $Na_2SO_4$, and evaporated. The residue was purified by column chromatography on silica-gel with $CHCl_3$-MeOH (50:1, v/v) as eluent to give methyl 4-[(4R)-acetoxy-1-[3-methoxy-4-[N'-(2-methylphenyl)ureido]phenylacetyl]-(2S)-pyrrolidinylmethoxy]benzoate (420 mg, 70%) as a white foam. $^1$H-NMR ($CDCl_3$) δ 1.99 (s, 3 H), 2.02–2.05 (m, 1 H), 2.15–2.41 (series of s and m, total 5 H), 3.55 (s, 3 H), 3.57 (s, 2 H), 3.63–3.73 (m, 2 H), 3.89 (s, 3 H), 4.07–4.10 (m, 1 H), 4.45–4.48 (m, 1 H), 4.57 (m, 1 H), 6.56 (s, 1 H), 6.66 (m, 1 H), 6.75–6.82 (m, 3 H), 7.11–7.24 (m, 4 H), 7.54–7.56 (m, 1 H), 7.92–7.94 (m, 2 H), 8.05–8.07 (m, 1 H); MS (FAB) m/z 590 (M$^+$+1).

To a stirred solution of methyl 4-[(4R)-acetoxy-1-[3-methoxy-4-[N'-(2-methylphenyl) ureido]phenylacetyl]-(2S)-pyrrolidinylmethoxy]benzoate (420 mg, 0.71 mmol) in THF (5 ml) was added 0.5 N NaOH (5 ml) and the reaction mixture was heated under reflux overnight. After cooled to room temperature, the mixture was poured into ice-1 N HCl and the resulting precipitate was collected under a reduced pressure. The crude solid was purified by recrystallization from $CHCl_3$-IPE to give 110 (182 mg, 48%) as a white crystalline powder. MW 533.57 mp 178–182° C.; $^1$H-NMR (DMSO-$d_6$) δ 1.92–2.10 (m, 2 H), 2.23 (s, 3 H), 3.40–3.44 (m, 1 H), 3.56–3.67 (m, 3 H), 3.78 (s, 3 H), 4.05–4.39 (series of m, total 4 H), 5.06 (m, 1 H), 6.71–7.01 (m, 5 H), 7.10–7.16 (m, 2 H), 7.77–7.79 (m, 1 H), 7.85–7.89 (m, 2 H), 7.98–8.00 (m, 1 H), 8.45 (s, 1 H), 8.54 (s, 1 H), 12.59 (br s, 1 H); MS (FAB) m/z 534 (M$^+$+1); Anal. Calcd for $C_{29}H_{31}N_3O_7 \cdot 1/2H_2O$: C, 64.20; H, 5.94; N, 7.74. Found: C, 64.35; H, 5.83; N, 7.68.

Example 103

4-[(4S)-fluoro-1-[3-methoxy-4-[N'-(2-methylphenyl)ureido]phenylacetyl]-2-pyrrolidinylmethyl]-1-piperazinylacetic acid

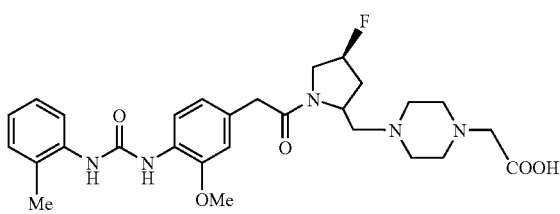

111

To a stirred solution of N-(tert-butoxycarbonyl) (4S)-fluoroprolinol (1.26 g, 5.75 mmol), Et₃N (4 ml, 28.5 mmol) and DMSO (4.1 ml, 57.5 mmol) in CH₂Cl₂ (20 ml) was added SO₃.pyridine (2.74 g, 17.2 mmol). After 5 h stirring, the mixture was evaporated to remove CH₂Cl₂ and diluted with Et₂O (200 ml). The solution was washed with 1 N HCl (200 ml) and brine (200 ml), dried over MgSO₄ and evaporated. The resulting residue was chromatographed on silica gel with hexane-EtOAc (4:1) to give N-(tert-butoxycarbonyl) (4S)-fluoroprolinal (628 mg, 50%) as a yellow oil. ¹H-NMR (CDCl₃) δ 1.41–1.47 (m, 9 H), 2.02–2.48 (m, 2 H), 3.47–3.94 (m, 2 H), 4.16 and 4.29 (each d, each J=9.8 Hz, total 1 H), 5.13 and 5.26 (each s, total 1 H).

To a stirred solution of N-(tert-butoxycarbonyl) (4S)-fluoroprolinal (1.44 g, 6.63 mmol), ethyl 1-piperazinylacetate (1.71 g, 9.94 mmol) and AcOH (759 ul, 13.3 mmol) in MeOH (20 ml) was added NaBH₃CN (880 mg, 13.3 mmol). The reaction mixture was stirred overnight and evaporated. The residue was quenched with sat. NaHCO₃ (100 ml) and evaporated with CHCl₃ (2×200 ml). The combined extracts were dried over MgSO₄ and evaporated. The oily residue was chromatographed on silica gel with CHCl₃-MeOH (20:1) to give ethyl 4-[1-(tert-butoxycarbonyl)-(4S)-fluoro-2-pyrrolidinylmethyl]-1-piperazinylacetate (2.38 g, 95%) as a yellow oil.

A mixture of ethyl 4-[1-(tert-butoxycarbonyl)-(4S)-fluoro-2-pyrrolidinylmethyl]-1-piperazinylacetate (2.38 g, 6.37 mmol), TFA (5 ml) and CH₂Cl₂ (5 ml) was stirred for 3 h. The mixture was evaporated and the residue was made basic with sat. NaHCO₃ (100 ml). The mixture was extracted with CHCl₃-MeOH (4:1, 2×150 ml) and the combined extracts were dried over K₂CO₃ and evaporated to give ethyl 4-[(4S)-fluoro-2-pyrrolidinylmethyl]-1-piperazinylacetate (1.44 g, 83%) as a brown oil. ¹H-NMR (CDCl₃) δ 1.27 (dt, J=7.1, 2.0 Hz, 3 H), 1.66–3.35 (series of m, 17 H), 4.18 (dq, J=7.1, 2.0 Hz, 2 H), 5.09 and 5.22 (each m, total 1 H).

A mixture of ethyl 4-[(4S)-fluoro-2-pyrrolidinylmethyl]-1-piperazinylacetate (1.44 g, 5.27 mmol), 3-methoxy-4-[N'-(2-methylphenyl)ureido]phenylacetic acid (1.66 g, 5.27 mmol), EDC.HCl (1.52 g, 7.91 mmol), HOBt (cat.) and DMAP (cat.) in DMF (10 ml) was stirred overnight. The mixture was diluted with EtOAc-MeOH (10:1, 220 ml). The solution was washed with brine (200 ml), dried over MgSO₄ and evaporated. The residue was chromatographed on silica gel with CHCl₃-MeOH (20:1) as eluent to give ethyl 4-[(4S)-fluoro-1-[3-methoxy-4-[N'-(2-methylphenyl) ureido]phenylacetyl]-2-pyrrolidinylmethyl]-1-piperazinylacetate (2.47 g, 82%) as a yellow viscous solid. ¹H-NMR (CDCl₃) δ 1.24–1.29 (m, 3 H), 1.92–4.36 (series of m, 7 H), 5.16 and 5.29 (each m, total 1 H), 6.43 (s, 1H), 6.74–6.81 (m, 2 H), 7.12–7.29 (m, 4 H), 7.50 (d, J=7.8 Hz, 1), 8.01–8.07 (m, 1 H).

A mixture of ethyl 4-[(4S)-fluoro-1-[3-methoxy-4-[N3-(2-methylphenyl)ureido]phenylacetyl]-2-pyrrolidinylmethyl]-1piperazinylacetate (1.0 g, 1.76 mmol) and 0.25 N NaOH (14 ml, 3.50 mmol) in THF (15 ml) was stirred overnight. The mixture was neutralized with 1 N HCl and evaporated. The residue was purified by ion exchange resin (DIAION, HP20) with H₂O to MeOH as eluent to give 111 MW 541.61 (400 mg, 40%) as a pale yellow amorphous solid. ¹H-NMR (CD₃OD) δ 2.00–3.95 (series of m, 24 H), 4.34–4.40 (m, 1 H), 5.23 and 5.36 (m, each, total 1 H), 6.78–6.82 (m, 1 H), 6.92 (m, 1 H), 7.00–7.04 (m, 1 H), 7.09–7.23 (m, 4 H), 7.59 (d, J=7.1 Hz, 1 H), 7.99–8.02 (m, 1 H); MS(FAB) m/z 542 (M⁺+1).

Example 104

4-[1-[4-[N'-(2-chlorophenyl)ureido]-3-methoxyphenylacetyl]-4,4difluoro-2-pyrrolidinylmethyl]-1-piperazinylacetic acid

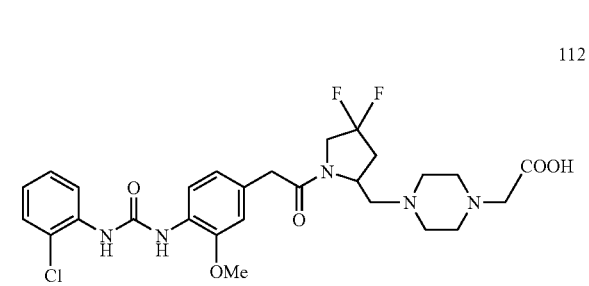

112

To a stirred mixture of 1-(tert-butoxycarbonyl)-4,4-difluoro-2-pyrrolidinylmethanol (2.11 g, 8.89 mmol), Et₃N (6.2 ml, 44.5 mmol), DMSO (6.3 ml, 88.9 mmol) in CH₂Cl₂ (20 ml) was added SO₃ pyridine (4.25 g, 26.7 mmol). After 3 h stirring, the mixture was concentrated in vacuo and diluted with Et₂O (200 ml). The resulting mixture was washed with 1 N HCl (100 ml) and brine (100 ml), dried over MgSO₄, and concentrated in vacuo. The residue was chromatographed on silica gel with hexane-EtOAc (4:1) as eluent to give 1-(tert-butoxycarbonyl)-4,4-difluoro-2-pyrrolidinecarbaldehyde (1.40 g, 67%) as a yellow oil. ¹H-NMR (CDCl₃) δ 1.45–1.52 (m, 9 H), 2.49 (m, 2 H), 3.75–3.88 (m, 2 H), 4.29–4.42 (m, 1 H), 9.54 and 9.60 (s, each, total 1 H).

To a stirred solution of 1-(tert-butoxycarbonyl)-4,4-difluoro-2-pyrrolidinecarbaldehyde (1.40 g, 5.95 mmol) and ethyl 1-piperazinylacetate (1.02 g, 5.95 mmol) in MeOH—AcOH (12:1, 13 ml) was added NaBH₃CN (787 mg, 11.9 mmol) at 0° C. After 3 days stirring, the mixture was quenched by addition of sat. NaHCO₃ (100 ml) and extracted with CHCl₃ (2×200 ml). The combined extracts were dried over MgSO₄ and concentrated in vacuo. The residue was chromatographed on silica gel with CHCl₃-MeOH (20:1) as eluent to give ethyl 4-[1-(tert-butoxycarbonyl)-4,4-difluoro-2-pyrrolidinylmethyl]-1-piperazinylacetate (822 mg, 35%) as a yellow oil. ¹H-NMR (CDCl₃) δ 1.27 (t, J=7.1 Hz, 3 H), 1.46 (m, 9 H), 1.64 (m, 2 H), 2.39–2.64 (m, 10 H), 3.19 (s, 2 H), 3.42–4.05 (series of m, 3 H), 4.18 (q, J=7.1 Hz, 2 H).

A solution of ethyl 4-[1-(tert-butoxycarbonyl)-4,4-difluoro-2-pyrrolidinylmethyl]-1-piperazinylacetate (820 mg, 2.09 mmol) and TFA (5 ml) in CH$_2$Cl$_2$ (5 ml) was stirred for 1 h. The mixture was concentrated in vacuo and the residue was made basic with sat. NaHCO$_3$. The resulting mixture was extracted with CHCl$_3$-MeOH (5:1, 2×200 ml). The combined extracts were dried over K$_2$CO$_3$ and concentrated in vacuo to give ethyl 4-(4,4-difluoro-2-pyrrolidinylmethyl)-1-piperazinylacetate (493 mg, 81%) as a brown oil. $^1$H-NMR (CDCl$_3$) δ 1.27 (t, J=7.1 Hz, 3H), 1.91 (m, 2 H), 2.27–2.60 (m, 10 H), 3.09–3.34 (m, 4 H), 3.46–3.53 (m, 1 H), 4.19 (q, J=7.1 Hz, 2 H).

A mixture of ethyl 4-(4,4-difluoro-2-pyrrolidinylmethyl)-1-piperazinylacetate (490 mg, 1.69 mmol), 4-[N'-(2-chlorophenyl)ureido]-3-methoxyphenylacetic acid (567 mg, 1.69 mmol), EDC.HCl (486 mg, 2.54 mmol), HOBt (cat.) and DMAP (cat.) in DMF (10 ml) was stirred overnight. The mixture was diluted with EtOAc (250 ml), washed with brine (2×200 ml), dried over MgSO$_4$, and concentrated in vacuo. The residue was chromatographed on silica gel with CHCl$_3$-EtOAc (4:1) to CHCl$_3$-MeOH (10:1) as eluent to give ethyl 4-[1-[4-[N'-(2-chlorophenyl) ureido]-3-methoxyphenylacetyl]-4,4-difluoro-2-pyrrolidinylmethyl]-1-piperazinylacetate (973 mg, 95%) as a yellow viscous oil. $^1$H-NMR (CDCl$_3$) δ 1.25 (t, J=7.1 Hz, 3 H), 2.31–2.68 (m, 12 H), 3.17–3.20 (m, 2 H), 3.52–3.91 (m, 4 H), 4.10–4.48 (series of m, 3 H), 6.75–6.84 (m, 2 H), 7.00 (dt, J=7.8, 1.5 Hz, 1 H), 7.16–7.29 (m, 3 H), 7.35 (dd, J=8.3, 1.5 Hz, 1 H), 8.00 (d, J=8.3 Hz, 1H), 8.18 (dd, J=8.3, 1.5 Hz, 1 H).

To a stirred solution of ethyl 4-[1-[4-[N'-(2-chlorophenyl) ureido]-3-methoxyphenylacetyl]-4,4-difluoro-2-pyrrolidinylmethyl]-1-piperazinylacetate (292 mg, 0.480 mmol) in THF (4 ml) was added 0.25 N NaOH (3.8 ml, 0.9690 mmol). After 2 days stirring, the mixture was neutralized with 1 N HCl and extracted with CHCl$_3$-MeOH (4:1, 2×200 ml). The combined extracts were dried over MgSO$_4$ and concentrated in vacuo. The residue was purified by tin layer column chromatography on silica gel with CHCl$_3$-MeOH (5:1) to give 112 MW 580.02 (81.7 mg, 29%) as a pale yellow amorphous solid. MW 580.02 $^1$H-NMR (DMSO-d$_6$) δ 2.24–2.50 (series of m, 12 H), 3.40–4.47 (series of m, 10 H), 6.76 (d, J=8.1 Hz, 1 H), 6.88 (s, 1 H), 7.02 (t, J=8.1 Hz, 1 H), 7.28 (t, J=8.1 Hz, 1 H), 7.44 (d, J=8.1 Hz, l1H), 7.97 (d, J=8.1 Hz, 1H), 8.08 (d, J=8.1 Hz, 1 H), 8.96–8.99 (m, 2 H). MS (FAB) m/z 580 (M$^+$+1).

Example 105

4-[1-[3-methoxy-4-[N'-(2-methylphenyl)ureido]phenylacetyl]-(4S)-phenoxy-(2S)-pyrrolidinyl]methyl-1-piperazinylacetic acid

113

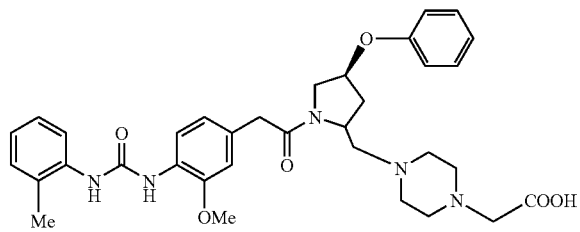

To a stirred mixture of methyl (2S,4R)-1-tert-butoxycarbonyl-4-hydroxy-2-pyrrolidinylcarboxylate (4.69 g, 19.1 mmol), phenol (1.98 g, 21.0 mmol) and PPh$_3$ (5.51 g, 21.0 mmol) in THF (80 ml) was added DIAD (4.13 ml, 21.0 mmol) at room temperature under an atmosphere of nitrogen. The mixture was stirred over night. After removal of the solvent, the resulting residue was chromatographed on silica gel [700 g, CHCl$_3$/EtOAc (10/1)], to give methyl (2S, 4S)-1tert-butoxycarbonyl-4-phenoxy-2-pyrrolidinylcarboxylate (5.31 g, 86%) as a colorless oil. $^1$H-NMR (CDCl$_3$) δ 1.43 (br, 9H, one of isomers), 1.48 (br, 9H, one of isomers), 2.48 (m, 1H), 3.75 (br, 3H), 4.42–4.96 (m, 2H), 6.88–7.35 (in, 5H).

To a stirred solution of methyl (2S,4S)-1-tert-butoxycarbonyl-4-phenoxy-2-pyrrolidinylcarboxylate (5.31 g, 16.5 mmol) in THF (132 ml) was added 0.25 N NaOH (132 ml, 33.0 mmol) at room temperature. The resulting mixture was stirred over night. After removal of the solvent, the mixture was acidified by the addition of 1 N HCl and extracted with CHCl$_3$. The combined extracts were washed with brine, dried over Na$_2$SO$_4$ and evaporated. The residue was recrystallized from n-hexane-CHCl$_3$, to give (2S, 4S)-1-tert-butoxycarbonyl-4-phenoxy-2-pyrrolidinylcarboxylic acid (2.96 g, 58%) as a white powder. $^1$H-NMR (DMSO-d$_6$) δ 1.36 (s, 9H), 2.16 (d, J=13.2 Hz, 1H), 2.56 (m, 1H ), 3.46 (m, 1H), 3.71 (dt, J=12.0, 5.4 Hz, 1H), 4.26 (dt, J=9.5, 7.1 Hz, 1H), 4.99 (m, 1H), 6.85 (m, 2H), 6.94 (t, J=7.3 Hz, 1H), 7.28 (t, J=7.3 Hz, 1H).

To a stirred solution of (2S, 4S)-1-tert-butoxycarbonyl-4-phenoxy-2-pyrrolidinylcarboxylic acid (2.39 g, 7.76 mmol) in THF (50 ml) was added BH$_3$.DMS (1.55 ml, 15.5 mmol) at 0° C. After 10 min. stirring at the same temperature, the mixture was allowed to room temperature and then heated at 50° C. for 2 h. After cooling to room temperature, the mixture was concentrated in vacuo and quenched by the addition of water at 0° C. The mixture was extracted with EtOAc. The combined extracts were washed with brine, dried over Na$_2$SO$_4$ and evaporated. The residue was chromatographed on silica gel [60 g, CHCl$_3$/MeOH (50/1)] to give (2S, 4S)-1-tert-butoxycarbonyl-4-phenoxy-2-pyrrolidinylmethanol (2.83 g, 100%) as a colorless oil. $^1$H-NMR (CDCl$_3$) δ 1.47 (s, 9H), 1.95 (br, 1H), 2.36 (m, 1H), 3.56–3.74 (m, 3H), 3.89–4.52 (m, 3H), 4.85 (br, 1H), 6.84 (dd, J=8.8, 1.2 Hz, 2H), 6.97 (t, J=7.2 Hz, 1H), 7.29 (t, 2H, J=7.8 Hz).

To a stirred mixture of (2S, 4S)-1-tert-butoxycarbonyl-4-phenoxy-2-pyrrolidinylmethanol (2.75 g, 9.37 mmol), Et$_3$ N (7.84 ml, 56.2 mmol), DMSO (6.66 ml, 9.37 mmol) in CH$_2$Cl$_2$ (30 ml) at 0° C. was added SO$_3$-pyridine (4.47 g, 28.1 mmol), then the resulting mixture was allowed to raise to room temperature. After 2.5 h stirring, the mixture was concentrated in vacuo. To the resulting mixture was added water and extracted with Et$_2$O. The combined extracts were washed with brine, dried over Na$_2$SO$_4$ and concentrated in vacuo. The residue was chromatographed on silica gel [100 g, CHCl$_3$/acetone (5/1)] to give (2S, 4S)-1-tert-butoxycarbonyl-4-phenoxy-2-pyrrolidine carbaldehyde (2.54 g, 93%) as a yellow oil. $^1$H-NMR (CDCl$_3$) δ 1.45 (s, 9H, one of isomers), 1.49 (s, 9H, one of isomers), 2.17 (br, 2H), 3.65–4.31 (m, 3H), 4.91 (br, 1H), 6.79 (d, J=7.8 Hz, 1H), 6.77 (m, 1H), 7.28 (m, 2H), 9.66 (m, 1H).

To a stirred mixture of 1-tert-butoxycarbonyl-(4S)-phenoxy-(2S)-pyrrolidinecarbaldehyde (1.36 g, 4.67 mmol), ethyl 1-piperazinylacetate (1.61 g, 9.37 mmol) in THF (30 ml) was added NaBH(OAc)$_3$ (1.98 g, 9.34 mmol) at room temperature. After 3 h stirring, the mixture was quenched by the addition of water and extracted with EtOAc. The combined extracts were washed with aq. NaHCO$_3$ and brine. The organic layer was dried over Na$_2$SO$_4$ and concentrated in vacuo. The residue was chromatographed on silica gel [50 g, CHCl₃/MeOH (10/1)], to give ethyl 4-[1-tert-butoxycarbonyl-(4S)-phenoxy-(2S)-pyrrolidinyl]methyl-1-piperazinylacetate (1.05 g, 50%) as a colorless oil. ¹H-NMR (CDCl₃) δ 1.27 (t, J=7.3 Hz, 3H), 1.57 (s, 9H), 2.18 (m, 1H), 2.33–2.74 (m, 9H), 3.17 (s, 2H), 3.52–4.10 (m, 5H), 4.17 (q, J=7.3 Hz, 2H), 4.89 (br, 1H), 6.84 (d, J=6.8 Hz, 2H), 6.95 (m, 1H), 7.26 (m, 3H).

To a stirred solution of ethyl 4-[1-tert-butoxycarbonyl-(4S)-phenoxy-(2S)-pyrrolidinyl]methyl-1-piperazinylacetate (1.05 g, 2.35 mmol) in CH₂Cl₂ (20 ml) was added TFA (20 ml) at room temperature. After 3 h stirring, the mixture was concentrated in vacuo, which was diluted with CHCl₃-MeOH (10/1) and made basic by the addition of 1 N NaOH. The combined reaction mixture was extracted with CHCl₃-MeOH (10/1). The organic layer was washed with brine, dried over NaSO₄ and concentrated, to give ethyl 4-[(4S)-phenoxy-(2S)-pyrrolidinyl]methyl-1-piperazinylacetate (1.12 g, quant.) as a brown oil, which was used without further purification. ¹H-NMR (CDCl₃) δ 1.25 (tt, J=7.1, 7.1 Hz, 3H), 1.91 (d, J=12.0 Hz, 1H), 2.42–2.85 (m, 10H), 3.22 (s, 2H), 3.50 (s, 2H), 3.54–3.82 (m, 2H), 4.15 (q, J=7.1 Hz, 2H), 4.98 (br, 1H), 6.84 (d, J=8.1 Hz, 2H), 6.76 (t, J=7.1 Hz, 1H), 7.26–7.31 (m, 3H), 7.40 (br, 1H).

A mixture of 4-[N'-(2-methylphenyl)ureido]-3-methoxyphenylacetic acid (337 mg, 1.07 mmol), ethyl 4-[(4S)-phenoxy-(2S)-pyrrolidinylmethyl]-1-piperazinylacetate (373 mg, 1.07 mmol), EDC.HCl (308 mg, 1.61 mmol) and DMAP (197 mg, 1.61 mmol) in DMF (6 ml) was stirred at room temperature for 18 h. The mixture was poured into ice water and extracted with EtOAc. The combined extracts were washed with ice water and brine. After dried over Na₂SO₄, the extracts were concentrated in vacuo. The residue was chromatographed on silica gel [50 g, CHCl₃/MeOH (50/1)], to give ethyl 4-[1-[3-methoxy-4-[N'-(2-methylphenyl)ureido]phenylacetyl]-(4S)-phenoxy-(2S)-pyrrolidinyl]methyl-1-piperazinylacetate (430 mg, 62%) as a colorless amorphous solid. ¹H-NMR (CDCl₃) δ 1.25 (t, J=7.8 Hz, 3H), 1.98–2.17 (m, 2H), 2.26 (s, 3H), 2.36–2.82 (m, 11H), 3.13 (s, 1H), 3.17 (s, 1H), 3.55 (d, J=2.4 Hz, 1H), 3.66 (d, J=0.9 Hz, 3H), 3.67–3.84 (m, 2H), 3.98–4.35 (m, 3H), 4.85–4.95 (m, 1H), 6.27–6.89 (m, 6H), 7.08 (t, J=7.3 Hz, 1H), 7.19 (d, J=6.8 Hz, H), 7.28 (m, 2H), 7.41 (d, J=4.9 Hz, 1H), 7.55 (d, J=7.8 Hz, 1H), 8.05 (dd, J=7.3, 2.2 Hz, 1H). For HCl salt: a pale brown amorphous solid. IR (KBr) 3265, 3059, 1747, 1533, 1225 cm⁻¹; MS (FAB) m/z 644 (M⁺+1); Anal. Calcd for C₃₆H₄₅N₅O₆.HCl.2.1H₂O: C, 60.22; H, 7.05; N, 9.75. Found: C, 59.97; H, 6.72; N, 9.54.

To a solution of ethyl 4-[1-[3-methoxy-4-[N-(2-methylphenyl)ureido]phenylacetyl]-(4S)-phenoxy-(2S)-pyrrolidinyl]methyl-1-piperazinylacetate (240 mg, 0.373 mmol) in THF (3.0 ml), 0.25 N NaOH (3.0 ml) was added. After stirring at room temperature for 20 h, the mixture was neutralized with 1 N HCl and extracted with CHCl₃-MeOH (10/1). The combined extracts were dried over Na₂SO₄ and concentrated in vacuo. The residue was triturated by the addition of ether, to give 113 MW 615.72 (143 mg, 62%) as a white powder. IR (KBr) 3346, 2949, 1633, 1533, 1227 cm⁻¹; ¹H-NMR (DMSO-d₆) δ 1.76 (m, 1H), 2.18 (br, 2H), 2.25 (s, 3H), 2.42–2.83 (m, 9H), 3.17 (s, 1H), 3.20 (s, 1H), 3.38 (m, 1H), 3.70 (s, 2H), 3.72–3.78 (m, 2H), 3.85 (s, 3H, one of isomers), 3.87 (s, 3H, one of isomers), 3.95 (m, 1H), 4.27 (br, 1H), 5.08 (m, 1H), 6.75 (d, J=8.3 Hz, 1H), 6.93 (m, 5H), 7.14 (m, 2H), 7.30 (d, J=7.6 Hz, 1H), 7.79 (d, J=9.0 Hz, 1H), 8.02 (m, 1H), 8.50 (s, 1H), 8.58 (s, 1H); MS (FAB) m/z 616(M⁺+1); Anal. Calcd for C₃₄H₄₁N₅O₆.0.1EtOH.2H₂O: C, 62.58; H, 7.00; N, 10.67. Found: C, 62.73; H, 6.58; N, 10.24.

Example 106

4-[1-(4-[N'-(2-chlorophenyl)ureido]-3-methoxyphenylacetyl]-(4S)-phenoxy-(2S)-pyrrolidinyl]methyl-1-piperazinylacetic acid

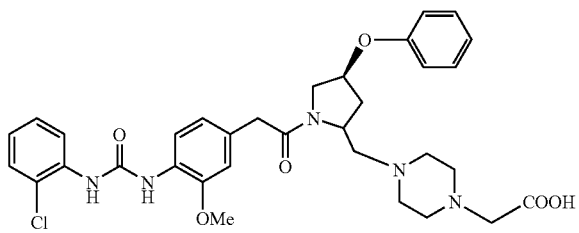

114

A mixture of 4-[N'-(2-chlorophenyl)ureido]-3-methoxyphenylacetic acid (358 mg, 1.07 mmol), ethyl 4-[(4S)-phenoxy-(2S)-pyrrolidinylmethyl]-1-piperazinylacetate (373 mg, 1.07 mmol), EDC.HCl (308 mg, 1.61 mmol) and DMAP (197 mg, 1.61 mmol) in DMF (6 ml) was stirred at room temperature for 18 h. The mixture was poured into ice water and extracted with EtOAc. The combined extracts were washed with ice water and brine. After dried over Na₂SO₄, the extracts were concentrated in vacuo. The residue was chromatographed on silica gel [50 g, CHCl₃/MeOH (50/1)] to give ethyl 4-[1-[4-[N'-(2-chlorophenyl)ureido]-3-methoxyphenylacetyl]-(4S)-phenoxy-(2S)-pyrrolidinyl]methyl-1-piperazinylacetate (320 mg, 45%) as a colorless amorphous solid. ¹H-NMR (CDCl₃) δ 1.25 (qq, J=7.3, 7.3 Hz, 3H), 2.05–2.20 (m, 2H), 2.35–2.80 (m, 1H), 3.12 and 3.18 (each s, 1H, amide isomers), 3.57 (d, J=5.4 Hz, 1H), 3.66 and 3.38 (each s, 3H, amide isomers), 3.70–3.90 (m, 2H), 4.02–4.43 (m, 3H), 4.88–4.97 (m, 1H), 6.83–6.99 (m, 6H), 7.18–7.32 (m, 3H), 7.68 (d, J=8.3 Hz, 1H), 7.74 (s, 1H), 8.16 (dd, J=8.3, 1.4 Hz, 1H). For HCl salt: a pale brown amorphous solid. IR (KBr) 3300, 2978, 1745, 1533, 1225 cm⁻¹; MS (FAB) m/z 664 (M⁺+1), 666 (⁺+3); Anal. Calcd for C₃₅H₄₂ClN₅O₆.HCl.2.4H₂O: C, 56.51; H, 6.48; N, 9.41. Found: C, 56.51; H, 6.18; N, 9.28.

To a solution of ethyl 4-[1-[4-[N'-(2-chlorophenyl)ureido]-3-methoxyphenylacetyl]-(4S)-phenoxy-(2S)-pyrrolidinyl]methyl-1-piperazinylacetate (181 mg, 0.273 mmol) in THF (2.2 ml), 0.25 N NaOH (2.2 ml) was added. After stirring at room temperature for 20 h, the mixture was neutralized with 1 N HCl and extracted with CHCl₃-MeOH (10/1). The combined extracts were dried over Na₂SO₄ and concentrated in vacuo. The residue was triturated by the addition of ether to give 114 (133 mg, 77%) as a white powder. MW 636.14 IR (KBr) 3317, 2949, 1701, 1631, 1595, 1225 cm⁻¹; ¹H-NMR (DMSO-d₆) δ 2.13–3.05 (m, 11H), 3.22 and 3.36 (each s, 2H, amide isomer), 3.38 (m, 1H), 3.60 (s, 2H), 3.71 (m, 1H), 3.85 (s, 3H), 3.95 (m, 1H), 4.28 (br, 1H), 5.06 (m, 1H), 6.76 (d, J=8.3 Hz, 1H), 6.91–7.03 (m, 5H), 7.29 (m, 3H), 7.44 (d, J=7.9 Hz, 1H), 7.97 (dd, J=8.1, 4.1 Hz, 1H), 8.08 (d, J=7.0 Hz, 1H), 8.91 (s, 1H), 8.95 (s, 1H); MS (FAB) m/z 636(M⁺+1), 638(M⁺+3); Anal. Calcd for C₃₃H₃₈ClN₅O₆.0.2EtOH.1.3H₂O: C, 59.98; H, 6.30; N, 10.47. Found: C, 60.25; H, 6.12; N, 10.11.

Example 107

4-[1-[4-[N'-(2-bromophenyl)ureido]-3-methoxyphenylacetyl]-(4S)-phenoxy-(2S)-pyrrolidinyl]methyl-1-piperazinylacetic acid

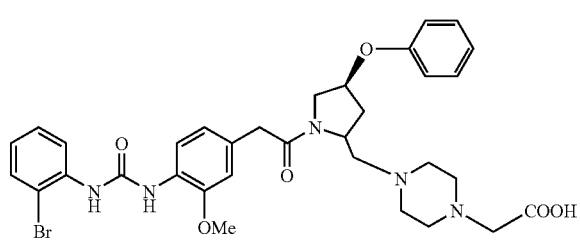

115

A mixture of 4-[N'-(2-bromophenyl)ureido]-3-methoxyphenylacetic acid (406 mg, 1.07 mmol), ethyl 4-[(4S)-phenoxy-(2S)-pyrrolidinyl]methyl-1-piperazinylacetate (373 mg, 1.07 mmol), EDC.HCl (308 mg, 1.61 mmol) and DMAP (197 mg, 1.61 mmol) in DMF (6 ml) was stirred at room temperature for 18 h. The mixture was poured into ice water and extracted with EtOAc. The combined extracts were washed with ice water and brine. After dried over $Na_2SO_4$, the extracts were concentrated in vacuo. The residue was chromatographed on silica gel [50 g, $CHCl_3$/MeOH (50/1)] to give ethyl 4-[1-[4-[N'-(2-bromophenyl)ureido]-3-methoxyphenylacetyl]-(4S)-phenoxy-(2S)-pyrrolidinyl]methyl-1-piperazinylacetate (560 mg, 74%) as a colorless amorphous solid. $^1$H-NMR ($CDCl_3$) δ 1.25 (tt, J=7.1, 7.1 Hz, 3H), 2.04–2.84 (m, 13I), 3.12 and 3.18 (each s, 1H, amide isomers), 3,57 (d, J=4.4 Hz, 1H), 3.66 and 3.68 (each s, 3H, amide isomers), 3.68–3.87 (m, 3H), 4.05–4.41 (m, 2H), 4.87–4.96 (m, 1H), 6.76–6.98 (m, 6H), 7.20–7.33 (m, 3H), 7.46 (d, J=8.1 Hz, 1H), 7.67 and 7.71 (each s, 1H, amide isomers), 7.78 and 7.81 (each s, 1H, amide isomers), 7.95 (d, J=8,3 Hz, 1H), 8.09 (d, J=8.1 Hz, 1H). For HCl salt: a pale brown amorphous solid. IR (KBr) 3384, 2978, 1745, 1340, 1120 cm$^{-1}$; MS (FAB) m/z 708 (M$^+$+1), 710 (M$^+$+3); Anal. Calcd for $C_{35}H_{42}BrN_5O_6$.HCl.2.5$H_2O$: C, 53.20; H, 6.12; N, 8.86. Found: C, 52.98; H, 5.79; N, 8.66.

To a solution of ethyl 4-[1-[4-[N'-(2-bromophenyl)ureido]-3-methoxyphenylacetyl]-(4S)-phenoxy-(2S)-pyrrolidinyl]methyl-1-piperazinylacetate (330 mg, 0.466 mmol) in THF (3.7 ml), 0.25 N NaOH (3.7 ml) was added. After stirring at room temperature for 20 h, the mixture was neutralized with 1 N HCl and extracted with $CHCl_3$-MeOH (10/1). The combined extracts were dried over $Na_2SO_4$ and concentrated in vacuo. The residue was triturated by the addition of ether, to give 115 (217 mg, 68%) as a white powder. MW 680.59 IR (KBr) 3315, 3095, 2941, 1631, 1529, 1435 cm$^{-1}$; $^1$H-NMR (DMSO-$d_6$) δ 1.75 (m, 1H), 2.18 and 2.23 (each s, 2H, amide isomers), 2.30–2.78 (m, 9H), 3.15 (2, 2H), 3.47 (m, 1H), 3.58 (s, 2H), 3.60–3.82 (m, 3H), 3.84 (m, 3H), 3.93 (m, 1H), 4.26 (br, 1H), 5.08 (m, 1H), 6.75 (d, J=7.8 Hz, 1H), 6.98 (m, 5H), 7.30 (m, 3H), 7.60 (dd, J=8.1, 2.2 Hz, 1H), 7.94 (m, 2H), 8.75 (s, 1H), 8.93 (s, 1H); MS(FAB) m/z 680(M$^+$+1), 82(M$^+$+3); Anal. Calcd for $C_{33}H_{38}BrN_5O_6$.0.2EtOH-2$H_2O$: C, 55.27; H, 6.00; N, 9.65. Found: C, 55.32; H, 5.56; N, 9.25.

Example 108

4-[(4S)-(4-carboxyphenoxy)-1-[3-methoxy-4-[N'-(2-methylphenyl)uriedo]phenylacetyl]-(2S)-pyrrolidinylmethoxy]benzoic acid

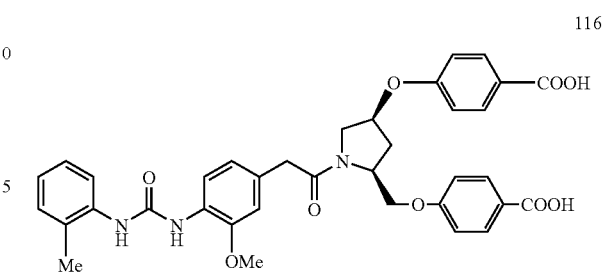

116

To a stirred solution of methyl 1-(tert-butoxycarbonyl)-(4R)-hydroxy-(2S)-pyrrolidinylcarboxylate (10.4 g, 0.04 mol) and imidazole (8.66 g, 0.13 mol) in DMF (40 ml) was added TBS-Cl (7.03 g, 0.05 mol) and the reaction mixture was stirred at 60° C. for 3 hr. After cooled to room temperature, the mixture was diluted with brine, and extracted with $Et_2O$. The extract was washed with brine, dried over $Na_2SO_4$, and evaporated. The residue was purified by column chromatography on silica-gel with n-hexane-EtOAc (5:1, v/v) as eluent to give methyl 1-(tert-butoxycarbonyl)-(4R)-(tert-butyldimethylsilyloxy)-(2S)-pyrrolidinylcarboxylate (15.0 g, 98%) as a colorless oil. $^1$H-NMR ($CDCl_3$) δ 0.06 (s, 6 H), 0.87 (s, 9 H), 1.41 and 1.46 (each s, 9 H), 1.99–2.03 (m, 1 H), 2.16–2.18 (m, 1 H), 3.31–3.42 (m, 1 H), 3.56–3.63 (m, 1 H), 3.73 and 3.74 (each s, 3 H), 4.31–4.42 (m, 2 H); MS (ESI) m/z 360 (M$^+$+1).

To a stirred solution of methyl 1-(tert-butoxycarbonyl)-(4R)-(tert-butyldimethylsilyloxy)-(2S)-pyrrolidinylcarboxylate (15.0 g, 0.04 mol) in THF (60 ml) was added 1 N NaOH (60 ml) and the reaction mixture was stirred at 60° C. for 2 hr. After cooled to room temperature, the mixture was concentrated to a small volume, acidified with 1 N HCl, and extracted with EtOAc. The extract was washed with brine, dried over $Na_2SO_4$, and evaporated to give 1-(tert-butoxycarbonyl)-(4R)-(tert-butyldimethylsilyloxy)-(2S)-pyrrolidinylcarboxylic acid (12.8 g, 89%) as a colorless oil. $^1$H-NMR ($CDCl_3$) δ 0.07 and 0.08 (each s, 6 H), 0.87 (s, 9 H), 1.49 (s, 9 H), 2.06–2.11 (m, 1 H), 2.41–2.44 (m, 1 H), 3.40–3.59 (m, 2 H), 4.36–4.50 (m, 2 H); MS (ESI) m/z 346 (M$^+$+1).

To a cooled (0° C.) stirred solution of 1-(tert-butoxycarbonyl)-(4R)-(tert-butyldimethylsilyloxy)-(2S)-pyrrolidinylcarboxylic acid (12.8 g, 0.04 mol) in THF (150 ml) was added dropwise $BH_3$.DMS (5.30 ml, 0.06 mol) and the reaction mixture was stirred at room temperature overnight. The reaction mixture was quenched by sat. $NH_4Cl$, and extracted with EtOAc. The extract was washed with brine, dried over $Na_2SO_4$, and evaporated. The residue was purified by column chromatography on silica-gel with toluene-acetone (5:1, v/v) as eluent to give 1-(tert-butoxy carbonyl)-(4R)-(tert-butyldimethylsilyloxy)-(2S)-prolinol (10.5 g, 85%) as a colorless oil. $^1$H-NMR ($CDCl_3$) δ 0.06 (s, 6 H), 0.87 (s, 9 H), 1.47 (s, 9 H), 1.58–1.63 (m, 1 H), 1.93–1.98 (m, 1 H), 3.32–3.44 (m, 2 H), 3.51–3.57 (m, 1 H), 3.67–3.71 (m, 1 H), 4.13–4.15 (m, 1 H), 4.27 (m, 1 H), 4.87–4.89 (m, 1 H).

To a cooled (0° C.), stirred solution of methyl 4-hydroxybenzoate (4.81 g, 0.03 mol), 1-(tert-butoxycarbonyl)-(4R)-

(tert-butyldimethylsilyloxy)-(2S)-prolinol (10.5 g, 0.03 mol), and Ph$_3$P (9.96 g, 0.04 mol) in THF (160 ml) was added dropwise DIAD (7.48 ml, 0.04 mol) and the reaction mixture was heated under reflux for 7 hr. After cooled to room temperature, the mixture was evaporated. The residue was purified by column chromatography on silica-gel with n-hexane-EtOAc (6:1, v/v) to give methyl 4-[1-(tert-butoxycarbonyl)-(4R)-(tert-butyldimethylsilyloxy)-(2S)-pyrrolidinylmethoxy]benzoate (9.58 g, 65%) as a white solid. mp 86–88° C.; $^1$H-NMR (CDCl$_3$) δ 0.08 (s, 6 H), 0.88 (s, 9 H), 1.46 (s, 9 H), 2.04–2.15 (m, 2 H), 3.29–3.48 (m, 2 H), 3.88 (s, 3 H), 4.06–4.30 (m, 3 H), 4.46–4.51 (m, 1 H). 6.91–6.93 (m, 2 H), 7.96–7.98 (m, 2 H); MS (ESI) m/z 466 (M$^+$+1).

To a cooled (0° C.), stirred solution of methyl 4-[1-(tert-butoxycarbonyl)-(4R)-(tert-butyldimethyl silyloxy)-(2S)-pyrrolidinylmethoxy]benzoate (1.49 g, 3.20 mmol) in THF (15 ml) was added TBAF (6.40 ml, 6.40 mmol, 1 M solution in TIM) and the reaction mixture was stirred at room temperature for 2 hr. The mixture was diluted with EtOAc, washed with H$_2$O, brine, dried over Na$_2$SO$_4$, and evaporated. The residue was purified by column chromatography on silica-gel with toluene-acetone (5:1, v/v) as eluent to give methyl 4-[1-(tert-butoxycarbonyl)-(4R)-hydroxy-(2S)-pyrrolidinylmethoxy]benzoate (1.05 g, 93%) as a white solid. mp 103–105° C.; $^1$H-NMR (CDCl$_3$) δ 1.46 (s, 9 H), 2.11–2.28 (m, 2 H), 3.49–3.60 (m, 2 H), 3.88 (s, 3 H), 4.15–4.34 (m, 3 H), 4.53–4.57 (m, 1 H), 6.91 (d, J=8.6 Hz, 2 H), 7.97 (d, J=8.6 Hz, 2 H); MS (ESI) m/z 352 (M$^+$+1).

To a cooled (0° C.), stirred solution of methyl 4-hydroxybenzoate (0.56 g, 3.68 mmol), methyl 4-[1-(tert-butoxycarbonyl)-(4R)-hydroxy-(2S)-pyrrolidinylmethoxy]benzoate (1.30 g, 3.70 mmol), and Ph$_3$P (1.16 g, 4.42 mmol) in THF (20 ml) was added dropwise DIAD (0.87 ml, 4.42 mmol) and the reaction mixture was stirred at room temperature for 3 hr. The mixture was evaporated and the residue was purified by column chromatography on silica-gel with n-hexane-EtOAc (6:1, v/v) as eluent to give methyl 4-[1-(tert-butoxycarbonyl)-(4S)-(4-methoxycarbonylphenoxy)-(2S)-pyrrolidinylmethoxy]benzoate (1.80 g, q.y.) as a colorless oil. $^1$H-NMR (CDCl$_3$) δ 1.49 (s, 9 H), 2.31–2.38 (m, 1 H), 2.45–2.49 (m, 1 H), 3.64–3.77 (m, 2 H), 3.88 (s, 6 H), 4.07–4.15 (m, 1 H), 4.33–4.44 (m, 2 H), 4.95–5.01 (m, 1 H), 6.85 (d, J=8.8 Hz, 2 H); 6.94 (br s, 2 H), 7.97 (d, J=8.8 Hz, 4 H); MS (ESI) m/z 486 (M$^+$+1).

To a stirred solution of methyl 4-[1-(tert-butoxycarbonyl)-(4S)-(4-methoxycarbonyl phenoxy)-(2S)-pyrrolidinylmethoxy]benzoate (1.80 g, 3.71 mmol) in CH$_2$Cl$_2$ (15 ml) was added TFA (15 ml) and the reaction mixture was stirred at room temperature for 1.5 hr. The mixture was concentrated in vacuo, made basic by sat. NaHCO$_3$, and extracted with CHCl$_3$. The extract was washed with brine, dried over K$_2$CO$_3$, and evaporated to give methyl 4-[(4S)-(4-methoxycarbonyl phenoxy)-(2S)-pyrrolidinylmethoxy]benzoate (1.50 g, q.y.) as a pale yellow oil. $^1$H-NMR (CDCl$_3$) δ 1.87–1.92 (m, 1 H), 2.41–2.48 (m, 1 H), 3.18–3.23 (m, 1 H), 3.34–3.37 (m, 1 H), 3.60–3.66 (m, 1 H), 3.88 (s, 3 H), 3.89 (s, 3 H), 4.04–4.13 (m, 2 H), 4.94–5.00 (m, 1 H), 6.87–6.93 (m, 4 H), 7.96–8.00 (m, 4 H); MS (ESI) m/z 386 (M$^+$+1).

A mixture of 3-methoxy-4-[N'-(2-methylphenyl)uriedo]phenylacetic acid (400 mg, 1.27 mmol), methyl 4-[(4S)-(4-methoxycarbonylphenoxy)-(2S)-pyrrolidinylmethoxy]benzoate (491 mg, 1.27 mmol), EDC.HCl (293 mg, 1.53 mmol), HOBt (207 mg, 1.53 mmol), and Et$_3$ N (215 μl, 1.54 mmol) in THF (10 ml) was stirred at room temperature overnight. The mixture was diluted with H$_2$O, and extracted with EtOAc. The extract was washed with brine, dried over Na$_2$SO$_4$, and evaporated. The residue was purified by column chromatography on silica-gel with CHCl$_3$-MeOH (60:1 to 50:1, v/v) as eluent to give methyl 4-[1-[3-methoxy-4-[N'-(2-methylphenyl)uriedo]phenylacetyl]-(4S)-(4-methoxycarbonylphenoxy)-(2S)-pyrrolidinylmethoxy]benzoate (532 mg, 61%) as a white foam. $^1$H-NMR (CDCl$_3$) δ 2.26–2.49 (series of s and m, total 5 H), 3.56–3.93 series of s and m, total 13 H), 4.07–4.59 (series of m, total 3 H), 5.01 (m, 1 H), 6.69–6.94 (m, 7 H), 7.09–7.13 (m, 1 H), 7.20–7.31 (m, 3 H), 7.52–7.57 (m, 1 H), 7.92–8.00 (m, 4 H), 8.06–8.09 (m, 1 H); MS (ESI) m/z 682 (M$^+$+1).

To a stirred solution of methyl 4-[1-[3-methoxy-4-[N'-(2-methylphenyl)uriedo]phenylacetyl]-(4S)-(4-methoxycarbonylphenoxy)-(2S)-pyrrolidinylmethoxy]benzoate (532 mg, 0.78 mmol) in THF (5 ml) was added 0.5 N NaOH (5 ml) and the reaction mixture was heated under reflux for 5 hr. After cooled to room temperature, the mixture was poured into ice-1 N HCl and the resulting precipitate was collected. The crude solid was recrystallized from MeOH—CHCl$_3$-Et$_2$O to give 116 (125 mg, 25%) as a pale yellow crystalline powder. MW 653.68 mp 154–159° C.; $^1$H-NMR (DMSO-d$_6$)2.24 (s, 3 H), 2.38–2.49 (m, 2 H), 3.63 (s, 2 H), 3.67–3.88 (series of s and m, total 4 H), 4.01–4.06 and 4.15–4.19 (each m, total 2 H), 4.27–4.31 and 4.38–4.42 (each m, total 2 H), 5.18–5.25 (m, 1 H), 6.72–6.77 (m, 1 H), 6.85–7.16 (series of m, total 8 H), 7.78–7.89 (m, 5 H), 7.99–8.02 (m, 1 H), 8.46 (s, 1 H), 8.57 (s, 1 H), 12.65 (br s, 2 H); MS (ESI) m/z 654 (M$^+$+1); Anal. Calcd for C$_{36}$H$_{35}$N$_3$O$_9$.1/2H$_2$O: C, 65.25; H, 5.48; N, 6.34. Found: C, 65.29; H, 5.54; N, 6.20.

Example 109

4-[(4S)-(4-carboxyphenoxy)-1-[4-[N'-(2-chlorophenyl)uriedo]-3-methoxyphenylacetyl]-(2S)-pyrrolidinylmethoxy]benzoic acid

117

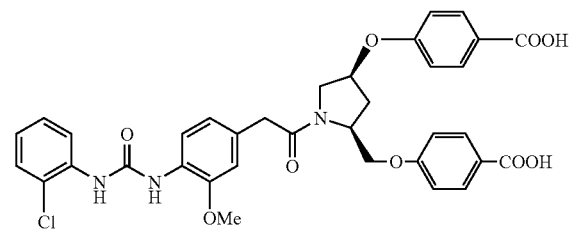

A mixture of 4-[N-(2-chlorophenyl)ureido]-3-methoxyphenylacetic acid (420 mg, 1.25 mmol), methyl 4-[(4S)-(4-methoxycarbonylphenoxy)-(2S)-pyrrolidinylmethoxy]benzoate (483 mg, 1.25 mmol), EDC.HCl (288 mg, 1.50 mmol), HOBt (203 mg, 1.50 mmol), and Et$_3$ N (210 μl, 1.51 mmol) in THF (10 ml) was stirred at room temperature overnight. The mixture was diluted-with H$_2$O, and extracted with EtOAc. The extract was washed with brine, dried over Na$_2$SO$_4$, and evaporated. The residue was purified by column chromatography on silica-gel with CHCl$_3$-MeOH (50:1, v/v) as eluent to give methyl 4-[1-[4-[N'-(2-chlorophenyl)uriedo]-3-methoxyphenylacetyl]-(4S)-(4-methoxycarbonylphenoxy)-(2S)-pyrrolidinylmethoxy]benzoate (488 mg, 55%) as a white foam. $^1$H-NMR (CDCl$_3$) δ 2.28–2.51 (m, 2 H), 3.62–3.94 (series of s and m, total 13 H), 4.07–4.62 (series of m, total 3 H), 4.99–5.03 (m, 1 H), 6.78–6.99 (m, 7 H), 7.23–7.34 (m, 2 H), 7.42–7.52 (m, 2 H), 7.92–8.01 (m, 5 H), 8.17–8.20 (m, 1 H); MS (ESI) m/z 702 (M$^+$+1).

To a stirred solution of methyl 4-[1-[4-[N-(2-chlorophenyl)uriedo]-3-methoxyphenylacetyl]-(4S)-(4-methoxycarbonylphenoxy)-(2S)-pyrrolidinylmethoxy]benzoate (488 mg, 0.70 mmol) in THF (5 ml) was added 0.5 N NaOH (5 ml) and the reaction mixture was heated under reflux for 3 hr. After cooled to room temperature, the mixture was poured into ice-1 N HCl and the resulting precipitate was collected. The crude solid was recrystallized from MeOH—CHCl$_3$-Et$_2$O to give 117 (137 mg, 29%) as a white crystalline powder. MW 674.10 mp 150–153° C.; $^1$H-NM (DMSO-d$_6$) δ and 4.17–4.21 (each m, total 2 H), 4.30–4.34 and 4.40–4.45 (each m, total 2 H), 5.20–5.27 (m, 1 H), 6.77–6.81 (m, 1 H), 6.89–6.92 (m, 1 H), 7.01–7.08 (m, 5 H), 7.27–7.31 (m, 1 H), 7.43–7.46 (m, 1), 7.86–7.92 (m, 4 H), 7.97–8.00 (m, 1 H), 8.10–8.12 (m, 1 H), 8.91 (s, 1 H), 8.96 (s, 1 H), 12.65 (br s, 2 H); MS (ESI) m/z 674 (M$^+$+1); Anal. Calcd for C$_{35}$H$_{32}$ClN$_3$O$_9$·1/4H$_2$O: C, 61.95; H, 4.83; N, 6.19; Cl,5.22. Found: C,61.77; H, 4.86; N, 6.13; Cl, 5.49.

Example 110

4-[1-[4-[N'-(2-bromophenyl)uriedo]-3-methoxyphenylacetyl]-(4S)-(4-carboxyphenoxy)-($^2$S)-pyrrolidinylmethoxy]benzoic acid

118

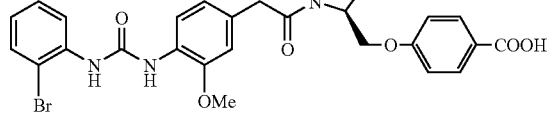

A mixture of 4-[N'-(2-bromophenyl)uriedo]-3-methoxyphenylacetic acid (464 mg, 1.22 mmol), methyl 4-[(4S)-(4-methoxycarbonylphenoxy)-(2S)-pyrrolidinylmethoxy]benzoate (472 mg, 1.22 mmol), EDC.HCl (282 mg, 1.47 mmol), HOBt (200 mg, 1.48 mmol), and Et$_3$ N (205 μl, 1.47 mmol) in THF (10 ml) was stirred at room temperature overnight. The mixture was diluted with H$_2$O, and extracted with EtOAc. The extract was washed with brine, dried over Na$_2$SO$_4$, and evaporated. The residue was purified by column chromatography on silica-gel with CHCl$_3$-MeOH (60:1 to 50:1, v/v) as eluent to give methyl 4-[1-[4-[N'-(2-bromophenyl)uriedo]-3-methoxyphenyl acetyl]-(4S)-(4-methoxycarbonylphenoxy)-(2S)-pyrrolidinylmethoxy]benzoate (379 mg, 41%) as a white foam. $^1$H-NMR (CDCl$_3$) δ 2.28–2.51 (m, 2 H), 3.59–3.95 (series of s and m, total 13 H), 4.07–4.62 (series of m, total 3 H), 4.99–5.03 (m, 1 H), 6.79–6.95 (m, 7 H), 7.27–7.36 (m, 3 H), 7.49–7.51 (m, 1 H), 7.93–8.01 (m, 5 H), 8.11–8.14 (m, 1 H); MS (ESI) m/z 747 (M$^+$+1).

To a stirred solution of methyl 4-[1-[4-[N'-(2-bromophenyl)uriedo]-3-methoxyphenylacetyl]-(4S)-(4-methoxycarbonylphenoxy)-(2S)-pyrrolidinylmethoxy]benzoate (379 mg, 0.51 mmol) in THF (5 ml) was added 0.5 N NaOH (5 ml) and the reaction mixture was heated under reflux for 5 hr. After cooled to room temperature, the mixture was poured into ice-1 N HCl and the resulting precipitate was collected. The crude solid was purified by preparative TLC to give 118 (51 mg, 14%) as a pale yellow amorphous solid. MW 718.55 $^1$H-NMR (DMSO-d$_6$) δ 2.20–2.40 (m, 2 H), 3.65–3.89 (series of m, total 6 H), 4.02–4.63 (series of m, total 4 H), 5.19–5.26 (m, 1 H), 6.74–7.06 (m, 7 H), 7.30–7.34 (m, 1 H), 7.59–7.61 (m, 1 H), 7.83–7.96 (m, 6 H), 8.74 (s, 1 H), 8.93 (s, 1 H); Anal. Calcd for C$_{35}$H$_{32}$BrN$_3$O$_9$·2H$_2$O: C, 55.71; H, 4.81; N, 5.57. Found: C, 55.92; H, 4.80; N, 5.30.

Example 111

4-[(4S)-(4-carboxyphenoxy)-1-[4-[N'-(2-methylphenyl)uriedo]phenylacetyl]-(2S)-pyrrolidinyl methoxy] benzoic acid

119

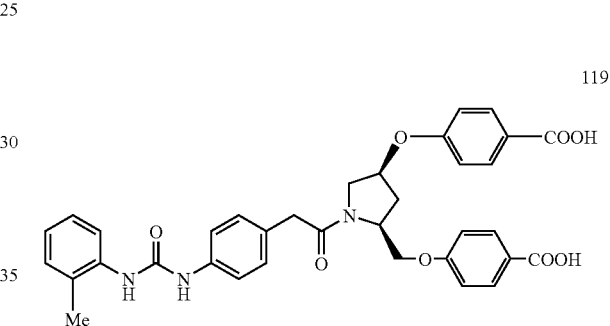

A mixture of 4-[N'-(2-methylphenyl)uriedo]phenylacetic acid (328 mg, 1.15 mmol), methyl 4-[(4S)-(4-methoxycarbonylphenoxy)-(2S)-pyrrolidinylmethoxy]benzoate (444 mg, 1.15 mmol), EDC.HCl (265 mg, 1.38 mmol), HOBt (187 mg, 1.38 mmol), and Et$_3$ N (195 μl, 1.40 mmol) in THF (10 ml) was stirred at room temperature overnight. The mixture was diluted with H$_2$O, and extracted with EtOAc. The extract was washed with brine, dried over Na$_2$SO$_4$, and evaporated. The residue was purified by column chromatography on silica-gel with CHCl$_3$-MeOH (60:1 to 50:1, v/v) as eluent to give methyl 4-[(4S)-(4-methoxycarbonylphenoxy)-1-[4-[N'-(2-methyl phenyl)uriedo]phenylacetyl]-(2S)-pyrrolidinylmethoxy]benzoate (332 mg, 44%) as a white foam. $^1$H-NMR (CDCl$_3$) δ 2.13 (s, 3 H), 2.24–2.48 (m, 2 H), 3.52–3.90 (series of s and m, total 10 H), 4.05–4.58 (series of m, total 3 H), 5.01 (m, 1 H), 6.78–6.90 (m, 4 H), 6.98–7.20 (m, 8 H), 7.51–7.56 (m, 2 H), 7.90–8.00 (m, 4 H); MS (ESI) m/z 652 (M$^+$+1).

To a stirred solution of methyl 4-[(4S)-(4-methoxycarbonylphenoxy)-1-[4-[N'-(2-methyl phenyl)uriedo]phenylacetyl]-(2S)-pyrrolidinylmethoxy]benzoate (332 mg, 0.51 mmol) in THF (5 ml) was added 0.5 N NaOH (5 ml) and the reaction mixture was heated under reflux for 3 hr. After cooled to room temperature, the mixture was poured into ice-1 N HCl and the resulting precipitate was collected. The crude solid was recrystallized from MeOH—CHCl$_3$-Et$_2$O to give 119 (118 mg, 37%) as a white crystalline powder. MW 623.65 mp 157–160° C.; $^{1}$H-NMR (DMSO-d$_{6}$) δ 2.20–2.25 (series of s and m, total 4 H), 2.39–2.47 (m, 1 H), 3.64 (s, 2 H), 3.68–3.89 (m, 1 H), 4.02–4.08 and 4.16–4.20 (each m, total 2 H), 4.29–4.33 and 4.39–4.43 (each m, total 2 H), 5.20–5.26 (m, 1 H), 6.92–6.96 (m, 1 H), 7.02–7.08 (m, 4 H), 7.12–7.18 (m, 4 H), 7.39–7.41 (m, 2 H), 7.84–7.92 (m, 6 H), 9.01 (s, 1 H), 12.65 (br s, 2 H); MS (ESI) m/z 624 (M$^{+}$+1); Anal. Calcd for C$_{35}$H$_{33}$N$_{3}$O$_{8}$.1H$_{2}$O: C, 65.51;. H, 5.50; N, 6.55. Found: C, 65.48; H, 5.36; N, 6.52.

Example 112

4-[4-(2,4-difluorophenoxy)-1-[3-methoxy-4-[N'-(2-methylphenyl)ureido]phenylacetyl]-2-pyrrolidinyl-methoxybenzoic acid

120

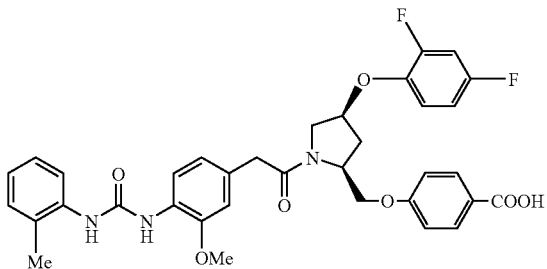

To a stirred solution of methyl 1-(tert-butoxycarbonyl)-4-hydroxyproline (4.0 g, 16.3 mmol), Ph$_{3}$P (5.14 g, 19.6 mmol), and 2,4-difluorophenol (2.55 g, 19.6 mmol) in THF (50 ml) was added DIAD (3.9 ml, 19.6 mmol), and the mixture was heated at reflux for 3 h. After cooling to room temperature, the mixture was concentrated in vacuo and the residue was chromatographed on silica gel with CHCl$_{3}$-EtOAc (4:1) to give methyl 1-(tert-butoxycarbonyl)-4-(2,4-difluorophenoxy) pyrrolidine-2carboxylate (5.82 g, quant) as yellow oil.

To a stirred solution of methyl 1-(tert-butoxycarbonyl)-4-(2,4 difluorophenoxy)pyrrolidine-2-carboxylate (5.82 g, 16.3 mmol) in THF (130 ml) was added 0.25 N NaOH (130 ml, 32.6 mmol). The resulting mixture was stirred overnight. The mixture was poured into 1 N HCl (100 ml) and extracted with CHCl$_{3}$ (2×200 ml). The extracts were dried over MgSO$_{4}$ and evaporated. The residue was chromatographed on silica gel with CHCl$_{3}$-EtOAc (4:1) as eluent to give 1-(tert-butoxycarbonyl)-4-(2,4-difluorophenoxy)pyrrolidine-2-carboxylic acid (2.55 g, 46%) as a colorless foam. $^{1}$H-NMR (CDCl$_{3}$) δ 1.42–1.47 (m, 9 H), 2.29–2.74 (series of m, 2 H), 3.66–3.71 (m, 2 H), 4.46–4.51 (m, 1 H), 4.83 (m, 1 H), 6.73–6.95 (m, 3 H).

To a stirred solution of 1-(tert-butoxycarbonyl)4-(2,4-difluorophenoxy)pyrrolidine-2-carboxylic acid (2.55 g, 7.43 mmol) in THF (50 ml) was added BH$_{3}$.DMS (452 ul, 7.43 mmol). The mixture was heated at reflux overnight. After cooling to room temperature, the mixture was concentrated in vacuo and quenched by the addition of H$_{2}$O (100 ml). The mixture was extracted with CHCl$_{3}$ (2×200 ml), dried over MgSO$_{4}$, and evaporated. The residue was chromatographed on silica gel with CHCl$_{3}$-EtOAc (4:1) as eluent to give 1-(tert-butoxycarbonyl)-4-(2,4-difluorophenoxy)-2-pyrrolidinylmethanol (1.76 g, 72%) as a colorless oil. $^{1}$H-NMR (CDCl$_{3}$) δ 1.45 (s, 9 H), 2.28–2.36 (m, 2 H), 3.58–4.99 (series of m, 8 H), 6.74–6.90 (m, 3 H).

To a stirred solution of 1-(tert-butoxycarbonyl)-4-(2,4-difluorophenoxy)-2-pyrrolidinylmethanol (500 mg, 1.52 mmol), methyl 4-hydroxybenzoate (277 mg, 1.82 mmol), and Ph3P (477 mg, 1.82 mmol) in THF (10 ml) was added DIAD (358 ul, 1.82 mmol), and the mixture was heated at reflux for 5 h; After cooling to room temperature, the mixture was concentrated in vacuo and the residue was chromatographed on silica gel with CHCl$_{3}$-EtOAc (20:1) as eluent to give methyl 4-[1-(tert-butoxycarbonyl)-4-(2,4-difluorophenoxy)-2-pyrrolidinylmethoxy]benzoate (529 mg, 75%) as a colorless oil. $^{1}$H-NMR (CDCl$_{3}$) δ 1.46 (s, 9 H), 2.20–2.47 (m, 2 H), 3.64 (m, 2 H), 3.86 (s, 3 H), 4.07–4.43 (m, 3 H), 4.86 (m, 1 H), 6.74–6.87 (m, 3 H), 6.94 (d, 2 H, J=8.5 Hz), 7.95 (d, 2 H, J=8.5 Hz).

To a stirred solution of methyl 4-[1-(tert-butoxycarbonyl)-4-(2,4-difluorophenoxy)-2-pyrrolidinyl methoxy]benzoate (529 mg, 1.15 mmol) in CH$_{2}$Cl$_{2}$ (5 ml) was added TFA (5 ml). The mixture was stirred overnight. The mixture was concentrated in vacuo and the residue was made basic by the addition of sat. NaHCO$_{3}$. The mixture was extracted with CHCl$_{3}$ (2×100 ml). The extracts were dried over K$_{2}$CO$_{3}$ and evaporated to give methyl 4-[4-(2,4-difluorophenoxy)-2-pyrrolidinyl methoxy]benzoate (385 mg, 92%) as a yellow oil. $^{1}$H-NMR (CDCl$_{3}$) δ 1.89–1.95 (m, 1 H), 2.28–2.35 (m, 1 H), 3.09 (dd, J=12.5, 4.9 Hz, 1 H), 3.33 (d, J=12.5 Hz, 1 H), 3.60 (m, 1 H), 3.86 (s, 3 H), 4.10 (d, J=5.6 Hz, 2H), 4.84(m, 1H), 6.73–6.89(m, 3 H), 6.91 (d, J=8.5 Hz, 2H), 7.96 (d, J=8.5 Hz, 2 H).

A mixture of methyl 4-[4-(2,4-difluorophenoxy)-2-pyrrolidinylmethoxy]benzoate (380 mg, 1.05 mmol), 3-methoxy-4-[N'-(2-methylphenyl)ureido]phenylacetic acid (329 mg, 1.05 mmol), EDC.HCl (302 mg, 1.58 mmol), and catalytic amount of HOBt and DMAP in DMF (10 ml) was stirred for 3 days. The mixture was diluted with EtOAc (200 ml) and washed with brine (2×200 ml). After removal of the solvent, residue was chromatographed on silica gel with CHCl$_{3}$-EtOAc (4:1) to CHCl$_{3}$-MeOH (10:1) as eluent to give methyl 4-[4-(2,4-difluorophenoxy)-1-[3-methoxy-4-[N'-(2-methylphenyl)ureido]phenylacetyl]-2-pyrrolidinylmethoxybenzoate (693 mg, quant) $^{1}$H-NMR (CDCl$_{3}$) δ2.16–2.53 (m, 5 H), 3.61–4.93 (series of m, 14 H), 6.48–8.12 (series of m, 16 H). To a stirred solution of methyl 4-[4-(2,4-difluorophenoxy)-1-[3-methoxy-4-[N'-(2-methylphenyl) ureido]phenylacetyl]-2-pyrrolidinylmethoxybenzoate (693 mg, 1.05 mmol) in THF (8 ml) was added 0.25 N NaOH (8.4 ml, 2.10 mmol). The mixture was stirred overnight. The mixture was poured into 1 N HCl (200 ml) and the resulting precipitate was collected with suction. The solid was chromatographed on silica gel with CHCl$_{3}$-MeOH (50:1 to 10:1) as eluent to give 120 (323 mg, 48%) as a colorless amorphous solid. MW 645.65 $^{1}$H-NMR (DMSO-d$_{6}$) δ 2.25 (s, 3 H), 2.35 (m, 2 H), 3.33–5.18 (series of m, 11 H), 6.75 (dd, 1 H, J=8.3, 1.7 Hz), 6.87–7.30 (series of m, 8 H), 7.79 (d, 1 H, J=8.3 Hz), 7.85–7.90 (m, 3 H), 8.01 (d, 1 H, J=8.3 Hz), 8.49 (s, 1 H), 8.57 (s, 1 H); MS (FAB) m/z, 646 (M$^{+}$+1).

Example 113

4-[1-[4-[N-(2-chlorophenyl)ureido]-3-methoxyphenylacetyl]-4-(6-quinolyloxy-2S-pyrrolidinyl]methoxybenzoic acid

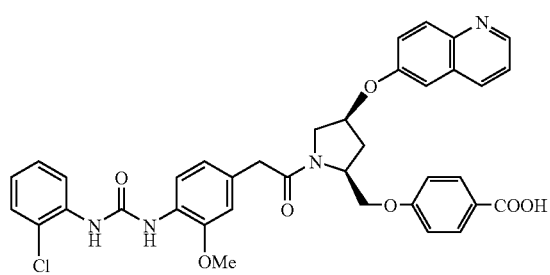

121

To a stirred solution of methyl (trans-1-tert-butoxycarbonyl-4-hydroxy-2-pyrrolidinyl) methoxy benzoate (1.0 g, 3.0 mmol), 6-hydroxyquinoline (435 mg, 3.0 mmol), and $Ph_3P$ (943 mg, 3.6 mmol) in THF (10 ml) was added DIAD (727 mg, 3.6 mmol) at 0° C. The reaction mixture was stirred at room temperature for 18 hr. The mixture was concentrated in vacuo. The residue was purified by column chromatography on silica gel with n-hexane-EtOAc (1:2, v/v). To a stirred solution of the product in $CH_2Cl_2$ (6.0 ml) was added TFA (6.0 ml) at 0° C. The reaction mixture was stirred at room temperature for 0.5 hr. The mixture was concentrated in vacuo. Sat. $NaHCO_3$ was added to the residue, and extracted with $CH_2Cl_2$. The extract was washed with brine, dried over $Na_2SO_4$, and concentrated in vacuo. The residue was purified by column chromatography on silica gel with MeOH—$CH_2Cl_2$(1% to 10%,v/v) as eluent to give methyl 4-[(4S)-[(6-quinolyloxy-(2S)-pyrrolidinyl)]methoxybenzoate (900 mg, 82%) as a pale yellow oil. $^1$H-NMR ($CDCl_3$) δ 1.92–2.10 (m, 1H), 2.45–2.55 (m, 1H), 3.20–3.30 (m, 1H), 3.38–3.50 (m, 1H), 3.60–3.70 (m, 1H), 3.88 (s, 3M), 4.05–4.18 (m, 2H), 5.03 (m, 1H), 6.91 (d, J=8.5 Hz, 1H), 7.02 (d, J=2.7 Hz, 1H), 7.35–7.38 (m, 2H), 7.96 (d, J=8.5 Hz, 1H), 8.00–8.05 (m, 2H), 8.76 (d, J=3.2 Hz, 1H).

To a stirred solution of methyl 4-(4S-(6-quinolyloxy-2S-pyrrolidinyl)methoxybenzoate (300 mg, 0.79 mmol), 4-[NA-(2-chlorophenyl)uredio]-3-methoxyphenylacetic acid (264 mg, 0.79 mmol), HOBt (107 mg, 0.79 mmol), and triethylamine (330 ml, 2.37 mmol) in THF (10.0 ml) and MeCN (10.0 ml) was added EDC.HCl (228 mg, 1.2 mmol) at 0° C. The reaction mixture was stirred at room temperature for 16 hr, and concentrated in vacuo. Water was added to the residue, and extracted with EtOAc. The extract was washed with sat. $NaHCO_3$ then dried over $Na_2SO_4$, and concentrated in vacuo. The residue was purified by column chromatography on silica gel with EtOAc to EtOH-EtOAc (10%, v/v) as eluent to give methyl 4-[1-[4-[N'-(2-chlorophenyl)ureido]-3-methoxyphenylacetyl]-4-(6-quinolyloxy-(2S)-pyrrolidinyl]methoxybenzoate (520 mg, 95%) as a colorless oil. $^1$H-NMR ($CDCl_3$) δ 2.30–2.60 (m, 3H), 3.64 (s, 2H), 3.73 (s, 3H), 3.80–3.95 (m, 1H), 3.87 (s, 3H), 4.15–4.30 (m, 1H), 4.50–4.70 (m, 2H), 5.11 (br s, 1H), 6.81–7.01 (m, 6H), 7.26–7.39 (m, 6H), 7.93–8:03 (m, 51), 8.19 (d, J=8.3 Hz, 1H), 8.80 (s, 1H).

To a stirred solution of methyl 4-[1-[4-[N'-(2-chlorophenyl)ureido]-3-methoxyphenyl acetyl]-4-(6-quinolyloxy-2S-pyrrolidinyl]methoxybenzoate (520 mg, 0.75 mmol) in THF (10.0 ml) and MeOH (5.0 ml) was added 1 N NaOH (1.5 ml, 1.5 mmol). The mixture was stirred at 60° C. for 18 hr. The mixture was concentrated in vacuo, water was added thereto, and neutralized with 1 N HCl. The resulting solid was collected, washed with water, and dried in vacuo to give 121 (450 mg, 88%) as a white crystalline solid. 681.13 mp 129–133° C.; IR (KBr) 3332, 1704, 1604, 1531, 1419, 1222, 1166 $cm^{-1}$; $^1$H-NMR (DMSO-$d_6$) δ 2.25–2.55 (m, 2H), 3.67 (s, 2H), 3.82 (s, 3H), 3.81–3.92 (m, 1H), 4.02–4.15 (m, 2H), 4.40–4.50 (m, 2H), 5.25–5.40 (m, 1H), 5.33–7.07 (m, 5H), 7.26–7.49 (m, 5H), 7.83–8.23 (m, 6H), 8.73–8.74 (m, 111), 8.90 (s, 1H), 8.94 (s, 1H); MS (FAB) m/z 681 ($M^+$+1); Anal. calcd for $C_{37}H_{33}N_4O_7Cl$·$0.5H_2O$: C, 64.39; H, 4.97; N, 8.12. Found: C, 64.22; H, 4.90; N, 7.96.

Example 114

4-[1-[4-[N'-(2-bromophenyl)ureido]-3-methoxyphenylacetyl]-(4S)-(6-quinolyloxy-(2S)-pyrrolidinyl]methoxybenzoic acid

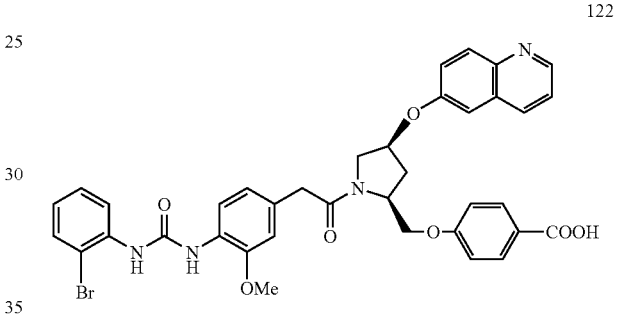

122

To a stirred solution of methyl 4-(4S-(6-quinolyloxy-2S-pyrrolidinyl)methoxybenzoate (300 mg, 0.79 mmol), 4-[N'-(2-bromophenyl)uredio]-3-methoxyphenylacetic acid (299 mg, 0.79 mmol), HOBt (107 mg, 0.79 mmol), and triethylamine (330 mmol, 2.37 mmol) in THF (10.0 ml) and MeCN (10.0 ml) was added EDC.HCl (228 mg, 1.2 mmol) at 0° C. The reaction mixture was stirred at room temperature for 16 hr, and concentrated in vacuo. Water was added to the residue, and extracted with EtOAc. The extract was washed with sat. $NaHCO_3$ then dried over $Na_2SO_4$, and concentrated in vacuo. The residue was purified by column chromatography on silica gel with EtOAc to EtOH-EtOAc (10%, v/v) as eluent to give methyl 4-[1-[4-[N'-(2-bromophenyl)ureido]-3-methoxyphenylacetyl]-(4S)-(6-quinolyloxy-(2S)-pyrrolidinyl]methoxybenzoate (530 mg, 91%) as a colorless oil. $^1$H-NMR ($CDCl_3$) δ 2.30–2.62 (m, 3H), 3.65 (s, 2H), 3.75 (s, 3H), 3.80–3.95 (m, 1H), 3.93 (s, 3H), 4.10–4.30 (m, 1H), 4.50–4.70 (m, 2H), 5.11 (br s, 1H), 6.82–6.98 (m, 6H), 7.15–7.39 (m, 5H), 7.52 (d, J=8.0 Hz, 1H), 7.93–8.03 (m, 5H), 8.14 (d, J=8.3 Hz, 1H), 8.80 (s, 1H).

To a stirred solution of methyl 4-[1-[4-[N'-(2-bromophenyl)ureido]-3-methoxyphenyl acetyl]-4-(6-quinolyloxy-2S-pyrrolidinyl]methoxybenzoate(530 mg, 0.72 mmol) in THF (10.0 ml) and MeOH (5.0 ml) was added 1 N NaOH (1.4 ml, 1.4 mmol). The mixture was stirred at 70° C. for 24 hr. The mixture was concentrated in vacuo, water was added thereto, and neutralized with 1 N HCl. The resulting solid was collected, washed with water, and dried in vacuo to give 122 (460 mg, 88%) as a white crystalline solid. MW 725.59 mp 149–153° C.; IR (KBr) 3332, 1704, 1604, 1527, 1222, 1164 $cm^{-1}$; $^1$H-NMR (DMSO-$d_6$) δ 2.28–2.58 (m, 2H), 3.67 (s, 2H), 3.82 (s, 3H), 3.85–3.90 (m, 1H), 4.05–4.15 (m, 2H), 4.40–4.50 (m, 2H), 5.20–5.32 (m, 1H), 6.77–7.07 (m, 5H), 7.31–7.61 (m, 5H), 7.83–7.97 (m, 5H), 8.21–8.22 (m, 1H), 8.73–8.74 (m, 2H), 8.92 (s, 1H); MS (FAB) m/z 725 (M$^+$), 727 (M$^+$+2); Anal. calcd for $C_{37}H_{33}N_4O_6Br \cdot 0.5H_2O$: C, 60.50; H, 4.67; N, 7.63; Br, 10.88. Found: C, 60.51; H, 4.60; N, 7.52; Br, 11.06.

Example 115

4-[(2S,4S)-1-[3-methoxy-4-[N'-(2-methylphenyl)ureido]phenylacetyl]4-(2-naphthyloxy)-2-pyrrolidinyl]methoxybenzoic acid

123

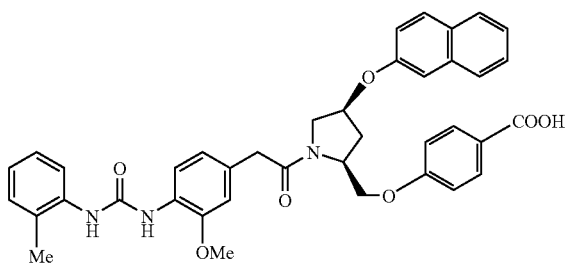

To a stirred mixture of methyl (2S, 4R)-1-tert-butoxycarbonyl-4-hydroxy-2-pyrrolidinylcarboxylate (4.22 g, 17.2 mmol), 2-naphthol (2.73 g, 18.9 mmol) and PPh$_3$ (4.96 g, 18.9 mmol) in THF (80 ml) was added DIAD (3.72 ml, 18.9 mmol) at room temperature under an atmosphere of nitrogen. After stirring over night, the mixture was concentrated in vacuo. The residue was chromatographed on silica gel [600 g, CHCl$_3$/EtOAc (10/1)], to give methyl (2S,4S)-1-tert-butoxycarbonyl-4-(2-naphthyloxy)-2-pyrrolidinylcarboxylate (5.37 g), which was used without further purification.

To a stirred solution of methyl (2S, 4S)-1-tert-butoxycarbonyl-4-(2-napthhyloxy)-2-pyrrolidinyl carboxylate (5.37 g) in THF (116 ml) was added 0.25 N NaOH (116 ml, 29.0 mmol) at room temperature. The resulting mixture was stirred over night. After removal of the solvent, the mixture was acidified by the addition of 1 N HCl and extracted with CHCl$_3$. The combined extracts were washed with brine, dried over Na$_2$SO$_4$ and evaporated. The residue was recrystallized from n-hexane-CHCl$_3$, to give (2S, 4S)-1-tert-butoxycarbonyl-4-(2-naphthyloxy)-2-pyrrolidinylcarboxylic acid [4.44 g, 85% (2 steps)] as a white powder. $^1$H-NMR (DMSO-d$_6$) δ 1.37 and 1.41 (s, 9H, amide isomers), 2.26 (d, J=13.9 Hz, 1H), 2.65 (m, 1H), 3.47 (d, J=11.5 Hz, 1H), 3.81 (m, 1H), 4.30 (m, 1H), 5.14 (m, 1H), 7.02–7.86 (m, 7H).

To a stirred solution of (2S, 4S)-1-tert-butoxycarbonyl-4-(2-naphthyloxy)-2-pyrrolidinylcarboxylic acid (1.12 g, 3.13 mmol) in THF (30 ml) was added BH$_3$.DMS (0.63 ml, 6.3 mmol) at 0° C. The mixture was raised to room temperature immediately and then heated at 50° C. for 1.5 h. After cooling to room temperature, the mixture was quenched by the addition of water at 0° C. and extracted with EtOAc. The combined extracts were washed with brine, dried over Na$_2$SO$_4$ and evaporated. The residue was chromatographed on silica gel [50 g, CHCl$_3$/MeOH (50/1)], to give (2S,4S)-1-tert-butoxycarbonyl-4-(2-naphthyloxy)-2-pyrrolidinylmethanol (1.10 g, 100%) as a pale yellow oil. $^1$H-NMR (CDCl$_3$) δ 1.48 (s, 9H), 2.45 (m, 1H), 3.58–4.80 (m, 4H), 5.01 (br, 1H), 7.04–7.99 (m, 7H).

To a stirred mixture of (2S,4S)-1-tert-butoxycarbonyl-4-(2-naphthyloxy)-2-pyrrolidinyl methanol (640 mg, 1.86 mmol), methyl 4-hydroxybenzoate (283 mg, 1.86 mmol) and PPh$_3$ (488 mg, 1.86 mmol) in THF (18 ml) was added DIAD (0.37 ml, 1.86 mmol) at room temperature under an atmosphere of nitrogen. The mixture was stirred over night. After removal of the solvent, the resulting residue was chromatographed on silica gel [100 g, n-hexane/EtOAc(2/1)], to give methyl 4-[(2S,4s)-1-tert-butoxycarbonyl-4-(2-naphthyloxy)-2-pyrrolidinyl]methoxybenzoate (830 mg, 93%) as a colorless oil. $^1$H-NM (CDCl$_3$) δ 1.50 (d, J=8.3 Hz, 9H), 2.34 (m, 1H), 2.53 (d, J=14.2 Hz, 1H), 3.72–3.85 (m, 1H), 3.86 and3.87 (s, 3H, amide isomers), 4.17 (m, 1H), 4.26–4.52 (m, 2H), 5.06 (br, 1H), 6.87 (d, J=8.8 Hz, 1H), 6.94 (d, J=8.8 Hz, 2H), 7.04 (br, 2H), 7.33 (t, J=7.3 Hz, 1H), 7.42 (t, J=7.3 Hz, 1H), 7.64–8.02 (m, 5H).

To a stirred solution of methyl 4-[(2S, 4S)-1-tert-butoxycarbonyl-4-(2-naphthyloxy)-2-pyrrolidinyl]methoxybenzoate (870 mg, 1.74 mmol) in CH$_2$Cl$_2$ (24 ml) was added TFA (6 ml) at room temperature. The mixture was stirred over night, which was concentrated in vacuo. The residue was diluted with CH$_2$Cl$_2$ and made basic by the addition of 1 N NaOH, which was extracted with CH$_2$Cl$_2$. The organic layer was washed with brine, dried over NaSO$_4$ and concentrated. The residue was chromatographed on silica gel [100 g, n-hexane/EtOAc(211)], to give methyl 4-[(2S, 4S)-4-(2-naphthyloxy)-2-pyrrolidinyl]methoxybenzoate (750 mg, 100%) as a black oil $^1$H-NMR (CDCl$_3$) δ 1.99 (dd, J=14.2, 5.6 Hz, 1H), 2.48 (m, 1H), 3.22 (dd, J=12.2, 4.6 Hz, 1H), 3.43 (d, J=12.5 Hz, 1H), 3.67 (m, 1H), 3.86 and 3.87 (s, 3H, amide isomers), 4.11 (m, 2H), 5.04 (m, 1H), 6.83 (d, J=8.5 Hz, 1H), 6.89 (d, J=8.8 Hz, 2H), 7.07 (d, J=2.0 Hz, 1H), 7.12 (d, J=9.0 Hz, 1H), 7.33 (dt, J=8.1, 1.2 Hz, 1H), 7.44 (dt, J=6.8, 1.2 Hz, 1H), 7.70 (d, J=8.1 Hz, 1H), 7.75 (dd, J=9.0, 5.1 Hz, 2H), 7.90 (d, J=8.5 Hz, 1H), 7.96 (dd, J=6.8, 2.0 Hz, 2).

A mixture of 3-methoxy-4-[N'-(2-methylphenyl)ureido] phenylacetic acid (333 mg, 0.106 mmol), methyl 4-[(2S, 4S)4-(2-naphthyloxy)-2-pyrrolidinyl]methoxybenzoate (400 mg, 1.06 mmol), EDC.HCl (305 mg, 1.59 mmol) and DMAP (194 mg, 1.59 mmol) in DMF (10 ml) was stirred at room temperature for 3 days. The mixture was poured into ice water and extracted with EtOAc. The combined extracts were washed with ice water and brine. After dried over Na$_2$SO$_4$, the extracts were concentrated in vacuo. The residue was chromatographed on silica gel [100 g, n-hexane/EtOAc(1/1)CHCl$_3$/MeOH(50/1)], to give methyl 4-[(2S, 4S)-1-[3-methoxy-4-[N'-(2-methylphenyl)ureido]phenylacetyl]-4-(2-naphthyloxy)-2-pyrrolidinyl]methoxybenzoate (520 mg, 73%) as a pale brown amorphous. $^1$H-NMR (CDCl$_3$) δ 2.28 (s, 3H), 2.29 (m, 1H), 2.55 (d, J=14.2 Hz, 1H), 3.60 (d, J=3.4 Hz, 2H), 3.66 (d, J=3.7 Hz, 3H), 3.68–4.00 (m, 5H), 4.05–4.67 (m, 3H), 5.09 (br, 1H), 6.61 (s, 1H), 6.77 (m, 2H), 6.87 (d, J=8.8 Hz, 1H), 6.94–7.54 (m, 8H), 7.68–8.09 (m, 8H); MS (ESI) m/z 674 (M$^+$+1).

To a solution of methyl 4-[(2S, 4S)-1-[3-methoxy-4-[N'-(2-methylphenyl)ureido]phenylacetyl]-4-(2-naphthyloxy)-2-pyrrolidinyl]methoxybenzoate (415 mg, 0.616 mmol) in THF (4.9 ml), 0.25 N NaOH (4.9 ml) was added. After stirring at room temperature for 3 days, the mixture was acidified with 1 N HCl and extracted with CHCl$_3$-MeOH (10/1). The combined extracts were dried over Na$_2$SO$_4$ and concentrated in vacuo. The residue was purified on TLC [CHCl$_3$/MeOH (10/1)], to give 123 (180 mg, 44%) as a colorless amorphous. MW 659.73 IR (KBr) 3354, 2937, 1685, 1601, 1533, 1255 cm$^{-1}$; $^1$H-NMR (DMSO-d$_6$) δ 2.24 (s, 3H), 2.25–2.43 (m, 2H), 3.65 (s, 2H), 3.81 (s, 3H), 3.83 (m, 1H), 4.05–4.70 (m, 4H), 5.21–5.33 (br, 1H), 6.76 (d, J=7.3 Hz, 1H), 6.86–7.35 (m, 9H), 7.44 (t, J=7.3 Hz, 1H), 7.76–7.89 (m, 6H), 8.01 (d, J=8.3 Hz, 1H), 8.48 (s, 1H), 8.56 (s, 1H); MS (FAB) m/z 660(N$^+$+1).

Example 116

4-[(2S,4S)-1-[4-[N'-(2-chlorophenyl)ureido]-3-methoxyphenylacetyl]-4-(2-naphtyloxy)-2-pyrrolidinyl]methoxybenzoic acid

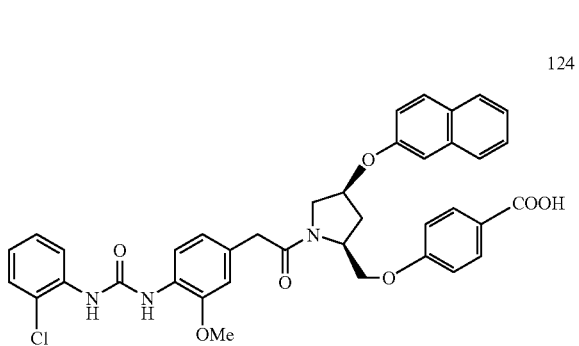

124

A mixture of 4-[N'-(2-chlorophenyl)ureido]-3-methoxyphenylacetic acid (310 mg, 0.93 mmol), methyl 4-[(2S, 4S)-4-(2-naphthyloxy)-2-pyrrolidinyl]methoxybenzoate (350 mg, 0.93 mmol), EDC.HCl (267 mg, 1.40 mmol) and DMAP (171 mg, 1.40 mmol) in DMF (10 ml) was stirred at room temperature for 3 days. The mixture was poured into ice water and extracted with EtOAc. The combined extracts were washed with ice water and brine. After dried over Na$_2$SO$_4$, the extracts were concentrated in vacuo. The residue was chromatographed on silica gel [100 g, n-hexane/EtOAc(1/1)CHCl$_3$/MeOH(50/1)], to give methyl 4-[(2S, 4S)-1-[4-[N'-(2-chlorophenyl) ureido]-3-methoxyphenylacetyl]-4-(2-naphthyloxy)-2-pyrrolidinyl]methoxybenzoate (450 mg, 68%) as a pale brown amorphous. $^1$H-NMR (CDCl$_3$) δ 2.32 (m, 1H), 2.58 (d, J=14.5 Hz, 1H), 3.63 (d, J=2.7 Hz, 1H), 3.70 (s, 3H), 3.86 (s, 3H), 3.84–3.95 (m, 2H), 4.15–4.64 (m, 4H), 5.11 (br, 1H), 6.79–7.06 (m, 7H), 7.21–7.46 (m, 7H), 7.66–7.77 (m, 3H), 7.92 (d, J=8.8 Hz, 1H), 7.97 (m, 1H), 8.17 (d, J=8.4 Hz, 1H); MS (ESI) m/z 694 (M$^+$+1), 696 (M$^+$+3).

To a solution of methyl 4-[(2S, 4S)-1-[4-[N'-(2-chlorophenyl)ureido]-3-methoxyphenyl acetyl]-4-(2-naphthyloxy)-2-pyrrolidinyl]methoxybenzoate (381 mg, 0.535 mmol) in THF (4.3 ml), 0.25 N NaOH (4.3 ml) was added. After stirring at room temperature for 3 days, the mixture was acidified with 1 N HCl and extracted with CHCl$_3$-MeOH (10/1). The combined extracts were dried over Na$_2$SO$_4$ and concentrated in vacuo. The residue was purified on TLC [CHCl$_3$/MeOH (10/1)] to give 124 (140 mg, 39%) as a colorless amorphous. MW 680.15 IR (KBr) 3323, 2935, 1704, 1601, 1529, 1529, 1508 cm$^{-1}$; $^1$H-NMR (DMSO-d$_6$) δ 2.27–2.49 (m, 2H), 3.65 (s, 2H), 3.81 (s, 3H), 3.83 (m, 1H), 4.05–4.71 (m, 4H), 5.30 (br, 1H), 6.77 (d, J=7.8 Hz, 1H), 6.87–7.16 (m, 4H), 7.14 (dd, J=8.8, 2.2 Hz, 1H), 7.27 (t, J=7.3 Hz, 1H), 7.29–7.46 (m, 4H), 7.76–7.86 (m, 5H), 7.96 (d, J=8.3 Hz, 1H), 8.08 (dd, J=8.3, 1.2 Hz, 1H), 8.90 (s, 1H), 8.93 (s, 1H); MS (FAB) m/z 680 (M$^+$+1), 682 (N$^+$+3); Anal. Calcd for C$_{38}$H$_{34}$ClN$_3$O$_7$.1H$_2$O: C, 65.37; H, 5.20; N, 6.02. Found: C, 65.43; H, 5.11; N, 5.93.

Example 117

2-[(2S,4S)-1-[3-methoxy-4-[N'-(2-methylphenyl) ureido]phenylacetyl]-4-(2-naphthyloxy)-2-pyrrolidinyl]methoxy-5-pyridinecarboxylic acid

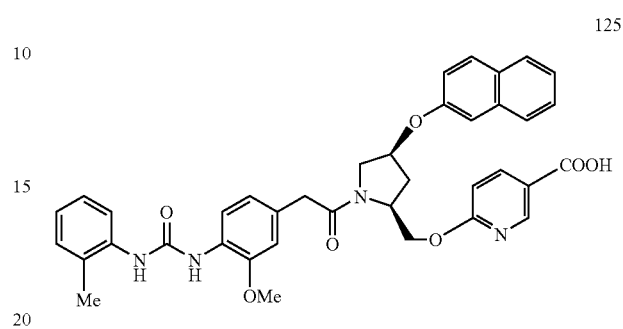

125

To a stirred mixture of methyl (2S, 4R)-1-tert-butoxycarbonyl-4-hydroxy-2-pyrrolidinylcarboxylate (4.22 g, 17.2 mmol), 2-naphthol (2.73 g, 18.9 mmol) and PPh$_3$ (4.96 g, 18.9 mmol) in THF (80 ml) was added DIAD (3.72 ml, 18.9 mmol) at room temperature under an atmosphere of nitrogen. After stirring over night, the mixture was concentrated in vacuo. The residue was chromatographed on silica gel [600 g, CHCl$_3$/EtOAc (10/1)], to give methyl (2S, 4S)-1-tert-butoxycarbonyl-4-(2-naphthyloxy)-2-pyrrolidinylcarboxylate (5.37 g), which was used to the next reaction without further purification.

To a stirred solution of methyl (2S, 4S)-1-tert-butoxycarbonyl-4-(2-naphthyloxy)-2-pyrrolidinyl carboxylate (5.37 g) in THF (116 ml) was added 0.25 N NaOH (116 ml, 29.0 mmol) at room temperature. The resulting mixture was stirred over night. After removal of the solvent, the mixture was acidified by the addition of 1 N HCl and extracted with CHCl$_3$. The combined extracts were washed with brine, dried over Na$_2$SO$_4$ and evaporated. The residue was recrystallized with n-hexane-CHCl$_3$, to give (2S, 4S)-1-tert-butoxycarbonyl-4-(2-naphthyloxy)-2-pyrrolidinylcarboxylic acid [4.44 g, 85%(2 steps)] as a white powder. $^1$H-NMR (DMSO-d$_6$) δ 1.37 and 1.41 (s, 9H, amide isomers), 2.26 (d, J=13.9 Hz, 1H), 2.65 (m, 1H), 3.47 (d, J=11.5 Hz, 1H), 3.81 (m, 1H), 4.30 (m, 1H), 5.14 (m, 1H), 7.02–7.86 (m, 7H).

To a stirred solution of (2S,4S)-1-tert-butoxycarbonyl-4-(2-naphthyloxy)-2-pyrrolidinylcarboxylic acid (1.12 g, 3.13 mmol) in THF (30 ml) was added BH$_3$.DMS (0.63 ml, 6.3 mmol) at 0° C. The mixture was raised to room temperature immediately and then heated at 50° C. for 1.5 h. After cooling to room temperature, the mixture was quenched by the addition of water at 0° C. and extracted with EtOAc. The combined extracts were washed with brine, dried over Na$_2$SO$_4$ and evaporated. The residue was chromatographed on silica gel [50 g, CHCl$_3$/MeOH (50/1)], to give (2S,4S)-1-tert-butoxycarbonyl-4-(2-naphthyloxy)-2-pyrrolidinyl-methanol (1.10 g, 100%) as a pale yellow oil. $^1$H-NMR (CDCl$_3$) δ 1.48 (s, 9H), 2.45 (m, 1H), 3.58–4.80 (m, 4H), 5.01 (br, 1H), 7.04–7.99 (m, 7H).

To a stirred mixture of (2S,4S)-1-tert-butoxycarbonyl-4-(2-naphthyloxy)-2-pyrrolidinylmethanol (484 mg, 1.41 mmol), methyl 2-hydroxy-5-pyridinecarboxylate (216 mg, 1.41 mmol) and PPh$_3$ (370 mg, 1.41 mmol) in THF (15 ml) was added DIAD (0.28 ml, 1.41 mmol) at room temperature under an atmosphere of nitrogen. The mixture was stirred over night. After removal of the solvent, the resulting residue was chromatographed on silica gel [50 g, n-hexane/ EtOAc(2/1)], to give methyl-2-[(2S,4S)-1-tert-butoxycarbonyl-4-(2-naphthyloxy)-2-pyrrolidinyl]methoxypyridine-5-carboxylate (170 mg, 25%) as a colorless oil. $^1$H-NMR (CDCl$_3$) δ 1.47 (s, 9H), 2.37 (m, 1H), 2.46 (d, J=14.2 Hz, 1H), 3.71–4.00 (m, 2H), 3.89 (s, 3H), 4.30–4.56 (m, 2H), 4.74 (dd, J=9.8, 4.6 Hz, 1H), 5.06 (br, 1H), 6.70 (d, J=8.8 Hz, 2H), 7.05–7.09 (m, 21H), 7.33 (t, J=6.9 Hz, 1H), 7.42 (t, J=6.9 Hz, 1H), 7.67–7.75 (m, 3H), 8.09 (d, J=8.8 Hz, 1H), 8.77 (d, J=2.2 Hz, 1H).

To a stirred solution of 5carboxymethyl-2-[(2S,4S)-1-tert-butoxycarbonyl-4-(2-napthyloxy)-2-pyrrolidinyl]methoxypyridine (170 mg, 0.36 mmol) in CH$_2$Cl$_2$ (5 ml) was added TFA (2 ml) at room temperature. After 2 h stirring, the mixture was concentrated in vacuo, which was diluted with CH$_2$Cl$_2$ and basified by the addition of 1 N NaOH. The combined reaction mixture was extracted with CH$_2$Cl$_2$. The organic layer was washed with brine, which were dried over NaSO$_4$ and concentrated. The residue was purified on TLC [CHCl$_3$/MeOH (10/1)], to give methyl 2-[(2S,4S)-4-(2-naphthyloxy)2-pyrrolidinyl]methoxypyridine-5-carboxylate (107 mg, 80%) as a colorless oil $^1$H-NMR (CDCl$_3$) δ 1.95 (m, 1H4), 2.27 (br, 1H), 2.46 (m, 1H), 3.19 (dd, J=12.2, 4.9 Hz, 1H), 3.41 (d, J=12.2 Hz, 1H), 3.65 (m, 1H), 3.89 (s, 3H), 4.58 (m, 2H), 5.00 (br, 1H), 6.77 (d, J=8.8 Hz, 1H), 7.06 (br, 1H), 7.11 (dd, J=8.8, 2.7 Hz, 1H), 7.31–7.45 (m, 2H), 7.69–7.76 (m, 3H), 8.13 (dd, J=8.8, 2.4 Hz, 14), 8.78 (d, J=2.2 Hz, 1H).

A mixture of 3-methoxy-4-[N'-(2-methylphenyl)ureido] phenylacetic acid (89 mg, 0.283 mmol), methyl-2-[(2S,4S)-4-(2-naphthyloxy)-2-pyrrolidinyl]methoxypyridine-5-carboxylate (107 mg, 0.78 mmol), EDC.HCl (81 mg, 0.425 mmol) and DMAP (52 mg, 0.425 mmol) in DMF (3 ml) was stirred at room temperature for 18 h. The mixture was poured into ice water and extracted with EtOAc. The combined extracts were washed with ice water and brine. After dried over Na$_2$SO$_4$, the extracts were concentrated in vacuo. The residue was purified on TLC [CHCl$_3$/MeOH (10/1)], to give 2-[(2S,4S)-1-[3-methoxy-4-[N'-(2-methylphenyl)ureido]phenylacetyl]-4-(2-naphthyloxy)-2-pyrrolidinyl]methoxy-5-pyridinecarboxylic acid methyl ester (193 mg, 100%) as a colorless amorphous. $^1$H-NMR (CDCl$_3$) δ 2.27 (d, J=3.2 Hz, 3H), 2.30 (m, 1H), 2.49 (dd, J=14.2, 2.0 Hz, 1H), 3.60 (d, J=3.9 Hz, 1H), 3.67 (d, J=5.9 Hz, 31), 3.81 (s, 1H), 3.85 (s, 1H), 3.88 and 3.91 (s, 3H, amide isomers), 3.95 (m, 1H), 4.02–5.09 (m, 4H), 6.67 (d, J=8.8 Hz, 1H), 6.73–7.13 (m, 3H), 7.20–7.45 (m, 7H), 7.53 (t, J=7.8 Hz, 1H), 7.67–7.77 (m, 3H), 8.02–8.84 (m, 3H).

For HCl salt: a pale brown amorphous. IR(KBr) 3346, 2951, 1720, 1601, 1533, 1281 cm$^{-1}$; MS (FAB) m/z 675 (M$^+$+1).

To a solution of 2-[(2S,4S)-1-[3-methoxy-4-[N'-(2-methylphenyl)ureido]phenylacetyl]-4-(2-naphthyloxy)-2-pyrrolidinyl]methoxy-5-pyridinecarboxylic acid methyl ester (158 mg, 0.23 mmol) in THF (1.8 ml), 0.25 N NaOH (1.8 ml) was added. After stirring at room temperature for 22 h, the mixture was neutralized with 1 N HCl and extracted with CHCl$_3$-MeOH (10/1). The combined extracts were dried over Na$_2$SO$_4$ and concentrated in vacuo. The residue was purified on TLC [CHCl$_3$/MeOH (5/1)] to give 125 (51 mg, 34%) as a colorless amorphous solid. MW 660.72 IR (KBr) 3354, 2956, 1601, 1533, 1255, 1022 cm$^{-1}$; $^1$H-NMR (DMSO-d$_6$) δ 2.24 (s, 3H), 3.30–5.32 (m, 13H), 6.72–8.82 (m, 19H); MS (FAB) m/z 661 (M$^+$+1); Anal. Calcd for C$_{38}$H$_{36}$N$_4$O$_7$·0.5EtOH·1H$_2$O: C, 66.75; H, 5.89; N, 7.98. Found: C, 66.39; H, 5.55; N, 7.66.

Example 118

4-[5-(R)-benzyloxymethyl-1-[4-[N'-(2-methylphenyl)ureido]phenylacetyl]-2-(S)-pyrrolidinyl methoxy]benzoic acid

126

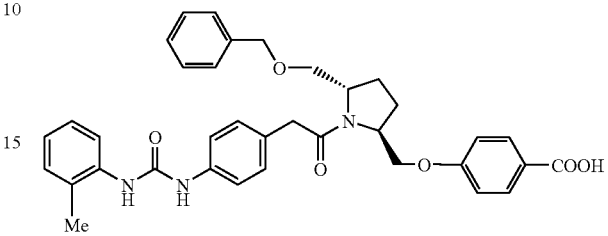

To a stirred solution of benzyl-(S)-glycidyl ether (5.0 g, 30.5 mmol) in THF (100 ml) was added allylmagnesium chloride (1.0 M in Et$_2$O, 30.5 ml, 30.5 mmol) at −78° C., and the resulting mixture was gradually warmed up to rt with stirring. The mixture was poured into water and concentrated in vacuo, then extracted with CHCl$_3$. The organic layer was dried over anhydrous Na$_2$SO$_4$ and concentrated in vacuo. The residue was chromatographed on silica gel with hexane-EtOAc (5:1) as eluent to give 1-benzyloxy-2-(R)-hydroxy-5-hexene (2.18 g, 35%) as a colorless oil: $^1$H-NMR (CDCl$_3$) δ 1.52–1.60 (m, 2 H), 2.11–2.25 (m, 2 H), 2.34 (d, J=3.2 Hz, 1 H), 3.35 (dd, J=9.6, 8.0 Hz, 1 H), 3.52 (dd, J=9.6, 3.2 Hz, 1 H), 3.84–3.86 (m, 1 H), 4.57.(s, 2 H), 4.96–5.07 (series of m, 2 H), 5.78–5.88 (m, 1 H), 7.29–7.38 (m, 5 H); MS (ESI) m/z, 224 (M$^+$+NH$_4^+$).

To a stirred solution of 1-benzyloxy-2-(R)-hydroxy-5-hexene (2.18 g, 10.5 mmol), triphenylphosphine (3.32 g, 12.7 mmol) and phthalimide (1.86 g, 12.7 mmol) was added diisopropyl azodicarboxylate (2.62 ml, 12.7 mmol) at rt, and the resulting mixture was stirred for overnight at rt. The mixture was concentrated in vacuo and extracted with EtOAc. The organic layer was washed with water, drying over anhydrous Na$_2$SO$_4$, then concentrated in vacuo. The residue was chromatographed on silica gel with hexane-EtOAc (5:1) as eluent to give 1-benzyloxy-2-(S)-phthalimido-5-hexene (2.95 g, 83%) as a colorless oil: $^1$H-NMR (CDCl$_3$) δ 1.76–1.84 (m, 2 H), 2.06 (dd, J=14.4, 6.8 Hz), 2 H, 2.12–2.22 (m, 1 H), 3.69 (dd, J=10.0, 5.6 Hz, 1 H), 4.00 (t, J=9.6 Hz, 1 H), 4.46 (d, J=12.0 Hz, 1 H), 4.53 (d, J=12.0 Hz, 1 H), 4.51–4.58 (m, 1 H), 4.91–4.99 (series of m, 2 H), 5.72–5.79 (m, 1 H)7.21–7.26 (m, 5 H), 7.71–7.83 (series of m, 2 H); MS (ESI) m/z, 336 (M$^+$+H).

To a stirred solution of 1-benzyloxy-2-(S)-phthalimido-5-hexene (2.95 g, 8.80 mmol) in EtOH (30 ml) was added hydrazine hydrate (80% in water, 460 ml, 11.4 mmol) at rt, and the resulting mixture was heated under reflux for 7.5 h with stirring. The solution was filtered, and the filtrate was concentrated in vacuo. The residue was poured into aq.NaHCO$_3$ and extracted with CHCl$_3$. The organic layer was dried over anhydrous Na$_2$SO$_4$, then concentrated in vacuo to give 2-(S)-amino-1benzyloxy-5-hexene (1.90 mg, quant.) as a colorless oil. $^1$H-NMR (CDCl$_3$) δ 1.37–1.55 (series of m, 4 H), 2.08–2.19 (m, 2 H), 2.99–3.03 (m, 1 H), 3.25 (dd, J=9.2, 7.6 Hz, 1 H), 3.45 (dd, J=9.2, 4.0 Hz, 1 H), 4.53 (s, 2 H), 4.94–5.06 (series of m, 2 H), 5.76–5.85 (m, 1 H), 7.27–7.37 (m, 5 H); MS (ESI) m/z, 206 (M$^+$+H), 247 (M$^+$+H+CH$_3$CN).

To a stirred solution of 2-(S)-amino-1-benzyloxy-5-hexene (1.89 g, 9.21 mmol) and triethylamine (1.28 ml, 9.21 mmol) in $CH_2Cl_2$ (20 ml) was added benzoyl chloride (1.07 ml, 9.21 mmol) at rt, and the resulting mixture was stirred for 23 h. The mixture was poured into water and extracted with $CH_2Cl_2$. The organic layer was washed with water, drying over anhydrous $Na_2SO_4$, then concentrated in vacuo. The residue was chromatographed on silica gel with hexane-EtOAc (5:1) as eluent to give N-[2-(S)-(1-benzyloxy)-5-hexenyl]benzamide (2.67 g, 94%) as a colorless needles. mp 78–79° C.; $^1$H-NMR ($CDCl_3$) δ 1.76–1.82 (m, 2 H), 2.11–2.17 (m, 2 H), 3.59 (br s, 2 H), 4.29–4.35 (m, 1 H), 4.54 (dd, J=19.2, 12.0 Hz, 2 H), 4.96–5.05 (series of m, 2 H), 5.78–5.89 (m, 1 H), 6.39 (d, J=8.0 Hz, 1 H), 7.27–7.51 (m, 8 H), 7.74 (d, J=7.2 Hz, 2 H); MS (ESI) m/z, 310 ($M^+$+H).

To a stirred solution of N-[2-(S)-(1-benzyloxy)-5-hexenyl]benzamide (2.41 g, 7.79 mmol) in $CH_3CN$—$H_2O$ (3:1, 40 ml) was added iodine (2.97 g, 23.4 mmol) in one portion, and the resulting mixture was stirred for 20 h. The mixture was poured into aq.$Na_2S_2O_3$ and concentrated in vacuo, then extracted with $CHCl_3$. The organic layer was washed with brine, drying over anhydrous $Na_2SO_4$, then concentrated in vacuo. The residue was dissolved in $CH_2Cl_2$ (30 ml) and was added di-tert-butyl dicarbonate (2.55 g, 11.7 mmol), $Et_3$ N (1.63 ml, 11.7 mmol) and N, N-dimethyl aminopyridine (180 mg, 1.47 mmol), and the resulting mixture was stirred overnight at rt. The mixture was poured into water and extracted with $CH_2Cl_2$. The organic layer was washed with water, drying over $Na_2SO_4$, and concentrated in vacuo. The residue was chromatographed on silica gel with hexane-EtOAc (5:1) to give N-Boc-2-(S)-benzoyloxymethyl-5-(S)-benzyloxy methylpyrrolidine (1.27 g, 38%) as a colorless oil. $^1$H-NMR ($CDCl_3$) δ 1.41 and 1.49 (s, total 9 H), 1.85–2.00 (series of m, 4 H), 3.33–4.59 (series of m, 8 H), 7.26–7.32 (m, 5 H), 7.41–7.46 (m, 2 H), 7.54–7.57 (m, 1 H), 8.02 (d, J=7.6 Hz, 2 H); MS (ESI) m/z, 426 ($M^+$+H), 448 ($M^+$+Na+).

To a stirred solution of N-Boc-2-(S)-benzoyloxymethyl-5-(S)-benzyloxy methylpyrrolidine (1.23 g, 2.89 mmol) in MeOH (30 ml) was added NaOH (1.0 M in water, 3.47 ml, 3.47 mmol) at rt, and the resulting mixture was stirred for 4 h. The mixture was neutralized with aq. 1N-HCl and concentrated in vacuo, then extracted with $CHCl_3$. The organic layer was washed with brine, drying over anhydrous $Na_2SO_4$, then concentrated in vacuo. The residue was chromatographed on silica gel with hexane-EtOAc (3:1) as eluent to give N-Boc-5-(S)-hydroxymethyl-2-(S)-benzyloxymethyl pyrrolidine (847 mg, 91%) as a colorless oil. $^1$H-NMR ($CDCl_3$) δ 1.41 (s, 9 H), 1.57 (br s, 1 H), 1.95–1.97 (m, 2 H), 2.05–2.18 (m, 1 H), 3.36 (t, J=8.4 Hz, 1 H), 3.56–3.62 (m, 2 H), 3.67–3.72 (m, 2 H), 3.95 (br s, 1 H), 4.03 (br s, 1 H), 4.51 (s, 1 H), 7.28–7.37 (m, 5H); MS (FAB) m/z, 322 ($M^+$+H).

To a stirred solution of N-Boc-2-(S)-hydroxymethyl-5-(S)-benzyloxymethylpyrrolidine (388 mg, 1.21 mmol), triphenylphosphine (380 mg, 1.45 mmol) and methyl 4-hydroxybenzoate (220 mg, 1.45 mmol) was added diisopropyl azodicarboxylate (200 ml, 1.45 mmol) at rt, and the resulting mixture was stirred overnight. The mixture was concentrated in vacuo and extracted with EtOAc. The organic layer was washed with water, drying over anhydrous $Na_2SO_4$, then concentrated in vacuo. The residue was chromatographed on silica gel with hexane-EtOAc (3:1) as eluent to give methyl 4-[2-(S)-(N-Boc-5-(S)-benzyloxymethyl)pyrrolidinylmethoxy]benzoate (462 mg, 84%) as a colorless oil: $^1$H-NMR ($CDCl_3$) δ 1.40 and 1.48 (s, total 9 H), 1.98–2.13 (m, 4 H), 3.83 and 3.85 (s, 3 H), 3.33–4.25 (series of m, 4 H), 4.47–4.59 (m, 2 H), 6.91–6.96 (m, 2 H), 7.26–7.34 (m, 5 H), 7.95–7.98 (m, 2 H); MS (FAB) m/z, 456 (N+H), 478 ($M^+$+Na+).

To a stirred solution of methyl 4-[2-(S)-(N-Boc-5-(S)-benzyloxymethyl)pyrrolidinyl methoxy]benzoate (446 mg, 0.98 mmol) in $CH_2Cl_2$ (10 ml) was added trifluoroaceticacid (10 ml) at rt, and the resulting mixture was stirred for 1 h. The mixture was concentrated in vacuo and poured into aq.$NaHCO_3$, then extracted with $CHCl_3$. The organic layer was washed with water, drying over anhydrous $Na_2SO_4$, then concentrated in vacuo to give methyl 4-[2-(S)-(5-(S)-benzyloxymethyl) pyrrolidinylmethoxy]benzoate (363 mg, quant.) as yellowish oil. The product was used for next reactions without further purification. $^1$H-NMR ($CDCl_3$) δ 1.43–1.65 (m, 2 H), 1.93–2.07 (m, 3 H), 3.36–3.68 (series of m, 4 H), 3.89 (s, 3 H), 3.86–3.93 (over lap, 2 H), 4.55 (s, 2 H), 6.90 (d, J=8.4 Hz, 2 H), 7.26–7.37 (m, 5 H), 7.97 (d, J=8.4 Hz, 2 H); MS (FAB) m/z, 356 ($M^+$+H).

To a stirred solution of methyl 4-[2-(S)-(5-(S)-benzyloxymethyl)pyrrolidinylmethoxy]benzoate (115 mg, 0.32 mmol), 4-[N'-(2-methylphenyl)ureido]phenylacetic acid (92.0 mg, 0.32 mmol) and N,N-dimethylaminopyridine (52.0 mg, 0.42 mmol) in DMF (10 ml) was added EDC.HCl (81.0 mg, 0.42 mmol) at rt, and the resulting mixture was stirred overnight. The reaction mixture was poured into water and extracted with $CHCl_3$. The organic layer was washed with brine, drying over anhydrous $Na_2SO_4$, then concentrated in vacuo. The residue was chromatographed on silica gel with $CHCl_3$-MeOH (20:1) as eluent to give methyl 4-[5-(R)-benzyl oxymethyl-1-[4-[N'-(2-methylphenyl)ureido]phenylacetamido]-2-(S)-pyrrolidinylmethoxy]benzoate (169 mg, 84%) as a colorless amorphous solid. $^1$H-NMR ($CDCl_3$), mixture of rotamars δ 1.92–2.18 (m, 3 H), 2.24 and 2.25 (s, total 3 H), 2.20–2.31 (overlap, 1 H), 3.39–3.70 (series of m, 4 H), 3.87 and 3.89 (s, total 3 H), 4.17 and 4.18 (s, total 2 H), 4.30–4.45 (series of m, 2 H), 4.53 (s, 2 H), 6.43–7.13 (series of m, 9 H), 7.20–7.36 (series of m, 7 H), 7.58–7.99 (series of m, 3 H); MS (FAB) m/z, 622 ($M^+$+H).

To a stirred solution of methyl 4-[5-(R)-benzyloxymethyl-1-[4-[N'-(2-methylphenyl) ureido]phenylacetyl]-2-(S)-pyrrolidinylmethoxy]benzoate (156 mg, 0.24 mmol) in MeOH-THF (1:5, 12 ml) was added 1.0M-NaOH (1.2 ml, 1.20 mmol) at rt, and the resulting mixture was heated at 80° C. with stirring for 7 h. The mixture was poured into 1N-HCl, then extracted with $CHCl_3$. The organic layer was washed with brine, drying over anhydrous $Na_2SO_4$, then concentrated in vacuo. The residue was chromatographed on silica gel with $CHCl_3$-MeOH (5:1) as eluent to give 126 (94.0 mg, 65%) as a colorless amorphous solid. MW 607.70 $^1$H-NMR ($CD_3OD$), mixture of rotamars δ 1.85–2.35 (series of m, 4 H), 2.43–2.92 (series of m, 5 H), 2.28 (s, 3 H), 3.55–4.55 (series of m, 10 H), 6.85–7.95 (series of m, 17 H); MS (ESI) m/z, 630 ($M^+$+Na+).

Example 119

4-[5-(R)-benzyloxymethyl-1-[4-[N'-(2-chlorophenyl)ureido]-3-methoxyphenylacetyl]-2-(S)-pyrrolidinylmethoxy]benzoic acid

127

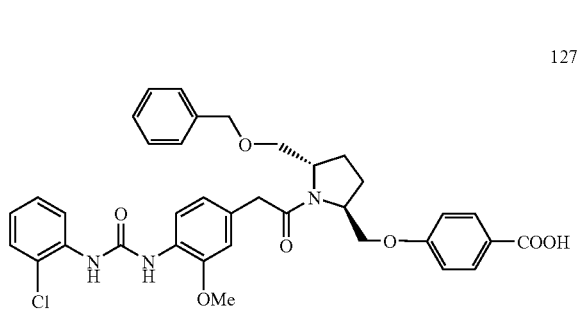

To a stirred solution of methyl 4-[2-(S)-(5-(S)-benzyloxymethyl)pyrrolidinylmethoxy]benzoate (117 mg, 0.33 mmol), 4-[N'-(2-chlorophenyl)ureido]-3-methoxyphenylacetic acid (110 mg, 0.33 mmol) and N,N-dimethylaminopyridine (50.0 mg, 0.40 mmol) in DMF (10 ml) was added EDC.HCl (76.0 mg, 0.40 mmol) at rt, and the resulting mixture was stirred overnight. The reaction mixture was poured into water and extracted with CHCl$_3$. The organic layer was washed with brine, drying over anhydrous Na$_2$SO$_4$, then concentrated in vacuo. The residue was chromatographed on silica gel with CHCl$_3$-MeOH (20:1) as eluent to give methyl 4-[5-(R)-benzyloxymethyl-1-[4-[N'-(2-chlorophenyl)ureido]-3-methoxyphenylacetyl]-2-(S)-pyrrolidinyl methoxy]benzoate (189 mg, 85%) as a colorless amorphous solid. $^1$H-NMR (CDCl$_3$), mixture of rotamars δ 1.91–2.30 (series of m, 4 H), 3.39–3.74 (series of m, 3 H), 3.73 (s, 2 H), 4.15–4.02 (m, 2 H), 4.32–4.44 (m, 1 H), 4.54 (s, 2 H), 6.71–7.02 (series of m, 5 H), 7.06 (s, 1 H), 7.17 (s, 1 H), 7.24–7.40 (series of m, 7 H), 7.89–8.22 (series of m, 4 H); MS (FAB) m/z, 672 (M$^+$+H).

To a stirred solution of methyl 4-[5-(R)-benzyloxymethyl-1-[4-[N'-(2-chlorophenyl) ureido]-3-methoxyphenylacetyl]-2-(S)-pyrrolidinylmethoxy]benzoate (169 mg, 0.25 mmol) in MeOH-THF (2:5, 7 ml) was added 1.0M-NaOH (750 ml, 0.75 mmol) at rt, and the resulting mixture was heated at 80° C. with stirring for 2 h. The mixture was poured into 1N-HCl, then extracted with CHCl$_3$. The organic layer was washed with brine, drying over anhydrous Na$_2$SO$_4$, then concentrated in vacuo. The residue was chromatographed on silica gel with CHCl$_3$-MeOH (15:1) as eluent to give 127 (114 mg, 69%) as a colorless amorphous solid. MW 658.14 $^1$H-NMR (CD$_3$OD), mixture of rotamars δ 1.88–2.37 (series of m, 4 H), 3.51–4.49 (series of m, 8H), 3.64 and 3.73 (s, total 3 H), 4.86 (s, 2 H), 6.85–7.95 (series of m, 16 H); MS (ESI) m/z, 658 (M$^+$+H), 680 (M$^+$30 Na$^+$); Anal. Calcd for C$_{36}$H$_{36}$ClN$_3$O$_7$.H$_2$O: C, 63.95; H, 5.66; N, 6.21. Found: C, 63.65; H, 5.40: N, 5.95.

Example 120

4-[5-(R)-benzyloxymethyl-1-[4-[N'-(2-bromophenyl)ureido]-3-methoxyphenylacetyl]-2-(S)-pyrrolidinylmethoxy]benzoic acid

128

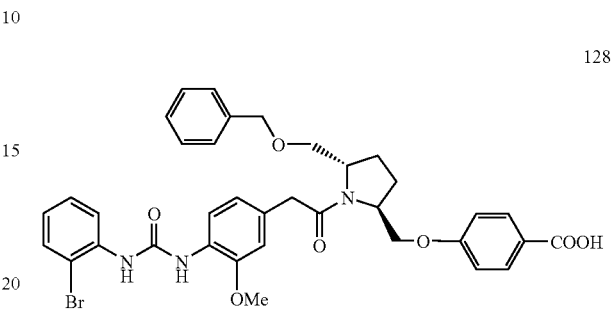

To a stirred solution of methyl 4-[2-(S)-(5-(S)-benzyloxymethyl)pyrrolidinylmethoxy]benzoate (119 mg, 0.34 mmol), 4-[N'-(2-bromophenyl)ureido]-3-methoxyphenylacetic acid (127 mg, 0.34 mmol) and N,N-dimethylaminopyridine (50.0 mg, 0.40 mmol) in DMF (10 ml) was added EDC.HCl (77.0 mg, 0.40 mmol) at rt, and the resulting mixture was stirred overnight. The reaction mixture was poured into water and extracted with CHCl$_3$. The organic layer was washed with brine, drying over anhydrous Na$_2$SO$_4$, then concentrated in vacuo. The residue was chromatographed on silica gel with CHCl$_3$-MeOH (20:1) as eluent to give methyl 4-[5-(R)-benzyloxymethyl-1-[4-[N'-(2-bromophenyl)ureido]-3-methoxyphenylacetyl]-2-(S)-pyrrolidinyl methoxy]benzoate (217 mg, 90%) as a colorless amorphous solid. $^1$H-NMR (CDCl$_3$), mixture of rotamars δ 1.92–2.31 (series of m, 4 H), 3.39–3.73 (series of m, 3 H), 3.65 (s, 2H), 4.15–4.02 (m, 2 H), 4.32–4.44 (m, 1 H), 4.54 (s, 2 H), 6.71–6.99 (series of m, 5 H), 7.04 (s, 1 H), 7.11 (s, 1 H), 7.22–7.39 (series of m, 7 H), 7.51–8.17 (series of m, 4 H); MS (FAB) m/z, 716 (M$^+$), 718 (M$^+$+2).

To a stirred solution of methyl 4-[5-(R)-benzyloxymethyl-1-[4-[N'-(2-bromophenyl) ureido]-3-methoxyphenylacetyl]-2-(S)-pyrrolidinylmethoxy]benzoate (178 mg, 0.25 mmol) in MeOH-THF (2:5, 7 ml) was added 1.0M-NaOH (750 ml, 0.75 mmol) at rt, and the resulting mixture was heated at 80° C. with stirring for 1.5 h. The reaction mixture was poured into 1N-HCl, then extracted with CHCl$_3$. The organic layer was washed with brine, drying over anhydrous Na$_2$SO$_4$, then concentrated in vacuo. The residue was chromatographed on silica gel with CHCl$_3$-MeOH (15:1) as eluent to give 128 (159 mg, 91%) as a colorless amorphous solid. MW 702.59 $^1$H-NMR (CD$_3$OD), mixture of rotamars δ 1.88–2.35 (series of m, 4 H), 3.51–4.49 (series of m, 8 H), 3.64 and 3.72 (s, total 3 H), 4.87 (s, 2 H), 6.65–8.05 (series of m, 16 H); MS (ESI) m/z, 702 (M$^+$), 704 (N$^+$+2); Anal. Calcd for C$_{36}$H$_{36}$BrN$_3$O$_7$.H$_2$O: C, 60.00; H, 5.32; N, 5.83. Found: C, 59.66; H, 5.04: N, 5.65.

Example 121

3-[5-(R)-benzyloxymethyl-1-[4-[N'-(2-methylphenyl)ureido]-3-methoxyphenylacetyl]-2-(S)-pyrrolidinylmethoxy]benzoic acid

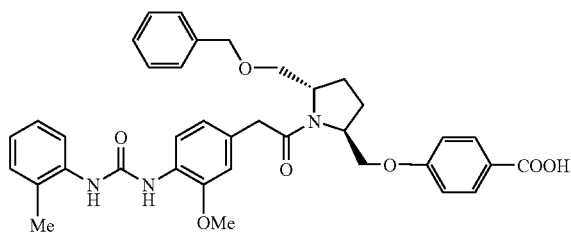

129

To a stirred solution of N-Boc-2-(S)-hydroxymethyl-5-(S)-benzyloxymethylpyrrolidine (415 mg, 1.29 mmol), triphenylphosphine (410 mg, 1.55 mmol) and methyl 3-hydroxybenzoate (240 mg, 1.55 mmol) was added diisopropyl azodicarboxylate (320 ml, 1.55 mmol) at rt, and the resulting mixture was stirred overnight. The mixture was concentrated in vacuo, then the residue was chromatographed on silica gel with hexane-EtOAc (3:1) as eluent to give methyl 3-[2-(S)-(N-Boc-5-(S)-benzyloxymethyl)pyrrolidinyl-methoxy]benzoate (513 mg, 87%) as a colorless oil: $^1$H-NMR (CDCl$_3$) δ 1.40 and 1.46 (s, total 9 H), 1.95–2.20 (series of m, 4 H), 3.33–3.72 (series of m, 2 H), 3.82–4.00 (m, 1 H), 3.90 and 3.91 (s, total 3 H), 4.09–4.21 (m, 3 H), 4.21–4.57 (m, 2 H), 7.11–7.15 (m, 1 H), 7.26–7.37 (m, 6 H), 7.53–7.65 (m, 2 H); MS (ESI) m/z, 456 (M$^+$+H).

To a stirred solution of methyl 3-[2-(S)-(N-Boc-5-(S)-benzyloxymethyl)pyrrolidinyl-methoxy]benzoate (501 mg, 1.10 mmol) in CH$_2$Cl$_2$ (10 ml) was added trifluoroacetic acid (10 ml) at rt, and the resulting mixture was stirred for 1 h. The mixture was concentrated in vacuo and poured into aq.NaHCO$_3$, the extracted with CHCl$_3$. The organic layer was washed with water, drying over anhydrous Na$_2$SO$_4$, and concentrated in vacuo to give methyl 3-[2-(S)-(5-(S)-benzyloxymethyl) pyrrolidinyl-methoxy]benzoate (387 mg, quant.) as yellowish oil. The product was used for next reactions without further purification. $^1$H-NMR (CDCl$_3$) δ 1.26–1.65 (m, 2 H), 1.94–2.04 (m, 3 H), 3.37–3.52 (m, 2 H), 3.63–3.66 (m, 1 H), 3.85–3.93 (m, 1 H), 3.91 (s, 3 H), 4.55 (s, 2 H), 7.09–7.11 (m, 1 H), 7.27–7.54 (m, 6 H), 7.54–7.55 (m, 1H), 7.61–7.63 (m, 2 H); MS (ESI) m/z, 35 (M$^+$+H).

To a stirred solution of methyl 3-[2-(S)-(5-(S)-benzyloxymethyl)pyrrolidinylmethoxy]benzoate (140 mg, 0.39 mmol), 4-[N'-(2-methylphenyl)ureido]-3-methoxyphenylacetic acid (125 mg, 0.39 mmol) and N,N-methylaminopyridine (58.0 mg, 0.47 mmol) in THF (15 ml) was added EDC.HCl (90.0 mg, 0.47 mmol) at rt, and the resulting mixture was stirred overnight. The reaction mixture was poured into water and extracted with CHCl$_3$. The organic layer was washed with brine, drying over anhydrous Na$_2$SO$_4$, then concentrated in vacuo. The residue was chromatographed on silica gel with CHCl$_3$-MeOH (10:1) as eluent to give methyl 3-[5-(R)-benzyloxymethyl-1-[4-[N'-(2-methylphenyl)ureido]-3-methoxyphenylacetyl]-2-(S)-pyrrolidinyl methoxy]benzoate (256 mg, quant.) as a colorless amorphous solid. $^1$H-NMR (CDCl$_3$), mixture of rotamars δ 1.67 (s, 3 H), 1.97–2.40 (series of m, 4 H), 3.42–3.85 (series of m, 5 H), 3.60 (s, 3 H), 3.95 and 3.97 (s, total 3 H), 4.15–4.26 (m, 2 H), 4.36–4.49 (m, 1 H), 4.59 (s, 2 H), 6.32 and 6.36 (s, total 1 H), 6.75–6.87 (series of m, 2 H), 7.20 (br s, 2 H), 7.16–7.72 (series of m, 10 H), 8.03–8.09 (m, 1 H); MS (ESI) m/z, 652 (M$^+$+H).

To a stirred solution of methyl 3-[5-(R)-benzyloxymethyl-1-[4-[N'-(2-methylphenyl) ureido]-3-methoxyphenylacetyl]-2-(S)-pyrrolidinylmethoxy]benzoate (185 mg, 0.28 mmol) in MeOH-THF (2:5, 7 ml) was added 1.0 M-NaOH (860 ml, 0.86 mmol) at rt, and the resulting mixture was heated at 60° C. with stirring for 1 h. The reaction mixture was poured into 1N-HCl, then extracted with CHCl$_3$. The organic layer was washed with brine, drying over anhydrous Na$_2$SO$_4$, then concentrated in vacuo. The residue was chromatographed on silica gel with CHCl$_3$-MeOH (5:1) as eluent to give129 (171 mg, 94%) as a colorless amorphous solid. MW 637.72 $^1$H-NMR (CD$_3$OD), mixture of rotamars δ 1.89–2.37 (series of m, 4 H), 2,29 (s, 3 H), 3.52–4.53 (series of m, 8 H), 3.66 and 3.74 (s, total 3 H), 4.85 (s, 2 H), 6.66–7.98 (series of m, 16 H); MS (ESI) m/z, 638 (M$^+$+H), 660 (M$^+$+Na$^+$); Anal. Calcd for C$_{37}$H$_{39}$N$_3$O$_7$.H$_2$O: C, 67.77; H, 6.30; N, 6.41. Found: C, 67.40; H, 5.95: N, 6.14.

Example 122

3-[5-(R)-benzyloxymethyl-1-[4-[N'-(2-chlorophenyl)ureido]-3-methoxyphenylacetyl]-2-(S)-pyrrolidinylmethoxy]benzoic acid

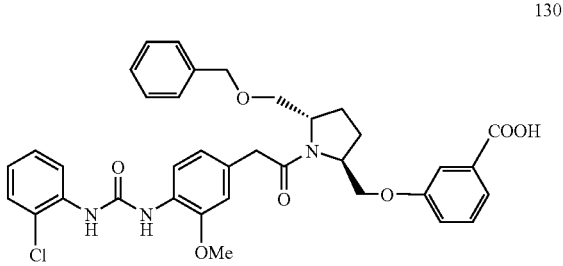

130

To a stirred solution of methyl 3-[2-(S)-(5-(S)-benzyloxymethyl)pyrrolidinylmethoxy]benzoate (118 mg, 0.33 mmol), 4-[N'-(2-chlorophenyl)ureido]-3-methoxyphenylacetic acid (112 mg, 0.33 mmol) and N,N-dimethylaminopyridine (50.0 mg, 0.40 mmol) in THF (15 ml) was added EDC.HCl (80.0 mg, 0.40 mmol) at rt, and the resulting mixture was stirred overnight. The reaction mixture was poured into water and extracted with CHCl$_3$. The organic layer was washed with brine, drying over anhydrous Na$_2$SO$_4$, then concentrated in vacuo. The residue was chromatographed on silica gel with CHCl$_3$-MeOH (10:1) as eluent to give methyl 3-[5-(R)-benzyloxymethyl-1-[4-[N'-(2-chlorophenyl)ureido]-3-methoxyphenylacetamido]-2-(S)-pyrrolidinylmethoxy]benzoate (226 mg, quant.) as a colorless amorphous solid. $^1$H-NMR (CDCl$_3$), mixture of rotamars δ 1.99–2.40 (series of m, 4 H), 3.43–3.92 (series of m, 5 H), 3.67 (s, 3 H), 3.98 and 4.02 (s, total 3 H), 4.18–4.29 (m, 2 H), 4.36–4.51 (m, 1 H), 4.60 (s, 2 H), 6.75–6.92 (series of m, 2 H), 7.01–7.22 (series of m, 4 H), 7.29–7.53 (series of m, 9 H), 7.62–8.26 (series of m, 3 H); MS (ESI) m/z, 672 (M$^+$+H).

To a stirred solution of methyl 3-[5-(R)-benzyloxymethyl-1-[4-[N'-(2-chlorophenyl) ureido]-3-methoxyphenylacetyl]-2-(S)-pyrrolidinylmethoxy]benzoate (169 mg, 0.25 mmol) in MeOH-THF (2:5, 7 ml) was added 1.0M-NaOH (760 ml, 0.76 mmol) at rt, and the resulting mixture was heated at 60° C. with stirring for 1.5 h. The reaction mixture was poured into 1N-HCl, then extracted with CHCl$_3$. The organic layer was washed with brine, dryed over anhydrous Na$_2$SO$_4$, then concentrated in vacuo. The residue was chromatographed on silica gel with CHCl$_3$-MeOH (5:1) as eluent to give 130 (155 mg, 94%) as a colorless amorphous solid. MW 658.14 $^1$H-NMR (CD$_3$OD), mixture of rotamars δ 1.89–2.35 (series of m, 4 H), 3.52–4.53 (series of m, 8 H), 3.68 and 3.75 (s, total 3 H), 4.85 (s, 2 H), 6.68–8.03 (series of m, 16 H); MS (ESI) m/z, 658 (M$^+$+H), 680 (M$^+$+Na$^+$); Anal. Calcd for C$_{36}$H$_{36}$ClN$_3$O$_7$.H$_2$O: C, 63.95; H, 5.66; N, 6.21. Found: C, 64.01; H, 5.38: N, 5.96.

Example 123

3-[5-(R)-benzyloxymethyl-1-[4-[N'-(2-bromophenyl)ureido]-3-methoxyphenylacetyl]-2-(S)-pyrrolidinylmethoxy]benzoic acid

131

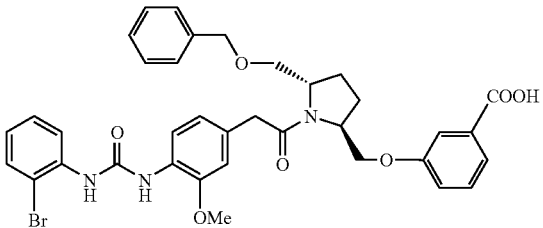

To a stirred solution of methyl 3-[2-(S)-(5-(S)-benzyloxymethyl)pyrrolidinylmethoxy]benzoate (116 mg, 0.33 mmol), 4-[N'-(2-bromophenyl)ureido]-3-methoxyphenylacetic acid (124 mg, 0.33 mmol) and N,N-dimethylaminopyridine (48.0 mg, 0.39 mmol) in THF (15 ml) was added EDC.HCl (75.0 mg, 0.39 mmol) at rt, and the resulting mixture was stirred overnight. The reaction mixture was poured into water and extracted with CHCl$_3$. The organic layer was washed with brine, drying over anhydrous Na$_2$SO$_4$, then concentrated in vacuo. The residue was chromatographed on silica gel with CHCl$_3$-MeOH (10:1) as eluent to give methyl 3-[5-(R)-benzyloxymethyl-1-[4-[N'-(2-bromophenyl)ureido]-3-methoxyphenylacetyl]-2-(S)-pyrrolidinyl methoxy]benzoate (209 mg, 89%) as a colorless amorphous solid. $^1$H-NMR (CDCl$_3$), mixture of rotamars δ 1.99–2.37 (series of m, 4 H), 3.43–3.91 (series of m, 5 H), 3.70 (s, 3 H), 3.93 and 3.96 (s, total 3 H), 4.19–4.28 (m, 2 H), 4.37–4.51 (m, 1 H), 4.60 (s, 2 H), 6.77–7.11 (series of m, 6 H), 7.28–7.74 (series of m, 10 H), 7.91–7.95 (series of m, 1 H), 8.20–8.23 (series of m, 1 H); MS (ESI) m/z 716 (M$^+$), 718 (M$^+$+2).

To a stirred solution of methyl 3-[5-(R)-benzyloxymethyl-1-[4-[N'-(2-bromophenyl) ureido]-3-methoxyphenylacetyl]-2-(S)-pyrrolidinylmethoxy]benzoate (176 mg, 0.25 mmol) in MeOH-THF (2:5, 7 ml) was added 1.0M-NaOH (760 ml, 0.76 mmol) at rt, and the resulting mixture was heated at 60° C. with stirring for 1.5 h. The reaction mixture was poured into 1N-HCl, then extracted with CHCl$_3$. The organic layer was washed with brine, drying over anhydrous Na$_2$SO$_4$, then concentrated in vacuo. The residue was chromatographed on silica gel with CHCl$_3$-MeOH (5:1) as eluent to give 131 (156 mg, 88%) as a colorless amorphous solid. MW 702.59 $^1$H-NMR (CD$_3$OD), mixture of rotamars δ 1.89–2.37 (series of m, 4 H), 2,29 (s, 3 H), 3.52–4.53 (series of m, 8 H), 3.68 and 3.75 (s, total 3 H), 4.85 (s, 2 H), 6.67–7.95 (series of m, 16 H); MS (ESI) m/z, 702 (M$^+$+H), 704 (M$^+$+Na$^+$); Anal. Calcd for C$_{36}$H$_{36}$BrN$_3$O$_7$.H$_2$O: C, 60.00; H, 5.32; N, 5.83. Found: C, 59.65; H, 5.02: N, 5.65.

Example 124

4-[(2S,4S)-4-methoxy-l1-[3-methoxy-4-[N'-(2-methylphenyl)ureido]phenylacetyl]-2-pyrrolidinyl]methoxybenzoic acid

132

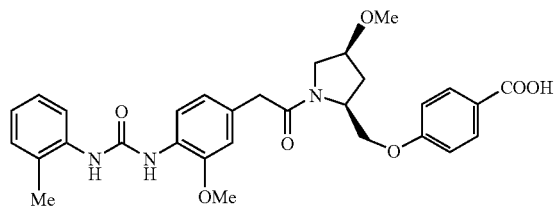

To a stirred mixture of (2S,4R)-1-tert-butoxycarbonyl-2-tert-butyldiphenylsilyloxymethy-4-hydroxypyrrolidine (21.7 g, 47.6 mmol), acetic acid (3.0 ml, 52.4 mmol) and PPh$_3$ (12.5 g, 52.4 mmol) in THF (330 ml) was added DIAD (9.4 ml, 47.6 mmol) at room temperature under an atmosphere of nitrogen. After 2 h stirring the same temperature, the mixture was heated at 50° C. for 2 h . After cooling to room temperature, the reaction mixture was concentrated in vacuo. The resulting residue was chromatographed on silica gel [1 Kg, n-hexane/EtOAc(5/1)], to give (2S,4S)4-acetoxy-1-tert-butoxycarbonyl-2-tert-butyldiphenylsilyloxymethy-pyrrolidine (23.3 g, 99%) as a colorless oil. $^1$H-NMR (CDCl$_3$) δ 1.06 (s, 9H), 1.35 and 1.43 (s, 9H, amide isomers), 1.92 (br, 3H), 2.20–2.45 (m, 2H), 3.31–4.07 (m, 5H), 5.17–5.30 (m, 1H), 7.36–7.44 (m, 6H), 7.65–7.71 (m, 4H).

To a stirred mixture of (2S,4S)-4-acetoxy-1-tert-butoxycarbonyl-2-tert-butyldiphenyl silyloxy methypyrrolidine (23.3 g, 46.9 mmol) and acetic acid (6.0 ml, 104.8 mmol) in THF (470 ml) was added TBAF (93.8 ml, 93.8 mmol) at 0° C. After 24 h stirring, the mixture was concentrated in vacuo. The resulting residue was diluted with EtOAC and aq. NH$_4$Cl and extracted with EtOAc. The combined extracts were washed with brine, which were dried over Na$_2$SO$_4$ and concentrated in vacuo. The residue was chromatographed on silica gel [700 g, CHCl$_3$/EtOAc (4/1)], to give (2S,4S)-4-acetoxy-1-tert-butoxycarbonyl-2-pyrrolidinemethanol (9.70 g, 8%) as a colorless oil. $^1$H-NMR (CDCl$_3$) δ 1.47 (s, 9H), 1.63 (m, 1H), 1.81 (m, 1H), 2.07 (s, 3H), 2.34 (m, 1H), 3.42 (dd, J=12.7, 0.9 Hz, 1H), 3.62–3.85 (m, 31H), 4.48 (br, 1H), 5.20 (br, 1H).

To a stirred mixture of (2S,4S)-4-acetoxy-1-tert-butoxycarbonyl-2-pyrrolidinemethanol (9.70 g, 37.4 mmol), p-hydroxybenzoic acid methyl ester (5.69 g, 37.4 mmol) and PPh$_3$ (10.8 g, 41.1 mmol) in THF (200 ml) was added DIAD (8.10 ml, 41.1 mmol) at room temperature. After 1.5 h stirring, the mixture was concentrated in vacuo. The resulting residue was chromatographed on silica gel [700 g, CHCl$_3$/EtOAc (10/1)], to give methyl 4-[(2S,4S)-4-acetoxy-1-tert-butoxycarbonyl-2-pyrrolidinyl]methoxybenzoate (11.8 g, 81%) as a pale yellow oil. $^1$H-NMR (CDCl$_3$) δ 1.48 (s, 9H), 2.03 (s, 3H), 2.27 (m, 2H), 3.46 (m, 1H), 3.72 (m, 1H), 3.88 (s, 3H), 3.98 (t, J=9.0 Hz, 1H), 4.21–4.47 (m, 2H), 5.31 (br, 1H), 6.96 (br, 2H), 7.98 (d, J=8.8 Hz, 2H).

To a stirred solution of methyl 4-[(2S,4S)-4-acetoxy-1-tert-butoxycarbonyl-4-hydroxy-2-pyrrolidinyl]methoxybenzoate (7.43 g, 18.9 mmol) in MeOH (150 ml) was added cat. $K_2CO_3$ at room temperature. After 1 day stirring, the mixture was concentrated in vacuo. The resulting residue was recrystallized by the addition of $CHCl_3$-n-hexane, to give methyl 4-[(2S,4S)-1-tert-butoxycarbonyl-4-hydroxy-2-pyrrolidinyl]methoxybenzoate (5.76 g, 87%) as a colorless solid. $^1$H-NMR ($CDCl_3$) δ 1.46 (s, 9H), 2.11 (m, 1H), 2.35 (br, 1H), 3.27–3.65 (m, 2H), 3.89 (s, 3H), 4.07–4.54 (m, 4H), 6.96 (d, J=6.9 Hz, 2H), 7.99 (d, J=6.9 Hz, 2H).

To a stirred solution of methyl 4-[(2S,4S)-1-tert-butoxycarbonyl-4-hydroxy-2-pyrrolidinyl]methoxybenzoate (2.10 g, 5.98 mmol) in THF (60 ml) was added 60% oil NaH (359 mg, 8.97 mmol) at 0° C. After 15 minutes stirring, MeI (1.20 ml, 8.97 mmol) was added to the mixture was added at same temperature, and the resulting mixture was allowed to raise to room temperature for over 1 h. Then 60% oil NaH (359 mg, 8.97 mmol) and MeI (1.20 ml, 8.97 mmol) was added to the reaction mixture at room temperature and stirred for 14 h. The reaction mixture was poured into ice water and extracted with $CHCl_3$. The combined extracts were washed with aq. $NaHCO_3$ and brine. After dried over $Na_2SO_4$, the extracts were concentrated in vacuo. The residue was chromatographed on silica gel [50 g, n-hexane/EtOAc(4/1)], to give methyl 4-[(2S,4S)-1-tert-butoxycarbonyl-4-methoxy-2-pyrrolidinyl]methoxybenzoate (1.32 g, 60%) as a colorless oil. $^1$H-NMR ($CDCl_3$) δ 1.48 (s, 9H), 2.05 (m, 1H), 2.29 (d, J=14.2 Hz, 1H), 3.30 (s, 3H), 3.36–4.38 (m, 4H), 6.76 (br, 2H), 7.97 (d, J=8.8 Hz, 2H).

To a stirred solution of methyl 4-[(2S,4S)-1-tert-butoxycarbonyl-4-methoxy-2-pyrrolidinyl]methoxybenzoate (2.38 g, 3.61 mmol) in $CH_2Cl_2$ (46 ml) was added TFA (23 ml) at room temperature. After 14 h stirring, the mixture was concentrated in vacuo. The residue was diluted by the addition of $CH_2Cl_2$ and 1 N NaOH, and extracted with $CH_2Cl_2$. The combined extracts were washed with brine, dried over $Na_2SO_4$, which was concentrated in vacuo. The residue was chromatographed on silica gel [50 g, $CHCl_3$/MeOH (20/1)], to give methyl 4-[(2S,4S)-4-methoxy-2-pyrrolidinyl]methoxybenzoate (950 mg, 99%) as a yellow oil. $^1$H-NMR ($CDCl_3$) δ 2.16 (t, J=5.3 Hz, 1H), 2.72 (s, 1H), 2.95 (d, J=6.8 Hz, 1H), 3.11 (d, J=11.0 Hz, 1H), 3.26 (t, J=1.9 Hz, 3H), 3.52 (br, 1H), 3.84 (d, J=1.7 Hz, 3H), 3.92 (s, 1H), 4.00 (d, J=4.1 Hz, 2H), 6.88 (m, 2H), 7.94 (m, 2H).

A mixture of 3-methoxy-4-[N'-(2-methylphenyl)ureido]phenylacetic acid (375 mg, 1.19 mmol), methyl 4-[(2S,4S) 4-methoxy-2-pyrrolidinyl]methoxybenzoate (317 mg, 1.19 mmol), EDC.HCl (342 mg, 1.79 mmol), HOBT (242 mg, 1.79 mmol) and $Et_3$ N (0.83 ml, 5.95 mmol) in DMF (5 ml) was stirred at room temperature for 13 h. The mixture was poured into ice water and extracted with EtOAc. The combined extracts were washed with ice water and brine. After dried over $Na_2SO_4$, the extracts were concentrated in vacuo. The residue was chromatographed on silica gel [50 g, $CHCl_3$/Aectone (10/1)$CHCl_3$/MeOH (20/1)], to give methyl 4-[(2S,4S)-4-methoxy-1-[3-methoxy-4-[N'-(2-methylphenyl)ureido]phenylacetyl]-2-pyrrolidinyl]methoxybenzoate (650 mg, 98%) as a pale brown amorphous solid $^1$H-NMR ($CDCl_3$) δ 2.03 (m, 1H), 2.31 (s, 3H), 2.32 (m, 1H), 3.29 (d, J=1.0 Hz, 3H), 3.57–3.68 (m, 5H), 3.88 (d, J=1.0 Hz, 3H), 3.99–4.06 (m, 2H), 4.46 (m, 1H), 6.19 (m, 1H), 6.80 (s, 1H), 6.81 (d, J=9.0 Hz, 1H), 6.96–7.19 (m, 4H), 7.29 (m, 2H), 7.50 (d, J=6.7 Hz, 1H), 7.95–8.10 (m, 3H); MS (ESI) m/z 562 (M$^+$+1).

To a solution of methyl 4-[(2S,4S)-4-methoxy-1-[3-methoxy-4-[N'-(2-methylphenyl) ureido]phenylacetyl]-2-pyrrolidinyl]methoxybenzoate (650 mg, 1.16 mmol) in THF (18.5 ml), 0.25 N NaOH (18.5 ml) was added. After stirring at room temperature for 12 h, the mixture was acidified with 1 N HCl and extracted with $CHCl_3$-MeOH (10/1). The combined extracts were dried over $Na_2SO_4$ and concentrated in vacuo. The residue was chromatographed on silica gel [50 g, $CHCl_3$/MeOH (20/1)] to give 132 (540 mg, 85%) as a colorless amorphous solid. MW 547.60 IR (KBr) 3354, 2937, 1709, 1685, 1604, 1533, 1454 cm$^{-1}$; $^1$H-NMR (DMSO-$d_6$) δ 2.11 (m, 2H), 2.25 (s, 3H), 3.22 (s, 3H), 3.49–3.78 (m, 4H), 3.82 and 3.86 (s, 3H, amide isomers), 3.87–4.52 (m, 4H), 6.71–7.17 (m, 71H), 7.79 (d, J=8.1 Hz, 1H), 7.86–8.03 (m, 3H), 8.45–8.57 (m, 2H), 12.64 (br, 1H); MS (ESI) m/z 548 (M$^+$+1); Anal. Calcd for $C_{30}H_{33}N_3O_7 \cdot 1Na \cdot 1.5H_2O$: C, 60.29; H, 6.07; N, 7.03. Found: C, 59.90; H, 5.59; N, 6.69.

Example 125

4-[(2S,4S)-1-[4-[N'-(2-chlorophenyl)ureido]-3-methoxyphenylacetyl]-4-methoxy-2-pyrrolidinyl]methoxybenzoic acid

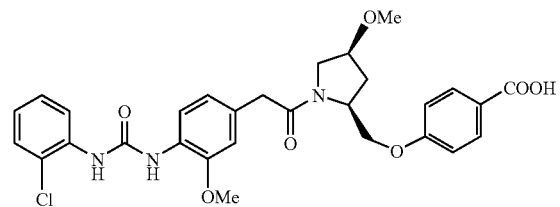

133

A mixture of 4-[N'-(2-chlorophenyl)ureido]-3-methoxyphenylacetic acid (398 mg, 1.19 mmol), methyl 4-[(2S, 4S)-4-methoxy-2-pyrrolidinyl]methoxybenzoate (317 mg, 1.19 mmol), EDC.HCl (342 mg, 1.79 mmol), HOBT (242 mg, 1.79 mmol) and $Et_3$ N (0.83 ml, 5.95 mmol) in DMF (5 ml) was stirred at room temperature for 13 h. The mixture was poured into ice water and extracted with EtOAc. The combined extracts were washed with ice water and brine. After dried over $Na_2SO_4$, the extracts were concentrated in vacuo. The residue was chromatographed on silica gel [50 g, $CHCl_3$/Aectone (10/1)$CHCl_3$/MeOH (20/1)], to give methyl 4-[(2S,4S)-1-[4-[N'-(2-chlorophenyl)ureido]-3-methoxyphenylacetyl]-4-methoxy-2-pyrrolidinyl]methoxybenzoate (600 mg, 87%) as a colorless amorphous solid $^1$H-NMR ($CDCl_3$) δ 1.99–2.06 (m, 1H), 2.34 (d, J=13.9 Hz, 1H), 3.30 (s, 3H), 3.59 (d, J=7.4 Hz, 1H), 3.62 (d, J=3.2 Hz, 2H), 3.83 (s, 3H), 3.88 (s, 3H), 4.00–4.18 (m, 3H), 4.42–4.51 (m, 2H), 6.82–7.07 (m, 7H), 7.28 (d, J=8.3 Hz, 1H), 7.35 (dd, J=7.9, 1.5 Hz, 1H), 7.94–8.00 (m, 3H), 8.18(d, J=8.3 Hz, 1H); MS (ESI) m/z 582 (M$^+$+1), 584 (M$^+$+3).

To a solution of methyl 4-[(2S,4S)-1-[4-[N'-(2-chlorophenyl)ureido]-3-methoxyphenyl acetyl]4-methoxy-2-pyrrolidinyl]methoxybenzoate (600 mg, 1.03 mmol) in THF (16 ml), 0.25 N NaOH (16 ml) was added. After stirring at room temperature for 12 h, the mixture was acidified with 1 N HCl and extracted with $CHCl_3$-MeOH (10/1). The combined extracts were dried over $Na_2SO_4$ and concentrated in vacuo. The residue was purified on TLC [$CHCl_3$/MeOH (10/1)] to give 133 (495 mg, 75%) as a colorless amorphous solid.

MW 568.02 IR (KBr) 3330, 3070, 2937, 1709, 1685, 1604, 1533 cm⁻; $^1$H-NMR (DMSO-d$_6$) δ 2.11 (m, 2H), 3.22 (s, 3H), 3.56–3.78 (m, 4H), 3.81 and 3.85 (s, 3H, amide isomers), 3.88–4.56 (m, 4H), 6.73 and 6.77 (d, J=8.1 Hz, 1H, amide isomers), 6.85 and 6.91 (s, 1H, amide isomers), 7.01–7.07 (m, 3H), 7.28 (t, J=8.1 Hz, 1H), 7.43 (d, J=8.1 Hz, 1H), 7.85–7.94 (m, 2H), 7.97 (d, J=8.6 Hz, 1H), 8.09 (d, J=8.3 Hz, 1H), 8.90–8.95 (m, 2H); MS (FAB) m/z 570 (M$^+$+1), 572 (M$^+$+3).

Example 126

4-[(2S,4S)-1-[4-[N'-(2-bromophenyl)ureido]-3-methoxyphenylacetyl]-4-methoxy-2-pyrrolidinyl]methoxybenzoic acid

134

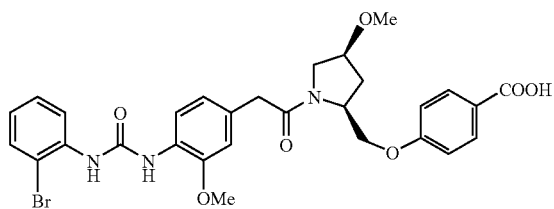

A mixture of 4-[N'-(2-bormophenyl)ureido]-3-methoxyphenylacetic acid (451 mg, 1.19 mmol), methyl 4-[(2S,4S)-4-methoxy-2-pyrrolidinyl]methoxybenzoate (317 mg, 1.19 mmol), EDC.HCl (342 mg, 1.79 mmol), HOBT (242 mg, 1.79 mmol) and Et$_3$N (0.83 ml, 5.95 mmol) in DMF (5 ml) was stirred at room temperature for 13 h. The mixture was poured into ice water and extracted with EtOAc. The combined extracts were washed with ice water and brine. After dried over Na$_2$SO$_4$, the extracts were concentrated in vacuo. The residue was chromatographed on silica gel [50 g, CHCl$_3$/Aectone (10/1)], to give methyl 4-[(2S,4S)-1-[4-[N'-(2-bromophenyl)ureido]-3-methoxy phenylacetyl]-4-methoxy-2-pyrrolidinyl]methoxybenzoate (760 mg, 100%) as a yellow oil. $^1$H-NMR (CDCl$_3$) δ 1.99–2.32 (m, 1H), 2.34 (d, J=13.4 Hz, 1H), 3.30 (s, 3H), 3.59 (m, 1H), 3.63 (d, J=3.2. Hz, 2H), 3.68 (dd, J=12.2, 5.1 Hz, 1H), 3.81 (br, 1H), 3.88 (s, 3H), 3.91–4.16 (m, 2H), 4.49–4.51 (m, 2H), 6.82–7.15 (m, 7H), 7.31 (t, J=8.1 Hz, 1H), 7.52 (d, J=8.1 Hz, 1H), 7.93–8.00 (m, 3H), 8.14 (d, J=8.3 Hz, 1H); MS (ESI) m/z 626 (M$^+$+1), 628 (M$^+$+3).

To a solution of methyl 4-[(2S,4S)-1-[4-[N'-(2-bromophenyl)ureido]phenylacetyl]-4-methoxy-2-pyrrolidinyl]methoxybenzoate (760 mg, 1.19 mmol) in THF (19 ml), 0.25 N NaOH (19 ml) was added. After stirring at room temperature for 12 h, the mixture was acidified with 1 N HCl and extracted with CHCl$_3$-MeOH (10/1). The combined extracts were dried over Na$_2$SO$_4$ and concentrated in vacuo. The residue was chromatographed on silica gel [50 g, CHCl$_3$/MeOH (20/1)] to give 134 (580 mg, 78%) as a colorless amorphous solid. MW 612.47 IR (KBr) 3330, 2935, 1709, 1685, 1604, 1529, 1434 cm⁻¹; $^1$H-NMR (DMSO-d$_6$) δ 2.11 (m, 2H), 3.22 (s, 3H), 3.58–3.78 (m, 4H), 3.81 and 3.86 (s, 3H, amide isomers), 3.92–4.52 (m, 4H), 6.72 (d, J=8.6 Hz, 1H), 6.77 (d, J=8.3 Hz, 1H), 6.85 and 6.91 (s, 1H, amide isomers), 6.97 (t, J=7.1 Hz, 1H), 7.02 and 7.06 (d, J=8.6 Hz, 2H, amide isomers), 7.32 (t, J=7.3 Hz, 1H), 7.59 (dd, J=8.1, 1.0 Hz, 1H), 7.94 (dd, J=8.1, 1.2 Hz, 2H), 7.95–7.98 (m, 2H), 8.74 (s, 1H), 8.94 (s, 1H), 12.63 (br, 1H); MS (FAB) m/z 612 (M$^+$+1), 614 (M$^+$+3).

Example 127

4-[(4R)-methoxy-1-[3-methoxy-4-[N'-(2-methylphenyl)ureido]phenylacetyl]-(2S)-pyrrolidinyl methoxy] benzoic acid

135

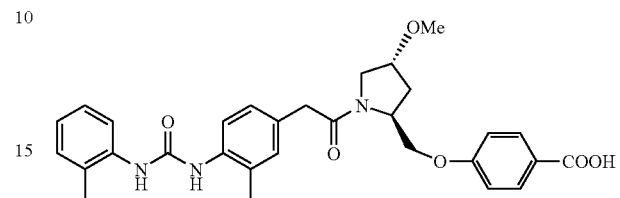

To a stirred solution of 1-(tert-butoxycarbonyl)-(4R)-methoxy-(2S)-pyrrolidinylcarboxylic acid (2.87 g, 11.7 mmol) in THF (25 ml) was added BH$_3$DMS (1.66 ml, 17.5 mmol) at room temperature and the reaction mixture was stirred at room temperature overnight. The mixture was evaporated and the residue was dissolved with CH$_2$Cl$_2$. The solution was washed with H$_2$O, brine, dried over Na$_2$SO$_4$, and evaporated. The residue was purified by column chromatography on silica-gel with CHCl$_3$-MeOH (50:1, v/v) as eluent to give 1-(tert-butoxycarbonyl)-(4R)-methoxy-(2S)-prolinol (1.79 g, 66%) as a colorless oil. $^1$H-NMR (CDCl$_3$) δ 1.47 (s, 9 H), 1.69–1.73 (m, 1 H), 2.12–2.17 (m, 1 H), 3.31 (s, 3 H), 3.37–3.40 (m, 1 H), 3.53–3.62 (m, 2 H), 3.68–3.73 (m, 1 H), 3.83–3.87 (m, 1 H), 4.04–4.07 (m, 1 H), 4.90–4.92 (m, 1 H); MS (FAB) m/z 232 (M$^+$+1).

To a stirred solution of methyl 4-hydroxybenzoate (1.18 g, 7.76 mmol), 1-(tert-butoxy carbonyl)-(4R)-methoxy-(2S)-prolinol (1.79 g, 7.74 mmol) and Ph$_3$P (2.44 g, 9.3.0 mmol) in THF (30 ml) was added DIAD (1.83 ml, 9.29 mmol) and the reaction mixture was heated under reflux for 5 hr. After cooled to room temperature, the mixture was evaporated. The residue was filtered on silica-gel with toluene-acetone (5:1, v/v) as eluent to give the crude product. The crude product was dissolved in CH$_2$Cl$_2$ (20 ml). The solution was added TFA (20 ml) and the reaction mixture was stirred at room temperature overnight. The mixture was concentrated in vacuo and made basic by sat. NaHCO$_3$. The mixture was extracted with CHCl$_3$, washed with brine, dried over K$_2$CO$_3$, and evaporated. The residue was purified by column chromatography on silica-gel with CHCl$_3$-MeOH (30:1 to 30:2, v/v) as eluent to give methyl 4-[(4R)-methoxy-(2S)-pyrrolidinyl methoxy]benzoate (1.67 g, 81% for 2 steps) as a reddish brown oil. $^1$H-NMR (CDCl$_3$) δ 1.65–1.72 (m, 1 H), 1.89 (bs, 1 H), 2.05–2.22 (m, 1 H), 2.95–3.15 (m, 2 H), 3.31 (s, 3 H), 3.69–3.76 (m, 1 H), 3.88 (s, 3 H), 3.91–4.06 (m, 3 H), 6.89–6.92 (m, 2 H), 7.96–7.98 (m, 2 H); MS (FAB) m/z 266 (M$^+$+1).

A mixture of 3-methoxy-4-[N'-(2-methylphenyl)ureido]phenylacetic acid (470 mg, 1.50 mmol), methyl 4-[(4R)-methoxy-(2S)-pyrrolidinylmethoxy]benzoate (396 mg, 1.49 mmol), EDC.HCl (343 mg, 1.79 mmol), HOBt (242 mg, 1.79 mmol) and Et$_3$N (250 ml, 1.79 mmol) in THF (10 ml) was stirred at room temperature overnight. The mixture was diluted with H$_2$O and extracted with EtOAc. The extract was washed with brine, dried over Na$_2$SO$_4$, and evaporated. The residue was purified by column chromatography on silica-gel with CHCl$_3$-MeOH (100:1, v/v) as eluent to give methyl 4-[(4R)-methoxy-1-[3-methoxy-4-[N'-(2-methylphenyl)ureido]phenyl acetyl]-(2S)-pyrrolidinylmethoxy]benzoate (822 mg, 98%) as a white foam. $^1$H-NMR (CDCl$_3$) δ 2.14–2.24 (m, 2 H), 2.27 (s, 3 H), 3.25 (s, 3 H), 3.51 (s, 3 H), 3.58–3.73 (m, 4 H), 3.88 (s, 3 H), 3.98–4.09 (m, 2 H), 4.40–4.53 (m, 2 H), 6.67–7.29 (series of m, total 9 H), 7.57–7.59 (m, 1 H), 7.91–7.93 (m, 2 H), 8.04–8.06 (m, 1 H); MS (FAB) m/z 562 (M$^+$+1).

To a stirred solution of methyl 4-[(4R)-methoxy-1-[3-methoxy-4-[N'-(2-methylphenyl) ureido]phenylacetyl]-(2S)-pyrrolidinylmethoxy]benzoate (517 mg, 0.92 mmol) in THF (5 ml) was added 0.5 N NaOH (5 ml) and the reaction mixture was heated under reflux for 3 hr. After cooled to room temperature, the mixture was poured into ice-1 N HCl and the resulting precipitate was collected under a reduced pressure. The crude solid was purified by recrystallization from MeOH—CHCl$_3$-IPE to give 135 (144 mg, 29%) as a white crystalline powder. MW 547.60 mp 112–115° C.; $^1$H-NMR (DMSO-d$_6$) δ 2.04–2.17 (m, 2 H), 2.25 (s, 3 H), 3.21 (s, 3 H), 3.56–3.75 (m, 4 H), 3.79 (s, 3 H), 4.04–4.35 (m, 4 H), 6.73–7.17 (series of m, total 7 H), 7.79–7.81 (m, 1 H), 7.87–7.89 (m, 2 H), 7.99–8.01 (m, 1 H), 8.47 (s, 1 H), 8.55 (s, 1 H), 12.63 (bs, 1 H); MS (FAB) m/z 548 (M$^+$+1); Anal. Calcd for C$_{30}$H$_{33}$N$_3$O$_7$·1/4H$_2$O: C, 65.26; H, 6.12; N, 7.61. Found: C, 65.36; H, 6.45; N, 7.24.

Example 128

4-[1-[4-[N'-(2-fluorophenyl)ureido]-3-methoxyphenylacetyl]-(4R)-methoxy-(2S)-pyrrolidinyl methoxy] benzoic acid

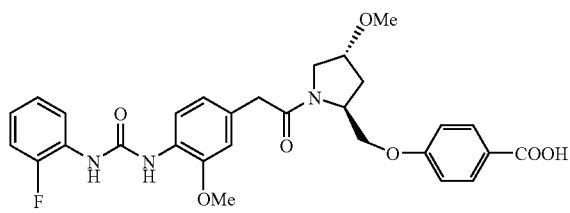

136

A mixture of 4-[N'-(2-fluorophenyl)ureido]-3-methoxyphenylacetic acid (476 mg, 1.50 mmol), methyl 4-[(4R)-methoxy-(2S)-pyrrolidinylmethoxy]benzoate (397 mg, 1.50 mmol), EDC.HCl (344 mg, 1.79 mmol), HOBt (243 mg, 1.80 mmol) and Et$_3$ N (250 ml, 1.79 mmol) in THF (10 ml) was stirred at room temperature overnight. The mixture was diluted with H$_2$O and extracted with EtOAc. The extract was washed with brine, dried over Na$_2$SO$_4$, and evaporated. The residue was purified by column chromatography on silica-gel with CHCl$_3$-MeOH (100:1, v/v) as eluent to give methyl 4-[1-[4-[N'-(2-fluorophenyl)ureido]-3-methoxyphenylacetyl]-(4R)-methoxy-(2S)-pyrrolidinylmethoxy]benzoate (806 mg, 95%) as a pale yellow foam. $^1$H-NMR (CDCl$_3$) δ 2.14–2.37 (m, 2 H), 3.28 (s, 3 H), 3.44 (s, 3 H), 3.48–3.74 (m, 4 H), 3.88 (s, 3 H), 4.02–4.15 (m, 2 H), 4.43–4.58 (m, 2 H), 6.63–7.10 (series of m, total 7 H), 7.68–7.73 (m, 1 H), 7.89–8.02 (m, 4 H), 8.16–8.20 (m, 1 H); MS (FAB) m/z 566 (M$^+$+1).

To a stirred solution of methyl 4-[1-[4-[N'-(2-fluorophenyl)ureido]-3-methoxyphenyl acetyl]-(4R)-methoxy-(2S)-pyrrolidinylmethoxy]benzoate (491 mg, 0.87 mmol) in THF (5 ml) was added 0.5 N NaOH (5 ml) and the reaction mixture was heated under reflux for 3 hr. After cooled to room temperature, the mixture was poured into ice-1 N HCl and the resulting precipitate was collected under a reduced pressure. The crude solid was purified by recrystallization from MeOH—CHCl$_3$-IPE to give 136 (173 mg, 36%) as a white crystalline powder. MW 551.56 mp 111–116° C.; $^1$H-NMR (DMSO-d$_6$) δ 2.08–2.17 (m, 2 H), 3.21 (s, 3 H), 3.56–3.73 (m, 4 H), 3.78 (s, 3 H), 4.04–4.33 (m, 4 H), 6.74–7.22 (series of m, total 7 H), 7.87–7.89 (m, 2 H), 7.99–8.01 (m, 1 H), 8.16–8.20 (m, 1 H), 8.70 (s, 1 H), 9.18 (s, 1 H), 12.64 (br s, 1 H); MS (FAB) m/z 552 (M$^+$+1); Anal. Calcd for C$_{29}$H$_{30}$N$_3$O$_7$·0.15H$_2$O: C, 62.84; H, 5.51; F, 3.43; N, 7.58. Found: C, 63.08; H, 5.83; F, 3.30; N, 7.15.

Example 129

4-[ 1-[4-[N'-(2-chlorophenyl)ureido]-3-methoxyphenylacetyl]-(4R)-methoxy-(2S)-pyrrolidinyl methoxy] benzoic acid

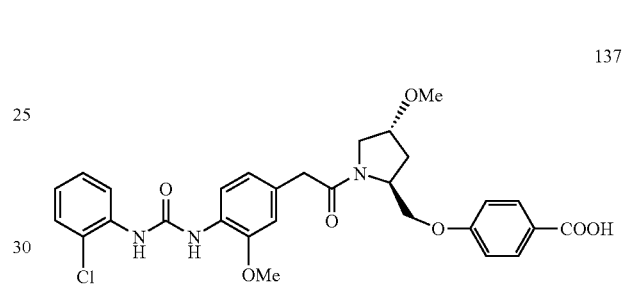

137

A mixture of 4-[N'-(2-chlorophenyl)ureido]-3-methoxyphenylacetic acid (460 mg, 1.37 mmol), methyl 4-[(4R)-methoxy-(2S)-pyrrolidinylmethoxy]benzoate (365 mg, 1.38 mmol), EDC.HCl (316 mg, 1.65 mmol), HOBt (223 mg, 1.65 mmol) and Et3 N (230 ml, 1.65 mmol) in THF (10 ml) was stirred at room temperature overnight. The mixture was diluted with H$_2$O and extracted with EtOAc. The extract was washed with brine, dried over Na$_2$SO$_4$ and evaporated. The residue was purified by column chromatography on silica-gel with CHCl$_3$-MeOH (100:1, v/v) as eluent to give methyl 4-[1-[4-[N'-(2chlorophenyl)ureido]-3-methoxyphenylacetyl]-(4R)-methoxy-(2S)-pyrrolidinylmethoxy]benzoate (801 mg, q. y.) as a white foam. $^1$H-NMR (CDCl$_3$) δ 2.13–2.36 (m, 2 H), 3.27 (s, 3 H), 3.58 (s, 3 H), 3.61–3.73 (m, 4 H), 3.88 (s, 3 H), 4.06–4.14 (m, 2 H), 4.43–4.56 (m, 2 H), 6.70–6.99 (series of m, total 5 H), 7.23–7.42 (m, 4 H), 7.90–8.00 (m, 3 H), 8.17–8.20 (m, 1 H); MS (FAB) m/z 582 (M$^+$+1).

To a stirred solution of methyl 4-[1-[4-[N'-(2-chlorophenyl)ureido]-3-methoxyphenyl acetyl]-(4R)-methoxy-(2S)-pyrrolidinylmethoxy]benzoate (541 mg, 0.93 mmol) in THF (5 ml) was added 0.5 N NaOH (5 ml) and the reaction mixture was heated under reflux for 3 hr. After cooled to room temperature, the mixture was poured into ice-1 N HCl and the resulting precipitate was collected under a reduced pressure. The crude solid was purified by recrystallization from MeOH—CHCl$_3$-IPE to give 137 (281 mg, 53%) as a white crystalline powder. MW 568.02 mp 116–119° C.; $^1$H-NMR (DMSO-d$_6$) δ 2.08–2.17 (m, 2 H), 3.21 (s, 3 H), 3.56–3.73 (m, 4 H), 3.79 (s, 3 H), 4.04–4.33 (m, 4 H), 6.75 (d, J=8.3 Hz, 1 H), 6.87 (s, 1 H), 7.02 (d, J=8.3 Hz, 3 H), 7.28 (t, J=7.8 Hz, 1 H), 7.44 (d, J=7.8 Hz, 1 H), 7.87–7.89 (m, 2H), 7.96(d, J=8.3 Hz, 1 H), 8.10 (d, J=8.3 Hz, 1 H), 8.89 (s, 1 H), 8.93 (s, 1 H), 12.63 (br s, 1 H); MS (FAB) m/z 568 (M⁺+1); Anal. Calcd for $C_{29}H_{30}ClN_3O_7 \cdot 1/4H_2O$: C, 60.84; H, 5.37; Cl, 6.19; N, 7.34. Found: C, 61.03; H, 5.56; Cl, 6.27; N, 7.03.

Example 130

4-[1-[4-[N'-(2-bromophenyl)ureido]-3-methoxyphenylacetyl]-(4R)-methoxy-(2S)-pyrrolidinyl methoxy]benzoic acid

138

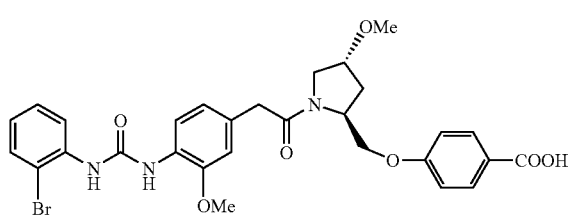

A mixture of 4-[N'-(2-bromophenyl)ureido]-3-methoxyphenylacetic acid (600 mg, 1.58 mmol), methyl 4-[(4R)-methoxy-(2S)-pyrrolidinylmethoxy]benzoate (420 mg, 1.58 mmol), EDC.HCl (364 mg, 1.90 mmol), HOBt (214 mg, 1.58 mmol) and Et₃N (265 ml, 1.90 mmol) in THF (15 ml) was stirred at room temperature overnight. The mixture was diluted with H₂O and extracted with EtOAc. The extract was washed with brine, dried over Na₂SO₄, and evaporated. The residue was purified by column chromatography on silica-gel with CHCl₃-MeOH (100:1, v/v) as eluent to give methyl 4-[1-[4-[N'-(2-bromophenyl)ureido]-3-methoxyphenylacetyl]-(4R)-methoxy-(2S)-pyrrolidinylmethoxy]benzoate (1.01 g, q.y.) as a pale yellow foam. ¹H-NMR (CDCl₃) δ 2.13–2.33 (m, 2 H), 3.27 (s, 3 H), 3.57 (s, 3 H), 3.61–3.72 (m, 4 H), 3.88 (s, 3 H), 4.05–4.14 (m, 2 H), 4.43–4.57 (m, 2 H), 6.70–7.00 (series of m, total 5 H), 7.29–7.52 (m, 4 H), 7.92–8.01 (m, 3 H), 8.12–8.15 (m, 1 H); MS (FAB) m/z 626 (M⁺+1).

To a stirred solution of methyl 4-[1-[4-[N'-(2-bromophenyl)ureido]-3-methoxyphenyl acetyl]-(4R)-methoxy-(2S)-pyrrolidinylmethoxy]benzoate (697 mg, 1.11 mmol) in THF (8 ml) was added 0.5 N NaOH (8 ml) and the reaction mixture was heated under reflux for 2 hr. After cooled to room temperature, the mixture was poured into ice-1 N HCl and the resulting precipitate was collected under a reduced pressure. The crude solid was purified by recrystallization from MeOH—CHCl₃-IPE to give 138 (252 mg, 37%) as a white crystalline powder. MW 612.47 mp 125–130° C.; ¹H-NMR (DMSO-d₆) δ 2.08–2.17 (m, 2 H), 3.21 (s, 3 H), 3.60–3.72 (m, 4 H), 3.79 (s, 3 H), 3.95–4.33 (m, 4 H), 6.75–7.08 (series of m, total 5 H), 7.31–7.34 (m, 1 H), 7.59–7.61 (m, 1 H), 7.87–7.89 (m, 2 H), 7.93–7.96 (m, 2 H), 8.73 (s, 1 H), 8.91 (s, 1 H), 12.63 (br s, 1 H); MS (FAB) m/z 612 (M⁺+1); Anal. Calcd for $C_{29}H_{30}BrN_3O_7$: C, 56.87; H, 4.94; Br, 13.05; N, 6.86. Found: C, 56.67; H, 4.97; Br, 13.07; N, 6.68.

Example 131

4-[4,4-difluoro-1-[3-methoxy-4-[N'-(2-methylphenyl)ureido]phenylacetyl]-2-pyrrolidinylmethoxy]benzoic acid

139

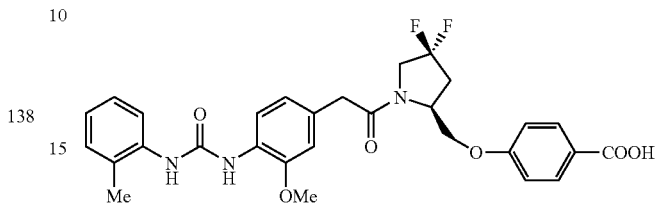

To a stirred solution of N-Boc proline methyl ester (2.0 g, 8.15 mmol) in CH₂Cl₂ were added 3 A molecular sieves (2 g) and PDC (4.60 g, 12.2 mmol). The mixture was stirred for 3 days. The mixture was filtered through a Celiete pad and the filtrate was evaporated. The residue was chromatographed on silica gel with CHCl₃-MeOH (10:1) as eluent to give methyl 1-(tert-butoxycarbonyl)-4-oxopyrrolidine-2-carboxylate (1.13 g, 57%) as a colorless oil. ¹H-NMR (CDCl₃) δ 1.46–1.48 (m, 9 H), 2.56–2.61 (m, 1 H), 2.88–3.00 (m, 1 H), 3.77 (s, 3 H), 3.82–3.88 (m, 2 H), 4.71–4.83 (m, 1 H).

To a cold (−78° C.), stirred solution of methyl 1-(tert-butoxycarbonyl)-4-oxopyrrolidine-2-carboxylate (1.13 g, 4.65 mmol) in CH₂Cl₂ (20 ml) was added methylDAST (1.1 ml, 11.6 mmol). The mixture was allowed to warm to room temperature. After 15 h stirring, the mixture was poured into H₂O (50 ml) and extracted with EtOAc (200 ml). The extract was washed with brine (2×200 ml), dried over MgSO₄, and evaporated. The residue was chromatographed on silica gel with CHCl₃-EtOAc (20:1) as eluent to give methyl 1-(tert-butoxycarbonyl)-4,4-difluoropyrrolidine-2-carboxylate (885 mg, 72%) as a yellow oil. ¹H-NMR (CDCl₃) δ 1.42 and 1.47 (s, each, total 9 H), 2.46 (ddd, d=26.9 13.7, 5.1 Hz, 1H), 2.62–2.78 (m, 1H), 3.75–3.95 (m, 5H), 4.43–4.57 (m, 1H).

To a stirred solution of methyl 1-(tert-butoxycarbonyl)-4,4-difluoropyrrolidine-2-carboxylate (885 mg, 3.34 mmol) in THF (25 ml) was added 0.25 N NaOH (26.7 ml, 6.67 mmol) and the stirring was continued for 1 h. The mixture was poured into 1 N HCl (100 ml) and extracted with CHCl₃ (2×200 ml). The combined extracts were washed with brine (100 ml), dried over MgSO₄, and evaporated to give 1-(tert-butoxycarbonyl)-4,4-difluoropyrrolidine-2-carboxylic acid (775 mg, 92%) as a yellow crystalline solid. mp 113–117° C.; ¹H-NMR (CDCl₃) δ 1.44 and 1.49 (s, each, total 9 H), 2.53–2.80 (m, 2 H), 3.71–3.90 (m, 2 H), 4.20–4.61 (m, 1 H); MS (FAB) m/z, 252 (M⁺+1); Anal. Calcd for $C_{10}H_{15}F_2O_4$: C, 47.81; H, 6.02; N, 5.58. Found: C, 48.06; H, 6.05; N, 5.45.

To a stirred solution of N-(tert-butoxycarbonyl) 4,4-difluoroproline (3.00 g, 11.9 mmol) in THF (20 ml) was added BH₃.DMS (1.1 ml, 11.9 mmol) at room temperature. The mixture was heated at reflux for 2 h. After cooling to room temperature, the mixture was concntrated in vacuo. The residue was quenched by the addition of H₂O (100 ml) and extracted with CHCl₃ (2×200 ml). The combined extracts were dried over MgSO₄ and evaporated. The residue was chromatographed on silica gel with CHCl₃-EtOAc (4:1) as eluent to give 1-(tert-butoxycarbonyl)-4,4-difluoro-2-pyrrolidinylmethanol (2.11 g, 75%) as a colorless oil. ¹H-NMR (CDCl₃) δ 1.48 (s, 9 H), 2.04–2.55 (m, 2 H), 3.59–4.17 (m, 5 H).

To a stirred mixture of 1-(tert-butoxycarbonyl)-4,4difluoro-2-pyrrolidinylmethanol (600 mg, 2.53 mmol), methyl 4-hydroxybenzoate (462 mg, 3.03 mmol), Ph₃P (795 mg, 3.03 mmol) in THF (10 ml) was added DIAD (597 ul, 3.03 mmol) at room temperature. The mixture was heated at reflux for 3 h with stirring. After cooling to room temperature, the mixture was concntrated in vacuo. The residue was chromatographed on silica gel with hexane-EtOAc (4:1) as eluent to give methyl 4-[1-(tert-butoxycarbonyl)-4,4-difluoro-2-pyrrolidinylmethoxy]benzoate (831 mg, 88%) as a colorless oil. ¹H-NMR (CDCl₃) δ 1.48 (s, 9 H), 2.53–2.61 (m, 2 H), 3.63–4.41 (series of m, total 8 H), 6.94 (d, J=8.8 Hz, 2H), 7.99(d, J=8.8 Hz, 2H).

A mixture of methyl 4-[1-(tert-butoxycarbonyl)-4,4-difluoro-2-pyrrolidinylmethoxy]benzoate (830 mg, 2.23 mmol) and TFA (5 ml) in CH₂Cl₂ (5 ml) was stirred for 3 h and concntrated in vacuo. The residue was made basic with sat. NaHCO₃ and extracted with CHCl₃ (2×200 ml). The combined extracts were dried over K₂CO₃ and concntrated in vacuo to give methyl 4-(4,4-difluoro-2-pyrrolidinylmethoxy)benzoate (550 mg, 91%) as a pale yellow solid. ¹H-NMR (CDCl₃) δ 2.19 (m, 1 H), 2.43 (m, 1 H), 3.19–3.41 (m, 2 H), 3.77 (m, 1 H), 3.89 (s, 3 H), 4.00–4.09 (m, 2 H), 6.92 (d, J=9.0 Hz, 2 H), 7.99 (d, J=9.0 Hz, 2 H); MS (FAB) m/z 272 (M⁺+1); Anal. Calcd for C₁₃H₁₅F₂NO₃: C, 57.56; H, 5.57; N, 5.16. Found: C, 57.65; H, 5.67; N, 5.16.

A mixture of methyl 4-(4,4 difluoro-2-pyrrolidinylmethoxy)benzoate (540 mg, 1.99 mmol), 3-methoxy-4-[N'-(2-methylphenyl)ureido]phenylacetic acid (626 mg, 1.99 mmol), EDC.HCl (572 mg, 2.99 mmol), HOBt (cat.), and DMAP (cat.) in DMF (10 ml) was stirred overnight. The mixture was diluted with EtOAc (300 ml), washed with brine (2×100 ml), dried over MgSO₄, and concntrated in vacuo. The residue was chromatographed on silica gel with CHCl₃-MeOH (20:1) as eluent to give methyl 4-[4,4-difluoro-1-[3-methoxy-4-[N'-(2-methylphenyl)ureido]phenylacetyl]-2-pyrrolidinylmethoxy]benzoate (1.00 g, 89%) as a colorless foam. ¹H-NMR (CDCl₃) δ 2.31 (s, 3 H), 2.47–2.63 (m, 2 H), 3.52–3.97 (series of s and m, total 10 H), 4.07–4.30 (mi 2 H), 4.67–4.69 (m, 1 H), 6.45 (s, 1 H), 6.65 (d, J=1.7 Hz, 1 H), 6.74–6.76 (m, 1 H), 6.84 (d, J=8.8 Hz, 2 H), 7.14 (m, 2 H), 7.24 (m, 2 H), 7.52–7.54 (m, 1 H), 7.94 (d, J=8.8 Hz, 2 H), 8.09 (d, J=8.1 Hz, 1H).

A mixture of methyl 4-[4,4-difluoro-1-[3-methoxy-4-[N'-(2-methylphenyl)ureido]phenyl-acetyl]-2-pyrrolidinylmethoxy]benzoate (1.00 g, 1.76 mmol) and 0.25 N NaOH (14 ml, 3.50 mmol) in THF (14 ml) was stirred overnight. The mixture was acidified with 1 N HCl and extracted with CHCl₃-MeOH (10:1, 2×200 ml). The combined extracts were dried over MgSO₄ and evaporated. The residue was chromatographed on silica gel with CHCl₃-MeOH (20:1 to 10:1) as eluent to give 139 (658 mg, 68%) as a colorless crystalline powder. MW 553.55 mp 135–140° C.; ¹H-NMR (DMSO-d₆) δ 2.23 (s, 3 H), 2.49–2.73 (m, 2 H), 3.36–4.55 (series of m, 10 H), 6.73 (d, J=8.3 Hz, 1 H), 6.84 (s, 1 H), 6.93 (t, J=7.3 Hz, 1 H), 7.00 (d, J=8.3 Hz, 2 H), 7.10–7.16 (m, 2 H), 7.78 (d, J=8.3 Hz, 1 H), 7.86 (d, J=8.3 Hz, 21H), 8.00 (d, J=8.3 Hz, 1 H), 8.47 (s, 1 H), 8.56 (s, 1 H); MS (FAB) m/z, 554 (M⁺+1); Anal. Calcd for C₂₉H₂₉F₂N₃O₆.3/4H₂O: C, 61.42; H, 5.44; N, 7.06. Found: C, 61.30; H, 5.44; N, 7.06.

Example 132

4-[1-[4-[N'-2-chlorophenyl)ureido]-3-methoxyphenylacetyl]-4,4-difluoro-2-pyrrolidinylmethoxy]benzoic acid

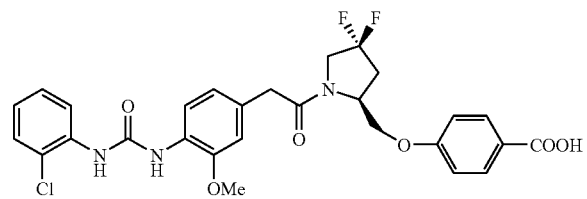

140

A mixture of methyl 4-(4,4 difluoro-2-pyrrolidinylmethoxy)benzoate (229 mg, 0.845 mmol), 4-[N'-(2-chlorophenyl)ureido]-3-methoxyphenylacetic acid (283 mg, 0.845 mmol), EDC.HCl (243 mg, 1.27 mmol), HOBt (cat.), DMAP (cat.), and DMF (10 ml) was stirred overnight. The mixture was diluted with EtOAc (300 ml). The solution was washed with brine (2×100 ml), dried over MgSO₄, and concntrated in vacuo. The residue was chromatographed on silica gel with CHCl₃-EtOAc (20:1 to 4:1) as eluent to give methyl 4-[1-[4-[N'-2-chlorophenyl)ureido]-3-methoxy phenylacetyl]-4,4-difluoro-2-pyrrolidinylmethoxy]benzoate (482 mg, 97%) as a colorless viscous solid. ¹H-NMR (CDCl₃) δ 2.50–2.67 (m, 2 H), 3.54–4.71 (series of m, 13 H), 6.69 (d, J=1.5 Hz, 1 H), 6.76 (d, J=8.3 Hz, 1 H), 6.84 (d, J=8.8 Hz, 2 H), 6.98 (dt, J=7.8, 1.5 Hz, 1 H), 7.23–7.27 (m, 1 H), 7.33 (d, J=8.3 Hz, 1 H), 7.39 (m, 2 H), 7.94 (d, J=8.8 Hz, 2 H), 8.00 (d, J=8.3 Hz, 1 H), 8.19 (dd, J=8.3, 1.5 Hz, 1 H).

A mixture of methyl methyl 4-[1-[4-[N'-(2chlorophenyl)ureido]-3-methoxyphenylacetyl]-4,4-difluoro-2-pyrrolidinylmethoxy]benzoate (480 mg, 0.816 mmol), 0.25 N NaOH (6.5 ml, 1.65 mmol), and THF (20 ml) was stirred for 3 days. The mixture was poured into 1 N HCl (100 ml) and extracted with CHCl₃-MeOH (5:1, 2×200 ml). The combined extracts were dried over MgSO₄ and concntrated in vacuo. The residue was chromatographed on silica gel with CHCl₃-MeOH (20:1 to 5:1) to give 140 (270 mg, 58%) as a pale yellow amorphous solid. MW 573.97 ¹H-NMR (DMSO-d₆) δ 2.45–2.74 (m, 2 H), 3.63–4.83 (series of m, 10 H), 6.76 (d, J=8.3 Hz, 1 H), 6.87 (s, 1 H), 7.00–7.05 (m, 3 H), 7.26–7.30 (m, 1 H), 7.44 (dd, J=8.3, 1.2 Hz, 1 H), 7.88–7.93 (m, 2 H), 7.98 (d, J=8.3 Hz, 1 H), 8.10 (d, J=8.3 Hz, 1 H), 8.92 (s, 1 H), 8.96 (s, 1 H); MS (FAB) m/z 574 (M⁺+1); Anal. Calcd for C₂₈H₂₆ClF₂N₃O₆.H₂O: C, 56.81; H, 4.77; N, 7.10. Found: C, 56.75; H, 4.69; N, 6.79.

Example 133

4-[(2R,3R,4S)-3,4-isopropylidenedioxy-1-[4-[N'-(2-methylphenyl)ureido]-3-methoxyphenylacetyl]-2-pyrrolidinyl]methoxybenzoic acid

141

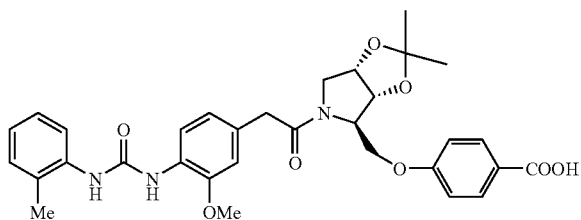

To a solution of methyl (2S,3R,4S)-1-benzyloxycarbonyl-3,4-isopropylidenedioxy-2-pyrrolidinyl carboxylate (10.7 g, 31.9 mmol) in THF (250 ml), 0.25 N NaOH (255 ml) was added. After stirring at room temperature for 24 h, the mixture was acidified with 1 N HCl and extracted with EtOAc. The combined extracts were washed with brine, which were dried over $Na_2SO_4$ and concentrated in vacuo, to give (2S,3R,4S)-1-benzyloxycarbonyl-3,4-isopropylidenedioxy-2-pyrrolidinylcarboxylic acid (9.87 g, 96%) as a colorless oil. $^1$H-NMR (CDCl$_3$) δ 1.32 (s, 3H), 1.46 (d, J=2.7 Hz, 3H), 3.61(m, 1H), 3.82 and 3.92 (d, J=12.7 Hz, 1H, amide isomers), 4.58 and 4.64 (s, 1H, amide isomers), 4.77 (t, J=5.1 Hz, 1H), 4.83 and 4.89 (d, J=5.9 Hz, 1H, amide isomers), 5.15 and 5.19 (m, 2H, amideisomers), 7.31–7.37 (m, 5H).

To a stirred solution of (2S,3R,4S)-1benzyloxycarbonyl-3,4-isopropylidenedioxy-2-pyrrolidinyl carboxylic acid (9.87 g, 30.7 mmol) in THF (200 ml) was added BH$_3$.DMS (6.14 ml, 61.4 mmol) at 0° C. The mixture was allowed to room temperature and then heated under reflux for 2 h. After cooling to room temperature, the mixture was concentrated in vacuo and quenched by the addition of water at 0° C. The mixture was extracted with EtOAc. The combined extracts were washed with water and brine, which were dried over Na$_2$SO$_4$ and concentrated in vacuo. The residue was chromatographed on silica gel [200 g, CHCl$_3$/MeOH (20/1)], to give (2R,3R,4S)-1benzyloxy carbonyl-3,4-isopropylidenedioxy-2-pyrrolidinylmethanol (10.1 g, 100%) as a colorless oil. $^1$H-NMR (CDCl$_3$) δ 1.31 (s, 3H), 1.45 (s, 3H), 3.56–4.74 (m, 7H), 5.14 (s, 2H), 7.34 (m, 5H).

To a stirred mixture of (2R,3R,4S)-1-benzyloxycarbonyl-3,4-isopropylidenedioxy-2-pyrrolidinyl methanol (312 mg, 0.64 mmol), methyl p-hydroxybenzoate (67 ml, 0.70 mmol), PPh$_3$ (184 mg, 0.70 mmol) in THF (7 ml) was added DIAD (138 ml, 0.70 mmol) at 0° C. under an atmosphere of nitrogen. The mixture was allowed to reach room temperature and stirred for 3 h. After removal of the solvent, the resulting residue was chromatographed on silica gel [10 g, n-hexane/EtOAc (4/1)], to give methyl 4-[(2R,3R,4S)-benzyloxycarbonyl-3,4-isopropylidenedioxy-2-pyrrolidinyl]methoxybenzoate (321 mg, 83%) as a colorless oil. $^1$H-NMR (CDCl$_3$) δ 1.01 (s, 6H), 1.03 (s, 3H), 2.23 (m, 1H), 2.63 (m, 1H), 3.61 (d, J=12.5 Hz, 1H), 3.80–4.27 (m, 4H), 4.84 (br, 1H), 5.01 and 5.08 (ABq, J=12.2 Hz, 1H, amide isomers), 6.75–6.87 (m, 3H), 7.19–7.63 (m, 15H).

A suspension of methyl 4-[(2R,3R,4S)-1benzyloxycarbonyl-3,4-isopropylidenedioxy-2-pyrrolidinyl]methoxybenzoate (2.37 g, 5.76 mmol) and 10% Pd/C (240 mg) in EtOH (170 ml) was stirred at room temperature under an atmosphere of hydrogen. After 1 day stirring, the catalyst and solvent were changed for 10% Pd/C (500 mg) and THF (50 ml). The suspension was stirred at room temperature under an atmosphere of hydrogen for 5 days. After removed the catalyst by filtration, the filtrates were concentrated in vacuo. The residue was chromatographed on silica gel [100 g, CHCl$_3$/acetone (20/1)], to give methyl 4-[(2R,3R,4S)-3,4-isopropylidenedioxy-2-pyrrolidinyl]methoxybenzoate (930 mg, 53%) as a brown oil. $^1$H-NMR (CDCl$_3$) δ 1.35 (s, 3H), 1.50 (s, 3H), 3.02 (dd, J=13.7, 4.1 Hz, 1H), 3.13(d, J=13.7 Hz, 1H), 3.58 (t, J=6.3 Hz, 1H), 3.88 (s, 3H), 3.90 (dd, J=9.3, 6.6 Hz, 11H), 4.02 (dd, J=9.5, 3.9 Hz, 1H), 4.74 (d, J=5.6 Hz, 1H), 4.79 (m, 1H), 6.90 (d, J=9.0 Hz, 2H), 7.98 (d, J=9.0 Hz, 2H).

A mixture of 3-methoxy-4-[N'-(2-methylphenyl)ureido]phenylacetic acid (437 mg, 1.39 mmol), methyl 4-[(2R,3R,4S)-3,4-isopropylidenedioxy-2-pyrrolidinyl]methoxybenzoate (428 mg, 1.39 mmol), EDC.HCl (400 mg, 2.09 mmol) and DMAP (170 mg, 1.39 mmol) in DMF (12 ml) was stirred at room temperature for 20 h. The mixture was poured into ice water and extracted with EtOAc. The combined extracts were washed with ice water and brine. After dried over Na$_2$SO$_4$, the extracts were concentrated in vacuo. The residue was chromatographed on silica gel [70 g, CHCl$_3$/acetone (10/1)], to give methyl 4-[(2R,3R,4S)-3,4-isopropylidenedioxy-1-[4-[N'-(2-methylphenyl)ureido]-3-methoxyphenylacetyl]-2-pyrrolidinyl]methoxybenzoate (840 mg, 100%) as a colorless amorphous solid IR (KBr) 3354, 2985, 2939, 1716, 1533, 1254 cm$^{-1}$; $^1$H-NMR (CDCl$_3$) δ 1.31 (s, 3H), 1.42 (s, 3H), 2.05 (s, 3H), 3.50 (s, 3H), 3.55–3.88 (m, 41H), 3.89 (s, 3H), 4.13 (m, 1H), 4.67 (br, 1H), 4.78 (d, J=6.1 Hz, 1H), 4.88 (t, J=5.6 Hz, 1H), 6.46 (s, 1H), 6.62 (d, J=1.5 Hz, 1H), 6.74 (m, 3H), 7.05 (s, 1H), 7.14 (d, J=7.3 Hz, 1H), 7.23 (m, 2H), 7.57 (d, J=7.8 Hz, 1H), 7.91–8.08 (m, 3H); MS (ESI) m/z 604 (M$^+$+1); Anal. Calcd for C$_{33}$H$_{37}$N$_3$O$_8$.0.6H$_2$O: C, 64.50; H, 6.27; N, 6.84. Found: C, 64.38; H, 6.18; N, 6.66.

A mixture of methyl 4-[(2R,3R,4S)-3,4-isopropylidenedioxy-1-[4-[N'-(2-methylphenyl)ureido]-3-methoxyphenylacetyl]-2-pyrrolidinyl]methoxybenzoate (183 mg, 0.303 mmol) and g.HCl-MeOH (6 ml) was stirred at room temperature for 17 h. The mixture was concentrated in vacuo. The residue was purified on TLC [CHCl$_3$/MeOH (10/1)], to give methyl 4-[(2R,3R,4S)-3,4-dihydroxy-1-[4-[N'-(2-methylphenyl)ureido]-3-methoxyphenylacetyl]-2-pyrrolidinyl]methoxybenzoate (162 mg, 95%) as a colorless amorphous solid IR (KBr) 3342, 1716, 1604, 1535, 1255 cm$^{-1}$; $^1$H-NMR (CDCl$_3$) δ 2.25 (br, 3H), 3.33–3.75 (m, 7H), 3.87 (s, 3H), 4.10 (d, J=8.3 Hz, 1H), 4.24 (s, 2H), 4.37 (m, 2H), 6.62–7.94 (m, 13H); MS (ESI) m/z 564 (M$^+$+1).

To a solution of methyl 4-[(2R,3R,4S)-3,4-isopropylidenedioxy-1-[4-[N'-(2-methylphenyl)ureido]-3-methoxyphenylacetyl]-2-pyrrolidinyl]methoxybenzoate (490 mg, 0.812 mmol) in THF (9.8 ml), 0.25 N NaOH (9.8 ml) was added. After stirring at room temperature for 4 days, the mixture was acidified with 1 N HCl and extracted with CHCl$_3$-MeOH (10/1). The combined extracts were dried over Na$_2$SO$_4$ and concentrated in vacuo to give 141 (445 mg, 93%) as a colorless amorphous solid. MW 689.64 IR (KBr) 3354, 2983, 2937, 1707, 1604, 1533 cm$^{-1}$; $^1$H-NMR (DMSO-d$_6$) 8.24 and 1.26 (s, 3H, amide isomers), 1.26 and 1.32 (s, 3H, amide isomers), 2.24 (s, 3H), 3.40 (dd, J=14.0, 5.1 Hz, 1H), 3.60 (m, 2H), 3.71 (m, 1H), 3.76 (s, 3H), 3.82 (s, 3H), 3.92–4.96 (m, 5H), 6.74 and 6.78 (m, 1H, amide isomers), 6.83–7.16 (m, 6H), 7.79 (d, J=8.3 Hz, 1H), 7.87 (t, J=9.1 Hz, 2H), 8.01 (m, 1H), 8.49 (d, J=3.4 Hz, 1H), 8.57

(s, 1H); MS (FAB) m/z 590(M++1); Anal. Calcd for C$_{32}$H$_{35}$N$_3$O$_8$·2.3H$_2$O: C, 60.90; H, 6.32; N, 6.66. Found: C, 61.00; H, 6.00; N, 6.27.

Example 134

4-[(2R,3R,4S)-3,4-dihydroxy-1-[4-[N'-(2-methylphenyl)ureido]-3-methoxyphenylacetyl]-2-pyrrolidinyl]methoxybenzoic acid

142

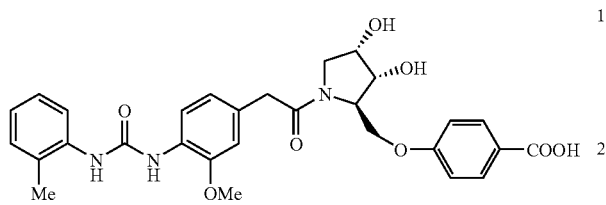

To a solution of methyl 4-[(2R,3R,4S)-3,4-dihydroxy-1-[4-[N'-(2-methylphenyl)ureido]-3-methoxyphenylacetyl]-2-pyrrolidinyl]methoxybenzoate (63 mg, 0.112 mmol) in THF (0.89 ml), 0.25 N NaOH (0.89 ml) was added. After stirring at room temperature for 3 days, the mixture was acidified with 1 N HCl and extracted with CHCl$_3$-MeOH (10/1). The combined extracts were dried over Na$_2$SO$_4$ and concentrated in vacuo to give 142 (54 mg, 88%) as a colorless amorphous solid. MW 549.57 IR (KBr) 3356, 2958, 2927, 1685, 1604, 1535, 1255 cm$^{-1}$; $^1$H-NMR (DMSO-d$_6$) δ 2.24 (s, 3H), 3.40 (m, 1H), 3.58 (s, 2H), 3.66 (dd, J=9.8, 6.6 Hz, 1H), 3.80 (s, 3H), 3.99–4.30 (m, 5H), 5.10 (br, 1H), 6.72 (d, J=8.1 Hz, 1H), 6.85 (s, 1H), 6.93 (t, J=7.3 Hz, 1H), 7.03 (d, J=8.8 Hz, 2H), 7.14 (t, J=8.8 Hz, 2H), 7.79 (d, J=8.1 Hz, 2H), 7.86 (d, J=8.8 Hz, 2H), 7.99 (d, J=8.3 Hz, 1H), 8.46 (s, 1H), 8.56 (s, 1H); MS (ESI) nm/i 550(M++1); Anal. Calcd for C$_{29}$H$_{31}$N$_3$O$_8$·0.85H$_2$O: C, 61.66; H, 5.83; N, 7.44. Found: C, 62.09; H, 5.93; N, 6.95.

Example 135

4-[(2R,3R,4S)-1-[4-[N'-(2-chlorophenyl)ureido]-3-methoxyphenylacetyl]-3,4-isopropylidenedioxy-2-pyrrolidinyl]methoxybenzoic acid

143

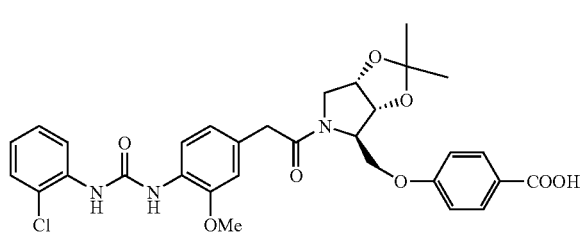

A mixture of 4-[N'-(2-chlorophenyl)ureido]-3-methoxyphenylacetic acid (487 mg, 1.45 mmol), methyl 4-[(2R,3R,4S)-3,4-isopropylidenedioxy-2-pyrrolidinyl]methoxybenzoate (447 mg, 1.45 mmol), EDC.HCl (418 mg, 2.18 mmol) and DMAP (177 mg, 1.45 mmol) in DMF (12 ml) was stirred at room temperature for 19 h. The mixture was poured into ice water and extracted with EtOAc. The combined extracts were washed with ice water and brine. After dried over Na$_2$SO$_4$, the extracts were concentrated in vacuo. The residue was chromatographed on silica gel [70 g, CHCl$_3$/acetone (10/1)], to give methyl 4-[(2R,3R,4S)-1-[4-[N'-(2-chlorophenyl)ureido]-3-methoxyphenylacetyl]-3,4-isopropylidenedioxy-2-pyrrolidinyl]methoxybenzoate (850 mg, 94%) as a colorless amorphous solid IR (KBr) 3329, 2939, 1716, 1627, 1531, 1254 cm$^{-1}$; $^1$H-NMR (CDCl$_3$) δ 1.33 (s, 3H), 1.43 (s, 3H), 3.56 (s, 3H), 3.61 (s, 1H), 3.64 (s, 1H), 3.70 (m, 1H), 3.79 (d, J=10.4 Hz, 1H), 3.88 (s, 3H), 4.14 (dd, J=9.8, 2.2 Hz, 1H), 4.40 (dd, J=9.8, 3.4 Hz, 1H), 4.67 (s, 1H), 4.80 (d, J=6.1 Hz, 1H), 4.90 (t, J=4.6 Hz, 1H), 6.65 (d, J=1.7 Hz, 1H), 6.71–6.84 (m, 3H), 6.98 (dt, J=7.6, 1.5 Hz, 1H), 7.27 (m, 2H), 7.33 (dd, J=8.0, 1.2 Hz, 2H), 7.90–8.01 (m, 3H), 8.20 (dd, J=8.3, 1.5 Hz, 1H); MS (ESI) m/z 624 (M++1), 626 (M++3); Anal. Calcd for C$_{32}$H$_{34}$N$_3$O$_8$·1.4H$_2$O: C, 59.19; H, 5.71; N, 6.47. Found: C, 58.85; H, 5.35; N, 6.21.

A mixture of methyl 4-[(2R,3R,4S)-1-[4-[N'-(2-chlorophenyl)ureido]-3-methoxyphenylacetyl]-3,4-isopropylidenedioxy-2-pyrrolidinyl]methoxybenzoate (177 mg, 0.284 mmol) and g.HCl-MeOH (4 ml) was stirred at room temperature for 2 days. The mixture was concentrated in vacuo. The residue was purified on TLC [CHCl$_3$/MeOH (15/1)], to give methyl 4-[(2R,3R,4S)-1-[4-[N'-2-chlorophenyl)ureido]-3-methoxyphenylacetyl]-3,4-isopropylidenedioxy-2-pyrrolidinyl]methoxybenzoate (140 mg, 85%) as a colorless amorphous solid IR (KBr) 3338, 2949, 1712, 1623, 1604, 1533 cm$^{-1}$; $^1$H-NMR (CDCl$_3$) δ 2.27 (m, 1H), 2.79 (m, 1H), 3.53 (dd, J=10.5, 5.9 Hz, 1H), 3.63 (s, 3H), 3.88 (s, 3H), 4.21 (d, J=7.8 Hz, 1H), 4.31 (m, 2H), 4.43 (dd, J=9.8, 4.4 Hz, 1H), 4.52 (t, J=4.6 Hz, 1H), 6.71 (s, 1H), 6.80 (m, 3H), 6.99 (t, J=7.3 Hz, 1H), 7.16 (s, 1H), 7.21 (s, 1H), 7.39 (d, J=8.1 Hz, 1H), 7.91 (d, J=8.6 Hz, 2H), 8.16 (d, J=8.3 Hz, 1H); MS (ESI) m/z 584 (M++1), 586 (M++3).

To a solution of methyl 4-[(2R,3R,4S)-1-[4-[N'-(2-chlorophenyl)ureido]-3-methoxyphenylacetyl]-3,4-isopropylidenedioxy-2-pyrrolidinyl]methoxybenzoate (511 mg, 0.819 mmol) in THF (9.8 ml), 0.25 N NaOH (9.8 ml) was added. After stirring at room temperature for 20 h, the mixture was acidified with 1 N HCl and extracted with CHCl$_3$-MeOH (10/1). The combined extracts were dried over Na$_2$SO$_4$ and concentrated in vacuo to give 143 (504 mg, 100%) as a colorless amorphous solid. MW 610.05 IR(KBr) 3330, 2983, 2937, 1711, 1689, 1604, 1533, 1252 cm$^{-1}$; $^1$H-NMR (DMSO-d$_6$) δ 1.26 (s, 3H), 1.32 (s, 3H), 3.40 (m, 1H), 3.60 and3.61 (d, J=2.5 Hz, 3H, amide isomers), 3.62 (m, 1H), 3.78 and 3.83 (s, 3H, amideisomers), 4.16 (m, 2H), 4.42–4.98 (m, 3H), 6.74–7.15 (m, 6H), 7.28 (t, J=7.3 Hz, 1H), 7.43 (d, J=8.1 Hz, 1H), 7.78–7.97 (m, 4H), 8.08 (d, J=8.3 Hz, 1H), 8.89 (s, 1H), 8.92 (s, 1H), 12.68 (br, 1H); MS (ESI) m/z 610 (M++1), 612 (M++3).

Example 136

4-[(2R,3R,4S)-1-[4-[N'-(2chlorophenyl)ureido]-3-methoxyphenylacetyl]-3,4-dihydroxy-2-pyrrolidinyl] methoxybenzoic acid

144

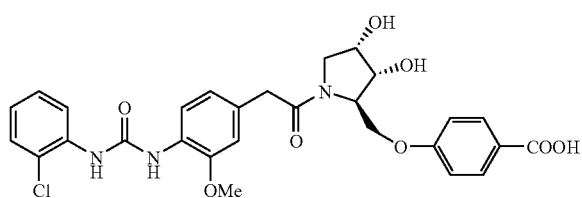

To a solution of methyl 4-[1-[4-[N'-(2-chlorophenyl)ureido]-3-methoxyphenylacetyl]-3,4-dihydroxy-2-pyrrolidinylmethoxy]benzoate (63 mg, 0.108 mmol) in THF (0.80 ml), 0.25 N NaOH (0.80 ml) was added. After stirring at room temperature for 3 days, the mixture was acidified with 1 N HCl and extracted with CHCl$_3$-MeOH (10/1). The combined extracts were dried over Na$_2$SO$_4$ and concentrated in vacuo to give 144 (61 mg, 100%) as a colorless amorphous solid. MW 569.99 IR (KBr) 3338, 1687, 1604, 1533; 1255, 1169, 1036 cm$^{-1}$; $^1$H-NMR (DMSO-d$_6$) δ 3.59 (d, J=5.5 Hz, 2H), 3.61 (m, 1H), 3.66 (dd, J=10.0, 7.1 Hz, 1H), 3.80 (s, 3H), 4.00–4.33 (m, 5H), 5.10 (br, 1H), 6.74 (d, J=8.3 Hz, 1H), 6.87 (s, 1H), 7.03 (m, 3H), 7.28 (t, J=8.3 Hz, 11H), 7.43 (d, J=6.6 Hz, 1H), 7.87 (d, J=8.5 Hz, 2H), 7.95 (d, J=8.3 Hz, 1H), 8.09 (d, J=8.3 Hz, 1H), 8.32 (s, 1H), 8.89 (s, 1H), 8.93 (s, 1H); MS (ESI) m/z 570 (M+1), 572 (M$^+$+3); Anal. Calcd for C$_{28}$H$_{28}$ClN$_3$O$_8$·1.4H$_2$O: C, 57.19; H, 5.14; N, 7.15. Found: C, 57.52; H, 5.22; N, 6.76.

Example 137

4-[1-[4-[N'-(2-methylphenyl)ureido]-3-methoxyphenylacetyl]-5-(R)-phenyl-2-(S)-pyrrolidinyl methoxy]benzoic acid

145

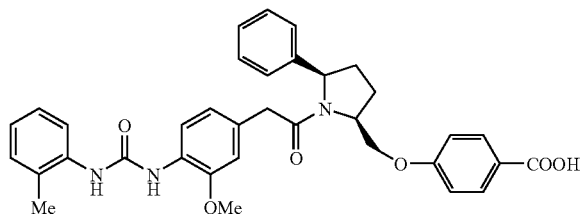

To a stirred solution of benzy N-Boc-pyrroglutarate (8.93 g, 28.0 mmol) in THF (100 ml) was added phenyllithium (1.0 M in Et$_2$O-cyclohexane, 33.5 ml, 33.5 mmol) at −78° C., and the resulting mixture was gradually warmed up to −40° C., then stirred overnight. aq.NH$_4$Cl was added to the reaction mixture, THF was removed in vacuo, then extracted with EtOAc. The organic layer was washed with water and, drying over anhydrous Na$_2$SO$_4$, then concentrated in vacuo. The residue was chromatographed on silica gel with hexane-EtOAc (4:1) as eluent, then recrystallized from hexane-EtOAc to give benzyl [2-(S)-(N-Boc-amino)-5-oxo-6-phenyl]pentanoate (5.02 g, 45%) as a colorless needles. mp 85–87° C.; $^1$H-NMR (CDCl$_3$) δ 1.43 (s, 9 H), 2.07–2.19 (m, 1 H), 2.27–2.36 (m, 1 H), 2.97–3.13 (m, 2 H), 4.44 (br s, 1 H), 5.19 (dd, J=25.2, 12.0 Hz, 2 H), 5.19 (overlap, 1 H), 7.28–7.98 (series of m, 10 H); MS (ESI) m/z, 322 (M$^+$+H).

To a stirred solution of benzyl [2-(S)-(N-Boc-amino)-5-oxo6-phenyl]pentanoate (2.20 g, 5.54 mmol) in CH$_2$Cl$_2$ (50 ml) was added trifluoroacetic acid (15 ml) at rt, and the resulting mixture was stirred for 2 h. The mixture was concentrated in vacuo and poured into aq.NaHCO$_3$, then extracted with EtOAc. The organic layer was dried over anhydrous Na$_2$SO$_4$, then concentrated in vacuo to give benzyl 5-phenyl-5-pyrroline-2-(S)-carboxylate (1.60 g, quant.) as yellowish solid. The product was used for next reaction without further purification: $^1$H-NM (CDCl$_3$) δ 2.20–2.29 (m, 1 H), 2.32–2.42 (m, 1 H), 2.96–3.05 (m, 1 H), 3.12–3.21 (m, 1 H), 4.96–5.00 (m, 1 H), 5.24 (s, 2 H), 7.31–7.49 (m, 8 H), 7.88–7.91 (m, 2 H); MS (ESI) m/z, 280 (M$^+$+H).

A mixture of benzyl 5-phenyl-5-pyrroline-2-(S)-carboxylate (1.59 g, 5.69 mmol) and Pd/C (10%, 128 mg) in MeOH (30 ml) was stirred under H$_2$ at rt for 28 h. The mixture was filtered and the filtrate was concentrated in vacuo. The residue was dissolved in CH$_3$CN—H$_2$O (3:2, 25 ml), then was added di-tert-butyl dicarbonate (1.86 g, 8.54 mmol) and 1.0 M-NaOH (8.54 ml, 8.54 mmol), and the resulting mixture was stirred for 30 min. The mixture was concentrated in vacuo and poured into aq.NaHCO$_3$, then extracted with EtOAc. The organic layer was washed with water, saturated brine, drying over anhydrous Na$_2$SO$_4$, then concentrated in vacuo. The residue was chromatographed on silica gel with CHCl$_3$-MeOH (9:1) and recrystallized from hexane-EtOAc to give N-Boc-5-(R)-phenyl-(S)-proline (810 mg, 49%) as a colorless solid. Mp 113–117° C.; $^1$H-NMR (CDCl$_3$) δ 1.13 (s, 9 H), 1.43 (br s, 1 H), 1.96 (br s, 1 H), 2.09 (br s, 1 H), 2.31–2.34 (m, 1 H), 2.46 (br s, 1 H), 4.52 (br s, 1 H), 4.69 (br s, 1 H), 7.22–7.37 (m, 5 H).

To a stirred solution of N-Boc-5-(R)-phenyl-2-(S)-proline (1.14 g, 3.91 mmol) in THF (20 ml) was added 10M-BH$_3$.Me$_2$S (780 ml, 7.82 mmol) at rt, and the resulting mixture was heated under reflux for 30 min. The mixture was poured into aq.1N-HCl and extracted with EtOAc. The organic layer was dried over anhydrous Na$_2$SO$_4$, then concentrated in vacuo. The residue was chromatographed on silica gel with CHCl$_3$-MeOH (10:1) as eluent to give N-Boc-2-(S)-hydoxymethyl-5-(R)-phenylpyrrolidine (1.11 g, quant.) as a colorless oil: $^1$H-NMR (CDCl$_3$) δ 1.19 (br s, 9 H), 1.65 (br s, 1 H), 1.83–1.90 (m, 1 H), 1.98–2.06 (m, 1 H), 2.22–2.31 (m, 1 H), 3.15–3.86 (m, 2 H), 4.16–4.19 (m, 1 H), 4;83 (t, J=6.8 Hz, 1 H), 4.89 (br s, 1 H), 7.19–7.31 (m, 5 H); MS (ESI) m/z, 278 (M⁺+H).

To a stirred solution of N-Boc-2-(S)-hydoxymethyl-5-(R)-phenylpyrrolidine (1.10 g, 3.97 mmol), triphenylphosphine (1.25 g, 4.76 mmol) and methyl 4-hydroxybenzoate (724 mg, 4.76 mmol) was added diisopropyl azodicarboxylate (955 ml, 4.76 mmol) at rt, and the resulting mixture was stirred at 60° C. for 45 min. The mixture was concentrated in vacuo, and the residue was chromatographed on silica gel with hexane-EtOAc (4:1) as eluent to give methyl 4-[N-Boc-5-(R)-phenyl-2-(S)-pyrrolidinylmethoxy]benzoate (1.31 g, 80%) as a colorless oil. ¹H-NMR (CDCl₃) δ 1.19 and 1.47 (br s, total 9 H), 2.09–2.15 (m, 3 H), 2.33–2.37 (m, 1 H), 3.94 (s, 3 H), 4.30 (br s, 1 H), 4.41 (br s, 2 H), 4.77 (br s, 1 H), 7.03 (d, J=8.8 Hz, 2 H), 7.24–7.36 (m, 5 H), 8.03–8.06 (m, 2 H); MS (ESI) m/z, 412 (M⁺+H).

To a stirred solution of methyl 4-[N-Boc-5-(R)-phenyl-2-(S)-pyrrolidinylmethoxy]benzoate (1.28 g, 3.11 mmol) in CH₂Cl₂ (30 ml) was added trifluoroacetic acid (10 ml) at rt, and the resulting mixture was stirred for 45 min. The mixture was concentrated in vacuo and poured into aq.NaHCO₃, then extracted with CHCl₃. The organic layer was washed with water, drying over anhydrous Na₂SO₄, and concentrated in vacuo to give methyl 4-[5-(R)-phenyl-2-(S)-pyrrolidinyl methoxy]benzate (363 mg, quant.) as yellowish oil. The product was used for next reactions without further purification. ¹H-NMR (CDCl₃) δ 1.71–1.83 (m, 2 H), 2.03–2.10 (m, 1 H), 2.15–2.24 (m, 1 H), 3.68–3.74 (m, 1 H), 3.89 (s, 3 H), 4.01–4.09 (m, 2 H), 4.28 (t, J=7.2 Hz, 1 H), 6.95 (d, J=8.8 Hz, 2 H), 7.22–7.27 (m, 1 H), 7.33 (t, J=8.0 Hz, 2 H), 7.42 (d, J=7.6 Hz, 2 H), 8.00 (d, J=8.8 Hz, 2 H); MS (ESI) m/z, 312 (M⁺+H) 353 (M⁺+CH₃CN).

To a stirred solution of methyl 4-[5-(R)-phenyl-2-(S)-pyrrolidinylmethoxy]benzoate (135 mg, 0.43 mmol), 4-[N'-(2-methylphenyl)ureido]-3-methoxyphenylacetic acid (136 mg, 0.43 mmol) and N,N-dimethylaminopyridine (52.9 mg, 0.43 mmol) in DMF (10 ml) was added EDC.HCl (90.8 mg, 0.48 mmol) at rt, and the resulting mixture was stirred overnight. The reaction mixture was poured into water and extracted with EtOAc. The organic layer was washed with brine, drying over anhydrous Na₂SO₄, then concentrated in vacuo. The residue was chromatographed on silica gel with hexane-EtOAc (1:5) as eluent to give methyl 4-[1-[4-[N'-(2-methylphenyl)ureido]-3-methoxyphenyl acetyl]-5-(R)-phenyl-2-(S)-pyrrolidinylmethoxy]benzoate (271 mg, quant.) as a colorless amorphous solid. ¹H-NMR (CDCl₃) δ 2.00–2.18 (m, 3 H), 2.31–2.41 (m, 1 H), 2.27 (s, 3 H), 3.31 (s, 2 H), 3.67 (s, 3 H), 3.89 (s, 3 H), 4.35–4.48 (m, 2H), 4.60 (br s, 1 H), 4.92 (t, J=6.8 Hz, 1 H), 6.51 (d, J=8.4 Hz, 1 H), 6.62 (s, 1 H), 6.96 (d, J=8.8 Hz, 1 H), 7.11–7.40 (series of m, 8 H), 7.51 (d, J=8.0 Hz, 1 H), 7.97–8.00 (m, 2 H); MS (ESI) m/z, 608 (M⁺+H).

To a stirred solution of methyl 4-[1-[4-[N'-(2-methylphenyl)ureido]-3-methoxyphenylacetyl]-5-(R)-phenyl-2-(S)-pyrrolidinylmethoxy]benzoate (243 mg, 0.40 mmol) in MeOH-THF (1:1, 10 ml) was added 1.0 M-NaOH (2.4 ml, 2.40 mmol) at rt, and the resulting mixture was heated at 60° C. with stirring for 1.5 h. The reaction mixture was poured into 1N-HCl, then extracted with CHCl₃. The organic layer was washed with brine and dried over anhydrous Na₂SO₄, then concentrated in vacuo. The residue was chromatographed on silica gel with CHCl₃-MeOH (10:1) to give 145 (224 mg, 94%) as a colorless amorphous solid. MW 593.67 ¹H-NMR (CD₃OD), mixture of rotamars, δ 2.00–2.19 (m, 3 H), 2.28 and 2.30 (s, total 3 H), 2.45–2.49 (m, 1 H), 3.37 (dd, J=39, 16 Hz, 2 H), 3.77 and 3.80 (s, total 3 H), 3.92–5.18 (series of m, 4 H), 6.48–8.03 (series of m, 16 H); MS (FAB) m/z, 594 (M⁺+H).

Example 138

4-[1-[4-[N'-(2-chlorophenyl)ureido]-3-methoxyphenylacetyl]-5-(R)-phenyl-2-(S)-pyrrolidinyl methoxy] benzoic acid

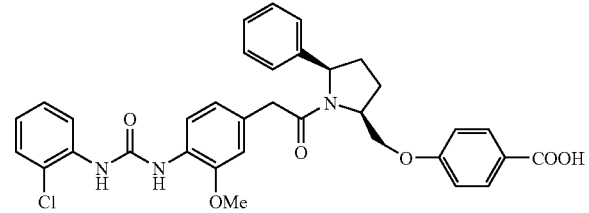

146

To a stirred solution of methyl 4-[5-(R)-phenyl-2-(S)-pyrrolidinylmethoxy]benzoate (142 mg, 0.46 mmol), 4-[N'-(2-chlorophenyl)ureido]-3-methoxyphenylacetic acid (153 mg, 0.46 mmol) and N,N-dimethylaminopyridine (55.7 mg, 0.46 mmol) in DMF (10 ml) was added EDC.HCl (95.7 mg, 0.50 mmol) at it, and the resulting mixture was stirred overnight. The reaction mixture was poured into water and extracted with EtOAc. The organic layer was washed with brine, drying over anhydrous Na₂SO₄, then concentrated in vacuo. The residue was chromatographed on silica gel with hexane-EtOAc (1:5) as eluent to give methyl 4-[1-[4-[N'-(2-chlorophenyl)ureido]-3-methoxyphenyl acetyl]-5-(R)-phenyl-2-(S)-pyrrolidinylmethoxy]benzoate (260 mg, 90%) as a colorless amorphous solid. ¹H-NMR (CDCl₃) δ 2.00–2.19 (m, 3 H), 2.35–2.44 (m, 1 H), 3.35 (s, 2 H), 3.76 (s, 3 H), 3.89 (s, 3 H), 4.38–4.48 (m, 2 H), 4.63 (br s, 1 H), 4.94 (t, J=7.2 Hz, 1 H), 6.53 (d, J=8.4 Hz, 1 H), 6.66 (s, 1 H), 6.96–7.01 (m, 3 H), 7.12–7.42 (series of m, 8 H), 7.87 (d, J=8.0 Hz, 1 H), 7.98 (d, J=8.8 Hz, 2 H), 8.17–8.19 (m, 1 H); MS (ESI) m/z, 627(+), 628 (M⁺+H).

To a stirred solution of methyl 4-[1-[4-[N'-(2-chlorophenyl)ureido]-3-methoxyphenylacetyl]-5-(R)-phenyl-2-(S)-pyrrolidinylmethoxy]benzoate (251 mg, 0.40 mmol) in MeOH-THF (1:1, 10 ml) was added 1.0M-NaOH-(2.4 ml, 2.40 mmol) at rt,. and the resulting mixture was heated at 60° C. with stirring for 1.5 h. The reaction mixture was poured into 1N-HCl, then extracted with CHCl₃. The organic layer was washed with brine and dried over anhydrous Na₂SO₄, then concentrated in vacuo. The residue was chromatographed on silica gel with CHCl₃-MeOH (10:1) to give 146 (181 mg, 74%) as a colorless amorphous solid.

MW 614.09 $^1$H-NMR (CD$_3$OD), mixture of rotamars, δ1.99–2.19 (m, 3 H), 2.42–2.53 (m, 1 H), 3.38 (dd, J=39, 15 Hz, 2 H), 3.79 and 3.80 (s, total 3 H), 3.94–5.19 (series of m, 4 H), 6.49–8.05 (series of m, 16 H); MS (FAB) m/z, 614 (M$^+$+H); Anal. Calcd for C$_{35}$H$_{34}$ClN$_3$O$_6$.H$_2$O: C, 65.06; H, 5.62; N, 6.50. Found: C, 65.03; H, 5.75; N, 6.45.

Example 139

4-[1-[4-[N'-(2-bromophenyl)ureido]-3-methoxyphenylacetyl]-5-(R)-phenyl-2-(S)-pyrrolidinyl ethoxy] benzoic acid

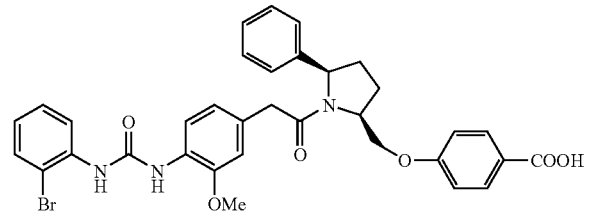

147

To a stirred solution of methyl 4-[5-(R)-phenyl-2-(S)-pirrolidinylmethoxy]benzoate (146 mg, 0.47 mmol), 4-[N'-(2-bromophenyl)ureido]-3-methoxyphenylacetic acid (178 mg, 0.47 mmol) and N,N-dimethylaminopyridine (57.4 mg, 0.47 mmol) in DMF (10 ml) was added EDC.HCl (99.0 mg, 0.52 mmol) at rt, and the resulting mixture was stirred overnight. The reaction mixture was poured into water and extracted with EtOAc. The organic layer was washed with brine, drying over anhydrous Na$_2$SO$_4$, then concentrated in vacuo. The residue was chromatographed on silica gel with hexane-EtOAc (1:5) as eluent to give methyl 4-[1-[4-[N'-(2-bromophenyl)ureido]-3-methoxyphenyl acetyl]-5-(R)-phenyl-2-(S)-pyrrolidinylmethoxy]benzoate (288 mg, 91%) as a colorless amorphous solid. $^1$H-NMR (CDCl$_3$) δ 2.00–2.20 (m, 3 H), 2.34–2.43 (m, 1 H), 3.35 (s, 2 H), 3.72 (s, 3 H), 3.89 (s, 3 H), 4.38–4.49 (m, 2 H), 4.62 (br s, 1 H), 4.94 (t, J=7.2 Hz, 1H), 6.54 (d, J=8.4 Hz, 1H), 6.67 (s, 1 H), 6.91–7.05 (m, 4 H), 7.28–7.42 (series of m, 7 H), 7.51 (d, J=8.0 Hz, 2 H), 7.87 (d, J=8.4 Hz, 1 H), 7.99 (d, J=8.8 Hz, 2 H), 8.14 (d, J=8.4 Hz, 2H); MS (ESI) m/z, 672 (M$^+$+2), 674 (M$^+$+2).

To a stirred solution of methyl 4-[1-[4-[N'-(2-bromophenyl)ureido]-3-methoxyphenylacetyl]-5-(R)-phenyl-2-(S)-pyrrolidinylmethoxy]benzoate (270 mg, 0.40 mmol) in MeOH-THF (1:1, 10 ml) was added 1.0M-NaOH (2.0 ml, 2.0 mmol) at rt, and the resulting mixture was heated at 60° C. with stirring for 1 h. The reaction mixture was poured into 1N-HCl, then extracted with CHCl$_3$. The organic layer was washed with brine and dried over anhydrous Na$_2$SO$_4$, then concentrated in vacuo. The residue was chromatographed on silica gel with CHCl$_3$-MeOH (10:1) to give147 (212 mg, 80%) as a colorless amorphous solid. MW 658.54 $^1$H-NMR (CD$_3$OD), mixture of rotamars, δ 1.99–2.19 (m, 3 H), 2.42–2.53 (m, 1 H), 3.38 (dd, J=39, 16 Hz, 2H), 3.79 and 3.80 (s, total 3 H), 3.94–5.19 (series of m, 4 H), 6.49–8.00 (series of m, 16 H); MS (FAB) m/z, 658 (M$^{30}$) 660 (M$^+$+2).

Example 140

4-[1-[4-[N'-(2,6-dichlorophenyl)ureido]-3-methoxyphenylacetyl]-5-(R)-phenyl-2-(S)-pyrrolidinyl methoxy]benzoic acid

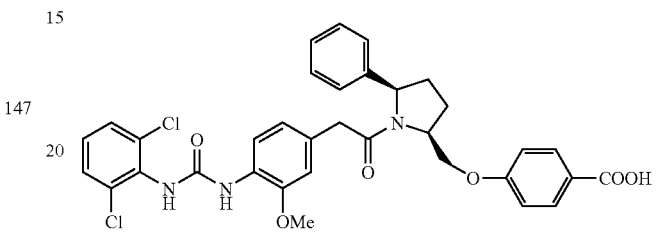

148

To a stirred solution of methyl 4-[5-(R)-phenyl-2-(S)-pirrolidinylmethoxy]benzoate (109 mg, 0.35 mmol), 4-[N'-(2,4-dichlorophenyl)ureido]-3-methoxyphenylacetic acid (129 mg, 0.35 mmol) and N,N-dimethylaminopyridine (42.8 mg, 0.35 mmol) in DMF (10 ml) was added EDC.HCl (73.4 mg, 0.39 mmol) at rt, and the resulting mixture was stirred for 6 h. The reaction mixture was poured into water and extracted with EtOAc. The organic layer was washed with brine, drying over anhydrous Na$_2$SO$_4$, then concentrated in vacuo. The residue was chromatographed on silica gel with hexane-EtOAc (1:4) as eluent to give methyl 4-[1-[4-[N'-(2,6-dichlorophenyl)ureido]-3-methoxyphenylacetyl]-5-(R)-phenyl-2-(S)-pyrrolidinylmethoxy]benzoate (208 mg, 90%) as a colorless amorphous solid. $^1$H-NMR (CDCl$_3$) δ 2.00–2.21 (m, 3 H), 2.33–2.39 (m, 1 H), 3.31 (s, 2 H), 3.69 (s, 3 H), 3.88 (s, 3 H), 4.34–4.45 (m, 2 H), 4.59 (br s, 1 H), 4.93 (t, J=6.8 Hz, 1 H), 6.47 (d, J=8.0 Hz, 1 H), 6.63 (s, 1 H), 6.68 (s, 1 H), 6.92–6.95 (m, 2 H), 7.12–7.41 (series of m, 9 H), 7.96–8.01 (m, 4 H); MS (FAB) m/z, 662 (M$^+$+H).

To a stirred solution of methyl 4-[1-[4-[N'-(2,6-dichlorophenyl)ureido]-3-methoxyphenylacetyl]-5-(R)-phenyl-2-(S)-pyrrolidinylmethoxy]benzoate (186 mg, 0.28 mmol) in MeOH-THF (1:1, 10 ml) was added 1.0M-NaOH (1.4 ml, 1.4 mmol) at rt, and the resulting mixture was heated at 60° C. with stirring for 2.5 h. The reaction mixture was poured into 1N-HCl, then extracted with CHCl$_3$. The organic layer was washed with brine and dried over anhydrous Na$_2$SO$_4$, then concentrated in vacuo. The residue was chromatographed on silica gel with CHCl$_3$-MeOH (10:1) to give 148 (166 mg, 91%) as a colorless amorphous solid. MW 648.53 $^1$H-NMR (CDCl$_3$) δ 2.00–2.18 (m, 3 H), 2.34–2.40 (m, 1 H), 3.33 (s, 2 H), 3.68 (s, 3 H), 4.37–4.47 (m, 2 H), 4.61 (br s, 1 H), 4.94 (t, J=6.8 Hz, 1 H), 6.48 (d, J=8.0 Hz, 1 H), 6.63 (s, 1 H), 6.96 (d, J=8.4 Hz, 3 H), 7.12–7.38 (series of m, 9 H), 7.95 (d, J=8.0 Hz, 1 H), 8.01 (d, J=8.8 Hz, 2 H); MS (FAB) m/z, 648 (M$^+$+H).

Example 141

4-[1-[4-[N'-(2bromophenyl)ureido]-3-methylphenylacetyl]-5-(R)-phenyl-2-(S)-pyrrolidinyl methoxy] benzoic acid

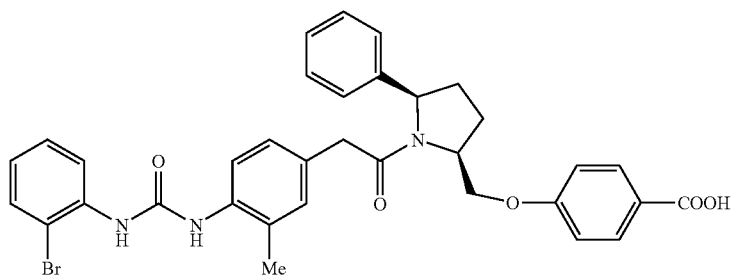

149

To a stirred solution of methyl 4-[5-(R)-phenyl-2-(S)-pirrolidinylmethoxy]benzoate (125 mg, 0.40 mmol), 4-[N'-(2-bromophenyl)ureido]-3-methylphenylacetic acid (146 mg, 0.40 mmol) and N,N-dimethylaminopyridine (49.0 mg, 0.40 mmol) in DMF (10 ml) was added EDC.HCl (84.1 mg, 0.44 mmol) at rt, and the resulting mixture was stirred for 6 h. The reaction mixture was poured into water and extracted with EtOAc. The organic layer was washed with brine, drying over anhydrous $Na_2SO_4$, then concentrated in vacuo. The residue was chromatographed on silica gel with hexane-EtOAc (1:4) as eluent to give methyl 4-[1-[4-[N'-(2-bromophenyl)ureido]-3-methylphenylacetyl]-5-(R)-phenyl-2-(S)-pyrrolidinylmethoxy]benzoate (238 mg, 90%) as a colorless amorphous solid. $^1$H-NMR (CDCl$_3$) δ 1.92 (s, 3 H), 2.09–2.27 (m, 3 H), 2.42–2.50 (m, 1 H), 3.22–3.41 (m, 2 H), 3.88 (s, 3 H), 4.39 (d, J=4.4 Hz, 1 H), 4.64 (br s, 1 H), 5.00 (t, J=6.8 Hz, 1 H), 6.72 (s, H), 6.81–6.93 (series of m, 8 H), 7.22–7.42 (series of m, 6 H), 8.01 (d, J=8.4 Hz, 2 H), 8.13 (d, J=8.0 Hz, 1H); MS (FAB) m/z, 656 (M$^+$), 658 (M$^+$+2).

To a stirred solution of methyl 4-[1-[4-[N'-(2-bromophenyl)ureido]-3-methylphenylacetyl]-5-(R)-phenyl-2-(S)-pyrrolidinylmethoxy]benzoate (216 mg, 0.33 mmol) in MEOH-THF (1:1, 10 ml).was added 1.0M-NaOH (1.7 ml, 1.7 mmol) at rt, and the resulting mixture was heated at 60° C. with stirring for 2.5 h. The reaction mixture was poured into 1N-HCl, then extracted with CHCl$_3$. The organic layer was washed with brine and dried over anhydrous Na$_2$SO$_4$, then concentrated in vacuo. The residue was chromatographed on silica gel with CHCl$_3$-MeOH (10:1) to give 149 (166 mg, 91%) as a colorless amorphous solid. MW 642.54 $^1$H-NMR (CDCl$_3$) δ 2.01 (s, 3 H), 2.05–2.25 (m, 3 H), 2.43–2.48 (m, 1 H), 3.34 (dd, J=45, 16 Hz, 2 H), 4.38–4.45 (m, 2 H), 4.66 (br s, 1 H), 4.99 (t, J=6.8 Hz, 1 H), 6.77 (s, 1 H), 6.82–6.88 (m, 2 H), 6.94 (d, J=8.8 Hz, 2H), 7.15–7.55 (series of m, 10 H), 8.00 (d, J=8.8 Hz, 2 H), 8.14 (d, J=7.2 Hz, 1 H); MS (FAB) m/z 642 (M$^+$), 644 (M$^+$+2).

Example 142

4-[1-[4-[N'-(2-methylphenyl)ureido]-3-methoxyphenylacetyl]-5-(R)-methyl-2-(S)-pyrrolidinyl methoxy] benzoic acid

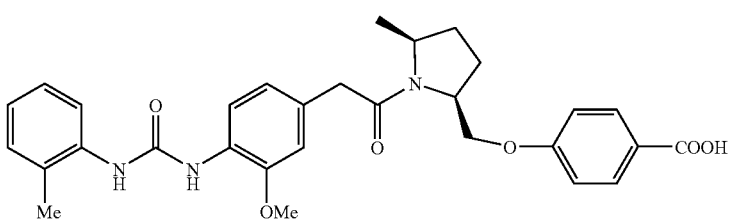

150

To a stirred solution of benzy N-Boc-pyrroglutarate (7.55 g, 23.6 mmol) in THF (100 ml) was added MeLi (1.1 Min Et$_2$O, 28.4 ml, 32.4 mmol) at −78° C., and the resulting mixture was gradually warmed up to it, then stirred overnight. aq.NH$_4$Cl was added to the reaction mixture, THF was removed in vacuo, then extracted with EtOAc. The organic layer was washed with water and, drying over anhydrous Na$_2$SO$_4$, then concentrated in vacuo. The residue was chromatographed on silica gel with hexane-EtOAc (3:1) as eluent to give benzyl [2-(S)-(N-Boc-amino)-5-oxo-6-methyl]pentanoate (5.02 g, 45%) as a colorless needles. mp 85–87° C.; $^1$H-NMR (CDCl$_3$) δ 1.43 (s, 9 H), 1.61–2.15 (series of m, 3 H), 2.09 (s, 3H), 2.41–2.55 (m, 2 H), 4.30 (br s, 1 H), 4.70 (d, J=5.6 Hz, 1 H), 5.12–5.21 (m, 2H), 7.29–7.37 (m, 5 H); MS (ESI) m/z, 336 (M$^+$+H).

To a stirred solution of benzyl [2-(S)-(N-Boc-amino)-5-oxo-6-methyl]pentanoate (4.46 g, 13.3 mmol) in CH$_2$Cl$_2$ (50 ml) was added trifluoroacetic acid (20 ml) at rt, and the resulting mixture was stirred for 1.5 h. The mixture was concentrated in vacuo, and dissolved in toluene, then evaporated to give benzyl 5-methyl-5-pyrroline-2-(S)-carboxylate trifluoroacetic acid salt (5.74 g, quant.) as a crude brown oil. This compound (1.97 g, 5.94 mmol) in MEOH (30 ml) was added Pd/C (10%, 153 mg), and the resulting mixture was stirred for 3 days under $H_2$ atomosphere. The mixture was filtered, and the filtrate was concentrated in vacuo to give 5-methyl-5-pyrrolidine-2-(S)-carboxylic acid trifluoroacetic acid salt (956 mg, 66%) as a crude white solid. To a solution of this compound (939 mg, 3.86 mmol) and di-tert-buyl dicarbonate in MeCN-water (15:1, 16 ml) was added 1.0M-NaOH (8.49 mmol, 8.49 ml) at rt, and the resulting mixture was stirred for 1 h. The resulting mixture was evaporated and poured into aq.-1N-HCl, then extracted with $CHCl_3$/MeOH (5:1). The organic layer was dried over anhydrous $Na_2SO_4$, then concentrated in vacuo. The residue was chromatographed on silica gel with $CHCl_3$-MeOH (7:1) to give N-Boc-5-(R)-methyl-(S)-proline (711 mg, 80%) as a colorless oil. $^1$H-NMR ($CD_3OD$) δ 1.27 (d, J=6.0 Hz, 3H), 1.41–1.46 (m, 9H), 1.62–1.64 (m, 1H), 1.96–2.01 (m, 2H), 2.22 (brs, 1H), 3.94 (br s, 1H), 4.17 (brs, 1H).; MS (ESI) m/z, 230 ($M^+$+H).

To a stirred solution of N-Boc-5-(R)-methyl-2-(S)-proline (1.03 g, 4.49 mmol) in THF (20 ml) was added 10M-$BH_3$·$Me_2S$ (1.57 ml, 15.7 mmol) at rt, and the resulting mixture was heated under reflux for 5 h. The mixture was poured into aq. 1N-HCl and extracted with EtOAc. The organic layer was dried over anhydrous $Na_2SO_4$, then concentrated in vacuo. The residue was chromatographed on silica gel with hexane-AcOEt (1:3) as eluent to give N-Boc-2-(S)-hydoxymethyl-5-R)-methylpyrrolidine (838 mg, 87%) as a colorless oil: $^1$H-NMR ($CDCl_3$) δ 1.17 (d, J=6.0 Hz, 3H), 1.48 (s, 9H), 1.48–1.64 (m, 2H), 1.90–2.11 (m, 2H), 3.52–3.57 (m, 1H), 3.68–3.70 (m, 1H), 3.94–4.13 (m, 1H).

To a stirred solution of N-Boc-2-S)-hydoxymethyl-5-(R)-methylpyrrolidine (820 mg, 3.81 mmol), triphenylphosphine (1.10 g, 4.19 mmol) and methyl 4-hydroxybenzoate (580 mg, 3.81 mmol) was added diisopropyl azodicarboxylate (841 ml, 4.19 mmol) at rt, and the resulting mixture was stirred at 60° C. for 1 h. The mixture was concentrated in vacuo, and the residue was chromatographed on silica gel with hexane-EtOAc (5:1) as eluent to give methyl 4-[N-Boc-5-(R)-methyl-2-(S)-pyrrolidinylmethoxy]benzoate (1.32 g, 80%) as a colorless oil. $^1$H-NMR ($CDCl_3$) δ 1.24 (br s, 3 H), 1.49 (s, 9 H), 1.55–1.70 (m, 2 H), 1.94–2.11 (m, 2 H), 3.88 (s, 3 H), 3.88 (overlap, 1H), 4.06–4.20 (m, 2H), 6.93–6.96 (m, 2H), 7.97 (d, J=8.8 Hz, 2 H); MS (ESI) m/z, 350 ($M^+$+H).

To a stirred solution of methyl 4-[N-Boc-5-(R)-methyl-2-(S)-pyrrolidinylmethoxy]benzoate (1.29 g, 3.70 mmol) in $CH_2Cl_2$ (30 ml) was added trifluoroacetic acid (10 ml) at rt, and the resulting mixture was stirred for 35 min. The mixture was concentrated in vacuo and poured into aq.$NaHCO_3$, then extracted with $CHCl_3$. The organic layer was washed with water, drying over anhydrous $Na_2SO_4$, and concentrated in vacuo to give methyl 4-[5-(R)-methyl-2-(S)-pyrrolidinyl methoxy]benzate (871 mg, 95%) as a colorless oil. The product was used for next reactions without further purification. $^1$H-NMR ($CDCl_3$) δ 1.18 (d, J=6.4 Hz, 3 H), 1.30–1.40 (m, 1 H), 1.59–1.67 (m, 1 H), 1.87–1.97 (m, 2 H), 3.19–3.27 (m, 1 H), 3.49–3.55 (m, 1 H), 3.87 (s, 3 1), 3.89–4.05 (m, 2 H), 6.89 (d, J=8.8 Hz, 2 H), 7.96 (d, J=8.8 Hz, 2 H); MS (ESI) m/z, 250 ($M^+$+H)

To a stirred solution of methyl 4-[5-(R)-methyl-2-(S)-pyrrolidinylmethoxy]benzoate (141 mg, 0.57 mmol), 4-[N'-(2-methylphenyl)ureido]-3-methoxyphenylacetic acid (178 mg, 0.57 mmol) and N,N-dimethylaminopyridine (69.0 mg, 0.57 mmol) in DMF (10 ml) was added EDC.HCl (120 mg, 0.62 mmol) at rt, and the resulting mixture was stirred overnight. The reaction mixture was poured into water and extracted with EtOAc. The organic layer was washed with brine, drying over anhydrous $Na_2SO_4$, then concentrated in vacuo. The residue was chromatographed on silica gel with EtOAc as eluent to give methyl 4-[1-[4-[N'-(2-methylphenyl)ureido]-3-methoxyphenyl acetyl]-5-(R)-methyl-2-(S)-pyrrolidinylmethoxy]benzoate (297 mg, 96%) as a colorless amorphous solid. $^1$H-NMR ($CDCl_3$) δ 1.24–1.34 (m, 3 H), 1.93–2.18 (series of m, 4 H), 2.28 (s, 3 H), 3.65 (s, 3 H), 3.88 (s, 3 H), 3.62–3.87 (m, 3 H), 4.11–4.38 (series of m, 3 H), 6.42–8.06 (series of m, 13 H); MS (ESI) m/z, 546 ($M^+$+H).

To a stirred solution of methyl 4-[1-[4-[N'-(2-methylphenyl)ureido]-3-methoxyphenylacetyl]-5-(R)-methyl-2-(S)-pyrrolidinylmethoxy]benzoate (279 mg, 0.51 mmol) in MeOH-THF (1:1, 10 ml) was added 1.0M-NaOH (2.56 ml, 2.56 mmol) at rt, and the resulting mixture was heated at 60° C. with stirring for 2 h. The reaction mixture was poured into 1N-HCl, then extracted with $CHCl_3$. The organic layer was washed with brine and dried over anhydrous $Na_2SO_4$, then concentrated in vacuo. The residue was chromatographed on silica gel with $CHCl_3$-MeOH (15:1) to give 150 (269 mg, 99%) as a colorless amorphous solid. MW 531.60 $^1$H-NMR ($CD_3OD$), mixture of rotamars, δ 1.28–1.35 (m, 3 H), 1.74–2.21 (series of m, 4 H), 2.28 (s, 3 H), 3.71–4.37 (series of m, 6 H), 6.76–7.99 (series of m, 11 H); MS (ESI) m/z, 532 ($M^+$+H).

Example 143

4-[trans-4-amino-1-[3-methoxy-4-[N'-(2-methylphenyl)ureido]phenylacetyl]-(2S)-pyrrolidinyl]methoxybenzoic acid

151

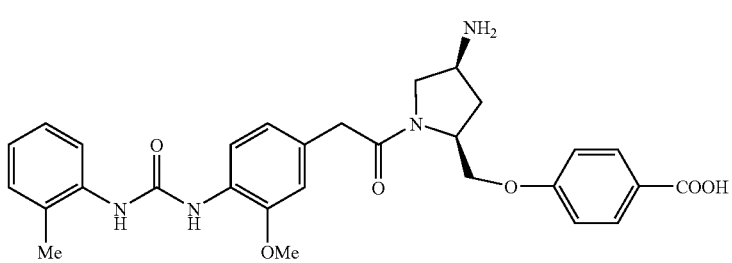

To a solution of methyl 4-(trans-4-amino-1-tert-butoxycarbonyl-(2S)-pyrrolidinyl) methoxybenzoate (1.0 g, 2.86 mmol) and TEA (1.2 ml, 8.6 mmol) in $CH_2Cl_2$ (20.0 ml) was added trifluoroacetic anhydride (720 mg, 3.43 mmol) at 0° C. After stirred for 2.5 hr at room temperature, water was added to the solution and extracted with $CH_2Cl_2$. The extract was washed with water, then dried over $Na_2SO_4$, and concentrated in vacuo. The residue was purified by column chromatography on silica gel with EtOAc-n-hexane (1:3, v/v) as eluent to give methyl 4-(trans-1tert-butoxycarbonyl-4-trifluoroacetamido-(2S)-pyrrolidinyl)methoxybenzoate (940 mg, 74%) as a colorless oil. $^1$H-NMR (CDCl$_3$) δ 1.46 (s, 9H), 2.02–2.18 (m, 1H), 2.41–2.52 (m, 1H), 3.30–3.45 (m, 1H), 3.80–3.90 (m, 1H), 3.88 (s, 3H), 4.00–4.30 (m, 3H), 4.65–4.75 (m, 1H), 6.50 (br s, 1H), 6.91–6.94 (m, 21H), 7.96–7.99 (m, 2H).

To a stirred solution of methyl 4-(trans-1tert-butoxycarbonyl-4-trifluoroacetamido-(2S)-pyrrolidinyl)methoxybenzoate (470 mg, 1.05 mmol) in $CH_2Cl_2$ (10.0 ml) was added TFA (5.0 ml) at 0° C. The reaction mixture was stirred at room temperature for 0.5 hr. The mixture was concentrated in vacuo. Sat. $NaHCO_3$ was added to the residue, and extracted with $CH_2Cl_2$. The extract was washed with brine, dried over $Na_2SO_4$, and concentrated in vacuo. The crude product was used to the subsequent reaction without further purification. To a stirred solution of the crude product, 3-methoxy-4-[N'-(2-methylphenyl)uredio]phenylacetic acid (314 mg, 1.0 mmol), HOBt (162 mg, 1.2 mmol), and triethylamine (417 ml, 3.0 mmol) in THF (10.0 ml) and MeCN (10.0 ml) was added EDC.HCl (288 mg, 1.5 mmol) at 0° C. The reaction mixture was stirred at room temperature for 16 hr, and concentrated in vacuo. Water was added to the residue, and extracted with EtOAc. The organic layer was washed with sat. $NaHCO_3$, 2-M citric acid, and sat. $NaHCO_3$, then dried over $Na_2SO_4$, and concentrated in vacuo. The residue was purified by column chromatography on silica gel with EtOAc-n-hexane (3:1, v/v) as eluent to give methyl 4-[trans-1-[3-methoxy-4-[N'-(2-methylphenyl)ureido]phenylacetyl]-4-trifluoroacetamido-(2S)-pyrrolidinyl]methoxybenzoate (350 mg, 52%) as a colorless oil. $^1$H-NMR (CDCl$_3$) δ 2.01–2.10 (m, 1H), 2.31 (s, 3H), 2.42–2.48 (m, 1H), 3.45–3.50 (m, 1H), 3.56–3.59 (m, 5H), 3.89 (s, 3H), 4.07–4.14 (m, 2H), 4.38–4.42 (m, 1H), 4.50–4.60 (m, 1H), 4.72–4.80 (m, 1H), 6.33 (s, 1H), 6.60–6.85 (m, 3H), 7.06–7.26 (m, 3H), 7.48–7.52 (m, 1H), 7.93–8.05 (m, 3H).

To a stirred solution of methyl 4-[trans-1-[3-methoxy-4-[N'-(2-methylphenyl)ureido]phenylacetyl]-4-trifluoroacetamido-(2S)-pyrrolidinyl]methoxybenzoate (150 mg, 0.23 mmol) in THF (3.0 ml) and MeOH (2.0 ml) was added 1 N NaOH (0.70 ml, 0.70 mmol). The mixture was stirred at 60° C. for 18 hr. The mixture was concentrated in vacuo, water was added thereto, and neutralized with 1 N HCl. The resulting solid was collected, washed with water, and dried in vacuo to give 151 (100 mg, 81%) as a white crystalline solid. MW 532.59 mp 170–171° C.; IR (KBr) 3264, 2937, 1604, 1535, 1415, 1376, 1255, 1224, 1033 cm$^{-1}$; $^1$H-NMR (DMSO-$d_6$) δ 1.80–1.90 (m, 1H), 2.10–2.20 (m, 1H), 2.24 (s, 3H), 3.55–3.80 (m, 3H), 3.57 (s, 2H), 4.08–4.18 (m, 2H), 4.36–4.60 (m, 1H), 6.72–7.16 (m, 7H), 7.77–8.01 (m, 4H), 8.46 (s, 1H), 8.54 (s, 1H); MS (FAB) m/z 532 (M$^+$+1); Anal. calcd for $C_{29}H_{32}N_4O_6 \cdot 2.0H_2O$: C, 61.26; H, 6.38; N, 9.85. Found: C, 61.07; H, 6.32; N, 9.58.

Example 144 methyl 4-[trans-4-amino-1-[3-methoxy-4-[N'-(2-methylphenyl)ureido]phenylacetyl]-(2S)-pyrrolidinyl]methoxybenzoate HCl salt

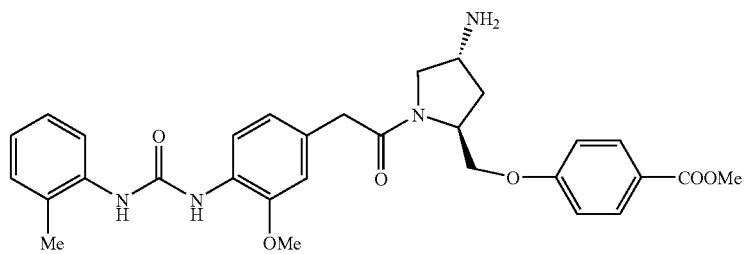

152

To a stirred solution of methyl 4-[trans-1-[3-methoxy-4-[N'-(2-methylphenyl)ureido]phenylacetyl]-4-trifluoroacetamido-(2S)-pyrrolidinyl]methoxybenzoate (200 mg, 0.31 mmol) in MeOH (4.0 mml) was added water (2.0 ml) and $K_2CO_3$ (138 mg, 1.0,mml) at room temperature. After stirred for 18 hr at room temperature, water was added to the mixture and extracted with $CH_2C_2$. The extract was washed with water, then dried over $Na_2SO_4$, and concentrated in vacuo. The residue was purified by column chromatography on silica gel with MeOH—$CH_2Cl_2$ (5:95 to 15:85, v/v) as eluent. The product was dissolved in EtOH (5.0 ml), and 1 N HCl (in EtOH) (1.0 ml, 1.0 mmol) was added thereto. The mixture was concentrated in vacuo to give 152 (120 mg, 63%) as an amorphous solid. MW 546.61 IR (KBr) 3382, 2948, 2879, 1604, 1533, 1286, 1255, 771 cm$^{-1}$; $^1$H-NMR (DMSO-$d_6$) δ 2.25 (s, 3H), 2.10–2.30 (m, 2H), 3.59–3.70 (m, 3H), 3.77–3.80 (m, 8H), 4.00–4.24 (m, 2H), 4.47–4.67 (m, 1H), 6.70–7.16 (m, 7H), 7.77–8.00 (m, 4H), 8.49 (s, 1H), 8.55 (s, 1H); MS (FAB) m/z 547 (M$^+$+1); Anal. calcd for $C_{30}H_{34}N_4O_6 \cdot HCl \cdot 1.4H_2O$: C, 59.24; H, 6.26; N, 9.21; Cl, 5.83 Found: C, 59.42; H, 6.42; N, 9.04; Cl, 6.11.

Example 145

4-[trans-1-[3-methoxy-4-[N'-(2-methylphenyl)ureido]phenylacetyl]4-methylamino-(2S)-pyrrolidinyl]methoxybenzoic acid

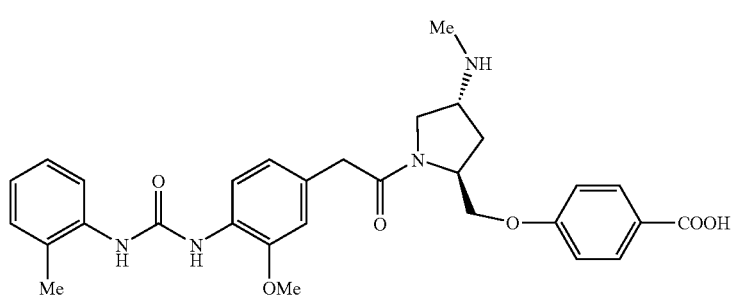

153

To a stirred solution of methyl 4-(trans-1-tert-butoxycarbonyl-4-trifluoroacetamido-(2S)-pyrrolidinyl)methoxybenzoate (520 mg, 1.17 mmol) in DMF (10.0 ml) was added $K_2CO_3$ (321 mg, 2.33 mmol) and MeI (330 mg, 2.33 mmol) at room temperature. The reaction mixture was stirred at 50° C. for 18 hr. Water was added to the mixture and extracted with EtOAc. The organic layer was washed with water, then dried over $Na_2SO_4$, and concentrated in vacuo. The residue was purified by column chromatography on silica gel with EtOAc-n-hexane (1:2, v/v) as eluent to give methyl 4-[trans-1-tert-butoxycarbonyl-4-(N-methyl-trifluoroacetamido)-(2S)-pyrrolidinyl]methoxybenzoate (390 mg, 73%) as a colorless oil. $^1$H-NMR (CDCl$_3$) δ 1.46 (9H, s), 2.12–2.40 (m, 2H), 2.96 and 3.05 (each s, total 3H), 3.28–3.70 (m, 2H), 3.88 (s, 3H), 3.95–4.42 (m, 3H), 5.10–5.40 (m, 1H), 6.89–6.91 (m, 2H), 7.96–8.00 (m, 2H).

To a stirred solution of methyl 4-[(trans-1-tert-butoxycarbonyl-4-(N-methyl-trifluoro acetamido)-(2S)-pyrrolidinyl]methoxybenzoate (390 mg, 0.85 mmol) in CH$_2$Cl$_2$ (8.0 ml) was added TFA (5.0 ml) at 0° C. The reaction mixture was stirred at room temperature for 0.5 hr. The mixture was concentrated in vacuo. Sat. NaHCO$_3$ was added to the residue, and extracted with CH$_2$Cl$_2$. The extract was washed with brine, dried over Na$_2$SO$_4$, and concentrated in vacuo. The crude product was used to the subsequent reaction without further purification. To a stirred solution of the crude product, 3-methoxy-4-[N'-(2-methylphenyl)uredio]phenylacetic acid (279 mg, 0.89 mmol), HOBt (143 mg, 1.1 mmol), and triethylamine (246 ml, 1.77 mmol) in THF (8.0 ml) and MeCN (8.0 ml) was added EDC.HCl (255 mg, 1.3 mmol) at 0° C. The reaction mixture was stirred at room temperature for 16 hr, and concentrated in vacuo. Water was added to the residue, and extracted with EtOAc. The extract was washed with sat. NaHCO$_3$, 2-M citric acid, and sat. NaHCO$_3$, then dried over Na$_2$SO$_4$, and concentrated in vacuo. The residue was purified by column chromatography on silica gel with EtOAc-n-hexane (4:1, v/v) as eluent to give methyl 4-[trans-1-[3-methoxy-4-[N'-(2-methylphenyl)ureido]phenylacetyl]-4-(N-methyl-trifluoroacetoamido)-(2S)-pyrrolidinyl]methoxybenzoate (480 mg, 82%) as a colorless oil. $^1$H-NMR (CDCl$_3$) δ 2.18–2.35 (m, 2H), 2.31 (s, 3H), 2.87 and 2.97 (each s, total 3H), 3.45–3.46 (m, 3H), 3.47 (s, 3H), 3.49 (s, 2H), 3.88 (s, 3H), 4.30–4.70 (m, 2H), 5.20–5.40 (m, 1H), 6.38–6.43 (m, 1H), 6.67–6.86 (m, 4H), 7.09–7.24 (m, 41H), 7.51–7.54 (m, 1H), 7.93–8.08 (m, 3H).

To a stirred solution of methyl 4-[trans-1-[3-methoxy-4-[N'-(2-methylphenyl)ureido]phenylacetyl]-4-(N-methyl-N-trifluoroacetylamino)-(2S)-pyrrolidinyl]methoxybenzoate (240 mg, 0.37 mmol) in THF (5.0 ml) and MEOH (3.0 ml) was added 1 N NaOH (1.27 ml, 1.27 mmol). The mixture was stirred at 60° C. for 18 hr. The mixture was concentrated in vacuo, water was added thereto, and neutralized with 1 N HCl. The resulting solid was collected, washed with water, and dried in vacuo to give 153 (140 mg, 70%) as a white crystalline solid. MW546.61 mp 162–164° C.; IR (KBr) 3338, 1604, 1535, 1255, 1033, 755 cm$^{-1}$; $^1$H-NMR (DMSO-d$_6$) δ 1.85–1.95 (m, 1H), 2.10–2.20 (m, 1H), 2.24 (s, 3H), 2.34 and 2.39 (each s, total 3H), 3.41–3.71 (m, 3H), 3.58 (s, 2H), 3.80 (s, 3H), 4.05–4.20 (m, 2H), 4.36–4.60 (m, 1H), 6.73–7.16 (m, 7H), 7.77–8.01 (m, 4H), 8.45 (s, 1H), 8.53 (s, 1H); MS (FAB) nm/z 547 (M$^+$+1); Anal. calcd for C$_{30}$H$_{34}$N$_4$O$_6$.2.5H$_2$O: C, 60.90; H, 6.64; N, 9.47. Found: C, 61.01; H, 6.50; N, 9.31.

Example 146 methyl 4-[trans-1-[3-methoxy-4-[N'-(2-methylphenyl)ureido]phenylacetyl]-4-methylamino-(2S)-pyrrolidinyl]methoxybenzoate

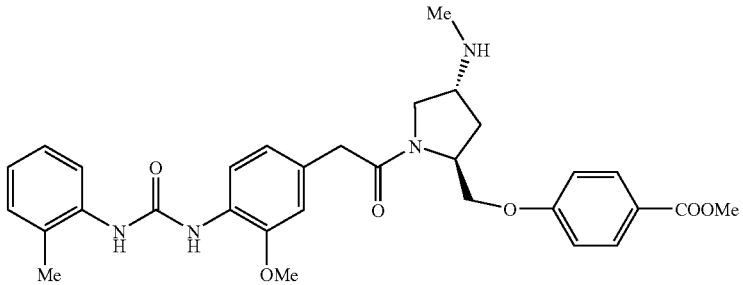

154

To a stirred solution of methyl 4-[trans-1-[3-methoxy-4-[N'-(2-methylphenyl)ureido]phenylacetyl]-4-(N-methyltrifluoroacetamido)-(2S)-pyrrolidinyl]methoxybenzoate (240 mg, 0.36 mmol) in THF (5.0 mml) and MeOH (5.0 ml) was added water (2.0 ml) and K$_2$CO$_3$ (138 mg, 1.0 mml) at room temperature. After stirred for 18 hr at room temperature, water was added to the mixture and extracted with CH$_2$Cl$_2$. The extract was washed with water, then dried over Na$_2$SO$_4$, and concentrated in vacuo. The residue was purified by column chromatography on silica gel with MeOH—CH$_2$Cl$_2$ (5/95 to 20/80, v/v) as eluent. The product was dissolved in EtOH (5.0 ml), and IN HCl (in EtOH) (0.71 ml, 0.71 mmol) was added thereto. The mixture was concentrated in vacuo to give 154 (180 mg, 85%) as an amorphous solid. MW 560.64 IR (KBr) 3311, 2692, 2453, 1712, 1604, 1533 cm$^{-1}$; $^1$H-NMR (DMSO-d$_6$) δ 2.24 (s, 3H), 2.15–2.30 (m, 2H), 2.60 (br s, 3H), 3.60–4.20 (m, 5H), 3.78–3.81 (m, 8H), 4.47–4.70 (m, 1H), 6.71–7.16 (m, 7H), 7.77–8.00 (m, 4H), 8.48 (s, 1H), 8.55 (s, 1H), 9.21 (br s, 2H); MS (FAB) m/z 561 (M$^+$+1); Anal. calcd for C$_{31}$H$_{36}$N$_4$O$_6$.HCl.1.4H$_2$O: C, 59.83; H, 6.45; N, 9.00; Cl, 5.70. Found: C, 60.08; H, 6.51; N, 8.68; Cl, 5.99.

Example 147

4-[trans-4dimethylamino-1-[3-methoxy-4-[N'-(2-methylphenyl)ureido]phenylacetyl]-(2S)-pyrrolidinyl]methoxybenzoic acid To a stirred solution of trans-1-tert-butoxycarbonyl-(2S)-hydroxymethyl-4-hydroxypyrrolidine (2.17 g, 10.0 mmol) and imidazole (2.04 g, 30.0 mmol) in DMF (50 ml) was added TBDPS-Cl (3.03 g, 11.0 mmol) at 0° C. The reaction mixture was stirred at room temperature for 18 hr. Water was added thereto, and extracted with EtOAc. The extract was washed with water, then dried over Na$_2$SO$_4$, and concentrated in vacuo. The residue was purified by column chromatography on silica gel with n-hexane-EtOAc(3:2, v/v) as eluent to give trans-1-tert-butoxycarbonyl-(2S)-(tert-butyldiphenylsilyloxy)methyl-4-hydroxypyrrolidine (1.5 g, 33%) as a white crystalline solid. $^1$H-NMR (CDCl$_3$) δ 1.03 (s9H), 1.25 and 1.32 (each s, 9H), 1.90–2.10 (m, 1H), 2.30–2.40 (m, 1H), 3.40–3.80 (m, 3H), 3.95–4.15 (m, 2H), 4.45–4.55 (m, 1H), 7.37–7.39 (m, 6H), 7.63–7.64 (m, 4H).

To a stirred solution of trans-1-tert-butoxycarbonyl-(2S)-(tert-butyldiphenylsilyloxy) methyl-4-hydroxypyrrolidine (910 mg, 2.0 mmol) and Ph$_3$P (628 mg, 2.4 mmol) in THF (20 ml) was added CBr$_4$ (993 mg, 3.0 mmol) at room temperature. The reaction mixture was stirred at room temperature for 0.5 hr. n-Hexane (40 ml) was added thereto. The resulting solid was filtered off, and dried in vacuo. The residue was purified by column chromatography on silica gel with n-hexane to n-hexane-EtOAc (3:2, v/v) as eluent to give cis-4-bromo-1-tert-butoxycarbonyl-(2S)-(tert-butyldiphenylsilyloxy)methylpyrrolidine (1.0 g, quant.) as a pale yellow oil. $^1$H-NMR (CDCl$_3$) δ 1.06 (s, 9H), 1.31 and 1.45 (each s, 9H), 2.63 (m, 2H), 3.49 (m, 1H), 3.89–4.14 (m, 5H), 7.35–7.42 (m, 6H), 7.64–7.66 (, 4Hm).

To a stirred solution of cis-4-bromo-1-tert-butoxycarbonyl-(2S)-(tert-butyldiphenylsilyloxy) methylpyrrolidine (480 mg, 0.93 mmol) in DMF (5 ml) was added NaN$_3$ (241 mg, 3.70 mmol) at room temperature. The reaction mixture was stirred at 70 for 3 days. Water was added thereto, and extracted with EtOAc. The extract was washed with water, then dried over Na$_2$SO$_4$, and concentrated in vacuo. The crude product was used to the subsequent reaction without further purification. The solution of the crude residue in EtOH (10 ml) was hydrogenated over 10% Pd—C under an atmospheric pressure at room temperature for 4 hr. The catalyst was filtered off, and the filtrate was concentrated in vacuo to give trans-4-amino-1tert-butoxycarbonyl-(2S)-(tert-butyldiphenylsilyloxy)methylpyrrolidine (400 mg, 95%) as a colorless oil. $^1$H-NMR (CDCl$_3$) δ 1.06 (s, 9H), 1.32 and 1.45 (each s, total 9H), 2.20–2.35 (m, 1H), 3.05–3.18 (m, 1H), 3.55–4.05 (m, 6H), 7.35–7.41 (m, 6H), 7.61–7.69 (m, 4H).

To a stirred solution of trans-4-amino-1-tert-butoxycarbonyl-(2S)-(tert-butyldiphenylsilyloxy) methylpyrrolidine (400 mg, 0.88 mmol), AcOH (120 ml, 2.0 mmol), and 37%

155

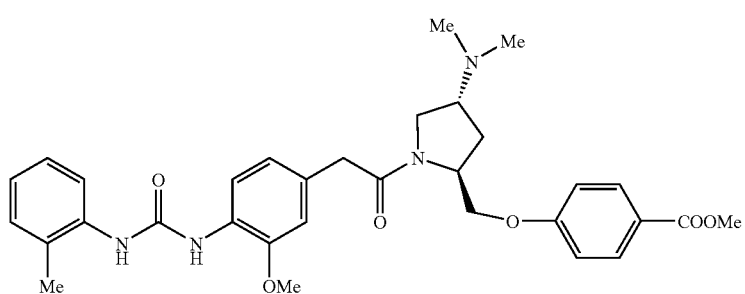

HCHO aq (500 ml) in MeOH (10 ml) was added NaBH$_3$CN (111 mg, 1.76 mmol) at 0° C. The reaction mixture was stirred at room temperature for 18 hr. After concentrated in vacuo, water was added and extracted with CH$_2$Cl$_2$. The extract was dried over Na$_2$SO$_4$ and concentrated in vacuo. The residue was purified by column chromatography on silica gel with MeOH—CH$_2$Cl$_2$ (3:97, v/v) as eluent to give trans-1-tert-butoxycarbonyl-(2S)-(tert-butyldiphenylsilyloxy)methyl-4-dimethylaminopyrrolidine (330 mg, 78%) as a pale yellow oil. $^1$H-NMR (CDCl$_3$) δ 1.06 (s, 9H), 1.33 and 1.45 (each s, total 9H), 1.80–2.25 (m, 2H), 2.23 (br s, 6H), 2.95–4.05 (m, 6H), 7.36–7.39 (m, 6H), 7.63–7.65 (m, 4H).

To a stirred solution of trans-1tert-butoxycarbonyl-(2S)-(tert-butyldiphenylsilyloxy)methyl-4-dimethylaminopyrrolidine (330 mg, 0.68 mmol) in THF (5 ml) was added TBAF (1.0 M solution in THF, 1.0 ml, 1.0 mmol) at 0° C. The reaction mixture was stirred at room temperature for 2 hr. The mixture was concentrated in vacuo. The residue was purified by column chromatography on silica gel with MeOH—CH$_2$Cl$_2$ (3:97 to 20:80, v/v) as eluent to give trans-1-tert-butoxycarbonyl-4-dimethylamino-(2S)-hydroxymethylpyrrolidine (180 mg, quant.) as a pale yellow oil. $^1$H-NMR (CDCl$_3$) δ 1.47 (s, 9H), 2.23 (s, 6H), 1.65–1.75 (m, 2H), 2.75–4.10 (m, 4H), 3.61 (d, J=5.6 Hz, 2H).

To a stirred solution of trans-1-tert-butoxycarbonyl-4-dimethylamino-(2S)-hydroxymethyl pyrrolidine (180 mg, 0.73 mmol), methyl 4-hydroxybenzoate (114 mg, 0.75 mmol), and Ph$_3$P (296 mg, 1.13 mmol) in THF (10 ml) was added DIAD (227 mg, 1.13 mmol) at 0° C. The reaction mixture was stirred at 70° C. for 18 hr. The mixture was concentrated in vacuo. The residue was purified by column chromatography on silica gel with n-hexane-EtOAc (1:2, v/v) to MeOH—CH$_2$Cl$_2$(5:95, v/v) as eluent to give methyl 4-[trans-1-tert-butoxycarbonyl-4-dimethylamino-(2S)-pyrrolidinyl]methoxybenzoate (180 mg, 68%) as a pale yellow oil. $^1$H-NMR (CDCl$_3$) δ 1.46 (s, 9H), 1.80–1.95 (m, 1H), 2.20–2.23 (m, 1H), 2.24 (s, 6H), 2.90–2.95 (m, 1H), 3.10–3.30 (m, 1H), 3.50–3.65 (m, 1H), 3.88 (s, 3H), 3.95–4.35 (m, 3H), 6.93–6.95 (m, 2H), 7.96–7.98 (m, 2H).

To a stirred solution of methyl 4-(trans-1-tert-butoxycarbonyl-4-dimethylamino-(2S)-pyrrolidinyl)methoxybenzoate (200 mg, 0.53 mmol) in CH$_2$Cl$_2$ (6 ml) was added TFA (3 ml) at 0° C. The reaction mixture was stirred at room temperature for 0.5 hr. The mixture was concentrated in vacuo. Sat. NaHCO$_3$ was added to the residue, and extracted with CH$_2$Cl$_2$. The extract was washed with brine, dried over Na$_2$SO$_4$, and concentrated in vacuo. The crude product was used to the subsequent reaction without further purification.

To a stirred solution of the crude product, 3-methoxy-4-[N'-(2-methylphenyl)uredio]phenylacetic acid (166 mg, 0.53 mmol), HOBt (71 mg, 0.53 mmol), and triethylamine (140 ml, 1.10 mmol) in THF (5 ml) and MeCN (5 ml) was added EDC.HCl (152 mg, 0.79 mmol) at 0° C. The reaction mixture was stirred at room temperature for 16 hr, and concentrated in vacuo. Water was added to the residue, and extracted with EtOAc. The extract was washed with sat. NaHCO$_3$, then dried over Na$_2$SO$_4$, and concentrated in vacuo. The residue was purified by column chromatography on silica gel with EtOAc to CH$_2$Cl$_2$-MeOH(8:92, v/v) as eluent to give methyl 4-[trans-4-dimethylamino-1-[3-methoxy-4-[N'-(2-methylphenyl) ureido]phenylacetyl]-(2S)-pyrrolidinyl]methoxybenzoate (260 mg, 86%) as a colorless oil. $^1$H-NMR (CDCl$_3$) δ 1.95–2.15 (m, 3H), 2.23 (s, 6H), 2.31 (s, 3H), 3.30–3.34 (m, 1H), 3.57 (s, 2H), 3.61 (s, 3H), 3.70–3.75 (m, 1H), 4.11–4.15 (m, 2H), 4.45–4.50 (m, 1H), 6.34 (s, 1H), 6.72–6.88 (m, 4H), 7.08–7.24 (m, 4H), 7.51–7.53 (m, 1H), 7.92–8.07 (m, 3H).

To a stirred solution of methyl 4-[trans-4-dimethylamino-1-[3-methoxy-4-[N'-(2-methylphenyl) ureido]phenylacetyl]-2-pyrrolidinyl]methoxybenzoate (260 mg, 0.45 mmol) in THF (4.0 ml) and MeOH (2.0 ml) was added 1 N NaOH (0.90 ml, 0.90 mmol). The mixture was stirred at 70° C. for 24 hr. The mixture was concentrate in vacuo, water was added thereto, and neutralized with 1 N HCl. The resulting solid was collected, washed with water, and dried in vacuo to give 155 (200 mg, 79%) as a white crystalline solid. MW 560.64 mp 145–150° C.; IR (KBr) 3355, 2948, 1698, 1604, 1533, 1454, 1417, 1255, 1226, 1166, 1035, 755 cm$^{-1}$; $^1$H-NMR (DMSO-d$_6$) δ 1.82–1.98 (m, 1H), 2.08–2.11 (m, 1H), 2.20 (s, 6H), 2.25 (s, 3H), 3.40–3.60 (m, 3H), 3.64 (s, 2H), 3.82 (s, 3H), 4.01–4.16 (m, 2H), 4.36 (m, 1H), 6.74–7.15 (m, 7H), 7.77–8.02 (m, 4H), 8.44 (s, 1H), 8.54 (s, 1H); MS (FAB) m/z 561 (M$^+$+1); Anal. calcd for C$_{31}$H$_{36}$N$_4$O$_6$. 1.2H$_2$O: C, 63.95; H, 6.65; N, 9.62. Found: C, 63.82; H, 6.72; N, 9.44.

Example 148 methyl 4-[trans-4-dimethylamino-1-[3-methoxy-4-[N'-(2-methylphenyl)ureido]phenylacetyl]-(2S)-pyrrolidinyl]methoxybenzoate HCl salt

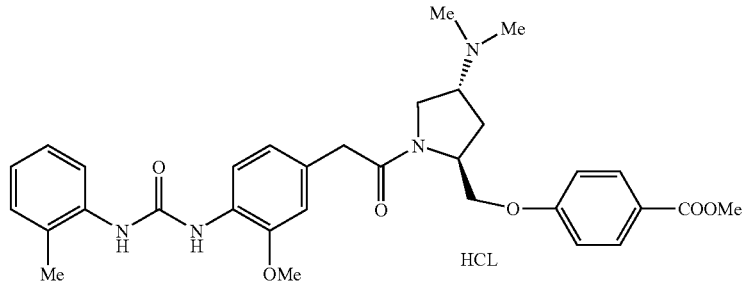

156

To a stirred solution of trans-4-[4-dimethylamino-1-[3-methoxy-4-[N'-(2-methylphenyl) ureido]phenylacetyl-(2S)-pyrrolidinyl]methoxybenzoic acid (80 mg, 0.14 mmol) in toluene (4.0 ml) and MeOH (1.0 ml) was added TMSCHN$_2$ (2.0 M in hexane, 100 ml, 0.20 mmol) at 0° C. The reaction mixture was stirred at room temperature for 1.5 hr. The mixture was concentrated in vacuo. The residue was purified by column chromatography on silica gel with MeOH—CH$_2$Cl$_2$(5:95, v/v) as eluent. The product was dissolved in EtOH (5.0 ml), and 1 N HCl (in EtOH) (244 μl, 0.244 mmol) was added thereto. The mixture was concentrated in vacuo to give 156 (72 mg, 88%) as an amorphous solid. MW 574.67 IR (KBr) 3345, 2950, 2586, 1712, 1604, 1511, 1454, 1284, 1255, 1170, 1114, 1029, 850, 771 cm$^{-1}$; $^1$H-NMR (DMSO-d$_6$) δ 2.25 (s, 3H), 2.35–2.37 (m, 2H), 2.77–2.81 (m, 6H), 3.62–3.71 (m, 2H), 3.79–3.81 (m, 8H), 3.99–4.16

(m, 3H), 4.50–4.70 (m, 1H), 6.74–7.16 (m, 7H), 7.77–8.01 (m, 4H), 8.48 (s, 1H), 8.55 (s, 1H); Anal. calcd for C32H38N4O6.1.0HCl 1.2 H2O: C, 60.74; H, 6.59; N, 8.85. Found: C, 61.03; H, 6.78; N, 8.33.

Example 149

4-[cis-4-&methylamino-1-[3-methoxy-4-[N'(2-methylphenyl)ureido]phenylacetyl]-(2S)-pyrrolidinyl] methoxybenzoic acid

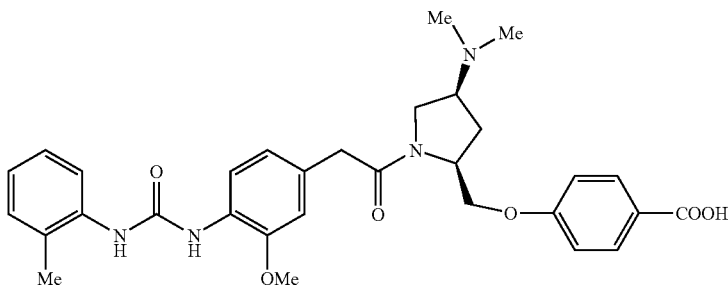

157

To a stirred solution of cis-1tert-butoxycarbonyl-(2S)-(tert-butyldiphenylsilyloxy)methyl-4-hydroxypyrrolidine (1.82 mg, 4.0 mmol), phthalimide (647 mg, 4.4 mmol), and Ph3P (1.26 g, 4.8 mmol) in THF (20 ml) was added DIAD (889 mg, 4.4 mmol) at 0° C. The reaction mixture was stirred at room temperature for 18 hr. The mixture was concentrated in vacuo. The residue was purified by column chromatography on silica gel with n-hexane-EtOAc (5/1, v/v) as eluent to give N-[cis-1tert-butoxycarbonyl-(2S)-(tert-butyldiphenylsilyloxy)methyl-4-pyrrolidinyl]phthalimide (1.6 g, 69%) as an amorphous solid. 1H-NMR (CDCl3) δ 1.07 (s, 9H), 1.30 and 1.44 (each s, total 9H), 2.27–2.37 (m, 1H), 2.94–2.96 (m, 1H), 3.81–4.09 (m, 51H), 4.72 (m, 1H), 7.37–7.38 (m, 6H), 7.67–7.74 (m, 6H), 7.84–7.86 (m, 2H).

To a stirred solution of N-[cis-1tert-butoxycarbonyl-(2S)-(tert-butyldiphenylsilyloxy) methyl-4-pyrrolidinyl]phthalimide (1.60 g, 2.74 mmol) in EtOH (8 ml) was added NH2NH2.H2O(206 mg, 4.11 mmol) at room temperature. The reaction mixture was stirred at 70 for 1 hr. The mixture was concentrated in vacuo. The resulting solid was filtered off, and washed with CHCl3. The filtrate was concentrated in vacuo. The resulting solid was filtered off, and washed with CHCl3. The filtrate was concentrated in vacuo to give cis-4-amino-1-tert-butoxycarbonyl-(2S)-(tert-butyl diphenylsilyloxy) methylpyrrolidine (1.3 g, quant) as a pale yellow oil. The crude product was used to the subsequent reaction without further purification. 1H-NMR (CDCl3) δ 1.06 (s, 9H), 1.30 and 1.45 (each s, total 91), 1.59 (m, 1H), 1.85 (m, 1H), 2.94 (m, 1H), 3.44 (m, 1H), 3.78–4.07 (m, 4H), 7.36–7.41 (m, 6H), 7.51–7.65 (m, 4H).

To a stirred solution of cis-4-amino-1-tert-butoxycarbonyl-(2S)-(tert-butyldiphenyl ilyloxy) methylpyrrolidine (1.24 g, 2.74 mmol), AcOH (374 μl, 5.48 mmol), and 37% HCHO aq (1.0 ml) in MeOH (20 ml) was added NaBH3CN (345 mg, 5.48 mmol) at 0° C. The reaction mixture was stirred at room temperature for 18 hr. After concentrated in vacuo, water was added and extracted with CH2Cl2. The extract was dried over Na2SO4, and concentrated in vacuo. The residue was purified by column chromatography on silica gel with MeOH—CH2Cl2 (3/97, v/v) as eluent to give cis-1-tert-butoxycarbonyl-(2S)-(tert-butyldiphenylsilyloxy) methyl-4-dimethylamino pyrrolidine (1.1 g, 83%) as a pale yellow oil. 1H-NMR (CDCl3) δ 1.05 (s, 9H), 1.29 and 1.45 (each s, total 9H), 1.95–2.04 (m, 1H), 2.20–2.26 (m, 1H), 2.27 (s, 6H), 2.54 (m, 1H), 3.00–3.02 (m, 1H), 3.62–4.03 (m, 4H), 7.34–7.41 (m, 61H), 7.63–7.65 (m, 4H).

To a stirred solution of cis-1-tert-butoxycarbonyl-2-(tert-butyldiphenylsilyloxy)methyl-4dimethyl amino pyrrolidine (1.1 g, 2.27 mmol) in THF (10 ml) was added TBAF (1.0 M solution in THF) (4.5 ml, 4.5 mmol) at 0° C. The reaction mixture was stirred at room temperature for 2 hr. The mixture was concentrated in vacuo. The residue was purified by column chromatography on silica gel with MeOH—CH2Cl2 (3/97 to 20/80, v/v) as eluent to give cis-1-tert-butoxycarbonyl-4-dimethylamino-(2S)-hydroxymethylpyrrolidine (580 mg, quant.) as a pale yellow oil. 1H-NMR (CDCl3) δ 1.47 (s, 9H), 1.25–1.96 (m, 2H), 2.25 (s, 6H), 2.53–2.58 (m, 1H), 3.17–4.02 (m, 5H).

To a stirred solution of cis-1-tert-butoxycarbonyl-4-dimethylamino-(2S)-hydroxymethylpyrrolidine (555 mg, 2.27 mmol), methyl 4-hydroxybenzoate (380 mg, 2.5 mmol), and Ph3P (1.07 g, 4.09 mmol) in THF (10 ml) was added DIAD (826 mg, 4.09 mmol) at 0° C. The reaction mixture was stirred at 70° C. for 18 hr. The mixture was concentrated in vacuo. The residue was purified by column chromatography on silica gel with n-hexane-EtOAc (1/2, v/v)MeOH—CH2Cl2(5/95, v/v) as eluent to give methyl 4-(cis-1-tert-butoxycarbonyl-4-dimethylamino-(2S)-pyrrolidinyl)methoxy benzoate (260 mg, 30%) as a pale yellow oil. 1H-NMR (CDCl3) δ 1.45 (s, 9H), 1.70–1.90 (m, 1H), 2.26 (s, 6H), 2.33 (m, 1H), 2.57 (m, 1H), 3.06 (m, 1H), 3.85–4.23 (m, 4H), 3.88 (s, 3H), 6.93 (m, 2H), 7.95 (m, 2H).

To a stirred solution of methyl 4-(cis-1-tert-butoxycarbonyl-4-dimethylamino-(2S)-pyrrolidinyl) methoxybenzoate (208 mg, 0.55 mmol) in CH2Cl2 (6 ml) was added TFA (3 ml) at 0° C. The reaction mixture was stirred at room temperature for 0.5 hr. The mixture was concentrated in vacuo. Sat. NaHCO3 was added to the residue, and extracted with CH2Cl2. The extract was washed with brine ,dried over Na2SO4, and concentrated in vacuo. The crude product was used to the subsequent reaction without further purification. To a stirred solution of the crude product, 3-methoxy-4-[N'-(2-methylphenyl)uredio]phenylacetic acid (173 mg, 0.55 mmol), HOBt (74 mg, 0.55 mmol), and triethylamine (153 μl, 1.1 mmol) in THF (6 ml) and MeCN (6 ml) was added EDC.HCl (160 mg, 0.83 mmol) at 0° C. The reaction mixture was stirred at room temperature for 16 hr, and concentrated in vacuo. Water was added to the residue, and extracted with EtOAc. The extract was washed with sat. NaHCO3, then dried over Na2SO4, and concentrated in vacuo. The residue was purified by column chromatography on silica gel with EtOAc-CH$_2$Cl$_2$-MeOH (5/95, v/v) as eluent to give methyl 4-[cis-4-methylamino-1-[3-methoxy-4-[N'-(2-methylphenyl) ureido]phenylacetyl]-(2S)-pyrrolidinyl]methoxybenzoate (270 mg, 47%) as a colorless oil. $^1$H-NMR (CDCl$_3$) δ 1.95–2.04 (m, 1H), 2.25 (s, 6H), 2.32 (s, 3H), 2.61 (m, 1H), 3.21 (m, 1H), 3.56–3.58 (m, 5H), 3.80–3.83 (m, 1H), 3.88 (s, 3H), 4.18–4.20 (m, 1H), 4.41–4.45 (m, 2H), 6.36 (s, 1H), 6.68–6.85 (m, 4H), 7.08–7.25 (m, 4H), 7.52–7.55 (m, 1H), 7.91–8.07 (m, 3H).

To a stirred solution of methyl 4-[cis-4diethylamino-1-[3-methoxy-4-[N'-(2-methylphenyl) ureido]phenylacetyl]-(2S)-pyrrolidinyl]methoxybenzoate (270 mg, 0.47 mmol) in THF (4.0 ml) and MeOH (2.0 ml) was added 1 N NaOH (1.0 ml, 1.0 mmol). The mixture was stirred at 70° C. for 18 hr. The mixture was concentrated in vacuo, water was added thereto, and neutralized with 1 N HCl. The resulting solid was collected, washed with water, and dried in vacuo to give 157 (170 mg, 65%) as a white crystalline solid. MW 560.64 mp 147–150° C.; IR (KBr) 3353, 2952, 1700, 1604, 1533, 1454, 1415, 1255, 1166, 1035, 755 cm$^{-1}$; $^1$H-NMR (DMSO-d$_6$) δ: 1.83–1.84 (m, 1H), 2.08–2.10 (m, 1H), 2.21 (br s, 6H), 2.24 (s, 3H), 3.00 (m, 2H), 3.60 (s, 2H), 3.78 (s, 3H), 3.85–4.29 (m, 4H), 6.71–7.16 (m, 7H), 7.77–8.01 (m, 4Hm), 8.46 (s, 1H), 8.54 (s, 1H); MS (FAB) m/z 561 (M+H)$^+$; Anal. calcd for C$_{31}$H$_{36}$N$_4$O$_6$.2 H$_2$O: C, 62.40; H, 6.76; N, 9.39. Found: C, 62.51; H, 6.60; N, 9.36.

Example 150 methyl 4-[cis-4-dimethylamino-1-[3-methoxy-4-[N'-(2-methylphenyl)ureido]phenylacetyl]-(2S)-pyrrolidinyl]methoxybenzoate HCl salt

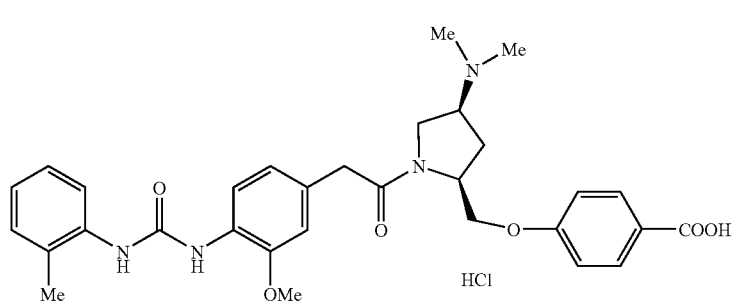

158

To a stirred solution of 4-[cis4-dimethylamino-1-[3-methoxy-4-[N'-(2-methylphenyl) ureido]phenylacetyl]-(2S)-pyrrolidinyl]methoxybenzoic acid (80 mg, 0.14 mmol) in toluene (4.0 ml) and MeOH (1.0 ml) was added TMSCHN$_2$ (2.0 M in hexane) (100 μl, 0.20 mmol) at 0° C. The reaction mixture was stirred at room temperature for 1.5 hr. The mixture was concentrated in vacuo. The residue was purified by column chromatography on silica gel with MeOH—CH$_2$Cl$_2$(5/95, v/v) as eluent. The product was dissolved in EtOH (5.0 ml), and 1 N HCl (in EtOH) (244 μl, 0.244 mmol) was added thereto. The mixture was concentrated in vacuo to give 158 (75 mg, 79%) as an amorphous solid. MW 574.67 IR (KBr) 3345, 2950, 2456, 1712, 1646, 1604, 1511, 1454, 1434, 1415, 1284, 1257, 1168, 1114, 1031, 771 cm$^{-1}$; $^1$H-NMR (DMSO-d$_4$) δ 2.10–2.20 (m, 2H), 2.25 (s, 3H), 2.83 (m, 6H), 3.60–3.62 (m, 2H), 3.76–3.81 (m, 8H), 4.20–4.33 (m, 4H), 6.71–7.17 (m, 6H), 7.77–7.98 (m, 5H), 8.47 (s, 1H), 8.55 (s, 1); MS (FAB) m/z 574 (M+H)$^+$; Anal. calcd for C$_{32}$H$_{38}$N$_4$O$_6$.1.0.HCl 1.3 H$_2$O: C, 60.57; H, 6.61; N, 8.83. Found: C, 60.80; H, 6.82; N, 8.44.

Example 151

4-[trans-1-[4-[N'-(2-chlorophenyl)ureido]-3-methoxyl phenylacetyl]-4-dimethylamino-(2S)-pyrrolidinyl]methoxybenzoic acid

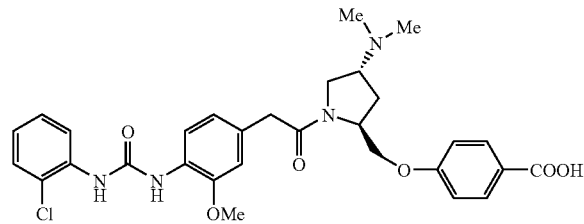

159

To a stirred solution of methyl 4-(trans-1-tert-butoxycarbonyl-4-dimethylamino-(2S)-pyrrolidinyl) methoxybenzoate (430 mg, 1.1 mmol) in CH$_2$Cl$_2$ (10.0 ml) was added TFA (5.0 ml) at 0° C. The reaction mixture was stirred at room temperature for 0.5 hr. The mixture was concentrated in vacuo. Sat. NaHCO$_3$ was added to the residue, and extracted with CH$_2$Cl$_2$. The extract was washed with brine, dried over Na$_2$SO$_4$, and concentrated in vacuo. The crude product was used to the subsequent reaction without further purification. To a stirred solution of the crude product, 4-[N'-(2-chlorophenyl)uredio]-3-methoxyphenylacetic acid (368 mg, 1.1 mmol), HOBt (162 mg, 1.2 mmol), and triethylamine (417 ml, 3.0 mmol) in THF (10.0 ml) and MeCN (10.0 ml) was added EDC.HCl (288 mg, 1.1 mmol) at 0° C. The reaction mixture was stirred at room temperature for 16 hr, and concentrated in vacuo. Water was added to the residue, and extracted with EtOAc. The extract was washed with sat. NaHCO$_3$, 2-M citric acid, and sat. NaHCO$_3$, then dried over Na$_2$SO$_4$, and concentrated in vacuo. The residue was purified by column chromatography on silica gel with n-hexane-EtOAc (1:1, v/v) as eluent to give 4-[trans-1-[4-[N'-(2-chlorophenyl) ureido]-3-methoxy-lphenylacetyl]-4-dimethylamino-(2S)-pyrrolidinyl]methoxy benzoate (530 mg, 78%) as a colorless oil. $^1$H-NMR (CDCl$_3$) δ 1.94–1.99 (m, 1H), 2.48 (s, 9H), 3.06–3.12 (m, 1H), 3.33–3.38 (m, 1H), 3.60 (s, 2H), 3.68 (s, 3H), 3.69–3.80 (m, 1H), 3.88 (s, 3H), 4.13–4.20 (m, 2H), 4.56 (m, 1H), 6.76–7.00 (m, 5H), 7.22–7.34 (m, 3H), 7.92–8.00 (m, 3H), 8.17–8.19 (m, 1H). For HCl salt: IR (KBr) 3324, 2950, 2454, 1710, 1604, 1511, 1284 cm$^{-1}$; $^1$H-NMR (DMSO-d$_6$) δ2.30–2.40 (m, 2H), 2.77–2.80 (m, 6H), 3.60–3.75 (m, 2H), 3.75–3.85 (m, 8H), 4.00–4.22 (m, 3H), 4.50–4.75 (m, 1H), 6.75–7.43 (m, 7H), 7.89–8.09 (m, 4H), 8.87 (s, 1H), 8.91 (s, 1H); MS (FAB) m/z 595 (M+H)$^+$; Anal. calcd for C$_{31}$H$_{36}$N$_4$O$_6$Cl.OHC.1.0H$_2$O: C, 57.23; H, 6.04; N, 8.61; Cl, 10.90. Found: C, 57.43; H, 6.08; N, 8.38; Cl, 10.73.

To a stirred solution of methyl 4-[trans-1-[4-[N'-(2-chlorophenyl)ureido]-3-methoxyl phenylacetyl]-4-dimethylamino-(2S)-pyrrolidinyl]methoxybenzoate (190 mg, 0.32 mmol) in THF (3.0 ml) and MeOH (2.0 ml) was added 1 N NaOH (0.64 ml, 0.64 mmol). The mixture was stirred at 70° C. for 24 hr. The mixture was concentrate in vacuo, water was added thereto, and neutralized with 1 N HCl. The resulting solid was collected, washed with water, and dried in vacuo to give 159 (150 mg, 83%) as a white crystalline solid. MW 581.06 mp 159–161° C.; IR (KBr) 3318, 2938, 1604, 1531, 1438, 1340 cm$^{-1}$; $^1$H-NMR (DMSO-d$_6$) δ 2.10–2.40 (m, 8H), 2.50–2.70 (m, 2H), 3.85–3.90 (m, 5H), 4.02–4.18 (m, 3H), 4.30–4.60 (m, 1H), 6.75–7.43 (m, 7H), 7.86–8.09 (m, 4H), 8.86 (s, 1H), 8.91 (s, 1H); MS (FAB) m/z 581 (M+H)$^+$; Anal. calcd for C$_{30}$H$_{33}$N$_4$O$_6$Cl.1.2H$_2$O: C, 59.79; H, 5.92; N, 9.30. Found: C, 59.69; H, 5.93; N, 9.09.

Example 152

4-[cis-1-[4-[N'-(2-chlorophenyl)ureido]-3-methoxyl phenylacetyl]-4-ethylamino-(2S)-pyrrolidinyl]methoxybenzoic acid

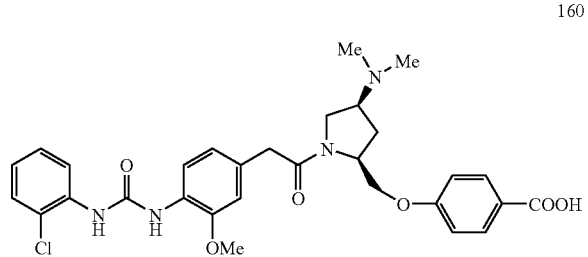

To a stirred solution of methyl 4-(cis-1-tert-butoxycarbonyl-4-dimethylamino-(2S)-pyrrolidinyl) methoxybenzoate (1.2 g, 3.2 mmol) in CH$_2$Cl$_2$ (10.0 ml) was added TFA (5.0 ml) at 0 ° C. The reaction mixture was stirred at room temperature for 0.5 hr. The mixture was concentrated in vacuo. Sat. NaHCO$_3$ was added to the residue, and extracted with CH$_2$Cl$_2$. The extract was washed with brine ,dried over Na$_2$SO$_4$, and concentrated in vacuo. The crude product was used to the subsequent reaction without further purification. To a stirred solution of the crude product (278 mg, 1.0 mmol), 4-[N'-(2-chlorophenyl)uredio]-3-methoxyphenylacetic acid (335 mg, 1.0 mmol), HOBt (135 mg, 1.0 mmol), and triethylamine (417 ml, 3.0 mmol) in THF (4.0 ml) and MeCN (4.0 ml) was added EDC.HCl (288 mg, 1.5 mmol) at 0° C. The reaction mixture was stirred at room temperature for 16 hr, and concentrated in vacuo. Water was added to the residue, and extracted with EtOAc. The extract was washed with sat. NaHCO$_3$, 2-M citric acid, and sat. NaHCO$_3$, then dried over Na$_2$SO$_4$, and concentrated in vacuo. The residue was purified by column chromatography on silica gel with n-hexane-EtOAc(1:1, v/v) as eluent to give methyl 4-[cis-1-[4-[N'-(2-chlorophenyl)ureido]-3-methoxylphenylacetyl]-4-dimethylamino-(2S)-pyrrolidinyl]methoxybenzoate (500 mg, 84%) as a colorless oil. $^1$H-NMR (CDCl$_3$) δ 1.98–2.50 (m, 1H), 2.26 (s, 3H), 2.25–2.40 (m, 1H), 2.58–2.65 (m, 1H), 3.20–3.30 (m, 1H), 3.60 (s, 2H), 3.64 (s, 3H), 3.80–3.90 (m, 1H), 3.88 (s, 3H), 4.18–4.20 (m, 1H), 4.42–4.46 (m, 2H), 6.72–7.00 (m, 4H), 7.20–7.35 (m, 5H), 7.91–7.94 (m, 3H), 8.18–8.21 (m, 1H).

To a stirred solution of methyl 4-[cis-1-[4-[N'-(2-chlorophenyl)ureido]-3-methoxyl phenylacetyl]-4-dimethylamino-(2S)-pyrrolidinyl]methoxybenzoate (250 mg, 0.42 mmol) in THF (5.0 ml) and MeOH (3.0 ml) was added 1 N NaOH (1.0 ml, 1.0 mmol). The mixture was stirred at 70° C. for 18 hr. The mixture was concentrated in vacuo, water was added thereto, and neutralized with 1 N HCl. The resulting solid was collected, washed with water, and dried in vacuo to give 160 (170 mg, 70%) as a white crystalline solid. MW 581.06 mp 165–167° C.; IR (KBr) 3328, 1604, 1531, 1164, 1033 cm$^-$; $^1$H-NMR (DMSO-d$_6$) δ 1.80–1.90 (m, 1H), 2.20–2.50 (m, 7H), 3.60–3.70 (m, 2H), 3.77–3.81 (m, 5H), 4.00–4.30 (m, 4H), 6.72–7.44 (m, 7H), 7.86–8.10 (m, 4H), 8.88–8.92 (m, 2H).; MS (FAB) m/z 581 (M$^+$+1); Anal. calcd for C$_{30}$H$_{33}$N$_4$O$_6$Cl.1.1H$_2$O: C, 59.87; H, 6.06; N, 9.31. Found: C, 59.65; H, .5.76; N, 9.09.

Example 153

4-[cis-1-[4-[N'-(2-chlorophenyl)ureido]-3-methoxylphenylacetyl]-4-(2-naphthalenesulfonamido)-(2S)-pyrrolidinyl]methoxybenzoic acid

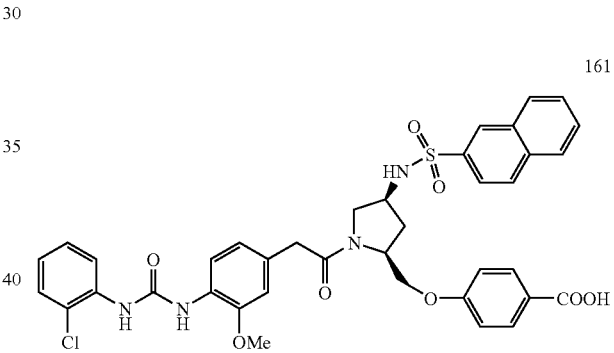

To a stirred solution of methyl 4-(cis-1-tert-butoxycarbonyl-4-amino-(2S)-pyrrolidinyl)methoxy benzoate (200 mg, 0.57 mmol) and TEA (317 ml, 2.3 mmol) in CHCl$_3$ (10.0 ml) was added (2-naphthyl)sulfonyl chloride (155 mg, 0.68 mmol) at 0° C. The reaction mixture was stirred at room temperature for 18 hr. The reaction mixture was concentrated in vacuo. The residue was purified by column chromatography on silica gel with n-hexane-EtOAc (2:1, v/v) as eluent to give methyl 4-(cis-1tert-butoxycarbonyl-4-(2-naphthylsulfonamido)-(2S)-pyrrolidinyl) methoxybenzoate (240 mg, 78%) as a pale yellow oil. $^1$H-NMR (CDCl$_3$) δ 1.25–1.45 (br s, 9H), 1.70–1.80 (m, 1H), 2.20–2.40 (m, 1H), 3.20–3.50 (m, 2H), 3.90 (s, 3H), 3.85–4.15 (m, 3H), 4.55–4.65 (m, 1H), 6.90–7.10 (m, 2H), 7.58–8.04 (m, 8H), 8.43(s, 1H).

To a stirred solution of methyl 4-(cis-1-tert-butoxycarbonyl-4-(2-naphthylsulfonamido)-(2S)-pyrrolidinyl) methoxybenzoate (240 mg, 0.44 mmol) in CH$_2$Cl$_2$ (5.0 ml) was added TFA (5.0 ml) at 0° C. The reaction mixture was stirred at room temperature for 0.5 hr. The mixture was concentrated in vacuo. Sat. NaHCO$_3$ was added to the residue, and extracted with CH$_2$Cl$_2$. The extract was washed with brine, dried over Na$_2$SO$_4$, and concentrated in vacuo. The crude product was used to the subsequent reaction without further purification. To a stirred solution of the crude product, 4-[N'-(2-chlorophenyl)uredio]-3-methoxyphenylacetic acid (147 mg, 0.44 mmol), HOBt (59 mg, 0.44 mmol), and triethylamine (275 ml, 1.9 mmol) in THF (6.0 ml) and MeCN (6.0 ml) was added EDC.HCl (127 mg, 0.66 mmol) at 0° C. The reaction mixture was stirred at room temperature for 16 hr, and concentrated in vacuo. Water was added to the residue, and extracted with EtOAc. The extract was washed with sat. NaHCO$_3$, 2-M citric acid, and sat. NaHCO$_3$, then dried over Na$_2$SO$_4$, and concentrated in vacuo. The residue was purified by column chromatography on silica gel with n-hexane-EtOAc (1:3, v/v) as eluent to give methyl 4-[cis-1-[4-[N'-(2-chlorophenyl)ureido]-3-methoxyphenylacetyl]-4-(2-naphthalenesulfonamido)-(2S)-pyrrolidinyl]methoxybenzoate (200 mg, 65%) as a colorless oil. $^1$H-NMR (CDCl$_3$) δ 1.75–1.80 (m, 1H), 2.25–2.40 (m, 1H), 3.43 (s, 2H), 3.40–3.50 (m, 1H), 3.60 (s, 3H), 3.65–3.75 (m, 1H), 3.90 (s, 3H), 3.85–3.92 (m, 1H), 3.95–4.00 (m, 1H), 4.30–4.40 (m, 1H), 4.65–4.75 (m, 1H), 6.26 (d, J=9.3 Hz, 1H), 6.50 (d, J=8.3 Hz, 1H), 6.23 (s, 1H), 6.86 (d, J=8.8 Hz, 2H), 6.75–7.01 (m, 1H), 7.23–7.36 (m, 3H), 7.61–7.96 (m, 9H), 8.20 (d, J=8.1 Hz, 1H), 8.43 (s, 1H).

To a stirred solution of methyl methyl 4-[cis-1-[4-[N'-(2-chlorophenyl)ureido]-3-methoxylphenyl acetyl]-4-(2-naphthalenesulfonamido)-(2S)-pyrrolidinyl]methoxybenzoate (200 mg, 0.26 mmol) in THF (6.0 ml) and MeOH (3.0 ml) was added 1 N NaOH (0.5 ml, 0.5 mmol). The mixture was stirred at 70° C. for 18 hr. The mixture was concentrated in vacuo, water was added thereto, and neutralized with 1 N HCl. The resulting solid was collected, washed with water, and dried in vacuo to give 161 (210 mg, quant) as a white crystalline solid. MW 743.22 mp 135–142° C.; IR (KBr) 3332, 1685, 1604, 1531, 1421, 1159 cm$^{-1}$; $^1$H-NMR (DMSO-d$_6$) δ 1.75–1.85 (m, 1H), 2.05–2.15 (m, 1H), 3.05–3.15 (m, 1H), 3.47 (s, 2H), 3.60–3.80 (m, 2H), 3.73 (s, 3H), 4.05–4.20 (m, 3H), 6.51 (d, J=8.5 Hz, 1H), 6.74–7.04 (m, 5H), 7.27–7.31 (m, 1H), 7.43–7.45 (m, 2H), 7.66–8.17 (m, 9H), 8.46 (s, 1H), 8.91 (d, J=9.5 Hz, 1H); MS (FAB) m/z743 (M$^+$+1); Anal. calcd for C$_{38}$H$_{35}$N$_4$O$_8$ClS. 0.5H$_2$O: C, 60.67; H, 4.82; N, 7.45; Cl, 4.26. Found: C, 60.77; H, 4.84; N, 7.21; Cl, 4.90.

Example 154

4-[1-[4-[N'-(2-bromophenyl)ureido]-3-methoxyphenylacetyl]-4-(2-mesitylenesulfonamido-(2S)-pyrrolidinyl]methoxybenzoic acid

162

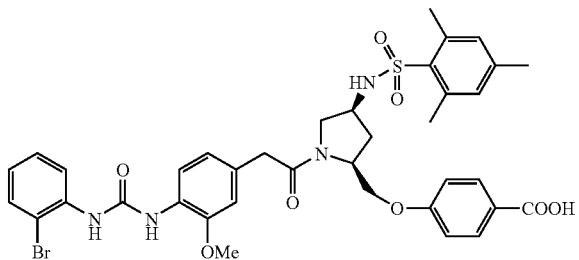

To a stirred solution of methyl 4-(cis-1-tert-butoxycarbonyl-4-amino-(2S)-pyrrolidinyl) methoxy benzoate (180 mg, 0.51 mmol) and TEA (283 ml, 2.0 mmol) in CHCl$_3$ (10.0 ml) was added (2-mesitylene)sulfonyl chloride (122 mg, 0.56 mmol) at 0° C. The reaction mixture was stirred at room temperature for 18 hr. The reaction mixture was concentrated in vacuo. The residue was purified by column chromatography on silica gel with n-hexane-EtOAc (3:1, v/v) as eluent to give methyl 4-(cis-1-tert-butoxycarbonyl-4-(2-mesitylenesulfonamido-(2S)-pyrrolidinyl) methoxy benzoate (170 mg, 62%) as a pale yellow oil. $^1$H-NMR (CDCl$_3$) δ 1.40 (s, 9H), 1.85–1.95 (m, 1H), 2.29 (s, 3H), 2.35–2.45 (m, 1H), 2.62 (s, 6H), 3.80–4.15 (m, 3H), 3.89 (s, 3H), 3.50–3.65 (m, 1H), 6.94 (s, 2H), 6.94–7.00 (m, 2H), 7.99 (d, J=8.8 Hz, 2H).

To a stirred solution of methyl (cis-1tert-butoxycarbonyl-4-(2-mesitylenesulfonamido)-(2S)-pyrrolidinyl)methoxybenzoate (170 mg, 0.32 mmol) in CH$_2$Cl$_2$ (5.0 ml) was added TFA (5.0 ml) at 0° C. The reaction mixture was stirred at room temperature for 0.5 hr. The mixture was concentrated in vacuo. Sat. NaHCO$_3$ was added to the residue, and extracted with CH$_2$Cl$_2$. The extract was washed with brine ,dried over Na$_2$SO$_4$, and concentrated in vacuo. The crude product was used to the subsequent reaction without further purification. To a stirred solution of the crude product, 4-[N'-(2-bromophenyl)uredio]-3-methoxyphenylacetic acid (121 mg, 0.32 mmol), HOBt (43 mg, 0.32 mmol), and triethylamine (139 ml, 1.0 mmol) in THF (5.0 ml) and MeCN (5.0 ml) was added EDC.HCl (91 mg, 0.48 mmol) at 0° C. The reaction mixture was stirred at room temperature for 16 hr, and concentrated in vacuo. Water was added to the residue, and extracted with EtOAc. The extract was washed with sat. NaHCO$_3$, 2-M citric acid, and sat. NaHCO$_3$, then dried over Na$_2$SO$_4$, and concentrated in vacuo. The residue was purified by column chromatography on silica gel with n-hexane-EtOAc(1:4, v/v) as eluent to give methyl 4-[1-[4-[N'-(2-bromophenyl)ureido]-3-methoxyphenylacetyl]-4-2-mesitylenesulfonamido)-(2S)-pyrrolidinyl]methoxybenzoate (210 mg, 83%) as a colorless oil. $^1$H-NMR (CDCl$_3$) δ 1.85–1.90 (m, 1H), 1.95–2.05 (m, 1H), 2.32 (s, 3H), 2.60 (s, 6H), 3.40–3.50 (m, 3H), 3.60–3.70 (m, 2H), 3.68 (s, 3H), 3.89 (s, 3H), 3.96–3.99 (m, 1H), 3.35–3.45 (m, 1H), 3.70–3.75 (m, 1H), 6.00 (d, J=9.5 Hz, 1H), 6.57–7.08 (m, 9H), 7.29–7.34 (m, 1H), 7.51–7.53 (m, 1H), 7.92–7.96 (m, 3H), 8.15 (d, J=6.8 Hz, 1H).

To a stirred solution of methyl 4-[1-[3-methoxy-4-[N'-(2-bromophenyl)ureido]phenylacetyl]-4-(2-mesitylenesulfonamido-(2S)-pyrrolidinyl]methoxybenzoate (210 mg, 0.26 mmol) in THF (5.0 ml) and MeOH (3.0 ml) was added 1 N NaOH (0.47 ml, 0.47 mmol). The mixture was stirred at 70° C. for 24 hr. The mixture was concentrated in vacuo, water was added thereto, and neutralized with 1 N HCl. The resulting solid was collected, washed with water, and dried in vacuo to give 162 (180 mg, 87%) as a white crystalline solid. MW 779.70 mp 130–132° C.; IR (KBr) 3332, 1689, 1604, 1529, 1155 cm$^{-1}$; $^1$H-NMR (DMSO-d$_6$) δ 1.70–1.85 (m, 1H), 2.02–2.12 (m, 1H), 2.25 (s, 3H), 2.52 (s, 6H), 3.05–3.12 (m, 1H), 3.48 (s, 2H), 3.60–3.70 (m, 2H), 3.77 (s, 3H), 3.90–4.20 (m, 3H), 6.59 (d, J=8.3 Hz, 1H), 6.77–6.80 (m, 1H), 6.95–7.01 (m, 4H), 7.31–7.35 (m, 1H), 7.60 (d, J=8.1 Hz, 1H), 7.86–7.97 (m, 5H), 8.72–8.76 (m, 1H), 8.89–8.93 (m, 1H); MS (FAB) m/z 779 (M$^+$), 781 (M$^+$+2);

Anal. calcd for $C_{37}H_{39}N_4O_8SBr.0.5H_2O$: C, 56.35; H, 5.11; N, 7.10; Br, 10.13. Found: C, 56.39; H, 5.07; N, 6.89; Br, 10.25.

Example 155

4-[1-[4-[N'-(2-bromophenyl)ureido]-3-methoxyphenylacetyl]-4dansylamino-(2S)-pyrrolidinyl]methoxybenzoic acid

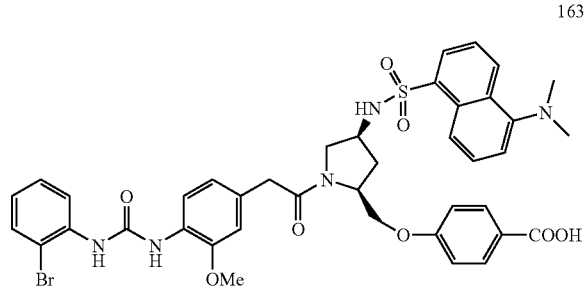

163

To a stirred solution of methyl 4-(cis-1-tert-butoxycarbonyl-4-amino-(2S)-pyrrolidinyl)methoxy benzoate (180 mg, 0.51 mmol) and TEA (283 ml, 2.0 mmol) in $CHCl_3$ (10.0 ml) was added dansyl chloride (155 mg, 0.68 mmol) at 0° C. The reaction mixture was stirred at room temperature for 18 hr. The reaction mixture was concentrated in vacuo. The residue was purified by column chromatography on silica gel with n-hexane-EtOAc (2:1, v/v) as eluent to give methyl 4-(cis-1-tert-butoxycarbonyl-4-dansylamino-(2S)-pyrrolidinyl)methoxy]benzoate (200 mg, 73%) as a pale yellow oil. $^1$H-NMR (CDCl$_3$) δ 1.34 (s, 9H), 1.50–1.60 (m, 1H), 2.15–2.25 (m, 1H), 2.87 (s, 6H), 3.15–3.22 (m, 1H), 3.35–3.45 (m, 1H), 3.48–3.52 (m, 1H), 3.80–4.10 (m, 3H), 3.91 (s, 3H), 7.01–7.25 (m, 4H), 7.50–7.53 (m, 1H), 8.03 (d, J=8.7 Hz, 2H), 8.16 (d, J=8.5 Hz, 1H), 8.28 (d, J=7.1 Hz, 1H), 8.53 (d, J=8.5 Hz, 1H).

To a stirred solution of methyl 4-(cis-1-tert-butoxycarbonyl-4-dansylamino-(2S)-pyrrolidinyl) methoxybenzoate (200 mg, 0.34 mmol) in $CH_2Cl_2$ (5.0 ml) was added TFA (5.0 ml) at 0° C. The reaction mixture was stirred at room temperature for 0.5 hr. The mixture was concentrated in vacuo. Sat. NaHCO$_3$ was added to the residue, and extracted with CH$_2$Cl$_2$. The extract was washed with brine, dried over Na$_2$SO$_4$, and concentrated in vacuo. The crude product was used to the subsequent reaction without further purification. To a stirred solution of the crude product, 4-[N'-(2-bromophenyl)uredio]-3-methoxyphenylacetic acid (129 mg, 0.34 mmol), HOBt (46 mg, 0.34 mmol), and triethylamine (142 ml, 1.0 mmol) in THF (5.0 ml) and MeCN (5.0 ml) was added EDC.HCl (98 mg, 0.51 mmol) at 0° C. The reaction mixture was stirred at room temperature for 16 hr, and concentrated in vacuo. Water was added to the residue, and extracted with EtOAc. The extract was washed with sat. NaHCO$_3$, 2-M citric acid, and sat. NaHCO$_3$, then dried over Na$_2$SO$_4$, and concentrated in vacuo. The residue was purified by column chromatography on silica gel with n-hexane-EtOAc(1:4, v/v) as eluent to give methyl 4-[1-[4-[N'-(2-bromophenyl) ureido]-3-methoxyphenylacetyl]-4dansylamino-(2S)-pyrrolidinyl]methoxybenzoate (250 mg, 88%) as a colorless oil. $^1$H-NMR (CDCl$_3$) δ 1.55–1.65 (m, 1H), 2.15–2.25 (m, 1H), 2.87 (s, 6H), 3.20–3.35 (m, 3H), 3.50–3.55 (m, 1H), 3.67 (s, 3H), 3.78–3.81 (m, 1H), 3.88–3.93 (m, 1H), 3.91 (s, 3H), 4.28–4.31 (m, 1H), 4.65–4.70 (m, 1H), 6.35 (d, J=9.5 Hz, 1H), 6.54 (d, J=8.5 Hz, 1H), 6.63 (s, 1H), 6.90–7.13 (m, 6H), 7.22–7.31 (m, 2H), 7.50–7.56 (m, 2H), 7.88 (d, J=8.0 Hz, 1H), 7.99 (d, J=9.0 Hz, 1H), 8.13–8.16 (m, 2H), 8.27 (d, J=7.6 Hz, 1H), 8.56 (d, J=8.3 Hz, 1H).

To a stirred solution of methyl 4-[1-[4-[N'-(2-bromophenyl)ureido]-3-methoxyphenylacetyl]-4-dansylamino-2S-pyrrolidinyl]methoxybenzoate (250 mg, 0.29 mmol) in THF (5.0 ml) and MeOH (3.0 ml) was added 1 N NaOH (0.52 ml, 0.52 mmol). The mixture was stirred at 70° C. for 24 hr. The mixture was concentrated in vacuo, water was added thereto, and neutralized with 1 N HCl. The resulting solid was collected, washed with water, and dried in vacuo to give 163 (230 mg, 94%) as a green crystalline solid. MW 830.74 mp 138–141° C.; IR (KBr) 3340, 2940, 1604, 1527, 1421, 1162, 1145 cm$^{-1}$; $^1$H-NMR (DMSO-d$_6$) δ 1.70–1.80 (m, 1H), 1.98–2.06 (m, 1H), 2.81 (s, 6H), 3.00–3.10 (m, 1H), 3.39–3.40 (m, 2H), 3.50–3.80 (m, 3H),; 3.76 (s, 3H), 3.90–4.15 (m, 2H), 6.52 (d, J=9.0 Hz, 1H), 6.73–7.00 (m, 4H), 7.22–7.35 (m, 2H), 7.55–7.64 (m, 3H), 7.83–8.48 (m, 8H), 8.71–8.76 (m, 1H), 8.88–8.92 (m, 1H); MS (FAB) m/z 830 (M$^+$), 832 (M$^+$+2); Anal. calcd for $C_{40}H_{40}N_5O_8BrS.0.7H_2O$: C, 56.97; H,. 95; N, 8.30; Br, 9.47.Found: C, 57.06; H, 4.86; N, 7.98; Br, 9.66.

Example 156

4-[4-methanesulfonamido-1-[4-[N'-(2-bromophenyl) ureido]-3-methoxyphenylacetyl]-(2S)-pyrrolidinyl] methoxybenzoic acid

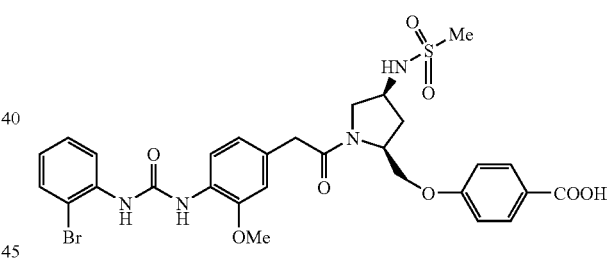

164

To a stirred solution of methyl 4-(cis-4-amino-1-tert-butoxycarbonyl(2S)-pyrrolidinyl)methoxy benzoate (180 mg, 0.51 mmol) and TEA (283 ml, 2.0 mmol) in CHCl$_3$ (10.0 ml) was added methanesulfonyl chloride (88 mg, 0.77 mmol) at 0° C. The reaction mixture was stirred at room temperature for 18 hr. The reaction mixture was concentrated in vacuo. The residue was purified by column chromatography on silica gel with n-hexane-EtOAc (1:1, v/v) as eluent to give methyl 4-(cis-1-tert-butoxycarbonyl-4-methanesulfonamido-(2S)-pyrrolidinyl) methoxybenzoate (150 mg, 69%) as a pale yellow oil. $^1$H-NMR (CDCl$_3$) δ 1.45 (s, 9H), 1.98–2.08 (m, 1H), 2.52–2.65 (m, 1H), 2.99 (s, 3H), 3.40–3.50 (m, 1H), 3.55–3.80 (m, 1H), 3.89 (s, 1H), 4.00–4.70 (m, 4H), 6.98–7.00 (m, 2H), 8.00 (d, J=8.8 Hz, 2H).

To a stirred solution of methyl 4-(cis-1-tert-butoxycarbonyl-4-methanesulfonamido-(2S)-pyrrolidinyl) methoxybenzoate (150 mg, 0.43 mmol) in CH$_2$Cl$_2$ (5.0 ml) was added TFA (5.0 ml) at 0° C. The reaction mixture was stirred at room temperature for 0.5 hr. The mixture was concentrated in vacuo. Sat. NaHCO$_3$ was added to the residue, and extracted with CH$_2$Cl$_2$. The extract was washed with brine, dried over Na$_2$SO$_4$, and concentrated in vacuo. The crude product was used to the subsequent reaction without further purification. To a stirred solution of the crude product, 4-[N'-(2-bromophenyl)uredio]-3-methoxyphenylacetic acid (163 mg, 0.42 mmol), HOBt (58 mg, 0.43 mmol), and triethylamine (179 ml, 1.3 mmol) in THF (5.0 ml) and MeCN (5.0 ml) was added EDC.HCl (144 mg, 0.75 mmol) at 0° C. The reaction mixture was stirred at room temperature for 16 hr, and concentrated in vacuo. Water was added to the residue, and extracted with EtOAc. The extract was washed with sat. NaHCO$_3$, 2-M citric acid, and sat. NaHCO$_3$, then dried over Na$_2$SO$_4$, and concentrated in vacuo. The residue was purified by column chromatography on silica gel with n-hexane-EtOAc (1:4, v/v) to EtOH-EtOAc (10%, v/v) as eluent to give methyl 4-[4-methanesulfonamido-1-[4-[N-(2-bromophenyl)ureido]-3-methoxyphenyl acetyl]-(2S)-pyrrolidinyl]methoxybenzoate (210 mg, 73%) as a colorless oil. $^1$H-NMR (CDCl$_3$) δ 1.95–2.00 (m, 1H), 2.55–2.65 (m, 1H), 2.17 (s, 3H), 3.55–3.70 (m, 1H), 3.60 (s, 2H), 3.67 (s, 3H), 3.85–3.90 (m, 1H), 3.89 (s, 3H), 3.95–4.18 (m, 2H), 4.45–4.55 (m, 1H), 4.70–4.80 (m, 1H), 5.87 (d, J=9.3 Hz, 1H), 6.73–6.95 (m, 5H), 7.09 (s, 2H), 7.28–7.33 (m, 1H), 7.51 (d, J=8.0 Hz, 1H), 7.93–7.97 (m, 3H), 8.13 (d, J=8.3 Hz, 1H).

To a stirred solution of methyl 4-[4-methanesulfonamido-1-[4-[N'-(2-bromophenyl) ureido]-3-methoxyphenylacetyl]-(2S)-pyrrolidinyl]methoxybenzoate (210 mg, 0.3 mmol) in THF (5.0 ml) and MeOH (3.0 ml) was added 1 N NaOH (0.8 ml, 0.8 mmol). The mixture was stirred at 70° C. for 24 hr. The mixture was concentrated in vacuo, water was added thereto, and neutralized with 1 N HCl. The resulting solid was collected, washed with water, and dried in vacuo to give 164 (170 mg, 83%) as a white crystalline solid. MW 675.55 mp 125–128° C.; IR (KBr) 3353, 1689, 1604, 1529, 1419, 1155 cm$^{-1}$; $^1$H-NMR (DMSO-d$_6$) δ 1.88–2.00 (m, 1H), 2.35–2.45 (m, 1H), 2.96 (m, 3H), 3.15–3.23 (m, 1H), 3.60 (s, 2H), 3.50–3.70 (m, 1H), 3.78 (s, 3H), 3.80–3.90 (m, 1H), 3.95–4.05 (m, 1H), 4.10–4.30 (m, 2H), 6.71–7.03 (m, 4H), 7.32 (m, 1H), 7.45 (d, J=6.8 Hz, 1H), 7.60 (d, J=7.8 Hz, 1H), 7.87–7.95 (m, 4H), 8.74 (s, 1H), 8.92 (s, 1H); MS (FAB) m/z 675 (M$^+$), 677 (M$^+$+2); Anal. calcd for C$_{29}$H$_{31}$N$_4$O$_8$BrS.0.6H$_2$O: C, 50.75; H, 4.73; N, 8.16. Found: C, 51.04; H, 4.62; N, 7.79.

Example 157

4-[1-[3-methoxy-4-[N'-(2-methylphenyl)ureido]phenylacetyl]-(2S)-octahydroindolylmethoxy]benzoic acid

165

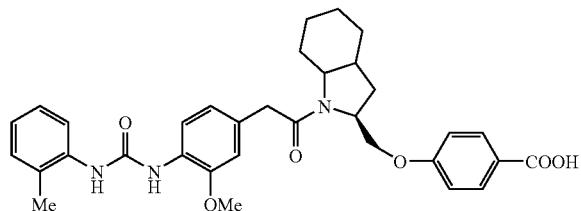

To a stirred solution of octahydroindole-(2S)-carboxylic acid (3.00 g, 17.7 mmol) in dioxane (20 ml) was added 1 N NaOH (45 ml) and the solution was stirred at 0° C. To the mixture was added (Boc)$_2$O (4.26 g, 19.5 mmol) in dioxane (25 ml) at 0° C. and the reaction mixture was stirred at room temperature for 1 day. The mixture was acidified with 1 N HCl and extracted with EtOAc. The extract was washed with brine, dried over Na$_2$SO$_4$ and evaporated to give 1-(tert-butoxy carbonyl)octahydroindole-(2S)-carboxylic acid (4.78 g, q.y.) as a colorless solid. mp 130–132° C.; $^1$H-NMR (CDCl$_3$) δ 1.10–1.46 (series of s and m, total 14 H), 1.65–1.76 (m, 3 H), 1.90–2.18 (m, 2 H), 2.26–2.35 (m, 1 H), 3.77–3.86 (m, 1 H), 4.22–4.34 (m, 1 H); MS (ESI) m/z 270 (N$^+$+1).

To a cooled (0° C.), stirred solution of 1-(tert-butoxycarbonyl)octahydroindole-(2S)-carboxylic acid (1.00 g, 3.71 mmol) in THF (10 ml) was added BH$_3$DMS (530 ml, 5.59 mmol) and the reaction mixture was stirred at room temperature overnight. The mixture was quenched by H$_2$O and extracted with EtOAc. The extract was washed with brine, dried over Na$_2$SO$_4$ and evaporated. The residue was purified by column chromatography on silica-gel with CHCl$_3$-MeOH (50:1, v/v) as eluent to give 1-(tert-butoxycarbonyl) octahydroindole-(2S)-methanol (940 mg, 99%) as a colorless oil. $^1$H-NMR (CDCl$_3$) δ 1.05–1.30 (m, 4 H), 1.47 (s, 9 H), 1.49–1.74 (m, 4 H), 1.82–1.93 (m, 3 H), 2.19–2.26 (m, 1 H), 3.56–3.61 (m, 1 H), 3.70–3.75 (m, 2 H), 3.94–3.96 (m, 1 H); MS (FAB) m/z 256 (M$^+$+1).

To a cooled (0° C.), stirred solution of methyl 4-hydroxybenzoate (560 mg, 3.68 mmol), 1-(tert-butoxycarbonyl) octahydroindole-(2S)-methanol (940 mg, 3.68 mmol) and Ph$_3$P (1.16 g, 4.42 mmol) in THF (20 ml) was added DIAD (870 ml, 4.42 mmol) and the reaction mixture was heated under reflux for 8 hr. After cooled to room temperature, the mixture was evaporated. The residue was purified by column chromatography on silica-gel with n-hexane-EtOAc (5:1, v/v) as eluent to give methyl 4-[1-(tert-butoxycarbonyl)-(2S)-octahydroindolylmethoxy]benzoate (1.16 g, 81%) as a colorless oil. $^1$H-NMR (CDCl$_3$) δ 1.14–1.47 (series of s and m, total 13 H), 1.60–2.13 (series of m, total 6 H), 2.22–2.28 (m, 1 H), 3.75–3.91 (series of s and m, total 4 H), 4.06–4.18 (m, 2 H), 4.37 (m, 1 H), 6.94–6.96 (m, 2 H), 7.96–7.98 (m, 2 H); MS (FAB) m/z 390 (M$^+$+1).

To a stirred solution of methyl 4-[1-(tert-butoxycarbonyl)-(2S)-octahydroindolylmethoxy]benzoate (1.16 g, 2.98 mmol) in CH$_2$Cl$_2$ (10 ml) was added TFA (10 ml) and the reaction mixture was stirred at room temperature for 2 hr. The mixture was concentrated in vacuo, made basic by sat. NaHCO$_3$, and extracted with CHCl$_3$. The extract was washed with brine, dried over K$_2$CO$_3$, and evaporated to give methyl 4-[(2S)-octahydroindolylmethoxy]benzoate (860 mg, q.y.) as a brown oil. $^1$H-NMR (CDCl$_3$) δ 1.23–1.78 (series of m, total 10 H), 2.00–2.09 (m, 2 H), 3.14–3.18 (m, 1 H), 3.55–3.62 (m, 1 H), 3.88 (s, 3 H), 3.96–4.06 (m, 2 H), 6.92 (d,J=9.1 Hz, 2 H), 7.97 (d, J=9.1 Hz, 2 H); MS (FAB) m/z 290 (M$^+$+1).

A mixture of 3-methoxy-4-[N'-(2-methylphenyl)ureido] phenylacetic acid (298 mg, 0.95 mmol), methyl 4-[(2S)-octahydroindolylmethoxy]benzoate (274 mg, 0.95 mmol), EDC.HCl (218 mg, 1.14 mmol), HOBt (154 mg, 1.14 mmol), Et$_3$ N (160 ml, 1.15 mmol) in THF (7 ml) was stirred at room temperature overnight. The mixture was diluted with H$_2$O and extracted with EtOAc. The extract was washed with brine, dried over Na$_2$SO$_4$, and evaporated. The residue was purified by column chromatography on silica-gel with CHCl$_3$-MeOH (100:1 to 50:1, v/v) as eluent to give methyl 4-[1-[3-methoxy-4-[N'-(2-methylphenyl)ureido] phenylacetyl]-(2S)-octahydroindolyl methoxy]benzoate (532 mg, 96%) as a white foam. $^1$H-NMR (CDCl$_3$) δ 1.13–2.05 (series of m, total 9 H), 2.14–2.24 (m, 2 H), 2.26

(s, 3 H), 3.60 (s, 2 H), 3.62 (s, 3 H), 3.80–3.85 (m, 1 H), 3.88 (s, 3H), 4.27–4.37 (m, 3 H), 6.62 (s, 1 H), 6.74–6.76 (m, 2 H), 6.91 (d, J=8.8 Hz, 2 H), 7.09–7.13 (m, 1 H), 7.20–7.24 (m, 3 H), 7.55 (d, J=7.8 Hz, 1 H), 7.94 (d, J=8.8 Hz, 2H), 8.04 (d, J=7.8 Hz, 1 H); MS (FAB) m/z 586 (M$^+$+1).

To a stirred solution of methyl 4-[1-[3-methoxy-4-[N'-(2-methylphenyl)ureido]phenyl acetyl]-(2S)-octahydroindolylmethoxy]benzoate (532 mg, 0.91 mmol) in THF (5 ml) was added 0.5 N NaOH (5 ml) and the reaction mixture was heated under reflux for 3 hr. After cooled to room temperature, the mixture was poured into ice-1 N HCl, and the resulting precipitate was collected. The crude solid was recrystallized from MeOH—CHCl$_3$-IPE to give 165 (278 mg, 54%) as a white crystalline powder. MW 571.66 mp 130–134° C.; $^1$H-NMR (DMSO-d$_6$) δ 1.16–2.10 (series of m, total 9 H), 2.15–2.30 (series of s and m, total 4 H), 3.55–3.79 (m, 3 H), 3.81 (s, 3 H), 3.90–3.95 (m, 1 H), 4.17–4.23 (m, 2 H), 4.34–4.36 (m, 1 H), 6.72–6.74 (m, 1 H), 6.87–6.88 (m, 1 H), 6.91–6.95 (m, 1 H), 7.03 (d, J=8.8 Hz, 2 H), 7.10–7.16 (m, 2 H), 7.78–7.80 (m, 1 H), 7.87 (d, J=8.8 Hz, 2 H), 7.98–8.00 (m, 1 H), 8.45 (s, 1 H), 8.54 (s, 1 H), 12.61 (br s, 1 H); MS (FAB) m/z 572 (M$^+$+1); Anal. Calcd for C$_{33}$H$_{37}$N$_3$O$_6$.1/4H$_2$O: C, 68.79; H, 6.56; N, 7.29. Found: C, 68.70; H, 6.82; N, 6.97.

Example 158

4-[1-[4-[N'-(2-chlorophenyl)ureido]-3-methoxyphenylacetyl]-(2S)-octahydroindolylmethoxy]benzoic acid

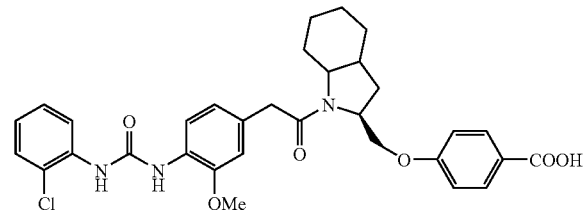

166

A mixture of 4-[N'-(2-chlorophenyl)ureido]-3-methoxyphenylacetic acid (307 mg, 0.92 mmol), methyl 4-[(2S)-octahydroindolylmethoxy]benzoate (265 mg, 0.92 mmol), EDC.HCl (211 mg, 1.10 mmol), HOBt (148 mg, 1.10 mmol), and Et$_3$ N (153 ml, 1.10 mmol) in THF (7 ml) was stirred at room temperature overnight. The mixture was diluted with H$_2$O and extracted with EtOAc. The extract was washed with brine, dried over Na$_2$SO$_4$, and evaporated. The residue was purified by column chromatography on silicagel with CHCl$_3$-MeOH (100:1 to 50:1, v/v) as eluent to give methyl 4-[1-[4-[N'-(2-chlorophenyl)ureido]-3-methoxyphenylacetyl]-(2S)-octahydroindolyl methoxy]benzoate (550 mg, 99%) as a white foam. $^1$H-NMR (CDCl$_3$) δ 1.15–2.02 (series of m, total 9 H), 2.17–2.33 (m, 2 H), 3.58 (s, 3 H), 3.62 (s, 2 H), 3.84–3.90 (series of s and m, total 4 H), 4.06–4.40 (m, 3 H), 6.71–6.74 (m, 2 H), 6.88–7.00 (m, 3 H), 7.21–7.30 (m, 2 H), 7.62 (s, 2 H), 7.91–7.95 (m, 3 H), 8.17–8.20 (m, 1 H); MS (FAB) m/z 606 (M$^+$+1).

To a stirred solution of methyl 4-[1-[4-[N'-(2-chlorophenyl)ureido]-3-methoxyphenylacetyl]-(2S)-octahydroindolylmethoxy]benzoate (550 mg, 0.91 mmol) in THF (5 ml) was added 0.5 N NaOH (5 ml) and the reaction mixture was heated under reflux for 5 hr. After cooled to room temperature, the mixture was poured into ice-1 N HCl, and the resulting precipitate was collected. The crude solid was recrystallized from MeOH—CHCl$_3$-IPE to give 166 (286 mg, 53%) as a white crystalline powder. MW 388.29 mp 133–136° C.; $^1$H-NMR (DMSO-d$_6$) δ 1.16–2.10 (series of m, total 10 H), 2.24–2.27 (m, 1 H), 3.55–3.75 (m, 2 H), 3.80 (s, 3 H), 3.90–3.96 (m, 1 H), 4.17–4.23 (m, 2 H), 4.34–4.36 (m, 1 H), 6.73–6.75 (m, 1 H), 6.88 (d, J=1.5 Hz, 1 H), 6.99–7.05 (m, 3 H), 7.25–7.30 (m, 1 H), 7.43 (dd, J=1.5, 8.1 Hz, 1 H), 7.87–7.89 (m, 2 H), 7.95 (d, J=8.1 Hz, 1 H), 8.08 (dd, J=1.5, 8.3 Hz, 1 H), 8.88 (s, 1 H), 8.92 (s, 1 H), 12.61 (br s, 1 H); MS (FAB) m/z 592 (M$^+$+1); Anal. Calcd for C$_{32}$H$_{34}$ClN$_3$O$_6$.1/4H$_2$O: C, 64.42; H, 5.83; N, 7.04; Cl, 5.94. Found: C, 64.55; H, 6.09; N, 6.64; Cl, 5.93.

Example 159

4-[1-[4-[N'-(2-bromophenyl)ureido]-3-methoxyphenylacetyl]-(2S)-octahydroindolylmethoxy]benzoic acid

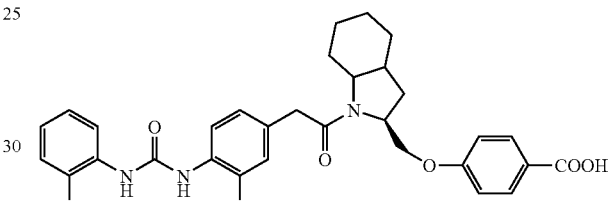

167

A mixture of 4-[N'-(2-bromophenyl)ureido]-3-methoxyphenylacetic acid (457 mg, 1.21 mmol), methyl 4-[(2S)-octahydroindolylmethoxy]benzoate (320 mg, 1.21 mmol), EDC.HCl (277 mg, 1.44 mmol), HOBt (196 mg, 1.45 mmol), and Et$_3$ N (200 ml, 1.43 mmol) in THF (7 ml) was stirred at room temperature overnight. The mixture was diluted with H$_2$O and extracted with EtOAc. The extract was washed with brine, dried over Na$_2$SO$_4$, and evaporated. The residue was purified by column chromatography on silicagel with CHCl$_3$-MeOH (100:1, v/v) as eluent to give methyl 4-[1-[4-[N'-(2-bromophenyl)ureido]-3-methoxyphenylacetyl]-(2S)-octahydroindolyl methoxy]benzoate (423 mg, 54%) as a white foam. $^1$H-NMR (CDCl$_3$) δ 1.15–1.89 (series of m, total 8 H), 1.96–2.02 (m, 1 H), 2.16–2.32 (m, 2 H), 3.63 (s, 2 H), 3.65 (s, 3 H), 3.82–3.86 (m, 1 H), 3.88 (s, 3 H), 4.30–4.39 (m, 3 H), 6.75–6.77 (m, 2 H), 6.88–6.93 (m, 3 H), 7.24–7.31 (m, 1 H), 7.37–7.50 (m, 3 H), 7.91–7.99 (m, 3 H), 8.12–8.15 (m, 1 H); MS (FAB) m/z 650 (M$^+$+1).

To a stirred solution of methyl 4-[1-[4-[N'-(2-bromophenyl)ureido]-3-methoxyphenyl acetyl]-(2S)-octahydroindolylmethoxy]benzoate (420 mg, 0.65 mmol) in THF (5 ml) was added 0.5 N NaOH (5 ml) and the reaction mixture was heated under reflux for 5 hr. After cooled to room temperature, the mixture was poured into ice-1 N HCl, and the resulting precipitate was collected. The crude solid was recrystallized from MeOH—CHCl$_3$-IPE to give 167 (197 mg, 48%) as a white crystalline powder. MW 636.53 mp 118–123° C.; $^1$H-NMR (DMSO-d$_6$) δ 1.16–2.27 (series of m, total 10 H), 3.56–3.75 (m, 3 H), 3.81 (s, 3 H), 3.90–3.96 (m, 1 H), 4.17–4.23 (m, 2 H), 4.34–4.36 (m, 1 H), 6.73–6.75 (m, 1 H), 6.88–7.05 (m, 4 H), 7.30–7.34 (m, 1 H), 7.59–7.61 (m, 1 H), 7.87–7.96 (m, 4 H), 8.73 (s, 1 H), 8.91 (s, 1 H), 12.64 (br s, 1 H); MS (FAB) m/z 636 (M$^+$+1); Anal. Calcd for C$_{32}$H$_{34}$BrN$_3$O$_6$·1/4H$_2$O: C, 59.96;H, 5.42;N, 6.55; Br, 12.46. Found: C, 60.12; H, ,5.86; N, 6.09; Br, 12.47.

Example 160

4-[3-[3-methoxy-4-[N'-(2-methylphenyl)ureido]phenyl]acetyl-4-thiazolidinyl]methoxybenzoic acid

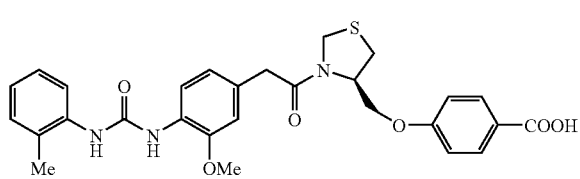

168

To a stirred solution of thiazolidine-4-carboxylic acid (5.0 g, 37.6 mmol) in DMF (50.0 ml) was added (Boc)$_2$O (9.8 g, 45.1 mmol) and TEA (8.0 ml). The reaction mixture was stirred at room temperature for 18 hr. Water was added to the mixture and extracted with EtOAc. The organic layer was washed with water, then dried over Na$_2$SO$_4$, and concentrated in vacuo. The residue was purified by column chromatography on silica gel with EtOAc-n-hexane (1:3, v/v) as eluent to give 3-tert-butoxycarbonylthiazolidine-4-carboxylic acid (6.5 g, 74%) as a white crystalline solid. $^1$H-NMR (CDCl$_3$) δ 1.49 (br s, 9H), 3.20–3.30 (m, 2H), 4.09–4.87 (m, 3H).

To a stirred solution of 3-tert-butoxycarbonylthiazolidine4-carboxylic acid (2.3 g, 10.0 mmol) in THF (30 ml) was added BH$_3$.THF(1.0 M solution in THF, 20.0 ml, 20.0 mmol) at 0° C. After stirred at room temperature for 1.0 h, the reaction mixture was heated under reflux for 1.0 hr. After cooled, the mixture was concentrated in vacuo. Water was added thereto at 0° C., and extracted with EtOAc. The extract was washed with water, then dried over Na$_2$SO$_4$, and concentrated in vacuo to give 3-tert-butoxycarbonyl-5-hydroxymethylthiazolidine (2.0 g , quant) as a a colorless oil. $^1$H-NMR (CDCl$_3$) δ 1.48 (s, 9H), 2.80–2.85 (m, 1H), 3.13–3.17 (m, 1H), 3.20–3.30 (m, 1H), 3.64–3.70 (m, 2H), 4.34 (br s, 1H), 4.60 (br s, 1H).

To a stirred solution of 3-tert-butoxycarbonyl-5-hydroxymethylthiazolidine (1.9 g, 8.7 mmol), methyl 4-hydroxybenzoate (1.3 g, 8.7 mmol), and Ph$_3$P (3.2 g, 12.2 mmol) in THF (10 ml) was added DIAD (2.2 g, 10.4 mmol) at 0° C. The reaction mixture was stirred at room temperature for 18 hr. The mixture was concentrated in vacuo. The residue was purified by column chromatography on silica gel with EtOAc-n-hexane (1:9, v/v) as eluent to give methyl 4-(3-tert-butoxycarbonyl-4-thiazolidinyl)methoxybenzoate (1.6 g, 52%) as a pale yellow oil. $^1$H-NMR (CDCl$_3$) δ 1.49 (s, 9H), 3.11–3.19 (m, 2H), 3.88 (s, 3H), 4.04–4.31 (m, 3H), 4.61 (m, 2H), 6.96 (d, J=8.8 Hz, 2H), 7.98 (d, J=8.8 Hz, 2H).

To a stirred solution of methyl 4-(3-tert-butoxycarbonyl-4-thiazolidinyl)methoxybenzoate (440 mg, 1.25 mmol) in CH$_2$Cl$_2$ (6 ml) was added TFA (3 ml) at 0° C. The reaction mixture was stirred at room temperature for 0.5 hr. The mixture was concentrated in vacuo. Sat. NaHCO$_3$ was added to the residue, and extracted with CH$_2$Cl$_2$. The extract was washed with brine ,dried over Na$_2$SO$_4$, and concentrated in vacuo. The crude product was used to the subsequent reaction without further purification. To a stirred solution of the crude product (0.6 mmol), 3-methoxy-4-[N'-(2-methyl phenyl)uredio]phenylacetic acid (188 mg, 0.6 mmol), HOBt (81 mg, 0.6 mmol), and triethylamine (280 ml, 2.0 mmol) in THF (5 ml) and MeCN (5 ml) was added EDC.HCl (173 mg, 0.9 mmol) at 0° C. The reaction mixture was stirred at room temperature for 16 hr, and concentrated in vacuo. Water was added to the residue, and extracted with EtOAc. The extract was washed with sat. NaHCO$_3$, 2-M citric acid, and sat. NaHCO$_3$, then dried over Na$_2$SO$_4$, and concentrated in vacuo. The residue was purified by column chromatography on silica gel with n-hexane-EtOAc (1:3, v/v) as eluent to give methyl 4-[3-[3-methoxy-4-[N'-(2-methylphenyl)ureido]phenyl]acetyl-4-thiazolidinyl]methoxybenzoate (340 mg, quant) as an amorphous solid. $^1$H-NMR (CDCl$_3$) δ 2.31 (s, 3H), 3.15–3.16 (m, 2H), 3.67–3.69 (m, 5H), 3.88 (s, 3H), 4.09–4.14 (m, 2H), 4.22–4.90 (m, 3H), 6.30 (m, 1H), 6.74–6.96 (m, 4H), 7.11–7.25 (m, 41H), 7.49–7.51 (m, 1H), 7.95–8.12 (m, 3H).

To a stirred solution of methyl 4-[3-[3-methoxy-4-[N'-(2-methylphenyl)ureido]phenyl]acetyl4-thiazolidinyl]methoxybenzoate (340 mg, 0.62 mmol) in THF (5.0 ml) and EtOH (3.0 ml) was added 1 N NaOH (0.62 ml, 0.62 mmol). The mixture was stirred at 70° C. for 18 hr. The mixture was concentrated in vacuo, water was added thereto, and neutralized with 1 N HCl. The resulting solid was collected, washed with water, and dried in vacuo to give 168 (290 mg, 88%) as a white crystalline solid. MW 535.62 mp 125–128° C.; IR (KBr) 3357, 2937, 1604, 1533, 1419, 1253, 1166, 1033, 773 cm$^{-1}$; $^1$H-NMR (DMSO-d$_6$) δ 2.25 (s, 3H), 3.05–3.20 (m, 2H), 3.71, 3.83, and 3.85 (each s, total 5H), 4.03–4.15 (m, 3H), 4.52–4.76 (m, 2H), 6.15–6.17 (m, 7H), 7.78–8.30 (m, 4H), 8.30 (m, 1H), 8.56 (m, 1H); MS (FAB) m/z 536 (M$^+$+1); Anal. calcd for C$_{28}$H$_{29}$N$_3$O$_6$S.0.5H$_2$O: C, 61.75; H, 5.55; N, 7.72. Found: C, 61.72; H, 5.55; N, 7.49.

Example 161

4-[3-[4-[N'-(2-chlorophenyl)ureido]-3-methoxyphenylacetyl]-4-thiazolidinyl]methoxybenzoic acid

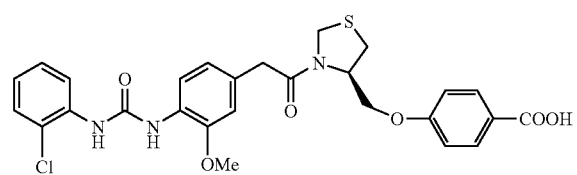

169

To a stirred solution of methyl 4-(3-tert-butoxycarbonyl-4-thiazolidinyl)methoxybenzoate (600 mg, 1.7 mmol) in CH$_2$Cl$_2$ (6,0 ml) was added TFA (6.0 ml) at 0° C. The reaction mixture was stirred at room temperature for 0.5 hr. The mixture was concentrated in vacuo. Sat. NaHCO$_3$ was added to the residue, and extracted with CH$_2$Cl$_2$. The extract was washed with brine ,dried over Na$_2$SO$_4$, and concentrated in vacuo. The crude product was used to the subsequent reaction without further purification. To a stirred solution of the crude product, 4-[N'-(2-chlorophenyl)uredio]-3-methoxyphenylacetic acid (570 mg, 1.7 mmol), HOBt (230 mg, 1.7 mmol), and triethylamine (709 ml, 5.1 mmol) in THF (10.0 ml) and MeCN (10.0 ml) was added EDC.HCl (490 mg, 2.55 mmol) at 0° C. The reaction mixture was stirred at room temperature for 16 hr, and concentrated in vacuo. Water was added to the residue, and extracted with EtOAc. The extract was washed with sat. NaHCO$_3$, 2-M citric acid, and sat. NaHCO$_3$, then dried over Na$_2$SO$_4$, and concentrated in vacuo. The residue was purified by column chromatography on silica gel with n-hexane-EtOAc (1:1, v/v) as eluent to give methyl 4-[3-[4-[N'-(2-chlorophenyl)ureido]-3-methoxyphenylacetyl]-4-thiazolidinyl]methoxybenzoate (900 mg, 93%) as a colorless oil. $^1$H-NMR (CDCl$_3$) δ 3.15–3.18 (m, 2H), 3.70 (s, 2H), 3.78 (s, 3H), 3.86 (s, 3H), 4.09–4.93 (m, 5H), 6.80–7.01 (m, 5H), 7.19–7.35 (m, 4H), 7.94–8.18 (m, 4H).

To a stirred solution of methyl 4-[3-[4-[N'-(2-chlorophenyl)ureido]-3-methoxyphenylacetyl]-4-thiazolidinyl]methoxybenzoate (900 mg, 1.6 mmol) in THF (8.0 ml) and MeOH (4.0 ml) was added 1 N NaOH (3.1 ml, 3.1 mmol). The mixture was stirred at 70° C. for 24 hr. The mixture was concentrated in vacuo, water was added thereto, and neutralized with 1 N HCl. The resulting solid was collected, washed with water, and dried in vacuo to give 169 (780 mg, 89%) as a white crystalline solid. MW 556.03 mp 126–129° C.; IR (KBr) 3343, 2937, 1604, 1531, 1421, 1245, 1166, 1035, 752 cm$^{-1}$; $^1$H-NMR (DMSO-d$_6$) δ 3.06–3.24 (m, 2H), 3.72–3.85 (m, 5H), 4.02–4.27 (m, 3H), 4.53–4.76 (m, 2H), 6.74–7.44 (m, 7H), 7.87–8.30 (m, 4H), 8.89–8.95 (m, 2H); MS (FAB) m/z 556 (M$^+$+1); Anal. calcd for C$_{27}$H$_{27}$N$_3$O$_6$ClS.0.7H$_2$O: C, 56.93; H, 5.03; N, 7.38; Cl, 6.22. Found: C, 56.89; H, 4.84; N, 7.42; Cl, 6.35.

Example 162

4-[3-[4-[N'-(2-bromophenyl)ureido]-3-methoxyphenylacetyl]-4-thiazolidinyl]methoxybenzoic acid

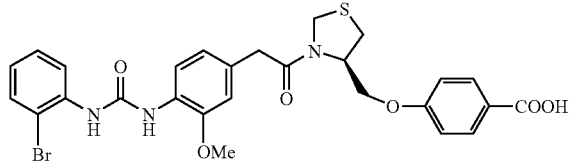

170

To a stirred solution of methyl 4-(3-tert-butoxycarbonyl-4-thiazolidinyl)methoxybenzoate (560 mg, 1.6 mmol) in CH$_2$Cl$_2$ (5.0 ml) was added TFA (5.0 ml) at 0° C. The reaction mixture was stirred at room temperature for 0.5 hr. The mixture was concentrated in vacuo. Sat. NaHCO$_3$ was added to the residue, and extracted with CH$_2$Cl$_2$. The extract was washed with brine, dried over Na$_2$SO$_4$, and concentrated in vacuo. The crude product was used to the subsequent reaction without further purification. To a stirred solution of the crude product, 4-[N'-(2-bromophenyl)uredio]-3-methoxy phenylacetic acid (599 mg, 1.6 mmol), HOBt (213 mg, 1.6 mmol), and triethylamine (659 ml, 4.7 mmol) in THF (10.0 ml) and MeCN (10.0 ml) was added EDC.HCl (455 mg, 2.4 mmol) at 0° C. The reaction mixture was stirred at room temperature for 16 hr, and concentrated in vacuo. Water was added to the residue, and extracted with EtOAc. The extract was washed with sat. NaHCO$_3$, 2-M citric acid, and sat. NaHCO$_3$, then dried over Na$_2$SO$_4$, and concentrated in vacuo. The residue was purified by column chromatography on silica gel with n-hexane-EtOAc (2:3, v/v) as eluent to give methyl 4-[3-[4-[N'-(2-bromophenyl)ureido]-3-methoxyphenylacetyl]-4-thiazolidinyl]methoxybenzoate (870 mg, 89%) as a colorless oil. $^1$H-NMR (CDCl$_3$) δ 3.00–3.20 (m, 3H), 3.70 (s, 2H), 3.81 (s, 3H), 3.88 (s, 3H), 4.09–4.23 (m, 1H), 4.42 (d, J=8.5 Hz, 1H), 4.59 (d, J=8.5 Hz, 1H), 4.70–4.92 (m, 1H), 6.81–7.53 (m, 9H), 7.95–8.15 (m, 4H).

To a stirred solution of methyl 4-[3-[4-[N'-(2-bromophenyl)ureido]-3-methoxyphenylacetyl]-4-thiazolidinyl]methoxybenzoate (870 mg, 1.4 mmol) in THF (8.0 ml) and MeOH (8.0 ml) was added 1 N NaOH (2.8 ml, 2.8 mmol). The mixture was stirred at 70° C. for 18 hr. The mixture was concentrated in vacuo, water was added thereto, and neutralized with 1 N HCl. The resulting solid was collected, washed with water, and dried in vacuo to give 170 (740 mg, 87%) as a white crystalline solid. MW 600.48 mp 125–133° C.; IR (KBr) 3332, 2935, 1604, 1527, 1421, 1245, 1166, 1027, 750 cm$^-$; $^1$H-NMR (DMSO-d$_6$) δ 3.01–3.25 (m, 2H), 3.72–3.85 (m, 5H), 4.02–4.30 (m, 2H), 4.54 (d, J=8.8 Hz, 1H), 4.74–4.87 (m, 2H), 6.76–7.07 (m, 5H), 7.30–7.34 (m, 1H), 7.59 (d, J=8.1 Hz, 1H), 7.86–7.98 (m, 4H), 8.74 (s, 1H), 8.92–8.94 (s, 1H); MS (FAB) m/z 600 (M$^+$+1); Anal. calcd for C$_{27}$H$_{26}$N$_3$O$_6$BrS.0.3H$_2$O: C, 53.52; H, 4.43 N 6.94 Found: C, 53.54; H, 4.45; N, 6.80.

Example 163 cis-4-[[1-[3-methoxy-4-[N'-(2-methylphenyl)ureido] phenylacetyl]-2-pyrrolidinyl]methylamino]cyclohexanecarboxylic acid

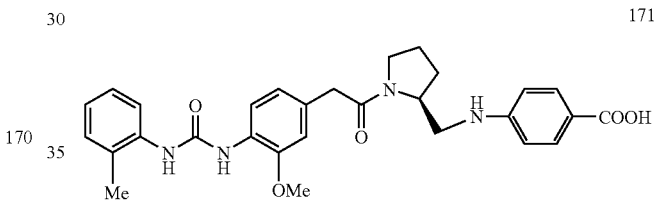

171

To a stirred solution of 2S-pyrrolidinemethanol (2.0 g, 20.0 mmol), 3-methoxy-4-[N'-(2-methyl phenyl)uredio]phenylacetic acid (6.28 g, 20.0 mmol), HOBt (71 mg, 0.53 mmol), and triethylamine (5.5 ml, 40.0 mmol) in THF (50.0 ml) and MeCN (40.0 ml) was added EDC.HCl (5.7 g, 30.0 mmol) at 0° C. The reaction mixture was stirred at room temperature for 16 hr, and concentrated in vacuo. Water was added to the residue, and extracted with EtOAc. The organic layer was washed with sat. NaHCO$_3$, 2-M citric acid, and sat. NaHCO$_3$, then dried over Na$_2$SO$_4$, and concentrated in vacuo. The residue was purified by column chromatography on silica gel with EtOAc to MeOH—CH$_2$Cl$_2$ (1:9, v/v) as eluent to give 1-[3-methoxy-4-[N'-(2-methylphenyl) ureido] phenylacetyl]-2S-pyrrolidinemethanol (7.0 g, 89%) as a white crystalline solid. $^1$H-NMR (CDCl$_3$) δ 1.54–1.58 (m, 1H), 1.80–2.04 (m, 3H), 2.27 (s, 3H), 3.42–3.46 (m, 1H), 3.54–3.65 (m, 2H), 3.62 (s, 2H), 3.69 (s, 3H), 4.21–4.23 (m, 1H), 5.04 (m, 1H), 6.68–6.79 (m, 3H), 7.09–7.31 (m, 4H), 7.52 (d, J=7.8 Hz, 1H), 8.07 (d, J=8.0 Hz, 1H).

To a stirred solution of oxalyl chloride (0.3 ml, 3.3 mmol) in CH$_2$Cl$_2$ (30.0 ml) was added DMSO (6.6 ml, 0.51 mmol) at −78° C. After 5 minutes, to the mixture was added 1-[3-methoxy-4-[N'-(2-methylphenyl)ureido]phenylacetyl]-2-pyrrolidinemethanol (1.2 g, 3.0 mmol) in CH$_2$Cl$_2$ (5.0 ml). The mixture was stirred for 30 minutes at −78° C., and triethylamine (2.1 ml, 15.0 mmol) was added. The mixture was stirred for 30 minutes at −78° C., and stirred for 30 minutes at room temperature. Water was added to the mixture, and extracted with CH$_2$Cl$_2$. The extract was washed with water, then dried over Na₂SO₄, and concentrated in vacuo. The crude product was used to the subsequent reaction without further purification. To a stirred solution of the crude product, benzyl cis-4-aminocyclohexanecarboxylate (769 mg, 3.3 mmol), and AcOH (0.32 ml) in DCE (10 ml) was added NaBH(OAc)₃ (1.1 g, 5.4 mmol) at 0° C. The reaction mixture was stirred at room temperature for 18 hr. The mixture was concentrated in vacuo. Sat. NaHCO₃ was added to the residue, and extracted with CH₂Cl₂. The extract was washed with brine, dried over Na₂SO₄, and concentrated in vacuo. The residue was purified by column chromatography on silica gel with MeOH—CH₂Cl₂ (1:9, v/v) as eluent to give benzylcis-4-[[1-[3-methoxy-4-[N'-(2-methylphenyl) ureido]phenylacetyl]-2-pyrrolidinyl]methylamino]cyclohexanecarboxylate (1.5 g, 83%) as an amorphous solid. ¹H-NMR (CDCl₃) δ 1.40–1.65 (m, 6H), 1.80–1.98 (m, 6H), 2.26 (s, 3H), 2.45–2.65 (m, 3H), 2.81–2.86 (m, 1H), 3.44–3.46 (m, 2H), 3.56 (s, 2H), 3.67 (s, 3H), 3.90–4.15 (m, 1H), 5.09 and 5.11 (each s, total 2H), 6.74–6.83 (m, 3H), 7.07–7.20 (m, 4H), 7.31–7.35 (m, 5H), 7.53–7.55 (m, 1H), 8.02–8.06 (m, 1H).

To a stirred solution of benzylcis-4-[[1-[3-methoxy-4-[N'-(2-methylphenyl)ureido]phenyl acetyl]-2-pyrrolidinyl]methylamino]cyclohexanecarboxylate (1.5 g, 2.45 mmol) in THF (10.0 ml) and MeOH (5.0 ml) was added 1 N NaOH (3.68 ml, 3.68 mmol). The mixture was stirred at 70° C. for 18 hr. The mixture was concentrated in vacuo, water was added thereto, and neutralized with 1 N HCl. The mixture was concentrated in vacuo. The residue was purified by column chromatography on silica gel with MeOH—CH₂C₂ (1:5, v/v) as eluent to give cis-4-[[1-[3-methoxy-4-[N'-(2-methyl phenyl)ureido]phenylacetyl]-2-pyrrolidinyl]methylamino]cyclohexanecarboxylic acid 171 (940 mg, 73%) as an amorphous solid. MW 522.64 IR (KBr) 3283, 2945, 2860, 1534, 1453, 1415 cm⁻¹; ¹H-NMR (DMSO-d₆) δ 1.38–2.00 (m, 12H), 2.45 (s, 3H), 2.30–3.95 (m, 4H), 3.22–3.75 (m, 2H), 3.58 (s, 2H), 3.86 (s, 3H), 4.12 (m, 1H), 6.73–7.16 (m, 5H), 7.77–7.79 (m, 1H), 7.98–8.02 (m, 1H), 8.51–8.52 (m, 1H), 8.57–8.59 (m, 1H); MS (FAB) m/z 523 (M⁺+1); Anal. calcd for C₂₉H₃₈N₄O₅.0.5NaCl.2.2H₂O: C, 58.89; H, 7.23; N, 9.47. Found: C, 59.21; H, 7.11; N, 9.11.

Example 164 methyl cis-4-[[1-[3-methoxy-4-[N'-(2-methylphenyl) ureido]phenylacetyl]-2-pyrrolidinyl]methyl amino] cyclohexanecarboxylate HCl salt

172

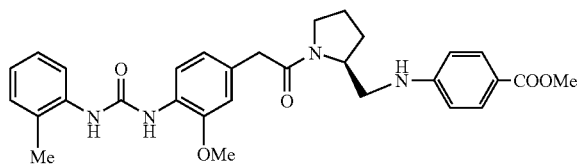

SOCl₂ was added to MeOH at 0° C. After stirred for 5 minutes, cis-4-[[1-[3-methoxy-4-[N'-(2-methylphenyl)ureido]phenylacetyl]-2-pyrrolidinyl]methylamino]cyclohexanecarboxylic acid (200 mg, 0.38 mmol) was added. The mixture was stirred at room temperature for 5 hr. The mixture was concentrated in vacuo. Aq. NaHCO₃ was added to the residue, and extracted with CH₂Cl₂. The extract was washed with brine, dried over Na₂SO₄, and concentrated in vacuo. The residue was purified by column chromatography on silica gel with MeOH—CH₂Cl₂ (5:95 to 18:92, v/v) as eluent. The product was dissolved in EtOH (5.0 ml), and 1 N HCl (in EtOH) (1.0 ml, 1.0 mmol) was added thereto. The mixture was concentrated in vacuo to give 172 (160 mg, 74%) as an amorphous solid; MW 536.66 IR (KBr) 3247, 2950, 2875, 1731, 1671, 1612, 1533, 1454, 1205 cm⁻¹; ¹H-NMR (DMSO-d₆) δ 1.45–2.10 (m, 12H), 2.25 (s, 3H), 2.60–2.70 (m, 1H), 2.90–3.20 (m, 31), 2.50–2.55 (m, 2H), 3.63 (m, 5H), 3.86 (s, 3H), 4.15–4.30 (m, 1H), 6.74–7.16 (m, 5H), 7.76–7.78 (m, 1H), 8.00–8.09 (m, 1H), 8.54–8.70 (m, 21); MS (FAB) m/z 537 (M⁺+1); Anal. calcd for C₃₀H₄₀N₄O₅.1.0HCl.1.0H₂O: C, 60.95; H, 7.33; N, 9.48; Cl, 6.00. Found: C, 60.87; H, 7.47; N, 8.97: Cl, 5.90.

Example 165

4-[N-[1-[3-methoxy-4-[N'-(2-methylphenyl)ureido] phenylacetyl]-2-pyrrolidinyl]methyl]-N-methylamino]cyclohexanecarboxylic acid

173

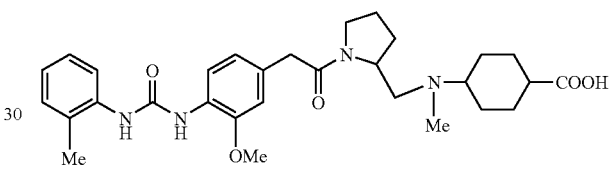

To a stirred solution of methyl cis-4-[[1-[3-methoxy-4-[N'-(2-methylphenyl)ureido]phenylacetyl]-2-pyrrolidinyl] methylamino]cyclohexanecarboxylate (300 mg, 0.55 mmol), HCHO (300 ml), and AcOH (66 mg, 1.1 mmol) in MeOH (10.0 ml) was added NaBH₃CN (70 mg, 1.1 mmol) at 0° C. The reaction mixture was stirred at room temperature for 18 hr. After concentrated in vacuo, water was added and extracted with CH₂Cl₂. The extract was washed with water, then dried over Na₂SO₄, and concentrated in vacuo. The residue was purified by TLC with MeOH—CH₂Cl₂ (3:97, v/v) as eluent to give methyl 4-[N-[1-[3-methoxy-4-[N'-(2-methylphenyl)ureido]phenylacetyl]-2-pyrrolidinylmethyl]-N-methylamino]cyclohexanecarboxylate (160 mg, 52%) as an amorphous solid. ¹H-NMR (CDCl₃) δ 1.30–2.20 (m, 12H), 2.27–2.37 (m, 6H), 2.50 –2.60 (m, 1H), 3.30–3.80 (m, 5H), 3.55 (s, 2H), 3.66–3.73 (m, 6H), 4.10–4.20 (m, 1H), 6.60–7.55 (m, 7H), 8.03 (m, 1H), 8.15 (m, 1H).

To a stirred solution of methyl 4-[N-[1-[3-methoxy-4-[N'-(2-methylphenyl)ureido]phenylacetyl]-2-pyrrolidinylmethyl]-N-methylamino]cyclohexanecarboxylate (100 mg, 0.18 mmol) in THF (5.0 ml) and MeOH (2.5 ml) was added 1 N NaOH (0.36 ml, 0.36 mmol). The mixture was stirred at 60° C. for 18 hr. The mixture was concentrated in vacuo, water was added thereto, and neutralized with 1 N HCl. The mixture was concentrated in vacuo. The residue was purified by TLC with MeOH—CH₂Cl₂ (1/4, v/v) as eluent to give 173 (10 mg, 10%) as an amorphous solid. MW 536.66 IR (KBr) 3440, 2954, 1697, 1533, 1454 cm⁻¹; ¹H-NMR (DMSO-d₆) δ 1.20–2.30 (m, 13H), 2.24 (s, 3H), 2.35–4.00 (m, 13H), 6.50–8.10 (m, 8H), 8.50 (m, 1H); MS (FAB) m/z 537 (M⁺+1); Anal. calcd for C₃₀H₄₀N₄O₅.2.0NaCl.0.8H₂O: C, 53.94; H, 6.28; N, 8.39. Found: C, 54.08; H, 6.52; N, 8.04.

Example 166

4-[[1-[3-methoxy-4-[N'(2-methylphenyl)ureido]phenylacetyl]-(2S)-pyrrolidinyl]methoxy]cyclohexanecarboxylic acid

174

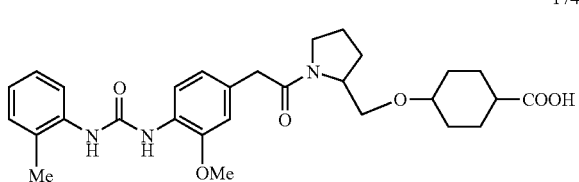

A mixture of methyl 4-(1-tert-butoxycarbonyl-(2S)-pyrrolidinyl)methoxybenzoate (1.0 g, 2.9 mmol) and 5% Rh on alumina (500 mg) in EtOH (10.0 ml) and AcOH (1.0 ml) was hydrogenated at room temperature at 5 atm for 36 hr. The catalyst was filtered off, and the filtrate was concentrated in vacuo. The residue was purified by column chromatography on silica gel with n-hexane-EtOAc (6:1, v/v) as eluent to give methyl cis-4-[(1-tert-butoxycarbonyl-(2S)-pyrrolidinyl) methoxy]cyclohexanecarboxylate (900 mg, 89%) as a pale yellow oil. $^1$H-NMR (CDCl$_3$) δ 1.46 (s, 9H), 1.46–2.00 (m, 12H), 2.34 (m, 1H), 3.20–3.55 (m, 5H), 3.67 (s, 3H), 3.84–3.92 (m, 1H).

To a stirred solution of methyl cis-4-[(1-tert-butoxycarbonyl-(2S)-pyrrolidinyl)methoxy]cyclohexanecarboxylate (900 mg, 2.6 mmol) in CH$_2$Cl$_2$ (5.0 ml) was added TFA (5.0 ml) at 0° C. The reaction mixture was stirred at room temperature for 0.5 hr. The mixture was concentrated in vacuo. Sat. NaHCO$_3$ was added to the residue, and extracted with CH$_2$Cl$_2$. The extract was washed with brine, dried over Na$_2$SO$_4$, and concentrated in vacuo. The crude product was used to the subsequent reaction without further purification. To a stirred solution of the crude product (200 mg, 0.83 mmol), 3-methoxy-4-[N'-(2-methylphenyl)uredio]phenylacetic acid (260 mg, 0.83 mmol), HOBt (135 mg, 1.0 mmol), and triethylamine (344 μl, 1.35–2.10 (m, 12H), 2.15–2.38 (m, 1H), 2.29 (m, 3H), 3.20–3.55 (m, 5H), 3.58 (s, 2H), 3.66 (s, 3H), 3.73 (s, 3H), 4.20–4.25 (m, 1H), 6.26–6.30 (m, 1H), 6.78–6.81(m, 2H), 7.06–7,23 (m, 3H), 7.51–7.52 (m, 1H), 8.01–8.03 (m, 1H).

To a stirred solution of methyl 4-[[1-[3-methoxy-4-[N'-(2-methylphenyl)ureido]phenylacetyl]-(2S)-pyrrolidinyl]methoxy]cyclohexanecarboxylate (460 mg, 0.86 mmol) in THF (10.0 ml) and EtOH (5.0 ml) was added 1 N NaOH (1.4 ml, 1.4 mmol). The mixture was stirred at 60° C. for 18 hr. The mixture was concentrated in vacuo, water was added thereto, and neutralized with 1 N HCl. The resulting solid was collected, washed with water, and dried in vacuo to give 174 (370 mg, 83%) as a white crystalline solid. MW 523.63 mp 110–113° C.; IR (KBr) 3345, 2937, 1612, 1533, 1454 cm$^-$; $^1$H-NMR (DMSO-d$_6$) δ 1.00–2.00 (m, 12H), 2.24 (s, 3H), 2.20–2.30 (m, 1H), 3.20–3.80 (m, 5H), 3.55 (s, 2H), 3.85 (s, 3H), 4.00–4.18 (m, 1H), 6.71–7.16 (m, 5H), 7.78 (d, J=8.0 Hz, 1H), 7.90 (d, J=8.3 Hz, 1H), 8.45 (s, 1H), 8.54 (s, 1H); MS (FAB) m/z 524 (M$^+$+1); Anal. calcd for C$_{29}$H$_{37}$N$_3$O$_6$.0.2H$_2$O: C, 66.07; H, 7.15; N, 7.97. Found: C, 66.02; H, 7.14; N, 7.87.

Example 167

4-[[1-[4-[N'-(2-chlorophenyl)ureido]-3-methoxylphenylacetyl]-(2S)-pyrrolidinyl]methoxy]cyclohexanecarboxylic acid

175

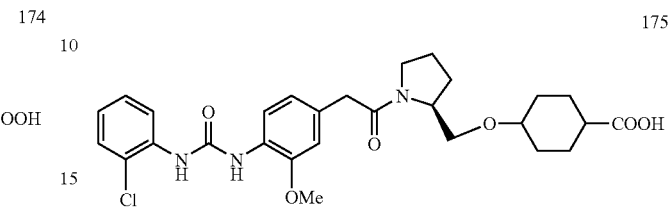

To a stirred solution of methyl 4-[(1-tert-butoxycarbonyl-2-pyrrolidinyl)methoxy]cyclohexane carboxylate (900 mg, 2.6 mmol) in CH$_2$Cl$_2$ (5.0 ml) was added TFA (5.0 ml) at 0° C. The reaction mixture was stirred at room temperature for 0.5 hr. The mixture was concentrated in vacuo. Sat. NaHCO$_3$ was added to the residue, and extracted with CH$_2$Cl$_2$. The extract was washed with brine dried over Na$_2$SO$_4$, and concentrated in vacuo. The crude product was used to the subsequent reaction without further purification. To a stirred solution of the crude product (200 mg, 0.83 mmol), 4-[N'-(2-chlorophenyl)uredio]-3-methoxyphenylacetic acid (277 mg, 0.83 mmol), HOBt (135 mg, 1.0 mmol), and triethylamine (344 ml, 2.48 mmol) in THF (10.0 ml) and MeCN (10.0 ml) was added EDC.HCl (238 mg, 1.24 mmol) at 0° C. The reaction mixture was stirred at room temperature for 16 hr, and concentrated in vacuo. Water was added to the residue, and extracted with EtOAc. The extract was washed with sat. NaHCO$_3$, 2-M citric acid, and sat. NaHCO$_3$, then dried over Na$_2$SO$_4$, and concentrated in vacuo. The residue was purified by column chromatography on silica gel with n-hexane-EtOAc (1:6, v/v) as eluent to give methyl 4-[[1-[4-[N'-(2-chlorophenyl)ureido]-3-methoxylphenylacetyl]-(2S)-pyrrolidinyl]methoxy]cyclohexane carboxylate (450 mg, 97%) as a colorless oil. $^1$H-NMR (CDCl$_3$) δ 1.35–2.15 (m, 12H), 2.25–2.40 (m, 1H), 3.40–3.70 (m, 5H), 3.61 (s, 2H), 3.66 (s, 3H), 3.81 (s, 3H), 4.20–4.30 (m, 1H), 6.81–6.99 (m, 3H), 7.17–7.34 (m, 3H), 7.92–7.94 (m, 2H), 8.17–8.19 (m, 2H).

To a stirred solution of methyl 4-[[-1–4-[N'-(2-chlorophenyl)ureido]-3-methoxylphenylacetyl]-(2S)-pyrrolidinyl]methoxy]cyclohexanecarboxylate (450 mg, 0.86 mmol) in THF (10.0 ml) and MeOH (5.0 ml) was added 1 N NaOH (1.4 ml, 1.4 mmol). The mixture was stirred at 70° C. for 24 hr. The mixture was concentrated in vacuo, water was added thereto, and neutralized with 1 N HCl. The resulting solid was collected, washed with water, and dried in vacuo to give 175 (370 mg, 84%) as a white crystalline solid. MW 544.04 mp 111–115° C.; IR (KBr) 3330, 2938, 1704, 1594, 1533, 1438, 1199 cm$^{-1}$; $^1$H-NMR (DMSO-d$_6$) δ 1.00–2.00 (m, 12H), 2.20–2.30 (m, 1H), 3.20–3.80 (m, 5H), 3.55 (s, 2H), 3.85 (s, 3H), 4.00–4.20 (m, 1H), 6.73–6.75 (m, 1H), 6.87 (s, 1H), 6.99–7.03 (m, 1H), 7.25–7.29 (m, 1H), 7.42 (d, J=7.1 Hz, 1H), 7.95 (d, J=8.3 Hz, 1H), 8.08 (d, J=8.0, 1H), 8.78 (s, 1H), 8.92 (s, 1H); MS (FAB) m/z 544 (M$^+$+1); Anal. calcd for C$_{28}$H$_{34}$N$_3$O$_6$Cl.0.2H$_2$O: C, 61.41; H, 6.33; N, 7.67; Cl, 6.47. Found: C, 61.37; H, 6.32; N, 7.56; Cl, 6.55.

Example 168

4-[1-[4-[N'-(2-bromophenyl)ureido]-3-methoxyphenylacetyl]-(2S)-pyrrolidinyl]methoxy cyclohexanecarboxilic acid

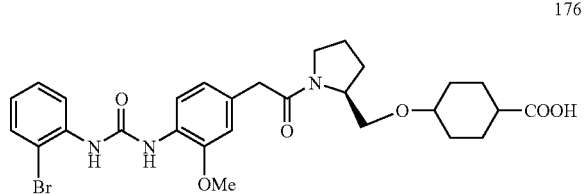

176

To a stirred solution of methyl 4-[(1-tert-butoxycarbonyl-2-pyrrolidinyl)methoxy]cyclohexane carboxylate (900 mg, 2.6 mmol) in CH$_2$Cl$_2$ (5.0 ml) was added TFA (5.0 ml) at 0° C. The reaction mixture was stirred at room temperature for 0.5 hr. The mixture was concentrated in vacuo. Sat. NaHCO$_3$ was added to the residue, and extracted with CH$_2$Cl$_2$. The extract was washed with brine, dried over Na$_2$SO$_4$, and concentrated in vacuo. The crude product was used to the subsequent reaction without further purification. To a stirred solution of the crude product (200 mg, 0.83 mmol), 4-[N'-(2-bromophenyl)uredio]-3-methoxyphenylacetic acid (314 mg, 0.83 mmol), HOBt (135 mg, 1.0 mmol), and triethylamine (344 ml, 2.48 mmol) in THF (10.0 ml) and MeCN (10.0 ml) was added EDC.HCl (238 mg, 1.24 mmol) at 0° C. The reaction mixture was stirred at room temperature for 16 hr, and concentrated in vacuo. Water was added to the residue, and extracted with EtOAc. The extract was washed with sat. NaHCO$_3$, 2-M citric acid, and sat. NaHCO$_3$, then dried over Na$_2$SO$_4$, and concentrated in vacuo. The residue was purified by column chromatography on silica gel with n-hexane-EtOAc (1:6, v/v) as eluent to give methyl [4-[1-[4-[N'-(2-bromophenyl)ureido]-3-methoxylphenylacetyl]-(2S)-pyrrolidinyl]methoxy]cyclohexane carboxylate (450 mg, 90%) as a colorless oil. $^1$H-NMR (CDCl$_3$) δ 1.30–2.10 (m, 12H), 2.35–2.40 (m, 1H), 3.25–3.70 (m, 5H), 3.84 (s, 3H), 4.10–4.25 (m, 1H), 6.81–7.06 (m, 4H), 7.25–7.32 (m, 2H), 7.50–7.52 (m, 1H), 7.90–7.92 (m, 1H), 8.13–8.15 (m, 1H).

To a stirred solution of methyl 4-[1-[4-[N'-(2-bromophenyl)ureido]-3-methoxyl phenylacetyl]-(2S)-pyrrolidinyl]methoxycyclohexanecarboxylate (450 mg, 0.74 mmol) in THF (10.0 ml) and MEOH (5.0 ml) was added 1 N NaOH (1.2 ml, 1.2 mmol). The mixture was stirred at 70° C. for 24 hr. The mixture was concentrated in vacuo, water was added thereto, and neutralized with 1 N HCl. The resulting solid was collected, washed with water, and dried in vacuo to give 176 (340 mg, 77%) as a white crystalline solid. MW 588.49 mp 108–111° C.; IR (KBr) 3328, 2938, 1702, 1594, 1529, 1434 cm$^{-1}$; $^1$H-NMR (DMSO-d$_6$) δ 1.00–2.00 (m, 12H), 2.15–2.25 (m, 1H), 3.40–3.75 (m, 5H), 3.48 (s, 2H), 3.85 (s, 3H), 4.04–4.15 (m, 1H), 6.70–6.72 (m, 1H), 6.87 (s, 1H), 6.94–6.98 (m, 1H), 7.29–7.33 (m, 1H), 7.59 (d, J=8.1 Hz, 1H), 7.93–7.95 (m, 2H), 8.73–8.74 (m, 1H), 8.91–8.92 (m, 1H); MS (FAB) m/z 589 (M$^+$+1); Anal. calcd for C$_{28}$H$_{34}$N$_3$O$_6$Br.0.2H$_2$O: C, 56.80; H, 5.86; N, 7.10; Br, 13.49. Found: C, 56.66; H, 5.83; N, 6.97; Br, 13.66.

Example 169

4-[[1-[4-[N'-(2-methylphenyl)ureido]phenylacetyl]-(2S)-pyrrolidinyl]methoxy]cyclohexane carboxylic acid

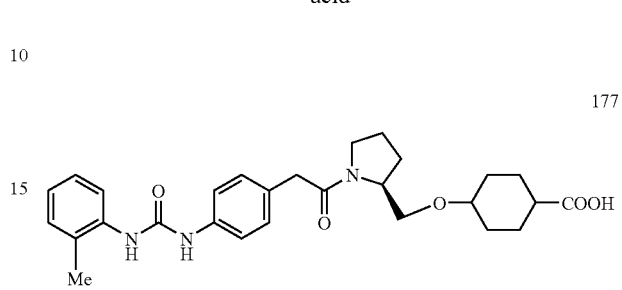

177

To a stirred solution of methyl 4-[(1-tert-butoxycarbonyl-2-pyrrolidinyl)methoxy]cyclohexane carboxylate (450 mg, 1.3 mmol) in CH$_2$Cl$_2$ (5.0 ml) was added TFA (5.0 ml) at 0° C. The reaction mixture was stirred at room temperature for 0.5 hr. The mixture was concentrated in vacuo. Sat. NaHCO$_3$ was added to the residue, and extracted with CH$_2$Cl$_2$. The extract was washed with brine, dried over Na$_2$SO$_4$, and concentrated in vacuo. The crude product was used to the subsequent reaction without further purification. To a stirred solution of the crude product, 4-[N'-(2-methylphenyl)ureidio]phenylacetic acid (375 mg, 1.3 mmol), HOBt (178 mg, 1.3 mmol), and triethylamine (550 ml, 3.9 mmol) in THF (6.0 ml) and MeCN (6.0 ml) was added EDC.HCl (380 mg, 1.9 mmol) at 0° C. The reaction mixture was stirred at room temperature for 16 hr, and concentrated in vacuo. Water was added to the residue, and extracted with EtOAc. The extract was washed with sat. NaHCO$_3$, 2-M citric acid, and sat. NaHCO$_3$, then dried over Na$_2$SO$_4$, and concentrated in vacuo. The residue was purified by column chromatography on silica gel with n-hexane-EtOAc (1:6, v/v) as eluent to give methyl 4-[[1-[4-[N'-(2-methylphenyl)ureido]phenylacetyl]-(2S)-pyrrolidinyl]methoxy]cyclohexanecarboxylate (520 mg, 78%) as a colorless oil. $^1$H-NMR (CDCl$_3$) δ 1.30–2.40 (m, 13H), 2.21 (s, 3H), 3.30–3.80 (m, 7H), 3.65 (s, 3H), 4.10–4.30 (m, 1H), 6.90–7.20 (m, 8H), 7.40–7.70 (m, 2H).

To a stirred solution of methyl 4-[[1-[4-[N'-(2-methylphenyl)ureido]phenylacetyl]-(2S)-pyrrolidinyl]methoxy]cyclohexanecarboxylate (520 mg, 1.0 mmol) in THF (10.0 ml) and MeOH (5.0 ml) was added 1 N NaOH (1.5 ml, 1.5 mmol). The mixture was stirred at 70° C. for 24 hr. The mixture was concentrated in vacuo, water was added thereto, and neutralized with 1 N HCl. The resulting solid was collected, washed with water, and dried in vacuo to give 177 (450 mg, 91%) as a white crystalline solid. MW 493.60 mp 107–111° C.; IR (KBr) 3353, 2938, 1704, 1540, 1454, 1240 cm$^{-1}$; $^1$H-NMR (DMSO-d$_6$) δ 1.20–2.00 (m, 12H), 2.23 (s, 3H), 2.22–2.24 (m, 1H), 3.20–3.80 (m, 7H), 4.00–4.18 (m, 1H), 6.90–6.94 (m, 1H), 7.10–7.16 (m, 5H), 7.36–7.38 (m, 2H), 7.82–7.87 (m, 2H), 8.89 (s, 1H), 12.0 (br s, 1H); MS (FAB) m/z 494 (M$^+$+1); Anal. calcd for C$_{28}$H$_{35}$N$_3$O$_5$.0.2H$_2$O: C, 67.64; H, 7.18; N, 8.45. Found: C, 67.66; H, 7.19; N, 8.24.

Example 170 cis-4-[1-[4-[N'-(2-chlorophenyl)ureido]-3-methoxy-lphenylacetyl]-(2S)-octahydroindolylmethoxy]cyclohexanecarboxylic acid

178

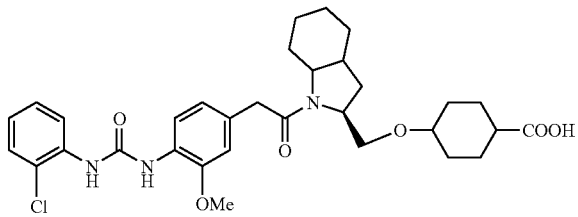

To a stirred solution of [1-tert-butoxycarbonyl-(2S)-octahydroindolyl]carboxylic acid (1.0 g, 3.7 mmol) in THF (10.0 ml) was added $BH_3 \cdot THF$(1.0 M in THF, 8.0 ml) at 0° C. After stirred at room temperature for 1.0 h, the reaction mixture was heated under reflux for 1.5 hr. After cooled, the mixture was concentrated in vacuo. Water was added thereto at 0° C., and extracted with EtOAc. The extract was washed with water, then dried over $Na_2SO_4$, and concentrated in vacuo to give [1-tert-butoxycarboyl-(2S)-octahydroindolyl]methanol (947 mg, quant) as a a colorless oil.

To a stirred solution of [1-tert-butoxycarboyl-(2S)-octahydroindolyl]methanol (947 mg, 3.7 mmol), methyl 4-hydroxybenzoate (565 mg, 3.7 mmol), and $Ph_3P$ (1.2 g, 4.5 mmol) in THF (10 ml) was added DIAD (984 mg, 4.5 mmol) at 0° C. The reaction mixture was stirred at room temperature for 18 hr. The mixture was concentrated in vacuo. The residue was purified by column chromatography on silica gel with n-hexane-EtOAc (9/1, v/v) as eluent to give methyl 4-[1-tert-butoxycarbonyl-(2S)-octahydroindolylmethoxy]benzoate (700 mg, 50%) as a pale yellow oil. $^1$H-NMR ($CDCl_3$) δ 1.10–2.25 (m, 11H), 1.45 (s, 9H), 3.88 (s, 3H), 3.70–4.20 (m, 3H), 4.36 (br s, 1H), 6.94 (d, J=8.8 H z, 2H), 7.96 (d, J=8.5 Hz, 2H).

A mixture of methyl 4-[1-tert-butoxycarbonyl-(2S)octahydroindolylmethoxy]benzoate (700 mg, 1.8 mmol) and 5% Rh on alumina (400 mg) in EtOH (10.0 ml) and AcOH (1.0 ml) was hydrogenated at room temperature at 5 atm for 48 hr. The catalyst was filtered off, and the filtrate was concentrated in vacuo. The residue was purified by column chromatography on silica gel with n-hexane-EtOAc (7:1, v/v) as eluent to give methyl cis-4-[1-tert-butoxycarbonyl-(2S)-octahydro indolylmethoxy]cyclohexanecarboxylate (600 mg, 85%) as a pale yellow oil. $^1$H-NMR ($CDCl_3$) δ 1.10–2.35 (m, 20H), 1.44 (s, 9H), 3.45–3.90 (m, 5H), 3.80 (s, 3H).

To a stirred solution of methyl cis-4-[1-tert-butoxycarbonyl-(2S)-octahydroindolylmethoxy]cyclohexanecarboxylate (600 mg, 1.5 mmol) in $CH_2Cl_2$ (6.0 ml) was added TFA (6.0 ml) at 0° C. The reaction mixture was stirred at room temperature for 0.5 hr. The mixture was concentrated in vacuo. Sat. $NaHCO_3$ was added to the residue, and extracted with $CH_2Cl_2$. The extract was washed with brine, dried over $Na_2SO_4$, and concentrated in vacuo. The crude product was used to the subsequent reaction without further purification. To a stirred solution of the crude product (221 mg, 0.75 mmol), 4-[N'-(2-chlorophenyl)uredio]-3-methoxyphenylacetic acid (250 mg, 0.75 mmol), HOBt (101 mg, 0.75 mmol), and triethylamine (312 ml, 2.3 mmol) in THF (10.0 ml) and MeCN (10.0 ml) was added EDC.HCl (216 mg, 1.1 mmol) at 0° C. The reaction mixture was stirred at room temperature for 16 hr, and concentrated in vacuo. Water was added to the residue, and extracted with EtOAc. The extract was washed with sat. $NaHCO_3$, 2-M citric acid, and sat. $NaHCO_3$, then dried over $Na_2SO_4$, and concentrated in vacuo. The residue was purified by column chromatography on silica gel with n-hexane-EtOAc(1:3, v/v) as eluent to give methyl cis4-[1-[4-[N'-(2-chlorophenyl)ureido]-3-methoxylphenylacetyl]-(2S)-octahydroindolylmethoxy]cyclohexane carboxylate (430 mg, 94%) as a colorless oil. $^1$H-NMR ($CDCl_3$) δ 1.10–2.40 (m, 20H), 3.45 (br s, 1H), 3.62 (s, 2H), 3.66 (s, 3H), 3.73 (s, 3H), 3.60–3.85 (m, 2H), 4.09–4.14 (m, 2H), 6.75–6.98 (m, 3H), 7.22–2.46 (m, 4H), 7.92 (d, J=8.0 Hz, 1H), 8.18 (d, J=8.3 Hz, 1H).

To a stirred solution of methyl cis-4-[1-[4-[N'-(2-chlorophenyl)ureido]-3-methoxylphenylacetyl]-(2S)-octahydroindolylmethoxy]cyclohexanecarboxylate (430 mg, 0.7 mmol) in THF (10.0 ml) and MeOH (5.0 ml) was added 1 N NaOH (1.4 ml, 1.4 mmol). The mixture was stirred at 70° C. for 24 hr. The mixture was concentrated in vacuo, water was added thereto, and neutralized with 1N HCl. The resulting solid was collected, washed with water, and dried in vacuo to give 178 (360 mg, 86%) as a white crystalline solid. MW 598.13 mp 120–121° C.; IR (KBr) 3338, 2933, 2859, 1614, 1533, 1438 cm$^{-1}$; $^1$H-NMR ($CDCl_3$) δ 1.05–2.40 (m, 20H), 3.38–3.50 (m, 2H), 3.63 and 3.65 (each s, total 2H), 3.71 and 3.75 (each s, total 3H), 3.70–3.80 (m, 1H), 3.93–3.97 (m, 1H), 4.15 (br s, 1H), 6.75–6.77 (m, 2H), 6.93–6.97 (m, 1H), 7.20–7.32 (m, 3H), 7.60–7.63 (m, 1H), 7.85 (d, J=8.3 Hz, 1H), 8.16 (d, J=8.3 Hz, 1H); MS (FAB) m/z 598 (M$^+$+1); Anal. calcd for $C_{32}H_{40}N_3O_6Cl \cdot 0.5H_2O$: C, 63.30; H, 6.81; N, 6.92; Cl, 5.84. Found: C, 63.68; H, 6.81; N, 6.81; Cl, 5.98.

Example 171 cis-4-[-1-[4-[N'-(2-bromophenyl)ureido]-3-methoxy-lphenylacetyl]-(2S)-octahydroindolylmethoxy]cyclohexanecarboxylic acid

179

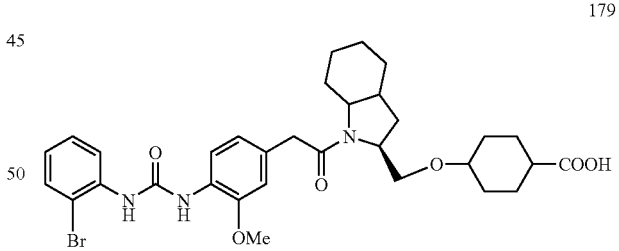

To a stirred solution of methyl cis-4-[1-tert-butoxycarbonyl-(2S)-octahydroindolylmethoxy]cyclohexanecarboxylate (600 mg, 1.5 mmol) in $CH_2Cl_2$ (6.0 ml) was added TFA (6.0 ml) at 0° C. The reaction mixture was stirred at room temperature for 0.5 hr. The mixture was concentrated in vacuo. Sat. $NaHCO_3$ was added to the residue, and extracted with $CH_2Cl_2$. The extract was washed with brine, dried over $Na_2SO_4$, and concentrated in vacuo. The crude product was used to the subsequent reaction without further purification. To a stirred solution of the crude product (221 mg, 0.75 mmol), 4-[N'-(2-bromophenyl)uredio]-3-methoxyphenylacetic acid (284 mg, 0.75 mmol), HOBt (101 mg, 0.75 mmol), and triethylamine (312 ml, 2.3 mmol) in THF (10.0 ml) and MeCN (10.0 ml) was added EDC.HCl (216 mg, 1.1 mmol) at 0° C. The reaction mixture was stirred at room temperature for 16 hr, and concentrated in vacuo. Water was added to the residue, and extracted with EtOAc. The extract was washed with sat. NaHCO$_3$, 2 M citric acid, and sat. NaHCO$_3$, then dried over Na$_2$SO$_4$, and concentrated in vacuo. The residue was purified by column chromatography on silica gel with n-hexane-EtOAc(1:3, v/v) as eluent to give methyl cis-4-[1-[4-[N'-(2-bromophenyl)ureido]-3-methoxylphenylacetyl]-(2S)octahydroindolylmethoxy]cyclohexane carboxylate (480 mg, 96%) as a colorless oil. $^1$H-NMR (CDCl$_3$) δ 1.10–2.40 (m, 20H), 3.45 (br s, 1H), 3.61 (s, 2H), 3.66 (s, 3H), 3.76 (s, 3H), 3.60–3.80 (m, 2H), 4.11–4.14 (m, 2H), 6.76–6.92 (m, 3H), 7.25–7.32 (m, 3H), 7.49 (d, J=7.1 Hz, 1H), 7.90 (d, J=8.0 Hz, 1H), 8.13 (d, J=8.0 Hz, 1H).

To a stirred solution of methyl cis-4-[1-[4-[N'-(2-bromophenyl)ureido]-3-methoxylphenylacetyl]-(2S)-octahydroindolylmethoxy]cyclohexanecarboxylate (480 mg, 0.73 mmol) in THF (10.0 ml) and MeOH (5.0 ml) was added 1 N NaOH (1.5 ml, 1.5 mmol). The mixture was stirred at 70° C. for 24 hr. The mixture was concentrated in vacuo, water was added thereto, and neutralized with 1N HCl. The resulting solid was collected, washed with water, and dried in vacuo to give 179 (400 mg, 85%) as a white crystalline solid. MW 642.58 mp 115–120° C.; IR (KBr) 3332, 2933, 2859, 1704, 1592, 1529, 1434 cm$^{-}$; $^1$H-NMR (CDCl$_3$) δ 1.10–2.40 (m, 20H), 3.40–3.50 (m, 2H), 3.61 and 3.63 (each s, total 214), 3.75 and 3.78 (each s, total 3H), 3.70–3.80 (m, 1H), 3.90–3.93 (m, 1H), 4.15 (br s, m), 6.76–6.92 (m, 3H), 7.26–7.30 (m, 1H), 7.43–7.52 (m, 3H), 7.84–7.86 (m, 1H), 8.10–8.12 (m, 1H); MS (FAB) m/z 643 (M$^+$+1); Anal. calcd for C$_{32}$H$_{40}$N$_3$O$_6$Br.0.4H$_2$O: C, 59.15; H, 6.33; N, 6.49; Br, 12.30. Found: C, 59.26; H, 6.33; N, 6.36; Br, 12.37.

Example 172

4-[[1-[3-methoxy-4-[N'-(2-methylphenyl)ureido]phenylacetyl]-2-pyrrolidinyl]carbonylamino]cyclohexanecarboxylic acid

180

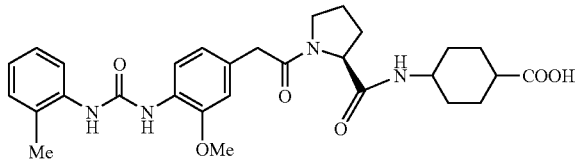

To a stirred solution of benzyl 4-aminocyclohexanecarboxylate (900 mg, 3.9 mmol), boc-proline (830 mg, 3.9 mmol), HOBt (521 mg, 3.9 mmol), and triethylamine (1.6 ml, 11.6 mmol) in CH$_2$Cl$_2$ (30.0 ml) was added EDC.HCl (1.1 g, 5.8 mmol) at 0° C. The reaction mixture was stirred at room temperature for 16 hr, and concentrated in vacuo. Water was added to the residue, and extracted with EtOAc. The extract was washed with sat. NaHCO$_3$, 2-M citric acid, and sat. NaHCO$_3$, then dried over Na$_2$SO$_4$, and concentrated in vacuo. The residue was purified by column chromatography on silica gel with n-hexane-EtOAc (6:1, v/v) as eluent to give benzylcis-4-[(1-tert-butoxycarbonyl-2-pyrrolidinyl)carbonylamino]cyclohexanecarboxylate (600 mg, 36%) as an amorphous solid. $^1$H-NMR (CDCl$_3$) δ 1.44 (s, 9H), 1.50–1.90 (m, 12H), 2.20–2.26 (m, 1H), 3.25–3.50 (m, 2H), 3.80–3.90 (m, 1H), 4.10–4.25 (m, 1H), 5.12 (s, 2H), 7.35–7.36 (m, 5H).

To a stirred solution of benzylcis-4-[(1-tert-butoxycarbonyl-2-pyrrolidinyl)carbonylamino]cyclohexanecarboxylate (600 mg, 1.4 mmol) in CH$_2$Cl$_2$ (6.0 ml) was added TFA (3.0 ml) at 0° C. The reaction mixture was stirred at room temperature for 0.5 hr. The mixture was concentrated in vacuo. Sat. NaHCO$_3$ was added to the residue, and extracted with CH$_2$Cl$_2$. The extract was washed with brine, dried over Na$_2$SO$_4$, and concentrated in vacuo. The crude product was used to the subsequent reaction without further purification. To a stirred solution of the crude product (300 mg, 0.7 mmol), 3-methoxy-4-[N'-(2-methylphenyl)uredio]phenylacetic acid (220 mg, 0.7 mmol), HOBt (94 mg, 0.7 mmol), and triethylamine (291 ml, 2.1 mmol) in THF (10.0 ml) and MeCN (10.0 ml) was added EDC.HCl (201 mg, 1.1 mmol) at 0° C. The reaction mixture was stirred at room temperature for 16 hr, and concentrated in vacuo. Water was added to the residue, and extracted with EtOAc. The extract was washed with sat. NaHCO$_3$, 2-M citric acid, and sat. NaHCO$_3$, then dried over Na$_2$SO$_4$, and concentrated in vacuo. The resulting solid was collected and washed with EtOAc to give benzyl 4-[[1-[3-methoxy-4-[N'-(2-methylphenyl)ureido]phenylacetyl]-2-pyrrolidinyl]carbonylamino]cyclohexanecarboxylate (380 mg, 87%) as a white crystalline solid. $^1$H-NMR (CDCl$_3$) δ 1.40–2.15 (m, 12H), 2.28 (m, 3H), 2.30–2.50 (m, 2H), 3.40–3.55 (m, 2H), 3.61 (s, 2H), 3.71 (s. 3H), 3.82 (m, 1H), 4.53 (d, J=6.3 Hz, 1H), 5.10 (s, 2H), 6.42 (s, 1H), 6.77–6.79 (m, 2H), 7.04–7.34 (m, 9H), 7.50–7.52 (m, 1H), 8.05–8.07 (m, 1H).

To a stirred solution of benzyl 4-[[1-[3-methoxy-4-[N'-(2-methylphenyl)ureido]phenylacetyl]-2-pyrrolidinyl]carbonylamino]cyclohexanecarboxylate (380 mg, 0.6 mmol) in THF (10.0 ml) and EtOH (5.0 ml) was added 1 N NaOH (0.9 ml, 0.9 mmol). The mixture was stirred at 50° C. for 18 hr. The mixture was concentrated in vacuo, water was added thereto, and neutralized with 1N HCl. The resulting solid was collected, washed with water, and dried in vacuo to give 180 (230 mg, 71%) as a white crystalline solid. MW 636.62 mp 136–142° C.; IR (KBr) 3345, 2940, 1650, 1625, 1535, 1454 cm$^{-1}$; $^1$H-NMR (DMSO-d$_6$) δ 1.40–2.00 (m, 12H), 2.24 (s, 3H), 2.30–2.40 (m, 1H), 3.45–3.80 (m, 5H), 3.86–3.87 (m, 3H), 4.304.43 (m, 1H), 6.65–7.30 (m, 5H), 7.70–7.80 (m, 1H), 7.98–8.09 (m, 1H), 8.46–8.57 (m, 1H); MS (FAB) m/z 537 (M$^+$+1); Anal. calcd for C$_{29}$H$_{36}$N$_4$O$_6$.0.5 H$_2$O: C, 63.84; H, 6.83; N, 10.27. Found: C, 64.18; H, 6.91; N, 9.85.

Example 173

4-[[1-[4-[N'-(2-chlorophenyl)ureido]-3-methoxylphenylacetyl]-2-pyrrolidinyl]carbonylamino]cyclohexanecarboxylic acid

181

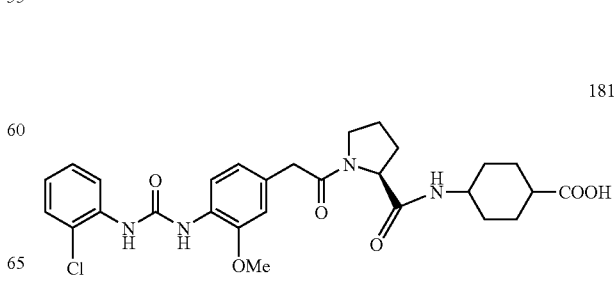

To a stirred solution of benzylcis-4-[(1-tert-butoxycarbonyl-2-pyrrolidinyl)carbonylamino]cyclohexanecarboxylate (600 mg, 1.4 mmol) in CH$_2$Cl$_2$ (6.0 ml) was added TFA (3.0 ml) at 0° C. The reaction mixture was stirred at room temperature for 0.5 hr. The mixture was concentrated in vacuo. Sat. NaHCO$_3$ was added to the residue, and extracted with CH$_2$Cl$_2$. The extract was washed with brine, dried over Na$_2$SO$_4$, and concentrated in vacuo. The crude product was used to the subsequent reaction without further purification. To a stirred solution of the crude product (300 mg, 0.7 mmol), 4-[N'-(2-chlorophenyl)uredio]-3-methoxyphenylacetic acid (237 mg, 0.7 mmol), HOBt (94 mg, 0.7 mmol), and triethylamine (291 ml, 2.1 mmol) in THF (10.0 ml) and MeCN (10.0 ml) was added EDC.HCl (201 mg, 1.1 mmol) at 0° C. The reaction mixture was stirred at room temperature for 16 hr, and concentrated in vacuo. Water was added to the residue, and extracted with EtOAc. The extract was washed with sat. NaHCO$_3$, 2-M citric acid, and sat. NaHCO$_3$, then dried over Na$_2$SO$_4$, and concentrated in vacuo. The resulting solid was collected and washed with EtOAc to give benzyl 4-[[1-[4-[N'-(2-chlorophenyl)ureido]-3-methoxyl phenylacetyl]-2-pyrrolidinyl]carbonylamino]cyclohexanecarboxylate (310 mg, 68%) as a white crystalline solid. $^1$H-NMR (CDCl$_3$) δ 1.40–2.15 (m, 12H), 2.30–2.60 (m, 2H), 3.42–3.55 (m, 2H), 3.64 (s, 2H), 3.84 (s, 3H), 4.55 (d, J=6.1 Hz, 1H), 5.12 (s, 2H), 6.81–7.35(m, 12H), 7.96–7.98 (m, 1H), 8.17–8.19 (m, 1H).

To a stirred solution of methyl benzyl 4-[[1-[4-[N'-(2-chlorophenyl)ureido]-3-methoxylphenyl acetyl]-2-pyrrolidinyl]carbonylamino]cyclohexanecarboxylate (310 mg, 0.86 mmol) in THF (10.0 ml) and MeOH (5.0 ml) was added 1 N NaOH (0.7 ml, 0.7 mmol). The mixture was stirred at 50 ° C. for 18 hr. The mixture was concentrated in vacuo, water was added thereto, and neutralized with 1 N HCl. The resulting solid was collected, washed with water, and dried in vacuo to give 181 (260 mg, 98%) as a white crystalline solid. MW 557.03 mp 135–140° C.; IR (KBr) 3328, 2938, 1594, 1533,1438, 1203 cm$^-$; $^1$H-NMR (DMSO-d$_6$) δ 1.40–2.20 (m, 12H), 2.30–2.40 (m, 1H), 3.40–3.80 (m, 5H), 3.65–3.85 (m, 3H), 4.30–4.43 (m, 1H), 6.66–7.31 (m, 5H), 7.42–8.10 (m, 2H), 8.89–8.94 (m, 2H); MS (FAB) m/z 557 (M$^+$+1); Anal. calcd for C$_{28}$H$_{33}$N$_4$O$_6$Cl.0.3H$_2$O: C, 59.79; H, 6.02; N, 9.96; Cl, 6.30. Found: C, 59.86; H, 6.10; N, 9.60; Cl, 6.34.

Example 174

4-[1-[3-methoxy-4-[N'-(2-methylphenyl)ureido]phenylacetyl]-(3S)-pyrrolidinyloxy]benzoic acid

182

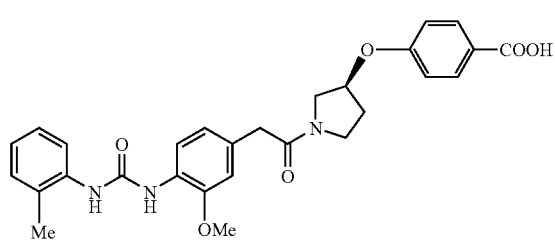

To a cooled (0° C.), stirred solution of methyl 4-hydroxybenzoate (1.84 g, 12.1 mmol), (R)-1-benzyl-3-pyrrolidinol (2.00 ml, 12.1 mmol), and Ph$_3$P (3.81 g, 14.5 mmol) in THF (25 ml) was added DIAD (2.86 ml, 14.5 mmol) and the reaction mixture was heated under reflux for 10 hr. After cooled to room temperature, the mixture was evaporated. The residue was purified by column chromatography on silica-gel with n-hexane-EtOAc (3:1, v/v) as eluent to give methyl 4-[1-benzyl-(3S)-pyrrolidinyloxy]benzoate (3.66 g, 97%) as a pale yellow oil. $^1$H-NMR (CDCl$_3$) δ 1.95–2.02 (m, 1 H), 2.28–2.37 (m, 1 H), 2.57–2.63 (m, 1 H), 2.72–2.81 (m, 2 H), 2.96–3.01 (m, 1 H), 3.63–3.71 (m, 2 H), 3.87 (s, 3 H), 4.84–4.89 (m, 1 H), 6.84 (d, J=8.8 Hz, 2 H), 7.23–7.34 (m, 5 H), 7.95 (d, J=8.8 Hz, 2 H).

A solution of methyl 4-[1-benzyl-(3S)-pyrrolidinyloxy]benzoate (3.66 g, 11.8 mmol) in MeOH (25 ml) was hydrogenated over Pd(OH)$_2$/C (0.73 g, 20 wt %) overnight. The reaction mixture was filtered to remove the catalyst and the solution was evaporated to give methyl 4-[(3S)-pyrrolidinyloxy]benzoate (2.60 g, q.y.) as a pale yellow oil. $^1$H-NMR (CDCl$_3$) δ 1.94–2.01 (m, 2 H), 2.09–2.18 (m, 1 H), 2.91–2.97 (m, 1 H), 3.04–3.09 (m, 1 H), 3.16–3.23 (m, 2 H), 3.88 (s, 3 H), 4.88–4.91 (m, 1 H), 6.86 (m, 2 H), 7.96–7.98 (m, 2 H); MS (ESI) m/z 222 (M$^+$+1).

A mixture of 3-methoxy-4-[N'-(2-methylphenyl)ureido] phenylacetic acid (449 mg, 1.43 mmol), methyl 4-[(3S)-pyrrolidinyloxy]benzoate (316 mg, 1.43 mmol), EDC.HCl (330 mg, 1.72 mmol), HOBt (193 mg, 1.43 mmol), and Et$_3$N (240 ml, 1.72 mmol) in THF (5 ml) was stirred at room temperature overnight. The reaction mixture was diluted with H$_2$O, and extracted with EtOAc. The extract was washed with brine, dried over Na$_2$SO$_4$, and evaporated. The residue was purified by column chromatography on silica-gel with CHCl$_3$-MeOH (100:1 to 50:1, v/v) as eluent to give methyl 4-[1-[3-methoxy-4-[N'-(2-methylphenyl)ureido] phenylacetyl]-(3S)-pyrrolidinyloxy]benzoate (735 mg, 99%) as a pale yellow oil. $^1$H-NMR (CDCl$_3$) δ 2.03–2.31 (series of s and m, total 5 H), 3.57–3.78 (series of m, total 9 H), 3.88 (s, 3 H), 4.95–4.99 (m, 1 H), 6.73–7.00 (m, 5 H), 7.06–7.10 (m, 1 H), 7.18–7.22 (m, 2 H), 7.42–7.46 (m, 1 H), 7.57–7.62 (m, 1 H), 7.95–8.08 (m, 3 H); MS (ESI) m/z 518 (M$^+$+1).

To a stirred solution of methyl 4-[1-[3-methoxy-4-[N'-(2-methylphenyl)ureido]phenylacetyl]-(3S)-pyrrolidinyloxy] benzoate (627 mg, 1.21 mmol) in THF (5 ml) was added 0.5 N NaOH (5 ml) and the reaction mixture was heated under reflux for 3 hr. After cooled to room temperature, the mixture was poured into ice-1 N HCl and the resulting precipitate was collected under a reduced pressure. The crude solid was recrystallized from MeOH—CHCl$_3$-IPE to give 182 (235 mg, 39%) as a white crystalline powder. MW 503.55 mp 131–135° C.; $^1$H-NMR (DMSO-d$_6$) δ 2.06–2.27 (series of m, total 5 H), 3.57–3.64 (m, 4 H), 3.71–3.88 (series of s and m, total 5 H), 5.11 and 5.20 (each m, total 1 H), 6.73–6.77 (m, 1 H), 6.88–6.95 (m, 2 H), 7.02–7.05 (m, 2 H), 7.11–7.17 (m, 2 H), 7.79–7.81 (m, 1 H), 7.88–7.90 (m, 2 H), 7.98–8.03 (m, 1 H), 8.45–8.47 (m, 1 H), 8.55–8.57 (m, 1 H), 12.66 (br s, 1 H); MS (ESI) m/z 504 (M$^+$+1); Anal. Calcd for C$_{28}$H$_{29}$N$_3$O$_6$.3/4H$_2$O: C, 65.04; H, 5.95; N, 8.13. Found: C, 65.11; H, 5.99; N, 7.66.

Example 175

4-[1-[4-[N'-(2-chlorophenyl)ureido]-3-methoxyphenylacetyl]-(3S)-pyrrolidinyloxy]benzoic acid

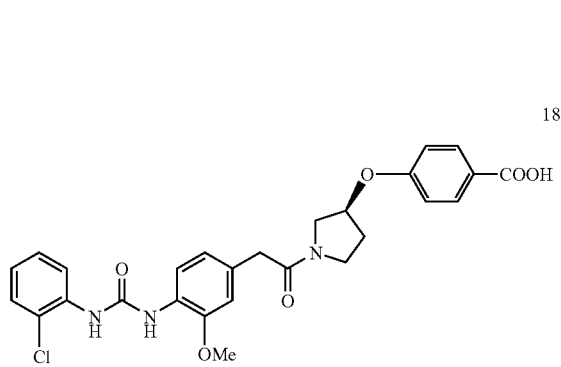

183

A mixture of 4-[N'-(2-chlorophenyl)ureido]-3-methoxyphenylacetic acid (410 mg, 1.22 mmol), methyl 4-[(3S)-pyrrolidinyloxy]benzoate (270 mg, 1.22 mmol), EDC.HCl (280 mg, 1.46 mmol), HOBt (200 mg, 1.48 mmol), and $Et_3N$ (205 ml, 1.47 mmol) in THF (8 ml) was stirred at room temperature overnight. The reaction mixture was diluted with $H_2O$, and extracted with EtOAc. The extract was washed with brine, dried over $Na_2SO_4$, and evaporated. The residue was purified by column chromatography on silica-gel with $CHCl_3$-MeOH (100:1 to 60:1, v/v) as eluent to give methyl 4-[1-[4-[N'-(2-chlorophenyl)ureido]-3-methoxyphenylacetyl]-(3S)-pyrrolidinyloxy]benzoate (652 mg, 99%) as a white solid. mp 200–203° C.; $^1$H-NMR ($CDCl_3$) δ 2.06–2.32 (m, 2 H), 3.60–3.82 (series of m, total 9 H), 3.88 (s, 3 H), 4.97–5.01 (m, 1 H), 6.76–6.86 (m, 4 H), 6.95–6.99 (m, 1 H), 7.23–7.47 (m, 4 H), 7.91–7.99 (m, 3 H), 8.19–8.21 (m, 1 H); MS (ESI) m/z 537 ($M^+$).

To a stirred solution of methyl 4-[1-[4-[N'-(2-chlorophenyl)ureido]-3-methoxyphenylacetyl]-(3S)-pyrrolidinyloxy]benzoate (650 mg, 1.21 mmol) in THF (5 ml) was added 0.5 N NaOH (5 ml) and the reaction mixture was heated under reflux for 5 hr. After cooled to room temperature, the mixture was poured into ice-1 N HCl and the resulting precipitate was collected under a reduced pressure. The crude solid was recrystallized from MeOH—$CHCl_3$-IPE to give 183 (443 mg, 70%) as a pale yellow crystalline powder. MW 523.97 mp 190–193° C.; $^1$H-NMR (DMSO-$d_6$) δ 2.06–2.27 (m, 2 H), 3.56–3.62 (m, 4 H), 3.71–3.88 (series of s and m, total 5 H), 5.11 and 5.20 (each m, total 1 H), 6.74–6.78 (m, 1 H), 6.89–6.91 (m, 1 H), 7.00–7.05 (m, 3 H), 7.26–7.30 (m, 1 H), 7.43–7.45 (m, 1 H), 7.88–7.98 (m, 3 H), 8.08–8.10 (m, 1 H), 8.89–8.95 (m, 2 H), 12.67 (br s, 1 H); MS (ESI) m/z 524 ($M^+$+1); Anal. Calcd for $C_{27}H_{26}ClN_3O_6 \cdot 1/4H_2O$: C, 61.36; H, 5.05; N, 7.95; Cl, 6.71. Found: C, 61.69; H, 5.45; N, 7.29; Cl, 6.91.

Example 176

4-[1-[4-[N'-(2-bromophenyl)ureido]-3-methoxyphenylacetyl]-(3S)-pyrrolidinyloxy]benzoic acid

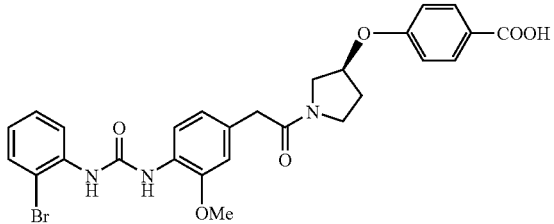

184

A mixture of 4-[N'-(2-bromophenyl)ureido]-3-methoxyphenylacetic acid (540 mg, 1.42 mmol), methyl 4-[(3S)-pyrrolidinyloxy]benzoate (315 mg, 1.42 mmol), EDC.HCl (328 mg, 1.71 mmol), HOBt (230 mg, 1.70 mmol), and $Et_3N$ (240 ml, 1.72 mmol) in THF (8 ml) was stirred at room temperature overnight. The reaction mixture was diluted with $H_2O$, and extracted with EtOAc. The extract was washed with brine, dried over $Na_2SO_4$, and evaporated. The residue was purified by column chromatography on silica-gel with $CHCl_3$-MeOH (100:1 to 50:1, v/v) as eluent to give methyl 4-[1-[4-[N'-(2-bromophenyl)ureido]-3-methoxyphenylacetyl]-(3S)-pyrrolidinyloxy]benzoate (620 mg, 74%) as a white foam. $^1$H-NMR ($CDCl_3$) δ 2.06–2.33 (m, 2 H), 3.60–3.82 (series of m, total 9 H), 3.89 (s, 3 H), 4.97–5.01 (m, 1 H), 6.77–7.00 (m, 5 H), 7.27–7.40 (m, 3 H), 7.49–7.51 (m, 1 H), 7.91–7.99 (m, 3 H), 8.13–8.17 (m, 1 H); MS (ESI) m/z 583 ($M^+$+1).

To a stirred solution of methyl 4-[1-[4-[N'-(2-bromophenyl)ureido]-3-methoxyphenyl acetyl]-(3S)-pyrrolidinyloxy]benzoate (620 mg, 1.06 mmol) in THF (5 ml) was added 0.5 N NaOH (5 ml) and the reaction mixture was heated under reflux for 2.5 hr. After cooled to room temperature, the mixture was poured into ice-1 N HCl and the resulting precipitate was collected under a reduced pressure. The crude solid was recrystallized from MeOH—$CHCl_3$-IPE to give 184 (421 mg, 70%) as a white crystalline powder. MW 568.42 mp 173–175° C.; $^1$H-NMR (DMSO-$d_6$) δ 2.06–2.28 (m, 2 H), 3.56–3.65 (m, 4 H), 3.71–3.88 (series of s and m, total 5 H), 5.12 and 5.20 (each m, total 1 H), 6.74–6.78 (m, 1 H), 6.89–7.05 (m, 4 H), 7.31–7.34 (m, 1 H), 7.59–7.61 (m, 1 H), 7.88–7.98 (m, 4 H), 8.73–8.74 (m, 1 H), 8.91–8.93 (m, 1 H), 12.67 (br s, 1 H); MS (ESI) m/z 569 ($M^+$+1); Anal. Calcd for $C_{27}H_{26}BrN_3O_6$: C, 57.05; H, 4.61; N, 7.39; Br, 14.06. Found: C, 57.57; H, 5.12; N, 6.81; Br, 13.96.

Example 177

4-[1-[3-methoxy-4-[N'-(2-methylphenyl)ureido]phenylacetyl]-(3R)-pyrrolidinyloxy]benzoic acid

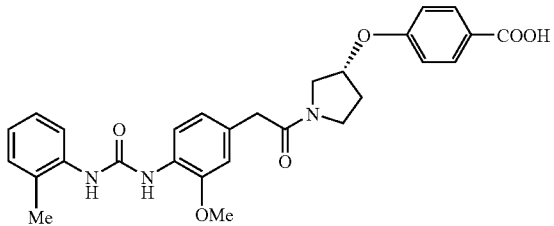

185

To a cooled (0° C.), stirred solution of methyl 4-hydroxybenzoate (1.78 g, 11.7 mmol), 1-benzyl-(3S)-pyrrolidinol (2.07 g, 11.7 mmol), and $Ph_3P$ (3.68 g, 14.0 mmol) in THF (25 ml) was added DIAD (2.76 ml, 14.0 mmol) and the reaction mixture was heated under reflux for, 10 hr. After cooled to room temperature, the mixture was evaporated. The residue was purified by column chromatography on silica-gel with n-hexane-EtOAc (3:1, v/v) as eluent to give methyl 4-[1-benzyl-(3R)-pyrrolidinyloxy]benzoate (3.56 g, 98%) as a pale yellow oil. $^1$H-NMR (CDCl$_3$) δ 1.95–2.03 (m, 1 H), 2.28–2.37 (m, 1 H), 2.57–2.63 (m, 1 H), 2.73–2.81 (m, 2 H), 2.97–3.01 (m, 1 H), 3.63–3.72 (m, 2 H), 3.87 (s, 3 H), 4.85–4.90 (m, 1 H), 6.83–6.85 (m, 2 H), 7.27–7.34 (m, 5 H), 7.94–7.97 (m, 2 H); MS (ESI) m/z 312 (M$^+$+1).

A solution of methyl 4-[1-benzyl-(3R)-pyrrolidinyloxy]benzoate (3.56 g, 11.4 mmol) in MeOH (25 ml) was hydrogenated over Pd(OH)$_2$/C (0.72 g, 20 wt %) overnight. The reaction mixture was filtered to remove the catalyst and the solution was evaporated to give methyl 4-[(3R)-pyrrolidinyloxy]benzoate (2.53 g, q.y.) as a pale yellow oil. $^1$H-NMR (CDCl$_3$) δ 1.94–2.18 (m, 3 H), 2.91–2.97 (m, 1 H), 3.04–3.09 (m, 1 H), 3.16–3.22 (m, 2 H), 3.88 (s, 3 H), 4.88–4.91 (m, 1 H), 6:86–6.89 (m, 2 H), 7.97–7.99 (m, 2 H); MS (ESI) m/z 263 [M$^+$+1+41, (+MeCN)].

A mixture of 3-methoxy-4-[N'-(2-methylphenyl)ureido]phenylacetic acid (460 mg, 1.46 mmol), methyl 4-[(3R)-pyrrolidinyloxy]benzoate (324 mg, 1.46 mmol), EDC.HCl (337 mg, 1.76 mmol), HOBt (237 mg, 1.75 mmol), and Et$_3$N (245 ml, 1.76 mmol) in THF (10 ml) was stirred at room temperature overnight. The reaction mixture was diluted with H$_2$O, and extracted with EtOAc. The extract was washed with brine, dried over Na$_2$SO$_4$, and evaporated. The residue was purified by column chromatography on silica-gel with CHCl$_3$-MeOH (100:1 to 50:1, v/v) as eluent to give methyl 4-[1-[3-methoxy-4-[N'-(2-methylphenyl)ureido]phenylacetyl]-(3R)-pyrrolidinyloxy]benzoate (583 mg, 77%) as a colorless oil. $^1$H-NMR (CDCl$_3$) δ 2.06–2.23 (m, 2 H), 2.30 (s, 3 H), 3.58–3.89 (series of s and m, total 12 H), 4.95–4.99 (m, 1 H), 6.75–7.00 (m, 4 H), 7.13–7.30 (m, 5 H), 7.52–7.57 (m, 1 H), 7.96–8.03 (m, 3 H); MS (ESI) m/z 518 (M$^+$+1).

To a stirred solution of methyl 4-[1-[3-methoxy-4-[N'-(2-methylphenyl)ureido]phenylacetyl]-(3R)-pyrrolidinyloxy]benzoate (583 mg, 1.13 mmol) in THF (5 ml) was added 0.5 N NaOH (5 ml) and the reaction mixture was heated under reflux for 3 hr. After cooled to room temperature, the mixture was poured into ice-1 N HCl and the resulting precipitate was collected under a reduced pressure. The crude solid was recrystallized from MeOH—CHCl$_3$-Et$_2$O to give 185 (297 mg, 52%) as a white crystalline powder. MW 503.55 mp 158–162° C.; $^1$H-NMR (DMSO-d$_6$) δ 2.08–2.31 (series of s and m, total 5 H), 3.54–3.89 (series of m, total 9 H), 5.11 and 5.20 (each m, total 1 H), 6.72–7.17 (series of m, total 6 H), 7.78–7.80 (m, 1 H), 7.87–7.90 (m, 2 H), 7.98–8.02 (m, 2 H), 8.46–8.47 (m, 1 H), 8.55–8.57 (m, 1 H), 12.66 (br s, 1 H); MS (ESI) m/z 504 (M$^+$+1); Anal. Calcd for C$_{28}$H$_{29}$N$_3$O$_6$.1/4H$_2$O: C, 66.19; H, 5.85; N, 8.27. Found: C, 66.12; H, 5.77; N, 8.21.

Example 178

4-[1-[4-[N'-(2-chlorophenyl)ureido]-3-methoxyphenylacetyl]-(3R)-pyrrolidinyloxy]benzoic acid

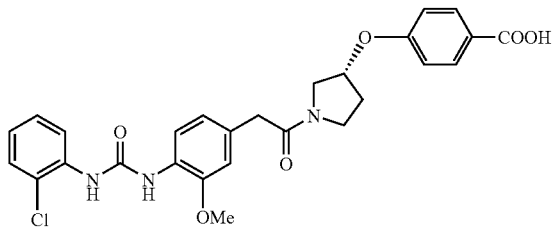

186

A mixture of 4-[N'-(2-chlorophenyl)ureido]-3-methoxyphenylacetic acid (498 mg, 1.49 mmol), methyl 4-[(3R)-pyrrolidinyloxy]benzoate (329 mg, 1.49 mmol), EDC.HCl (342 mg, 1.78 mmol), HOBt (241 mg, 1.78 mmol), and Et$_3$N (250 ml, 1.79 mmol) in THF (10 ml) was stirred at room temperature overnight. The reaction mixture was diluted with H$_2$O, and extracted with EtOAc. The extract was washed with brine, dried over Na$_2$SO$_4$, and evaporated. The residue was purified by column chromatography on silica-gel with CHCl$_3$-MeOH (100:1 to 50:1, v/v) as eluent to give methyl 4-[1-[4-[N'-(2-chlorophenyl)ureido]-3-methoxyphenylacetyl]-(3R)-pyrrolidinyloxy]benzoate (561 mg, 70%) as a white form. $^1$H-NMR (CDCl$_3$) δ 2.05–2.34 (m, 2 H), 3.59–4.07 (series of s and m, total 12 H), 4.97–5.02 (m, 1 H), 6.75–6.86 (m, 4 H), 6.94–7.00 (m, 1 H), 7.22–7.33 (m, 2H), 7.59–7.66 (m, 2H), 7.92–7.99 (m, 3H), 8.19–8.22 (m, 1H); MS (ESI) m/z 538 (M$^+$+1).

To a stirred solution of methyl 4-[1-[4-[N'-(2-chlorophenyl)ureido]-3-methoxyphenyl acetyl]-(3R)-pyrrolidinyloxy]benzoate (561 mg, 1.04 mmol) in THF (5 ml) was added 0.5 N NaOH (5 ml) and the reaction mixture was heated under reflux for 5 hr. After cooled to room temperature, the mixture was poured into ice-1 N HCl and the resulting precipitate was collected under a reduced pressure. The crude solid was recrystallized from MeOH—CHCl$_3$-Et$_2$O to give 186 (361 mg, 66%) as a white crystalline powder. MW 523.97 mp 193–194° C.; $^1$H-NMR (DMSO-d$_6$) δ 2.06–2.28 (m, 2 H), 3.58–3.62 (m, 4 H), 3.71–3.76 (m, 1 H), 3.83–3.89 (series of s and m, total 4 H), 5.12 and 5.20 (each m, total 1 H), 6.74–6.78 (m, 1 H), 6.90–6.91 (m, 1 H), 7.01–7.05 (m, 3 H), 7.27–7.30 (m, 1 H), 7.43–7.45 (m, 1 H), 7.88–7.98 (m, 3 H), 8.08–8.10 (m, 1 H), 8.89–8.96 (m, 2 H), 12.67 (br s, 1 H); MS (ESI) m/z 524 (M$^+$+1); Anal. Calcd for C$_{27}$H$_{26}$ClN$_3$O$_6$.1/4H$_2$O: C, 61.36; H, 5.05; N, 7.95; Cl, 6.71. Found: C, 61.49; H, 5.11; N, 7.72; Cl, 7.08.

Example 179

4-[1-[4-[N'-(2-bromophenyl)ureido]-3-methoxyphenylacetyl]-(3R)-pyrrolidinyloxy]benzoic acid

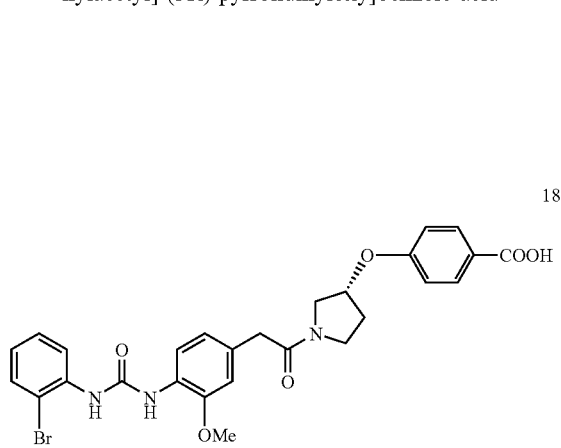

187

A mixture of 4-[N'-(2-bromophenyl)ureido]-3-methoxyphenylacetic acid (460 mg, 1.21 mmol), methyl 4-[(3R)-pyrrolidinyloxy]benzoate (269 mg, 1.21 mmol), EDC.HCl (280 mg, 1.46 mmol), HOBt (197 mg, 1.46 mmol), and Et$_3$N (205 ml, 1.47 mmol) in THF (10 ml) was stirred at room temperature overnight. The reaction mixture was diluted with H$_2$O, and extracted with EtOAc. The extract was washed with brine, dried over Na$_2$SO$_4$, and evaporated. The residue was purified by column chromatography on silica-gel with CHCl$_3$-MeOH (100:1 to 60:1, v/v) as eluent to give methyl 4-[1-[4-[N'-(2-bromophenyl)ureido]-3-methoxyphenylacetyl]-(3R)-pyrrolidinyloxy]benzoate (555 mg, 78%) as a white foam. $^1$H-NMR (CDCl$_3$) δ 2.05–2.33 (m, 2 H), 3.60–4.07 (series of s and m, total 12 H), 4.96–5.01 (m, 1 H), 6.76–6.93 (m, 5 H), 7.28–7.30 (m, 1 H), 7.48–7.58 (m, 3 H), 7.92–7.99 (m, 3 H), 8.12–8.16 (m, 1 H); MS (ESI) m/z 582 (M$^+$).

To a stirred solution of methyl 4-[1-[4-[N'-(2-bromophenyl)ureido]-3-methoxyphenylacetyl]-(3R)-pyrrolidinyloxy]benzoate (555 mg, 0.95 mmol) in THF (5 ml) was added 0.5 N NaOH (5 ml) and the reaction mixture was heated under reflux for 5 hr. After cooled to room temperature, the mixture was poured into ice-1 N HCl and the resulting precipitate was collected under a reduced pressure. The crude solid was recrystallized from MeOH—CHCl$_3$-Et$_2$O to give 187 (330 mg, 61%) as a white crystalline powder. MW 568.42 mp 175–177° C.; $^1$H-NMR (DMSO-d$_6$) δ 1.99–2.27 (m, 2 H), 3.56–3.63 (m, 4 H), 3.71–3.76 (m, 1 H), 3.83–3.89 (series of s and m, 4 H), 5.12 and 5.20 (each m, total 1 H), 6.74–6.78 (m, 1 H), 6.89–7.05 (m, 4 H), 7.30–7.35 (m, 1 H), 7.59–7.61 (m, 1 H), 7.88–7.98 (m, 4 H), 8.74–8.76 (m, 1 H), 8.92–8.95 (m, 1 H), 12.68 (br s, 1 H); MS (ESI) m/z 569 (M$^+$+1); Anal. Calcd for C$_{27}$H$_{26}$BrN$_3$O$_6$: C, 57.05; H, 4.61; N, 7.39; Br, 14.06. Found: C, 56.91; H, 4.66; N, 7.20; Br, 14.59.

Example 180

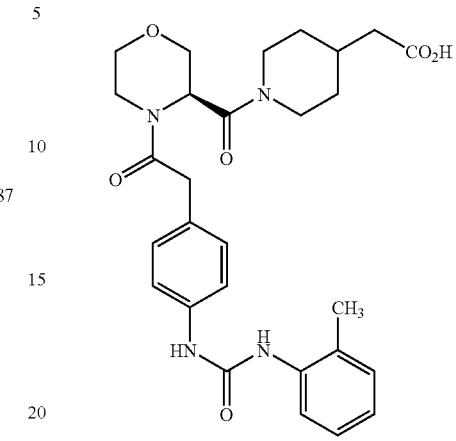

188

1 gram of Tentagel PHB resin (loading 0.29 mmol) was taken up in DMF 25 mL and Fmoc-(4-carboxymethyl)-piperidine (318 mg, 0.87 mmol) was added. The resin was shaken for 5 min then DIC (220 mg, 0.27 mL, 1.74 mmol) and DMAP (106 mg, 0.87 mmol) were added and the resin was shaken for 24 hr.

The resin was drained and washed with DMF (3×), CH$_3$OH (3×) and CH$_2$Cl$_2$ (3×) then dried under vacuum. The resin gave a negative bromophenylblue test. The resin was taken up in 20% piperidine in DMF and shaken for 4 hr. The resin was drained and washed with DMF (3×), CH$_3$OH (3×) and CH$_2$Cl$_2$ (3×) then dried under vacuum. The resin gave a positive bromophenylblue test. The resin was taken up in 25 mL of DMF and Fmoc-L-morpholine-2-carboxylic acid (307 mg, 0.87 mmol) was added. The resin was shaken for 5 min then PyBroP (406 mg, 0.87 mmol) and DIEA (123 mg, 0.15 mL, 0.87 mmol) were added and the resin was shaken for 24 hr.

The resin was drained and washed with DMF (3×), CH$_3$OH (3×) and CH$_2$Cl$_2$ (3×) then dried under vacuum. The resin gave a negative bromophenylblue test. The resin was taken up in 20% piperidine in DMF and shaken for 4 hr. The resin was drained and washed with DMF (3×), CH$_3$OH (3×) and CH$_2$Cl$_2$ (3×) then dried under vacuum. The resin gave a positive bromophenylblue test. The resin was taken up in 25 mL. of DMF and 4-o-tolylureidophenylacetic acid (247 mg, 0.87 mmol) was added and the resin was shaken for 5 min. PyBroP (406 mg, 0.87 mmol) and DIEA (123 mg, 0.15 mL, 0.87 mmol) was added and the resin was shaken for 24 hr.

The resin was drained and washed with DMF (3×), CH$_3$OH (3×) and CH$_2$Cl$_2$ (3×) then dried under vacuum. The resin gave a negative bromophenylblue test. The resin was then taken up in 90% TFA in CH$_2$Cl$_2$ and shaken for 4 hr. The resin was drained and the eluate collected. The resin was taken up in fresh CH$_2$Cl$_2$ and shaken for 30 min. The resin was drained and the eluate collected and combined with the first fraction. The solvent was removed under vacuum and the residue was recrystallized from ethyl acetate-hexane, yielding 85 mg 188.

Example 181

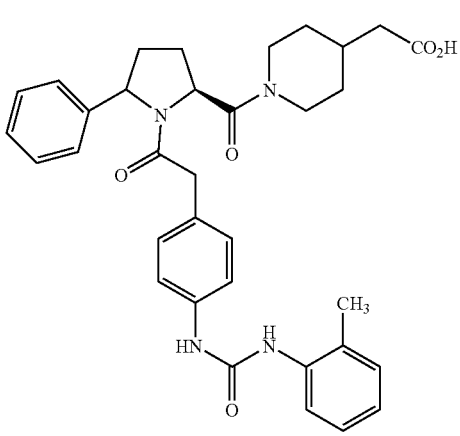

189

1 gram of Tentagel PHB resin (loading 0.29 mmol/gm) was taken up in DMF 25 mL and Fmoc-(4-carboxymethy)-piperidine (318 mg, 0.87 mmol) was added. The resin was shaken for 5 min then DIC (220 mg, 0.27 mL, 1.74 mmol) and DMAP (106 mg, 0.87 mmol) were added and the resin was shaken for 24 hr.

The resin was drained and washed with DMF (3×), $CH_3OH$ (3×) and $CH_2Cl_2$ (3×) then dried under vacuum. The resin gave a negative bromophenylblue test. The resin was taken up in 20% piperidine in DMF and shaken for 4 hr. The resin was drained and washed with DMF (3×), $CH_3OH$ (3×) and $CH_2Cl_2$ (3×) then dried under vacuum. The resin gave a positive bromophenylblue test. The resin was taken up in 25 mL of DMF and Fmoc-L-4-phenylproline (307 mg, 0.87 mmol) was added. The resin was shaken for 5 min then PyBroP (406 mg, 0.87 mmol) and DIEA (123 mg, 0.15 mL, 0.87 mmol) were added and the resin was shaken for 24 hr.

The resin was drained and washed with DMF (3×), $CH_3OH$ (3×) and $CH_2Cl_2$ (3×) then dried under vacuum. The resin gave a negative bromophenylblue test. The resin was taken up in 20% piperidine in DMF and shaken for 4 hr. The resin was drained and washed with DMF (3×), $CH_3OH$ (3×) and $CH_2Cl_2$ (3×) then dried under vacuum. The resin gave a positive bromophenylblue test. The resin was taken up in 25mL of DMF and 4-o-tolylureidophenylacetic acid (247 mg, 0.87 mmol) was added and the resin was shaken for 5 min. PyBroP (406 mg, 0.87 mmol) and DIEA (123 mg, 0.15 mL, 0.87 mmol) was added and the resin shaken for 24 hr.

The resin was drained and washed with DMF (3×), $CH_3OH$ (3×) and $CH_2Cl_2$ (3×) then dried under vacuum. The resin gave a negative bromophenylblue test. The resin was then taken up in 90% TFA in $CH_2Cl_2$ and shaken for 4 hr. The resin was drained and the eluate collected.

The resin was taken up in fresh $CH_2Cl_2$ and shaken for 30 min. The resin was drained and the eluate collected and combined with the first fraction. The solvent was removed under vacuum and the residue was recrystallized from ethyl acetate-hexane, yielding 82 mg 189.

Example 182

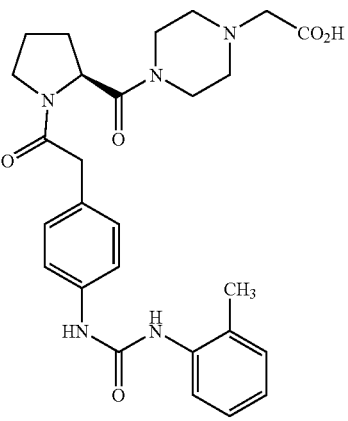

190

1 gram of Tentagel PHB resin (loading 0.29 mmol/gm) was taken up in DMF 25 mL and Fmoc-4-carboxymethyl-piperazine (318 mg, 0.87 mmol) was added. The resin was shaken for 5 min DIC (220 mg, 0.27 mL, 1.74 mmol) and DMAP (106 mg, 0.87 mmol) were added and the resin was shaken for 24 hr.

The resin was drained and washed with DMF (3×), $CH_3OH$ (3×) and $CH_2Cl_2$ (3×) then dried under vacuum. The resin gave a negative bromophenylblue test. The resin was taken up in 20% piperidine in DMF and shaken for 4 hr. The resin was drained and washed with DMF (3×), $CH_3OH$ (3×) and $CH_2Cl_2$ (3×) then dried under vacuum. The resin gave a positive bromophenylblue test. The resin was taken up in 25 mL of DMF and Fmoc-L-proline (294 mg, 0.87 mmol) was added. The resin was shaken for 5 min. then PyBroP (406 mg, 0.87 mmol) and DIEA (123 mg, 0.15 mL, 0.87 mmol) were added and the resin was shaken for 24 hr.

The resin was drained and washed with DMF (3×), $CH_3OH$ (3×) and $CH_2Cl_2$ (3×) then dried under vacuum. The resin gave a negative bromophenylblue test. The resin was taken up in 20% piperidine in DMF and shaken for 4 hr. The resin was drained and washed with DMF (3×), $CH_3OH$ (3×) and $CH_2Cl_2$ (3×) then dried under vacuum. The resin gave a positive bromophenylblue test. The resin was taken up in 25 mL of DMF and 4-o-tolylureidophenyl acetic acid (247 mg, 0.87 mmol) was added and the resin was shaken for 5 min. PyBroP (406 mg, 0.87 mmol) and DIEA (123 mg, 0.15 mL, 0.87 mmol) was added and the resin was shaken for 24 hr.

The resin was drained and washed with DMF (3×), $CH_3OH$ (3×) and $CH_2Cl_2$ (3×) then dried under vacuum. The resin gave a negative bromophenylblue test. The resin was then taken up in 90% TFA in $CH_2Cl_2$ and shaken for 4 hr. The resin was drained and the eluate collected. The resin was taken up in fresh $CH_2Cl_2$ and shaken for 30 min. The resin was drained and the eluate collected and combined with the first fraction. The solvent was removed under vacuum and the residue was recrystallized from ethyl acetate-hexane, yielding 78 mg 190.

Example 183

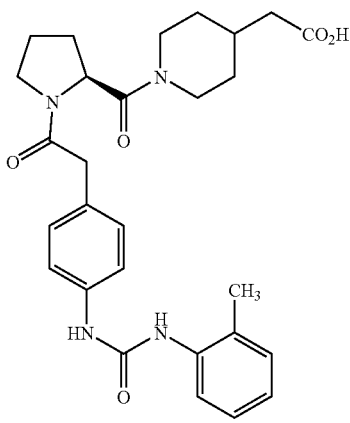

191

1 gram of Tentagel PHB resin (loading 0.29 mmol/gm) was taken up in DMF 25 mL and Fmoc-isonipecotic acid (306 mg, 0.87 mmol) was added. The resin was shaken for 5 min then DIC (220 mg, 0.27 mL, 1.74 mmol) and DMAP (106 mg, 0.87 mmol) were added and the resin was shaken for 24 hr.

The resin was drained and washed with DMF (3×), $CH_3OH$ (3×) and $CH_2Cl_2$ (3×) then dried under vacuum. The resin gave a negative bromophenylblue test. The resin was taken up in 20% piperidine in DMF and shaken for 4 hr. The resin was drained and washed with DMF (3×), $CH_3OH$ (3×) and $CH_2Cl_2$ (3×) then dried under vacuum. The resin gave a positive bromophenylblue test. The resin was taken up in 25 mL of DMF and Fmoc-L-proline (294 mg, 0.87 mmol) was added. The resin was shaken for 5 min then PyBroP (406 mg, 0.87 mmol) and DIEA (123 mg, 0.15 mL, 0.87 mmol) were added and the resin was shaken for 24 hr.

The resin was drained and washed with DMF (3×), $CH_3OH$ (3×) and $CH_2Cl_2$ (3×) then dried under vacuum. The resin gave a negative bromophenylblue test. The resin was taken up in 20% piperidine in DMF and shaken for 4 hr. The resin was drained and washed with DMF (3×), $CH_3OH$ (3×) and $CH_2Cl_2$ (3×) then dried under vacuum. The resin gave a positive bromophenylblue test. The resin was taken up in 25 mL of DMF and 4-o-tolylureidophenyl acetic acid (247 mg, 0.87 mmol) was added and the resin was shaken for 5 min. PyBroP (406 mg, 0.87 mmol) and DIEA (123 mg, 0.15 mL, 0.87 mmol) was added and the resin was shaken for 24 hr.

The resin was drained and washed with DMF (3×), $CH_3OH$ (3×) and $CH_2Cl_2$ (3×) then dried under vacuum. The resin gave a negative bromophenylblue test. The resin was then taken up in 90% TFA in $CH_2Cl_2$ and shaken for 4 hr. The resin was drained and the eluate collected. The resin was taken up in fresh $CH_2Cl_2$ and shaken for 30 min. The resin was drained and the eluate collected and combined with the first fraction. The solvent was removed under vacuum and the residue was recrystallized from ethyl acetate-hexane, yielding 73 mg 191.

Example 184

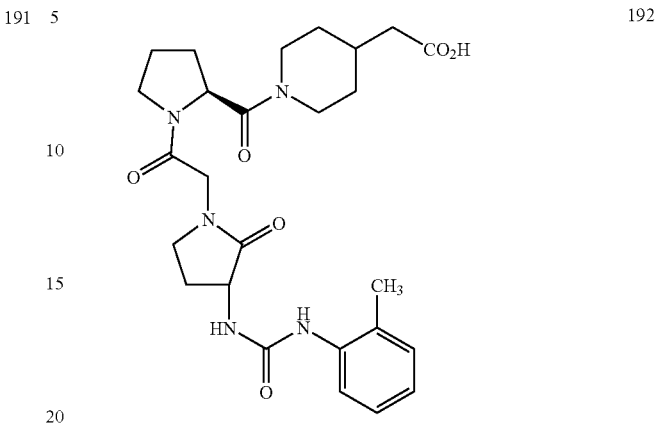

192

1 gram of Tentagel PHB resin (loading 0.29 mmol/gm) was taken up in DMF 25 mL and Fmoc-(4-carboxymethy)-piperidine (318 mg, 0.87 mmol) was added. The resin was shaken for 5 min then DIC (220 mg, 0.27 mL, 1.74 mmol) and DMAP (106 mg, 0.87 mmol) were added and the resin was shaken for 24 hr.

The resin was drained and washed with DMF (3×), $CH_3OH$ (3×) and $CH_2Cl_2$ (3×) then dried under vacuum. The resin gave a negative bromophenylblue test. The resin was taken up in 20% piperidine in DMF and shaken for 4 hr. The resin was drained and washed with DMF (3×), $CH_3OH$ (3×) and $CH_2Cl_2$ (3×) then dried under vacuum. The resin gave a positive bromophenylblue test. The resin was taken up in 25 mL of DMF and Fmoc-L-proline (294 mg, 0.87 mmol) was added. The resin was shaken for 5 min. then PyBroP (406 mg, 0.87 mmol) and DIEA (123 mg, 0.15 mL, 0.87 mmol) were added and the resin was shaken for 24 hr.

The resin was drained and washed with DMF (3×), $CH_3OH$ (3×) and $CH_2Cl_2$ (3×) then dried under vacuum. The resin gave a negative bromophenylblue test. The resin was taken up in 20% piperidine in DMF and shaken for 4 hr. The resin was drained and washed with DMF (3×), $CH_3OH$ (3×) and $CH_2Cl_2$ (3×) then dried under vacuum. The resin gave a positive bromophenylblue test. The resin was taken up in 25 mL of DMF and Fmoc-3-amino-2-oxo-1-pyrrolidineacetate (331 mg, 0.87 mmol) was added and the resin was shaken for 5 min. PyBroP (406 mg, 0.87 mmol) and DEA (123 mg, 0.15 mL, 0.87 mmol) was added and the resin was shaken for 24 hr.

The resin was drained and washed with DMF (3×), $CH_3OH$ (3×) and $CH_2Cl_2$ (3×) then dried under vacuum. The resin gave a negative bromophenylblue test. The resin was taken up in 20% piperidine in DMF and shaken for 4 hr. The resin was drained and washed with DMF (3×), $CH_3OH$ (3×) and $CH_2Cl$ (3×) then dried under vacuum. The resin gave a positive bromophenylblue test. The resin was taken up in $CH_2Cl_2$ and o-tolyl isocyanate (193 mg, 1.45 mmol, 0.18 mL) was added. The resin was shaken for 24 hr.

The resin was drained and washed with DMF (3×), $CH_3OH$ (3×) and $CH_2Cl_2$ (3×) then dried under vacuum. The resin gave a negative bromophenylblue test. The resin was then taken up in 90% TFA in $CH_2Cl_2$ and shaken for 4 hr. The resin was drained and the eluate collected. The resin was taken up in fresh $CH_2Cl_2$ and shaken for 30 min. The resin was drained and the eluate collected and combined with the

Example 185

193

In a 250 mL round-bottomed flask was placed o-tolyl-isothiocyanate (10.0 g, 67.1 mmol) in 150 mL of $CH_2Cl_2$. This solution was cooled to minus 78° C. and ammonia gas (excess) was bubbled through for ~10 min. A precipitate immediately formed and was found to be the desired product o-tolylthiourea. The reaction mixture was filtered and the solid collected by washing thoroughly with cooled $CH_2Cl_2$. The white solid was dried under vacuum to provide 10.12 g (92% yield) of the desired o-tolylthiourea.

The o-tolylthiourea (10.12 g, 61 mmol) was then methylated by addition of methyl iodide (9.1 g, 62 mmol) in anhydrous methanol (100 mL). The reaction was stirred at room temp for 6 hr and then concentrated in vacuo. The residue was poured into aqueous ammonium chloride and extracted 3× with EtOAc. The combined organics were dried and concentrated in vacuo to give 8.7 g (84% yield) of 2-methyl-2-thio-o-tolylpseudourea. The pseudourea (8.7 g, 51 mmol) was dissolved in methanol (100 mL) and piperidine (8.7 g, 102 mmol) at room temp. The mixture was stirred overnight and then concentrated in vacuo to afford 9.2 g of the product ester as a pale yellow solid. This solid was saponified with LiOH to give 9.0 g of the desired final carboxylic acid 193.

Example 186

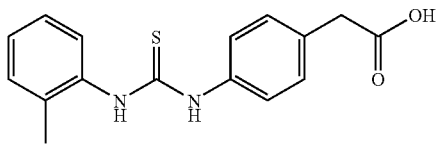

194

Methyl-4-aminophenylacetate (4.0 g, 25 mmol) was dissolved in $CH_2Cl_2$ (100 mL) and to this solution was added o-tolylisothiocyante (3.7 g, 25 mmol). The reaction mixture was heated to reflux for 4 hr and then cooled to room temp. The solution was poured in to 1 N HCl and then extracted 3× with EtOAc, dried over $MgSO_4$, and concentrated in vacuo to afford 5.2 g (67% yield) of thiourea methyl ester. The ester was saponified using LiOH to give 5.0 g of the desired 4-(o-tolylthioureido)phenylacetic acid 194.

Example 187

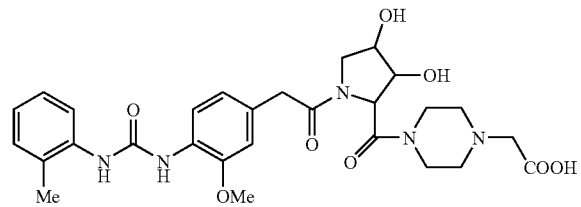

195

A solution of ethyl 4-[1-[3-methoxy-4-[N'-(2-methylphenyl)ureido]phenylacetyl]-(2S,3R, 4R)-3,4-isopropylidenedioxy-2-pyrrolidinylcarbonyl]-1-piperazinylacetate (1.27 g, 1.99 mmol) in sat. HCl (gas)-MeOH (20 mL) was stirred at room temp. for 2 hr, and MEOH was evaporated off. The residue was taken up with sat. $NaHCO_3$ solution, and extracted with $CHCl_3$-MeOH (4:1, v/v). The extracts were washed with brine, dried over $MgSO_4$, and concentrated to dryness. Chromatography of the residue with $CHCl_3$-MEOH (5:1, v/v) as eluent gave ethyl 4-[1-[3-methoxy-4-[N'-(2-methylphenyl)ureido]phenylacetyl]-(2S,3R, 4R)-3,4-dihydroxy-2-pyrrolidinyl carbonyl]-1-piperazinylacetate (990 mg, 83%) as a yellow amorphous solid. IR (KBr) 3338, 2937, 2830, 1743, 1625, 1600, 1532, 1454 cm$^{-1}$; $^1$H-NMR ($CDCl_3$) d 1.25 (t, J=7.1 Hz, 3H), 2.20 (s, 3H), 2.46–2.56 (m, 4H), 3.15 (s, 2H), 3.40–3.72 (m, 9H), 3.62 (s, 3H), 4.01–4.08 (m, 2H), 4.16 (q, J=7.1 Hz, 2H), 4.22 (m, 1H), 4.72 (d, J=2.9 Hz, 1H), 6.68 (d, J=7.6 Hz, 1H), 6.72 (s, 1H), 7.06 (t, J=7.6 Hz, 1H), 7.15–7.18 (m, 3H), 7.52–7.56 (m, 2H), 7.90 (d, J=8.3 Hz, 1H); MS (FAB) m/z 598 (M$^+$+1).

To a solution of ethyl 4-[1-[3-methoxy-4-[N'-(2-methylphenyl)ureido]phenylacetyl]-(2S, 3R, 4R)-3,4-dihydroxy-2-pyrrolidinylcarbonyl]-1-piperazinylacetate (870 mg, 1.46 mmol) in THF (15 mL) was added 0.25 N NaOH (7.00 mL, 1.75 mmol). After being stirred at room temp. for 3.5 hr, the reaction mixture was concentrated. The residue was diluted with water and neutralized with 1 N HCl at 0° C. The mixture was concentrated and purified by ion-exchanged resin (HP-20, Mitsubishi Chemical) to give 195 (645 mg, 78%) as a colorless amorphous solid. IR (KBr) 3330, 2937, 1627, 1535, 1454 cm$^{-1}$; $^1$H NMR (DMSO-d$_6$) d 2.25 (s, 3H), 2.38 (m, 1H), 2.42–2.58 (m, 2H), 2.64 (m, 1H), 3.01 (s, 2H), 3.13–3.71 (m, 8H), 3.88 (s, 3H), 3.89 (m, 1H), 4.05 (m, 1H), 4.58 (d, J=3.2 Hz, 1H), 6.76 (dd, J=8.3, 1.5 Hz, 1H), 6.91–6.95 (m, 2H), 7.10–7.16 (m, 2H), 7.79 (d, J=8.3 Hz, 1H), 8.00 (d, J=8.3 Hz, 1H), 8.49 (s, 1H), 8.57 (s, 1H); MS (FAB) m/z 570 (M$^+$+1); Anal. Calcd for $C_{28}H_{35}N_5O_8 \cdot 2.75H_2O$: C, 54.32; H, 6.59; N, 11.31. Found: C, 54.07; H, 6.11; N, 11.00.

Example 188

196

To a suspension of 2-amino-4-thiazoleacetic acid (4 g, 25 mmol) in 1:1 CH$_2$Cl:acetone (100 mL) was added o-tolylisocyanate (3.5 g, 26 mmol). The mixture was heated to reflux for 8 hr at which time a yellow precipitate had formed. the precipitate was filtered and the solid washed generously with 1:1 CH$_2$Cl$_2$:acetone. The solid was recrystallized with hot methanol and dried under vaccum to yield 4.8 g (66% yield) of the desired 2-(o-tolylureido)-4-thiazoleacetic acid 196.

Example 189

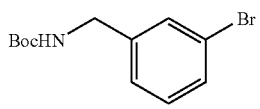
197

In a round bottom flask, 3-bromobenzyl amine (3.00 g, 16.13 mmole) was dissolved in dioxane-water (1:1) and solid Na$_2$CO$_3$ was added till the pH was 8–9. Boc$_2$O (3.87 g, 17.74 mmole) was added and the reaction was stirred for 12 hr at room temp. The reaction mixture was poured into 1 N HCl and the aqueous layer was extracted 3× with ethyl acetate. The combined organic layers were then washed with water, brine then dried over anhydrous MgSO$_4$. The solution was filtered and the solvent was removed under reduced pressure. The product was purified by flash chromatography. (4:1 hexane-ethyl acetate) Yield 4.39 g 197.

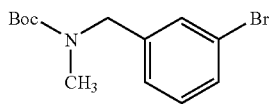
198

The Boc-protected benzyl amine (2.00 g, 6.99 mmole) was dissolved in dry THF under argon. The reaction was cooled to minus 78° C. Lithium bis(trimethylsilyl)amide (13.98 mL, 13.98 mmole) was added over 10 min. The reaction was stirred for one hr at minus 78° C. then iodomethane (1.98 g, 13.98 mmole, 0.87 mL) was added rapidly. The reaction was allowed to slowly warm to room temp and stir overnight. The reaction was poured into 1 N HCl and the aqueous layer was extracted 3× with ethyl acetate. The solution was filtered and the solvent was removed under reduced pressure. The product was isolated by flash chromatography. (7:1 hexane-ethyl acetate) Yield 1.68 g 198.

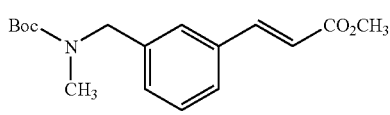
199

In a pressure tube was placed the Boc-protected 3-bromobenzyl methylamine (1.68 g, 5.60 mmole). The tube was then charged with DMF, sodium acetate (0.51 g 6.16 mmole), P(o-tolyl)$_3$ (0.51 g, 6.16 mmole), and Pd(OAc)$_2$ (0.25 g, 1.12 mmole) The tube was flushed with argon for 10 min then methyl acrylate (0.53 g, 0.53 mmole, 0.55 mL) was added. The tube was sealed and heated to 135° C. for 24 hr. The reaction was cooled to 0° C. and the tube was slowly opened. The solution was poured into 1 N HCl and the aqueous layer was extracted 3× with ethyl acetate. The combined organic layers were washed with water, brine then dried over MgSO$_4$. The solution was filtered and the solvent was removed under reduced pressure. The product was isolated by flash chromatography. (6:1 hexane-ethyl acetate) Yield 1.60 g 199.

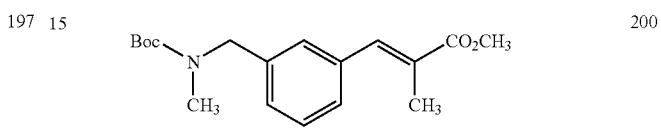
200

In a pressure tube was placed the Boc-protected 3-bromobenzyl methylamine (1.00 g, 3.33 mmole). The tube was then charged with DMF, sodium acetate (0.30 g, 3.36 mmole), P(o-tolyl)$_3$(0.20, 0.66 mmole), and Pd(OAc)$_2$ (0.15 g, 0.66 mmole). The tube was flushed with argon for 10 min then methyl methacrylate (0.37 g, 3.66 mmole, 0.39 mL) was added. The tube was sealed and heated to 135° C. for 24 hr; The reaction was cooled to 0° C. and the tube was slowly opened. The solution was poured into 1 N HCl and the aqueous layer was extracted 3× with ethyl acetate. The combined organic layers were washed with water, brine then dried over MgSO$_4$. The solution was filtered and the solvent was removed under reduced pressure. The product was isolated by flash chromatography. (6:1 hexane-ethyl acetate) Yield 1.01 g 200.

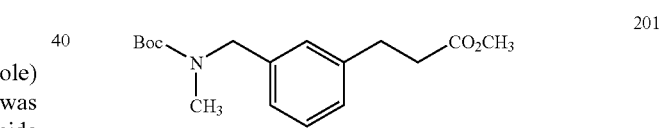
201

The α, β-unsaturated ester (1.60 g, 5.49 mmole) was placed in a Paar vessel and dissolved in ethyl acetate. Pd/C (0.3 g) was added and the vessel was pressured to 50 psi with H$_2$. The vessel was agitated for 12 hr. The Paar vessel was flushed with argon and the catalyst was removed by filtration through celite. The solvent was removed under reduced pressure. Yield 1.60 g 201.

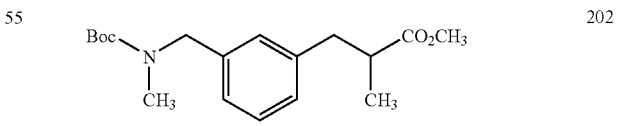
202

The α-methyl-, β-unsaturated ester (1.01 g, 3.16 mmole) was placed in a Paar vessel and dissolved in ethyl acetate. Pd/C was added and the vessel was pressured to 50 psi with H$_2$. The vessel was agitated for 12 hr. The Paar vessel was flushed with argon and the catalyst was removed by filtration through celite. The solvent was removed under reduced pressure. Yield 996.41 mg 202.

203

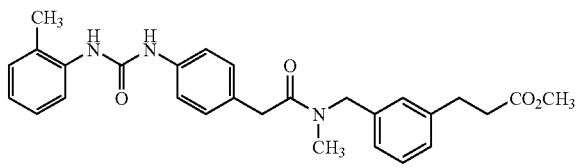

The Boc ester (304 mg, 1.04 mmole) was taken up in CH$_2$Cl$_2$ and excess trifluoroacetic acid was added. The reaction was then stirred for 2 hr. The solvent was removed and the residue was taken up. in ethyl acetate and washed with sat. NaHCO$_3$ solution. The organic layer was washed with water, brine then dried over Na$_2$SO$_4$. The solution was filtered and the solvent was removed under reduced pressure. The residue was taken up in CH$_2$Cl$_2$-DMF and HOBt (154.30 mg, 1.14 mmole), 4-[N'-(o-tolylurea)-phenylacetic acid (324.11 mg, 1.14 mmole) and EDCI (218.53 mg, 1.14 mmole) were added. The reaction was stirred for 24 hr. The solution was poured into 1 N HCl and the aqueous layer was extracted 3× with ethyl acetate. The combined organic layers were washed with water, brine then dried over MgSO$_4$. The solution was filtered and the solvent was removed under reduced pressure. The product was isolated by flash chromatography. (ethyl acetate) Yield 380.32 mg 203.

204

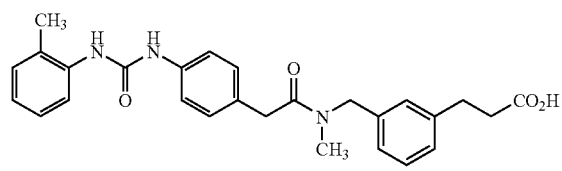

The ester (380.32 mg, 0.80 mmole) was taken up in ethanol-water (4:1) and NaOH was added. The reaction was then heated to 50° C. for 2 hr. The TLC (ethyl acetate) showed no starting material present. The reaction was cooled to room temp. The solution was poured into 1 N HCl and the aqueous layer was extracted 3× ethyl acetate. The combined organic layers were washed with water, brine then dried over MgSO$_4$. The solution was filtered and the solvent was removed under reduced pressure. The residue was recrystallized from ethyl acetate-hexane. Yield 319.40 mg 204.

Example 190

205

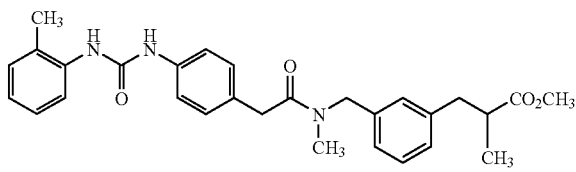

The Boc ester (209.60, 0.65 mmole) was taken up in CH$_2$Cl$_2$ and excess trifluoroacetic acid was added. The reaction was then stirred for 2 hr. The solvent was removed and the residue was taken up in ethyl acetate and washed with sat. NaHCO$_3$ solution. The organic layer was washed with water, brine then dried over Na$_2$SO$_4$. The solution was filtered and the solvent was removed under reduced pressure. The residue was taken up in CH$_2$Cl$_2$-DMF and HOBt (97.45 mg, 0.72 mmole), 4-[N'-(o-tolylurea)-phenylacetic acid (204.70 mg, 0.72 mmole) and EDCI (138.03 mg, 0.72 mmole) were added. The reaction was stirred for 24 hr. The solution was poured into 1 N HCl and the aqueous layer was extracted 3× with ethyl acetate. The combined organic layers were washed with water, brine then dried over MgSO$_4$. The solution was filtered and the solvent was removed under reduced pressure. The product was isolated by flash chromatography. (ethyl acetate) Yield 237.8 mg 205.

206

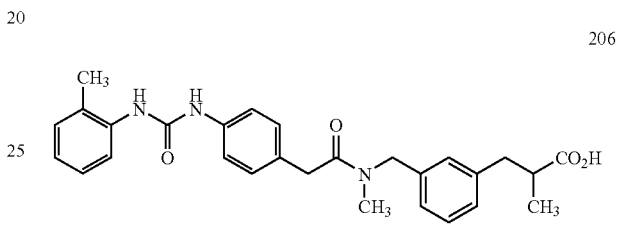

The ester (237.8 mg, 0.49 mmole) was taken up in ethanol-water (4:1) and NaOH added. The reaction was heated to 50° C. for 2 hr. The TLC (ethyl acetate) showed no starting material present. The reaction was cooled to room temp. The solution was poured into 1 N HCl and the aqueous layer was extracted 3× with ethyl acetate. The combined organic layers were washed with water, brine then dried over MgSO$_4$. The solution was filtered and the solvent was removed under reduced pressure. The residue was recrystalized from ethyl acetate-hexane. Yield 207.8 mg 206.

Example 191

207

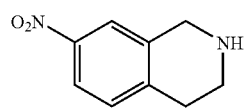

The 1,2,3,4-tetrahydroisoquinoline (12.20 g, 91.60 mmole) was taken up in H$_2$SO$_4$(40 mL) and cooled to minus 10° C. Concentrated HNO$_3$ (9.0 mL) was slowly added to the solution while maintaining the internal temp at minus 10° C. On completion of the addition the reaction was allowed to stand and slowly warm to room temp over 12 hr. The reaction mixture was slowly added to ice and the aqueous solution was basified with NH$_4$OH. The aqueous layer was extracted 4 times with CHCl$_3$. The combined organic layers were washed with water then dried over Na$_2$SO$_4$. The solution was filtered and the solvent was removed under reduced pressure. The resulting brown oil was taken up in ethanol and concentrated HCl was added. The resulting white solid was collected by filtration and dried under vacuum. Yield 8.0 g 207.

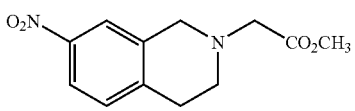
208

The 6-nitro-1,2,3,4-tetrahydroisoquinoline (1.00 g, 5.61 mmole) was taken up in ethanol. Methyl bromoacetate (0.86 g, 5.61 mmole, 0.53 mL) and triethylamine (1.17 g, 11.59 mmole, 1.62 mL) were then added and the mixture was heated to reflux for 5 hr. The solution was cooled to room temp and the solution was concentrated under vacuum. The solution was added to water and the aqueous layer was extracted 3× with ethyl acetate. The combined organic layers were dried over $Na_2SO_4$, filtered and the solvent was removed under reduced pressure. The product was isolated by flash chromatography (3:1 hexane-ethyl acetate). Yield 702 mg 208.

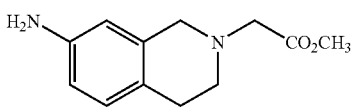
209

The above ester (702 mg, 2.81 mmole) was placed in a Paar vessel and dissolved in ethanol. Pd/C (100 mg) was added and the vessel was pressured to 50 psi with $H_2$. The vessel was agitated for 24 hr. The Paar vessel was flushed with argon and the catalyst was removed by filtration through celite. The solvent was removed under reduced pressure. 1H-NMR showed only desired product. Yield 587 mg 209.

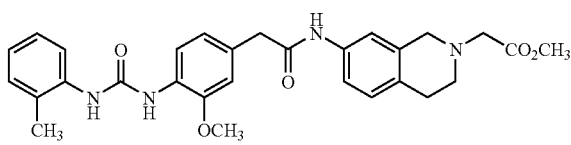
210

The aniline (587.0 mg, 2.66 mmole) was taken up in dry $CH_2Cl_2$ and pyridine under argon. The reaction was cooled to 0° C. A $CH_2Cl_2$ solution of 3-methoxy-4-(N'phenylureido) phenylacetyl chloride (837.70 mg, 2.66 mmole) was added over 5 min. The reaction was then allowed to warm to room temp and stir overnight. The reaction mixture was then poured into 1 N HCl and the aqueous layer was extracted 3× with ethyl acetate. The combined organic layers were then washed with sat. $NaHCO_3$, water, brine then dried over $MgSO_4$. The solution was filtered and the solvent was removed under reduced pressure. The product was isolated by flash chromatography (ethyl acetate). Yield 618.36 mg 210.

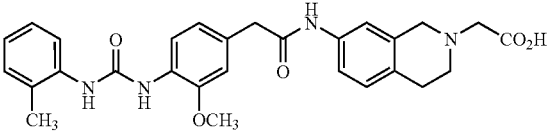
211

The methyl ester (618.36 mg, 1.20 mmole) above was taken up in $THF-H_2O$ and LiOH (558.07 mg, 13.30 mmole) was added. The reaction mixture was stirred at room temp for 24 hr. The reaction was poured into 1 N HCl and the aqueous layer was extracted 3× with ethyl acetate. The combined organic layers were then washed with water, brine then dried over $MgSO_4$. The solution was filtered and the solvent was removed under reduced pressure. The product was purified by recrystallization. (hexane-ethyl acetate). Yield 600 mg 211.

Example 192

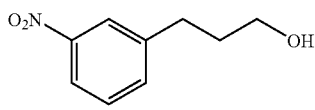
212

The 3-nitro-phenyl propionic acid (1.00 g, 5.12 mmole) was taken up in dry THF under argon. The reaction was cooled to 0° C. and $BH_3$-THF (1.0M, 15.37 mmole, 15.37 mL) was added over 10 min. The reaction was stirred at 0° C. for 1 hr then slowly quenched with water. The solution was slowly warmed to room temp then poured into 1 N HCl. The aqueous layer was extracted 3× with ethyl acetate. The combined organic layers were then washed with sat. $NaHCO_3$, water, brine then dried over $MgSO_4$. The solution was filtered and the solvent was removed under reduced pressure. The product was isolated by flash chromatography (1:1 hexane-ethyl acetate) Yield 909.0 mg 212.

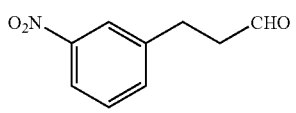
213

The 3-nitro-phenyl propanol (909.0 mg, 5.02 mmole) was taken up in dry $CH_2Cl_2$. In a second round bottom flask $(COCl)_2$ (700.65 mg, 5.52 mmole, 0.48 mL) was added to dry $CH_2Cl_2$ under argon. The $(COCl)_2$—$CH_2Cl_2$ solution was then cooled to minus 60° C. and DMSO (862.56 mg, 11.4 mmole, 0.78 mL) was slowly added. The reaction was stirred at minus 60° C. for 5 min then the alcohol solution was added via a cannula over 5 min. The reaction mixture was stirred at minus 60° C. for 1 hr then Et3 N (2.54 g, 25.10 mmole, 3.50 mL) was added and the reaction was allowed to slowly warn to room temp. The reaction was poured into 1 N HCl and the aqueous layer was extracted 3× with ethyl acetate. The combined organic layers were washed with sat.

NaHCO$_3$, water, brine then dried over MgSO$_4$. The solution was filtered and the solvent was removed under reduced pressure. H1-NMR showed no starting material present. The aldehyde 213 was used as is without further purification.

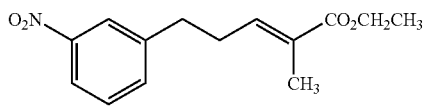
214

In a round bottom flask NaH (132.48 mg, 5.52 mmole) was slurried in dry. THF under argon. Triethyl 2-phosphonopropionate (1.31 g, 5.52 mmole, 1.18 mL) dissolve in dry THF was added slowly via a syringe. The reaction mixture was stirred for 30 min at room temp. The above aldehyde, dissolved in dry THF under argon, was added to the phosphonate solution via syringe over 10 min. The reaction mixture was stirred for 12 hr. The reaction was poured into 1 N HCl and the aqueous layer was extracted 3× with ethyl acetate. The combined organic layers were washed with sat. NaHCO$_3$, water, brine then dried over MgSO$_4$. The solution was filtered and the solvent was removed under reduced pressure. The product was isolated by flash chromatography. (1:1 ethyl acetate-hexane) Yield 992.0 mg 214.

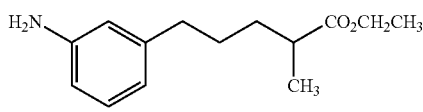
215

The above α,β-unsaturated ester (992.0 mg, 3.77 mmole) was placed in a Paar vessel and dissolved in ethanol. The vessel was flushed with argon and Pd/C (200.0 mg) was added. The argon atmosphere was replaced with H$_2$ at 50 psi. The Paar vessel was then shaken for 12 hr. The hydrogen was flushed from the vessel with argon and the catalyst was removed by filtration through celite. The solvent was removed under reduced pressure. 1H-NMR showed only the desired product. Yield 851.2 mg 215.

The above aniline (850.0 mg, 3.61 mmole) was taken up in dry CH$_2$Cl$_2$ and pyridine under argon. The reaction was cooled to 0° C. A CH$_2$Cl$_2$ solution of 3-methoxy-4-(N'phenylureido) phenylacetyl chloride (1.14 g, 3.61 mmole) was added over 5 min. The reaction was then allowed to warm to room temp and stir overnight. The reaction mixture was then poured into 1 N HCl and the aqueous layer was extracted 3× with ethyl acetate. The combined organic layers were then washed with sat. NaHCO$_3$, water, brine then dried over MgSO$_4$. The solution was filtered and the solvent was removed under reduced pressure. The product was isolated by flash chromatography (ethyl acetate) Yield 576.0 mg 216.

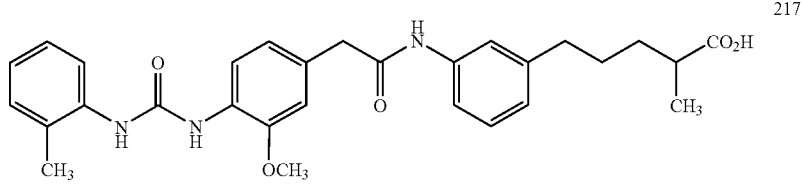
217

The above ethyl ester (576.0 mg, mmole) was taken up in ethanol-water and NaOH was added. The reaction mixture was heated to 50° C. for 2 hr. The reaction was cooled to room temp and then poured into 1 N HCl. The aqueous layer was extracted 3× times with ethyl acetate. The combined organic layers were then washed with water, brine then dried over MgSO$_4$. The solution was filtered and the solvent was removed under reduced pressure. The product was purified by Sep-Pak column. Yield 534 mg 217.

Example 193

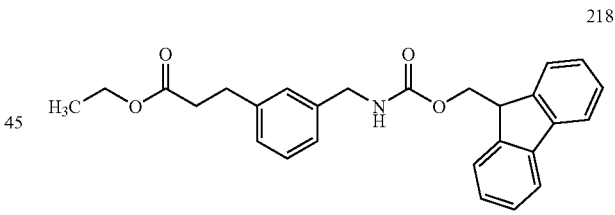
218

One gram of Wang resin (tentagel S-PHB 0.3 mmole loading) was suspended in a solution of 3-(Fmoc-amino) phenylpropionic acid (361.31 mg, 0.90 mmole), DMAP (109.95 mg, 0.90 mmole), HOBt 243.63 mg, 0.90 mmole), and DIC (227.16 mg, 1.80 mmole, 0.28 mL) in a mixture of DMF and CH$_2$Cl$_2$. The mixture was shaken for 20 hr and

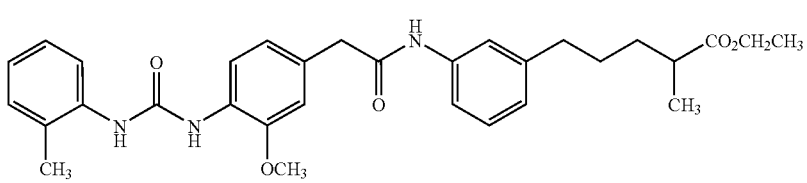
216 drained. The resin 218 was washed with DMF, MeOH, CH₂Cl₂ and dried under reduced pressure.

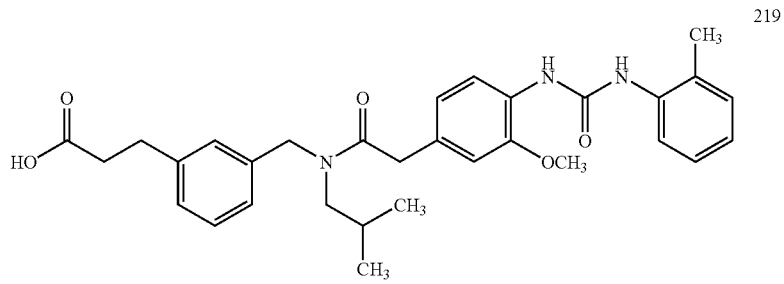

To the above resin (500 mg, 0.15 mmole) was added a solution of piperidine-DMF (50% v/v, 4 mL) and the mixture was shaken for 4 hr. The resin was washed with DMF, MeOH, CH₂Cl₂. To the resin was added TMOF and isobutrylaldehyde (108.17 mg, 1.50 mmole, 0.14 mL). The mixture was shaken for 4 hr. The resin was drained and fresh TMOF and isobutrylaldehyde was added. The mixture was then shaken for 12 hr. The resin was drained and taken up in MeOH-1% AcOH and NaCNBH₃ (150.0 mg, 2.39 mmole) was added. The resin was shaken for 6 hr. The resin was drained and washed with MeOH, MeOH-Et₃N, MeOH, DMF, CH₂Cl₂. The resin was taken up in DMF and 3-methoxy-4-(N'-phenylureido)phenylacetic acid (141.45 mg, 0.45 mmole), PyBrop (209.78 mg, 0.45 mmole), and DIEA (58.16 mg, 0.45 mmole, 0.08 mL) were added. The resin was then shaken for 24 hr then drained. The resin was washed with DMF, MeOH, CH₂Cl₂. To the resin was added a solution of TFA in CH₂Cl₂ (30% v/v 3 mL) and the mixture was shaken for 5 hr. The mixture was filtered and the filtrate was concentrated in vacuo. The residue was purified by Sep-Pak column. After removal of the solvent, Et₂O was added to the residue and the solid was collected to afford 15 mg 219 as a crystalline solid.

Example 194

Tentagel PHB resin (1.0 g, loading 0.29 mmole/gm) was taken up in 25 mL of DMF and 6-bromohexanoic acid (169 mg, 0.87 mmol) was added. The resin was shaken for 5 min then DIC (220 mg, 0.27 mL, 1.74 mmoles) and DMAP (35 mg, 0.29 mmole) were added and the resin was shaken for 14 hr. The resin was drained and washed with DMF (3×), CH₃OH (3×) and CH₂Cl₂ (3×) then dried under vacuum.

To this resin was added 2,2-dimethyl-1,3-dioxolane-4-methanamine (227 mg, 1.74 mmol) and lithium iodide (232 mg, 1.74 mmol) in 15 mL of DMF. The resins was shaken for 14 hr at room temp. The resin was drained and washed with DMF (3×), CH₃OH (3×) and CH₂Cl₂ (3×) then dried under vacuum. The resin gave a positive bromophenylblue test.

The resin was taken up in 25 mL of DMF and 4-o-tolylureido-3-methoxyphenylacetic acid (247 mg, 0.87 mmole) was added and the resin was shaken for 5 min. PyBrOP (406 mg, 0.87 mmole) and DIEA (123 mg, 0.15 mL, 0.87 mmole) was added and the resin was shaken for 14 hr. The resin was drained and washed with DMF (3×), CH₃OH (3×) and CH₂Cl₂ (3×) then dried under vacuum. The resin gave a negative bromophenylblue test.

The resin was then taken up in 90% TFA in CH₂Cl₂ and shaken for 4 hr. The resin was drained and the elutant

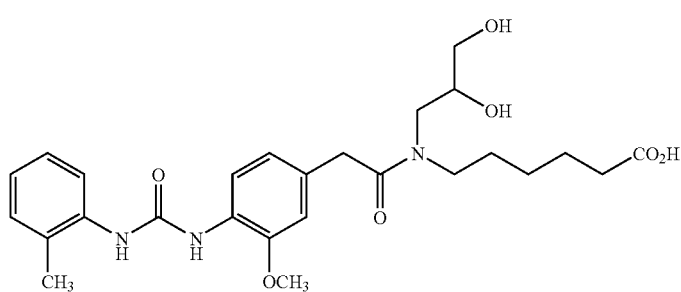

collected. The resin was taken up in fresh CH$_2$Cl$_2$ and shaken for 30 min. The resin was drained and the elutant collected and combined with the first fraction. The solvent was removed under vacuum and the residue was recrystallized from ethyl acetate-hexane, yield 56 mg 220.

Example 195

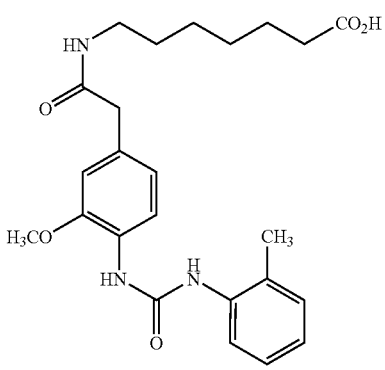
221

1 gram of Tentagel PHB resin (loading 0.29 mmole/gm) was taken up in DMF 25 mL and Fmoc-7-aminoheptanoic acid (319 mg, 0.87 mmole) was added. The resin was shaken for 5 min then DIC (220 mg, 0.27 mL, 1.74 mmol) and DMAP (106 mg, 0.87 mmole) were added and the resin was shaken for 24 hr. The resin was drained and washed with DMF (3×), CH$_3$OH (3×) and CH$_2$Cl$_2$ (3×) then dried under vacuum. The resin gave a negative bromophenylblue test. The resin was taken up in 20% piperidine in DMF and shaken for 4 hr. The resin was drained and washed with DMF (3×), CH$_3$OH (3×) and CH$_2$Cl$_2$ (3×) then dried under vacuum. The resin gave a positive bromophenylblue test.

The resin was taken up in 25 mL of DMF and 4-o-tolylureido-3-methoxyphenylacetic acid (247 mg, 0.87 mmole) was added and the resin was shaken for 5 min. PyBrOP (406 mg, 0.87 mmole) and DIEA (123 mg, 0.15 mL, 0.87 mmole) was added and the resin was shaken for 14 hr. The resin was drained and washed with DMF (3×), CH$_3$OH (3×) and CH$_2$Cl$_2$ (3×) then dried under vacuum. The resin gave a negative bromophenylblue test.

The resin was then taken up in 90% TFA in CH$_2$Cl$_2$ and shaken for 4 hr. The resin was drained and the elutant collected. The resin was taken up in fresh CH$_2$Cl$_2$ and shaken for 30 min. The resin was drained and the elutant collected and combined with the first fraction. The solvent was removed under vacuum and the residue was recrystallized from ethyl acetate-hexane, yield 66 mg 221.

Example 196

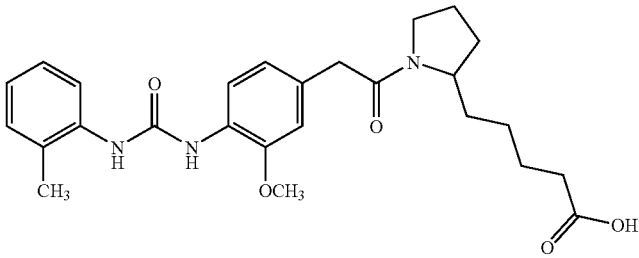
222

To a solution of oxalyl chloride (3.8 g, 30 mmol) in CH$_2$Cl$_2$ (100 mL) was added DMSO (2.4 g, 31 mmol) dropwise over 30 min at minus 78° C. To this solution was added N-Boc-prolinol (5.0 g, 25 mmol) dropwise over 15 min. The reaction was stirred at minus 78° C. for 3 hr and then quenched by the cold addition of 1 N HCl, extracted 3× with EtOAc, dried, and concentrated in vacuo to afford the crude prolinal which was chromatographed (25% EtOAc/hexanes) to yield 3.8 g of the desired product.

A solution of Methyl (triphenylphosphoranylidene)butanoate (6.9 g, 19 mmol) in THF (100 mL) was generated. LiHMDS (10 mL of a 2.0M soln, 20 mmol) was added at minus 78° C. and then stirred for 1 hr. The above prolinal (3.8 g, 19 mmol) was then added in one portion and the mixture was allowed to warm to room temp over 4 hr. The reaction was quenched by the addition of 1 N HCl, extracted 3× with EtOAc, dried, and concentrated in vacuo to afford the crude alkene which was chromatographed (25% EtOAc/hexanes) to yield 2.9 g of he desired product.

Hydrogenation of the alkene was performed by placing the alkene (2.9 g, 10 mmol) in ethanol (20 mL) and adding a catalytic amount of 10% Pd/C followed by Parr hydrogenation at 40 psi for 4 hr, the resulting alkane was used without purification. The Boc group was removed by the addition of 1:1 TFA/CH$_2$Cl$_2$ at room temp. The reaction was stirred for 2 hr and the solvent was removed in vacuo. The crude amine 1.9 g was used without further purification.

A solution of the above free amine (1.9 g, 10 mmol) in CH$_2$Cl$_2$ (100 mL) was generated. To this solution was added EDCI (2.95 g, 10 mmol), DMAP (1.2 g, 10 mmol), and 4-o-tolylureido-3-methoxyphenylacetic acid (3.15 g, 10 mmol) at room temp. The reaction mixture was stirred for 4 hr and then quenched by the addition of 1 N HCl, extracted 3× with EtOAc, dried, and concentrated in vacuo. The crude amide was chromatographed (5% MeOH/CH$_2$Cl$_2$) to yield 1.95 g of the desired product.

The ester (1.95 g, 4.2 mmol) was taken up in 1:1 THF-H$_2$O and LiOH was added at room temp. The reaction mixture was then stirred for 3 hr. The solution was poured into 1 N HCl and the aqueous layer was extracted 3× with EtOAc. The combine organic layers were washed with water, brine and dried over anhydrous magnesium sulfate. The solution was filtered and the solvent removed under reduced pressure. The solid was then triturated with cold ether to give 1.65 g of the desired carboxylic acid 222.

Example 197

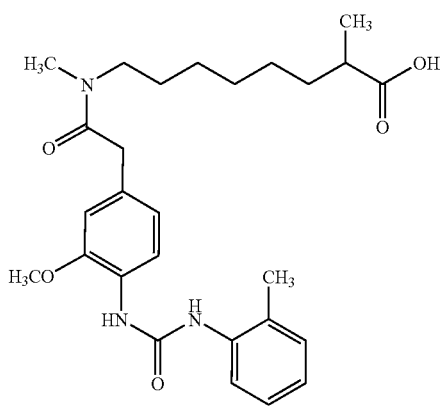

223

To a solution of methyl 8-aminooctanoate (2.0 g, 12 mmol) in 1:1 dioxane:water (100 mL) was added Boc anhydride (2.8 g, 13 mmol) and K$_2$CO$_3$ (10 g). This solution was allowed to stir at room temp for 14 hr. The reaction was then poured onto 1 N HCl, extracted 3× with EtOAc, dried, and concentrated in vacuo. The crude carbamate was chromatographed (50% EtOAc/hexanes) to yield 2.7 g of the desired product.

The Boc-protected amine was methylated by placing it in THF (75 mL), followed by the addition of LiHMDS (25 mL of a 2.0M soln., 50 mmol) at minus 78° C., this solution was then stirred for 30 min and methyl iodide (7.2 g, 50 mmol) was added in one portion the reaction mixture was allowed to warm to room temp overnight. The reaction was quenched by the addition of 1 N HCl, extracted 3× with EtOAc, dried, and concentrated in vacuo. The crude methylated carbamate was chromatographed (50% EtOAc/hexanes) to yield 1.9 g of the desired dimethyl product.

The Boc group was removed by the addition of 1:1 TFA/CH$_2$Cl$_2$ at room temp. The reaction was stirred for 2 hr and the solvent was removed in vacuo. The crude amine 900 mg was used without further purification.

A solution of the above free amine (900 mg, 4.5 mmol) in CH$_2$Cl$_2$ (100 mL) was generated. To this solution was added EDCI (1.33 g, 4.5 mmol), DMAP (567 mg, 4.5 mmol), and 4-o-tolylureido-3-methoxyphenylacetic acid (1.45 g, 4.6 mmol) at room temp. The reaction mixture was stirred for 4 hr and then quenched by the addition of 1 N HCl, extracted 3× with EtOAc, dried, and concentrated in vacuo. The crude amide was chromatographed (5% MeOH/CH$_2$Cl$_2$) to yield 1.2 g of the desired product.

The ester (1.2 g, 2.4 mmol) was taken up in 1:1 THF-H$_2$O and LiOH was added at room temp. The reaction mixture was then stirred for 3 hr. The solution was poured into 1 N HCl and the aqueous layer was extracted 3× with EtOAc. The combine organic layers were washed with water, brine and dried over anhydrous magnesium sulfate. The solution was filtered and the solvent removed under reduced pressure. The solid was then triturated with cold ether to give 1.01 g of the desired carboxylic acid 223.

Example 198

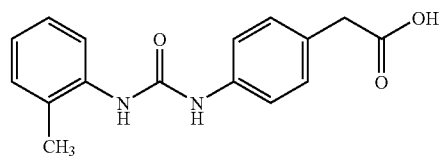

224

To a suspension of 4-aminophenylacetic acid (10 g, 66 mmol) in 1:1 CH$_2$Cl$_2$:acetone (100 mL) was added o-tolyisocyanate (8.8 g, 66 mmol). The mixture was heated to reflux for 4 hr at which time a white precipitate had formed. The precipitate was filtered and the solid washed generously with 1:1 CH$_2$Cl$_2$:acetone. The solid was recrystallized with hot methanol and dried under vacuum to yield 14.1 g (75% yield) of the desired 4-(o-tolylureido)phenylacetic acid 224.

Example 199

225

To a suspension of 2-amino-4-thiazoleacetic acid (4 g, 25 mmol) in 1:1 CH$_2$Cl:acetone (100 mL) was added o-tolylisocyanate (3.5 g, 26 mmol). The mixture was heated to reflux for 8 hr at which time a yellow precipitate had formed. the precipitate was filtered and the solid washed generously with 1:1 CH$_2$Cl$_2$:acetone. The solid was recrystallized with hot methanol and dried under vacuum to yield 4.8 g (66% yield) of the desired 2-(o-tolylureido)-4-thiazoleacetic acid 225.

Example 200

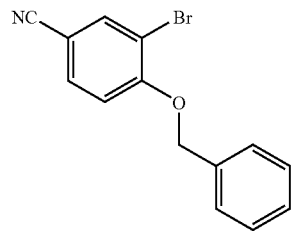

226

3-Bromo-4-hydroxybenzonitrile (5.00 g, 25.25 mmol) was taken up in DMF. Benzyl bromide (4.75 g, 27.78 mmol, 3.30 mL) and Cs$_2$CO$_3$ (16.45 g, 50.50mmol) were added and the reaction was heated to 50° C. for 2 hr. The solution was cooled to room temperature and poured into 1 N HCl. The aqueous layer was extracted 3× with ethyl acetate. The combined organic layers were washed with water, brine then dried over MgSO$_4$. The solution was filtered and the solvent was removed under reduced pressure. The product was isolated by flash chromatography. (hexane to 8:1 hexane-ethyl acetate) Yield 8.90 g 226.

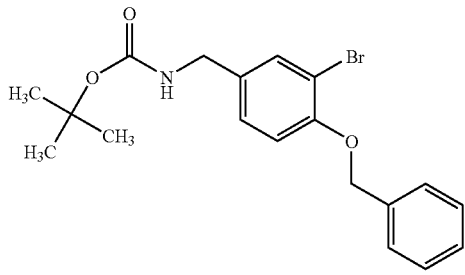

227

3-Bromo-4-benzyloxybenzonitrile (1.50 g, 5.21 mmol) was taken up in dry THF under argon and the solution was cooled to 0° C. BH$_3$-THF (10.41 mL, 10.41 mmol) was added via syringe over 5 min. The reaction mixture was then warmed to room temp then heated to reflux for 12 hr. The solution was cooled to 0° C. and methanol was slowly added. When no more gas evolution was observed the solution was warmed to room temp and excess 1 N NaOH solution was added. Boc$_2$O (1.25 g, 5.73 mmol) was added and the reaction mixture was stirred at room temp for 12 hr. The solution was poured into 1 N HCl and the aqueous layer was extracted 3× with ethyl acetate. The combined organic layers were washed with water, brine then dried over MgSO$_4$. The solution was filtered and the solvent was removed under reduced pressure. The product was isolated by flash chromatography. (7:1 ethyl acetate-hexane) Yield 1.80 g 227

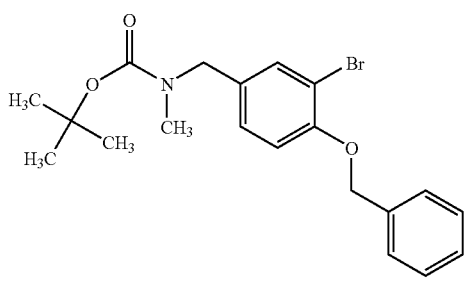

228

The Boc-protected benzyl amine (1.80 g, 4.59 mmol) was dissolved in dry THF under argon. The reaction was cooled to minus 78° C. Lithium bis(trimethylsilyl)amide (13.77 mL, 13.77 mmol) was added over 10 min. The reaction was stirred for 1 hr at minus 78° C., then iodomethane (1.95 mL, 13.77 mmol, 0.86 mL) was added rapidly. The reaction was allowed to slowly warm to room temp and stir overnight. The reaction was poured into 1 N HCl and the aqueous layer was extracted 3× with ethyl acetate. The solution was filtered and the solvent was removed under reduced pressure. The product was isolated by flash chromatography. (7:1 hexane-ethyl acetate) Yield 1.70 g 228.

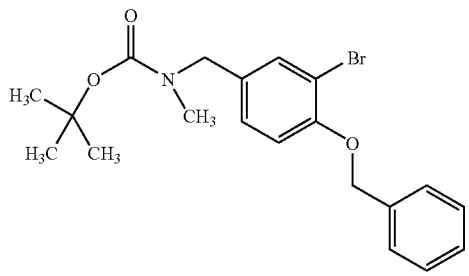

229

In a pressure tube was placed the 4-(N-methyl-Boc-aminomethyl)-2-bromobenzyloxy phenol (1.70 g, 4.18 mmol). The tube was then charged with DMF, sodium acetate (0.38 g, 4.60 mmol), dppp (0.35 g, 0.84 mmol), and Pd(OAc)$_2$ (0.19 g, 0.84 mmol) The tube was flushed with argon for 10 min and then methyl acrylate (0.40 g, 4.60 mmol, 0.41 mL) was added. The tube was sealed and heated to 135° C. for 24 hr. The reaction was cooled to 0° C. and the tube was slowly opened. The solution was poured into 1 N HCl and the aqueous layer was extracted 3× with ethyl acetate. The combined organic layers were washed with water, brine then dried over MgSO$_4$. The solution was filtered and the solvent was removed under reduced pressure. The product was isolated by flash chromatography. (6:1 hexane-ethyl acetate) Yield 1.12 g 229

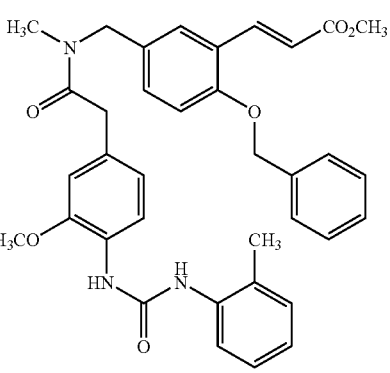

230

The unsaturated ester (307.40 mg, 0.75 mmol) was taken up in CH$_2$Cl$_2$ and excess TFA was added. The reaction was stirred for 4 hr at room temp. The solvent was removed under reduced pressure and the residue was dried under high vacuum. The solvent was removed and the residue was taken up in ethyl acetate and washed with sat. NaHCO$_3$ solution. The organic layer was washed with water, brine then dried over Na$_2$SO$_4$. The solution was filtered and the solvent was removed under reduced pressure. The residue was taken up in CH$_2$Cl$_2$-DMF and HOBt (110.99 mg, 0.82 mmol), 3-methoxy-4-(N'-phenylureido) phenylacetic acid (258.31 mg, 0.82 mmol) and EDCI (157.20 mg, 0.82 mmol) were added. The reaction was stirred for 24 hr. The solution was poured into 1 N HCl and the aqueous layer was extracted 3× with ethyl acetate. The combined organic layers were washed with water, brine then dried over MgSO$_4$. The solution was filtered and the solvent was removed under reduced pressure. The product was isolated by flash chromatography. (ethyl acetate) Yield 296.30 mg 230

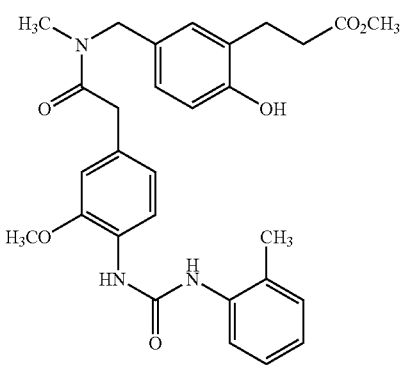

231

The unsaturated ester (296.30 mg, 0.49 mmol) was taken up in EtOAc and Pd/C (75 mg) was added under argon. The argon atmosphere was replaced with hydrogen at 1 atmosphere and stirred for 24 hr. The hydrogen atmosphere was removed and replaced with argon. The catalyst was removed by filtration through celite and the celite pad was washed with ethyl acetate 3×. The solvent was removed under reduced pressure. H$^1$-NMR showed only the desired product. No further purification was needed. Yield 233.00 mg 231

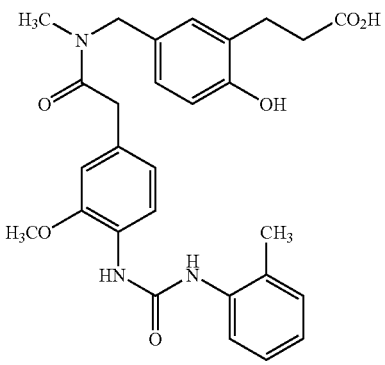

232

The ester (233.00 mg, 0.45 mmol) was taken up in THF-H$_2$O (4:1) and LiOH (94.41 mg, 2.25 mmol) was added. The reaction mixture was stirred at room temp for 24 hr. The solution was poured into 1 N HCl and the aqueous layer was extracted 3× with ethyl acetate. The combined organic layers were washed with water, brine then dried over MgSO$_4$. The solution was filtered and the solvent was removed under reduced pressure. The product was washed with ether-hexane (1:1) and dried under high vacuum. Yield 211.58 mg 232

Example 201

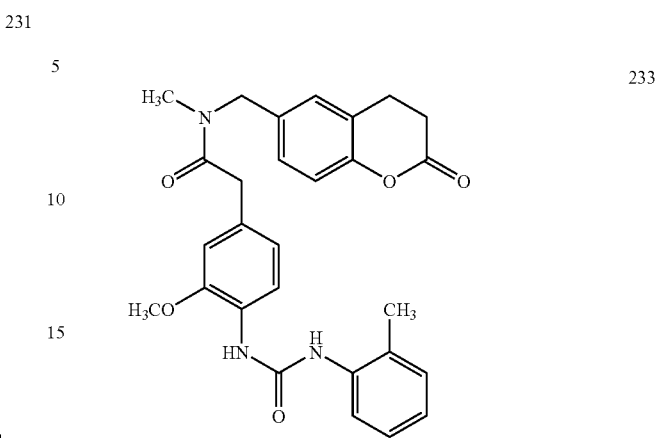

233

The carboxylic acid (65.00 mg, 0.13 mmol) was taken up in benzene and para-toluenesulfonic acid (10.00 mg, 0.06 mmol) was added. A Dean-Stark trap was added and the solution was heated to reflux for 24 hr. The reaction was cooled to room temp and poured into sat. NaHCO$_3$. The organic layer was seperated and the aqueous layer was extracted 3× with ethyl acetate. The combined organic layers were washed with water, brine and dried over MgSO$_4$. The solution was filtered and the solvent was removed under reduced pressure. The product was isolated by flash chromatography (4:1 hexane-ethyl acetate to ethyl acetate) Yield 29.00 mg 233

Example 202

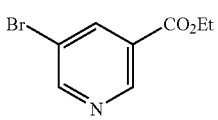

234

5-Bromonicotinic acid (5.15 g, 25.49 mmol) was taken up in EtOH and H$_2$SO$_4$ (1 mL) was added and the solution heated to reflux for 24 hr. The solution was cooled to rt and concentrated. The solution was then added to sat. NaHCO$_3$ and the aqueous layer were extracted 3× with Et$_2$O. The combined organic layers were dried over Na$_2$SO$_4$, filtered and the solvent was removed under reduced pressure. The product was sufficiently pure for the next step. Yield 5.42 g 234

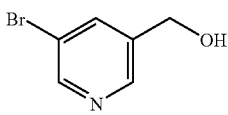

235

The ethyl 5-Bromonicotinate (5.40 g, 23.47 mmol) was taken up in 95% EtOH and NaBH$_4$ (8.31 g, 225.69 mmol) was added slowly at room temp. After addition the solution was stirred for 24 hr at room temp. Water was slowly added to the solution, then the mixture was stirred for 4 hr. The EtOH was removed under reduced pressure and the aqueous layer was extracted 3× with $CH_2Cl_2$. The combined organic layers were dried over $Na_2SO_4$, filtered and the solvent was removed under reduced pressure. The product was isolated by flash chromatography. (2:1 ethyl acetate-hexane) Yield 2.12 g 235

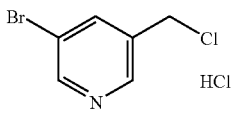

236

The benzyl alcohol (2.12 g, 11.28 mmol) was taken up $Et_2O$ and $HCl_{(g)}$ was bubbled through the solution for 10 min. The solution was stirred at room temp for 1 hr and then the solid was collected by filtration. The solid was washed with $Et_2O$ and the then dried. The HCl salt was added to $SOCl_2$ and the mixture was heated to reflux for 1.5 hr. The solution was cooled to room temp and $Et_2O$ was added to precipitate the product. The solid was collected by filtration, washed with $Et_2O$ and dried under vacuum. Yield 2.42 g 236

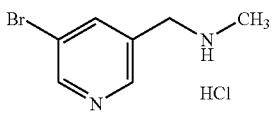

237

The benzyl chloride (2.42 g, 9.96 mmol) was added over 1 hr to $CH_3NH_2$ (75.9 mL, 2.5M in EtOH) at room temp. The reaction was stirred at room temp for 48 hr. The solution was concentrated and added to sat. $NaHCO_3$. The aqueous layer was extracted 3× with ethyl acetate. The combined organic layers were dried over $Na_2SO_4$, filtered and the solvent was removed under reduced pressure. Yield 1.19 g 237

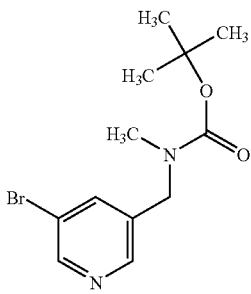

238

The 3-bromo-5-(N-methyl-aminomethyl)-pyridine(1.19 g, 5.01 mmol) was taken up in DMF and triethylamine (0.90 g, 1.24 mL, 8.89 mmol) was added. Boc2O (1.55 g, 7.10 mmol) was added and the reaction mixture was stirred at room temp for 48 hr. The solution was poured into 1 N HCl and the aqueous layer was extracted 3× with ethyl acetate. The combined organic layers were washed with water, brine then dried over $MgSO_4$. The solution was filtered and the solvent was removed under reduced pressure. The product was isolated by flash chromatography (2% methanol-$CH_2Cl_2$) Yield 1.6 g 238

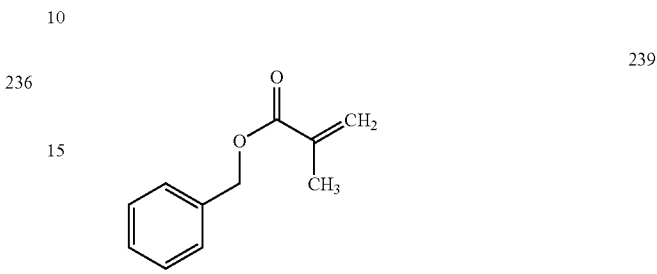

239

The sodium salt of a-methyl acrylic acid (5.00 g, 46.27 mmol) was dissolved in DMF and benzyl bromide (8.70 g, 50.89 mmol) was added at room temp. Potassium carbonate (7.03 g, 50.89 mmol) was then added and the solution was heated to 50° C. for 24 hr. The solution was poured into 1 N HCl and the aqueous layer was extracted 3× with diethyl ether. The combined organic layers were washed with water, brine then dried over $MgSO_4$. The solution was filtered and the solvent was removed carefully under reduced pressure. The product was isolated by flash chromatography (2% ether-pentane) Yield 6.93 g 239

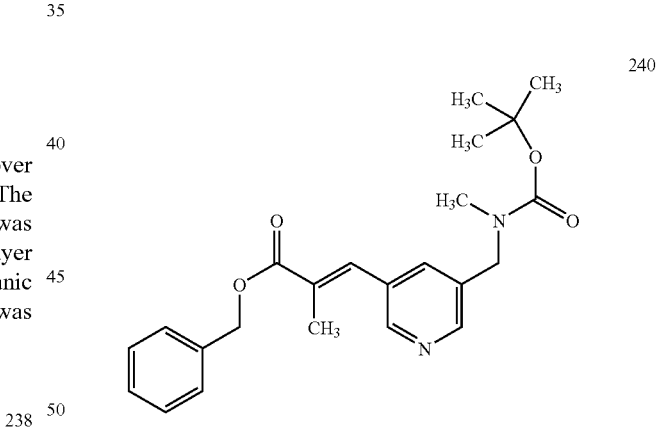

240

In a pressure tube was placed the 3-bromo-5-(N-methyl-Boc-aminomethyl)-pyridine (700.00 mg, 2.33 mmol). The tube was then charged with DMF, triethylamine (260.05 mg, 2.57 mmol, 0.36 mL), dppp (193.85 mg, 0.47 mmol), and $Pd(OAc)_2$ (105.52 mg, 0.47 mmol) The tube was flushed with argon for 10 min then benzyl methacrylate (452.86 mg, 2.57 mmol) was added. The tube was sealed and heated to 135° C. for 24 hr. The reaction was cooled to 0° C. and the tube was slowly opened. The solution was poured into 1 N HCl and the aqueous layer was extracted 3× with ethyl acetate. The combined organic layers were washed with water, brine then dried over $MgSO_4$. The solution was filtered and the solvent was removed under reduced pressure. The product was isolated by flash chromatography. (6:1 hexane-ethyl acetate) Yield 785.23 mg 240

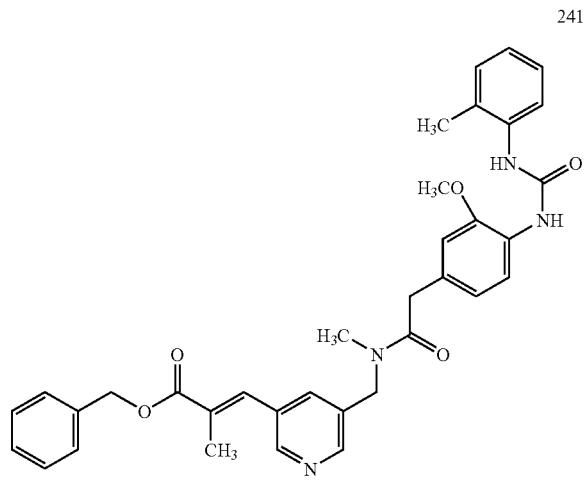

241

The unsaturated ester (392.61 mg, 0.99 mmol) was taken up in CH$_2$Cl$_2$ and excess TFA was added. The reaction was stirred for 4 hr at room temp. The solvent was removed under reduced pressure and the residue was dried under high vacuum. The solvent was removed and the residue was taken up in ethyl acetate and washed with sat. NaHCO$_3$ solution. The organic layer was washed with water, brine then dried over Na$_2$SO$_4$. The solution was filtered and the solvent was removed under reduced pressure. The residue was taken up in CH$_2$Cl$_2$-DMF and HOBt (147.53 mg, 1.09 mmol), 3-methoxy-4-(N'-phenylureido)phenylacetic acid (342.64 mg, 1.09 mmol) and EDCI (208.96 mg, 1.09 mmol) were added. The reaction was stirred for 24 hr. The solution was poured into 1 N HCl and the aqueous layer was extracted 3× with ethyl acetate. The combined organic layers were washed with water, brine then dried over MgSO$_4$. The solution was filtered and the solvent was removed under reduced pressure. The product was isolated by flash chromatography. (ethyl acetate) 363.79 mg 241

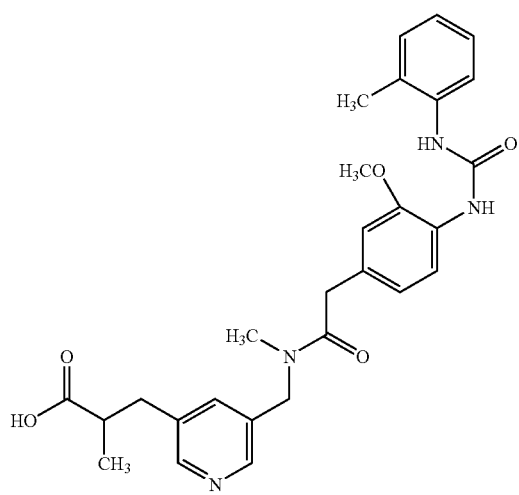

242

The unsaturated ester (363.00 mg, 0.61 mmol) was taken up in CH$_3$OH and Pd/C (100.00 mg) was added under argon. The argon atmosphere was replaced with hydrogen at 1 atmosphere and stirred for 24 hr. The hydrogen atmosphere was removed and replaced with argon. The catalyst was removed by filtration through celite and the celite pad was washed with ethyl acetate 3×. The solvent was removed under reduced pressure. H$^1$-NMR showed only the desired product. The solid was washed with ether and then dried under high vacuum. Yield 254.79 mg 242

Example 203

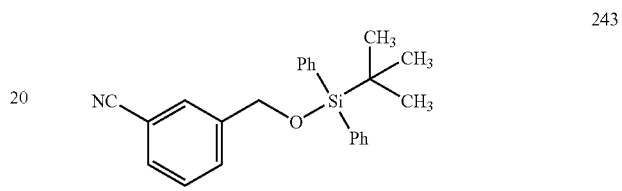

243

3-Cyanobenzaldehyde (9.41 g, 71.76 mmol) was taken up in ethanol and cooled to 0° C. The NaBH$_4$ (2.71 g, 71.76 mmol) was added in small portions. The solutions was stirred for 30 min at 0° C. then allowed to warm to room temp and stirred for 1 hr. The reaction was slowly poured into 1NHCl and the aqueous layer was extracted 3× with ethyl acetate. The combined organic layers were washed with water, brine then dried over MgSO$_4$. The solution was filtered and the solvent was removed under reduced pressure. The residue was taken up in DMF and imidazole (2.08 g, 30.50 mmol) was added. TBDPSCl (4.61 g, 16.78 mmol, 4.36 mL) was then. added and the reaction was stirred at room temp for 12 hr. The solution was poured into 1 N HCl and the aqueous layer was extracted 3× with ethyl acetate. The combined organic layers were washed with water, brine then dried over MgSO$_4$. The solution was filtered and the solvent was removed under reduced pressure. The product was isolated by flash chromatography. (7:1 hexane-ethyl acetate to 4:1 hexane-ethyl acetate) Yield 16.23 g 243

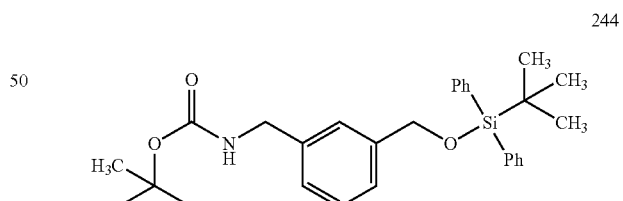

244

The silyl protected 3-cyanobenzyl alcohol (8.50 g, 34.36 mmol) was taken up in ethyl acetate and Boc$_2$O (8.25 g, 37.79 mmol) was added. Pd/C (1.0 g) was added and the Parr vessel was pressurized with hydrogen at 50 psi. The vessel was shaken for 24 hr then the hydrogen was flushed with argon and the catalyst was removed by filtration through a celite pad. The celite was washed 3× with ethyl acetate. The solvent was removed under reduced pressure and the product was isolated by flash chromatography (10:1 hexane-ethyl acetate) Yield 11.10 log 244

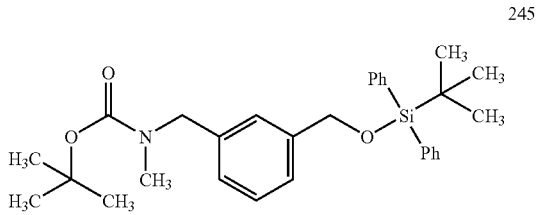

245

The O-silyl-N-Boc-protected benzyl alcohol (5.00 g, 14.22 mmol) was dissolved in dry THF under argon. The reaction was cooled to minus 78° C. Lithium bis(trimethylsilyl)amide (42.67 mL, 42.67 mmol) was added over 10 min. The reaction was stirred for 1 hr at minus 78° C. then iodomethane (6.06 g, 42.67 mmol, 2.66 mL) was added rapidly. The reaction was allowed to slowly warm to room temp and stir overnight. The reaction was poured into 1 N HCl and the aqueous layer was extracted 3× with ethyl acetate. The solution was filtered and the solvent was removed under reduced pressure. The product was isolated by flash chromatography. (2% ethyl acetate-hexane) Yield 4.7 g 245

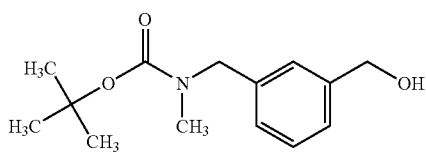

246

The O-silyl-Boc-N-methyl protected benzyl alcohol (4.7 g, 9.60 mmol) was taken up in THF and TBAF (14.39 mL, 1.0M in THF) at room temp. The solution was stirred for 4 hr. TLC showed no starting material present. The reaction was poured into 1 N HCl and the aqueous layer was extracted 3× with ethyl acetate. The solution was filtered and the solvent was removed under reduced pressure. The product was isolated by flash chromatography. (4:1 hexane-ethyl acetate to 1:1 hexane-ethyl acetate) Yield 2.39 g 246

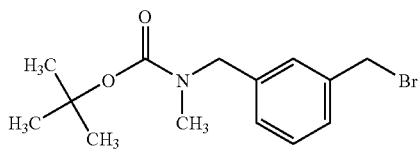

247

The N-methyl Boc protected benzyl alcohol (1.00 g, 3.98 mmol) was taken up in dry $CH_2Cl_2$ under argon. Triphenylphosphine (1.46 g, 5.57 mmol) was added and the solution was cooled to 0° C. Carbon tetrabromide (1.85 g, 5.57 mmol) dissolved in dry $CH_2Cl_2$ was added over 10 min. The solution was stirred for 1 h at 0° C. then the solvent was removed under reduced pressure. The residue was taken up in $Et_2O$ and the resulting solid was removed by filtration and the filtrate was collected and the solvent was removed under reduced pressure. The product was isolated by flash chromatography (2% ether-pentane) Yield 1.15 g 247

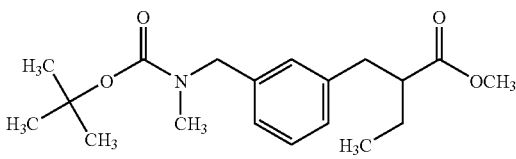

248

LHMDS (3.23 mL, 3.23 mmol) was added to dry DME under argon at minus 78° C. Methyl butyrate (300 mg, 2.94 mmol, 0.33 mL) dissolved in dry DME was added to the LHMDS over 15 min and the solution was stirred for 1 hr at minus 78° C. 3-N-methyl-N-Boc protected benzyl bromide (1.02 g, 3.23 mmol) dissolved in dry DME was added to the enolate solution over 15 min then the solution was allowed to slowly warm to minus 20° C. and stirred for 4 hr. The reaction was poured into 1 N HCl and the aqueous layer was extracted 3× with ethyl acetate. The solution was filtered and the solvent was removed under reduced pressure. The product was isolated by flash chromatography. (3% ethyl acetate-hexane) Yield 414 mg 248.

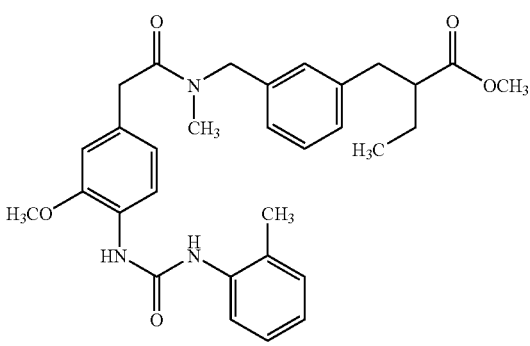

249

The Boc ester (121.60 mg, 0.36 mmol) was taken up in $CH_2Cl_2$ and excess trifluoroacetic acid was added. The reaction was then stirred for 2 hr. The solvent was removed and the residue was taken up in ethyl acetate and washed with sat. $NaHCO_3$ solution. The organic layer was washed with water, brine then dried over $Na_2SO_4$. The solution was filtered and the solvent was removed under reduced pressure. The residue was taken up in $CH_2Cl_2$-DMF and HOBt (54.10 mg, 0.40 mmol) 3-methoxy-4-(N'-phenylureido)phenylacetic acid (125.74 mg, 0.40 mmol) and EDCI (77.0 mg, 0.40 mmol) were added. The reaction was stirred for 24 hr. The solution was poured into 1 N HCl and the aqueous layer was extracted 3× with ethyl acetate. The combined organic layers were washed with water, brine then dried over $MgSO_4$. The solution was filtered and the solvent was removed under reduced pressure. The product was isolated by flash chromatography. (ethyl acetate) Yield 165.20 mg 249

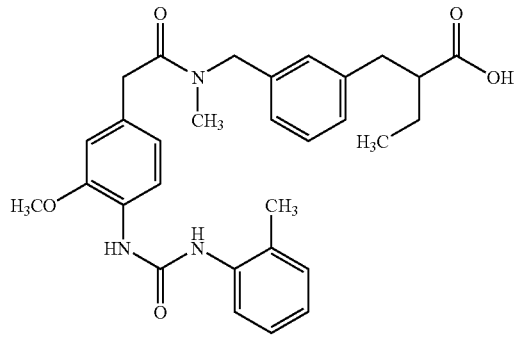

The ester (165.20, 0.31 mmol) was taken up in ethanol-water (4:1) and NaOH was added. The reaction was then heated to 50° C. for 2 hr. The TLC (ethyl acetate) showed no starting material present. The reaction was cooled to room temp. The solution was poured into 1 N HCl and the aqueous layer was extracted 3× with ethyl acetate. The combined organic layers were washed with water, brine then dried over MgSO$_4$. The solution was filtered and the solvent was removed under reduced pressure. The residue was recrystallized from ethyl acetate-hexane. Yield 120.00 mg 250

Example 204

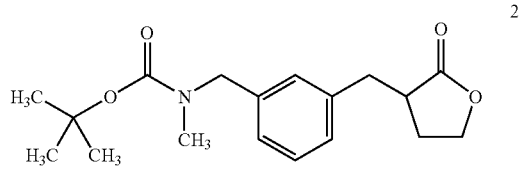

Butyrolactone (250 mg, 2.90 mmol, 223.20 mL) was added to LHMDS (2.90 mL, 1.0M in hexane) in THF at minus 78° C. under argon over 10 min. The solution was stirred at minus 78° C. for 1 hr. 3-N-methyl-N-Boc protected benzyl bromide (991.24 mg, 2.90 mmol) dissolved in dry DME was added to the enolate solution over 15 min then the solution was allowed to slowly warm to room temp and stirred for 12 hr. The reaction was poured into 1 N HCl and the aqueous layer was extracted 3× with ethyl acetate. The solution was filtered and the solvent was removed under reduced pressure. The product was isolated by flash chromatography. (4:1 hexane-ethyl acetate to 1:1 ethyl acetate-hexane) Yield 501.18 mg 251

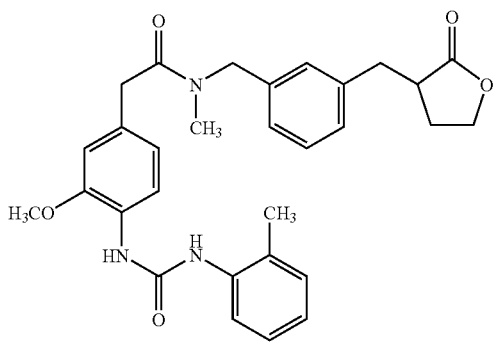

The Boc ester (250.00 mg, 0.78 mmol) was taken up in CH$_2$Cl$_2$ and excess trifluoroacetic acid was added. The reaction was then stirred for 2 hr. The solvent was removed and the residue was taken up in ethyl acetate and washed with sat. NaHCO$_3$ solution. The organic layer was washed with water, brine then dried over Na$_2$SO$_4$. The solution was filtered and the solvent was removed under reduced pressure. The residue was taken up in CH$_2$Cl$_2$-DMF and HOBt (116.40 mg, 0.86 mmol) 3-methoxy-4-(N'-phenylureido) phenylacetic acid (270.33 mg, 0.86 mmol) and EDCI (165.06 mg, 0.86 mmol) were added. The reaction was stirred for 24 hr. The solution was poured into 1 N HCl and the aqueous layer was extracted 3× with ethyl acetate. The combined organic layers were washed with water, brine then dried over MgSO$_4$. The solution was filtered and the solvent was removed under reduced pressure. The product was isolated by flash chromatography. (ethyl acetate) Yield 119.00 mg 252

Example 205

3-methoxy-4-[2-[3-methoxy-4-[N'-(2-methylphenyl) ureido]phenylacetyl]-N-methylaminoethoxy]benzoic acid

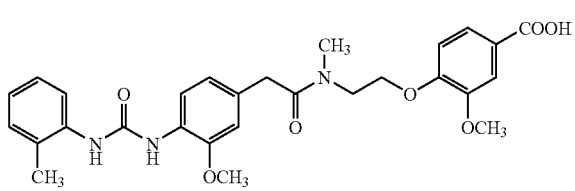

To a stirred and cooled (0° C.) solution of N-methyl ethanolamine (3.10 g, 41.27 mmol), Et$_3$N (11.80 mL, 84.66 mmol) in DMF-H2O (3:1, v/v, 40 mL) was added dropwise 30% toluene solution of benzyl chloroformate (25.40 g, 49.13 mmol) for over 15 min. The resulting mixture was stirred for 1 day at room temp. The mixture was extracted with EtOAc. The extract was washed with sat. NaHCO₃, brine, dried over Na₂SO₄, and evaporated. The residue was purified by column chromatography on silica-gel with n-hexane:EtOAc (3:1, v/v) then CHCl₃ as eluent to give 4.67 g (54%) N-methyl-N-(benzyloxy carbonyl)ethanolamine as a colorless oil. ¹H-NMR (CDCl₃) d 1.82 (bs, 1 H), 3.00 (s, 3 H), 3.46 (bs, 2 H), 3.77 (bs, 2 H), 5.13 (s, 2 H), 7.29–7.36 (m, 5 H).

To a stirred solution of ethyl 4-hydoxy-3-methoxybenzoate (2.01 g, 10.25 mmol), N-methyl-N-(benzyloxycarbonyl)ethanolamine (2.11 g, 10.08 mmol), PPh₃ (3.26 g, 12.43 mmol) in THF was added DIAD (2.65 mL, 13.46 mmol) and the reaction mixture was heated under reflux overnight. The mixture was evaporated, and the residue was subjected to short column chromatography on silica-gel with n-hexane/EtOAc (5:1, v/v) as eluent to give ethyl 3-methoxy-4-[2-methyl-2-(benzyloxycarbonyl)aminoethoxy]benzoate as a crude product.

To a solution of the crude product (5.20 g, 13.42 mmol) in EtOH (50 mL) was added AcOH (5 mL) and the solution was hydrogenated over 5% Pd/C for 4 hr. The mixture was filtered to remove the catalyst and the filtrate was evaporated. The residue was diluted with CHCl₃ and washed with sat. NaHCO₃, brine, dried over Na₂SO₄, and evaporated. The residue was chromatographed on silica-gel with CHCl₃:MeOH (10:1, v/v) as eluent to give 510 mg (2 steps 20%) ethyl 3-methoxy-4-(2-methylamino ethoxy) benzoate as a yellow oil. ¹H-NMR (CDCl₃) d 1.39 (t, 3 H, J=7.3 Hz), 1.82 (bs, 1 H), 2.52 (s, 3 H), 3.04 (t, 2 H, J=5.3 Hz), 3.91 (s, 3 H), 4.18 (t, 2 H, J=5.3 Hz), 4.36 (q, 2 H, J=7.3 Hz), 6.90 (d, 1 H, J=8.3 Hz), 7.55 (d, 1 H, J=2.0 Hz), 7.65 (dd, 1 H, J=2.0, 8.3 Hz).

To a stirred solution of ethyl 3-methoxy-4-(2-methylaminoethoxy) benzoate (510 mg, 2.01 mmol) in DMF (13 mL) was added pentafluorophenyl ester of 3-methoxy-4-[N'-(2-methylphenyl) ureido]phenylacetic acid (900 mg, 1.87 mmol) and Et₃N (0.420 mL, 3.01 mmol), and the resulting mixture was stirred for 2 days. The mixture was diluted with EtOAc, washed with 1 N HCl, sat. NaHCO₃, brine, and dried over Na₂SO₄. After being evaporated, the residue was purified by column chromatography on silica-gel with CHCl₃:MeOH (50:1, v/v) to give 880 mg (85%) ethyl 3-methoxy-4-[2-[3-methoxy-4-[N'-(2-methylphenyl)ureido]phenylacetyl]-N-methylaminoethoxy]benzoate as a colorless amorphous solid. ¹H-NMR (CDCl₃) δ 1.37–1.41 (m, 3 H), 2.28 (s, 3 H), 3.03 and 3.18 (s, 3 H), 3.56 (s, 2 H), 3.65 (s, 2 H), 3.75–3.87 (m, 6 H), 4.06–4.24 (2 H, m), 4.33–4.39 (m, 2 H), 6.68–8.08 (series of m, 12 H).

To a solution of ethyl 3-methoxy-4-[2-[3-methoxy-4-[N'-(2-methylphenyl)ureido]phenylacetyl]-N-methylaminoethoxy]benzoate (880 mg, 1.601 mmol) in THF (15 mL) was added 0.25 N NaOH (15 mL). Then the reaction mixture was heated under reflux overnight. The mixture was poured into 1 N HCl (100 mL), and the solid was collected. The crude solid was recrystallized from MeOH—CHCl₃ to give 253 as a white powder. IR (KBr) 1700 cm⁻¹; ¹H-NMR (DMSO-d₆) δ 2.25 (s, 3 H), 2.50 (s, 2 H), 2.91 and 3.12 (s, 3 H) 3.53–3.76 (m, 2 H), 3.80 (s, 3 H), 3.84 (s, 3 H), 4.16–4.21 (m, 2 H), 6.72–8.56 (series of m, 12 H), 12.68 (bs, 1 H); MS (FAB) m/z 522 (M⁺+1); Anal. Calcd. for C₂₈H₃₁N₃O₇.1H₂O: C, 62.33; H, 6.16; N, 6.63. Found: C, 62.17; H, 6.05; N, 7.57.

Example 206

4-[[2-[3-methoxy-4-[N'-(2-methylphenyl)ureido]phenylacetyl]methylamino]ethoxy]isophthalic acid

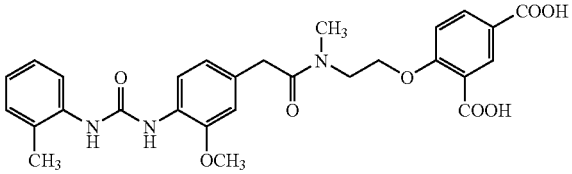

254

To a stirred solution of N-methyl-N-benzyloxycarbonylethanolamine (1.05 g, 5.02 mmol), dimethyl 4-hydroxy isophthalate (1.05 g, 5.00 mmol), Ph₃P (1.59 g, 6.06 mmol) in THF (20 mL) was added DIAD (1.28 mL, 6.50 mmol) at room temp. The resulting mixture was then heated under reflux overnight. After cooling to room temp, the mixture was evaporated. The residue was dissolved in EtOH and added 5% Pd/C (200 mg). The stirred resulting mixture was hydrogenated for 2 hr at 1 atm. The mixture was filtered to remove the catalyst, and the filtrate was evaporated. The residue was purified by column chromatography on silica-gel with CHCl₃-MeOH (30:1, v/v) as eluent to give 480 mg (36% for 2 steps) dimethyl 4-(2-methylaminoethoxy) isophthalate as an oil. ¹H-NMR (CDCl₃) δ 1.68 (s, 1 H), 2.53 (s, 3 H), 3.01–3.04 (m, 2 H), 3.89 (s, 3 H), 3.90 (s, 3 H), 4.21–4.23 (m, 2 H), 7.00 (d, 1 H, J=8.8 Hz), 8.14 (dd, 1 H, J=2.4, 8.8 Hz), 8.50 (d, 1 H, J=2.4 Hz); MS (FAB), m/z 268 (M⁺+1).

To a stirred solution of dimethyl 4-(2-methylaminoethoxy)isophthalate (410 mg, 1.53 mmol) in DMF (13 mL) was added pentafluorophenyl ester of 3-methoxy-4-[N'-(2-methylphenyl)ureido]phenylaceic acid (700 mg, 1.46 mmol) and Et₃N (340 µl, 2.44 mmol), and the resulting mixture was stirred overnight. The mixture was diluted with EtOAc, washed with 1 N HCl, sat. NaHCO₃, and brine. The solution was dried over Na₂SO₄ and evaporated to give 780 mg (95%) dimethyl 4-[2-[3-methoxy-4-[N'-(2-methylphenyl)ureido]phenylacetyl]methylamino ethoxy]isophthalate as a crystalline powder. ¹H-NMR (CDCl₃) δ 2.29 (s, 3 H), 3.24 (s, 3 H), 3.59 (s, 3 H), 3.67–3.68 (m, 2 H), 3.84 (s, 3 H), 3.91 (s, 3 H), 3.81–3.86 (m, 2 H), 4.25–4.28 (m, 2 H), 6.51–8.48 (series of m, 12 H); MS (FAB) m/z 564 (M⁺+1).

To a solution of dimethyl 4-[2-[3-methoxy-4-[N'-(2-methylphenyl)ureido]phenylacetyl]methylaminoethoxy]isophthalate (780 mg, 1.384 mmol) in THF (30 mL) was added 0.25 N NaOH (30 mL). The resulting mixture was then heated under reflux overnight. The mixture was poured into ice-1 N HCl (200 mL) and the solid was collected. The crude solid was recrystallized from MeOH—CHCl₃ to give 420 mg (57%) 4-[[2-[3-methoxy-4-[N'-(2-methylphenyl)ureido]phenyl acetyl]methylamino]ethoxy]isophthalic acid 254 as a white crystalline powder. mp 139–141° C. IR (KBr) 1700 cm⁻¹; ¹H-NMR (DMSO-d₆) d 2.94 (s, 3 H), 3.18 (s, 3 H) 3.62–3.86 (m, total 8 H), 4.24–4.28 (m, 2 H), 6.74–8.58 (series of m, total 12 H), 12.91 (bs, 1 H); MS (FAB) m/z 536 (M⁺+1); Anal. Calcd. for C₂₈H₂₉N₃O₈.2.5HCl: C, 53.66; H, 5.07; N, 6.70. Found: C, 53.80; H, 4.64; N, 6.70.

Example 207

3-methoxy-4-[2-[3-methoxy-4-[N'-(2-methylphenyl)ureido]phenylacetyl]aminoethoxy]benzoic acid

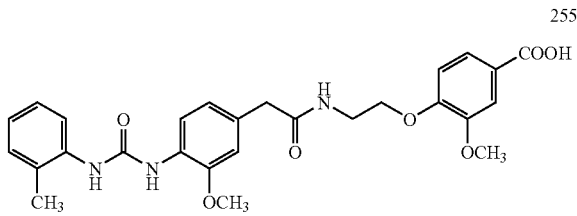

255

To a solution of 2-ethanolamine (5.16 g, 84.48 mmol), Et$_3$N (23.50 mL, 168.60 mL) in dioxane-H$_2$O (1/1, 160 mL) was added dropwise (Boc)$_2$O (23.40 mL, 101.86 mmol) at room temp. The reaction mixture was stirred for 2 days at room temp. The resulting mixture was diluted with CHCl$_3$, washed with 0.5 N HCl, sat. NaHCO$_3$, and brine. The separated organic layer was dried over Na$_2$SO$_4$ and evaporated to give 11.86 g (87%) N-Boc-2-ethanolamine as an oil. $^1$H-NMR (CDCl$_3$) δ 1.45 (s, 9 H), 3.29–3.31 (m, 2 H), 3.71–3.72 (m, 2 H).

To a stirred solution of ethyl 4-hydroxy-3-methoxybenzoate (1.46 g, 7.44 mmol), N-Boc ethanolamine (1.19 g, 7.38 mmol), PPh$_3$ (2.53 g, 9.65 mmol) in THF (30 mL) was added DIAD (1.90 mL, 9.65 mmol), and the resulting mixture was then heated under reflux overnight. The mixture was evaporated to give a crude gum. The crude product was dissolved in CH$_2$Cl$_2$ (20 mL) and TFA (20 mL). The resulting mixture was stirred for 2.5 hr at room temp. The mixture was concentrated in vacuo and the residue was made basic with sat. NaHCO$_3$ and extracted with CHCl$_3$. The extract was washed with brine, dried over Na$_2$SO$_4$, and evaporated to give the 1.61 g (90% for 2 steps) ethyl 3-methoxy-4-(2-aminoethoxy) benzoate as a yellow oil. $^1$H-NMR (CDCl$_3$) d 1.39 (t, 3 H, J=7.3 Hz), 3.14–3.17 (m, 2 H), 3.92 (s, 3 H), 4.09–4.11 (m, 2 H), 4.36 (q, 2 H, J=7.3 Hz), 6.89 (d, 1 H, J=8.3 Hz), 7.56 (d, 1 H, J=2.0 Hz), 7.66 (dd, 1 H, J=2.0, 8.3 Hz).

To a stirred solution of ethyl 3-methoxy-4-(2-aminoethoxy)benzoate (250 mg, 1.04 mmol) and pentafluorophenyl ester of 3-methoxy-4-[N'-(2-methylphenyl)ureido]phenylacetic acid (500 mg, 1.04 mmol) was added Et$_3$ N (210 μl, 3.01 mmol), and the resulting mixture was stirred for 2 days. 0.25 N NaOH (20 mL) and THF (20 mL) was added to the mixture and the resulting mixture was heated under reflux overnight. After cooling, the mixture was evaporated and the residue was acidified by the addition of 1 N HCl. The mixture was extracted with CHCl$_3$, and the extract was washed with brine, dried over Na$_2$SO$_4$, and evaporated. The obtained crude solid was recrystallized from CHCl$_3$ to give 110 mg (20% for 2 steps) 3-methoxy-4-[2-[3-methoxy-4-[N'-(2-methylphenyl)ureido]phenylacetyl]aminoethoxy] benzoic acid 255 as a white crystalline powder. mp 180–181° C.; IR (KBr) 1687 cm$^{-1}$; $^1$H-NMR (DMSO-d$_6$) δ 2.24 (s, 3 H), 3.37 (s, 2 H), 3.38 (s, 2 H), 3.41–3.50 (m, 2 H), 3.81 (s, 3 H), 3.83 (s, 3 H), 4.06–4.08 (m, 2 H), 6.76–8.55 (series of m, total 12 H); MS (FAB) m/z 508 (M$^+$+1); Anal. Calcd for C$_{27}$H$_{29}$N$_3$O$_7$·1/2H$_2$O: C, 62.78; H, 5.85; N, 8.13. Found: C, 62.46; H, 5.69; N, 8.03.

Example 208

3-methoxy-4-[2-[3-methoxy-4-[N'-(2-methylphenyl)ureido]phenylacetyl]ethylaminoethoxy]benzoic acid

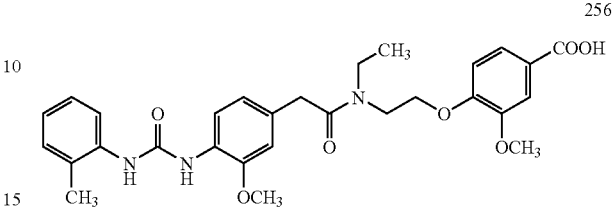

256

To a cooled (0° C.) solution of ethyl 3-methoxy-4-(2-aminoethoxy)benzoate (1.93 g, 8.07 mmol) and Et$_3$ N (2.00 mL, 14.35 mmol) was added TFAA (1.35 mL, 9.56 mmol) and the resulting mixture was stirred overnight at room temp. The resulting mixture was diluted with Et$_2$O and washed successively with sat. NaHCO$_3$, 1 N HCl, H$_2$O, and brine. The extract was dried over Na$_2$SO$_4$ and evaporated to give 1.22 g (45%) ethyl 3-methoxy-4-(2-N-trifluoroacetamidoethoxy)benzoate as an oil. $^1$H-NMR (CDCl$_3$) δ 1.39 (t, 3 H, J=7.3 Hz), 3.77–3.81 (m, 2 H), 3.92 (s, 3 H), 4.18–4.20 (m, 2 H), 4.37 (q, 2 H, J=7.3 Hz), 6.92 (d, 1 H, J=8.7 Hz), 7.59 (d, 1 H, J=2.0 Hz), 7.67 (dd, 1 H, J=2.0, 8.7 Hz); MS (FAB) m/z 335 (M$^+$), 290 (M$^+$-OEt).

To a stirred solution of ethyl 3-methoxy-4-(2-N-trifluoroacetamidoethoxy)benzoate (1.20 g, 3.58 mmol) in DMF (15 mL) was added K$_2$CO$_3$ (0.98 g, 7.09 mmol) and EtI (0.43 mL, 5.38 mmol) at room temp. The resulting mixture was stirred for 2 days at 60° C. The mixture was diluted with EtOAc, washed successively with 1 N HCl, brine, and dried over Na$_2$SO$_4$. The solvent was evaporated and the residue was purified by column chromatography on silica-gel with n-hexane-EtOAc (2:1, v/v) as eluent to give 990 mg (76%) ethyl 3-methoxy-4-[2-(N-ethyl-N-trifluoroacetamido)ethoxybenzoate as a yellow crystalline solid. $^1$H-NMR (CDCl$_3$) δ 1.28–1.31 (m, 3 H), 1.37–1.40 (m, 3 H), 3.64–3.69 (m, 2 H), 3.81–3.84 (m, 2 H), 3.92 (s, 3 H), 4.27–4.30 (m, 2 H), 4.34–4.39 (m, 2 H), 6.89 (d, 1 H, J=8.3 Hz), 7.55 (d, 1 H, J=2.0 Hz), 7.66 (dd, 1 H, J=2.0, 8.3 Hz); MS (FAB) m/z 364 (M$^+$+1).

To a stirred solution of ethyl 3-methoxy-4-(2-(N-ethyl-N-trifluoroacetamido)ethoxybenzoate (990 mg, 2.73 mmol) in THF-MeOH-H$_2$O (2:1:1, v/v, 20 mL) was added K$_2$CO$_3$ (560 mg, 4.05 mmol), and the resulting mixture was stirred overnight. The resulting mixture was diluted with H$_2$O and extracted with EtOAc. The extract was washed successively with sat. NaHCO$_3$, brine, dried over Na$_2$SO$_4$, and evaporated to give 800 mg (q.y.) ethyl 3-methoxy-4-(2-ethylaminoethoxy)benzoate as an oil. $^1$H-NMR (CDCl$_3$) δ 1.15 (t, 3 H, J=7.3 Hz), 1.39 (t, 3 H, J=7.3 Hz), 1.76 (bs, 1 H), 2.74 (q, 2 H, J=7.3 Hz), 3.08 (t, 2 H, J=5.4 Hz), 3.91 (s, 3 H), 4.18 (t, 2 H, J=5.4 Hz), 4.36 (q, 2 H, J=7.3 Hz), 6.90 (d, 1 H, J=8.3 Hz), 7.55 (d, 1 H, J=2.0 Hz), 7.66 (dd, 1 H, J=2.0, 8.3 Hz); MS (FAB) m/z 268 (M$^+$+1).

To a stirred solution of ethyl 3-methoxy-4-(2-ethylaminoethoxy)benzoate (290 mg, 1.08 mmol) and pentafluorophenyl ester of 3-methoxy-4-[N-(2-methylphenyl)ureido]phenylacetic acid (502 mg, 1.05 mmol) in DMF (7 mL) was added Et$_3$ N (250 μl, 1.79 mmol), and the resulting mixture was stirred overnight. The mixture was diluted with EtOAc, washed with 0.5 N HCl, brine, and dried over Na$_2$SO$_4$. The solvent was evaporated and the residue was purified by column chromatography on silica-gel with CHCl$_3$-MeOH (40:1, v/v) as an eluent to give 550 mg (93%) ethyl 3-methoxy-4-[2-[3-methoxy-4-[N'-(2-methylphenyl)ureido]phenylacetyl]ethylaminoethoxy]benzoate as an amorphous solid. $^1$H-NMR (CDCl$_3$) δ 1.11–1.18 (m, 3 H), 1.37–1.41 (m, 3 H), 2.30 (s, 3 H), 3.47–3.53 (m, 2 H), 3.61–3.75 (m, 7 H), 3.84 (s, 3 H), 4.03–4.27 (m, 2 H), 4.33–4.39 (m, 2 H), 6.34–8.07 (series of m, total 12 H).

To a solution of ethyl 3-methoxy-4-[2-[3-methoxy-4-[N'-(2-methylphenyl)ureido]phenylacetyl]ethylaminoethoxy]benzoate (550 mg, 0.98 mmol) in THF (15 mL) was added 0.25 N NaOH (15 mL). The resulting mixture was then heated under reflux for 2 days. The mixture was poured into 1 N HCl and the solid was collected. The crude solid was recrystallized from EtOH—CHCl$_3$ to give 182 mg (35%) 3-methoxy-4-[2-[3-methoxy-4-[N'-(2-methylphenyl)ureido]phenylacetyl]ethylaminoethoxy]benzoic acid 256 as a white crystalline powder. mp 115–118° C.; IR (KBr) 1707 cm$^-$; $^1$H-NMR (DMSO-d$_6$) δ 1.02–1.12 (m, 3 H), 2.25 (s, 3 H), 2.50 (s, 2 H), 3.35–3.89 (m, 10 H), 4.11–4.16 (m, 2H), 6.71–8.56 (series of m, total 12H), 12.65 (br s, 1H); MS (FAB) m/z 536 (M$^{30}$ +1); Anal. Calcd for C$_{29}$H$_{33}$N$_3$O$_7$.3/4H$_2$O: C, 63.43; H, 6.33; N, 7.65. Found: 63.34; H, 6.28; N, 7.28.

Example 209

3-nitro-4-[2-[3-methoxy-4-[N'-(2-methylphenyl)ureido]phenylacetyl]aminoethoxy]benzoic acid CHCl$_3$-MeOH (20:1, v/v) as eluent to give 930 mg (27% for 2 steps ) methyl 3-nitro4-(2-aminoethoxy)benzoate as gum. $^1$H-NMR (CDCl$_3$) δ 3.16–3.19 (m, 1 H), 3.53–3.57 (m, 1 H), 3.90 and 3.94 (s, 3 H), 3.95–3.98 (m, 1 H), 4.21–4.24 (m, 1 H), 6.89–6.91 and 7.11–7.13 (m, 1 H), 8.03–8.19 and 8.21 (m, 1 H), 8.52 and 8.86 (m, 1 H).

To a stirred solution of pentafluorophenyl ester of 3-methoxy-4-[N'-(2-methylphenyl)ureido]phenylacetic acid (1.86 g, 3.87 mmol) and methyl 3-nitro-4-(2-aminoethoxy)benzoic acid (0.93 g, 3.87 mmol) in DMF (27 mL) was added Et$_3$ N (0.90 mL, 6.46 mmol), and the resulting mixture was stirred overnight. The mixture was poured into 0.5 N HCl and the resulting solid was collected. The crude solid was dissolved in THF-0.25 N NaOH (1/1, 20 mL) and the resulting mixture was heated under reflux overnight. The mixture was extracted with EtOAc, washed with brine, dried over Na$_2$SO$_4$, and evaporated. The crude solid was recrystallized from CHCl$_3$-EtOH to give 60 mg (3% for 2 steps) 3-nitro-4-[2-[3-methoxy-4-[N-(2-methylphenyl)ureido]phenylacetyl]aminoethoxy]benzoic acid 257 as a yellow crystalline solid. mp 112–115° C.; $^1$H-NMR (DMSO-d$_6$) d 2.24 (s, 3 H), 3.37–3.66 (m, 7 H), 3.84 (s, 3 H), 4.27–4.30 (m, 1 H), 6.74–8.56 (series of m, total 12 H); MS (FAB) m/z 523 (M$^+$+1); Anal. Calcd for C$_{26}$H$_{26}$N$_4$O$_8$.3/2H$_2$O: C, 56.83; H, 5.32; N, 10.20. Found: C, 56.66; H, 4.90; N, 9.33.

Example 210

3-methoxy-4-[2-[3-methoxy-4-[N'-(2-fluorophenyl)ureido]phenylacetyl]ethylaminoethoxy]benzoic acid

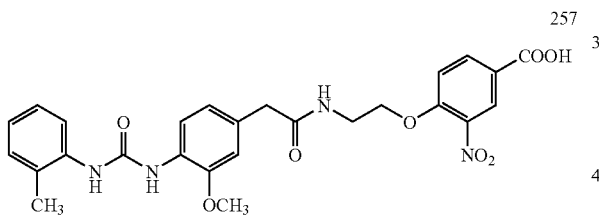

257

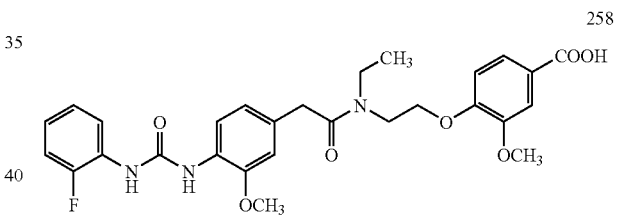

258

To a stirred solution of 4-hydroxy-3-nitrobenzoic acid (5.18 g, 28.29 mmol) in benzene-MeOH (4:1, v/v, 140 mL) was added TMSCHN$_2$ (14.10 mL, 28.20 mmol, 2 M solution in hexane) at room temp, and the resulting mixture was stirred overnight. The mixture was evaporated and the residue was purified by column chromatography on silica-gel with CHCl$_3$ as eluent to give 4.18 g (75%) methyl 3-nitro-4-hydroxybenzoate as a yellow crystalline solid. $^1$H-NMR (CDCl$_3$) δ 3.95 (s, 3H), 7.22 (d, 1H, J=8.8 Hz), 8.24 (dd, 1 , J=2.0, 8.8 Hz), 8.83 (d, 1H, J=2.0 Hz), 10.89 (s, 1H).

To a stirred solution of methyl 3-nitro-4-hydroxybenzoate (1.98 g, 10.04 mmol), N-Boc ethanolamine (1.63 g, 10.11 mmol) and PPh$_3$ (3.43 g, 13.08 mmol) in THF (40 mL) was added DIAD (2.57 mL, 13.05 mmol), and the reaction mixture was then heated under reflux overnight. The resulting mixture was evaporated to give a gum. The residual crude gum was dissolved in CH$_2$Cl$_2$ (30 mL) and TFA (30 mL), and the mixture was stirred for 1 hr at room temp. The mixture was concentrated in vacuo and made basic with sat. NaHCO$_3$. The mixture was extracted with CHCl$_3$, washed with brine, and dried over Na$_2$SO$_4$. The solvent was evaporated in vacuo to give the oily residue, which was purified by column chromatography on silica -gel with CHCl$_3$ then To a stirred solution of pentafluorophenyl ester of 3-methoxy-4-[N'-(2-fluorophenyl)ureido]phenylacetic acid (135 mg, 0.28 mmol) and ethyl 3-methoxy-4-(2-ethylaminoethoxy)benzoate (78 mg, 0.29 mmol) was added Et$_3$ N (0.1 mL, 0.72 mmol), and the resulting mixture was stirred overnight. The mixture was diluted with EtOAc, washed successively with 0.5 N HCl, brine, dried over Na$_2$SO$_4$, and evaporated. The residue was purified by column chromatography on silica-gel with CHCl$_3$-MeOH (50:1, v/v) as eluent to give 160 mg(q.y.) ethyl 3-methoxy-4-[2-[3-methoxy-4-[N'-(2-fluorophenyl)ureido]phenylacetyl]ethylaminoethoxy]benzoate as an oil. $^1$H-NMR (CDCl$_3$) δ 1.13–1.23 (m, 3 H), 1.37–1.40 (m, 3 H), 2.90–3.89 (m, 12 H), 4.09–4.28 (m, 2 H), 4.33–4.39 (m, 2 H), 6.70–8.21 (series of m, total 12 H).

To a stirred solution of ethyl 3-methoxy-4-[2-[3-methoxy-4-[N-(2-fluorophenyl)ureido]phenylacetyl]ethylaminoethoxy]benzoate (160 mg, 0.28 mmol) in THF (5 mL) was added 0.25 N NaOH (5 mL) and the resulting mixture was the heated under reflux overnight. The mixture was poured into 1 N HCl and the solid was collected. The crude solid was recrystallized from EtOH—CHCl$_3$-n-hexane to give 70 mg (46%) 3-methoxy-4-[2-[3-methoxy-4-[AN-(2-fluorophenyl)ureido]phenylacetyl]ethylaminoethoxy]benzoic acid 258 as a yellow crystalline powder. mp 105–110° C.; IR (KBr) 1687 cm$^{-1}$; $^1$H-NMR (DMSO-d6) δ 1.00–1.10 (m, 3 H), 2.48 (s, 2 H), 3.35–3.81 (m, 10 H), 4.13–4.14 (m, 2 H), 6.70–9.15 (series of m, 12 H); MS (FAB) m/z 540 (M$^+$+1); Anal. Calcd for $C_{28}H_{30}FN_3O_7 \cdot 1/2H_2O$: C, 61.31; H, 5.82; N, 7.47. Found: C, 61.05; H, 5.82; N, 7.47.

Example 211

4-[4-[3-methoxy-4-[N'-(2-methylphenyl)ureido]phenyl]acetyl-1-piperazinylbenzoic acid

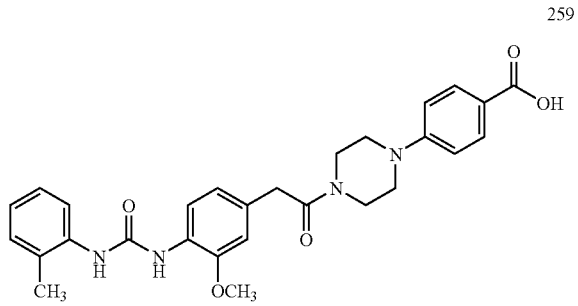

259

A stirred mixture of tert-butyl 1-piperazinecarboxylate (1.00 g, 5.37 mmol), ethyl 4-fluorobenzoate (903 mg, 5.37 mmol), and $K_2CO_3$ (1.11 g, 8.06 mmol) in DMF (10 mL) was heated at 120° C. overnight. After cooling, the mixture was diluted with EtOAc (300 mL), followed by washing with brine (2×200 mL), drying over $MgSO_4$, and evaporation. The residue was chromatographed on silica-gel with $CHCl_3$-EtOAc (20:1 to 4:1, v/v) as eluent to give 257 mg (14%) ethyl 4-[4-(tert-butyloxycarbonyl)-1-piperazinyl]benzoate as a pale yellow amorphous solid. IR (KBr) 1701, 1612 cm$^{-1}$; $^1$H-NMR (CDCl$_3$) d 1.37 (3 H, t, J=7.3 Hz), 1.49 (9 H, s), 3.30 (4 H, t, J=5.4 Hz), 3.58 (4 H, t, J=5.4 Hz), 4.33(2 H, q, J=7.3 Hz), 6.87(2 H, d, J=8.8 Hz), 7.94 (2 H, dt, J=8.8, 2.4 Hz); MS (FAB) m/z 335 (M$^+$+1); Anal. Calcd for $C_{18}H_{26}N_2O_4$: C, 64.54; H, 7.84; N, 8.38. Found: C, 64.39; H, 7.89; N, 8.38.

To a stirred solution of ethyl 4-[4-(tert-butyloxycarbonyl)-1-piperazinyl]benzoate (240 mg, 0.718 mmol) in $CH_2Cl_2$ (5 mL) was added TFA (5 mL), and the resulting mixture was stirred for 3 hr. The mixture was concentrated in vacuo and the residue was made basic by the addition of sat. $NaHCO_3$, followed by extraction with $CHCl_3$ (2×100 mL). The combined extracts were dried over $Na_2CO_3$ and evaporated to give 168 mg ethyl 4-(1-piperazinyl)benzoate (100%) as a yellow oil. $^1$H-NMR (CDCl$_3$) δ 1.37 (3 H, t, J=7.3 Hz), 3.03 (4 H, t, J=4.9 Hz), 3.29 (4 H, t, J=4.9 Hz), 4.33 (2 H, q, J=7.3 Hz), 6.87 (2 H, dt, J=8.8, 2.4 Hz), 7.91–7.94 (2 H, m).

To a stirred solution of ethyl 4-(1-piperazinyl)benzoate (170 mg, 0.730 mmol) and 3-methoxy-4-[N'-(2-methylphenyl)ureido]phenylacetic acid (229 mg, 0.730 mmol) in DMF (10 mL) was added EDC.HCl (210 mg, 1.10 mmol), DMAP (catalytic amount), and HOBt (catalytic amount), and the mixture was stirred overnight. The mixture was poured into $H_2O$ (100 mL) and the solid was collected with suction. The residue was recrystallized from CHCl$_3$-n-hexane to give 290 mg (75%) ethyl 4-[4-[3-methoxy-4-[N'-(2-methylphenyl)ureido]phenyl]acetyl-1-piperazinyl benzoate as a colorless crystalline powder. mp 208–210° C.; IR (KBr) 1711, 1695 cm$^{-1}$; $^1$H-NMR (CDCl$_3$) δ 1.37 (3 H, t, J=7.3 Hz), 2.29(3 H, s), 3.14 (2 H, t, J=4.9 Hz), 3.28 (2 H, t, J=4.9 Hz), 3.62 (2 H, t, J=4.9 Hz), 3.71 (3 H, s), 3.72 (2 H, s), 3.79 (2 H, t, J=4.9 Hz), 4.33 (2 H, q, J=7.3 Hz), 6.38 (1 H,s), 6.78–6.99 (4 H, m), 7.13–7.24 (4 H, m), 7.50 (1 H, d, J=7.8 Hz), 7.92 (2 H, d, J=8.8 Hz), 8.12 (1 H, d, J=7.8 Hz); MS (FAB) m/z 531 (M$^+$+1); Anal. Calcd for $C_{30}H_{34}N_4O_5 \cdot 0.5H_2O$: C, 66.77; H, 6.54; N, 10.38. Found: C, 66.89; H, 6.39; N, 10.45.

To a stirred solution of ethyl 4-[4-[3-methoxy-4-[N'-(2-methylphenyl)ureido]phenyl]-acetyl-1-piperazinylbenzoate (290 mg, 0.547 mmol) in MEOH-THF (2:1, v/v, 15 mL) was added 0.25 N NaOH (5 mL, 1.25 mmol) and the mixture was heated under reflux for 3 hr. The mixture was poured into ice-1 N HCl (100 mL) and the solid was collected with suction. The residue was recrystallized from CHCl$_3$-MeOH to give 190 mg (69%) 4-[4-[3-methoxy-4-[N'-(2-methylphenyl)ureido]phenyl]acetyl-1-piperazinylbenzoic acid 259 as a yellow crystalline powder. mp 240–245° C.; $^1$H-NMR (DMSO) d 2.24 (3 H, s), 3.17–3.50 (8 H, m), 3.72 (2 H, s), 3.86 (3 H, s), 6.77 (1 H, d, J=8.3 Hz), 6.90 (1 H, s), 6.91–6.96 (3 H, m), 7.11–7.17 (2H, m), 7.76–7.80 (3 H, m), 8.03 (1 H, d, J=8.3 Hz), 8.47 (1 H, s), 8.58 (1 H, s), 12.30 (1 H, s); Anal.Calcd for $C_{28}H_{30}N_4O_5 \cdot H_2O$: C, 64.60; H, 6.20; N, 10.76. Found: C, 64.64; H, 5.85; N, 10.51.

Example 212

(R)-3-methoxy-4-[2-[3-methoxy-4-[N'-(2-methylphenyl)ureido]phenylacetylamino]-1-propoxy]benzoic acid

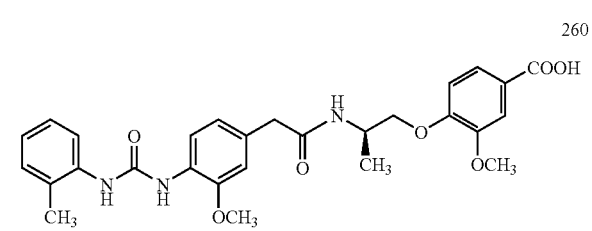

260

To a cooled (0° C.) solution of (R)-2-amino-1-propanol (3.01 g, 0.04 mmol) and Et$_3$N (6.70 mL, 0.05-mmol) in DMF-H$_2$O (1:1, v/v)(40 mL) was added (Boc)$_2$O (10.0 mL, 0.04 mmol), and the resulting mixture was stirred at room temp for 2 days. The mixture was diluted with EtOAc, washed with H$_2$O, brine, dried over Na$_2$SO$_4$ and evaporated to give 6.91 g (98%) (R)-2-N-tert-butoxycarbonylamino-1-propanol as a colorless oil. $^1$H-NMR (CDCl$_3$) δ1.15 (d, 3 H, J=6.8 Hz), 1.45 (s, 9 H), 3.48–3.53 (m, 1 H), 3.62–3.66 (m, 1 H), 3.76–3.77 (m, 1 H); MS (FAB) m/z 176 (M$^+$+1), 120 (M$^+$-$^t$Bu).

To a stirred solution of ethyl 4-hydroxy-3-methoxybenzoate (7.74 g, 0.04 mmol), (R)-2-N-tert-butoxycarbonylamino-1propanol (6.91 g, 0.04 mmol) and Ph$_3$P (13.44 g, 0.05 mmol) in THF (70 mL) was added diisopropyl azodicarboxylate(DIAD)(10.0 mL, 0.05 mmol), and the resulting mixture was heated under reflux overnight. After cooling to room temp, the solvent was evaporated. The mixture was dissolved in CH$_2$Cl$_2$ (50 mL) and TFA (30 mL) and the solution was stirred at room temp for 1 hr. After concentration in vacuo, the residue was poured into sat.

NaHCO$_3$ and extracted with CHCl$_3$. The extract was washed with brine, dried over Na$_2$SO$_4$ and evaporated. The residue was purified by column chromatography on silica-gel with 5% MeOH in CHCl$_3$ as eluent to give 7.93 g (2 steps 79%) ethyl (R)-3-methoxy-4-(2-amino-1propoxy)benzoate as a yellow oil. $^1$H-NMR (CDCl$_3$) δ 1.90 (d, 3 H, J=6.8 Hz), 1.39 (t, 3 H, J=7.3 Hz), 1.72 (bs, 2 H), 3.42–3.47 (m, 1 H), 3.74–3.89 (m, 1 H), 3.91 (s, 3 H), 3.96–4.00 (m, 1 H), 4.35 (q, 2 H, J=7.3 Hz), 6.88 (d, 1 H, J=8.3 Hz), 7.55 (d, 1 H, J=2.0 Hz), 7.65 (dd, 1 H, J=2.0, 8.3 Hz); MS (FAB) m/z 254 (M$^+$+1).

To a stirred solution of pentafluorophenyl 3-methoxy-4-[N'-(2-methylphenyl)ureido]phenylacetate (459 mg, 0.96 mmol) and ethyl (R)-3-methoxy-4-(2-aminopropoxy)benzoate (242 mg, 0.96 mmol) in DMF (5 mL) was added Et$_3$N (200 μl, 1.43 mmol), and the resulting mixture was stirred for 2 hr. The mixture was diluted with EtOAc, washed with 0.5 N HCl, brine, dried over Na$_2$SO$_4$ and evaporated. The residue was purified by column chromatography on silica-gel with CHCl$_3$-MeOH (50:1, v/v) as eluent to give 360 mg (69%) ethyl (R)-3-methoxy-4-[2-[3-methoxy-4-[N'-(2-methylphenyl)ureido]phenylacetylamino]-1-propoxy]benzoate as a colorless crystalline solid. $^1$H-NMR (CDCl$_3$) δ 1.23–1.28 (m, 3 H), 1.38–1.41 (t, 3 H, J=7.3 Hz), 2.32 (s, 3 H), 3.50–4.13 (m, total 11 H), 4.36 (q, 2 H, J=7.3 Hz), 6.65–8.13 (series of m, total 12 H).

To a stirred solution of ethyl (R)-3-methoxy-4-[2-[3-methoxy-4-[N'-(2-methylphenyl)ureido]phenylacetylamino]-1propoxy]benzoate (360 mg, 0.66 mmol) in THF-MeOH (20 mL, 9:1, v/v) was added 0.25 N NaOH (10 mL), and the resulting mixture was heated under reflux overnight. The mixture was poured into ice-1 N HCl, and precipitate was collected. The crude solid was recrystallized from CHCl$_3$-n-hexane to give 172 mg(50%) 260 as a white crystalline powder. mp 168–169° C.; IR (KBr) 1687 cm$^{-1}$; $^1$H-NMR (DMSO-d$_6$) δ 1.18 (d, 3 H, J=6.8 Hz), 2.24 (s, 3 H), 2.50–2.51 (m, 2 H), 3.80 (s, 3 H), 3.84 (s, 3 H), 3.87–4.06 (m, 2 H), 4.07–4.14 (m, 1 H), 6.76–8.57 (series of m, total 12 H), 12.66 (bs, 1 H); MS (FAB) m/z 522 (M$^+$+1); Anal. Calcd for C$_{28}$H$_{31}$N$_3$O$_7$.3/4 H$_2$O: C, 62.85; H, 6.12; N, 7.85. Found: C, 62.77; H, 5.95 N, 7.79.

Example 213

4-[[2-[3-methoxy-4-[N'-(2-methylphenyl)ureido]phenylacetyl]allylamino]ethoxy]benzoic acid

261

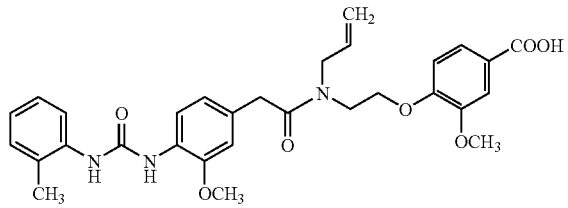

To a stirred mixture of ethyl 4-(2-N-trifluoroacetylaminoethoxy)-3-methoxy benzoate (3.5 g, 10.4 mmol)and K$_2$CO$_3$ (2.3 g, 16.4 mmol) in DMF (20 mL) was added allyl bromide (14.2 mL, 16.5 mmol), and the resulting mixture was stirred for 45 min at 65° C. After cooling, water was added to the mixture and extracted with EtOAc. The extract was washed with brine, dried over Na$_2$SO$_4$, and evaporated in vacuo. The residue was dissolved in THF-MeOH-H$_2$O (1:1:1 v/v/v) (30 mL) and added K$_2$CO$_3$ (2.3 g, 16.4 mmol). The resulting mixture was stirred for 16 hr at room temp. The mixture was diluted with EtOAc, washed with brine, dried over Na$_2$SO$_4$, and evaporated. The residue was chromatographed on silica-gel with CHCl$_3$:MeOH (95:5 to 95:5, v/v) as eluent to give 2.9 g (100%) ethyl 4-(2-allylaminoethoxy)-3-methoxybenzoate as a pale-yellow oil. $^1$H-NMR (CDCl$_3$, 400 MHz) δ 1.39 (t, 3H, J=7.3 Hz), 3.07 (t, 2H, J=5.3 Hz), 3.34 (d, 2H, J=5.9 Hz), 3.91 (s, 3H), 4.18 (t, 2H, J=5.4 Hz), 4.35 (dd, 2H, J=7.3 Hz, 14.1 Hz), 5.12 (d, 1H, J=10.3 Hz), 5.22 (dd, 1H, J=1.5 Hz, 17.1 Hz), 5.92 (m, 2H), 6.90 (d, 1H, J=8.3 Hz), 7.55 (d, 1H, J=1.5 Hz), 7.65 (dd, 1H, J=2.0 Hz, 8.3 Hz); MS(FAB) m/z 278, 280(M+H)$^+$.

To a stirred mixture of ethyl 4-(2-allylaminoethoxy)-3-methoxy benzoate (578 mg, 2.1 mmol), 3-methoxy-4-[N'-(2-methylphenyl)ureido]phenylaceticacid (650 mg, 2.1 mmol), HOBt (420 mg, 3.11 mmol), and DMAP (catalytic amount) in DMF (4 mL) was added EDC (596 mg, 3.11 mmol) at room temp. The resulting mixture was stirred for a further 18 hr at room temp. The mixture was poured into 1 N HCl and extracted with EtOAc. The extract was washed with brine, dried over Na$_2$SO$_4$, and evaporated in vacuo. The residue was chromatographed on silica-gel with CHCl$_3$: EtOAc (95:5 to 1:1, v/v) as eluent to give 1 g (84%) 3-methoxy-4-[[2-[3-methoxy-4-[N'-(2-methylphenyl)ureido]phenylacetyl]allylamino]ethoxy]benzoic acid as a pale-yellow gum. $^1$H-NMR(CDCl$_3$, 400 MHz) δ 1.39 (t, 3H, J=7.3 Hz), 2.29 (s, 3H), 3.58 and 3.63 (s, total 3H), 3.70–3.77 (m, 2H), 3.83 and 3.87 (s, 3H), 4.05–4.13 (m, 2H), 4.25 (m, 1H), 4.36 (q, 1H, J=7.0 Hz), 5.04–5.22 (m, 2H), 5.73 (m, 1H), 6.32 and 6.47 (s, 1H), 6.69–6.85 (m, 2H), 7.12 (m, 2H), 7.23 (m, 2H), 7.50–7.65 (m, 2H), 8.05 (d, 1H, J=7.8 Hz); MS (FAB) m/z 576(M+H)$^+$.

A mixture of 3-methoxy-4-[[2-[3-methoxy-4-[N'-(2-methylphenyl)ureido]phenylacetyl]allylamino]ethoxy]benzoic acid (50 mg, 0.09 mmol) in THF-MeOH (1:1, v/v) (2 mL) and 1 N NaOH (0.135 mL, 0.135 mmol was stirred for 15 hr at room temp and 3 hr at 50° C. The mixture was poured into ice-1 N HCl. Solid was collected, washed with water, and air-dried. The crude solid was recrystallized from CHCl$_3$-n-hexane to give 38 mg (77%) 261 as a white crystalline material. mp 125–130° C.; IR(KBr), 3319, 2939, 1687, 1647, 1601, 1535, 1456, 1417, 1269, 1223, 1034, 760cm$^{-1}$; $^1$H-NMR(DMSO-d$_6$, 400 MHz) δ 2.29 (s, 3H), 3.68 (s, 2H), 3.75–3.85 (m, 8H), 4.05 (br, 1H), 4.19 (m, 3H), 5.10–5.25 (m, 2H), 5.65–5.90 (m, 1H), 6.75 (m, 1H), 6.85 (s, 1H), 6.92 (m, 1H), 7.02–7.20 (m, 3H), 7.48 (d, 1H, J=10.2 Hz), 7.56 (m, 1H), 7.79 (d, 1H, J=6.8 Hz), 8.01 (m, 1H), 8.46 (s, 1H), 8.56 (d, 1H, J=4.4 Hz), 12.7 (br, 1H); MS (FAB) m/z 548(M+H)$^+$; Anal. calcd. for C$_{30}$H$_{33}$N$_3$O$_7$.0.5 H$_2$O, C, 64.74; H, 6.16; N, 7.55. Found, C, 64.72; H, 6.07; N, 7.55.

Example 214

3-methoxy-4-[[2-[3-methoxy-4-[N'-(2-methylphenyl)ureido]phenylacetyl]-(2-morpholino) ethylamino]ethoxy]benzoic acid

262

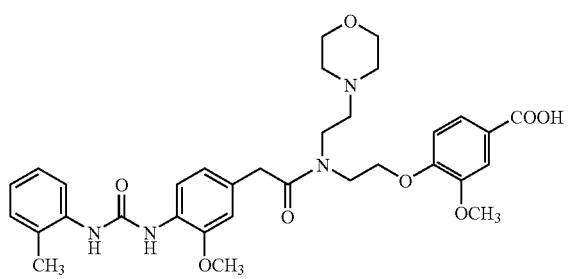

To a stirred solution of 3-methoxy-4-[[2-[3-methoxy-4-[N'-(2-methylphenyl)ureido]phenylacetyl]allylamino]ethoxy]benzoic acid (950 mg, 1.65 mmol) in THF:H$_2$O (7 mL) was added N-methylmorpholine-N-oxide (579 mg, 4.95 mmol) and osmium tetroxide (0.2M solution in water) (0.413 mL, 0.08 mmol). The resulting mixture was stirred for 3 hr at room temp. Sat. NaHSO$_3$ was added to the mixture, and the mixture was filtered through Celite. The filtrate was extracted with EtOAc. The extract was washed with brine, dried over MgSO$_4$, and evaporated in vacuo. The residue was dissolved in MeOH-THF-H$_2$O (1:1:1, v/v) (12 mL) and added sodium periodate (318 mg, 1.5 mmol). The resulting mixture was stirred at an ambient temp for 1 hr. The mixture was diluted with EtOAc, washed with brine, and dried over MgSO$_4$. Solvent was evaporated in vacuo to afford 862 mg (90%) ethyl 3-methoxy-4-[[2-[3-methoxy-4-[N'-(2-methylphenyl)ureido]phenylacetyl]-N-formylmethylamino]ethoxy]benzoate as a pale-yellow gum. $^1$H-NMR (CDCl$_3$, 400 MHz) δ 1.39 (t, 3H, J=7.3 Hz), 2.29 (s, 3H), 3.31–3.95 (m, 11H), 4.10–4.42 (m, 5H), 6.51–6.82 (m, 3H), 7.10–7.25 (m, 3H), 7.50 (m, 2H), 7.60 (m, 1H), 8.10 (m, 1H), 9.50 (m, 1H); MS (FAB) m/z 578 (M+H)$^+$.

To a stirred mixture of ethyl 3-methoxy-4-[[2-[3-methoxy-4-[N'-(2-methylphenyl)ureido]phenylacetyl]-N-formylmethylamino]ethoxy]benzoate (265 mg, 0.46 mmol), morpholine (0.40 mL, 4.59 mmol), and AcOH (0.263 mL, 4.6 mmol) in EtOH (3 mL) was added NaBH$_3$CN (288 mg, 4.6 mmol) at room temp. The resulting mixture was stirred for 15 hr at room temp and the mixture was diluted with EtOAc and added sat. NaHCO$_3$ at 0° C. The resulting mixture was stirred for 0.5 hr at 0° C. The mixture was extracted with EtOAc. The extract was washed with brine, dried over MgSO$_4$, and evaporated in vacuo. The residue was chromatographed on silica-gel with CHCl$_3$:MeOH (95:5, v/v) as eluent to give 213 mg (71%) ethyl 3-methoxy-4-[[2-[3-methoxy-4-[N'-(2-methylphenyl)ureido]phenylacetyl]-(2-morpholino)ethylamino]ethoxy]benzoate as an oil. $^1$H-NMR (CDCl$_3$, 400 MHz) δ 1.28 (t, 3H, J=7.0 Hz), 2.31(s, 3H), 2.48 (br s, 4H), 2.52 (m, 2H), 3.60–3.91 (m, 16H), 4.11 and 4.28 (m, total 2H), 4.39 (q, 2H, J=7.0 Hz), 6.70–6.85 (m, 4H), 7.15 (m, 2H), 7.50–7.63 (m, 3H), 8.08 (d, 1H, J=8.0 Hz); MS (FAB) m/z 649(M+H)$^+$.

A mixture of ethyl 3-methoxy-4-[[2-[3-methoxy-4-[N'-(2-methylphenyl)ureido]phenyl acetyl]-(2-morpholino)ethylamino]ethoxy]benzoate (265 mg, 0.46 mmol) in THF (4 mL) and 1N NaOH (0.984 mL) was stirred at 50° C. for 15 hr. The pH of the mixture was adjusted to 7.4 by the addition of 1 N HCl, and extracted with CHCl$_3$:MeOH(9:1, v/v). The extract was washed with brine, dried over MgSO$_4$, and evaporated in vacuo. The residue was crystallized with Et$_2$O to give 160 mg(78%) 262 as a white crystalline material. mp 125–130° C.; IR (KBr), 3346, 2956, 2937, 1705, 1622, 1599, 1537, 1456, 1417, 1299, 1114, 1032, 752cm$^{-1}$; $^1$H-NMR (CD$_3$OD, 400 MHz) 2.29 (s, 3H), 2.49–2.64 (m, 6H), 3.65–3.85 (m, 16H), 4.13 (m 1H), 4.26 (m, 1H), 6.78–7.04 (m, 4H), 7.18 (m, 2H), 7.55–7.64 (m, 3H), 7.99 (m, 2H); MS (FAB) m/z 621(M+H)$^+$; Anal. Calcd. for C$_{33}$H$_{40}$N$_4$O$_8$.2.5H$_2$O, C, 59.54; H, 6.81; N, 8.42. Found, C, 59.71; H, 6.35; N, 7.98.

Example 215

3-methoxy-4-[[2-[3-methoxy-4-[N'-(2-methylphenyl)ureido]phenylacetyl]-[2-[4-methyl-1-piperazinyl]ethylamino]ethoxy]benzoic acid

263

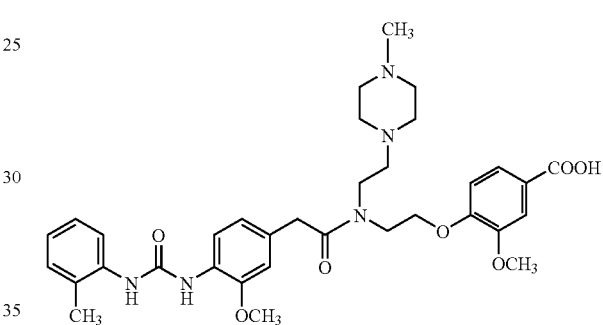

To a stirred mixture of ethyl 3-methoxy-4-[[2-[3-methoxy-4-N'-(2-methylphenyl)ureido]phenylacetyl]-N-formylmethylamino]ethoxy]benzoate (242 mg, 0.42 mmol), N-methylpiperazine (0.465 mL, 4.2 mmol), and AcOH (0.240 mL, 4.2 mmol) in EtOH (3 mL) was added NaBH$_3$CN (263 mg, 4.2 mmol) at room temp. The resulting mixture was stirred for 15 hr at room temp. The mixture was diluted with EtOAc and added sat. NaHCO$_3$ at 0° C. The resulting mixture was stirred for 0.5 hr at 0° C. The mixture was extracted with EtOAc. The extract was washed with brine, dried over MgSO$_4$, and evaporated in vacuo. The residue was chromatographed on silica-gel with CHCl$_3$:MeOH (95:5, v/v) as eluent to give 195 mg (70%) ethyl 3-methoxy-4-[[2-[3-methoxy-4-[N'-(2-methylphenyl)ureido]phenylacetyl]-[2-(4-methyl-1-piperazinyl]ethylamino]ethoxy]benzoate as an oil. $^1$H-NMR (CDCl$_3$, 400 MHz) δ 1.23 (t, 3H, J=7.0 Hz), 2.25 (s, 3H), 2.29 (s, 3H), 2.50 (br m, 12H), 3.44–3.85 (m, 12H), 4.10 (br, 1H), 4.22 (br, 1H), 4.35 (m, 2H), 6.70–6.85 (m, 3H), 6.98 (s, 1H), 7.10 (m, 1H), 7.20 (m, 2H), 7.40 (m, 1H), 7.60–7.70 (m, 3H), 8.05 (d, 1H, J=7.8 Hz); MS (FAB) m/z 662(M+H)$^+$.

A mixture of ethyl 3-methoxy-4-[[2-[3-methoxy-4-[N'-(2-methylphenyl)ureido]phenylacetyl]-[2-(4-methyl-1-piperazinyl]ethylamino]ethoxy]benzoate (195 mg, 0.30 mmol) in THF:MeOH(4:1, v/v) (5 mL) and 1 N NaOH (0.885 mL) was stirred at 50° C. for 15 hr. The pH of the mixture was adjusted to 7.4 by the addition of 1 N HCl, and extracted with CHCl$_3$:MeOH(9:1, v/v). The extract was washed with brine, dried over MgSO$_4$, and evaporated in vacuo. The residue was crystallized with Et$_2$O to give 141 mg(75%) 263 as a white crystalline material. mp 155–160° C.; IR (KBr), 2937, 1537, 783 cm⁻; ¹H-NMR (CD₃OD, 400M) δ 2.29 (s, 3H), 2.49–2.80 (m, 15H), 3.60–3.85 (m, 9H), 3.92 (s, 1H), 4.12 (m, 1H), 4.25 (m, 1H), 6.78–7.20 (m, 6H), 7.61 (m, 3H), 8.00 (m, 1H); MS (FAB) m/z 632(M)⁺; Anal. Calcd. for C₃₄H₄₃N₅O₇.2.5H₂O, C, 60.16; H, 7.13; N, 10.32. Found, C, 59.72; H, 6.86; N, 9.97.

Example 216

3-methoxy-4-[[2-[3-methoxy-4-[N'-(2-methylphenyl)ureido]phenylacetyl]-2-cyclopropylamino]ethylamino]ethoxy]benzoic acid

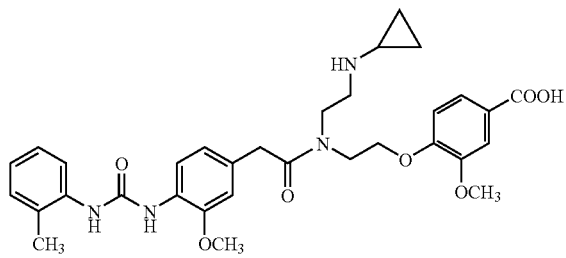

264

To a stirred mixture of ethyl 3-methoxy-4-[[2-[3-methoxy-4-[N'-(2-methylphenyl)ureido]phenylacetyl]-N-formylmethylamino]ethoxy]benzoate (267 mg, 0.46 mmol), cyclopropylamine (0.32 mL, 4.6 mmol), and AcOH (0.264 mL, 4.6 mmol) in EtOH (3 mL) was added NaBH₃CN (290 mg, 4.6 mmol) at room temp. The resulting mixture was stirred for 15 hr at room temp. The mixture was diluted with EtOAc and added sat. NaHCO₃ at 0° C. The resulting mixture was stirred for 0.5 hr at 0° C. The mixture was extracted with EtOAc. The extract was washed with brine, dried over MgSO₄, and evaporated in vacuo. The residue was chromatographed on silica-gel with CHCl₃:MeOH (95:5, v/v) as eluent to give 156 mg (55%) ethyl 3-methoxy-4-[[2-[3-methoxy-4-[N'-(2-methylphenyl)ureido]phenylacetyl]-[2-cyclopropylamino]ethylamino]ethoxy]benzoate as an oil. ¹H-NMR (CDCl₃, 400 MHz) δ 0.35 (m, 4H), 1.22 (br s, 3H), 2.10 (m, 1H), 2.20 (s, 3H), 2.42 (br, 2H), 2.90 (br s, 2H), 3.60–3.80 (m, 10H), 4.10 (br, 1H), 4.22 (br, 1H), 4.33 (br, 2H), 6.72 (m, 3H), 7.05–7.30 (m, 4H), 7.55 (m, 4H), 8.06 (br s, 1H); MS (FAB) m/z 619(M+H)⁺.

A mixture of ethyl 3-methoxy-4-[[2-[3-methoxy-4-[N'-(2-methylphenyl)ureido]phenylacetyl]-N-[2-cyclopropylamino]ethylamino]ethoxy]benzoate (195 mg, 0.30 mmol)) in THF:MeOH(4:1, v/v) (5 mL) and 1 N NaOH (0.756 mL) was stirred at 50° C. for 15 hr. The pH of the mixture was adjusted to 7.4 by the addition of 1 N HCl, and extracted with CHCl₃:MeOH(9:1, v/v). The extract was washed with brine, dried over MgSO₄, and evaporated in vacuo. The residue was crystallized with Et₂O to give 57 mg (38%) 3-methoxy-4-[[2-[3-methoxy-4-[N'-(2-methyl phenyl)ureido]phenylacetyl]-[2-cyclopropylamino]ethylamino] ethoxy]benzoic acid 264 as a white crystalline material. mp 135–140° C.; IR (KBr), 3324, 2937, 1535, 1032, 754 cm⁻¹; ¹H-NMR (CD₃OD, 400 MHz) δ 0.50–0.73 (m, 4H), 2.29 (s, 3H), 2.53 (m, 3H), 2.98 (m, 1H), 3.21 (m, 1H), 3.58–3.88 (m, 11H), 3.91 (s, 1H), 4.09 (m, 1H), 4.25 (m, 1H), 6.76–6.92 (m, 3H), 7.01 (m, 1H), 7.18 (m, 2H), 7.60 (m, 3H), 8.00 (d, J=8.3 Hz, 1H); MS (FAB) m/z 591(M+H)⁺; Anal. Calcd. for C₃₂H₃₈N₄O₇.3.0H₂O, C, 59.62; H, 6.88; N, 8.69. Found, C, 59.25; H, 6.29; N, 8.29.

Example 217

4-[[2-[3-methoxy-4-[N'-(2-fluorophenyl)ureido]phenylacetyl]-N-methylamino]ethoxy]benzoic acid

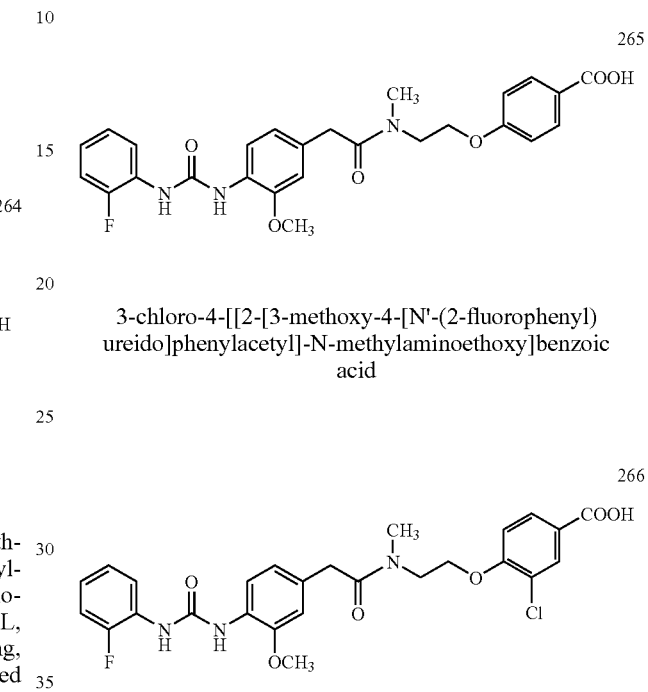

265

3-chloro-4-[[2-[3-methoxy-4-[N'-(2-fluorophenyl)ureido]phenylacetyl]-N-methylaminoethoxy]benzoic acid

266

To a stirred cold (0° C.) solution of 2-(N-benzyloxycarbonyl-N-methyl)ethanolamine (3.01 g, 14.4 mmol), methyl 3chloro-4-hydroxybenzoate (2.68 g, 14.4 mmol), Ph₃P (5.65 g, 21.5 mmol) in THF (30 mL) was added diisopropyl azodicarboxylate (DIAD) (4.25 mL, 21.6 mmol), and the resulting mixture was heated under reflux overnight. The solution was evaporated off and the residue was purified by column chromatography on silica-gel with CHCl₃ as eluent to give 3.90 g (72%) methyl 3-chloro-4-[2-(N-benzyloxycarbonyl-N-methylamino)ethoxy]benzoate as a pale yellow solid. ¹H-NMR (CDCl₃) δ 3.15 (s, 3 H), 3.74–3.76 (m, 2 H), 3.89 (s, 3 H), 4.17–4.27 (m, 2 H), 5.14 (s, 2 H), 6.81–6.94 (m, 1 H), 7.33–7.36 (m, 5H), 7.85–7.92 (m, 1 H), 8.05 (bs, 1 H).

A solution of methyl 3-chloro-4-[2-(N-benzyloxycarbonyl-N-methylamino)ethoxy]benzoate (3.90 g, 10.3 mmol) in EtOAc-AcOH (40 mL, 1:1, v/v) was hydrogenated over 5% Pd—C (1.95 g, 50 wt %) at 3 atm for 2 hr. The mixture was filtered and the filtrate was washed with sat. NaHCO₃ and the basic aqueous layer was extracted with CHCl₃, washed with brine and evaporate to give unseparable mixture of methyl 3-chloro-4-(N-methylaminoethoxy)benzoate and methyl 4-[2-(N-methylamino) ethoxy]benzoate the title compound (1.61 g) as a pale yellow oil. ¹H-NMR (CDCl₃) δ 2.52–2.52 and 2.53–2.54 (each m, 3 H), 2.98–3.00 and 3.03–3.05 (each m, each 2 H), 3.88 and 3.99 (each s, each 3 H), 4.11–4.14 and 4.18–4.20 (each m, each 2 H), 6.91–6.96 and 7.90–8.05 (series of m, total 7 H).

A mixture of 3-methoxy-4-[N'-(2-fluorophenyl)ureido] phenylacetic acid (392 mg), a mixture of methyl 3-chloro-4-[2-(N-methylamino)ethoxy]benzoate and methyl 4-[2-(N- methylamino)ethoxy]benzoate (305 mg), EDC (hydrochloride) (354 mg), HOBt (250 mg), and DMAP (250 mg) in DMF (8 mL) was stirred at room temp for 6 hr. The mixture was diluted with EtOAc, washed with 0.5 N HCl, brine, dried over $Na_2SO_4$ and evaporated. The residue was purified by column chromatography on silica-gel with 1% MeOH in $CHCl_3$ as eluent to give a mixture of methyl 3-chloro-4-[[2-[3-methoxy-4-[N'-(2-fluorophenyl) ureido]phenylacetyl]-N-methylaminoethoxy]benzoate and methyl 4-[[2-[3-methoxy-4-[N'-(2-fluorophenyl)ureido]phenylacetyl]-N-methylaminoethoxy]benzoate (550 mg) as a brown amorphous solid.

To a stirred solution of this mixture (550 mg) of methyl 3-chloro-4-[[2-[3-methoxy-4-[N'-(2-fluorophenyl)ureido]phenylacetyl]-N-methylaminoethoxy]benzoate and methyl 4-[[2-[3-methoxy-4-[N'-(2-fluorophenyl)ureido]phenylacetyl]-N-methylaminoethoxy]benzoate in THF-MeOH (20 mL, 1:1, v/v) was added 0.5 N NaOH (10 mL), and the resulting mixture was heated under reflux for 6 hr. The mixture was poured into ice-1 N HCl, and the solid was collected. The crude solid was purified by preparative TLC with 10% MeOH in $CHCl_3$ as eluent to give 265 (56 mg, as a white amorphous solid) and 266 (88 mg, as a brown amorphous solid).

Example 218

4-[[2-[3-methoxy-4-[N-(2-methylphenyl)ureido] phenylacetyl]methylamino]ethoxy]benzoic acid

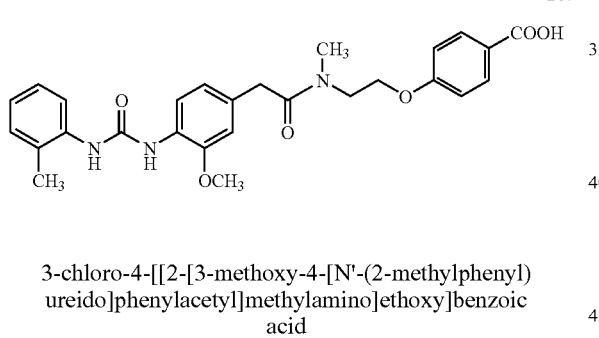

267

3-chloro-4-[[2-[3-methoxy-4-[N'-(2-methylphenyl)ureido]phenylacetyl]methylamino]ethoxy]benzoic acid

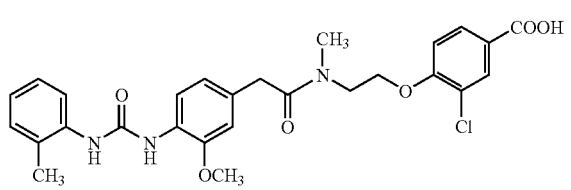

268

A mixture of methyl 4-[2-(N-methyl-2-amino)ethoxy]-3-chlorobenzoate (292 mg, 1.2 mmol), 3-methoxy-4-[N'-(2-methylphenyl)ureido]phenylaceticacid (377 mg, 1.2 mmol), EDC (345 mg, 1.8 mmol), HOBt(243 mg, 1.8 mmol), and DMAP(29 mg, 0.24 mmol) in DMF(2.7 mL) was stirred for 6 hr at room temp. The mixture was poured into ice-1 N HCl and extracted with EtOAc. The extract was washed with brine, dried over $MgSO_4$, and evaporated in vacuo. The residue was chromatographed on silica-gel with $CHCl_3$:EtOAc (95:5 to 0:100, v/v) as eluent to give unseparable mixture (489 mg) of methyl 3-chloro-4-[[2-[3-methoxy-4-[N'-(2-methylphenyl)ureido]phenylacetyl]methylamino] ethoxy]benzoate and methyl 4-[[2-[3-methoxy-4-[N'-(2-methylphenyl)ureido]phenyl acetyl]methylamino]ethoxy] benzoate as pale-yellow oil.

A mixture (480 mg as mixture) of methyl 3-chloro-4-[[2-[3-methoxy-4-[N'-(2-methyl phenyl)ureido]phenylacetyl]methylamino]ethoxy]benzoate and methyl 4-[[2-[3-methoxy-4-[N'-(2-methylphenyl)ureido]phenylacetyl]methylamino]ethoxy]benzoate in THF-MeOH(4 mL, 1:1, v/v) was stirred at 50° C. for 15 hr. The mixture was poured into ice-1 N HCl. The solid was collected, washed with water, and air-dried. The crude solid was purified by preparative TLC $CHCl_3$:MeOH (93:7, v/v) as eluent to afford 267 (180 mg, 2steps 31% as a crystalline material) and 268 (280 mg, 2 steps 44% as a crystalline material). 267: mp 145–150° C.; $^1$H-NMR (DMSO-$_6$, 400 MHz) δ 2.31 (s, 3H), 3.05 and 3.19 (s, 3H), 3.35 and 3.38 (s, 3H), 3.72–3.85 (m, 7H), 4.09 and 4.23 (m, total 2H), 6.79–7.20 (m, 7H), 7.60 (m, 1H), 7.86–8.09 (m, 3H); MS (FAB) m/z 493(M+H)$^+$; Anal. calcd. for $C_{27}H_{29}N_3O_6$.1.75$H_2O$, C, 62.00; H, 6.26; N, 8.03. Found, C, 62.16; H, 5.88; N, 7.82. 268: mp 145–150° C.; $^1$H-NMR (DMSO-$_6$, 400 MHz) δ 2.29 (s, 3H), 3.06 and 3.26 (s, 3H), 3.31 and 3.35 (s, 3H), 3.85–3.94 (m, 4H), 4.18 and 4.32 (m, total 2H), 6.75–6.85 (m, 2H), 6.99–7.20 (m, 4H), 7.59 (m, 1H), 7.90–8.02 (m, 3H); MS (FAB) m/z 526(M+H)$^+$; Anal. calcd. for $C_{27}H_{28}ClN_3O_6$.2.0$H_2O$, C, 57.70; H, 5.74; N, 7.48. Found, C, 57.99; H, 5.53; N, 7.07.

Example 219

4-[3-[3-methoxy-4-[N'-(2-methylphenyl)ureido]phenylacetyl]-N-methylamino]-1-propyl]benzoic acid

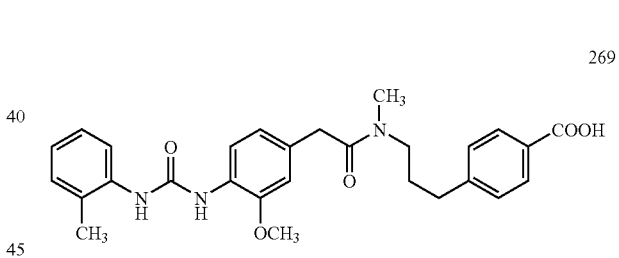

269

To a stirred cold (minus 78° C.) solution of triethyl 4-phosphonomethylbenzoate (1.22 g, 4.05 mmol) in THF (10 mL) was added NaHMDS (1.0 M in THF (4.0 mL, 4.0 mmol), and the resulting mixture was stirred for 1 hr at the same temp. A solution of 2-(N-benzyloxycarbonyl-N-methylamino) acetaldehyde (700 mg, 3.38 mmol),in THF (5 mL) was slowly added to this solution at that temp, and the mixture was allowed to warm to room temp for over 2 hr with stirring. The solution was quenched by the addition of sat. $NH_4Cl$ (100 mL), and extracted with EtOAc. The extract was washed with brine (200 mL), dried over $MgSO_4$, and evaporated. The residue was chromatographed on silica gel with $CHCl_3$-EtOAc (20:1, v/v) as eluent to give 810 mg (68%) ethyl (E)-4-[3-(N-benzyloxycarbonyl-N-methylamino)-1-propenylbenzoate as a yellow oil. $^1$H-NMR ($CDCl_3$) δ 1.40 (t, J=7.3 Hz, 3 H), 2.95 (m, 2 H), 4.09 (m, 2 H), 4.35–4.40 (m, 2 H), 5.17 (s, 2 H), 6.26–6.64 (series of m, 2 H), 7.36 (m, 7 H), 7.99 (d, J=8.3 Hz, 2 H).

A stirred solution of ethyl (E)4-[3-(N-benzyloxycarbonyl-N-methylamino)-1-propenyl benzoate (810 mg, 2.29 mmol) in EtOH—AcOH (10:1, v/v, 22 mL) was hydrogenated over 5% Pd—C (1 g) for 3 days. The mixture was filtered and the filtrate was evaporated. The residue was made basic with sat. NaHCO$_3$ and extracted with CHCl$_3$. The extract was dried over Na$_2$CO$_3$ and evaporated to give 438 mg (86%) ethyl 4-(3-methylamino-1-propyl)benzoate as a yellow oil. $^1$H-NMR (CDCl$_3$) δ 1.39 (t, J=7.3 Hz, 3 H), 1.82 (m, 2 H), 2.43 (s, 3 H), 2.61 (t, J=7.3 Hz, 2 H), 2.72 (t, J=7.3 Hz, 2 H), 3.33 (br s, 1H), 4.36 (q, J=7.3 Hz, 2H), 7.25 (d, J=8.3 Hz, 2H), 7.96 (d, J=8.3 Hz, 2 H).

To a stirred solution of 3-methoxy-4-[N'-(2-methylphenyl)ureido]phenylacetic acid (456 mg, 1.45 mmol) and ethyl 4-(3-methylamino-1-propyl)benzoate (220 mg, 1.45 mmol) were added EDC.HCl (417 mg, 2.16 mmol), HOBt (cat.), and DMAP (catalytic amount) in DMF (10 mL), and the resulting mixture was stirred overnight. The mixture was diluted with EtOAc (300 mL), washed with brine, dried over MgSO$_4$, and evaporated. The residue was chromatographed on silica-gel with CHCl$_3$-EtOH (10:1) to give 503 mg (71%) ethyl 4-[3-[3-methoxy-4-[N'-(2-methylphenyl) ureido]phenylacetyl-N-methylamino]-1-propyl]benzoate as a yellow oil. MS (FAB) m/z 518(M+H)$^+$.

To a stirred solution of ethyl 4-[3-[3-methoxy-4-[N'-(2-methylphenyl)ureido]phenyl acetyl-N-methylamino]-1propyl]benzoate (500 mg, 0.966 mmol) in THF (8 mL) was added 0.25 N NaOH (8 mL), and the mixture was heated under reflux overnight. The resulting solution was poured into ice-1 N HCl (100 mL) and the solid was collected with suction. The solid was dissolved in CHCl$_3$ (100 mL) and dried over MgSO$_4$. After removal of the solvent, the residue was chromatographed on silica gel with CHCl$_3$-MeOH (10:1 to 5:1, v/v) to give 131 mg (28%) 4-[3-[3-methoxy-4-[N'-(2-methylphenyl)ureido]phenylacetyl-N-methylamino]-1-propyl]benzoic acid 269 as a pale yellow amorphous solid. $^1$H-NMR (DMSO-d$_6$) δ 1.68–1.80 (m, 2 H), 2.24 (s, 3 H), 2.57 (m, 2 H), 2.81 and 2.97 (s, each, total 3 H), 3.33 (m, 2 H), 3.57–3.61 (m, 2 H), 3.84 (s, 3 H), 6.71 (dd, J=29.8, 8.3 Hz, 1H), 6.87 (d, J=11.2 Hz, 1H), 6.93 (t, J=7.3 Hz, 1H), 7.15 (m, 2H), 7.28 (m, 2 H), 7.79 (d, J=8.3 Hz, 1 H), 7.84–7.87 (m, 2 H), 8.02 (d, J=8.3 Hz, 1 H), 8.49 (d, J=7.3 Hz, 1 H), 8.58 (d, J=4.9 Hz, 1 H); MS (FAB) m/z 490 (M$^+$+1); Anal. Calcd for C$_{28}$H$_{31}$N$_3$O$_5$.1/2H$_2$O: C, 67.45; H, 6.47; N, 8.43. Found: C, 67.27; H, 6.51; N, 8.02.

Example 220

4-[[2-[4-[N'-(2-methylphenyl)ureido]phenylacetyl]-N-methylamino]ethoxy]benzoic acid

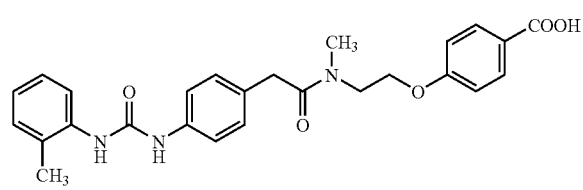

270

3-chloro-4-[[2-[4-[N'-(2-methylphenyl)ureido]phenylacetyl]-N-methylamino]ethoxy]benzoic acid

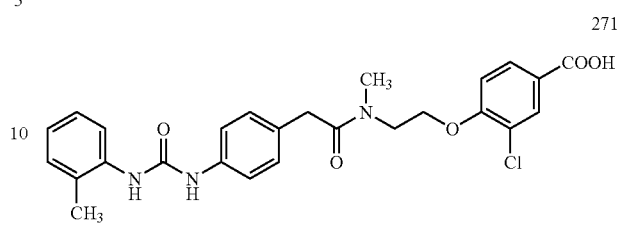

271

A solution of pentafluorophenyl 4-[N'-(2-methylphenyl)ureido]phenylacetate (562 mg, 1.29 mmol), a mixture (304 mg) of methyl 3-chloro-4-[2-(N-methylamino)ethoxy]benzoate and methyl 4-[2-(N-methyl amino)ethoxy]benzoate and Et$_3$ N (260 mL) in DMF (8 mL) was stirred at room temp for 4 hr. The mixture was diluted with EtOAc, washed with 0.5 N HCl, brine, dried over Na$_2$SO$_4$ and evaporated. The residue was purified by column chromatography on silicagel with CHCl$_3$-MeOH (50:1, v/v) as eluent to give a mixture (670 mg) of methyl 3-chloro-4-[[2-[4-[N'-(2-methylphenyl)ureido) phenylacetyl]-N-methylamino) ethoxy] benzoate and methyl-4-[[2-[4-[N'-(2-methylphenyl)ureido] phenylacetyl]-N-methylamino)ethoxy]benzoate as an oil.

To a stirred suspension of this mixture (670 mg) in THF-MeOH (20 mL, 1:1, v/v) was added 0.5 N NaOH (10 mL) and the resulting mixture was heated under reflux for 6 hr. The solution was poured into ice-1 N HCl and the solid was collected. The crude solid was purified by preparative thin layer chromatography (TLC) with 10% MeOH in CHCl$_3$ as eluent to give 73 mg 270 as an amorphous solid and 110 mg 271 as a white amorphous solid. 270 MS (FAB) m/z 462 (M$^+$+1). 271 MS (FAB) m/z 496 (M$^+$+1).

Example 221

(S)-4-[2-[3-methoxy-4-[N'-(2-methylphenyl)ureido] phenylacetylamino]-1-propoxy]benzoic acid

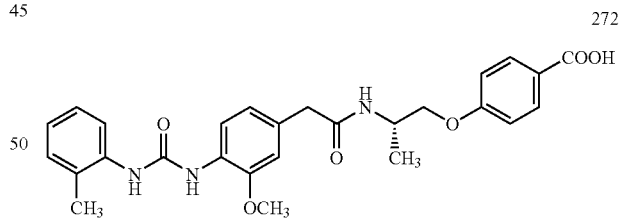

272

To a cooled (0° C.) solution of (S)-2-amino-1-propanol (2.08 g, 27.7 mmol) and Et$_3$N (4.63 mL, 33.2 mmol) in DMF-H$_2$O (40 mL, 1:1, v/v) was added (Boc)$_2$O (6.36 mL, 27.7 mmol), and the resulting solution was stirred at room temp for 2 days. H$_2$O was added to the mixture and extracted with EtOAc. The extract was washed with brine and dried over Na$_2$SO$_4$. The solvent was evaporated to give 4.24 g (87%) (S)-2-(N-tert-butoxycarbonylamino)-1-propanol as a colorless oil. $^1$H-NMR (CDCl$_3$) δ 1.14 (d, 3 H, J=6.8 Hz), 1.45 (s, 9 H), 3.51–3.52 (m, 1 H), 3.63–3.66 (m, 1 H), 7.77 (m, 1 H), 4.62 (m, 1 H).

To a cooled (0° C.) solution of (S)-2-(N-tert-butoxycarbonylamino)-1-propanol (1.02 g, 5.82 mmol), methyl 4-hydroxybenzoate (0.89 g, 5.85 mmol), and Ph₃P (1.98 g, 7.55 mmol) in THF (20 mL) was added diisopropyl azodicarboxylate (DIAD) (1.49 mL, 7.57 mmol), and the resulting mixture was heated under reflux overnight. The solution was evaporated and the residue was dissolved in CH₂Cl₂ (20 mL) and TFA (10 mL). The mixture was stirred at room temp for 1.5 hr. The solution was concentrated in vacuo and the residue was treated with sat. NaHCO₃. The mixture was extracted with CHCl₃, washed with brine, dried over Na₂SO₄ and evaporated. The residue was purified by column chromatography on silica-gel with CHC₃:MeOH (50:1, v/v) to give 480 mg (2 steps 39%) methyl (S)-4-(2-amino-1-prophyl) benzoate as a pale yellow oil. ¹H-NMR (CDCl₃) δ 1.19 (d, 3 H, J=6.4 Hz), 3.35–3.39 (m, 1 H), 3.72–3.76 (m, 1 H), 3.89 (s, 3 H), 3.90–3.94 (m 1 H), 6.92 (d, 2 H, J=8.8 Hz), 7.99 (d, 2H, J=8.8 Hz).

A mixture of pentafluorophenyl 3-methoxy-4-[N'-(2-methylphenyl)ureido]phenylacetate (505 mg, 1.05 mmol), methyl (S)-4-(2-amino-1-propoxy)benzoate (220 mg, 1.05 mmol), and Et₃N (0.220 mL, 1.58 mmol) in DMF (8 mL) was stirred at room temp for 3 hr. The mixture was diluted with EtOAc, washed with 0.5 N HCl, brine and dried over Na₂SO₄. After removal of the solvent, the residue was recrystallized from MeOH—CHCl₃-n-hexane to give 290 mg (55%) methyl (S)-4-[2-[3-methoxy-4-[N'-(2-methylphenyl) ureido]phenylacetylamino]-1-propoxy]benzoate as a white crystalline powder. ¹H-NMR (DMSO-d₆) δ 1.18 (d, 3 H, J=6.8 Hz), 2.24 (s, 3 H), 3.36 (s, 2H), 3.80 (s, 3H), 3.82 (s, 3H), 3.93–4.03 (m, 2H), 4.09–4.14 (m, 1H), 6.75–8.57 (series of m, total 13 H).

To a stirred solution of methyl (S)-4-[2-[3-methoxy-4-[N'-(2-methylphenyl)ureido]phenyl acetylamino]-1-propoxy]benzoate (290 mg, 0.57 mmol) in THF-MeOH (20 mL, 1:1, v/v) was added 0.5 N NaOH (20 mL) and the solution was heated under reflux for 2 hr. The mixture was poured into ice-1 N HCl and extracted with CHCl₃-MeOH (10:1, v/v). The extract was washed with brine, dried over Na₂SO₄ and evaporated. The residue was recrystallized from MeOH—CHCl₃-n-hexane to give 158 mg (56%) 272 as a white crystalline powder. mp 198–201° C.; ¹H-NMR (DMSO-d₆) δ 1.18 (d, 3 H, J=6.3 Hz), 2.24 (s, 3 H), 3.36 (s, 2 H), 3.82 (s, 3 H), 3.87–4.10 (m, 2 H), 4.10–4.16 (m, 1 H), 6.75–6.78 (m, 1 H), 6.92–7.02 (m, 4 H), 7.11–7.18 (m, 2 H), 7.78–7.80 (m, 1 H), 7.86–7.89 (m, 2 H), 7.98–8.00 (m, 1 H), 8.12–8.14 (m, 1 H), 8.46 (s, 1 H), 8.55 (s, 1 H), 12.62 (bs, 1 H); MS (FAB) m/z 492 (M⁺+1); Anal. Calcd for C₂₇H₂₉N₃O₆.1/2H₂O: C, 64.79; H, 6.04; N, 8.21. Found: C, 64.36; H, 5.85; N, 8.21.

Example 222

(S)-4-[2-[4-[N'-(2-methylphenyl)ureido]phenylacetylamino]-1-propoxy]benzoic acid

273

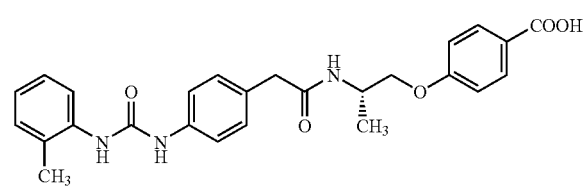

A mixture of pentafluorophenyl 4-[N'-(2-methylphenyl) ureido]phenylacetate (560 mg, 1.24 mmol), methyl (S)-4-(2-amino-1-propoxy)benzoate (260 mg, 1.24 mmol), Et₃N (0.260 mL, 1.87 mmol) in DMF (8 mL) was stirred at room temp for 3 hr. The mixture was diluted with EtOAc and the solution was washed with 0.5 N HCl, brine, and dried over Na₂SO₄. After removal of the solvent, the residue was purified by recrystallization from MeOH—CHCl₃-n-hexane to give 210 mg (36%) (S)-4-[2-[3-methoxy-4-[N'-(2-methylphenyl)ureido]phenylacetylamino]-1-propoxy]benzoic acid as a white crystalline powder. ¹H-NMR (DMSO-d₆) δ 1.17 (d, 3 H, J=6.8 Hz), 2.24 (s, 3 H), 3.32 (s, 2 H), 3.81 (s, 3 H), 3.92–4.03 (m, 2 H), 4.08–4.15 (m, 1 H), 6.92–6.95 (m, 1 H), 7.04–7.06 (m, 2 H), 7.12–7.18 (m, 4 H), 7.35–7.39 (m, 2 H), 7.83–7.85 (m, 1 H), 7.89–7.92 (m, 3 H), 8.12–8.14 (m, 1 H), 8.97 (s, 1 H).

To a stirred solution of methyl (S)-4-[2-[4-[N'-(2-methylphenyl)ureido]phenylacetyl amino]-1-propoxy]benzoate (200 mg, 0.42 mmol) in THF-MeOH (10 mL, 1:1, v/v) was added 0.5 N NaOH (10 mL), and the mixture was heated under reflux for 2 hr. The mixture was poured into ice-1 N HCl, and the solid was collected. The crude solid was recrystallized from MeOH—CHCl₃-n-hexane to give 68 mg (34%) 273 as a white crystalline powder. mp 262–265° C.; ¹H-NMR (DMSO-d₆) δ 1.17 (d, 3 H, J=6.8 Hz), 2.24 (s, 3 H), 3.32 (s, 2 H), 3.91–4.02 (m, 2 H), 4.09–4.15 (m, 1 H), 6.92–6.96 (m, 1 H), 7.01–7.03 (m, 2 H), 7.12–7.20 (m, 4 H), 7.36–7.40 (m, 2 H), 7.83–7.95 (m, 4 H), 8.12–8.14 (m, 1 H), 8.99 (s, 1 H), 12.63 (bs, 1 H); MS (FAB) m/z 462 (M⁺+1); Anal. Calcd for C₂₆H₂₇N₃O₅.1/4H₂O: C, 67.01; H, 5.95; N, 9.02. Found: C, 67.13; H, 5.90; N, 9.02.

Example 223

(S)-3-chloro-4-[2-[4-[N'-(2-methylphenyl)ureido] phenylacetylamino]-1-propoxy]benzoic acid

274

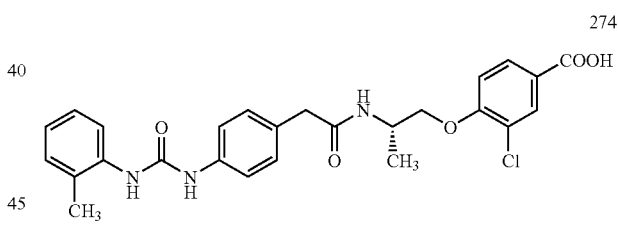

To a cooled (0° C.) solution of (S)-2-(N-tert-butoxycarbonylamino)-1-propanol (1.05 g, 5.99 mmol), methyl 3-chloro-4-hydroxybenzoate (1.12 g, 6.00 mmol), and Ph₃P (2.36 g, 9.00 mmol) in THF (20 mL) was added diisopropyl azodicarboxylate (DIAD) (1.77 mL, 8.99 mmol), and the resulting mixture was heated under reflux for 2 days. The solution was evaporated off and the residue was dissolved in CH₂Cl₂ (20 mL) and TFA (10 mL). The resulting mixture was stirred at room temp for 1.5 hr. The solution was concentrated in vacuo, and the residue was dissolved in CHCl₃. The mixture was extracted with H₂O, and the aqueous layer was made basic by the addition of sat. NaHCO₃. This basic aqueous layer was extracted with CHCl₃. The extract was washed with brine, dried over Na₂SO₄ and evaporated to give 660 mg (2 steps, 32%) methyl (S)-3-chloro-4-(2-amino-1-propoxy)benzoate as a colorless oil. ¹H-NMR (CDCl₃) δ 1.21 (d, 3 H, J=6.4 Hz), 3.41–3.48 (m, 1 H), 3.77–3.81 (m, 1 H), 3.89 (s, 3 H), 3.98–4.01 (m, 1 H), 6.91–6.94 (m, 1 H), 7.90–7.93 (m, 1 H), 8.05–8.06 (m, 1 H).

A mixture of pentafluorophenyl 4-[N'-2-methylphenyl)ureido]phenylacetate (508 mg, 1.13 mmol), methyl (S)-3-chloro-4-(2-amino-1-propoxy)benzoate (275 mg, 1.13 mmol) and Et$_3$N (0.240 mL, 1.72 mmol) in DMF (10 mL) was stirred at room temp overnight. The mixture was diluted with EtOAc, and the solution was washed with 0.5 N HCl, sat. NaHCO$_3$, brine, dried over Na$_2$SO$_4$, and evaporated. The residue was recrystallized from MeOH—CHCl$_3$-n-hexane to give 240 mg (42%) methyl (S)-3chloro-4-[2-[4-[N'-(2-methylphenyl)ureido]phenylacetylamino]-1-propoxy]benzoate as a white crystalline powder. $^1$H-NMR (DMSO-d$_6$) δ 1.21 (d, 3 H, J=6.4 Hz), 2.25 (s, 3 H), 3.33 (s, 2 H), 3.82 (s, 3H), 4.04–4.14 (m, 3H), 6.90–6.94 (m, 1H), 7.11–7.16 (m, 4H), 7.29–7.38 (m, 3H), 7.83–7.94 (m, 3H), 8.13–8.17 (m, 2H), 9.34 (s, 1 H); MS(FAB) m/z 510 (M$^+$).

To a stirred solution of methyl (S)-3-chloro-4-[2-[4-[N'-(2-methylphenyl)ureido]phenylacetylamino]-1-propoxy]benzoate (240 mg, 0.47 mmol) in THF-MeOH (10 mL, 1:1, v/v) was added 0.5 N NaOH (10 mL), and the resulting mixture was heated under reflux overnight. The mixture was poured into ice-1 N HCl and the solid was collected. The crude solid was recrystallized from MeOH—CHCl$_3$-n-hexane to give 98 mg (42%) 274 as a white crystalline powder. mp 228–231° C.; $^1$H-NMR (DMSO-d$_6$) δ 1.20 (d, 3 H, J=6.3 Hz), 2.24 (s, 3 H), 3.34 (s, 2 H), 4.02–4.18 (m, 3 H), 6.92–6.95 (m, 1 H), 7.12–7.42 (series of m, total 7 H), 7.82–8.18 (series of m, total 5 H), 9.12 (s, 1 H); MS (FAB) m/z 496 (M+), 497 (M$^+$+1); Anal. Calcd for C$_{26}$H$_{26}$ClN$_3$O$_5$.1/2H$_2$O: C, 61.84; H, 5.39; Cl, 7.02; N, 8.32. Found: C, 61.76; H, 5.25; Cl, 7.09; N, 8.25.

Example 224

(S)-3-chloro-4-[2-[3-methoxy-4-[N'-(2-methylphenyl)ureido]phenylacetylamino]-1-propoxy]benzoic acid

275

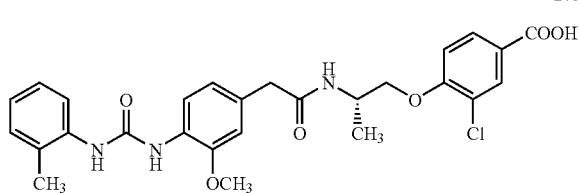

A mixture of pentafluorophenyl 3-methoxy-4-[N'-(2-methylphenyl)ureido]phenylacetate (513 mg, 1.07 mmol), methyl (S)-3-chloro-4-(2-amino-1-propoxy)benzoate (260 mg, 1.07 mmol) and Et$_3$ N (220 μl, 1.58 mmol) in DMF (10 mL) was stirred at room temp overnight. The mixture was diluted with EtOAc and the solution was washed with sat. NaHCO$_3$, dried over Na$_2$SO$_4$, and evaporated. The residue was recrystallized from MeOH—CHCl$_3$-EtOAc-n-hexane to give 400 mg (69%) methyl (S)-3-chloro-4-[2-[3-methoxy-4-[N'-(2-methylphenyl)ureido]phenylacetylamino]-1-propoxy]benzoate as pale brown crystalline powder. $^1$H-NMR (DMSO-d$_6$) δ 1.21 (d, 3 H, J=6.4 Hz), 2.24 (s, 3 H), 3.37 (s, 2 H), 3.82(s, 3 H), 3.83 (s, 3 H), 4.04–4.12 (m, 3 H), 6.75–6.77 (m, 1 H), 6.91–6.95 (m, 2 H), 7.11–7.17 (m, 2 H), 7.29–7.31 (m, 1 H), 7.78–7.99 (m, 4 H), 8.12–8.13 (m, 1H), 8.46 (s, 1 H), 8.55 (s, 1 H).

To a stirred solution of methyl (S)-3-chloro-4-[2-[3-methoxy-4-[N'-(2-methylphenyl) ureido]phenylacetylamino]-1propoxy]benzoate (400 mg, 0.74 mmol) in THF-MeOH (20 mL, 1:1, v/v) was added 0.5 N NaOH (20 mL), and the resulting mixture was heated under reflux overnight. The mixture was poured into ice-1 N HCl and the solid was collected. The crude solid was recrystallized from MeOH—CHCl$_3$-Et$_2$O to give 200 mg (51%) 275 as a pale brown crystalline powder. mp 198–201° C.; $^1$H-NMR (DMSO-d$_6$) δ 1.21 (d, 3 H, J=6.8 Hz), 2.24 (s, 3 H), 3.37 (s, 2 H), 3.84 (s, 3 H), 4.00–4.15 (m, 3 H), 6.76–7.28 (series of m, total 6 H), 7.77–8.14 (series of m, total 5 H), 8.46 (s, 1 H), 8.56 (s, 1 H); MS (FAB) m/z 526 (M$^+$), 528 (M$^+$+2); Anal. Calcd for C$_{27}$H$_{28}$ClN$_3$O$_6$.1/4H$_2$O: C, 61.13;H, 5.42;Cl, 6.68;N, 7.92. Found: C, 60.97; H,5.48; Cl,6.86; N, 7.89.

Example 225

3-dimethylamino-4-[[2-[3-methoxy-4-[N'-(2-methylphenyl)ureido]phenylacetyl]methylamino]ethoxy]benzoic acid

276

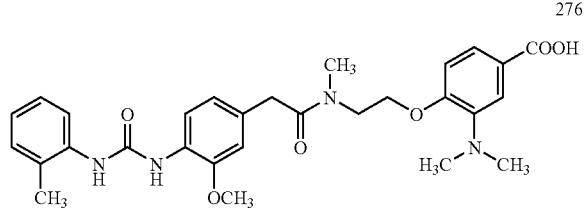

To a stirred and cooled (0° C.) solution of 2-(N-Boc-N-methylamino)ethanol (3 g, 17 mmol), methyl 4-hydroxy-3-nitro benzoate (3.38 g, 17 mmol), and Ph$_3$P (5.4 g, 21 mmol) in THF (20 mL) was added diisopropyl azodicarboxylate (DIAD) (4 mL, 21 mmol), and the resulting mixture was heated under reflux for 15 hr. The solution was evaporated off. The residue was chromatographed on silica-gel with CHCl$_3$:MeOH (100:0 to 4:1, v/v) as eluent to give 2.5 g (39%) methyl 4-[2-(N-methyl-2-amino)ethoxy]-3-nitro benzoate as a pale yellow oil. $^1$H-NMR (CDCl$_3$, 400 MHz) δ 2.82 (s, 3H), 3.50 (t, 2H, J=4.5 Hz), 3.95 (s, 3H), 4.54 (t, 2H, J=4.5 Hz), 7.26 (d, 1H, J=8.8 Hz), 8.25 (d, 1H, J=8.8 Hz), 8.56 (s, 1H); MS (FAB) m/z 255 (M$^+$+1).

A mixture of 3-methoxy-4-[N'-(2-methylphenyl)ureido]phenylacetic acid (992 mg, 3.11 mmol), methyl 4-(N-methyl-2-aminoethoxy)-3-nitro benzoate (800 mg, 3.11 mmol) and 4-DMAP (77 mg, 0.63 mmol), HOBt (640 mg, 4.7 mmol), and EDC (904 mg, 4.7 mmol) in DMF (20 mL) was stirred at room temp overnight. The mixture was diluted with EtOAc, and the solution was washed with 0.5 N HCl, sat. NaHCO$_3$, brine, , dried over Na$_2$SO$_4$, and evaporated. The residue was chromatographed on silica-gel with CHCl$_3$:EtOAc (95:5 to 0:100, v/v) as eluent to give 587 mg (34%) methyl 3-nitro-4-[[2-[3-methoxy-4-[N'-(2-methylphenyl)ureido]phenylacetyl]methylamino]ethoxy]benzoate as a pale yellow oil. $^1$H-NMR (CDCl$_3$, 400 MHz) δ 2.31 (s, 3H), 3.05 (s, 1H), 3.23 (s, 2H), 3.71 (s, 2H), 3.83 (s, 3H), 3.85 (m, 3H), 3.94 (s, 3H), 4.19 and 4.39 (m, total 2H), 6.80 (m, 2H), 7.05 (m, 1H), 7.22 (m, 31H), 7.62 (d, 1H, J=8.2 Hz), 8.02 (d, 1H, J=8.2 Hz), 8.21 (dd, 1H, J=2.1 Hz, 8.8 Hz, 8.55 (d, 1H, J=2.1 Hz); MS (FAB) m/z 551(M$^+$+1).

A mixture of methyl 3-nitro-4-[[2-[3-methoxy-4-[N'-(2-methylphenyl)ureido]phenyl acetyl]methylamino]ethoxy]benzoate (587 mg, 1.1 mmol) and 5% -Pd—C (600 mg) in THF-MeOH—AcOH (1:1:1, v/v, 150 mL) was hydrogenated at 45 psi for 18 hr. Insoluble catalyst was removed with suction, and the filtrate was evaporated in vacuo to afford 555 mg (100%) methyl 3-amino-4-[[2-[3-methoxy-4-[N'-(2-methylphenyl)ureido]phenylacetyl]methylamino]ethoxy]benzoate as a pale yellow gum. $^1$H-NMR (CDCl$_3$, 400 MHz) δ 2.29 (s, 3H), 3.08 (m, 1H), 3.19 (s, 2H), 3.65 (s, 1H), 3.73–3.80 (m, 3H), 3.84 (s, 3H), 3.87 (s, 3H), 4.19 and 4.40 (m, total 2H), 6.70–6.82 (m, 2H), 7.02–7.29 (m, 6H), 7.60 (d, 1H, J=7.8 Hz), 7.92–7.99 (m, 3H); MS (FAB) m/z 521 (M$^+$+1).

To a stirred solution of methyl 3-amino-4-[[2-[3-methoxy-4-[N'-(2-methylphenyl)ureido]phenylacetyl]methylamino]ethoxy]benzoate (555 mg, 1.1 mmol), formaldehyde (10 mL), and AcOH (0.58 mL, 10 mmol) in MeCN (10 mL) was added NaBH$_3$CN (0.67 g, 10 mmol) at room temp, and the resulting mixture was stirred for 15 hr at the same temp. Sat. NaHCO$_3$ was added to the mixture and extracted with CHCl$_3$. The extract was washed with brine, dried over MgSO$_4$, and evaporated in vacuo. The residue was chromatographed on silica-gel with toluene:acetone (7:3 to 1:1, v/v) as eluent to give 123 mg (21%) methyl 3-dimethylamino-4-[[2-[3-methoxy-4-[N'-(2-methylphenyl) ureido]phenylacetyl]methylamino]ethoxy]benzoate as an oil. $^1$H-NMR (CDCl$_3$, 400 MHz) δ 2.30 (s, 3H), 2.70 (s, 3H), 2.75 (s, 3H), 3.05 (s, 1H), 3.18 (s, 2H), 3.61 (s, 3H), 3.70 (s, 1H), 3.80 (m, 3H), 3.86 (s, 3H), 4.07 and 4.22 (m, total 2H), 6.28 (m, 1H), 6.70–6.80 (m, 3H), 7.03 (m, 1H), 7.15–7.25 (m, 4H), 7.46–7.65 (m, 2H), 8.02 (m, 1H); MS (FAB) m/z 548 (M$^+$+1).

A stirred mixture of methyl 3-dimethylamino-4-[[2-[3-methoxy-4-[N'-(2-methylphenyl) ureido]phenylacetyl]methylamino]ethoxy]benzoate (123 mg, 0.22 mmol) in THF (15 mL) and 1N NaOH (0.885 mL, 0.885 mmol) was heated under reflux for 15 hr. The pH of the mixture was adjusted to 5.0 by the addition of 1 N HCl, and extracted with CHCl$_3$—MeOH(9:1, v/v). The extract was washed with brine, dried over MgSO$_4$, and evaporated in vacuo. The residue was crystallized with Et$_2$O-n:hexane to give 118 mg(100%) 276 as a white crystalline material. mp 125–130° C.; IR (KBr) 3346, 2940, 1620, 1597, 1535, 1456, 1417, 1227, 1039, 754 cm$^{-1}$; $^1$H-NMR (CD$_3$OD, 400 MHz) δ 2.29 (s, 3H), 2.70 (s, 3H), 2.79 (s, 2H), 3.05 (s, 1H), 3.22 (s, 2H), 3.75 (s, 3H), 3.85 (m, 4H), 4.15 and 4.28 (m, 2H), 6.78–7.05 (m, 4H), 7.18 (m, 2H), 7.55–7.70 (m, 3H), 7.98 (m, 1H); MS (FAB) m/z 535(M$^+$+1); Anal. calcd. for C$_{29}$H$_{34}$N$_4$O$_6$.2.0H$_2$O: C, 61.04; H, 6.71; N, 9.82. Found: C, 61.15; H, 6.43; N, 8.94.

Example 226

3-dimethylamino-4-[[2-[3-methoxy-4-[N'-(2-fluorophenyl)ureido]phenylacetyl]methylamino]ethoxy]benzoic acid

277

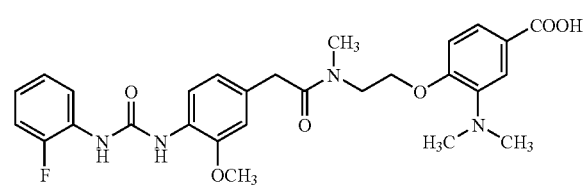

A mixture of 3-methoxy-4-[N'-(2-fluorophenyl)ureido]phenylacetic acid(1 g, 3.11 mmol), methyl 4-[2-(N-methyl-2-amino)ethoxy]-3-nitrobenzoate (800 mg, 3.11 mmol) and 4-DMAP (77 mg, 0.63 mmol), HOBt(640 mg, 4.7 mmol), and EDC (904 mg, 4.7 mmol) in DMF (20 mL) was stirred at room temp overnight. The mixture was diluted with EtOAc, and the solution was washed with 0.5 N HCl, sat. NaHCO$_3$, brine, , dried over Na$_2$SO$_4$, and evaporated. The residue was chromatographed on silica-gel with CHCl$_3$-EtOAc (95:5 to 0:100, v/v) as eluent to give 420 mg (19%) methyl 3-nitro-4-[[2-[3-fluoro-4-[N'-(2-fluorophenyl)ureido]phenylacetyl]methylamino]ethoxy]benzoate as a pale yellow oil. $^1$H-NMR (CDCl$_3$, 400 MHz) δ 3.04 (s, 1H), 3.24 (s, 2H), 3.72 (s, 1H), 3.85 (s, 3H), 3.90 (m, 3H), 3.93 (s, 3H), 4.16 and 4.39 (2m, 3H), 6.80 (m, 2H), 6.99 (m, 1H), 7.05 (m, 2H), 7.22 (d, 1H, J=8.8 Hz), 7.51 (s, 2H), 8.00 (m, 1H), 8.08 (m, 1H), 8.21 (d, 1H, J=8.6 Hz), 8.51 (s, 1H); MS (FAB) m/z 555 (M$^+$+1).

A mixture of methyl 3-nitro-4-[[2-[3-methoxy-4-[N'-(2-fluorophenyl)ureido]phenylacetyl]methylamino]ethoxy]benzoate (420 mg, 0.76 mmol) and 5% -Pd—C (1 g) in THF-MeOH—AcOH (1:1:1, v/v, 150 mL) was hydrogenated at 45 psi for 18 hr. Insoluble catalyst was removed with suction, and the filtrate was evaporated in vacuo to afford 397 mg (100%) methyl 3-amino-4-[[2-[3-methoxy-4-[N'-(2-fluorophenyl)ureido]phenylacetyl]methylamino]ethoxy]benzoate as a pale yellow gum. $^1$H-NMRv (CDCl$_3$, 400 MHz) δ 3.05 and 3.13 (s, total 3H), 3.66 (s, 3H), 3.70 (s, 2H), 3.65–3.90 (m, 4H), 3.86 (s, 3H), 4.10 and 4.23 (m, 2H), 6.70–6.83 (m, 3H), 6.98–7.15 (m, 6H), 7.25–7.43 (m, 2H), 7.99 (m, 1H), 8.13 (m, 1H); MS (FAB) m/z 525 (M$^+$+1).

To a stirred solution of methyl 3-amino-4-[[2-[3-methoxy-4-[N'-(2-fluorophenyl)ureido]phenylacetyl]methylamino]ethoxy]benzoate (397 mg, 0.76 mmol), formaldehyde (10 mL), and AcOH (0.43 mL, 7.6 mmol) in MeCN (10 mL) was added NaBH$_3$CN (0.48 g, 7.6 mmol) at room temp, and the resulting mixture was stirred for 15 hr at the same temp. Sat. NaHCO$_3$ was added to the mixture-and extracted with CHCl$_3$. The extract was washed with brine, dried over MgSO$_4$, and evaporated in vacuo. The residue was chromatographed on silica-gel with toluene:acetone (7:3 to 1:1, v/v) as eluent to give 123 mg (21%) methyl 3-dimethylamino-4-[[2-[3-methoxy-4-[N'-(2-methylphenyl)ureido]phenylacetyl]methylamino]ethoxy]benzoate as an oil. $^1$H-NMR (CDCl$_3$, 400 MHz) δ 2.74 (s, 3H), 2.77 (s, 3H), 3.08 (s, 1H), 3.22 (s, 2H), 3.52 (s, 3H), 3.61 (s, 1H), 3.83 (m, 3H), 3.88 (s, 3H), 4.12 and 4.23 (m, total 2H), 6.68 (s, 1H), 6.78 (m, 2H), 6.98 (m, 2H), 7.10 (m, 1H), 7.55–7.68 (m, 4H), 7.99 (m, 1H), 8.16 (t, 1H, J=8.3 Hz); MS (FAB) m/z 553 (M$^+$+1).

A stirred mixture of methyl 3-dimethylamino-4-[[2-[3-methoxy-4-[N'-(2-fluorophenyl) ureido]phenylacetyl]methylamino]ethoxy]benzoate (61 mg, 0.11 mmol) in THF (15 mL) and 1N NaOH (0.22 mL, 0.22 mmol) was heated under reflux for 15 hr. The pH of the mixture was adjusted to 5.0 by the addition of 1 N HCl, and extracted with CHCl$_3$:MeOH(9:1, v/v). The extract was washed with brine, MeOH:acetone (93:7, v/v) as eluent to give 37 mg (63%) 277 as a white crystalline material. mp 120–125° C.; $^1$H-NMR (CD$_3$OD, 400 MHz) δ 2.60 (s, 4H), 2.78 (s, 2H), 3.06 (s, 1H), 3.22 (s, 2H), 3.75 (s, 3H), 3.85–3.92 (m, 4H), 4.17 and 4.29 (m, total 2H), 6.80–7.12 (m, 6H), 7.61–7.70 (m, 2H), 8.00 (m, 1H), 8.08 (m, 1H); MS (FAB) 539 (M$^+$+1); Anal. calcd. for C$_{28}$H$_{31}$FN$_4$O$_6$.2.75H$_2$O: C, 57.18; H, 6.26; N, 9.53. Found, C, 57.20; H, 5.62; N, 9.06.

Example 227

3-methylamino-4-[[2-[4-[N'-(2-methylphenyl)ure-ido]phenylacetyl]methylamino]ethoxy]benzoic acid

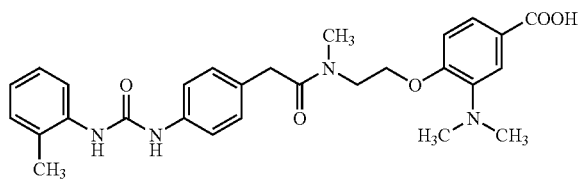

278

A mixture of pentafluorophenyl [4-[N'-(2-methylphenyl) ureido]phenyl]acetate (1.42 g, 3.15 mmol), methyl 4-[2-(N-methyl-2-amino)ethoxy]-3-nitro benzoate (800 mg, 3.15 mmol) and triethylamine (0.66 mL, 4.73 mmol) in DMF (8 mL) was stirred at 50° C. for 15 hr. The mixture was poured into ice-1 N HCl and extracted with CHCl₃. The extract was brine, dried over Na₂SO₄, and evaporated. The residue was chromatographed on silica-gel with CHCl₃:EtOAc (95:5 to 0:100, v/v) as eluent to give 1.04 g (63%) methyl 3-nitro-4-[[2-[4-[N'-(2-methylphenyl)ureido]phenylacetyl]methylamino]ethoxy]benzoate as a pale yellow oil. ¹H-NMR (CDCl₃, 400 MHz) δ 2.30 (s, 3H), 2.90, 3.02 and 3.05 (s, total 1H), 3.22 (s, 2H), 3.71 (s, 1H), 3.85 (3H), 3.93 (s, 3H), 4.19 and 4.39 (m, 2H), 7.02 (m, 1H), 7.19 (m, 4H), 7.35 (d, 1H, J=8.3 Hz), 7.40 (d, 1H, J=8.0 Hz), 7.55 (s, 2H), 7.70 (m, 1H), 8.22 (d, 1H, J=6.7 Hz), 8.51 (s, 1H); MS (FAB) m/z 521(M⁺+1).

A mixture of methyl 3-nitro-4-[[2-[4-[N'-(2-methylphenyl)ureido]phenylacetyl]methylamino]ethoxy]benzoate (1.04 g, 2 mmol) and 5% -Pd—C (1.2 g) in THF-MeOH—AcOH (1:1:1, v/v, 150 mL) was hydrogenated at 45 psi for 18 hr. Insoluble catalyst was removed with suction, and the filtrate was evaporated in vacuo to afford methyl 3-amino-4-[[2-[4-[N'-(2-methylphenyl) ureido]phenylacetyl]methylamino]ethoxy]benzoate as a pale yellow gum.

To a stirred solution of 3-amino-4-[[2-[4-[N'-(2-methylphenyl)ureido]phenylacetyl]methylamino]ethoxy]benzoate, formaldehyde (5 mL), and AcOH (1.14 mL, 20 mmol) in MeCN (5 mL) was added NaBH₃CN (1.26 g, 20 mmol) at room temp, and the resulting mixture was stirred for 15 hr at the same temp. Sat. NaHCO₃ was added to the mixture and extracted with CHCl₃. The extract was washed with brine, dried over MgSO₄, and evaporated in vacuo. The residue was chromatographed on silica-gel with toluene:acetone (7:3 to 1:1, v/v) as eluent to give 85 mg (2 steps, 8%) methyl 3-dimethylamino-4-[[2-[4-[N'-(2-methylphenyl)ureido]phenylacetyl]methyl amino]ethoxy]benzoate as an oil. ¹H-NMR (CDCl₃, 400 MHz) δ 2.12 (s, 3H), 2.73 (s, 3H), 2.75 (s, 3H), 3.05 (s, 1H), 3.20 (s, 2H), 3.60 (s, 1H), 3.80 (m, 3H), 3.88 (s, 3H), 4.17 (m, 2H), 6.95–7.28 (m, 8H), 7.55–7.75 (m, 3H); MS (FAB) m/z 518 (M⁺+1).

A stirred mixture of methyl 3-dimethylamino-4-[[2-[4-[N'-(2-methylphenyl)ureido]phenylacetyl]methylamino] ethoxy]benzoate(ap315201)(85 mg, 0.16 mmol) in THF (15 mL) and 1N NaOH (0.32 mL, 0.32 mmol) was heated under reflux for 15 hr. The pH of the mixture was adjusted to 5.0 by the addition of 1 N HCl, and extracted with CHCl₃: MeOH(9:1, v/v). The extract was washed with brine, dried over MgSO₄, and evaporated in vacuo. The residue was crystallized from Et₂O to give 53 mg(65%) 278 as a white crystalline material. mp 110–115° C.; ¹H-NMR (CD₃OD, 400 MHz) δ 2.29 (s, 3H), 2.75 (s, 3H), 2.76 (s, 3H), 3.02 (s, 1H), 3.20 (s, 2H), 3.72 (s, 1H), 3.85 (m, 3H), 4.18 and 4.28 (m, total 2H), 6.95–7.03 (m, 2H), 7.18 (m, 4H), 7.34 (d, 1H, J=8.3 Hz), 7.38 (d, 1H, J=8.8 Hz), 7.62 (d, 1H, J=8.3 Hz), 7.66 (s, 1H), 7.80 (m, 1H); MS (FAB) m/z 505 (M⁺+1).

Example 228

3-isopropylamino-4-[[2-[3-methoxy-4-[N'-(2-fluorophenyl)ureido]phenylacetyl]methylamino]ethoxy]benzoic acid

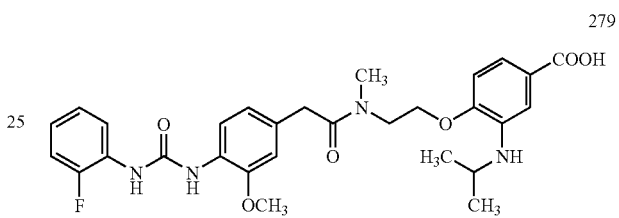

279

To a stirred cold (0° C.) solution of methyl 3-amino-4-[[2-[3-methoxy-4-[N'-(2-fluoro phenyl)ureido]phenylacetyl]methylamino]ethoxy]benzoate (100 mg, 0.19 mmol) in acetone/AcOH/DMF (13 mL, 6:6:1, v/v/v) was added NaBH₃CN (300 mg), and the resulting mixture was stirred for 60 hr at room temp. The mixture was pored into sat. NaHCO₃ and the solid was collected with suction. The precipitate was dissolved in CHCl₃ (20 mL), and the solution was washed with brine, dried over MgSO₄, and evaporated under a reduced pressure. The residue was chromatographed on silica-gel plate with toluene:acetone (2:1, v/v) as eluent to give 108 mg (100%) methyl 3-isopropylamino-4-[[2-[3-methoxy-4-[N'-(2-fluorophenyl)ureido]phenylacetyl]methylamino]ethoxy]benzoate as a colorless oil. ¹H-NMR (CDCl₃, 400 MHz) δ 1.20 (m, 1H), 2.88 (s, 6H), 3.02 and 3.12 (s, total 3H), 3.53 (s, 2H), 3.60–3.80 (m, 7H), 3.85 (s, 3H), 4.10 and 4.20 (m, 2H), 6.65–675 (m, 2H), 6.90–7.08 (m, 2H), 7.22–7.35 (m, 2H), 8.02 (s, 2H), 8.10 (m, 2H), 8.21 (br, 1H), 8.33 (br, 1H); MS (FAB) m/z 566 (M⁺+1).

A stirred mixture of methyl 3-isopropylamino-4-[[2-[3-methoxy-4-[N'-(2-fluorophenyl) ureido]phenylacetyl]methylamino]ethoxy]benzoate (116 mg, 0.2 mmol), 0.25 N NaOH (6 mL), and THF (6 mL) was heated under reflux for 8 hr. The mixture was poured into water (200 mL), acidified by 1 N HCl and the solid was collected with suction. The solid was recrystallized from CHCl₃-n-hexane-diisopropylether to give 56 mg (50%) 279 as a colorless crystalline powder. mp 195–200° C.; ¹H-NMR (CD₃OD, 400 MHz) δ 1.15–1.20 (m, 6H), 3.01 (s, 1H), 3.12 (s, 2H), 3.48–3.60 (m, 1H), 3.68 (s, 3H), 3.75 (s, 2H), 3.82 (s, 1H), 3.86 (m, 3H), 4.15–4.23 (m, 2H), 6.80 (m, 3H), 4.15–4.23 (m, 2H), 6.80 (m, 3H), 6.98 (m, 1H), 7.10 (m, 2H), 7.20 and 7.25 (s, total 1H), 7.32 (m, 1H), 7.98 (m, 1H), 8.05 (m, 1H); MS (FAB) m/z 552 (M+H)⁺; Anal. calcd. for C₂₉H₃₃FN₄O₆·1.0H₂O: C, 61.04; H, 6.18; N, 9.82. Found, C, 61.36; H, 6.25; N, 9.45.

Example 229

4-[[1-[4-[N'-(2-fluorophenyl)ureido]-3-methoxyphenylacetyl]-2-methylamino]-2-methyl-2-propoxy] benzoic acid

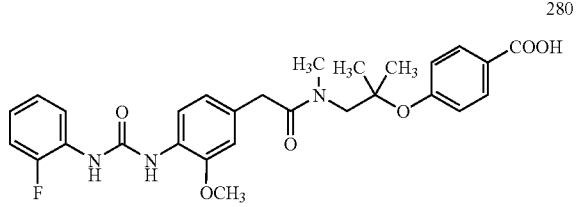

To a stirred solution of 2-amino-2-methyl-1-propanol (8.4 g, 93.89 mmol) and triethylamine (11.4 g, 0.113 mol) in DMF-water (1:1, v/v, 100 mL) was added di-tert-butyl dicarbonate (25 g, 0.15 mol) at 5 to 10° C. The resulting solution was stirred for 2 hr at room temp. The mixture was diluted with water(100 mL) and extracted with EtOAc. The extract was washed with brine, dried over Na$_2$SO$_4$, and evaporated. The residue was chromatographed on silica-gel with CH$_2$Cl$_2$ as eluent to give 12 g (68%) 2-tert-butoxycarbonylamino-2-methyl-1-propanol as a syrup. $^1$H-NMR (CDCl$_3$) δ 1.25 (s, 6H), 1.43 (s, 9H), 3.59 (d, J=8.3 Hz, 2H), 4.68 (br, 1H).

To a stirred suspension of 2-tert-butoxycarbonylamino-2-methyl-1-propanol (5.7 g, 30.11 mmol) and powdered NaOH(6.7 g, 0.151 mol) in Et$_2$O(200 mL) was added p-toluenesulfonyl chloride (6.9 g, 36.14 mmol) at room temp. The stirred resulting mixture was heated under reflux for 8 hr. After cooling, ice-water(100 mL) was added to the solution. Separated Et$_2$O layer was washed with brine, dried over Na$_2$SO$_4$, and evaporated. To the residue was added n-hexane and triturated. The solid was collected to afford 8.5 g (82.2%) 2-tert-butoxycarbonylamino-2-methyl-1-propyl p-toluenesulfonate as a crystalline material. $^1$H-NMR (CDCl$_3$) δ 1.26 (s, 6H), 1.38 (s, 9H), 2.37 (s, 3H), 4.05 (s, 2H), 4.49 (br, 1H), 7.34 (d, J=7.8 Hz, 2H), 7.78 (d, J=7.8 Hz, 2H).

A stirred mixture of 2-tert-butoxycarbonylamino-2-methyl-1-propyl p-toluenesulfonate (8.2 g, 23.88 mmol) and powdered NaOH (6.7 g, 0.151 mol) in Et$_2$O (200 mL) was heated under reflux for 10 hr. After cooling, the mixture was filtered. And the filtrate was washed with water, brine, dried over Na$_2$SO$_4$, and evaporated. The residue was chromatographed on silica-gel with n-hexane:EtOAc (6:1 v/v) as eluent to give 2.7 g (66.2%) 1-tert-butoxycarbonyl-2-methylpropylene imine as an oil. $^1$H-NMR (CDCl$_3$) δ 1.29 (s, 61H), 1.47 (s, 9H), 2.05 (s, 2H).

To a stirred solution of 1-tert-butoxycarbony-2-methylpropyleneimine (1.03 g, 6.10 mmol) and methyl 4-hydroxybenzoate (800 mg, 6.26 mmol) in CH$_2$Cl$_2$ (10 mL) was added boron trifluoride diethyl ether (0.127 mL, 1 mmol) at ambient temp. The resulting solution was stirred for a further 3 hr at the same temp. The mixture was washed with water, brine, dried over Na$_2$SO$_4$, and evaporated. The residue was chromatographed on silica-gel with n-hexane:EtOAc (6:1, v/v) as eluent to give 550 mg (33%) methyl 4-(1-tert-butoxycarbonylamino-2-methyl-2-propoxy)benzoate as a gum. $^1$H-NMR (CDCl$_3$) δ 1.33 (s, 6H), 1.47 (s, 9H), 3.36 (d, J=6.3 Hz, 2H), 3.90 (s, 3H), 5.05 (br, 1H), 6.99 (d, J=8.8 Hz, 2H), 7.97 (d, J=8.8 Hz, 2H).

A mixture of methyl 4-(1-tert-butoxycarbonylamino-2-methyl-2-propoxy)benzoate (460 mg, 1.42 mmol) and anisole (0.155 mL, 1.42 mmol) in CH$_2$Cl$_2$(15 mL) and TFA (3 mL) was stirred for 3 hr at room temp. The mixture was evaporated off. The residue was dissolved in CH$_2$Cl$_2$ (30 mL) and made basic by the addition of 0.5 N NaOH. The CH$_2$Cl$_2$ layer was separated, dried over Na$_2$SO$_4$, and evaporated. The residue was chromatographed on silica-gel with CH$_2$Cl$_2$ as eluent to give 370 mg (100%) methyl 4-(1-amino-2-methyl-2-propoxy)benzoate as a gum. $^1$H-NMR (CDCl$_3$) δ 1.34 (s, 6H), 2.87 (s, 2H), 3.90 (s, 3H), 7.10 (d, J=8.8 Hz, 2H), 7.97 (d, J=8.8 Hz, 2H).

To a stirred solution of methyl 4-(1-amino-2-methyl-2-propoxy)benzoate (370 mg, 1.66 mmol) and triethylamine (0.35 mL, 2.49 mmol) in CH$_2$Cl$_2$ (15 mL) was added trifluoroacetic anhydride (0.316 mL, 2.24 mmol) at 0° C. After stirred for 1 hr at the same temp, water was added to the solution. CH$_2$Cl$_2$ layer was separated, washed with water, dried over Na$_2$SO$_4$, and evaporated. The residue was chromatographed on silica-gel(20 mL) with CH$_2$Cl$_2$ as eluent to give 530 mg (100%) methyl 4-(1-trifluoroacetamido-2-methyl-2-propoxy)benzoate as a gum. This compound was used to the subsequent reaction without further purification.

To a stirred mixture of methyl 4-(1-trifluoroacetamido-2-methyl-2-propoxy)benzoate (530 mg, 1.66 mmol) and K$_2$CO$_3$ (345 mg, 2.49 mmol) in DMF (10 mL) was added MeI (0.14 mL, 2.37 mmol) at room temp. The resulting mixture was stirred for 18 hr at room temp. The mixture was poured into water, and extracted with EtOAc. The extract was washed with washed with brine, dried over Na$_2$SO$_4$, and evaporated. The residual gum was used to the subsequent reaction without further purification.

The above crude residue was dissolved in MeOH(10 mL). To the stirred solution was added water (5 mL) and Na$_2$CO$_3$ (352 mg, 3.32 mmol), arid the resulting mixture was stirred for 5 hr at room temp. The mixture was poured into water and extracted with CHCl$_3$. The extract was washed with water, dried over Na$_2$SO$_4$, and evaporated. The residue was chromatographed on silica-gel with CHCl$_3$ as eluent to give 390 mg (100%) methyl 4-(1-methylamino-2-methyl-2-propoxy)benzoate as a gum. $^1$H-NMR (CDCl$_3$) δ 1.37 (s, 6H), 2.51 (s, 3H), 3.89 (s, 3H), 6.92 (d, J=8.8 Hz, 2H), 7.97 (d, J=8.8 Hz, 2H).

To a stirred mixture of methyl 4-(1-methylamino-2-methyl-2-propoxy)benzoate (200 mg, 0.84 mmol), 4-[N'-(2-fluorophenyl)ureido]-3-methoxyphenylacetic acid (268 mg, 0.84 mmol), 4-DMAP(125 mg, 1.0 mmol) in DMF(5 mL) was added EDC(220 mg, 1.14 mmol) at ambient temp. The resulting mixture was stirred for a further 10 hr at ambient temp. The mixture was poured into water, and extracted with EtOAc. The extract was washed with brine, dried over Na$_2$SO$_4$, and evaporated. The residual gum was triturated with CH$_2$Cl$_2$ and Et$_2$O to give 200 mg (44.1%) methyl 4-[[1-[4-[N'-(2-fluorophenyl)ureido]-3-methoxyphenylacetyl]methylamino]-2-methyl-2-propoxy]benzoate as a crystalline material. $^1$H-NMR (CDCl$_3$) δ 1.36 and 1.31 (each s, 6H), 3.24–3.88 (series of s, 13 H), 6.65–8.20 (seris of m, 14H).

A mixture of methyl 4-[[1-[4-[N'-(2-fluorophenyl)ureido]-3-methoxyphenylacetyl]methylamino]-2-methyl-2-propoxy]benzoate(180 mg, 0.335 mmol) in THF(3 mL) and 0.25N NaOH(4 mL) was stirred for 5 hr at room temp. The mixture was poured into ice-1 N HCl(5 mL). The solid was collected, washed with water, and air-dried. The crude solid was recrystallized from EtOH—CHCl$_3$-n-hexane to give 70 mg (40%)280 as fine needles. mp 200–207° C.; $^1$H-NMR (DMSO-d$_6$) δ 1.26 and 1.33 (each s, 6H), 3.70–3.81 (series of s, 7H), 3.83 (s, 3H), 6.75–8.20 (series of m, 10H), 8.71 (s, 1H), 9.17 (br s, 1H), 12.72 (s, 1H).

Example 230

(S)-3-chloro-4-[2-[3-methoxy-4-[N'-(2-fluorophenyl) ureido]phenylacetylamino]-1-propoxy]benzoic acid

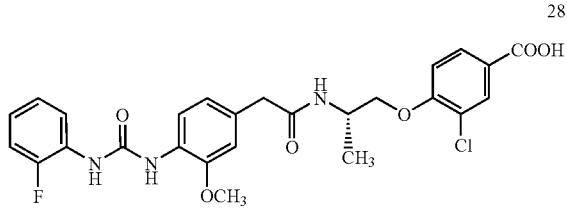

281

A mixture of 3-methoxy-4-[N'-(2-fluorophenyl)ureido] phenylacetic acid (327 mg, 1.03 mmol), methyl (S)-3-chloro-4-(2-amino-1propoxy)benzoate (250 mg, 1.03 mmol), EDC(hydrochloride) (295 mg, 1.54 mmol), HOBt (208 mg, 1.54 mmol), and DMAP (25 mg, 0.20 mmol) in DMF (8 mL) was stirred at room temp overnight. The mixture was diluted with EtOAc, washed with 0.5 N HCl, brine, dried over Na$_2$SO$_4$ and evaporated. The residue was recrystallized from CHCl$_3$-EtOAc to give 308 mg (55%) as a white crystalline powder. $^1$H-NMR (CDCl$_3$) δ 1.29 (d, 3 H, J=6.8 Hz), 3.51 (s, 2 H), 3.84 (s, 3 H), 3.88 (s, 3 H), 4.01–4.08 (m, 2 H), 4.38–4.39 (m, 1 H), 6.25 (d, 1 H, J=8.3 Hz), 6.78–6.83 (m, 2 H), 6.90–6.95 (m, 2 H), 7.02–7.11 (m, 2 H), 7.89 (dd, 1 H, J=2.0, 8.8 Hz), 8.02 (d, 1 H, J=2.4 Hz), 8.20 (d, 1 H, J=8.3 Hz), 8.27–8.31 (m, 1 H), 8.53 (s, 1 H), 8.84 (s, 1 H).

To a stirred solution of methyl (S)-3-chloro-4-[2-[3-methoxy-4-[N'-(2-fluorophenyl) ureido]phenylacetylamino]-1-propoxy]benzoate (308 mg, 0.57 mmol) in THF-MeOH (10 mL, 1:1, v/v) was added 0.5 N NaOH (10 mL), and the reaction mixture was heated under reflux for 1 hr. The mixture was poured into ice-1 N HCl and the solid was collected. The crude solid was purified by recrystallization from MeOH—CHCl$_3$-n-hexane to give 196 mg (65%) 281 as a white crystalline powder. mp 188–191° C.; $^1$H-NMR (DMSO-d$_6$) δ 1.21 (d, 3 H, J=6.4 Hz), 3.38 (s, 2 H), 3.83 (s, 3 H), 4.02–4.18 (m, 3 H), 6.78–7.29 (series of m, total 6 H), 7.85–8.00 (m, 3 H), 8.12–8.19 (m, 2 H), 8.70 (s, 1 H), 9.17 (s, 1 H), 12.98 (bs, 1 H); MS (FAB) m/z 530 (M$^+$), 531 (M$^+$+1), 532 (M$^+$+2); Anal. Calcd for C$_{26}$H$_{25}$ClFN$_3$O$_6$.1/4H$_2$O: C, 58.43; H, 4.81; Cl, 6.63; F, 3.55; N, 7.86. Found: C, 58.45; H, 4.83; Cl, 6.68; F, 3.38; N, 7.79.

Example 231

4-[[2-[3-methoxy-4-[N'-(2-methylphenyl)ureido] phenylacetyl]methylamino]ethylamino]benzoic acid

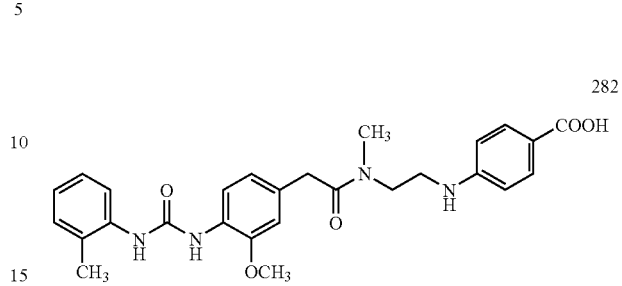

282

A stirred solution of N-benzyloxycarbonyl-N-methylaminoacetaldehyde (1.77 g, 1.1 mmol) in toluene (3 mL) was added methyl-4-aminobenzoate (1.29 g, 8.5 mmol), and the mixture was stirred for 1 hr at room temp. The reaction mixture was evaporated under a reduced pressure and the residue was dissolved into MeCN(15 mL). To the solution was added AcOH (2.44 mL, 43 mmol) and NaBH$_3$CN (2.67 g, 43 mmol), and the resulting mixture was stirred for 15 hr at room temp. The reaction was quenched by the addition of sat. NaHCO$_3$. The mixture was extracted with EtOAc, washed with brine, dried over MgSO$_4$, and evaporated. The residue was chromatographed on silica-gel with n-hexane: EtOAc (7:3, v/v) as eluent to give 1.26 g (43%) methyl 4-[2-(N-benzyloxy carbonyl-N-methylamino)-ethylamino] benzoate as a colorless oil. $^1$H-NMR (CDCl$_3$, 400 MHz) δ 2.96 (s, 3H), 3.32 (br m, 2H), 3.50–3.60 (m, 2H), 3.82 (s, 3H), 5.15 (each d, 2H, J=14.6 Hz), 6.35 and 6.58 (m, total 2H), 7.36 (s, 5H), 7.76 and 7.84 (m, total 2H); MS (FAB) m/z 342 (M$^+$+1).

To a stirred solution of methyl 4-[2-(N-benzyloxycarbonyl-N-methylamino)ethylamino]benzoate (1.26 g, 3.68 mmol) in MeOH(20 mL) was added 5 wt. Pd—C (700 mg), and the mixture was hydrogenated (3 atm) for 4 hr at room temp. The mixture was filtered, and the filtrate was evaporated under a reduced pressure to give 600 mg (78%) methyl 4-[2-(N-methylamino) ethylamino]benzoate as a colorless oil. $^1$H-NMR (CDCl$_3$, 400 MHz) δ 2.46 (s, 3H), 2.88 (t, 2H, J=5.5 Hz), 3.27 (br s, 2H), 3.85 (s, 3H), 6.57 (d, 2H, J=8.8 Hz), 7.85 (d, 2H, J=8.8 Hz); MS (FAB) m/z 209 (M$^+$+1).

To a stirred solution of methyl 4-[2-(N-methylamino) ethylamino]benzoate (590 mg, 2.83 mmol)3-methoxy-4-[N'-(2-methylphenyl)ureido]phenylacetic acid (891 mg, 2.83 mmol) in DMF(14 mL) was added EDC (815 mg, 4.25 mmol), HOBt (574 mg, 4.25 mmol), and 4-DMAP (519 mg, 4.25 mmol), and the resulting mixture was stirred overnight at room temp. The mixture was poured into 1 N HCl and the solid was collected with suction. The crude solid was purified by chromatography on silica-gel (middle pressure) with CHCl$_3$-EtOAc (10:0 to 7:3, v/v) as eluent to give 1.25 g (87%) methyl 4-[[2-[3-methoxy-4-[N'-(2-methylphenyl) ureido]phenylacetyl]methylamino]ethylamino]benzoate as a light yellow oil. $^1$H-NMR (CDCl$_3$, 400 MHz) δ 3.18 (s, 2H), 3.05 and 3.32 (s, total 2H), 3.72–3.85 (m, 9H), 4.12 and 4.23 (m, total 2H), 6.78 (m, 3H), 7.05 (t, 1H, J=7.5 Hz), 7.20 (m, 2H), 7.43–7.50 (m, 3H), 7.62 (d, 1H, J=8.8 Hz), 8.05 (d, 1H, J=8.8 Hz); MS (FAB) m/z 505 (M$^+$+1).

A stirred mixture of methyl 4-[[2-[3-methoxy-4-[N'-(2-methylphenyl)ureido]phenylacetyl]methylamino]ethylamino]benzoate (300 mg, 0.6 mmol) in 0.25 N NaOH (6 mL) and THF (6 mL) was heated under reflux for 8 hr. The mixture was poured into water, and acidified with 1 N HCl. The solid was collected with suction. The crude solid was recrystallized from n-hexane-diisopropylether to give 202 mg (69%) 282 as a pale yellow crystalline powder. mp 115–120° C.; IR(KBr) 3346, 2935, 1603, 1531, 1454, 1417, 1257, 1174, 1036, 754 cm$^{-1}$; $^1$H-NMR (CD$_3$OD, 400 MHz) δ 2.28 (s, 3H), 2.98 (s, 1H), 3.10 (s, 2H), 3.35–3.42 (m, 2H), 3.53–3.65 (m, 3H), 3.70 (s, 1H), 3.80 and 3.82 (s, 3H), 6.60–6.85 (m, 4H), 7.02 (m, 1H), 7.18 (m, 2H), 7.58 (m, 1H), 7.82 (m, 2H), 7.96 (m, 1H); MS (FAB) m/z 491 (M$^+$+1).

Example 232

(S)-3-chloro-4-[2-[N-methyl-N-[3-methoxy-4-[N'-(2-fluorophenyl)ureido]phenylacetyl]amino]-1-propoxy]benzoic acid

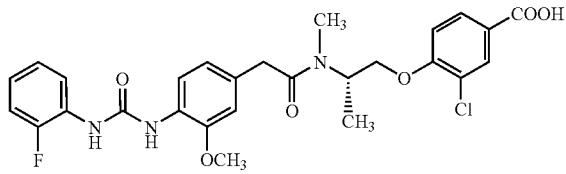

283

To a cooled (0° C.) solution of methyl (S)-3-chloro-4-(2-amino-1-propoxy)benzoate (1.74 g, 7.14 mmol) in CH$_2$Cl$_2$ (20 mL) was added Et$_3$N (1.19 mL, 8.54 mmol) and trifluoroacetic anhydride (TFAA) (1.11 mL, 7.86 mmol), and the reaction mixture was stirred at room temp overnight. The mixture was diluted with CHCl$_3$, washed with 0.5 N HCl, brine, dried over Na$_2$SO$_4$ and evaporated. The residue was recrystallized from CHCl$_3$-n-hexane to give 1.59 g (66%) (S)-3-chloro-4-(2-trifluoroacetamido-1-propoxy)benzoate as a white crystalline material. mp 122–125° C.; $^1$H-NMR (CDCl$_3$) δ 1.48 (d, 3 H, J=6.8 Hz), 3.91 (s, 3 H), 4.10–4.19 (m, 2 H), 4.47–4.52 (m, 1 H), 6.68 (bs, 1 H), 6.92–6.94 (m, 1 H), 7.93–7.95 (m, 1 H), 8.07–8.08 (m, 1 H); MS (FAB) m/z 340 (M$^+$+1); Anal. Calcd for C$_{13}$H$_{13}$ClF$_3$NO$_4$: C, 45.96; H, 3.86; Cl, 10.44; F, 16.78; N, 4.12. Found: C, 45.88; H, 3.97; Cl, 10.24, F, 16.72; N, 4.18.

To a stirred solution of methyl (S)-3-chloro-4-(2-trifluoroacetamido-1-propoxy)benzoate (800 mg, 2.36 mmol) in DMF (5 mL) was added K$_2$CO$_3$ (651 mmol, 4.71 mmol) and MeI (0.22 mL, 3.53 mmol), and the reaction mixture was stirred at 60° C. overnight. The mixture was diluted with EtOAc, washed with 0.5 N HCl, brine, dried over Na$_2$SO$_4$ and evaporated. The residue was purified by column chromatography on silica-gel with 5% EtOAc in CHCl$_3$ as eluent to give 850 mg (100%) methyl (S)-3-chloro-4-[2-(N-methyl-N-trifluoroacetamido)-1-propoxy]benzoate as a colorless oil. $^1$H-NMR (CDCl$_3$) δ 1.43–1.46 (m, 3 H), 3.03 and 3.21 (s, 3 H), 3.90 (s, 3 H), 4.04–4.22 (m, 2 H), 4.81–4.87 (m, 1 H), 6.91 (d, 1 H, J=8.3 Hz), 7.93 (dd, 1 H, J=2.0, 8.3 H), 8.06 (d, 1 H, J=2.0 Hz).

To a stirred solution of methyl (S)-3-chloro-4-[2-(N-methyl-N-trifluoroacetamido)-1-propoxy]benzoate (880 mg, 2.49 mmol) in MeOH—H$_2$O (10 mL, 1:1, v/v) was added K$_2$CO$_3$ (516 mg, 3.73 mmol), and the resulting mixture was stirred at room temp overnight. The mixture was diluted with EtOAc, washed with H$_2$O, brine, dried over Na$_2$SO$_4$ and evaporated to give 460 mg (72%) (S)-3-chloro-4-(2-methylamino-1-propoxy)benzoate as a colorless oil. $^1$H-NMR (CDCl$_3$) δ 1.20(d, 3 H, J=6.4 Hz), 2.51 (s, 3 H), 3.07–3.12 (m, 1 H), 3.89 (s, 3 H), 392–4.04 (m, 2H), 6.93–6.95 (m, 1 H), 7.90–7.93 (m, 1 H), 8.05–8.06 (m, 1 H).

A mixture of 3-methoxy-4-[N'-(2-fluorophenyl)ureido] phenylacetic acid (296 mg, 0.93 mmol), methyl (S)-3-chloro-4-(2-methylamino-1-propoxy)benzoate (240 mg, 0.93 mmol), EDC(hydrochloride) (268 mg, 1.40 mmol), HOBt (189 mg, 1.40 mmol), and DMAP (23 mg, 0.19 mmol) in DMF (8 mL) was stirred at room temp for 1.5 hr. The mixture was diluted with EtOAc, washed with 0.5 N HCl, brine, dried over Na$_2$SO$_4$ and evaporated. The residue was purified by column chromatography on silica-gel with 5% MeOH in CHCl$_3$ as eluent to give 520 mg (100%) methyl (S)-3-chloro-4-[2-[N-methyl-N-[3-methoxy-4-[N'-(2-fluorophenyl)ureido]phenylacetyl]amino]-1-propoxy]benzoate as a red-brown amorphous solid.

To a stirred solution of this product (520 mg, 0.93 mmol) in THF (10 mL) was added 0.5 N NaOH (10 mL), and the resulting mixture was heated under reflux for 3 hr. The mixture was poured into ice-1 N HCl and the solid was collected. The crude solid was recrystallized from CHCl$_3$-Et$_2$O to give 170 mg (2 steps, 37%) 283 as a white crystalline powder. mp 142–147° C.; $^1$H-NMR (DMSO-d$_6$) δ 1.13–1.20 (m, 3 H), 2.74 and 2.94 (s, 3 H), 3.65 (s, 2 H), 3.82 and 3.84 (s, 3 H), 4.13–4.22 (m, 2 H), 4.53 and 4.91–4.92 (m, 1 H), 6.71–7.29 (series of m, total 6 H), 7.86–8.02 (m, 3 H), 8.15–8.19 (m, 1 H), 8.71 (s, 1 H), 9.17 (s, 1H), 13.00 (bs, 1 H); MS (FAB) m/z 544 (M$^+$), 545 (M$^+$+1); Anal. Calcd for C$_{27}$H$_{27}$ClFN$_3$O$_6$.1/4H$_2$O: C, 59.13; H, 5.05; Cl, 6.46; F, 3.46; N, 7.66. Found: C, 59.19; H, 4.99; Cl, 6.64; F, 3.23; N, 7.55.

Example 233

(S)-3-chloro-4-[2-[N-methyl-N-[3-methoxy-4-[N'-(2-methylphenyl)ureido]phenylacetyl]amino]-1-propoxy]benzoic acid

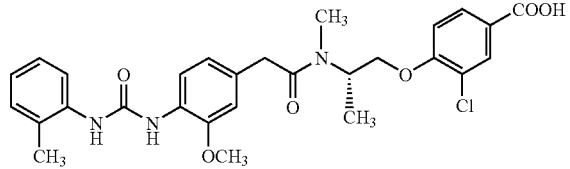

284

A mixture of 3-methoxy-4-[N'-(2-methylphenyl)ureido] phenylacetic acid (261 mg, 0.83 mmol), methyl (S)-3-chloro-4-(2-methylamino-1-propoxy)benzoate (214 mg, 0.83 mmol), EDC(hydrochloride) (239 mg, 1.25 mmol), HOBt (168 mg, 1.24 mmol), and DMAP (20 mg, 0.16 mmol) in DMF (8 mL) was stirred at room temp for 2 hr. The mixture was diluted with EtOAc, washed with 0.5 N HCl, brine, dried over Na$_2$SO$_4$ and evaporated. The residue was purified by column chromatography on silica-gel with CHCl$_3$-MeOH (50:1, v/v) as eluent to give 470 mg (100%) methyl (S)-3-chloro-4-[2-[N-methyl-N-[3-methoxy-4-[N'-(2-methylphenyl)ureido]phenylacetyl]amino]-1propoxy] benzoate as a pale yellow amorphous solid.

To a stirred solution of the above product (470 mg, 0.95 mmol) in THF (10 mL) was added 0.5 N NaOH (10 mL) and the reaction mixture was heated under reflux for 3 hr. The

Example 234

3-isopropylamino-4-[[2-[3-methoxy-4-['-(2-methylphenyl)ureido]phenylacetyl]methylamino]ethoxy]benzoic acid

285

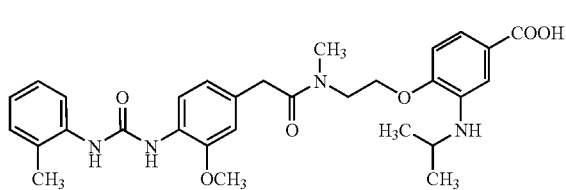

To a cold (0° C.), stirred solution of methyl 3-amino-4-[[2-[3-methoxy-4-[N'-(2-methyl phenyl) ureido]phenylacetyl]methylamino]ethoxy]benzoate (300 mg, 0.58 mmol) in acetone-AcOH-DMF (13 mL, 6:6:1, v/v/v) was added NaBH$_3$CN (300 mg) and the resulting mixture was stirred for 60 hr at room temp. The mixture was poured into sat. NaHCO$_3$ and extracted with CHCl$_3$. The extract was washed with brine, dried over MgSO$_4$, and evaporated to give 280 mg (86%) methyl 3-isopropylamino-4-[[2-[3-methoxy-4-[N'-(2-methylphenyl)ureido]phenylacetyl]methylamino]ethoxy]benzoate as a colorless oil. $^1$H-NMR (CDCl$_3$, 400 MHz) δ 1.21 (m, 6H), 2.30 (s, 3H), 3.05 and 3.10 (s, total 2H), 3.59 (s, 3H), 3.62–3.81 (m, 6H), 3.89 (s, 3H), 4.10 and 4.21 (m, 2H), 6.65–6.80 (m, 4H), 7.10 (m, 1H), 7.20 (s, 3H), 7.32 (m, 2H), 7.54 (d, 1H, J=8.3 Hz), 8.00 (s, 1H), 8.07 (d, 1H, J=8.3 Hz); MS (FAB) m/z 563 (M$^+$+1).

A stirred mixture of methyl 3-isopropylamino-4-[[2-[3-methoxy-4-[N'-(2-methylphenyl) ureido]phenylacetyl]methylamino]ethoxy]benzoate (280 mg, 0.5 mmol), 0.25 N NaOH (6 mL), and THF (6 mL) was heated under reflux for 8 hr. The mixture was poured into water (200 mL), acidified with 1 N HCl and the solid was collected with suction. The solid was recrystallized from CHCl$_3$-n-hexane-diisopropylether to give 202 mg (74%) 285 as a light yellow crystalline powder. mp 130–135° C.; $^1$H-NMR (CD$_3$OD, 400 MHz) δ 1.18 and 1.22 (d, total 6H, J=6.3 Hz), 2.29 and 2.32 (s, total 3H), 3.04 and 3.14 (s, total 2H), 3.60–3.90 (m, 9H), 4.16 and 4.25 (m, total 2H), 6.80 (m, 3H), 7.02 (m, 1H), 7.12–7.24 (m, 3H), 7.29–7.38 (m, 1H), 7.59 (m, 1H), 8.02 (m, 1H); MS (FAB) m/z 548 (M+H)$^+$; Anal. calcd. for C$_{30}$H$_{36}$N$_4$O$_6$: C, 65.68; H, 6.61. Found: C, 65.80; H, 6.83.

Example 235

4-[[2-[3-methoxy-4-[N'-(2-methylphenyl)ureido]phenylacetyl]methylamino]ethyl]methylamino benzoic acid

286

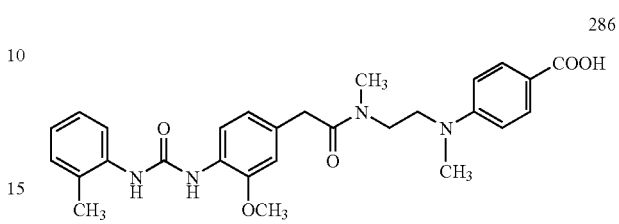

To a stirred cold (0° C.) solution of methyl 4-[[2-[3-methoxy-4-[N'-(2-methylphenyl) ureido]phenylacetyl]methylamino]ethyl]aminobenzoate (300 mg, 0.6 mmol) in MeCN-formaldehyde-AcOH (11 mL, 8:2:1, v/v/v) was added NaBH$_3$CN (187 mg, 2.40 mmol), and the resulting mixture was stirred for 18 hr at room temp. The mixture was poured into sat. NaHCO$_3$ and extracted with CHCl$_3$. The extract was washed with brine, dried over MgSO$_4$, and evaporated to give 309 mg (100%) methyl 4-[[2-[3-methoxy-4-[N'-(2-methylphenyl)ureido]phenylacetyl]-2-'-methylamino]ethyl]N-methylaminobenzoate as a colorless oil. $^1$H-NMR (CDCl$_3$, 400 MHz) δ 2.30 (m, 3H), 2.98 (m, 7H), 3.46–3.72 (m, 9H), 3.82 (m, 3H), 6.32 (m, 1H), 6.55–6.75 (m, 4H), 7.05–7.50 (m, 2H), 7.82–8.02 (m, 4H); MS (FAB) m/z 518 (M$^+$+1).

A stirred mixture of methyl 4-[[2-[3-methoxy-4-[N'-(2-methylphenyl)ureido]phenylacetyl]-2-N'-methylamino]ethyl]methylaminobenzoate (309 mg, 0.6 mmol) in 1 N NaOH (2.4 mL), and THF (10 mL) was heated under reflux for 8 hr. The mixture was poured into water (200 mL), acidified by the addition of 1 N HCl. The solid was collected with suction. The crude solid was recrystallized from CHCl$_3$-n-hexane-isopropylether to give 211 mg (70%) 286 as a light yellow crystalline powder. mp 125–130° C.; IR(KBr) 3338, 2933, 1601, 1529, 1182, 1036, 752 cm$^{-1}$; $^1$H-NMR (CD$_3$OD, 400 MHz) δ 2.28 and 2.29 (s, 3H), 2.95–3.02 (m, 6H), 3.60 (br, 6H), 3.80 (s, 1H), 3.86 (s, 2H), 6.60–6.82 (m, 4H), 7.01–7.18 (m, 3H), 7.58 (m, 1H), 7.82–7.99 (m, 3H); MS (FAB) m/z 504 (M$^+$+1).

Example 236

(S)-3-chloro-4-[2-[N-benzyl-N-[3-methoxy-4-[N'-(2-fluorophenyl)ureido]phenylacetyl]amino]-1-propoxy]benzoic acid

287

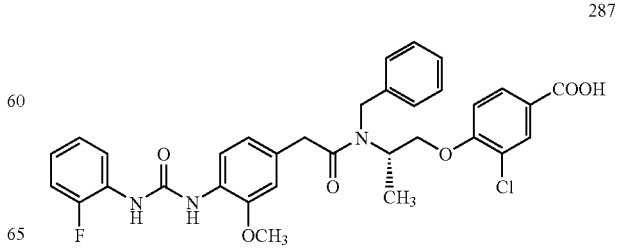

To a stirred solution of NaBH₃CN (985 mg, 15.68 mmol) in MeOH (5 mL) was added a solution of methyl (S)-3-chloro-4-(2-amino-1-propoxy)benzoate (382 mg, 1.57 mmol) and benzaldehyde (0.19 mL) in MeOH (5 mL), and the resulting mixture was stirred at room temp overnight. The mixture was quenched by H₂O and extracted with CHCl₃. The extract was washed with brine, dried over Na₂SO₄ and evaporated. The residue was purified by column chromatography on silica-gel with CHCl₃:MeOH (30:1, v/v) as eluent to give 336 mg (64%) (S)-3-chloro-4-(2-N-benzylamino-1-propoxy)benzoate as a colorless oil. ¹H-NMR (CDCl₃) δ 1.22 (d, 3 H, J=6.4 Hz), 3.21–3.25 (m, 1 H), 3.84–4.03 (m, total 7 H), 6.89–6.91 (m, 1 H), 7.23–7.37 (m, 5 H), 7.89–7.91 (m, 1 H), 8.05 (m, 1 H).

A mixture of 3-methoxy-4-[N'-(2-fluorophenyl)ureido] phenylacetic acid (320 mg, 1.01 mmol), methyl (S)-3-chloro-4-(2-N-benzylamino-1-propoxy)benzoate (336 mg, 1.01 mmol); EDC (hydrochloride) (289 mg, 1.51 mmol), HOBt (204 mg, 1.51 mmol) and DMAP (25 mg, 0.20 mmol) in DMF (7 mL) was stirred at room temp for 2 days. The mixture was diluted with EtOAc, washed with 0.5 N HCl, brine, dried over Na₂SO₄ and evaporated. The residue was purified by column chromatography on silica-gel with CHCl₃:MeOH (50:1, v/v) as eluent to give 607 mg (95%) methyl (S)-3-chloro-4-[2-[N-benzyl-N-[3-methoxy-4-[N'-(2-fluorophenyl)ureido]phenyl acetyl]amino]-1propoxy] benzoate as a pale yellow amorphous solid. ¹H-NMR (CDCl₃) δ 1.20–1.27 (m, 3 H), 3.62 (s, 2 H), 3.73–4.16 (series of m, total 9 H), 4.71 (bs, 2 H), 6.67–7.38 (series of m, total 12 H), 7.77–8.17 (series of m, total 5 H).

To a stirred solution of methyl (S)-3-chloro-4-[2-[N-benzyl-N-[3-methoxy-4-[N'-(2-fluorophenyl) ureido]phenylacetyl]amino]-1-propoxy]benzoate (607 mg, 0.96 mmol) in THF (6 mL) was added 0.5 N NaOH (6 mL), and the resulting mixture was heated under reflux overnight. The mixture was poured into ice-1 N HCl and the solid was collected. The crude solid was recrystallized to give 192 mg (32%) 287 as a white crystalline powder. mp 125–130° C.; ¹H-NMR (DMSO-d₆) δ 1.07–1.23 (m, 3 H), 3.76 (s, 2 H), 3.85 (s, 3 H), 3.90–4.26 (m, 3 H), 4.56 (s, 2 H), 6.66–7.38 (series of m, total 10 H), 7.82–8.20 (series of m, total 5 H), 8.70–8.74 (m, 1 H), 9.18–9.20 (m, 1 H), 13.02 (bs, 1 H); MS (FAB) m/z 621 (M⁺+1); Anal. Calcd for C₃₃H₃₁ClFN₃O₆.1/4H₂O: C, 63.46; H, 5.08; Cl, 5.68; F, 3.04; N, 6.73. Found: C, 63.67; H, 5.16; Cl, 5.75; F, 2.95; N, 6.55.

Example 237

3-(N-isopropyl-N-methylamino)-4-[[2-[3-methoxy-4-[N'-(2-methylphenyl)ureido]phenylacetyl]methylamino]ethoxy]benzoic acid

288

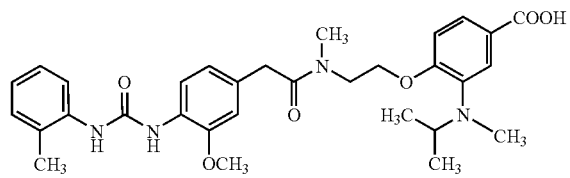

To a stirred cold (0° C.) solution of methyl 3-isopropylamino-4-[[2-[3-methoxy-4-[N'-(2-methylphenyl)ureido] phenylacetyl]methylamino]ethoxy]benzoate (324 mg, 0.58 mmol) in CH₃CN-formaldehyde-AcOH (11 mL, 8:2:1, v/v/v) was added NaBH₃CN (145 mg, 2.30 mmol), and the resulting mixture was stirred for 18 hr at room temp. The mixture was poured sat. NaHCO₃ and the solid was collected with suction. The crude solid was dissolved in CHCl₃ (20 mL), and the solution was washed with brine, dried over MgSO₄, and evaporated to give 317 mg (95%) methyl 3-(N-isopropyl-N-methylamino)-4-[[2-[3-methoxy-4-[N'-(2-methylphenyl)ureido]phenylacetyl]methylamino]ethoxy] benzoate as a colorless oil. ¹H-NMR (CDCl₃) δ 1.02 (m, 6H), 2.29 (s, 3H), 2.63 (m, 3H), 3.02–3.20 (m, 3H), 3.49–3.80 (m, 8H), 3.88 (s, 3H), 4.06 and 4.21 (m, total 2H), 6.59 (m, 1H), 6.76 (m, 2H), 7.11–7.23 (m, 3H), 7.50–7.62 (m, 3H), 8.05 (d, 1H, J=8.3 Hz); MS (FAB) m/z 576 (M⁺+1).

A stirred mixture of methyl 3-(N-isopropyl-N-methylamino)-4-[[2-[3-methoxy-4-[N'-(2-methylphenyl)ureido] phenylacetyl]methylamino]ethoxy]benzoate(317 mg, 0.55 mmol) in 0.25 N NaOH (8.2 mL) and THF (8 mL) was heated under reflux for 8 hr. The mixture was poured into water (200 mL), acidified by the addition of 1 N HCl and the solid was collected with suction. The crude solid was recrystallized from CHCl₃-n-hexane-diisopropylether to give 288 as a light yellow crystalline powder. mp 130–135° C.; IR (KBr) 2970, 1537, 1038, 754 cm⁻¹; ¹H-NMR (CD₃OD) δ 1.12(m, 6H), 2.29 (s, 3H), 2.76 (m, 1H), 2.89 (s, 2H), 3.02 (s, 1H), 3.21 (s, 2H), 3.72 (s, 2H), 3.80 (s, 3H), 3.84 (m, 3H), 4.13 and 4.40 (m, total 2H), 6.76 (d, 1H, J=7.8 Hz), 6.86 (s, 1H), 7.00 (m, 2H), 7.18 (m, 3H), 7.57 (d, 1H, J=7.8 Hz), 7.95 (m, 2H); MS (FAB) m/z 562 (M⁺+1); Anal. Calcd for C₃₁H₃₈N₄O₆.2.0H₂O: C, 62.19; H, 7.07; N, 9.36. Found: C, 62.54; H, 6.85; N, 8.90.

Example 238

3-(1-piperidinyl)-4-[[2-[3-methoxy-4-[N'-(2-fluorophenyl)ureido]phenylacetyl]methylamino]ethoxy] benzoic acid

289

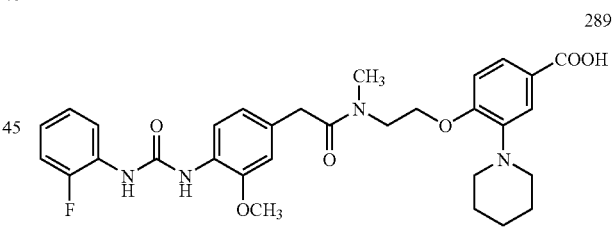

To a stirred solution of methyl 3-amino-4-[[2-[3-methoxy-4-[N'-(2-fluorophenyl)ureido]phenylacetyl]methylamino]ethoxy]benzoate (300 mg, 0.57 mmol) in THF (2 mL) was added a solution of glutaraldehyde (50% aqueous solution) (0.13 mL, 0.69 mmol) in MeOH (1.4 mL), THF (0.993 mL), and 3 N H₂SO₄ (0.952 mL) at 020 C. To the solution was added NaBH₃CN (150 mg), DMF (5 mL), and MeOH (2 mL) at room temp, and the resulting mixture was stirred for 15 hr. The mixture was poured into sat. NaHCO₃ and extracted with CHCl₃. The extract was washed with brine, dried over MgSO₄, and evaporated under a reduced pressure. The residue was chromatographed on silica gel with toluene:acetone (7:3, v/v) as eluent to give 145 mg (43%) methyl 3-(1-piperidinyl)-4-[[2-[3-methoxy-4-[N'-(2-fluorophenyl)ureido]phenylacetyl]methyl amino]ethoxy] benzoate as a colorless oil. ¹H-NMR (CDCl₃, 400 MHz) δ 1.58–1.72 (m, 6H), 2.80–2.92 (m, 4H), 3.26 (s, 2H), 3.58 (s, 2H), 3.69 (s, 2H), 3.80–3.89 (m, 7H), 4.22 (m, 2H), 6.72 (s, 1H), 6.78 (m, 2H), 6.95–7.18 (m, 2H), 7.32 (s, 1H), 7.60 (s, 1H), 7.63 (d, 1H, J=7.8 Hz), 7.98. (d, 1H, J=7.8 Hz), 8.18 (m, 1H); MS (FAB) m/z 593 (M$^+$+1).

A stirred mixture of methyl 3-(1-piperidinyl)-4-[[2-[3-methoxy-4-[N'-(2-fluorophenyl) ureido]phenylacetyl]methylamino]ethoxy]benzoate (290 mg, 0.49 mmol), 1 N NaOH (1.95 mL) in MeOH(5 mL) and THF (10 mL) was heated under reflux for 4 hr. The mixture was poured into water (200 mL), acidified with 1 N HCl (pH=4.0), and extracted with CHCl$_3$-MeOH(9:1, v/v). The combined extract was dried over MgSO$_4$, and evaporated. The residue was crystallized from diisopropylether-hexane to give 201 mg (71%)289 as a light yellow crystalline powder. mp 125–130° C.; IR (KBr) 3338, 2935, 1599, 1537, 1041, 752 cm$^{-1}$; $^1$H-NMR (CD$_3$OD) δ 1.52–1.73 (m, 6H), 2.88 (s, 3H), 2.98 (br, 1H), 3.09 (s, 1H), 3.23 (s, 2H), 3.66 (s, 2H), 3.75 (s, 1H), 3.82 (s, 4H), 4.13 and 4.29 (m, total 2H), 6.78 (m, 2H), 6.99 (m, 2H), 7.10 (m, 2H), 7.60–7.70 (m, 2H), 7.96–8.07 (m, 2H); MS (FAB) m/z 578 (M$^+$+1); Anal. Calcd for C$_{31}$H$_{35}$FN$_4$O$_6$.0.5H$_2$O: C, 63.36; H, 6.17; N, 9.53. Found: C, 63.22; H, 6.15; N, 9.16.

Example 239

3-amino-4-[[2-[3-methoxy-4-[N'-(2-methylphenyl) ureido]phenylacetyl]methylamino]ethoxy]benzoic acid

290

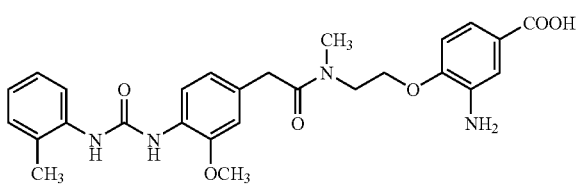

To a stirred solution of methyl 3-amino-4-[[2-[3-methoxy-4-[N'-(2-methylphenyl)ureido]phenylacetyl]methylamino]ethoxy]benzoate (300 mg, 0.58 mmol) in MeOH-THF (2:1, v/v, 12 mL) was added 0.25 N NaOH (9 mL), and the resulting mixture was heated under reflux for 16 hr. The mixture was poured into water (100 mL) and acidified by the addition of 1 N HCl. The solid was collected with suction. The residue was recrystallized from diisopropylether to give 243 mg (83%) 290 as a yellow crystalline powder. mp 125–130° C.; IR (KBr) 3346, 2935, 1533, 1211, 1034, 756, 637 cm$^{-1}$; $^1$H-NMR (DMSO-d$_6$) δ 2.29 (s, 3H), 3.05 (s, 1H), 3.72–3.85 (m, 7H), 4.12 and 4.25 (m, total 2H), 6.76–6.89 (m, 3H), 7.00 (m, 1H), 7.18 (m, 2H), 7.39 (m, 2H), 7.60 (d, 1H, J=7.8 Hz), 7.96 (m, 1H); Anal.Calcd for C$_{27}$H$_{30}$N$_4$O$_6$.0.5H$_2$O: C, 62.90; H, 6.06; N, 10.87. Found: C, 63.03; H, 6.14; N, 10.56.

Example 240

3-(1-piperidinyl)-4-[[2-[3-methoxy-4-[N'-(2-methylphenyl)ureido]phenylacetyl]methylamino]ethoxy] benzoic acid

291

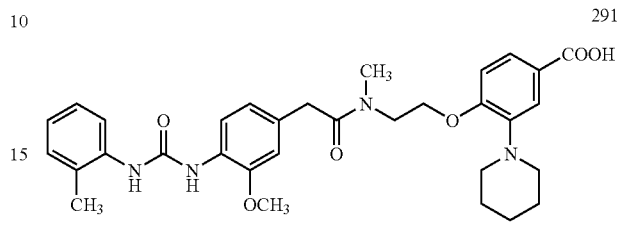

To a cooled and stirred solution of methyl 3-amino-4-[[2-[3-methoxy-4-[N'-(2-methylphenyl) ureido]phenylacetyl]methylamino]ethoxy]benzoate (573 mg, 1.1 mmol) in THF-MeOH (2:1, v/v, 6 mL) was added glutaraldehyde (0.423 mL, 2.2 mmol), 3 N H$_2$SO$_4$(1.83 mL, 5.5 mmol), and NaBH$_3$CN (276 mg, 4.4 mmol). The resulting mixture was stirred for 18 hr at room temp. The mixture was poured into sat. NaHCO$_3$(100 mL) and the solid was collected with suction. The crude solid was purified by column chromatography on silica-gel with toluene-acetone (10:0 to 4:1, v/v) to give 240 mg (37%) methyl 3-(1-piperidinyl)-4-[[2-[3-methoxy-4-[N'-(2-methyl phenyl)ureido]phenylacetyl]methylamino]ethoxy]benzoate as a gum. $^1$H-NMR (CD$_3$OD) δ 1.52–1.72 (m, 6H), 2.30 (s, 3H), 2.36 (s, 2H), 2.89 (br s, 3H), 2.98 (m, 1H), 3.05 (s, 1H), 3.20 (s, 2H), 3.68 (s, 2H), 3.69 (m, 2H), 3.79 (m, 2H), 3.88 (s, 2H), 4.08 and 4.21 (m, 2H), 6.35 and 6.42 (s, total 1H), 6.70 (s, 1H), 6.70 (s, 1H), 6.79 (m, 2H), 7.09–7.24 (m, 4H), 7.50–7.65 (m, 3H), 8.05 (d, 1H, J=8.3 Hz); MS (FAB) m/z 588 (M$^+$+1).

A stirred mixture of methyl 3-(1-piperidinyl)-4-[[2-[3-methoxy-4-[N'-(2-methylphenyl) ureido]phenylacetyl]methylamino]ethoxy]benzoate (240 mg, 0.41 mmol), 1 N NaOH (1.63 mL) in MeOH (6.5 mL), H$_2$O (5 mL), and THF (6.5 mL) was heated under reflux for 11 hr. The mixture was poured into water (200 mL), acidified by the addition of 1 N HCl until pH=4.0, and the solid was collected with suction. The aqueous layer was extracted with CHCl$_3$-MeOH (9:1, v/v, 30 mL×3). The precipitate was dissolved in the combined organic extract. The organic layer was dried over MgSO$_4$ and evaporated. The residue was crystallized from diisopropylether to give 151 mg (65%) 291 as a light yellow crystalline powder. mp 120–125° C.; IR (KBr) 3354, 2935, 1535, 1252, 1217, 1034, 754, 638 cm$^{-1}$; $^1$H-NMR (CD$_3$OD) δ 1.55–1.72 (m, 6H), 2.30 (s, 31H), 2.89 (br, 2H), 2.98 (br, 1H), 3.09 (s, 1H), 3.22 (s, 2H), 3.69 (s, 3H), 3.74 (s, 1H), 3.83 (m, 4H), 4.12 and 4.28 (m, total 2H), 6.75 (m, 2H), 6.88–7.02 (m, 1H), 7.17 (m, 2H), 7.58–7.73 (m, 4H), 7.99 (d, 1H, J=8.3 Hz); MS (FAB) m/z 574 (M$^+$+1); Anal. Calcd for C$_{32}$H$_{38}$N$_4$O$_6$.0.5H$_2$O: C, 65.85; H, 6.73; N, 9.60. Found: C, 65.94; H, 6.88; N, 9.03.

Example 241

3-amino-4-[[2-[3-methoxy-4-[N'-(2-fluorophenyl)ureido]phenylacetyl]methylamino]ethoxy]benzoic acid

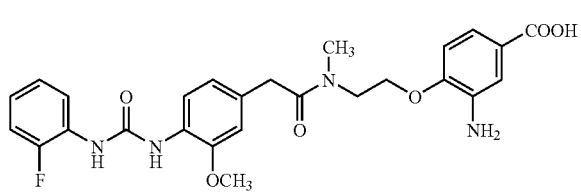

292

A stirred mixture of methyl 3-amino-4-[[2-[3-methoxy-4-[N'-(2-fluorophenyl)ureido]phenylacetyl]methylamino]ethoxy]benzoate (250 mg, 0.48 mmol) in 1 N NaOH (1.91 mL), MeOH (8 mL), H$_2$O (6 mL), and THF (8 mL) was heated under reflux for 10 hr. The mixture was poured into water (200 mL), acidified by the addition of 1 N HCl (pH=4.8), and the solid was collected with suction. The crude solid was recrystallized from diisopropylether to give 209 mg (86%) 292 as a pale yellow crystalline powder. mp 125–130° C.; IR (KBr) 3325, 2935, 1537, 1209, 1032, 752, 449 cm$^{-1}$; $^1$H-NMR (CD$_3$OD) δ 3.05 (s, 1H), 3.31 (s, 2H), 3.77 (m, 3H), 3.80 (s, 1H), 3.84 (m, 3H), 4.14–4.26 (m, 2H), 6.80–6.87 (m, 3H), 7.01 (m, 1H), 7.10 (m, 2H), 7.39 (m, 2H), 7.80 (m, 1H), 8.07 (m, 1H); MS (FAB) m/z 510 (M$^+$+1); Anal. Calcd for C$_{26}$H$_{27}$FN$_4$O$_6$.0.5H$_2$O: C, 60.11; H, 5.43; F, 3.66; N, 10.78. Found: C, 60.29; H, 5.40; F, 3.60; N, 10.59.

Example 242

(S)-3-amino-4-[2-[3-methoxy-4-[N'-(2-methylphenyl)ureido]phenylacetylamino]-1-propoxy]benzoic acid

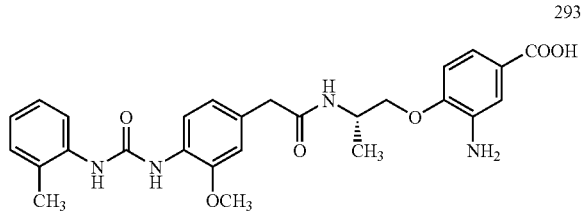

293

To a stirred solution of (S)-2-(N-tert-butoxycarbonylamino)-1-propanol (0.90 g, 5.13 mmol), methyl 4-hydroxy-3-nitrobenzoate (1.01 g, 5.12 mmol), and Ph$_3$P (1.75 g, 6.67 mmol) in THF (15 mL) was added diisopropyl azodicarboxylate (DIAD) (1.31 mL, 6.65 mmol) at room temp, and the resulting mixture was heated under reflux overnight. The solution was evaporated and the residue was dissolved in CH$_2$Cl$_2$ (20 mL) and TFA (10 mL). The mixture was stirred at room temp for 3 hr. The mixture was concentrated in vacuo. The residue was dissolved in CHCl$_3$, washed with sat. NaHCO$_3$, brine, dried over Na$_2$SO$_4$ and evaporated. The residue was purified by column chromatography on silica-gel with 5% MeOH in CHCl$_3$ as eluent to give 313 mg (24%) methyl(S)-3-nitro-4-(2-amino-1-propoxy)benzoate as a pale yellow oil. $^1$H-NMR (CDCl$_3$) δ 1.22 (d, 3 H, J=6.8 Hz), 3.43–3.48 (m, 1 H), 3.69–3.87 (m, 2 H), 3.89 (s, 3 H), 6.93–6.95 (m, 1 H), 7.99–8.02 (m, 1 H), 8.18–8.21 (m, 1 H).

A mixture of pentafluorophenyl 3-methoxy-4-[N'-(2-methylphenyl)ureido]phenylacetate (591 mg, 1.23 mmol), methyl (S)-3-nitro-4-(2-amino-1-propoxy)benzoate (313 mg, 1.23 mmol), and Et$_3$N (257 mL, 1.84 mmol) in DMF (5 mL) was stirred at room temp for 2 days. The mixture was diluted with EtOAc, washed with 0.5 N HCl, brine, dried over Na$_2$SO$_4$, and evaporated. The residue was purified by column chromatography on silica-gel with 5% MeOH in CHCl$_3$ as eluent to give 310 mg (46%) methyl (S)-3-nitro-4-[2-[3-methoxy-4-[N'-(2-methylphenyl)ureido]phenylacetylamino]-1-propoxy]benzoate as a gum. $^1$H-NMR (CDCl$_3$) δ 1.28 (d, 3 H, J=6.8 Hz), 2.31 (s, 3 H), 3.49 (s, 2H), 3.71 (s, 3 H), 3.92 (s, 3 H), 4.14–4.16 (m, 2 H), 4.38–4.41 (m, 1 H), 5.88–5.90 (m, 1 H), 6.49 (s, 1 H), 6.70–6.71 (m, 1 H), 6.77–6.79 (m, 1 H), 7.05–7.30 (m, 4 H), 7.55–7.57 (m, 1 H), 8.02–8.06 (m, 2 H), 8.16–8.19 (m, 1 H), 8.51–8.52 (m, 1 H); MS (FAB) m/z 551 (M$^+$+1).

A stirred solution of methyl (S)-3-nitro-4-[2-[3-methoxy-4-[N'-(2-methylphenyl)ureido]phenylacetylamino]-1-propoxy]benzoate (310 mg, 0.56 mmol) in MeOH-THF (10 mL, 1:1, v/v) was hydrogenated over 5% Pd—C (50 mg, 16 wt %) overnight. The mixture was filtered to remove the catalyst and the filtrate was evaporated to give methyl (S)-3-amino-4-[2-[3-methoxy-4-[N'-(2-methylphenyl)ureido]phenylacetylamino]-1-propoxy]benzoate (240 mg) as a gum.

To a stirred solution of the above crude product (220 mg) in THF-MeOH (10 mL, 1:1, v/v) was added 0.5 N NaOH (10 mL), and the resulting mixture was heated under reflux for 2 hr. The mixture was poured into ice-H$_2$O, and the aqueous layer was made acidic (pH 4.8) by the addition of 1 N HCl. The solid was collected and the crude solid was recrystallized from MeOH—CHCl$_3$-n-hexane to give 116 mg (2 steps, 44%) 293 as a pale yellow crystalline powder. mp 200–204° C.; $^1$H-NMR (DMSO-d$_6$) δ 1.21 (d, 3 H, J=6.8 Hz), 2.24 (s, 3 H), 3.37 (s, 2 H), 3.80 (s, 3 H), 3.83–3.99 (m, 2 H), 4.10–4.19 (m, 1 H), 4.99 (bs, 2 H), 6.75–7.23 (series of m, total 8 H), 7.79 (d, 1 H, J=7.8 Hz), 7.98 (d, 1 H, J=7.8 Hz), 8.17 (d, 1 H, J=8.3 Hz), 8.46 (s, 1 H), 8.55 (s, 1 H); MS (FAB) m/z 507 (M$^+$+1); Anal. Calcd for C$_{27}$H$_{30}$N$_4$O$_6$.1/2H$_2$O: C, 62.90; H, 6.06; N, 10.87. Found: C, 62.85; H, 6.10; N, 10.51.

Example 243

(S)-4-[2-[3-methoxy-4-[N'-(2-bromophenyl)ureido]phenylacetylamino]-1-propoxy]benzoic acid

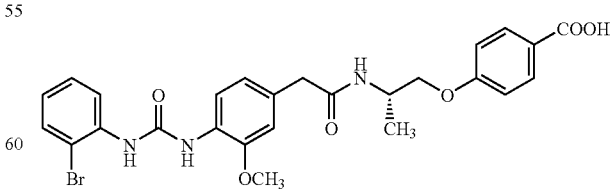

294

To a stirred and cooled (0° C.) solution of (S)-2-(N-tert-butoxycarbonylamino)-1-propanol (6.74 g, 0.04 mol), benzyl 4-hydroxybenzoate (8.78g, 0.04 mol), and Ph$_3$P (15.13 g, 0.06 mol) in THF (100 mL) was added diisopropyl azodicarboxylate (DIAD) (11.4 mL, 0.06 mol), and the resulting mixture was heated under reflux overnight. The solution was evaporated and the residue was dissolved in CH$_2$Cl$_2$ (30 mL) and TFA (30 mL). The resulting solution was stirred at room temp for 30 min., and the solution was evaporated in vacuo. The residue was dissolved in CHCl$_3$, washed with sat. NaHCO$_3$, dried over Na$_2$SO$_4$ and evaporated. The residue was purified by column chromatography on silica-gel with CHCl$_3$ to CHCl$_3$:MeOH (9:1, v/v) as eluent to give 6.63 g (2 steps, 60%) benzyl (S)-4-(2-amino-1-propoxy) benzoate as a yellow oil. $^1$H-NMR (CDCl$_3$) δ 1.18 (d, J=6.3 Hz, 3 H), 3.35–3.39 (m, 1 H), 3.71–3.75 (m, 1 H), 3.90–3.93 (m, 1 H), 5.34 (s, 2 H), 6.90–6.93 (m, 2 H), 7.32–7.46 (m, 5 H), 8.01–8.04 (m, 2 H).

A mixture of 3-methoxy-4-[N'-(2-bromophenyl)ureido]phenylacetic acid (480 mg, 1.27 mmol), benzyl (S)-4-(2-amino-1-propoxy)benzoate (361 mg, 1.27 mmol), EDC(hydrochloride) (364 mg, 1.90 mmol), HOBt (256 mg, 1.89 mmol), and 4-DMAP (31 mg, 0.25 mmol) in DMF (8 mL) was stirred at room temp. overnight. The mixture was diluted with EtOAc, washed with 0.5 N HCl, brine, dried over Na$_2$SO$_4$, and evaporated. The residue was purified by column chromatography on silica-gel with CHCl$_3$ to 5% MeOH in CHCl$_3$ as eluent to give 476 mg (58%) benzyl (S)-4-[2-[3-methoxy-4-[N'-(2-bromophenyl)ureido]phenylacetylamino]-1-propoxy]benzoate as a brown solid. $^1$H-NMR (CDCl$_3$) δ 1.25–1.28 (m, 3 H), 3.51 (s, 2 H), 3.74 (s, 3 H), 3.95–3.97 (m, 2 H), 4.36–4.39 (m, 1 H), 5.33 (s, 2 H), 6.75–6.94 (m, 5 H), 7.26–7.70 (m, 8 H), 7.99–8.26 (m, 5 H).

To a stirred solution of benzyl (S)-4-[2-[3-methoxy-4-[N'-(2-bromophenyl)ureido]phenylacetylamino]-1-propoxy]benzoate (476 mg, 1.39 mmol) in THF (10 mL) was added 0.5 N NaOH (10 mL), and the resulting mixture was heated under reflux for 2 hr. The mixture was poured into ice-1 N HCl, and the solid was collected. The crude solid was recrystallized from MeOH—CHCl$_3$-n-hexane to give 240 mg (59%) 294 as a white crystalline powder. mp 202–205° C.; $^1$H-NMR (DMSO-d$_6$) δ 1.18 (d, J=6.8 Hz, 3 H), 3.37 (s, 2 H), 3.82 (s, 3 H), 3.92–4.00 (m, 2 H), 4.03–4.15 (m, 1 H), 6.77–6.79 (m, 1 H), 6.93–7.03 (m, 4 H), 7.30–7.34 (m, 1 H), 7.59–7.61 (m, 1 H), 7.87–7.97 (m, 4 H), 8.13–8.15 (m, 1 H), 8.73 (s, 1 H), 8.91 (s, 1 H), 12.63 (bs, 1 H); MS (FAB) m/z 557 (M$^+$+1); Anal. Calcd for C$_{26}$H$_{26}$BrN$_3$O$_6$: C, 56.12; H, 4.71; Br, 14.36; N, 7.55. Found: C, 56.11; H, 4.74; Br, 14.56; N, 7.49.

Example 244

(S)-4-[[2-[3-methoxy-4-[N'-(2-methylphenyl)ureido]phenylacetyl]-(2-aminobenzyl)amino]-1-propoxy]benzoic acid

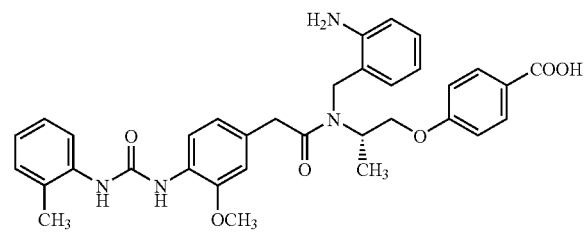

295

To a stirred cooled (0° C.) solution of benzyl (S)-4-(2-amino-1-propoxy)benzoate (1.50 g, 5.26 mmol) and 2-nitrobenzaldehyde (0.87 g, 5.76 mmol) in MeOH—AcOH (16 mL, 15:1, v/v) was added NaBH$_3$CN (1.65 g, 26.3 mmol), and the resulting mixture was stirred at room temp overnight. The mixture was quenched by sat. NaHCO$_3$ and extracted with EtOAc. The extract was washed with brine, dried over Na$_2$SO$_4$, and evaporated. The residue was purified by column chromatography on silica-gel with CHCl$_3$ to 5% MeOH in CHCl$_3$ as eluent to give 931 mg (42%) benzyl (S)-4-[2-(2-nitrobenzylamino)-1-propoxy]benzoate as a yellow oil. $^1$H-NMR (CDCl$_3$) δ 1.21 (d, J=6.4 Hz, 3 H), 3.13–3.18 (m, 1 H), 3.88–3.97 (m, 2 H), 4.06–4.20 (m, 2 H), 5.34 (s, 2 H), 6.89–6.94 (m, 2 H), 7.29–7.65 (m, 8 H), 7.94–8.03 (m, 3 H); MS (FAB) m/z 421 (M$^+$+1).

A mixture of pentafluorophenyl 3-methoxy-4-[N'-(2-methylphenyl)ureido]phenylacetate (460 mg, 0.96 mmol), benzyl (S)-4-[2-(2-nitrobenzylamino)-1propoxy]benzoate (403 mg, 0.96 mmol), and Et$_3$N (200 mL, 1.43 mmol) in DMF (8 mL) was stirred at room temp overnight. The mixture was diluted with EtOAc, washed with 0.5 N HCl, brine, dried over Na$_2$SO$_4$, and evaporated. The residue was purified by column chromatography on silica-gel with 1% MeOH in CHCl$_3$ as eluent to give 504 mg (73%) benzyl (S)-4-[[2-[3-methoxy-4-[N'-(2-methylphenyl)ureido]phenylacetyl]-(2-nitrobenzyl)amino]-1-propoxy]benzoate as a brown amorphous solid. MS (FAB) m/z 717 (M$^+$+1).

A stirred solution of benzyl (S)-4-[[2-[3-methoxy-4-[N'-(2-methylphenyl)ureido]phenyl acetyl]-(2-nitrobenzyl)amino]-1-propoxy]benzoate (504 mg, 0.70 mmol) in MeOH-THF (11 mL, 10:1, v/v) was hydrogenated over 5% Pd—C (100 mg, 20 wt %) at 3 atm overnight. The mixture was filtered to remove the catalyst and the filtrate was evaporated. The residue was purified by preparative TLC with 5% MeOH in CHCl$_3$ as eluent to give 115 mg (27%) 295 as a white powder. MS (FAB) m/z 597 (M$^+$+1).

Example 245

(S)-4-[[2-[3-methoxy-4-[N'-(2-bromophenyl)ureido]phenylacetyl]-(2-nitrobenzyl)amino]-1-propoxy]benzoic acid

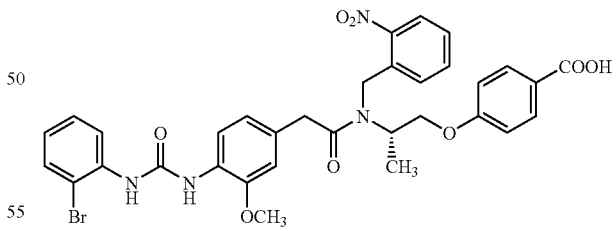

296

To a stirred and cooled (0° C.) solution of benzyl (S)-4-(2-amino-1-propoxy)benzoate (1.50 g, 5.26 mmol) and 2-nitrobenzaldehyde (0.87 g, 5.76 mmol) in MeOH—AcOH (16 mL, 15:1, v/v) was added NaBH$_3$CN (1.65 g, 26.3 mmol), and the resulting mixture was stirred at room temp overnight. The mixture was quenched by sat. NaHCO$_3$ and extracted with EtOAc. The extract was washed with brine, dried over Na$_2$SO$_4$ and evaporated. The residue was purified by column chromatography on silica-gel with CHCl$_3$ to 5% MeOH in CHCl$_3$ as eluent to give 931 mg (42%) benzyl (S)-4-[2-(2-nitrobenzylamino)-1-propoxy]benzoate as a yellow oil. $^1$H-NMR (CDCl$_3$) δ 1.21 (d, 3 H, J=6.4 Hz), 3.13–3.18 (m, 1 H), 3.88–3.97 (m, 2 H), 4.06–4.20 (m, 2 H), 5.34 (s, 2 H), 6.89–6.94 (m, 2 H), 7.29–7.65 (m, 8 H), 7.94–8.03 (m, 3 H); MS (FAB) m/z 421 (M$^+$+1).

A mixture of 3-methoxy-4-[N'-(2-bromophenyl)ureido] phenylacetic acid (476 mg, 1.26 mmol), benzyl (S)-4-[2-(2-nitrobenzylamino)-1-propoxy]benzoate (528 mg, 1.26 mmol), EDC(hydrochloride) (361 mg, 1.88 mmol), HOBt (255 mg, 1.89 mmol), and DMAP (30 mg, 0.25 mmol) in DMF (10 mL) was stirred at room temp. overnight and at 60° C. for 1 day. The mixture was diluted with EtOAc, washed with 0.5 N HCl, brine, dried over Na$_2$SO$_4$ and evaporated. The residue was purified by column chromatography on silica-gel with CHCl$_3$ to 2% MeOH in CHCl$_3$ as eluent to give benzyl (S)-4-[[2-[3-methoxy-4-[N'-(2-bromophenyl)ureido]phenylacetyl]-(2-nitrobenzyl)amino]-1-propoxy]benzoic acid as an oil, which is used to the subsequent reaction without further purification.

To a stirred solution of the above crude in THF-MeOH (10 mL, 1:1, v/v) was added 0.5 N NaOH (10 mL), and the resulting mixture was heated under reflux for 3 hr. The mixture was poured into ice-H$_2$O, and the basic aqueous layer was made acidic (pH 4.3) with 1 N HCl. The solid was collected, and the crude solid was purified by preparative TLC with 5% MeOH in CHCl$_3$ as eluent to give 162 mg (2 steps, 19%) 296 as a white amorphous solid. MS (FAB) m/z 692 (M$^+$+1); Anal. Calcd for C$_{33}$H$_{31}$BrN$_4$O$_8$.7/4H$_2$O: C, 54.82; H, 4.81; N, 7.75. Found: C, 54.80; H, 4.61; N, 7.24.

Example 246

4-[2-N-[3-methoxy-4-[N'-(2-methylphenyl)ureido] phenylacetamido]ethoxy]benzoic acid

297

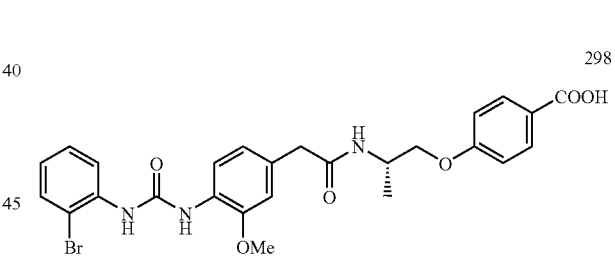

To a cooled (0° C.) solution of 2-(N-tert-butoxycarbonylamino)ethanol (3.20 g, 19.9 mmol), methyl 4-hydroxybenzoate (3.02 g, 19.9 mmol) and Ph$_3$P (6.25 g, 23.8 mmol) in THF (50 ml) was added dropwise DIAD (4.69 ml, 23.8 mmol) over for 5 min. The reaction mixture was heated under reflux for 3 hr. The mixture was evaporated and the residue was dissolved in CH$_2$Cl$_2$ (30 ml) and TFA (30 ml). The reaction mixture was stirred at room temperature overnight. The mixture was concentrated in vacuo and the residue was dissolved in CHCl$_3$ and H$_2$O. The solution was made basic by sat. NaHCO$_3$ and extracted with CHCl$_3$. The extract was washed with brine, dried over Na$_2$SO$_4$ and evaporated. The residue was purified by column chromatography on silica-gel with CHCl$_3$-MeOH (30:1, v/v) as eluent to give methyl 4-(2-aminoethoxy)benzoate (1.03 g, 34% for 2 steps) as a colorless oil. $^1$H-NMR (CDCl$_3$) δ 3.10–3.13 (m, 2 H), 3.89 (s, 3 H), 4.03–4.06 (m, 2 H), 6.92–6.94 (m, 2 H), 7.98–8.00 (m, 2 H).

A mixture of 3-methoxy-4-[N'-(2-methylphenyl)ureido] phenylacetic acid (557 mg, 1.77 mmol), methyl 4-(2-aminoethoxy)benzoate (346 mg, 1.77 mmol), EDC.HCl (408 mg, 2.13 mmol), HOBt (287 mg, 2.12 mmol) and DMAP (52 mg, 0.43 mmol) in DMF (10 ml) was stirred at room temperature for 2 days. The mixture was diluted with EtOAc and H$_2$O. The resulting precipitate was collected to give methyl 4-[2-N-[3-methoxy-4-[N'-(2-methylphenyl)ureido] phenylacetamido]ethoxy]benzoate (598 mg, 69%) as a white crystalline powder. $^1$H-NMR (DMSO-d$_6$) δ 2.23 (s, 3 H), 3.36 (s, 2 H), 3.42–3.45 (m, 2 H), 3.79 (s, 3 H), 3.81 (s, 3 H), 4.02–4.09 (m, 2 H), 6.73–6.75 (m, 1 H), 6.90–6.94 (m, 2 H), 7.02–7.04 (m, 2 H), 7.09–7.15 (m, 2 H), 7.77–7.79 (m, 1 H), 7.88–7.90 (m, 2 H), 7.95–7.98 (m, 1 H), 8.23–8.24 (m, 1 H), 8.44 (s, 1 H), 8.53 (s, 1 H); MS (FAB), m/z 492 (M$^+$+1); Anal. Calcd for C$_{27}$H$_{29}$N$_3$O$_6$.1/4H$_2$O: C, 65.38; H, 5.99; N, 8.47. Found: C, 65.26; H, 5.99; N, 8.49.

To a stirred solution of methyl 4-[2-N-[3-methoxy-4-[N'-(2-methylphenyl)ureido]phenylacetamido]ethoxy]benzoate (280 mg, 0.57 mmol) in THF-MeOH (10 ml, 1:1, v/v) was added 0.5 N NaOH (10 ml) and the reaction mixture was heated under reflux for 5 hr. The mixture was cooled to room temperature and poured into ice-1 N HCl. The resulting precipitate was collected and recrystallized from Et$_2$O—CHCl$_3$-MeOH to give 297 (135 mg, 50%) as a white crystalline powder. MW 477.51 $^1$H-NMR (DMSO-d$_6$) δ 2.24 (s, 3 H), 3.38 (s, 2 H), 3.43–3.47 (m, 2 H), 3.82 (s, 3 H), 4.06–4.09 (, 2 H), 6.76–6.78 (m, 1 H), 6.92–7.17 (m, 6 H), 7.79 (d, J=8.1 Hz, 1 H), 7.88–7.89 (m, 2 H), 7.98 (d, J=8.1 Hz, 1 H), 8.24–8.27 (m, 1 H), 8.45 (s, 1 H), 8.55 (s, 1 H); MS (FAB) m/z 478 (M$^+$+1); Anal. Calcd for C$_{26}$H$_{27}$N$_3$O$_6$.1/4H$_2$O: C, 64.79; H, 5.75; N, 8.72. Found: C, 64.67; H, 5.63; N, 8.60.

Example 247

(S)-4-[2-N-[4-[N'-(2-bromophenyl)ureido]-3-methoxyphenylacetamido]-1-propoxy]benzoic acid

298

To a cooled (0° C.), stirred solution of (S)-2-(N-tert-butoxycarbonylamino)-1-propanol (6.74 g, 0.04 mol), benzyl 4-hydroxybenzoate (8.78 g, 0.04 mol), and Ph$_3$P (15.13 g, 0.06 mol) in THF (100 ml) was added DIAD (11.4 ml, 0.06 mol), and the reaction mixture was heated under reflux overnight. The solution was evaporated and the residue was dissolved in CH$_2$Cl$_2$ (30 ml) and TFA (30 ml). The solution was stirred at room temperature for 30 min. and the solution was concentrated in vacuo. The residue was dissolved in CHCl$_3$, washed with sat. NaHCO$_3$, dried over Na$_2$SO$_4$ and evaporated. The residue was purified by column chromatography on silica-gel with CHCl$_3$ to CHCl$_3$-MeOH (9:1, v/v) as eluent to give benzyl (S)-4-(2-amino-1-propoxy) benzoate (6.63 g, 2 steps, 60%) as a yellow oil. $^1$H-NMR (CDCl$_3$) δ 1.18 (d, J=6.3 Hz, 3 H), 3.35–3.39 (m, 1 H), 3.71–3.75 (m, 1 H), 3.90–3.93 (m, 1 H), 5.34 (s, 2 H), 6.90–6.93 (m, 2H), 7.32–7.46 (m, 5H), 8.01–8.04 (m, 2H).

A mixture of 4-[N'-(2-bromophenyl)ureido]-3-methoxyphenylacetic acid (480 mg, 1.27 mmol), benzyl (S)-4-(2- amino-1-propoxy)benzoate (361 mg, 1.27 mmol), EDC.HCl (364 mg, 1.90 mmol), HOBt (256 mg, 1.89 mmol) and DMAP (31 mg, 0.25 mmol) in DMF (8 ml) was stirred at room temperature overnight. The mixture was diluted with EtOAc, washed with 0.5 N HCl, brine, dried over $Na_2SO_4$ and evaporated. The residue was purified by column chromatography on silica-gel with $CHCl_3$ to 5% MeOH in $CHCl_3$ as eluent to give benzyl (S)-4-[2-[4-[N'-(2-bromophenyl) ureido]-3-methoxyphenylacetamido]-1-propoxy]benzoate (476 mg, 58%) as a brown solid. $^1$H-NMR ($CDCl_3$) δ 1.25–1.28 (m, 3 H), 3.51 (s, 2 H), 3.74 (s, 3 H), 3.95–3.97 (m, 2 H), 4.36–4.39 (m, 1 H), 5.33 (s, 2 H), 6.75–6.94 (m, 5 H), 7.26–7.70 (m, 8 H), 7.99–8.26 (m, 5 H).

The a stirred solution of benzyl (S)-4-[2-[4-[N'-(2-bromophenyl)ureido]-3-methoxyphenyl acetamido]-1-propoxy]benzoate (476 mg, 1.39 mmol) in THF (10 ml) was added 0.5 N NaOH (10 ml), and the reaction mixture was heated under reflux for 2 hr. The mixture was poured into ice-1 N HCl, and the resulting precipitate was collected. The crude solid was purified by recrystallization from MeOH—$CHCl_3$-n-hexane to give 298 (240 mg, 59%) as a white crystalline powder. MW 556.41 $^1$H-NMR (DMSO-$d_6$) δ 1.18 (d, J=6.8 Hz, 3 H), 3.37 (s, 2 H), 3.82 (s, 3H), 3.92–4.00 (m, 2 H), 4.03–4.15 (m, 1 H), 6.77–6.79 (m, 1 H), 6.93–7.03 (m, 4 H), 7.30–7.34 (m, 1 H), 7.59–7.61 (m, 1 H), 7.87–7.97 (m, 4 H), 8.13–8.15 (m, 1 H), 8.73 (s, 1 H), 8.91 (s, 1 H), 12.63 (bs, 1 H); MS (FAB) m/z 557 (M$^+$+1); Anal. Calcd for $C_{26}H_{26}BrN_3O_6$: C, 56.12; H, 4.71; Br, 14.36; N, 7.55. Found: C, 56.11; H, 4.74; Br, 14.56; N, 7.49.

Example 248

(S)-4-[2-N-[[3-methoxy-4-[N'-(2-methylphenyl)ureido]phenyl]-N-methylacetamido]-1-propoxy] benzoic acid mixture was concentrated in vacuo, and made basic by sat. $NaHCO_3$. The mixture was extracted with $CHCl_3$, washed with brine, dried over $K_2CO_3$ and evaporated to give methyl (S)-4-(2-amino-1-propoxy) benzoate (790 mg, 94%) as a yellow oil. $^1$H-NMR ($CDCl_3$) δ 1.19 (d, J=6.7 Hz, 3 H), 3.34–3.42 (m, 1 H), 3.70–3.77 (m, 1 H), 3.86–3.94 (series of s and m, total 4 H), 6.92 (d, J=9.0 Hz, 2 H), 7.98 (d, J=9.0 Hz, 2 H).

To a cooled (0° C.) solution of methyl (S)-4-(2-amino-1-propoxy)benzoate (790 mg, 3.78 mmol) and $Et_3$N (630 ml, 4.52 mmol) in THF (10 ml) was added TFAA (640 ml, 4.53 mmol) and the reaction mixture was stirred at room temperature for 4 days. The mixture was diluted with 0.5 N HCl and extracted with $CHCl_3$. The extract was washed with brine, dried over $K_2CO_3$, and evaporated. The residue was purified by recrystallization from n-hexane-$CHCl_3$ to give methyl (S)-4-[2-(trifluoroacetamido)-1-propoxy]benzoate (790 mg, 69%) as a white crystalline material. $^1$H-NMR ($CDCl_3$) δ 1.42 (d, J=6.8 Hz, 3 H), 3.89 (s, 3 H), 4.01–4.13 (m, 2 H), 4.44–4.50 (m, 1 H), 6.57–6.61 (m, 1 H), 6.92 (d, J=9.0 Hz, 2 H), 8.00 (d, J=9.0 Hz, 2 H); MS (FAB) m/z 306 (M$^+$+1); Anal. Calcd for $C_{13}H_{14}F_3NO_4$: C, 51.15; H, 4.62; F, 18.67; N, 4.59. Found: C, 51.14; H, 4.60; F, 18.50; N, 4.54.

To a stirred solution of methyl (S)-4-[2-(trifluoroacetamido)-1-propoxy]benzoate (695 mg, 2.28 mmol) and $K_2CO_3$ (630 mg, 4.56 mmol) in DMF (10 ml) was added MeI (210 ml, 3.37 mmol) and the reaction mixture was stirred at room temperature for 2 days. The mixture was diluted with $H_2O$ and extracted with EtOAc. The extract was washed with brine, dried over $Na_2SO_4$, and evaporated. The residue was purified by column chromatography on silica-gel with EtOAc-$CHCl_3$ (1:19, v/v) as eluent to give methyl (S)-4-[2-[(N-methyl)trifluoroacetamido]-1-propoxy]benzoate (720 mg, 99%) as a white solid. mp 73–75° C.; $^1$H-NMR ($CDCl_3$)

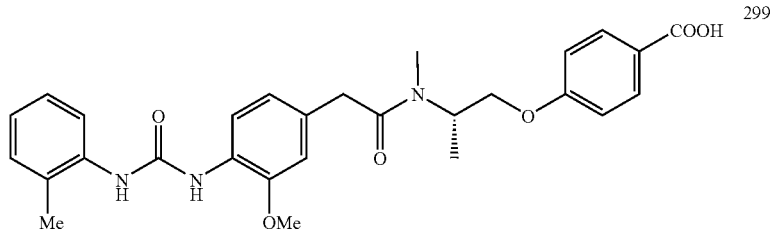

299

δ 1.36–1.39 (m, 3 H), 2.96 and 3.10 (each s, total 3 H), 3.89 (s, 3 H), 3.99–4.14 (m, 2 H), 4.84–4.92 (m, 1 H), 6.88–6.92 (m, 2 H), 7398–8.00 (m, 2 H); MS (FAB) m/z 320 (M$^+$+1); Anal. Calcd for $C_{14}H_{16}F_3NO_4$: C, 52.67; H, 5.05; F, 17.85; N, 4.39. Found: C, 52.76; H, 5.09; F, 17.53; N, 4.32.

To a stirred solution of methyl (S)-4-[2-[(N-methyl)trifluoroacetamido]-1-propoxy]benzoate (710 mg, 2.22 mmol) in MeOH—$H_2O$ (10 ml, 1:1, v/v) was added $K_2CO_3$ (460 mg, 3.33 mmol) and the reaction mixture was stirred at room temperature overnight. The mixture was diluted with $H_2O$ and extracted with EtOAc. The extract was washed with brine, dried over $Na_2SO_4$, and evaporated to give methyl (S)-4-[2-(N-methylamino)-1-propoxy]benzoate (430 mg, 87%) as a colorless oil. $^1$H-NMR ($CDCl_3$) δ 1.17 (d, J=6.6 Hz, 3 H), 2.48 (s, 3 H), 2.98–3.06 (m, 1 H), 3.86–3.96 (series of s and m, total 5 H), 6.92 (d, J=9.0 Hz, 2 H), 7.98 (d, J=9.0 Hz, 2 H).

To a cooled (0° C.) solution of (S)-2-[(N-tert-butoxycarbonyl)amino]-1-propanol (3.08 g, 17.6 mmol), methyl 4-hydroxybenzoate (2.67 g, 17.6 mmol) and $Ph_3P$ (5.53 g, 21.1 mmol) in THF (35 ml) was added dropwise DIAD (4.15 ml, 21.1 mmol). The reaction mixture was heated under reflux overnight. The mixture was evaporated and the residue was purified by column chromatography on silica-gel with n-hexane-EtOAc (5:1, v/v) as eluent to give methyl (S)-4-[2-[(N-tert-butoxycarbonyl)amino]-1-propoxy]benzoate (1.24 g, 23%) as a white solid. $^1$H-NMR ($CDCl_3$) δ 1.30 (d, J=6.8 Hz, 3 H), 1.45 (s, 9 H), 3.89 (s, 3 H), 3.98–3.99 (m, 2 H), 4.07 (m, 1 H), 4.76 (m, 1 H), 6.91–6.93 (m, 2 H), 7.98–8.00 (m, 2 H); MS (FAB) m/z 310 (M$^+$+1).

To a stirred solution of methyl (S)-4-[2-[(N-tert-butoxycarbonyl)amino]-1-propoxy]benzoate (1.24 g, 4.01 mmol) in $CH_2Cl_2$ (10 ml) was added TFA (10 ml) and the reaction mixture was stirred at room temperature overnight. The A mixture of 3-methoxy-4-[N'-(2-methylphenyl)ureido]phenylacetic acid (605 mg, 1.93 mmol), methyl (S)-4-[2-(N-methylamino)-1-propoxy]benzoate (430 mg, 1.93 mmol), EDC.HCl (444 mg, 2.32 mmol), HOBt (313 mg, 2.32 mmol), Et$_3$N (320 ml, 2.30 mmol) in THF (13 ml) was stirred at room temperature overnight. The mixture was diluted with H$_2$O and extracted with EtOAc. The extract was washed with brine, dried over Na$_2$SO$_4$, and evaporated. The residue was purified by column chromatography on silica-gel with CHCl$_3$-MeOH (100:1 to 75:1, v/v) as eluent to give methyl (S)-4-[2-N-[[3-methoxy-4-[N'-(2-methylphenyl)ureido]phenyl]-N-methylacetamido]-1-propoxy]benzoate (953 mg, 95%) as a white foam. $^1$H-NMR (CDCl$_3$) δ 1.12–1.13 and 1.25–1.27 (each m, total 3 H), 2.27 (s, 3 H), 2.84 and 2.92 (each s, total 3 H), 3.63 (s, 3 H), 3.67 (s, 2 H), 3.71–4.05 (series of s and m, total 5 H), 4.39–4.44 and 4.96–5.01 (each m, total 1 H), 6.66–6.85 (m, 5 H), 7.09–7.27 (m, 4 H), 7.53–7.55 (m, 1 H), 7.92–7.98 (m, 2 H), 8.04–8.08 (m, 1 H); MS (FAB) m/z 520 (M$^+$+1); Anal. Calcd for C$_{29}$H$_{33}$N$_3$O$_6$.11/4H$_2$O: C, 61.20; H, 6.82; N, 7.38. Found: C, 61.14; H, 5.86; N, 7.16.

To a stirred solution of methyl (S)-4-[2-N-[[3-methoxy-4-[N'-(2-methylphenyl)ureido]phenyl]-N-methylacetamido]-1-propoxy]benzoate (663 mg, 1.28 mmol) in THF (5 ml) was added 0.5 N NaOH (5 ml) and the reaction mixture was heated under reflux for 5 hr. After cooled to room temperature, the mixture was poured into ice-1 N HCl and the resulting precipitate was collected under a reduced pressure. The crude solid was dissolved in CHCl$_3$ and evaporated. The residue was washed with Et$^2$O to give 299 (465 mg, 72%) as a white amorphous solid. MW 505.56 $^1$H-NMR (DMSO-d$_6$) δ 1.11–1.15 (m, 3 H), 2.25 (s, 3 H), 2.73 and 2.88 (each s, total 3 H), 3.60–3.76 (m, 2 H), 3.83 (s, 3 H), 4.03–4.12 (m, 2 H), 4.41–4.50 and 4.48–4.94 (each m, total 1 H), 6.71–6.76 (m, 1 H), 6.84–6.86 (m, 1 H), 6.91–7.01 (m, 3 H), 7.11–7.12 (m, 2 H), 7.78–7.80 (m, 1 H), 7.86–7.90 (m, 2 H), 8.01–8.03 (m, 1 H), 8.45 (s, 1 H), 8.54 (s, 1H); MS (FAB) m/z 520 (M$^+$+1); Anal. Calcd for C$_{28}$H$_{31}$N$_3$O$_6$.3/2H$_2$O: C, 63.15; H, 6.43; N, 7.89. Found: C, 63.09; H, 5.99; N, 7.64.

Example 249

4-[2-N-[3-methoxy-4-[N'-(2-methylphenyl)ureido]phenylacetamido]-2-methyl-1-propoxy]benzoic acid A stirred mixture of methyl 4-hydroxybenzoate (3 g, 19.72 mmol), K$_2$CO$_3$ (6.8 g, 49.3 mmol), 3-chloropivalic acid (2.9 g, 21.69 mmol) and catalytic amount of KI (200 mg) in DMF (70 ml) was heated at 100° C. for 14 days under a current of nitrogen. The mixture was poured into ice-water, and extracted with EtOAc. The extracts were washed with brine, dried over Na$_2$SO$_4$, and evaporated. The residue was chromatographed on silica gel (50 ml) with CHCl$_3$-EtOH (10:1, v/v) as eluent to give the title compound (1 g, 23%) as an amorphous solid. $^1$H-NMR (CDCl$_3$) δ 1.37 (s, 6 H), 3.89 (s, 3 H), 4.03 (s, 2 H), 6.92 (d, J=9 Hz, 2 H), 7.98 (d, J=9 Hz, 2 H).

To a stirred mixture of 2,2-dimethyl-3-(4-methoxycarbonyl)phenoxypropionic acid (720 mg, 2.85 mmol) and triethylamine (0.46 ml, 3.28 mmol) in tert-BuOH (10 ml) and benzene (10 ml) was added a solution of diphenyl phosphoryl azide (870 mg, 3.14 mmol) in benzene (3 ml) at room temperature. The resulting mixture was heated at reflux for 20 hr. After cooling, ice and 1N HCl (5 ml) was added to the mixture and extracted with toluene. The extracts were washed with brine, dried over Na$_2$SO$_4$, and evaporated. The residue was chromatographed on silica gel (50 ml) with toluene-EtOAc (10:1, v/v) as eluent to give methyl 4-[1-(2-amino-2-methyl)prpoxy]benzoate as a gum (520 mg), which was used to the subsequent reaction without further purification. $^1$H-NMR (CDCl$_3$) δ 1.41 (s, 9 H), 3.89 (s, 3 H), 4.04 (s, 2 H), 4.69 (br s, 1H), 6.94 (dd, J=2 and 7 Hz, 2 H), 7.98 (dd, J=2 and 7 Hz).

A solution of methyl 4-[1-(2-methyl-2-tert-butoxycarbonylamino-)prpoxy]benzoate (520 mg) and anisole (0.175 ml, 1.61 mmol) in CH$_2$Cl$_2$ (5 ml) and TFA (3 ml) was stirred at room temperature for 18 hr. The mixture was evaporated off. The residue was dissolved in CH$_2$Cl$_2$, and the mixture was made basic by the addition of sat. NaHCO$_3$. Separated CH$_2$Cl$_2$ layer was dried over Na$_2$SO$_4$ and Na$_2$CO$_3$, and evaporated. The residue was chromatographed on silica gel with CHCl$_3$-EtOH (10:1, v/v) as eluent to give methyl 4-[1-(2-amino-2-methyl)prpoxy]benzoate (250 mg, 39% in two steps) as a gum. $^1$H-NMR (CDCl$_3$) δ 3.75 (s, 2 H), 3.89 (s, 3 H), 6.93 (d, J=8.8 Hz, 2 H), 7.98 (d, J=8.8 Hz, 2 H).

To a stirred mixture of methyl 4-[1-(2-amino-2-methyl)prpoxy]benzoate (250 mg, 1.12 mmol), 3-methoxy-4-[N'-(2-methylphenyl)ureido]phenylacetic acid (352 mg, 1.12 mmol), 4-DMAP (165 mg, 1.34 mmol) in DMF (10 ml) was added EDC.HCl (290 mg, 1.51 mmol) at room temperature. The resulting mixture was stirred at room temperature for 18 hr. The mixture was pored into ice-water. The solid was collected, washed with water and air-red. The crude solid was purified by silica gel column chromatography with CHCl$_3$-EtOH (4:1, v/v) as eluent to give methyl 4-[2-N-[3-methoxy-4-[N'-(2-methylphenyl)ureido]phenylacetamido]-2-methyl-1-propoxy]benzoate (580 mg, q.y.) as a crystalline material. IR (KBr) 3350, 3286, 1712, 1687, 1637, 1606 cm$^{-1}$; $^1$H-NMR (CDCl$_3$) δ 1.39 (s, 6 H), 2.33 (s, 3 H), 3.41 (s, 2 H), 3.63 (s, 3 H), 3.88 (s, 3H), 4.05 (s, 2 H), 5.44 (br s, 1 H), 6.33 (br s, 1H), 6.79 (d, J=8.3 Hz, 2 H), 7.12 (s, 1 H), 7.18 (t, J=7.5 Hz, 1 H), 7.53 (d, J=7.8 Hz, 1 H), 7.94 (d, J=7.8 Hz, 2 H), 8.14 (d, J=8.3 Hz, 1 H); MS (FAB) m/z 520

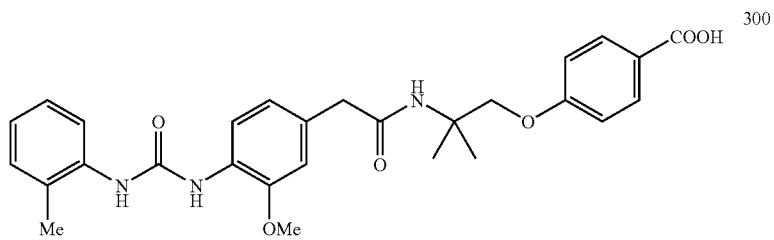

300

(M++1); Anal. Calcd for $C_{29}H_{33}N_3O_6$: C, 67.04; H, 6.40; N, 8.09. Found: C, 66.86; H, 6.36; N, 8.22.

To a stirred solution of methyl 4-[2-[3-methoxy-4-[N'-(2-methylphenyl)ureido]phenyl acetamido]-2-methyl-2-propoxy]benzoate (510 mg, 0.98 mmol) was added 0.25 N NaOH (8 ml, 2 mmol) at room temperature. The resulting mixture was stirred at an ambient temperature for 18 hr. The mixture was pored into ice-1 N HCl (5 ml). the solid was collected, washed with water and air-dried. The crude solid was recrystallized from $CHCl_3$-EtOH-$Et_2O$ to give 300 (480 mg, 97%) as fine needles. MW 505.56 IR (KBr) n 3346, 3294, 1687, 1637, 1604 cm$^{-1}$; $^1$H-NMR (DMSO-$d_6$) δ 1.35 (s, 6 H), 2.24 (s, 3 H), 3.33 (s, 2 H), 3.80 (s, 3 H), 4.15 (s, 2 H), 6.75 (d, J=8.3 Hz, 1 H), 6.88 (s, 1 H), 6.95–6.99 (m, 3 H), 7.11–7.17 (m, 3 H), 7.80 (d, J=8.3 Hz, 1 H), 7.82 (s, 1 H), 7.87 (d, J=8.8 Hz, 2 H), 7.98 (d, J=7.8 Hz, 1 H), 8.45 (s, 1 H), 8.54 (s, 1 H), 12.62 (br s, 1 H); MS (FAB) m/z 506 (M++1); Anal. Calcd for $C_{28}H_{31}N_3O_6$: C, 66.52; H, 6.18; N, 8.31. Found: C, 66.22; H, 6.28; N, 8.11.

Example 250

3-amino-4-[2-N-[4-[N'-(2-chlorophenyl)ureido]-3-methoxyphenylacetamido]-2-methyl-1-propoxy] benzoic acid

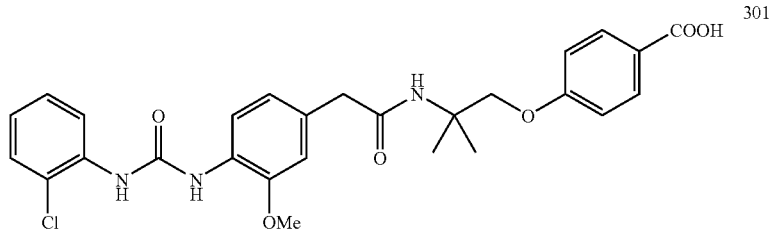

301

To a stirred solution of 4-amino-2-nitrophenol (10 g, 64.88 mmol) in AcOH (70 ml) and DMSO (20 ml) was added c. $H_2SO_4$ at 0–5° C. To a stirred this solution was added dropwise a solution of $NaNO_2$ (5.4 g, 77.9 mmol) in water (5 ml) below 20° C. for over 10 min. The resulting mixture was further stirred for 0.5 hr at 5° C. This mixture was poured into a stirred solution of KI (30 g, 0.182 mol) and catalytic amount of Cu powder (200 mg) in ice-water (200 ml) for over 10 min. The resulting mixture was for a further 1 hr at an ambient temperature. The mixture was extracted with $CH_2Cl_2$. The extracts were washed successively with sat. $Na_2S_2O_3$ and brine. The organic layer was dried over $Na_2SO_4$, and evaporated. The residue was chromatographed on silica-gel (50 ml) with $CHCl_3$-EtOAc (3:1, v/v) as eluent to give 4-iodo-2-nitrophenol (2.5 g, 15%) as a yellow crystalline material. $^1$H-NMR (CDCl$_3$) δ 6.94 (d, J=8.8 Hz, 1 H), 7.82 (dd, J=2 and 8.8 Hz, 1 H), 8.42 (d, J=2 Hz, 1H), 10.49 (s, 1 H).

To a stirred solution of 4-iodo-2-nitrophenol (2 g, 7.75 mmol), hydroxypivalic acid methyl ester (1.05 g, 7.92 mmol) and PPh$_3$ (2.3 g, 8.68 mmol) in THF (10 ml) was added dropwise a solution of DIAD (1.77 g, 8.30 mmol) in THF (2 ml) under ice-water bath cooling. The resulting mixture was then heated under reflux for 18hr. After cooling, the mixture was evaporated off. The residue was chromatographed on silica gel (100 ml) with with toluene-EtOAc (4:1, v/v) as eluent to give methyl 3-(4-iodo-2-nitro)phenoxy-2,2-dimethylpropionate (2.9 g, q.y.) as a crystalline material. $^1$H-NMR (CDCl$_3$) δ 1.34 (s, 6 H), 3.71 (s, 3 H), 4.08 (s, 2 H), 6.86 (d, J=8.8 Hz, 1 H), 7.78 (dd, J=2 and 8.8 Hz, 1 H), 8.12 (d, J=2 Hz, 1H).

A mixture of methyl 3-(4-iodo-2-nitro)phenoxy-2,2-dimethylpropionate (2.8 g, 7.38 mmol) in THF (15 ml) and 0.25 N NaOH (60 ml, 15 mol) at an ambient temperature for 18 hr. The mixture was poured into ice-1 N HCl (20 ml). The solid was collected, washed with water and air-dried. The crude solid was recrystallized from $CHCl_3$-EtOH-IPE to afford 3-(4-iodo-2-nitro)phenoxy-2,2-methylpropionic acid (2.0 g, 74%) as a crystalline material. Mp 165–182° C.; IR (KBr) n 1716, 1525, 1344 cm$^{-1}$; $^1$H-NMR (CDCl$_3$) δ 1.38 (s, 6 H), 4.10 (s, 2 H), 6.86 (d, J=8.8 Hz, 1 H), 7.79 (dd, J=2.2 and 8.8 Hz, 1 H), 8.12 (d, J=2 Hz, 1H); MS (FAB) m/z 366 (M++1); Anal. Calcd for $C_{29}H_{33}N_3O_6$: C, 36.18; H, 3.18; N, 3.84. Found: C, 36.85; H, 3.35; N, 3.79.

To a stirred mixture of 3-(4-iodo-2-nitro)phenoxy-2,2,2-dimethylpropionic acid (1.93 g, 5.29 mmol) and triethylamine (590 mg, 5.81 mmol) in tert-BuOH (15 ml) and toluene (15 ml) was added a solution of diphenyl phosphoryl azide (1.53 g, 5.55 mmol) in toluene (3 ml) at room temperature. The resulting mixture was then heated at reflux for 20 hr. After cooling, ice and 1N HCl (5 ml) was added to the mixture and extracted with toluene. The extracts were washed with brine, dried over $Na_2SO_4$, and evaporated. The residue was chromatographed on silica gel (50 ml) with toluene-EtOAc (10:1, v/v) as eluent to give 3-nitro-4-(2-tert-butoxycarbonylamino-2-methyl-1-propoxy)iodobenzene (1.91 g, 83%) as a gum. $^1$H-NMR (CDCl$_3$) δ 1.38 (s, 9 H), 1.39 (s, 6 H), 4.19 (s, 2 H), 4.67 (br s, 1 H), 6.88 (d, J=8.8 Hz, 1 H), 7.77 (dd, J=2.0 and 8.8 Hz, 1 H), 8.12 (d, J=2.0 Hz, 1 H).

A mixture of 3-nitro-4-(2-tert-butoxycarbonylamino-2-methyl-1-propoxy)iodobenzene (1.9 g, 4.36 mmol), Pd(OAc)$_2$ and 1,3-bis(diphenylphosphino)propane (dppp) (90 mg, 0.22 mmol) in triethylamine-MeOH-DMSO (1:2:5, v/v, 48 ml) was stirred under a current of CO (gas) at 70° C. for 6 hr. After cooling, the mixture was poured into water and extracted with EtOAc. The extracts were washed with brine, dried over $Na_2SO_4$, and evaporated. The residue was chromatographed on silica gel (50 ml) with toluene-EtOAc (6:1, v/v) as eluent to give methyl 4-(2-tert-butoxycarbonyl amino-2-methyl-1-propoxy)-3-nitrobenzoate (820 mg, 51%) as a gum. $^1$H-NMR (CDCl$_3$) δ 1.38 (s, 9 H), 1.42 (s, 61 H), 3.93 (s, 3 H), 4.29 (s, 2 H), 4.67 (br s, 1 H), 7.15 (d, J=8.8 Hz, 1 H), 8.18 (dd, J=1.7 and 8.8 Hz, 1 H), 8.52 (d, J=1.7 Hz, 1H).

A stirred mixture of methyl 4-(2-tert-butoxycarbonylamino-2-methyl-1-propoxy)-3-nitrobenzoate (350 mg, 0.95 mmol) and 5% Pd—C (70 mg) in EtOH (30 ml) was hydrogenated in an atmospheric hydrogen pressure at room temperature for 20 hr. Insoluble Pd-catalyst was removed with suction and washed with EtOH. The filtrate was evaporated off to afford methyl 4-(2-tert-butoxycarbonyl amino-2-methyl)-1-propoxy-3-aminobenzoate as a gum, which was used to the subsequent reaction without further purification. $^1$H-NMR (CDCl$_3$) δ 1.41 (s, 9 H), 1.43 (s, 6 H), 3.86 (s, 3 H), 4.07 (s, 2 H), 4.67 (br s, 1 H), 6.80 (d, J=8.5 Hz, 1 H), 7.39 (d, J=2.2 Hz, 1H), 7.44 (dd, J=2.2 and 8.5 Hz, 1 H).

To a stirred mixture of the above methyl 4-(2-tert-butoxycarbonylamino-2-methyl)-1-propoxy-3-aminobenzoate and triethylamine (0.20 ml, 1.43 mmol) in CH$_2$Cl$_2$ (10 ml) was added a solution of trifluoroacetic anhydride (0.182 ml, 1.28 mmol) in CH$_2$Cl$_2$ (3 ml) at 0–5° C. The resulting mixture was stirred at room temperature for 1 hr. Ice-sat. NaHCO$_3$ was added to the mixture, and extracted with CH$_2$Cl$_2$. The extracts were washed with brine, dried over Na$_2$SO$_4$, and evaporated. The residue was dissolved in CH$_2$Cl$_2$ (5 ml) and added anisole (0.105 ml, 0.95 mmol) and TFA (2 ml). The resulting mixture was stirred at room temperature for 18 hr. The mixture was evaporated in vacuo, and the residue was diluted with CH$_2$Cl$_2$ and made basic by the addition of sat. NaHCO$_3$. The separated CH$_2$Cl$_2$ layer was dried over Na$_2$SO$_4$, and evaporated. The residue was chromatographed on silica gel (50 ml) with CHCl$_3$-EtOH (99:1, v/v) as eluent to give methyl 4-(2-amino-2-methyl-1-propoxy)-3-trifluoroacetamidobenzoate (631 mg, 63% in 3-steps) as a gum. $^1$H-NMR (CDCl$_3$) δ 1.29 (s, 9 H, tert-Bu), 3.86 (s, 2 H, CH$_2$), 3.91 (s, 3 H, ), 6.99 (d, J=8.5 Hz, 1 H), 7.91 (dd, J=2.0 and 8.5 Hz, 1H), 8.83 (d, J=8.5 Hz, 1 H).

To a stirred mixture of methyl 4-(2-amino-2-methyl)-1-propoxy-3-trifluoroacetamido benzoate (200 mg, 0.598 mmol), 4-[N'-(2-chlorophenyl)ureido]-3-methoxyphenylacetic acid (210 mg, 0.598 mmol), 4-DMAP (90 mg, 0.72 mmol) in DMF (7 ml) was added EDC.HCl (160 mg, 0.81 mmol) at room temperature. The resulting mixture was stirred at room temperature for 20 hr. The mixture was pored into ice-water. The solid was collected, washed with water and air-dried. The crude solid was purified by silica gel column chromatography with CHCl$_3$-EtOH (98:2, v/v) as eluent to give methyl 4-[2-N-[4-[N'-(2-chlorophenyl)ureido]-3-methoxyphenylacetamido]-2-methyl-1-propoxy]-3-trifluoroacetamidobenzoate (580 mg, q.y.) as a crystalline material. $^1$H-NMR (CDCl$_3$) δ 1.42 (s, 6 H), 3.42 (s, 2 H), 3.69 (s, 3 H), 3.89 (s, 3 H), 4.23 (s, 2 H), 5.33 (br s, 1 H), 6.66 (s, 1 H), 6.71 (m, 1 H), 6.92 (d, J=8.5 Hz, 1 H), 7.02 (m, 1 H), 7.09 (m, 1 H), 7.29 (m, 1 H), 7.37 (d, J=8.0 Hz, 1H), 7.87 (dd, J=2 and 8.5 Hz, 1 H), 7.97 (d, J=8.0 Hz, 1 H), 8.19 (d, J=8.2 Hz, 1 H), 8.59 (br s, 1 H), 8.74 (d, J=2.0 Hz, 1 H).

To a stirred solution of methyl 4-[2-N-[4-[N'-(2-chlorophenyl)ureido]-3-methoxyphenyl acetamido]-2-methyl-1-propoxy]-3-trifluoroacetamidobenzoate (320 mg, 0.492 mmol) in THF (2 ml) was added 0.25 N NaOH (6 ml, 1.5 mmol) at an ambient temperature. And the resulting mixture was stirred for 20 hr. The mixture was poured into ice-1 N HCl (2 ml). The solid was collected, washed with water and air-dried. The crude solid was recrystallized from CHCl$_3$-EtOH-Et$_2$O to give 301 (240 mg, 89%) as fine needles. MW 541.00 IR (KBr) n 3338, 3296, 1691, 1641 cm$^{-1}$; $^1$H-NMR (CDCl$_3$) δ $^1$H-NMR (DMSO-d$_6$) δ 1.37 (s, 6 H), 3.35 (s, 2 H), 3.77 (s, 3 H), 4.05 (s, 2 H), 4.96(br s, 1 H), 6.75 (br d, J=8.3 Hz, 1 H), 6.78 (d, J=8:3 Hz, 1 H), 6.87 (d, J=1.7 Hz, 1 H), 7.01 (m, 1 H), 7.15 (dd, J=2 and 8.5 Hz, 1H), 7.24 (d, J=2 Hz, 1 H), 7.27 (dt, J=2.0 and 8.5 Hz, 1 H), 7.43 (dd, J=2 and 8.0 Hz, 1 H), 7.78 (br s, 1 H), 7.90 (d, J=8.0 Hz, 1 H), 8.08 (dd, J=2 and 8.3 Hz, 1 H), 8.85 (s, 1 H), 8.89 (s, 1 H), 12.23 (br s, 1 H); MS (FAB) m/z 541 (M$^+$+1); Anal. Calcd for C$_{27}$H$_{29}$ClN$_4$O$_6$: C, 58.00; H, 5.59; N, 10.02. Found: C, 57.97; H, 5.39; N, 10.01.

Example 251

2-acetylamino-4-[2-N-[3-methoxy-4-[N'-(2-methylphenyl)ureido]phenyl]-N-methylacetamido]ethylaminobenzoateic acid

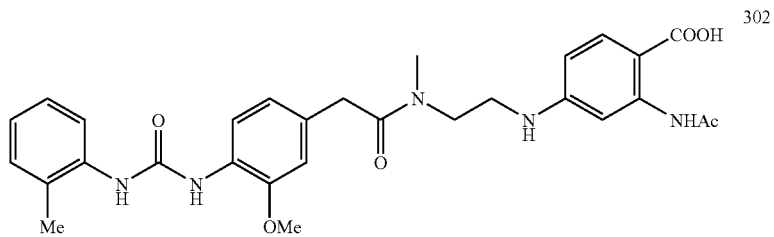

302

To a stirred solution of 2-acetylamino-4-nitrobenzoic acid (1.28 g, 5.71 mmol) in benzene-MeOH (4:1, v/v, 25 mL), was added trimethylsilyldiazomethane (2.0 M solution in n-hexane, 4.28 ml, 8.56 mmol) at 0° C. The stirring was continued for 18 hours at rt. The reaction was poured into hexane, and the resulting precipitate was collected by filtration to give methyl 2-acetylamino-4-nitrobenzoate (1.32 g, 97%) as a white solid; mp no data; $^1$H-NMR (400 MHz, CDCl$_3$) δ 2.30 (s, 3 H), 4.00 (s, 3 H), 7.88 (m, 1 H), 8.18 (dd, J=2.0 Hz, 8.8 Hz, 1 H), 9.60 (t, J=2.2 Hz, 1 H), 11.10 (s, 1 H); MS (ESI) m/z 238 (M$^+$).

To a solution of methyl 2-acetylamino-4-nitrobenzoate (1.31 g, 5.50 mmol) in MeOH (30 mL) was added 5% Pd on carbon (195 mg), and the stirring under H$_2$ gas (3 atm) was continued for 18 hours at rt. The catalyst was filtered off and the mixture was evaporated. The resulting crude solid was recrystallized with CHCl$_3$-MeOH-hexane to give methyl 2-acetylamino-4-aminobenzoate (1.03 g, 90%) as a white solid. $^1$H-NMR (400 MHz, CDCl$_3$) δ 2.23 (s, 3 H), 3.82 (s, 3H), 4.20 (s, 2 H), 6.30 (dd, J=2.5 Hz, 8.8 Hz, 1 H), 7.80 (d, J=8.8 Hz, 1 H), 8.06 (s, 1 H), 11.26 (s, 1 H); MS (FAB), m/z 208 (M$^+$).

To a cooled solution of methyl 2-acetylamino-4-aminobenzoate (300 mg, 1.44 mmol) and N-tert-butoxycarbonyl-N-methylglycinal (499 mg, 2.88 mmol) in 1,2-dichloroethane (30 ml), was added NaBH(OAc)$_3$ (964 mg, 4.32 mmol) and the stirring was continued for 64 h at 0° C. The mixture was poured into sat. NaHCO$_3$ and was extracted with CHCl$_3$ (50 ml×3), washed with brine, and dried over MgSO$_4$. After removal of the solvent in vacuo, the residue was chromatographed on silica gel (middle pressure chromatography system: YAMAZEN YFLC-5404-FC, linear gradient of hexane-EtOAc from 9:1 to 2:1) to give methyl 2-acetylamino-4-[2-(N-tert-butoxycarbonyl-N-methylamino)ethylamino]benzoate (451 mg, 86%) as a colorless oil. $^1$H-NMR (CDCl$_3$, 400 MHz) δ 1.48 (s, 9 H), 2.22 (s, 3 H), 2.90 (s, 3 H), 3.32 (m, 2 H), 3.50 (m, 2 H), 3.80 (s, 3 H), 6.20 (dd, J=2.2 Hz, 8.8 Hz, 1 H), 7.80 (m, 1 H), 7.95 (m, 1 H), 11.30 (br s, 1 H); MS (FAB) m/z 366 (M$^+$+1).

To a stirred solution of methyl methyl 2-acetylamino-4-[2-(N-tert-butoxycarbonyl-N-methylamino)ethylamino]benzoate (450 mg, 1.23 mmol) in dichloromethane (5 mL), was added TFA (5 mL) and the stirring was continued for 18 h at rt. After removal of the solvent in vacuo, the residue was dissolved in CHCl$_3$ (200 mL), washed with brine, sat. NaHCO$_3$, and dried over MgSO$_4$. The solvent was removed to give methyl 2-acetylamino-4-[2-(N-methylamino) ethylamino]benzoate (298 mg, 88%) as a colorless oil. $^1$H-NMR (CDCl$_3$, 400 MHz) δ 2.21 (s, 3 H), 2.46 (s, 3 H), 2.88 (m, 2 H), 3.31 (m, 2 H), 3.83 (s, 3 H), 4.85 (br, 1 H), 6.24 (dd, J=2.5 Hz, 8.8 Hz, 1 H), 7.80 (d, J=8.8 Hz, 1 H), 7.99 (d, J=2.5 Hz, 1 H); MS (FAB), m/z 266 (M$^+$+1).

A mixture of methyl 2-acetylamino-4-[2-(N-methylamino)ethylamino]benzoate (145 mg, 0.55 mmol), 3-methoxy-4-[N'-(2-methylphenyl)ureido]phenylacetic acid (172 mg, 0.55 mmol), EDC.HCl (158 mg, 0.83 mmol), HOBt (141 mg, 1.05 mmol), and DMAP (13 mg, 0.11 mmol) in DMF (10 ml) was stirred for 18 hours. The mixture was diluted with EtOAc (300 ml), washed with brine, and dried over MgSO$_4$. After removal of the solvent, residue was chromatographed on silica gel (middle pressure chromatography system: YAMAZEN YFLC-5404-FC, linear gradient of CHCl$_3$-MeOH from 100:0 to 70:30) to give methyl 2-acetylamino-4-[2-N-[3-methoxy-4-[N'-(2-methylphenyl)ureido]phenyl]-N-methylacetamido]ethylaminobenzoate (309 mg, 100%) as an amorphous foam. $^1$H-NMR (CDCl$_3$) δ 2.22 (s, 3 H), 2.30 (s, 3 H), 3.02 (s, 3 H), 3.35 (m, 2 H), 3.58 (s, 3 H), 3.50–3.74 (m, 4 H), 3.85 (s, 3 H), 6.20 (m, 1 H), 6.58 (s, 1 H), 6.65–6.75 (m, 3 H), 7.13 (m, 2 H), 7.40–7.50 (m, 2 H), 7.75 (m, 2 H), 7.90 (m, 1 H), 8.00 (m, 1 H), 11.32 (s, 1 H); MS (FAB) m/z 562 (M$^+$+1).

To a solution of methyl 2-acetylamino-4-[2-N-[3-methoxy-4-[N'-(2-methylphenyl)ureido]phenyl]-N-methylacetamido]ethylaminobenzoate (309 mg, 0.55 mmol) in THF-MeOH (1:1, v/v, 9 ml), was added 0.25 N NaOH (4.4 ml, 1.1 mmol) at rt, and heated to reflux. The stirring was continued for 18 hours at reflux. The reaction mixture was poured into water, and acidified to pH 5.0 with 1.0 N HCl. The resulting precipitate was recrystallized with hexane-diethylether to give 302 (175 mg, 58%) as a pale red powder. MW 547.60 $^1$H-NMR (CD$_3$OD) δ 2.16 (d, J=4.8 Hz, 3 H), 2.28 (d, J=4.2 Hz, 3 H), 2.98 and 3.10(2 s, total 3 H), 3.35 (m, 2 H), 3.68 (m, 4 H), 3.81 and 3.84 (2 s, total 3 H), 6.30 (m, 1 H), 6.60–6.82 (m, 2 H), 7.00 (m, 1 H), 7.15 (m, 2 H), 7.53 (m, 1 H), 7.77–7.96 (m, 3 H); MS FAB) m/z 548 (M$^+$+1); Anal. Calcd for C$_{29}$H$_{33}$N$_5$O$_6$.0.5 H$_2$O: C, 62.58; H, 6.16; N, 12.58. Found: C, 62.55; H, 6.31; N, 12.15.

Example 252

2-acetylamino-4-[2-N-[4-[N'-(2-bromophenyl)ureido]-3-methoxyphenyl]-N-methylacetamido]ethylaminobenzoic acid

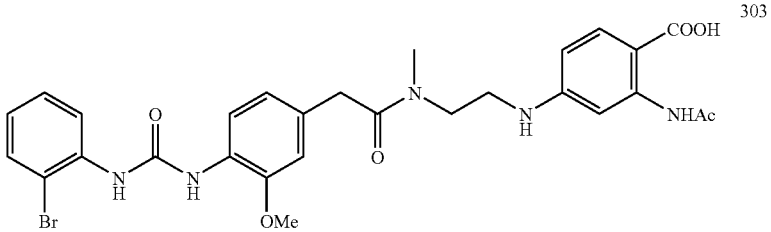

303

A mixture of methyl 2-acetylamino-4-(2-N-methylamino-1-ethylamino)benzoate (145 mg, 0.55 mmol), 3-methoxy-4-[N'-(2-bromophenyl)ureido]phenylacetic acid (209 mg, 0.55 mmol), EDC.HCl (158 mg, 0.83 mmol), HOBt (141 mg, 1.05 mmol), and DMAP (13 mg, 0.11 mmol) in DMF (10 ml) was stirred for 18 hours. The mixture was diluted with EtOAc (300 ml), washed with brine, and dried over MgSO$_4$. After removal of the solvent, residue was chromatographed on silica gel (middle pressure chromatography system: YAMAZEN YFLC-5404-FC, linear gradient of CHCl$_3$-MeOH from 100:0 to 70:30) to give methyl 2-acetylamino-4-[2-N-[4-[N'-(2-bromo phenyl)ureido]-3-methoxyphenyl]-N-methylacetamido]ethylaminobenzoate (294 mg, 85%) as an amorphous foam. $^1$H-NMR (CDCl$_3$) δ 2.21 (s, 3 H), 3.05 (s, 3 H), 3.40 (m, 2 H), 3.65–3.70 (m, 4 H), 3.78 (s, 3 H), 3.86 (s, 3 H), 6.21 (m, 1 H), 6.79 (m, 2 H), 6.93 (m, 1 H), 7.10 (d, J=10.3 Hz, 1 H), 7.30 (m, 1 h), 7.42 (m, 1 H), 7.61 (m, 1 H), 7.78–7.85 (m, 2 H), 7.93 (m, 2 H), 8.13 (m, 1 H); MS (FAB), m/z 627 (M$^+$).

To a solution of methyl 2-acetylamino-4-[3-methoxy-4-[N'-(2-bromophenyl)ureido]phenylacetamido]-2-N-methylamino-1-ethylaminobenzoate (294 mg, 0.47 mmol) in THF-MeOH (1:1, v/v, 8 ml), was added 0.25 N NaOH (3.8 ml, 0.94 mmol) at rt, and heated to reflux. The stirring was continued for 18 hours at reflux. The reaction mixture was poured into water, and acidified to pH 5.0 with 1.0 N HCl. The resulting precipitate was recrystallized with hexane-diethylether to give 303 as a white powder (210 mg, 73%). MW 612.47 mp 155–160° C.; $^1$H-NMR (CD$_3$OD) δ 22.18 (d, J=5.5 Hz, 3 H), 3.00 and 3.12 (2 s, total 3 H), 3.39 (m, 1 H), 3.60 (m, 4 H), 3.70 (s, 1 H), 3.85 and 3.86 (2 s, total 3 H), 6.31 (m, 1 H), 6.68 (m, 1 H), 6.78 (m, 1 H), 6.78 and 6.85 (2 m, total 1 H), 6.97 (m, H), 7.30 (m, 1 H), 7.56 (m, 1 H), 7.80 –7.95 (m, 4 H); MS (ESI) m/z 613 (M$^+$); Anal. Calcd for C$_{28}$H$_{31}$Br$_1$N$_5$O$_6$.0.75 H$_2$O: C, 53.64; H, 5.22; N, 11.17. Found: C, 53.89; H, 5.23; N, 10.69.

Example 253

4-[2-N-[[4-[N'-(2-chlorophenyl)ureido]-3-methoxyphenyl]-N-phenylacetamido]ethoxy]benzoic acid

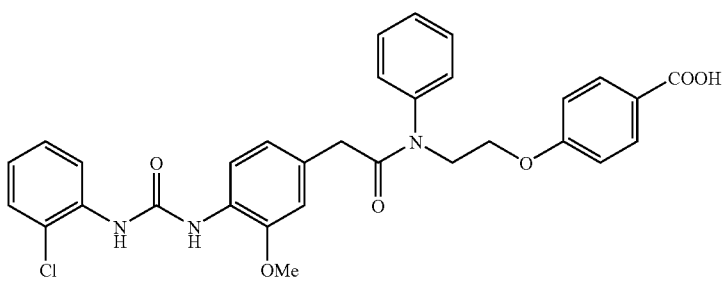

304

To a solution of methyl 4-[2-(methanesulfonyloxy)ethoxy]benzoate (2.74 g, 10 mmol) in MeCN (50 ml), was added aniline (9.1 ml, 100 mmol) at rt. The reaction was stirred for 64 hours at reflux. The mixture was poured into H$_2$O (200 mL), extracted with EtOAc (100 mL×2), dried over MgSO$_4$. After removal of the solvent in vacuo, the unreacted aniline was removed in vacuo by co-evaporation with toluene (10 mL×3) at 80° C. The residue was chromatographed on silica gel (middle pressure chromatography system: YAMAZEN YFLC-5404-FC, f50 mm×150 mm, CHCl$_3$) to give methyl 4-[2-(N-phenylamino)ethoxy]benzoate (2.23 g, 82%) as a colorless oil. $^1$H-NMR (CDCl$_3$) δ 3.56 (t, J=5.1 Hz, 2 H), 3.90 (s, 3 H), 4.21 (t, J=5.1 Hz, 2), 6.68 (dd, J=1.0 Hz, 8.6 Hz, 2 H), 6.75 (t, J=7.3 Hz, 1 H), 7.20 (AB type d, J=7.3 Hz, 2 H), 8.00 (d, J=9.1 Hz, 2 H); MS (ESI) m/z 272 (M$^+$+1).

A mixture of methyl 4-[2-(N-phenylamino)ethoxy]benzoate (136 mg, 0.5 mmol), 3-methoxy-4-[N'-(2-chlorophenyl)ureido]phenylacetic acid (167 mg, 0.5 mmol) and PyBOP (781 mg, 0.75 mmol), i-PrNEt$_2$ (261 ml, 0.96 mmol) in DMF (10 ml) was stirred for 18 hours. The mixture was diluted with EtOAc (100 mL), washed with 1 N HCl, brine and dried over MgSO$_4$. The residue was co-evaporated with toluene (10 ml×3) to remove DMF. The residue was chromatographed on TLC (MERCK, silicagel 60, 2 mm, 2 plates, CHCl$_3$-MeOH, 20:1) to give methyl 4-[2-N-[[4-[N'-(2-chlorophenyl)ureido]-3-methoxyphenyl]-N-phenylacetamido]ethoxy]benzoate (129 mg, 44%) as a white amorphous foam. $^1$H-NMR (CDCl$_3$) δ 3.42 (s, 1 H), 3.69 (d, J=8.3 Hz, 1 H), 3.74 (s, 3 H), 3.87 (s, 3 H), 4.10 (m, 2 H), 4.23 (m, 2 H), 6.48–7.44 (m, 13 H), 7.93 (d, J=9.3 Hz, 2 H), 8.18 (dd, J=1.5 Hz, 8.3 Hz, 1 H); MS (ESI) m/z 588 (M$^+$).

To a solution of methyl 4-[2-N-[[4-[N'-(2-chlorophenyl)ureido]-3-methoxyphenyl]-N-phenyl acetamido]ethoxy] benzoate (124 mg, 0.19 mmol) in THF-MeOH (6:1, v/v, 3 ml), was added 0.5 N NaOH (2 ml, 1 mmol) at rt, and heated to reflux in a sealed bottle. The stirring was continued for 15 hours at reflux. The reaction mixture was poured into water, acidified with 1.0 N HCl, extracted with CHCl$_3$-MeOH (2:1, 20 mL×3), and dried over MgSO$_4$. After removal of the solvent, the residue was crystallized with CHCl$_3$-hexane-diethylether to give 304 (77 mg, 64%) as a white powder. MW 574.02 $^1$H-NMR (CD$_3$OD) δ 3.45 (s, 2 H), 3.79 (s, 3 H), 4.12 (m, 2 H), 4.22 (m, 2 H), 6.48 (dd, J=2.0 Hz, 8.3 Hz, 1 H), 6.61 (d, J=2.0 Hz, 1 H), 6.87 (d, J=8.8 Hz, 2 H), 7.00 (m, 1 H), 7.22 (m, 3 H), 7.36 (m, 1 H), 7.43 (m, 3 H), 7.90 (d, J=8.3 Hz, 1 H), 7.95 (d, J=8.8 Hz, 2 H), 8.02 (dd, J=1.5 Hz, 8.3 Hz, 1 H); MS (ESI) m/z 574 (M$^+$); Anal. Calcd for C$_{31}$H$_{28}$ClN$_3$O$_6$.0.5 H$_2$O: C, 63.86; H, 5.01; N, 7.21. Found: C, 63.67; H, 4.91; N, 6.99.

Example 254

(S)-4-[2-N-[[3-methoxy-4-[N'-(2-methylphenyl)ureido]phenyl]-N-(2-aminobenzyl)acetamido]-1-propoxy]benzoic acid

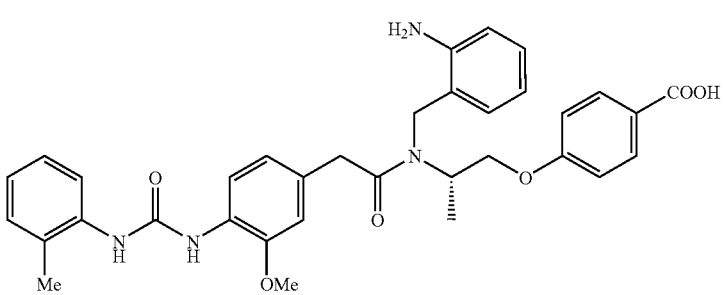

305

To a cooled (0° C.) solution of benzyl (S)-4-(2-amino-1-propoxy)benzoate (1.50 g, 5.26 mmol) and 2-nitrobenzaldehyde (0.87 g, 5.76 mmol) in MeOH—AcOH (16 ml, 15:1, v/v) was added NaBH$_3$CN (1.65 g, 26.3 mmol) and the reaction mixture was stirred at room temperature overnight. The mixture was quenched by sat. NaHCO$_3$ and extracted with EtOAc. The extract was washed with brine, dried over Na$_2$SO$_4$ and evaporated. The residue was purified by column chromatography on silica gel with CHCl₃ to 5% MEOH in CHCl₃ as eluent to give benzyl (S)-4-[2-(2-nitrobenzylamino)-1-propoxy]benzoate (931 mg, 42%) as a yellow oil. ¹H-NMR (CDCl₃) δ 1.21 (d, J=6.4 Hz, 3 H), 3.13–3.18 (m, 1 H), 3.88–3.97 (m, 2 H), 4.06–4.20 (m, 2 H), 5.34 (s, 2 H), 6.89–6.94 (m, 2 H), 7.29–7.65 (m, 8 H), 7.94–8.03 (m, 3 H); MS (FAB) m/z 421 (M⁺+1).

A mixture of pentafluorophenyl 3-methoxy-4-[N'-(2-methylphenyl)ureido]phenylacetate (460 mg, 0.96 mmol), benzyl (S)-4-[2-(2-nitrobenzylamino)-1-propoxy]benzoate (403 mg, 0.96 mmol) and Et₃N (200 ml, 1.43 mmol) in DMF (8 ml) was stirred at room temperature overnight. The mixture was diluted with EtOAc, washed with 0.5 N HCl, brine, dried over Na₂SO₄, and evaporated. The residue was purified by column chromatography on silica-gel with 1% MeOH in CHCl₃ as eluent to give benzyl (S)-4-[2-N-[[3-methoxy-4-[N'-(2-methylphenyl)ureido]phenyl]-N-(2-nitrobenzyl)acetamido]-1-propoxy]benzoate (504 mg, 73%) as a brown amorphous solid. MS (FAB), m/z 717 (M⁺+1).

A stirred solution of benzyl (S)-4-[2-N-[[3-methoxy-4-[N'-(2-methylphenyl)ureido]phenyl]-N-(2-nitrobenzyl)acetamido]-1-propoxy]benzoate (504 mg, 0.76 mmol) in MeOH-THF (11 ml, 10:1, v/v) was hydrogenated over 5% Pd—C (100 mg, 20 wt %) at 3 atm overnight. The mixture was filtered to remove the catalyst and the filtrate was evaporated. The residue was purified by preparative thin layer chromatography with 5% MeOH in CHCl₃ as eluent to give 305 (115 mg, 27%) as a white powder. MW 596.67 MS (FAB), m/z 597 (M⁺+1).

Example 255

(S)-4-[2-N-[[4-[N'-(2-bromophenyl)ureido]-3-methoxyphenyl]-N-(2-nitrobenzyl)acetamido]-1-propoxy]benzoic acid To a cooled (0) solution of benzyl (S)-4-(2-amino-1-propoxy)benzoate (1.50 g, 5.26 mmol) and 2-nitrobenzaldehyde (0.87 g, 5.76 mmol) in MeOH—AcOH (16 ml, 15:1, v/v) was added NaBH₃CN (1.65 g, 26.3 mmol) and the reaction mixture was stirred at room temperature overnight. The mixture was quenched by sat. NaHCO₃ and extracted with EtOAc. The extract was washed with brine, dried over Na₂SO₄ and evaporated. The residue was purified by column chromatography on silica gel with CHCl₃ to 5% MeOH in CHCl₃ as eluent to give benzyl (S)-4-[2-(2-nitrobenzylamino)-1-propoxy]benzoate (931 mg, 42% /) as a yellow oil. ¹H-NMR (CDCl₃) δ 1.21 (d, J=6.4 Hz, 3 H), 3.13–3.18 (m, 1 H), 3.88–3.97 (m, 2 H), 4.06–4.20 (m, 2 H), 5.34 (s, 2 H), 6.89–6.94 (m, 2 H), 7.29–7.65 (m, 8 H), 7.94–8.03 (m, 3 H); FAB-MAS, m/z 421 (M⁺+1).

A mixture of 4-[N'-(2-bromophenyl)ureido]-3-methoxyphenylacetic acid (476 mg, 1.26 mmol), benzyl (S)-4-[2-(2-nitrobenzylamino)-1-propoxy]benzoate (528 mg, 1.26 mmol), EDC.HCl (361 mg, 1.88 mmol), HOBt (255 mg, 1.89 mmol) and DMAP (30 mg, 0.25 mmol) in DMF (10 ml) was stirred at room temperature overnight. And the reaction could not be completed, so the reaction mixture was stirred at 60° C. for 1 day. The mixture was diluted with EtOAc, washed with 0.5 N HCl, brine, dried over Na₂SO₄ and evaporated. The residue was purified by column chromatography on silica-gel with CHCl₃ to 2% MeOH in CHCl₃ as eluent to give the title compound as a crude oil. To a stirred solution of the crude product in THF-MeOH (10 ml, 1:1, v/v) was added 0.5 N NaOH (10 ml) and the reaction mixture was heated under reflux for 3 hr. The mixture was poured into ice-H₂O and the basic aqueous layer was acidified (pH 4.3) with 1 N HCl. The resulting precipitate was collected and the crude solid was purified by preparative thin layer chromatography with 5% MeOH in CHCl₃ as eluent to give 306 (162 mg, 2 steps, 19%) as a white amorphous solid. MW 691.53 MS (FAB), m/z 692 (M³⁰ +1); Anal. Calcd for C₃₃H₃₁BrN₄O₈.7/4H₂O: C, 54.82; H, 4.81; N, 7.75. Found: C, 54.80; H, 4.61; N, 7.24.

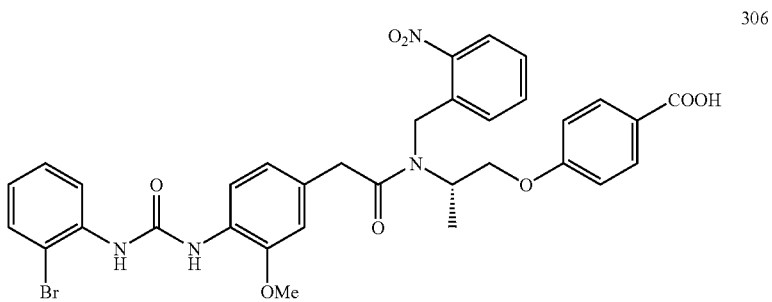

306

Example 256

4-[2-N-cyclopropyl-N-[4-[N'-(2-chlorophenyl)ureido]-3-methoxyphenyl]acetamido]ethoxybenzoic acid

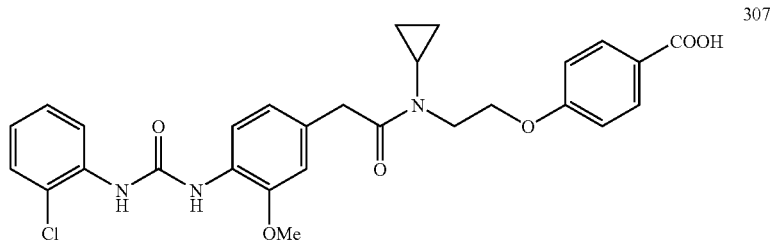

307

A mixture of methyl 4-(2-cyclopropylaminoethoxy)benzoate (290 mg, 1.23 mmol), 4-[N'-(2-chlorophenyl)ureido]-3-methoxyphenylacetic acid (412 mg, 1.23 mmol), EDC.HCl (354 mg, 1.85 mmol), HOBt (cat.), and DMAP (cat.) in DMF (10 ml) was stirred overnight. The mixture was partitioned between EtOAc (300 ml) and H₂O (100 ml). The organic phase was separated, washed with brine (2×100 ml), dried over MgSO₄, and evaporated. The residue was chromatographed on silica gel with CHCl₃-MeOH (20:1) as eluent to give methyl 4-[2-N-cyclopropyl-N-[4-[N'-(2-chlorophenyl)ureido]-3-methoxyphenyl]acetamido]ethoxybenzoate (506 mg, 75%) as a yellow viscous oil. $^1$H-NMR (CDCl₃) δ 0.90–0.97 (m, 4 H), 2.75 (m, 1 H), 3.61 (s, 3 H), 3.79 (t, J=5.4 Hz, 2 H), 3.87 (s, 3 H), 3.88 (s, 2 H), 4.16 (t, J=5.4 Hz, 2 H), 6.76–6.80 (m, 4 H), 6.95 (dt, J=7.8, 1.5 Hz, 1 H), 7.21–7.31 (m, 2 H), 7.53 (s, 1 H), 7.56 (s, 1 H), 7.93 (d, J=8.3 Hz, 3 H), 8.19 (dd, J=8.3, 1.5 Hz, 1 H).

To a stirred solution of methyl 4-[2-N-cyclopropyl-N-[4-[N'-(2-chlorophenyl)ureido]-3-methoxyphenyl]acetamido]ethoxybenzoate (506 mg, 0.917 mmol) in THF (7 ml) was added 0.25 N NaOH (7.3 ml, 1.83 mmol). After stirring overnight, the mixture was poured into 1 N HCl (50 ml) and extracted with CHCl₃-MeOH (4:1, 2×200 ml). The combined extracts were dried over MgSO₄ and evaporated. The residue was chromatographed on silica gel with CHCl₃-MeOH (20:1 to 10:1) as eluent to give 307 (403 mg, 82%) as a colorless amorphous solid. MW 537.99 $^1$H-NMR (DMSO) δ 0.86–0.91 (m, 4 H), 2.75 (m, 1 H), 3.69 (t, J=5.5 Hz, 2 H); 3.81 (s, 3 H), 3.84 (s, 2 H), 4.16 (t, J=5.5 Hz, 2 H), 6.76 (d, J=8.3 Hz, 1 H), 6.88 (s, 1 H), 6.97–7.04 (m, 3 H), 7.28 (t, J=7.8 Hz, 1 H), 7.44 (d, J=7.8 Hz, 1 H), 7.88 (d, J=8.8 Hz, 2 H), 7.96 (d, J=8.1 Hz, 1 H), 8.10 (d, J=8.3 Hz, 1 H), 8.89 (s, 1 H), 8.93 (s, 1 H), 12.65 (s, br s); MS (FAB), m/z 538 (M⁺+1); Anal. Calcd for C₂₈H₂₈ClN₃O₆: C, 62.51, H, 5.25; N, 7.81. Found: C, 61.85; H, 5.42; N, 7.41.

Example 257

4-[2-N-cyclohexyl-N-[3-methoxy-4-[N'-(2-methylphenyl)ureido]phenyl]acetamido]ethoxybenzoic acid

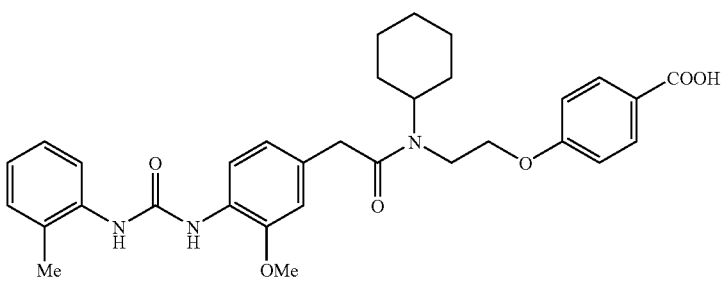

308

To a solution of methyl 4-[(2-methanesulfonyloxy)-1-ethoxy]benzoate (2.74 g, 10 mmol) in MeCN (50 ml), was added cyclohexylamine (5.72 ml, 50 mmol) at rt. The reaction was stirred for 18 hours at reflux. The mixture was poured into H₂O (200 mL), extracted with EtOAc (100 mL×2), dried over MgSO₄. After removal of the solvent, residue was chromatographed on silica gel (middle pressure chromatography system: YAMAZEN YFLC-5404-FC, f50 mm×150 mm, linear gradient of CHCl₃-EtOAc from 10:0 to 1:1) to give methyl 4-(2-N-cyclohexylamino)ethoxy benzoate (2.43 g, 88%) as a colorless oil. $^1$H-NMR (CDCl₃) δ 1.10 (m, 2 H), 1.25 (m, 2 H), 1.60 (br, 2 H), 1.73 (m, 2 H), 1.90 (br, 2 H), 2.49 (m, 1 H), 3.02 (t, J=5.2 Hz, 2 H), 3.88 (s, 3 H), 4.12 (t, J=5.2 Hz, 2 H), 6.90 (d, J=6.90 Hz, 2 H), 7.99 (d, J=7.99 Hz, 2 H); MS (ESI) m/z 278 (M⁺+1).

A mixture of methyl 4-(2-N-cyclohexylamino)ethoxybenzoate (139 mg, 0.5 mmol), 3-methoxy-4-[N'-(2-methylphenyl)ureido]phenylacetic acid (157 mg, 0.5 mmol), EDC.HCl (144 mg, 0.75 mmol), HOBt (128 mg, 0.95 mmol), and DMAP (12 mg, 0.1 mmol) in DMF (2.5 ml) was stirred for 18 hours. The mixture was diluted with EtOAc (200 ml), washed with 1 N HCl and brine, and dried over MgSO$_4$. After removal of the solvent, residue was chromatographed on silica gel (middle pressure chromatography system: YAMAZEN YFLC-5404-FC, linear gradient CHCl$_3$-EtOAc 10:0 to 1:4) to give methyl 4-[2-N-cyclohexyl-N-[3-methoxy-4-[N'-(2-methylphenyl) ureido]phenyl]acetamido] ethoxybenzoate (247 mg, 86%) as an amorphous foam. $^1$H-NMR (CDCl$_3$) δ 1.08–1.80 (m, 10 H), 2.30 (s, 3 H), 3.60–3.79 (m, 8 H), 3.88 (s, 3 H), 4.16 (m, 2 H), 6.30 (s, 1 H), 6.70–6.83 (m, 2 H), 6.88 (d, 2 H, J=9.0 Hz), 7.12 (m, 2 H), 7.23 (m, 1 H), 7.60 (d, 1 H, J=8.3 Hz), 7.92 (d, 2 H, J=9.0 Hz), 8.10 (d, 1 H, J=8.0 Hz); MS (ESI) m/z 574 (M$^+$+1).

To a solution of methyl 4-[2-N-cyclohexyl-N-[3-methoxy-4-[N'-(2-methylphenyl)ureido]phenyl]acetamido] ethoxybenzoate (247 mg, 0.43 mmol) in THF-MeOH (6:1, v/v, 7 ml), was added 0.5 N NaOH (3.4 ml, 0.84 mmol) at rt, and heated to reflux in a sealed bottle. The stirring was continued for 18 hours at reflux. The reaction mixture was poured into water, acidified with 1.0 N HCl, extracted with CHCl$_3$-MeOH (2:1, 20 mL×3), and dried over MgSO$_4$. After removal of the solvent, the residue was crystallized with CHCl$_3$-hexane-diethylether to give 308 (196 mg, 81%) as a white powder. MW 559.62 $^1$H-NMR (CD$_3$OD) δ 0.90–1.82 (m, 10 H), 2.29 (s, 3 H), 3.62 (m, 2 H), 3.78 (s, 3 H), 3.80 (m, 3 H), 4.12 (m, 2 H), 6.82 (m, 2 H), 6.96 (m, 3 H), 7.16 (m, 2 H), 7.58 (d, J=7.7 Hz, 1 H), 7.92 (m, 3 H); MS (ESI) nm/z 560 (M$^+$+1); Anal. Calcd for C$_{32}$H$_{37}$N$_3$O$_6$.0.5 H$_2$O: C, 67.59; H, 6.74; N, 7.39. Found: C, 67.83; H, 6.80; N, 7.13.

Example 258

4-[2-N-[4-[N'-(2-chlorophenyl)ureido]-3-methoxyphenyl]-N-propargylacetamido]-ethoxybenzoic acid

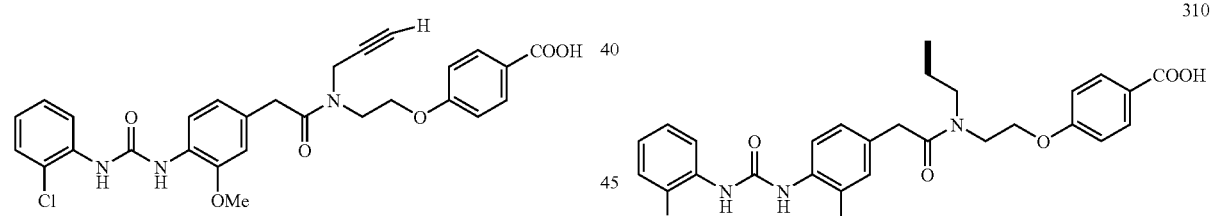

To a solution of methyl 4-[(2-methanesulfonyloxy)-1ethoxy]benzoate (2.74 g, 10 mmol) in MeCN (50 ml), was added propargylamine (3.43 ml, 50 mmol) at rt. The reaction was stirred for 18 hours at reflux. The mixture was poured into H$_2$O (200 mL), extracted with EtOAc (100 mL×2), dried over MgSO$_4$. After removal of the solvent in vacuo, the residue was chromatographed on silica gel (middle pressure chromatography system: YAMAZEN YFLC-5404-FC, f50 mm×150 mm, linear gradient of CHCl$_3$-EtOAc from 10:0 to 9:1) to give methyl 4-(2-N-propargylamino) ethoxybenzoate (2.33 g, 100%) as a colorless oil. $^1$H-NMR (CDCl$_3$) δ 2.28 (d, J=2.4 Hz, 1 H), 3.11 (t, J=5.1 Hz, 2 H), 3.52 (d, J=2.4 Hz, 2 H), 3.88 (s, 3 H), 4.15 (t, J=5.1 Hz, 2 H), 6.90 (d, J=8.8 Hz, 2 H), 7.98 (d, J=8.8 Hz, 2 H); MS (ESI) m/z 234 (M$^+$+1).

A mixture of methyl 4-(2-N-propargylamino)ethoxybenzoate (117 mg, 0.5 mmol), 3-methoxy-4-[N'-(2-chlorophenyl)ureido]phenylacetic acid (167 mg, 0.5 mmol), EDC.HCl (144 mg, 0.75 mmol), HOBt (128 mg, 0.96 mmol), and DMAP (12 mg, 0.1 mmol) in DMF (10 ml) was stirred for 18 hours. The mixture was diluted with EtOAc (100 mL), washed with 1 N HCl, brine and dried over MgSO$_4$. The residue was co-evaporated with toluene (10 ml×3) to remove DMF. The residue was chromatographed on TLC (MERCK, silicagel 60, 2 mm, 2 plates, CHCl$_3$-MeOH, 20:1) to give methyl 4-[2-N-[4-[N'-(2-chlorophenyl)ureido]-3-methoxyphenyl]-N-propargyl acetamido]ethoxybenzoate (244 mg, 89%) as a white amorphous foam. $^1$H-NMR (CDCl$_3$) δ 2.20 and 2.32 (2 m, total 1 H), 3.72 (s, 2 H), 3.83 (m, 5 H), 3.88 (s, 3 H), 4.09–4.35 (m, 4 H), 6.77–6.86 (m, 4H), 6.99 (m, 1 H), 7.11 (m, 2 H), 7.24 (m, 1 H), 7.34 (d, J=7.9 Hz, 1 H), 7.96 (m, 3 H), 8.18 (dd, J=1.5 Hz, 8.3 Hz, 1 H); MS (ESI) m/z 550 (M$^+$).

To a solution of methyl 4-[2-N-[4-[N'-(2-chlorophenyl) ureido]-3-methoxyphenyl]-N-propargyl acetamido]ethoxybenzoate (240 mg, 0.44 mmol) in THF-MeOH—H$_2$O (2:2:1, v/v, 10 ml), was added NaOH (500 mg, 12.5 mmol) at rt. The stirring was continued for 2 hours at rt. The reaction mixture was poured into water, acidified with 1.0 N HCl, extracted with CHCl$_3$-MeOH (2:1, 20 mL×3), and dried over MgSO$_4$. The residue was chromatographed on TLC (Whatman, 1 mm, 3 plates, CHCl$_3$-MeOH, 92:8) to give 309 (202 mg, 86%) as a white solid. MW 535.98 $^1$H-NMR (CD$_3$OD) δ 2.60 and 2.81 (2d, J=2.5 Hz, total 1 H), 3.79–3.94 (m, 4 H), 3.85 (s, 3 H), 4.15 (m, 1 H), 4.24 (m, 1 H), 4.32 (m, 2), 6.80 (d, J=8.3 Hz, 1 H), 6.85 (d, J=4.3 Hz, 1 H), 6.94 (m, 2 H), 7.02 (m, 1 H), 7.25 (m, 1 H), 7.38 (m, 1 H), 7.87–8.02 (m, 4 H); MS (ESI) m/z 536 (M$^+$+1); Anal. Calcd for C$_{28}$H$_{26}$ClN$_3$O$_6$.2.25 H$_2$O: C, 58.33; H, 5.33; N, 7.29. Found: C, 58.23; H, 4.77; N, 6.91.

Examples 259 and 260

4-[2-N-allyl-N-[4-[N'-(2-chlorophenyl)ureido]-3-methoxyphenyl]acetamido]ethoxybenzoic acid A mixture of methyl 4-(2-N-allylamino)ethoxybenzoate (118 mg, 0.5 mmol), 3-methoxy-4-[N'-(2-chlorophenyl)ureido]phenylacetic acid (167 mg, 0.5 mmol), EDC.HCl (144 g, 0.75 mmol), HOBt (128 mg, 0.95 mmol), and DMAP (12 mg, 0.1 mmol) in DMF (2.5 ml) was stirred for 18 hours. The mixture was diluted with EtOAc (300 ml), washed with 1 N HCl and brine, and dried over MgSO$_4$. After removal of the solvent, residue was chromatographed on silica gel (middle pressure chromatography system: YAMAZEN YFLC-5404-FC, linear gradient CHCl$_3$-EtOAc 100:0 to 85:15) to give methyl 4-[2-N-allyl-N-[4-[N'-(2-chlorophenyl)ureido]-3-methoxyphenyl]acetamido]ethoxybenzoate (253 mg, 92%) as an amorphous foam. $^1$H-NMR (CDCl$_3$) δ 3.65–3.85 (m, 4 H), 3.73 (s, 3 H), 3.88 (s, 3 H), 5.08 (m, 2 H), 4.22 (m, 2 H), 5.10–5.24 (m, 2 H), 5.76 (m, 1 H), 6.77 (m, 2 H), 6.85 (m, 2 H), 6.99 (m, 1 H), 7.06 (m, 2 H), 7.26 (m, 1 H), 7.34 (d, 1 H, J=8.1 Hz), 7.94 (d, 2 H, J=8.8 Hz), 7.98 (m, 1 H), 8.18 (d, 1 H, J=6.9 Hz); MS (FAB) m/z 552 (M$^+$).

To a solution of methyl 4-[2-N-allyl-N-[4-[N'-(2-chlorophenyl)ureido]-3-methoxyphenyl]acetamido]ethoxybenzoate (250 mg, 0.45 mmol) in THF-MeOH (1:1, v/v, 8 ml), was added 0.25 N NaOH (3.6 ml, 0.91 mmol) at rt, and heated to reflux. The stirring was continued for 18 hours at reflux. The reaction mixture was poured into water, and acidified with 1.0 N HCl. The resulting precipitate was collected by filtration. The precipitate was recrystallized with hexane-diethylether to give 310 as a white powder (195 mg, 80%). MW 537.99 $^1$H-NMR (CD$_3$OD) δ 3.61 (s, 1 H), 3.76 (s, 3 H), 3.82 (m, 1 H), 3.85 (s, 1 H), 3.88 (m, 1 H), 4.11–4.25 (m, 4 H), 5.12–5.25 (m, 2 H), 5.81 (m, 1 H), 6.78 (d, 1 H, J=8.3 Hz), 6.82 (m, 1 H), 6.92 (m, 2 H), 7.01 (m, 1 H), 7.26 (m, 1 H), 7.37 (m, 1 H), 7.96 (m, 3 H), 8.02 (m, 1 H); MS (FAB) m/z 537 (M$^+$); Anal. Calcd for C$_{28}$H$_{28}$ClN$_3$O$_6$.1/4 H$_2$O: C, 61.99; H, 5.30; N, 7.75. Found: C, 62.00; H, 5.56; N, 7.76.

Example 261

4-[2-N-allyl-N-[4-[N'(2-bromophenyl)ureido]-3-methoxyphenyl]acetamido]ethoxybenzoic acid

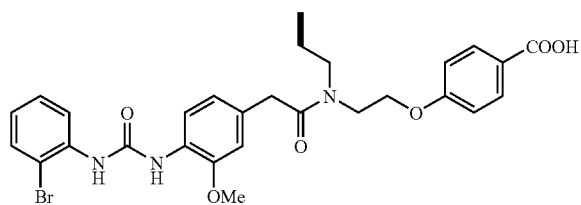

311

A mixture of methyl 4-(2-N-allylamino)ethoxybenzoate (118 mg, 0.5 mmol), 4-[N'-(2-bromophenyl)ureido]-3-methoxyphenylacetic acid (190 mg, 0.5 mmol), EDC.HCl (144 mg, 0.75 mmol), HOBt (128 mg, 0.95 mmol), and DMAP (12 mg, 0.1 mmol) in DMF (2.5 ml) was stirred for 18 hours. The mixture was diluted with EtOAc (300 ml), washed with 1 N HCl and brine, and dried over MgSO$_4$. After removal of the solvent, residue was chromatographed on silica gel (middle pressure chromatography system: YAMAZEN YFLC-5404-FC, linear gradient CHCl$_3$-EtOAc 100:0 to 70:30) to give methyl 4-[2-N-allyl-N-[4-[N'-(2-bromophenyl)ureido]-3-methoxyphenyl]acetamido]ethoxybenzoate (251 mg, 84%) as an amorphous foam. $^1$H-NMR (CDCl$_3$) δ 3.65–3.85 (m, 4 H), 3.73(s, 3 H), 3.88 (s, 3 H), 4.08 (m, 2 H), 4.22 (m, 2 H), 5.10–5.25 (m, 2 H), 5.78 (m, 1 H), 6.79 (m, 1 H), 6.85 (m, 3.1 H), 6.93 (m, 1 H), 7.02 (m, 2 H), 7.30 (m, 1 H), 7.51 (m, 1 H), 7.94 (d, 2 H, J=8.8 Hz), 7.97 (m, 1 H), 8.14 (m, 1 H); MS (FAB) m/z 596 (M$^+$).

To a solution of methyl 4-[2-N-allyl-N-[4-[N'-(2-bromophenyl)ureido]-3-methoxyphenyl]acetamido]ethoxybenzoate (251 mg, 0.42 mmol) in THF-MeOH (1:1, v/v, 8 ml), was added 0.25 N NaOH (3.4 ml, 0.84 mmol) at rt, and heated to reflux. The stirring was continued for 18 hours at reflux. The reaction mixture was poured into water, and acidified with 1.0 N HCl. The resulting precipitate was collected by filtration. The precipitate was recrystallized with Hexane-diethylether to give 311 (192 mg, 78%) as a white powder. MW 582.44 $^1$H-NMR (CD$_3$OD) δ 3.61 (s, 3 H), 3.77 (s, 3 H), 3.80 (m, 1 H), 3.85 (s, 1 H), 3.88 (s, 1 H), 4.12–4.25 (m, 4 H), 5.12–5.23 (m, 2 H), 5.81 (m, 1 H), 6.76 (m, 1 H), 6.82 (m, 1 H), 6.93 (m, 3 H), 7.29 (m, 1 H), 7.56 (m, 1 H), 7.94 (m, 4 H); MS (FAB), m/z 582 (M$^+$); Anal. Calcd for C$_{28}$H$_{28}$BrN$_3$O$_6$: C, 57.74; H, 4.85; N, 7.21. Found: C, 57.40; H, 5.07; N, 7.04. For HCl salt of 311 : Anal. Calcd for C$_{28}$H$_{27}$BrN$_3$O$_6$.0.25 H$_2$O: C, 55.23; H, 4.55; N, 6.90. Found: C, 54.98; H, 4.71; N, 6.53.

Example 262

4-[2-N-allyl-N-[3-methyl-4-[N'-(2-methylphenyl)ureido]phenyl]acetamido]ethoxybenzoic acid

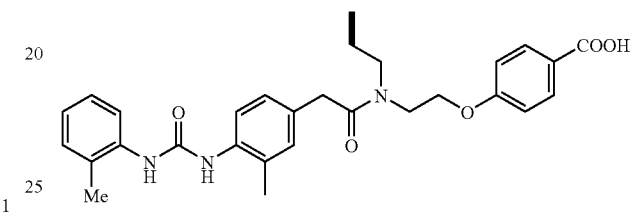

312

A mixture of methyl 4-(2-N-allylamino-1-ethyl)ethoxybenzoate (87 mg, 0.37 mmol), 3-methyl-4-[N'-(2-methylphenyl)ureido]phenylacetic acid (100 mg, 0.37 mmol), EDC.HCl (105 mg, 0.56 mmol), HOBt (95 mg, 0.70 mmol), and DMAP (9 mg, 0.07 mmol) in DMF (7.4 ml) was stirred for 18 hours. The mixture was diluted with EtOAc (100 ml), washed with 1 N HCl and brine, and dried over MgSO$_4$. The residue was co-evaporated with toluene (10 ml×3) to remove DMF. The residue was chromatographed on TLC (Whatman, PLK-5F, 2 plates, CHCl$_3$-MeOH, 97:3) to give methyl 4-[2-N-allyl-N-[3-methyl-4-[N'-(2-methylphenyl)ureido]phenyl]acetamido]ethoxybenzoate (190 mg, 100%) as a white amorphous foam. $^1$H-NMR (CDCl$_3$) δ 2.05 and 2.09 (2s, total 3 H), 2.20 and 2.21 (s, total 3 H), 3.62 (s, 2 H), 3.76 (m, 2 H), 3.90 (s, 3 H), 3.88 (m, 1 H), 4.08 (m, 2 H), 4.11 (m, 1 H), 6.28 (m, 2 H), 5.78 (m, 1 H), 6.88 (d, J=8.8 Hz, 2 H), 7.05 (m, 1 H), 7.12 (m, 1 H), 7.21 (m, 1 H), 7.58 (m, 2 H), 7.95 (d, J=8.8 Hz, 2 H), 8.02 (m, 1 H); MS (FAB), m/z 516 (M$^+$+1).

To a solution of methyl 4-[2-N-allyl-N-[3-methyl-4-[N'-(2-methylphenyl)ureido]phenyl]acetamido]ethoxybenzoate (217 mg, 0.43 mmol) in THF-MeOH (6:1, v/v, 7 ml), was added 0.5 N NaOH (1.9 ml, 0.86 mmol) at rt, and heated to reflux. The stirring was continued for 2 hours at reflux in a sealed bottle. The reaction mixture was poured into water, acidified with 1.0 N HCl, extracted with CHCl$_3$-MeOH (2:1, 20 mL×3), and dried over MgSO$_4$. After removal of the solvent, the residue was crystallized with CHCl$_3$-hexane-diethylether to give 312 (84 mg, 38%) as a white powder. MW 501.57 $^1$H-NMR (CD$_3$OD) δ 2.18 and 2.24 (s, total 3 H), 2.30 (d, J=4.9 Hz, 3 H), 3.70 (s, 1 H), 3.78 (m, 2 H), 3.88 (s, 1 H), 4.12 (m, 4 H), 5.20 (m, 2 H), 5.81 (m, 1 H), 6.92–7.20 (m, 7 H), 7.58 (m, 2 H), 7.96 (m, 2 H); MS (ESI) m/z 502 (M$^+$); Anal. Calcd for C$_{29}$H$_{31}$N$_3$O$_5$: C, 69.44; H, 6.23; N, 8.38. Found: C, 68.99; H, 6.39; N, 8.03.

Example 263

4-[2-N-allyl-N-[3-chloro-4-[N'-(2-methylphenyl)ureido]phenyl]acetamido]ethoxybenzoic acid

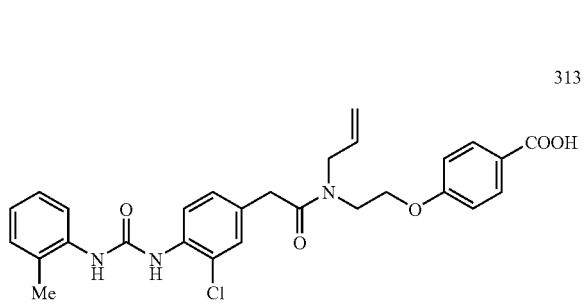

313

Example 264 methyl 4-[2-N-[2-(4-morpholinyl)ethyl]-N-[3-methoxy-4-[N'-(2-methylphenyl)ureido]phenyl]-acetamido]ethoxybenzoate

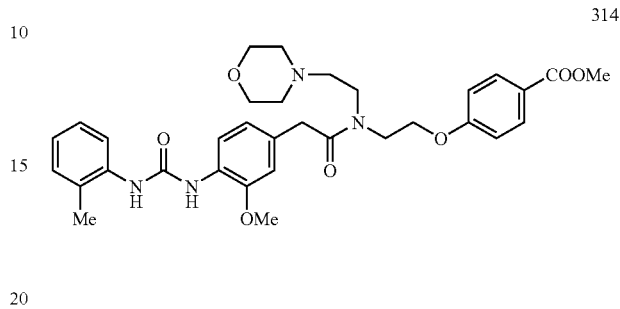

314

To a stirred solution of methyl 4-(2-N-allylaminoethoxy)benzoate (141 mg, 0.60 mmol) and 3-chloro-4-[N'-(2-methylphenyl)ureido]phenylacetic acid (191 mg, 0.60 mmol) in DMF (5 mL) were-added EDC-HCl (172.5 mg, 0.90 mmol), HOBt (154 mg, 1.14 mmol), and DMAP (15 mg, 0.12 mmol), and the stirring was continued overnight at rt. The mixture was diluted with EtOAc (50 mL) and washed with 1M HCl (×3), 1M NaOH (×1), and brine. The mixture was dried over anhydrous $MgSO_4$ and concentrated under a reduced pressure to give methyl 4-[2-N-allyl-N-[3-chloro-4-[N'-(2-methylphenyl)ureido]phenyl]acetamido]ethoxybenzoate (350 mg, 109%) as a white powder. $^1$H-NMR ($CDCl_3$) δ 2.35 (s, 3 H), 3.60 (s, 1 H), 3.75 (m, 2 H), 3.90 (s, 3 H), 4.10 (m, 4 H), 4.21 (m, 1 H), 5.20 (m, 2 H), 5.80 (m, 1 H), 6.50 (s, 1 H), 6.85 (m, 2 H), 7.08 (m, 2 H), 7.20 (m, 4 H), 7.50 (d, J=8.1 Hz, 1 H), 7.95 (d, J=8.1 Hz, 2 H), 8.12 (d, J=8.1 Hz, 1 H); MS (ESI) m/z: 536 ($M^+$+H).

To a stirred solution of methyl 4-[2-N-allyl-N-[3-chloro-4-[N'-(2-methylphenyl)ureido]phenyl]acetamido]ethoxybenzoate (321 mg, 0.6 mmol) in TBF-MeOH—$H_2O$ (2:2:1, v/v, 30 ml), was added NaOH (500 mg, 12.5 mmol) at rt. The stirring was continued for 18 hours at rt. The reaction mixture was poured into water, washed with diethyl ether, acidified with 1M HCl, extracted with $CHCl_3$-MeOH (2:1, 20 mL×3), dried over anhydrous $MgSO_4$, and concentrated under a reduced pressure. The residue was solidified with $CHCl_3$/n-hexane to give 313 (283 mg, 83%) as a white solid. IR (KBr): 3345, 1581, 1529, 1243, 1167 $cm^{-1}$; $^1$H-NMR ($CD_3OD$) δ 2.30 (s, 3 H), 3.71 (s, 1 H), 3.78 (m, 1 H), 3.82 (m, 1 H), 3.89 (s, 1 H), 4.10 (m, 1 H), 4.19 (m, 2 H), 4.21 (t, J=5.4 Hz, 1 H), 5.20 (m, 2 H), 5.82 (m, 1 H), 6.95 (m, 2 H), 7.03 (m, 1 H), 7.18 (m, 3 H), 7.28 (s, 1 H), 7.60 (d, J=8.1 Hz, 1 H), 7.99 (m, 3 H); MS (ESI) m/z 522 ($M^+$+1); Anal. Calcd for $C_{28}H_{28}ClN_3O_5$·1.75 $H_2O$: C, 60.76; H, 5.74; N, 7.59. Found: C, 60.43; H, 5.34; N, 7.17.

To a stirred solution of methyl 4-[2-N-(2,3-dihydroxy-1-propyl)-[3-methoxy-4-[N'-(2-methylphenyl) ureido]phenylacetamido]ethoxy]benzoate (1.83 g, 3.24 mmol) in THF-MeOH—$H_2O$ (1:1:1, v/v/v, 15 mL) was added sodium periodate (2.08 g, 9.71 mmol), and stirred for 18 hours at rt. A saturated $Na_2S_2O_3$ (50 ml) was added to the reaction mixture and the mixture was stirred for 1 hour. The mixture was extracted with EtOAc (100 ml×3), washed with brine, dried over $MgSO_4$. The solvent was removed to give the title compound (1.73 g, 100%) as an amorphous foam. $^1$H-NMR ($CDCl_3$) δ 2.32 (t, 3 H, J=2.8 Hz), 3.33–4.30 (m, 8 H), 3.72 (s, 3 H), 3.86 (s, 3 H), 6.20 (m, 1 H), 6.70 (m, 1 H), 6.80 (m, 4 H), 7.06 (m, 1 H), 7.18 (m, 1 H), 7.26 (m, 1 H), 7.49 (d, 1 H, J=7.4 Hz), 7.96 (m, 2 H), 8.10 (m, 1 H), 9.57 and 9.63 (2 s, total 1 H); MS (FAB), m/z 534 ($M^+$+1).

To a stirred solution of methyl 4-[2-N-formylmethyl-N-[3-methoxy-4-[N'-(2-methyl phenyl)ureido]phenylacetamido]ethoxy]benzoate (400 mg, 0.75 mmol) in EtOH (7.5 ml), were added morpholine (654 ml, 7.5 mmol) and acetic acid (429 ml, 7.5 mmol) at rt. The reaction was stirred for 5 min. at rt, then cooled to 0° C. To the cooled solution, was added $NaBH_3CN$ (471 mg, 7.5 mmol) and the stirring was continued for 1 h at rt. The mixture was poured into sat. $NaHCO_3$ and was extracted with EtOAc (50 ml×3), washed with brine, and dried over $MgSO_4$. After removal of the solvent in vacuo, the residue was chromatographed on silica gel (middle pressure chromatography system: YAMAZEN YFLC-5404-FC, linear gradient toluene-acetone 100:0 to 1:1) to give 314 (346 mg, 76%) as a white amorphous foam. $^1$H-NMR ($CDCl_3$, 400 MHz) δ 2.31 (s, 3 H), 2.46 (m, 4 H), 3.52–3.79 (m, 12 H), 3.70 (d, 3 H, J=2.7 Hz), 4.05 and 4.22 (m, total 2 H), 6.24 and 6.29 (s, total 1 H), 6.73 (m, 2 H), 6.85 (m, 2 H), 7.07 (s, 1 H), 7.17 (m, 1 H), 7.25 (m, 2 H), 7.50 (t, 1 H, J=7.3 Hz), 7.96 (m, 2 H), 8.08 (m, 1 H); MS (FAB), m/z 605 ($M^+$+1); Anal. Calcd for $C_{33}H_{40}N_4O_7$·1/2 $H_2O$: C, 64.58; H, 6.73; N, 9.13. Found: C, 64.95; H, 6.88; N, 8.82. HCl salt of 314: Anal. Calcd for $C_{33}H_{41}ClN_4O_7$·2.5 $H_2O$: C, 57.76; H, 6.76; N, 8.16; Cl, 5.17; Found: C, 58.29; H, 6.81; N, 7.42; Cl, 5.05.

Example 265

4-[2-N-[2-(4-morpholinyl)ethyl]-N-[3-methoxy-4-[N'-(2-methylphenyl)ureido]phenyl]acetamido]ethoxybenzoic acid

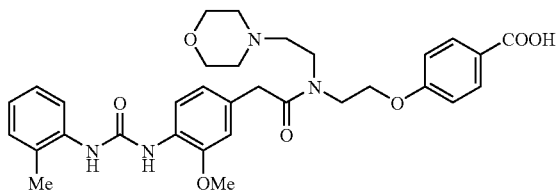

315

To a solution of methyl 4-[2-N-[2-(4-morpholinyl)ethyl]-N-[3-methoxy-4-[N'-(2-methylphenyl) ureido]phenyl]acetamido]ethoxybenzoate (146 mg, 0.24 mmol) in THF-MeOH (1:1,v/v, 6 ml), was added 0.25 N NaOH (1.9 ml, 0.48 mmol) at rt, and heated to reflux. The stirring was continued for 18 hours at reflux. The reaction mixture was poured into water, and acidified with 1.0 N HCl. The mixture was extracted with CHCl$_3$-MeOH (3:1, v/v, 30 ml×5). The combined organic solvent was dried over MgSO$_4$. After removal of solvent, the residue was crystallized with diethylether to give 315 (102 mg, 71%) as a white powder. $^1$H-NMR (CD$_3$OD) δ 2.28 (d, J=3.0 Hz, 3 H), 2.46 (m, 1 H), 2.40 (m, 1 H), 2.56 (m, 1 H), 2.63 (m, 1 H), 3.62–3.80 (m, 12 H), 3.85 (s, 3 H), 4.12 (m, 1 H), 4.26 (m, 1 H), 6.82 (m, 2 H), 6.96 (m, 2 H), 7.01 (m, 1 H), 7.17 (m, 2 H), 7.58 (d, J=7.8 Hz, 1 H), 7.93 (m, 3 H); MS (FAB) m/z 591 (M$^+$); Anal. Calcd for C$_{32}$H$_{38}$N$_4$O$_7$·1.0 H$_2$O: C, 63.14; H, 6.62; N, 9.20. Found: C, 63.48; H, 6.66; N, 8.79.

Example 266

4-[2-N-cyclopropyl-N-[3-methoxy-4-[N'-(2-methylphenyl)ureido]phenyl]acetamido]ethoxybenzoic acid

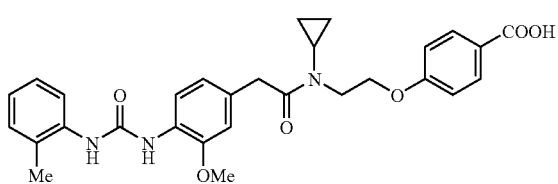

316

To a stirred solution of methyl 4-(2-hydroxyethyloxy)benzoate (5.00 g, 25.5 mmol), DMSO (18.1 ml, 255 mmol), Et$_3$N (17.7 ml, 127.5 mmol) in CH$_2$Cl$_2$ (200 ml) was added SO$_3$·Py (12.2 g, 76.5 mmol). After stirring for 5 h, the mixture was concentrated in vacuo and the residue was diluted with H$_2$O (100 ml). The mixture was extracted with EtOAc (2×200 ml). The combined extracts were washed with brine (100 ml), dried over (MgSO$_4$), and evaporated. The residue was chromatographed on silica gel with hexane-EtOAc (4:1) to give 4:1 mixture of methyl 4-formyl methyloxybenzoate and methyl 4-hydroxybenzoate (2.00 g) as a white solid. $^1$H-NMR (CDCl$_3$) δ 3.90 (s, 3 H), 4.64 (d, J=1.0 Hz, 2 H), 6.92 (d, J=9.0 Hz, 2 H), 8.02 (d, J=9.0 Hz, 2 H), 9.86 (d, J=1.0 Hz, 1 H).

To a stirred solution of 4:1 mixture of methyl 4-formylmethyloxybenzoate and methyl 4-hydroxybenzoate (1.00 g) and cyclopropylamine (425 ml, 6.18 mmol) in MeOH—AcOH (10:1, 11 ml) was added NaBH$_3$CN (681 mg, 10.3 mmol). After stirring overnight, the mixture was quenched by addition of sat. NaHCO$_3$ (50 ml) and extracted with CHCl$_3$ (2×200 ml). The combined extracts were dried over MgSO$_4$ and evaporated. The residue was chromatographed on silica gel with CHCl$_3$-MeOH (20:1) to give methyl 4-(2-cyclopropyl aminoethoxy)benzoate (595 mg, 49%) as a colorless oil. $^1$H-NMR (CDCl$_3$)δ 0.37–0.49 (m, 4 H), 1.91 (m, 1 H), 2.18–2.23 (m, 1 H), 3.11 (t, J=5.2 Hz, 2 H), 3.88 (s, 3 H), 4.12 (t, J=5.2 Hz, 2 H), 6.92 (d, J=8.8 Hz, 2 H), 7.98 (d, J=8.8 Hz, 2 H).

A mixture of methyl 4-(2-cyclopropylaminoethoxy)benzoate (290 mg, 1.23 mmol), 3-methoxy-4-[N'-(2-methylphenyl)ureido]phenylacetic acid (387 mg, 1.23 mmol), EDC·HCl (354 mg, 1.85 mmol), HOBt (cat.), and DMAP (cat.) in DMF (10 ml) was stirred overnight. The mixture was partitioned between EtOAc (300 ml) and H$_2$O (100 ml). The organic phase was separated, washed with brine (2×100 ml), dried over MgSO$_4$, and evaporated. The residue was chromatographed on silica gel with CHCl$_3$-MeOH (50:1) to give the title compound (426 mg, 65%) as a yellow viscous oil. $^1$H-NMR (CDCl$_3$)δ 0.90–0.97 (m, 4 H), 2.28 (s, 3 H), 3.60 (s, 3 H), 3.77 (t, J=5.4 Hz, 2 H), 3.85 (s, 2 H), 3.87 (s, 3 H), 4.15 (t, J=5.4 Hz, 2 H), 6.60–6.81 (m, 5 H), 7.09–7.23 (m, 4 H), 7.57 (d, J=8.3 Hz, 1 H), 7.92–7.95 (m, 2 H), 8.04 (d, J=8.3 Hz, 1 H).

To a stirred solution of methyl 4-[2-[N cyclopropyl-[3-methoxy-4-[N'-(2-methylphenyl) ureido]phenyl]acetamido]ethoxy]benzoate (426 mg, 0.801 mmol) in THF (7 ml) was added 0.25 N NaOH (6.4 ml, 1.60 mmol). After stirring overnight, the mixture was poured into 1 N HCl (50 ml) and extracted with CHCl$_3$-MeOH (4:1, 2×200 ml). The combined extracts were dried over MgSO$_4$ and evaporated. The residue was chromatographed on silica gel with CHCl$_3$-MeOH (20:1 to 10:1) as eluent to give 316 (333 mg, 80%) as a colorless amorphous solid. $^1$H-NMR (DMSO) δ 0.86–0.91 (m, 4 H), 2.25 (s, 3 H), 2.74 (m, 1 H), 3.69 (t, J=5.5 Hz, 2 H), 3.81 (s, 3 H), 3.83 (s, 2 H), 4.15 (t, J=5.5 Hz, 2 H), 6.75 (d, J=8.3 Hz, 1 H), 6.87 (s, 1 H), 6.92–6.99 (m, 3 H), 7.11–7.17 (m, 2 H), 7.81 (d, J=8.1 Hz, 1 H), 7.88 (d, J=8.5 Hz, 2 H), 8.01 (d, J=8.1 Hz, 1 H), 8.47 (s, 1 H), 8.55 (s, 1 H), 12.96 (s, br s); MS (FAB), m/z 518 (MW+1); Anal. Calcd for C$_{29}$H$_{31}$N$_3$O$_6$: C, 67.30; H, 6.04; N, 8.12. Found: C, 66.71; H, 6.26; N, 7.82.

Example 267

4-[2-N-[2-(N', N'-dimethylamino)-1-ethyl)-N-[4-[N'-(2-chlorophenyl)ureido]-3-methoxphenyl]acetamido]ethoxybenzoic acid

317

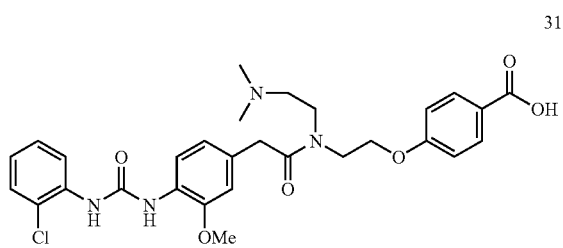

To a solution of methyl 4-[2-N-[2-(N', N'-dimethylamino)-1-ethyl)-N-[-4-[N''-(2-chlorophenyl) ureido]-3-methoxphenyl]acetamido]ethoxybenzoate (100 mg, 0.17 mmol) in THF-MeOH (1:1, v/v, 3 ml), was added 0.25 N NaOH (2.0 ml, 0.5 mmol) at rt, and heated to reflux. The stirring was continued for 3 hours at reflux. The reaction mixture was poured into water, and acidified to pH 5.0 with 1.0 N HCl. After removal of the organic solvent in vacuo, the resulting mixture was chromatographed with HP-20 ($H_2O$-MeOH 100:0 to 0:100) to give 317 (63 mg, 64%) as a white powder. $^1$H-NMR ($CD_3OD$) δ 2.41 (s, 2 H), 2.65 (s, 3 H), 2.69 (s, 3 H), 3.02 (m, 2 H), 3.62–3.85 (m, 4 H), 3.84 (s, 3 H), 4.05 and 4.22 (m, total 2 H), 6.82–6.88 (m, 4 H), 7.02 (m, 1 H), 7.25 (m, 1 H), 7.38 (m, 1 H), 7.92 (m, 2 H), 8.01 (m, 2H); MS (FAB), m/z 569 ($M^+$); Anal. Calcd for $C_{29}H_{33}ClN_4O_6$·3.0 $H_2O$: C, 55.90; H, 6.31; N, 8.99. Found: C, 56.40; H, 6.50; N, 8.08.

Example 268 isopropyl 4-[2-N-[2-(4-morpholinyl)ethyl]-N-[3-methoxy-4-[N'-(2-methylphenyl)ureido]phenyl]acetamido]ethoxybenzoate

318

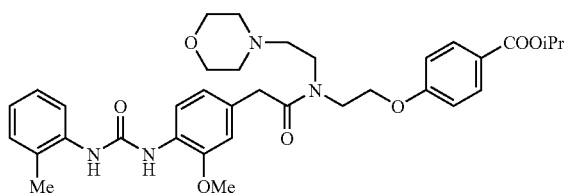

To a stirred solution of 4-[2-N-[2-(4-morpholinyl)ethyl]-N-[3-methoxy-4-[N'-(2-methylphenyl) ureido]phenyl]acetamido]ethoxybenzoic acid (250 mg, 0.42 mmol) in DMF (2 mL), were added isopropyl iodide (264 ml, 2.53 mmol) and $K_2CO_3$ (88 mg, 0.64 mmol) at rt. The reaction was stirred for 2 hours at 50° C. The mixture was poured into brine and was extracted with $CHCl_3$ (50 ml×3), washed with brine, and dried over $MgSO_4$. After removal of the solvent in vacuo, the residue was chromatographed on silica gel (middle pressure chromatography system: YAMAZEN YFLC-5404-FC, linear gradient toluene-acetone 100:0 to 40:60) to give 318 (261 mg, 97%) as a white amorphous foam. $^1$H-NMR ($CDCl_3$, 400 MHz) δ 1.35 (s, 3 H), 1.36 (s, 3 H), 2.31 (s, 3 H), 2.45 (m, 4 H), 2.50 (m, 2 H), 3.55–3.78 (m, 10 H), 3.70 (s, 3 H), 4.05 and 4.20 (t, J=5.2 Hz, total 2 H), 5.22 (m, 1 H), 6.24 and 6.33 (2 s, total 1 H), 6.70–6.83 (m, 4 H), 7.08 (s, 1 H), 7.15 (m, 1 H), 7.22 (m, 1 H), 7.40 (t, J=9.0 Hz, 1 H), 7.93 (d, J=8.8 Hz, 1 H), 7.97 (d, J=8.8 Hz, 1 H), 8.07 (t, J=7.8 Hz, 1 H); MS (FAB), m/z 633 ($M^+$+1); Anal. Calcd for $C_{35}H_{44}N_4O_7$·0.75 $H_2O$: C, 65.05; H, 7.10; N, 8.67. Found: C, 65.19; H, 7.09; N, 8.50.

Example 269

4-[2-N-[2-(3,3-difluoro-1-pyrrolidinyl)ethyl]-N-[4-[N'-(2-bromophenyl)ureido]-3-methoxyphenyl]acetamido]ethoxybenzoic acid sodium salt

319

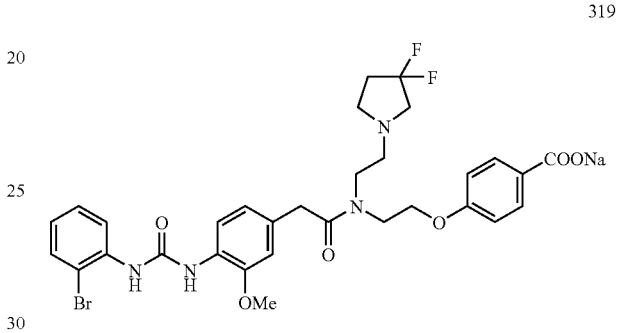

To a stirred solution of methyl 4-[2-N-formylmethyl-N-[3-methoxy-4-[N'-(2-bromophenyl)ureido]phenyl]acetamido]ethoxybenzoate (300 mg, 0.5 mmol) in 1,2-dichloroethane (3.6 ml), was added 3,3-difluoropyrrolidine AcOH salt (420 mg, 2.5 mmol) at rt. The reaction was stirred for 5 min. at rt, then cooled to 0° C. To the cooled solution, was added $NaBH(OAc)_3$ (530 mg, 2.5 mmol), and the stirring was continued for 4 h at rt. The mixture was poured into sat. $NaHCO_3$, was extracted with $CHCl_3$ (50 mL×3), washed with brine, and dried over $MgSO_4$. After removal of the solvent in vacuo, the residue was chromatographed on silica gel (middle pressure chromatography system: YAMAZEN YFLC-5404-FC, linear gradient $CHCl_3$-MeOH 10:0 to 97:3) to give methyl 4-[2-N-[2-(3,3-difluoro-1-pyrrolidinyl)ethyl]-N-[4-[N'-(2-bromophenyl) ureido]-3-methoxyphenyl]acetamido]ethoxybenzoate (345 mg, 100%) as a white amorphous foam. $^1$H-NMR ($CDCl_3$, 400 MHz) δ 2.20–2.80 (m, 6 H), 3.48 (m, 2 H), 3.70–3.80 (m, 9 H), 3.89 (s, 3 H), 4.09 (m, 1 H), 4.21 (m, 1 H), 6.79–6.85 (m, 4 H), 6.93 (m, 1 H), 7.08 (m, 2 H), 7.30 (m, 1 H), 7.50 (m, 1 H), 7.96 (m, 3 H), 8.13 (dd, J=1.5 Hz, 8.3 Hz, 1 H); MS ESI m/z 689 ($M^+$).

To a solution of methyl 4-[2-N-[2-(3,3-difluoro-1-pyrrolidinyl)ethyl]-N-[4-[N'-(2-bromophenyl) ureido]-3-methoxyphenyl]acetamido]ethoxybenzoate (345 mg, 0.5 mmol) in THF-MeOH (1:1, v/v, 8 ml), was added 0.25 N NaOH (4 ml, 1.0 mmol) at rt, and heated to reflux. The stirring was continued for 6 hours at reflux. The solvent was removed, and the residue was chromatographed on HP-20 ($H_2O$-MeOH, 0:100 to 100:0) to give 319 (306 mg, 91%) as a pale red powder. $^1$H-NMR ($CD_3OD$, 400 MHz) δ 2.20–2.90 (m, 6 H), 3.60 (m, 2 H), 3.70–3.92 (m, 9 H), 4.10 (m, 1 H), 4.22 (m, 1 H), 6.84 (m, 4 H), 6.96 (m, 1 H), 7.30 (m, 1 H), 7.55 (m, 1 H), 7.93 (m, 3H), 7.97 (m, 1 H); MS (ESI) /z 676 ($M^+$+1); Anal. Calcd for $C_{31}H_{32}BrF_2N_4O_6$·2.5 $H_2O$: C, 52.85; H, 5.29; N, 7.95. Found: C, 52.67; H, 5.20; N, 8.11.

Example 270

4-[2-N-(N'-methoxy-N'-methylamino)ethyl-N-[3-methoxy-4-[N''-(2-methylphenyl)ureido]phenyl]acetamido]ethoxybenzoic acid sodium salt

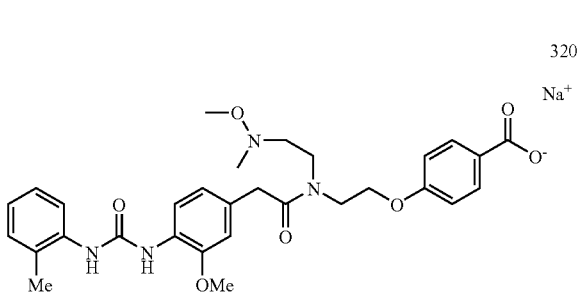

320

To a stirred solution of methyl 4-[2-N-formylmethyl-[3-methoxy-4-[N'-(2-methylphenyl) ureido]phenylacetamido]ethoxy]benzoate (350 mg, 0.66 mmol) in EtOH (13 ml), was added N-methoxy-N-methylamine hydrochloride (637 mg, 6.6 mmol) at rt. The reaction was sonicated for 5 min. at rt, then cooled to 0° C. To the cooled solution, was added NaBH$_3$CN (105 mg, 1.65 mmol) and the stirring was continued for 18 h at rt. The mixture was poured into sat. NaHCO$_3$ and was extracted with CHCl$_3$ (50 ml×3), washed with brine, and dried over MgSO$_4$. After removal of the solvent in vacuo, the residue was chromatographed on silica gel (middle pressure chromatography system: YAMAZEN YFLC-5404-FC, linear gradient toluene-acetone 9:1 to 2:3) to give the title compound (344 mg, 91%) as a white amorphous foam. $^1$H-NMR (CDCl$_3$, 400 MHz) δ 2.29 (s, 3 H), 2.52 and 2.58 (s, total 3 H), 2.79 (m, 2 H), 3.49–3.76 (m, 9 H), 3.88 (s, 3 H), 4.05 and 4.20 (m, total 2 H), 6.69–6.86 (m, 5 H), 7.10 (m, 1 H), 7.20 (m, 2 h), 7.29 (m, 1 H), 7.44 (m, 1 H), 7.94 and 7.99 (d, J=8.6 Hz, total 2 H), 8.06 (m, 1 H); MS (FAB), m/z 579 (M$^+$+1); Anal. Calcd for C$_{31}$H$_{38}$N$_4$O$_7$.2.5H$_2$O: C, 59.70; H, 6.95; N, 8.98. Found: C, 59.58; H, 6.65; N, 8.90.

To a solution of methyl 4-[2-N-(N'-methoxy-N'-methylamino)ethyl-N-[3-methoxy-4-[N''-(2-methylphenyl)ureido]phenyl]acetamido]ethoxybenzoate (138 mg, 0.24 mmol) in THF-MeOH (1:1, v/v, 4 ml), was added 0.25 N NaOH (1.9 ml, 0.48 mmol) at rt, and heated to reflux. The stirring was continued for 18 hours at reflux. The solvent was removed, and the residue was chromatographed on HP-20 (H$_2$O-MeOH, 100:0 to 0:100) to give 320 (140 mg, 100%) as a white powder. $^1$H-NMR (CD$_3$OD) δ 2.29 (s, 3 H), 2.54 and 2.56 (2 s, total 3 H), 2.82 (m, 2 H), 3.48 (m, 2 H), 3.65–5.80 (m, 9 H), 4.09 and 4.21 (2 m, total 2 H), 6.80 (m, 4 H), 7.00 (t, J=7.5 Hz, 1 H), 7.18 (m, 2 H), 7.57 (d, J=7.8 Hz, 1 H), 7.88 (m, 2 H), 7.99 (m, 1 H); MS (FAB), m/z 565 (M$^+$+1); Anal. Calcd for C$_{30}$H$_{35}$N$_4$O$_7$Na.1.0 H$_2$O: C, 59.59; H, 6.17; N, 9.27. Found: C, 59.10; H, 6.28; N, 8.86.

Example 271

4-[2-N-(N'-methoxy-N'-methylamino)ethyl-N-[4-[N'-(2-bromophenyl)ureido]-3-methoxyphenyl acetamido]ethoxy]benzoic acid

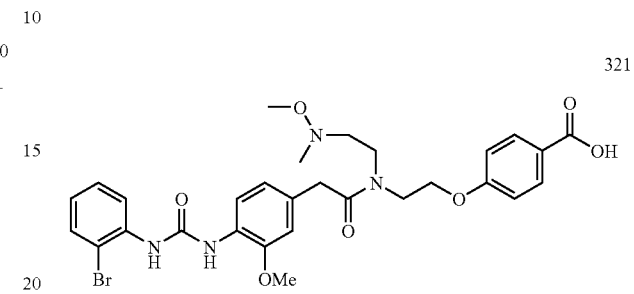

321

To a stirred solution of methyl 4-[2-N-formylmethyl-N-[3-methoxy-4-[N'-(2-bromophenyl)ureido]phenyl]acetamido]ethoxybenzoate (209 mg, 0.35 mmol) in EtOH (7 ml), was added N-methoxy-N-methylamine HCl salt (341 mg, 3.5 mmol) at rt. The reaction was sonicated for 5 min. at rt, then cooled to 0° C. To the cooled solution, was added NaBH(OAc)$_3$ (370 mg, 1.75 mmol) and the stirring was continued for 18 h at rt. The mixture was poured into sat. NaHCO$_3$, extracted with CHCl$_3$ (50 ml×3), and dried over MgSO$_4$. After removal of the solvent, the residue was chromatographed on TLC (Whatman, PLK-5F, 2 plates, CHCl$_3$-MeOH, 98:2) to give methyl 4-[2-N-(N'-methoxy-N'-methylamino)ethyl-N-[4-[N'-(2-bromophenyl)ureido]-3-methoxyphenyl acetamido]ethoxy]benzoate (89 mg, 40%) as a white amorphous foam. $^1$H-NMR (CDCl$_3$, 400 MHz) δ 2.52 and 2.60 (2 s, 3 H), 2.80 (m, 2 H), 3.48 and 3.50 (2 s, total 3 H), 3.65 (m, 2 H), 3.72 (s, 3 H), 3.77 (m, 4 H), 3.90 (s, 3 H), 4.08 (m, 1 H), 4.22 (m, 1 H), 6.82 (m, 5 H), 7.12 (s, 2 H), 7.30 (m, 1 H), 7.52 (d, J=8.1 Hz, 1 H), 7.94 (m, 3 H), 8.15 (d, J=8.3 Hz, 1 H);MS (ESI) m/z 643 (M$^+$).

To a solution of methyl 4-[2-N-(N'-methoxy-N'-methylamino)ethyl-N-[4-[N'-(2-bromophenyl)ureido]-3-methoxyphenylacetamido]ethoxy]benzoate (89 mg, 0.14 mmol) in THF-MeOH (5:1, v/v, 6 ml), was added 0.5 N NaOH (1.4 ml, 0.7 mmol) at rt, and heated to reflux in a glass sealed bottle. The stirring was continued for 3 hours at reflux. The reaction was poured into water, and was acidified with 1 N HCl to pH 5, extracted with CHCl$_3$-MeOH (2:1, v/v, 30 mL×3), dried over MgSO$_4$. The solvent was removed in vacuo to give 321 (53 mg, 60%) as a white powder. $^1$H-NMR (CD$_3$OD, 400 MHz)δ 2.62 and 2.64 (2 s, total 3 H), 2.80 (m, 2 H), 3.50 (d, J=7.3 Hz, 3 H), 3.63–3.88 (m, 6 H), 4.12 (m, 1 H), 4.25 (m, 1 H), 6.82–7.00 (m, 5 H), 7.30 (m, 1 H), 7.58 (m, 1H), 7.95 (m, 4 H); MS (FAB), m/z 629 (M+); Anal. Calcd for C$_{29}$H$_{33}$BrN$_4$O$_7$.0.25 H$_2$O: C, 54.94; H, 5.33; N, 8.84. Found: C, 55.39; H, 5.53; N, 8.23.

Example 272

4-[2-N-(N', N'-diallyl)ethyl-N-[3-methoxy-4-[N"-(2-methylphenyl)ureido]phenyl]acetamido]ethoxybenzoic acid sodium salt

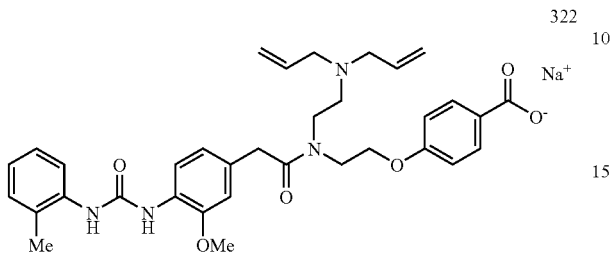

322

To a stirred solution of methyl 4-[2-N-formylmethyl-N-[3-methoxy-4-[N'-(2-methylphenyl)ureido]phenyl]acetamido]ethoxybenzoate (400 mg, 0.75 mmol) in EtOH (15 ml), were added diallylamine (926 ml, 7.5 mmol) and acetic acid (429 ml, 7.5 mmol) at rt. The reaction was stirred for 5 min. at rt, then cooled to 0° C. To the cooled solution, was added NaBH$_3$CN (118 mg, 1.9 mmol) and the stirring was continued for 1 h at rt. The mixture was poured into sat. NaHCO$_3$ and was extracted with EtOAc (50 ml×3), washed with brine, and dried over MgSO$_4$. After removal of the solvent in vacuo, the residue was chromatographed on silica gel (middle pressure chromatography system: YAMAZEN YFLC-5404-FC, linear gradient toluene-acetone 9:1 to 1:1) to give methyl 4-[2-N-(N', N'-diallyl)ethyl-N-[3-methoxy-4-[N"-(2-methylphenyl)ureido]phenyl]acetamido]ethoxybenzoate (385 mg, 84%) as a white amorphous foam. $^1$H-NMR (CDCl$_3$, 400 MHz) δ 2.30 (s, 3 H), 2.60 (m, 2 H), 3.09 (m, 4 H), 3.49 (m, 2 H), 3.60 (s, 2 H), 3.70 (m, 5 H), 3.89 (s, 3 H), 4.02 and 4.19 (2 m, total 2 H), 5.01–5.20 (m, 4 H), 4.79 (m, 2 H), 6.30 and 6.32 (2 s, total 1 H), 6.70–6.84 (m, 5 H), 7.08 (m, 1 H), 7.14 (m, 1 H), 7.25 (m, 1 H), 7.60 (m, 1 H), 7.93 and 7.98(2 d, J=8.8 Hz, 2. H), 8.03 and 8.06 (2 d, J=8.3 Hz, 1 H); MS (FAB), m/z 615 (M$^+$+1).

To a stirred solution of methyl 4-[2-N-(N', N'-diallyl)ethyl-N-[3-methoxy-4-[N"-(2-methylphenyl) ureido]phenyl]acetamido]ethoxybenzoate (385 mg, 0.63 mmol) in MeOH (3 ml), was added 1 N HCl (756 ml, 0.76 mmol) at rt. The reaction was stirred for 5 min. at rt, then evaporated to give methyl 4-[2-N-(N', N'-diallyl)ethyl-N-[3-methoxy-4-[N"-(2-methylphenyl) ureido]phenyl]acetamido]ethoxybenzoate HCl salt (385 mg, 99%) as an amorphous foam. Anal. Calcd for C$_{35}$H$_{43}$ClN$_4$O$_6$.0.5 H$_2$O: C, 63.67; H, 6.72; N, 8.49. Found: C, 63.67; H, 6.69; N, 8.43.

To a solution of 4-[2-N-(N', N'-diallyl)ethyl-N-[3-methoxy-4-[N"-(2-methylphenyl) ureido]phenyl]acetamido] ethoxybenzoate (175 mg, 0.29 mmol) in THF-MeOH (1:1, v/v, 20 ml), was added 0.25 N, NaOH (2.5 ml, 0.63 mmol) at rt, and heated to reflux. The stirring was continued for 1 hours at reflux. The solvent was removed, and the residue was chromatographed on HP-20 (H$_2$O-MeOH, 100:0 to 0:100) to give 322 (160 mg, 94%) as a white powder. $^1$H-NMR (CD$_3$OD) δ 2.29 (s, 3 H), 2.60 (t, J=6.9 Hz, 1 H), 2.67 (t, J=7.0 Hz, 1 H), 3.10 (d, J=6.6 Hz, 2 H), 3.14 (d, J=6.6 Hz, 2 H), 3.59 (m, 2 H), 3.69–3.80 (m, 4 H), 3.80 (s, 3 H), 4.06 (t, J=5.2 Hz, 4.21 (t, J=5.1 Hz, 1 H), 5.15 (m, 4 H), 5.80 (m, 2 H), 6.79 (m, 2 H), 6.84 (d, J=8.8 Hz, 2 H), 7.00 (t, J=7.5 Hz, 1 H), 7.14 (m, 2 h), 7.48 (m, 1 H), 7.91 (dd, J=6.1 Hz, 8.8 Hz, 2 H), 8.00 (m, 1 H); MS (FAB), m/z 601 (M$^+$); Anal. Calcd for C$_{34}$H$_{39}$N$_4$O$_6$Na.0.5 H$_2$O: C, 64.65; H, 6.38; N, 8.87. Found: C, 64.53; H, 6.58; N, 8.78.

Example 273

4-[2-N-(N', N'-diallyl)ethyl-N-[4-[N'-(2-chlorophenyl)ureido]-3-methoxyphenylacetamido]ethoxy] benzoic acid sodium salt

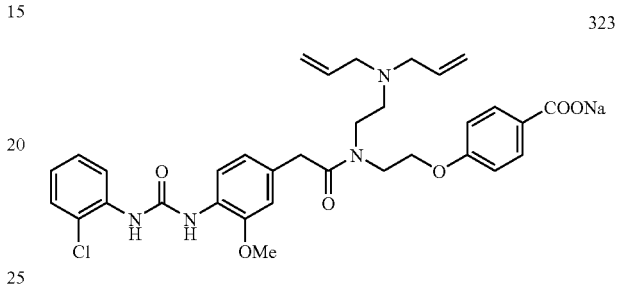

323

To a stirred solution of methyl 4-[2-N-formylmethyl-N-[4-[N'-(2-chlorophenyl)ureido]-3-methoxy phenylacetamido]ethoxy]benzoate (100 mg, 0.18 mmol) in EtOH (3.6 ml), was added diallylamine (223 ml, 1.81 mmol) at rt. The reaction was stirred for 5 min. at rt, then cooled to 0° C. To the cooled solution, were added AcOH (104 ml, 1.81 mmol) and NaBH$_3$CN (28 mg, 0.45 mmol), and the stirring was continued for 18 h at rt. The mixture was poured into sat. NaHCO$_3$, was extracted with CHCl$_3$ (30 mL×3), washed with brine, and dried over MgSO$_4$. After removal of the solvent in vacuo, the residue was chromatographed on silica gel (middle pressure chromatography system: YAMAZEN YFLC-5404-FC, linear gradient CHCl$_3$-MeOH 10:0 to 20:1) to give methyl 4-[2-N-(N', N'-diallyl)ethyl-N-[4-[N'-(2-chlorophenyl)ureido]-3-methoxyphenyl acetamido]ethoxy]benzoate (96 mg, 83%) as a white amorphous foam. $^1$H-NMR (CDCl$_3$, 400 MHz) δ 2.60 (m, 2 H), 3.09 (d, J=6.4 Hz, 1 H), 3.11 (d, J=6.4 Hz, 3 H), 3.52 (m, 2 H), 3.61 (s, 2 H), 3.70–3.80 (m, 5 H), 3.86 (s, 3 H), 4.05 and 4.20 (2 m, total 2 H), 5.06–5.21 (m, 4 H), 5.80 (m, 2 H), 6.71–6.85 (m, 4 H), 6.98 (m, 1 H), 7.22 (m, 1 H), 7.32 (m, 3 H), 7.93 (d, J=7.8 Hz, 2 H), 7.98 (m, 1 H), 8.18 (dd, J=1.5 Hz, 8.2 Hz, 1 H); MS (ESI) m/z 635 (M$^+$).

To a solution of methyl 4-[2-N-(N', N'diallyl)ethyl-N-[4-[N'-2-chlorophenyl)ureido]-3-methoxy phenylacetamido] ethoxy]benzoate (96 mg, 0.15 mmol) in THF-MeOH (1:1, v/v, 8 ml), was added 0.25 N NaOH (3.91 ml, 0.98 mmol) at rt, and heated to 50° C. The stirring was continued for 6 hours at reflux. The solvent was removed, and the residue was chromatographed on HP-20 (H$_2$O-MeOH, 0:100 to 100:0) to give 323 (88 mg, 94%) as a white powder. $^1$H-NMR (CD$_3$OD, 400 MHz) δ 2.61 (m, 2 H), 3.10 (s, 2 H), 3.12 (s, 2 H), 3.59 (m, 2 H), 3.70 (s, 2 H), 3.78 (m, 2 H), 3.82 (s, 3 H), 4.10 (m, 1 H), 4.21 (m, 1 H), 5.18 (m, 4 H), 5.81 (m, 2 H), 6.82 (m, 4 H), 7.01 (t, J=7.8 Hz, 1 H), 7.25 (m, 1 H), 7.39 (d, J=7.8 Hz, 1 H), 7.90(m, 2 H), 8.02(m, 2 H);MS (ESI) m/z 621 (M$^+$); Anal. Calcd for C$_{33}$H$_{36}$ClN$_4$O$_6$Na.1.25 H$_2$O: C, 59.55; H, 5.83; N, 8.42. Found: C, 59.90; H, 5.74; N, 7.96.

Example 274

4-[2-N-[3-methoxy-4-[N'-(2-methylphenyl)ureido]phenyl]-N-methylacetoamido]ethyl-1-piperazinylacetic acid

324

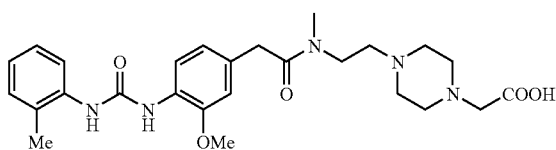

To a stirred suspension of 1-(2-hydroxyethyl)piperazine (5.21 g, 40.0 mmol) and K$_2$CO$_3$ (8.76 g, 63.4 mmol) in CH$_3$CN (100 ml) was added ethyl bromoacetate (5.60 ml, 50.5 mmol) at 0° C. The reaction mixture was heated under reflux for 5 h, diluted with EtOAc, and washed with water and brine. The extract dried over Na$_2$SO$_4$, concentrated to dryness and afforded ethyl 4-(2-hydroxyethyl)-1-piperazinylacetate (9.65 g, 100%) as a yellow oil. $^1$H-NMR (CDCl$_3$) δ 1.23 (t, 3H, J=7.3 Hz), 2.51–2.61(m, 11H), 3.22(s, 2H), 3.61(t, 2H, J=5.4 Hz), 4.19(q, 2H, J=7.3 Hz).

To a solution of 2,4-dinitrobenzenesulfonyl chloride (1.0 g, 3.75 mmol) and pyridine (0.34 ml, 4.20 mmol) in THF (19 ml) was added dropwise methylamine (2.0M THF solution, 2.3 ml, 4.60 mmol) at 0° C. The reaction mixture was stirred for 1 hr, quenched by the addition of 1 N HCl solution, and extracted with EtOAc. The extract was washed with sat. NaHCO$_3$ solution and brine, dried over Na$_2$SO$_4$, and concentrated to dryness. The residue was recrystallized from EtOAc-Et$_2$O to give methyl 2,4-dinitrobenzenesulfonamide (546 mg, 56%) as a colorless solid. $^1$H-NMR (DMSO) δ 2.60 (d, 3H, J=4.9 Hz), 8.22 (d, 1H, J=8.8 Hz), 8.31 (q, 1H, J=4.9 Hz), 8.66 (dd, 1H, J=8.8, 2.0 Hz), 8.90 (d, 1H, J=2.0 Hz).

To a solution of ethyl 4-(2-hydroxyethyl)-1-piperazinylacetate (452 mg, 2.09 mmol), methyl 2,4-dinitrobenzenesulfon-amide (546 mg, 2.09 mmol) and PPh$_3$ (658 mg, 2.51 mmol) in THF was added DIAD (0.50 ml, 251 mmol) at 0° C. After stirring 17h at room temperature, the reaction mixture was concentrated to dryness. Chromatography of the residue with EtOAc-MeOH (10:1) to afford ethyl 4-[2-[N-(2,4-dinitrobenzensulfonyl)-N-methylamino]ethyl]-1-piperazinylacetate (864 mg, 90%) as a reddish oil. $^1$H-NMR (CDCl$_3$) δ 1.27 (t, 3H, J=6.8 Hz), 2.35–2.63 (m, 10H), 2.98 (s, 3H), 3.20 (s, 2H), 3.41 (t, 2H, J=6.8 Hz), 4.17 (q, 2H, J=6.8 Hz), 8.33 (d, 1H, J=8.3 Hz), 8.46 (d, 1H, J=2.0 Hz), 8.50 (dd, 1H, J=8.3, 2.0 Hz).

A solution of ethyl 4-[2-[N-(2,4-dinitrobenzensulfonyl)-N-methylamino]ethyl]-1-piperazinylacetate (864 mg, 1.88 mmol), mercaptoacetic acid (0.17 ml, 2.44 mmol) and Et$_3$N (0.53 ml, 3.76 mmol) in CH$_2$Cl$_2$ (25 ml) was stirred at rt for 3hr. The reaction mixture ethyl 4-(2-methylaminoethyl)-1-piperazinylacetate (388 mg, 90%) as reddish oil. $^1$H-NMR (CDCl$_3$) δ 1.27 (t, 3H, J=6.8 Hz), 2.50 (s, 3H), 2.53–2.60 (m, 8H), 2.75 (t, 2H, J=5.9 Hz), 3.20 (s, 2H), 4.18 (q, 2H, J=6.8 Hz).

To a solution of ethyl 4-(2-methylaminoethyl)-1-piperazinylacetate (388 mg, 1.69 mmol), Et$_3$ N (0.32 ml, 2.25 mmol) and DMAP (46 mg, 0.38 mmol) in DMF (15 ml) was stirred for 15 min at room temperature, then (532 mg, 1.69 mmol), HOBt (103 mg, 0.76 mmol) and EDC.HCl (486 mg, 2.53 mmol) was added to the reaction mixture which was stirred for 15 h at room temperature The reaction mixture was diluted with EtOAc, which was washed with brine, dried over Na$_2$SO$_4$, and concentrated to dryness. Chromatography of the residue with CHCl$_3$-MeOH (10:1, v/v) to afford ethyl 4-[2-N-[3-methoxy-4-[N'-(2-methylphenyl)ureido]phenyl]-N-methylacetoamido]ethyl-1-piperazinylacetate (889 mg, mixture of DMF) as a reddish oil. $^1$H-NMR (CDCl$_3$) δ 1.25–1.29 (m, 3H), 2.29 (s, 3H), 2.42–2.63 (m, 10H), 3.20, 3.18 (each s, total 3H), 3.55, 3.40 (each t, total 2H, J=6.8 Hz), 3.65, 3.69 (each s, total 2H), 3.72 (s, 3H), 4.15–4.21 (m, 2H), 6.50 (m, 1H), 6.77–6.81 (m, 8H), 7.11–7.24 (m, 3H), 7.53 (d, 1H, J=8.3 Hz), 8.02 (s, 1H), 8.06 (d, 1H, J=7.8 Hz).

To a stirred solution of ethyl 44-[2-N-[3-methoxy-4-[N'-(2-methylphenyl)ureido]phenyl]-N-methylacetoamido]ethyl-1-piperazinylacetate (889 mg, 1.69 mmol) in THF-EtOH (5:1, v/v, 18 ml) was added 4 N NaOH (0.84 ml, 3.38 mmol). The reaction mixture was stirred at rt for 4 h, adjusted to pH 7.5 with 1 N HCl and extracted with CHCl$_3$-MeOH (4:1, v/v). The combined extracts were dried over MgSO$_4$ and concentrated to afforded 324 (218 mg, 26% 2steps) as a brown amorphous foam. IR(KBr)n 3299, 3004, 1700, 1627, 1598, 1536 cm$^{-1}$; $^1$H-NMR (DMSO) δ 2.25 (s, 3H), 2.36–2.62 (m, 10H), 2.84, 2.99 (each s, total 3H), 3.13, 3.14 (each s, total 2H), 3.38–3.45 (m, 2H), 3.61, 3.65 (each s, total 2H), 3.86 (s, 3H), 6.74 (t, 1H, J=7.8 Hz), 6.87 (s, 1H), 6.93 (t, 1H, J=7.8 Hz), 7.11–7.17 (m, 2H), 7.79 (d, 1H, J=7.8 Hz), 8.01 (d, 1H, J=7.8 Hz), 8.47 (s, 1H), 8.57 (s, 1H); MS (FAB) m/z 498 (M$^+$+1); Anal. Calcd for C$_{26}$H$_{35}$N$_5$O$_5$O.2HCl.H$_2$O: C, 53.06; H, 6.67; N, 11.89. Found: C, 53.04; H, 6.15; N, 11.09.

Example 275

1-[2-[N-methyl-N-[3-methoxy-4-[N'-(2-methylphenyl)ureido]phenyl]acetamido]ethyl]-4-piperidinylacetic acid

325

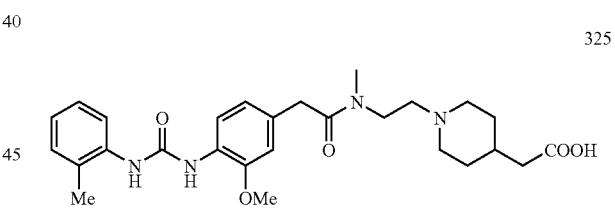

To a stirred solution of 2-(N-benzyloxycarbonyl-N-methylamino)acetaldehyde (2.07 g, 10.0 mmol) and ethyl 4-piperidinylideneacetate (1.69 g, 10.0 mmol) in MeOH—AcOH (10:1, v/v, 22 ml) was added NaBH$_3$CN (1.32 g, 20 mmol) and the stirring was continued overnight. The mixture was quenched by addition of sat. NaHCO$_3$ (200 ml) and extracted with CHCl$_3$ (3×150 ml). The combined extracts were dried over MgSO$_4$ and evaporated. The residue was chromatographed on silica-gel with CHCl$_3$-EtOH (40:1, v/v) to give ethyl 1-[2-(N-benzyloxycarbonyl-N-methylamino)ethyl]-4-piperidinylideneacetate (1.71 g, 47%) as a colorless oil. $^1$H-NMR (CDCl$_3$) δ 1.25 (t, J=7.3 Hz, 3 H), 2.16 (m, 2 H), 2.57 (m, 4 H), 2.95 (m, 7 H), 3.44 (m, 2 H), 4.13 (q, J=7.3 Hz, 2 H), 5.12 (s, 2 H), 5.49–5.53 (m, 1 H), 7.35 (m, 5 H).

A solution of ethyl 1-[2-(N-benzyloxycarbonyl-N-methylamino)ethyl]-4-piperidinylidene acetate (1.70 g, 4.72 mmol) in EtOH—AcOH (20:1, v/v, 21 ml) was hydrogenated over 5% Pd/C (2 g) for 3 days with stirring. The mixture was filtered and the filtrate was concentrated in vacuo. The residue was made basic with sat. NaHCO₃ and extracted with CHCl₃ (300 ml). The extract was dried over Na₂CO₃ and evaporated to give ethyl 1-(2-methylaminoethyl)-4-piperidinylacetate (813 mg, 75%) as a yellow oil. ¹H-NMR (CDCl₃) δ 1.25 (t, J=7.3 Hz, 3 H), 1.68–1.81 (m, 5 H), 1.97 (t, J=11.2 Hz, 2 H), 2.22 (d, J=7.3 Hz, 2 H), 2.43–2.47 (m, 5 H), 2.66 (t, J=6.4 Hz, 2 H), 2.85–2.90 (m, 2 H), 4.13 (q, J=7.3 Hz, 2 H).

To a stirred solution of 3-methoxy-4-[N'-(2-methylphenyl)ureido]phenylacetic acid (550 mg, 1.75 mmol) and ethyl 1-(2-methylaminoethyl)-4-piperidinylacetate (400 mg, 1.75 mmol) in DMF (10 ml) were added EDC.HCl (503 mg, 2.63 mmol), HOBt (cat.), and DMAP (cat.) and the stirring was continued overnight. The mixture was diluted with EtOAc (300 ml), washed with brine (200 ml), dried over MgSO₄, and evaporated. The residue was chromatographed on silica gel with CHCl₃-EtOH (10:1, v/v) to give ethyl 1-[2-[N-methyl-N-[3-methoxy-4-[N'-(2-methylphenyl) ureido]phenyl]acetamido]ethyl]-4-piperidinylacetate (697 mg, 76%) as a yellow gum. ¹H-NMR (CDCl₃) δ 1.19–2.06 (series of m, 12 H), 2.21 (t, J=7.8 Hz, 2 H), 2.28 (s, 3 H), 2.41 (t, J=7.3 Hz, 1 H), 2.46 (t, J=7.3 Hz, 1 H), 2.80–2.89 (m, 2 H), 2.95 and 3.01 (s, each, total 3 H), 3.40 and 3.50 (t, J=6.8 Hz, each, total 2 H), 3.64–3.75 (m, 5 H), 4.09–4.16 (m, 2 H), 6.59 (s, 1 H), 6.77–6.79 (m, 2 H), 7.12 (t, J=7.3 Hz, 1 H), 7.21–7.27 (m, 3 H), 7.54 (d, J=8.3 Hz, 1 H), 8.06 (dd, J=8.3, 2.4 Hz, 1 H).

To a stirred solution of ethyl 1-[2-[N-methyl-N-[3-methoxy-4-[N'-(2-methylphenyl) ureido]phenyl]acetamido] ethyl]4-piperidinylacetate (690 mg, 1.32 mmol) in THF (11 ml) was added 0.25 N aq. NaOH (11 ml, 2.75 mmol) and the stirring was continued overnight. The mixture was diluted with H₂O (50 ml), neutralized with 1 N HCl, and extracted with CHCl₃-MeOH (2:1, v/v, 3×100 ml). The combined extracts were dried over MgSO₄ and evaporated. The residue was dissolved in MeOH (50 ml) and activated carbon (2 g) was added to this solution. The suspension was refluxed for 30 min with stirring and filtered through Celite. The filtrate was evaporated and the residue was triturated by taking up CHCl₃ and adding hexane until a precipitate formed. This precipitate was collected and dried in vacuo to give 325 (75 mg, 11%) as a white amorphous solid. ¹H-NMR (DMSO) δ 1.19–2.99 (series of m, total 17 H), 3.32–3.43 (m, 4 H), 3.62–3.65 (m, 2H), 3.86 (s, 3 H), 6.73 (t, J=8.3 Hz, 1 H), 6.87 (s, 1 H), 6.93 (t, J=7.8 Hz, 1 H), 7.11–7.17 (m, 2 H), 7.79 (d, J=8.3 Hz, 1 H), 8.01 (d, J=8.3 Hz, 1 H), 8.47 (s, 1 H), 8.57 (s, 1 H); MS-FAB m/z 497 (M⁺+1); Anal. Calcd for C₂₇H₃₆N₄O₅.HCl: C, 60.84; H, 7.00; N, 10.51. Found: C, 60.97; H, 7.14; N, 10.17.

Example 276

1-[2-[N-methyl-N-[4-[N'-(2-methylphenyl)ureido]phenyl]acetamido]ethyl]-4-piperidinylacetic acid

326

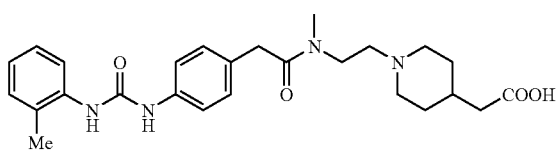

To a stirred solution of ethyl 1-(2-methylaminoethyl)-4-piperidinylacetate (400 mg; 1.75 mmol) and Et₃ N (366 ul, 2.63 mmol) in DMF (10 ml) was added pentafluorophenyl 4-(N'-(2-methylphenyl)ureido)phenylacetate (788 mg, 1.75 mmol) and the stirring was continued overnight. The mixture was diluted with EtOAc (300 ml), washed with brine (200 ml), dried over MgSO₄, and evaporated. The residue was chromatographed on silica-gel with CHCl₃-EtOH (10:1, v/v) to give ethyl 1-[2-[N-methyl-N-[4-[N'-(2-methylphenyl)ureido]phenyl]acetamido]ethyl]-4-piperidinyl acetate (630 mg, 73%) as a colorless oil.

To a stirred solution of ethyl 1-[2-[N-methyl-N-[4-[N'-(2-methylphenyl)ureido]phenyl]acetamido]ethyl]-4-piperidinylacetate (630 mg, 1.27 mmol) in THF (10 ml) was added 0.25 N aq. NaOH (10 ml) and the stirring was continued overnight. The reaction mixture was diluted with H₂O (1.00 ml), neutralized with 1 N HCl, and extracted with CHCl₃-MeOH (2:1, v/v, 3×100 ml). The combined extracts were dried over MgSO₄ and evaporated. The residue was triturated by taking up CHCl₃ and adding hexane until precipitate formed. This precipitate was collected and dried in vacuo to give 326 (20 mg, 3%) as a white amorphous solid. ¹H-NMR (DMSO)δ 1.69 (m, 5 H), 2.15 (m, 4 H), 2.24 (s, 2 H), 2.50 (m, 2 H), 2.83 and 2.99 (s, each, total 3 H), 3.32–3.49 (m, 4 H), 3.63 (d, J=6.8 Hz, 2 H), 6.91–6.95 (m, 1 H), 7.13 (m, 4 H), 7.39 (d, J=8.3 Hz, 2 H), 7.83 (d, J=7.3 Hz, 1 H), 7.97 (m, 1 H), 9.12 (m, 1 H); MS (FAB): m/z 467 (M⁺+1).

Example 277

4-[2-N-[4-[N'-(2-methylphenyl)ureido]phenyl]-N-methylacetamido]ethyl-1-piperazinylacetic acid

327

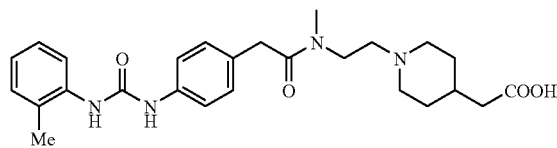

To a solution of ethyl 4-(2-methylaminoethyl)-1-piperazinylacetate (700 mg, 3.05 mmol), Et₃ N (0.64 ml, 4.58 mmol) and DMAP (75 mg, 0.61 mmol) in THF (15 ml) was stirred for 30 min at rt, then 4-[N'-(2-methylphenyl)ureido]phenylacetic acid (917 mg, 3.05 mmol), HOBt (82 mg, 0.61 mmol) and EDC.HCl (879 mg, 4.58 mmol) was added to the reaction mixture which was stirred for 12 h at rt. The reaction mixture was diluted with EtOAc, which was washed with brine, dried over Na₂SO₄, and concentrated to dryness. Chromatography of the residue with CHCl₃-MeOH (10:1, v/v) afforded ethyl 4-[2-N-[4-[N'-(2-methylphenyl)ureido]phenyl]-N-methylacetamido]ethyl-1-piperazinylacetate (996 mg, 66%) as a yellow amorphous foam. ¹H-NMR (CDCl₃) δ 1.25–1.29 (m, 3H), 2.20 (s, 3H), 2.47–2.58 (m, 10H), 2.97, 3.05 (each s, total 3H), 3.17, 3.20 (each s, total 2H), 3.45, 3.52 (each d, total 2H, J=6.8 Hz), 3.64, 3.68 (each s, 2H), 4.15–4.21 (m, 2H), 7.01–7.19 (m, 8H), 7.48 (m, 1H), 7.64 (m, 1H); MS (FAB) m/z 496 (M⁺+1).

To a stirred solution of ethyl 4-[2-N-[4-[N'-(2-methylphenyl)ureido]phenyl]-N-methyl acetamido]ethyl-1-piperazinylacetate (996 mg, 2.01 mmol) in THF-EtOH (5:1, 12 ml) was added 4 N NaOH (1.0 ml, 4.00 mmol). The reaction mixture was stirred at rt for 4 h, adjusted to pH 7.5 with 1

N HCl and extracted with CHCl₃-MeOH (4:1, v/v). The combined extracts were dried over MgSO₄ and concentrated to afforded 327 (73 mg, 8%) as a yellow amorphous foam. IR(KBr) n 3338, 2925, 2850, 2821, 1704, 1627, 1540 cm⁻¹; ¹H-NMR (DMSO) δ 2.24 (s, 3H), 2.33–2.61 (m, 10H), 2.82, 2.95 (each s, total 3H), 3.00, 3.02 (each s, total 2H), 3.39 (t, 2H, J=6.8 Hz), 3.60, 3.62 (each s, total 2H), 6.92 (t, 1H, J=7.8 Hz), 7.09–7.16 (m, 4H), 7.41–7.44 (m, 2H), 7.76, 7.77 (each d, 2H, J=7.8 Hz), 8.46, 8.53 (each s, 1H), 9.54, 9.59 (each s, 1H); MS (FAB) m/z 468 (M⁺+1); Anal. Calcd for C₂₅H₃₃N₅O₅.2HCl: C, 55.56; H, 6.53; N, 12.96. Found: C, 54.99; H, 6.45; N, 11.58.

Example 278

4-[2-N-[4-[N'-(2-fluorophenyl)ureido]-3-methoxyphenyl]-N-methylacetamido]ethyl-1-piperazinylacetic acid

328

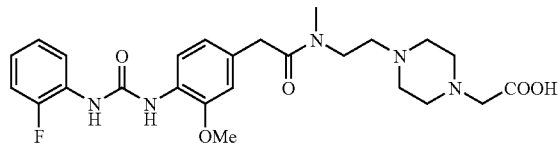

To a solution of ethyl 4-(2-methylaminoethyl)-1-piperazinylacetate (695 mg, 3.03 mmol), Et₃ N (0.64 ml, 4.58 mmol) and DMAP (75 mg, 0.61 mmol) in DMF (15 ml) was stirred for 15 min at rt, then 4-[N'-(2-fluorophenyl)ureido]-3-methoxyphenylacetic acid (965 mg, 3.03 mmol), HOBt (82 mg, 0.61 mmol) and EDC.HCl (872 mg, 4.54 mmol) was added to the reaction mixture which was stirred for 12 h at rt. The reaction mixture was diluted with EtOAc, which was washed with brine, dried over Na₂SO₄, and concentrated to dryness. Chromatography of the residue with CHCl₃-MeOH (10:1, v/v) afforded ethyl 4-[2-N-[4-[N'-(2-fluorophenyl)ureido]-3-methoxyphenyl]-N-methyl acetamido]ethyl-1-piperazinylacetate (1.21 g, mixture of DMF) as a black oil. ¹H-NMR (CDCl₃) δ 1.24–1.29 (m, 3H), 2.45–2.59 (m, 10H), 2.98, 3.05 (each s, total 3H), 3.17, 3.20 (each s, total 2H), 3.44, 3.52 (each t, total 2H, J=6.8 Hz), 3.66 (s, 2H), 4.15–4.21 (m, 2H), 6.77–6.78 (m, 2H), 6.79–7.11 (m, 3H), 7.68–7.95 (m, 2H), 7.64 (broad s, 1H), 8.20 (t, 1H, J=7.8 Hz); MS (FAB) m/z 530 (M⁺+1).

To a stirred solution of ethyl 4-[2-N-[4-[N'-(2-fluorophenyl)ureido]-3-methoxyphenyl]-N-methyl acetamido]ethyl-1-piperazinylacetate (1.21 g, mixture of DMF) in TBF-EtOH (5:1, v/v, 12 ml) was added 4 N NaOH (1.0 ml, 4.00 mmol). The reaction mixture was stirred at rt for 4 h, adjusted to pH 7.5 with 1 N HCl and extracted with CHCl₃-MeOH (4:1, v/v). The combined extracts were dried over MgSO₄ and concentrated to afforded 328 (78 mg, 5% 2 steps) as a brown amorphous foam. IR(KBr) n 3299, 2940, 2830, 1704, 1627, 1598, 1536 cm⁻¹; ¹H-NMR (DMSO) δ 2.36–2.61 (m, 10H), 2.83, 2.98 (each s, total 3H), 3.11 (s, 2H), 3.37–3.43 (m, 2H), 3.62, 3.65 (each s, total 2H), 3.85 (s, 3H), 6.75 (m, 1H), 6.87 (s, 1H), 6.98 (s, 1H), 7.12 (t, 1H, J=7.8 Hz), 7.20, 7.23 (each d, 2H, J=7.8 Hz), 8.01 (d, 1H, J=7.8 Hz), 8.17 (t, 1H, J=7.8 Hz), 8.72 (s, 1H), 9.19 (s, 1H); MS (FAB) m/z 502 (M⁺+1); Anal. Calcd for C₂₅H₃₂FN₅O₅.2HCl.0.5H₂O: C, 51.46; H, 6.05; N, 12.00. Found: C, 51.08; H, 5.69; N, 11.27.

Example 279

3-fluoro-1-[2-N-methyl-N-[3-methoxy-4-[N'-(2-methylphenyl)ureido]phenyl]acetamido]ethyl-4-piperidinylacetic acid

329

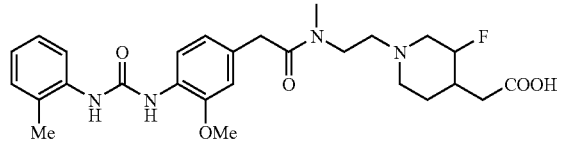

To a stirred solution of 1-tert-butoxycarbonyl-4-piperidone (14.9 g, 74.8 mmol) in DMF (35 mL) was added TMSCl (11.4 mL, 89.7 mmol) and then Et₃ N (25.0 mL, 179 mmol) dropwise at room temperature, and the reaction mixture was heated at 80° C. for 18 hr. Hexane was added to the reaction mixture, and the resulting mixture was washed with sat. NaHCO₃ and brine, dried over Na₂SO₄, and concentrated to dryness. Chromatography of the residue with hexane-EtOAc (5:1, v/v) as eluent gave 1-tert-butoxycarbonyl-1,2,3,6-tetrahydro-4-(trimethylsilyloxy)pyridine (20.4 g, 99%) as a yellow oil. ¹H-NMR (CDCl₃) δ 0.19 (s, 9H), 1.46 (s, 9H), 2.05–2.15 (m, 2H), 3.48–3.56 (m, 2H), 3.83–3.91 (m, 2H), 4.79 (broad s, 1H).

To a solution of 1-tert-butoxycarbonyl-1,2,3,6-tetrahydro-4-(trimethylsilyloxy)pyridine (20.4 g, 75.0 mmol) in CH₃CN (500 mL) was added Selectfluor™ (29.2 g, 82.5 mmol) at room temperature, and the reaction mixture was stirred for 2 hr. EtOAc was added to the reaction mixture, and the mixture was washed with brine, dried over Na₂SO₄, and concentrated to dryness. Chromatography of the residue with CHCl₃-MeOH (6:1, v/v) as eluent gave 1-tert-butoxycarbonyl-3-fluoro-4-piperidone (14.5 g, 89%) as a colorless oil. ¹H-NMR (CDCl₃) δ 1.50 (s, 9H), 2.44 (t, J=6.9 Hz, 1H), 2.48–2.63 (m, 2H), 3.26 (ddd, J=13.5, 10.5, 3.9 Hz, 1H), 3.72 (t, J=6.9 Hz, 1H), 4.16 (m, 1H), 4.42 (m, 1H), 4.83 (dt, 49.2, 6.9 Hz, 1H).

To a solution of triethyl phosphonoacetate (3.72 g, 16.6 mmol) in THF (70 mL) was added lithium bis(trimethylsilyl)amide (1.0M THF solution, 15.5 mL, 15.5 mmol) at −78° C. After being stirred at the same temperature for 1 hr, 1-tert-butoxycarbonyl-3-fluoro-4-piperidone (3.02 g, 13.9 mmol) was added to the reaction mixture. The mixture was stirred for 30 min at the same temperature, quenched by the addition of sat. NH₄Cl solution and extracted with EtOAc. The extracts were washed with brine, dried over Na₂SO₄, and concentrated to dryness. Chromatography of the residue with hexane-EtOAc (8:1, v/v) as eluent gave ethyl (1-butoxycarbonyl-3-fluoropiperidin-4-yliden)acetate (3.23 g, 81%) as a colorless solid. ¹H-NMR δ 1.30 (t, J=7.1 Hz, 3H), 1.48 (s, 9H), 2.10 (m, 1H), 2.56 (m, 1H), 2.77 (m, 1H), 3.13–3.54 (m, 2H), 3.70 (m, 1H), 4.17 4.18 (each q, J=7.1 Hz, total 2H), 5.82 5.98 (each s, total 1H), 6.41 (each d, J=46.9 Hz, total 1H); MS (FAB) m/z 288 (M⁺+1).

A solution of ethyl (1-butoxycarbonyl-3-fluoropiperidin-4-yliden)acetate (1.32 g, 4.59 mmol) in THF (30 mL) was hydrogenated over Pd—C (TMEDA complex, 66.0 mg) at room temperature for 2 hr under hydrogen atmosphere. The catalyst was filtered off and the filtrate was concentrated to dryness. Chromatography of the residue with hexane-EtOAc (9:1, v/v) as eluent gave ethyl 1-tert-butoxycarbonyl-3- fluoro-4-piperidinylacetate (653 mg, 73%) as a colorless oil. $^1$H-NMR (CDCl$_3$) δ 1.26 (t, J=7.1 Hz, 3H), 1.45 (s, 9H), 1.53–1.79 (m, 2H), 1.92–2.09 (m, 2H), 2.31 (dd, J=16.4, 6.9 Hz, 1H), 2.52 (dd, J=16.4, 7.3 Hz, 1H), 2.61–3.06 (m, 2H), 4.14 (q, J=7.1 Hz, 2H), 4.28–4.77 (m, 2H); $^{13}$C NMR (CDCl$_3$) 14.29, 25.80, 28.42, 35.99, 36.20, 60.55, 79.78, 86.72, 88.48, 154.94, 171.93; FAB-MS m/z 290 (M$^+$+1).

To a solution of ethyl 1-tert-butoxycarbonyl-3-fluoro-4-piperidinylacetate (653 mg, 2.26 mmol) in CH$_2$Cl$_2$ (10 mL) was added TFA (5 mL) at 0° C. After being stirred at room temperature for 4 hr, the reaction mixture was concentrated. The residue was taken up with sat. NaHCO$_3$ solution and extracted with THF-EtOAc (1:1, v/v). The extracts were dried over MgSO$_4$ and concentrated to afford ethyl 3-fluoro-4-piperidinylacetate (420 mg, 98%) as a yellow oil. $^1$H-NMR (CDCL$_3$) δ 1.26 (t, J=7.4 Hz, 3H), 1.68–1.80 (m, 2H), 2.18 (m, 1H), 2.32 (dd, J=16.6, 6.8 Hz, 1H), 2.54 (dd, J=16.6, 7.5 Hz, 1H), 2.82 (m, 1H), 2.90, 3.00 (each d, J=14.4 Hz, total 1H), 3.31 (m, 1H), 3.51 (m, 1H), 4.15 (q, J=7.4 Hz, 2H), 4.82, 4.71 (each broad s, total 1H).

To a solution of ethyl 3-fluoro-4-piperidinylacetate (230 mg, 1.22 mmol) and 2-(N-tert-butoxy carbonyl-N-methylamino)acetaldehyde (211 mg, 1.22 mmol) in THF (5 mL) was added NaBH(OAc)$_3$ (386 mg, 1.82 mmol) and acetic acid (70.0 mL, 1.22 mmol) at room temperature After being stirred for 24 hr, the reaction mixture was quenched by the addition of sat. NaHCO$_3$ solution and extracted with EtOAc. The extracts were washed with brine, dried over Na$_2$CO$_3$, and concentrated to dryness. Chromatography of the residue with CHCl$_3$-MeOH (6:1, v/v) as eluent gave ethyl 3-fluoro-1-[2-(N-tert-butoxycarbonyl-N-methylamino)ethyl]-4-piperidinylacetate (236 mg, 56%) as a reddish oil. $^1$H-NMR (CDCl$_3$) δ 1.25 (t, J=7.1 Hz, 3H), 1.45 (s, 9H), 1.53 1.79 (m, 2H), 1.90–2.09 (m, 2H), 2.15 (dd, J=16.4, 7.1 Hz, 1H), 2.45–2.58 (m, 2H), 2.87 (s, 3H), 2.90–2.99 (m, 2H), 3.20 (m, 1H), 3.24–3.45 (m, 2H), 4.14 (q, J=7.1 Hz, 2H), 4.61, 4.73 (each broad s, 1H); ESI-MS m/z 347.

To a solution of ethyl 3-fluoro-1-[2-(N-tert-butoxycarbonyl-N-methylamino)ethyl]4-piperidinylacetate (236 mg, 0.68 mmol) in CH$_2$Cl$_2$ (10 mL) was added TFA (5 mL) at 0° C. After being stirred at room temperature for 4 hr, the reaction mixture was concentrated. The residue was taken up with sat. NaHCO$_3$ solution and extracted with CHCl$_3$. The extracts were dried over MgSO$_4$ and concentrated to afford ethyl 3-fluoro-1-[2-(N-methylamino)ethyl]4-piperidinylacetate (117 mg, 70%) as a reddish oil. $^1$H-NMR (CDCl$_3$)δ 1.26 (t, J=7.1 Hz, 3H), 1.58 (m, 1H), 1.70 (m, 1H), 1.99 (m, 1H), 2.14 (m, 1H), 2.27–2.33 (m, 1H), 2.47 (s, 3H), 2.48–2.56 (m, 4H), 2.72 (t, J=6.3 Hz, 2H), 2.90 (m, 1H), 3.16 (m, 1H), 4.14 (q, J=7.1 Hz, 2H), 4.67 (d, J=48.3 Hz, 1H); ESI-MS m/z 247 (M$^+$+1)

To a solution of 3-methoxy-4-[N'-(2-methylphenyl)ureido]phenylacetic acid (164 mg, 0.52 mmol), ethyl 3-fluoro-1-[2-(N-methylamino)ethyl]-4-piperidinylacetate (117 mg, 0.47 mmol), Et$_3$N (0.10 mL, 0.71 mmol), and HOBt (13.0 mg, 0.09 mmol) in THF (5 mL) was added EDC.HCl (137 mg, 0.71 mmol). After being stirred at room temperature for 8 hr, the reaction mixture was diluted with water and extracted with EtOAc. The extracts were washed with brine, dried over Na$_2$SO$_4$, and concentrated to dryness. Chromatography of the residue with toluene-acetone (1:2, v/v) as eluent gave ethyl 3-fluoro-1-[2-N-methyl-N-[3-methoxy-4-[N'-(2-methylphenyl)ureido]phenyl]acetamido]ethyl-4-piperidinylacetate (160 mg, 62%) as a yellow amorphous solid. $^1$H-NMR (CDCl$_3$) δ 1.24–1.28 (m, 3H), 1.51–2.23 (m 7H), 2.26 (s, 3H), 2.35 (s, 2H), 2.39–2.56 (m, 3H), 2.88 (m, 1H), 2.95, 3.03 (each s, total 3H), 3.11 (m, 1H), 3.44 (m, 1H), 3.56 (m, 1H), 3.64 (s, 2H), 3.68 (s, 3H), 4.11–4.17 (m, 2H), 4.57, 4.69 (each s, total 1H), 6.72–6.82 (m, 2H), 7.10–7.33 (m, 5H), 7.54 (d, J=8.1 Hz, 1H), 8.06 (d, J=8.1 Hz, 1H); ESI-MS m/z 543 (M$^+$+1).

To a solution of ethyl 3-fluoro-1-[2-N-methyl-N-[3-methoxy-4-[N'-(2-methylphenyl) ureido]phenyl]acetamido] ethyl-4-piperidinylacetate (160 mg, 0.29 mmol) in THF (3 mL) was added 0.25 N NaOH (1.30 mL, 0.32 mmol). After being stirred at room temperature for 1 hr, the reaction mixture was concentrated. The residue was diluted with water and neutralized with 1N HCl at 0° C. The mixture was concentrated and purified by ion-exchanged resin (HP-20, Mitsubishi Chemical) to give 329 (110 mg, 74%) as a yellow amorphous solid. IR (KBr) 3343, 2937, 1700, 1617, 1589, 1535, 1486, 1455, 1417 cm$^{-1}$; $^1$H-NMR (CD$_3$OD) δ 1.57–1.72 (m, 2H), 1.98 (m, 1H), 2.26 (m, 1H), 2.28 (s, 3H), 2.37–2.59 (m, 3H), 2.66–2.89 (m, 2H), 2.95, 3.09 (each s, total 31), 3.14 (m, 1H), 3.40 (m, 1H), 3.51 (m, 1H), 3.59 (m, 1H), 3.71 (s, 21), 3.78 (m, 1H), 3.89 (s, 3H), 4.69, 4.81 (each s, total 1H), 6.79 (dd, J=8.1, 1.5 Hz, 1H), 6.90 (broad s, 1H), 7.01 (t, J=7.8 Hz, 1H), 7.13–7.19 (m, 2H), 7.58 (d, J=7.8 Hz, 1H), 8.00 (d, J=8.1 Hz, 1H); ESI-MS m/z 515 (M$^+$+1); Anal. Calcd for C$_{27}$H$_{35}$FN$_4$O$_5$.H$_2$O: C, 60.89; H, 7.00; N, 10.52. Found: C, 61.09; H, 6.80; N, 9.87.

Example 280

4-[2-N-[2-(4-fluorophenoxy)ethyl]-N-[3-methoxy-4-[N'-(2-methylphenyl)ureido]phenyl]acetamido]ethylpiperazinyl-1-acetic acid

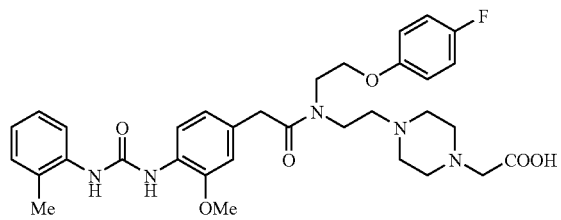

330

To a solution of 2-(N-benzyl-N-tert-butoxycarbonylamino)ethanol (6.85 g, 27.3 mmol), 4-fluorophenol (3.07 g, 27.3 mmol) and PPh$_3$ (7.83 g, 30.0 mmol) in THF (100 mL) was added DIAD (6.00 mL, 30.0 mmol) at room temperature After being stirred for 3 hr, the reaction mixture was concentrated. Chromatography of the residue with hexane-EtOAc (8:1, v/v) as eluent gave 1-[2-(N-benzyl-N-tert-butoxycarbonylamino)ethoxy]-4-fluorobenzene (8.19 g, 64%) as a yellow oil. $^1$H-NMR (CDCl$_3$)δ 1.42–1.50 (m, 9H), 3.41–3.67 (m, 21H), 3.92–4.11 (m, 2H), 4.51–4.63 (m, 21), 6.73–6.85 (m, 2H), 6.89–6.98 (m, 21H), 7.24 (m 5H); FAB-MS m/z 346 (M$^+$+1).

To a solution of 1-[2-(N-benzyl-N-tert-butoxycarbonylamino)ethoxy]-4-fluorobenzene (8.19 g, 23.7 mmol) in CH$_2$Cl$_2$ (50 mL) was added TFA (40 mL) at 0° C. After being stirred at room temperature for 1 hr, the reaction mixture was concentrated. The residue was taken up with sat. NaHCO$_3$ solution and extracted with CHCl$_3$. The extracts were washed with brine, dried over Na$_2$SO$_4$, and concentrated to give 1-(2-N-benzylaminoethoxy)-4-fluorobenzene (4.38 g, 75%) as a reddish oil. $^1$H-NMR (CDCl$_3$)δ 3.00 (t, J=5.2 Hz, 2H), 3.87 (s, 2H), 4.04 (t, J=5.2 Hz, 2H), 6.80–6.85 (m, 2H), 6.92–6.98 (m, 2H), 7.23–7.36 (m, 5H); FAB-MS m/z 246 (M$^+$+1).

A mixture of 1-(2-N-benzylaminoethoxy)-4-fluorobenzene (1.08 g, 4.40 mmol), ethyl 4-(2-bromoethyl)piperazinyl-1-acetate (1.23 g, 4.40 mmol), and K$_2$CO$_3$ (0.61 g, 17.9 mmol) in CH$_3$CN (50 mL) was heated under reflux for 8 hr. The resulting mixture was filtered and the filtrate was concentrated to dryness. Chromatography of the residue with toluene-acetone (3:1, v/v) as eluent gave ethyl 4-[2-N-benzyl-N-[2-(4-fluorophenoxy)ethyl]amino]ethylpiperazinyl-1-acetate (1.51 g, 77%) as a reddish oil. $^1$H-NMR (CDCl$_3$)δ 1.27 (t, J=7.1 Hz, 3H), 2.31–2.66 (m, 10H), 2.75 (t, J=6.6 Hz, 2H), 2.90 (t, J=6.1 Hz, 2H), 3.18 (s, 2H), 3.72 (s, 2H), 3.97 (t, J=6.1 Hz, 2H), 4.17 (q, J=7.1 Hz, 2H), 6.75–6.79 (m, 2H), 6.91–6.96 (m, 2H), 7.21–7.35 (m, 5H); FAB-MS m/z 444 (M$^+$+1).

A solution of ethyl 4-[2-N-benzyl-N-[2-(4-fluorophenoxy)ethyl]amino]ethylpiperazinyl-1-acetate (1.50 g, 3.38 mmol) in EtOH (30 mL) was hydrogenated over 5% Pd—C (53.1% wet, 0.73 g) under hydrogen atmosphere for 4 hr. The catalyst was filtered off and the filtrate was concentrated. The residue was taken up with sat. NaHCO$_3$ solution and extracted with CHCl$_3$. The extracts were washed with brine, dried over Na$_2$SO$_4$, and concentrated to afford ethyl 4-[2-N-[2-(4-fluorophenoxy)ethyl]amino]ethylpiperazinyl-1-acetate (1.12 g, 94%) as a reddish oil. $^1$H-NMR (CDCl$_3$) δ 1.27 (t, J=7.1 Hz, 31), 1.81 (broad s, 1H), 2.47–2.66 (m, 12H), 3.00 (t, J=5.4 Hz, 2H), 3.20 (s, 2H), 4.03 (t, J=5.4 Hz, 2H), 4.18 (q, J=7.1 Hz, 2H), 6.81–6.85 (m, 2H), 6.90–6.99 (m, 2H); FAB-MS m/z 354 (M$^+$+1).

To a solution of 3-methoxy-4-[N'-(2-methylphenyl)ureido]phenylacetic acid (485 mg, 1.54 mmol), ethyl 4-[2-N-[2-(4-fluorophenoxy)ethyl]amino]ethylpiperazinyl-1-acetate (545 mg, 1.54 mmol), Et$_3$ N (0.32 mL, 2.32 mmol), and HOBt (41.5 mg, 0.31 mmol) in THF (15 mL) was added EDC.HCl (883 mg, 2.32 mmol) at room temperature After stirring for 24 hr, the reaction mixture was diluted with water and extracted with CHCl$_3$-MeOH (10:1, v/v). The extracts were washed with brine, dried over Na$_2$SO$_4$, and concentrated to dryness. Chromatography of the residue with CHCl$_3$-MeOH (4:1, v/v) as eluent to give ethyl 4-[2-N-[2-(4-fluorophenoxy)ethyl]-N-[3-methoxy-4-[N'-(2-methylphenyl)ureido]phenyl]acetamido]ethylpiperazinyl-1-acetate (532 mg, 53%) as a yellow amorphous solid. $^1$H-NMR (CDCl$_3$) δ 1.26, 1.27 (each t, J=7.1 Hz, total 3H), 2.27 (s, 3H), 2.51–2.63 (m, 10H), 3.16, 3.19 (each s, total 2H), 3.51–3.56 (m, 2H), 3.63, 3.67 (each s, total 2H), 3.69–3.81 (m, 5H), 3.95, 4.10 (each t, J=5.2 Hz, total 2H), 4.16, 4.18 (each q, J=7.1 Hz, total 2H), 6.56 (d, J=8.1 Hz, 1H), 6.72–6.78 (m, 4H), 6.89–6.98 (m, 2H), 7.12 (t, J=7.6 Hz, 1H), 7.20–7.23 (m, 3H), 7.51 (d, J=7.6 Hz, 1H), 8.04 (d, J=8.1 Hz, 1H); FAB-MS m/z 650 (M$^+$+1).

To a solution of ethyl 4-[2-N-[2-(4-fluorophenoxy)ethyl]-N-[3-methoxy-4-[N'-(2-methylphenyl) ureido]phenyl]acetamido]ethylpiperazinyl-1-acetate (532 mg, 0.82 mmol) in dioxane (8 mL) was added dropwise 0.25 N NaOH (5.00 mL, 1.25 mmol) at room temperature, and the reaction mixture was stirred for 1 hr. The resulting mixture was concentrated, diluted with water, and neutralized with 1 N HCl at 0° C. The mixture was extracted with CHCl$_3$-MeOH (4:1, v/v). The extracts were washed with brine, dried over Na$_2$SO$_4$, and concentrated to dryness. Chromatography of the residue with CHCl$_3$-MeOH (3:1, v/v) as eluent gave 330 (168 mg, 33%) as a pale yellow amorphous solid. IR (KBr) 3338, 2938, 2829, 1635, 1533, 1506, 1454, 1415 cm$^{-1}$; $^1$H-NMR (DMSO-d$_6$)δ 2.25 (s, 3H), 2.37–2.48 (m, 6H), 2.53–2.67 (m, 6H), 3.09 (m, 2H), 3.44–3.49 (m, 2H), 3.64–3.69 (m, 2H), 3.72 (s, 2H), 3.80, 3.84 (each s, total 3H), 4.06–4.09 (m, 2H), 6.73 (m, 1H), 6.85 (s, 1H), 6.91–6.97 (m , 3H), 7.07–7.18 (m, 4H), 7.78 (d, J=8.1 Hz, 1H), 8.00 (dd, J=8.1, 2.7 Hz, 1H), 8.53 (m, 1H), 8.59 (m, 1H); FAB-MS m/z 622 (M$^+$+1); Anal. Calcd for C$_{33}$H$_{40}$FN$_5$O$_6$.2HCl: C, 57.06; H, 6.09; N, 10.08. Found: C, 56.83; H, 6.05; N, 9.90.

Example 281

4-[2-N-[2-(4-acetylphenoxy)ethyl]-N-[3-methoxy-4-[N'-(2-methylphenyl)ureido]phenyl]acetamido]ethylpiperazinyl-1-acetic acid

331

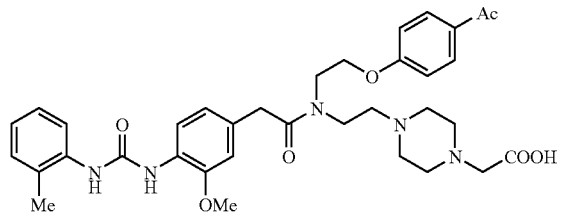

To a solution of 2-(N-benzyl-N-tert-butoxycarbonylamino)ethanol (5.90 g, 23.5 mmol), 4-hydroxyacetophenone (3.18 g, 23.5 mmol) and PPh$_3$ (6.74 g, 25.8 mmol) in THF (100 mL) was added DIAD (5.20 mL, 25.8 mmol) at room temperature The reaction mixture was heated under reflux for 4 hr and concentrated. Chromatography of the residue with hexane-EtOAc (5:1, v/v) as eluent gave 4-[2-(N-benzyl-N-tert-butoxycarbonylamino)ethoxy]acetophenone (3.64 g, 42%) as a yellow oil. $^1$H-NMR (CDCl$_3$) δ 1.43–1.65 (m, 9H), 2.55 (s, 3H), 3.41–3.69 (m, 2H), 4.02–4.24 (m, 2H), 4.49–4.66 (m, 2H), 6.81–6.93 (m, 2H), 7.19–7.37 (m, 5H), 7.91 (d, J=8.8 Hz, 2H); FAB-MS m/z 370 (M$^+$+1).

To a solution of 4-[2-(N-benzyl-N-tert-butoxycarbonylamino)ethoxy]acetophenone (3.05 g, 8.26 mmol) in CH$_2$Cl$_2$ (30 mL) was added TFA (20 mL) at 0° C. After being stirred at room temperature for 2 hr, the reaction mixture was concentrated. The residue was taken up with sat. NaHCO$_3$ solution and extracted with CHCl$_3$. The extracts were washed with brine, dried over Na$_2$SO$_4$, and concentrated to give 4-(2-N-benzylaminoethoxy)acetophenone (2.21 g, 99%) as a reddish oil. $^1$H-NMR (CDCl$_3$) δ 2.04 (broad s, 1H), 2.55 (s, 3H), 3.05 (t, J=5.4 Hz, 2H), 3.88 (s, 2H), 4.15 (t, J=5.4 Hz, 2H), 6.92 (d, J=8.9 Hz, 2H), 7.24–7.36 (m, 5H), 7.91 (d, J=8.9 Hz, 2H); FAB-MS m/z 270 (M$^+$+1).

To a solution of ethyl 4-(2-hydroxyethyl)piperazinyl-1-acetate (11.3 g, 52.1 mmol) and CBr$_4$ (20.7 g, 62.5 mmol) in CH$_2$Cl$_2$ (200 mL) was added PPh$_3$ (19.2 g, 73.0 mmol) portionwise at 0° C. and the reaction mixture was stirred for 30 min. Hexane was added to the mixture, the precipitates were filtered off, and the filtrate was concentrated to afford ethyl 4-(2-bromoethyl) piperazinyl-1-acetate (13.7 g, 94%) as a yellow oil. $^1$H-NMR (CDCl$_3$)δ 1.27 (t, J=7.1 Hz, 3H), 2.61–2.78 (m, 8H), 2.81 (t, J=7.6 Hz, 2H), 3.20 (s, 2H), 3.42 (t, J=7.6 Hz, 3H), 4.18 (q, J=7.1 Hz, 2H).

A mixture of 4-(2-N-benzylaminoethoxy)acetophenone (681 mg, 2.52 mmol), ethyl 4-(2-bromoethyl)piperazinyl-1-acetate (705 mg, 2.52 mmol), and K$_2$CO$_3$ (349 g, 2.52 mmol) in CH$_3$CN (10 mL) was heated under reflux for 22 hr.

The resulting mixture was filtered and the filtrate was concentrated to dryness. Chromatography of the residue with toluene-acetone (1:1, v/v) as eluent gave ethyl 4-[2-[N-benzyl-N-[2-(4-acetylphenoxy)ethyl]amino]ethylpiperazinyl-1-acetate (920 mg, 78%) as a reddish oil. $^1$H-NMR (CDCl$_3$) δ 1.27 (t, J=7.1 Hz, 3H), 2.45–2.53 (m, 10H), 2.55 (s, 3H), 2.76 (t, J=6.8 Hz, 2H), 2.94 (t, J=6.1 Hz, 2H), 3.18 (s, 2H), 3.73 (s, 2H), 4.06 (t, J=6.1 Hz, 2H), 4.17 (q, J=7.1 Hz, 2H), 6.85 (d, J=7.1 Hz, 2H), 7.22–7.35 (m, 5H), 7.90 (d, J=7.1 Hz, 2H); FAB-MS m/z 468 (M$^+$+1).

A solution of ethyl 4-[2-[N-benzyl-N-[2-(4-acetylphenoxy)ethyl]amino]ethylpiperazinyl-1-acetate (920 mg, 1.97 mmol) in EtOH (30 mL) was hydrogenated over 5% Pd—C (53.1% wet, 510 mg) under hydrogen atmosphere for 4 hr. The catalyst was filtered off and the filtrate was concentrated. The residue was taken up with sat. NaHCO$_3$ solution and extracted with CHCl$_3$. The extracts were washed with brine, dried over Na$_2$SO$_4$, and concentrated to afford ethyl 4-[2-N-[2-(4-acetyl phenoxy)ethyl]amino]ethylpiperazinyl-1-acetate (690 mg, 93%) as a reddish-oil. $^1$H-NMR (CDCl$_3$) δ 1.27 (t, J=7.1 Hz, 3H), 2.55 (s, 3H), 2.46–2.54 (m, 10H), 2.78 (t, J=6.2 Hz, 2H), 3.04 (t, J=5.2 Hz, 2H), 3.20 (s, 2H), 4.13 (t, J=5.2 Hz, 2H), 4.18 (q, J=7.1 Hz, 2H), 6.92 (d, J=8.8 Hz, 2H), 7.92 (d, J=8.8 Hz, 2H); FAB-MS m/z 378 (M$^+$+1).

To a solution of 3-methoxy-4-[N'-(2-methylphenyl)ureido]phenylacetic acid (558 mg, 1.77 mmol), ethyl 4-[2-N-[2-(4-acetylphenoxy)ethyl]amino]ethylpiperazinyl-1-acetate (670 mg, 1.77 mmol), Et$_3$ N (0.38 mL, 2.66 mmol), and HOBt (50.0 mg, 0.35 mmol) in THF (10 mL) was added EDC.HCl (883 mg, 2.32 mmol) at room temperature After stirring for 15 hr, the reaction mixture was diluted with water and extracted with CHCl$_3$-MeOH (10:1, v/v). The extracts were washed with brine, dried over Na$_2$SO$_4$, and concentrated to dryness. Chromatography of the residue with CHCl$_3$-MeOH (4:1, v/v) as eluent to give ethyl 4-[2-N-[2-(4-acetylphenoxy)ethyl]-N-[3-methoxy-4-[N'-(2-methylphenyl)ureido]phenyl]acetamido]ethylpiperazinyl-1-acetate (724 mg, 61%) as a yellow amorphous solid. $^1$H-NMR (CDCl$_3$) δ 1.25, 1.27 (each t, J=7.1 Hz, total 3H), 2.29 (s, 3H), 2.45–2.51 (m, 8H), 2.54 (s, 3H), 2.55–2.63 (m, 2H), 3.17, 3.19 (each s, total 2H), 3.51–3.55 (m, 2H), 3.60 (s, 2H), 3.69 (s, 3H), 3.71–3.78 (m, 2H), 4.04–4.23 (m, 4H), 6.47 (m, 1H, J=8.1 Hz), 6.72–6.76 (m, 2H), 6.85 (d, J=8.8 Hz, 2H), 7.12–7.19 (m, 2H), 7.20–7.24 (m, 2H), 7.51 (d, 8.1 Hz, 1H), 7.88 (d, J=8.8 Hz, 2H), 8.04 (d, J=8.1 Hz, 1H); FAB-MS m/z 674 (M$^+$+1).

To a solution of ethyl 4-[2-N-[2-(4-acetylphenoxy)ethyl]-N-[3-methoxy-4-[N'-(2-methylphenyl) ureido]phenyl]acetamido]ethylpiperazinyl-1-acetate (724 mg, 1.07 mmol) in THF (10 mL) was added dropwise 0.25 N NaOH (6.50 mL, 1.61 mmol) at room temperature, and the reaction mixture was stirred for 1 hr. The resulting mixture was concentrated, diluted with water, and neutralized with 1 N HCl at 0° C. The mixture was extracted with CHCl$_3$-MeOH (4:1, v/v). The extracts were washed with brine, dried over Na$_2$SO$_4$, and concentrated to dryness. Chromatography of the residue with CHCl$_3$-MeOH (3:1, v/v) as eluent gave 331 (450 mg, 65%) as a pale yellow amorphous solid. IR (KBr) 3345, 2938, 2821, 1673, 1631, 1598, 1533, 1455, 1417 cm$^{-1}$; $^1$H-NMR (DMSO-d$_6$) δ 2.25 (s, 3H), 2.35–2.47 (m, 8H), 2.51 (s, 3H), 2.53–2.58 (m, 2H), 2.96 (s, 2H), 3.46–3.50 (m, 2H), 3.69 (s, 2H), 3.73–3.77 (m, 2H), 3.80, 3.83 (each s, total 3H), 4.19–4.22 (m, 2H), 6.73 (m, 1H), 6.85 (s, 1H), 6.92 (t, J=7.3 Hz, 1H), 7.30 (d, J=7.3 Hz, 2H), 7.10–7.16 (m, 2H), 7.79 (d, J=8.3 Hz, 1H), 7.90–7.95 (m, 2H), 8.00 (t, J=8.3 Hz, 1H), 8.55 (m, 1H), 8.61 (m, 1H); FAB-MS m/z 646 (M$^+$+1); Anal. Calcd for C$_{35}$H$_{43}$N$_5$O$_7$.2HCl.1H$_2$O: C, 57.06; H, 6.43; N, 9.51. Found: C, 59.17; H, 6.32; N, 9.61.

Example 282

4-[2-N-[4-[N'-(2-bromophenyl)ureido]3-methoxyphenyl]-N-benzylacetamido]ethyl-1-piperidinylacetic acid

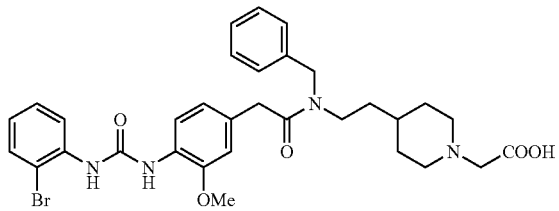

332 methyl 4-[2-N-[4-[N'-(2-bromophenyl)ureido]-3-methoxyphenyl]-N-benzylacetamido]ethyl-1-piperidinylacetate

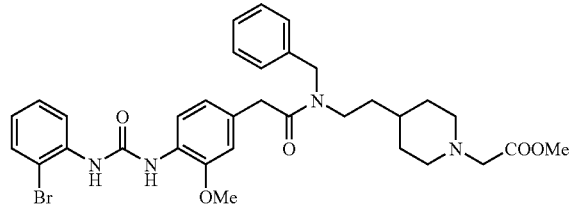

333

A mixture of piperidine ethanol (10.0 g, 77.4 mmol), benzyl 2-bromoacetate (17.8 g, 77.6 mmol) and K$_2$CO$_3$ (21.4 g, 155 mmol) in CH$_3$CN (200 ml) was heated under reflux with stirring for 2 h. The insoluble solid was removed by filtration, and the filtrate was concentrated in vacuo. The residue was poured into ice cooled 1N-HCl and extracted with CHCl$_3$. The organic layer was washed with water, drying over anhydrous Na$_2$SO$_4$, and concentrated in vacuo. The residue was chromatographed on silica gel with EtOAc as eluent to give benzyl 4-(2-hydroxyethyl)-1-piperidinylacetate (16.3 g, 76%) as a colorless oil. $^1$H-NMR (CDCl$_3$)δ 1.31–1.40 (m, 3 H), 1.52 (dd, J=12.8, 6.3 Hz, 2H), 1.68 (brd, J=10.0 Hz, 3 H), 2.16 (t, J=11.6 Hz, 2 H), 2.92 (brd, J=11.6 Hz, 2 H), 3.24 (s, 2 H), 3.69 (t, J=6.8 Hz, 2 H), 5.16 (s, 2 H), 7.35 (m, 5 H).

To a stirred solution of benzyl 4-(2-hydroxyethyl)-1-piperidinylacetate (14.9 g, 53.8 mmol) in CH$_2$Cl$_2$ (150 ml) was added Et$_3$ N (37.5 ml, 269 mmol) and DMSO (41.6 ml, 538 mmol). The reaction mixture was cooled to 0° C. and SO$_3$Py (25.7 g, 161 mmol) was added portion wise, and the resulting mixture was stirred at rt overnight. The mixture was concentrated in vacuo, and the residue was diluted with water, followed by extracted with Et$_2$O. The organic layer was washed with water, dried over anhydrous Na$_2$CO$_3$ and concentrated in vacuo. The residue was chromatographed on silica gel with EtOAc-hexane (2:1) as eluent to give (4-N-carbobenzyloxy methylpiperidinyl)acetaldehyde (4.63 g, 31%) as a colorless oil. $^1$H-NMR (CDCl$_3$) δ 1.36–1.46 (m, 2 H), 1.69 (br s, 2 H), 1.72 (br s, 1 H), 1.90 (m, 1 H), 2.21 (dt, J=11.6, 2.4 Hz, 2 H), 2.37 (dd, J=6.8, 1.6 Hz, 2 H), 2.92 (d, J=11.6 Hz, 2 H), 3.25 (s, 2 H), 5.16 (s, 2 H), 7.35 (m, 5 H), 9.77 (t, J=2.0 Hz, 1 H).

To a stirred solution of N-benzylamine (1.06 ml, 9.75 mmol) in MeOH (20 ml) was added AcOH (560 ml, 9.75 mmol) and (4-N-carbobenzyloxymethylpiperidinyl)acetaldehyde (1.79 g, 6.50 mmol) in MeOH (5 ml) and cooled to 0° C. NaBH$_3$CN (645 mg, 9.75 mmol) was added in one portion, and the resulting mixture was stirred overnight at rt. The mixture was concentrated in vacuo, and the residue was poured into aq.NaHCO$_3$, then extracted with CHCl$_3$. The organic layer was washed with water, dried over anhydrous Na$_2$SO$_4$ and concentrated in vacuo. The residue was chromatographed on silica gel with CHCl$_3$-MeOH-EtOAc (10:1:1) as eluent to give N-benzyl-2-[4-(N-carbobenzyloxymethylpiperidinyl)]ethylamine (872 mg, 37%) as a colorless oil. $^1$H-NMR (CDCl$_3$) δ 1.36–1.46 (m, 2 H), 1.69 (br s, 2 H), 1.72 (br s, 1 H), 1.90 (m, 1 H), 2.21 (dt, J=11.6,2.4 Hz, 2 H), 2.37 (dd, J=6.8, 1.6 Hz, 2 H), 2.92 (d, J=11.6 Hz, 2 H), 3.25(s, 2 H), 5.16 (s, 2 H), 7.35 (m, 5 H), 9.77 (t, J=2.0 Hz, 1 H).

To a stirred solution of N-benzyl-2-[4-(N-carbobenzyloxymethylpiperidinyl)]ethylamine (356 mg, 0.972 mmol), 4-[N'-(2-bromophenyl)ureido]-3-methoxyphenylacetic acid (369 mg, 0.972 mmol) and N,N-dimethylaminopyridine (119 mg, 0.972 mmol) in DMF (15 ml) was added EDC.HCl (372 mg, 1.94 mmol) at rt, and the resulting mixture was stirred overnight. The reaction mixture was poured into water and extracted with EtOAc. The organic layer was washed with brine and dried over anhydrous Na$_2$SO$_4$, then concentrated in vacuo. The residue was chromatographed on silica gel with CHCl$_3$-MeOH (10:1) as eluent to give benzyl 4-[2-N-[4-[N'-(2-bromophenyl)ureido]3-methoxyphenyl]-N-benzylacetamido]ethyl-1-piperidinylacetate (611 mg, 86%) as a colorless oil. $^1$H-NMR (CDCl$_3$) mixture of rotamars δ 1.15–2.09 (series of m, 7 H), 2.06–2.14 (m, 2 H), 2.84–2.96 (m, 2 H), 3.17–3.23 (s, total 2 H), 3.21 and 3.23(s, total 2 H), 3.38–3.42 (m, 1 H), 3.65 and 3.73 (s, total 2 H), 3.83 and 3.84 (s, total 3 H), 4.49 (s, 1 H), 4.60 (s, 1 H), 5.15 (d, J=2.8 Hz, 2 H), 6.74–7.83 (series of m, 16 H), 7.51–7.53 (m, 1 H), 7.94–8.02 (m, 1 H), 8.18 (d, J=8.4 Hz, 2 H); MS (FAB) m/z 727 (M$^+$), 729 (M$^+$+2).

To a stirred solution of benzyl 4-[2-N-[4-[N'-(2-bromophenyl)ureido]3-methoxyphenyl]-N-benzylacetamido]ethyl-1-piperidinylacetate (347 mg, 0.477 mmol) in MeOH—H$_2$O (5:1, 6 ml) was added LiOH (13.6 mg, 0.57 mmol) at rt, and the resulting mixture was stirred for overnight. The reaction mixture was poured into water and the solution was neutralized with aq. 1N-HCl, then extracted with CHCl$_3$. The organic layer was washed with brine and dried over anhydrous Na$_2$SO$_4$, then concentrated in vacuo. The residue was chromatographed on silica gel with CHCl$_3$-MeOH (10:1) as eluent to give 332 (97.3 mg, 32%) as a colorless amorphous solid, and 333 (168 mg, 54%) as a colorless amorphous solid, respectively. 332 $^1$H-NMR (CD$_3$OD), mixture of rotamars δ 1.29–1.90 (series of m, 7 H), 2.75–2.86 (m, 2 H), 3.28–3.51 (series of m, 6 H), 3.74 and 3.78 (s, total 2 H), 3.87 and 3.89 (s, total 3 H), 4.66 (s, 1 H), 4.85 (s, 1 H), 6.79–7.00 (series of m, 3 H), 7.16 (d, J=7.2 Hz, 1 H), 7.23–7.37 (m, 5 H), 7.57 (dd, J=8.4, 1.2 Hz, 1 H), 7.88–8.00 (series of m, 2 H); MS (FAB) nm/z 637 (M$^+$), 639 (M$^+$+2). 333 $^1$H-NMR (CDCl$_3$), mixture of rotamars δ 1.15–2.11 (series of m, 7 H), 2.89–2.97 (m, 2 H), 3.17–3.49 (series of m, 6 H), 3.17 and 3.18 (s, total 3 H), 3.70 and 3.71 (s, total 3 H), 3.83 and 3.84 (s, total 2 H), 4.49, 4.60 and 4.71 (s, total 2 H), 6.75–8.16 (series of m, 14 H); MS (FAB) m/z 651 (M$^+$), 653 (M$^+$+2).

Example 283

4-[2-N-[4-[N'-(2-chlorophenyl)-3-methoxyureido]phenyl]-N-benzylacetamido]ethyl-1-piperidinyl acetic acid

334

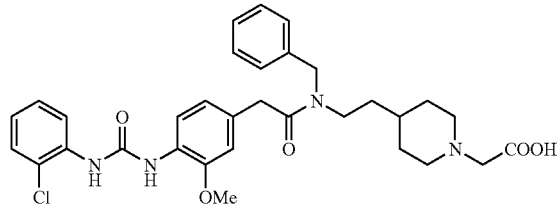

To a stirred solution of N-benzyl-2-[4-(N-carbobenzyloxymethylpiperidinyl)]ethylamine (372 mg, 1.11 mmol), 4-[N'-(2-chlorophenyl)ureido]-3-methoxyphenyl]acetic acid (758 mg, 1.11 mmol) and N,N-dimethylaminopyridine (136 mg, 1.11 mmol) in DMF (15 ml) was added EDC.HCl (426 mg, 2.22 mmol) at rt, and the resulting mixture was stirred for 12 h. The reaction mixture was poured into water and extracted with EtOAc. The organic layer was washed with brine and dried over anhydrous Na$_2$SO$_4$, then concentrated in vacuo. The residue was chromatographed on silica gel with CHCl$_3$-MeOH (10:1) as eluent to give benzyl 4-[2-N-[4-[N'-(2-chlorophenyl)-3-methoxyureido]phenyl]-N-benzylacetamido]ethyl-1-piperidinylacetate (668 mg, 88%) as a pale yellowish oil. $^1$H-NMR (CDCl$_3$) mixture of rotamars δ 1.15–1.83 (series of m, 7 H), 2.04–2.13 (m, 2 H), 2.83–2.95 (m, 2 H), 2.88 and 2.99 (s, total 2 H), 3.20 and 3.23 (s, total 2 H), 3.20–3.23 (overlap, 1 H), 3.38–3.42 (m, 1 H), 3.65–3.74 (m, 3 H), 4.50 (s, 1 H), 4.61 (s, 1 H), 5.14 (d, J=4.4 Hz, 2 H), 6.72–6.82 (series of m, 2 H), 6.94–6.99 (m, 1 H), 7.13–7.50 (series of m, 14 H), 7.94–8.02 (m, 1 H), 8.18 (d, J=8.0 Hz, 2 H); MS (FAB) m/z 683 (M$^+$+H).

To a stirred solution of benzyl 4-[2-N-[4-[N'-(2-chlorophenyl)-3-methoxyureido]phenyl]-N-benzylacetamido]ethyl-1-piperidinylacetate (633 mg, 0.93 mmol) in MeOH—H$_2$O (10:1, 10 ml) was added LiOH (24.4 mg, 1.02 mmol) at rt, and the resulting mixture was stirred overnight. The reaction mixture was poured into water and the solution was neutralized with aq. 1N-HCl, then extracted with CHCl$_3$. The organic layer was washed with brine and dried over anhydrous Na$_2$SO$_4$, then concentrated in vacuo. The residue was chromatographed on silica gel with CHCl$_3$-MeOH (20:1) as eluent to give methyl 4-[2-N-[4-[N'-(2-chlorophenyl)-3-methoxyureido]phenyl]-N-benzylacetamido]ethyl-1-piperidinylacetate (504 mg, 89%) as a colorless amorphous solid. $^1$H-NMR (CDCl$_3$), mixture of rotamars δ 1.26–1.64 (series of m, 7 H), 2.02–2.10 (m, 2 H), 2.86 (t, J=10.4 Hz, 2 H), 3.17 (d, J=8.0 Hz, 2 H), 3.16–3.22 (m, overlap, 1 H), 3.40 (t, J=7.6 Hz, 1 H), 3.48 (s, 1 H), 3.65 and 3.73 (s, total 2 H), 3.70 and 3.71 (s, total 3 H), 3.79 and 3.80 (s, total 3 H), 4.50, 4.60 and 4.70 (s, total 2 H), 6.73–6.85 (series of m, 2 H), 6.98 (t, J=7.6 Hz, 1 H), 7.13–7.37 (series of m, 9 H), 7.96 (m, 1 H), 8.18 (d, J=8.0 Hz, 2 H); MS (FAB) m/z 607 (M$^+$+H).

To a stirred solution of methyl 4-[2-N-[4-[N'-(2-chlorophenyl)-3-methoxyureido]phenyl]-N-benzylacetamido]

ethyl-1-piperidinylacetate (177 mg, 0.292 mmol) in MeOH—H$_2$O (5:1, 6 ml) was added LiOH (21.6 mg, 0.90 mmol), and the resulting mixture was stirred for 4 h at rt. The mixture was poured into water, and the solution was neutrallized with aq. 1N-HCl, then extracted with CHCl$_3$. The organic layer was washed with brine and dried over anhydrous Na$_2$SO$_4$, then concentrated to yield 334 (155 mg, 92%) as a colorless amorphous solid. $^1$H-NMR (CD$_3$OD) mixture of rotamars δ 1.28–1.90 (series of m, 7 H), 2.84 (br s, 2 H), 3.30–3.52 (series of m, 6 H), 3.74 and 3.82 (s, total 2 H), 3.87 and 3.88 (s, total 3 H), 4.63 (s, 1 H), 4.66 (s, 1 H), 6.79–7.05 (series of m, 3 H), 7.16 (d, J=7.2 Hz, 1 H), 7.24–7.40 (m, 5 H), 7.88 (s, 1 H), 7.98–8.04 (series of m, 2 H); MS (ESI) m/z 593 (M$^+$), 615 (M$^+$+Na$^+$).

It should be understood that while this invention has been described herein in terms of specific embodiments set forth in detail, such embodiments are presented by way of illustration of general principles, and the invention is not necessarily limited thereto. Modifications and variations in any given material or process step will be readily apparent to those skilled in the art without departing from the true spirit and scope of the following claims, and all such modifications are included within the scope of the present invention.

We claim:

1. A compound represented by Formula I, or a salt thereof,

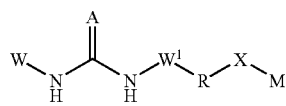

wherein
W is chosen from aryl group, substituted aryl group, heteroaryl group and substituted heteroaryl group;
W$^1$ is chosen from arylene group, substituted arylene group, heterocyclylene group and substituted heteroarylene group;
A is chosen from =O, =S and =NH;
R is chosen from a direct bond, alkenylene group and —(CH$_2$)$_n$—,
wherein
n is chosen from 1 and 2;
X is chosen from —C(O)—, —CH$_2$— and S(O)$_2$;
M is chosen from

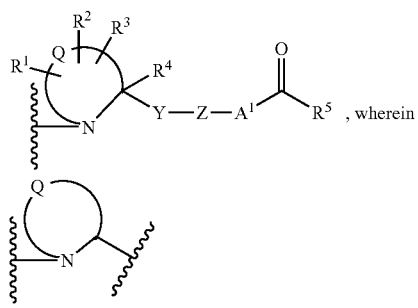

is a divalent thiazolidine moiety, wherein the nitrogen atom is the point of attachment to X;
R$^1$, R$^2$ and R$^3$ are independently chosen from —H, —OH, —NH$_2$, halogen atom, alkyl group, substituted alkyl group, aryl group, substituted aryl group, alkoxy group, substituted alkoxy group, monoalkylamino group, substituted monoalkylamino group, dialkylamino group, substituted dialkylamino group, cycloalkylamino group, substituted cycloalkylamino group, alkylsulfonylamino group, substituted alkylsulfonylamino group, arylsulfonylamino group, substituted arylsulfonylamino group, aryloxy group, substituted aryloxy group, heteroaryloxy group, substituted heteroaryloxy group, benzyloxy group and substituted benzyloxy group;
R$^4$ is chosen from —H and lower alkyl group;
Y is a direct bond or a divalent radical chosen from —C(O)—, —C(O)NH—, alkenylene group, alkynylene group and —(CH$_2$)$_k$Y$^2$,
wherein
k is chosen from 1, 2 and 3; and
Y$^2$ is a direct bond or a divalent radical chosen from —O—, —S—, —S(O), —S(O)$_2$— and —NY$^3$—,
wherein
Y$^3$ is chosen from —H and lower alkyl group;
Z is chosen from arylene group, substituted arylene group, heterocyclylene group, substituted heterocyclylene group, cycloalkylene group and substituted cycloalkylene group, with the proviso that when Y is a direct bond, Z is not a five-membered substituted or unsubstituted nitrogen-containing heterocyclylene group;
A$^1$ is a direct bond or a divalent radical chosen from alkenylene group, alkynylene group, —(CH$_2$)$_t$— and —O(CH$_2$)$_v$,
wherein
t is chosen from 1, 2 and 3; and
v is chosen from 0, 1, 2, and 3; and
R$^5$ is chosen from —OH, lower alkoxy group, —N(H)OH,

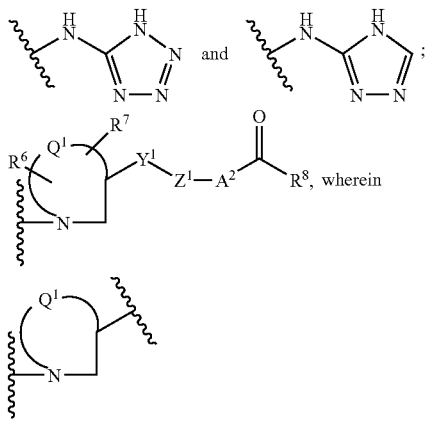

is a divalent thiazolidine moiety, wherein the nitrogen atom is the point of attachment to X;
R$^6$ and R$^7$ are independently chosen from —H, —OH, halogen atom, alkyl group and alkoxy group;
Y$^1$ is a divalent radical chosen from —O—, —S—, —S(O)—, —S(O)$_2$— and —NY$^4$—,
wherein
Y$^4$ is chosen from —H and lower alkyl group;
Z$^1$ is a divalent radical chosen from arylene group, substituted arylene group, heterocyclylene group, substituted heterocyclylene group, cycloalkylene group and substituted cycloalkylene group;
A$^2$ is a direct bond or a divalent radical chosen from alkenylene group, alkynylene group and —(CH$_2$)$_e$ wherein e is chosen from 1, 2 and 3; and R⁸ is chosen from —OH, lower alkoxy group, —N(H)OH,

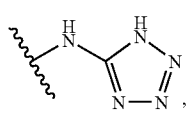 , 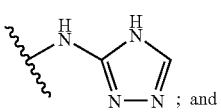 ; and

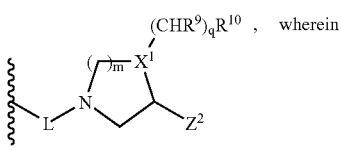 , wherein

L is

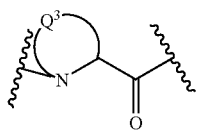

wherein

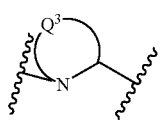

is a divalent thiazolidine moiety, wherein the nitrogen atom is the point of attachment to X, optionally substituted with from 1 to 3 substitutents chosen independently from alkyl group, alkoxy group, hydroxyalkyl group, —OH, benzyloxy group, —NH₂, halogen atom, aryl group and heteroaryl group;

m and q are independently chosen from 0, 1, 2 and 3;

X¹ is chosen from —CH= and —N=;

R⁹ is chosen from —H and lower alkyl group;

R¹⁰ is chosen from —COOH, lower alkoxycarbonyl group,

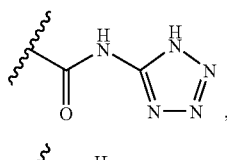 , 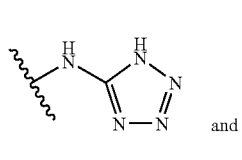 and

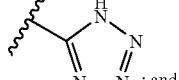 ; and

Z² is chosen from —H, COOH and lower alkoxycarbonyl group.

2. A compound according to claim 1, or a salt thereof, wherein M is

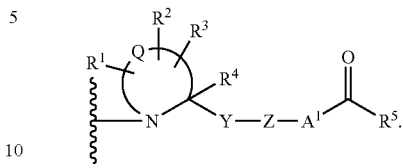

3. A compound according to claim 1, or a salt thereof, wherein M is

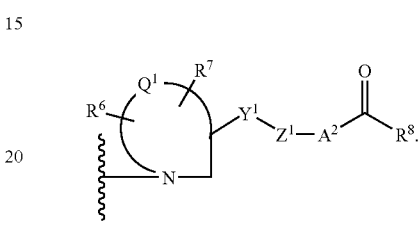

4. A compound according to claim 1, or a salt thereof, wherein M is

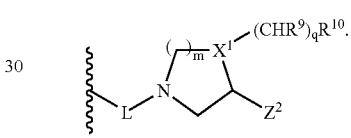

5. A compound according to claim 2, or a salt thereof, wherein at least one radical of R¹, R² and R³ is —OH or halogen atom.

6. A compound according to claim 5, or a salt thereof, wherein A is =O, R is —(CH₂)ₙ— and X is —C(O)—.

7. A compound according to claim 6, or a salt thereof, wherein Y is chosen from alkenylene group, alkynylene group and —(CH₂)ₖY²; Y² is chosen from a direct bond, —O—, —S(O) and —NY³—; and Y³ is —H.

8. A compound according to claim 7, or a salt thereof, wherein Y is chosen from —O— and —NY³—.

9. A compound according to claim 2, or a salt thereof, wherein W is unsubstituted phenyl group or phenyl group having one or two substituents chosen from lower alkyl group and halogen atom at the ortho positions thereof.

10. A compound according to claim 9, or a salt thereof, wherein W¹ is unsubstituted phenylene group or phenylene group having a substituent chosen from methoxy group, lower alkyl group and halogen atom at the ortho position to the —NH— thereof.

11. A compound according to claim 2, or a salt thereof, wherein W¹ is phenylene group having a substituent chosen from methoxy group, lower alkyl group and halogen atom at the ortho position to the —NH— thereof and having 1 to 3 substituents chosen from lower alkyl group and halogen atom.

12. A compound according to claim 2, or a salt thereof, wherein A¹ is a direct bond or —(CH₂)ₜ—.

13. A compound according to claim 12, or a salt thereof, wherein A¹ is a direct bond.

14. A compound according to claim 13, or a salt thereof, wherein R⁵ is —OH.

15. A compound according to claim 2, or a salt thereof, wherein W is unsubstituted phenyl group or phenyl group having one or two substituents chosen from lower alkyl group and halogen atom at the ortho positions thereof; $W^1$ is unsubstituted phenylene group or phenylene group having a substituent chosen from methoxy group, lower alkyl group and halogen atom at the ortho position to the —NH— thereof; R is —CH$_2$—; X is —C(O)— and $R^5$ is —OH.

16. A compound according to claim 2, or a salt thereof, wherein $R^5$ is lower alkoxy group.

17. A compound according to claim 15, or a salt thereof, chosen from the group consisting of

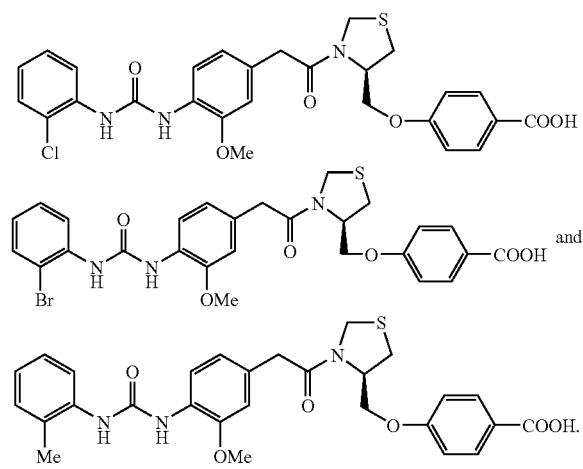

18. A compound according to claim 17, or a salt thereof which is

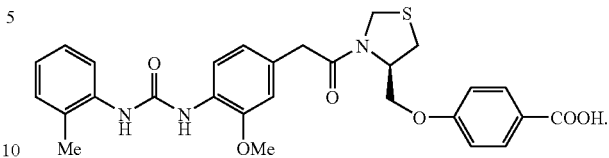

19. A pharmaceutical composition comprising as a therapeutic agent, a compound according to claim 1 and a pharmaceutically acceptable carrier or excipient.

20. A pharmaceutical composition according to claim 19, further comprising one or more additional therapeutic agents.

21. A pharmaceutical composition according to claim 20, wherein said one or more additional therapeutic agents are chosen from the group consisting of antiinflammatory, antirheumatic, corticosteroid, immunosuppressive, antipsoriatic, bronchodilator, antiasthmatic and antidiabetic agents.

22. A pharmaceutical composition according to claim 21, wherein one of said one or more additional therapeutic agents is an antiinflammatory agent.

23. A pharmaceutical composition according to claim 22, wherein said antiinflammatory agent is chosen from a steroid and an NSAID.

24. A method of treating a condition associated with VLA-4 mediated cell adhesion in a mammal, said condition being selected from asthma and arthritis, said method comprising administering to said mammal an effective amount of a compound according to claim 1.

* * * * *

UNITED STATES PATENT AND TRADEMARK OFFICE
CERTIFICATE OF CORRECTION

| | | |
|---|---|---|
| PATENT NO. | : 7,179,819 B2 | Page 1 of 1 |
| APPLICATION NO. | : 10/787905 | |
| DATED | : February 20, 2007 | |
| INVENTOR(S) | : Baldwin et al. | |

It is certified that error appears in the above-identified patent and that said Letters Patent is hereby corrected as shown below:

On the title page item [75]:
The eighth inventor's name should read --Shin Iimura--.

Signed and Sealed this

Seventeenth Day of April, 2007

JON W. DUDAS
*Director of the United States Patent and Trademark Office*